US011684659B2

(12) United States Patent
Ferraro et al.

(10) Patent No.: US 11,684,659 B2
(45) **Date of Patent: *Jun. 27, 2023**

(54) TUMOR CELL VACCINES

(71) Applicant: NEUVOGEN, INC., San Diego, CA (US)

(72) Inventors: Bernadette Ferraro, San Diego, CA (US); Justin James Arndt, San Diego, CA (US); Todd Merrill Binder, San Diego, CA (US); Matthias Hundt, San Diego, CA (US); Kendall M. Mohler, San Diego, CA (US); Jian Yan, San Diego, CA (US)

(73) Assignee: NEUVOGEN, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/726,295

(22) Filed: Apr. 21, 2022

(65) Prior Publication Data

US 2022/0257737 A1 Aug. 18, 2022

Related U.S. Application Data

(63) Continuation of application No. 17/109,757, filed on Dec. 2, 2020.

(60) Provisional application No. 62/943,055, filed on Dec. 3, 2019.

(51) Int. Cl.
*A61K 39/00* (2006.01)
*A61K 35/00* (2006.01)
*A61K 35/13* (2015.01)

(52) U.S. Cl.
CPC .......... *A61K 39/0011* (2013.01); *A61K 35/00* (2013.01); *A61K 35/13* (2013.01); *A61K 2039/5152* (2013.01); *A61K 2039/545* (2013.01); *A61K 2039/575* (2013.01); *A61K 2039/80* (2018.08)

(58) Field of Classification Search
CPC ..... A61K 35/00; A61K 35/13; A61K 39/0011
See application file for complete search history.

(56) References Cited

U.S. PATENT DOCUMENTS

| | | | |
|---|---|---|---|
| 5,057,540 | A | 10/1991 | Kensil et al. |
| 5,273,965 | A | 12/1993 | Kensil et al. |
| 5,352,449 | A | 10/1994 | Beltz et al. |
| 5,443,829 | A | 8/1995 | Kensil et al. |
| 5,560,398 | A | 10/1996 | Pfleger |
| 5,679,356 | A | 10/1997 | Bonnem et al. |
| 5,772,995 | A | 6/1998 | Fakhrai et al. |
| 7,101,543 | B2 | 9/2006 | Fakhrai |
| 7,635,468 | B2 | 12/2009 | Dobric et al. |
| 7,740,837 | B2 | 6/2010 | Fakhrai |
| 8,293,252 | B2 | 10/2012 | Fakhrai et al. |
| 8,444,964 | B2 | 5/2013 | Habib et al. |
| 9,296,784 | B2 | 3/2016 | Jaffee et al. |
| 10,279,020 | B2 | 5/2019 | Podack |
| 10,335,472 | B2 | 7/2019 | Khamar et al. |
| 10,391,158 | B2 | 8/2019 | Lawman et al. |
| 10,404,662 | B1 | 9/2019 | Ben-Dor et al. |
| 10,751,400 | B2 | 8/2020 | Lawman et al. |
| 2002/0006413 | A1 | 1/2002 | Sobol et al. |
| 2002/0168370 | A1 | 11/2002 | McDonald et al. |
| 2002/0177551 | A1 | 11/2002 | Terman |
| 2003/0185808 | A1 | 10/2003 | Thraves et al. |
| 2006/0165668 | A1 | 7/2006 | Liu et al. |
| 2009/0162404 | A1 | 6/2009 | Podack |
| 2010/0119537 | A1 | 5/2010 | Podack |
| 2010/0310562 | A1 | 12/2010 | Kroczek |
| 2011/0014228 | A1 | 1/2011 | Reiss et al. |
| 2011/0250233 | A1 | 10/2011 | Link et al. |
| 2012/0034242 | A1 | 2/2012 | Jooss et al. |
| 2013/0052215 | A9 | 2/2013 | Podack |
| 2013/0251752 | A1 | 9/2013 | Antonia et al. |
| 2014/0050751 | A1 | 2/2014 | Jaffee et al. |

(Continued)

FOREIGN PATENT DOCUMENTS

| | | | |
|---|---|---|---|
| CA | 2683629 | A1 | 10/2008 |
| WO | 00/04926 | A2 | 2/2000 |

(Continued)

OTHER PUBLICATIONS

"A549, CCL-185", retrieved at https://www.atcc.org/products/ccl-185, retrieved on Jun. 30, 2021, updated on Jun. 12, 2021, pp. 7.

(Continued)

*Primary Examiner* — Stephen L Rawlings
(74) *Attorney, Agent, or Firm* — Marshall, Gerstein & Borun LLP

(57) ABSTRACT

The present disclosure provides an allogeneic whole cell cancer vaccine platform that includes compositions and methods for treating and preventing cancer. Provided herein are compositions containing a therapeutically effective amount of cells from one or more cancer cell lines, some or all of which are modified to (i) inhibit or reduce expression of one or more immunosuppressive factors by the cells, and/or (ii) express or increase expression of one or more immunostimulatory factors by the cells, and/or (iii) express or increase expression of one or more tumor-associated antigens (TAAs), including TAAs that have been mutated, and which comprise cancer cell lines that natively express a heterogeneity of tumor associated antigens and/or neoantigens. Also provided herein are methods of making the vaccine compositions, methods of preparing, and methods of use thereof.

4 Claims, 163 Drawing Sheets

Specification includes a Sequence Listing.

(56) References Cited

U.S. PATENT DOCUMENTS

| | | | |
|---|---|---|---|
| 2016/0030557 | A1 | 2/2016 | Weiner et al. |
| 2016/0175416 | A1 | 6/2016 | Peretz et al. |
| 2018/0073038 | A1 | 3/2018 | Nemunaitis et al. |
| 2019/0046624 | A1 | 2/2019 | Wagner et al. |
| 2019/0070278 | A1 | 3/2019 | Fucikova et al. |
| 2019/0175706 | A1 | 6/2019 | Podack |
| 2019/0262443 | A1 | 8/2019 | Khamar et al. |
| 2019/0365878 | A1 | 12/2019 | Zheng |
| 2020/0179447 | A1 | 6/2020 | Gaensler |

FOREIGN PATENT DOCUMENTS

| | | | |
|---|---|---|---|
| WO | 01/54716 | A2 | 8/2001 |
| WO | 2005/030136 | A2 | 4/2005 |
| WO | 2005/063280 | A1 | 7/2005 |
| WO | 2007/085648 | A1 | 8/2007 |
| WO | 2008/126039 | A2 | 10/2008 |
| WO | 2009/117566 | A1 | 9/2009 |
| WO | 2012/156969 | A1 | 11/2012 |
| WO | 2016/156202 | A1 | 10/2016 |
| WO | 2018/098279 | A1 | 5/2018 |
| WO | 2019/104327 | A1 | 5/2019 |
| WO | 2019/112942 | A1 | 6/2019 |
| WO | 2019/191681 | A1 | 10/2019 |
| WO | 2020/076568 | A1 | 4/2020 |
| WO | 2020/185449 | A1 | 9/2020 |

OTHER PUBLICATIONS

"CTCFL CCCTC-binding factor like [ *Homo sapiens* (human) ]", Gene ID: 140690, retrieved at https://www.ncbi.nlm.nih.gov/gene/140690, retrieved on Jun. 30, 2021, updated on Jun. 20, 2021, pp. 14.

"Phase III Lucanix™ Vaccine Therapy in Advanced Non-small Cell Lung Cancer (NSCLC) Following Front-line Chemotherapy (STOP)," U.S National Library of Medicine, Clinical Trials.gov, retrieved at https://www.clinicaltrials.gov/ct2/show/study/NCT00676507, retrieved on Jun. 30, 2021, last updated May 8, 2015, pages.

A549 cell line data sheet, retrieved on Jan. 28, 2022 from https://www.atcc.org/products/ccl-185 (2022).

Abdalla et al., Idiotype vaccination in patients with myeloma reduced circulating myeloma cells (CMC), Ann. Oncol., 19:1172-1179 (2008).

Airoldi et al., IL-12 can target human lung adenocarcinoma cells and normal bronchial epithelial cells surrounding tumor lesions, PLoS One, 4(7):e6119:1-11 (2009).

Ara et al., Multiple effects of CD40-CD40L axis in immunity against infection and cancer, Immunotargets Ther., 7:55-61 (2018).

Barretina et al., The cancer cell line encyclopedia enables predictive modelling of anticancer drug sensitivity, Nature, 483(7391):603-607 (2012).

Barrett et al., Regulated intratumoral expression of IL-12 using a RheoSwitch Therapeutic System (Registered) (RTS(Registered)) gene switch as gene therapy for the treatment of glioma, Cancer Gene. Ther., 25:106-116 (2018).

Bastos et al., What kind of message does IL-12/IL-23 bring to macrophages and dendritic cells?, Microbes and Infection, 6:630-636 (2004).

Blair et al., IDO1 inhibition potentiates vaccine-induced immunity against pancreatic adenocarcinoma, J. Clin. Invest., 129(4):1742-1755 (2019).

Boehm et al., Cellular responses to interferon-gamma, Ann. Rev. Immunol., 15:749-795 (1997).

Borch et al., mRNA-transfected dendritic cell vaccine in combination with metronomic cyclophosphamide as treatment for patients with advanced malignant melanoma, Oncoimmunol, 5(9):e1207842 (2016).

Briones et al., In vivo antitumor effect of CD40L-transduced tumor cells as a vaccine for B-cell lymphoma, Cancer Res., 62:3195-3199 (2002).

Bruttel et al., Cancer stem cell immunology: key to understanding tumorigenesis and tumor immune escape?, Front Immunol., 5:360 (2014).

Cai et al., Improving cancer vaccine efficiency by nanomedicine, Adv. Biosyst., 3(3):e1800287 (2019).

Cerami et al., The cBio cancer genomics portal: an open platform for exploring multidimensional cancer genomics data, Cancer Discovery, 2(5):401-404 (2012).

Change et al., Granulocyte-macrophage colony stimulating factor: an adjuvant for cancer vaccines, Hematology, 9(3):207-215 (2004).

Cheever et al., PROVENGE (Sipuleucel-T) in prostate cancer: the first FDA-approved therapeutic cancer vaccine, Clin. Cancer Res., 17:3520-3526 (2011).

Chen et al., Anti-tumour effects of a xenogeneic fibroblast activation protein-based whole cell tumour vaccine in murine tumour models, Artif. Cells Nanomed Biotechnol., 47(1):4182-4193 (2019).

Chen et al., Oncology meets immunology: the cancer-immunity cycle, Immunity, 39:1-10 (2013).

Choi et al., Strengthening of antitumor immune memory and prevention of thymic atrophy mediated by adenovirus expressing IL-12 and GM-CSF, Gene. Ther., 19(7):711-723 (2012).

Cicchelero et al., Various ways to improve whole cancer cell vaccines, Expert Rev. Vaccines, 13:721-735 (2014).

Cohen et al., Cell-surface marker discovery for lung cancer, Oncotarget, 8:113373-402 (2017).

Contardi et al., CTLA-4 is constitutively expressed on tumor cells and can trigger apoptosis upon ligand interaction, Int. J. Cancer, 117:538-550 (2005).

Creelan et al., Phase II trial of a GM-CSF-producing and CD40L-expressing bystander cell line combined with an allogeneic tumor cell-based vaccine for refractory lung adenocarcinoma, J. Immunother., 36:442-450 (2013).

Curry et al., Vaccination with Irradiated Autologous Tumor Cells Mixed with Irradiated GM-K562 Cells Stimulates Antitumor Immunity and T Lymphocyte Activation in Patients with Recurrent Malignant Glioma, Clin. Cancer Res., 22:2885-2896 (2016).

Czerwinska et al., Therapeutic melanoma vaccine with cancer stem cell phenotype represses exhaustion and maintains antigen-specific T cell sternness by up-regulating BCL6, Oncoimmunology, 9(1):1710063 (2020).

Dahmani et al., TGF-beta in T Cell Biology: Implications for Cancer Immunotherapy, Cancers (Basel), 10(6):194 (2018).

Daris et al., Cannabinoids in cancer treatment: Therapeutic potential and legislation, Bosn. J. Basic. Med. Sci., 19(1):14-23 (2019).

Deguchi et al., Increased immunogenicity of tumor-associated antigen, mucin 1, engineered to express alpha-gal epitopes: a novel approach to immunotherapy in pancreatic cancer, Cancer Res., 70(13):5259-5269 (2010).

Dessureault et al., A GM-CSF/CD40L producing cell augments anti-tumor T cell responses, J. Surg. Res., 125(2): 173-181 (2005).

Dirkse et al., Stem cell-associated heterogeneity in Glioblastoma results from intrinsic tumor plasticity shaped by the microenvironment, Nat. Commun., 10:1787 (2019).

Djureinovic et al., Profiling cancer testis antigens in non-small-cell lung cancer, JCI Insight, 1(10):e86837:1-18 (2016).

DMS 53 cell line data sheet, retrieved on Jan. 28, 2022 from https://www.atcc.org/products/crl-2062 (2022).

DMS 53, CRL-2062, retrieved at https://www.atcc.org/products/crl-2062, retrieved on Jun. 30, 2021, updated on May 19, 20201, pp. 6.

Dorigo et al., Combination of transforming growth factor beta antisense and interleukin-2 gene therapy in the murine ovarian teratoma model, Gynecol Oncol., 71:204-210 (1998).

Dranoff, GM-CSF-based cancer vaccines, Immunol. Rev., 188:147-154 (2002).

Dudek et al., Immature, semi-mature, and fully mature dendritic cells: toward a DC-cancer cells interface that augments anticancer immunity, Front. Immunol., 4:438 (2013).

Ebert et al., A cancer vaccine induces expansion of NY-ESO-1-specific regulatory T cells in patients with advanced melanoma, PLoS One, 7:e48424 (2012).

Egilmez, Chap. 14 in Vaccine Adjuvants and Delivery Systems, John Wiley & Sons, Inc. (2007).

(56) References Cited

OTHER PUBLICATIONS

Elgueta et al., Molecular mechanism and function of CD40/CD40L engagement in the immune system, Immunological reviews, 229:152-172 (2009).
Fakhrai et al., Cytokine gene therapy with interleukin-2-transduced fibroblasts: effects of IL-2 dose on anti-tumor immunity, Hum. Gene. Ther., 6:591-601 (1995).
Fakhrai et al., Eradication of established intracranial rat gliomas by transforming growth factor beta antisense gene therapy, Proc. Natl. Acad. ScL U S A, 93:2909-2914 (1996).
Fakhrai et al., Phase 1 clinical trial of a TGF-beta antisense-modified tumor cell vaccine in patients with advanced glioma, Cancer Gene. Ther., 13:1052-1060 (2006).
Floudas et al., A Pilot Study of the PD-1 Targeting Agent AMP-224 Used With Low-Dose Cyclophosphamide and Stereotactic Body Radiation Therapy in Patients With Metastatic Colorectal Cancer, Clin. Colorectal Cancer, (2019).
Franken et al., Clonogenic assay of cells in vitro, Nat. Protoc., 1:2315-2319 (2006).
Fujita et al., Involvement of Sonic hedgehog in the cell growth of LK-2 cells, human lung squamous carcinoma cells, Biochem. Biophys. Res. Commun., 238(2):658-664 (1997).
Fukuyama et al., Identification of a new cancer/germline gene, KK-LC-1, encoding an antigen recognized by autologous CTL induced on human lung adenocarcinoma, Cancer Res., 66:4922-4928 (2006).
Gandhi et al., Pembrolizumab plus Chemotherapy in Metastatic Non-Small-Cell Lung Cancer, N. Engl. J. Med., 378:2078-2092 (2018).
Gao et al., Integrative analysis of complex cancer genomics and clinical profiles using the cBioPortal, Sci. Signal., 6(269):pl1 (2013).
Gatza et al., Roles for the type III TGF-beta receptor in human cancer, Cell Signal, 22:1163-1174 (2010).
Ge et al., Metronomic cyclophosphamide treatment in metastasized breast cancer patients: immunological effects and clinical outcome, Cancer Immunol. Immunother., 61:353-362 (2011).
Geissmann et al., TGF-(Beta)1 Prevents the Noncognate Maturation of Human Dendritic Langerhans Cells, J. Immun., 162:4567-4575(1999).
Ghiringhelli et al., Metronomic cyclophosphamide regimen selectively depletes CD4+CD25+ regulatory T cells and restores T and NK effector functions in end stage cancer patients, Cancer Immunol. Immunother., 56:641-648 (2007).
Giaccone et al., A phase III study of belagenpumatucel-L, an allogeneic tumour cell vaccine, as maintenance therapy for non-small cell lung cancer, Eur. J. Cancer, 51(16):2321-2329 (2015).
Giard et al., In vitro cultivation of human tumors: establishment of cell lines derived from a series of solid tumors, J. Natl. Cancer Inst., 51:1417-1423 (1973).
Gilbert et al., Cancer stem cells: cell culture, markers, and targets for new therapies, J. Cell Biochem., 108(5):1031-1038 (2009).
Giovanni et al., Cancer vaccines co-targeting HER2/Neu and IGF1R, Cancers (Basel), 11(4):517 (2019).
Gray et al., A phase I/randomized phase II study of GM.CD40L vaccine in combination with CCL21 in patients with advanced lung adenocarcinoma, Cancer Immunol. Immunother., (2018).
Greten et al., Low-dose cyclophosphamide treatment impairs regulatory T cells and unmasks AFP-specific CD4+ T-cell responses in patients with advanced HCC, J. Immunother., 33(2):211-218 (2010).
Gulley, Therapeutic vaccines: the ultimate personalized therapy?, Hum. Vaccin. Immunother., 9:219-221 (2013).
Gure et al., Cancer-testis genes are coordinately expressed and are markers of poor outcome in non-small cell lung cancer, Clin. Cancer Res., 11:8055-8062 (2005).
Hamid et al., Alum with interleukin-12 augments immunity to a melanoma peptide vaccine: correlation with time to relapse in patients with resected high-risk disease, Clin. Cancer Res., 13:215-222 (2007).
Hansson et al., Long-term idiotype vaccination combined with interleukin-12 (IL-12), or IL-12 and granulocyte macrophage colony-stimulating factor, in early-stage multiple myeloma patients, Clin. Cancer Res., 13:1503-1510 (2007).
Hirschowitz et al., Pilot study of 1650-G: a simplified cellular vaccine for lung cancer, J. Thorac. Oncol., 6:169-173 (2011).
Ho et al., Mesothelin expression in human lung cancer, Clin. Cancer Res., 13:1571-1575 (2007).
Hollingsworth et al., Turning the corner on therapeutic cancer vaccines, NPJ Vaccines, 4(7):1-10 (2019).
Hyun et al., Comprehensive analysis of cytomegalovirus pp65 antigen-specific CD8 + T Cell responses according to human leukocyte antigen class I allotypes and intraindividual dominance, Front. Immunol., 8:1591 (2017).
International Application No. PCT/US2020/062840, International Search Report and Written Opinion, dated May 25, 2021.
Jiang et al., Vaccinations for colorectal cancer: Progress, Strategies, and novel adjuvants, Int. J. Mol. Sci., 20(14):3403 (2019).
Jones et al., Immune response to polyvalent melanoma cell vaccine in AJCC stage III melanoma: an immunologic survival model, Ann. Surg. Oncol., 3:437-445 (1996).
Jurtz et al., NetMHCpan-4.0: Improved Peptide-MHC Class I Interaction Predictions Integrating Eluted Ligand and Peptide Binding Affinity Data, J. Immunol., 199:3360-3368 (2017).
Kareva, A Combination of Immune Checkpoint Inhibition with Metronomic Chemotherapy as a Way of Targeting Therapy-Resistant Cancer Cells, Int. J. Mol. Sci., 18(10):2134 (2017).
Karimi-Busheri et al., Pivotal role of CD38 biomarker in combination with CD24, EpCAM, and ALDH for identification of H460 derived lung cancer stem cells, J. Stem. Cells, 6:9-20 (2011).
Karsten et al., What makes cancer stem cell markers different?, SpringerPlus, 2(1):301 (2013).
Keenan et al., Whole cell vaccines—past progress and future strategies, Semin. Oncol., 39:276-286 (2012).
Kim et al., Histone deacetylase inhibitors: molecular mechanisms of action and clinical trials as anti-cancer drugs, Am. J. Transl. Res., 3(2):166-179 (2011).
Kim, Development of genetically modified tumor cell containing co-stimulatory molecule, Biomedical Science Letters, 25(4):398-406 (2019).
Kozlowska et al., Therapeutic gene modified cell based cancer vaccines, Gene., 525(2):200-207 (2013).
Kubiczkova et al., TGF-(Beta)—an excellent servant but a bad master, J. transl. med., 10:183 (2012).
Laheru et al., Allogeneic granulocyte macrophage colony-stimulating factor-secreting tumor immunotherapy alone or in sequence with cyclophosphamide for metastatic pancreatic cancer: a pilot study of safety, feasibility, and immune activation, Clin. Cancer Res., 14:1455-1463 (2008).
Lasek et al., Interleukin 12: still a promising candidate for tumor immunotherapy?, Cancer Immunol. Immunother., 63:419-435 (2014).
Le et al. Regulatory T-cell modulation using cyclophosphamide in vaccine approaches: a current perspective, Cancer Res., 72:3439-3444 (2012).
Le et al., Results from a Phase IIb, Randomized, Multicenter study of GVAX pancreas and CRS-207 compared with chemotherapy in adults with previously treated metastatic pancreatic adenocarcinoma (ECLIPSE Study), Clin. Cancer Res., 25(18):5493-5502 (2019).
Leko et al., Identification of neoantigen-reactive tumor-infiltrating lymphocytes in primary bladder cancer, J. Immunol., 202(12):3458-3467 (2019).
Li et al., Transforming growth factor-beta regulation of immune responses, Annu. Rev. Immunol., 24:99-146 (2006).
Li et al., Vaccination with CD47 deficient tumor cells elicits an antitumor immune response in mice, Nat. Commun., 11(1):581 (2020).
Lieber et al. A continuous tumor-cell line from a human lung carcinoma with properties of type II alveolar epithelial cells, Int. J. Cancer, 17:62-70 (1976).
Lin et al., Present status of the use of cytokines as adjuvants with vaccines to protect against infectious diseases, Clin. Infec. Dis., 21(6):1439-1449 (1995).
Lindenberg et al., Induction of dendritic cell maturation in the skin microenvironment by soluble factors derived from colon carcinoma, Hum. Vaccin Immunother., 10:1622-1632 (2014).

(56) References Cited

OTHER PUBLICATIONS

Lipson et al., Safety and immunologic correlates of Melanoma GVAX, a GM-CSF secreting allogeneic melanoma cell vaccine administered in the adjuvant setting, J. Transl. Med., 13:214 (2015).
Liu et al., Interleukin-12: an update on its immunological activities, signaling and regulation of gene expression, Curr. Immunol. Rev., 1(2):119-137 (2005).
LK-2 cell line data sheet, retrieved on Jan. 28, 2022 from https://cellbank.nibiohn.go.jp/~cellbank/en/search_res_det.cgi?ID=540 (2022).
Luiten et al., Immunogenicity, including vitiligo, and feasibility of vaccination with autologous GM-CSF-transduced tumor cells in metastatic melanoma patients, J. Clin. Oncol., 23:8978-8991 (2005).
Luksza et al., A neoantigen fitness model predicts tumor response to checkpoint blockade immunotherapy, Nature, 551(7681):517-520 (2017).
Lund et al., Definition of supertypes for HLA molecules using clustering of specificity matrices, Immunogenetics, 55:797-810 (2004).
Machiels et al., Cyclophosphamide, doxorubicin, and paclitaxel enhance the antitumor immune response of granulocyte/macrophage-colony stimulating factor-secreting whole-cell vaccines in HER-2/neu tolerized mice, Cancer Res., 61:3689-3697 (2001).
Mackiewicz et al., Long-term survival of high-risk melanoma patients immunized with a Hyper-IL-6-modified allogeneic whole-cell vaccine after complete resection, Expert Opin. Investig. Drugs, 21(6):773-783 (2012).
Madondo et al., Low dose cyclophosphamide: Mechanisms of T cell modulation, Cancer Treat. Rev., 42:3-9 (2016).
Maiers et al., High-resolution HLA alleles and haplotypes in the United States population, Human Immunology, 68:779-788 (2007).
Majzner et al., Tumor Antigen Escape from CAR T-cell Therapy, Cancer Discov., 8:1219-1226 (2018).
Mao et al., Selective blockade of B7-H3 enhances antitumour immune activity by reducing immature myeloid cells in head and neck squamous cell carcinoma, J. Cell. Mol. Med., 21:2199-2210 (2017).
Marcinkowski et al., Cancer targeting by TCR gene-engineered T cells directed against Kita-Kyushu Lung Cancer Antigen-1, J. Immunother Cancer, 7:229 (2019).
McGranahan et al., Clonal neoantigens elicit T cell immunoreactivity and sensitivity to immune checkpoint blockade, Science, 351:1463-1469 (2016).
Meeker et al., Emergence of idiotype variants during treatment of B-cell lymphoma with anti-idiotype antibodies, N. Engl. J. Med., 312:1658-1665 (1985).
Miao et al., Adaptive Immune Resistance Emerges from Tumor-Initiating Stem Cells, Cell., 2019.
Michael et al., Delayed disease progression after allogeneic cell vaccination in hormone-resistant prostate cancer and correlation with immunologic variables, Clin. Cancer Res., 11(12):4469-4478 (2005).
Miguel et al., Comparative antitumor effect among GM-CSF, IL-12 and GM-CSF+IL-12 genetically modified tumor cell vaccines, Cancer Gene. Ther., 20:576-581 (2013).
Miyazono et al., Intracellular and extracellular TGF-beta signaling in cancer: some recent topics, Front Med., 12:387-411 (2018).
Mohamadzadeh et al., Interleukin 15 skews monocyte differentiation into dendritic cells with features of Langerhans cells, J. Exp. Med., 194:1013-1020 (2001).
Najafi et al., Contribution of regulatory T cells to cancer: A review, J. Cell Physiol., (2018).
NCI-H23 cell line data sheet, retrieved on Jan. 28, 2022 from https://www.atcc.org/products/crl-5800 (2022).
NCI-H460 cell line data sheet, retrieved on Jan. 28, 2022 from https://www.atcc.org/products/htb-177 (2022).
NCI-H520 cell line data sheet, retrieved on Jan. 28, 2022 from https://www.atcc.org/products/htb-182 (2022).
Nelson, IL-2, regulatory T cells, and tolerance, J. Immunol., 172(7):3983-3988 (2004).
Nemunaitis et al. Phase II trial of Belagenpumatucel-L, a TGF-beta2 antisense gene modified allogeneic tumor vaccine in advanced non small cell lung cancer (NSCLC) patients, Cancer Gene. Ther., 16:620-624 (2009).
Nemunaitis et al., Granulocyte-macrophage colony-stimulating factor gene-modified autologous tumor vaccines in non-small-cell lung cancer, J. Natl. Cancer Inst., 96(4):326-331 (2004).
Nemunaitis et al., Phase 1/2 trial of autologous tumor mixed with an allogeneic GVAX vaccine in advanced-stage non-small-cell lung cancer, Cancer Gene. Ther., 13:555-562 (2006).
Nemunaitis et al., Phase II study of belagenpumatucel-L, a transforming growth factor beta-2 antisense gene-modified allogeneic tumor cell vaccine in non-small-cell lung cancer, J. Clin. Oncol., 24:4721-4730 (2006).
Niyongere et al., Immunotherapy combination strategies (non-chemotherapy) in non-small cell lung cancer, J. Thorac. Dis., 10(Suppl. 3):S433-S450 (2018).
Obeid et al., Calreticulin exposure dictates the immunogenicity of cancer cell death, Nat. Med., 13:54-61 (2007).
Odunsi et al., Epigenetic potentiation of NY-ESO-1 vaccine therapy in human ovarian cancer, Cancer Immunol. Res., 2(1):37-49 (2014).
Olivares et al., Phase I trial of TGF-beta 2 antisense GM-CSF gene-modified autologous tumor cell (TAG) vaccine, Clin. Cancer Res., 17:183-192 (2011).
Oser et al., Transformation from non-small-cell lung cancer to small-cell lung cancer: molecular drivers and cells of origin, Lancet Oncol., 16:e165-72 (2015).
Page et al., Novel technologies and emerging biomarkers for personalized cancer immunotherapy, J. Immunother. Cancer, 4:3 (2016).
Pardoll, The blockade of immune checkpoints in cancer immunotherapy, Nature, 12(4):252-264 (2012).
Paz-Ares et al., Pembrolizumab plus Chemotherapy for Squamous Non-Small-Cell Lung Cancer, N. Engl. J. Med., 379:2040-2051 (2018).
Pedersen et al., Transcriptional gene expression profiling of small cell lung cancer cells, Cancer Res., 63(8): 1943-1953 (2003).
Pettengill et al., Isolation and growth characteristics of continuous cell lines from small-cell carcinoma of the lung, Cancer, 45:906-918 (1980).
Phelps et al., NCI-Navy Medical Oncology Branch cell line data base, J. Cell. Biochem. Suppl., 24:32-91 (1996).
Podaza et al., Evaluation of T-cell responses against shared melanoma associated antigens and predicted neoantigens in cutaneous melanoma patients treated with the CSF-470 allogeneic cell vaccine plus BCG and GM-CSF, Front Immunol., 11:1147 (2020).
Portielje et al., IL-12: a promising adjuvant for cancer vaccination, Cancer Immunol. Immunother., 52(3):133-144 (2003).
Raez et al., Induction of CD8 T-cell-Ifn-gamma response and positive clinical outcome after immunization with gene-modified allogeneic tumor cells in advanced non-small-cell lung carcinoma, Cancer Gene. Ther., 10(11):850-858 (2003).
Rahma et al., Is the "3+3" dose-escalation phase I clinical trial design suitable for therapeutic cancer vaccine development? A recommendation for alternative design, Clin. Cancer Res., 20:4758-4767 (2014).
Rijavec et al., Belagenpumatucel-L for the treatment of non-small cell lung cancer, Expert Opin. Biol. Ther., 15(9):1371-1379 (2015).
Rizvi et al., Cancer immunology, Mutational landscape determines sensitivity to PD-1 blockade in non-small cell lung cancer, Science, 348:124-128 (2015).
Rosenthal et al., Neoantigen-directed immune escape in lung cancer evolution, Nature, (2019).
Rukmini et al., Inducing tumor suppressive microenvironments through genome edited CD47 -/- syngeneic cell vaccination, Sci. Rep., 9(1):20057 (2019).
Salas et al., Vaccination for pancreatic ductal adenocarcinoma: A hard nut to crack, Clin. Cancer Res., 25(18):5435-5437 (2019).
Sastry et al., Titering lentiviral vectors: comparison of DNA, RNA and marker expression methods, Gene. Ther., 9:1155-1162 (2002).
Schlom, Therapeutic cancer vaccines: current status and moving forward, J. Natl. Cancer Inst., 104:599-613 (2012).

(56) References Cited

OTHER PUBLICATIONS

Sebastian et al., Phase lb study evaluating a self-adjuvanted mRNA cancer vaccine (RNActive(R)) combined with Tocal radiation as consolidation and maintenance treatment for patients with stage IV non-small cell lung cancer, BMC Cancer, 14:748 (2014).
Seeger et al., The TGF-beta superfamily in dendritic cell biology, Cytokine Growth Factor Rev., 26:647-657 (2015).
Senzer et al., Phase I trial of "bi-shRNAi(furin)/GMCSF DNA/autologous tumor cell" vaccine (FANG) in advanced cancer, Mol. Ther., 20:679-686 (2012).
Shawler et al., Antigenic and immunologic characterization of an allogeneic colon carcinoma vaccine, Clin. Exp. Immunol., 129:99-106 (2002).
Shawler et al., Comparison of gene therapy with interleukin-2 gene modified fibroblasts and tumor cells in the murine CT-26 model of colorectal carcinoma, J. Immunother. Emphasis Tumor Immunol., 17:201-208 (1995).
Shawler et al., Gene therapy approaches to enhance antitumor immunity, Adv. Pharmacol., 40:309-337 (1997).
Shawler et al., Interleukin-2 (IL-2) gene therapy with allogeneic fibroblasts in the CT-26 model of murine colorectal carcinoma, Oncol. Rep., 4:135-138 (1997).
Siegel et al., Cancer statistics, 2019, CA Cancer J. Clin., 69:7-34 (2019).
Soares et al., PD-1/PD-L1 blockade together with vaccine therapy facilitates effector T-cell infiltration into pancreatic tumors, J. Immunother., 38:1-11 (2015).
Sobol et al., Interleukin 2 gene therapy of colorectal carcinoma with autologous irradiated tumor cells and genetically engineered fibroblasts: a Phase I study, Clin. Cancer Res., 5:2359-2365 (1999).
Sobol et al., Interleukin-2 gene therapy in a patient with glioblastoma, Gene. Ther., 2:164-167 (1995).
Soiffer et al., Vaccination with irradiated autologous melanoma cells engineered to secrete human granulocyte-macrophage colony-stimulating factor generates potent antitumor immunity in patients with metastatic melanoma, Proc. Natl. Acad. Sci. U S A, 95:13141-13146 (1998).
Soiffer et al., Vaccination with irradiated, autologous melanoma cells engineered to secrete granulocyte-macrophage colony-stimulating factor by adenoviral-mediated gene transfer augments antitumor immunity in patients with metastatic melanoma, J. Clin. Oncol., 21:3343-3350 (2003).
Soliman et al., A GM-CSF and CD40L bystander vaccine is effective in a murine breast cancer model. Breast Cancer (Dove Med Press), 7:389-397 (2015).
Srivatsan et al., Allogeneic tumor cell vaccines: the promise and limitations in clinical trials, Hum. Vaccin. Immunother., 10(1):52-63 (2014).
Stronen et al., Targeting of cancer neoantigens with donor-derived T cell receptor repertoires, Science, 352(6291):1337-1341 (2016).
Suh et al., The B7 family member B7-H3 preferentially down-regulates T helper type 1-mediated immune responses, Nat. Immun., 4:899 (2003).
Sun et al., Vaccination with IL-12 gene-modified autologous melanoma cells: preclinical results and a first clinical phase I study, Gene. Ther., 5:481-490 (1998).
Taylor, Cytokines as adjuvants for vaccines: antigen-specific responses differ from polyclonal responses, Infect. Immunl., 63(9):3241-3244 (1995).
Theofilopoulos et al., Type I interferons (alpha/beta) in immunity and autoimmunity, Ann. Rev. Immunol., 23:307-336 (2005).
Thi et al., Cell-based IL-15:IL-15R (Alpha) secreting vaccine as an effective therapy for CT26 colon cancer in mice, Mol. Cells., 42(12):869-883 (2019).
Thomas et al., High mesothelin expression in advanced lung adenocarcinoma is associated with KRAS mutations and a poor prognosis, Oncotarget, 6:11694-11703 (2015).
Thomas et al., Why has active immunotherapy not worked in lung cancer?, Annals Oncol., 26:(11)2213-2220 (2015).
Trinchieri, Interleukin-12 and the regulation of innate resistance and adaptive immunity, Nat. Rev. Immunol., 3(2):133-146 (2003).
Tsujikawa et al., Evaluation of cyclophosphamide/GVAX pancreas followed by listeria-mesothelin (CRS-207) with or without nivolumab in patients with pancreatic cancer, Clin. Cancer Res., 26(14):3578-3588 (2020).
Uemura et al., Effects of granulocyte colony-stimulating factor and granulocyte-macrophage colony-stimulating factor on lung cancer: roles of cyclooxygenase-2, Oncol. Rep., 17:955-961 (2007).
Ulrich et al., Chapter 21 in Vaccine Design, the Subunit and Adjuvant Approach, Powell, M.F. and Newman, M.J., eds. Plenum Press, NY (1995).
Van De Laar et al., Regulation of dendritic cell development by GM-CSF: molecular control and implications for immune homeostasis and therapy, Blood, 119:3383-3393 (2012).
Vilella et al., Treatment of patients with progressive unresectable metastatic melanoma with a heterologous polyvalent melanoma whole cell vaccine, Int. J. Cancer, 106:626-631 (2003).
Visser et al., Effects of TGF-beta on the immune system: implications for cancer immunotherapy, Leukemia., 13:1188-1199 (1999).
Vonderheide, The Immune Revolution: A Case for Priming, Not Checkpoint, Cancer Cell, 33:563-569 (2018).
Voorwerk et al., Immune induction strategies in metastatic triple-negative breast cancer to enhance the sensitivity to PD-1 blockade: the TONIC trial, Nat. Med., 25:920-928 (2019).
Wang et al., B7-H3-mediated tumor immunology: Friend or foe?, Int. J. Cancer, 134:2764-2771 (2014).
Wei et al., Silencing of the TGF-(Beta)1 gene increases the immunogenicity of cells from human ovarian carcinoma, J. Immunother., 35(3):267-275 (2012).
Wu et al., A phase II study of allogeneic GM-CSF-transfected pancreatic tumor vaccine (GVAX) with ipilimumab as maintenance treatment for metastatic pancreatic cancer, Clin. Cancer Res., 26(19):5129-5139 (2020).
Xia et al., Whole-cell cancer vaccines induce large antibody responses to carbohydrates and glycoproteins, Cell. Chem. Biol., 23:1515-1525 (2016).
Xu et al., Membrane-Bound CD40L Promotes Senescence and Initiates Senescence-Associated Secretory Phenotype via NF-?B Activation in Lung Adenocarcinoma, Cell. Physiol. Biochem., 48(4):1793-1803 (2018).
Xu et al., WT1 promotes cell proliferation in non-small cell lung cancer cell lines through up-regulating cyclin D1 and p-pRb in vitro and in vivo, PLoS One, 8(8):e68837:1-10 (2013).
Yamashita et al., Local increase in polymorphonuclear leukocyte elastase is associated with tumor invasiveness in non-small cell lung cancer, Chest, 109:1328-1334 (1996).
Yan et al., Recent progress in GM-CSF-based cancer immunotherapy, Immunotherapy, 9:347-360 (2017).
Yarchoan et al., A phase 2 study of GVAX colon vaccine with cyclophosphamide and pembrolizumab in patients with mismatch repair proficient advanced colorectal cancer, Cancer Med., 9(4):1485-1494 (2020).
Yu et al., Novel GM-CSF-based vaccines: One small step in GM-CSF gene optimization, one giant leap for human vaccines, Hum. Vaccin Immunother., 12:3020-3028 (2016).
Zhang et al., Brother of regulator of imprinted sites inhibits cisplatin-induced DNA damage in non-small cell lung cancer, OncoL Lett., 20(5):251 (2020).
Zhang et al., Megakaryocytic potentiating factor and mature mesothelin stimulate the growth of a lung cancer cell line in the peritoneal cavity of mice, PLoS One, 9(8):e104388:1-7 (2014).
Zhang et al., Optimizing DC vaccination by combination with oncolytic adenovirus coexpressing IL-12 and GM-CSF, Mol. Ther., 19:1558-1568 (2011).
Zhang et al., Personalized cancer vaccines: Targeting the cancer mutanome, Vaccine, 35:1094-100 (2017).
Zhang et al., Prognostic Significance of CD276 in Non-small Cell Lung Cancer, Open Med. (Wars)., 14:805-812 (2019).
Zhao et al., Allogenic mouse cell vaccine inhibits lung cancer progression by inhibiting angiogenesis, Hum. Vaccin Immunother., 1-16 (2020).

(56) References Cited

OTHER PUBLICATIONS

Zhao et al., Stemness-related markers in cancer, Cancer Transl. Med., 3(3):87-95 (2017).
Zhenjiang et al., Mesothelin-specific Immune Responses Predict Survival of Patients With Brain Metastasis, EBioMedicine, 23:20-24 (2017).
Zhong et al., Conjugation of TLR7 agonist combined with demethylation treatment improves whole-cell tumor vaccine potency in acute myeloid leukemia, Int. J. Med. Sci., 17(15):2346-2356 (2020).

FIG. 16A
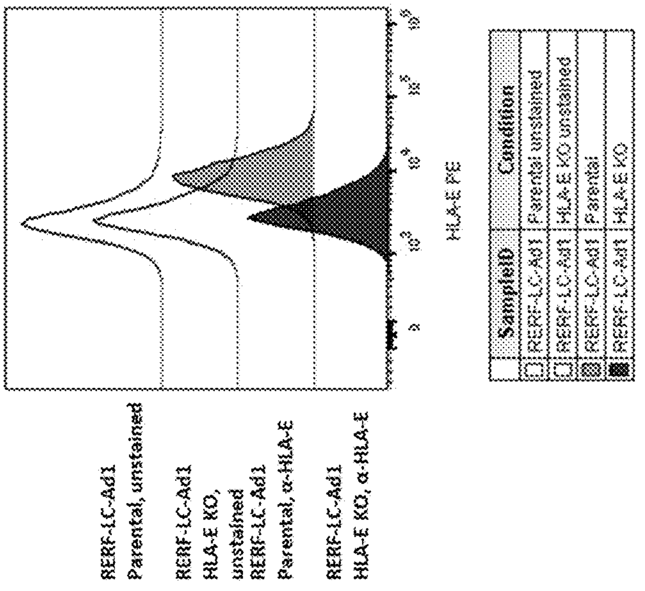
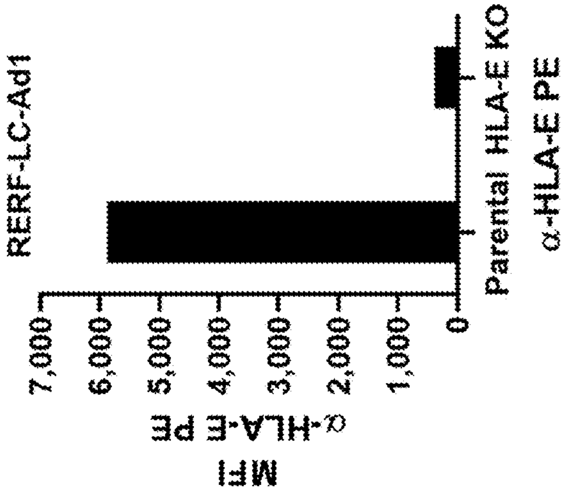
FIG. 16B
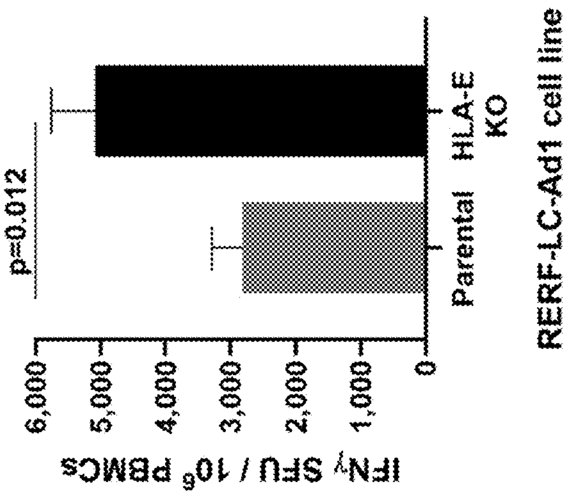

TGFβ1 Secretion
p=0.0286
ND
TGFβ1 Secretion (pg / 10^6 cells / mL/ 24h)
2,000
1,500
1,000
500
0
Parental TGFβ1 TGFβ2 KD
NCI-H2023 CD47 modified cell line TGFβ2 Secretion
TGFβ2 Secretion (pg / 10^6 cells / mL/ 24h)
500
400
300
200
100
0
Parental TGFβ1 TGFβ2 KD
NCI-H2023 CD47 modified cell line NCI-H2023
αCD47 BV421 MFI
300,000
200,000
100,000
1,000
800
600
400
200
0
Parental
TGFβ1/β2 KD CD47 KO NCI-H2023 Parental. Unstained.
NCI-H2023 TGFβ1β2 KD CD47 KO. Unstained.
NCI-H2023 Parental. BV421-αCD47.
NCI-H2023 TGFβ1β2 KD CD47 KO. BV421-αCD47.
CD47 BV421

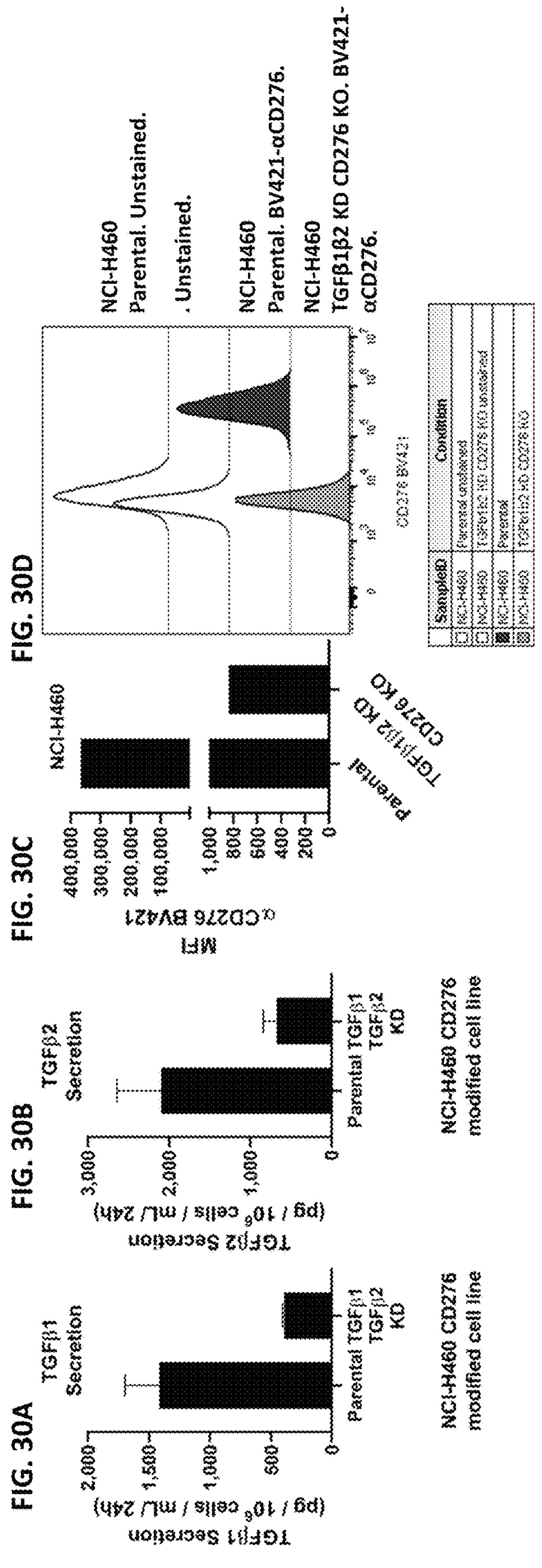
FIG. 30A
TGFβ1 Secretion
TGFβ1 Secretion (pg / 10^6 cells / mL / 24h)
2,000
1,500
1,000
500
0
Parental
TGFβ1 TGFβ2 KD
NCI-H460 CD276 modified cell line
FIG. 30B
TGFβ2 Secretion
TGFβ2 Secretion (pg / 10^6 cells / mL / 24h)
3,000
2,000
1,000
0
Parental
TGFβ1 TGFβ2 KD
NCI-H460 CD276 modified cell line
FIG. 30C
NCI-H460
MFI αCD276 BV421
400,000
300,000
200,000
100,000
1,000
800
600
400
200
0
Parental
TGFβ1β2 KD CD276 KO
FIG. 30D
NCI-H460 Parental. Unstained.
. Unstained.
NCI-H460 Parental. BV421-αCD276.
NCI-H460 TGFβ1β2 KD CD276 KO. BV421-αCD276.
CD276 BV421
SampleID
Condition
NCI-H460
Parental unstained
NCI-H460
TGFb1b2 KD CD276 KO unstained
NCI-H460
Parental
NCI-H460
TGFb1b2 KD CD276 KO

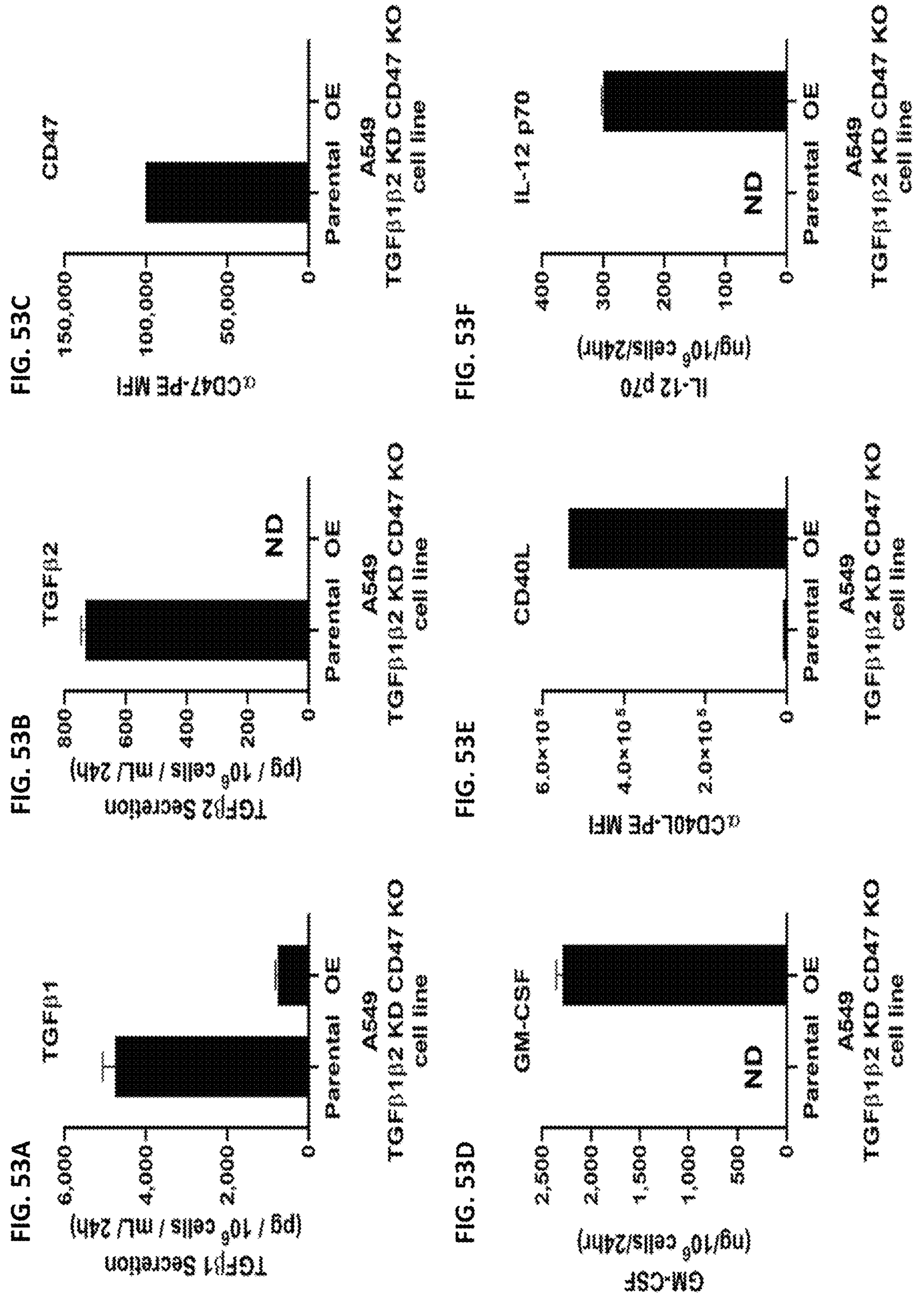
FIG. 53A
TGFβ1
TGFβ1 Secretion (pg / 10^6 cells / mL/ 24h)
6,000
4,000
2,000
0
Parental OE
A549
TGFβ1β2 KD CD47 KO
cell line
FIG. 53B
TGFβ2
TGFβ2 Secretion (pg / 10^6 cells / mL/ 24h)
800
600
400
200
0
ND
Parental OE
A549
TGFβ1β2 KD CD47 KO
cell line
FIG. 53C
CD47
αCD47-PE MFI
150,000
100,000
50,000
0
Parental OE
A549
TGFβ1β2 KD CD47 KO
cell line
FIG. 53D
GM-CSF
GM-CSF (ng/10^6 cells/24hr)
2,500
2,000
1,500
1,000
500
0
ND
Parental OE
A549
TGFβ1β2 KD CD47 KO
cell line
FIG. 53E
CD40L
αCD40L-PE MFI
6.0×10^5
4.0×10^5
2.0×10^5
0
Parental OE
A549
TGFβ1β2 KD CD47 KO
cell line
FIG. 53F
IL-12 p70
IL-12 p70 (ng/10^6 cells/24hr)
400
300
200
100
0
ND
Parental OE
A549
TGFβ1β2 KD CD47 KO
cell line

| TAA | # of cell lines |
|---|---|
| MAGEA1 | 1 |
| MAGEA3 | 4 |
| MAGEA4 | 2 |
| TERT | 4 |
| STEAP1 | 6 |
| CEA | 1 |
| Her2 | 6 |
| MUC1 | 2 |
| LY6K | 1 |
| MSLN | 1 |
| NUF2 | 6 |
| PRAME | 5 |
| Survivin | 6 |
| WT1 | 1 |
| 5T4 | 5 |
| DEPDC1 | 6 |
| BORIS | 0 |
| EGFR | 4 |
| KIF20A | 6 |
| MPHOSPH1 | 6 |
| PSMA | 2 |
| TTK | 6 |
| IGF2BP3 | 5 |
| Brachyury | 2 |

FIG. 69A
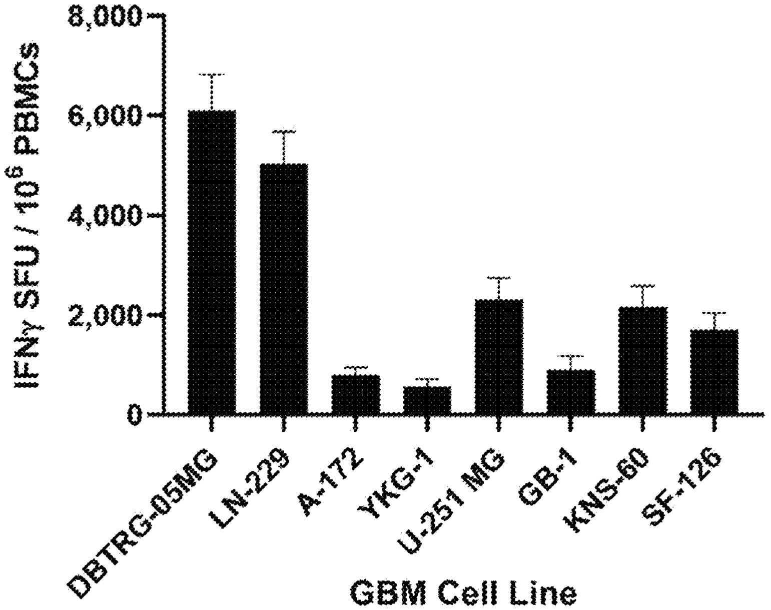
FIG. 69B
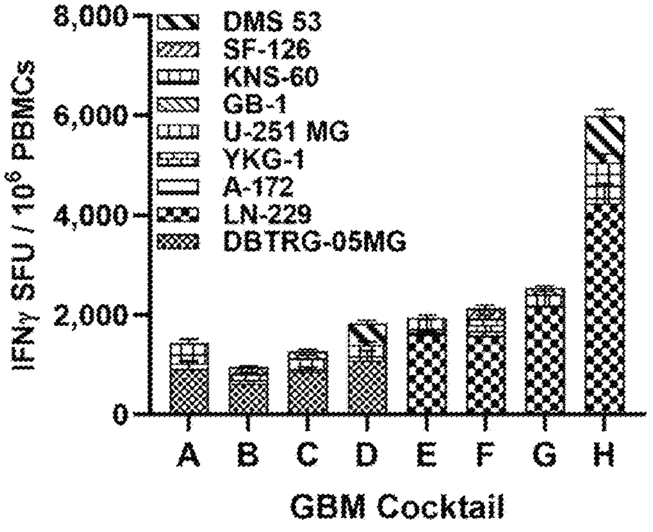
FIG. 69C
| Cocktail | Component Cell Lines |
|---|---|
| A | DBTRG-05MG, A-172, KNS-60 |
| B | DBTRG-05MG, YKG-1, SF-126 |
| C | DBTRG-05MG, U-251 MG, GB-1 |
| D | DBTRG-05MG, U-251 MG, DMS 53 |
| E | LN-229, A-172, KNS-60 |
| F | LN-229, YKG-1, SF-126 |
| G | LN-229, U-251 MG, GB-1 |
| H | LN-229, U-251 MG, DMS 53 |

| Minimum # of TAAs | % of GBM tumors (n=170) |
|---|---|
| 18 | 100% |
| 19 | 97.6% |
| 20 | 79.4% |
| 21 | 32.9% |
| 22 | 1.8% |

FIG. 76A
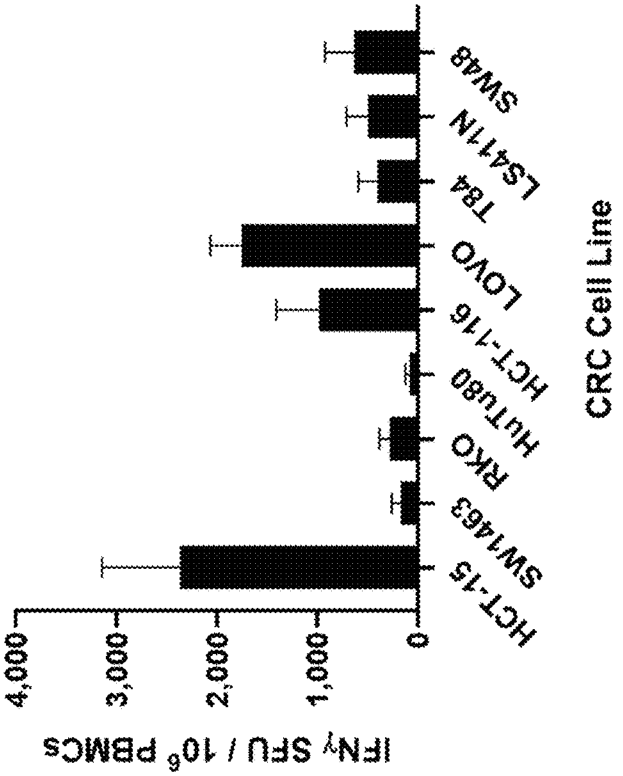
FIG. 76B
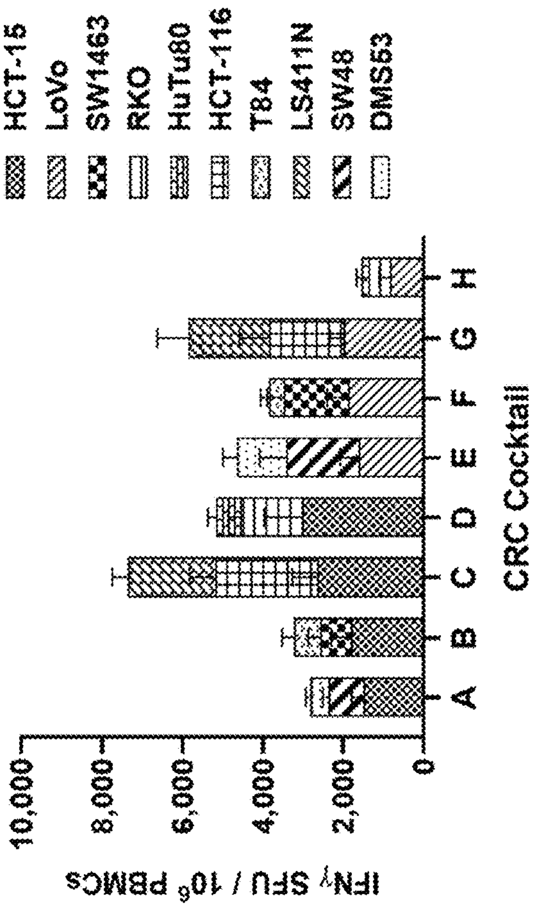
FIG. 76C
| Cocktail | Component Cell Lines |
|---|---|
| A | HCT-15, SW48, DMS 53 |
| B | HCT-15, SW1463, T84 |
| C | HCT-15, HCT-116, LS411N |
| D | HCT-15, RKO, HuTu80 |
| E | LoVo, SW48, DMS 53 |
| F | LoVo, SW1463, T84 |
| G | LoVo, HCT-116, LS411N |
| H | LoVo, RKO, HuTu80 |

| Cocktail | Component Cell Lines |
|---|---|
| A | HCT-15, SW48, DMS 53 |
| B | HCT-15, SW1463, T84 |
| C | HCT-15, HCT-116, LS411N |
| D | HCT-15, RKO, HuTu80 |
| E | LoVo, SW48, DMS 53 |
| F | LoVo, SW1463, T84 |
| G | LoVo, HCT-116, LS411N |
| H | LoVo, RKO, HuTu80 |

| Minimum # of Prioritized TAAs | % CRC Tumors (n=365) |
|---|---|
| 14 | 100% |
| 15 | 94.5% |
| 16 | 65.8% |
| 17 | 42.2% |
| 18 | 25.8% |
| 19 | 11.5% |
| 20 | 1.4% |

| Minimum # of Prioritized TAAs | % PCa Tumors (n=460) |
|---|---|
| 18 | 100% |
| 19 | 99.3% |
| 20 | 75.4% |
| 21 | 21.1% |
| 22 | 1.5% |

FIG. 86A
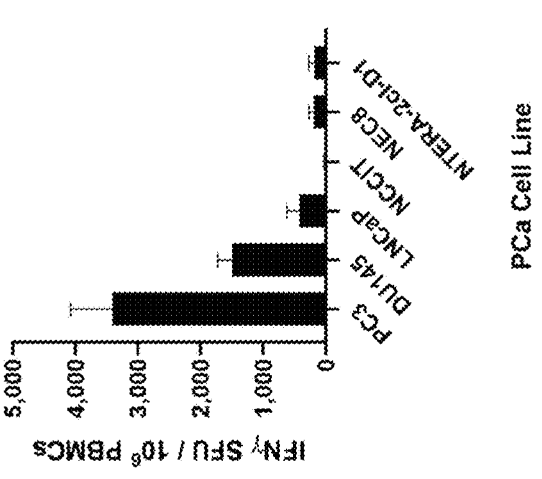
FIG. 86B
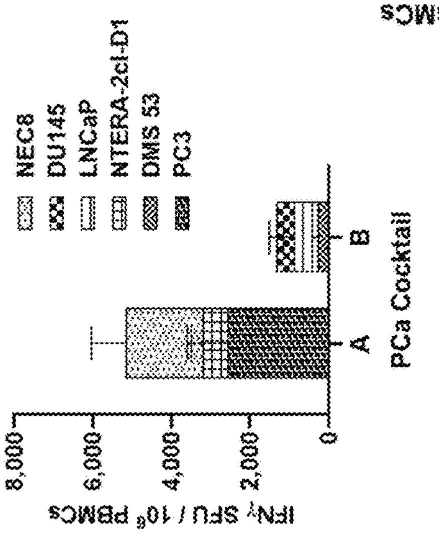
FIG. 86C
| Cocktail | Component Cell Lines |
|---|---|
| A | PC3, NEC8, NTERA-2cl-D1 |
| B | DU145, LNCaP, DMS 53 |
FIG. 86D
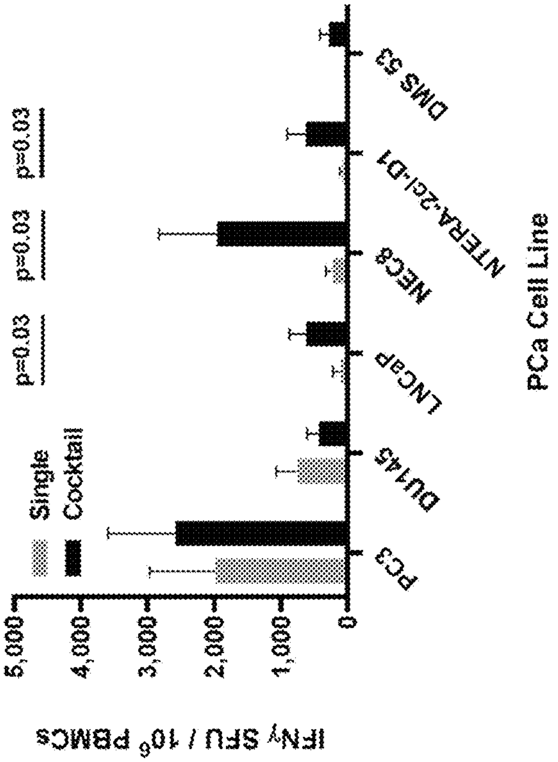

FIG. 93A
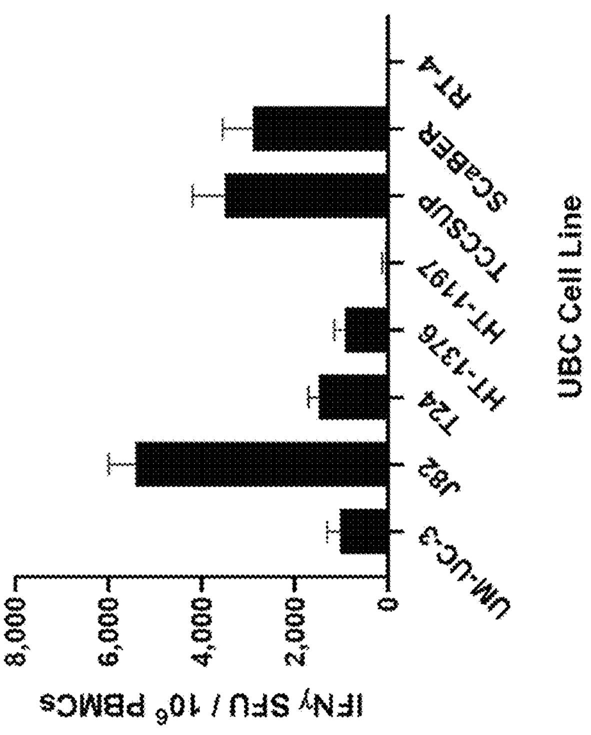
FIG. 93B
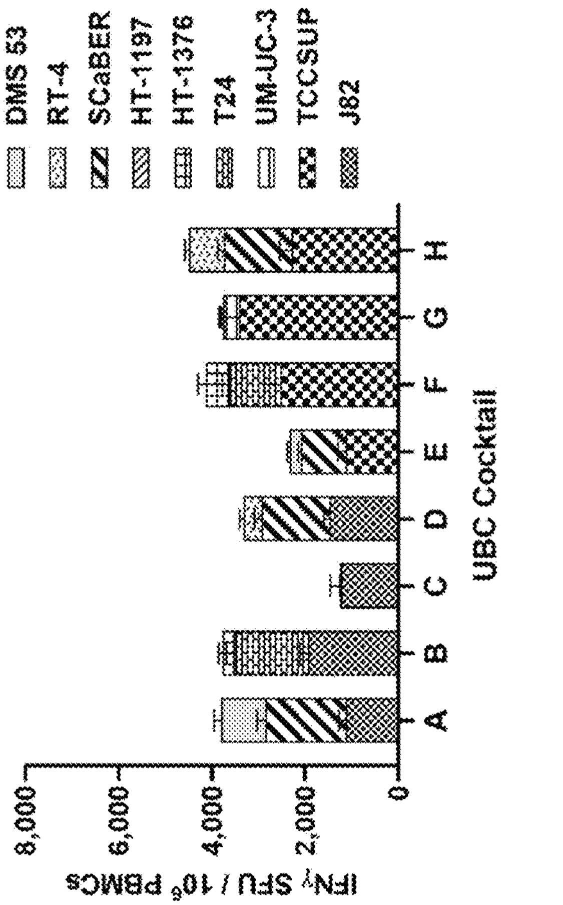
| Cocktail | Component Cell Lines |
|---|---|
| A | J82, SCaBER, DMS 53 |
| B | J82, T24, HT-1376 |
| C | J82, UM-UC-3, HT-1197 |
| D | J82, SCaBER, RT-4 |
| E | TCCSUP, SCaBER, DMS 53 |
| F | TCCSUP, T24, HT-1376 |
| G | TCCSUP, UM-UC-3, HT-1197 |
| H | TCCSUP, SCaBER, RT-4 |
FIG. 93C

| Minimum # of TAAs | % UBC Tumors (n=407) |
|---|---|
| 15 | 100.0% |
| 16 | 99.3% |
| 17 | 96.8% |
| 18 | 90.7% |
| 19 | 80.3% |
| 20 | 68.6% |
| 21 | 56.3% |
| 22 | 41.3% |
| 23 | 27.5% |
| 24 | 9.1% |

FIG. 100A
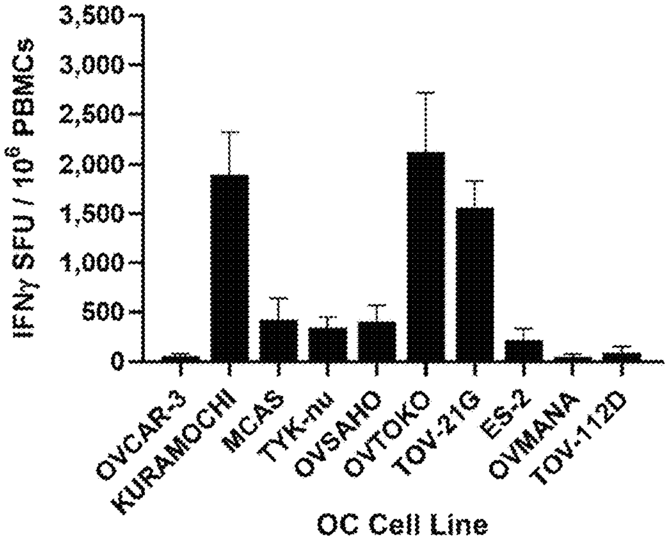
FIG. 100B
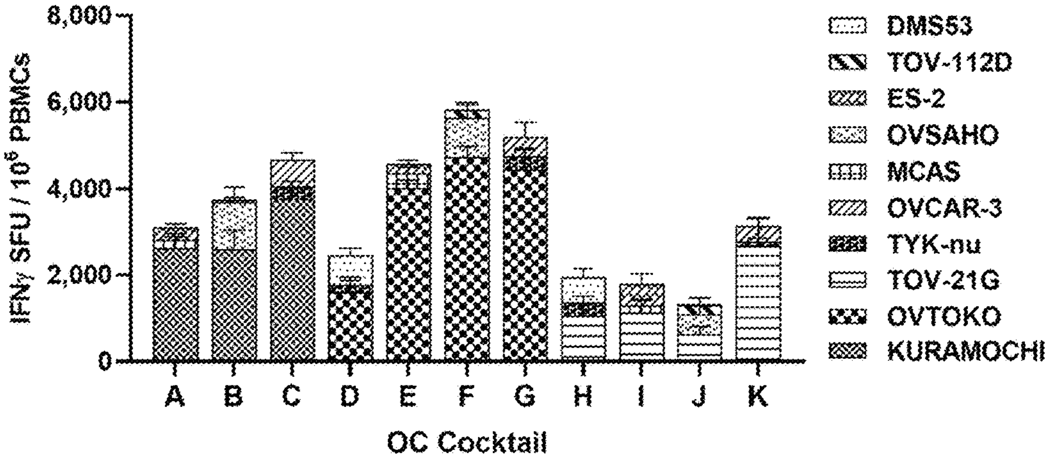
FIG. 100C
| Cocktail | Component Cell Lines |
|---|---|
| A | KURAMOCHI, MCAS, ES-2 |
| B | KURAMOCHI, OVSAHO, TOV-112D |
| C | KURAMOCHI, OVCAR-3, TYK-nu |
| D | OVTOKO, TYK-nu, DMS 53 |
| E | OVTOKO, MCAS, ES-2 |
| F | OVTOKO, OVSAHO, TOV-112D |
| G | OVTOKO, OVCAR-3, TYK-nu |
| H | TOV-21G, TYK-nu, DMS 53 |
| I | TOV-21G, MCAS, ES-2 |
| J | TOV-21G, OVSAHO, TOV-112D |
| K | TOV-21G, OVCAR-3, TYK-nu |

| Minimum # of TAAs | %OC Tumors (n=307) |
|---|---|
| 15 | 100.0% |
| 16 | 98.0% |
| 17 | 79.8% |
| 18 | 43.3% |
| 19 | 16.6% |
| 20 | 3.9% |

| Minimum # of Prioritized TAAs | % HN Tumors (n=515) |
|---|---|
| 14 | 100% |
| 15 | 97.5% |
| 16 | 89.5% |
| 17 | 79.8% |
| 18 | 61.0% |
| 19 | 35.1% |
| 20 | 10.9% |

FIG. 109A
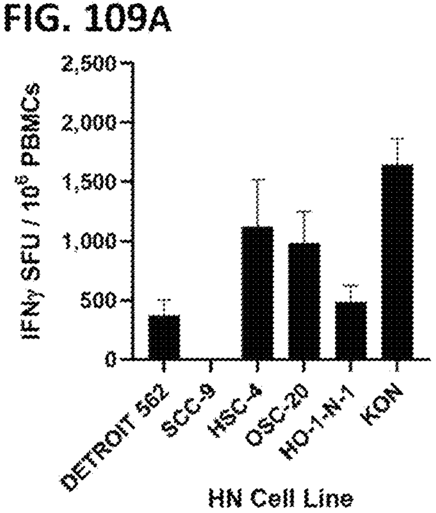
FIG. 109B
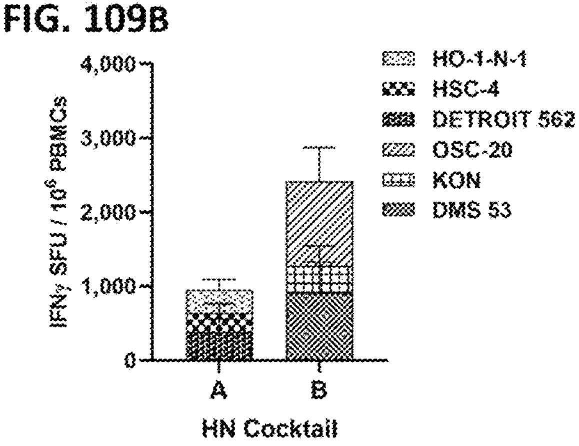
FIG. 109C
| Cocktail | Component Cell Lines |
| --- | --- |
| A | HSC-4, HO-1-N-1, DETROIT 562 |
| B | KON, OSC-20, DMS 53 |
FIG. 109D
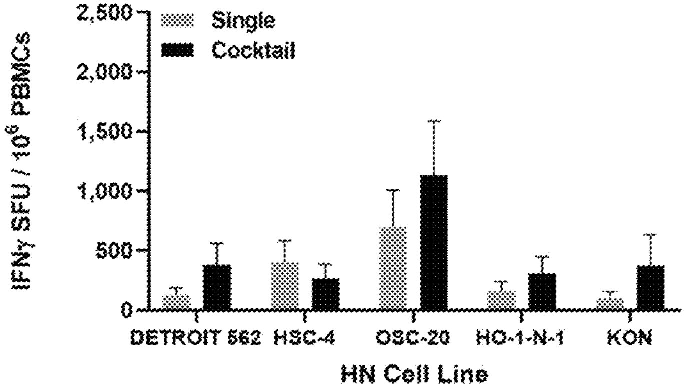
FIG. 109E
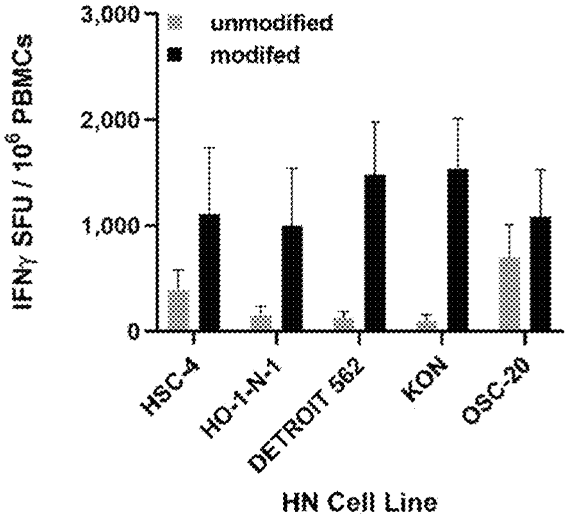

FIG. 115A
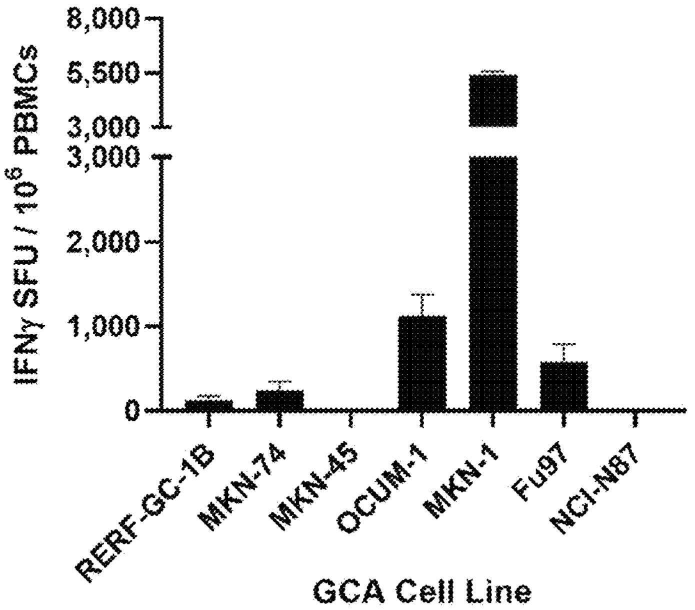
FIG. 115B
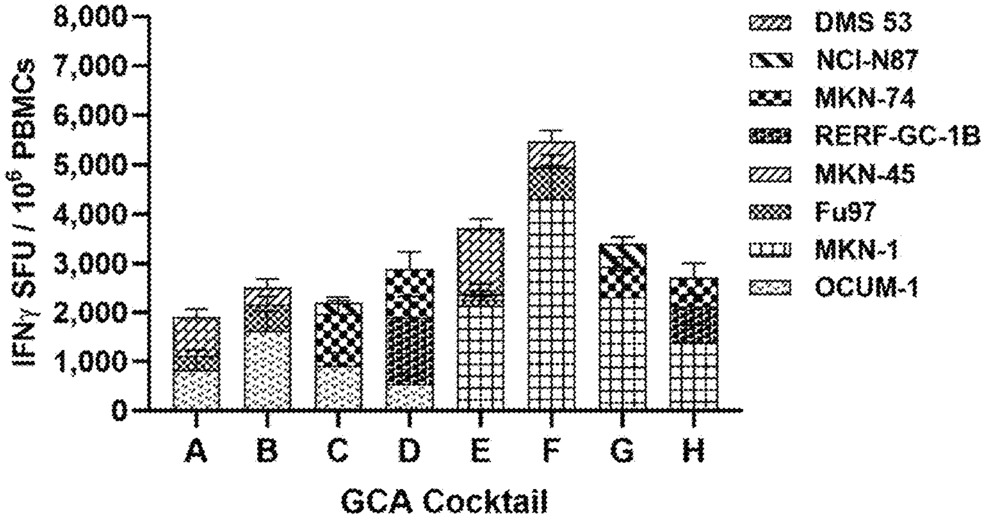
FIG. 115C
| Cocktail | Component Cell Lines |
|---|---|
| A | OCUM-1, Fu97, DMS 53 |
| B | OCUM-1, MKN-45, Fu97 |
| C | OCUM-1, MKN-74, NCI-N87 |
| D | OCUM-1, RERF-GC-1B, MKN-74 |
| E | MKN-1, Fu97, DMS 53 |
| F | MKN-1, MKN-45, Fu97 |
| G | MKN-1, MKN-74, NCI-N87 |
| H | MKN-1, RERF-GC-1B, MKN-74 |

| Minimum # of TAAs | %GCA Tumors (n=371) |
|---|---|
| 11 | 100.0% |
| 12 | 99.5% |
| 13 | 98.9% |
| 14 | 94.9% |
| 15 | 83.0% |
| 16 | 67.1% |
| 17 | 43.4% |
| 18 | 24.5% |
| 19 | 8.6% |
| 20 | 0.3% |

FIG. 122A
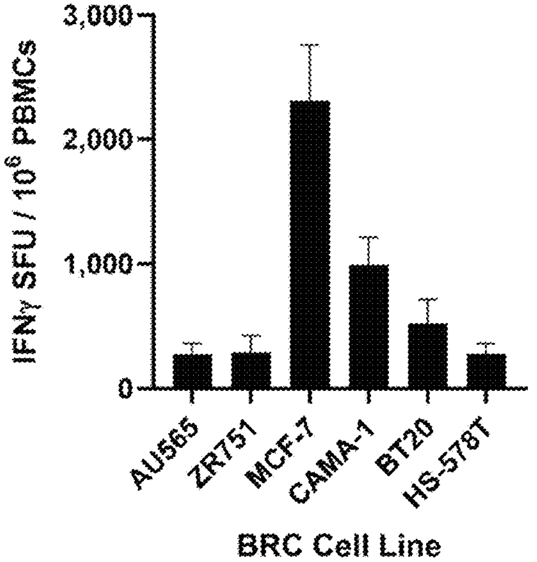
FIG. 122B
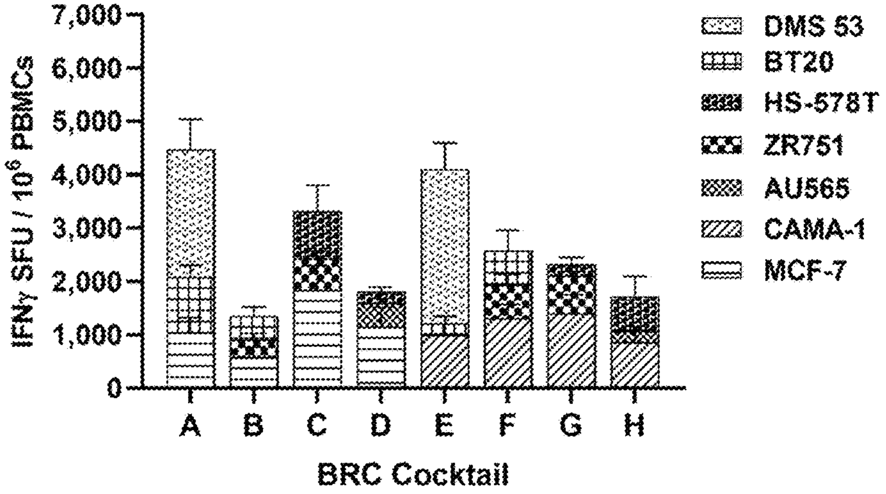
FIG. 122C
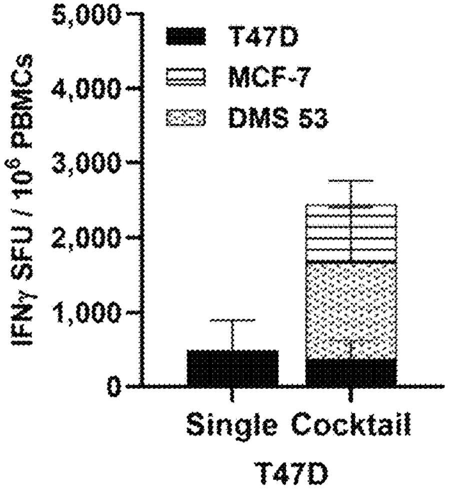
| Cocktail | Component Cell Lines |
|---|---|
| A | MCF-7, BT20, DMS 53 |
| B | MCF-7, ZR751, BT20 |
| C | MCF-7, ZR751, HS-578T |
| D | MCF-7, AU565, HS-578T |
| E | CAMA-1, BT20, DMS 53 |
| F | CAMA-1, ZR751, BT20 |
| G | CAMA-1, ZR751, HS-578T |
| H | CAMA-1, AU565, HS-578T |
FIG. 122D

| Minimum # of TAAs | %BCA Tumors (n=1082) |
|---|---|
| 15 | 100.0% |
| 16 | 99.9% |
| 17 | 99.3% |
| 18 | 95.1% |
| 19 | 79.9% |
| 20 | 47.6% |
| 21 | 17.1% |
| 22 | 3.4% |

FIG. 124
FIG. 124E
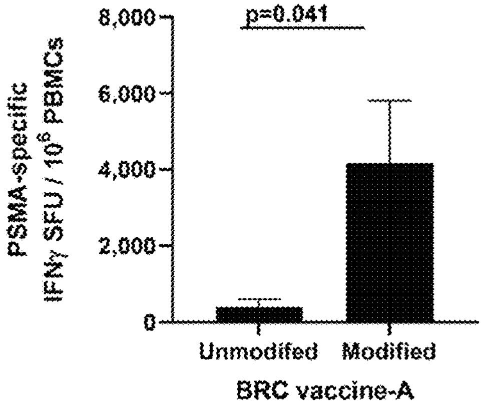
FIG. 124F
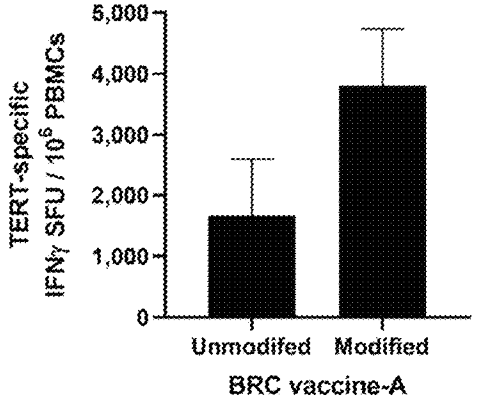
FIG. 124G
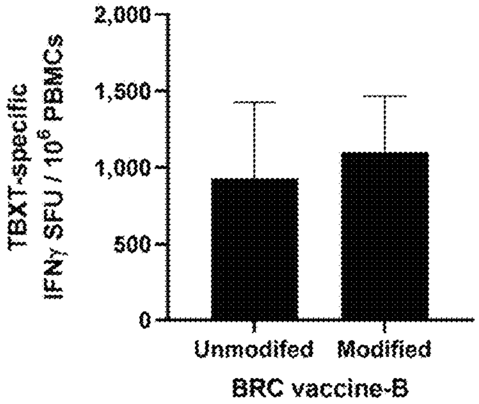
FIG. 124H
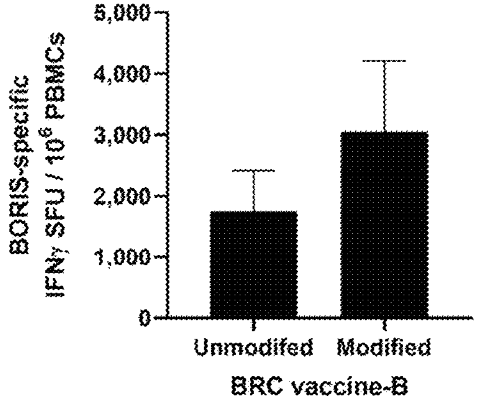

FIG. 129 modPSMA 1 MWNLLHETDSAVAT[illegible]RRPRWLCAGALVLAGGFFLLGFLFGWFIKSSNEATNITPKHNMKAFLDELKAENIKKFLYNFT[illegible]IPHLAGTEQNFQLAKQIQSQW
huPSMA 1 MWNLLHETDSAVAT[illegible]RRPRWLCAGALVLAGGFFLLGFLFGWFIKSSNEATNITPKHNMKAFLDELKAENIKKFLYNFT[illegible]IPHLAGTEQNFQLAKQIQSQW modPSMA 101 KEFGLDSVELAHYDVLLSYPNKTHPNYISIINEDGNEIFNTSLFEPPPPGYENVSDIVPPFSAFSPQ[illegible]MPEG[illegible]LVYVNYARTEDFFKLE[illegible]DMKI[illegible]CSGKI
huPSMA 101 KEFGLDSVELAHYDVLLSYPNKTHPNYISIINEDGNEIFNTSLFEPPPPGYENVSDIVPPFSAFSPQ[illegible]MPEG[illegible]LVYVNYARTEDFFKLE[illegible]DMKI[illegible]CSGKI modPSMA 201 VIARY[illegible]KVFR[illegible]NKVKNAQLAGAKGVILYSDPADYFAPGVKSYPDGWN[illegible]PGGGVQR[illegible]NILNLNGAGDPLTPGYPANEYAYR[illegible]GIAEAVGLPSIPVHP[illegible]YY
huPSMA 201 VIARY[illegible]KVFR[illegible]NKVKNAQLAGAKGVILYSDPADYFAPGVKSYPDGWN[illegible]PGGGVQR[illegible]NILNLNGAGDPLTPGYPANEYAYR[illegible]GIAEAVGLPSIPVHP[illegible]YY modPSMA 301 DAQKLLEKMGGSAPPDSSWRGSLKVPYNVGPGFTGNFSTQKVKMHIHSTNEVTRIYNVIGTLRGAVEPD[illegible]YVILGGHRDSWVFGGIDPQSGAAVV[illegible]EIVR
huPSMA 301 DAQKLLEKMGGSAPPDSSWRGSLKVPYNVGPGFTGNFSTQKVKMHIHSTNEVTRIYNVIGTLRGAVEPD[illegible]YVILGGHRDSWVFGGIDPQSGAAVV[illegible]EIVR modPSMA 401 SFGTLKKEGWRPRRTILFASWDAEEFGLLGSTEWAEENSRLLQERGVAYINADSSIEGNYTLR[illegible]DCTPLMYSLVHNLTKELKSPDEGFEGKSLY[illegible]SWTKK
huPSMA 401 SFGTLKKEGWRPRRTILFASWDAEEFGLLGSTEWAEENSRLLQERGVAYINADSSIEGNYTLR[illegible]DCTPLMYSLVHNLTKELKSPDEGFEGKSLY[illegible]SWTKK modPSMA 501 SPSPEFSGMPRISKL[illegible]SGN[illegible]FEVFFQRLGIASG[illegible]ARYTKNWETNKFSGYPLYHSVYETYELVEKFYDPMFKYHLTVAQVRGGMVFELANSIVLPF[illegible]CRDY
huPSMA 501 SPSPEFSGMPRISKL[illegible]SGN[illegible]FEVFFQRLGIASG[illegible]ARYTKNWETNKFSGYPLYHSVYETYELVEKFYDPMFKYHLTVAQVRGGMVFELANSIVLPF[illegible]CRDY modPSMA 601 AVVLRKYADKIYSISMKHPQEMKTYSVSFDSLF[illegible]AVKNFT[illegible]IASKFSERLQDFDKSNPIVLRMMNDQLMFLERAFI[illegible]PLGLPDRPFYRHVI[illegible]APSSHNKY
huPSMA 601 AVVLRKYADKIYSISMKHPQEMKTYSVSFDSLF[illegible]AVKNFT[illegible]IASKFSERLQDFDKSNPIVLRMMNDQLMFLERAFI[illegible]PLGLPDRPFYRHVI[illegible]APSSHNKY modPSMA 701 AGESFPGIYDALFDIES[illegible]V[illegible]PSKAWGEVKRQIYVAAFTVQAAAETLSEVA
huPSMA 701 AGESFPGIYDALFDIES[illegible]V[illegible]PSKAWGEVKRQIYVAAFTVQAAAETLSEVA

FIG. 130B

| | Total Sample | | Analyzed Sample | | |
|---|---|---|---|---|---|
| Ethnic subset | n | % of total | n | % of subset | % of total |
| European | 15,734 | 56.1 | 13,605 | 86.5 | 48.5 |
| African | 4,796 | 17.1 | 3,073 | 64.1 | 11.0 |
| Hispanic | 3,972 | 14.2 | 2,696 | 67.9 | 9.6 |
| Asian | 3,532 | 12.6 | 2,595 | 73.5 | 9.3 |
| **Total** | 28,034 | 100.0 | 21,969 | n/a | 78.4 |

FIG. 130C

| Ethnic subset | Min % freq. | Max % freq. | Total % freq. | * Outlier % freq. | % Analyzed |
|---|---|---|---|---|---|
| European | 0.07 | 9.55 | 91.2 | 4.7 | 86.5 |
| African | 0.14 | 2.96 | 74.4 | 10.3 | 64.1 |
| Hispanic | 0.13 | 2.54 | 74.4 | 6.6 | 67.9 |
| Asian | 0.15 | 4.53 | 76.3 | 2.9 | 73.5 |

* Number of A & B pairs analyzed after removal of haplotypes where the A or B haplotype is not classified into a supertype.

SEQUENCE LISTING

<160> NUMBER OF SEQ ID NOS: 143

<210> SEQ ID NO 1
<211> LENGTH: 786
<212> TYPE: DNA
<213> ORGANISM: Artificial Sequence
<220> FEATURE:
<223> OTHER INFORMATION: Synthetic

<400> SEQUENCE: 1
atgatcgaaa catacaacca aacttctccc cgatctgcgg ccactggact gcccatcagc 60
atgaaaattt ttatgtattt acttactgtt tttcttatca cccagatgat tgggtcagca 120
ctttttgctg tgtatcttca tagaaggttg gacaagatag aagatgaaag gaatcttcat 180
gaagattttg tattcatgaa aacgatacag agatgcaaca caggagaaag atccttatcc 240
ttactgaact gtgaggagat taaaagccag tttgaaggct ttgtgaagga tataatgtta 300
aacaaagagg agacgaagaa agaaaacagc tttgaaatgc ctcgtggtga agaggatagt 360
caaattgcgg cacatgtcat aagtgaggcc agcagtaaaa caacatctgt gttacagtgg 420
gctgaaaaag gatactacac catgagcaac aacttggtaa ccctggaaaa tgggaaacag 480
ctgaccgtta aaagacaagg actctattat atctatgccc aagtcacctt ctgttccaat 540
cgggaagctt cgagtcaagc tccatttata gccagcctct gcctaaagtc cccccggtaga 600 ttcgagagaa tcttactcag agctgcaaat acccacagtt ccgccaaacc ttgcgggcaa 660
caatccattc acttgggagg agtatttgaa ttgcaaccag gtgcttcggt gtttgtcaat 720
gtgactgatc caagccaagt gagccatggc actggcttca cgtcctttgg cttactcaaa 780
ctctga 786

<210> SEQ ID NO 2
<211> LENGTH: 786
<212> TYPE: DNA
<213> ORGANISM: Artificial Sequence
<220> FEATURE:
<223> OTHER INFORMATION: Synthetic

<400> SEQUENCE: 2
atgatcgaaa cctacaacca gacctcacca cgaagtgccg ccaccggact gcctattagt 60
atgaaaatct ttatgtacct gctgacagtg ttcctgatca cccagatgat cggctccgcc 120
ctgtttgccg tgtacctgca ccggagactg gacaagatcg aggatgagcg gaacctgcac 180
gaggacttcg tgtttatgaa gaccatccag cggtgcaaca caggcgagag aagcctgtcc 240

```
ctgctgaatt gtgaggagat caagagccag ttcgagggct ttgtgaagga catcatgctg    300

aacaaggagg agacaaagaa ggagaacagc ttcgagatgc ccagaggcga ggaggattcc    360

cagatcgccg cccacgtgat ctctgaggcc agctccaaga ccacaagcgt gctgcagtgg    420

gccgagaagg gctactatac catgtctaac aatctggtga cactggagaa cggcaagcag    480

ctgaccgtga agaggcaggg cctgtactat atctatgccc aggtgacatt ctgcagcaat    540

cgcgaggcct ctagccaggc cccctttatc gccagcctgt gcctgaagag ccctggcagg    600

ttcgagcgca tcctgctgag agccgccaac acccactcct ctgccaagcc atgcggacag    660

cagtcaatcc acctgggagg cgtgttcgag ctgcagccag gagcaagcgt gttcgtgaat    720

gtgactgacc catcacaggt gtctcacggc actggattca catcatttgg actgctgaaa    780

ctgtga                                                               786
```

```
<210> SEQ ID NO 3
<211> LENGTH: 261
<212> TYPE: PRT
<213> ORGANISM: Artificial Sequence
<220> FEATURE:
<223> OTHER INFORMATION: Synthetic

<400> SEQUENCE: 3

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Pro Arg Gly Glu Glu Asp Ser Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
```

260

<210> SEQ ID NO 4
<211> LENGTH: 723
<212> TYPE: DNA
<213> ORGANISM: Artificial Sequence
<220> FEATURE:
<223> OTHER INFORMATION: Synthetic

<400> SEQUENCE: 4
atggctcagc atggggctat gggggccttc agggctctgt gcggactggc tctgctgtgc 60
gctctgtcac tggggcagag accaacagga ggaccaggat gcggacctgg caggctgctg 120
ctgggcaccg gcacagacgc aaggtgctgt agagtgcaca ccacaaggtg ctgtcgcgac 180
taccctggcg aggagtgctg ttctgagtgg gattgcatgt gcgtgcagcc agagtttcac 240
tgtggcgatc cctgctgtac cacatgccgc caccacccat gtccacctgg acagggagtg 300
cagtctcagg gcaagttcag ctttggcttc cagtgcatcg actgtgcaag cggcaccttt 360
tccggaggac acgagggaca ctgcaagccc tggaccgatt gtacacagtt tggcttcctg 420
accgtgttcc ctggcaacaa gacacacaat gccgtgtgcg tgcctggctc cccaccagca 480
gagcccctgg gctggctgac cgtggtgctg ctggccgtgg cagcatgcgt gctgctgctg 540
acaagcgccc agctgggact gcacatctgg cagctgcggt cccagtgtat gtggccaaga 600
gagacccagc tgctgctgga ggtgcctcca tccacagagg acgcccggtc ttgccagttc 660
cccgaagagg agagggggga aagaagtgcc gaagaaaagg gaaggctggg agacctgtgg 720
gtg 723

<210> SEQ ID NO 5
<211> LENGTH: 241
<212> TYPE: PRT
<213> ORGANISM: Artificial Sequence
<220> FEATURE:
<223> OTHER INFORMATION: Synthetic

<400> SEQUENCE: 5

Met Ala Gln His Gly Ala Met Gly Ala Phe Arg Ala Leu Cys Gly Leu
1 5 10 15

Ala Leu Leu Cys Ala Leu Ser Leu Gly Gln Arg Pro Thr Gly Gly Pro
20 25 30

Gly Cys Gly Pro Gly Arg Leu Leu Leu Gly Thr Gly Thr Asp Ala Arg
35 40 45

Cys Cys Arg Val His Thr Thr Arg Cys Cys Arg Asp Tyr Pro Gly Glu
50 55 60

Glu Cys Cys Ser Glu Trp Asp Cys Met Cys Val Gln Pro Glu Phe His
65 70 75 80

Cys Gly Asp Pro Cys Cys Thr Thr Cys Arg His His Pro Cys Pro Pro
85 90 95

Gly Gln Gly Val Gln Ser Gln Gly Lys Phe Ser Phe Gly Phe Gln Cys
100 105 110

Ile Asp Cys Ala Ser Gly Thr Phe Ser Gly Gly His Glu Gly His Cys
115 120 125

Lys Pro Trp Thr Asp Cys Thr Gln Phe Gly Phe Leu Thr Val Phe Pro
130 135 140

Gly Asn Lys Thr His Asn Ala Val Cys Val Pro Gly Ser Pro Pro Ala
145 150 155 160

Glu Pro Leu Gly Trp Leu Thr Val Val Leu Leu Ala Val Ala Ala Cys

```
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val


<210> SEQ ID NO 6
<211> LENGTH: 435
<212> TYPE: DNA
<213> ORGANISM: Artificial Sequence
<220> FEATURE:
<223> OTHER INFORMATION: Synthetic

<400> SEQUENCE: 6

atgtggctgc agagcctgct gctcttgggc actgtggcct gcagcatctc tgcacccgcc     60

cgctcgccca gccccagcac gcagccctgg gagcatgtga atgccatcca ggaggcccgg    120

cgtctcctga acctgagtag agacactgct gctgagatga atgaaacagt agaagtcatc    180

tcagaaatgt ttgacctcca ggagccgacc tgcctacaga cccgcctgga gctgtacaag    240

cagggcctgc ggggcagcct caccaagctc aagggcccct tgaccatgat ggccagccac    300

tacaagcagc actgccctcc aaccccggaa acttcctgtg caacccagat tatcaccttt    360

gaaagtttca aagagaacct gaaggacttt ctgcttgtca tcccctttga ctgctgggag    420

ccagtccagg agtga                                                     435


<210> SEQ ID NO 7
<211> LENGTH: 435
<212> TYPE: DNA
<213> ORGANISM: Artificial Sequence
<220> FEATURE:
<223> OTHER INFORMATION: Synthetic

<400> SEQUENCE: 7

atgtggctgc agtctctgct gctgctgggc accgtcgcct gttctatttc cgcacccgct     60

cgctcccctt ctccctcaac tcagccttgg gagcacgtga acgccatcca ggaggcccgg    120

agactgctga atctgtcccg ggacaccgcc gccgagatga acgagacagt ggaagtgatc    180

tctgagatgt tcgatctgca ggagcccacc tgcctgcaga caaggctgga gctgtacaag    240

cagggcctgc gcggctctct gaccaagctg aagggcccac tgacaatgat ggccagccac    300

tataagcagc actgcccccc tacccccgag acaagctgtg ccacccagat catcacattc    360

gagtccttta aggagaacct gaaggacttt ctgctggtca ttccatttga ttgttgggag    420

cccgtgcagg agtga                                                     435


<210> SEQ ID NO 8
<211> LENGTH: 144
<212> TYPE: PRT
<213> ORGANISM: Artificial Sequence
<220> FEATURE:
<223> OTHER INFORMATION: Synthetic

<400> SEQUENCE: 8

Met Trp Leu Gln Ser Leu Leu Leu Leu Gly Thr Val Ala Cys Ser Ile
```

```
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140


<210> SEQ ID NO 9
<211> LENGTH: 1710
<212> TYPE: DNA
<213> ORGANISM: Artificial Sequence
<220> FEATURE:
<223> OTHER INFORMATION: Synthetic

<400> SEQUENCE: 9

atgtgccatc agcaactggt tatatcttgg ttcagtctcg tctttctcgc gtcacccttg     60

gtcgctatct gggagcttaa aaaagatgtc tacgtcgttg aacttgattg gtaccctgat    120

gctccggggg aaatggtggt tttgacttgc gatacgccag aagaggatgg cataacgtgg    180

acactggacc agtcttcaga ggttctcggg tctggtaaga cactcactat acaggtgaag    240

gagtttggtg acgcaggaca atatacttgc cataaaggcg gcgaggtgct ctcccatagc    300

cttctgctcc ttcataaaaa agaggacggg atatggtcaa ctgacattct gaaggatcag    360

aaagaaccga agaacaaaac tttcctcaga tgcgaggcaa agaactattc aggccgcttt    420

acttgctggt ggctcactac catcagcact gacctcactt tcagcgtcaa gagcagtaga    480

ggctcaagtg acccacaagg ggttacatgc ggggccgcta cgttgtctgc cgagcgagtc    540

aggggagata ataaggaata tgagtatagc gttgaatgcc aagaagattc agcctgccca    600

gccgcagaag agagtcttcc catagaagtt atggtggacg cagttcataa actgaagtat    660

gagaactata catcttcctt ctttattcgc gatatcataa agcctgatcc tccgaaaaac    720

ttgcaactca agccgttgaa gaatagccga caggtcgagg tctcttggga gtatccagat    780

acgtggtcta ccccgcactc ctatttcagt ctcaccttct gtgtgcaggt gcaggggaaa    840

agtaagcggg aaaaaaagga ccgggtattt actgataaga cctccgctac agtgatttgt    900

agaaagaacg cctctatcag cgtgagagcc caggatagat attattctag tagttggtct    960

gagtgggcct ccgtcccttg ttccggaagc ggagccacga acttctctct gttaaagcaa   1020

gcaggagatg ttgaagaaaa ccccgggcct atgtgtccag cgcgcagcct cctccttgtg   1080

gctaccctgg tcctcctgga ccacctcagt ttggcccgaa acctgccggt cgctacaccc   1140

gatcctggaa tgtttccctg ccttcatcac agccagaatc tgctgagggc agtcagtaac   1200

atgctgcaga aggcgcggca aactctggag ttctatccat gtacctccga ggaaattgat   1260

cacgaggaca ttactaagga taaaacaagt acagtagaag cctgtttgcc tcttgagctc   1320
```

actaaaaatg agtcatgctt gaacagtcga gagacgagtt ttatcactaa cggttcatgc 1380
ttggcgtcca ggaagacaag ctttatgatg gcgctctgcc tgtcttctat atatgaagac 1440
cttaaaatgt accaagttga gtttaagacc atgaacgcca aacttttgat ggaccccaag 1500
aggcagatct tccttgatca gaatatgttg gcggtgatcg atgaacttat gcaagctttg 1560
aacttcaaca gtgagacagt gcctcagaaa agttccttgg aggaaccgga cttctataag 1620
accaagatca aactgtgcat tttgctgcat gcatttagaa ttcgagccgt tacaatcgac 1680
cgggtgatgt catatttgaa tgcatcataa 1710

<210> SEQ ID NO 10
<211> LENGTH: 569
<212> TYPE: PRT
<213> ORGANISM: Artificial Sequence
<220> FEATURE:
<223> OTHER INFORMATION: Synthetic

<400> SEQUENCE: 10

Met Cys His Gln Gln Leu Val Ile Ser Trp Phe Ser Leu Val Phe Leu
1 5 10 15

Ala Ser Pro Leu Val Ala Ile Trp Glu Leu Lys Lys Asp Val Tyr Val
20 25 30

Val Glu Leu Asp Trp Tyr Pro Asp Ala Pro Gly Glu Met Val Val Leu
35 40 45

Thr Cys Asp Thr Pro Glu Glu Asp Gly Ile Thr Trp Thr Leu Asp Gln
50 55 60

Ser Ser Glu Val Leu Gly Ser Gly Lys Thr Leu Thr Ile Gln Val Lys
65 70 75 80

Glu Phe Gly Asp Ala Gly Gln Tyr Thr Cys His Lys Gly Gly Glu Val
85 90 95

Leu Ser His Ser Leu Leu Leu Leu His Lys Lys Glu Asp Gly Ile Trp
100 105 110

Ser Thr Asp Ile Leu Lys Asp Gln Lys Glu Pro Lys Asn Lys Thr Phe
115 120 125

Leu Arg Cys Glu Ala Lys Asn Tyr Ser Gly Arg Phe Thr Cys Trp Trp
130 135 140

Leu Thr Thr Ile Ser Thr Asp Leu Thr Phe Ser Val Lys Ser Ser Arg
145 150 155 160

Gly Ser Ser Asp Pro Gln Gly Val Thr Cys Gly Ala Ala Thr Leu Ser
165 170 175

Ala Glu Arg Val Arg Gly Asp Asn Lys Glu Tyr Glu Tyr Ser Val Glu
180 185 190

Cys Gln Glu Asp Ser Ala Cys Pro Ala Ala Glu Glu Ser Leu Pro Ile
195 200 205

Glu Val Met Val Asp Ala Val His Lys Leu Lys Tyr Glu Asn Tyr Thr
210 215 220

Ser Ser Phe Phe Ile Arg Asp Ile Ile Lys Pro Asp Pro Pro Lys Asn
225 230 235 240

Leu Gln Leu Lys Pro Leu Lys Asn Ser Arg Gln Val Glu Val Ser Trp
245 250 255

Glu Tyr Pro Asp Thr Trp Ser Thr Pro His Ser Tyr Phe Ser Leu Thr
260 265 270

Phe Cys Val Gln Val Gln Gly Lys Ser Lys Arg Glu Lys Lys Asp Arg
275 280 285

```
Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Ser Gly Ala Thr Asn Phe Ser
                325                 330                 335

Leu Leu Lys Gln Ala Gly Asp Val Glu Glu Asn Pro Gly Pro Met Cys
            340                 345                 350

Pro Ala Arg Ser Leu Leu Leu Val Ala Thr Leu Val Leu Leu Asp His
        355                 360                 365

Leu Ser Leu Ala Arg Asn Leu Pro Val Ala Thr Pro Asp Pro Gly Met
    370                 375                 380

Phe Pro Cys Leu His His Ser Gln Asn Leu Leu Arg Ala Val Ser Asn
385                 390                 395                 400

Met Leu Gln Lys Ala Arg Gln Thr Leu Glu Phe Tyr Pro Cys Thr Ser
                405                 410                 415

Glu Glu Ile Asp His Glu Asp Ile Thr Lys Asp Lys Thr Ser Thr Val
            420                 425                 430

Glu Ala Cys Leu Pro Leu Glu Leu Thr Lys Asn Glu Ser Cys Leu Asn
        435                 440                 445

Ser Arg Glu Thr Ser Phe Ile Thr Asn Gly Ser Cys Leu Ala Ser Arg
    450                 455                 460

Lys Thr Ser Phe Met Met Ala Leu Cys Leu Ser Ser Ile Tyr Glu Asp
465                 470                 475                 480

Leu Lys Met Tyr Gln Val Glu Phe Lys Thr Met Asn Ala Lys Leu Leu
                485                 490                 495

Met Asp Pro Lys Arg Gln Ile Phe Leu Asp Gln Asn Met Leu Ala Val
            500                 505                 510

Ile Asp Glu Leu Met Gln Ala Leu Asn Phe Asn Ser Glu Thr Val Pro
        515                 520                 525

Gln Lys Ser Ser Leu Glu Glu Pro Asp Phe Tyr Lys Thr Lys Ile Lys
    530                 535                 540

Leu Cys Ile Leu Leu His Ala Phe Arg Ile Arg Ala Val Thr Ile Asp
545                 550                 555                 560

Arg Val Met Ser Tyr Leu Asn Ala Ser
                565
```

<210> SEQ ID NO 11
<211> LENGTH: 402
<212> TYPE: DNA
<213> ORGANISM: Artificial Sequence
<220> FEATURE:
<223> OTHER INFORMATION: Synthetic

<400> SEQUENCE: 11

```
atgtatagga tgcagctgct gtcatgtatc gcactgtccc tggcactggt gactaactct      60

aactgggtga atgtgatctc cgacctgaag aagatcgagg acctgatcca gtctatgcac     120

atcgatgcca ccctgtacac agagtccgac gtgcacccct cttgcaaggt gaccgccatg     180

aagtgtttcc tgctggagct gcaggtcatc agcctggaga gcggcgacgc atccatccac     240

gataccgtgg agaacctgat catcctggcc aacaatagcc tgagctccaa cggcaatgtg     300

acagagtccg gctgcaagga gtgtgaggag ctggaggaga agaatatcaa agagttcctg     360

cagtcattcg tccatatcgt ccagatgttt atcaatacca gt                        402
```

<210> SEQ ID NO 12
<211> LENGTH: 134
<212> TYPE: PRT
<213> ORGANISM: Artificial Sequence
<220> FEATURE:
<223> OTHER INFORMATION: Synthetic

<400> SEQUENCE: 12

```
Met Tyr Arg Met Gln Leu Leu Ser Cys Ile Ala Leu Ser Leu Ala Leu
1               5                   10                  15

Val Thr Asn Ser Asn Trp Val Asn Val Ile Ser Asp Leu Lys Lys Ile
            20                  25                  30

Glu Asp Leu Ile Gln Ser Met His Ile Asp Ala Thr Leu Tyr Thr Glu
        35                  40                  45

Ser Asp Val His Pro Ser Cys Lys Val Thr Ala Met Lys Cys Phe Leu
    50                  55                  60

Leu Glu Leu Gln Val Ile Ser Leu Glu Ser Gly Asp Ala Ser Ile His
65                  70                  75                  80

Asp Thr Val Glu Asn Leu Ile Ile Leu Ala Asn Asn Ser Leu Ser Ser
                85                  90                  95

Asn Gly Asn Val Thr Glu Ser Gly Cys Lys Glu Cys Glu Glu Leu Glu
            100                 105                 110

Glu Lys Asn Ile Lys Glu Phe Leu Gln Ser Phe Val His Ile Val Gln
        115                 120                 125

Met Phe Ile Asn Thr Ser
    130
```

<210> SEQ ID NO 13
<211> LENGTH: 1608
<212> TYPE: DNA
<213> ORGANISM: Artificial Sequence
<220> FEATURE:
<223> OTHER INFORMATION: Synthetic

<400> SEQUENCE: 13

```
atgtgccatc agcagctggt cattagttgg tttagcctgg tctttctggc ctcacccctg     60

gtcgcaatct gggaactgaa gaaggacgtg tacgtggtgg agctggactg gtatccagat    120

gcaccaggag agatggtggt gctgacctgc gacacacctg aggaggatgg catcacctgg    180

acactggatc agagctccga ggtgctgggc agcggcaaga ccctgacaat ccaggtgaag    240

gagttcggcg acgccggcca gtacacatgt cacaagggcg gcgaggtgct gtcccactct    300

ctgctgctgc tgcacaagaa ggaggacggc atctggtcca cagacatcct gaaggatcag    360

aaggagccaa agaacaagac cttcctgcgg tgcgaggcca agaattatag cggccggttc    420

acctgttggt ggctgaccac aatctccacc gatctgacat tttctgtgaa gtctagcagg    480

ggctcctctg acccccaggg agtgacatgc ggagcagcca ccctgagcgc cgagcgggtg    540

agaggcgata acaaggagta cgagtattct gtggagtgcc aggaggacag cgcctgtcca    600

gcagcagagg agtccctgcc tatcgaagtg atggtggatg ccgtgcacaa gctgaagtac    660

gagaattata caagctcctt ctttatcagg gacatcatca agccagatcc ccctaagaac    720

ctgcagctga agcccctgaa gaatagccgc caggtggagg tgtcctggga gtaccctgac    780

acctggtcca caccacactc ttatttcagc ctgacctttt gcgtgcaggt gcagggcaag    840

agcaagaggg agaagaagga ccgcgtgttc accgataaga catccgccac cgtgatctgt    900

cggaagaacg ccagcatctc cgtgagggcc caggatcgct actattctag ctcctggagc    960

gagtgggcct ccgtgccatg ctctggagga ggaggcagcg gcggaggagg ctccggaggc   1020
```

```
ggcggctctg gcggcggcgg ctccctgggc tctcgggccg tgatgctgct gctgctgctg   1080

ccctggaccg cacagggaag agccgtgcca ggaggctcta gcccagcatg gacacagtgc   1140

cagcagctgt cccagaagct gtgcaccctg gcatggtctg cccaccctct ggtgggccac   1200

atggacctga gagaggaggg cgatgaggag accacaaacg acgtgcctca catccagtgc   1260

ggcgacggct gtgatccaca gggcctgagg gacaattctc agttctgtct gcagcgcatc   1320

caccagggcc tgatcttcta cgagaagctg ctgggcagcg atatctttac aggagagccc   1380

agcctgctgc ctgactcccc agtgggacag ctgcacgcct ctctgctggg cctgagccag   1440

ctgctgcagc cagagggaca ccactgggag acccagcaga tcccttctct gagcccatcc   1500

cagccttggc agcggctgct gctgcggttc aagatcctga gaagcctgca ggcattcgtc   1560

gcagtcgcag ccagggtgtt cgcccacgga gccgctactc tgagccca                 1608
```

<210> SEQ ID NO 14
<211> LENGTH: 536
<212> TYPE: PRT
<213> ORGANISM: Artificial Sequence
<220> FEATURE:
<223> OTHER INFORMATION: Synthetic

<400> SEQUENCE: 14

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255
```

```
Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Gly Ser Gly Gly Gly
                325                 330                 335

Gly Ser Gly Gly Gly Gly Ser Gly Gly Gly Gly Ser Leu Gly Ser Arg
            340                 345                 350

Ala Val Met Leu Leu Leu Leu Leu Pro Trp Thr Ala Gln Gly Arg Ala
        355                 360                 365

Val Pro Gly Gly Ser Ser Pro Ala Trp Thr Gln Cys Gln Gln Leu Ser
    370                 375                 380

Gln Lys Leu Cys Thr Leu Ala Trp Ser Ala His Pro Leu Val Gly His
385                 390                 395                 400

Met Asp Leu Arg Glu Glu Gly Asp Glu Glu Thr Thr Asn Asp Val Pro
                405                 410                 415

His Ile Gln Cys Gly Asp Gly Cys Asp Pro Gln Gly Leu Arg Asp Asn
            420                 425                 430

Ser Gln Phe Cys Leu Gln Arg Ile His Gln Gly Leu Ile Phe Tyr Glu
        435                 440                 445

Lys Leu Leu Gly Ser Asp Ile Phe Thr Gly Glu Pro Ser Leu Leu Pro
    450                 455                 460

Asp Ser Pro Val Gly Gln Leu His Ala Ser Leu Leu Gly Leu Ser Gln
465                 470                 475                 480

Leu Leu Gln Pro Glu Gly His His Trp Glu Thr Gln Gln Ile Pro Ser
                485                 490                 495

Leu Ser Pro Ser Gln Pro Trp Gln Arg Leu Leu Leu Arg Phe Lys Ile
            500                 505                 510

Leu Arg Ser Leu Gln Ala Phe Val Ala Val Ala Ala Arg Val Phe Ala
        515                 520                 525

His Gly Ala Ala Thr Leu Ser Pro
    530                 535
```

<210> SEQ ID NO 15
<211> LENGTH: 342
<212> TYPE: DNA
<213> ORGANISM: Artificial Sequence
<220> FEATURE:
<223> OTHER INFORMATION: Synthetic

<400> SEQUENCE: 15

```
atgaggctgc tgattctggc actgctgggc atctgctctc tgaccgctta catcgtggaa      60

ggagtcggct ctgaagtctc tgacaagcgc acatgcgtgt ctctgaccac acagcgcctg     120

cccgtgagcc ggatcaagac ctacacaatc accgagggca gcctgagagc cgtgatcttc     180

atcacaaaga ggggcctgaa ggtgtgcgcc gaccctcagg caacctgggt gcgggacgtg     240

gtgagaagca tggataggaa gtccaacacc cggaacaata tgatccagac aaaacccaca     300

ggaacccagc agagcactaa tacagccgtg acactgaccg gg                        342
```

<210> SEQ ID NO 16
<211> LENGTH: 114

<212> TYPE: PRT
<213> ORGANISM: Artificial Sequence
<220> FEATURE:
<223> OTHER INFORMATION: Synthetic

<400> SEQUENCE: 16

```
Met Arg Leu Leu Ile Leu Ala Leu Leu Gly Ile Cys Ser Leu Thr Ala
1               5                   10                  15

Tyr Ile Val Glu Gly Val Gly Ser Glu Val Ser Asp Lys Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly
```

<210> SEQ ID NO 17
<211> LENGTH: 1899
<212> TYPE: DNA
<213> ORGANISM: Artificial Sequence
<220> FEATURE:
<223> OTHER INFORMATION: Synthetic

<400> SEQUENCE: 17

```
atggctctgc ctaccgcaag acccctgctg ggctcctgtg ggactcctgc tctgggatca     60

ctgctgtttc tgctgttttc actgggctgg gtgcagcctt cccgcaccct ggcaggagag    120

acaggacagg aggcagcacc actggacggc gtgctggcca accccccctaa tatcagctcc    180

ctgtctcctc ggcagctgct gggcttccca tgtgcagagg tgagcggact gtccaccgag    240

agggtgcgcg agctggcagt ggccctggca cagaagaacg tgaagctgag cacagagcag    300

ctgaggtgcc tggcacacag gctgtccgag ccaccagagg acctggatgc actgccactg    360

gacctgctgc tgttcctgaa cccagatgcc ttttccggcc cccaggcctg taccaggttc    420

ttttctcgca tcacaaaggc caatgtggat ctgctgccca gaggcgcacc tgagaggcag    480

agactgctgc cagccgccct ggcatgctgg ggcgtgaggg gctctctgct gagcgaggca    540

gacgtgcgcg ccctgggagg actggcctgt gatctgccag gccgctttgt ggcagagagc    600

gccgaggtgc tgctgccacg gctggtgtcc tgccctggcc cactggacca ggatcagcag    660

gaggcagccc gggccgccct gcagggcggc ggccctccct acggcccccc ttccacctgg    720

tctgtgagca caatggacgc actgagagga ctgctgcctg tgctgggaca gccaatcatc    780

aggtctatcc cccagggcat cgtggcagca tggaggcagc ggagcagccg ggaccccagc    840

tggcggcagc ctgagagaac catcctgcgg cctagattcc ggagagaggt ggagaagaca    900

gcctgtccat ctggcaagaa ggccagagag atcgacgaga gcctgatctt ttacaagaag    960

tgggagctgg aggcctgcgt ggacgccgcc ctgctggcta cccagatgga cagggtgaat   1020

gccatcccct tcacctacga gcagctggac gtgctgaagc acaagctgga tgagctgtac   1080

ccacagggct atcccgagtc cgtgatccag cacctgggct acctgtttct gaagatgtcc   1140

cccgaggata tcagaaagtg gaacgtgacc tctctggaga cactgaaggc cctgctggag   1200
```

```
gtcaataagg gccacgagat gagccctcag gtggccaccc tgatcgaccg gttcgtgaag   1260

ggcagaggcc agctggacaa ggatacactg gataccctga cagcctttta ccccggctac   1320

ctgtgctccc tgtctcctga ggagctgtcc tctgtgccac ccagctccat ctgggccgtg   1380

cggccacagg acctggatac ctgcgacccc cggcagctgg acgtgctgta ccctaaggcc   1440

aggctggcct tccagaacat gaatggctct gagtatttcg tgaagatcca gagctttctg   1500

ggaggagcac ctaccgagga cctgaaggcc ctgagccagc agaacgtgag catggacctg   1560

gccaccttta tgaagctgcg cacagatgcc gtgctgccac tgaccgtggc agaggtgcag   1620

aagctgctgg gacctcacgt ggagggcctg aaggcagagg agaggcacag gccagtgcgg   1680

gactggattc tgcggcagag acaggacgat ctggataccc tgggactggg actgcaggga   1740

ggcatcccaa atggaggcag cacatccggc tctggcaagc caggctccgg agagggctct   1800

accaagggaa tgcaggaggc cctgagcggc acaccttgcc tgctgggacc tggacctgtg   1860

ctgactgtgc tggctctgct gctggcatct actctggct                          1899
```

<210> SEQ ID NO 18
<211> LENGTH: 633
<212> TYPE: PRT
<213> ORGANISM: Artificial Sequence
<220> FEATURE:
<223> OTHER INFORMATION: Synthetic

<400> SEQUENCE: 18

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240
```

```
Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Gly Ser Thr Ser Gly Ser Gly
            580                 585                 590

Lys Pro Gly Ser Gly Glu Gly Ser Thr Lys Gly Met Gln Glu Ala Leu
        595                 600                 605

Ser Gly Thr Pro Cys Leu Leu Gly Pro Gly Pro Val Leu Thr Val Leu
    610                 615                 620

Ala Leu Leu Leu Ala Ser Thr Leu Ala
625                 630

<210> SEQ ID NO 19
<211> LENGTH: 339
```

<212> TYPE: DNA
<213> ORGANISM: Artificial Sequence
<220> FEATURE:
<223> OTHER INFORMATION: Synthetic

<400> SEQUENCE: 19
atgaactttt acctgctgct ggcatcctca atcctgtgcg ccctgatcgt gttttggaaa 60
taccgacgct ttcagagaaa tactggcgag atgagcagca acagcaccgc cctggccctg 120
gtgcggccct ctagctccgg cctgatcaac tctaatacag acaacaatct ggccgtgtac 180
gacctgtctc gggatatcct gaacaatttc cctcacagca tcgcccggca gaagagaatc 240
ctggtgaacc tgagcatggt ggagaataag ctggtggagc tggaacatac actgctgagt 300
aagggcttta ggggggcttc accacatcgc aagtcaaca 339

<210> SEQ ID NO 20
<211> LENGTH: 113
<212> TYPE: PRT
<213> ORGANISM: Artificial Sequence
<220> FEATURE:
<223> OTHER INFORMATION: Synthetic

<400> SEQUENCE: 20

Met Asn Phe Tyr Leu Leu Leu Ala Ser Ser Ile Leu Cys Ala Leu Ile
1 5 10 15

Val Phe Trp Lys Tyr Arg Arg Phe Gln Arg Asn Thr Gly Glu Met Ser
20 25 30

Ser Asn Ser Thr Ala Leu Ala Leu Val Arg Pro Ser Ser Ser Gly Leu
35 40 45

Ile Asn Ser Asn Thr Asp Asn Asn Leu Ala Val Tyr Asp Leu Ser Arg
50 55 60

Asp Ile Leu Asn Asn Phe Pro His Ser Ile Ala Arg Gln Lys Arg Ile
65 70 75 80

Leu Val Asn Leu Ser Met Val Glu Asn Lys Leu Val Glu Leu Glu His
85 90 95

Thr Leu Leu Ser Lys Gly Phe Arg Gly Ala Ser Pro His Arg Lys Ser
100 105 110

Thr

<210> SEQ ID NO 21
<211> LENGTH: 2301
<212> TYPE: DNA
<213> ORGANISM: Artificial Sequence
<220> FEATURE:
<223> OTHER INFORMATION: Synthetic

<400> SEQUENCE: 21
atgaatttct acctgctgct ggcatcttca atcctgtgcg ccctgatcgt cttttggaag 60
tatcgccgct ttcagaggaa cactggcgag atgagcagca acagcaccgc cctggccctg 120
gtgcggcctt ctagctccgg cctgatcaac tctaatacag acaacaatct ggccgtgtat 180
gacctgtccc gggatatcct gaacaatttc ccacactcta tcgccaggca gaagcgcatc 240
ctggtgaacc tgagcatggt ggagaataag ctggtggagc tggagcacac cctgctgagc 300
aagggcttcc ggggagcatc ccccacacaga aagtctaccg gcagcggcgc cacaaacttt 360
tctctgctga agcaggcagg cgacgtggag gagaatcctg gaccagccct gccaaccgcc 420
agacccctgc tgggcagctg tggcacaccc gccctgggct ctctgctgtt cctgctgttt 480
agcctgggat gggtgcagcc atcaaggacc ctggcaggag agacaggaca ggaggcagca 540

```
cccctggatg gcgtgctggc caacccccct aatatctcta gcctgagccc aagacagctg    600

ctgggcttcc catgtgcaga ggtgtccgga ctgtctaccg agagggtgcg cgagctggca    660

gtggccctgg cacagaagaa tgtgaagctg tctacagagc agctgaggtg cctggcacac    720

agactgagcg agccaccaga ggacctggat gcactgcctc tggacctgct gctgttcctg    780

aaccccgatg cctttagcgg acctcaggcc tgcacccggt tcttttccag aatcacaaag    840

gccaatgtgg atctgctgcc taggggcgca ccagagaggc agagactgct gccagccgcc    900

ctggcctgct ggggcgtgag ggcagcctg ctgtccgagg cagacgtgcg cgccctggga    960

ggactggcct gtgatctgcc aggccgcttt gtggcagagt ctgccgaggt gctgctgcct   1020

aggctggtga gctgcccagg acctctggac caggatcagc aggaggcagc ccgggccgcc   1080

ctgcagggcg gcggccctcc atacggcccc ccttccacct ggtccgtgtc tacaatggac   1140

gcactgagag gactgctgcc agtgctggga cagccaatca tcaggagcat cccccagggc   1200

atcgtggcag catggaggca gcggagcagc cgggacccct cctggaggca gccagagagg   1260

accatcctgc ggccaagatt ccggagagag gtggagaaga cagcatgtcc atccggcaag   1320

aaggcccgcg agatcgacga gtctctgatc ttttacaaga agtgggagct ggaggcctgc   1380

gtggacgccg ccctgctggc tacccagatg gaccgggtga acgccatccc cttcacctac   1440

gagcagctgg acgtgctgaa gcacaagctg gatgagctgt acccccaggg ctatcctgag   1500

tccgtgatcc agcacctggg ctacctgttt ctgaagatga gccccgagga tatccggaag   1560

tggaacgtga cctccctgga gacactgaag gccctgctgg aggtcaataa gggccacgag   1620

atgagccctc aggtggccac cctgatcgac aggttcgtga agggccgcgg ccagctggac   1680

aaggatacac tggataccct gacagccttt taccctggct acctgtgcag cctgtcccca   1740

gaggagctga gctccgtgcc accctctagc atctgggccg tgcggcccca ggacctggat   1800

acctgcgacc ctagacagct ggatgtgctg tacccaaagg ccaggctggc cttccagaac   1860

atgaatggct ctgagtattt cgtgaagatc cagagctttc tgggaggagc accaaccgag   1920

gacctgaagg ccctgtccca gcagaacgtg tctatggacc tggccacctt tatgaagctg   1980

agaacagatg ccgtgctgcc tctgaccgtg gcagaggtgc agaagctgct gggaccacac   2040

gtggagggcc tgaaggcaga ggagaggcac aggcctgtga gggactggat tctgcggcag   2100

agacaggacg atctggatac cctgggactg ggactgcagg gaggcatccc caatggcggc   2160

tctacaagcg gctccggcaa gcctggctct ggagagggca gcaccaaggg aatgcaggag   2220

gccctgagcg gcacaccctg tctgctggga cctggacccg tgctgactgt gctggctctg   2280

ctgctggctt caaccctggc a                                              2301
```

```
<210> SEQ ID NO 22
<211> LENGTH: 767
<212> TYPE: PRT
<213> ORGANISM: Artificial Sequence
<220> FEATURE:
<223> OTHER INFORMATION: Synthetic

<400> SEQUENCE: 22

Met Asn Phe Tyr Leu Leu Leu Ala Ser Ser Ile Leu Cys Ala Leu Ile
1               5                   10                  15

Val Phe Trp Lys Tyr Arg Arg Phe Gln Arg Asn Thr Gly Glu Met Ser
            20                  25                  30

Ser Asn Ser Thr Ala Leu Ala Leu Val Arg Pro Ser Ser Ser Gly Leu
        35                  40                  45
```

-continued

```
Ile Asn Ser Asn Thr Asp Asn Asn Leu Ala Val Tyr Asp Leu Ser Arg
    50                  55                  60

Asp Ile Leu Asn Asn Phe Pro His Ser Ile Ala Arg Gln Lys Arg Ile
65                  70                  75                  80

Leu Val Asn Leu Ser Met Val Glu Asn Lys Leu Val Glu Leu Glu His
                85                  90                  95

Thr Leu Leu Ser Lys Gly Phe Arg Gly Ala Ser Pro His Arg Lys Ser
            100                 105                 110

Thr Gly Ser Gly Ala Thr Asn Phe Ser Leu Leu Lys Gln Ala Gly Asp
        115                 120                 125

Val Glu Glu Asn Pro Gly Pro Ala Leu Pro Thr Ala Arg Pro Leu Leu
    130                 135                 140

Gly Ser Cys Gly Thr Pro Ala Leu Gly Ser Leu Leu Phe Leu Leu Phe
145                 150                 155                 160

Ser Leu Gly Trp Val Gln Pro Ser Arg Thr Leu Ala Gly Glu Thr Gly
                165                 170                 175

Gln Glu Ala Ala Pro Leu Asp Gly Val Leu Ala Asn Pro Pro Asn Ile
            180                 185                 190

Ser Ser Leu Ser Pro Arg Gln Leu Leu Gly Phe Pro Cys Ala Glu Val
        195                 200                 205

Ser Gly Leu Ser Thr Glu Arg Val Arg Glu Leu Ala Val Ala Leu Ala
    210                 215                 220

Gln Lys Asn Val Lys Leu Ser Thr Glu Gln Leu Arg Cys Leu Ala His
225                 230                 235                 240

Arg Leu Ser Glu Pro Pro Glu Asp Leu Asp Ala Leu Pro Leu Asp Leu
                245                 250                 255

Leu Leu Phe Leu Asn Pro Asp Ala Phe Ser Gly Pro Gln Ala Cys Thr
            260                 265                 270

Arg Phe Phe Ser Arg Ile Thr Lys Ala Asn Val Asp Leu Leu Pro Arg
        275                 280                 285

Gly Ala Pro Glu Arg Gln Arg Leu Leu Pro Ala Ala Leu Ala Cys Trp
    290                 295                 300

Gly Val Arg Gly Ser Leu Leu Ser Glu Ala Asp Val Arg Ala Leu Gly
305                 310                 315                 320

Gly Leu Ala Cys Asp Leu Pro Gly Arg Phe Val Ala Glu Ser Ala Glu
                325                 330                 335

Val Leu Leu Pro Arg Leu Val Ser Cys Pro Gly Pro Leu Asp Gln Asp
            340                 345                 350

Gln Gln Glu Ala Ala Arg Ala Ala Leu Gln Gly Gly Gly Pro Pro Tyr
        355                 360                 365

Gly Pro Pro Ser Thr Trp Ser Val Ser Thr Met Asp Ala Leu Arg Gly
    370                 375                 380

Leu Leu Pro Val Leu Gly Gln Pro Ile Ile Arg Ser Ile Pro Gln Gly
385                 390                 395                 400

Ile Val Ala Ala Trp Arg Gln Arg Ser Ser Arg Asp Pro Ser Trp Arg
                405                 410                 415

Gln Pro Glu Arg Thr Ile Leu Arg Pro Arg Phe Arg Arg Glu Val Glu
            420                 425                 430

Lys Thr Ala Cys Pro Ser Gly Lys Lys Ala Arg Glu Ile Asp Glu Ser
        435                 440                 445

Leu Ile Phe Tyr Lys Lys Trp Glu Leu Glu Ala Cys Val Asp Ala Ala
    450                 455                 460
```

```
Leu Leu Ala Thr Gln Met Asp Arg Val Asn Ala Ile Pro Phe Thr Tyr
465                 470                 475                 480

Glu Gln Leu Asp Val Leu Lys His Lys Leu Asp Glu Leu Tyr Pro Gln
                485                 490                 495

Gly Tyr Pro Glu Ser Val Ile Gln His Leu Gly Tyr Leu Phe Leu Lys
            500                 505                 510

Met Ser Pro Glu Asp Ile Arg Lys Trp Asn Val Thr Ser Leu Glu Thr
        515                 520                 525

Leu Lys Ala Leu Leu Glu Val Asn Lys Gly His Glu Met Ser Pro Gln
    530                 535                 540

Val Ala Thr Leu Ile Asp Arg Phe Val Lys Gly Arg Gly Gln Leu Asp
545                 550                 555                 560

Lys Asp Thr Leu Asp Thr Leu Thr Ala Phe Tyr Pro Gly Tyr Leu Cys
                565                 570                 575

Ser Leu Ser Pro Glu Glu Leu Ser Ser Val Pro Pro Ser Ser Ile Trp
            580                 585                 590

Ala Val Arg Pro Gln Asp Leu Asp Thr Cys Asp Pro Arg Gln Leu Asp
        595                 600                 605

Val Leu Tyr Pro Lys Ala Arg Leu Ala Phe Gln Asn Met Asn Gly Ser
    610                 615                 620

Glu Tyr Phe Val Lys Ile Gln Ser Phe Leu Gly Gly Ala Pro Thr Glu
625                 630                 635                 640

Asp Leu Lys Ala Leu Ser Gln Gln Asn Val Ser Met Asp Leu Ala Thr
                645                 650                 655

Phe Met Lys Leu Arg Thr Asp Ala Val Leu Pro Leu Thr Val Ala Glu
            660                 665                 670

Val Gln Lys Leu Leu Gly Pro His Val Glu Gly Leu Lys Ala Glu Glu
        675                 680                 685

Arg His Arg Pro Val Arg Asp Trp Ile Leu Arg Gln Arg Gln Asp Asp
    690                 695                 700

Leu Asp Thr Leu Gly Leu Gly Leu Gln Gly Gly Ile Pro Asn Gly Gly
705                 710                 715                 720

Ser Thr Ser Gly Ser Gly Lys Pro Gly Ser Gly Glu Gly Ser Thr Lys
                725                 730                 735

Gly Met Gln Glu Ala Leu Ser Gly Thr Pro Cys Leu Leu Gly Pro Gly
            740                 745                 750

Pro Val Leu Thr Val Leu Ala Leu Leu Leu Ala Ser Thr Leu Ala
        755                 760                 765
```

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
tacagctgca aggacaacca g 21

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
aatctgatat agctcaatcc g 21

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
tttccaccat tagcacgcgg g 21

<210> SEQ ID NO 26
<211> LENGTH: 36
<212> TYPE: DNA
<213> ORGANISM: Artificial Sequence
<220> FEATURE:
<223> OTHER INFORMATION: Synthetic

<400> SEQUENCE: 26
ggcagccctg gcatgggtgt gcatgtgggt gcagcc 36

<210> SEQ ID NO 27
<211> LENGTH: 36
<212> TYPE: DNA
<213> ORGANISM: Artificial Sequence
<220> FEATURE:
<223> OTHER INFORMATION: Synthetic

<400> SEQUENCE: 27
cacacaggaa actacacttg tgaagtaaca gaatta 36

<210> SEQ ID NO 28
<211> LENGTH: 43
<212> TYPE: DNA
<213> ORGANISM: Artificial Sequence
<220> FEATURE:
<223> OTHER INFORMATION: Synthetic

<400> SEQUENCE: 28
ccagtcacct ctgaacatga actgacatgt caggctgagg gct 43

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
gcttgctcag gatctgcccg 20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
gcactaccag agctaactca 20

<210> SEQ ID NO 31
<211> LENGTH: 38
<212> TYPE: DNA
<213> ORGANISM: Artificial Sequence
<220> FEATURE:
<223> OTHER INFORMATION: Synthetic

<400> SEQUENCE: 31
ctcgccagcc ccccgagcca gggggaggtg ccgcccgg 38

<210> SEQ ID NO 32
<211> LENGTH: 44
<212> TYPE: DNA
<213> ORGANISM: Artificial Sequence
<220> FEATURE:
<223> OTHER INFORMATION: Synthetic

<400> SEQUENCE: 32
agctcaccag tcccccagaa gactatcctg agcccgagga agtc 44

<210> SEQ ID NO 33
<211> LENGTH: 44
<212> TYPE: DNA
<213> ORGANISM: Artificial Sequence
<220> FEATURE:
<223> OTHER INFORMATION: Synthetic

<400> SEQUENCE: 33
tactcctctc ggaggccctg gcccttaccc agacctgggc gggt 44

<210> SEQ ID NO 34
<211> LENGTH: 43
<212> TYPE: DNA
<213> ORGANISM: Artificial Sequence
<220> FEATURE:
<223> OTHER INFORMATION: Synthetic

<400> SEQUENCE: 34
cctaatggct tccctggatg cagagaaggc ccaaggacaa aag 43

<210> SEQ ID NO 35
<211> LENGTH: 3402
<212> TYPE: DNA
<213> ORGANISM: Homo Sapiens

<400> SEQUENCE: 35
atgcctagag cacctagatg tagagctgtg cggagcctgc tgcggagcca ctatagagaa 60
gttctgcccc tggccacctt cgtgcgtaga cttggacctc aaggatggcg gctggtgcag 120
agaggcgatc ctgctgcttt tagagccctg gtggcccagt gtctcgtgtg cgttccatgg 180
gatgctagac ctccaccagc tgctcccagc ttcagacagg tgtcctgcct gaaagaactg 240
gtggccagag tgctgcagcg gctgtgtgaa aggggcgcca aaaatgtgct ggccttcggc 300
tttgccctgc tggatgaagc tagaggcgga cctcctgagg cctttacaac aagcgtgcgg 360
agctacctgc ctaacaccgt gacagatgcc ctgagaggat ctggcgcttg gggactgctg 420
ctgagaagag tgggagatga cgtgctggtg catctgctgg cccactgtgc tctgtttgtg 480
ctggtggctc ctagctgcgc ctaccaagtt tgcggccctc tgctgtatca gctgggcgct 540
gctacacagg ctagaccacc tccacatgcc agcggaccta gaagaaggct gggctgcgaa 600
agagcctgga accactctgt tagagaagcc ggcgtgccac tgggattgcc tgcacctggt 660
gctcggagaa gagatggcag cgcctctaga tctctgcctc tgcctaagag gcccagaaga 720
ggcgcagcac ctgagcctga gagaacccct atcggccaag gatcttgggc ccatcctggc 780
agaacaagag gccctagcga tagaggcttc tgcgtggtgt ctcctgccag acctgccgag 840

-continued

```
gaagctacat ctcttgacgg cgccctgagc ggcacaagac actctcatcc atctgtgggc    900
tgccagcacc atgccggacc tccatctaca agcagaccac ctagaccttg ggacacccct    960
tgtcctccag tgtacgccga gacaaagcac ttcctgtaca gcagcggcga caaagagcag   1020
ctgaggccta gcttcctgct gagctttctg aggccaagcc tgacaggcgc cagacggctg   1080
ctggaaacaa tcttcctggg cagcagaccc tggatgcctg gcacacttag aaggctgcct   1140
agactgcccc agcggtactg gcaaatgagg cccctgtttc tggaactgct gggcaaccac   1200
gctcagtgcc cttatggcgt gctgctgaaa acccactgtc cactgagagc cgtggttact   1260
ccagctgctg gcgtgtgtgc cagagagaag ccacagggat ctgtggtggc ccctgaggaa   1320
gaggacaccg atcctagaag gctcgtgcag ctgctgaggc agcatagctc tccatggcag   1380
gtctacggat tcgtgcgggc ctgtctgcat agactggttc cacctggact gtggggctcc   1440
agacacaacg agcggcggtt tctgcggaac accaagaagt tcatcagcct gggaaagcac   1500
gccaagctga gcctgcaaga gctgacctgg aagatgagcg tgtgggattg tgcttggctg   1560
cggagaagtc ctggcgtggg atgtgttcct gccgccgaac acagactgcg ggaagagatc   1620
ctggccaagt tcctgcactg gctgatgtcc gtgtacgtgg tcgaactgct gcggtccctg   1680
ttctgcgtga ccgagacaac cttccagaag aaccggctgt tcttctaccg gaagtccgtg   1740
tggtccaagc tgcagagcat cggcatccgg cagcatctga agagagtgca gctgagagag   1800
ctgctcgaag ccgaagttcg gcagcacaga aaagccagac tggccctgct gaccagcagg   1860
ctgagattca tccccaagca cgatggcctg cggcctattg tgaacatgga ctacgttgtg   1920
ggcgccagaa ccttccaccg ggaaaagaga gccgagcggc tgacctctag agtgaaggcc   1980
ctgtttagcg tgctgaacta cgagcgggcc agaaggccat ctctgctggg agcctttgtg   2040
ctcggcctgg acgatattca tagagcctgg cggacattcg tgctgagagt cagagcccag   2100
gatagccctc ctgagctgta cttcgtgaag gccgatgtga tgggcgccta caacacaatc   2160
cctcaggacc ggctgaccga gatcattgcc agcatcatca agccccagaa catgtactgt   2220
gtgcggagat acgccgtggt gcagaaagcc acacatggcc acgtgcgcaa ggccttcaag   2280
agccatgtgt ctaccctgac cgacctgcag ccttacatga gacagttcgt ggcctatctg   2340
caagagacaa gccctctgag ggacgccgtg atcatcgaac agagcagcag cctgaatgag   2400
gccagctccg gcctgtttga cgtgttcctc agattcatgt gccaccacgc cgtgcggatc   2460
agaggcaaga gctacatcca gtgccagggc attccacagg gctccatcct gagcacactg   2520
ctgtgcagcc tgtgctacgg cgacatggaa aacaagctgt tcgccggcat tcggcgcgac   2580
ggactgcttc ttagactggt ggacgacttc ctgctcgtga cccctcatct gacccacgcc   2640
aagacctttc tgaaaacact cgtgcggggc gtgcccgagt atggctgtgt ggtcaatctg   2700
agaaagaccg tggtcaactt ccccgtcgag gatgaagccc tcggcggcac agcttttgtg   2760
cagatgcctg ctcacggact gttcccttgg tgctccctgc tgctggacac tagaaccctg   2820
gaagtgcaga gcgactacag cagctatgcc cggacctcta tcagagccag cctgaccttc   2880
aaccggggct ttaaggccgg cagaaacatg cggagaaagc tgtttggagt gctgcggctg   2940
aagtgccaca gcctgttcct cgacctgcaa gtgaacagcc tgcagaccgt gtgcaccaat   3000
atctacaaga ttctgctgct gcaagcctac cggttccacg cctgtgttct gcagctgccc   3060
ttccaccagc aagtgtggaa gaaccctaca ttcttcctgc ggatcatcag cgacaccgcc   3120
agcctgtgtt acagcatcct gaaggccaag aacgccggca tgtctctggg agctaaaggc   3180
gctgcaggac ccctgccttt tgaagctgtt cagtggctgt gtcaccaggc ctttctgctg   3240
```

```
aagctgaccc ggcacagagt gacatatgtg cccctgctgg gctccctgag aacagctcag   3300

atgcagctgt ccagaaagct gccaggcaca accctgacag ccctggaagc tgctgctaac   3360

cctgctctgc ccagcgactt caagaccatc ctggactgat ga                     3402


<210> SEQ ID NO 36
<211> LENGTH: 1132
<212> TYPE: PRT
<213> ORGANISM: Homo Sapiens

<400> SEQUENCE: 36

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Glu Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala His Cys Ala Leu Phe Val
145                 150                 155                 160

Leu Val Ala Pro Ser Cys Ala Tyr Gln Val Cys Gly Pro Leu Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Asp Gly Ser Ala Ser Arg Ser Leu Pro Leu Pro Lys Arg Pro Arg Arg
225                 230                 235                 240

Gly Ala Ala Pro Glu Pro Glu Arg Thr Pro Ile Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Asp Gly Ala
        275                 280                 285

Leu Ser Gly Thr Arg His Ser His Pro Ser Val Gly Cys Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Phe Leu Arg Pro
```

```
            340                 345                 350

Ser Leu Thr Gly Ala Arg Arg Leu Leu Glu Thr Ile Phe Leu Gly Ser
        355                 360                 365

Arg Pro Trp Met Pro Gly Thr Leu Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Val Val Thr Pro Ala Ala Gly Val Cys Ala Arg Glu Lys Pro Gln
            420                 425                 430

Gly Ser Val Val Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu His Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Trp Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Leu
545                 550                 555                 560

Phe Cys Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Leu Glu Ala Glu Val Arg Gln
        595                 600                 605

His Arg Lys Ala Arg Leu Ala Leu Leu Thr Ser Arg Leu Arg Phe Ile
    610                 615                 620

Pro Lys His Asp Gly Leu Arg Pro Ile Val Asn Met Asp Tyr Val Val
625                 630                 635                 640

Gly Ala Arg Thr Phe His Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Ser Leu Leu Gly Ala Phe Val Leu Gly Leu Asp Asp Ile His Arg
        675                 680                 685

Ala Trp Arg Thr Phe Val Leu Arg Val Arg Ala Gln Asp Ser Pro Pro
    690                 695                 700

Glu Leu Tyr Phe Val Lys Ala Asp Val Met Gly Ala Tyr Asn Thr Ile
705                 710                 715                 720

Pro Gln Asp Arg Leu Thr Glu Ile Ile Ala Ser Ile Ile Lys Pro Gln
                725                 730                 735

Asn Met Tyr Cys Val Arg Arg Tyr Ala Val Val Gln Lys Ala Thr His
            740                 745                 750

Gly His Val Arg Lys Ala Phe Lys Ser His Val Ser Thr Leu Thr Asp
        755                 760                 765
```

Leu Gln Pro Tyr Met Arg Gln Phe Val Ala Tyr Leu Gln Glu Thr Ser
770 775 780

Pro Leu Arg Asp Ala Val Ile Ile Glu Gln Ser Ser Ser Leu Asn Glu
785 790 795 800

Ala Ser Ser Gly Leu Phe Asp Val Phe Leu Arg Phe Met Cys His His
805 810 815

Ala Val Arg Ile Arg Gly Lys Ser Tyr Ile Gln Cys Gln Gly Ile Pro
820 825 830

Gln Gly Ser Ile Leu Ser Thr Leu Leu Cys Ser Leu Cys Tyr Gly Asp
835 840 845

Met Glu Asn Lys Leu Phe Ala Gly Ile Arg Arg Asp Gly Leu Leu Leu
850 855 860

Arg Leu Val Asp Asp Phe Leu Leu Val Thr Pro His Leu Thr His Ala
865 870 875 880

Lys Thr Phe Leu Lys Thr Leu Val Arg Gly Val Pro Glu Tyr Gly Cys
885 890 895

Val Val Asn Leu Arg Lys Thr Val Val Asn Phe Pro Val Glu Asp Glu
900 905 910

Ala Leu Gly Gly Thr Ala Phe Val Gln Met Pro Ala His Gly Leu Phe
915 920 925

Pro Trp Cys Ser Leu Leu Leu Asp Thr Arg Thr Leu Glu Val Gln Ser
930 935 940

Asp Tyr Ser Ser Tyr Ala Arg Thr Ser Ile Arg Ala Ser Leu Thr Phe
945 950 955 960

Asn Arg Gly Phe Lys Ala Gly Arg Asn Met Arg Arg Lys Leu Phe Gly
965 970 975

Val Leu Arg Leu Lys Cys His Ser Leu Phe Leu Asp Leu Gln Val Asn
980 985 990

Ser Leu Gln Thr Val Cys Thr Asn Ile Tyr Lys Ile Leu Leu Leu Gln
995 1000 1005

Ala Tyr Arg Phe His Ala Cys Val Leu Gln Leu Pro Phe His Gln
1010 1015 1020

Gln Val Trp Lys Asn Pro Thr Phe Phe Leu Arg Ile Ile Ser Asp
1025 1030 1035

Thr Ala Ser Leu Cys Tyr Ser Ile Leu Lys Ala Lys Asn Ala Gly
1040 1045 1050

Met Ser Leu Gly Ala Lys Gly Ala Ala Gly Pro Leu Pro Phe Glu
1055 1060 1065

Ala Val Gln Trp Leu Cys His Gln Ala Phe Leu Leu Lys Leu Thr
1070 1075 1080

Arg His Arg Val Thr Tyr Val Pro Leu Leu Gly Ser Leu Arg Thr
1085 1090 1095

Ala Gln Met Gln Leu Ser Arg Lys Leu Pro Gly Thr Thr Leu Thr
1100 1105 1110

Ala Leu Glu Ala Ala Ala Asn Pro Ala Leu Pro Ser Asp Phe Lys
1115 1120 1125

Thr Ile Leu Asp
1130

<210> SEQ ID NO 37
<211> LENGTH: 2256
<212> TYPE: DNA
<213> ORGANISM: Homo Sapiens

<400> SEQUENCE: 37

```
atgtggaatc tgctgcacga gacagatagc gccgtggcta ccgttagaag gcccagatgg     60
ctttgtgctg gcgctctggt tctggctggc ggcttttttc tgctgggctt cctgttcggc    120
tggttcatca agagcagcaa cgaggccacc aacatcaccc ctaagcacaa catgaaggcc    180
tttctggacg agctgaaggc cgagaatatc aagaagttcc tgtacaactt cacgcacatc    240
cctcacctgg ccggcaccga gcagaatttt cagctggcca agcagatcca gagccagtgg    300
aaagagttcg gcctggactc tgtggaactg gcccactacg atgtgctgct gagctacccc    360
aacaagacac accccaacta catcagcatc atcaacgagg acggcaacga gatcttcaac    420
accagcctgt tcgagcctcc acctcctggc tacgagaacg tgtccgatat cgtgcctcca    480
ttcagcgctt tcagcccaca gcggatgcct gagggctacc tggtgtacgt gaactacgcc    540
agaaccgagg acttcttcaa gctggaatgg gacatgaaga tcagctgcag cggcaagatc    600
gtgatcgccc ggtacagaaa ggtgttccgc gagaacaaag tgaagaacgc ccagctggca    660
ggcgccaaag gcgtgatcct gtatagcgac cccgccgact attttgcccc tggcgtgaag    720
tcttaccccg acggctggaa ttttcctggc ggcggagtgc agcggcggaa catccttaat    780
cttaacggcg ctggcgaccc tctgacacct ggctatcctg ccaatgagta cgcctacaga    840
cacggaattg ccgaggctgt gggcctgcct tctattcctg tgcaccctgt gcggtactac    900
gacgcccaga aactgctgga aaagatgggc ggaagcgccc ctcctgactc ttcttggaga    960
ggctctctga aggtgcccta caatgtcggc ccaggcttca ccggcaactt cagcacccag   1020
aaagtgaaaa tgcacatcca cagcaccaac gaagtgaccc ggatctacaa cgtgatcggc   1080
acactgagag gcgccgtgga acccgacaaa tacgtgatcc tcggcggcca cagagacagc   1140
tgggtgttcg gaggaatcga ccctcaatct ggcgccgctg tggtgtatga gatcgtgcgg   1200
tctttcggca ccctgaagaa agaaggatgg cggcccagac ggaccatcct gtttgcctct   1260
tgggacgccg aggaatttgg cctgctggga tctacagagt gggccgaaga gaacagcaga   1320
ctgctgcaag aaagaggcgt ggcctacatc aacgccgaca gcagcatcga gggcaactac   1380
accctgcgga tcgattgcac ccctctgatg tacagcctgg tgcacaacct gaccaaagag   1440
ctgaagtccc ctgacgaggg ctttgagggc aagagcctgt acaagagctg gaccaagaag   1500
tccccatctc ctgagttcag cggcatgccc agaatctcta agctggaaag cggcaacaac   1560
ttcgaggtgt tcttccagcg gctgggaatc gcctctggaa tcgccagata caccaagaac   1620
tgggagacaa acaagttctc cggctatccc ctgtaccaca gcgtgtacga gacatacgag   1680
ctggtggaaa agttctacga ccccatgttc aagtaccacc tgacagtggc ccaagtgcgc   1740
ggaggcatgg tgttcgaact ggccaatagc atcgtgctgc ccttcaactg cagagactac   1800
gccgtggtgc tgcggaagta cgccgacaag atctacagca tcagcatgaa gcacccgcaa   1860
gagatgaaga cctacagcgt gtccttcgac tccctgttct tcgccgtgaa gaacttcacc   1920
aagatcgcca gcaagttcag cgagcggctg caggacttcg acaagagcaa ccctatcgtg   1980
ctgaggatga tgaacgacca gctgatgttc ctggaacggg ccttcatcaa ccctctggga   2040
ctgcccgaca gacccttcta caggcacgtg atctgtgccc ctagcagcca caacaaatac   2100
gccggcgaga gcttccccgg catctacgat gccctgttcg acatcgagag caacgtgaac   2160
cctagcaagg cctggggcga agtgaagaga cagatctacg tggccgcatt cacagtgcag   2220
gccgctgccg aaacactgtc tgaggtggcc tgatga                             2256
```

<210> SEQ ID NO 38
<211> LENGTH: 750
<212> TYPE: PRT
<213> ORGANISM: Homo Sapiens

<400> SEQUENCE: 38

```
Met Trp Asn Leu Leu His Glu Thr Asp Ser Ala Val Ala Thr Val Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr His Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Arg Met Pro Glu Gly Tyr Leu Val Tyr
                165                 170                 175

Val Asn Tyr Ala Arg Thr Glu Asp Phe Phe Lys Leu Glu Trp Asp Met
            180                 185                 190

Lys Ile Ser Cys Ser Gly Lys Ile Val Ile Ala Arg Tyr Arg Lys Val
        195                 200                 205

Phe Arg Glu Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Phe Pro Gly Gly Gly Val Gln Arg Arg
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg His Gly Ile Ala Glu Ala Val Gly
        275                 280                 285

Leu Pro Ser Ile Pro Val His Pro Val Arg Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Lys Tyr Val Ile Leu Gly Gly His Arg Asp Ser Trp Val Phe Gly
    370                 375                 380
```

```
Gly Ile Asp Pro Gln Ser Gly Ala Ala Val Val Tyr Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Ile
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Lys Ser
                485                 490                 495

Trp Thr Lys Lys Ser Pro Ser Pro Glu Phe Ser Gly Met Pro Arg Ile
            500                 505                 510

Ser Lys Leu Glu Ser Gly Asn Asn Phe Glu Val Phe Phe Gln Arg Leu
        515                 520                 525

Gly Ile Ala Ser Gly Ile Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asn Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Phe Ala Val Lys Asn Phe Thr
625                 630                 635                 640

Lys Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asn Pro Leu Gly Leu Pro Asp Arg Pro Phe Tyr Arg
        675                 680                 685

His Val Ile Cys Ala Pro Ser Ser His Asn Lys Tyr Ala Gly Glu Ser
    690                 695                 700

Phe Pro Gly Ile Tyr Asp Ala Leu Phe Asp Ile Glu Ser Asn Val Asn
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750
```

<210> SEQ ID NO 39
<211> LENGTH: 2697
<212> TYPE: DNA
<213> ORGANISM: Homo Sapiens

<400> SEQUENCE: 39

```
atgtctctcg aacagagaag cctgcactgc aagcccgagg aagctctgga agctcagcaa     60
```

```
gaggctctgg gccttgtgtg tgttcaggcc gctgccagca gcttttctcc tctggtgctg    120
ggcacactgg aagaggtgcc aacagccggc tctaccgatc ctcctcaatc tcctcaaggc    180
gccagcgcct ttcctaccac catcaacttc acccggcaga gacagcctag cgagggctct    240
agctctcacg aggaaaaggg ccctagcacc agctgcatcc tggaaagcct gttccgggcc    300
gtgatcacaa agaaagtggc cgacctcgtg ggcttcctgc tgctgaagta cagagccaga    360
gaacccgtga ccaaggccga gatgctggaa agcgtgatca agaactacaa gcactgcttc    420
agcgagatct tcggcaaggc cagcgagtct ctgcagctcg tgtttggcat cgacgtgaaa    480
gaggccgatc ctaccggcca cagctacgtg ttcgtgacat gtctgggcct gagctacgat    540
ggcctgctgg gcgacaatca gattatgctg aaaaccggct tcctgatcat cgtgctggtc    600
atgatcgcca tggaaggctc tcacgcccct aaagaggaaa tctgggaaga actgagcgtg    660
atggaagtgt acgacggcag agagcatagc gcctacggcg agcctagaaa actgctgacc    720
caggacctgg tgcaagagaa gtacctcgag tacagacagg tgcccgacag cgaccctgcc    780
agatacgaat ttctgtgggg ccctagagca ctggccgaga caagctatgt gaaggtgctg    840
gaatacgtca tcaaggtgtc cgccagagtg tgcttcttct tcccatctct gcgggaagcc    900
gctctgcgcg aagaggaaga aggcgtcaga ggccggaaga gaagaagcct ggaagagaaa    960
aagggcaact acgtggtcac cgaccactgc agaggcagaa agcggagaag cgagtctaga   1020
ggcagacggt gccctgagat gattagcgtg ctgggcccta tctctggcca cgtgctgaag   1080
gccgtgttca gcagaggcga tacacctgtg ctgccccacg agacaagact gctgcagaca   1140
ggcatccatg tgcgggtgtc acagccaagc ctgatcctgg tgtctcagta cacccctgac   1200
agcacccctt gtcacagagg cgacaaccag ctccaggtgc agcacaccta ctttaccggc   1260
agcgaggtgg aaaacgtgtc cgtgaacgtg cacaatccca ccggcagatc catctgtccc   1320
agccaagagc ctatgagcat ctacgtgtac gccctgcctc tgaagatgct gaacatcccc   1380
agcatcaatg tgcatcacta cccctctgcc gccgagcgga aacacagaca tctgcctgtg   1440
gccgatgccg tgattcacgc ctctggaaag cagatgtggc aggccagact gacagtgtcc   1500
ggactggctt ggaccagaca gcagaaccag tggaaagaac ccgacgtgta ctacacctcc   1560
gccttcgtgt tccccacaaa ggacgtggcc ctgagacacg ttgtgtgcgc ccatgaactc   1620
gtgtgcagca tggaaaacac ccgggccacc aagatgcaag tgatcggcga ccagtacgtg   1680
aaggtgtacc tggaatcctt ctgcgaggac gtgccaagcg gcaagctgtt catgcacgtg   1740
accctgggct ccgatgtgga agaggacctg accatgacca gaaatcccca gcctttcatg   1800
cggcctcacg agagaaatgg cttcaccgtg ctgtgcccca agaacatgat catcaagccc   1860
ggcaagatca gccacatcat gctggatgtg gccttcacca gccacgagca cttcggactg   1920
ctgtgtccta agagcatccc cggcctgagc atcagcggca acctgctgat gaatggccag   1980
cagatcttcc tggaagtgca ggccattcgg gaaaccgtgg aactgagaca gtacgaccct   2040
gtggctgccc tgttcttctt cgacatcgat ctgctgctcc agagaggccc tcagtacagc   2100
gagcacccaa cctttaccag ccagtacaga atccagggca agctggaata tcggcacacc   2160
tgggatagac acgatgaggg tgctgcacag ggcgacgatg atgtgtggac aagcggcagc   2220
gatagcgacg aggaactggt caccaccgag agaaagaccc ctagagttac aggcggaggc   2280
gcaatggctg gcgcttctac atctgccgga cgcaagagaa agagcgcctc ttctgccacc   2340
gcctgtacaa gcggcgtgat gacaagaggc aggctgaaag ccgagagcac agtggcccct   2400
gaggaagata cagacgagga cagcgacaac gagattcaca accccgccgt gtttacctgg   2460
```

```
cctccttggc aggctggcat tctggctaga aacctggtgc ctatggtggc cacagtgcag   2520

ggccagaacc tgaagtacca agagttcttc tgggacgcca acgacatcta ccggatcttc   2580

gccgaactgg aaggcgtgtg gcaaccagcc gctcagccca aaagacgcag acacagacag   2640

gacgctctgc ccggaccttg tattgccagc acacccaaga aacaccgggg ctgataa      2697


<210> SEQ ID NO 40
<211> LENGTH: 897
<212> TYPE: PRT
<213> ORGANISM: Homo Sapiens

<400> SEQUENCE: 40

Met Ser Leu Glu Gln Arg Ser Leu His Cys Lys Pro Glu Glu Ala Leu
1               5                   10                  15

Glu Ala Gln Gln Glu Ala Leu Gly Leu Val Cys Val Gln Ala Ala Ala
            20                  25                  30

Ser Ser Phe Ser Pro Leu Val Leu Gly Thr Leu Glu Glu Val Pro Thr
        35                  40                  45

Ala Gly Ser Thr Asp Pro Pro Gln Ser Pro Gln Gly Ala Ser Ala Phe
    50                  55                  60

Pro Thr Thr Ile Asn Phe Thr Arg Gln Arg Gln Pro Ser Glu Gly Ser
65                  70                  75                  80

Ser Ser His Glu Glu Lys Gly Pro Ser Thr Ser Cys Ile Leu Glu Ser
                85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
        115                 120                 125

Leu Glu Ser Val Ile Lys Asn Tyr Lys His Cys Phe Ser Glu Ile Phe
    130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Phe Val Thr Cys Leu Gly
                165                 170                 175

Leu Ser Tyr Asp Gly Leu Leu Gly Asp Asn Gln Ile Met Leu Lys Thr
            180                 185                 190

Gly Phe Leu Ile Ile Val Leu Val Met Ile Ala Met Glu Gly Ser His
        195                 200                 205

Ala Pro Lys Glu Glu Ile Trp Glu Glu Leu Ser Val Met Glu Val Tyr
    210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
        275                 280                 285

Arg Val Cys Phe Phe Phe Pro Ser Leu Arg Glu Ala Ala Leu Arg Glu
    290                 295                 300

Glu Glu Glu Gly Val Arg Gly Arg Lys Arg Arg Ser Leu Glu Glu Lys
305                 310                 315                 320

Lys Gly Asn Tyr Val Val Thr Asp His Cys Arg Gly Arg Lys Arg Arg
                325                 330                 335
```

```
Ser Glu Ser Arg Gly Arg Arg Cys Pro Glu Met Ile Ser Val Leu Gly
            340                 345                 350

Pro Ile Ser Gly His Val Leu Lys Ala Val Phe Ser Arg Gly Asp Thr
        355                 360                 365

Pro Val Leu Pro His Glu Thr Arg Leu Leu Gln Thr Gly Ile His Val
    370                 375                 380

Arg Val Ser Gln Pro Ser Leu Ile Leu Val Ser Gln Tyr Thr Pro Asp
385                 390                 395                 400

Ser Thr Pro Cys His Arg Gly Asp Asn Gln Leu Gln Val Gln His Thr
                405                 410                 415

Tyr Phe Thr Gly Ser Glu Val Glu Asn Val Ser Val Asn Val His Asn
            420                 425                 430

Pro Thr Gly Arg Ser Ile Cys Pro Ser Gln Glu Pro Met Ser Ile Tyr
        435                 440                 445

Val Tyr Ala Leu Pro Leu Lys Met Leu Asn Ile Pro Ser Ile Asn Val
    450                 455                 460

His His Tyr Pro Ser Ala Ala Glu Arg Lys His Arg His Leu Pro Val
465                 470                 475                 480

Ala Asp Ala Val Ile His Ala Ser Gly Lys Gln Met Trp Gln Ala Arg
                485                 490                 495

Leu Thr Val Ser Gly Leu Ala Trp Thr Arg Gln Gln Asn Gln Trp Lys
            500                 505                 510

Glu Pro Asp Val Tyr Tyr Thr Ser Ala Phe Val Phe Pro Thr Lys Asp
        515                 520                 525

Val Ala Leu Arg His Val Val Cys Ala His Glu Leu Val Cys Ser Met
    530                 535                 540

Glu Asn Thr Arg Ala Thr Lys Met Gln Val Ile Gly Asp Gln Tyr Val
545                 550                 555                 560

Lys Val Tyr Leu Glu Ser Phe Cys Glu Asp Val Pro Ser Gly Lys Leu
                565                 570                 575

Phe Met His Val Thr Leu Gly Ser Asp Val Glu Glu Asp Leu Thr Met
            580                 585                 590

Thr Arg Asn Pro Gln Pro Phe Met Arg Pro His Glu Arg Asn Gly Phe
        595                 600                 605

Thr Val Leu Cys Pro Lys Asn Met Ile Ile Lys Pro Gly Lys Ile Ser
    610                 615                 620

His Ile Met Leu Asp Val Ala Phe Thr Ser His Glu His Phe Gly Leu
625                 630                 635                 640

Leu Cys Pro Lys Ser Ile Pro Gly Leu Ser Ile Ser Gly Asn Leu Leu
                645                 650                 655

Met Asn Gly Gln Gln Ile Phe Leu Glu Val Gln Ala Ile Arg Glu Thr
            660                 665                 670

Val Glu Leu Arg Gln Tyr Asp Pro Val Ala Ala Leu Phe Phe Phe Asp
        675                 680                 685

Ile Asp Leu Leu Leu Gln Arg Gly Pro Gln Tyr Ser Glu His Pro Thr
    690                 695                 700

Phe Thr Ser Gln Tyr Arg Ile Gln Gly Lys Leu Glu Tyr Arg His Thr
705                 710                 715                 720

Trp Asp Arg His Asp Glu Gly Ala Ala Gln Gly Asp Asp Asp Val Trp
                725                 730                 735

Thr Ser Gly Ser Asp Ser Asp Glu Glu Leu Val Thr Thr Glu Arg Lys
            740                 745                 750
```

```
Thr Pro Arg Val Thr Gly Gly Gly Ala Met Ala Gly Ala Ser Thr Ser
        755                 760                 765

Ala Gly Arg Lys Arg Lys Ser Ala Ser Ser Ala Thr Ala Cys Thr Ser
    770                 775                 780

Gly Val Met Thr Arg Gly Arg Leu Lys Ala Glu Ser Thr Val Ala Pro
785                 790                 795                 800

Glu Glu Asp Thr Asp Glu Asp Ser Asp Asn Glu Ile His Asn Pro Ala
                805                 810                 815

Val Phe Thr Trp Pro Pro Trp Gln Ala Gly Ile Leu Ala Arg Asn Leu
            820                 825                 830

Val Pro Met Val Ala Thr Val Gln Gly Gln Asn Leu Lys Tyr Gln Glu
        835                 840                 845

Phe Phe Trp Asp Ala Asn Asp Ile Tyr Arg Ile Phe Ala Glu Leu Glu
    850                 855                 860

Gly Val Trp Gln Pro Ala Ala Gln Pro Lys Arg Arg Arg His Arg Gln
865                 870                 875                 880

Asp Ala Leu Pro Gly Pro Cys Ile Ala Ser Thr Pro Lys Lys His Arg
                885                 890                 895

Gly


<210> SEQ ID NO 41
<211> LENGTH: 3318
<212> TYPE: DNA
<213> ORGANISM: Homo Sapiens

<400> SEQUENCE: 41

atgtctagcc ctggaacaga gtctgccggc aagagcctgc agtacagagt ggaccatctg     60

ctgagcgccg tggaaaatga actgcaggcc ggaagcgaga agggcgatcc tacagagcac    120

gagctgagag tcggcctgga agagtctgag ctgtggctgc ggttcaaaga actgaccaac    180

gagatgatcg tgaccaagaa cggcagacgg atgttccccg tgctgaaagt gaacgtgtcc    240

ggactggacc ccaacgccat gtacagcttt ctgctggact tcgtggtggc cgacaaccac    300

agatggaaat acgtgaacgg cgagtgggtg ccaggcggaa aacctcaact gcaagcccct    360

agctgcgtgt acattcaccc tgacagcccc aatttcggcg cccactggat gaaggcccct    420

gtgtccttca gcaaagtgaa gctgaccaac aagctgaacg gcggaggcca gatcatgctg    480

aacagcctgc acaaatacga gcccagaatc cacatcgtca gagtcggcgg accccagaga    540

atgatcacca gccactgctt ccccgagaca cagtttatcg ccgtgaccgc ctaccagaac    600

gaggaaatca ccacactgaa gatcaagtac aacccccttcg ccaaggcctt cctggacgcc    660

aaagagcgga gcgaccacaa agagatgatc aaagagcccg gcgacagcca gcagccaggc    720

tattctcaat ggggatggct gctgccaggc accagcacat tgtgccctcc agccaatcct    780

cacagccagt ttggaggcgc cctgagcctg tctagcaccc acagctacga cagatacccc    840

acactgcgga gccacagaag cagcccctat ccttctcctt acgctcaccg gaacaacagc    900

cccacctaca gcgataatag ccccgcctgt ctgagcatgc tgcagtccca cgataactgg    960

tccagcctga gaatgcctgc tcacccttcc atgctgcccg tgtctcacaa tgcctctcca   1020

cctaccagca gctctcagta ccctagcctt tggagcgtgt ccaatggcgc cgtgacactg   1080

ggatctcagg cagccgctgt gtctaatgga ctgggagccc agttcttcag aggcagccct   1140

gctcactaca cccctctgac acatcctgtg tctgccccta gcagcagcgg cttccctatg   1200

tataagggcg ctgccgccgc taccgacatc gtggattctc agtatgatgc cgccgcacag   1260
```

ggacacctga tcgcctcttg gacacctgtg tctccacctt ccatgagagg cagaaagaga 1320
agatccgccg ccaccgagat cagcgtgctg agcgagcagt tcaccaagat caaagaattg 1380
aagctgatgc tcgagaaggg gctgaagaaa gaagagaagg acggcgtctg ccgcgagaag 1440
aatcacagaa gccctagcga gctggaagcc cagagaacat ctggcgcctt ccaggacagc 1500
atcctggaag aagaggtgga actggttctg gcccctctgg aagagagcaa gaagtacatc 1560
ctgacactgc agaccgtgca cttcacctct gaagccgtgc agctccagga catgagcctg 1620
ctgtctatcc agcagcaaga gggcgtgcag gttgtggttc agcaacctgg acctggactg 1680
ctctggctgc aagagggacc tagacagtcc ctgcagcagt gtgtggccat cagcatccag 1740
caagagctgt atagccctca agagatggaa gtgctgcagt ttcacgccct cgaagagaac 1800
gtgatggtgg ccatcgagga cagcaagctg gctgtgtctc tggccgaaac aaccggcctg 1860
atcaagctgg aagaggaaca agagaagaac cagctgctgg ccgagaaaac aaaaaagcaa 1920
ctgttcttcg tggaaaccat gagcggcgac gagagaagcg acgagatcgt gctgacagtg 1980
tccaacagca acgtggaaga acaagaggac cagcctaccg cctgtcaggc cgatgccgag 2040
aaagccaagt ttaccaagaa ccagagaaag accaagggcg ccaagggcac cttccactgc 2100
aacgtgtgca tgttcaccag cagccggatg agcagcttca actgccacat gaagacccac 2160
accagcgaga agccccatct gtgtcacctg tgcctgaaaa ccttccggac agtgacactg 2220
ctgtggaact atgtgaacac ccacacaggc acccggcctt acaagtgcaa cgactgcaac 2280
atggccttcg tgaccagcgg agaactcgtg cggcacagaa gatacaagca cacccacgag 2340
aaacccttca agtgcagcat gtgcaaatac gcatccatgg aagcctccaa gctgaagtgc 2400
cacgtgcgct ctcacacagg cgagcaccct ttccagtgct gtcagtgtag ctacgccagc 2460
cgggacacct ataagctgaa gcggcacatg agaacccact ctggcgaaaa gccctacgag 2520
tgccacatct gccacaccag attcacccag agcggcacca tgaagattca catcctgcag 2580
aaacacggca agaacgtgcc caagtaccag tgtcctcact gcgccaccat tatcgccaga 2640
aagtccgacc tgcgggtgca catgaggaat ctgcacgcct attctgccgc cgagctgaaa 2700
tgcagatact gcagcgccgt gttccacaag agatacgccc tgatccagca ccagaaaacc 2760
cacaagaacg agaagcggtt taagtgcaag cactgcagct acgcctgcaa gcaagagcgc 2820
cacatgatcg cccacatcca cacacacacc ggggagaagc cttttacctg cctgagctgc 2880
aacaagtgct tccggcagaa acagctgctc aacgcccact tcagaaagta ccacgacgcc 2940
aacttcatcc ccaccgtgta caagtgctcc aagtgcggca agggcttcag ccggtggatc 3000
aatctgcacc ggcacctgga aaagtgcgag tctggcgaag ccaagtctgc cgcctctggc 3060
aagggcagaa gaacccggaa gagaaagcag accatcctga aagaggccac caagagccag 3120
aaagaagccg ccaagcgctg gaaagaggct gccaacggcg acgaagctgc tgccgaagaa 3180
gccagcacaa caaagggcga acagttcccc gaagagatgt tccctgtggc ctgcagagaa 3240
accacagcca gagtgaagca agaggtcgac cagggcgtga cctgcgagat gctgctgaac 3300
accatggaca agtgatga 3318

<210> SEQ ID NO 42
<211> LENGTH: 1104
<212> TYPE: PRT
<213> ORGANISM: Homo Sapiens

<400> SEQUENCE: 42

Met Ser Ser Pro Gly Thr Glu Ser Ala Gly Lys Ser Leu Gln Tyr Arg

-continued

```
1               5                   10                  15

Val Asp His Leu Leu Ser Ala Val Glu Asn Glu Leu Gln Ala Gly Ser
            20                  25                  30

Glu Lys Gly Asp Pro Thr Glu His Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Val
                85                  90                  95

Ala Asp Asn His Arg Trp Lys Tyr Val Asn Gly Glu Trp Val Pro Gly
            100                 105                 110

Gly Lys Pro Gln Leu Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Thr Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Ile Lys Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Ser Gln Phe Gly Gly Ala Leu Ser Leu Ser Ser
            260                 265                 270

Thr His Ser Tyr Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Arg Met Pro Ala His Pro Ser Met Leu Pro Val Ser His
                325                 330                 335

Asn Ala Ser Pro Pro Thr Ser Ser Ser Gln Tyr Pro Ser Leu Trp Ser
            340                 345                 350

Val Ser Asn Gly Ala Val Thr Leu Gly Ser Gln Ala Ala Ala Val Ser
        355                 360                 365

Asn Gly Leu Gly Ala Gln Phe Phe Arg Gly Ser Pro Ala His Tyr Thr
    370                 375                 380

Pro Leu Thr His Pro Val Ser Ala Pro Ser Ser Ser Gly Phe Pro Met
385                 390                 395                 400

Tyr Lys Gly Ala Ala Ala Ala Thr Asp Ile Val Asp Ser Gln Tyr Asp
                405                 410                 415

Ala Ala Ala Gln Gly His Leu Ile Ala Ser Trp Thr Pro Val Ser Pro
            420                 425                 430
```

-continued

```
Pro Ser Met Arg Gly Arg Lys Arg Arg Ser Ala Ala Thr Glu Ile Ser
        435                 440                 445

Val Leu Ser Glu Gln Phe Thr Lys Ile Lys Glu Leu Lys Leu Met Leu
    450                 455                 460

Glu Lys Gly Leu Lys Lys Glu Glu Lys Asp Gly Val Cys Arg Glu Lys
465                 470                 475                 480

Asn His Arg Ser Pro Ser Glu Leu Glu Ala Gln Arg Thr Ser Gly Ala
                485                 490                 495

Phe Gln Asp Ser Ile Leu Glu Glu Glu Val Glu Leu Val Leu Ala Pro
            500                 505                 510

Leu Glu Glu Ser Lys Lys Tyr Ile Leu Thr Leu Gln Thr Val His Phe
        515                 520                 525

Thr Ser Glu Ala Val Gln Leu Gln Asp Met Ser Leu Leu Ser Ile Gln
    530                 535                 540

Gln Gln Glu Gly Val Gln Val Val Val Gln Gln Pro Gly Pro Gly Leu
545                 550                 555                 560

Leu Trp Leu Gln Glu Gly Pro Arg Gln Ser Leu Gln Gln Cys Val Ala
                565                 570                 575

Ile Ser Ile Gln Gln Glu Leu Tyr Ser Pro Gln Glu Met Glu Val Leu
            580                 585                 590

Gln Phe His Ala Leu Glu Glu Asn Val Met Val Ala Ile Glu Asp Ser
        595                 600                 605

Lys Leu Ala Val Ser Leu Ala Glu Thr Thr Gly Leu Ile Lys Leu Glu
    610                 615                 620

Glu Glu Gln Glu Lys Asn Gln Leu Leu Ala Glu Lys Thr Lys Lys Gln
625                 630                 635                 640

Leu Phe Phe Val Glu Thr Met Ser Gly Asp Glu Arg Ser Asp Glu Ile
                645                 650                 655

Val Leu Thr Val Ser Asn Ser Asn Val Glu Glu Gln Glu Asp Gln Pro
            660                 665                 670

Thr Ala Cys Gln Ala Asp Ala Glu Lys Ala Lys Phe Thr Lys Asn Gln
        675                 680                 685

Arg Lys Thr Lys Gly Ala Lys Gly Thr Phe His Cys Asn Val Cys Met
    690                 695                 700

Phe Thr Ser Ser Arg Met Ser Ser Phe Asn Cys His Met Lys Thr His
705                 710                 715                 720

Thr Ser Glu Lys Pro His Leu Cys His Leu Cys Leu Lys Thr Phe Arg
                725                 730                 735

Thr Val Thr Leu Leu Trp Asn Tyr Val Asn Thr His Thr Gly Thr Arg
            740                 745                 750

Pro Tyr Lys Cys Asn Asp Cys Asn Met Ala Phe Val Thr Ser Gly Glu
        755                 760                 765

Leu Val Arg His Arg Arg Tyr Lys His Thr His Glu Lys Pro Phe Lys
    770                 775                 780

Cys Ser Met Cys Lys Tyr Ala Ser Met Glu Ala Ser Lys Leu Lys Cys
785                 790                 795                 800

His Val Arg Ser His Thr Gly Glu His Pro Phe Gln Cys Cys Gln Cys
                805                 810                 815

Ser Tyr Ala Ser Arg Asp Thr Tyr Lys Leu Lys Arg His Met Arg Thr
            820                 825                 830

His Ser Gly Glu Lys Pro Tyr Glu Cys His Ile Cys His Thr Arg Phe
        835                 840                 845
```

Thr Gln Ser Gly Thr Met Lys Ile His Ile Leu Gln Lys His Gly Lys
850 855 860

Asn Val Pro Lys Tyr Gln Cys Pro His Cys Ala Thr Ile Ile Ala Arg
865 870 875 880

Lys Ser Asp Leu Arg Val His Met Arg Asn Leu His Ala Tyr Ser Ala
885 890 895

Ala Glu Leu Lys Cys Arg Tyr Cys Ser Ala Val Phe His Lys Arg Tyr
900 905 910

Ala Leu Ile Gln His Gln Lys Thr His Lys Asn Glu Lys Arg Phe Lys
915 920 925

Cys Lys His Cys Ser Tyr Ala Cys Lys Gln Glu Arg His Met Ile Ala
930 935 940

His Ile His Thr His Thr Gly Glu Lys Pro Phe Thr Cys Leu Ser Cys
945 950 955 960

Asn Lys Cys Phe Arg Gln Lys Gln Leu Leu Asn Ala His Phe Arg Lys
965 970 975

Tyr His Asp Ala Asn Phe Ile Pro Thr Val Tyr Lys Cys Ser Lys Cys
980 985 990

Gly Lys Gly Phe Ser Arg Trp Ile Asn Leu His Arg His Leu Glu Lys
995 1000 1005

Cys Glu Ser Gly Glu Ala Lys Ser Ala Ala Ser Gly Lys Gly Arg
1010 1015 1020

Arg Thr Arg Lys Arg Lys Gln Thr Ile Leu Lys Glu Ala Thr Lys
1025 1030 1035

Ser Gln Lys Glu Ala Ala Lys Arg Trp Lys Glu Ala Ala Asn Gly
1040 1045 1050

Asp Glu Ala Ala Ala Glu Glu Ala Ser Thr Thr Lys Gly Glu Gln
1055 1060 1065

Phe Pro Glu Glu Met Phe Pro Val Ala Cys Arg Glu Thr Thr Ala
1070 1075 1080

Arg Val Lys Gln Glu Val Asp Gln Gly Val Thr Cys Glu Met Leu
1085 1090 1095

Leu Asn Thr Met Asp Lys
1100

<210> SEQ ID NO 43
<211> LENGTH: 3216
<212> TYPE: DNA
<213> ORGANISM: Homo Sapiens

<400> SEQUENCE: 43
atggctctgc tgctggtttc tctgctggcc ctgctgtctc tcggctctgg atgtcaccac 60
agaatctgcc actgcagcaa ccgggtgttc ctgtgccaga aaagcaaagt gaccgagatc 120
ctgagcgacc tgcagcggaa tgccatcgag ctgagattcg tgctgaccaa gctgcaagtg 180
atccagaagg gcgccttcag cggcttcggc gacctggaaa agatcgagat cagccagaac 240
aacgtgctgg aagtgatcga ggcccacgtg ttcagcaacc tgcctaagct gcacgagatc 300
agaatcgaga aggccaacaa cctgctgtac atcaaccccg aggccttcca gaacttcccc 360
aacctgcagt acctgctgat ctccaacacc ggcatcaaac atctgcccga cgtgcacaag 420
atccacagcc tgcagaaggt gctgctggac atccaggaca acatcaacat ccacacaatc 480
gagcggaact acttcctggg cctgagcttc gagagcgtga tcctgtggct gaacaagaac 540
ggcatccaag agatccacaa ctgcgccttc aatggcaccc agctggacga gctgaacctg 600

-continued

```
tccgacaaca acaatctgga agaactgccc aacgacgtgt tccacagagc cagcggacct    660
gtgatcctgg acatcagcag aaccagaatc cactctctgc ccagctacgg cctggaaaac    720
ctgaagaagc tgcgggccag aagcacctac aatctgaaaa agctgcctac gctggaaacc    780
ctggtggccc tgatggaagc cagcctgaca taccctagcc actgctgcgc ctttgccaac    840
tggcggagac agatctctga gctgcacccc atctgcaaca agagcatcct gcggcaagag    900
gtggactaca tgacacaggc cagaggccag agattcagcc tggccgagga taacgagagc    960
agctacagca gaggcttcga catgacctac accgagttcg actacgacct gtgcaacaag   1020
gtggtggacg tgacatgcag ccccaagcct gatgccttca atccctgcga ggacatcatg   1080
ggctacaaca tcctgagagt gctgatctgg ttcatcagca tcctggccat caccgagaac   1140
atcatcgtgc tggtcatcct gaccaccagc cagtacaagc tgaccgtgcc tatgttcctg   1200
atgtgcaacc tggccttcgc cgatctgtgc atcggcatct acctgctgct gatcgccagc   1260
gtggacattc acaccaagag ccagtaccac aactacgcca tcgactggca gacaggcgcc   1320
ggatgtgatg ccgccggatt ctttacagtg ttcgccagcg agctgtccgt gtacaccctg   1380
acagctatca ccctggaacg gtggcacacc atcacacacg ctatgcagct ggactgcaaa   1440
gtgcacctga gacacagcgc ctccgtgatg gttatgggct ggatcttcgc cttcgctgcc   1500
gctctgttcc ccatctttgg catcagctcc tacatgaagg tgtccatcta tctgcccatg   1560
gacatcgaca gccctctgag ccagctgtac gtgatgagtc tgctggtgct gaatgtgctg   1620
gcctttgtgg tcatctgcgg ctgctacatc tatatctacc tgacagtgcg gaaccccaac   1680
atcgtgtcca gctccagcga cacccggatc gctaagagaa tggccatgct gatcttcacc   1740
gactttctgt gcatggcccc tatcagcctg ttcgccatta gcgctagcct gaaggtgccc   1800
ctgatcaccg tgtccaaggc caagattctg ctggtcctgt tctaccccat caacagctgc   1860
gccaatcctt tcctgtacgc catcttcacc aagaacttca ggcggaactt cttcatcctg   1920
ctgagcaagc ggggctgtta caagatgcag gcccagatct accggaccga gacactgtcc   1980
accgtgcaca acacacaccc cagaaacggc cactgtagca gcgcccctag agtgacaaat   2040
ggctccacct acatcctggt gccactgagc catctggccc agaacagagg ccggaagaga   2100
agaagcccca gggctcccaa gagacagaga tgcatgcccg aagaggacct gcagagccag   2160
agcgaaacac agggactcga aggtgctcag gctcctctgg ccgtggaaga agatgccagc   2220
agctctacca gcacctccag cagcttccct agcagctttc cattcagctc ctctagctct   2280
agcagcagct gttaccctct gatccccagc acacccgaga aggtgttcgc cgacgacgag   2340
acacctaatc cactgcagtc tgcccagatc gcctgcagca gtacactggt ggttgctagc   2400
ctgcctctgg accagtctga tgagggaagc agcagccaga aagaggaaag ccctagcaca   2460
ctccaggtgc tgcccgatag cgagagcctg cctagaagcg agatctacaa gaaaatgacc   2520
gacctggtgc agttcctcct gttcaagtac cagatgaagg aacccatcac caaggccgaa   2580
atcctggaaa gcgtgatcag aaactacgag gaccactttc cactgctgtt cagcgaggcc   2640
agcgagtgca tgctgctcgt gtttagcatc gacgtgaaga aggtggaccc caccggccac   2700
agctttgtgc tggttacaag cctgggactg acctacgacg gcatgctgtc cgatgtgcag   2760
agcatgccta agaccggcat cctgatcctg attctgagca tcgtgttcat cgagggctac   2820
tgcacccctg aggaagtgat ttgggaagcc ctgaacatga tgggcctgta cgatggcatg   2880
gaacacctga tctacggcga gcccagaaaa ctgctgaccc aggactgggt gcaagagaac   2940
tacctggaat accggcagat gcccggcagc gatcctgcca gatatgagtt tctgtggggc   3000
```

cctagagcac atgccgagat ccggaagatg agcctgctga agttcctggc caaagtgaac 3060
ggcagcgacc caatcagctt cccactttgg tacgaagagg ccctgaagga cgaggaagag 3120
agagcccagg atagaatcgc caccaccgac gacacaacag ccatggcctc tgcctcttct 3180
agcgccaccg gcagctttag ctaccccgag tgataa 3216

<210> SEQ ID NO 44
<211> LENGTH: 1070
<212> TYPE: PRT
<213> ORGANISM: Homo Sapiens

<400> SEQUENCE: 44

Met Ala Leu Leu Leu Val Ser Leu Leu Ala Leu Leu Ser Leu Gly Ser
1 5 10 15

Gly Cys His His Arg Ile Cys His Cys Ser Asn Arg Val Phe Leu Cys
20 25 30

Gln Lys Ser Lys Val Thr Glu Ile Leu Ser Asp Leu Gln Arg Asn Ala
35 40 45

Ile Glu Leu Arg Phe Val Leu Thr Lys Leu Gln Val Ile Gln Lys Gly
50 55 60

Ala Phe Ser Gly Phe Gly Asp Leu Glu Lys Ile Glu Ile Ser Gln Asn
65 70 75 80

Asn Val Leu Glu Val Ile Glu Ala His Val Phe Ser Asn Leu Pro Lys
85 90 95

Leu His Glu Ile Arg Ile Glu Lys Ala Asn Asn Leu Leu Tyr Ile Asn
100 105 110

Pro Glu Ala Phe Gln Asn Phe Pro Asn Leu Gln Tyr Leu Leu Ile Ser
115 120 125

Asn Thr Gly Ile Lys His Leu Pro Asp Val His Lys Ile His Ser Leu
130 135 140

Gln Lys Val Leu Leu Asp Ile Gln Asp Asn Ile Asn Ile His Thr Ile
145 150 155 160

Glu Arg Asn Tyr Phe Leu Gly Leu Ser Phe Glu Ser Val Ile Leu Trp
165 170 175

Leu Asn Lys Asn Gly Ile Gln Glu Ile His Asn Cys Ala Phe Asn Gly
180 185 190

Thr Gln Leu Asp Glu Leu Asn Leu Ser Asp Asn Asn Asn Leu Glu Glu
195 200 205

Leu Pro Asn Asp Val Phe His Arg Ala Ser Gly Pro Val Ile Leu Asp
210 215 220

Ile Ser Arg Thr Arg Ile His Ser Leu Pro Ser Tyr Gly Leu Glu Asn
225 230 235 240

Leu Lys Lys Leu Arg Ala Arg Ser Thr Tyr Asn Leu Lys Lys Leu Pro
245 250 255

Thr Leu Glu Thr Leu Val Ala Leu Met Glu Ala Ser Leu Thr Tyr Pro
260 265 270

Ser His Cys Cys Ala Phe Ala Asn Trp Arg Arg Gln Ile Ser Glu Leu
275 280 285

His Pro Ile Cys Asn Lys Ser Ile Leu Arg Gln Glu Val Asp Tyr Met
290 295 300

Thr Gln Ala Arg Gly Gln Arg Phe Ser Leu Ala Glu Asp Asn Glu Ser
305 310 315 320

Ser Tyr Ser Arg Gly Phe Asp Met Thr Tyr Thr Glu Phe Asp Tyr Asp
325 330 335

```
Leu Cys Asn Lys Val Val Asp Val Thr Cys Ser Pro Lys Pro Asp Ala
            340                 345                 350

Phe Asn Pro Cys Glu Asp Ile Met Gly Tyr Asn Ile Leu Arg Val Leu
        355                 360                 365

Ile Trp Phe Ile Ser Ile Leu Ala Ile Thr Glu Asn Ile Ile Val Leu
    370                 375                 380

Val Ile Leu Thr Thr Ser Gln Tyr Lys Leu Thr Val Pro Met Phe Leu
385                 390                 395                 400

Met Cys Asn Leu Ala Phe Ala Asp Leu Cys Ile Gly Ile Tyr Leu Leu
                405                 410                 415

Leu Ile Ala Ser Val Asp Ile His Thr Lys Ser Gln Tyr His Asn Tyr
            420                 425                 430

Ala Ile Asp Trp Gln Thr Gly Ala Gly Cys Asp Ala Ala Gly Phe Phe
        435                 440                 445

Thr Val Phe Ala Ser Glu Leu Ser Val Tyr Thr Leu Thr Ala Ile Thr
    450                 455                 460

Leu Glu Arg Trp His Thr Ile Thr His Ala Met Gln Leu Asp Cys Lys
465                 470                 475                 480

Val His Leu Arg His Ser Ala Ser Val Met Val Met Gly Trp Ile Phe
                485                 490                 495

Ala Phe Ala Ala Ala Leu Phe Pro Ile Phe Gly Ile Ser Ser Tyr Met
            500                 505                 510

Lys Val Ser Ile Tyr Leu Pro Met Asp Ile Asp Ser Pro Leu Ser Gln
        515                 520                 525

Leu Tyr Val Met Ser Leu Leu Val Leu Asn Val Leu Ala Phe Val Val
    530                 535                 540

Ile Cys Gly Cys Tyr Ile Tyr Ile Tyr Leu Thr Val Arg Asn Pro Asn
545                 550                 555                 560

Ile Val Ser Ser Ser Ser Asp Thr Arg Ile Ala Lys Arg Met Ala Met
                565                 570                 575

Leu Ile Phe Thr Asp Phe Leu Cys Met Ala Pro Ile Ser Leu Phe Ala
            580                 585                 590

Ile Ser Ala Ser Leu Lys Val Pro Leu Ile Thr Val Ser Lys Ala Lys
        595                 600                 605

Ile Leu Leu Val Leu Phe Tyr Pro Ile Asn Ser Cys Ala Asn Pro Phe
    610                 615                 620

Leu Tyr Ala Ile Phe Thr Lys Asn Phe Arg Arg Asn Phe Phe Ile Leu
625                 630                 635                 640

Leu Ser Lys Arg Gly Cys Tyr Lys Met Gln Ala Gln Ile Tyr Arg Thr
                645                 650                 655

Glu Thr Leu Ser Thr Val His Asn Thr His Pro Arg Asn Gly His Cys
            660                 665                 670

Ser Ser Ala Pro Arg Val Thr Asn Gly Ser Thr Tyr Ile Leu Val Pro
        675                 680                 685

Leu Ser His Leu Ala Gln Asn Arg Gly Arg Lys Arg Arg Ser Pro Arg
    690                 695                 700

Ala Pro Lys Arg Gln Arg Cys Met Pro Glu Glu Asp Leu Gln Ser Gln
705                 710                 715                 720

Ser Glu Thr Gln Gly Leu Glu Gly Ala Gln Ala Pro Leu Ala Val Glu
                725                 730                 735

Glu Asp Ala Ser Ser Ser Thr Ser Thr Ser Ser Ser Phe Pro Ser Ser
            740                 745                 750
```

```
Phe Pro Phe Ser Ser Ser Ser Ser Ser Ser Ser Cys Tyr Pro Leu Ile
        755                 760                 765

Pro Ser Thr Pro Glu Lys Val Phe Ala Asp Asp Glu Thr Pro Asn Pro
    770                 775                 780

Leu Gln Ser Ala Gln Ile Ala Cys Ser Ser Thr Leu Val Val Ala Ser
785                 790                 795                 800

Leu Pro Leu Asp Gln Ser Asp Glu Gly Ser Ser Ser Gln Lys Glu Glu
                805                 810                 815

Ser Pro Ser Thr Leu Gln Val Leu Pro Asp Ser Glu Ser Leu Pro Arg
            820                 825                 830

Ser Glu Ile Tyr Lys Lys Met Thr Asp Leu Val Gln Phe Leu Leu Phe
        835                 840                 845

Lys Tyr Gln Met Lys Glu Pro Ile Thr Lys Ala Glu Ile Leu Glu Ser
    850                 855                 860

Val Ile Arg Asn Tyr Glu Asp His Phe Pro Leu Leu Phe Ser Glu Ala
865                 870                 875                 880

Ser Glu Cys Met Leu Leu Val Phe Ser Ile Asp Val Lys Lys Val Asp
                885                 890                 895

Pro Thr Gly His Ser Phe Val Leu Val Thr Ser Leu Gly Leu Thr Tyr
            900                 905                 910

Asp Gly Met Leu Ser Asp Val Gln Ser Met Pro Lys Thr Gly Ile Leu
        915                 920                 925

Ile Leu Ile Leu Ser Ile Val Phe Ile Glu Gly Tyr Cys Thr Pro Glu
    930                 935                 940

Glu Val Ile Trp Glu Ala Leu Asn Met Met Gly Leu Tyr Asp Gly Met
945                 950                 955                 960

Glu His Leu Ile Tyr Gly Glu Pro Arg Lys Leu Leu Thr Gln Asp Trp
                965                 970                 975

Val Gln Glu Asn Tyr Leu Glu Tyr Arg Gln Met Pro Gly Ser Asp Pro
            980                 985                 990

Ala Arg Tyr Glu Phe Leu Trp Gly  Pro Arg Ala His Ala  Glu Ile Arg
        995                 1000                1005

Lys Met  Ser Leu Leu Lys Phe  Leu Ala Lys Val Asn  Gly Ser Asp
    1010                1015                1020

Pro Ile  Ser Phe Pro Leu Trp  Tyr Glu Glu Ala Leu  Lys Asp Glu
    1025                1030                1035

Glu Glu  Arg Ala Gln Asp Arg  Ile Ala Thr Thr Asp  Asp Thr Thr
    1040                1045                1050

Ala Met  Ala Ser Ala Ser Ser  Ser Ala Thr Gly Ser  Phe Ser Tyr
    1055                1060                1065

Pro Glu
    1070
```

<210> SEQ ID NO 45
<211> LENGTH: 3216
<212> TYPE: DNA
<213> ORGANISM: Homo Sapiens

<400> SEQUENCE: 45

```
atggctctgc tgctggtttc tctgctggcc ctgctgtctc tcggctctgg atgtcaccac      60

agaatctgcc actgcagcaa ccgggtgttc ctgtgccaga aaagcaaagt gaccgagatc     120

ctgagcgacc tgcagcggaa tgccatcgag ctgagattcg tgctgaccaa gctgcaagtg     180

atccagaagg gcgccttcag cggcttcggc gacctggaaa agatcgagat cagccagaac     240
```

-continued

```
aacgtgctgg aagtgatcga ggcccacgtg ttcagcaacc tgcctaagct gcacgagatc    300
agaatcgaga aggccaacaa cctgctgtac atcaaccccg aggccttcca gaacttcccc    360
aacctgcagt acctgctgat ctccaacacc ggcatcaaac atctgcccga cgtgcacaag    420
atccacagcc tgcagaaggt gctgctggac atccaggaca acatcaacat ccacacaatc    480
gagcggaact acttcctggg cctgagcttc gagagcgtga tcctgtggct gaacaagaac    540
ggcatccaag agatccacaa ctgcgccttc aatggcaccc agctggacga gctgaacctg    600
tccgacaaca acaatctgga agaactgccc aacgacgtgt tccacagagc cagcggacct    660
gtgatcctgg acatcagcag aaccagaatc cactctctgc ccagctacgg cctggaaaac    720
ctgaagaagc tgcgggccag aagcacctac aatctgaaaa agctgcctac gctggaaacc    780
ctggtggccc tgatggaagc cagcctgaca taccctagcc actgctgcgc ctttgccaac    840
tggcggagac agatctctga gctgcacccc atctgcaaca agagcatcct gcggcaagag    900
gtggactaca tgacacaggc cagaggccag agattcagcc tggccgagga taacgagagc    960
agctacagca gaggcttcga catgacctac accgagttcg actacgacct gtgcaacaag   1020
gtggtggacg tgacatgcag ccccaagcct gatgccttca atccctgcga ggacatcatg   1080
ggctacaaca tcctgagagt gctgatctgg ttcatcagca tcctggccat caccgagaac   1140
atcatcgtgc tggtcatcct gaccaccagc cagtacaagc tgaccgtgcc tatgttcctg   1200
atgtgcaacc tggccttcgc cgatctgtgc atcggcatct acctgctgct gatcgccagc   1260
gtggacattc acaccaagag ccagtaccac aactacgcca tcgactggca gacaggcgcc   1320
ggatgtgatg ccgccggatt ctttacagtg ttcgccagcg agctgtccgt gtacaccctg   1380
acagctatca ccctggaacg gtggcacacc atcacacacg ctatgcagct ggactgcaaa   1440
gtgcacctga gacacagcgc ctccgtgatg gttatgggct ggatcttcgc cttcgctgcc   1500
gctctgttcc ccatctttgg catcagctcc tacatgaagg tgtccatcta tctgcccatg   1560
gacatcgaca gccctctgag ccagctgtac gtgatgagtc tgctggtgct gaatgtgctg   1620
gcctttgtgg tcatctgcgg ctgctacatc tatatctacc tgacagtgcg gaaccccaac   1680
atcgtgtcca gctccagcga cacccggatc gctaagagaa tggccatgct gatcttcacc   1740
gactttctgt gcatggcccc tatcagcctg ttcgccatta gcgctagcct gaaggtgccc   1800
ctgatcaccg tgtccaaggc caagattctg ctggtcctgt tctaccccat caacagctgc   1860
gccaatcctt tcctgtacgc catcttcacc aagaacttca ggcggaactt cttcatcctg   1920
ctgagcaagc ggggctgtta caagatgcag gcccagatct accggaccga gacactgtcc   1980
accgtgcaca acacacaccc cagaaacggc cactgtagca gcgcccctag agtgacaaat   2040
ggctccacct acatcctggt gccactgagc catctggccc agaacagagg ccggaagaga   2100
agaagcccca gggctcccaa gagacagaga tgcatgcccg aagaggacct gcagagccag   2160
agcgaaacac agggactcga aggtgctcag gctcctctgg ccgtggaaga agatgccagc   2220
agctctacca gcacctccag cagcttccct agcagctttc cattcagctc ctctagctct   2280
agcagcagct gttaccctct gatccccagc acacccgaga aggtgttcgc cgacgacgag   2340
acacctaatc cactgcagtc tgcccagatc gcctgcagca gtacactggt ggttgctagc   2400
ctgcctctgg accagtctga tgagggaagc agcagccaga aagaggaaag ccctagcaca   2460
ctccaggtgc tgcccgatag cgagagcctg cctagaagcg agatctacaa gaaaatgacc   2520
gacctggtgc agttcctcct gttcaagtac cagatgaagg aacccatcac caaggccgaa   2580
atcctggaaa gcgtgatcag aaactacgag gaccactttc cactgctgtt cagcgaggcc   2640
```

agcgagtgca tgctgctcgt gtttagcatc gacgtgaaga aggtggaccc caccggccac 2700
agctttgtgc tggttacaag cctgggactg acctacgacg gcatgctgtc cgatgtgcag 2760
agcatgccta agaccggcat cctgatcctg attctgagca tcgtgttcat cgagggctac 2820
tgcacccctg aggaagtgat ttgggaagcc ctgaacatga tgggcctgta cgatggcatg 2880
gaacacctga tctacggcga gcccagaaaa ctgctgaccc aggactgggt gcaagagaac 2940
tacctggaat accggcagat gcccggcagc gatcctgcca gatatgagtt tctgtggggc 3000
cctagagcac atgccgagat ccggaagatg agcctgctga agttcctggc caaagtgaac 3060
ggcagcgacc caatcagctt cccactttgg tacgaagagg ccctgaagga cgaggaagag 3120
agagcccagg atagaatcgc caccaccgac gacacaacag ccatggcctc tgcctcttct 3180
agcgccaccg gcagctttag ctaccccgag tgataa 3216

<210> SEQ ID NO 46
<211> LENGTH: 814
<212> TYPE: PRT
<213> ORGANISM: Homo Sapiens

<400> SEQUENCE: 46

Met Ser Ser Pro Gly Thr Glu Ser Ala Gly Lys Ser Leu Gln Tyr Arg
1 5 10 15

Val Asp His Leu Leu Ser Ala Val Glu Asn Glu Leu Gln Ala Gly Ser
20 25 30

Glu Lys Gly Asp Pro Thr Glu His Glu Leu Arg Val Gly Leu Glu Glu
35 40 45

Ser Glu Leu Trp Leu Arg Phe Lys Glu Leu Thr Asn Glu Met Ile Val
50 55 60

Thr Lys Asn Gly Arg Arg Met Phe Pro Val Leu Lys Val Asn Val Ser
65 70 75 80

Gly Leu Asp Pro Asn Ala Met Tyr Ser Phe Leu Leu Asp Phe Val Val
85 90 95

Ala Asp Asn His Arg Trp Lys Tyr Val Asn Gly Glu Trp Val Pro Gly
100 105 110

Gly Lys Pro Gln Leu Gln Ala Pro Ser Cys Val Tyr Ile His Pro Asp
115 120 125

Ser Pro Asn Phe Gly Ala His Trp Met Lys Ala Pro Val Ser Phe Ser
130 135 140

Lys Val Lys Leu Thr Asn Lys Leu Asn Gly Gly Gly Gln Ile Met Leu
145 150 155 160

Asn Ser Leu His Lys Tyr Glu Pro Arg Ile His Ile Val Arg Val Gly
165 170 175

Gly Pro Gln Arg Met Ile Thr Ser His Cys Phe Pro Glu Thr Gln Phe
180 185 190

Ile Ala Val Thr Ala Tyr Gln Asn Glu Glu Ile Thr Thr Leu Lys Ile
195 200 205

Lys Tyr Asn Pro Phe Ala Lys Ala Phe Leu Asp Ala Lys Glu Arg Ser
210 215 220

Asp His Lys Glu Met Ile Lys Glu Pro Gly Asp Ser Gln Gln Pro Gly
225 230 235 240

Tyr Ser Gln Trp Gly Trp Leu Leu Pro Gly Thr Ser Thr Leu Cys Pro
245 250 255

Pro Ala Asn Pro His Ser Gln Phe Gly Gly Ala Leu Ser Leu Ser Ser
260 265 270

-continued

```
Thr His Ser Tyr Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Arg Met Pro Ala His Pro Ser Met Leu Pro Val Ser His
                325                 330                 335

Asn Ala Ser Pro Pro Thr Ser Ser Ser Gln Tyr Pro Ser Leu Trp Ser
            340                 345                 350

Val Ser Asn Gly Ala Val Thr Leu Gly Ser Gln Ala Ala Ala Val Ser
        355                 360                 365

Asn Gly Leu Gly Ala Gln Phe Phe Arg Gly Ser Pro Ala His Tyr Thr
    370                 375                 380

Pro Leu Thr His Pro Val Ser Ala Pro Ser Ser Ser Gly Phe Pro Met
385                 390                 395                 400

Tyr Lys Gly Ala Ala Ala Ala Thr Asp Ile Val Asp Ser Gln Tyr Asp
                405                 410                 415

Ala Ala Ala Gln Gly His Leu Ile Ala Ser Trp Thr Pro Val Ser Pro
            420                 425                 430

Pro Ser Met Arg Gly Arg Lys Arg Arg Ser Pro Pro Val Pro Gly Val
        435                 440                 445

Pro Phe Arg Asn Val Asp Asn Asp Ser Leu Thr Ser Val Glu Leu Glu
    450                 455                 460

Asp Trp Val Asp Ala Gln His Pro Thr Asp Glu Glu Glu Glu Glu Ala
465                 470                 475                 480

Ser Ser Ala Ser Ser Thr Leu Tyr Leu Val Phe Ser Pro Ser Ser Phe
                485                 490                 495

Ser Thr Ser Ser Ser Leu Ile Leu Gly Gly Pro Glu Glu Glu Glu Val
            500                 505                 510

Pro Ser Gly Val Ile Pro Asn Leu Thr Glu Ser Ile Pro Ser Ser Pro
        515                 520                 525

Pro Gln Gly Pro Pro Gln Gly Pro Ser Gln Ser Pro Leu Ser Ser Cys
    530                 535                 540

Cys Ser Ser Phe Leu Trp Ser Ser Phe Ser Glu Glu Ser Ser Ser Gln
545                 550                 555                 560

Lys Gly Glu Asp Thr Gly Thr Cys Gln Gly Leu Pro Asp Ser Glu Ser
                565                 570                 575

Ser Phe Thr Tyr Thr Leu Asp Glu Lys Val Ala Lys Leu Val Glu Phe
            580                 585                 590

Leu Leu Leu Lys Tyr Glu Ala Glu Glu Pro Val Thr Glu Ala Glu Met
        595                 600                 605

Leu Met Ile Val Ile Lys Tyr Lys Asp Tyr Phe Pro Val Ile Leu Lys
    610                 615                 620

Arg Ala Arg Glu Phe Met Glu Leu Leu Phe Gly Leu Ala Leu Ile Glu
625                 630                 635                 640

Val Gly Pro Asp His Phe Cys Val Phe Ala Asn Thr Val Gly Leu Thr
                645                 650                 655

Asp Glu Gly Ser Asp Asp Glu Gly Met Pro Glu Asn Ser Leu Leu Ile
            660                 665                 670

Ile Ile Leu Ser Val Ile Phe Ile Lys Gly Asn Cys Ala Ser Glu Glu
        675                 680                 685
```

```
Val Ile Trp Glu Val Leu Asn Ala Val Gly Val Tyr Ala Gly Arg Glu
    690                 695                 700

His Phe Val Tyr Gly Lys Pro Arg Glu Leu Leu Thr Asn Val Trp Val
705                 710                 715                 720

Gln Gly His Tyr Leu Glu Tyr Trp Glu Val Pro His Ser Ser Pro Leu
                725                 730                 735

Tyr Tyr Glu Phe Leu Trp Gly Pro Arg Ala His Ser Glu Ser Ile Lys
            740                 745                 750

Lys Lys Val Leu Glu Phe Leu Ala Lys Leu Asn Asn Thr Val Pro Ser
        755                 760                 765

Phe Phe Pro Ser Trp Tyr Lys Asp Ala Leu Lys Asp Val Glu Glu Arg
    770                 775                 780

Val Gln Ala Thr Ile Asp Thr Ala Asp Asp Ala Thr Val Met Ala Ser
785                 790                 795                 800

Glu Ser Leu Ser Val Met Ser Ser Asn Val Ser Phe Ser Glu
                805                 810
```

<210> SEQ ID NO 47
<211> LENGTH: 2895
<212> TYPE: DNA
<213> ORGANISM: Homo Sapiens

<400> SEQUENCE: 47

```
atgtctagcc ctggaacaga gtctgccggc aagagcctgc agtacagagt ggaccatctg     60

ctgagcgccg tggaaaatga actgcaggcc ggaagcgaga agggcgatcc tacagagcac    120

gagctgagag tcggcctgga agagtctgag ctgtggctgc ggttcaaaga actgaccaac    180

gagatgatcg tgaccaagaa cggcagacgg atgttccccg tgctgaaagt gaacgtgtcc    240

ggactggacc ccaacgccat gtacagcttt ctgctggact tcgtggtggc cgacaaccac    300

agatggaaat acgtgaacgg cgagtgggtg ccaggcggaa aacctcaact gcaagcccct    360

agctgcgtgt acattcaccc tgacagcccc aatttcggcg cccactggat gaaggcccct    420

gtgtccttca gcaaagtgaa gctgaccaac aagctgaacg gcggaggcca gatcatgctg    480

aacagcctgc acaaatacga gcccagaatc cacatcgtca gagtcggcgg accccagaga    540

atgatcacca gccactgctt ccccgagaca cagtttatcg ccgtgaccgc ctaccagaac    600

gaggaaatca ccacactgaa gatcaagtac aaccccttcg ccaaggcctt cctggacgcc    660

aaagagcgga gcgaccacaa agagatgatc aaagagcccg gcgacagcca gcagccaggc    720

tattctcaat ggggatggct gctgccaggc accagcacat tgtgccctcc agccaatcct    780

cacagccagt ttggaggcgc cctgagcctg tctagcaccc acagctacga cagatacccc    840

acactgcgga gccacagaag cagcccctat ccttctcctt acgctcaccg gaacaacagc    900

cccacctaca gcgataatag ccccgcctgt ctgagcatgc tgcagtccca cgataactgg    960

tccagcctga gaatgcctgc tcacccttcc atgctgcccg tgtctcacaa tgcctctcca   1020

cctaccagca gctctcagta ccctagcctt tggagcgtgt ccaatggcgc cgtgacactg   1080

ggatctcagg cagccgctgt gtctaatgga ctgggagccc agttcttcag aggcagccct   1140

gctcactaca cccctctgac acatcctgtg tctgccccta gcagcagcgg cttccctatg   1200

tataagggcg ctgccgccgc taccgacatc gtggattctc agtatgatgc cgccgcacag   1260

ggacacctga tcgcctcttg gacacctgtg tctccacctt ccatgagagg cagaaagcgg   1320

agaagcgact tcctgctgct gcagaaccct gcctctacct gtgtgcctga accagcctct   1380

cagcacaccc tgagatctgg ccctggatgt ctccagcagc ctgaacagca gggcgttaga   1440
```

```
gatcctggcg gaatctgggc caaactggga gctgccgaag cctctgccga atgtctgcag   1500

ggcagaagaa gcagaggcgc cagcggatct gaacctcacc agatgggaag cgacgtgcac   1560

gacctgaatg ctctgttgcc tgccgtgcca tctcttggcg gaggcggagg atgtgctttg   1620

cctgtttctg gtgctgccca gtgggctccc gtgctggatt ttgctcctcc tggcgcttct   1680

gcctatggct ctcttggagg acctgctcct ccaccagctc cacctccacc gccgcctcca   1740

ccacctcaca gctttatcaa gcaagagccc tcctggggcg gagccgagcc tcacgaaaaa   1800

cagtgtctga gcgccttcac cgtgcacttt ttcggccagt ttaccggcac cgtgggcgcc   1860

tgtagatacg gcccttttgg accaccacca cctagccagg cttctagcgg acaggccaga   1920

atgttcccca acgctcctta cctgcctagc tgcctggaaa gccagcctac catcagaaac   1980

cagggcttca gcaccgtgac cttcgacggc atgcctagct atggccacac accatctcac   2040

cacgccgctc agttccccaa tcacagcttc aagcacgagg accctatggg ccagcaggga   2100

tctctgggag agcagcagta tagcgtgcca cctcctgtgt acggctgtca cacccctacc   2160

gatagctgca caggcaatca ggctctgctg ctgaggatgc ctttcagcag cgacaacctg   2220

taccagatga caagccagct ggaatgcatg atttggaacc agatgaacct gggcgccact   2280

ctgaaaggcg tggccgctgg atctagcagc tccgtgaaat ggacagccgg ccagagcaat   2340

cactccaccg gctacgagag cgacaatcac accatgccta tcctgtgtgg ggcccagtac   2400

cggattcaca cacacggcgt gttcaggggc attcaggatg tgcgaagagt gcctggcgtg   2460

gcccctacac ttgtgggatc tgccagcgaa accagcgaga agcacccctt catgtgcgcc   2520

tatccaggct gcaacaagcg gtacttcaag ctgagccacc tgaagatgca cagccggaag   2580

cacacaggcg agaagctgta ccagtgcgac ttcaaggact gcgagcggag attcagctgc   2640

agcgaccagc tgaagagaca ccagagaagg cacaccggcg tgaagccctt tcagtgcaag   2700

acctgccagc ggaccttctc ctggtccaac cacctgaaaa cccacacaag aacccacacc   2760

ggcaagacca tcgagaagcc cttcagctgt agatggccca gctgccagaa gaagttcgcc   2820

cggtctaacg agctggtgca tcaccacaac atgcaccaga ggaacatgac caaactgcag   2880

ctggtgctgt gatga                                                    2895
```

<210> SEQ ID NO 48
<211> LENGTH: 963
<212> TYPE: PRT
<213> ORGANISM: Homo Sapiens

<400> SEQUENCE: 48

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu His Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Val
                85                  90                  95

Ala Asp Asn His Arg Trp Lys Tyr Val Asn Gly Glu Trp Val Pro Gly
            100                 105                 110
```

```
Gly Lys Pro Gln Leu Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Thr Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Ile Lys Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Ser Gln Phe Gly Gly Ala Leu Ser Leu Ser Ser
            260                 265                 270

Thr His Ser Tyr Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Arg Met Pro Ala His Pro Ser Met Leu Pro Val Ser His
                325                 330                 335

Asn Ala Ser Pro Pro Thr Ser Ser Ser Gln Tyr Pro Ser Leu Trp Ser
            340                 345                 350

Val Ser Asn Gly Ala Val Thr Leu Gly Ser Gln Ala Ala Ala Val Ser
        355                 360                 365

Asn Gly Leu Gly Ala Gln Phe Phe Arg Gly Ser Pro Ala His Tyr Thr
    370                 375                 380

Pro Leu Thr His Pro Val Ser Ala Pro Ser Ser Ser Gly Phe Pro Met
385                 390                 395                 400

Tyr Lys Gly Ala Ala Ala Ala Thr Asp Ile Val Asp Ser Gln Tyr Asp
                405                 410                 415

Ala Ala Ala Gln Gly His Leu Ile Ala Ser Trp Thr Pro Val Ser Pro
            420                 425                 430

Pro Ser Met Arg Gly Arg Lys Arg Arg Ser Asp Phe Leu Leu Leu Gln
        435                 440                 445

Asn Pro Ala Ser Thr Cys Val Pro Glu Pro Ala Ser Gln His Thr Leu
    450                 455                 460

Arg Ser Gly Pro Gly Cys Leu Gln Gln Pro Glu Gln Gln Gly Val Arg
465                 470                 475                 480

Asp Pro Gly Gly Ile Trp Ala Lys Leu Gly Ala Ala Glu Ala Ser Ala
                485                 490                 495

Glu Cys Leu Gln Gly Arg Arg Ser Arg Gly Ala Ser Gly Ser Glu Pro
            500                 505                 510

His Gln Met Gly Ser Asp Val His Asp Leu Asn Ala Leu Leu Pro Ala
        515                 520                 525
```

```
Val Pro Ser Leu Gly Gly Gly Gly Gly Cys Ala Leu Pro Val Ser Gly
    530                 535                 540

Ala Ala Gln Trp Ala Pro Val Leu Asp Phe Ala Pro Pro Gly Ala Ser
545                 550                 555                 560

Ala Tyr Gly Ser Leu Gly Gly Pro Ala Pro Pro Pro Ala Pro Pro Pro
                565                 570                 575

Pro Pro Pro Pro Pro Pro His Ser Phe Ile Lys Gln Glu Pro Ser Trp
            580                 585                 590

Gly Gly Ala Glu Pro His Glu Lys Gln Cys Leu Ser Ala Phe Thr Val
        595                 600                 605

His Phe Phe Gly Gln Phe Thr Gly Thr Val Gly Ala Cys Arg Tyr Gly
    610                 615                 620

Pro Phe Gly Pro Pro Pro Pro Ser Gln Ala Ser Ser Gly Gln Ala Arg
625                 630                 635                 640

Met Phe Pro Asn Ala Pro Tyr Leu Pro Ser Cys Leu Glu Ser Gln Pro
                645                 650                 655

Thr Ile Arg Asn Gln Gly Phe Ser Thr Val Thr Phe Asp Gly Met Pro
            660                 665                 670

Ser Tyr Gly His Thr Pro Ser His His Ala Ala Gln Phe Pro Asn His
        675                 680                 685

Ser Phe Lys His Glu Asp Pro Met Gly Gln Gln Gly Ser Leu Gly Glu
    690                 695                 700

Gln Gln Tyr Ser Val Pro Pro Pro Val Tyr Gly Cys His Thr Pro Thr
705                 710                 715                 720

Asp Ser Cys Thr Gly Asn Gln Ala Leu Leu Leu Arg Met Pro Phe Ser
                725                 730                 735

Ser Asp Asn Leu Tyr Gln Met Thr Ser Gln Leu Glu Cys Met Ile Trp
            740                 745                 750

Asn Gln Met Asn Leu Gly Ala Thr Leu Lys Gly Val Ala Ala Gly Ser
        755                 760                 765

Ser Ser Ser Val Lys Trp Thr Ala Gly Gln Ser Asn His Ser Thr Gly
    770                 775                 780

Tyr Glu Ser Asp Asn His Thr Met Pro Ile Leu Cys Gly Ala Gln Tyr
785                 790                 795                 800

Arg Ile His Thr His Gly Val Phe Arg Gly Ile Gln Asp Val Arg Arg
                805                 810                 815

Val Pro Gly Val Ala Pro Thr Leu Val Gly Ser Ala Ser Glu Thr Ser
            820                 825                 830

Glu Lys His Pro Phe Met Cys Ala Tyr Pro Gly Cys Asn Lys Arg Tyr
        835                 840                 845

Phe Lys Leu Ser His Leu Lys Met His Ser Arg Lys His Thr Gly Glu
    850                 855                 860

Lys Leu Tyr Gln Cys Asp Phe Lys Asp Cys Glu Arg Arg Phe Ser Cys
865                 870                 875                 880

Ser Asp Gln Leu Lys Arg His Gln Arg Arg His Thr Gly Val Lys Pro
                885                 890                 895

Phe Gln Cys Lys Thr Cys Gln Arg Thr Phe Ser Trp Ser Asn His Leu
            900                 905                 910

Lys Thr His Thr Arg Thr His Thr Gly Lys Thr Ile Glu Lys Pro Phe
        915                 920                 925

Ser Cys Arg Trp Pro Ser Cys Gln Lys Lys Phe Ala Arg Ser Asn Glu
    930                 935                 940

Leu Val His His His Asn Met His Gln Arg Asn Met Thr Lys Leu Gln
```

-continued 945 950 955 960

Leu Val Leu

<210> SEQ ID NO 49
<211> LENGTH: 2965
<212> TYPE: DNA
<213> ORGANISM: Homo Sapiens

<400> SEQUENCE: 49
agagtctgag ctgtggctgc ggttcaaaga actgaccaac gagatgatcg tgaccaagaa 60
cggcagacgg atgttccccg tgctgaaagt gaacgtgtcc ggactggacc ccaacgccat 120
gtacagcttt ctgctggact tcgtggtggc cgacaaccac agatggaaat acgtgaacgg 180
cgagtgggtg ccaggcggaa aacctcaact gcaagcccct agctgcgtgt acattcaccc 240
tgacagcccc aatttcggcg cccactggat gaaggcccct gtgtccttca gcaaagtgaa 300
gctgaccaac aagctgaacg gcggaggcca gatcatgctg aacagcctgc acaaatacga 360
gcccagaatc cacatcgtca gagtcggcgg accccagaga atgatcacca gccactgctt 420
ccccgagaca cagtttatcg ccgtgaccgc ctaccagaac gaggaaatca ccacactgaa 480
gatcaagtac aacccccttcg ccaaggcctt cctggacgcc aaagagcgga gcgaccacaa 540
agagatgatc aaagagcccg gcgacagcca gcagccaggc tattctcaat ggggatggct 600
gctgccaggc accagcacat tgtgccctcc agccaatcct cacagccagt ttggaggcgc 660
cctgagcctg tctagcaccc acagctacga cagatacccc acactgcgga gccacagaag 720
cagcccctat ccttctcctt acgctcaccg gaacaacagc cccacctaca gcgataatag 780
ccccgcctgt ctgagcatgc tgcagtccca cgataactgg tccagcctga gaatgcctgc 840
tcacccttcc atgctgcccg tgtctcacaa tgcctctcca cctaccagca gctctcagta 900
ccctagcctt tggagcgtgt ccaatggcgc cgtgacactg ggatctcagg cagccgctgt 960
gtctaatgga ctgggagccc agttcttcag aggcagccct gctcactaca cccctctgac 1020
acatcctgtg tctgccccta gcagcagcgg cttccctatg tataagggcg ctgccgccgc 1080
taccgacatc gtggattctc agtatgatgc cgccgcacag ggacacctga tcgcctcttg 1140
gacacctgtg tctccacctt ccatgagagg cagaaagcgg agaagcgact tcctgctgct 1200
gcagaaccct gcctctacct gtgtgcctga accagcctct cagcacaccc tgagatctgg 1260
ccctggatgt ctccagcagc ctgaacagca gggcgttaga gatcctggcg gaatctgggc 1320
caaactggga gctgccgaag cctctgccga atgtctgcag ggcagaagaa gcagaggcgc 1380
cagcggatct gaacctcacc agatgggaag cgacgtgcac gacctgaatg ctctgttgcc 1440
tgccgtgcca tctcttggcg gaggcggagg atgtgctttg cctgtttctg gtgctgccca 1500
gtgggctccc gtgctggatt ttgctcctcc tggcgcttct gcctatggct ctcttggagg 1560
acctgctcct ccaccagctc cacctccacc gccgcctcca ccacctcaca gctttatcaa 1620
gcaagagccc tcctggggcg gagccgagcc tcacgaaaaa cagtgtctga gcgccttcac 1680
cgtgcacttt ttcggccagt ttaccggcac cgtgggcgcc tgtagatacg gccctttttgg 1740 accaccacca cctagccagg cttctagcgg acaggccaga atgttcccca acgctcctta 1800
cctgcctagc tgcctggaaa gccagcctac catcagaaac cagggcttca gcaccgtgac 1860
cttcgacggc atgcctagct atggccacac accatctcac cacgccgctc agttccccaa 1920
tcacagcttc aagcacgagg accctatggg ccagcaggga tctctgggag agcagcagta 1980
tagcgtgcca cctcctgtgt acggctgtca cacccctacc gatagctgca caggcaatca 2040
ggctctgctg ctgaggatgc ctttcagcag cgacaacctg taccagatga caagccagct 2100
ggaatgcatg atttggaacc agatgaacct gggcgccact ctgaaaggcg tggccgctgg 2160
atctagcagc tccgtgaaat ggacagccgg ccagagcaat cactccaccg gctacgagag 2220
cgacaatcac accatgccta tcctgtgtgg ggcccagtac cggattcaca cacacggcgt 2280
gttcaggggc attcaggatg tgcgaagagt gcctggcgtg gcccctacac ttgtgggatc 2340
tgccagcgaa accagcgaga agcacccctt catgtgcgcc tatccaggct gcaacaagcg 2400
gtacttcaag ctgagccacc tgaagatgca cagccggaag cacacaggcg agaagctgta 2460
ccagtgcgac ttcaaggact gcgagcggag attcagctgc agcgaccagc tgaagagaca 2520
ccagagaagg cacaccggcg tgaagccctt tcagtgcaag acctgccagc ggaccttctc 2580
ctggtccaac cacctgaaaa cccacacaag aacccacacc ggcaagacca tcgagaagcc 2640
cttcagctgt agatggccca gctgccagaa gaagttcgcc cggtctaacg agctggtgca 2700
tcaccacaac atgcaccaga ggaacatgac caaactgcag ctggtgctga ggggaagaaa 2760
gaggcggtcc accgagtaca agctggtggt tgttggagcc gatggcgtgg gaaagagcgc 2820
cctgacaatt cagctgatcc agaaccactt cgtgcgcggc agaaagagaa gatctacaga 2880
gtataagctc gtggtcgtgg gcgctgtcgg agtgggaaaa tctgccctga ccatccaact 2940
cattcagaat cactttgtgt gatga 2965

<210> SEQ ID NO 50
<211> LENGTH: 1033
<212> TYPE: PRT
<213> ORGANISM: Homo Sapiens

<400> SEQUENCE: 50

Met Ser Ser Pro Gly Thr Glu Ser Ala Gly Lys Ser Leu Gln Tyr Arg
1 5 10 15

Val Asp His Leu Leu Ser Ala Val Glu Asn Glu Leu Gln Ala Gly Ser
20 25 30

Glu Lys Gly Asp Pro Thr Glu His Glu Leu Arg Val Gly Leu Glu Glu
35 40 45

Ser Glu Leu Trp Leu Arg Phe Lys Glu Leu Thr Asn Glu Met Ile Val
50 55 60

Thr Lys Asn Gly Arg Arg Met Phe Pro Val Leu Lys Val Asn Val Ser
65 70 75 80

Gly Leu Asp Pro Asn Ala Met Tyr Ser Phe Leu Leu Asp Phe Val Val
85 90 95

Ala Asp Asn His Arg Trp Lys Tyr Val Asn Gly Glu Trp Val Pro Gly
100 105 110

Gly Lys Pro Gln Leu Gln Ala Pro Ser Cys Val Tyr Ile His Pro Asp
115 120 125

Ser Pro Asn Phe Gly Ala His Trp Met Lys Ala Pro Val Ser Phe Ser
130 135 140

Lys Val Lys Leu Thr Asn Lys Leu Asn Gly Gly Gly Gln Ile Met Leu
145 150 155 160

Asn Ser Leu His Lys Tyr Glu Pro Arg Ile His Ile Val Arg Val Gly
165 170 175

Gly Pro Gln Arg Met Ile Thr Ser His Cys Phe Pro Glu Thr Gln Phe
180 185 190

Ile Ala Val Thr Ala Tyr Gln Asn Glu Glu Ile Thr Thr Leu Lys Ile
195 200 205

```
Lys Tyr Asn Pro Phe Ala Lys Ala Phe Leu Asp Ala Lys Glu Arg Ser
    210                 215                 220

Asp His Lys Glu Met Ile Lys Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Ser Gln Phe Gly Gly Ala Leu Ser Leu Ser Ser
            260                 265                 270

Thr His Ser Tyr Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Arg Met Pro Ala His Pro Ser Met Leu Pro Val Ser His
                325                 330                 335

Asn Ala Ser Pro Pro Thr Ser Ser Ser Gln Tyr Pro Ser Leu Trp Ser
            340                 345                 350

Val Ser Asn Gly Ala Val Thr Leu Gly Ser Gln Ala Ala Ala Val Ser
        355                 360                 365

Asn Gly Leu Gly Ala Gln Phe Phe Arg Gly Ser Pro Ala His Tyr Thr
    370                 375                 380

Pro Leu Thr His Pro Val Ser Ala Pro Ser Ser Ser Gly Phe Pro Met
385                 390                 395                 400

Tyr Lys Gly Ala Ala Ala Ala Thr Asp Ile Val Asp Ser Gln Tyr Asp
                405                 410                 415

Ala Ala Ala Gln Gly His Leu Ile Ala Ser Trp Thr Pro Val Ser Pro
            420                 425                 430

Pro Ser Met Arg Gly Arg Lys Arg Arg Ser Asp Phe Leu Leu Leu Gln
        435                 440                 445

Asn Pro Ala Ser Thr Cys Val Pro Glu Pro Ala Ser Gln His Thr Leu
    450                 455                 460

Arg Ser Gly Pro Gly Cys Leu Gln Gln Pro Glu Gln Gln Gly Val Arg
465                 470                 475                 480

Asp Pro Gly Gly Ile Trp Ala Lys Leu Gly Ala Ala Glu Ala Ser Ala
                485                 490                 495

Glu Cys Leu Gln Gly Arg Arg Ser Arg Gly Ala Ser Gly Ser Glu Pro
            500                 505                 510

His Gln Met Gly Ser Asp Val His Asp Leu Asn Ala Leu Leu Pro Ala
        515                 520                 525

Val Pro Ser Leu Gly Gly Gly Gly Gly Cys Ala Leu Pro Val Ser Gly
    530                 535                 540

Ala Ala Gln Trp Ala Pro Val Leu Asp Phe Ala Pro Pro Gly Ala Ser
545                 550                 555                 560

Ala Tyr Gly Ser Leu Gly Gly Pro Ala Pro Pro Pro Ala Pro Pro Pro
                565                 570                 575

Pro Pro Pro Pro Pro Pro His Ser Phe Ile Lys Gln Glu Pro Ser Trp
            580                 585                 590

Gly Gly Ala Glu Pro His Glu Lys Gln Cys Leu Ser Ala Phe Thr Val
        595                 600                 605

His Phe Phe Gly Gln Phe Thr Gly Thr Val Gly Ala Cys Arg Tyr Gly
    610                 615                 620
```

Pro Phe Gly Pro Pro Pro Pro Ser Gln Ala Ser Ser Gly Gln Ala Arg
625 630 635 640

Met Phe Pro Asn Ala Pro Tyr Leu Pro Ser Cys Leu Glu Ser Gln Pro
645 650 655

Thr Ile Arg Asn Gln Gly Phe Ser Thr Val Thr Phe Asp Gly Met Pro
660 665 670

Ser Tyr Gly His Thr Pro Ser His His Ala Ala Gln Phe Pro Asn His
675 680 685

Ser Phe Lys His Glu Asp Pro Met Gly Gln Gln Gly Ser Leu Gly Glu
690 695 700

Gln Gln Tyr Ser Val Pro Pro Pro Val Tyr Gly Cys His Thr Pro Thr
705 710 715 720

Asp Ser Cys Thr Gly Asn Gln Ala Leu Leu Leu Arg Met Pro Phe Ser
725 730 735

Ser Asp Asn Leu Tyr Gln Met Thr Ser Gln Leu Glu Cys Met Ile Trp
740 745 750

Asn Gln Met Asn Leu Gly Ala Thr Leu Lys Gly Val Ala Ala Gly Ser
755 760 765

Ser Ser Ser Val Lys Trp Thr Ala Gly Gln Ser Asn His Ser Thr Gly
770 775 780

Tyr Glu Ser Asp Asn His Thr Met Pro Ile Leu Cys Gly Ala Gln Tyr
785 790 795 800

Arg Ile His Thr His Gly Val Phe Arg Gly Ile Gln Asp Val Arg Arg
805 810 815

Val Pro Gly Val Ala Pro Thr Leu Val Gly Ser Ala Ser Glu Thr Ser
820 825 830

Glu Lys His Pro Phe Met Cys Ala Tyr Pro Gly Cys Asn Lys Arg Tyr
835 840 845

Phe Lys Leu Ser His Leu Lys Met His Ser Arg Lys His Thr Gly Glu
850 855 860

Lys Leu Tyr Gln Cys Asp Phe Lys Asp Cys Glu Arg Arg Phe Ser Cys
865 870 875 880

Ser Asp Gln Leu Lys Arg His Gln Arg Arg His Thr Gly Val Lys Pro
885 890 895

Phe Gln Cys Lys Thr Cys Gln Arg Thr Phe Ser Trp Ser Asn His Leu
900 905 910

Lys Thr His Thr Arg Thr His Thr Gly Lys Thr Ile Glu Lys Pro Phe
915 920 925

Ser Cys Arg Trp Pro Ser Cys Gln Lys Lys Phe Ala Arg Ser Asn Glu
930 935 940

Leu Val His His His Asn Met His Gln Arg Asn Met Thr Lys Leu Gln
945 950 955 960

Leu Val Leu Arg Gly Arg Lys Arg Arg Ser Thr Glu Tyr Lys Leu Val
965 970 975

Val Val Gly Ala Asp Gly Val Gly Lys Ser Ala Leu Thr Ile Gln Leu
980 985 990

Ile Gln Asn His Phe Val Arg Gly Arg Lys Arg Arg Ser Thr Glu Tyr
995 1000 1005

Lys Leu Val Val Val Gly Ala Val Gly Val Gly Lys Ser Ala Leu
1010 1015 1020

Thr Ile Gln Leu Ile Gln Asn His Phe Val
1025 1030

<210> SEQ ID NO 51
<211> LENGTH: 2361
<212> TYPE: DNA
<213> ORGANISM: Homo Sapiens

<400> SEQUENCE: 51
atggactttc tgctgctgca gaaccctgcc agcacctgtg ttccagaacc tgcctctcag 60
cacaccctga gatctggccc tggatgtctc cagcagcctg aacagcaggg cgttagagat 120
cctggcggaa tctgggccaa actgggagcc gctgaagcct ctgccgaatg tctgcagggc 180
agaagaagca gaggcgccag cggatctgaa cctcaccaga tgggaagcga cgtgcacgac 240
ctgaatgctc tgctgcctgc cgtgccatct cttggcggag gcggaggatg tgctttgcct 300
gtttctggtg ctgcccagtg ggctcccgtg ctggattttg ctcctcctgg cgcttctgcc 360
tatggctctc ttggaggacc tgctcctcca ccagctccac ctccaccgcc gcctccacca 420
cctcacagct ttatcaagca agagccctcc tggggcggag ccgagcctca cgaaaaacag 480
tgtctgagcg ccttcaccgt gcactttttc ggccagttta ccggcacagt gggcgcctgt 540
agatacggcc cttttggacc accaccacct agccaggcta gctctggaca ggccagaatg 600
ttccccaacg ctccctacct gcctagctgc ctggaaagcc agcctaccat cagaaaccag 660
ggcttcagca ccgtgacctt cgacggcatg cctagctatg gccacacacc atctcaccac 720
gccgctcagt tccccaatca cagcttcaag cacgaggacc ctatgggcca gcagggatct 780
ctgggagagc agcagtatag cgtgccacct cctgtgtacg gctgtcacac ccctaccgat 840
agctgcacag gcaatcaggc cctgctgctg aggatgccct tcagcagcga caacctgtac 900
cagatgacaa gccagctgga atgcatgatc tggaaccaga tgaacctggg cgccacactg 960
aaaggcgtgg ccgctggatc tagcagcagc gtgaaatgga cagccggcca gagcaatcac 1020
tccaccggct acgagtccga caaccacacc atgcctattc tgtgcggagc ccagtacaga 1080
atccacacac acggcgtgtt ccggggcatt caggatgtgc gaagagtgcc tggcgtggcc 1140
cctacacttg tgggatctgc ctctgagaca agcgagaagc accccttcat gtgcgcctat 1200
cctggctgca acaagcggta cttcaagctg agccacctga agatgcacag ccggaagcac 1260
acaggcgaga agctgtacca gtgcgacttc aaggactgcg agcggagatt cagctgcagc 1320
gaccagctga agagacacca gagaaggcac accggcgtga agcccttcca gtgcaagacc 1380
tgccagcgga cctttagctg gtccaaccac ctgaaaaccc acacaagaac ccacaccggc 1440
aagaccatcg agaagccttt cagctgtaga tggcccagct gccagaagaa gttcgcccgg 1500
tctaacgagc tggtgcatca ccacaacatg caccagagga acatgaccaa actgcagctg 1560
gtgctgaggg gaagaaagcg gagaagcgcc cagagaatga ccacacagtt gctgctgctc 1620
ctcgtgtggg ttgccgttgt gggagaagtg cagaccagaa tcgcctgggc cagaaccgag 1680
ctgctgaacg tgtgcatgaa cgccaagcac cacaagaaga agcccgatcc tgaggacaag 1740
ctgcacgagc agtgtcggcc ttggagaaag aacgcctgct gtagcaccaa caccagccaa 1800
gaggcccaca agaacgtgtc ctacctgtac cggttcaact ggaaccactg cggcgagatg 1860
acacccgcct gcaagagaca cttcatccag gatacctgcc tgtacgagtg cagccccaat 1920
ctcggcccct ggattcagca agtggaccag agctggcgga aagaactggt cctgaatgtg 1980
cccctgtgca aagaggattg cgagcagtgg tgggaagatt gcagaaccag ctacacatgc 2040
aagagcaact ggcacaaagg ctggaactgg accagcggct tcaacaagtg tgccgtggga 2100
gctgcctgtc agcctttcca cttctacttt cacacaccca ccgtgctgtg caacaagatc 2160
tggacccaca gctacaaggt gtccaactac agcagaggca gcggccggtg tatccagatg 2220
tggttcgatc ccgccaaggg caaccccaat gaggaagtgg ccagattcta cgccgctgcc 2280
atgtctggtg caggaccttg ggctgcttgg ccctttctgc tttcactggc cctgatgctg 2340
ctgtggctgc tgagctgata a 2361

<210> SEQ ID NO 52
<211> LENGTH: 785
<212> TYPE: PRT
<213> ORGANISM: Homo Sapiens

<400> SEQUENCE: 52

Met Asp Phe Leu Leu Leu Gln Asn Pro Ala Ser Thr Cys Val Pro Glu
1 5 10 15

Pro Ala Ser Gln His Thr Leu Arg Ser Gly Pro Gly Cys Leu Gln Gln
20 25 30

Pro Glu Gln Gln Gly Val Arg Asp Pro Gly Gly Ile Trp Ala Lys Leu
35 40 45

Gly Ala Ala Glu Ala Ser Ala Glu Cys Leu Gln Gly Arg Arg Ser Arg
50 55 60

Gly Ala Ser Gly Ser Glu Pro His Gln Met Gly Ser Asp Val His Asp
65 70 75 80

Leu Asn Ala Leu Leu Pro Ala Val Pro Ser Leu Gly Gly Gly Gly Gly
85 90 95

Cys Ala Leu Pro Val Ser Gly Ala Ala Gln Trp Ala Pro Val Leu Asp
100 105 110

Phe Ala Pro Pro Gly Ala Ser Ala Tyr Gly Ser Leu Gly Gly Pro Ala
115 120 125

Pro Pro Pro Ala Pro Pro Pro Pro Pro Pro Pro Pro Pro His Ser Phe
130 135 140

Ile Lys Gln Glu Pro Ser Trp Gly Gly Ala Glu Pro His Glu Lys Gln
145 150 155 160

Cys Leu Ser Ala Phe Thr Val His Phe Phe Gly Gln Phe Thr Gly Thr
165 170 175

Val Gly Ala Cys Arg Tyr Gly Pro Phe Gly Pro Pro Pro Pro Ser Gln
180 185 190

Ala Ser Ser Gly Gln Ala Arg Met Phe Pro Asn Ala Pro Tyr Leu Pro
195 200 205

Ser Cys Leu Glu Ser Gln Pro Thr Ile Arg Asn Gln Gly Phe Ser Thr
210 215 220

Val Thr Phe Asp Gly Met Pro Ser Tyr Gly His Thr Pro Ser His His
225 230 235 240

Ala Ala Gln Phe Pro Asn His Ser Phe Lys His Glu Asp Pro Met Gly
245 250 255

Gln Gln Gly Ser Leu Gly Glu Gln Gln Tyr Ser Val Pro Pro Pro Val
260 265 270

Tyr Gly Cys His Thr Pro Thr Asp Ser Cys Thr Gly Asn Gln Ala Leu
275 280 285

Leu Leu Arg Met Pro Phe Ser Ser Asp Asn Leu Tyr Gln Met Thr Ser
290 295 300

Gln Leu Glu Cys Met Ile Trp Asn Gln Met Asn Leu Gly Ala Thr Leu
305 310 315 320

Lys Gly Val Ala Ala Gly Ser Ser Ser Ser Val Lys Trp Thr Ala Gly
325 330 335

-continued

```
Gln Ser Asn His Ser Thr Gly Tyr Glu Ser Asp Asn His Thr Met Pro
            340                 345                 350

Ile Leu Cys Gly Ala Gln Tyr Arg Ile His Thr His Gly Val Phe Arg
        355                 360                 365

Gly Ile Gln Asp Val Arg Arg Val Pro Gly Val Ala Pro Thr Leu Val
    370                 375                 380

Gly Ser Ala Ser Glu Thr Ser Glu Lys His Pro Phe Met Cys Ala Tyr
385                 390                 395                 400

Pro Gly Cys Asn Lys Arg Tyr Phe Lys Leu Ser His Leu Lys Met His
                405                 410                 415

Ser Arg Lys His Thr Gly Glu Lys Leu Tyr Gln Cys Asp Phe Lys Asp
            420                 425                 430

Cys Glu Arg Arg Phe Ser Cys Ser Asp Gln Leu Lys Arg His Gln Arg
        435                 440                 445

Arg His Thr Gly Val Lys Pro Phe Gln Cys Lys Thr Cys Gln Arg Thr
    450                 455                 460

Phe Ser Trp Ser Asn His Leu Lys Thr His Thr Arg Thr His Thr Gly
465                 470                 475                 480

Lys Thr Ile Glu Lys Pro Phe Ser Cys Arg Trp Pro Ser Cys Gln Lys
                485                 490                 495

Lys Phe Ala Arg Ser Asn Glu Leu Val His His His Asn Met His Gln
            500                 505                 510

Arg Asn Met Thr Lys Leu Gln Leu Val Leu Arg Gly Arg Lys Arg Arg
        515                 520                 525

Ser Ala Gln Arg Met Thr Thr Gln Leu Leu Leu Leu Leu Val Trp Val
    530                 535                 540

Ala Val Val Gly Glu Val Gln Thr Arg Ile Ala Trp Ala Arg Thr Glu
545                 550                 555                 560

Leu Leu Asn Val Cys Met Asn Ala Lys His His Lys Lys Lys Pro Asp
                565                 570                 575

Pro Glu Asp Lys Leu His Glu Gln Cys Arg Pro Trp Arg Lys Asn Ala
            580                 585                 590

Cys Cys Ser Thr Asn Thr Ser Gln Glu Ala His Lys Asn Val Ser Tyr
        595                 600                 605

Leu Tyr Arg Phe Asn Trp Asn His Cys Gly Glu Met Thr Pro Ala Cys
    610                 615                 620

Lys Arg His Phe Ile Gln Asp Thr Cys Leu Tyr Glu Cys Ser Pro Asn
625                 630                 635                 640

Leu Gly Pro Trp Ile Gln Gln Val Asp Gln Ser Trp Arg Lys Glu Leu
                645                 650                 655

Val Leu Asn Val Pro Leu Cys Lys Glu Asp Cys Glu Gln Trp Trp Glu
            660                 665                 670

Asp Cys Arg Thr Ser Tyr Thr Cys Lys Ser Asn Trp His Lys Gly Trp
        675                 680                 685

Asn Trp Thr Ser Gly Phe Asn Lys Cys Ala Val Gly Ala Ala Cys Gln
    690                 695                 700

Pro Phe His Phe Tyr Phe His Thr Pro Thr Val Leu Cys Asn Lys Ile
705                 710                 715                 720

Trp Thr His Ser Tyr Lys Val Ser Asn Tyr Ser Arg Gly Ser Gly Arg
                725                 730                 735

Cys Ile Gln Met Trp Phe Asp Pro Ala Lys Gly Asn Pro Asn Glu Glu
            740                 745                 750

Val Ala Arg Phe Tyr Ala Ala Ala Met Ser Gly Ala Gly Pro Trp Ala
```

```
        755                 760                 765

Ala Trp Pro Phe Leu Leu Ser Leu Ala Leu Met Leu Leu Trp Leu Leu
    770                 775                 780

Ser
785


<210> SEQ ID NO 53
<211> LENGTH: 2838
<212> TYPE: DNA
<213> ORGANISM: Homo Sapiens

<400> SEQUENCE: 53

atgtggaatc tgctgcacga gacagatagc gccgtggcta ccgttagaag gcccagatgg      60

ctttgtgctg gcgctctggt tctggctggc ggcttttttc tgctgggctt cctgttcggc     120

tggttcatca agagcagcaa cgaggccacc aacatcaccc ctaagcacaa catgaaggcc     180

tttctggacg agctgaaggc cgagaatatc aagaagttcc tgtacaactt cacgcacatc     240

cctcacctgg ccggcaccga gcagaatttt cagctggcca agcagatcca gagccagtgg     300

aaagagttcg gcctggactc tgtggaactg gcccactacg atgtgctgct gagctacccc     360

aacaagacac accccaacta catcagcatc atcaacgagg acggcaacga gatcttcaac     420

accagcctgt tcgagcctcc acctcctggc tacgagaacg tgtccgatat cgtgcctcca     480

ttcagcgctt tcagcccaca gcggatgcct gagggctacc tggtgtacgt gaactacgcc     540

agaaccgagg acttcttcaa gctggaatgg gacatgaaga tcagctgcag cggcaagatc     600

gtgatcgccc ggtacagaaa ggtgttccgc gagaacaaag tgaagaacgc ccagctggca     660

ggcgccaaag gcgtgatcct gtatagcgac cccgccgact attttgcccc tggcgtgaag     720

tcttaccccg acggctggaa ttttcctggc ggcggagtgc agcggcggaa catccttaat     780

cttaacggcg ctggcgaccc tctgacacct ggctatcctg ccaatgagta cgcctacaga     840

cacggaattg ccgaggctgt gggcctgcct tctattcctg tgcaccctgt gcggtactac     900

gacgcccaga aactgctgga aaagatgggc ggaagcgccc ctcctgactc ttcttggaga     960

ggctctctga aggtgcccta caatgtcggc ccaggcttca ccggcaactt cagcacccag    1020

aaagtgaaaa tgcacatcca cagcaccaac gaagtgaccc ggatctacaa cgtgatcggc    1080

acactgagag gcgccgtgga acccgacaaa tacgtgatcc tcggcggcca cagagacagc    1140

tgggtgttcg gaggaatcga ccctcaatct ggcgccgctg tggtgtatga gatcgtgcgg    1200

tctttcggca ccctgaagaa agaaggatgg cggcccagac ggaccatcct gtttgcctct    1260

tgggacgccg aggaatttgg cctgctggga tctacagagt gggccgaaga gaacagcaga    1320

ctgctgcaag aaagaggcgt ggcctacatc aacgccgaca gcagcatcga gggcaactac    1380

accctgcgga tcgattgcac ccctctgatg tacagcctgg tgcacaacct gaccaaagag    1440

ctgaagtccc ctgacgaggg ctttgagggc aagagcctgt acaagagctg gaccaagaag    1500

tccccatctc ctgagttcag cggcatgccc agaatctcta agctggaaag cggcaacaac    1560

ttcgaggtgt tcttccagcg gctgggaatc gcctctggaa tcgccagata caccaagaac    1620

tgggagacaa acaagttctc cggctatccc ctgtaccaca gcgtgtacga gacatacgag    1680

ctggtggaaa agttctacga ccccatgttc aagtaccacc tgacagtggc ccaagtgcgc    1740

ggaggcatgg tgttcgaact ggccaatagc atcgtgctgc ccttcaactg cagagactac    1800

gccgtggtgc tgcggaagta cgccgacaag atctacagca tcagcatgaa gcacccgcaa    1860

gagatgaaga cctacagcgt gtccttcgac tccctgttct tcgccgtgaa gaacttcacc    1920
```

aagatcgcca gcaagttcag cgagcggctg caggacttcg acaagagcaa ccctatcgtg 1980
ctgaggatga tgaacgacca gctgatgttc ctggaacggg ccttcatcaa ccctctggga 2040
ctgcccgaca gacccttcta caggcacgtg atctgtgccc ctagcagcca caacaaatac 2100
gccggcgaga gcttccccgg catctacgat gccctgttcg acatcgagag caacgtgaac 2160
cctagcaagg cctggggcga agtgaagaga cagatctacg tggccgcatt cacagtgcag 2220
gccgctgccg aaacactgtc tgaagtggcc agaggccgga agagaagatc cgactgcaga 2280
aagatggccc ggttcagcta ctccgtgatc tggatcatgg ccatctccaa ggccttcgag 2340
ctgagactgg ttgccggact gggccaccaa gagtttgcca gacctagctg gggctatctg 2400
gccttccggg acgatagcat ctggccccaa gaggaacctg ccatcagacc cagatctagc 2460
cagcgggtgc cacctatgga aatccagcac agcaaagaac tgaaccggac ctgctgcctg 2520
aacggcagaa cctgtatgct gggcagcttc tgcgcctgtc ctcctagctt ctacggccgg 2580
aattgcgagc acgacgtgcg gaaagaaaac tgcggcagcg tgccacacga tacctggctg 2640
cctaagaaat gcagcctgtg caagtgttgg cacggccagc tgcggtgttt ccccagagct 2700
tttctgcccg tgtgtgacgg cctggtcatg gatgaacacc tggtggccag cagaacccct 2760
gagcttcctc caagcgccag gaccaccacc tttatgctcg tgggcatctg cctgagcatc 2820
cagagctact actgatga 2838

<210> SEQ ID NO 54
<211> LENGTH: 944
<212> TYPE: PRT
<213> ORGANISM: Homo Sapiens

<400> SEQUENCE: 54

Met Trp Asn Leu Leu His Glu Thr Asp Ser Ala Val Ala Thr Val Arg
1 5 10 15

Arg Pro Arg Trp Leu Cys Ala Gly Ala Leu Val Leu Ala Gly Gly Phe
20 25 30

Phe Leu Leu Gly Phe Leu Phe Gly Trp Phe Ile Lys Ser Ser Asn Glu
35 40 45

Ala Thr Asn Ile Thr Pro Lys His Asn Met Lys Ala Phe Leu Asp Glu
50 55 60

Leu Lys Ala Glu Asn Ile Lys Lys Phe Leu Tyr Asn Phe Thr His Ile
65 70 75 80

Pro His Leu Ala Gly Thr Glu Gln Asn Phe Gln Leu Ala Lys Gln Ile
85 90 95

Gln Ser Gln Trp Lys Glu Phe Gly Leu Asp Ser Val Glu Leu Ala His
100 105 110

Tyr Asp Val Leu Leu Ser Tyr Pro Asn Lys Thr His Pro Asn Tyr Ile
115 120 125

Ser Ile Ile Asn Glu Asp Gly Asn Glu Ile Phe Asn Thr Ser Leu Phe
130 135 140

Glu Pro Pro Pro Pro Gly Tyr Glu Asn Val Ser Asp Ile Val Pro Pro
145 150 155 160

Phe Ser Ala Phe Ser Pro Gln Arg Met Pro Glu Gly Tyr Leu Val Tyr
165 170 175

Val Asn Tyr Ala Arg Thr Glu Asp Phe Phe Lys Leu Glu Trp Asp Met
180 185 190

Lys Ile Ser Cys Ser Gly Lys Ile Val Ile Ala Arg Tyr Arg Lys Val
195 200 205

```
Phe Arg Glu Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Phe Pro Gly Gly Gly Val Gln Arg Arg
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg His Gly Ile Ala Glu Ala Val Gly
        275                 280                 285

Leu Pro Ser Ile Pro Val His Pro Val Arg Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Lys Tyr Val Ile Leu Gly Gly His Arg Asp Ser Trp Val Phe Gly
    370                 375                 380

Gly Ile Asp Pro Gln Ser Gly Ala Ala Val Val Tyr Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Ile
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Lys Ser
                485                 490                 495

Trp Thr Lys Lys Ser Pro Ser Pro Glu Phe Ser Gly Met Pro Arg Ile
            500                 505                 510

Ser Lys Leu Glu Ser Gly Asn Asn Phe Glu Val Phe Phe Gln Arg Leu
        515                 520                 525

Gly Ile Ala Ser Gly Ile Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asn Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620
```

```
Tyr Ser Val Ser Phe Asp Ser Leu Phe Phe Ala Val Lys Asn Phe Thr
625                 630                 635                 640

Lys Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asn Pro Leu Gly Leu Pro Asp Arg Pro Phe Tyr Arg
        675                 680                 685

His Val Ile Cys Ala Pro Ser Ser His Asn Lys Tyr Ala Gly Glu Ser
    690                 695                 700

Phe Pro Gly Ile Tyr Asp Ala Leu Phe Asp Ile Glu Ser Asn Val Asn
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala Arg Gly
            740                 745                 750

Arg Lys Arg Arg Ser Asp Cys Arg Lys Met Ala Arg Phe Ser Tyr Ser
        755                 760                 765

Val Ile Trp Ile Met Ala Ile Ser Lys Ala Phe Glu Leu Arg Leu Val
    770                 775                 780

Ala Gly Leu Gly His Gln Glu Phe Ala Arg Pro Ser Trp Gly Tyr Leu
785                 790                 795                 800

Ala Phe Arg Asp Asp Ser Ile Trp Pro Gln Glu Glu Pro Ala Ile Arg
                805                 810                 815

Pro Arg Ser Ser Gln Arg Val Pro Pro Met Glu Ile Gln His Ser Lys
            820                 825                 830

Glu Leu Asn Arg Thr Cys Cys Leu Asn Gly Arg Thr Cys Met Leu Gly
        835                 840                 845

Ser Phe Cys Ala Cys Pro Pro Ser Phe Tyr Gly Arg Asn Cys Glu His
    850                 855                 860

Asp Val Arg Lys Glu Asn Cys Gly Ser Val Pro His Asp Thr Trp Leu
865                 870                 875                 880

Pro Lys Lys Cys Ser Leu Cys Lys Cys Trp His Gly Gln Leu Arg Cys
                885                 890                 895

Phe Pro Arg Ala Phe Leu Pro Val Cys Asp Gly Leu Val Met Asp Glu
            900                 905                 910

His Leu Val Ala Ser Arg Thr Pro Glu Leu Pro Pro Ser Ala Arg Thr
        915                 920                 925

Thr Thr Phe Met Leu Val Gly Ile Cys Leu Ser Ile Gln Ser Tyr Tyr
    930                 935                 940
```

<210> SEQ ID NO 55
<211> LENGTH: 2373
<212> TYPE: DNA
<213> ORGANISM: Homo Sapiens

<400> SEQUENCE: 55

```
atggactttc tgctgctgca gaaccctgcc agcacctgtg ttccagaacc tgcctctcag      60

cacaccctga gatctggccc tggatgtctc cagcagcctg aacagcaggg cgttagagat     120

cctggcggaa tctgggccaa actgggagcc gctgaagcct ctgccgaatg tctgcagggc     180

agaagaagca gaggcgccag cggatctgaa cctcaccaga tgggaagcga cgtgcacgac     240

ctgaatgctc tgctgcctgc cgtgccatct cttggcggag gcggaggatg tgctttgcct     300

gtttctggtg ctgcccagtg ggctcccgtg ctggattttg ctcctcctgg cgcttctgcc     360
```

```
tatggctctc ttggaggacc tgctcctcca ccagctccac ctccaccgcc gcctccacca    420
cctcacagct ttatcaagca agagccctcc tggggcggag ccgagcctca cgaaaaacag    480
tgtctgagcg ccttcaccgt gcactttttc ggccagttta ccggcacagt gggcgcctgt    540
agatacggcc cttttggacc accaccacct agccaggcta gctctggaca ggccagaatg    600
ttccccaacg ctccctacct gcctagctgc ctggaaagcc agcctaccat cagaaaccag    660
ggcttcagca ccgtgacctt cgacggcatg cctagctatg gccacacacc atctcaccac    720
gccgctcagt tccccaatca cagcttcaag cacgaggacc ctatgggcca gcagggatct    780
ctgggagagc agcagtatag cgtgccacct cctgtgtacg gctgtcacac ccctaccgat    840
agctgcacag gcaatcaggc cctgctgctg aggatgccct tcagcagcga caacctgtac    900
cagatgacaa gccagctgga atgcatgatc tggaaccaga tgaacctggg cgccacactg    960
aaaggcgtgg ccgctggatc tagcagcagc gtgaaatgga cagccggcca gagcaatcac   1020
tccaccggct acgagtccga caaccacacc atgcctattc tgtgcggagc ccagtacaga   1080
atccacacac acggcgtgtt ccggggcatt caggatgtgc gaagagtgcc tggcgtggcc   1140
cctacacttg tgggatctgc ctctgagaca agcgagaagc accccttcat gtgcgcctat   1200
cctggctgca acaagcggta cttcaagctg agccacctga agatgcacag ccggaagcac   1260
acaggcgaga agctgtacca gtgcgacttc aaggactgcg agcggagatt cagctgcagc   1320
gaccagctga agagacacca gagaaggcac accggcgtga agcccttcca gtgcaagacc   1380
tgccagcgga cctttagctg gtccaaccac ctgaaaaccc acacaagaac ccacaccggc   1440
aagaccatcg agaagccttt cagctgtaga tggcccagct gccagaagaa gttcgcccgg   1500
tctaacgagc tggtgcatca ccacaacatg caccagagga acatgaccaa actgcagctg   1560
gtgctgaggg gaagaaagcg gagatctgcc gtgacagcct gtcagagcct gggctttgtg   1620
gtgtccctga tcgagatcgt gggcatcatt gccgctacct gcatggacca gtggtctacc   1680
caggacctgt acaacaaccc tgtgaccgcc gtgttcaact accaaggcct gtggcacagc   1740
tgcatgagag agagcagcgg cttcaccgag tgcagaggct acttcaccct gctggaactg   1800
cctgccatgc tgcaggctgt gcaggccctt atgatcgtgg gaattgtgct gggagccatc   1860
ggcctgctgg tgtccatttt cgccctgaag tgcatccgga tcggcagcat ggaagatagc   1920
gccaaggcca acatgaccct gaccagcggc atcatgttca tcgtgtccgg cctgtgcgcc   1980
attgctggcg tgtccgtgtt tgccaatatg ctcgtgacca acttctggct gagcaccgcc   2040
aacatgtaca ccggcatggg cgagatggtg cagaccgtgc agacacggta cacatttggc   2100
gccgctctgt ttgtcggatg ggttgcaggc ggactgacac tgattggcgg cgtgatgatg   2160
tgtatcgcct gcagaggact ggcccctgag gaaacaaact acaaggccgt gtactaccac   2220
gcctccggac acagcgtggc atacaaacct ggcggcttta aggccagcac cggcttcggc   2280
agcaacacca agaacaagaa gatctacgac ggcggagcac acaccgagga tgaggtgcag   2340
agctacccca gcaagcacga ctacgtgtga tga                                2373
```

<210> SEQ ID NO 56
<211> LENGTH: 789
<212> TYPE: PRT
<213> ORGANISM: Homo Sapiens

<400> SEQUENCE: 56

```
Met Asp Phe Leu Leu Leu Gln Asn Pro Ala Ser Thr Cys Val Pro Glu
1               5                   10                  15
```

-continued

```
Pro Ala Ser Gln His Thr Leu Arg Ser Gly Pro Gly Cys Leu Gln Gln
            20                  25                  30

Pro Glu Gln Gln Gly Val Arg Asp Pro Gly Gly Ile Trp Ala Lys Leu
        35                  40                  45

Gly Ala Ala Glu Ala Ser Ala Glu Cys Leu Gln Gly Arg Arg Ser Arg
    50                  55                  60

Gly Ala Ser Gly Ser Glu Pro His Gln Met Gly Ser Asp Val His Asp
65                  70                  75                  80

Leu Asn Ala Leu Leu Pro Ala Val Pro Ser Leu Gly Gly Gly Gly Gly
                85                  90                  95

Cys Ala Leu Pro Val Ser Gly Ala Ala Gln Trp Ala Pro Val Leu Asp
            100                 105                 110

Phe Ala Pro Pro Gly Ala Ser Ala Tyr Gly Ser Leu Gly Gly Pro Ala
        115                 120                 125

Pro Pro Pro Ala Pro Pro Pro Pro Pro Pro Pro Pro Pro His Ser Phe
    130                 135                 140

Ile Lys Gln Glu Pro Ser Trp Gly Gly Ala Glu Pro His Glu Lys Gln
145                 150                 155                 160

Cys Leu Ser Ala Phe Thr Val His Phe Phe Gly Gln Phe Thr Gly Thr
                165                 170                 175

Val Gly Ala Cys Arg Tyr Gly Pro Phe Gly Pro Pro Pro Pro Ser Gln
            180                 185                 190

Ala Ser Ser Gly Gln Ala Arg Met Phe Pro Asn Ala Pro Tyr Leu Pro
        195                 200                 205

Ser Cys Leu Glu Ser Gln Pro Thr Ile Arg Asn Gln Gly Phe Ser Thr
    210                 215                 220

Val Thr Phe Asp Gly Met Pro Ser Tyr Gly His Thr Pro Ser His His
225                 230                 235                 240

Ala Ala Gln Phe Pro Asn His Ser Phe Lys His Glu Asp Pro Met Gly
                245                 250                 255

Gln Gln Gly Ser Leu Gly Glu Gln Gln Tyr Ser Val Pro Pro Pro Val
            260                 265                 270

Tyr Gly Cys His Thr Pro Thr Asp Ser Cys Thr Gly Asn Gln Ala Leu
        275                 280                 285

Leu Leu Arg Met Pro Phe Ser Ser Asp Asn Leu Tyr Gln Met Thr Ser
    290                 295                 300

Gln Leu Glu Cys Met Ile Trp Asn Gln Met Asn Leu Gly Ala Thr Leu
305                 310                 315                 320

Lys Gly Val Ala Ala Gly Ser Ser Ser Ser Val Lys Trp Thr Ala Gly
                325                 330                 335

Gln Ser Asn His Ser Thr Gly Tyr Glu Ser Asp Asn His Thr Met Pro
            340                 345                 350

Ile Leu Cys Gly Ala Gln Tyr Arg Ile His Thr His Gly Val Phe Arg
        355                 360                 365

Gly Ile Gln Asp Val Arg Arg Val Pro Gly Val Ala Pro Thr Leu Val
    370                 375                 380

Gly Ser Ala Ser Glu Thr Ser Glu Lys His Pro Phe Met Cys Ala Tyr
385                 390                 395                 400

Pro Gly Cys Asn Lys Arg Tyr Phe Lys Leu Ser His Leu Lys Met His
                405                 410                 415

Ser Arg Lys His Thr Gly Glu Lys Leu Tyr Gln Cys Asp Phe Lys Asp
            420                 425                 430
```

-continued

```
Cys Glu Arg Arg Phe Ser Cys Ser Asp Gln Leu Lys Arg His Gln Arg
        435                 440                 445

Arg His Thr Gly Val Lys Pro Phe Gln Cys Lys Thr Cys Gln Arg Thr
    450                 455                 460

Phe Ser Trp Ser Asn His Leu Lys Thr His Thr Arg Thr His Thr Gly
465                 470                 475                 480

Lys Thr Ile Glu Lys Pro Phe Ser Cys Arg Trp Pro Ser Cys Gln Lys
                485                 490                 495

Lys Phe Ala Arg Ser Asn Glu Leu Val His His His Asn Met His Gln
            500                 505                 510

Arg Asn Met Thr Lys Leu Gln Leu Val Leu Arg Gly Arg Lys Arg Arg
        515                 520                 525

Ser Ala Val Thr Ala Cys Gln Ser Leu Gly Phe Val Val Ser Leu Ile
    530                 535                 540

Glu Ile Val Gly Ile Ile Ala Ala Thr Cys Met Asp Gln Trp Ser Thr
545                 550                 555                 560

Gln Asp Leu Tyr Asn Asn Pro Val Thr Ala Val Phe Asn Tyr Gln Gly
                565                 570                 575

Leu Trp His Ser Cys Met Arg Glu Ser Ser Gly Phe Thr Glu Cys Arg
            580                 585                 590

Gly Tyr Phe Thr Leu Leu Glu Leu Pro Ala Met Leu Gln Ala Val Gln
        595                 600                 605

Ala Leu Met Ile Val Gly Ile Val Leu Gly Ala Ile Gly Leu Leu Val
    610                 615                 620

Ser Ile Phe Ala Leu Lys Cys Ile Arg Ile Gly Ser Met Glu Asp Ser
625                 630                 635                 640

Ala Lys Ala Asn Met Thr Leu Thr Ser Gly Ile Met Phe Ile Val Ser
                645                 650                 655

Gly Leu Cys Ala Ile Ala Gly Val Ser Val Phe Ala Asn Met Leu Val
            660                 665                 670

Thr Asn Phe Trp Leu Ser Thr Ala Asn Met Tyr Thr Gly Met Gly Glu
        675                 680                 685

Met Val Gln Thr Val Gln Thr Arg Tyr Thr Phe Gly Ala Ala Leu Phe
    690                 695                 700

Val Gly Trp Val Ala Gly Gly Leu Thr Leu Ile Gly Gly Val Met Met
705                 710                 715                 720

Cys Ile Ala Cys Arg Gly Leu Ala Pro Glu Glu Thr Asn Tyr Lys Ala
                725                 730                 735

Val Tyr Tyr His Ala Ser Gly His Ser Val Ala Tyr Lys Pro Gly Gly
            740                 745                 750

Phe Lys Ala Ser Thr Gly Phe Gly Ser Asn Thr Lys Asn Lys Lys Ile
        755                 760                 765

Tyr Asp Gly Gly Ala His Thr Glu Asp Glu Val Gln Ser Tyr Pro Ser
    770                 775                 780

Lys His Asp Tyr Val
785
```

<210> SEQ ID NO 57
<211> LENGTH: 2769
<212> TYPE: DNA
<213> ORGANISM: Homo Sapiens

<400> SEQUENCE: 57

```
atgtggaatc tgctgcacga gacagatagc gccgtggcta ccgttagaag gcccagatgg      60
```

-continued

```
ctttgtgctg gcgctctggt tctggctggc ggcttttttc tgctgggctt cctgttcggc    120
tggttcatca agagcagcaa cgaggccacc aacatcaccc ctaagcacaa catgaaggcc    180
tttctggacg agctgaaggc cgagaatatc aagaagttcc tgtacaactt cacgcacatc    240
cctcacctgg ccggcaccga gcagaatttt cagctggcca agcagatcca gagccagtgg    300
aaagagttcg gcctggactc tgtggaactg gcccactacg atgtgctgct gagctacccc    360
aacaagacac accccaacta catcagcatc atcaacgagg acggcaacga gatcttcaac    420
accagcctgt tcgagcctcc acctcctggc tacgagaacg tgtccgatat cgtgcctcca    480
ttcagcgctt tcagcccaca gcggatgcct gagggctacc tggtgtacgt gaactacgcc    540
agaaccgagg acttcttcaa gctggaatgg gacatgaaga tcagctgcag cggcaagatc    600
gtgatcgccc ggtacagaaa ggtgttccgc gagaacaaag tgaagaacgc ccagctggca    660
ggcgccaaag gcgtgatcct gtatagcgac cccgccgact attttgcccc tggcgtgaag    720
tcttaccccg acggctggaa ttttcctggc ggcggagtgc agcggcggaa catccttaat    780
cttaacggcg ctggcgaccc tctgacacct ggctatcctg ccaatgagta cgcctacaga    840
cacggaattg ccgaggctgt gggcctgcct tctattcctg tgcaccctgt gcggtactac    900
gacgcccaga aactgctgga aaagatgggc ggaagcgccc ctcctgactc ttcttggaga    960
ggctctctga aggtgcccta caatgtcggc ccaggcttca ccggcaactt cagcacccag   1020
aaagtgaaaa tgcacatcca cagcaccaac gaagtgaccc ggatctacaa cgtgatcggc   1080
acactgagag gcgccgtgga acccgacaaa tacgtgatcc tcggcggcca cagagacagc   1140
tgggtgttcg gaggaatcga ccctcaatct ggcgccgctg tggtgtatga gatcgtgcgg   1200
tctttcggca ccctgaagaa agaaggatgg cggcccagac ggaccatcct gtttgcctct   1260
tgggacgccg aggaatttgg cctgctggga tctacagagt gggccgaaga gaacagcaga   1320
ctgctgcaag aaagaggcgt ggcctacatc aacgccgaca gcagcatcga gggcaactac   1380
accctgcgga tcgattgcac ccctctgatg tacagcctgg tgcacaacct gaccaaagag   1440
ctgaagtccc ctgacgaggg ctttgagggc aagagcctgt acaagagctg gaccaagaag   1500
tccccatctc ctgagttcag cggcatgccc agaatctcta agctggaaag cggcaacaac   1560
ttcgaggtgt tcttccagcg gctgggaatc gcctctggaa tcgccagata caccaagaac   1620
tgggagacaa acaagttctc cggctatccc ctgtaccaca gcgtgtacga gacatacgag   1680
ctggtggaaa agttctacga ccccatgttc aagtaccacc tgacagtggc ccaagtgcgc   1740
ggaggcatgg tgttcgaact ggccaatagc atcgtgctgc ccttcaactg cagagactac   1800
gccgtggtgc tgcggaagta cgccgacaag atctacagca tcagcatgaa gcacccgcaa   1860
gagatgaaga cctacagcgt gtccttcgac tccctgttct tcgccgtgaa gaacttcacc   1920
aagatcgcca gcaagttcag cgagcggctg caggacttcg acaagagcaa ccctatcgtg   1980
ctgaggatga tgaacgacca gctgatgttc ctggaacggg ccttcatcaa ccctctggga   2040
ctgcccgaca gacccttcta caggcacgtg atctgtgccc ctagcagcca caacaaatac   2100
gccggcgaga gcttccccgg catctacgat gccctgttcg acatcgagag caacgtgaac   2160
cctagcaagg cctggggcga agtgaagaga cagatctacg tggccgcatt cacagtgcag   2220
gccgctgccg aaacactgtc tgaagtggcc agaggccgga agagaagaag tgctctgctg   2280
gcactgctgc tggtggtggc tttgcctaga gtgtggaccg acgccaatct gacagtgcgg   2340
cagagagatc ctgaggacag ccagagaacc gacgacggcg ataacagagt gtggtgccac   2400
gtgtgcgagc gcgagaatac cttcgagtgt cagaacccca gacggtgcaa gtggaccgag   2460
```

```
ccttactgtg tgatcgccgc cgtgaaaatc ttcccacggt tcttcatggt ggtcaagcag   2520

tgcagcgctg gctgtgccgc tatggaaaga cccaagcctg aggaaaagcg gttcctgctc   2580

gaggaaccca tgctgttctt ctacctgaag tgctgcaaaa tctgctactg caacctggaa   2640

ggccctccta tcaacagcag cgtcctgaaa gaatatgccg gcagcatggg cgagtcttgt   2700

ggtggactgt ggctggccat tctgctgctg cttgcctcta ttgccgcctc tctgagcctg   2760

agctgatga                                                           2769
```

<210> SEQ ID NO 58
<211> LENGTH: 921
<212> TYPE: PRT
<213> ORGANISM: Homo Sapiens

<400> SEQUENCE: 58

```
Met Trp Asn Leu Leu His Glu Thr Asp Ser Ala Val Ala Thr Val Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr His Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Arg Met Pro Glu Gly Tyr Leu Val Tyr
                165                 170                 175

Val Asn Tyr Ala Arg Thr Glu Asp Phe Phe Lys Leu Glu Trp Asp Met
            180                 185                 190

Lys Ile Ser Cys Ser Gly Lys Ile Val Ile Ala Arg Tyr Arg Lys Val
        195                 200                 205

Phe Arg Glu Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Phe Pro Gly Gly Gly Val Gln Arg Arg
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg His Gly Ile Ala Glu Ala Val Gly
        275                 280                 285

Leu Pro Ser Ile Pro Val His Pro Val Arg Tyr Tyr Asp Ala Gln Lys
    290                 295                 300

Leu Leu Glu Lys Met Gly Gly Ser Ala Pro Pro Asp Ser Ser Trp Arg
```

-continued

```
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Lys Tyr Val Ile Leu Gly Gly His Arg Asp Ser Trp Val Phe Gly
    370                 375                 380

Gly Ile Asp Pro Gln Ser Gly Ala Ala Val Val Tyr Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Ile
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Lys Ser
                485                 490                 495

Trp Thr Lys Lys Ser Pro Ser Pro Glu Phe Ser Gly Met Pro Arg Ile
            500                 505                 510

Ser Lys Leu Glu Ser Gly Asn Asn Phe Glu Val Phe Phe Gln Arg Leu
        515                 520                 525

Gly Ile Ala Ser Gly Ile Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asn Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Phe Ala Val Lys Asn Phe Thr
625                 630                 635                 640

Lys Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asn Pro Leu Gly Leu Pro Asp Arg Pro Phe Tyr Arg
        675                 680                 685

His Val Ile Cys Ala Pro Ser Ser His Asn Lys Tyr Ala Gly Glu Ser
    690                 695                 700

Phe Pro Gly Ile Tyr Asp Ala Leu Phe Asp Ile Glu Ser Asn Val Asn
705                 710                 715                 720

Pro Ser Lys Ala Trp Gly Glu Val Lys Arg Gln Ile Tyr Val Ala Ala
                725                 730                 735
```

```
Phe Thr Val Gln Ala Ala Ala Glu Thr Leu Ser Glu Val Ala Arg Gly
            740                 745                 750

Arg Lys Arg Arg Ser Ala Leu Leu Ala Leu Leu Leu Val Val Ala Leu
        755                 760                 765

Pro Arg Val Trp Thr Asp Ala Asn Leu Thr Val Arg Gln Arg Asp Pro
    770                 775                 780

Glu Asp Ser Gln Arg Thr Asp Asp Gly Asp Asn Arg Val Trp Cys His
785                 790                 795                 800

Val Cys Glu Arg Glu Asn Thr Phe Glu Cys Gln Asn Pro Arg Arg Cys
                805                 810                 815

Lys Trp Thr Glu Pro Tyr Cys Val Ile Ala Ala Val Lys Ile Phe Pro
            820                 825                 830

Arg Phe Phe Met Val Val Lys Gln Cys Ser Ala Gly Cys Ala Ala Met
        835                 840                 845

Glu Arg Pro Lys Pro Glu Glu Lys Arg Phe Leu Leu Glu Glu Pro Met
    850                 855                 860

Leu Phe Phe Tyr Leu Lys Cys Cys Lys Ile Cys Tyr Cys Asn Leu Glu
865                 870                 875                 880

Gly Pro Pro Ile Asn Ser Ser Val Leu Lys Glu Tyr Ala Gly Ser Met
                885                 890                 895

Gly Glu Ser Cys Gly Gly Leu Trp Leu Ala Ile Leu Leu Leu Leu Ala
            900                 905                 910

Ser Ile Ala Ala Ser Leu Ser Leu Ser
        915                 920
```

<210> SEQ ID NO 59
<211> LENGTH: 1995
<212> TYPE: DNA
<213> ORGANISM: Homo Sapiens

<400> SEQUENCE: 59

```
atggccgcta cagagattag cgtgctgagc gagcagttca ccaagatcaa agaactgaag     60

ctgatgctcg agaagggcct gaagaaagaa gagaaggacg gcgtctgccg cgagaagaac    120

cacagaagcc catctgagct ggaagcccag agaacctctg gcgccttcca ggacagcatc    180

ctggaagagg aagtggaact ggttctggcc cctctggaag agagcaagaa gtacatcctg    240

acactgcaga ccgtgcactt cacctctgaa gccgtgcagc tccaggacat gagcctgctg    300

tctatccagc agcaagaggg cgtgcaggtt gtggttcagc aacctggacc tggactgctg    360

tggctgcaag agggacctag acagagcctg cagcagtgtg tggccatcag catccagcaa    420

gagctgtact cccctcaaga gatggaagtg ctgcagtttc acgccctgga agaaaacgtg    480

atggtggcca tcgaggacag caagctggct gtgtctctgg ccgaaaccac cggcctgatc    540

aagctggaag aagaacaaga gaagaatcag ctgctcgccg aaaagaccaa aaagcaactg    600

ttcttcgtgg aaaccatgag cggcgacgag cggagcgacg aaatcgtgct gaccgtgtcc    660

aacagcaacg tcgaggaaca agaggaccag cctacagcct gtcaggccga tgccgagaaa    720

gccaagttta ccaagaacca gagaaagacc aagggcgcca agggcacctt ccactgcaac    780

gtgtgcatgt tcaccagcag ccggatgagc agcttcaact gccacatgaa gacccacacc    840

agcgagaagc cccacctgtg ccatctgtgc ctgaaaacct tccggaccgt gactctgctg    900

tggaactacg tgaacaccca cacaggcacc cggccttaca agtgcaacga ctgcaacatg    960

gccttcgtga ccagcggaga actcgtgcgg cacagaagat acaagcacac ccacgagaaa   1020
```

cccttcaagt gcagcatgtg caaatacgcc agcatggaag cctccaagct gaagtgtcac 1080
gtgcggagcc atacaggcga gcaccctttc cagtgctgcc agtgtagcta cgcctccagg 1140
gacacctata agctgaagcg gcacatgaga acccactctg ggagaagcc ttacgagtgc 1200 cacatctgcc acaccagatt cacccagagc ggcaccatga agattcacat cctgcagaaa 1260
cacggcaaga acgtgcccaa gtaccagtgt cctcactgcg ccaccattat cgccagaaag 1320
tccgacctgc gggtgcacat gaggaatctg cacgcctatt ctgccgccga gctgaaatgc 1380
agatactgca gcgccgtgtt ccacaagaga tacgccctga tccagcacca gaaaacccac 1440
aagaacgaga agcggtttaa gtgcaagcac tgctcctacg cctgcaagca agagcgccac 1500
atgatcgccc acatccacac acacaccggc gaaaagcctt tcacctgtct gagctgcaac 1560
aagtgcttcc ggcagaaaca gctgctgaac gcccacttca gaaagtacca cgacgccaac 1620
ttcatcccca ccgtgtacaa gtgctccaag tgcggcaagg gcttcagccg gtggatcaat 1680
ctgcaccggc acctggaaaa gtgcgagtct ggcgaagcca agtctgccgc ctctggcaag 1740
ggcagaagaa cccggaagag aaagcagacc attctgaaag aggccaccaa gagccagaaa 1800
gaagccgcca agcgctggaa agaggctgcc aacggcgacg aagctgccgc tgaagaagcc 1860
agcacaacaa agggcgaaca gttccccgaa gagatgttcc ccgtggcctg cagagaaacc 1920
acagccagag tgaagcaaga ggtggaccag ggcgtcacat gcgagatgct gctgaatacc 1980
atggacaagt gatga 1995

<210> SEQ ID NO 60
<211> LENGTH: 663
<212> TYPE: PRT
<213> ORGANISM: Homo Sapiens

<400> SEQUENCE: 60

Met Ala Ala Thr Glu Ile Ser Val Leu Ser Glu Gln Phe Thr Lys Ile
1               5                   10                  15

Lys Glu Leu Lys Leu Met Leu Glu Lys Gly Leu Lys Lys Glu Glu Lys
            20                  25                  30

Asp Gly Val Cys Arg Glu Lys Asn His Arg Ser Pro Ser Glu Leu Glu
        35                  40                  45

Ala Gln Arg Thr Ser Gly Ala Phe Gln Asp Ser Ile Leu Glu Glu Glu
    50                  55                  60

Val Glu Leu Val Leu Ala Pro Leu Glu Glu Ser Lys Lys Tyr Ile Leu
65                  70                  75                  80

Thr Leu Gln Thr Val His Phe Thr Ser Glu Ala Val Gln Leu Gln Asp
                85                  90                  95

Met Ser Leu Leu Ser Ile Gln Gln Gln Glu Gly Val Gln Val Val Val
            100                 105                 110

Gln Gln Pro Gly Pro Gly Leu Leu Trp Leu Gln Glu Gly Pro Arg Gln
        115                 120                 125

Ser Leu Gln Gln Cys Val Ala Ile Ser Ile Gln Gln Glu Leu Tyr Ser
    130                 135                 140

Pro Gln Glu Met Glu Val Leu Gln Phe His Ala Leu Glu Glu Asn Val
145                 150                 155                 160

Met Val Ala Ile Glu Asp Ser Lys Leu Ala Val Ser Leu Ala Glu Thr
                165                 170                 175

Thr Gly Leu Ile Lys Leu Glu Glu Glu Gln Glu Lys Asn Gln Leu Leu
            180                 185                 190

Ala Glu Lys Thr Lys Lys Gln Leu Phe Phe Val Glu Thr Met Ser Gly

```
        195                 200                 205

Asp Glu Arg Ser Asp Glu Ile Val Leu Thr Val Ser Asn Ser Asn Val
    210                 215                 220

Glu Glu Gln Glu Asp Gln Pro Thr Ala Cys Gln Ala Asp Ala Glu Lys
225                 230                 235                 240

Ala Lys Phe Thr Lys Asn Gln Arg Lys Thr Lys Gly Ala Lys Gly Thr
                245                 250                 255

Phe His Cys Asn Val Cys Met Phe Thr Ser Ser Arg Met Ser Ser Phe
            260                 265                 270

Asn Cys His Met Lys Thr His Thr Ser Glu Lys Pro His Leu Cys His
        275                 280                 285

Leu Cys Leu Lys Thr Phe Arg Thr Val Thr Leu Leu Trp Asn Tyr Val
    290                 295                 300

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Met
            340                 345                 350

Glu Ala Ser Lys Leu Lys Cys His Val Arg Ser His Thr Gly Glu His
        355                 360                 365

Pro Phe Gln Cys Cys Gln Cys Ser Tyr Ala Ser Arg Asp Thr Tyr Lys
    370                 375                 380

Leu Lys Arg His Met Arg Thr His Ser Gly Glu Lys Pro Tyr Glu Cys
385                 390                 395                 400

His Ile Cys His Thr Arg Phe Thr Gln Ser Gly Thr Met Lys Ile His
                405                 410                 415

Ile Leu Gln Lys His Gly Lys Asn Val Pro Lys Tyr Gln Cys Pro His
            420                 425                 430

Cys Ala Thr Ile Ile Ala Arg Lys Ser Asp Leu Arg Val His Met Arg
        435                 440                 445

Asn Leu His Ala Tyr Ser Ala Ala Glu Leu Lys Cys Arg Tyr Cys Ser
    450                 455                 460

Ala Val Phe His Lys Arg Tyr Ala Leu Ile Gln His Gln Lys Thr His
465                 470                 475                 480

Lys Asn Glu Lys Arg Phe Lys Cys Lys His Cys Ser Tyr Ala Cys Lys
                485                 490                 495

Gln Glu Arg His Met Ile Ala His Ile His Thr His Thr Gly Glu Lys
            500                 505                 510

Pro Phe Thr Cys Leu Ser Cys Asn Lys Cys Phe Arg Gln Lys Gln Leu
        515                 520                 525

Leu Asn Ala His Phe Arg Lys Tyr His Asp Ala Asn Phe Ile Pro Thr
    530                 535                 540

Val Tyr Lys Cys Ser Lys Cys Gly Lys Gly Phe Ser Arg Trp Ile Asn
545                 550                 555                 560

Leu His Arg His Leu Glu Lys Cys Glu Ser Gly Glu Ala Lys Ser Ala
                565                 570                 575

Ala Ser Gly Lys Gly Arg Arg Thr Arg Lys Arg Lys Gln Thr Ile Leu
            580                 585                 590

Lys Glu Ala Thr Lys Ser Gln Lys Glu Ala Ala Lys Arg Trp Lys Glu
        595                 600                 605

Ala Ala Asn Gly Asp Glu Ala Ala Ala Glu Glu Ala Ser Thr Thr Lys
    610                 615                 620
```

Gly Glu Gln Phe Pro Glu Glu Met Phe Pro Val Ala Cys Arg Glu Thr
625 630 635 640

Thr Ala Arg Val Lys Gln Glu Val Asp Gln Gly Val Thr Cys Glu Met
645 650 655

Leu Leu Asn Thr Met Asp Lys
660

<210> SEQ ID NO 61
<211> LENGTH: 1896
<212> TYPE: DNA
<213> ORGANISM: Homo Sapiens

<400> SEQUENCE: 61
atggcattgc ctacagctag acctctgctg ggcagctgtg gaacaccagc tctgggaagc 60
ctgctgtttc tgctgttcag cctcggatgg gtgcagcctt ctagaacact ggccggcgag 120
acaggacaag aagctgctcc tcttgacggc gtgctggcca atcctcctaa tatcagctct 180
ctgagcccca gacagctgct cggctttcct tgtgccgaag tgtctggcct gagcaccgag 240
agagtgtggg aacttgctgt ggccctggct cagaaaaacg tgaagctgag cacagagcag 300
ctgagatgtc tggcccacca gctgagtgaa cctccagagg atctggatgc cctgcctctg 360
gacctgctgc tgttcctgaa tcctgacgcc tttagcggcc ctcaggcctg caccagattc 420
ttcagcagaa tcaccaaggc caatgtggat ctgctgccca gaggcgcccc tgagagacaa 480
agacttctgc ctgctgctct ggcctgttgg ggcgttagag gatctctgct gtctgaggcc 540
gatgtgctgg ctcttggagg cctggcttgt aacctgcctg gcagatttgt ggccgagtct 600
gctgaggtgc tgctgcctag actggtgtcc tgtcctggac ctctggatca ggaccagcaa 660
gaagccgcta gagctgcact tcaaggcggc ggacctcctt atggacctcc tctgacttgg 720
agcgtgtcca ccatggacgc tctgagagga ctgctgcctg ttctgggcca gcctatcatc 780
cggtctatcc ctcagggaat tgtggccgct tggcggcaga gaagcttcag agatccctct 840
tggagacagc ccaagcagac catcctgtgg cctcggttca gatgggaagt cgagaaaacc 900
gcctgtccta gcggcaagaa ggccagagag atcgacgaga gcctgatctt ctacaagaag 960
tgggaactcg aggcctgcgt ggacgctgct ctgctggcta cacagatgga cagagtgaac 1020
gctatcccct tcacctatga gcagctggac gtgctgaagc acaagctgga tgagctgtac 1080
cctcagggct accccgagtc tgtgattcag cacctgggct acctgtttct gaagatgagc 1140
cccgaggaca tccggaagtg gaacgtgacc agcctggaaa ccctgaaggc cctgctggaa 1200
gtgaacaagg gccacgagat gtccccacag gctcctagaa ggcctctgcc tcaagtggcc 1260
acactgatcg acagattcgt gaaaggcagg ggccagctgg acaaggacac cctggataca 1320
ctgaccgcct tctatcccgg ctatctgtgc agcctgtctc ctgaggaact gtcctctgtg 1380
cctcctagct ctatttgggc tgtgcggcct caggacctgg atacctgtga tcctagacag 1440
ctggatgtcc tgtatcctaa ggctcggctg gccttccaga acatgaacgg cagcgagtac 1500
ttcgtgaaga tccagttctt ccttggcggc gctcccaccg aggatctgaa agctctgtcc 1560
cagcagaatg tgtctatgga cctggccacc tttatgaagc tgcggaccga tgctgtgctg 1620
cctctgacag tggccgaggt gcaaaaactg ctgggccctc atgtggaagg actgaaggcc 1680
gaagaacggc acagacccgt cagagactgg attctgagac agcggcagga cgacctggac 1740
acactggaac ttggactgca aggcggcatc cccaatggct acctggtgct ggatctgagc 1800
gtgcaagagg ccctctctgg cacaccttgt ttgctcggac ctggaccagt gctgacagtg 1860
ttggctctgc tgctggcctc tacactggcc tgataa 1896

<210> SEQ ID NO 62
<211> LENGTH: 630
<212> TYPE: PRT
<213> ORGANISM: Homo Sapiens

<400> SEQUENCE: 62

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Trp Glu Leu Ala Val Ala Leu Ala Gln Lys Asn Val Lys Leu
                85                  90                  95

Ser Thr Glu Gln Leu Arg Cys Leu Ala His Gln Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Leu Ala Leu Gly Gly Leu Ala Cys Asn Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Leu Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Phe Arg Asp Pro Ser Trp Arg Gln Pro Lys Gln Thr Ile
        275                 280                 285

Leu Trp Pro Arg Phe Arg Trp Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365
```

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Phe Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
    530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Glu Leu Gly Leu Gln Gly Gly Ile Pro Asn
            580                 585                 590

Gly Tyr Leu Val Leu Asp Leu Ser Val Gln Glu Ala Leu Ser Gly Thr
        595                 600                 605

Pro Cys Leu Leu Gly Pro Gly Pro Val Leu Thr Val Leu Ala Leu Leu
    610                 615                 620

Leu Ala Ser Thr Leu Ala
625                 630

<210> SEQ ID NO 63
<211> LENGTH: 2947
<212> TYPE: DNA
<213> ORGANISM: Homo Sapiens

<400> SEQUENCE: 63
cctgaacgtg accttcagct acaagatatt cttccccaac tggatctccg gccaagagta 60
cctgcaccag agcgccgaca acaacatcgt gctgtacaac atcgagacag gccagagcta 120
caccatcatg agcaaccgga ccatgaagtc cgtgaacgcc agcaactacg gactgagccc 180
cgattggcag ttcgtgtacc tggaaagcga ctacagcaag ctgtggcggt acagctacac 240
cgccacctac tacatctacg acctgagcaa cggcgagttc gtgaagggca acgagctgcc 300
ccatcctatc cagtacctgt gttggagccc tgtgggctcc aagctggcct acgtgtacca 360
gaacaacatc tacctgaagc agcggcctgg cgaccctcca ttccagatca ccttcaacgg 420
cagagagaac aagatcttta acggcatccc cgactgggtg tacgaggaag agatgctggc 480
caccaaatac gccctgtggt ggtcccctaa cggcaagttt ctggcctatg ccgacttcaa 540
cgacacagac atccccgtga tcgcctacag ctactacggc aatgagcagt accccaggac 600

```
catcaacatc agctacccca aagccggcgc taagaaccct gtcgtgcgga tcttcatcat    660
cgacaccacc tatcctgtgt acgtgggccc tcaagaggtg ccagtgcctg ccatgattgc    720
cagcagcgac tactacttca gctggctgac ctgggtcacc gacgagcgag tttgtctgca    780
gtggctgaag cgggtgcaga acatcagcgt gctgagcatc tgcgacttca gaaaggactg    840
gcagacatgg gactgcccca acacacagca gcacatcgag gaaagcagaa ccggctgggc    900
tggcggcttc tttgtgtcta cccctgtgtt cagctacgac gccatcctgt actataagat    960
cttcagcgac aaggacggct acaagcacat ccactacatc aagtacaccg tcgagaacgt   1020
gatccagatt accagcggca agtgggaagc catcaatatc ttcagagtga tccagtacag   1080
cctgttctac agcagcaacg agttcgagga ataccccggc agacggaaca tctacagaat   1140
cagcatcggc agctacccgc ctagcaagaa atgcgtgacc tgccacctga gaaaagagcg   1200
gtgccagtac tacacagcca gcttctccaa ctacgccaag tactacgccc tcgtgtgtta   1260
cggccctggc atccctatca gcacactgca cgatggcaga accgaccaag agatcaagat   1320
cctggaagaa aacaaagagc tggaaaacgc cctgaagaac atccagctgc ctaaagagga   1380
aatcaagaag ctggaagtcg acgagatcac cctgtggtac aagatgatcc tgcctcctca   1440
gttcgaccgg tccaagaagt accctctgct gatccaggtg tacggcggac cttgttctca   1500
gtctgtgcgc tccgtgttcg ccgtgaattg gatcagctat ctggccagca aagaaggcat   1560
ggttatcgcc ctggtggacg gcagaggcac agcttttcaa ggcgacaagc tgctgtacgc   1620
cgtgtatcag aaactgggcg tgtacgaagt ggaagatcag atcaccgccg tgcggaagtt   1680
catcgagatg ggcttcatcg acgagaagcg gatcgccatc tggggctggt cttacggcgg   1740
ctatattagc tctctggccc tggcctctgg caccggcctg tttaagtgtg gaattgccgt   1800
ggctcccgtg tccagctggg agtactatac cagcgtgtac accgagcggt tcatgggcct   1860
gcctaccaag gacgacaacc tggaacacta caagaactct accgtgatgg ccagagccga   1920
gtacttccgg aacgtggact acctgctgat tcacggcacc gccgacgaca acgtgcactt   1980
ccaaaacagc gcccagatcg ctaaggccct cgtgaatgcc caggtggact ttcaggccat   2040
gtggtacagc gaccagaacc acggactgtc tggcctgagc accaaccacc tgtacaccca   2100
catgacccac tttctgaaac agtgcttcag cctgagcgac cggggcagaa agagaagatc   2160
tgccgtcaca gcctgtcaga gcctgggctt tgtggtgtcc ctgatcgaga tcgtgggcat   2220
cattgccgct acctgcatgg accagtggtc tacccaggac ctgtataaca accccgtgac   2280
cgccgtgttc aactaccaag gcctgtggca cagctgcatg agagagagca gcggcttcac   2340
cgagtgcagg ggctacttta ccctgctgga actgccagcc atgctgcagg ctgtgcaggc   2400
ccttatgatc gtgggaattg tgctgggcgc catcggcctg ctggtgtcta tttttgccct   2460
gaagtgcatc cggatcggca gcatggaaga tagcgccaag gccaacatga ccctgacctc   2520
cggcatcatg ttcatcgtgt ccggcctgtg tgccattgca ggcgtgtccg tgtttgccaa   2580
tatgctcgtg accaacttct ggctgtccac cgccaacatg tacaccggca tgggcgagat   2640
ggtgcagacc gtgcagacac ggtacacatt tggcgccgct ctgtttgtcg gatgggttgc   2700
aggcggactg actctgattg gcggcgtgat gatgtgtatc gcctgcagag gactggcccc   2760
tgaggaaaca aactacaagg ccgtgtacta ccacgccagc ggacacagcg tggcatacaa   2820
accaggcggc tttaaggcca gcacaggctt cggcagcaac accaagaaca agaagatcta   2880
cgacggcgga gcccataccg aggatgaggt gcagagctac cctagcaagc acgactacgt   2940
```

gtgatga 2947

<210> SEQ ID NO 64
<211> LENGTH: 1027
<212> TYPE: PRT
<213> ORGANISM: Homo Sapiens

<400> SEQUENCE: 64

Met Lys Thr Leu Val Lys Ile Val Phe Gly Val Ala Thr Ser Ala Val
1 5 10 15

Leu Ala Leu Leu Val Met Cys Ile Val Leu His Pro Ser Arg Val His
20 25 30

Asn Ser Glu Glu Asn Thr Met Arg Ala Leu Thr Leu Lys Asp Ile Leu
35 40 45

Asn Val Thr Phe Ser Tyr Lys Ile Phe Phe Pro Asn Trp Ile Ser Gly
50 55 60

Gln Glu Tyr Leu His Gln Ser Ala Asp Asn Asn Ile Val Leu Tyr Asn
65 70 75 80

Ile Glu Thr Gly Gln Ser Tyr Thr Ile Met Ser Asn Arg Thr Met Lys
85 90 95

Ser Val Asn Ala Ser Asn Tyr Gly Leu Ser Pro Asp Trp Gln Phe Val
100 105 110

Tyr Leu Glu Ser Asp Tyr Ser Lys Leu Trp Arg Tyr Ser Tyr Thr Ala
115 120 125

Thr Tyr Tyr Ile Tyr Asp Leu Ser Asn Gly Glu Phe Val Lys Gly Asn
130 135 140

Glu Leu Pro His Pro Ile Gln Tyr Leu Cys Trp Ser Pro Val Gly Ser
145 150 155 160

Lys Leu Ala Tyr Val Tyr Gln Asn Asn Ile Tyr Leu Lys Gln Arg Pro
165 170 175

Gly Asp Pro Pro Phe Gln Ile Thr Phe Asn Gly Arg Glu Asn Lys Ile
180 185 190

Phe Asn Gly Ile Pro Asp Trp Val Tyr Glu Glu Glu Met Leu Ala Thr
195 200 205

Lys Tyr Ala Leu Trp Trp Ser Pro Asn Gly Lys Phe Leu Ala Tyr Ala
210 215 220

Asp Phe Asn Asp Thr Asp Ile Pro Val Ile Ala Tyr Ser Tyr Tyr Gly
225 230 235 240

Asn Glu Gln Tyr Pro Arg Thr Ile Asn Ile Ser Tyr Pro Lys Ala Gly
245 250 255

Ala Lys Asn Pro Val Val Arg Ile Phe Ile Ile Asp Thr Thr Tyr Pro
260 265 270

Val Tyr Val Gly Pro Gln Glu Val Pro Val Pro Ala Met Ile Ala Ser
275 280 285

Ser Asp Tyr Tyr Phe Ser Trp Leu Thr Trp Val Thr Asp Glu Arg Val
290 295 300

Cys Leu Gln Trp Leu Lys Arg Val Gln Asn Ile Ser Val Leu Ser Ile
305 310 315 320

Cys Asp Phe Arg Lys Asp Trp Gln Thr Trp Asp Cys Pro Asn Thr Gln
325 330 335

Gln His Ile Glu Glu Ser Arg Thr Gly Trp Ala Gly Gly Phe Phe Val
340 345 350

Ser Thr Pro Val Phe Ser Tyr Asp Ala Ile Leu Tyr Tyr Lys Ile Phe
355 360 365

```
Ser Asp Lys Asp Gly Tyr Lys His Ile His Tyr Ile Lys Tyr Thr Val
    370                 375                 380

Glu Asn Val Ile Gln Ile Thr Ser Gly Lys Trp Glu Ala Ile Asn Ile
385                 390                 395                 400

Phe Arg Val Ile Gln Tyr Ser Leu Phe Tyr Ser Ser Asn Glu Phe Glu
                405                 410                 415

Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
        435                 440                 445

Gln Tyr Tyr Thr Ala Ser Phe Ser Asn Tyr Ala Lys Tyr Tyr Ala Leu
    450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Glu Ile Lys Lys Leu Glu
            500                 505                 510

Val Asp Glu Ile Thr Leu Trp Tyr Lys Met Ile Leu Pro Pro Gln Phe
        515                 520                 525

Asp Arg Ser Lys Lys Tyr Pro Leu Leu Ile Gln Val Tyr Gly Gly Pro
    530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
                565                 570                 575

Thr Ala Phe Gln Gly Asp Lys Leu Leu Tyr Ala Val Tyr Gln Lys Leu
            580                 585                 590

Gly Val Tyr Glu Val Glu Asp Gln Ile Thr Ala Val Arg Lys Phe Ile
        595                 600                 605

Glu Met Gly Phe Ile Asp Glu Lys Arg Ile Ala Ile Trp Gly Trp Ser
    610                 615                 620

Tyr Gly Gly Tyr Ile Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Thr Ser Val Tyr Thr Glu Arg Phe Met Gly Leu Pro Thr Lys Asp Asp
            660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn
    690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
                725                 730                 735

Ser Gly Leu Ser Thr Asn His Leu Tyr Thr His Met Thr His Phe Leu
            740                 745                 750

Lys Gln Cys Phe Ser Leu Ser Asp Arg Gly Arg Lys Arg Arg Ser Ala
        755                 760                 765

Val Thr Ala Cys Gln Ser Leu Gly Phe Val Val Ser Leu Ile Glu Ile
    770                 775                 780

Val Gly Ile Ile Ala Ala Thr Cys Met Asp Gln Trp Ser Thr Gln Asp
```

```
785                 790                 795                 800

Leu Tyr Asn Asn Pro Val Thr Ala Val Phe Asn Tyr Gln Gly Leu Trp
                805                 810                 815

His Ser Cys Met Arg Glu Ser Ser Gly Phe Thr Glu Cys Arg Gly Tyr
            820                 825                 830

Phe Thr Leu Leu Glu Leu Pro Ala Met Leu Gln Ala Val Gln Ala Leu
        835                 840                 845

Met Ile Val Gly Ile Val Leu Gly Ala Ile Gly Leu Leu Val Ser Ile
    850                 855                 860

Phe Ala Leu Lys Cys Ile Arg Ile Gly Ser Met Glu Asp Ser Ala Lys
865                 870                 875                 880

Ala Asn Met Thr Leu Thr Ser Gly Ile Met Phe Ile Val Ser Gly Leu
                885                 890                 895

Cys Ala Ile Ala Gly Val Ser Val Phe Ala Asn Met Leu Val Thr Asn
            900                 905                 910

Phe Trp Leu Ser Thr Ala Asn Met Tyr Thr Gly Met Gly Glu Met Val
        915                 920                 925

Gln Thr Val Gln Thr Arg Tyr Thr Phe Gly Ala Ala Leu Phe Val Gly
    930                 935                 940

Trp Val Ala Gly Gly Leu Thr Leu Ile Gly Gly Val Met Met Cys Ile
945                 950                 955                 960

Ala Cys Arg Gly Leu Ala Pro Glu Glu Thr Asn Tyr Lys Ala Val Tyr
                965                 970                 975

Tyr His Ala Ser Gly His Ser Val Ala Tyr Lys Pro Gly Gly Phe Lys
            980                 985                 990

Ala Ser Thr Gly Phe Gly Ser Asn  Thr Lys Asn Lys Lys  Ile Tyr Asp
        995                 1000                1005

Gly Gly  Ala His Thr Glu Asp  Glu Val Gln Ser Tyr  Pro Ser Lys
    1010                1015                1020

His Asp  Tyr Val
    1025


<210> SEQ ID NO 65
<211> LENGTH: 2856
<212> TYPE: DNA
<213> ORGANISM: Homo Sapiens

<400> SEQUENCE: 65

atggaaagaa gaaggctctg gggcagcatc cagagccggt acatcagcat gagcgtgtgg     60

acaagccctc ggagactggt ggaactggct ggacagagcc tgctgaagga tgaggccctg    120

gccattgctg ctctggaact gctgcctaga gagctgttcc ctcctctgtt catggccgcc    180

ttcgacggca gacacagcca gacactgaaa gccatggtgc aggcctggcc tttcacctgt    240

ctgcctctgg gagtgctgat gaagggccag catctgcacc tggaaacctt caaggccgtg    300

ctggatggcc tggatgtgct gctggctcaa gaagtgcggc ctcggcgttg gaaactgcag    360

gttctggatc tgctgaagaa cagccaccag gatttctgga ccgtttggag cggcaacaga    420

gccagcctgt acagctttcc tgagcctgaa gccgctcagc ccatgaccaa gaaaagaaag    480

gtggacggcc tgagcaccga ggccgagcag ccttttattc ccgtggaagt gctggtggac    540

ctgttcctga aagaaggcgc ctgcgacgag ctgttcagct acctgaccga gaaagtgaag    600

cagaagaaga acgtcctgca cctgtgctgc aagaagctga agatctttgc catgcctatg    660

caggacatca agatgatcct gaagatggtg cagctggaca gcatcgagga cctggaagtg    720
```

-continued

```
acctgtacct ggaagctgcc cacactggcc aagttcttta gctacctggg ccagatgatc    780

aacctgcgga gactgctgct gagccacatc cacgccagct cctacatcag ccccgagaaa    840

gaggaacagt acatctccca gttcacctct cagtttctga gcctgcagtg tctgcaggcc    900

ctgtacgtgg acagcctgtt cttcctgaga ggcaggctgg accagctgct gagacacgtg    960

atgaaccctc tggaaaccct gagcatcacc aactgcagac tgctggaagg cgacgtgatg   1020

cacctgtctc agagcccatc tgtgtcccag ctgagcgtgc tgtctctgtc tggcgtgatg   1080

ctgaccgatg tgtcccctga acctctgcag gcactgctga aaaaggccag cgccactctg   1140

caggacctgg tgtttgatga gtgcggcatc atggacgacc agctgtttgc cctgctgcca   1200

agcctgagcc actgtagcca actgaccaca ctgagcttct acggcaacag catctacatc   1260

tctgccctgc agagcctcct gcagcacctg atcggactga gcaatctgac ccacgtgctg   1320

tacccagtgc tgctcgagag ctacgaggac atccacgtga ccctgcacca agagagactg   1380

gcctatctgc atgcccggct gagagaactg ctgtgcgaac tgggcagacc cagcatggtt   1440

tggctgagcg ctaatctgtg ccctcactgc ggcgacagaa ccttctacga ccccaagctg   1500

atcatgtgcc cctgcttcat gcccaaccgg ggcagaaaga gaagaagctc tagccctggc   1560

acagagagcg ccggaaagtc cctgcagtac agagtggatc atctgctgag cgccgtggaa   1620

aacgaactgc aggccggatc tgagaagggc gatcctacag agcacgagct gagagtcggc   1680

ctggaagagt ctgagctgtg gctgcggttc aaagaactga ccaacgagat gatcgtcacc   1740

aagaacggca gacggatgtt ccccgtgctg aaagtgaacg tgtccggact ggaccccaac   1800

gccatgtata gctttctgct ggacttcgtg gtggccgaca accacagatg gaaatacgtg   1860

aacggcgagt gggtgccagg cggaaaacct caactgcaag cccctagctg cgtgtacatt   1920

caccctgaca gccccaattt cggcgcccac tggatgaagg cccctgtgtc ctttagcaaa   1980

gtcaagctga ccaacaagct gaacggcgga ggccagatca tgctgaactc cctgcacaaa   2040

tacgagccca gaatccacat cgtcagagtc ggcggacccc agagaatgat caccagccac   2100

tgcttccccg agacacagtt tatcgccgtg accgcctacc agaacgagga aatcacaacc   2160

ctgaagatca agtacaaccc cttcgccaag gccttcctgg acgccaaaga gcggagcgac   2220

cacaaagaaa tgatcaaaga gcccggcgac tcccagcagc caggctattc tcaatgggga   2280

tggctgctgc caggcaccag cacattgtgc cctccagcca atcctcacag ccagtttgga   2340

ggcgctctgt ccctgagcag cacacacagc tacgacagat accccacact gcggagccac   2400

agaagcagcc cctatccttc tccttacgct caccggaaca acagccccac ctacagcgat   2460

aatagccccg cctgtctgag catgctgcag tcccacgata attggagcag cctgcggatg   2520

cctgctcacc cttctatgct gcccgtgtct cacaacgcct ctccacctac aagcagctct   2580

cagtacccca gcctttggag cgtgtccaat ggcgctgtga cactgggatc tcaggccgct   2640

gctgtgtcta atggactggg agcccagttc ttcagaggca gccctgctca ctacacccct   2700

ctgacacatc ctgtgtcagc cccttctagc agcggcttcc ctatgtacaa aggcgccgct   2760

gccgccaccg atatcgtgga ttctcagtac gatgccgccg ctcagggcca cctgattgca   2820

tcttggacac ctgtgtctcc accttccatg tgatga                             2856
```

<210> SEQ ID NO 66
<211> LENGTH: 950
<212> TYPE: PRT
<213> ORGANISM: Homo Sapiens

<400> SEQUENCE: 66

```
Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser Leu Leu Lys Asp Glu Ala Leu Ala Ile Ala Ala Leu Glu Leu Leu
        35                  40                  45

Pro Arg Glu Leu Phe Pro Pro Leu Phe Met Ala Ala Phe Asp Gly Arg
    50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Leu Lys Asn Ser
        115                 120                 125

His Gln Asp Phe Trp Thr Val Trp Ser Gly Asn Arg Ala Ser Leu Tyr
    130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Thr Glu Lys Val Lys Gln Lys Lys Asn Val Leu His Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Phe Ser Tyr Leu
                245                 250                 255

Gly Gln Met Ile Asn Leu Arg Arg Leu Leu Leu Ser His Ile His Ala
            260                 265                 270

Ser Ser Tyr Ile Ser Pro Glu Lys Glu Glu Gln Tyr Ile Ser Gln Phe
        275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Leu Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365

Leu Gln Ala Leu Leu Lys Lys Ala Ser Ala Thr Leu Gln Asp Leu Val
    370                 375                 380

Phe Asp Glu Cys Gly Ile Met Asp Asp Gln Leu Phe Ala Leu Leu Pro
385                 390                 395                 400

Ser Leu Ser His Cys Ser Gln Leu Thr Thr Leu Ser Phe Tyr Gly Asn
                405                 410                 415
```

```
Ser Ile Tyr Ile Ser Ala Leu Gln Ser Leu Leu Gln His Leu Ile Gly
            420                 425                 430

Leu Ser Asn Leu Thr His Val Leu Tyr Pro Val Leu Leu Glu Ser Tyr
        435                 440                 445

Glu Asp Ile His Val Thr Leu His Gln Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Leu Cys Pro His Cys Gly Asp Arg Thr Phe Tyr
                485                 490                 495

Asp Pro Lys Leu Ile Met Cys Pro Cys Phe Met Pro Asn Arg Gly Arg
            500                 505                 510

Lys Arg Arg Ser Ser Ser Pro Gly Thr Glu Ser Ala Gly Lys Ser Leu
        515                 520                 525

Gln Tyr Arg Val Asp His Leu Leu Ser Ala Val Glu Asn Glu Leu Gln
    530                 535                 540

Ala Gly Ser Glu Lys Gly Asp Pro Thr Glu His Glu Leu Arg Val Gly
545                 550                 555                 560

Leu Glu Glu Ser Glu Leu Trp Leu Arg Phe Lys Glu Leu Thr Asn Glu
                565                 570                 575

Met Ile Val Thr Lys Asn Gly Arg Arg Met Phe Pro Val Leu Lys Val
            580                 585                 590

Asn Val Ser Gly Leu Asp Pro Asn Ala Met Tyr Ser Phe Leu Leu Asp
        595                 600                 605

Phe Val Val Ala Asp Asn His Arg Trp Lys Tyr Val Asn Gly Glu Trp
    610                 615                 620

Val Pro Gly Gly Lys Pro Gln Leu Gln Ala Pro Ser Cys Val Tyr Ile
625                 630                 635                 640

His Pro Asp Ser Pro Asn Phe Gly Ala His Trp Met Lys Ala Pro Val
                645                 650                 655

Ser Phe Ser Lys Val Lys Leu Thr Asn Lys Leu Asn Gly Gly Gly Gln
            660                 665                 670

Ile Met Leu Asn Ser Leu His Lys Tyr Glu Pro Arg Ile His Ile Val
        675                 680                 685

Arg Val Gly Gly Pro Gln Arg Met Ile Thr Ser His Cys Phe Pro Glu
    690                 695                 700

Thr Gln Phe Ile Ala Val Thr Ala Tyr Gln Asn Glu Glu Ile Thr Thr
705                 710                 715                 720

Leu Lys Ile Lys Tyr Asn Pro Phe Ala Lys Ala Phe Leu Asp Ala Lys
                725                 730                 735

Glu Arg Ser Asp His Lys Glu Met Ile Lys Glu Pro Gly Asp Ser Gln
            740                 745                 750

Gln Pro Gly Tyr Ser Gln Trp Gly Trp Leu Leu Pro Gly Thr Ser Thr
        755                 760                 765

Leu Cys Pro Pro Ala Asn Pro His Ser Gln Phe Gly Gly Ala Leu Ser
    770                 775                 780

Leu Ser Ser Thr His Ser Tyr Asp Arg Tyr Pro Thr Leu Arg Ser His
785                 790                 795                 800

Arg Ser Ser Pro Tyr Pro Ser Pro Tyr Ala His Arg Asn Asn Ser Pro
                805                 810                 815

Thr Tyr Ser Asp Asn Ser Pro Ala Cys Leu Ser Met Leu Gln Ser His
            820                 825                 830

Asp Asn Trp Ser Ser Leu Arg Met Pro Ala His Pro Ser Met Leu Pro
```

```
        835                 840                 845

Val Ser His Asn Ala Ser Pro Pro Thr Ser Ser Ser Gln Tyr Pro Ser
    850                 855                 860

Leu Trp Ser Val Ser Asn Gly Ala Val Thr Leu Gly Ser Gln Ala Ala
865                 870                 875                 880

Ala Val Ser Asn Gly Leu Gly Ala Gln Phe Phe Arg Gly Ser Pro Ala
                885                 890                 895

His Tyr Thr Pro Leu Thr His Pro Val Ser Ala Pro Ser Ser Ser Gly
            900                 905                 910

Phe Pro Met Tyr Lys Gly Ala Ala Ala Ala Thr Asp Ile Val Asp Ser
        915                 920                 925

Gln Tyr Asp Ala Ala Ala Gln Gly His Leu Ile Ala Ser Trp Thr Pro
    930                 935                 940

Val Ser Pro Pro Ser Met
945                 950


<210> SEQ ID NO 67
<211> LENGTH: 1617
<212> TYPE: DNA
<213> ORGANISM: Homo Sapiens

<400> SEQUENCE: 67

atgcaccaga aacggaccgc catgtttcag gaccctcaag agaggcccag aaagctgcct     60

cacctgtgta ccgagctgca gaccaccatc cacgacatca tcctggaatg cgtgtactgc    120

aagcagcagc tcctgcggag agaggtgtac gatttcgcct tccgggacct gtgcatcgtg    180

tacagagatg gcaacccta cgccgtgtgc aacaagtgcc tgaagttcta cagcaagatc    240

agcgagtacc gctactactg ctacagcgtg tacggcacca cactggaaca gcagtacaac    300

aagcccctgt gcgacctgct gatccggtgc atcaactgcc agaaacctct gtgccccgag    360

gaaaagcagc ggcacctgga caagaagcag cggttccaca acatcagagg ccggtggacc    420

ggcagatgca tgagctgttg tcggagcagc cggaccagaa gagagacaca gctgagaggc    480

cggaagagaa gaagccacgg cgataccct acactgcacg agtacatgct ggacctgcag    540

cctgagacaa ccgacctgta ctgctacgag cagctgaacg acagcagcga ggaagaggac    600

gagattgacg gacctgccgg acaggccgaa cctgatagag cccactacaa tatcgtgacc    660

ttctgctgca agtgcaacag caccctgaga ctgtgcgtgc agagcaccca cgtggacatc    720

agaaccctgg aagatctgct gatgggcacc ctgggaatcg tgtgccctat ctgcagccag    780

aagcctagag gcagaaagcg gagaagcgcc agattcgacg accccaccag aaggccttac    840

aagctgcctg atctgtgcac tgaactgaac accagcctgc aggacatcga gattacctgt    900

gtgtattgca agaccgtgct ggaactgacc gaggtgttcg agtttgcctt taaggacctg    960

ttcgtggtgt accgggacag cattcctcac gccgcctgcc acaagtgcat cgacttctac   1020

agccggatca gagagctgcg gcactacagc gattctgtgt acggggacac cctggaaaag   1080

ctgaccaaca ccggcctgta caacctgctc atcagatgcc tgcggtgtca gaagcccctg   1140

aatcctgccg agaagctgag acacctgaac gagaagcgga gattccacaa tatcgccggc   1200

cactacagag gccagtgcca cagctgttgc aaccgggcca gacaagagag actgcagaga   1260

aggcgggaaa cccaagtgcg gggcagaaag agaagatctc acggccctaa ggccacactg   1320

caggatatcg tgctgcacct ggaacctcag aacgagatcc ccgtggatct gctgtgccat   1380

gagcagctgt ccgactccaa agaggaaaac gacgaaatcg acggcgtgaa ccaccagcat   1440
```

ctgcctgcca gaagggccga accacagaga cacaccatgc tgtgcatgtg ttgcaagtgc 1500
gaggcccgga ttgagctggt ggtggaaagc tctgccgacg acctgagagc cttccagcag 1560
ctgttcctga acaccctgag cttcgtgtgt ccttggtgcg ccagccagca gtgataa 1617

<210> SEQ ID NO 68
<211> LENGTH: 537
<212> TYPE: PRT
<213> ORGANISM: Homo Sapiens

<400> SEQUENCE: 68

Met His Gln Lys Arg Thr Ala Met Phe Gln Asp Pro Gln Glu Arg Pro
1 5 10 15

Arg Lys Leu Pro His Leu Cys Thr Glu Leu Gln Thr Thr Ile His Asp
20 25 30

Ile Ile Leu Glu Cys Val Tyr Cys Lys Gln Gln Leu Leu Arg Arg Glu
35 40 45

Val Tyr Asp Phe Ala Phe Arg Asp Leu Cys Ile Val Tyr Arg Asp Gly
50 55 60

Asn Pro Tyr Ala Val Cys Asn Lys Cys Leu Lys Phe Tyr Ser Lys Ile
65 70 75 80

Ser Glu Tyr Arg Tyr Tyr Cys Tyr Ser Val Tyr Gly Thr Thr Leu Glu
85 90 95

Gln Gln Tyr Asn Lys Pro Leu Cys Asp Leu Leu Ile Arg Cys Ile Asn
100 105 110

Cys Gln Lys Pro Leu Cys Pro Glu Glu Lys Gln Arg His Leu Asp Lys
115 120 125

Lys Gln Arg Phe His Asn Ile Arg Gly Arg Trp Thr Gly Arg Cys Met
130 135 140

Ser Cys Cys Arg Ser Ser Arg Thr Arg Arg Glu Thr Gln Leu Arg Gly
145 150 155 160

Arg Lys Arg Arg Ser His Gly Asp Thr Pro Thr Leu His Glu Tyr Met
165 170 175

Leu Asp Leu Gln Pro Glu Thr Thr Asp Leu Tyr Cys Tyr Glu Gln Leu
180 185 190

Asn Asp Ser Ser Glu Glu Glu Asp Glu Ile Asp Gly Pro Ala Gly Gln
195 200 205

Ala Glu Pro Asp Arg Ala His Tyr Asn Ile Val Thr Phe Cys Cys Lys
210 215 220

Cys Asn Ser Thr Leu Arg Leu Cys Val Gln Ser Thr His Val Asp Ile
225 230 235 240

Arg Thr Leu Glu Asp Leu Leu Met Gly Thr Leu Gly Ile Val Cys Pro
245 250 255

Ile Cys Ser Gln Lys Pro Arg Gly Arg Lys Arg Arg Ser Ala Arg Phe
260 265 270

Asp Asp Pro Thr Arg Arg Pro Tyr Lys Leu Pro Asp Leu Cys Thr Glu
275 280 285

Leu Asn Thr Ser Leu Gln Asp Ile Glu Ile Thr Cys Val Tyr Cys Lys
290 295 300

Thr Val Leu Glu Leu Thr Glu Val Phe Glu Phe Ala Phe Lys Asp Leu
305 310 315 320

Phe Val Val Tyr Arg Asp Ser Ile Pro His Ala Ala Cys His Lys Cys
325 330 335

Ile Asp Phe Tyr Ser Arg Ile Arg Glu Leu Arg His Tyr Ser Asp Ser
340 345 350

Val Tyr Gly Asp Thr Leu Glu Lys Leu Thr Asn Thr Gly Leu Tyr Asn
355 360 365

Leu Leu Ile Arg Cys Leu Arg Cys Gln Lys Pro Leu Asn Pro Ala Glu
370 375 380

Lys Leu Arg His Leu Asn Glu Lys Arg Arg Phe His Asn Ile Ala Gly
385 390 395 400

His Tyr Arg Gly Gln Cys His Ser Cys Cys Asn Arg Ala Arg Gln Glu
405 410 415

Arg Leu Gln Arg Arg Arg Glu Thr Gln Val Arg Gly Arg Lys Arg Arg
420 425 430

Ser His Gly Pro Lys Ala Thr Leu Gln Asp Ile Val Leu His Leu Glu
435 440 445

Pro Gln Asn Glu Ile Pro Val Asp Leu Leu Cys His Glu Gln Leu Ser
450 455 460

Asp Ser Lys Glu Glu Asn Asp Glu Ile Asp Gly Val Asn His Gln His
465 470 475 480

Leu Pro Ala Arg Arg Ala Glu Pro Gln Arg His Thr Met Leu Cys Met
485 490 495

Cys Cys Lys Cys Glu Ala Arg Ile Glu Leu Val Val Glu Ser Ser Ala
500 505 510

Asp Asp Leu Arg Ala Phe Gln Gln Leu Phe Leu Asn Thr Leu Ser Phe
515 520 525

Val Cys Pro Trp Cys Ala Ser Gln Gln
530 535

<210> SEQ ID NO 69
<211> LENGTH: 2253
<212> TYPE: DNA
<213> ORGANISM: Homo Sapiens

<400> SEQUENCE: 69
atgtggaatc tccttcacga aaccgactcg gctgtggcca ccgcgcgccg cccgcgctgg 60
ctgtgcgctg gggcgctggt gctggcgggt ggcttctttc tcctcggctt cctcttcggg 120
tggtttataa aatcctccaa tgaagctact aacattactc caaagcataa tatgaaagca 180
tttttggatg aattgaaagc tgagaacatc aagaagttct tatataattt tacacagata 240
ccacatttag caggaacaga acaaaacttt cagcttgcaa agcaaattca atcccagtgg 300
aaagaatttg gcctggattc tgttgagcta gcacattatg atgtcctgtt gtcctaccca 360
aataagactc atcccaacta catctcaata attaatgaag atggaaatga gattttcaac 420
acatcattat ttgaaccacc tcctccagga tatgaaaatg tttcggatat tgtaccacct 480
ttcagtgctt tctctcctca aggaatgcca gagggcgatc tagtgtatgt taactatgca 540
cgaactgaag acttctttaa attggaacgg gacatgaaaa tcaattgctc tgggaaaatt 600
gtaattgcca gatatgggaa agttttcaga ggaaataagg ttaaaaatgc ccagctggca 660
ggggccaaag gagtcattct ctactccgac cctgctgact actttgctcc tggggtgaag 720
tcctatccag atggttggaa tcttcctgga ggtggtgtcc agcgtggaaa tatcctaaat 780
ctgaatggtg caggagaccc tctcacacca ggttacccag caaatgaata tgcttatagg 840
cgtggaattg cagaggctgt tggtcttcca agtattcctg ttcatccaat tggatactat 900
gatgcacaga agctcctaga aaaaatgggt ggctcagcac caccagatag cagctggaga 960
ggaagtctca aagtgcccta caatgttgga cctggcttta ctggaaactt ttctacacaa 1020
aaagtcaaga tgcacatcca ctctaccaat gaagtgacaa gaatttacaa tgtgataggt 1080
actctcagag gagcagtgga accagacaga tatgtcattc tgggaggtca ccgggactca 1140
tgggtgtttg gtggtattga ccctcagagt ggagcagctg ttgttcatga aattgtgagg 1200
agctttggaa cactgaaaaa ggaagggtgg agacctagaa gaacaatttt gtttgcaagc 1260
tgggatgcag aagaatttgg tcttcttggt tctactgagt gggcagagga gaattcaaga 1320
ctccttcaag agcgtggcgt ggcttatatt aatgctgact catctataga aggaaactac 1380
actctgagag ttgattgtac accgctgatg tacagcttgg tacacaacct aacaaaagag 1440
ctgaaaagcc ctgatgaagg ctttgaaggc aaatctcttt atgaaagttg gactaaaaaa 1500
agtccttccc cagagttcag tggcatgccc aggataagca aattgggatc tggaaatgat 1560
tttgaggtgt tcttccaacg acttggaatt gcttcaggca gagcacggta tactaaaaat 1620
tgggaaacaa acaaattcag cggctatcca ctgtatcaca gtgtctatga aacatatgag 1680
ttggtggaaa agttttatga tccaatgttt aaatatcacc tcactgtggc ccaggttcga 1740
ggagggatgg tgtttgagct agccaattcc atagtgctcc cttttgattg tcgagattat 1800
gctgtagttt taagaaagta tgctgacaaa atctacagta tttctatgaa acatccacag 1860
gaaatgaaga catacagtgt atcatttgat tcactttttt ctgcagtaaa gaattttaca 1920
gaaattgctt ccaagttcag tgagagactc caggactttg acaaaagcaa cccaatagta 1980
ttaagaatga tgaatgatca actcatgttt ctggaaagag catttattga tccattaggg 2040
ttaccagaca ggccttttta taggcatgtc atctatgctc caagcagcca caacaagtat 2100
gcaggggagt cattcccagg aatttatgat gctctgtttg atattgaaag caaagtggac 2160
ccttccaagg cctggggaga agtgaagaga cagatttatg ttgcagcctt cacagtgcag 2220
gcagctgcag agactttgag tgaagtagcc taa 2253

<210> SEQ ID NO 70
<211> LENGTH: 750
<212> TYPE: PRT
<213> ORGANISM: Homo Sapiens

<400> SEQUENCE: 70

Met Trp Asn Leu Leu His Glu Thr Asp Ser Ala Val Ala Thr Ala Arg
1 5 10 15

Arg Pro Arg Trp Leu Cys Ala Gly Ala Leu Val Leu Ala Gly Gly Phe
20 25 30

Phe Leu Leu Gly Phe Leu Phe Gly Trp Phe Ile Lys Ser Ser Asn Glu
35 40 45

Ala Thr Asn Ile Thr Pro Lys His Asn Met Lys Ala Phe Leu Asp Glu
50 55 60

Leu Lys Ala Glu Asn Ile Lys Lys Phe Leu Tyr Asn Phe Thr Gln Ile
65 70 75 80

Pro His Leu Ala Gly Thr Glu Gln Asn Phe Gln Leu Ala Lys Gln Ile
85 90 95

Gln Ser Gln Trp Lys Glu Phe Gly Leu Asp Ser Val Glu Leu Ala His
100 105 110

Tyr Asp Val Leu Leu Ser Tyr Pro Asn Lys Thr His Pro Asn Tyr Ile
115 120 125

Ser Ile Ile Asn Glu Asp Gly Asn Glu Ile Phe Asn Thr Ser Leu Phe
130 135 140

Glu Pro Pro Pro Pro Gly Tyr Glu Asn Val Ser Asp Ile Val Pro Pro
145 150 155 160

-continued

```
Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575
```

```
Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750
```

<210> SEQ ID NO 71
<211> LENGTH: 58
<212> TYPE: DNA
<213> ORGANISM: Homo Sapiens

<400> SEQUENCE: 71

```
ccggtgctgg agaaagatca aacagctcga gctgtttgat ctttctccag catttttt        58
```

<210> SEQ ID NO 72
<211> LENGTH: 927
<212> TYPE: DNA
<213> ORGANISM: Homo Sapiens

<400> SEQUENCE: 72

```
atgtctctcg aacagagaag cctgcactgc aagcccgagg aagctctgga agctcagcaa      60

gaggctctgg gccttgtgtg tgttcaggcc gctgccagca gcttttctcc tctggtgctg     120

ggcacactgg aagaggtgcc aacagccggc tctaccgatc ctcctcaatc tcctcaaggc     180

gccagcgcct ttcctaccac catcaacttc acccggcaga gacagcctag cgagggctct     240

agctctcacg aggaaaaggg ccctagcacc agctgcatcc tggaaagcct gttccgggcc     300

gtgatcacaa agaaagtggc cgacctcgtg ggcttcctgc tgctgaagta cagagccaga     360

gaacccgtga ccaaggccga gatgctggaa agcgtgatca agaactacaa gcactgcttc     420

agcgagatct tcggcaaggc cagcgagtct ctgcagctcg tgtttggcat cgacgtgaaa     480

gaggccgatc ctaccggcca cagctacgtg ttcgtgacat gtctgggcct gagctacgat     540

ggcctgctgg gcgacaatca gattatgctg aaaaccggct tcctgatcat cgtgctggtc     600

atgatcgcca tggaaggctc tcacgcccct aaagaggaaa tctgggaaga actgagcgtg     660

atggaagtgt acgacggcag agagcatagc gcctacggcg agcctagaaa actgctgacc     720

caggacctgg tgcaagagaa gtacctcgag tacagacagg tgcccgacag cgaccctgcc     780

agatacgaat ttctgtgggg ccctagagca ctggccgaga caagctatgt gaaggtgctg     840
```

gaatacgtca tcaaggtgtc cgccagagtg tgcttcttct tcccatctct gcgggaagcc 900
gctctgcgcg aagaggaaga aggcgtc 927

<210> SEQ ID NO 73
<211> LENGTH: 309
<212> TYPE: PRT
<213> ORGANISM: Homo Sapiens

<400> SEQUENCE: 73

Met Ser Leu Glu Gln Arg Ser Leu His Cys Lys Pro Glu Glu Ala Leu
1 5 10 15

Glu Ala Gln Gln Glu Ala Leu Gly Leu Val Cys Val Gln Ala Ala Ala
20 25 30

Ser Ser Phe Ser Pro Leu Val Leu Gly Thr Leu Glu Glu Val Pro Thr
35 40 45

Ala Gly Ser Thr Asp Pro Pro Gln Ser Pro Gln Gly Ala Ser Ala Phe
50 55 60

Pro Thr Thr Ile Asn Phe Thr Arg Gln Arg Gln Pro Ser Glu Gly Ser
65 70 75 80

Ser Ser His Glu Glu Lys Gly Pro Ser Thr Ser Cys Ile Leu Glu Ser
85 90 95

Leu Phe Arg Ala Val Ile Thr Lys Lys Val Ala Asp Leu Val Gly Phe
100 105 110

Leu Leu Leu Lys Tyr Arg Ala Arg Glu Pro Val Thr Lys Ala Glu Met
115 120 125

Leu Glu Ser Val Ile Lys Asn Tyr Lys His Cys Phe Ser Glu Ile Phe
130 135 140

Gly Lys Ala Ser Glu Ser Leu Gln Leu Val Phe Gly Ile Asp Val Lys
145 150 155 160

Glu Ala Asp Pro Thr Gly His Ser Tyr Val Phe Val Thr Cys Leu Gly
165 170 175

Leu Ser Tyr Asp Gly Leu Leu Gly Asp Asn Gln Ile Met Leu Lys Thr
180 185 190

Gly Phe Leu Ile Ile Val Leu Val Met Ile Ala Met Glu Gly Ser His
195 200 205

Ala Pro Lys Glu Glu Ile Trp Glu Glu Leu Ser Val Met Glu Val Tyr
210 215 220

Asp Gly Arg Glu His Ser Ala Tyr Gly Glu Pro Arg Lys Leu Leu Thr
225 230 235 240

Gln Asp Leu Val Gln Glu Lys Tyr Leu Glu Tyr Arg Gln Val Pro Asp
245 250 255

Ser Asp Pro Ala Arg Tyr Glu Phe Leu Trp Gly Pro Arg Ala Leu Ala
260 265 270

Glu Thr Ser Tyr Val Lys Val Leu Glu Tyr Val Ile Lys Val Ser Ala
275 280 285

Arg Val Cys Phe Phe Phe Pro Ser Leu Arg Glu Ala Ala Leu Arg Glu
290 295 300

Glu Glu Glu Gly Val
305

<210> SEQ ID NO 74
<211> LENGTH: 42
<212> TYPE: DNA
<213> ORGANISM: Homo Sapiens

<400> SEQUENCE: 74
ctggaagaga aaaagggcaa ctacgtggtc accgaccact gc 42

<210> SEQ ID NO 75
<211> LENGTH: 14
<212> TYPE: PRT
<213> ORGANISM: Homo Sapiens

<400> SEQUENCE: 75

Leu Glu Glu Lys Lys Gly Asn Tyr Val Val Thr Asp His Cys
1 5 10

<210> SEQ ID NO 76
<211> LENGTH: 1680
<212> TYPE: DNA
<213> ORGANISM: Homo Sapiens

<400> SEQUENCE: 76
gagtctagag gcagacggtg ccctgagatg attagcgtgc tgggccctat ctctggccac 60
gtgctgaagg ccgtgttcag cagaggcgat acacctgtgc tgccccacga gacaagactg 120
ctgcagacag gcatccatgt gcgggtgtca cagccaagcc tgatcctggt gtctcagtac 180
acccctgaca gcaccccttg tcacagaggc gacaaccagc tccaggtgca gcacacctac 240
tttaccggca gcgaggtgga aaacgtgtcc gtgaacgtgc acaatcccac cggcagatcc 300
atctgtccca gccaagagcc tatgagcatc tacgtgtacg ccctgcctct gaagatgctg 360
aacatcccca gcatcaatgt gcatcactac ccctctgccg ccgagcggaa acacagacat 420
ctgcctgtgg ccgatgccgt gattcacgcc tctggaaagc agatgtggca ggccagactg 480
acagtgtccg gactggcttg gaccagacag cagaaccagt ggaaagaacc cgacgtgtac 540
tacacctccg ccttcgtgtt ccccacaaag gacgtggccc tgagacacgt tgtgtgcgcc 600
catgaactcg tgtgcagcat ggaaaacacc cgggccacca agatgcaagt gatcggcgac 660
cagtacgtga aggtgtacct ggaatccttc tgcgaggacg tgccaagcgg caagctgttc 720
atgcacgtga ccctgggctc cgatgtggaa gaggacctga ccatgaccag aaatccccag 780
cctttcatgc ggcctcacga gagaaatggc ttcaccgtgc tgtgccccaa gaacatgatc 840
atcaagcccg gcaagatcag ccacatcatg ctggatgtgg ccttcaccag ccacgagcac 900
ttcggactgc tgtgtcctaa gagcatcccc ggcctgagca tcagcggcaa cctgctgatg 960
aatggccagc agatcttcct ggaagtgcag gccattcggg aaaccgtgga actgagacag 1020
tacgaccctg tggctgccct gttcttcttc gacatcgatc tgctgctcca gagaggccct 1080
cagtacagcg agcacccaac ctttaccagc cagtacagaa tccagggcaa gctggaatat 1140
cggcacacct gggatagaca cgatgagggt gctgcacagg gcgacgatga tgtgtggaca 1200
agcggcagcg atagcgacga ggaactggtc accaccgaga gaaagacccc tagagttaca 1260
ggcggaggcg caatggctgg cgcttctaca tctgccggac gcaagagaaa gagcgcctct 1320
tctgccaccg cctgtacaag cggcgtgatg acaagaggca ggctgaaagc cgagagcaca 1380
gtggcccctg aggaagatac agacgaggac agcgacaacg agattcacaa ccccgccgtg 1440
tttacctggc ctccttggca ggctggcatt ctggctagaa acctggtgcc tatggtggcc 1500
acagtgcagg gccagaacct gaagtaccaa gagttcttct gggacgccaa cgacatctac 1560
cggatcttcg ccgaactgga aggcgtgtgg caaccagccg ctcagcccaa aagacgcaga 1620
cacagacagg acgctctgcc cggaccttgt attgccagca cacccaagaa acaccggggc 1680

```
<210> SEQ ID NO 77
<211> LENGTH: 560
<212> TYPE: PRT
<213> ORGANISM: Homo Sapiens

<400> SEQUENCE: 77

Glu Ser Arg Gly Arg Arg Cys Pro Glu Met Ile Ser Val Leu Gly Pro
1               5                   10                  15

Ile Ser Gly His Val Leu Lys Ala Val Phe Ser Arg Gly Asp Thr Pro
            20                  25                  30

Val Leu Pro His Glu Thr Arg Leu Leu Gln Thr Gly Ile His Val Arg
        35                  40                  45

Val Ser Gln Pro Ser Leu Ile Leu Val Ser Gln Tyr Thr Pro Asp Ser
    50                  55                  60

Thr Pro Cys His Arg Gly Asp Asn Gln Leu Gln Val Gln His Thr Tyr
65                  70                  75                  80

Phe Thr Gly Ser Glu Val Glu Asn Val Ser Val Asn Val His Asn Pro
                85                  90                  95

Thr Gly Arg Ser Ile Cys Pro Ser Gln Glu Pro Met Ser Ile Tyr Val
            100                 105                 110

Tyr Ala Leu Pro Leu Lys Met Leu Asn Ile Pro Ser Ile Asn Val His
        115                 120                 125

His Tyr Pro Ser Ala Ala Glu Arg Lys His Arg His Leu Pro Val Ala
    130                 135                 140

Asp Ala Val Ile His Ala Ser Gly Lys Gln Met Trp Gln Ala Arg Leu
145                 150                 155                 160

Thr Val Ser Gly Leu Ala Trp Thr Arg Gln Gln Asn Gln Trp Lys Glu
                165                 170                 175

Pro Asp Val Tyr Tyr Thr Ser Ala Phe Val Phe Pro Thr Lys Asp Val
            180                 185                 190

Ala Leu Arg His Val Val Cys Ala His Glu Leu Val Cys Ser Met Glu
        195                 200                 205

Asn Thr Arg Ala Thr Lys Met Gln Val Ile Gly Asp Gln Tyr Val Lys
    210                 215                 220

Val Tyr Leu Glu Ser Phe Cys Glu Asp Val Pro Ser Gly Lys Leu Phe
225                 230                 235                 240

Met His Val Thr Leu Gly Ser Asp Val Glu Glu Asp Leu Thr Met Thr
                245                 250                 255

Arg Asn Pro Gln Pro Phe Met Arg Pro His Glu Arg Asn Gly Phe Thr
            260                 265                 270

Val Leu Cys Pro Lys Asn Met Ile Ile Lys Pro Gly Lys Ile Ser His
        275                 280                 285

Ile Met Leu Asp Val Ala Phe Thr Ser His Glu His Phe Gly Leu Leu
    290                 295                 300

Cys Pro Lys Ser Ile Pro Gly Leu Ser Ile Ser Gly Asn Leu Leu Met
305                 310                 315                 320

Asn Gly Gln Gln Ile Phe Leu Glu Val Gln Ala Ile Arg Glu Thr Val
                325                 330                 335

Glu Leu Arg Gln Tyr Asp Pro Val Ala Ala Leu Phe Phe Phe Asp Ile
            340                 345                 350

Asp Leu Leu Leu Gln Arg Gly Pro Gln Tyr Ser Glu His Pro Thr Phe
        355                 360                 365

Thr Ser Gln Tyr Arg Ile Gln Gly Lys Leu Glu Tyr Arg His Thr Trp
    370                 375                 380
```

```
Asp Arg His Asp Glu Gly Ala Ala Gln Gly Asp Asp Asp Val Trp Thr
385                 390                 395                 400

Ser Gly Ser Asp Ser Asp Glu Glu Leu Val Thr Thr Glu Arg Lys Thr
                405                 410                 415

Pro Arg Val Thr Gly Gly Gly Ala Met Ala Gly Ala Ser Thr Ser Ala
            420                 425                 430

Gly Arg Lys Arg Lys Ser Ala Ser Ser Ala Thr Ala Cys Thr Ser Gly
        435                 440                 445

Val Met Thr Arg Gly Arg Leu Lys Ala Glu Ser Thr Val Ala Pro Glu
    450                 455                 460

Glu Asp Thr Asp Glu Asp Ser Asp Asn Glu Ile His Asn Pro Ala Val
465                 470                 475                 480

Phe Thr Trp Pro Pro Trp Gln Ala Gly Ile Leu Ala Arg Asn Leu Val
                485                 490                 495

Pro Met Val Ala Thr Val Gln Gly Gln Asn Leu Lys Tyr Gln Glu Phe
            500                 505                 510

Phe Trp Asp Ala Asn Asp Ile Tyr Arg Ile Phe Ala Glu Leu Glu Gly
        515                 520                 525

Val Trp Gln Pro Ala Ala Gln Pro Lys Arg Arg Arg His Arg Gln Asp
    530                 535                 540

Ala Leu Pro Gly Pro Cys Ile Ala Ser Thr Pro Lys Lys His Arg Gly
545                 550                 555                 560
```

<210> SEQ ID NO 78
<211> LENGTH: 1305
<212> TYPE: DNA
<213> ORGANISM: Homo Sapiens

<400> SEQUENCE: 78

```
atgtctagcc ctggaacaga gtctgccggc aagagcctgc agtacagagt ggaccatctg      60

ctgagcgccg tggaaaatga actgcaggcc ggaagcgaga agggcgatcc tacagagcac     120

gagctgagag tcggcctgga agagtctgag ctgtggctgc ggttcaaaga actgaccaac     180

gagatgatcg tgaccaagaa cggcagacgg atgttccccg tgctgaaagt gaacgtgtcc     240

ggactggacc ccaacgccat gtacagcttt ctgctggact tcgtggtggc cgacaaccac     300

agatggaaat acgtgaacgg cgagtgggtg ccaggcggaa aacctcaact gcaagcccct     360

agctgcgtgt acattcaccc tgacagcccc aatttcggcg cccactggat gaaggcccct     420

gtgtccttca gcaaagtgaa gctgaccaac aagctgaacg gcggaggcca gatcatgctg     480

aacagcctgc acaaatacga gcccagaatc cacatcgtca gagtcggcgg accccagaga     540

atgatcacca gccactgctt ccccgagaca cagtttatcg ccgtgaccgc ctaccagaac     600

gaggaaatca ccacactgaa gatcaagtac aacccccttcg ccaaggcctt cctggacgcc     660

aaagagcgga gcgaccacaa agagatgatc aaagagcccg gcgacagcca gcagccaggc     720

tattctcaat ggggatggct gctgccaggc accagcacat tgtgccctcc agccaatcct     780

cacagccagt ttggaggcgc cctgagcctg tctagcaccc acagctacga cagatacccc     840

acactgcgga gccacagaag cagcccctat ccttctcctt acgctcaccg gaacaacagc     900

cccacctaca gcgataatag ccccgcctgt ctgagcatgc tgcagtccca cgataactgg     960

tccagcctga gaatgcctgc tcacccttcc atgctgcccg tgtctcacaa tgcctctcca    1020

cctaccagca gctctcagta ccctagcctt tggagcgtgt ccaatggcgc cgtgacactg    1080

ggatctcagg cagccgctgt gtctaatgga ctgggagccc agttcttcag aggcagccct    1140
```

```
gctcactaca cccctctgac acatcctgtg tctgccccta gcagcagcgg cttccctatg   1200

tataagggcg ctgccgccgc taccgacatc gtggattctc agtatgatgc cgccgcacag   1260

ggacacctga tcgcctcttg gacacctgtg tctccacctt ccatg                   1305


<210> SEQ ID NO 79
<211> LENGTH: 435
<212> TYPE: PRT
<213> ORGANISM: Homo Sapiens

<400> SEQUENCE: 79

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu His Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Val
                85                  90                  95

Ala Asp Asn His Arg Trp Lys Tyr Val Asn Gly Glu Trp Val Pro Gly
            100                 105                 110

Gly Lys Pro Gln Leu Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Thr Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Ile Lys Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Ser Gln Phe Gly Gly Ala Leu Ser Leu Ser Ser
            260                 265                 270

Thr His Ser Tyr Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Arg Met Pro Ala His Pro Ser Met Leu Pro Val Ser His
                325                 330                 335

Asn Ala Ser Pro Pro Thr Ser Ser Ser Gln Tyr Pro Ser Leu Trp Ser
            340                 345                 350
```

-continued

```
Val Ser Asn Gly Ala Val Thr Leu Gly Ser Gln Ala Ala Ala Val Ser
        355                 360                 365

Asn Gly Leu Gly Ala Gln Phe Phe Arg Gly Ser Pro Ala His Tyr Thr
    370                 375                 380

Pro Leu Thr His Pro Val Ser Ala Pro Ser Ser Ser Gly Phe Pro Met
385                 390                 395                 400

Tyr Lys Gly Ala Ala Ala Ala Thr Asp Ile Val Asp Ser Gln Tyr Asp
                405                 410                 415

Ala Ala Ala Gln Gly His Leu Ile Ala Ser Trp Thr Pro Val Ser Pro
            420                 425                 430

Pro Ser Met
        435


<210> SEQ ID NO 80
<211> LENGTH: 1563
<212> TYPE: DNA
<213> ORGANISM: Homo Sapiens

<400> SEQUENCE: 80

gacttcctgc tgctgcagaa ccctgcctct acctgtgtgc ctgaaccagc ctctcagcac      60

accctgagat ctggccctgg atgtctccag cagcctgaac agcagggcgt tagagatcct     120

ggcggaatct gggccaaact gggagctgcc gaagcctctg ccgaatgtct gcagggcaga     180

agaagcagag gcgccagcgg atctgaacct caccagatgg gaagcgacgt gcacgacctg     240

aatgctctgt tgcctgccgt gccatctctt ggcggaggcg gaggatgtgc tttgcctgtt     300

tctggtgctg cccagtgggc tcccgtgctg gattttgctc ctcctggcgc ttctgcctat     360

ggctctcttg gaggacctgc tcctccacca gctccacctc caccgccgcc tccaccacct     420

cacagcttta tcaagcaaga gccctcctgg ggcggagccg agcctcacga aaaacagtgt     480

ctgagcgcct tcaccgtgca ctttttcggc cagtttaccg gcaccgtggg cgcctgtaga     540

tacggcccct ttggaccacc accacctagc caggcttcta gcggacaggc cagaatgttc     600

cccaacgctc cttacctgcc tagctgcctg gaaagccagc ctaccatcag aaaccagggc     660

ttcagcaccg tgaccttcga cggcatgcct agctatggcc acacaccatc tcaccacgcc     720

gctcagttcc ccaatcacag cttcaagcac gaggaccccta tgggccagca gggatctctg     780

ggagagcagc agtatagcgt gccacctcct gtgtacggct gtcacacccc taccgatagc     840

tgcacaggca atcaggctct gctgctgagg atgcctttca gcagcgacaa cctgtaccag     900

atgacaagcc agctggaatg catgatttgg aaccagatga acctgggcgc cactctgaaa     960

ggcgtggccg ctggatctag cagctccgtg aaatggacag ccggccagag caatcactcc    1020

accggctacg agagcgacaa tcacaccatg cctatcctgt gtggggccca gtaccggatt    1080

cacacacacg gcgtgttcag gggcattcag gatgtgcgaa gagtgcctgg cgtggcccct    1140

acacttgtgg gatctgccag cgaaaccagc gagaagcacc ccttcatgtg cgcctatcca    1200

ggctgcaaca agcggtactt caagctgagc cacctgaaga tgcacagccg gaagcacaca    1260

ggcgagaagc tgtaccagtg cgacttcaag gactgcgagc ggagattcag ctgcagcgac    1320

cagctgaaga gacaccagag aaggcacacc ggcgtgaagc cctttcagtg caagacctgc    1380

cagcggacct tctcctggtc caaccacctg aaaacccaca caagaaccca caccggcaag    1440

accatcgaga agcccttcag ctgtagatgg cccagctgcc agaagaagtt cgcccggtct    1500

aacgagctgg tgcatcacca caacatgcac cagaggaaca tgaccaaact gcagctggtg    1560
```

ctg 1563

<210> SEQ ID NO 81
<211> LENGTH: 521
<212> TYPE: PRT
<213> ORGANISM: Homo Sapiens

<400> SEQUENCE: 81

Asp Phe Leu Leu Leu Gln Asn Pro Ala Ser Thr Cys Val Pro Glu Pro
1 5 10 15

Ala Ser Gln His Thr Leu Arg Ser Gly Pro Gly Cys Leu Gln Gln Pro
20 25 30

Glu Gln Gln Gly Val Arg Asp Pro Gly Gly Ile Trp Ala Lys Leu Gly
35 40 45

Ala Ala Glu Ala Ser Ala Glu Cys Leu Gln Gly Arg Arg Ser Arg Gly
50 55 60

Ala Ser Gly Ser Glu Pro His Gln Met Gly Ser Asp Val His Asp Leu
65 70 75 80

Asn Ala Leu Leu Pro Ala Val Pro Ser Leu Gly Gly Gly Gly Gly Cys
85 90 95

Ala Leu Pro Val Ser Gly Ala Ala Gln Trp Ala Pro Val Leu Asp Phe
100 105 110

Ala Pro Pro Gly Ala Ser Ala Tyr Gly Ser Leu Gly Gly Pro Ala Pro
115 120 125

Pro Pro Ala Pro Pro Pro Pro Pro Pro Pro Pro Pro His Ser Phe Ile
130 135 140

Lys Gln Glu Pro Ser Trp Gly Gly Ala Glu Pro His Glu Lys Gln Cys
145 150 155 160

Leu Ser Ala Phe Thr Val His Phe Phe Gly Gln Phe Thr Gly Thr Val
165 170 175

Gly Ala Cys Arg Tyr Gly Pro Phe Gly Pro Pro Pro Pro Ser Gln Ala
180 185 190

Ser Ser Gly Gln Ala Arg Met Phe Pro Asn Ala Pro Tyr Leu Pro Ser
195 200 205

Cys Leu Glu Ser Gln Pro Thr Ile Arg Asn Gln Gly Phe Ser Thr Val
210 215 220

Thr Phe Asp Gly Met Pro Ser Tyr Gly His Thr Pro Ser His His Ala
225 230 235 240

Ala Gln Phe Pro Asn His Ser Phe Lys His Glu Asp Pro Met Gly Gln
245 250 255

Gln Gly Ser Leu Gly Glu Gln Gln Tyr Ser Val Pro Pro Pro Val Tyr
260 265 270

Gly Cys His Thr Pro Thr Asp Ser Cys Thr Gly Asn Gln Ala Leu Leu
275 280 285

Leu Arg Met Pro Phe Ser Ser Asp Asn Leu Tyr Gln Met Thr Ser Gln
290 295 300

Leu Glu Cys Met Ile Trp Asn Gln Met Asn Leu Gly Ala Thr Leu Lys
305 310 315 320

Gly Val Ala Ala Gly Ser Ser Ser Ser Val Lys Trp Thr Ala Gly Gln
325 330 335

Ser Asn His Ser Thr Gly Tyr Glu Ser Asp Asn His Thr Met Pro Ile
340 345 350

Leu Cys Gly Ala Gln Tyr Arg Ile His Thr His Gly Val Phe Arg Gly
355 360 365

```
Ile Gln Asp Val Arg Arg Val Pro Gly Val Ala Pro Thr Leu Val Gly
    370                 375                 380

Ser Ala Ser Glu Thr Ser Glu Lys His Pro Phe Met Cys Ala Tyr Pro
385                 390                 395                 400

Gly Cys Asn Lys Arg Tyr Phe Lys Leu Ser His Leu Lys Met His Ser
                405                 410                 415

Arg Lys His Thr Gly Glu Lys Leu Tyr Gln Cys Asp Phe Lys Asp Cys
            420                 425                 430

Glu Arg Arg Phe Ser Cys Ser Asp Gln Leu Lys Arg His Gln Arg Arg
        435                 440                 445

His Thr Gly Val Lys Pro Phe Gln Cys Lys Thr Cys Gln Arg Thr Phe
    450                 455                 460

Ser Trp Ser Asn His Leu Lys Thr His Thr Arg Thr His Thr Gly Lys
465                 470                 475                 480

Thr Ile Glu Lys Pro Phe Ser Cys Arg Trp Pro Ser Cys Gln Lys Lys
                485                 490                 495

Phe Ala Arg Ser Asn Glu Leu Val His His His Asn Met His Gln Arg
            500                 505                 510

Asn Met Thr Lys Leu Gln Leu Val Leu
        515                 520


<210> SEQ ID NO 82
<211> LENGTH: 84
<212> TYPE: DNA
<213> ORGANISM: Homo Sapiens

<400> SEQUENCE: 82

accgagtaca agctggtggt tgttggagcc gatggcgtgg gaaagagcgc cctgacaatt     60

cagctgatcc agaaccactt cgtg                                            84


<210> SEQ ID NO 83
<211> LENGTH: 28
<212> TYPE: PRT
<213> ORGANISM: Homo Sapiens

<400> SEQUENCE: 83

Thr Glu Tyr Lys Leu Val Val Val Gly Ala Asp Gly Val Gly Lys Ser
1               5                   10                  15

Ala Leu Thr Ile Gln Leu Ile Gln Asn His Phe Val
            20                  25


<210> SEQ ID NO 84
<211> LENGTH: 84
<212> TYPE: DNA
<213> ORGANISM: Homo Sapiens

<400> SEQUENCE: 84

acagagtata agctcgtggt cgtgggcgct gtcggagtgg gaaaatctgc cctgaccatc     60

caactcattc agaatcactt tgtg                                            84


<210> SEQ ID NO 85
<211> LENGTH: 28
<212> TYPE: PRT
<213> ORGANISM: Homo Sapiens

<400> SEQUENCE: 85

Thr Glu Tyr Lys Leu Val Val Val Gly Ala Val Gly Val Gly Lys Ser
1               5                   10                  15
```

Ala Leu Thr Ile Gln Leu Ile Gln Asn His Phe Val
20 25

<210> SEQ ID NO 86
<211> LENGTH: 1116
<212> TYPE: DNA
<213> ORGANISM: Homo Sapiens

<400> SEQUENCE: 86
cctcctgtgc ctggcgtgcc cttcagaaac gtggacaacg atagcctgac cagcgtggaa 60
ctggaagatt gggtcgacgc ccagcatcct accgacgagg aagaggaaga agccagctct 120
gccagcagca ccctgtacct ggtgtttagc cccagcagct tctccaccag ctctagcctg 180
attctcggag gccccgaaga agaagaggtc ccaagcggcg tgatccccaa tctgacagag 240
agcatcccaa gcagccctcc acagggacca ccacaaggac cttctcagag ccctctgagc 300
agctgttgca gcagtttcct gtggtccagc ttcagcgagg aaagcagctc ccagaaaggc 360
gaggataccg gcacttgtca gggcctgcca gatagcgaga gcagcttcac ctacacactg 420
gacgagaagg tggccaagct ggtcgagttc ctgctgctga agtacgaggc cgaggaacct 480
gtgacagagg ccgagatgct gatgatcgtc atcaagtata aggactactt ccccgtgatc 540
ctgaagcggg ccagagaatt catggaactg ctgttcggac tggccctgat cgaagtgggc 600
cccgatcact tctgcgtgtt cgctaacaca gtgggcctga ccgatgaggg ctccgatgat 660
gagggaatgc ccgagaactc cctgctgatc atcatcctga gcgtcatctt catcaagggc 720
aactgcgcct ccgaggaagt gatctgggaa gtcctgaatg ccgtgggcgt ttacgccggc 780
agagaacact ttgtgtacgg caagccccgc gagctgctga ccaatgtttg ggtgcagggc 840
cactacctgg aatactggga agtgcctcac tctagccctc tgtactacga gtttctgtgg 900
ggccctagag cacacagcga gtccatcaag aaaaaggtgc tggaattcct ggccaaactg 960
aacaataccg tgcctagctt cttcccgtcc tggtacaagg atgccctgaa ggacgtggaa 1020
gagagagtgc aggccaccat cgacaccgcc gatgatgcta cagtgatggc cagcgagagc 1080
ctgagcgtga tgagcagcaa cgtgtccttt agcgag 1116

<210> SEQ ID NO 87
<211> LENGTH: 372
<212> TYPE: PRT
<213> ORGANISM: Homo Sapiens

<400> SEQUENCE: 87

Pro Pro Val Pro Gly Val Pro Phe Arg Asn Val Asp Asn Asp Ser Leu
1 5 10 15

Thr Ser Val Glu Leu Glu Asp Trp Val Asp Ala Gln His Pro Thr Asp
20 25 30

Glu Glu Glu Glu Glu Ala Ser Ser Ala Ser Ser Thr Leu Tyr Leu Val
35 40 45

Phe Ser Pro Ser Ser Phe Ser Thr Ser Ser Ser Leu Ile Leu Gly Gly
50 55 60

Pro Glu Glu Glu Glu Val Pro Ser Gly Val Ile Pro Asn Leu Thr Glu
65 70 75 80

Ser Ile Pro Ser Ser Pro Pro Gln Gly Pro Pro Gln Gly Pro Ser Gln
85 90 95

Ser Pro Leu Ser Ser Cys Cys Ser Ser Phe Leu Trp Ser Ser Phe Ser
100 105 110

Glu Glu Ser Ser Ser Gln Lys Gly Glu Asp Thr Gly Thr Cys Gln Gly

-continued

```
        115                 120                 125

Leu Pro Asp Ser Glu Ser Ser Phe Thr Tyr Thr Leu Asp Glu Lys Val
    130                 135                 140

Ala Lys Leu Val Glu Phe Leu Leu Leu Lys Tyr Glu Ala Glu Glu Pro
145                 150                 155                 160

Val Thr Glu Ala Glu Met Leu Met Ile Val Ile Lys Tyr Lys Asp Tyr
                165                 170                 175

Phe Pro Val Ile Leu Lys Arg Ala Arg Glu Phe Met Glu Leu Leu Phe
            180                 185                 190

Gly Leu Ala Leu Ile Glu Val Gly Pro Asp His Phe Cys Val Phe Ala
        195                 200                 205

Asn Thr Val Gly Leu Thr Asp Glu Gly Ser Asp Asp Glu Gly Met Pro
    210                 215                 220

Glu Asn Ser Leu Leu Ile Ile Ile Leu Ser Val Ile Phe Ile Lys Gly
225                 230                 235                 240

Asn Cys Ala Ser Glu Glu Val Ile Trp Glu Val Leu Asn Ala Val Gly
                245                 250                 255

Val Tyr Ala Gly Arg Glu His Phe Val Tyr Gly Lys Pro Arg Glu Leu
            260                 265                 270

Leu Thr Asn Val Trp Val Gln Gly His Tyr Leu Glu Tyr Trp Glu Val
        275                 280                 285

Pro His Ser Ser Pro Leu Tyr Tyr Glu Phe Leu Trp Gly Pro Arg Ala
    290                 295                 300

His Ser Glu Ser Ile Lys Lys Lys Val Leu Glu Phe Leu Ala Lys Leu
305                 310                 315                 320

Asn Asn Thr Val Pro Ser Phe Phe Pro Ser Trp Tyr Lys Asp Ala Leu
                325                 330                 335

Lys Asp Val Glu Glu Arg Val Gln Ala Thr Ile Asp Thr Ala Asp Asp
            340                 345                 350

Ala Thr Val Met Ala Ser Glu Ser Leu Ser Val Met Ser Ser Asn Val
        355                 360                 365

Ser Phe Ser Glu
    370
```

<210> SEQ ID NO 88
<211> LENGTH: 561
<212> TYPE: DNA
<213> ORGANISM: Homo Sapiens

<400> SEQUENCE: 88

```
gactgcagaa agatggcccg gttcagctac tccgtgatct ggatcatggc catctccaag     60

gccttcgagc tgagactggt tgccggactg ggccaccaag agtttgccag acctagctgg    120

ggctatctgg ccttccggga cgatagcatc tggccccaag aggaacctgc catcagaccc    180

agatctagcc agcgggtgcc acctatggaa atccagcaca gcaaagaact gaaccggacc    240

tgctgcctga acggcagaac ctgtatgctg ggcagcttct gcgcctgtcc tcctagcttc    300

tacggccgga attgcgagca cgacgtgcgg aaagaaaact gcggcagcgt gccacacgat    360

acctggctgc ctaagaaatg cagcctgtgc aagtgttggc acggccagct gcggtgtttc    420

cccagagctt ttctgcccgt gtgtgacggc ctggtcatgg atgaacacct ggtggccagc    480

agaacccctg agcttcctcc aagcgccagg accaccacct ttatgctcgt gggcatctgc    540

ctgagcatcc agagctacta c                                              561
```

<210> SEQ ID NO 89
<211> LENGTH: 187
<212> TYPE: PRT
<213> ORGANISM: Homo Sapiens

<400> SEQUENCE: 89

```
Asp Cys Arg Lys Met Ala Arg Phe Ser Tyr Ser Val Ile Trp Ile Met
1               5                   10                  15

Ala Ile Ser Lys Ala Phe Glu Leu Arg Leu Val Ala Gly Leu Gly His
            20                  25                  30

Gln Glu Phe Ala Arg Pro Ser Trp Gly Tyr Leu Ala Phe Arg Asp Asp
        35                  40                  45

Ser Ile Trp Pro Gln Glu Glu Pro Ala Ile Arg Pro Arg Ser Ser Gln
    50                  55                  60

Arg Val Pro Pro Met Glu Ile Gln His Ser Lys Glu Leu Asn Arg Thr
65                  70                  75                  80

Cys Cys Leu Asn Gly Arg Thr Cys Met Leu Gly Ser Phe Cys Ala Cys
                85                  90                  95

Pro Pro Ser Phe Tyr Gly Arg Asn Cys Glu His Asp Val Arg Lys Glu
            100                 105                 110

Asn Cys Gly Ser Val Pro His Asp Thr Trp Leu Pro Lys Lys Cys Ser
        115                 120                 125

Leu Cys Lys Cys Trp His Gly Gln Leu Arg Cys Phe Pro Arg Ala Phe
    130                 135                 140

Leu Pro Val Cys Asp Gly Leu Val Met Asp Glu His Leu Val Ala Ser
145                 150                 155                 160

Arg Thr Pro Glu Leu Pro Pro Ser Ala Arg Thr Thr Thr Phe Met Leu
                165                 170                 175

Val Gly Ile Cys Leu Ser Ile Gln Ser Tyr Tyr
            180                 185
```

<210> SEQ ID NO 90
<211> LENGTH: 2268
<212> TYPE: DNA
<213> ORGANISM: Homo Sapiens

<400> SEQUENCE: 90

```
ggatccgcca ccatgtggaa tctgctgcac gagacagata gcgccgtggc taccgttaga     60

aggcccagat ggctttgtgc tggcgctctg gttctggctg gcggcttttt tctgctgggc    120

ttcctgttcg gctggttcat caagagcagc aacgaggcca ccaacatcac ccctaagcac    180

aacatgaagg cctttctgga cgagctgaag gccgagaata tcaagaagtt cctgtacaac    240

ttcacgcaca tccctcacct ggccggcacc gagcagaatt ttcagctggc caagcagatc    300

cagagccagt ggaaagagtt cggcctggac tctgtggaac tggcccacta cgatgtgctg    360

ctgagctacc ccaacaagac acaccccaac tacatcagca tcatcaacga ggacggcaac    420

gagatcttca acaccagcct gttcgagcct ccacctcctg gctacgagaa cgtgtccgat    480

atcgtgcctc cattcagcgc tttcagccca cagcggatgc ctgagggcta cctggtgtac    540

gtgaactacg ccagaaccga ggacttcttc aagctggaat gggacatgaa gatcagctgc    600

agcggcaaga tcgtgatcgc ccggtacaga aaggtgttcc gcgagaacaa agtgaagaac    660

gcccagctgg caggcgccaa aggcgtgatc ctgtatagcg accccgccga ctattttgcc    720

cctggcgtga agtcttaccc cgacggctgg aattttcctg gcggcggagt gcagcggcgg    780

aacatcctta atcttaacgg cgctggcgac cctctgacac ctggctatcc tgccaatgag    840
```

-continued

```
tacgcctaca gacacggaat tgccgaggct gtgggcctgc cttctattcc tgtgcaccct    900

gtgcggtact acgacgccca gaaactgctg gaaaagatgg gcggaagcgc ccctcctgac    960

tcttcttgga gaggctctct gaaggtgccc tacaatgtcg gcccaggctt caccggcaac   1020

ttcagcaccc agaaagtgaa aatgcacatc cacagcacca acgaagtgac ccggatctac   1080

aacgtgatcg gcacactgag aggcgccgtg gaacccgaca aatacgtgat cctcggcggc   1140

cacagagaca gctgggtgtt cggaggaatc gaccctcaat ctggcgccgc tgtggtgtat   1200

gagatcgtgc ggtctttcgg caccctgaag aaagaaggat ggcggcccag acggaccatc   1260

ctgtttgcct cttgggacgc cgaggaattt ggcctgctgg gatctacaga gtgggccgaa   1320

gagaacagca gactgctgca agaaagaggc gtggcctaca tcaacgccga cagcagcatc   1380

gagggcaact acaccctgcg gatcgattgc acccctctga tgtacagcct ggtgcacaac   1440

ctgaccaaag agctgaagtc ccctgacgag ggctttgagg gcaagagcct gtacaagagc   1500

tggaccaaga agtccccatc tcctgagttc agcggcatgc ccagaatctc taagctggaa   1560

agcggcaaca acttcgaggt gttcttccag cggctgggaa tcgcctctgg aatcgccaga   1620

tacaccaaga actgggagac aaacaagttc tccggctatc ccctgtacca cagcgtgtac   1680

gagacatacg agctggtgga aaagttctac gaccccatgt tcaagtacca cctgacagtg   1740

gcccaagtgc gcggaggcat ggtgttcgaa ctggccaata gcatcgtgct gcccttcaac   1800

tgcagagact acgccgtggt gctgcggaag tacgccgaca agatctacag catcagcatg   1860

aagcacccgc aagagatgaa gacctacagc gtgtccttcg actccctgtt cttcgccgtg   1920

aagaacttca ccaagatcgc cagcaagttc agcgagcggc tgcaggactt cgacaagagc   1980

aaccctatcg tgctgaggat gatgaacgac cagctgatgt tcctggaacg ggccttcatc   2040

aaccctctgg gactgcccga cagacccttc tacaggcacg tgatctgtgc ccctagcagc   2100

cacaacaaat acgccggcga gagcttcccc ggcatctacg atgccctgtt cgacatcgag   2160

agcaacgtga accctagcaa ggcctggggc gaagtgaaga gacagatcta cgtggccgca   2220

ttcacagtgc aggccgctgc cgaaacactg tctgaagtgg ccagaggc                2268
```

<210> SEQ ID NO 91
<211> LENGTH: 1566
<212> TYPE: DNA
<213> ORGANISM: Homo Sapiens

<400> SEQUENCE: 91

```
atggactttc tgctgctgca gaaccctgcc agcacctgtg ttccagaacc tgcctctcag     60

cacaccctga gatctggccc tggatgtctc cagcagcctg aacagcaggg cgttagagat    120

cctggcggaa tctgggccaa actgggagcc gctgaagcct ctgccgaatg tctgcagggc    180

agaagaagca gaggcgccag cggatctgaa cctcaccaga tgggaagcga cgtgcacgac    240

ctgaatgctc tgctgcctgc cgtgccatct cttggcggag gcggaggatg tgctttgcct    300

gtttctggtg ctgcccagtg ggctcccgtg ctggattttg ctcctcctgg cgcttctgcc    360

tatggctctc ttggaggacc tgctcctcca ccagctccac ctccaccgcc gcctccacca    420

cctcacagct ttatcaagca agagccctcc tggggcggag ccgagcctca cgaaaaacag    480

tgtctgagcg ccttcaccgt gcactttttc ggccagttta ccggcacagt gggcgcctgt    540

agatacggcc cttttggacc accaccacct agccaggcta gctctggaca ggccagaatg    600

ttccccaacg ctccctacct gcctagctgc ctggaaagcc agcctaccat cagaaaccag    660

ggcttcagca ccgtgacctt cgacggcatg cctagctatg gccacacacc atctcaccac    720
```

gccgctcagt tccccaatca cagcttcaag cacgaggacc ctatgggcca gcagggatct 780
ctgggagagc agcagtatag cgtgccacct cctgtgtacg gctgtcacac ccctaccgat 840
agctgcacag gcaatcaggc cctgctgctg aggatgccct tcagcagcga caacctgtac 900
cagatgacaa gccagctgga atgcatgatc tggaaccaga tgaacctggg cgccacactg 960
aaaggcgtgg ccgctggatc tagcagcagc gtgaaatgga cagccggcca gagcaatcac 1020
tccaccggct acgagtccga caaccacacc atgcctattc tgtgcggagc ccagtacaga 1080
atccacacac acggcgtgtt ccggggcatt caggatgtgc gaagagtgcc tggcgtggcc 1140
cctacacttg tgggatctgc ctctgagaca agcgagaagc acccccttcat gtgcgcctat 1200 cctggctgca acaagcggta cttcaagctg agccacctga agatgcacag ccggaagcac 1260
acaggcgaga agctgtacca gtgcgacttc aaggactgcg agcggagatt cagctgcagc 1320
gaccagctga agagacacca gagaaggcac accggcgtga agcccttcca gtgcaagacc 1380
tgccagcgga cctttagctg gtccaaccac ctgaaaaccc acacaagaac ccacaccggc 1440
aagaccatcg agaagccttt cagctgtaga tggcccagct gccagaagaa gttcgcccgg 1500
tctaacgagc tggtgcatca ccacaacatg caccagagga acatgaccaa actgcagctg 1560
gtgctg 1566

<210> SEQ ID NO 92
<211> LENGTH: 768
<212> TYPE: DNA
<213> ORGANISM: Homo Sapiens

<400> SEQUENCE: 92
gcccagagaa tgaccacaca gttgctgctg ctcctcgtgt gggttgccgt tgtgggagaa 60
gtgcagacca gaatcgcctg ggccagaacc gagctgctga acgtgtgcat gaacgccaag 120
caccacaaga agaagcccga tcctgaggac aagctgcacg agcagtgtcg gccttggaga 180
aagaacgcct gctgtagcac caacaccagc caagaggccc acaagaacgt gtcctacctg 240
taccggttca actggaacca ctgcggcgag atgacacccg cctgcaagag acacttcatc 300
caggatacct gcctgtacga gtgcagcccc aatctcggcc cctggattca gcaagtggac 360
cagagctggc ggaaagaact ggtcctgaat gtgcccctgt gcaaagagga ttgcgagcag 420
tggtgggaag attgcagaac cagctacaca tgcaagagca actggcacaa aggctggaac 480
tggaccagcg gcttcaacaa gtgtgccgtg ggagctgcct gtcagccttt ccacttctac 540
tttcacacac ccaccgtgct gtgcaacaag atctggaccc acagctacaa ggtgtccaac 600
tacagcagag gcagcggccg gtgtatccag atgtggttcg atcccgccaa gggcaacccc 660
aatgaggaag tggccagatt ctacgccgct gccatgtctg gtgcaggacc ttgggctgct 720
tggccctttc tgctttcact ggccctgatg ctgctgtggc tgctgagc 768

<210> SEQ ID NO 93
<211> LENGTH: 256
<212> TYPE: PRT
<213> ORGANISM: Homo Sapiens

<400> SEQUENCE: 93

Ala Gln Arg Met Thr Thr Gln Leu Leu Leu Leu Leu Val Trp Val Ala
1 5 10 15

Val Val Gly Glu Val Gln Thr Arg Ile Ala Trp Ala Arg Thr Glu Leu
20 25 30

-continued

```
Leu Asn Val Cys Met Asn Ala Lys His His Lys Lys Lys Pro Asp Pro
        35                  40                  45

Glu Asp Lys Leu His Glu Gln Cys Arg Pro Trp Arg Lys Asn Ala Cys
    50                  55                  60

Cys Ser Thr Asn Thr Ser Gln Glu Ala His Lys Asn Val Ser Tyr Leu
65                  70                  75                  80

Tyr Arg Phe Asn Trp Asn His Cys Gly Glu Met Thr Pro Ala Cys Lys
                85                  90                  95

Arg His Phe Ile Gln Asp Thr Cys Leu Tyr Glu Cys Ser Pro Asn Leu
            100                 105                 110

Gly Pro Trp Ile Gln Gln Val Asp Gln Ser Trp Arg Lys Glu Leu Val
        115                 120                 125

Leu Asn Val Pro Leu Cys Lys Glu Asp Cys Glu Gln Trp Trp Glu Asp
    130                 135                 140

Cys Arg Thr Ser Tyr Thr Cys Lys Ser Asn Trp His Lys Gly Trp Asn
145                 150                 155                 160

Trp Thr Ser Gly Phe Asn Lys Cys Ala Val Gly Ala Ala Cys Gln Pro
                165                 170                 175

Phe His Phe Tyr Phe His Thr Pro Thr Val Leu Cys Asn Lys Ile Trp
            180                 185                 190

Thr His Ser Tyr Lys Val Ser Asn Tyr Ser Arg Gly Ser Gly Arg Cys
        195                 200                 205

Ile Gln Met Trp Phe Asp Pro Ala Lys Gly Asn Pro Asn Glu Glu Val
    210                 215                 220

Ala Arg Phe Tyr Ala Ala Ala Met Ser Gly Ala Gly Pro Trp Ala Ala
225                 230                 235                 240

Trp Pro Phe Leu Leu Ser Leu Ala Leu Met Leu Leu Trp Leu Leu Ser
                245                 250                 255
```

<210> SEQ ID NO 94
<211> LENGTH: 2085
<212> TYPE: DNA
<213> ORGANISM: Homo Sapiens

<400> SEQUENCE: 94

```
atggctctgc tgctggtttc tctgctggcc ctgctgtctc tcggctctgg atgtcaccac     60

agaatctgcc actgcagcaa ccgggtgttc ctgtgccaga aaagcaaagt gaccgagatc    120

ctgagcgacc tgcagcggaa tgccatcgag ctgagattcg tgctgaccaa gctgcaagtg    180

atccagaagg gcgccttcag cggcttcggc gacctggaaa agatcgagat cagccagaac    240

aacgtgctgg aagtgatcga ggcccacgtg ttcagcaacc tgcctaagct gcacgagatc    300

agaatcgaga aggccaacaa cctgctgtac atcaaccccg aggccttcca gaacttcccc    360

aacctgcagt acctgctgat ctccaacacc ggcatcaaac atctgcccga cgtgcacaag    420

atccacagcc tgcagaaggt gctgctggac atccaggaca acatcaacat ccacacaatc    480

gagcggaact acttcctggg cctgagcttc gagagcgtga tcctgtggct gaacaagaac    540

ggcatccaag agatccacaa ctgcgccttc aatggcaccc agctggacga gctgaacctg    600

tccgacaaca acaatctgga agaactgccc aacgacgtgt tccacagagc cagcggacct    660

gtgatcctgg acatcagcag aaccagaatc cactctctgc ccagctacgg cctggaaaac    720

ctgaagaagc tgcgggccag aagcacctac aatctgaaaa agctgcctac gctggaaacc    780

ctggtggccc tgatggaagc cagcctgaca taccctagcc actgctgcgc ctttgccaac    840

tggcggagac agatctctga gctgcacccc atctgcaaca agagcatcct gcggcaagag    900
```

```
gtggactaca tgacacaggc cagaggccag agattcagcc tggccgagga taacgagagc    960

agctacagca gaggcttcga catgacctac accgagttcg actacgacct gtgcaacaag   1020

gtggtggacg tgacatgcag ccccaagcct gatgccttca atccctgcga ggacatcatg   1080

ggctacaaca tcctgagagt gctgatctgg ttcatcagca tcctggccat caccgagaac   1140

atcatcgtgc tggtcatcct gaccaccagc cagtacaagc tgaccgtgcc tatgttcctg   1200

atgtgcaacc tggccttcgc cgatctgtgc atcggcatct acctgctgct gatcgccagc   1260

gtggacattc acaccaagag ccagtaccac aactacgcca tcgactggca gacaggcgcc   1320

ggatgtgatg ccgccggatt ctttacagtg ttcgccagcg agctgtccgt gtacaccctg   1380

acagctatca ccctggaacg gtggcacacc atcacacacg ctatgcagct ggactgcaaa   1440

gtgcacctga gacacagcgc ctccgtgatg gttatgggct ggatcttcgc cttcgctgcc   1500

gctctgttcc ccatctttgg catcagctcc tacatgaagg tgtccatcta tctgcccatg   1560

gacatcgaca gccctctgag ccagctgtac gtgatgagtc tgctggtgct gaatgtgctg   1620

gcctttgtgg tcatctgcgg ctgctacatc tatatctacc tgacagtgcg gaaccccaac   1680

atcgtgtcca gctccagcga cacccggatc gctaagagaa tggccatgct gatcttcacc   1740

gactttctgt gcatggcccc tatcagcctg ttcgccatta gcgctagcct gaaggtgccc   1800

ctgatcaccg tgtccaaggc caagattctg ctggtcctgt tctaccccat caacagctgc   1860

gccaatcctt tcctgtacgc catcttcacc aagaacttca ggcggaactt cttcatcctg   1920

ctgagcaagc ggggctgtta caagatgcag gcccagatct accggaccga gacactgtcc   1980

accgtgcaca acacacaccc cagaaacggc cactgtagca gcgcccctag agtgacaaat   2040

ggctccacct acatcctggt gccactgagc catctggccc agaac                   2085
```

<210> SEQ ID NO 95
<211> LENGTH: 695
<212> TYPE: PRT
<213> ORGANISM: Homo Sapiens

<400> SEQUENCE: 95

```
Met Ala Leu Leu Leu Val Ser Leu Leu Ala Leu Leu Ser Leu Gly Ser
1               5                   10                  15

Gly Cys His His Arg Ile Cys His Cys Ser Asn Arg Val Phe Leu Cys
            20                  25                  30

Gln Lys Ser Lys Val Thr Glu Ile Leu Ser Asp Leu Gln Arg Asn Ala
        35                  40                  45

Ile Glu Leu Arg Phe Val Leu Thr Lys Leu Gln Val Ile Gln Lys Gly
    50                  55                  60

Ala Phe Ser Gly Phe Gly Asp Leu Glu Lys Ile Glu Ile Ser Gln Asn
65                  70                  75                  80

Asn Val Leu Glu Val Ile Glu Ala His Val Phe Ser Asn Leu Pro Lys
                85                  90                  95

Leu His Glu Ile Arg Ile Glu Lys Ala Asn Asn Leu Leu Tyr Ile Asn
            100                 105                 110

Pro Glu Ala Phe Gln Asn Phe Pro Asn Leu Gln Tyr Leu Leu Ile Ser
        115                 120                 125

Asn Thr Gly Ile Lys His Leu Pro Asp Val His Lys Ile His Ser Leu
    130                 135                 140

Gln Lys Val Leu Leu Asp Ile Gln Asp Asn Ile Asn Ile His Thr Ile
145                 150                 155                 160
```

-continued

```
Glu Arg Asn Tyr Phe Leu Gly Leu Ser Phe Glu Ser Val Ile Leu Trp
                165                 170                 175

Leu Asn Lys Asn Gly Ile Gln Glu Ile His Asn Cys Ala Phe Asn Gly
            180                 185                 190

Thr Gln Leu Asp Glu Leu Asn Leu Ser Asp Asn Asn Asn Leu Glu Glu
        195                 200                 205

Leu Pro Asn Asp Val Phe His Arg Ala Ser Gly Pro Val Ile Leu Asp
    210                 215                 220

Ile Ser Arg Thr Arg Ile His Ser Leu Pro Ser Tyr Gly Leu Glu Asn
225                 230                 235                 240

Leu Lys Lys Leu Arg Ala Arg Ser Thr Tyr Asn Leu Lys Lys Leu Pro
                245                 250                 255

Thr Leu Glu Thr Leu Val Ala Leu Met Glu Ala Ser Leu Thr Tyr Pro
            260                 265                 270

Ser His Cys Cys Ala Phe Ala Asn Trp Arg Arg Gln Ile Ser Glu Leu
        275                 280                 285

His Pro Ile Cys Asn Lys Ser Ile Leu Arg Gln Glu Val Asp Tyr Met
    290                 295                 300

Thr Gln Ala Arg Gly Gln Arg Phe Ser Leu Ala Glu Asp Asn Glu Ser
305                 310                 315                 320

Ser Tyr Ser Arg Gly Phe Asp Met Thr Tyr Thr Glu Phe Asp Tyr Asp
                325                 330                 335

Leu Cys Asn Lys Val Val Asp Val Thr Cys Ser Pro Lys Pro Asp Ala
            340                 345                 350

Phe Asn Pro Cys Glu Asp Ile Met Gly Tyr Asn Ile Leu Arg Val Leu
        355                 360                 365

Ile Trp Phe Ile Ser Ile Leu Ala Ile Thr Glu Asn Ile Ile Val Leu
    370                 375                 380

Val Ile Leu Thr Thr Ser Gln Tyr Lys Leu Thr Val Pro Met Phe Leu
385                 390                 395                 400

Met Cys Asn Leu Ala Phe Ala Asp Leu Cys Ile Gly Ile Tyr Leu Leu
                405                 410                 415

Leu Ile Ala Ser Val Asp Ile His Thr Lys Ser Gln Tyr His Asn Tyr
            420                 425                 430

Ala Ile Asp Trp Gln Thr Gly Ala Gly Cys Asp Ala Ala Gly Phe Phe
        435                 440                 445

Thr Val Phe Ala Ser Glu Leu Ser Val Tyr Thr Leu Thr Ala Ile Thr
    450                 455                 460

Leu Glu Arg Trp His Thr Ile Thr His Ala Met Gln Leu Asp Cys Lys
465                 470                 475                 480

Val His Leu Arg His Ser Ala Ser Val Met Val Met Gly Trp Ile Phe
                485                 490                 495

Ala Phe Ala Ala Ala Leu Phe Pro Ile Phe Gly Ile Ser Ser Tyr Met
            500                 505                 510

Lys Val Ser Ile Tyr Leu Pro Met Asp Ile Asp Ser Pro Leu Ser Gln
        515                 520                 525

Leu Tyr Val Met Ser Leu Leu Val Leu Asn Val Leu Ala Phe Val Val
    530                 535                 540

Ile Cys Gly Cys Tyr Ile Tyr Ile Tyr Leu Thr Val Arg Asn Pro Asn
545                 550                 555                 560

Ile Val Ser Ser Ser Ser Asp Thr Arg Ile Ala Lys Arg Met Ala Met
                565                 570                 575

Leu Ile Phe Thr Asp Phe Leu Cys Met Ala Pro Ile Ser Leu Phe Ala
```

```
            580                 585                 590

Ile Ser Ala Ser Leu Lys Val Pro Leu Ile Thr Val Ser Lys Ala Lys
        595                 600                 605

Ile Leu Leu Val Leu Phe Tyr Pro Ile Asn Ser Cys Ala Asn Pro Phe
    610                 615                 620

Leu Tyr Ala Ile Phe Thr Lys Asn Phe Arg Arg Asn Phe Phe Ile Leu
625                 630                 635                 640

Leu Ser Lys Arg Gly Cys Tyr Lys Met Gln Ala Gln Ile Tyr Arg Thr
                645                 650                 655

Glu Thr Leu Ser Thr Val His Asn Thr His Pro Arg Asn Gly His Cys
            660                 665                 670

Ser Ser Ala Pro Arg Val Thr Asn Gly Ser Thr Tyr Ile Leu Val Pro
        675                 680                 685

Leu Ser His Leu Ala Gln Asn
    690                 695
```

<210> SEQ ID NO 96
<211> LENGTH: 1104
<212> TYPE: DNA
<213> ORGANISM: Homo Sapiens

<400> SEQUENCE: 96

```
cccagggctc ccaagagaca gagatgcatg cccgaagagg acctgcagag ccagagcgaa     60

acacagggac tcgaaggtgc tcaggctcct ctggccgtgg aagaagatgc cagcagctct    120

accagcacct ccagcagctt ccctagcagc tttccattca gctcctctag ctctagcagc    180

agctgttacc ctctgatccc cagcacaccc gagaaggtgt tcgccgacga cgagacacct    240

aatccactgc agtctgccca gatcgcctgc agcagtacac tggtggttgc tagcctgcct    300

ctggaccagt ctgatgaggg aagcagcagc cagaaagagg aaagccctag cacactccag    360

gtgctgcccg atagcgagag cctgcctaga agcgagatct acaagaaaat gaccgacctg    420

gtgcagttcc tcctgttcaa gtaccagatg aaggaaccca tcaccaaggc cgaaatcctg    480

gaaagcgtga tcagaaacta cgaggaccac tttccactgc tgttcagcga ggccagcgag    540

tgcatgctgc tcgtgtttag catcgacgtg aagaaggtgg accccaccgg ccacagcttt    600

gtgctggtta caagcctggg actgacctac gacggcatgc tgtccgatgt gcagagcatg    660

cctaagaccg gcatcctgat cctgattctg agcatcgtgt tcatcgaggg ctactgcacc    720

cctgaggaag tgatttggga agccctgaac atgatgggcc tgtacgatgg catggaacac    780

ctgatctacg gcgagcccag aaaactgctg acccaggact gggtgcaaga gaactacctg    840

gaataccggc agatgcccgg cagcgatcct gccagatatg agtttctgtg ggccctaga    900

gcacatgccg agatccggaa gatgagcctg ctgaagttcc tggccaaagt gaacggcagc    960

gacccaatca gcttcccact ttggtacgaa gaggccctga aggacgagga agagagagcc   1020

caggatagaa tcgccaccac cgacgacaca acagccatgg cctctgcctc ttctagcgcc   1080

accggcagct ttagctaccc cgag                                          1104
```

<210> SEQ ID NO 97
<211> LENGTH: 368
<212> TYPE: PRT
<213> ORGANISM: Homo Sapiens

<400> SEQUENCE: 97

```
Pro Arg Ala Pro Lys Arg Gln Arg Cys Met Pro Glu Glu Asp Leu Gln
1               5                   10                  15
```

```
Ser Gln Ser Glu Thr Gln Gly Leu Glu Gly Ala Gln Ala Pro Leu Ala
            20                  25                  30

Val Glu Glu Asp Ala Ser Ser Ser Thr Ser Thr Ser Ser Ser Phe Pro
        35                  40                  45

Ser Ser Phe Pro Phe Ser Ser Ser Ser Ser Ser Ser Ser Cys Tyr Pro
    50                  55                  60

Leu Ile Pro Ser Thr Pro Glu Lys Val Phe Ala Asp Asp Glu Thr Pro
65                  70                  75                  80

Asn Pro Leu Gln Ser Ala Gln Ile Ala Cys Ser Ser Thr Leu Val Val
                85                  90                  95

Ala Ser Leu Pro Leu Asp Gln Ser Asp Glu Gly Ser Ser Ser Gln Lys
            100                 105                 110

Glu Glu Ser Pro Ser Thr Leu Gln Val Leu Pro Asp Ser Glu Ser Leu
        115                 120                 125

Pro Arg Ser Glu Ile Tyr Lys Lys Met Thr Asp Leu Val Gln Phe Leu
    130                 135                 140

Leu Phe Lys Tyr Gln Met Lys Glu Pro Ile Thr Lys Ala Glu Ile Leu
145                 150                 155                 160

Glu Ser Val Ile Arg Asn Tyr Glu Asp His Phe Pro Leu Leu Phe Ser
                165                 170                 175

Glu Ala Ser Glu Cys Met Leu Leu Val Phe Ser Ile Asp Val Lys Lys
            180                 185                 190

Val Asp Pro Thr Gly His Ser Phe Val Leu Val Thr Ser Leu Gly Leu
        195                 200                 205

Thr Tyr Asp Gly Met Leu Ser Asp Val Gln Ser Met Pro Lys Thr Gly
    210                 215                 220

Ile Leu Ile Leu Ile Leu Ser Ile Val Phe Ile Glu Gly Tyr Cys Thr
225                 230                 235                 240

Pro Glu Glu Val Ile Trp Glu Ala Leu Asn Met Met Gly Leu Tyr Asp
                245                 250                 255

Gly Met Glu His Leu Ile Tyr Gly Glu Pro Arg Lys Leu Leu Thr Gln
            260                 265                 270

Asp Trp Val Gln Glu Asn Tyr Leu Glu Tyr Arg Gln Met Pro Gly Ser
        275                 280                 285

Asp Pro Ala Arg Tyr Glu Phe Leu Trp Gly Pro Arg Ala His Ala Glu
    290                 295                 300

Ile Arg Lys Met Ser Leu Leu Lys Phe Leu Ala Lys Val Asn Gly Ser
305                 310                 315                 320

Asp Pro Ile Ser Phe Pro Leu Trp Tyr Glu Glu Ala Leu Lys Asp Glu
                325                 330                 335

Glu Glu Arg Ala Gln Asp Arg Ile Ala Thr Thr Asp Asp Thr Thr Ala
            340                 345                 350

Met Ala Ser Ala Ser Ser Ser Ala Thr Gly Ser Phe Ser Tyr Pro Glu
        355                 360                 365
```

<210> SEQ ID NO 98
<211> LENGTH: 1527
<212> TYPE: DNA
<213> ORGANISM: Homo Sapiens

<400> SEQUENCE: 98

```
atggaaagaa gaaggctctg gggcagcatc cagagccggt acatcagcat gagcgtgtgg      60

acaagccctc ggagactggt ggaactggct ggacagagcc tgctgaagga tgaggccctg     120
```

-continued

```
gccattgctg ctctggaact gctgcctaga gagctgttcc ctcctctgtt catggccgcc    180

ttcgacggca gacacagcca gacactgaaa gccatggtgc aggcctggcc tttcacctgt    240

ctgcctctgg gagtgctgat gaagggccag catctgcacc tggaaacctt caaggccgtg    300

ctggatggcc tggatgtgct gctggctcaa gaagtgcggc ctcggcgttg gaaactgcag    360

gttctggatc tgctgaagaa cagccaccag gatttctgga ccgtttggag cggcaacaga    420

gccagcctgt acagctttcc tgagcctgaa gccgctcagc ccatgaccaa gaaaagaaag    480

gtggacggcc tgagcaccga ggccgagcag ccttttattc ccgtggaagt gctggtggac    540

ctgttcctga aagaaggcgc ctgcgacgag ctgttcagct acctgaccga gaaagtgaag    600

cagaagaaga acgtcctgca cctgtgctgc aagaagctga agatctttgc catgcctatg    660

caggacatca agatgatcct gaagatggtg cagctggaca gcatcgagga cctggaagtg    720

acctgtacct ggaagctgcc cacactggcc aagttcttta gctacctggg ccagatgatc    780

aacctgcgga gactgctgct gagccacatc cacgccagct cctacatcag ccccgagaaa    840

gaggaacagt acatctccca gttcacctct cagtttctga gcctgcagtg tctgcaggcc    900

ctgtacgtgg acagcctgtt cttcctgaga ggcaggctgg accagctgct gagacacgtg    960

atgaaccctc tggaaaccct gagcatcacc aactgcagac tgctggaagg cgacgtgatg   1020

cacctgtctc agagcccatc tgtgtcccag ctgagcgtgc tgtctctgtc tggcgtgatg   1080

ctgaccgatg tgtcccctga acctctgcag gcactgctga aaaaggccag cgccactctg   1140

caggacctgg tgtttgatga gtgcggcatc atggacgacc agctgtttgc cctgctgcca   1200

agcctgagcc actgtagcca actgaccaca ctgagcttct acggcaacag catctacatc   1260

tctgccctgc agagcctcct gcagcacctg atcggactga gcaatctgac ccacgtgctg   1320

tacccagtgc tgctcgagag ctacgaggac atccacgtga ccctgcacca agagagactg   1380

gcctatctgc atgcccggct gagagaactg ctgtgcgaac tgggcagacc cagcatggtt   1440

tggctgagcg ctaatctgtg ccctcactgc ggcgacagaa ccttctacga ccccaagctg   1500

atcatgtgcc cctgcttcat gcccaac                                        1527
```

<210> SEQ ID NO 99
<211> LENGTH: 509
<212> TYPE: PRT
<213> ORGANISM: Homo Sapiens

<400> SEQUENCE: 99

```
Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser Leu Leu Lys Asp Glu Ala Leu Ala Ile Ala Ala Leu Glu Leu Leu
        35                  40                  45

Pro Arg Glu Leu Phe Pro Pro Leu Phe Met Ala Ala Phe Asp Gly Arg
    50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Leu Lys Asn Ser
        115                 120                 125
```

-continued

His Gln Asp Phe Trp Thr Val Trp Ser Gly Asn Arg Ala Ser Leu Tyr
    130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Thr Glu Lys Val Lys Gln Lys Lys Asn Val Leu His Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Phe Ser Tyr Leu
                245                 250                 255

Gly Gln Met Ile Asn Leu Arg Arg Leu Leu Leu Ser His Ile His Ala
            260                 265                 270

Ser Ser Tyr Ile Ser Pro Glu Lys Glu Glu Gln Tyr Ile Ser Gln Phe
        275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Leu Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365

Leu Gln Ala Leu Leu Lys Lys Ala Ser Ala Thr Leu Gln Asp Leu Val
    370                 375                 380

Phe Asp Glu Cys Gly Ile Met Asp Asp Gln Leu Phe Ala Leu Leu Pro
385                 390                 395                 400

Ser Leu Ser His Cys Ser Gln Leu Thr Thr Leu Ser Phe Tyr Gly Asn
                405                 410                 415

Ser Ile Tyr Ile Ser Ala Leu Gln Ser Leu Leu Gln His Leu Ile Gly
            420                 425                 430

Leu Ser Asn Leu Thr His Val Leu Tyr Pro Val Leu Leu Glu Ser Tyr
        435                 440                 445

Glu Asp Ile His Val Thr Leu His Gln Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Leu Cys Pro His Cys Gly Asp Arg Thr Phe Tyr
                485                 490                 495

Asp Pro Lys Leu Ile Met Cys Pro Cys Phe Met Pro Asn
            500                 505

<210> SEQ ID NO 100
<211> LENGTH: 1302
<212> TYPE: DNA
<213> ORGANISM: Homo Sapiens

<400> SEQUENCE: 100
tctagccctg gcacagagag cgccggaaag tccctgcagt acagagtgga tcatctgctg 60
agcgccgtgg aaaacgaact gcaggccgga tctgagaagg gcgatcctac agagcacgag 120
ctgagagtcg gcctggaaga gtctgagctg tggctgcggt tcaaagaact gaccaacgag 180
atgatcgtca ccaagaacgg cagacggatg ttccccgtgc tgaaagtgaa cgtgtccgga 240
ctggacccca acgccatgta tagctttctg ctggacttcg tggtggccga caaccacaga 300
tggaaatacg tgaacggcga gtgggtgcca ggcggaaaac ctcaactgca agcccctagc 360
tgcgtgtaca ttcaccctga cagccccaat ttcggcgccc actggatgaa ggcccctgtg 420
tcctttagca aagtcaagct gaccaacaag ctgaacggcg gaggccagat catgctgaac 480
tccctgcaca aatacgagcc cagaatccac atcgtcagag tcggcggacc ccagagaatg 540
atcaccagcc actgcttccc cgagacacag tttatcgccg tgaccgccta ccagaacgag 600
gaaatcacaa ccctgaagat caagtacaac cccttcgcca aggccttcct ggacgccaaa 660
gagcggagcg accacaaaga aatgatcaaa gagcccggcg actcccagca gccaggctat 720
tctcaatggg gatggctgct gccaggcacc agcacattgt gccctccagc caatcctcac 780
agccagtttg gaggcgctct gtccctgagc agcacacaca gctacgacag ataccccaca 840
ctgcggagcc acagaagcag cccctatcct tctccttacg ctcaccggaa caacagcccc 900
acctacagcg ataatagccc cgcctgtctg agcatgctgc agtcccacga taattggagc 960
agcctgcgga tgcctgctca cccttctatg ctgcccgtgt ctcacaacgc ctctccacct 1020
acaagcagct ctcagtaccc cagcctttgg agcgtgtcca atggcgctgt gacactggga 1080
tctcaggccg ctgctgtgtc taatggactg ggagcccagt tcttcagagg cagccctgct 1140
cactacaccc ctctgacaca tcctgtgtca gccccttcta gcagcggctt ccctatgtac 1200
aaaggcgccg ctgccgccac cgatatcgtg gattctcagt acgatgccgc cgctcagggc 1260
cacctgattg catcttggac acctgtgtct ccaccttcca tg 1302

<210> SEQ ID NO 101
<211> LENGTH: 474
<212> TYPE: DNA
<213> ORGANISM: Homo Sapiens

<400> SEQUENCE: 101
atgcaccaga aacggaccgc catgtttcag gaccctcaag agaggcccag aaagctgcct 60
cacctgtgta ccgagctgca gaccaccatc cacgacatca tcctggaatg cgtgtactgc 120
aagcagcagc tcctgcggag agaggtgtac gatttcgcct tccgggacct gtgcatcgtg 180
tacagagatg gcaaccccta cgccgtgtgc aacaagtgcc tgaagttcta cagcaagatc 240
agcgagtacc gctactactg ctacagcgtg tacggcacca cactggaaca gcagtacaac 300
aagcccctgt gcgacctgct gatccggtgc atcaactgcc agaaacctct gtgccccgag 360
gaaaagcagc ggcacctgga caagaagcag cggttccaca acatcagagg ccggtggacc 420
ggcagatgca tgagctgttg tcggagcagc cggaccagaa gagagacaca gctg 474

<210> SEQ ID NO 102
<211> LENGTH: 158
<212> TYPE: PRT
<213> ORGANISM: Homo Sapiens

<400> SEQUENCE: 102

Met His Gln Lys Arg Thr Ala Met Phe Gln Asp Pro Gln Glu Arg Pro

```
1               5                   10                  15

Arg Lys Leu Pro His Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asn Lys Cys Leu Lys Phe Tyr Ser Lys Ile
65                  70                  75                  80

Ser Glu Tyr Arg Tyr Tyr Cys Tyr Ser Val Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155


<210> SEQ ID NO 103
<211> LENGTH: 291
<212> TYPE: DNA
<213> ORGANISM: Homo Sapiens

<400> SEQUENCE: 103

cacggcgata cccctacact gcacgagtac atgctggacc tgcagcctga gacaaccgac      60

ctgtactgct acgagcagct gaacgacagc agcgaggaag aggacgagat tgacggacct     120

gccggacagg ccgaacctga tagagcccac tacaatatcg tgaccttctg ctgcaagtgc     180

aacagcaccc tgagactgtg cgtgcagagc acccacgtgg acatcagaac cctggaagat     240

ctgctgatgg gcaccctggg aatcgtgtgc cctatctgca gccagaagcc t              291


<210> SEQ ID NO 104
<211> LENGTH: 97
<212> TYPE: PRT
<213> ORGANISM: Homo Sapiens

<400> SEQUENCE: 104

His Gly Asp Thr Pro Thr Leu His Glu Tyr Met Leu Asp Leu Gln Pro
1               5                   10                  15

Glu Thr Thr Asp Leu Tyr Cys Tyr Glu Gln Leu Asn Asp Ser Ser Glu
            20                  25                  30

Glu Glu Asp Glu Ile Asp Gly Pro Ala Gly Gln Ala Glu Pro Asp Arg
        35                  40                  45

Ala His Tyr Asn Ile Val Thr Phe Cys Cys Lys Cys Asn Ser Thr Leu
    50                  55                  60

Arg Leu Cys Val Gln Ser Thr His Val Asp Ile Arg Thr Leu Glu Asp
65                  70                  75                  80

Leu Leu Met Gly Thr Leu Gly Ile Val Cys Pro Ile Cys Ser Gln Lys
                85                  90                  95

Pro


<210> SEQ ID NO 105
<211> LENGTH: 471
<212> TYPE: DNA
```

<213> ORGANISM: Homo Sapiens

<400> SEQUENCE: 105

```
gccagattcg acgaccccac cagaaggcct tacaagctgc ctgatctgtg cactgaactg     60

aacaccagcc tgcaggacat cgagattacc tgtgtgtatt gcaagaccgt gctggaactg    120

accgaggtgt tcgagtttgc ctttaaggac ctgttcgtgg tgtaccggga cagcattcct    180

cacgccgcct gccacaagtg catcgacttc tacagccgga tcagagagct gcggcactac    240

agcgattctg tgtacgggga caccctggaa aagctgacca acaccggcct gtacaacctg    300

ctcatcagat gcctgcggtg tcagaagccc ctgaatcctg ccgagaagct gagacacctg    360

aacgagaagc ggagattcca caatatcgcc ggccactaca gaggccagtg ccacagctgt    420

tgcaaccggg ccagacaaga gagactgcag agaaggcggg aaacccaagt g             471
```

<210> SEQ ID NO 106
<211> LENGTH: 157
<212> TYPE: PRT
<213> ORGANISM: Homo Sapiens

<400> SEQUENCE: 106

```
Ala Arg Phe Asp Asp Pro Thr Arg Arg Pro Tyr Lys Leu Pro Asp Leu
1               5                   10                  15

Cys Thr Glu Leu Asn Thr Ser Leu Gln Asp Ile Glu Ile Thr Cys Val
            20                  25                  30

Tyr Cys Lys Thr Val Leu Glu Leu Thr Glu Val Phe Glu Phe Ala Phe
        35                  40                  45

Lys Asp Leu Phe Val Val Tyr Arg Asp Ser Ile Pro His Ala Ala Cys
    50                  55                  60

His Lys Cys Ile Asp Phe Tyr Ser Arg Ile Arg Glu Leu Arg His Tyr
65                  70                  75                  80

Ser Asp Ser Val Tyr Gly Asp Thr Leu Glu Lys Leu Thr Asn Thr Gly
                85                  90                  95

Leu Tyr Asn Leu Leu Ile Arg Cys Leu Arg Cys Gln Lys Pro Leu Asn
            100                 105                 110

Pro Ala Glu Lys Leu Arg His Leu Asn Glu Lys Arg Arg Phe His Asn
        115                 120                 125

Ile Ala Gly His Tyr Arg Gly Gln Cys His Ser Cys Cys Asn Arg Ala
    130                 135                 140

Arg Gln Glu Arg Leu Gln Arg Arg Arg Glu Thr Gln Val
145                 150                 155
```

<210> SEQ ID NO 107
<211> LENGTH: 312
<212> TYPE: DNA
<213> ORGANISM: Homo Sapiens

<400> SEQUENCE: 107

```
cacggcccta aggccacact gcaggatatc gtgctgcacc tggaacctca gaacgagatc     60

cccgtggatc tgctgtgcca tgagcagctg tccgactcca aagaggaaaa cgacgaaatc    120

gacggcgtga accaccagca tctgcctgcc agaagggccg aaccacagag acacaccatg    180

ctgtgcatgt gttgcaagtg cgaggcccgg attgagctgg tggtggaaag ctctgccgac    240

gacctgagag ccttccagca gctgttcctg aacaccctga gcttcgtgtg tccttggtgc    300

gccagccagc ag                                                        312
```

<210> SEQ ID NO 108
<211> LENGTH: 104
<212> TYPE: PRT
<213> ORGANISM: Homo Sapiens

<400> SEQUENCE: 108

His Gly Pro Lys Ala Thr Leu Gln Asp Ile Val Leu His Leu Glu Pro
1 5 10 15

Gln Asn Glu Ile Pro Val Asp Leu Leu Cys His Glu Gln Leu Ser Asp
20 25 30

Ser Lys Glu Glu Asn Asp Glu Ile Asp Gly Val Asn His Gln His Leu
35 40 45

Pro Ala Arg Arg Ala Glu Pro Gln Arg His Thr Met Leu Cys Met Cys
50 55 60

Cys Lys Cys Glu Ala Arg Ile Glu Leu Val Val Glu Ser Ser Ala Asp
65 70 75 80

Asp Leu Arg Ala Phe Gln Gln Leu Phe Leu Asn Thr Leu Ser Phe Val
85 90 95

Cys Pro Trp Cys Ala Ser Gln Gln
100

<210> SEQ ID NO 109
<211> LENGTH: 780
<212> TYPE: DNA
<213> ORGANISM: Homo Sapiens

<400> SEQUENCE: 109
gccgtgacag cctgtcagag cctgggcttt gtggtgtccc tgatcgagat cgtgggcatc 60
attgccgcta cctgcatgga ccagtggtct acccaggacc tgtacaacaa ccctgtgacc 120
gccgtgttca actaccaagg cctgtggcac agctgcatga gagagagcag cggcttcacc 180
gagtgcagag gctacttcac cctgctggaa ctgcctgcca tgctgcaggc tgtgcaggcc 240
cttatgatcg tgggaattgt gctgggagcc atcggcctgc tggtgtccat tttcgccctg 300
aagtgcatcc ggatcggcag catggaagat agcgccaagg ccaacatgac cctgaccagc 360
ggcatcatgt tcatcgtgtc cggcctgtgc gccattgctg gcgtgtccgt gtttgccaat 420
atgctcgtga ccaacttctg gctgagcacc gccaacatgt acaccggcat gggcgagatg 480
gtgcagaccg tgcagacacg gtacacattt ggcgccgctc tgtttgtcgg atgggttgca 540
ggcggactga cactgattgg cggcgtgatg atgtgtatcg cctgcagagg actggcccct 600
gaggaaacaa actacaaggc cgtgtactac cacgcctccg gacacagcgt ggcatacaaa 660
cctggcggct ttaaggccag caccggcttc ggcagcaaca ccaagaacaa gaagatctac 720
gacggcggag cacacaccga ggatgaggtg cagagctacc ccagcaagca cgactacgtg 780

<210> SEQ ID NO 110
<211> LENGTH: 260
<212> TYPE: PRT
<213> ORGANISM: Homo Sapiens

<400> SEQUENCE: 110

Ala Val Thr Ala Cys Gln Ser Leu Gly Phe Val Val Ser Leu Ile Glu
1 5 10 15

Ile Val Gly Ile Ile Ala Ala Thr Cys Met Asp Gln Trp Ser Thr Gln
20 25 30

Asp Leu Tyr Asn Asn Pro Val Thr Ala Val Phe Asn Tyr Gln Gly Leu
35 40 45

```
Trp His Ser Cys Met Arg Glu Ser Ser Gly Phe Thr Glu Cys Arg Gly
    50                  55                  60

Tyr Phe Thr Leu Leu Glu Leu Pro Ala Met Leu Gln Ala Val Gln Ala
65                  70                  75                  80

Leu Met Ile Val Gly Ile Val Leu Gly Ala Ile Gly Leu Leu Val Ser
                85                  90                  95

Ile Phe Ala Leu Lys Cys Ile Arg Ile Gly Ser Met Glu Asp Ser Ala
            100                 105                 110

Lys Ala Asn Met Thr Leu Thr Ser Gly Ile Met Phe Ile Val Ser Gly
        115                 120                 125

Leu Cys Ala Ile Ala Gly Val Ser Val Phe Ala Asn Met Leu Val Thr
    130                 135                 140

Asn Phe Trp Leu Ser Thr Ala Asn Met Tyr Thr Gly Met Gly Glu Met
145                 150                 155                 160

Val Gln Thr Val Gln Thr Arg Tyr Thr Phe Gly Ala Ala Leu Phe Val
                165                 170                 175

Gly Trp Val Ala Gly Gly Leu Thr Leu Ile Gly Gly Val Met Met Cys
            180                 185                 190

Ile Ala Cys Arg Gly Leu Ala Pro Glu Glu Thr Asn Tyr Lys Ala Val
        195                 200                 205

Tyr Tyr His Ala Ser Gly His Ser Val Ala Tyr Lys Pro Gly Gly Phe
    210                 215                 220

Lys Ala Ser Thr Gly Phe Gly Ser Asn Thr Lys Asn Lys Lys Ile Tyr
225                 230                 235                 240

Asp Gly Gly Ala His Thr Glu Asp Glu Val Gln Ser Tyr Pro Ser Lys
                245                 250                 255

His Asp Tyr Val
            260
```

<210> SEQ ID NO 111
<211> LENGTH: 492
<212> TYPE: DNA
<213> ORGANISM: Homo Sapiens

<400> SEQUENCE: 111

```
gctctgctgg cactgctgct ggtggtggct ttgcctagag tgtggaccga cgccaatctg      60

acagtgcggc agagagatcc tgaggacagc cagagaaccg acgacggcga taacagagtg     120

tggtgccacg tgtgcgagcg cgagaatacc ttcgagtgtc agaaccccag acggtgcaag     180

tggaccgagc cttactgtgt gatcgccgcc gtgaaaatct tcccacggtt cttcatggtg     240

gtcaagcagt gcagcgctgg ctgtgccgct atggaaagac ccaagcctga ggaaaagcgg     300

ttcctgctcg aggaacccat gctgttcttc tacctgaagt gctgcaaaat ctgctactgc     360

aacctggaag gccctcctat caacagcagc gtcctgaaag aatatgccgg cagcatgggc     420

gagtcttgtg gtggactgtg gctggccatt ctgctgctgc ttgcctctat tgccgcctct     480

ctgagcctga gc                                                         492
```

<210> SEQ ID NO 112
<211> LENGTH: 164
<212> TYPE: PRT
<213> ORGANISM: Homo Sapiens

<400> SEQUENCE: 112

```
Ala Leu Leu Ala Leu Leu Leu Val Val Ala Leu Pro Arg Val Trp Thr
1               5                   10                  15
```

-continued

```
Asp Ala Asn Leu Thr Val Arg Gln Arg Asp Pro Glu Asp Ser Gln Arg
            20                  25                  30

Thr Asp Asp Gly Asp Asn Arg Val Trp Cys His Val Cys Glu Arg Glu
        35                  40                  45

Asn Thr Phe Glu Cys Gln Asn Pro Arg Arg Cys Lys Trp Thr Glu Pro
    50                  55                  60

Tyr Cys Val Ile Ala Ala Val Lys Ile Phe Pro Arg Phe Phe Met Val
65                  70                  75                  80

Val Lys Gln Cys Ser Ala Gly Cys Ala Ala Met Glu Arg Pro Lys Pro
                85                  90                  95

Glu Glu Lys Arg Phe Leu Leu Glu Glu Pro Met Leu Phe Phe Tyr Leu
            100                 105                 110

Lys Cys Cys Lys Ile Cys Tyr Cys Asn Leu Glu Gly Pro Pro Ile Asn
        115                 120                 125

Ser Ser Val Leu Lys Glu Tyr Ala Gly Ser Met Gly Glu Ser Cys Gly
    130                 135                 140

Gly Leu Trp Leu Ala Ile Leu Leu Leu Leu Ala Ser Ile Ala Ala Ser
145                 150                 155                 160

Leu Ser Leu Ser


<210> SEQ ID NO 113
<211> LENGTH: 1986
<212> TYPE: DNA
<213> ORGANISM: Homo Sapiens

<400> SEQUENCE: 113

gccgccaccg agatcagcgt gctgagcgag cagttcacca agatcaaaga attgaagctg      60

atgctcgaga aggggctgaa gaaagaagag aaggacggcg tctgccgcga gaagaatcac     120

agaagcccta gcgagctgga agcccagaga acatctggcg ccttccagga cagcatcctg     180

gaagaagagg tggaactggt tctggcccct ctggaagaga gcaagaagta catcctgaca     240

ctgcagaccg tgcacttcac ctctgaagcc gtgcagctcc aggacatgag cctgctgtct     300

atccagcagc aagagggcgt gcaggttgtg gttcagcaac ctggacctgg actgctctgg     360

ctgcaagagg gacctagaca gtccctgcag cagtgtgtgg ccatcagcat ccagcaagag     420

ctgtatagcc ctcaagagat ggaagtgctg cagtttcacg ccctcgaaga gaacgtgatg     480

gtggccatcg aggacagcaa gctggctgtg tctctggccg aaacaaccgg cctgatcaag     540

ctggaagagg aacaagagaa gaaccagctg ctggccgaga aaacaaaaaa gcaactgttc     600

ttcgtggaaa ccatgagcgg cgacgagaga agcgacgaga tcgtgctgac agtgtccaac     660

agcaacgtgg aagaacaaga ggaccagcct accgcctgtc aggccgatgc cgagaaagcc     720

aagtttacca agaaccagag aaagaccaag ggcgccaagg gcaccttcca ctgcaacgtg     780

tgcatgttca ccagcagccg gatgagcagc ttcaactgcc acatgaagac ccacaccagc     840

gagaagcccc atctgtgtca cctgtgcctg aaaaccttcc ggacagtgac actgctgtgg     900

aactatgtga acacccacac aggcacccgg ccttacaagt gcaacgactg caacatggcc     960

ttcgtgacca gcggagaact cgtgcggcac agaagataca agcacaccca cgagaaaccc    1020

ttcaagtgca gcatgtgcaa atacgcatcc atggaagcct ccaagctgaa gtgccacgtg    1080

cgctctcaca caggcgagca ccctttccag tgctgtcagt gtagctacgc cagccgggac    1140

acctataagc tgaagcggca catgagaacc cactctggcg aaaagcccta cgagtgccac    1200

atctgccaca ccagattcac ccagagcggc accatgaaga ttcacatcct gcagaaacac    1260
```

ggcaagaacg tgcccaagta ccagtgtcct cactgcgcca ccattatcgc cagaaagtcc 1320
gacctgcggg tgcacatgag gaatctgcac gcctattctg ccgccgagct gaaatgcaga 1380
tactgcagcg ccgtgttcca caagagatac gccctgatcc agcaccagaa aacccacaag 1440
aacgagaagc ggtttaagtg caagcactgc agctacgcct gcaagcaaga gcgccacatg 1500
atcgcccaca tccacacaca caccggggag aagcctttta cctgcctgag ctgcaacaag 1560
tgcttccggc agaaacagct gctcaacgcc cacttcagaa agtaccacga cgccaacttc 1620
atccccaccg tgtacaagtg ctccaagtgc ggcaagggct tcagccggtg gatcaatctg 1680
caccggcacc tggaaaagtg cgagtctggc gaagccaagt ctgccgcctc tggcaagggc 1740
agaagaaccc ggaagagaaa gcagaccatc ctgaaagagg ccaccaagag ccagaaagaa 1800
gccgccaagc gctggaaaga ggctgccaac ggcgacgaag ctgctgccga agaagccagc 1860
acaacaaagg gcgaacagtt ccccgaagag atgttccctg tggcctgcag agaaaccaca 1920
gccagagtga agcaagaggt cgaccagggc gtgacctgcg agatgctgct gaacaccatg 1980
gacaag 1986

<210> SEQ ID NO 114
<211> LENGTH: 2280
<212> TYPE: DNA
<213> ORGANISM: Homo Sapiens

<400> SEQUENCE: 114
atgaagaccc tggtcaagat cgtgtttggc gtggccacat ctgccgtgct ggctctgctg 60
gtcatgtgca ttgtgctgca ccccagcaga gtgcacaaca gcgaagagaa caccatgcgg 120
gccctgacac tgaaggacat cctgaacgtg accttcagct acaagatatt cttccccaac 180
tggatctccg gccaagagta cctgcaccag agcgccgaca acaacatcgt gctgtacaac 240
atcgagacag gccagagcta caccatcatg agcaaccgga ccatgaagtc cgtgaacgcc 300
agcaactacg gactgagccc cgattggcag ttcgtgtacc tggaaagcga ctacagcaag 360
ctgtggcggt acagctacac cgccacctac tacatctacg acctgagcaa cggcgagttc 420
gtgaagggca acgagctgcc ccatcctatc cagtacctgt gttggagccc tgtgggctcc 480
aagctggcct acgtgtacca gaacaacatc tacctgaagc agcggcctgg cgaccctcca 540
ttccagatca ccttcaacgg cagagagaac aagatcttta acggcatccc cgactgggtg 600
tacgaggaag agatgctggc caccaaatac gccctgtggt ggtcccctaa cggcaagttt 660
ctggcctatg ccgacttcaa cgacacagac atccccgtga tcgcctacag ctactacggc 720
aatgagcagt accccaggac catcaacatc agctacccca aagccggcgc taagaaccct 780
gtcgtgcgga tcttcatcat cgacaccacc tatcctgtgt acgtgggccc tcaagaggtg 840
ccagtgcctg ccatgattgc cagcagcgac tactacttca gctggctgac ctgggtcacc 900
gacgagcgag tttgtctgca gtggctgaag cgggtgcaga acatcagcgt gctgagcatc 960
tgcgacttca gaaaggactg gcagacatgg gactgcccca acacacagca gcacatcgag 1020
gaaagcagaa ccggctgggc tggcggcttc tttgtgtcta cccctgtgtt cagctacgac 1080
gccatcctgt actataagat cttcagcgac aaggacggct acaagcacat ccactacatc 1140
aagtacaccg tcgagaacgt gatccagatt accagcggca agtgggaagc catcaatatc 1200
ttcagagtga tccagtacag cctgttctac agcagcaacg agttcgagga ataccccggc 1260
agacggaaca tctacagaat cagcatcggc agctacccgc ctagcaagaa atgcgtgacc 1320
tgccacctga gaaaagagcg gtgccagtac tacacagcca gcttctccaa ctacgccaag 1380

-continued

```
tactacgccc tcgtgtgtta cggccctggc atccctatca gcacactgca cgatggcaga   1440

accgaccaag agatcaagat cctggaagaa aacaaagagc tggaaaacgc cctgaagaac   1500

atccagctgc ctaaagagga aatcaagaag ctggaagtcg acgagatcac cctgtggtac   1560

aagatgatcc tgcctcctca gttcgaccgg tccaagaagt accctctgct gatccaggtg   1620

tacggcggac cttgttctca gtctgtgcgc tccgtgttcg ccgtgaattg gatcagctat   1680

ctggccagca aagaaggcat ggttatcgcc ctggtggacg gcagaggcac agcttttcaa   1740

ggcgacaagc tgctgtacgc cgtgtatcag aaactgggcg tgtacgaagt ggaagatcag   1800

atcaccgccg tgcggaagtt catcgagatg ggcttcatcg acgagaagcg gatcgccatc   1860

tggggctggt cttacggcgg ctatattagc tctctggccc tggcctctgg caccggcctg   1920

tttaagtgtg gaattgccgt ggctcccgtg tccagctggg agtactatac cagcgtgtac   1980

accgagcggt tcatgggcct gcctaccaag gacgacaacc tggaacacta caagaactct   2040

accgtgatgg ccagagccga gtacttccgg aacgtggact acctgctgat tcacggcacc   2100

gccgacgaca acgtgcactt ccaaaacagc gcccagatcg ctaaggccct cgtgaatgcc   2160

caggtggact ttcaggccat gtggtacagc gaccagaacc acggactgtc tggcctgagc   2220

accaaccacc tgtacaccca catgacccac tttctgaaac agtgcttcag cctgagcgac   2280
```

```
<210> SEQ ID NO 115
<211> LENGTH: 760
<212> TYPE: PRT
<213> ORGANISM: Homo Sapiens

<400> SEQUENCE: 115

Met Lys Thr Leu Val Lys Ile Val Phe Gly Val Ala Thr Ser Ala Val
1               5                   10                  15

Leu Ala Leu Leu Val Met Cys Ile Val Leu His Pro Ser Arg Val His
            20                  25                  30

Asn Ser Glu Glu Asn Thr Met Arg Ala Leu Thr Leu Lys Asp Ile Leu
        35                  40                  45

Asn Val Thr Phe Ser Tyr Lys Ile Phe Phe Pro Asn Trp Ile Ser Gly
    50                  55                  60

Gln Glu Tyr Leu His Gln Ser Ala Asp Asn Asn Ile Val Leu Tyr Asn
65                  70                  75                  80

Ile Glu Thr Gly Gln Ser Tyr Thr Ile Met Ser Asn Arg Thr Met Lys
                85                  90                  95

Ser Val Asn Ala Ser Asn Tyr Gly Leu Ser Pro Asp Trp Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Lys Gly Asn
    130                 135                 140

Glu Leu Pro His Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Glu Met Leu Ala Thr
        195                 200                 205

Lys Tyr Ala Leu Trp Trp Ser Pro Asn Gly Lys Phe Leu Ala Tyr Ala
```

-continued

```
    210                 215                 220

Asp Phe Asn Asp Thr Asp Ile Pro Val Ile Ala Tyr Ser Tyr Tyr Gly
225                 230                 235                 240

Asn Glu Gln Tyr Pro Arg Thr Ile Asn Ile Ser Tyr Pro Lys Ala Gly
                245                 250                 255

Ala Lys Asn Pro Val Val Arg Ile Phe Ile Ile Asp Thr Thr Tyr Pro
            260                 265                 270

Val Tyr Val Gly Pro Gln Glu Val Pro Val Pro Ala Met Ile Ala Ser
        275                 280                 285

Ser Asp Tyr Tyr Phe Ser Trp Leu Thr Trp Val Thr Asp Glu Arg Val
    290                 295                 300

Cys Leu Gln Trp Leu Lys Arg Val Gln Asn Ile Ser Val Leu Ser Ile
305                 310                 315                 320

Cys Asp Phe Arg Lys Asp Trp Gln Thr Trp Asp Cys Pro Asn Thr Gln
                325                 330                 335

Gln His Ile Glu Glu Ser Arg Thr Gly Trp Ala Gly Gly Phe Phe Val
            340                 345                 350

Ser Thr Pro Val Phe Ser Tyr Asp Ala Ile Leu Tyr Tyr Lys Ile Phe
        355                 360                 365

Ser Asp Lys Asp Gly Tyr Lys His Ile His Tyr Ile Lys Tyr Thr Val
    370                 375                 380

Glu Asn Val Ile Gln Ile Thr Ser Gly Lys Trp Glu Ala Ile Asn Ile
385                 390                 395                 400

Phe Arg Val Ile Gln Tyr Ser Leu Phe Tyr Ser Ser Asn Glu Phe Glu
                405                 410                 415

Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
        435                 440                 445

Gln Tyr Tyr Thr Ala Ser Phe Ser Asn Tyr Ala Lys Tyr Tyr Ala Leu
    450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Glu Ile Lys Lys Leu Glu
            500                 505                 510

Val Asp Glu Ile Thr Leu Trp Tyr Lys Met Ile Leu Pro Pro Gln Phe
        515                 520                 525

Asp Arg Ser Lys Lys Tyr Pro Leu Leu Ile Gln Val Tyr Gly Gly Pro
    530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
                565                 570                 575

Thr Ala Phe Gln Gly Asp Lys Leu Leu Tyr Ala Val Tyr Gln Lys Leu
            580                 585                 590

Gly Val Tyr Glu Val Glu Asp Gln Ile Thr Ala Val Arg Lys Phe Ile
        595                 600                 605

Glu Met Gly Phe Ile Asp Glu Lys Arg Ile Ala Ile Trp Gly Trp Ser
    610                 615                 620

Tyr Gly Gly Tyr Ile Ser Ser Leu Ala Leu Ala Ser Gly Thr Gly Leu
625                 630                 635                 640
```

```
Phe Lys Cys Gly Ile Ala Val Ala Pro Val Ser Ser Trp Glu Tyr Tyr
                645                 650                 655

Thr Ser Val Tyr Thr Glu Arg Phe Met Gly Leu Pro Thr Lys Asp Asp
            660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn
    690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
                725                 730                 735

Ser Gly Leu Ser Thr Asn His Leu Tyr Thr His Met Thr His Phe Leu
            740                 745                 750

Lys Gln Cys Phe Ser Leu Ser Asp
        755                 760


<210> SEQ ID NO 116
<211> LENGTH: 780
<212> TYPE: DNA
<213> ORGANISM: Homo Sapiens

<400> SEQUENCE: 116

gccgtcacag cctgtcagag cctgggcttt gtggtgtccc tgatcgagat cgtgggcatc      60

attgccgcta cctgcatgga ccagtggtct acccaggacc tgtataacaa ccccgtgacc     120

gccgtgttca actaccaagg cctgtggcac agctgcatga gagagagcag cggcttcacc     180

gagtgcaggg gctactttac cctgctggaa ctgccagcca tgctgcaggc tgtgcaggcc     240

cttatgatcg tgggaattgt gctgggcgcc atcggcctgc tggtgtctat ttttgccctg     300

aagtgcatcc ggatcggcag catggaagat agcgccaagg ccaacatgac cctgacctcc     360

ggcatcatgt tcatcgtgtc cggcctgtgt gccattgcag gcgtgtccgt gtttgccaat     420

atgctcgtga ccaacttctg gctgtccacc gccaacatgt acaccggcat gggcgagatg     480

gtgcagaccg tgcagacacg gtacacattt ggcgccgctc tgtttgtcgg atgggttgca     540

ggcggactga ctctgattgg cggcgtgatg atgtgtatcg cctgcagagg actggcccct     600

gaggaaacaa actacaaggc cgtgtactac cacgccagcg gacacagcgt ggcatacaaa     660

ccaggcggct ttaaggccag cacaggcttc ggcagcaaca ccaagaacaa gaagatctac     720

gacggcggag cccataccga ggatgaggtg cagagctacc ctagcaagca cgactacgtg     780


<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117

tgcccaccag tgccaccact                                                  20


<210> SEQ ID NO 118
<211> LENGTH: 21
<212> TYPE: DNA
<213> ORGANISM: Artificial Sequence
<220> FEATURE:
<223> OTHER INFORMATION: Synthetic
```

<400> SEQUENCE: 118
cggactgctg tgtcctaaga g 21

<210> SEQ ID NO 119
<211> LENGTH: 22
<212> TYPE: DNA
<213> ORGANISM: Artificial Sequence
<220> FEATURE:
<223> OTHER INFORMATION: Synthetic

<400> SEQUENCE: 119
gctgtcctcg tctgtatctt cc 22

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
tgtgaaggtg ctggaatacg 20

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
gccggtaaag taggtgtgct 20

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
tgtctagggg aagggtgtgg 20

<210> SEQ ID NO 123
<211> LENGTH: 21
<212> TYPE: DNA
<213> ORGANISM: Artificial Sequence
<220> FEATURE:
<223> OTHER INFORMATION: Synthetic

<400> SEQUENCE: 123
tgccccagac tgaccaaata c 21

<210> SEQ ID NO 124
<211> LENGTH: 22
<212> TYPE: DNA
<213> ORGANISM: Artificial Sequence
<220> FEATURE:
<223> OTHER INFORMATION: Synthetic

<400> SEQUENCE: 124
gaagcccttc agctgtagat gg 22

<210> SEQ ID NO 125
<211> LENGTH: 19

<212> TYPE: DNA
<213> ORGANISM: Artificial Sequence
<220> FEATURE:
<223> OTHER INFORMATION: Synthetic

<400> SEQUENCE: 125
ctgaattgtc agggcgctc 19

<210> SEQ ID NO 126
<211> LENGTH: 22
<212> TYPE: DNA
<213> ORGANISM: Artificial Sequence
<220> FEATURE:
<223> OTHER INFORMATION: Synthetic

<400> SEQUENCE: 126
catgcaccag aggaacatga cc 22

<210> SEQ ID NO 127
<211> LENGTH: 22
<212> TYPE: DNA
<213> ORGANISM: Artificial Sequence
<220> FEATURE:
<223> OTHER INFORMATION: Synthetic

<400> SEQUENCE: 127
gagttggatg gtcagggcag at 22

<210> SEQ ID NO 128
<211> LENGTH: 28
<212> TYPE: DNA
<213> ORGANISM: Artificial Sequence
<220> FEATURE:
<223> OTHER INFORMATION: Synthetic

<400> SEQUENCE: 128
gatcacttct gcgtgttcgc taacacag 28

<210> SEQ ID NO 129
<211> LENGTH: 23
<212> TYPE: DNA
<213> ORGANISM: Artificial Sequence
<220> FEATURE:
<223> OTHER INFORMATION: Synthetic

<400> SEQUENCE: 129
ctcatcacgc tcaggctctc gct 23

<210> SEQ ID NO 130
<211> LENGTH: 21
<212> TYPE: DNA
<213> ORGANISM: Artificial Sequence
<220> FEATURE:
<223> OTHER INFORMATION: Synthetic

<400> SEQUENCE: 130
gagaagtgca gaccagaatc g 21

<210> SEQ ID NO 131
<211> LENGTH: 22
<212> TYPE: DNA
<213> ORGANISM: Artificial Sequence
<220> FEATURE:
<223> OTHER INFORMATION: Synthetic

<400> SEQUENCE: 131
tctgctgtag ttggacacct tg 22

<210> SEQ ID NO 132
<211> LENGTH: 27
<212> TYPE: DNA
<213> ORGANISM: Artificial Sequence
<220> FEATURE:
<223> OTHER INFORMATION: Synthetic

<400> SEQUENCE: 132
atgcatgccc gaagaggacc tgcagag 27

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
gctctgcaca tcggacagca t 21

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
ttccagtgct gccagtgtag 20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
agcacttgtt gcagctcaga 20

<210> SEQ ID NO 136
<211> LENGTH: 22
<212> TYPE: DNA
<213> ORGANISM: Artificial Sequence
<220> FEATURE:
<223> OTHER INFORMATION: Synthetic

<400> SEQUENCE: 136
ccctcaagag aggcccagaa ag 22

<210> SEQ ID NO 137
<211> LENGTH: 23
<212> TYPE: DNA
<213> ORGANISM: Artificial Sequence
<220> FEATURE:
<223> OTHER INFORMATION: Synthetic

<400> SEQUENCE: 137
tacacgatgc acaggtcccg gaa 23

<210> SEQ ID NO 138
<211> LENGTH: 21
<212> TYPE: DNA
<213> ORGANISM: Artificial Sequence -continued

```
<220> FEATURE:
<223> OTHER INFORMATION: Synthetic

<400> SEQUENCE: 138

cacggcgata cccctacact g                                          21


<210> SEQ ID NO 139
<211> LENGTH: 23
<212> TYPE: DNA
<213> ORGANISM: Artificial Sequence
<220> FEATURE:
<223> OTHER INFORMATION: Synthetic

<400> SEQUENCE: 139

ccatcagcag atcttccagg gtt                                        23


<210> SEQ ID NO 140
<211> LENGTH: 23
<212> TYPE: DNA
<213> ORGANISM: Artificial Sequence
<220> FEATURE:
<223> OTHER INFORMATION: Synthetic

<400> SEQUENCE: 140

tgaacaccag cctgcaggac atc                                        23


<210> SEQ ID NO 141
<211> LENGTH: 26
<212> TYPE: DNA
<213> ORGANISM: Artificial Sequence
<220> FEATURE:
<223> OTHER INFORMATION: Synthetic

<400> SEQUENCE: 141

gcatctgatg agcaggttgt acaggc                                     26


<210> SEQ ID NO 142
<211> LENGTH: 24
<212> TYPE: DNA
<213> ORGANISM: Artificial Sequence
<220> FEATURE:
<223> OTHER INFORMATION: Synthetic

<400> SEQUENCE: 142

tgtgccatga gcagctgtcc gact                                       24


<210> SEQ ID NO 143
<211> LENGTH: 23
<212> TYPE: DNA
<213> ORGANISM: Artificial Sequence
<220> FEATURE:
<223> OTHER INFORMATION: Synthetic

<400> SEQUENCE: 143

aaggctctca ggtcgtcggc aga                                        23
```

TUMOR CELL VACCINES

CROSS-REFERENCE TO RELATED APPLICATIONS

This application is a continuation of U.S. patent application Ser. No. 17/109,757 filed Dec. 2, 2020, which claims priority to U.S. Provisional Patent Application No. 62/943,055 filed Dec. 3, 2019. The entire contents of these applications are incorporated herein by reference in their entirety.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "54907D_Seqlisting.txt", which was created on Apr. 19, 2022 and is 343,888 bytes in size. The subject matter of the Sequence Listing is incorporated herein in its entirety by reference.

BACKGROUND

Cancer is a leading cause of death. Recent breakthroughs in immunotherapy approaches, including checkpoint inhibitors, have significantly advanced the treatment of cancer, but these approaches are neither customizable nor broadly applicable across indications or to all patients within an indication. Furthermore, only a subset of patients are eligible for and respond to these immunotherapy approaches. Therapeutic cancer vaccines have the potential to generate anti-tumor immune responses capable of eliciting clinical responses in cancer patients, but many of these therapies have a single target or are otherwise limited in scope of immunomodulatory targets and/or breadth of antigen specificity. The development of a therapeutic vaccine customized for an indication that targets the heterogeneity of the cells within an individual tumor remains a challenge.

A vast majority of therapeutic cancer vaccine platforms are inherently limited in the number of antigens that can be targeted in a single formulation. The lack of breadth in these vaccines adversely impacts efficacy and can lead to clinical relapse through a phenomenon called antigen escape, with the appearance of antigen-negative tumor cells. While these approaches may somewhat reduce tumor burden, they do not eliminate antigen-negative tumor cells or cancer stem cells. Harnessing a patient's own immune system to target a wide breadth of antigens could reduce tumor burden as well as prevent recurrence through the antigenic heterogeneity of the immune response. Thus, a need exists for improved whole cell cancer vaccines. Provided herein are methods and compositions that address this need.

SUMMARY

In various embodiments, the present disclosure provides an allogeneic whole cell cancer vaccine platform that includes compositions and methods for treating and preventing cancer. The present disclosure provides compositions and methods that are customizable for the treatment of various solid tumor indications and target the heterogeneity of the cells within an individual tumor. The compositions and methods of embodiments of the present disclosure are broadly applicable across solid tumor indications and to patients afflicted with such indications. In some embodiments, the present disclosure provides compositions of cancer cell lines that (i) are modified as described herein and (ii) express a sufficient number and amount of tumor associated antigens (TAAs) such that, when administered to a subject afflicted with a cancer, cancers, or cancerous tumor (s), a TAA-specific immune response is generated.

In one embodiment, provided herein is a composition comprising a therapeutically effective amount of at least 1 cancer cell line, wherein the cell line or a combination of the cell lines comprises cells that express at least 5 tumor associated antigens (TAAs) associated with a cancer of a subject intended to receive said composition, and wherein said composition is capable of eliciting an immune response specific to the at least 5 TAAs. In another embodiment, provided herein is a composition comprising a therapeutically effective amount of at least 1 cancer cell line, wherein the cell line or a combination of the cell lines comprises cells that express at least 10 tumor associated antigens (TAAs) associated with a cancer of a subject intended to receive said composition, and wherein said composition is capable of eliciting an immune response specific to the at least 10 TAAs. In another embodiment, provided herein is a composition comprising a therapeutically effective amount of at least 1 cancer cell line, wherein the cell line or a combination of the cell lines comprises cells that express at least 15 tumor associated antigens (TAAs) associated with a cancer of a subject intended to receive said composition, and wherein said composition is capable of eliciting an immune response specific to the at least 15 TAAs. In another embodiment, provided herein is a composition comprising a therapeutically effective amount of at least 2 cancer cell lines, wherein each cell line or a combination of the cell lines comprises cells that express at least 5 tumor associated antigens (TAAs) associated with a cancer of a subject intended to receive said composition, and wherein each cell line or the combination of the cell lines are modified to express or increase expression of at least 1 immunostimulatory factor. In another embodiment, provided herein is a composition comprising a therapeutically effective amount of at least 2 cancer cell lines, wherein each cell line or a combination of the cell lines comprises cells that express at least 15 tumor associated antigens (TAAs) associated with a cancer of a subject intended to receive said composition, and wherein each cell line or the combination of the cell lines are modified to express or increase expression of at least 2 immunostimulatory factor. In still another embodiment, provided herein is an aforementioned composition wherein said composition is capable of stimulating a 1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, or 25-fold or higher increase in IFNγ production compared to a composition comprising unmodified cancer cell lines.

In another embodiment, provided herein is a composition comprising a therapeutically effective amount of at least 2 cancer cell lines, wherein each cell line or a combination of the cell lines comprises cells that express at least 5 tumor associated antigens (TAAs) associated with a cancer of a subject intended to receive said composition, and wherein each cell line or the combination of the cell lines are modified to inhibit or decrease expression of at least 1 immunosuppressive factor. In another embodiment, provided herein is a composition comprising a therapeutically effective amount of at least 2 cancer cell lines, wherein each cell line or a combination of the cell lines comprises cells that express at least 5 tumor associated antigens (TAAs) associated with a cancer of a subject intended to receive said composition, and wherein each cell line or the combination of the cell lines are modified to (i) express or increase expression of at least 1 immunostimulatory factor, and (ii) inhibit or decrease expression of at least 1 immunosuppressive factor. In another embodiment, provided herein is an aforementioned composition wherein each cell line or the combination of the cell lines comprises cells that express 5, 6, 7, 8, 9, 10, 11, 12, 13, 14, 15, 16, 17, 18, 19, 20, 21, 22, 23, 24, 25, 26, 27, 28, 29, or 30 TAAs associated with the cancer of the subject intended to receive said composition. In another embodiment, the composition comprises 2, 3, 4, 5, or 6 cancer cell lines. In still another embodiment, each cell line or a combination of the cell lines are modified to express or increase expression of 1, 2, 3, 4, 5, 6, 7, or 8 immunostimulatory factors. In yet another embodiment, each cell line or a combination of the cell lines are modified to inhibit or decrease expression of 1, 2, 3, 4, 5, 6, 7, or 8 immunosuppressive factors.

In still another embodiment of the present disclosure, provided herein is a composition comprising a therapeutically effective amount of at least 2 cancer cell lines, wherein each cell line or a combination of the cell lines comprises cells that are modified to express or increase expression of at least 2 immunostimulatory factors. In another embodiment, provided herein is a composition comprising a therapeutically effective amount of at least 2 cancer cell lines, wherein each cell line or a combination of the cell lines comprises cells that are modified to express or increase expression of at least 1 immunostimulatory factor, and wherein at least 1 of the cell lines is modified to knockdown or knockout one or more of CD276, TGFβ1, and TGFβ2. In another embodiment, provided herein is a composition comprising a therapeutically effective amount of at least 2 cancer cell lines, wherein each cell line or a combination of the cell lines comprises cells that are modified to express or increase expression of at least 1 immunostimulatory factor, and wherein said at least 1 immunostimulatory factor increases dendritic cell maturation. In another embodiment, provided herein is a composition comprising a therapeutically effective amount of at least 2 cancer cell lines, wherein each cell line or a combination of the cell lines comprises cells that are modified to express or increase expression of at least 1 immunostimulatory factor, and wherein said composition is capable of stimulating a 1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, or 25-fold or higher increase in IFNγ production compared to a composition comprising unmodified cancer cell lines. In another embodiment, provided herein is a composition comprising a therapeutically effective amount of at least 2 cancer cell lines, wherein each cell line or a combination of the cell lines comprises cells that are modified to (i) express or increase expression of at least 1 immunostimulatory factor, and (ii) inhibit or decrease expression of at least 1 immunosuppressive factor, and wherein said composition is capable of stimulating at least a 1.5-fold increase in IFNγ production compared to a composition comprising unmodified cancer cell lines. In another embodiment, provided herein is a composition comprising a therapeutically effective amount of at least 2 cancer cell lines, wherein each cell line or a combination of the cell lines comprises cells that are modified to (i) express or increase expression of at least 2 immunostimulatory factors, and (ii) inhibit or decrease expression of at least 1 immunosuppressive factor, and wherein said composition is capable of stimulating at least a 1.5-fold increase in IFNγ production compared to a composition comprising unmodified cancer cell lines. In still another embodiment, provided herein is a composition comprising a therapeutically effective amount of at least 3 cancer cell lines, wherein each cell line or a combination of the cell lines comprises cells that are modified to (i) express or increase expression of at least 2 immunostimulatory factors, and (ii) inhibit or decrease expression of at least 1 immunosuppressive factor, and wherein said composition is capable of stimulating at least a 1.7-fold increase in IFNγ production compared to a composition comprising unmodified cancer cell lines. In yet another embodiment, provided herein is a composition comprising a therapeutically effective amount of at least 3 cancer cell lines, wherein each cell line or a combination of the cell lines comprises cells that are modified to (i) express or increase expression of at least 2 immunostimulatory factors, and (ii) inhibit or decrease expression of at least 2 immunosuppressive factors, and wherein said composition is capable of stimulating at least a 2.0-fold increase in IFNγ production compared to a composition comprising unmodified cancer cell lines.

In one embodiment, provided herein is an immunogenic composition comprising a therapeutically effective amount of at least 1 cancer cell line, wherein the cell line or a combination of the cell lines comprises cells that are modified to (i) express or increase expression of at least 1 immunostimulatory factor, and (ii) increase expression of at least 1 tumor associated antigen (TAA) that is either not expressed or minimally expressed by 1 cell line or the combination of the cell lines. In another embodiment, provided herein is an immunogenic composition comprising a therapeutically effective amount of at least 2 cancer cell lines, wherein the cell line or a combination of the cell lines comprises cells that are modified to (i) express or increase expression of at least 2 immunostimulatory factors, and (ii) increase expression of at least 2 tumor associated antigens (TAAs) that are either not expressed or minimally expressed by 1 cell line or the combination of the cell lines. In another embodiment, provided herein is an immunogenic composition comprising a therapeutically effective amount of at least 3 cancer cell lines, wherein the cell line or a combination of the cell lines comprises cells that are modified to (i) express or increase expression of at least 2 immunostimulatory factors, and (ii) increase expression of at least 2 tumor associated antigens (TAAs) that are either not expressed or minimally expressed by 1 cell line or the combination of the cell lines.

In another embodiment, provided herein is an aforementioned immunogenic composition wherein each cell line or a combination of the cell lines are modified to (i) express or increase expression of 3, 4, 5, 6, 7, 8, 9 or 10 immunostimulatory factors, and/or (iii) increase expression of 3, 4, 5, 6, 7, 8, 9 or 10 TAAs that are either not expressed or minimally expressed by 1 cell line or the combination of the cell lines. In another embodiment, provided herein is an aforementioned immunogenic composition capable of stimulating at least a 1, 1.3, 1.4, 1.5, 1.6, 1.7, or 2-fold increase in IFNγ production compared to a composition comprising unmodified cancer cell lines.

In yet another embodiment, provided herein is an immunogenic composition comprising a therapeutically effective amount of at least 1 cancer cell line, wherein the cell line or a combination of the cell lines comprises cells that are modified to (i) express or increase expression of at least 1 immunostimulatory factor, (ii) inhibit or decrease expression of at least 1 immunosuppressive factor, and (iii) increase expression of at least 1 tumor associated antigen (TAA) that is either not expressed or minimally expressed by 1 cell line or the combination of the cell lines. In another embodiment, provided herein is an immunogenic composition comprising a therapeutically effective amount of at least 2 cancer cell lines, wherein each cell line or a combination of the cell lines comprises cells that are modified to (i) express or increase expression of at least 2 immunostimulatory factors, (ii) inhibit or decrease expression of at least 2 immunosuppressive factors, and (iii) increase expression of at least 2 tumor associated antigens (TAAs) that are either not expressed or minimally expressed by 1 cell line or the combination of the cell lines. In another embodiment, provided herein is an immunogenic composition comprising a therapeutically effective amount of at least 3 cancer cell lines, wherein each cell line or a combination of the cell lines comprises cells that are modified to (i) express or increase expression of at least 2 immunostimulatory factors, (ii) inhibit or decrease expression of at least 2 immunosuppressive factors, and (iii) increase expression of at least 1 tumor associated antigen (TAA) that is either not expressed or minimally expressed by 1 cell line or the combination of the cell lines. In another embodiment, provided herein is an immunogenic composition comprising a therapeutically effective amount of at least 3 cancer cell lines, wherein each cell line or a combination of the cell lines comprises cells that are modified to (i) express or increase expression of at least 2 immunostimulatory factors, (ii) inhibit or decrease expression of at least 2 immunosuppressive factors, and (iii) increase expression of at least 2 tumor associated antigens (TAAs) that are either not expressed or minimally expressed by 1 cell line or the combination of the cell lines.

In some embodiments, an aforementioned immunogenic composition is provided wherein the composition comprises 4, 5, or 6 cancer cell lines. In some embodiments, each cell line or a combination of the cell lines comprises cells that are modified to increase expression of at least 3, 4, 5, 6, 7, 8, 9, or 10 or more TAAs that are either not expressed or minimally expressed by 1 cell line or the combination of the cell lines. In another embodiment, n each cell line or a combination of the cell lines are modified to (i) express or increase expression of 3, 4, 5, 6, 7, 8, 9 or 10 immunostimulatory factors, (ii) inhibit or decrease expression of 3, 4, 5, 6, 7, 8, 9 or 10 immunosuppressive factors, and/or (iii) increase expression of 3, 4, 5, 6, 7, 8, 9 or 10 TAAs that are either not expressed or minimally expressed by 1 cell line or the combination of the cell lines.

In still another embodiment of the present disclosure, provided herein is an immunogenic composition comprising a therapeutically effective amount of at least 3 cancer cell lines, wherein each cell line or a combination of the cell lines comprises cells that are modified to (i) express or increase expression of at least 2 immunostimulatory factors, (ii) inhibit or decrease expression of at least 2 immunosuppressive factors, and/or (iii) express or increase expression of one or more of CT83, MSLN, TERT, PSMA, MAGEA1, EGFRvIII, hCMVpp65, TBXT, BORIS, FSHR, MAGEA10, MAGEC2, WT1, FBP, TDGF1, Claudin 18, LYK6K, FAP, PRAME, HPV16/18 E6/E7, or mutated versions thereof. In some embodiments, the mutated versions comprise: (i) a modified version selected from the group consisting of modTERT, modPSMA, modMAGEA1, modTBXT, modBORIS, modFSHR, modMAGEA10, modMAGEC2, modWT1, modKRAS, modFBP, modTDGF1, modClaudin 18, modLY6K, modFAP, and modPRAME; or (ii) a fusion protein selected from the group consisting of modCT83-MSLN, modMAGEA1-EGFRvIII-pp65, modTBXT-modBORIS, modFSHR-modMAGEA10, modTBXT-modMAGEC2, modTBXT-modWT1, modTBXT-modWT1-KRAS, modWT1-modFBP, modPSMA-modTDGF1, modWT1-modClaudin 18, modPSMA-modLY6K, modFAP-modClaudin 18, and modPRAME-modTBXT. In still other embodiments, the mutated versions comprise: (i) a modified version selected from the group consisting of modMesothelin (SEQ ID NO: 62), modTERT (SEQ ID NO: 36), modPSMA (SEQ ID NO: 38), modMAGEA1 (SEQ ID NO: 73), modTBXT (SEQ ID NO: 79), modBORIS(SEQ ID NO: 60), modFSHR (SEQ ID NO: 95), modMAGEA10 (SEQ ID NO: 97), modMAGEC2 (SEQ ID NO: 87), modWT1 (SEQ ID NO: 81), KRAS G12D (SEQ ID NO: 83) or KRAS G12V (SEQ ID NO:85), modFBP (SEQ ID NO: 93), modTDGF1 (SEQ ID NO: 89), modClaudin 18 (SEQ ID NO: 110), modLYK6K (SEQ ID NO: 112), modFAP (SEQ ID NO: 115), and modPRAME (SEQ ID NO:99); or (ii) a fusion protein selected from the group consisting of CT83-MSLN (SEQ ID NO: 22), modMAGEA1-EGFRvIII-pp65 (SEQ ID NO: 40), modTBXT-modBORIS (SEQ ID NO:42), modFSHR-modMAGEA10 (SEQ ID NO: 44), modTBXT-modMAGEC2 (SEQ ID NO: 46), modTBXT-modWT1 (SEQ ID NO: 48), modTBXT-modWT1 (KRAS) (SEQ ID NO: 50), modWT1-modFBP (SEQ ID NO: 52), modPSMA-modTDGF1 (SEQ ID NO: 54), modWT1-modClaudin 18 (SEQ ID NO: 56), modPSMA-modLY6K (SEQ ID NO: 58), and modPRAME-modTBXT (SEQ ID NO: 66).

In still another embodiment of the present disclosure, provided herein is a composition comprising a therapeutically effective amount of a cancer stem cell line, wherein said cancer stem cell line is modified to express or increase expression of at least 1 immunostimulatory factor. In another embodiment, provided herein is a composition comprising a therapeutically effective amount of a cancer stem cell line, wherein said cancer stem cell line is modified to (i) express or increase expression of at least 1 immunostimulatory factor, and (ii) inhibit or decrease expression of at least 1 immunosuppressive factor. In another embodiment, provided herein is a composition comprising a therapeutically effective amount of a cancer stem cell line, wherein said cell line is modified to (i) express or increase expression of at least 1 immunostimulatory factor, and (ii) increase expression of at least 1 TAA that is either not expressed or minimally expressed by the cancer stem cell line. In some embodiments, the at least 1 TAA is selected from the group consisting of TERT, PSMA, MAGEA1, EGFRvIII, hCMV pp65, TBXT, BORIS, FSHR, MAGEA10, MAGEC2, WT1, KRAS, FBP, TDGF1, Claudin 18, LY6K, FAP, PRAME, HPV16/18 E6/E7, and FAP, or mutated versions thereof.

In still another embodiment of the present disclosure, provided herein is a composition comprising a therapeutically effective amount of a cancer stem cell line, wherein said cancer stem cell line is modified to (i) express or increase expression of at least 1 immunostimulatory factor, (ii) inhibit or decrease expression of at least 1 immunosuppressive factor, and (iii) increase expression of at least 1 tumor associated antigen (TAA) that is either not expressed or minimally expressed by the cancer stem cell line. In another embodiment, provided herein is a composition comprising a therapeutically effective amount of a cancer stem cell line, wherein said cancer stem cell line is modified to (i) express or increase expression of at least 2 immunostimulatory factors, (ii) inhibit or decrease expression of at least 2 immunosuppressive factor, and (iii) increase expression of at least 2 tumor associated antigens (TAAs) that are either not expressed or minimally expressed by the cancer stem cell line. In some embodiments, the cancer stem cell line is selected from the group consisting of JHOM-2B, OVCAR-3, OV56, JHOS-4, JHOC-5, OVCAR-4, JHOS-2, EFO-21, CFPAC-1, Capan-1, Panc 02.13, SUIT-2, Panc 03.27, SK-MEL-28, RVH-421, Hs 895.T, Hs 940.T, SK-MEL-1, Hs 936.T, SH-4, COLO 800, UACC-62, NCI-H2066, NCI- H1963, NCI-H209, NCI-H889, COR-L47, NCI-H1092, NCI-H1436, COR-L95, COR-L279, NCI-H1048, NCI-H69, DMS 53, HuH-6, Li7, SNU-182, JHH-7, SK-HEP-1, Hep 3B2.1-7, SNU-1066, SNU-1041, SNU-1076, BICR 18, CAL-33, YD-8, CAL-29, KMBC-2, 253J, 253J-BV, SW780, SW1710, VM-CUB-1, BC-3C, KNS-81, TM-31, NMC-G1, GB-1, SNU-201, DBTRG-05MG, YKG-1, ECC10, RERF-GC-1B, TGBC-11-TKB, SNU-620, GSU, KE-39, HuG1-N, NUGC-4, SNU-16, OCUM-1, C2BBe1, Caco-2, SNU-1033, SW1463, COLO 201, GP2d, LoVo, SW403, CL-14, HCC2157, HCC38, HCC1954, HCC1143, HCC1806, HCC1599, MDA-MB-415, CAL-51, K052, SKNO-1, Kasumi-1, Kasumi-6, MHH-CALL-3, MHH-CALL-2, JVM-2, HNT-34, HOS, OUMS-27, T1-73, Hs 870.T, Hs 706.T, SJSA-1, RD-ES, U20S, SaOS-2, SK-ES-1, MKN-45, HSC-3, HSC-4, DETROIT 562, and SCC-9.

In still another embodiment of the present disclosure, provided herein is a composition comprising a therapeutically effective amount of small cell lung cancer cell line DMS 53, wherein said cell line DMS 53 is (i) modified to knockdown TGFβ2, (ii) knockout CD276, and (iii) upregulate expression of GM-CSF, membrane bound CD40L, and IL-12. In another embodiment of the present disclosure, provided herein is a composition comprising a therapeutically effective amount of small cell lung cancer cell line DMS 53, wherein said cell line DMS 53 is (i) modified to knockdown TGFβ2, (ii) knockout CD276, and (iii) upregulate expression of GM-CSF and membrane bound CD40L. In still another embodiment of the present disclosure, provided herein is a vaccine composition comprising a therapeutically effective amount of small cell lung cancer cell line DMS 53, wherein said composition stimulates an immune response specific to at least 1 tumor associated antigen (TAA) expressed by said cell line DMS 53. In still another embodiment of the present disclosure, provided herein is a composition comprising a therapeutically effective amount of at least 2 cancer cell lines, wherein at least 1 of the cell lines comprises cells that are modified to express or increase expression of at least 1 immunostimulatory factor, and wherein at least 1 of the cell lines is small cell lung cancer cell line DMS 53 and comprises cells that are modified to express or increase expression of at least 1 immunostimulatory factor or inhibit or decrease expression of at least 1 immunosuppressive factor. In still another embodiment of the present disclosure, provided herein is a composition comprising a therapeutically effective amount of at least 2 cancer cell lines, wherein at least 1 cell line comprises cells that are modified to express or increase expression of at least 1 immunostimulatory factor, and wherein 1 cell line is small cell lung cancer DMS 53.

In yet another embodiment of the present disclosure, provided herein is a composition comprising a therapeutically effective amount of small cell lung cancer cell line DMS 53, wherein said cell line is modified to (i) express or increase expression of at least 1 immunostimulatory factor, and (ii) inhibit or decrease expression of at least 1 immunosuppressive factor. In still another embodiment of the present disclosure, provided herein is a composition comprising a therapeutically effective amount of 3 cancer cell lines, wherein each cell line comprises cells that are modified to (i) express or increase expression of at least 2 immunostimulatory factors, and (ii) inhibit or decrease expression of at least 1 immunosuppressive factors, and wherein 1 of the cell lines is small cell lung cancer cell line DMS 53.

In some embodiments, an aforementioned composition is provided wherein said composition is a vaccine composition. In some embodiments, an aforementioned composition is provided wherein said composition is capable of eliciting an immune response in a subject. In some embodiments, an aforementioned composition is provided wherein said composition comprises 3, 4, 5, 6, 7, 8, 9 or 10 cancer cell lines. In some embodiments, an aforementioned composition is provided wherein said composition comprises modifications to express or increase expression of 2, 3, 4, 5, 6, 7, 8, 9, or 10 immunostimulatory factors. In some embodiments, an aforementioned composition is provided wherein said composition comprises modifications to inhibit or decrease expression of 2, 3, 4, 5, 6, 7, 8, 9, or 10 immunosuppressive factors. In some embodiments, an aforementioned composition is provided wherein said composition comprises modifications to express or increase expression of 2, 3, 4, 5, 6, 7, 8, 9, or 10 TAAs. In one embodiment, the amino acid sequence of one or more of the TAAs has been modified to include a mutation or a neoepitope.

In some embodiments of the present disclosure, an aforementioned composition is provided wherein said immune response is an innate immune response, an adaptive immune response, a cellular immune response, and/or a humoral response. In one embodiment the immune response is an adaptive immune response. In some embodiments, the adaptive immune response comprises the production of antigen specific cells selected from the group consisting of $CD4^+$ T cells, $CD8^+$ T cells, gamma-delta T cells, natural killer T cells, and B cells. In other embodiments of the present disclosure, the antigen specific $CD4^+$ T cells comprise memory cells, T helper type 1 cells, T helper type 9 cells, T helper type 17 cells, T helper type 22 cells, and T follicular helper cells. In some embodiments, the antigen specific $CD8^+$ T cells comprise memory cells and cytotoxic T lymphocytes. In other embodiments, the antigen specific B cells comprise memory cells, immunoglobulin M, immunoglobulin G, immunoglobulin D, immunoglobulin E, and immunoglobulin A. In some embodiments, each cell line or a combination of the cell lines express at least 10 TAAs. In other embodiments, the TAAs are also expressed in a cancer of a subject intended to receive said composition.

In some embodiments, an aforementioned composition is provided wherein the therapeutically effective amount comprises approximately $8\times10^6$ cells of each cell line. In another embodiment, the therapeutically effective amount comprises approximately $1\times10^7$ cells of each cell line. In some embodiments, the therapeutically effective amount comprises approximately $1.0\times10^6$-$6.0\times10^7$ cells of each cell line. In some embodiments, an aforementioned composition is provided wherein the therapeutically effective amount comprises approximately an equal number of cells of each cell line. In some embodiments, an aforementioned composition is provided herein the cell lines are genetically heterogeneous allogeneic, genetically homogeneous allogeneic, genetically heterogeneous xenogeneic, genetically homogeneous xenogeneic, or a combination of allogeneic and xenogeneic.

Provided herein in various embodiments is an aforementioned composition wherein the cell lines are from parental cell lines of solid tumors originating from the lung, prostate, testis, breast, colon, bladder, gastrointestinal system, brain, spinal cord, urinary tract, colon, rectum, stomach, head and neck, liver, kidney, central nervous system, endocrine system, mesothelium, ovaries, endometrium, pancreas, esophagus, neuroendocrine system, uterus, or skin. In some embodiments, the parental cell lines comprise cells selected from the group consisting of squamous cells, carcinoma cells, adenocarcinoma cells, adenosquamous cells, large cell cells, small cell cells, sarcoma cells, clear cell carcinoma cells, carcinosarcoma cells, mixed mesodermal cells, and teratocarcinoma cells. In some embodiments, the sarcoma cells comprise osteosarcoma, chondrosarcoma, leiomyosarcoma, rhabdomyosarcoma, mesothelioma, fibrosarcoma, angiosarcoma, liposarcoma, glioma, gliosarcoma, astrocytoma, myxosarcoma, mesenchymous or mixed mesodermal. In some embodiments, the cell line or cell lines are non-small cell lung cancer cell lines or small cell lung cancer cell lines. In other embodiments, the cell lines are selected from the group consisting of NCI-H460, NCIH520, A549, DMS 53, LK-2, and NCI-H23. In some embodiments, the cell line or cell lines are small cell lung cancer cell lines. In other embodiments, the cell lines are selected from the group consisting of DMS 114, NCI-H196, NCI-H1092, SBC-5, NCI-H510A, NCI-H889, NCI-H1341, NCIH-1876, NCI-H2029, NCI-H841, DMS 53, and NCI-H1694. In other embodiments, the cell line or cell lines are prostate cancer cell lines or testicular cancer cell lines. In some embodiments, the cell lines are selected from the group consisting of PC3, DU-145, LNCAP, NEC8, and NTERA-2cl-D1. In some embodiments, the cell line or cell lines are colorectal cancer cell lines. In other embodiments, the cell lines are selected from the group consisting of HCT-15, RKO, HuTu-80, HCT-116, and LS411N. In some embodiments, the cell line or cell lines are breast or triple negative breast cancer cell lines. In some embodiments, the cell lines are selected from the group consisting of Hs 578T, AU565, CAMA-1, MCF-7, and T-47D. In other embodiments, the cell line or cell lines are bladder or urinary tract cancer cell lines. In some embodiments, the cell lines are selected from the group consisting of UM-UC-3, J82, TCCSUP, HT-1376, and SCaBER. In other embodiments, the cell line or cell lines are head and neck cancer cell lines. In some embodiments, the cell lines are selected from the group consisting of HSC-4, Detroit 562, KON, HO-1-N-1, and OSC-20. In other embodiments, the cell line or cell lines are gastric or stomach cancer cell lines. In some embodiments, the cell lines are selected from the group consisting of Fu97, MKN74, MKN45, OCUM-1, and MKN1. In other embodiments, the cell line or cell lines are liver cancer or hepatocellular cancer (HCC) cell lines. In some embodiments, the cell lines are selected from the group consisting of Hep-G2, JHH-2, JHH-4, JHH-5, JHH-6, Li7, HLF, HuH-1, HuH-6, and HuH-7. In some embodiments, the cell line or cell lines are glioblastoma cancer cell lines. In some embodiments, the cell lines are selected from the group consisting of DBTRG-05MG, LN-229, SF-126, GB-1, and KNS-60. In other embodiments, the cell line or cell lines are ovarian cancer cell lines. In some embodiments, the cell lines are selected from the group consisting of TOV-112D, ES-2, TOV-21G, OVTOKO, and MCAS. In some embodiments, the cell line or cell lines are esophageal cancer cell lines. In other embodiments, the cell lines are selected from the group consisting of TE-10, TE-6, TE-4, EC-GI-10, OE33, TE-9, TT, TE-11, OE19, and OE21. In some embodiments, the cell line or cell lines are kidney or renal cell carcinoma cancer cell lines. In some embodiments, the cell lines are selected from the group consisting of A-498, A-704, 769-P, 786-0, ACHN, KMRC-1, KMRC-2, VMRC-RCZ, and VMRC-RCW. In other embodiments, the cell line or cell lines are pancreatic cancer cell lines. In some embodiments, the cell lines are selected from the group consisting of PANC-1, KP-3, KP-4, SUIT-2, and PSN11. In some embodiments, the cell line or cell lines are endometrial cancer cell lines. In other embodiments, the cell lines are selected from the group consisting of SNG-M, HEC-1-B, JHUEM-3, RL95-2, MFE-280, MFE-296, TEN, JHUEM-2, AN3-CA, and Ishikawa. In some embodiments, the cell line or cell lines are skin or melanoma cancer cell lines. In some embodiments, the cell lines are selected from the group consisting of RPMI-7951, MeWo, Hs 688(A).T, COLO 829, C32, A-375, Hs 294T, Hs 695T, Hs 852T, and A2058. In other embodiments, the cell line or cell lines are mesothelioma cancer cell lines. In some embodiments, the cell lines are selected from the group consisting of NCI-H28, MSTO-211H, IST-Mes1, ACC-MESO-1, NCI-H2052, NCI-H2452, MPP 89, and IST-Mes2.

In some embodiments, the present disclosure provides an aforementioned composition further comprising a cancer stem cell line. In some embodiments, the present disclosure provides an aforementioned composition further comprising cell line DMS 53. In some embodiments, the present disclosure provides an aforementioned composition wherein 1 of the cell lines is of a different cancer than at least 1 of the other cell lines. In another embodiment, at least 3 cell lines are each of the same type of cancer. In some embodiments, at least 3 cell lines are each of a different cell histology type or molecular subtype. In some embodiments, the present disclosure provides an aforementioned composition wherein the cell histology type is selected from the group consisting of squamous, carcinoma, adenocarcinoma, large cell, small cell, and sarcoma.

In some embodiments, the present disclosure provides an aforementioned composition wherein the modification to increase expression of the at least 1 immunostimulatory factor comprises use of a lentiviral vector or vectors encoding the at least 1 immunostimulatory factor. In one embodiment, the at least 1 immunostimulatory factor is expressed at a level at least 2.0-fold higher compared to unmodified cell lines. In another embodiment, the at least 1 immunostimulatory factor is selected from the group consisting of GM-CSF, membrane bound CD40L, GITR, IL-15, IL-23, and IL-12. In another embodiment, the immunostimulatory factors are GM-CSF, membrane bound CD40L, and IL-12. In another embodiment, the immunostimulatory factors are GM-CSF, membrane bound CD40L, and IL-15. In another embodiment, the GM-CSF comprises SEQ ID NO: 8. In another embodiment, the membrane bound CD40L comprises SEQ ID NO: 3. In another embodiment, the IL-12 comprises SEQ ID NO: 10.

In some embodiments, the present disclosure provides an aforementioned composition wherein the modification to inhibit or decrease expression of the at least 1 immunosuppressive factor comprises a knockout or a knockdown of said at least 1 immunosuppressive factor. In om embodiments, expression of the at least 1 immunosuppressive factor is decreased by at least approximately 5, 10, 15, 20, 25, or 30%. In another embodiment, the modification is a knockdown.

In some embodiments, the present disclosure provides an aforementioned composition wherein the modifications to inhibit or decrease expression of the at least 1 immunosuppressive factor comprise a combination of knocking down expression of the at least 1 immunosuppressive factor and knocking out expression of a different immunosuppressive factor. In some embodiments, the at least 1 immunosuppressive factor is selected from the group consisting of CD276, CD47, CTLA4, HLA-E, HLA-G, IDO1, IL-10, TGFβ1, TGFβ2, and TGFβ3. In another embodiment, the at least 1 immunosuppressive factor is selected from the group consisting of CD276, HLA-E, HLA-G, TGFβ1, and TGFβ2. In another embodiment, the immunosuppressive factors are TGFβ1, TGFβ2, and CD276. In still another embodiment, the immunosuppressive factors are TGFβ2 and CD276. In yet another embodiment of the present disclosure, the immunosuppressive factors are TGFβ1 and CD276. In some embodiments, the TGFβ1 is knocked down using short hairpin RNA comprising SEQ ID NO: 25. In other embodiments, TGFβ2 is knocked down using short hairpin RNA comprising SEQ ID NO: 24. In still other embodiments, CD276 is knocked out using a zinc finger nuclease pair that targets a CD276 genomic DNA sequence comprising SEQ ID NO: 26.

In some embodiments, the present disclosure provides an aforementioned composition wherein the composition comprises cell lines that express a heterogeneity of HLA supertypes, and wherein at least 2 different HLA-A and at least 2 HLA-B supertypes are represented. In some embodiments, the composition expresses major histocompatibility complex molecules in the HLA-A24, HLA-A01, HLA-A03, HLA-B07, HLA-B08, HLA-B27, and HLA-B44 supertypes. In other embodiments, the composition expresses major histocompatibility complex molecules in the HLA-A24, HLA-A03, HLA-A01, HLA-B07, HLA-B27, and HLA-B44 supertypes. In yet other embodiments, the composition expresses HLA-A01, HLA-A03, HLA-B07, HLA-B08, and HLA-B44 supertypes. In some embodiments, the present disclosure provides an aforementioned composition wherein the cell line(s) is a genetically homogeneous cell line. In some embodiments, the present disclosure provides an aforementioned composition wherein the cell line(s) is a genetically heterogeneous cell line.

Various methods are contemplated and provided by the present disclosure. In one embodiment, the present disclosure provides a method of stimulating an immune response in a subject comprising administering to the subject a therapeutically effective amount of an aforementioned composition. In one embodiment, the present disclosure provides a method of stimulating an immune response specific to at least 5, 6, 7, 8, 9, 10, 11, 12, 13, 14, 15, 16, 17, 18, 19, 20, 21, 22, 23, 24, 25, 26, 27, 28, 29, or 30 or more tumor associated antigens (TAAs) in a subject comprising administering to the subject a therapeutically effective amount of an aforementioned composition. In some embodiments, provided herein is a method of stimulating an immune response in a subject comprising administering to the subject a therapeutically effective amount of 2 aforementioned compositions In one embodiment, provided herein is a method of stimulating an immune response in a subject comprising administering to the subject a therapeutically effective amount of 2 or more compositions described herein, wherein the compositions comprise different combinations of cell lines. In one embodiment, provided herein is a method of stimulating an immune response in a subject comprising administering to the subject a therapeutically effective amount of 2 compositions described herein, wherein the compositions each comprise 3 different cell lines. In some embodiments, the immune response comprises increased production of antigen specific or vaccine specific immunoglobulin G antibodies. In other embodiments, the immune response comprises increased production of one or more of IL-1β, IL-6, IL-8, IL-12, IL-17A, IL-20, IL-22, TNFα, IFNγ, CCL5, or CXCL10. In one embodiment, the immune response comprises increased production of IFNγ. In some embodiments, the immune response comprises increased production of Granzyme A, Granzyme B, Perforin, and CD107a. In other embodiments, the immune response comprises decreased levels of regulatory T cells, mononuclear monocyte derived suppressor cells, and polymorphonuclear derived suppressor cells. In still other embodiments, the immune response comprises decreased levels of circulating tumor cells (CTCs), neutrophil to lymphocyte ratio (NLR), and platelet to lymphocyte ratio (PLR). In other embodiments, the immune response comprises changes in immune infiltrate in the tumor microenvironment.

In one embodiment, provided herein is a method of treating cancer in a subject comprising administering to the subject a therapeutically effective amount of a composition described herein. In one embodiment, provided herein is a method of treating cancer in a subject comprising administering to the subject a therapeutically effective amount of 2 or more compositions described herein, wherein the compositions comprise different combinations of cell lines. In one embodiment, provided herein is a method of treating cancer in a subject comprising administering to the subject a therapeutically effective amount of 2 compositions described herein, wherein the compositions each comprise 3 different cell lines. In one embodiment, provided herein is a method of treating cancer in a subject comprising administering to the subject a therapeutically effective amount of a composition described herein, and further comprising administering to the subject a therapeutically effective amount of a chemotherapeutic agent. In one embodiment, provided herein is a method of treating cancer in a subject comprising administering to the subject a therapeutically effective amount of one or more compositions described herein, and further comprising administering to the subject a therapeutically effective amount of cyclophosphamide. In some embodiments, the therapeutically effective amount of cyclophosphamide comprises 50 mg/day for 1-10 days prior to the administration of the therapeutically effective amount of the composition.

In one embodiment, the present disclosure provides a method of treating cancer in a subject comprising administering to the subject a therapeutically effective amount of a composition described herein, and further comprising administering to the subject a therapeutically effective amount of a checkpoint inhibitor. In another embodiment, the checkpoint inhibitor is selected from the group consisting of an inhibitor of CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, BTLA, SIGLEC9, and 2B4. In some embodiments, the checkpoint inhibitor is selected from the group consisting of pembrolizumab, avelumab, atezolizumab, cetrelimab, dostarlimab, cemiplimab, spartalizumab, camrelizumab, durvalumab, and nivolumab. In other embodiments, an aforementioned method is provided further comprising administering to the subject an isolated tumor associated antigen (TAA). In one embodiment, provided herein is a method of treating cancer in a subject comprising administering to the subject a therapeutically effective amount of a composition described herein, and further comprising administering to the subject one or more inhibitors selected from the group consisting of inhibitors of ALK, PARP, VEGFRs, EGFR, FGFR1-3, HIF1α, PDGFR1-2, c-Met, c-KIT, Her2, Her3, AR, PR, RET, EPHB4, STAT3, Ras, HDAC1-11, mTOR, and CXCR4.

In one embodiment, provided herein is a method of treating cancer in a subject comprising administering to the subject a therapeutically effective amount of a composition provided herein, and further comprising administering to the subject a therapeutically effective amount of radiation therapy. In one embodiment, provided herein is a method of treating cancer in a subject comprising administering a therapeutically effective amount of a composition described herein, and further comprising administering to the patient a cancer treatment surgery. In one embodiment, provided herein is a method of concurrently treating two or more cancers in a subject comprising administering to the subject a therapeutically effective amount of a composition described herein.

In another embodiment, provided herein is a method of preparing a vaccine composition described herein, comprising the steps of: (a) selecting one or more cancer cell lines that express at least, 5, 10, 15 or 20 or more TAAs; and (b) modifying each of the one or more cancer cell lines of (a), wherein the cell line or a combination of the cell lines comprises cells that are modified to (i) express or increase expression of at least 1 immunostimulatory factor, and/or (ii) increase expression of at least 1 TAA that is either not expressed or minimally expressed by 1 cell line or the combination of the cell lines. In one embodiment, the cell line or a combination of the cell lines comprises cells that are additionally modified to inhibit or decrease expression of at least 1 immunosuppressive factor. In another embodiment, the modifying step comprises introducing one or more vectors into one or more of the cell lines. In yet another embodiment, the one or more vectors are lentiviral vectors. In still another embodiment, the method further comprises the step of adapting the modified cell lines to a xeno-free media. In another embodiment, the method further comprises the step of irradiating the cell lines. In another embodiment, the method further comprises the step of adapting the cells to a cryopreservation media.

In various embodiments, the present disclosure provides an aforementioned method wherein the composition or compositions are administered to the subject by a route selected from the group consisting of parenteral, enteral, oral, intramuscular, intradermal, subcutaneous, intratumoral, intranodal, intranasal, transdermal, inhalation, mucosal, and topical. In one embodiment, the route is intradermal. In some embodiments, the composition or compositions are administered to an administration site on the subject selected from the group consisting of arm or arms, thigh or thighs, and back. In another embodiment, the compositions are intradermally administered at different administration sites on the subject. In another embodiment, the composition is intradermally administered by injection with a syringe positioned at an angle between 5 and 15 degrees from the surface of the administration site. In some embodiments, a method of treating cancer in a subject is provided comprising administering to the subject a therapeutically effective amount of a first dose and therapeutically effective amounts of subsequent doses of one or more compositions provided herein, wherein the one or more compositions are administered 1-24 times in year one, 1-16 times in year two, and 1-14 times in year three. In another embodiment, the present disclosure provides a method of stimulating an immune response in a subject comprising administering to the subject a first dose of a therapeutically effective amount of two compositions provided herein, wherein the first four doses are administered every 21 days up to day 63, and then every 42 days for three additional doses up to day 189. In one embodiment, the method further comprises administering five additional doses at 42-day intervals up to day 399, and then at least at two 84-day intervals thereafter.

In another embodiment, the present disclosure provides a method of stimulating an immune response in a subject comprising administering to the subject a first dose and subsequent doses of a therapeutically effective amount of two compositions provided herein, wherein the first four doses are administered every 14 days up to day 42, and then every 42 days for three additional doses up to day 168. In one embodiment, the method further comprises administering to the subject five additional doses at 42-day intervals up to day 378, and then at least at two 84-day intervals thereafter.

In another embodiment, the present disclosure provides a method of treating a cancer in a subject comprising administering to the subject a therapeutically effective amount of two compositions, wherein each composition comprises at least 2 cancer cell lines modified to (i) express or increase expression of at least 1 immunostimulatory factor, (ii) inhibit or decrease expression of at least 1 immunosuppressive factor, and (iii) increase expression of at least 1 tumor associated antigen (TAA) that is either not expressed or minimally expressed by 1 cell line or the combination of the cell lines, wherein one composition is administered to the upper body of the subject, and the other composition is administered to the lower body of the subject. In another embodiment, the present disclosure provides a method of treating a cancer in a subject comprising administering to the subject a first dose and subsequent doses of a therapeutically effective amount of two compositions, wherein each composition comprises at least 2 cancer cell lines modified to (i) express or increase expression of one or more of GM-CSF, IL-12, and membrane bound CD40L, (ii) inhibit or decrease expression of one or more of TGFβ1, TGFβ2, and CD276, and (iii) increase expression of at least 1 TAA that is either not expressed or minimally expressed by 1 cell line or the combination of the cell lines, wherein one composition is administered to the upper body of the subject, and the other composition is administered to the lower body of the subject. In some embodiments, the methods provided herein further comprises administering to the subject one or more therapeutic agents or treatments. In other embodiments, the subject refrains from treatment with other vaccines or therapeutic agents. In some embodiments, the therapeutic agent or treatment is selected from the group consisting of radiotherapy, chemotherapy, surgery, small molecule inhibitors, and checkpoint inhibitors. In one embodiment, the therapeutic agent is cyclophosphamide. In other embodiments, the checkpoint inhibitor is selected from the group consisting of an inhibitor of CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, BTLA, SIGLEC9, and 2B4. In some embodiments, the checkpoint inhibitor is pembrolizumab, avelumab, atezolizumab, cetrelimab, dostarlimab, cemiplimab, spartalizumab, camrelizumab, durvalumab, or nivolumab. In some embodiments, the one or more therapeutic agents or treatments are administered prior to at least 1 administration of said first dose and/or said subsequent doses. In other embodiments, the one or more therapeutic agents or treatments are administered prior to, concurrently, or subsequent to each administration of said composition. In still other embodiments, a first therapeutic agent is administered prior to said first dose, and wherein a second therapeutic agent is administered concurrently with said first dose and said subsequent doses.

In another embodiment, the present disclosure provides a method of stimulating an immune response in a subject comprising: a. administering to the subject a first dose of a therapeutically effective amount of two compositions provided herein, wherein said two compositions are administered concurrently at different sites, and administering to the subject subsequent doses of said two compositions after administering said first dose, wherein said two compositions are administered concurrently at different sites; and b. optionally administering to the subject therapeutically effective doses cyclophosphamide for 1-10 days prior to administering the first dose of (a), and optionally for 1-10 days prior to administering said subsequent doses of (a); c. optionally administering to the subject a checkpoint inhibitor either (i) concurrently with each dose of (a), or (ii) every one, two, three, or four weeks following the first dose of (a). In another embodiment, the present disclosure provides a method of treating cancer in a subject comprising: a. administering to the subject a first dose of a therapeutically effective amount of two compositions described herein, and administering to the subject subsequent doses of said two compositions after administering said first dose, wherein said two compositions are administered concurrently at different sites; b. optionally administering to the subject cyclophosphamide for 1-10 days prior to administering the first dose of (a), and optionally for 1-10 days prior to administering said subsequent doses of (a); c. optionally administering to the subject a checkpoint inhibitor either (i) concurrently with each dose of (a), or (ii) every one, two, three, or four weeks following the first dose of (a). In another embodiment, the present disclosure provides a method of treating cancer in a subject comprising: a. administering to the subject a first dose of a therapeutically effective amount of two compositions according to any one of claims 1-138, and administering to the subject subsequent doses of said two compositions after administering said first dose, wherein said two compositions are administered concurrently at different sites, and wherein said subsequent doses are administered at 3, 6, 9, 15, 21, and 27 weeks following administration of said first dose; b. administering to the subject cyclophosphamide daily for 7 days prior to administering said first dose and said subsequent doses of (a); c. administering to the subject a checkpoint inhibitor at 3, 6, 9, 12, 15, 18, 21, 24, and 27 weeks following said first dose of (a). In one embodiment, cyclophosphamide is administered orally and the checkpoint inhibitor is pembrolizumab and is administered intravenously. In another embodiment, cyclophosphamide is administered orally at a dosage of 50 mg and the checkpoint inhibitor is pembrolizumab and is administered intravenously at a dosage of 200 mg.

In another embodiment, the present disclosure provides a method of treating cancer in a subject comprising: a. administering to the subject a first dose of a therapeutically effective amount of two compositions provided herein, and administering to the subject subsequent doses of said two compositions after administering said first dose, wherein said two compositions are administered concurrently at different sites, and wherein said subsequent doses are administered at 2, 4, 6, 12, 18, and 24 weeks following administration of said first dose; b. administering to the subject cyclophosphamide daily for 7 days prior to administering said first dose and said subsequent doses of (a); and c. administering to the subject a checkpoint inhibitor at 2, 4, 6, 8, 10, 12, 14, 16, 18, 20, 22, 24, 26, 28, and 30 weeks following said first dose of (a). In one embodiment, cyclophosphamide is administered orally at a dosage of 50 mg and the checkpoint inhibitor is durvalumab and is administered intravenously at a dosage of 10 mg/kg. In other embodiments, the methods further comprise the step of abstaining from cannabinoid administration for 1, 2, 3, 4, 5, 6, 7, 8, 9, or 10 days prior to administration of the compositions and 1, 2, 3, 4, 5, 6, 7, 8, 9, or 10 days after administration of the compositions.

In some embodiments, each embraced in groups or individually, the subject suffers from a cancer selected from the group consisting of lung cancer, prostate cancer, breast cancer, esophageal cancer, colorectal cancer, bladder cancer, gastric cancer, head and neck cancer, liver cancer, renal cancer, glioma, endometrial cancer, ovarian cancer, pancreatic cancer, melanoma, and mesothelioma. In one embodiment, the breast cancer is triple negative breast cancer. In another embodiment, the glioma is an astrocytoma. In still another embodiment, the astrocytoma is glioblastoma multiform (GBM).

The present disclosure also provides kits. In one embodiment, the present disclosure provides a kit comprising one or more compositions provided herein. In another embodiment, the present disclosure provides a kit comprising at least 1 vial, said vial comprising a composition described herein. In another embodiment, the present disclosure provides a kit comprising a first vaccine composition in a first vial and a second vaccine composition in a second vial, wherein said first and second vaccine compositions each comprise at least 2 cancer cell lines that are modified to express or increase expression of at least 2 immunostimulatory factors. In yet another embodiment, the present disclosure provides a A kit comprising 6 vials, wherein the vials each contain a composition comprising a cancer cell line, and wherein at least 4 of the 6 vials comprise a cancer cell line that is modified to (i) express or increase expression of at least 2 immunostimulatory factors, and/or (ii) inhibit or decrease expression of at least 2 immunosuppressive factors, and/or (iii) increase expression of at least 1 TAA that is either not expressed or minimally expressed by 1 cell line or the combination of the cell lines, wherein at least 4 of the vials contain different compositions. In some embodiments, the kit further comprises instructions for use. In some embodiments, the kit is used for the treatment of cancer.

Unit doses of the composition provided herein are also contemplated. In one embodiment, the present disclosure provides a unit dose of a medicament for treating cancer comprising 6 compositions of different cancer cell lines, wherein at least 4 compositions comprise a cell line that is modified to (i) express or increase expression of at least 2 immunostimulatory factors, and (ii) inhibit or decrease expression of at least 2 immunosuppressive factors. In some embodiments, cell lines comprise: (a) non-small cell lung cancer cell lines and/or small cell lung cancer cell lines selected from the group consisting of NCI-H460, NCIH520, A549, DMS 53, LK-2, and NCI-H23; (b) DMS 53 and five small cell lung cancer cell lines selected from the group consisting of DMS 114, NCI-H196, NCI-H1092, SBC-5, NCI-H510A, NCI-H889, NCI-H1341, NCIH-1876, NCI-H2029, NCI-H841, DMS 53, and NCI-H1694; (c) DMS 53 and prostate cancer cell lines or testicular cancer cell lines PC3, DU-145, LNCAP, NEC8, and NTERA-2cl-D1; (d) DMS 53 and colorectal cancer cell lines HCT-15, RKO, HuTu-80, HCT-116, and LS411N; (e) DMS 53 and breast or triple negative breast cancer cell lines Hs 578T, AU565, CAMA-1, MCF-7, and T-47D; (f) DMS 53 and bladder or urinary tract cancer cell lines UM-UC-3, J82, TCCSUP, HT-1376, and SCaBER; (g) DMS 53 and head or neck cancer cell lines HSC-4, Detroit 562, KON, HO-1-N-1, and OSC-20; (h) DMS 53 and gastric or stomach cancer cell lines Fu97, MKN74, MKN45, OCUM-1, and MKN1; (i) DMS 53 and five liver cancer or hepatocellular cancer (HCC) cell lines selected from the group consisting of Hep-G2, JHH-2, JHH-4, JHH-5, JHH-6, Li7, HLF, HuH-1, HuH-6, and HuH-7; (j) DMS 53 and glioblastoma cancer cell lines DBTRG-05MG, LN-229, SF-126, GB-1, and KNS-60; (k) DMS 53 and ovarian cancer cell lines selected from the group consisting of TOV-112D, ES-2, TOV-21G, OVTOKO, and MCAS; (I) DMS 53 and five esophageal cancer cell lines selected from the group consisting of TE-10, TE-6, TE-4, EC-GI-10, OE33, TE-9, TT, TE-11, OE19, and OE21; (m) DMS 53 and five kidney or renal cell carcinoma cancer cell lines selected from the group consisting of A-498, A-704, 769-P, 786-0, ACHN, KMRC-1, KMRC-2, VMRC-RCZ, and VMRC-RCW; (n) DMS 53 and pancreatic cancer cell lines PANC-1, KP-3, KP-4, SUIT-2, and PSN11; (o) DMS 53 and five endometrial cancer cell lines selected from the group consisting of SNG-M, HEC-1-B, JHUEM-3, RL95-2, MFE-280, MFE-296, TEN, JHUEM-2, AN3-CA, and Ishikawa; (p) DMS 53 and five skin or melanoma cancer cell lines selected from the group consisting of RPMI-7951, MeWo, Hs 688(A).T, COLO 829, C32, A-375, Hs 294T, Hs 695T, Hs 852T, and A2058; or (q) DMS 53 and five mesothelioma cancer cell lines selected from the group consisting of NCI-H28, MSTO-211H, IST-Mes1, ACC-MESO-1, NCI-H2052, NCI-H2452, MPP 89, and IST-Mes2.

In another embodiment, the present disclosure provides a unit dose of a medicament for treating cancer comprising 6 compositions of different cancer cell lines, wherein each cell line is modified to (i) express or increase expression of at least 2 immunostimulatory factors, (ii) inhibit or decrease expression of at least 2 immunosuppressive factors, and/or (iii) express or increase expression of at least 1 TAA that is either not expressed or minimally expressed by the cancer cell lines. In some embodiments, two compositions comprising 3 cell lines each are mixed.

In another embodiment, the present disclosure provides a vaccine composition comprising therapeutically effective amounts of lung cancer cell lines NCI-H460, NCI-H520, and A549; wherein (a) NCI-H460 is modified to (i) increase expression of GM-CSF, IL-12, and membrane bound CD40L, and (ii) decrease expression of TGFβ1, TGFβ2, and CD276; (b) NCI-H520 is modified to (i) increase expression of GM-CSF and membrane bound CD40L, and (ii) decrease expression of TGFβ1, TGFβ2, and CD276; and (c) A549 is modified to (i) increase expression of GM-CSF, IL-12, and membrane bound CD40L, and (ii) decrease expression of TGFβ1, TGFβ2, and CD276. In another embodiment, the present disclosure provides a vaccine composition comprising therapeutically effective amounts of lung cancer cell lines NCI-H460, NCIH520, and A549; wherein (a) NCI-H460 is modified to (i) increase expression of GM-CSF, IL-12, and membrane bound CD40L, and (ii) decrease expression of TGFβ1, TGFβ2, and CD276; (b) NCI-H520 is modified to (i) increase expression of GM-CSF and membrane bound CD40L, and (ii) decrease expression of TGFβ1, TGFβ2, and CD276; and (c) A549 is modified to (i) increase expression of GM-CSF, IL-12, and membrane bound CD40L, and (ii) decrease expression of TGFβ1, TGFβ2, and CD276; wherein said therapeutically effective amount is approximately $1.0\times10^7$ cells for each cell line or approximately $6\times10^7$ cells. In still another embodiment, the present disclosure provides a vaccine composition comprising therapeutically effective amounts of lung cancer cell lines DMS 53, LK-2, and NCI-H23, wherein (a) DMS 53 is modified to (i) increase expression of GM-CSF and membrane bound CD40L, and (ii) decrease expression of TGFβ2 and CD276; (b) LK-2 is modified to (i) increase expression of GM-CSF and membrane bound CD40L, (ii) decrease expression of TGFβ1, TGFβ2, and CD276, and (iii) to express MSLN and CT83; and (c) NCI-H23 is modified to (i) increase expression of GM-CSF, IL-12, and membrane bound CD40L, and (ii) decrease expression of TGFβ1, TGFβ2, and CD276. In another embodiment, the present disclosure provides a vaccine composition comprising therapeutically effective amounts of lung cancer cell lines DMS 53, LK-2, and NCI-H23; wherein (a) DMS 53 is modified to (i) increase expression of GM-CSF and membrane bound CD40L, and (ii) decrease expression of TGFβ2 and CD276; (b) LK-2 is modified to (i) increase expression of GM-CSF and membrane bound CD40L, (ii) decrease expression of TGFβ1, TGFβ2, and CD276, and (iii) to express MSLN and CT83; and (c) NCI-H23 is modified to (i) increase expression of GM-CSF, IL-12, and membrane bound CD40L, and (ii) decrease expression of TGFβ1, TGFβ2, and CD276; wherein said therapeutically effective amount is approximately $1.0\times10^7$ cells for each cell line or approximately $6\times10^7$ cells.

In another embodiment, the present disclosure provides a vaccine composition comprising therapeutically effective amounts of cancer cell lines LN-229, GB-1, and SF-126, wherein: (a) LN-229 is modified to (i) increase expression of GM-CSF, IL-12, and membrane bound CD40L; (ii) decrease expression of TGFβ1 and CD276; and (iii) modified to express modPSMA; (b) GB-1 is modified to (i) increase expression of GM-CSF and membrane bound CD40L; and (ii) decrease expression of TGFβ1 and CD276; and (c) SF-126 is modified to (i) increase expression of GM-CSF, IL-12, and membrane bound CD40L; (ii) decrease expression of TGFβ1, TGFβ2, and CD276; and (iii) modified to express modTERT. In another embodiment, the present disclosure provides a vaccine composition comprising therapeutically effective amounts of cancer cell lines DBTRG-05MG, KNS 60, and DMS 53, wherein: (a) DMS 53 is modified to (i) increase expression of GM-CSF and membrane bound CD40L; and (ii) decrease expression of TGFβ2 and CD276; (b) DBTRG-05MG is modified to (i) increase expression of GM-CSF, IL-12, and membrane bound CD40L; and (ii) decrease expression of TGFβ1 and CD276; and (c) KNS 60 is modified to (i) increase expression of GM-CSF, IL-12, and membrane bound CD40L; (ii) decrease expression of TGFβ1, TGFβ2, and CD276; and (iii) modified to express modMAGEA1, EGFRvIII, and hCMV pp65.

In yet another embodiment, the present disclosure provides a vaccine composition comprising therapeutically effective amounts of cancer cell lines HCT-15, RKO, and HuTu-80, wherein: (a) HCT-15 is modified to (i) increase expression of GM-CSF, IL-12, and membrane bound CD40L; and (ii) decrease expression of TGFβ1 and CD276; (b) RKO is modified to (i) increase expression of GM-CSF, IL-12, and membrane bound CD40L; and (ii) decrease expression of TGFβ1 and CD276; and (c) HuTu-80 is modified to (i) increase expression of GM-CSF, IL-12, and membrane bound CD40L; (ii) decrease expression of TGFβ1, TGFβ2, and CD276; and (iii) modified to express modPSMA. In another embodiment, the present disclosure provides a vaccine composition comprising therapeutically effective amounts of cancer cell lines HCT-116, LS411N and DMS 53, wherein: (a) HCT-116 is modified to (i) increase expression of GM-CSF and membrane bound CD40L; (ii) decrease expression of TGFβ1 and CD276; and (iii) modified to express modTBXT, modWT1, KRAS G12D and KRAS G12V; (b) LS411N is modified to (i) increase expression of GM-CSF, IL-12, and membrane bound CD40L; and (ii) decrease expression of TGFβ1 and CD276; and (c) DMS 53 is modified to (i) increase expression of GM-CSF and membrane bound CD40L; and (ii) decrease expression of TGFβ2 and CD276. In another embodiment, the present disclosure provides a vaccine composition comprising therapeutically effective amounts of cancer cell lines PC3, NEC8, NTERA-2cl-D1, wherein: (a) PC3 is modified to (i) increase expression of GM-CSF, IL-12, and membrane bound CD40L; (ii) decrease expression of TGFβ1, TGFβ2, and CD276; and (iii) modified to express modTBXT and modMAGEC2; (b) NEC8 is modified to (i) increase expression of GM-CSF, IL-12, and membrane bound CD40L; and (ii) decrease expression of CD276; and (c) NTERA-2cl-D1 is modified to (i) increase expression of GM-CSF, IL-12, and membrane bound CD40L; and (ii) decrease expression of CD276. In another embodiment, the present disclosure provides a vaccine composition comprising therapeutically effective amounts of cancer cell lines DU-145, LNCaP, and DMS 53, wherein: (a) DU-145 is modified to (i) increase expression of GM-CSF, IL-12, and membrane bound CD40L; (ii) decrease expression of CD276; and (iii) modified to express modPSMA; (b) LNCaP is modified to (i) increase expression of GM-CSF, IL-12, and membrane bound CD40L; and (ii) decrease expression of CD276; and (c) DMS 53 is modified to (i) increase expression of GM-CSF and membrane bound CD40L; and (ii) decrease expression of TGFβ2 and CD276. In another embodiment, the present disclosure provides a vaccine composition comprising therapeutically effective amounts of cancer cell lines J82, HT-1376, and TCCSUP, wherein: (a) J82 is modified to (i) increase expression of GM-CSF, IL-12, and membrane bound CD40L; (ii) decrease expression of TGFβ2 and CD276; and (iii) modified to express modPSMA; (b) HT-1376 is modified to (i) increase expression of GM-CSF, IL-12, and membrane bound CD40L; and (ii) decrease expression of TGFβ1, TGFβ2, and CD276; and (c) TCCSUP is modified to (i) increase expression of GM-CSF, IL-12, and membrane bound CD40L; and (ii) decrease expression of TGFβ1, TGFβ2, and CD276.

In another embodiment, the present disclosure provides a vaccine composition comprising therapeutically effective amounts of cancer cell lines SCaBER, UM-UC-3 and DMS 53, wherein: (a) SCaBER is modified to (i) increase expression of GM-CSF, IL-12, and membrane bound CD40L; (ii) decrease expression of TGFβ1, TGFβ2, and CD276; and (iii) modified to express modWT1 and modFOLR1; (b) UM-UC-3 is modified to (i) increase expression of GM-CSF, IL-12, and membrane bound CD40L; and (ii) decrease expression of TGFβ1 and CD276; and (c) DMS 53 is modified to (i) increase expression of GM-CSF and membrane bound CD40L; and (ii) decrease expression of TGFβ2 and CD276. In another embodiment, the present disclosure provides a vaccine composition comprising therapeutically effective amounts of cancer cell lines OVTOKO, MCAS, TOV-112D, wherein: (a) OVTOKO is modified to (i) increase expression of GM-CSF, IL-12, and membrane bound CD40L; and (ii) decrease expression of TGFβ1 and CD276; (b) MCAS is modified to (i) increase expression of GM-CSF, IL-12, and membrane bound CD40L; (ii) decrease expression of TGFβ1, TGFβ2, and CD276; and (iii) modified to express modhTERT; (c) TOV-112D is modified to (i) increase expression of GM-CSF, IL-12, and membrane bound CD40L; (ii) decrease expression of TGFβ1, TGFβ2, and CD276; and (iii) modified to express modFSHR and modMAGEA10. In another embodiment, the present disclosure provides a vaccine composition comprising therapeutically effective amounts of cancer cell lines TOV-21G, ES-2 and DMS 53, wherein: (a) TOV-21G is modified to (i) increase expression of GM-CSF, IL-12, and membrane bound CD40L; (ii) decrease expression of CD276; and (iii) modified to express modWT1 and modFOLR1; (b) ES2 is modified to (i) increase expression of GM-CSF, IL-12, and membrane bound CD40L; (ii) decrease expression of TGFβ1, TGFβ2, and CD276; and (iii) modified to express modBORIS; and (c) DMS 53 is modified to (i) increase expression of GM-CSF and membrane bound CD40L; and (ii) decrease expression of TGFβ2 and CD276.

In another embodiment, the present disclosure provides a vaccine composition comprising therapeutically effective amounts of cancer cell lines HSC-4, HO-1-N-1, and DETROIT 562, wherein: (a) HSC-4 is modified to (i) increase expression of GM-CSF, IL-12, and membrane bound CD40L; (ii) decrease expression of TGFβ1, TGFβ2, and CD276; and (iii) modified to express modPSMA; (b) HO-1-N-1 is modified to (i) increase expression of GM-CSF, IL-12, and membrane bound CD40L; (ii) decrease expression of TGFβ1, TGFβ2, and CD276; and (iii) modified to express modPRAME and modTBXT; and (c) DETROIT 562 is modified to (i) increase expression of GM-CSF, IL-12, and membrane bound CD40L; and (ii) decrease expression of TGFβ1, TGFβ2, and CD276. In another embodiment, the present disclosure provides a vaccine composition comprising therapeutically effective amounts of cancer cell lines KON, OSC-20 and DMS 53, wherein: (a) KON is modified to (i) increase expression of GM-CSF, IL-12, and membrane bound CD40L; (ii) decrease expression of TGFβ1, TGFβ2, and CD276; and (iii) modified to express HPV16 E6 and E7 and HPV18 E6 and E7; (b) OSC-20 is modified to (i) increase expression of GM-CSF, IL-12, and membrane bound CD40L; and (ii) decrease expression of TGFβ2 and CD276; and (c) DMS 53 is modified to (i) increase expression of GM-CSF and membrane bound CD40L; and (ii) decrease expression of TGFβ2 and CD276. In another embodiment, the present disclosure provides a vaccine composition comprising therapeutically effective amounts of cancer cell lines MKN-1, MKN-45, and MKN-74, wherein: (a) MKN-1 is modified to (i) increase expression of GM-CSF, IL-12, and membrane bound CD40L; (ii) decrease expression of TGFβ1, TGFβ2, and CD276; and (iii) modified to express modPSMA and modLYK6; (b) MKN-45 is modified to (i) increase expression of GM-CSF, IL-12, and membrane bound CD40L; (ii) decrease expression of TGFβ1 and CD276; and (c) MKN-74 is modified to (i) increase expression of GM-CSF, IL-12, and membrane bound CD40L; and (ii) decrease expression of TGFβ1, and CD276. In another embodiment, the present disclosure provides a vaccine composition comprising therapeutically effective amounts of cancer cell lines OCUM-1, Fu97 and DMS 53, wherein: (a) OCUM-1 is modified to (i) increase expression of GM-CSF and membrane bound CD40L; (ii) decrease expression of CD276; (b) Fu97 is modified to (i) increase expression of GM-CSF, IL-12, and membrane bound CD40L; and (ii) decrease expression of TGFβ1 and CD276; and (iii) modified to express modWT1 and modCLDN18; and (c) DMS 53 is modified to (i) increase expression of GM-CSF and membrane bound CD40L; and (ii) decrease expression of TGFβ2 and CD276.

In another embodiment, the present disclosure provides a vaccine composition comprising therapeutically effective amounts of cancer cell lines CAMA-1, AU565, and HS-578T, wherein: (a) CAMA-1 is modified to (i) increase expression of GM-CSF, IL-12, and membrane bound CD40L; (ii) decrease expression of TGFβ2, and CD276; and (iii) modified to express modPSMA; (b) AU565 is modified to (i) increase expression of GM-CSF, IL-12, and membrane bound CD40L; (ii) decrease expression of TGFβ2 and CD276; and (iii) modified to express modTERT; and (c) HS-578T is modified to (i) increase expression of GM-CSF, IL-12, and membrane bound CD40L; and (ii) decrease expression of TGFβ1, TGFβ2 and CD276. In another embodiment, the present disclosure provides a vaccine composition comprising therapeutically effective amounts of cancer cell lines MCF-7, T47D and DMS 53, wherein: (a) MCF-7 is modified to (i) increase expression of GM-CSF, IL-12, and membrane bound CD40L; and (ii) decrease expression of TGFβ1, TGFβ2 and CD276; (b) T47D is modified to (i) increase expression of GM-CSF, IL-12, and membrane bound CD40L; and (ii) decrease expression of CD276; and (iii) modified to express modTBXT and modBORIS; and (c) DMS 53 is modified to (i) increase expression of GM-CSF and membrane bound CD40L; and (ii) decrease expression of TGFβ2 and CD276. In another embodiment, the present disclosure provides an aforementioned vaccine composition wherein said therapeutically effective amount is approximately $1.0\times10^7$ cells for each cell line or approximately $6\times10^7$ cells.

In one embodiment, the present disclosure provides a composition comprising a first cocktail and a second cocktail; wherein said first cocktail comprises therapeutically effective amounts of at least 2 irradiated cancer cell lines modified to (i) increase expression of GM-CSF, IL-12, and membrane bound CD40L, and (ii) decrease expression of TGFβ1, TGFβ2, and CD276; and wherein said second cocktail comprises cell line DMS 53 modified to (i) increase expression of GM-CSF and membrane bound CD40L, and (ii) decrease expression of TGFβ2 and CD276. In one embodiment, said first cocktail and/or said second cocktail comprises one or more cell lines modified to express or increase expression of CT83, MSLN, TERT, PSMA, MAGEA1, EGFRvIII, hCMV pp65, TBXT, BORIS, FSHR, MAGEA10, MAGEC2, WT1, KRAS, FBP, TDGF1, Claudin 18, LYK6K, PRAME, HPV16/18 E6/E7, or mutated versions thereof.

In another embodiment, the present disclosure provides a method of stimulating an immune response specific to tumor associated antigens (TAAs) associated with non-small cell lung cancer (NSCLC) in a human subject comprising administering (i) a therapeutically effective amount of a first vaccine composition comprising therapeutically effective amounts of lung cancer cell lines NCI-H460, NCI-H520, and A549; wherein (a) NCI-H460 is modified to (i) increase expression of GM-CSF, IL-12, and membrane bound CD40L; and (ii) decrease expression of TGFβ1, TGFβ2, and CD276; (b) NCI-H520 is modified to (i) increase expression of GM-CSF and membrane bound CD40L; and (ii) decrease expression of TGFβ1, TGFβ2, and CD276; and (c) A549 is modified to (i) increase expression of GM-CSF, IL-12, and membrane bound CD40L; and (ii) decrease expression of TGFβ1, TGFβ2, and CD276; and (ii) a therapeutically effective amount of a second vaccine composition comprising therapeutically effective amounts of lung cancer cell lines DMS 53, LK-2, and NCI-H23; wherein (d) DMS 53 is modified to (i) increase expression of GM-CSF and membrane bound CD40L; and (ii) decrease expression of TGFβ2 and CD276; (e) LK-2 is modified to (i) increase expression of GM-CSF and membrane bound CD40L; and (ii) decrease expression of TGFβ1, TGFβ2, and CD276; (iii) to express MSLN and CT83; and (f) NCI-H23 is modified to (i) increase expression of GM-CSF, IL-12, and membrane bound CD40L; and (ii) decrease expression of TGFβ1, TGFβ2, and CD276; wherein the first vaccine composition is administered intradermally in the subject's arm, and the second vaccine composition is administered intradermally in the subject's thigh. In another embodiment, the present disclosure provides a method of treating non-small cell lung cancer (NSCLC) cancer in a human subject comprising administering (i) a therapeutically effective amount of a first vaccine composition comprising therapeutically effective amounts of lung cancer cell lines NCI-H460, NCI-H520, and A549; wherein (a) NCI-H460 is modified to (i) increase expression of GM-CSF, IL-12, and membrane bound CD40L; and (ii) decrease expression of TGFβ1, TGFβ2, and CD276; (b) NCI-H520 is modified to (i) increase expression of GM-CSF and membrane bound CD40L; and (ii) decrease expression of TGFβ1, TGFβ2, and CD276; and (c) A549 is modified to (i) increase expression of GM-CSF, IL-12, and membrane bound CD40L; and (ii) decrease expression of TGFβ1, TGFβ2, and CD276; and (ii) a therapeutically effective amount of a second vaccine composition comprising therapeutically effective amounts of lung cancer cell lines DMS 53, LK-2, and NCI-H23; wherein (d) DMS 53 is modified to (i) increase expression of GM-CSF, and membrane bound CD40L; and (ii) decrease expression of TGFβ2 and CD276; (e) LK-2 is modified to (i) increase expression of GM-CSF and membrane bound CD40L; and (ii) decrease expression of TGFβ1, TGFβ2, and CD276; (iii) to express MSLN and CT83; and (f) NCI-H23 is modified to (i) increase expression of GM-CSF, IL-12, and membrane bound CD40L; and (ii) decrease expression of TGFβ1, TGFβ2, and CD276; wherein the first vaccine composition is administered intradermally in the subject's arm, and the second vaccine composition is administered intradermally in the subject's thigh.

In another embodiment, the present disclosure provides a method of stimulating an immune response specific to tumor associated antigens (TAAs) associated with glioblastoma in a human subject comprising administering (i) a therapeutically effective amount of a first vaccine composition comprising therapeutically effective amounts of cancer cell lines LN-229, GB-1, SF-126; wherein: (a) LN-229 is modified to (i) increase expression of GM-CSF, IL-12, and membrane bound CD40L; (ii) decrease expression of TGFβ1 and CD276; and (iii) modified to express modPSMA; (b) GB-1 is modified to (i) increase expression of GM-CSF and membrane bound CD40L; and (ii) decrease expression of TGFβ1 and CD276; and (c) SF-126 is modified to (i) increase expression of GM-CSF, IL-12, and membrane bound CD40L; (ii) decrease expression of TGFβ1, TGFβ2, and CD276; and (iii) modified to express modhTERT; and (ii) a therapeutically effective amount of a second vaccine composition comprising therapeutically effective amounts of cancer cell lines DBTRG-05MG, KNS 60, and DMS 53; wherein: (d) DMS 53 is modified to (i) increase expression of GM-CSF and membrane bound CD40L; and (ii) decrease expression of TGFβ2 and CD276; (e) DBTRG-05MG is modified to (i) increase expression of GM-CSF, IL-12, and membrane bound CD40L; and (ii) decrease expression of TGFβ1 and CD276; and (f) KNS 60 is modified to (i) increase expression of GM-CSF, IL-12, and membrane bound CD40L; (ii) decrease expression of TGFβ1, TGFβ2, and CD276; and (iii) modified to express modMAGEA1, EGFRvIII, and hCMV pp65; wherein the first vaccine composition is administered intradermally in the subject's arm, and the second vaccine composition is administered intradermally in the subject's thigh. In another embodiment, the present disclosure provides a method of treating glioblastoma in a human subject comprising administering (i) a therapeutically effective amount of a first vaccine composition comprising therapeutically effective amounts of cancer cell lines LN-229, GB-1, SF-126; wherein: (a) LN-229 is modified to (i) increase expression of GM-CSF, IL-12, and membrane bound CD40L; (ii) decrease expression of TGFβ1 and CD276; and (iii) modified to express modPSMA; (b) GB-1 is modified to (i) increase expression of GM-CSF and membrane bound CD40L; and (ii) decrease expression of TGFβ1 and CD276; and (c) SF-126 is modified to (i) increase expression of GM-CSF, IL-12, and membrane bound CD40L; (ii) decrease expression of TGFβ1, TGFβ2, and CD276; and (iii) modified to express modTERT; and (ii) a therapeutically effective amount of a second vaccine composition comprising therapeutically effective amounts of cancer cell lines DBTRG-05MG, KNS 60, and DMS 53; wherein: (d) DMS 53 is modified to (i) increase expression of GM-CSF and membrane bound CD40L; and (ii) decrease expression of TGFβ2 and CD276; (e) DBTRG-05MG is modified to (i) increase expression of GM-CSF, IL-12, and membrane bound CD40L; and (ii) decrease expression of TGFβ1 and CD276; and (f) KNS 60 is modified to (i) increase expression of GM-CSF, IL-12, and membrane bound CD40L; (ii) decrease expression of TGFβ1, TGFβ2, and CD276; and (iii) modified to express modMAGEA1, EGFRvIII, and hCMV pp65; wherein the first vaccine composition is administered intradermally in the subject's arm, and the second vaccine composition is administered intradermally in the subject's thigh.

In another embodiment, the present disclosure provides a method of stimulating an immune response specific to tumor associated antigens (TAAs) associated with colorectal cancer in a human subject comprising administering (i) a therapeutically effective amount of a first vaccine composition comprising therapeutically effective amounts of cancer cell lines HCT-15, RKO, and HuTu-80, wherein: (a) HCT-15 is modified to (i) increase expression of GM-CSF, IL-12, and membrane bound CD40L; and (ii) decrease expression of TGFβ1 and CD276; (b) RKO is modified to (i) increase expression of GM-CSF, IL-12, and membrane bound CD40L; and (ii) decrease expression of TGFβ1 and CD276; and (c) HuTu-80 is modified to (i) increase expression of GM-CSF, IL-12, and membrane bound CD40L; (ii) decrease expression of TGFβ1, TGFβ2, and CD276; and (iii) modified to express modPSMA; and (ii) a therapeutically effective amount of a second vaccine composition comprising therapeutically effective amounts of cancer cell lines HCT-116, LS411N and DMS 53; wherein: (d) HCT-116 is modified to (i) increase expression of GM-CSF and membrane bound CD40L; (ii) decrease expression of TGFβ1 and CD276; and (iii) modified to express modTBXT, modWT1, KRAS G12D and KRAS G12V; (e) LS411N is modified to (i) increase expression of GM-CSF, IL-12, and membrane bound CD40L; and (ii) decrease expression of TGFβ1 and CD276; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh. In another embodiment, the present disclosure provides a method of treating colorectal cancer in a human subject comprising administering (i) a therapeutically effective amount of a first vaccine composition comprising therapeutically effective amounts of cancer cell lines HCT-15, RKO, and HuTu-80, wherein: (a) HCT-15 is modified to (i) increase expression of GM-CSF, IL-12, and membrane bound CD40L; and (ii) decrease expression of TGFβ1 and CD276; (b) RKO is modified to (i) increase expression of GM-CSF, IL-12, and membrane bound CD40L; and (ii) decrease expression of TGFβ1 and CD276; and (c) HuTu-80 is modified to (i) increase expression of GM-CSF, IL-12, and membrane bound CD40L; (ii) decrease expression of TGFβ1, TGFβ2, and CD276; and (iii) modified to express modPSMA; and (ii) a therapeutically effective amount of a second vaccine composition comprising therapeutically effective amounts of cancer cell lines HCT-116, LS411N and DMS 53; wherein: (d) HCT-116 is modified to (i) increase expression of GM-CSF and membrane bound CD40L; (ii) decrease expression of TGFβ1 and CD276; and (iii) modified to express modTBXT, modWT1, KRAS G12D and KRAS G12V; (e) LS411N is modified to (i) increase expression of GM-CSF, IL-12, and membrane bound CD40L; and (ii) decrease expression of TGFβ1 and CD276; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh. In another embodiment, the present disclosure provides a method of stimulating an immune response specific to tumor associated antigens (TAAs) associated with prostate cancer in a human subject comprising administering (i) a therapeutically effective amount of a first vaccine composition comprising therapeutically effective amounts of cancer cell lines PC3, NEC8, NTERA-2cl-D1, wherein: (a) PC3 is modified to (i) increase expression of GM-CSF, IL-12, and membrane bound CD40L; (ii) decrease expression of TGFβ1, TGFβ2, and CD276; and (iii) modified to express modTBXT and modMAGEC2; (b) NEC8 is modified to (i) increase expression of GM-CSF, IL-12, and membrane bound CD40L; and (ii) decrease expression of CD276; and (c) NTERA-2cl-D1 is modified to (i) increase expression of GM-CSF, IL-12, and membrane bound CD40L; and (ii) decrease expression of CD276; and (ii) a therapeutically effective amount of a second vaccine composition comprising therapeutically effective amounts of cancer cell lines DU-145, LNCaP, and DMS 53, wherein: (d) DU-145 is modified to (i) increase expression of GM-CSF, IL-12, and membrane bound CD40L; (ii) decrease expression of CD276; and (iii) modified to express modPSMA; (e) LNCaP is modified to (i) increase expression of GM-CSF, IL-12, and membrane bound CD40L; and (ii) decrease expression of CD276; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh.

In another embodiment, the present disclosure provides a method of treating prostate cancer in a human subject comprising administering (i) a therapeutically effective amount of a first vaccine composition comprising therapeutically effective amounts of cancer cell lines PC3, NEC8, NTERA-2cl-D1, wherein: (a) PC3 is modified to (i) increase expression of GM-CSF, IL-12, and membrane bound CD40L; (ii) decrease expression of TGFβ1, TGFβ2, and CD276; and (iii) modified to express modTBXT and modMAGEC2; (b) NEC8 is modified to (i) increase expression of GM-CSF, IL-12, and membrane bound CD40L; and (ii) decrease expression of CD276; and (c) NTERA-2cl-D1 is modified to (i) increase expression of GM-CSF, IL-12, and membrane bound CD40L; and (ii) decrease expression of CD276; and (ii) a therapeutically effective amount of a second vaccine composition comprising therapeutically effective amounts of cancer cell lines DU-145, LNCaP, and DMS 53, wherein: (d) DU 145 is modified to (i) increase expression of GM-CSF, IL-12, and membrane bound CD40L; (ii) decrease expression of CD276; and (iii) modified to express modPSMA; (e) LNCaP is modified to (i) increase expression of GM-CSF, IL-12, and membrane bound CD40L; and (ii) decrease expression of CD276; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh. In another embodiment, the present disclosure provides a method of stimulating an immune response specific to tumor associated antigens (TAAs) associated with bladder cancer in a human subject comprising administering (i) a therapeutically effective amount of a first vaccine composition comprising therapeutically effective amounts of cancer cell lines J82, HT-1376, and TCCSUP, wherein: (a) J82 is modified to (i) increase expression of GM-CSF, IL-12, and membrane bound CD40L; (ii) decrease expression of TGFβ2 and CD276; and (iii) modified to express modPSMA; (b) HT-1376 is modified to (i) increase expression of GM-CSF, IL-12, and membrane bound CD40L; and (ii) decrease expression of TGFβ1, TGFβ2, and CD276; and (c) TCCSUP is modified to (i) increase expression of GM-CSF, IL-12, and membrane bound CD40L; and (ii) decrease expression of TGFβ1, TGFβ2, and CD276; and (ii) a therapeutically effective amount of a second vaccine composition comprising therapeutically effective amounts of cancer cell lines SCaBER, UM-UC-3 and DMS 53, wherein: (d) SCaBER is modified to (i) increase expression of GM-CSF, IL-12, and membrane bound CD40L; (ii) decrease expression of TGFβ1, TGFβ2, and CD276; and (iii) modified to express modWT1 and modFOLR1; (e) UM-UC-3 is modified to (i) increase expression of GM-CSF, IL-12, and membrane bound CD40L; and (ii) decrease expression of TGFβ1 and CD276; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh.

In another embodiment, the present disclosure provides a method of treating bladder cancer in a human subject comprising administering (i) a therapeutically effective amount of a first vaccine composition comprising therapeutically effective amounts of cancer cell lines J82, HT-1376, and TCCSUP, wherein: (a) J82 is modified to (i) increase expression of GM-CSF, IL-12, and membrane bound CD40L; (ii) decrease expression of TGFβ2 and CD276; and (iii) modified to express modPSMA; (b) HT-1376 is modified to (i) increase expression of GM-CSF, IL-12, and membrane bound CD40L; and (ii) decrease expression of TGFβ1, TGFβ2, and CD276; and (c) TCCSUP is modified to (i) increase expression of GM-CSF, IL-12, and membrane bound CD40L; and (ii) decrease expression of TGFβ1, TGFβ2, and CD276; and (ii) a therapeutically effective amount of a second vaccine composition comprising therapeutically effective amounts of cancer cell lines SCaBER, UM-UC-3 and DMS 53, wherein: (d) SCaBER is modified to (i) increase expression of GM-CSF, IL-12, and membrane bound CD40L; (ii) decrease expression of TGFβ1, TGFβ2, and CD276; and (iii) modified to express modWT1 and modFOLR1; (e) UM-UC-3 is modified to (i) increase expression of GM-CSF, IL-12, and membrane bound CD40L; and (ii) decrease expression of TGFβ1 and CD276; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh.

In another embodiment, the present disclosure provides a method of stimulating an immune response specific to tumor associated antigens (TAAs) associated with ovarian cancer in a human subject comprising administering (i) a therapeutically effective amount of a first vaccine composition comprising therapeutically effective amounts of cancer cell lines OVTOKO, MCAS, TOV-112D, wherein: (a) OVTOKO is modified to (i) increase expression of GM-CSF, IL-12, and membrane bound CD40L; and (ii) decrease expression of TGFβ1 and CD276; (b) MCAS is modified to (i) increase expression of GM-CSF, IL-12, and membrane bound CD40L; (ii) decrease expression of TGFβ1, TGFβ2, and CD276; and (iii) modified to express modhTERT; (c) TOV-112D is modified to (i) increase expression of GM-CSF, IL-12, and membrane bound CD40L; (ii) decrease expression of TGFβ1, TGFβ2, and CD276; and (iii) modified to express modFSHR and modMAGEA10; and (ii) a therapeutically effective amount of a second vaccine composition comprising therapeutically effective amounts of cancer cell lines TOV-21G, ES-2 and DMS 53, wherein: (d) TOV-21G is modified to (i) increase expression of GM-CSF, IL-12, and membrane bound CD40L; (ii) decrease expression of CD276; and (iii) modified to express modWT1 and modFOLR1; (e) ES2 is modified to (i) increase expression of GM-CSF, IL-12, and membrane bound CD40L; (ii) decrease expression of TGFβ1, TGFβ2, and CD276; and (iii) modified to express modBORIS; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh. In another embodiment, the present disclosure provides a method of treating ovarian cancer in a human subject comprising administering (i) a therapeutically effective amount of a first vaccine composition comprising therapeutically effective amounts of cancer cell lines OVTOKO, MCAS, TOV-112D, wherein: (a) OVTOKO is modified to (i) increase expression of GM-CSF, IL-12, and membrane bound CD40L; and (ii) decrease expression of TGFβ1 and CD276; (b) MCAS is modified to (i) increase expression of GM-CSF, IL-12, and membrane bound CD40L; (ii) decrease expression of TGFβ1, TGFβ2, and CD276; and (iii) modified to express modhTERT; (c) TOV-112D is modified to (i) increase expression of GM-CSF, IL-12, and membrane bound CD40L; (ii) decrease expression of TGFβ1, TGFβ2, and CD276; and (iii) modified to express modFSHR and modMAGEA10; and (ii) a therapeutically effective amount of a second vaccine composition comprising therapeutically effective amounts of cancer cell lines TOV-21G, ES-2 and DMS 53, wherein: (d) TOV-21G is modified to (i) increase expression of GM-CSF, IL-12, and membrane bound CD40L; (ii) decrease expression of CD276; and (iii) modified to express modWT1 and modFOLR1; (e) ES2 is modified to (i) increase expression of GM-CSF, IL-12, and membrane bound CD40L; (ii) decrease expression of TGFβ1, TGFβ2, and CD276; and (iii) modified to express modBORIS; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh.

In another embodiment, the present disclosure provides a method of stimulating an immune response specific to tumor associated antigens (TAAs) associated with head and neck cancer in a human subject comprising administering (i) a therapeutically effective amount of a first vaccine composition comprising therapeutically effective amounts of cancer cell lines HSC-4, HO-1-N-1, DETROIT 562, wherein: (a)

HSC-4 is modified to (i) increase expression of GM-CSF, IL-12, and membrane bound CD40L; (ii) decrease expression of TGFβ1, TGFβ2, and CD276; and (iii) modified to express modPSMA; (b) HO-1-N-1 is modified to (i) increase expression of GM-CSF, IL-12, and membrane bound CD40L; (ii) decrease expression of TGFβ1, TGFβ2, and CD276; and (iii) modified to express modPRAME and modTBXT; and (c) DETROIT 562 is modified to (i) increase expression of GM-CSF, IL-12, and membrane bound CD40L; and (ii) decrease expression of TGFβ1, TGFβ2, and CD276; and (ii) a therapeutically effective amount of a second vaccine composition comprising therapeutically effective amounts of cancer cell lines KON, OSC-20 and DMS 53, wherein: (d) KON is modified to (i) increase expression of GM-CSF, IL-12, and membrane bound CD40L; (ii) decrease expression of TGFβ1, TGFβ2, and CD276; and (iii) modified to express HPV16 E6 and E7 and HPV18 E6 and E7; (e) OSC-20 is modified to (i) increase expression of GM-CSF, IL-12, and membrane bound CD40L; and (ii) decrease expression of TGFβ2 and CD276; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh. In another embodiment, the present disclosure provides a method of treating head and neck cancer in a human subject comprising administering (i) a therapeutically effective amount of a first vaccine composition comprising therapeutically effective amounts of cancer cell lines HSC-4, HO-1-N-1, DETROIT 562, wherein: (a) HSC-4 is modified to (i) increase expression of GM-CSF, IL-12, and membrane bound CD40L; (ii) decrease expression of TGFβ1, TGFβ2, and CD276; and (iii) modified to express modPSMA; (b) HO-1-N-1 is modified to (i) increase expression of GM-CSF, IL-12, and membrane bound CD40L; (ii) decrease expression of TGFβ1, TGFβ2, and CD276; and (iii) modified to express modPRAME and modTBXT; and (c) DETROIT 562 is modified to (i) increase expression of GM-CSF, IL-12, and membrane bound CD40L; and (ii) decrease expression of TGFβ1, TGFβ2, and CD276; and (ii) a therapeutically effective amount of a second vaccine composition comprising therapeutically effective amounts of cancer cell lines KON, OSC-20 and DMS 53, wherein: (d) KON is modified to (i) increase expression of GM-CSF, IL-12, and membrane bound CD40L; (ii) decrease expression of TGFβ1, TGFβ2, and CD276; and (iii) modified to express HPV16 E6 and E7 and HPV18 E6 and E7; (e) OSC-20 is modified to (i) increase expression of GM-CSF, IL-12, and membrane bound CD40L; and (ii) decrease expression of TGFβ2 and CD276; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh.

In another embodiment, the present disclosure provides a method of stimulating an immune response specific to tumor associated antigens (TAAs) associated with gastric cancer in a human subject comprising administering (i) a therapeutically effective amount of a first vaccine composition comprising therapeutically effective amounts of cancer cell lines MKN-1, MKN-45, and MKN-74; wherein (a) MKN-1 is modified to (i) increase expression of GM-CSF, IL-12, and membrane bound CD40L; (ii) decrease expression of TGFβ1, TGFβ2, and CD276; and (iii) modified to express modPSMA and modLYK6; (b) MKN-45 is modified to (i) increase expression of GM-CSF, IL-12, and membrane bound CD40L; (ii) decrease expression of TGFβ1 and CD276; (c) MKN-74 is modified to (i) increase expression of GM-CSF, IL-12, and membrane bound CD40L; and (ii) decrease expression of TGFβ1, and CD276; and (ii) a therapeutically effective amount of a second vaccine composition comprising therapeutically effective amounts of cancer cell lines OCUM-1, Fu97 and DMS 53, wherein (d) OCUM-1 is modified to (i) increase expression of GM-CSF and membrane bound CD40L; (ii) decrease expression of CD276; (e) Fu97 is modified to (i) increase expression of GM-CSF, IL-12, and membrane bound CD40L; and (ii) decrease expression of TGFβ1 and CD276; and (iii) modified to express modWT1 and modCLDN18; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh. In another embodiment, the present disclosure provides a method of treating gastric cancer in a human subject comprising administering (i) a therapeutically effective amount of a first vaccine composition comprising therapeutically effective amounts of cancer cell lines MKN-1, MKN-45, and MKN-74; wherein (a) MKN-1 is modified to (i) increase expression of GM-CSF, IL-12, and membrane bound CD40L; (ii) decrease expression of TGFβ1, TGFβ2, and CD276; and (iii) modified to express modPSMA and modLYK6; (b) MKN-45 is modified to (i) increase expression of GM-CSF, IL-12, and membrane bound CD40L; (ii) decrease expression of TGFβ1 and CD276; (c) MKN-74 is modified to (i) increase expression of GM-CSF, IL-12, and membrane bound CD40L; and (ii) decrease expression of TGFβ1, and CD276; and (ii) a therapeutically effective amount of a second vaccine composition comprising therapeutically effective amounts of cancer cell lines OCUM-1, Fu97 and DMS 53, wherein (d) OCUM-1 is modified to (i) increase expression of GM-CSF and membrane bound CD40L; (ii) decrease expression of CD276; (e) Fu97 is modified to (i) increase expression of GM-CSF, IL-12, and membrane bound CD40L; and (ii) decrease expression of TGFβ1 and CD276; and (iii) modified to express modWT1 and modCLDN18; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh.

In another embodiment, the present disclosure provides a method of stimulating an immune response specific to tumor associated antigens (TAAs) associated with breast cancer in a human subject comprising administering (i) a therapeutically effective amount of a first vaccine composition comprising therapeutically effective amounts of cancer cell lines CAMA-1, AU565, HS-578T, MCF-7, T47D and DMS 53, wherein: (a) CAMA-1 is modified to (i) increase expression of GM-CSF, IL-12, and membrane bound CD40L; (ii) decrease expression of TGFβ2, and CD276; and (iii) modified to express modPSMA; (b) AU565 is modified to (i) increase expression of GM-CSF, IL-12, and membrane bound CD40L; (ii) decrease expression of TGFβ2 and CD276; and (iii) modified to express modTERT; and (c) HS-578T is modified to (i) increase expression of GM-CSF, IL-12, and membrane bound CD40L; and (ii) decrease expression of TGFβ1, TGFβ2 and CD276; and (ii) a therapeutically effective amount of a second vaccine composition comprising therapeutically effective amounts of cancer cell lines MCF-7, T47D and DMS 53, wherein: (d) MCF-7 is modified to (i) increase expression of GM-CSF, IL-12, and membrane bound CD40L; and (ii) decrease expression of TGFβ1, TGFβ2 and CD276; (e) T47D is modified to (i) increase expression of GM-CSF, IL-12, and membrane bound CD40L; and (ii) decrease expression of CD276; and (iii) modified to express modTBXT and modBORIS; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh. In another embodiment, the present disclosure provides a method of treating breast cancer in a human subject comprising administering (i) a therapeutically effective amount of a first vaccine composition comprising therapeutically effective amounts of cancer cell lines CAMA-1, AU565, and HS-578T, wherein: (a) CAMA-1 is modified to (i) increase expression of GM-CSF, IL-12, and membrane bound CD40L; (ii) decrease expression of TGFβ2, and CD276; and (iii) modified to express modPSMA; (b) AU565 is modified to (i) increase expression of GM-CSF, IL-12, and membrane bound CD40L; (ii) decrease expression of TGFβ2 and CD276; and (iii) modified to express modTERT; and (c) HS-578T is modified to (i) increase expression of GM-CSF, IL-12, and membrane bound CD40L; and (ii) decrease expression of TGFβ1, TGFβ2 and CD276; and (ii) a therapeutically effective amount of a second vaccine composition comprising therapeutically effective amounts of cancer cell lines MCF-7, T47D and DMS 53, wherein: (d) MCF-7 is modified to (i) increase expression of GM-CSF, IL-12, and membrane bound CD40L; and (ii) decrease expression of TGFβ1, TGFβ2 and CD276; (e) T47D is modified to (i) increase expression of GM-CSF, IL-12, and membrane bound CD40L; and (ii) decrease expression of CD276; and (iii) modified to express modTBXT and modBORIS; and (f) DMS 53 is modified to (i) increase expression of GM-CSF and membrane bound CD40L; and (ii) decrease expression of TGFβ2 and CD276; wherein the first vaccine composition is administered intradermally in the subject's arm, and the second vaccine composition is administered intradermally in the subject's thigh.

In another embodiment, the present disclosure provides a method of stimulating an immune response specific to tumor associated antigens (TAAs) associated with NSCLC in a human subject comprising: a. orally administering cyclophosphamide daily for one week at a dose of 50 mg/day; b. after said one week in (a), further administering a first dose of a vaccine comprising a first and second composition, wherein the first composition comprises therapeutically effective amounts of lung cancer cell lines NCI-H460, NCI-H520, and A549; wherein (a) NCI-H460 is modified to (i) increase expression of GM-CSF, IL-12, and membrane bound CD40L; and (ii) decrease expression of TGFβ1, TGFβ2, and CD276; (b) NCI-H520 is modified to (i) increase expression of GM-CSF and membrane bound CD40L; and (ii) decrease expression of TGFβ1, TGFβ2, and CD276; and (c) A549 is modified to (i) increase expression of GM-CSF, IL-12, and membrane bound CD40L; and (ii) decrease expression of TGFβ1, TGFβ2, and CD276; and the second composition comprises therapeutically effective amounts of lung cancer cell lines DMS 53, LK-2, and NCI-H23; wherein (d) DMS 53 is modified to (i) increase expression of GM-CSF and membrane bound CD40L; and (ii) decrease expression of TGFβ2 and CD276; (e) LK-2 is modified to (i) increase expression of GM-CSF and membrane bound CD40L; and (ii) decrease expression of TGFβ1, TGFβ2, and CD276; (iii) to express MSLN and CT83; and (f) NCI-H23 is modified to (i) increase expression of GM-CSF, IL-12, and membrane bound CD40L; c. after said one week in (a), further administering via injection a first dose of a composition comprising pembrolizumab at a dosage of 200 mg; d. further administering subsequent doses of the first and second compositions at 3, 6, 9, 15, 21, and 27 weeks following administration of said first dose in (b), and wherein 50 mg of cyclophosphamide is orally administered for 7 days leading up to each subsequent dose; e. further administering intravenously subsequent doses of the composition comprising pembrolizumab at 3, 6, 9, 12, 15, 18, 21, 24, and 27 weeks following said first dose in (c) at a dosage of 200 mg; wherein the first composition is administered intradermally in the subject's arm, and the second composition is administered intradermally in the subject's thigh.

In still another embodiment, the present disclosure provides a method of stimulating an immune response specific to tumor associated antigens (TAAs) associated with a cancer in a human subject comprising: a. orally administering cyclophosphamide daily for one week at a dose of 50 mg/day; b. after said one week in (a), further administering a first dose of a vaccine comprising a first and second composition, wherein the first composition is a composition provided herein; and the second composition is a different composition provided herein; c. after said one week in (a), further administering via injection a first dose of a composition comprising pembrolizumab at a dosage of 200 mg; d. further administering subsequent doses of the first and second compositions at 3, 6, 9, 15, 21, and 27 weeks following administration of said first dose in (b), and wherein 50 mg of cyclophosphamide is orally administered for 7 days leading up to each subsequent dose; e. further administering intravenously subsequent doses of the composition comprising pembrolizumab at 3, 6, 9, 12, 15, 18, 21, 24, and 27 weeks following said first dose in (c) at a dosage of 200 mg; wherein the first composition is administered intradermally in the subject's arm, and the second composition is administered intradermally in the subject's thigh.

In another embodiment, the present disclosure provides a method of stimulating an immune response specific to TAAs associated with NSCLC in a human subject comprising: a. orally administering cyclophosphamide daily for one week at a dose of 50 mg/day; b. after said one week in (a), further administering a first dose of a vaccine comprising a first and second composition, wherein the first composition comprises therapeutically effective amounts of lung cancer cell lines NCI-H460, NCI-H520, and A549; wherein (a) NCI-H460 is modified to (i) increase expression of GM-CSF, IL-12, and membrane bound CD40L; and (ii) decrease expression of TGFβ1, TGFβ2, and CD276; (b) NCI-H520 is modified to (i) increase expression of GM-CSF and membrane bound CD40L; and (ii) decrease expression of TGFβ1, TGFβ2, and CD276; and (c) A549 is modified to (i) increase expression of GM-CSF, IL-12, and membrane bound CD40L; and (ii) decrease expression of TGFβ1, TGFβ2, and CD276; and the second composition comprises therapeutically effective amounts of lung cancer cell lines DMS 53, LK-2, and NCI-H23; wherein (d) DMS 53 is modified to (i) increase expression of GM-CSF and membrane bound CD40L; and (ii) decrease expression of TGFβ2 and CD276; (e) LK-2 is modified to (i) increase expression of GM-CSF and membrane bound CD40L; and (ii) decrease expression of TGFβ1, TGFβ2, and CD276; (iii) to express MSLN and CT83; and (f) NCI-H23 is modified to (i) increase expression of GM-CSF, IL-12, and membrane bound CD40L; c. after said one week in (a), further administering via injection a first dose of a composition comprising durvalumab at a dosage of 10 mg/kg; d. further administering subsequent doses of the first and second compositions at 2, 4, 10, 16, 22, and 28 weeks following administration of said first dose in (b), and wherein 50 mg of cyclophosphamide is orally administered for 7 days leading up to each subsequent dose; e. further administering intravenously subsequent doses of the composition comprising durvalumab at 2, 4, 6, 8, 10, 12, 14, 16, 18, 20, 22, 24, 26, 28 and 30 weeks following said first dose in (c) at a dosage of 10 mg/kg; wherein the first composition is administered intradermally in the subject's arm, and the second composition is administered intradermally in the subject's thigh.

In another embodiment, the present disclosure provides a method of stimulating an immune response specific to TAAs associated with NSCLC in a human subject comprising: a. orally administering cyclophosphamide daily for one week at a dose of 50 mg/day; b. after said one week in (a), further administering a first dose of a vaccine comprising a first and second composition, wherein the first composition is a composition provided herein and the second composition is a different composition provided herein; c. after said one week in (a), further administering via injection a first dose of a composition comprising durvalumab at a dosage of 10 mg/kg; d. further administering subsequent doses of the first and second compositions at 2, 4, 10, 16, 22, and 28 weeks following administration of said first dose in (b), and wherein 50 mg of cyclophosphamide is orally administered for 7 days leading up to each subsequent dose; e. further administering intravenously subsequent doses of the composition comprising durvalumab at 2, 4, 6, 8, 10, 12, 14, 16, 18, 20, 22, 24, 26, 28 and 30 weeks following said first dose in (c) at a dosage of 10 mg/kg; wherein the first composition is administered intradermally in the subject's arm, and the second composition is administered intradermally in the subject's thigh.

In yet another embodiment, the present disclosure provides a kit comprising six vials, wherein each vial comprises cells of lung cancer cell lines NCI-H460, NCIH520, A549, DMS 53, LK-2, and NCI-H23, and wherein: (a) NCI-H460 is modified to (i) increase expression of GM-CSF, IL-12, and membrane bound CD40L; and (ii) decrease expression of TGFβ1, TGFβ2, and CD276; (b) NCI-H520 is modified to (i) increase expression of GM-CSF and membrane bound CD40L; and (ii) decrease expression of TGFβ1, TGFβ2, and CD276; (c) A549 is modified to (i) increase expression of GM-CSF, IL-12, and membrane bound CD40L; and (ii) decrease expression of TGFβ1, TGFβ2, and CD276; (d) DMS 53 is modified to (i) increase expression of GM-CSF, and membrane bound CD40L; and (ii) decrease expression of TGFβ2 and CD276; (e) LK-2 is modified to (i) increase expression of GM-CSF and membrane bound CD40L; and (ii) decrease expression of TGFβ1, TGFβ2, and CD276; (iii) to express MSLN and CT83; and (f) NCI-H23 is modified to (i) increase expression of GM-CSF, IL-12, and membrane bound CD40L; and (ii) decrease expression of TGFβ1, TGFβ2, and CD276. In another embodiment, the present disclosure provides a kit comprising six vials, wherein each vial comprises cells of cancer cell lines LN-229, GB-1, SF-126, DBTRG-05MG, KNS 60, and DMS 53, wherein: (a) LN-229 is modified to (i) increase expression of GM-CSF, IL-12, and membrane bound CD40L; (ii) decrease expression of TGFβ1 and CD276; and (iii) modified to express modPSMA; (b) GB-1 is modified to (i) increase expression of GM-CSF and membrane bound CD40L; and (ii) decrease expression of TGFβ1 and CD276; (c) SF-126 is modified to (i) increase expression of GM-CSF, IL-12, and membrane bound CD40L; (ii) decrease expression of TGFβ1, TGFβ2, and CD276; and (iii) modified to express modTERT; (d) DMS 53 is modified to (i) increase expression of GM-CSF and membrane bound CD40L; and (ii) decrease expression of TGFβ2 and CD276; (e) DBTRG-05MG is modified to (i) increase expression of GM-CSF, IL-12, and membrane bound CD40L; and (ii) decrease expression of TGFβ1 and CD276; and (f) KNS 60 is modified to (i) increase expression of GM-CSF, IL-12, and membrane bound CD40L; (ii) decrease expression of TGFβ1, TGFβ2, and CD276; and (iii) modified to express modMAGEA1, EGFRvIII, and hCMV pp65. In another embodiment, the present disclosure provides a kit comprising six vials, wherein each vial comprises cells of cancer cell lines HCT-15, RKO, HuTu-80, HCT-116, LS411N and DMS 53, wherein: (a) HCT-15 is modified to (i) increase expression of GM-CSF, IL-12, and membrane bound CD40L; and (ii) decrease expression of TGFβ1 and CD276; (b) RKO is modified to (i) increase expression of GM-CSF, IL-12, and membrane bound CD40L; and (ii) decrease expression of TGFβ1 and CD276; (c) HuTu-80 is modified to (i) increase expression of GM-CSF, IL-12, and membrane bound CD40L; (ii) decrease expression of TGFβ1, TGFβ2, and CD276; and (iii) modified to express modPSMA; (d) HCT-116 is modified to (i) increase expression of GM-CSF and membrane bound CD40L; (ii) decrease expression of TGFβ1 and CD276; and (iii) modified to express modTBXT, modWT1, KRAS G12D and KRAS G12V; (e) LS411N is modified to (i) increase expression of GM-CSF, IL-12, and membrane bound CD40L; and (ii) decrease expression of TGFβ1 and CD276; and (f) DMS 53 is modified to (i) increase expression of GM-CSF and membrane bound CD40L; and (ii) decrease expression of TGFβ2 and CD276.

In still another embodiment, the present disclosure provides a kit comprising six vials, wherein each vial comprises cells of cancer cell lines PC3, NEC8, NTERA-2cl-D1, DU-145, LNCaP, and DMS 53, wherein: (a) PC3 is modified to (i) increase expression of GM-CSF, IL-12, and membrane bound CD40L; (ii) decrease expression of TGFβ1, TGFβ2, and CD276; and (iii) modified to express modTBXT and modMAGEC2; (b) NEC8 is modified to (i) increase expression of GM-CSF, IL-12, and membrane bound CD40L; and (ii) decrease expression of CD276; (c) NTERA-2cl-D1 is modified to (i) increase expression of GM-CSF, IL-12, and membrane bound CD40L; and (ii) decrease expression of CD276; (d) DU-145 is modified to (i) increase expression of GM-CSF, IL-12, and membrane bound CD40L; (ii) decrease expression of CD276; and (iii) modified to express modPSMA; (e) LNCaP is modified to (i) increase expression of GM-CSF, IL-12, and membrane bound CD40L; and (ii) decrease expression of CD276; and (f) DMS 53 is modified to (i) increase expression of GM-CSF and membrane bound CD40L; and (ii) decrease expression of TGFβ2 and CD276. In another embodiment, the present disclosure provides a kit comprising six vials, wherein each vial comprises cells of cancer cell lines J82, HT-1376, TCCSUP, SCaBER, UM-UC-3 and DMS 53, wherein: (a) J82 is modified to (i) increase expression of GM-CSF, IL-12, and membrane bound CD40L; (ii) decrease expression of TGFβ2 and CD276; and (iii) modified to express modPSMA; (b) HT-1376 is modified to (i) increase expression of GM-CSF, IL-12, and membrane bound CD40L; and (ii) decrease expression of TGFβ1, TGFβ2, and CD276; (c) TCCSUP is modified to (i) increase expression of GM-CSF, IL-12, and membrane bound CD40L; and (ii) decrease expression of TGFβ1, TGFβ2, and CD276; (d) SCaBER is modified to (i) increase expression of GM-CSF, IL-12, and membrane bound CD40L; (ii) decrease expression of TGFβ1, TGFβ2, and CD276; and (iii) modified to express modWT1 and modFOLR1; (e) UM-UC-3 is modified to (i) increase expression of GM-CSF, IL-12, and membrane bound CD40L; and (ii) decrease expression of TGFβ1 and CD276; and (f) DMS 53 is modified to (i) increase expression of GM-CSF and membrane bound CD40L; and (ii) decrease expression of TGFβ2 and CD276.

In another embodiment, the present disclosure provides a kit comprising six vials, wherein each vial comprises cells of cancer cell lines OVTOKO, MCAS, TOV-112D, TOV-21G, ES-2 and DMS 53, wherein: (a) OVTOKO is modified to (i) increase expression of GM-CSF, IL-12, and membrane bound CD40L; and (ii) decrease expression of TGFβ1 and CD276; (b) MCAS is modified to (i) increase expression of GM-CSF, IL-12, and membrane bound CD40L; (ii) decrease expression of TGFβ1, TGFβ2, and CD276; and (iii) modified to express modhTERT; (c) TOV-112D is modified to (i) increase expression of GM-CSF, IL-12, and membrane bound CD40L; (ii) decrease expression of TGFβ1, TGFβ2, and CD276; and (iii) modified to express modFSHR and modMAGEA10; (d) TOV-21G is modified to (i) increase expression of GM-CSF, IL-12, and membrane bound CD40L; (ii) decrease expression of CD276; and (iii) modified to express modWT1 and modFOLR1; (e) ES2 is modified to (i) increase expression of GM-CSF, IL-12, and membrane bound CD40L; (ii) decrease expression of TGFβ1, TGFβ2, and CD276; and (iii) modified to express modBORIS; and (f) DMS 53 is modified to (i) increase expression of GM-CSF and membrane bound CD40L; and (ii) decrease expression of TGFβ2 and CD276. In another embodiment, the present disclosure provides a kit comprising six vials, wherein each vial comprises cells of cancer cell lines HSC-4, HO-1-N-1, DETROIT 562, KON, OSC-20 and DMS 53, wherein: (a) HSC-4 is modified to (i) increase expression of GM-CSF, IL-12, and membrane bound CD40L; (ii) decrease expression of TGFβ1, TGFβ2, and CD276; and (iii) modified to express modPSMA; (b) HO-1-N-1 is modified to (i) increase expression of GM-CSF, IL-12, and membrane bound CD40L; (ii) decrease expression of TGFβ1, TGFβ2, and CD276; and (iii) modified to express modPRAME and modTBXT; (c) DETROIT 562 is modified to (i) increase expression of GM-CSF, IL-12, and membrane bound CD40L; and (ii) decrease expression of TGFβ1, TGFβ2, and CD276; (d) KON is modified to (i) increase expression of GM-CSF, IL-12, and membrane bound CD40L; (ii) decrease expression of TGFβ1, TGFβ2, and CD276; and (iii) modified to express HPV16 E6 and E7 and HPV18 E6 and E7; (e) OSC-20 is modified to (i) increase expression of GM-CSF, IL-12, and membrane bound CD40L; and (ii) decrease expression of TGFβ2 and CD276; and (f) DMS 53 is modified to (i) increase expression of GM-CSF and membrane bound CD40L; and (ii) decrease expression of TGFβ2 and CD276.

In yet another embodiment, the present disclosure provides a kit comprising six vials, wherein each vial comprises approximately cells of cancer cell lines MKN-1, MKN-45, MKN-74, OCUM-1, Fu97 and DMS 53, wherein: (a) MKN-1 is modified to (i) increase expression of GM-CSF, IL-12, and membrane bound CD40L; (ii) decrease expression of TGFβ1, TGFβ2, and CD276; and (iii) modified to express modPSMA and modLYK6; (b) MKN-45 is modified to (i) increase expression of GM-CSF, IL-12, and membrane bound CD40L; (ii) decrease expression of TGFβ1 and CD276; (c) MKN-74 is modified to (i) increase expression of GM-CSF, IL-12, and membrane bound CD40L; and (ii) decrease expression of TGFβ1, and CD276; (d) OCUM-1 is modified to (i) increase expression of GM-CSF and membrane bound CD40L; (ii) decrease expression of CD276; (e) Fu97 is modified to (i) increase expression of GM-CSF, IL-12, and membrane bound CD40L; and (ii) decrease expression of TGFβ1 and CD276; and (iii) modified to express modWT1 and modCLDN18; and (f) DMS 53 is modified to (i) increase expression of GM-CSF and membrane bound CD40L; and (ii) decrease expression of TGFβ2 and CD276. In another embodiment, the present disclosure provides a kit comprising six vials, wherein each vial comprises cells of cancer cell lines CAMA-1, AU565, HS-578T, MCF-7, T47D and DMS 53, wherein: (a) CAMA-1 is modified to (i) increase expression of GM-CSF, IL-12, and membrane bound CD40L; (ii) decrease expression of TGFβ2, and CD276; and (iii) modified to express modPSMA; (b) AU565 is modified to (i) increase expression of GM-CSF, IL-12, and membrane bound CD40L; (ii) decrease expression of TGFβ2 and CD276; and (iii) modified to express modTERT; and (c) HS-578T is modified to (i) increase expression of GM-CSF, IL-12, and membrane bound CD40L; and (ii) decrease expression of TGFβ1, TGFβ2 and CD276; (d) MCF-7 is modified to (i) increase expression of GM-CSF, IL-12, and membrane bound CD40L; and (ii) decrease expression of TGFβ1, TGFβ2 and CD276; (e) T47D is modified to (i) increase expression of GM-CSF, IL-12, and membrane bound CD40L; and (ii) decrease expression of CD276; and (iii) modified to express modTBXT and modBORIS; and (f) DMS 53 is modified to (i) increase expression of GM-CSF and membrane bound CD40L; and (ii) decrease expression of TGFβ2 and CD276.

In another embodiment, the present disclosure provides a unit dose of a lung cancer vaccine comprising six compositions wherein each composition comprises approximately $1.0\times10^7$ cells of lung cancer cell lines NCI-H460, NCIH520, A549, DMS 53, LK-2, and NCI-H23; wherein: (a) NCI-H460 is modified to (i) increase expression of GM-CSF, IL-12, and membrane bound CD40L; and (ii) decrease expression of TGFβ1, TGFβ2, and CD276; (b) NCI-H520 is modified to (i) increase expression of GM-CSF and membrane bound CD40L; and (ii) decrease expression of TGFβ1, TGFβ2, and CD276; (c) A549 is modified to (i) increase expression of GM-CSF, IL-12, and membrane bound CD40L; and (ii) decrease expression of TGFβ1, TGFβ2, and CD276; (d) DMS 53 is modified to (i) increase expression of GM-CSF and membrane bound CD40L; and (ii) decrease expression of TGFβ2 and CD276; (e) LK-2 is modified to (i) increase expression of GM-CSF and membrane bound CD40L; and (ii) decrease expression of TGFβ1, TGFβ2, and CD276; (iii) to express MSLN and CT83; and (f) NCI-H23 is modified to (i) increase expression of GM-CSF, IL-12, and membrane bound CD40L; and (ii) decrease expression of TGFβ1, TGFβ2, and CD276. In another embodiment, the present disclosure provides a unit dose of a cancer vaccine comprising six compositions wherein each composition comprises approximately $1.0\times10^7$ cells of cancer cell lines LN-229, GB-1, SF-126, DBTRG-05MG, KNS 60, and DMS 53, wherein: (a) LN-229 is modified to (i) increase expression of GM-CSF, IL-12, and membrane bound CD40L; (ii) decrease expression of TGFβ1 and CD276; and (iii) modified to express modPSMA (b) GB-1 is modified to (i) increase expression of GM-CSF and membrane bound CD40L; and (ii) decrease expression of TGFβ1 and CD276; (c) SF-126 is modified to (i) increase expression of GM-CSF, IL-12, and membrane bound CD40L; (ii) decrease expression of TGFβ1, TGFβ2, and CD276; and (iii) modified to express modhTERT; (d) DMS 53 is modified to (i) increase expression of GM-CSF and membrane bound CD40L; and (ii) decrease expression of TGFβ2 and CD276; (e) DBTRG-05MG is modified to (i) increase expression of GM-CSF, IL-12, and membrane bound CD40L; and (ii) decrease expression of TGFβ1 and CD276; and (f) KNS 60 is modified to (i) increase expression of GM-CSF, IL-12, and membrane bound CD40L; (ii) decrease expression of TGFβ1, TGFβ2, and CD276; and (iii) modified to express modMAGEA1, EGFRvIII, and hCMV pp65.

In another embodiment, the present disclosure provides a unit dose of a cancer vaccine comprising six compositions wherein each composition comprises approximately $1.0\times 10^7$ cells of cancer cell lines HCT-15, RKO, HuTu-80, HCT-116, LS411N and DMS 53, wherein: (a) HCT-15 is modified to (i) increase expression of GM-CSF, IL-12, and membrane bound CD40L; and (ii) decrease expression of TGFβ1 and CD276; (b) RKO is modified to (i) increase expression of GM-CSF, IL-12, and membrane bound CD40L; and (ii) decrease expression of TGFβ1 and CD276; (c) HuTu-80 is modified to (i) increase expression of GM-CSF, IL-12, and membrane bound CD40L; (ii) decrease expression of TGFβ1, TGFβ2, and CD276; and (iii) modified to express modPSMA; (d) HCT-116 is modified to (i) increase expression of GM-CSF and membrane bound CD40L; (ii) decrease expression of TGFβ1 and CD276; and (iii) modified to express modTBXT, modWT1, KRAS G12D and KRAS G12V; (e) LS411N is modified to (i) increase expression of GM-CSF, IL-12, and membrane bound CD40L; and (ii) decrease expression of TGFβ1 and CD276; and (f) DMS 53 is modified to (i) increase expression of GM-CSF and membrane bound CD40L; and (ii) decrease expression of TGFβ2 and CD276. In another embodiment, the present disclosure provides a unit dose of a cancer vaccine comprising six compositions wherein each composition comprises approximately $1.0\times 10^7$ cells of cancer cell lines PC3, NEC8, NTERA-2cl-D1, DU-145, LNCaP, and DMS 53, wherein: (a) PC3 is modified to (i) increase expression of GM-CSF, IL-12, and membrane bound CD40L; (ii) decrease expression of TGFβ1, TGFβ2, and CD276; and (iii) modified to express modTBXT and modMAGEC2; (b) NEC8 is modified to (i) increase expression of GM-CSF, IL-12, and membrane bound CD40L; and (ii) decrease expression of CD276; (c) NTERA-2cl-D1 is modified to (i) increase expression of GM-CSF, IL-12, and membrane bound CD40L; and (ii) decrease expression of CD276; (d) DU-145 is modified to (i) increase expression of GM-CSF, IL-12, and membrane bound CD40L; (ii) decrease expression of CD276; and (iii) modified to express modPSMA; (e) LNCaP is modified to (i) increase expression of GM-CSF, IL-12, and membrane bound CD40L; and (ii) decrease expression of CD276; and (f) DMS 53 is modified to (i) increase expression of GM-CSF and membrane bound CD40L; and (ii) decrease expression of TGFβ2 and CD276.

In another embodiment, the present disclosure provides a unit dose of a cancer vaccine comprising six compositions wherein each composition comprises approximately $1.0\times 10^7$ cells of cancer cell lines J82, HT-1376, TCCSUP, SCaBER, UM-UC-3 and DMS 53, wherein: (a) J82 is modified to (i) increase expression of GM-CSF, IL-12, and membrane bound CD40L; (ii) decrease expression of TGFβ2 and CD276; and (iii) modified to express modPSMA; (b) HT-1376 is modified to (i) increase expression of GM-CSF, IL-12, and membrane bound CD40L; and (ii) decrease expression of TGFβ1, TGFβ2, and CD276; (c) TCCSUP is modified to (i) increase expression of GM-CSF, IL-12, and membrane bound CD40L; and (ii) decrease expression of TGFβ1, TGFβ2, and CD276; (d) SCaBER is modified to (i) increase expression of GM-CSF, IL-12, and membrane bound CD40L; (ii) decrease expression of TGFβ1, TGFβ2, and CD276; and (iii) modified to express modWT1 and modFOLR1; (e) UM-UC-3 is modified to (i) increase expression of GM-CSF, IL-12, and membrane bound CD40L; and (ii) decrease expression of TGFβ1 and CD276; and (f) DMS 53 is modified to (i) increase expression of GM-CSF and membrane bound CD40L; and (ii) decrease expression of TGFβ2 and CD276. In another embodiment, the present disclosure provides a unit dose of a cancer vaccine comprising six compositions wherein each composition comprises approximately $1.0\times 10^7$ cells of cancer cell lines OVTOKO, MCAS, TOV-112D, TOV-21G, ES-2 and DMS 53, wherein: (a) OVTOKO is modified to (i) increase expression of GM-CSF, IL-12, and membrane bound CD40L; and (ii) decrease expression of TGFβ1 and CD276; (b) MCAS is modified to (i) increase expression of GM-CSF, IL-12, and membrane bound CD40L; (ii) decrease expression of TGFβ1, TGFβ2, and CD276; and (iii) modified to express modTERT; (c) TOV-112D is modified to (i) increase expression of GM-CSF, IL-12, and membrane bound CD40L; (ii) decrease expression of TGFβ1, TGFβ2, and CD276; and (iii) modified to express modFSHR and modMAGEA10; (d) TOV-21G is modified to (i) increase expression of GM-CSF, IL-12, and membrane bound CD40L; (ii) decrease expression of CD276; and (iii) modified to express modWT1 and modFOLR1; (e) ES2 is modified to (i) increase expression of GM-CSF, IL-12, and membrane bound CD40L; (ii) decrease expression of TGFβ1, TGFβ2, and CD276; and (iii) modified to express modBORIS; and (f) DMS 53 is modified to (i) increase expression of GM-CSF and membrane bound CD40L; and (ii) decrease expression of TGFβ2 and CD276.

In yet another embodiment, the present disclosure provides a unit dose of a cancer vaccine comprising six compositions wherein each composition comprises approximately $1.0\times 10^7$ cells of cancer cell lines HSC-4, HO-1-N-1, DETROIT 562, KON, OSC-20 and DMS 53, wherein: (a) HSC-4 is modified to (i) increase expression of GM-CSF, IL-12, and membrane bound CD40L; (ii) decrease expression of TGFβ1, TGFβ2, and CD276; and (iii) modified to express modPSMA; (b) HO-1-N-1 is modified to (i) increase expression of GM-CSF, IL-12, and membrane bound CD40L; (ii) decrease expression of TGFβ1, TGFβ2, and CD276; and (iii) modified to express modPRAME and modTBXT; (c) DETROIT 562 is modified to (i) increase expression of GM-CSF, IL-12, and membrane bound CD40L; and (ii) decrease expression of TGFβ1, TGFβ2, and CD276; (d) KON is modified to (i) increase expression of GM-CSF, IL-12, and membrane bound CD40L; (ii) decrease expression of TGFβ1, TGFβ2, and CD276; and (iii) modified to express HPV16 E6 and E7 and HPV18 E6 and E7; (e) OSC-20 is modified to (i) increase expression of GM-CSF, IL-12, and membrane bound CD40L; and (ii) decrease expression of TGFβ2 and CD276; and (f) DMS 53 is modified to (i) increase expression of GM-CSF and membrane bound CD40L; and (ii) decrease expression of TGFβ2 and CD276. In another embodiment, the present disclosure provides a unit dose of a cancer vaccine comprising six compositions wherein each composition comprises approximately $1.0\times 10^7$ cells of cancer cell lines MKN-1, MKN-45, MKN-74, OCUM-1, Fu97 and DMS 53, wherein: (a) MKN-1 is modified to (i) increase expression of GM-CSF, IL-12, and membrane bound CD40L; (ii) decrease expression of TGFβ1, TGFβ2, and CD276; and (iii) modified to express modPSMA and modLYK6; (b) MKN-45 is modified to (i) increase expression of GM-CSF, IL-12, and membrane bound CD40L; (ii) decrease expression of TGFβ1 and CD276; (c) MKN-74 is modified to (i) increase expression of GM-CSF, IL-12, and membrane bound CD40L; and (ii) decrease expression of TGFβ1, and CD276; (d) OCUM-1 is modified to (i) increase expression of GM-CSF and membrane bound CD40L; (ii) decrease expression of CD276; (e) Fu97 is modified to (i) increase expression of GM-CSF, IL-12, and membrane bound CD40L; and (ii) decrease expression of TGFβ1 and CD276; and (iii) modified to express modWT1 and modCLDN18; and (f) DMS 53 is modified to (i) increase expression of GM-CSF and membrane bound CD40L; and (ii) decrease expression of TGFβ2 and CD276.

In still another embodiment, the present disclosure provides a unit dose of a cancer vaccine comprising six compositions wherein each composition comprises approximately $1.0\times10^7$ cells of cancer cell lines CAMA-1, AU565, HS-578T, MCF-7, T47D and DMS 53, wherein: (a) CAMA-1 is modified to (i) increase expression of GM-CSF, IL-12, and membrane bound CD40L; (ii) decrease expression of TGFβ2, and CD276; and (iii) modified to express modPSMA; (b) AU565 is modified to (i) increase expression of GM-CSF, IL-12, and membrane bound CD40L; (ii) decrease expression of TGFβ2 and CD276; and (iii) modified to express modTERT; and (c) HS-578T is modified to (i) increase expression of GM-CSF, IL-12, and membrane bound CD40L; and (ii) decrease expression of TGFβ1, TGFβ2 and CD276 (d) MCF-7 is modified to (i) increase expression of GM-CSF, IL-12, and membrane bound CD40L; and (ii) decrease expression of TGFβ1, TGFβ2 and CD276; (e) T47D is modified to (i) increase expression of GM-CSF, IL-12, and membrane bound CD40L; and (ii) decrease expression of CD276; and (iii) modified to express modTBXT and modBORIS; and (f) DMS 53 is modified to (i) increase expression of GM-CSF and membrane bound CD40L; and (ii) decrease expression of TGFβ2 and CD276.

In some embodiments, an aforementioned composition is provided wherein DMS 53 is further modified to increase expression of IL-12. In some embodiments, the present disclosure provides an aforementioned unit dose wherein DMS 53 is further modified to increase expression of IL-12. In other embodiments, an aforementioned kit is provided wherein DMS 53 is further modified to increase expression of IL-12. In still other embodiments, the present disclosure provides an aforementioned method wherein DMS 53 is further modified to increase expression of IL-12.

BRIEF DESCRIPTION OF THE DRAWINGS

FIGS. 16A and B show reduction of HLA-E expression in the RERF-LC-Ad1 cell line increases cellular immune responses.

FIGS. 30A-D show reduction of CD276 expression and TGFβ1 and TGFβ2 secretion in the NCI-H460 cell line.

FIGS. 53A-F show secretion of GM-CSF, expression of membrane bound CD40L, and secretion of IL-12 in the A549 TGFβ1 TGFβ2 KD CD47 KO cell line.

FIGS. 69A-C show IFNγ responses elicited by single candidate GBM vaccine cell lines (FIG. 69A) and in cocktails of cell lines (FIGS. 69B-C).

FIGS. 76A-C show IFNγ responses elicited by single candidate CRC vaccine cell lines (FIG. 76A) and in cocktails (FIGS. 76B and C).

FIGS. 86A-D show IFNγ responses elicited by individual PCa candidate vaccine cell lines alone (FIG. 86A) and in cocktails (FIGS. 86B-C) of cell lines and that unmodified LNCaP, NEC8, and NTERA-2cl-D1 cell lines are more immunogenic in cocktails (FIG. 86D)

FIG. 91A shows IFNγ responses to individual PCA vaccine-A cell lines. Pca vaccine-A (FIG. 91B and FIG. 91D) and PCa vaccine-B (FIG. 91C and FIG. 91E) induce more robust IFNγ responses than single component cell lines to parental cell lines and PCa antigens.

FIGS. 93A-C show IFNγ responses elicited by individual UBC candidate vaccine cell lines alone (FIG. 93A) and in cocktails (FIG. 93B and FIG. 93C).

FIGS. 100A-C show IFNγ responses elicited by individual OC candidate vaccine cell lines alone (FIG. 100A) and in cocktails (FIG. 100B and FIG. 1000).

FIGS. 109A-E show IFNγ responses elicited by individual HN candidate vaccine cell lines alone (FIG. 109A), and in cocktails of cell lines (FIG. 109B and FIG. 109C), most HN cell lines are more immunogenic in cocktails (FIG. 109D), and the modified HN vaccine component cell lines are more immunogenic than the parental cell lines (FIG. 109E).

FIGS. 115A-C show IFNγ responses elicited by individual GCA candidate vaccine cell lines alone (FIG. 115A) and in cocktails (FIG. 115B and FIG. 115C).

Figure 119C:
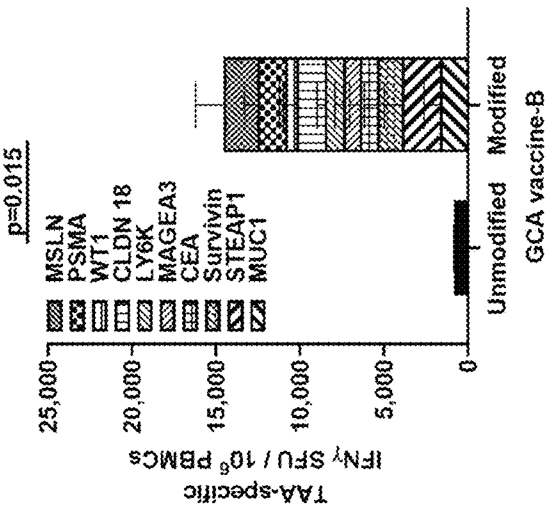
Figure 119B:
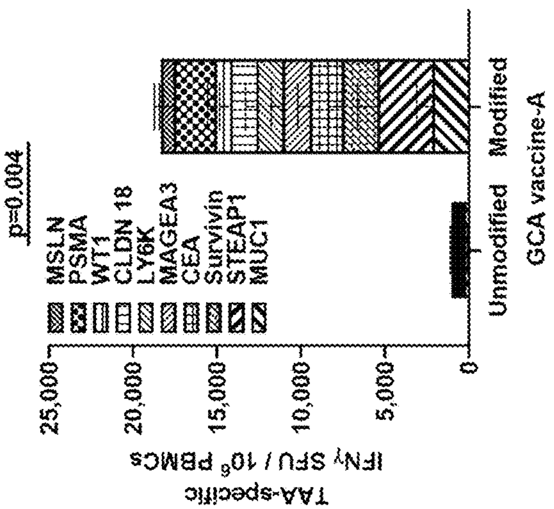
Figure 119A:
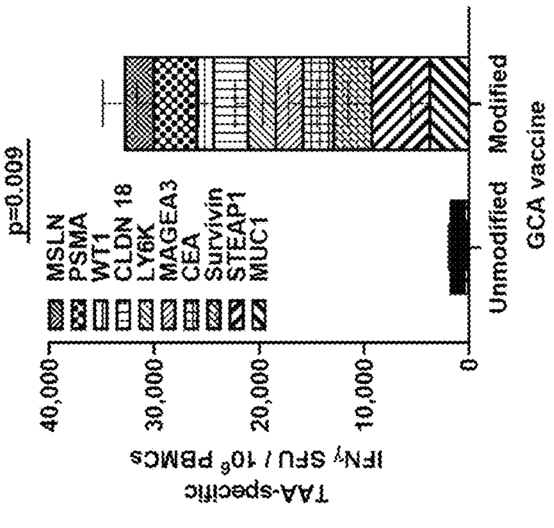

FIGS. 119A-C show antigen specific IFNγ responses induced by the unit dose of the GCA vaccine (FIG. 119A), GCA vaccine-A (FIG. 119B), and GCA vaccine-B (FIG. 119C) compared to unmodified controls.

Figure 120:
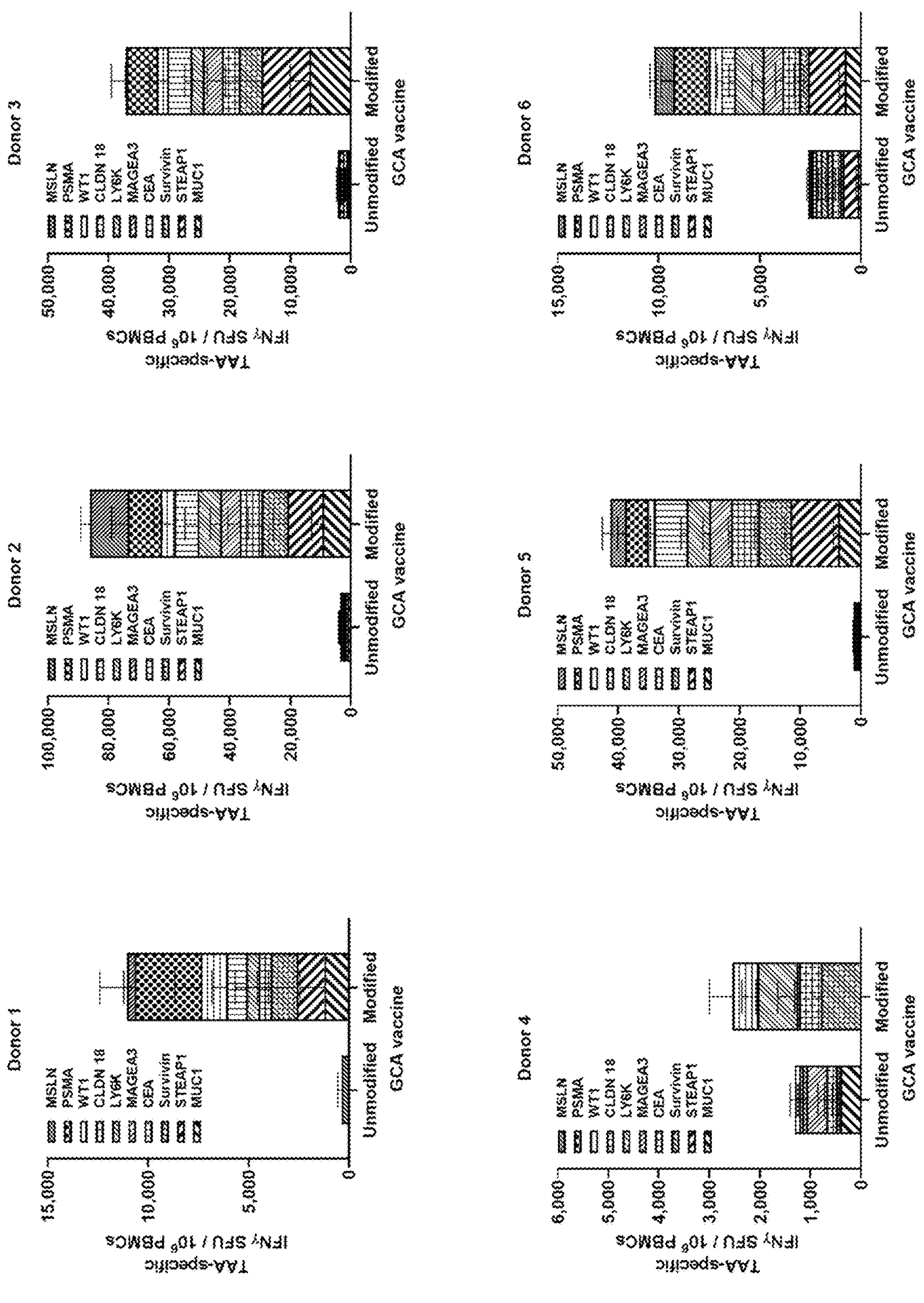

FIG. 120 shows antigen specific IFNγ responses induced by the unit dose of the GCA vaccine in individual donors compared to unmodified controls.

Figure 121A:
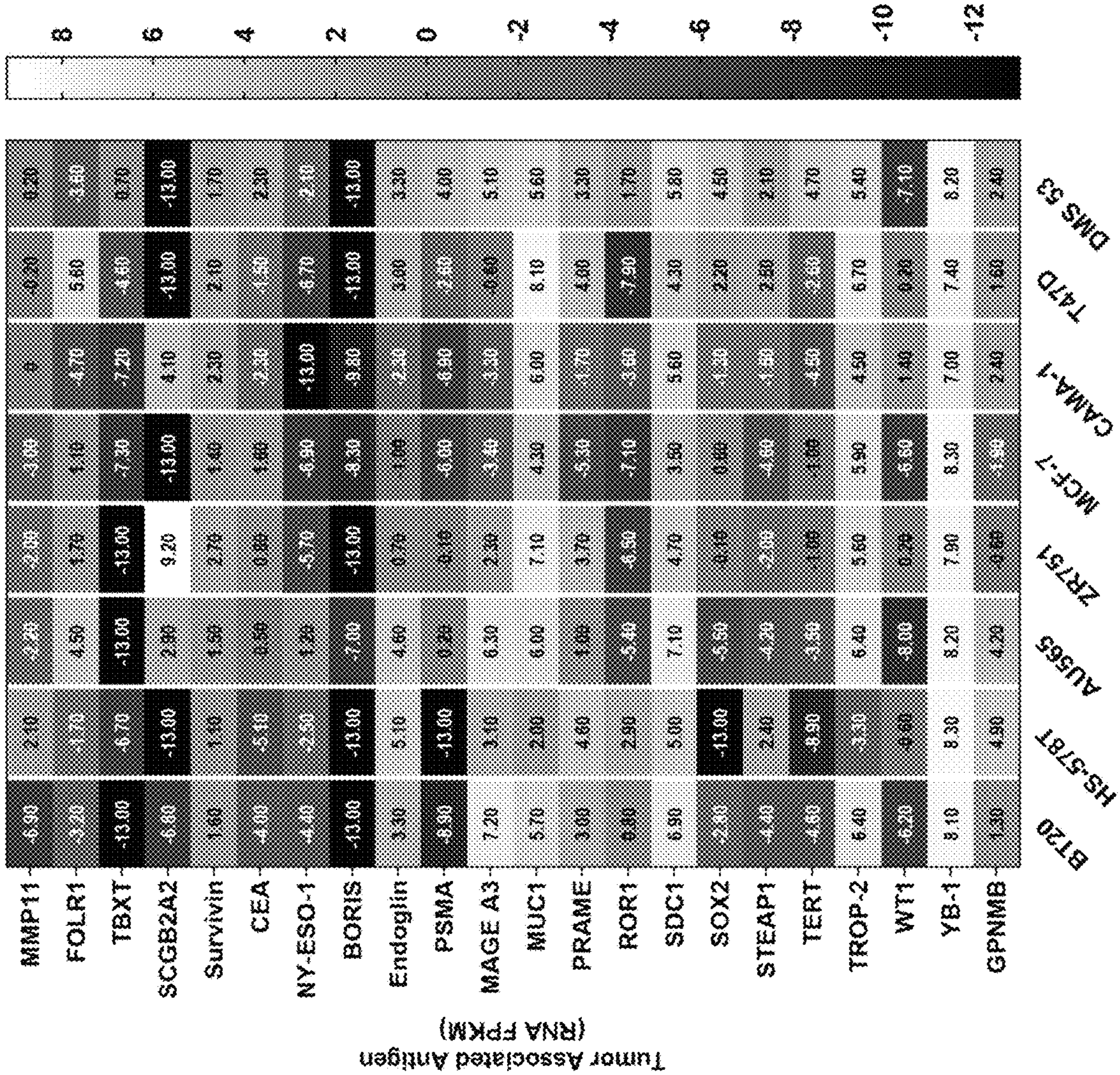

FIGS. 121A and B show endogenous expression of breast cancer antigens (FIG. 121A) and breast cancer CSC-like markers (FIG. 121B) by candidate breast cancer vaccine component cell lines.

FIGS. 122A-D show IFNγ responses elicited by individual BRC candidate vaccine cell lines alone (FIG. 122A and FIG. 122C) and in cocktails (FIG. 122B, FIG. 122C, and FIG. 122D).

Figure 123A:
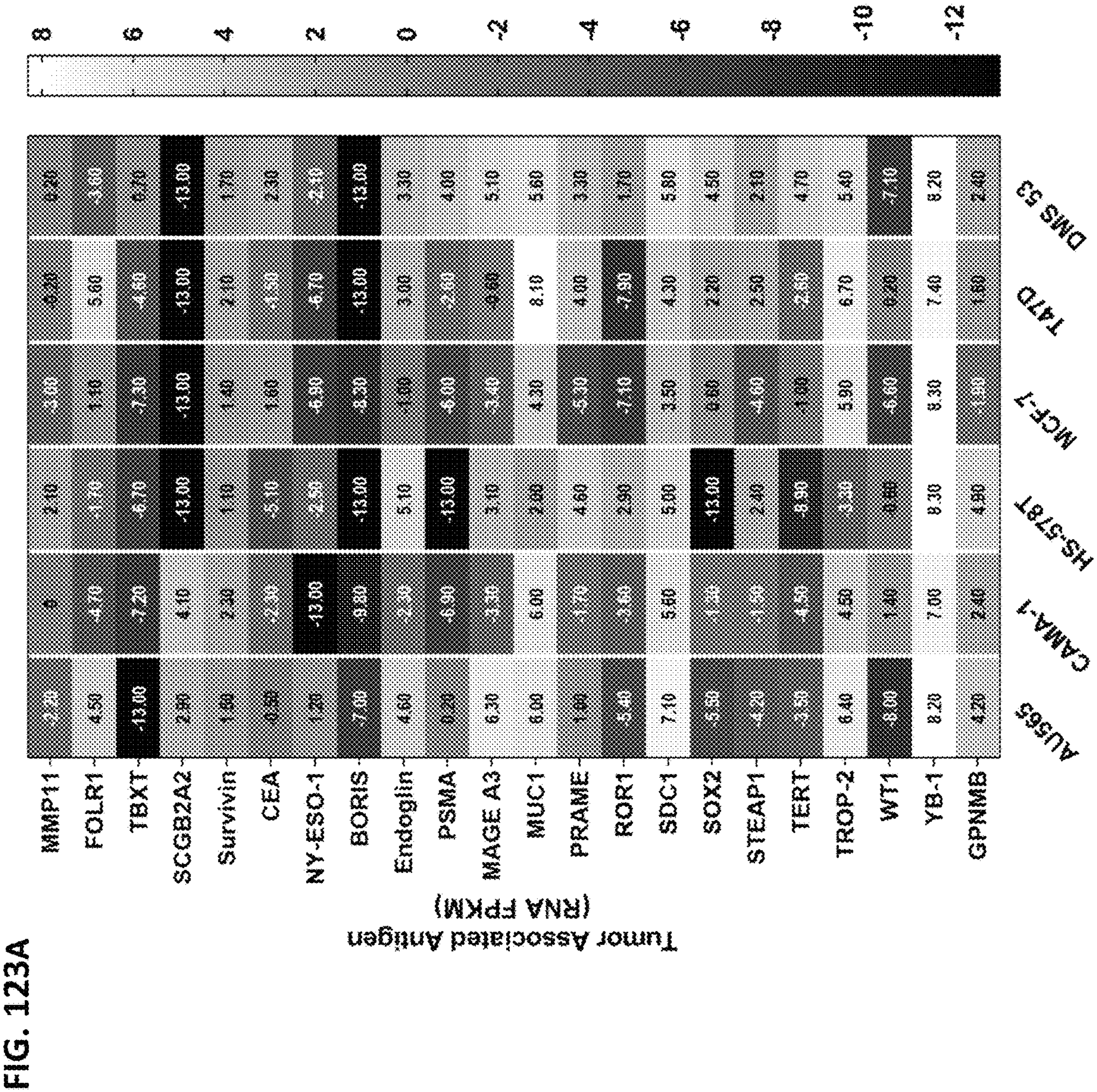
Figure 123B:
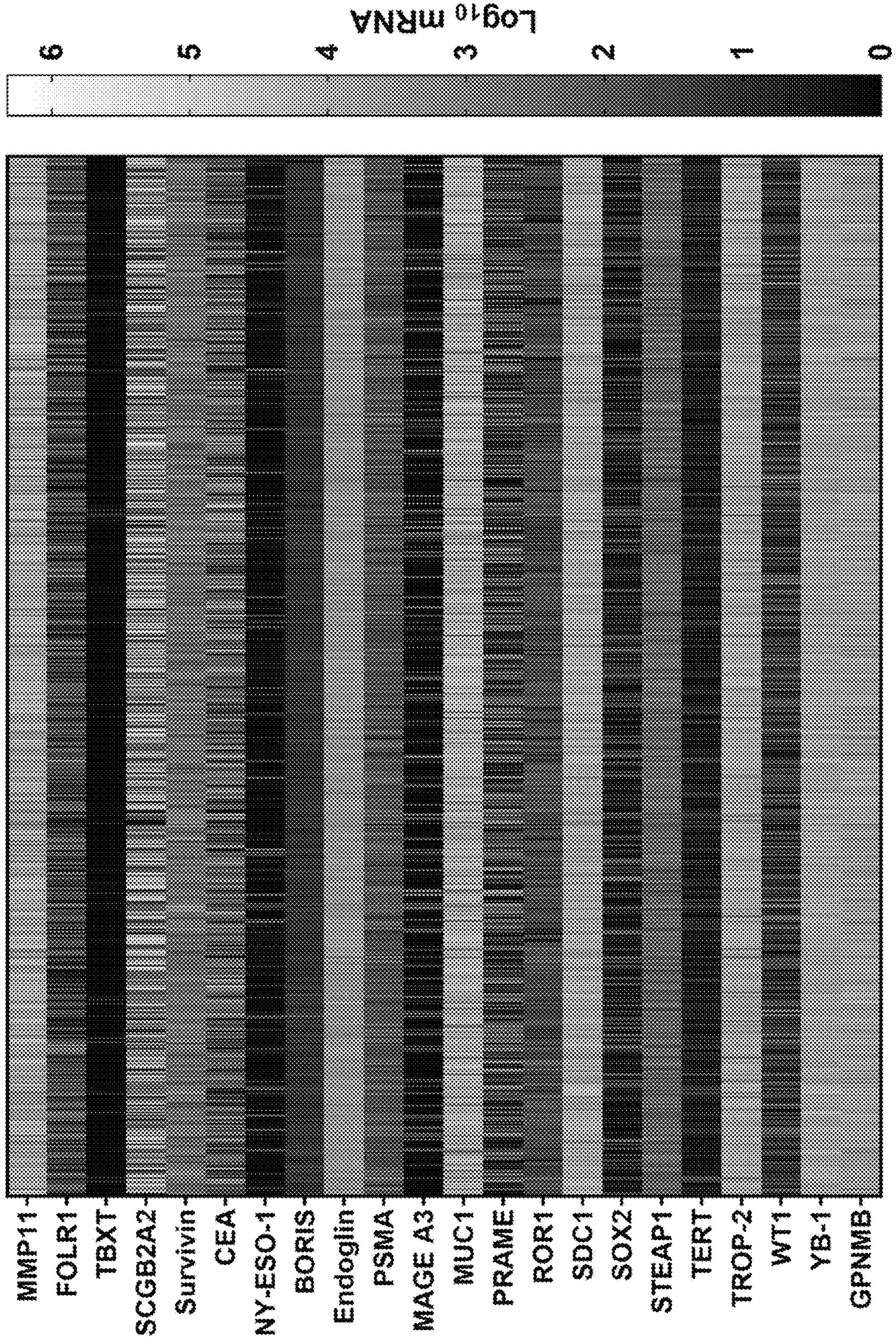
Figure 123C:
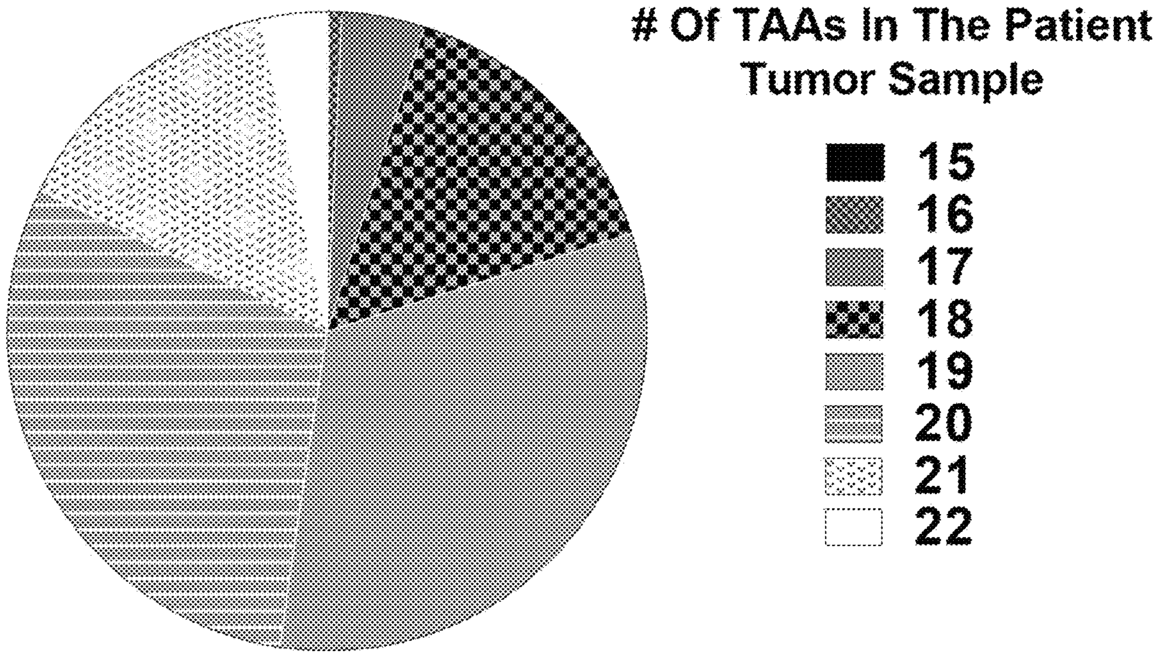

FIGS. 123A-C show endogenous antigen expression by selected BRC vaccine component cell lines (FIG. 123A) expression of these antigens in patient tumors (FIG. 123B) and breast cancer patient tumors (FIG. 123C).

Figure 124A:
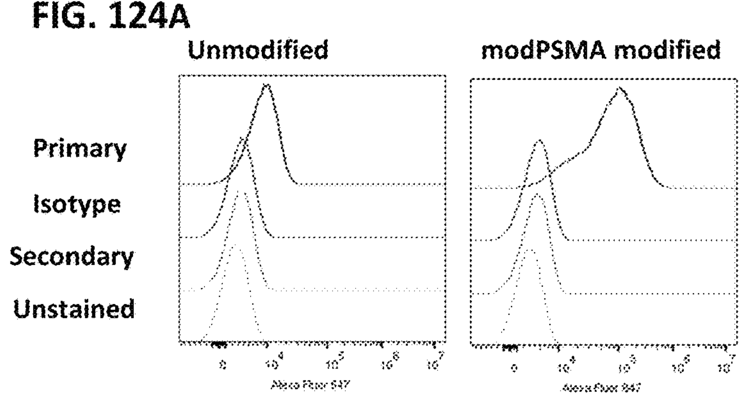

FIGS. 124A-H show expression of modPSMA by CAMA-1 (FIG. 124A) and IFNγ responses to PSMA (FIG. 124E), show expression of modTERT by AU565 (FIG. 124B) and IFNγ responses to TERT (FIG. 124F), and show expression of modTBXT (FIG. 124C) and ModBORIS (FIG. 124D) by T47D and IFNγ responses to TBXT (FIG. 124G) and BORIS (FIG. 124H).

Figure 125:
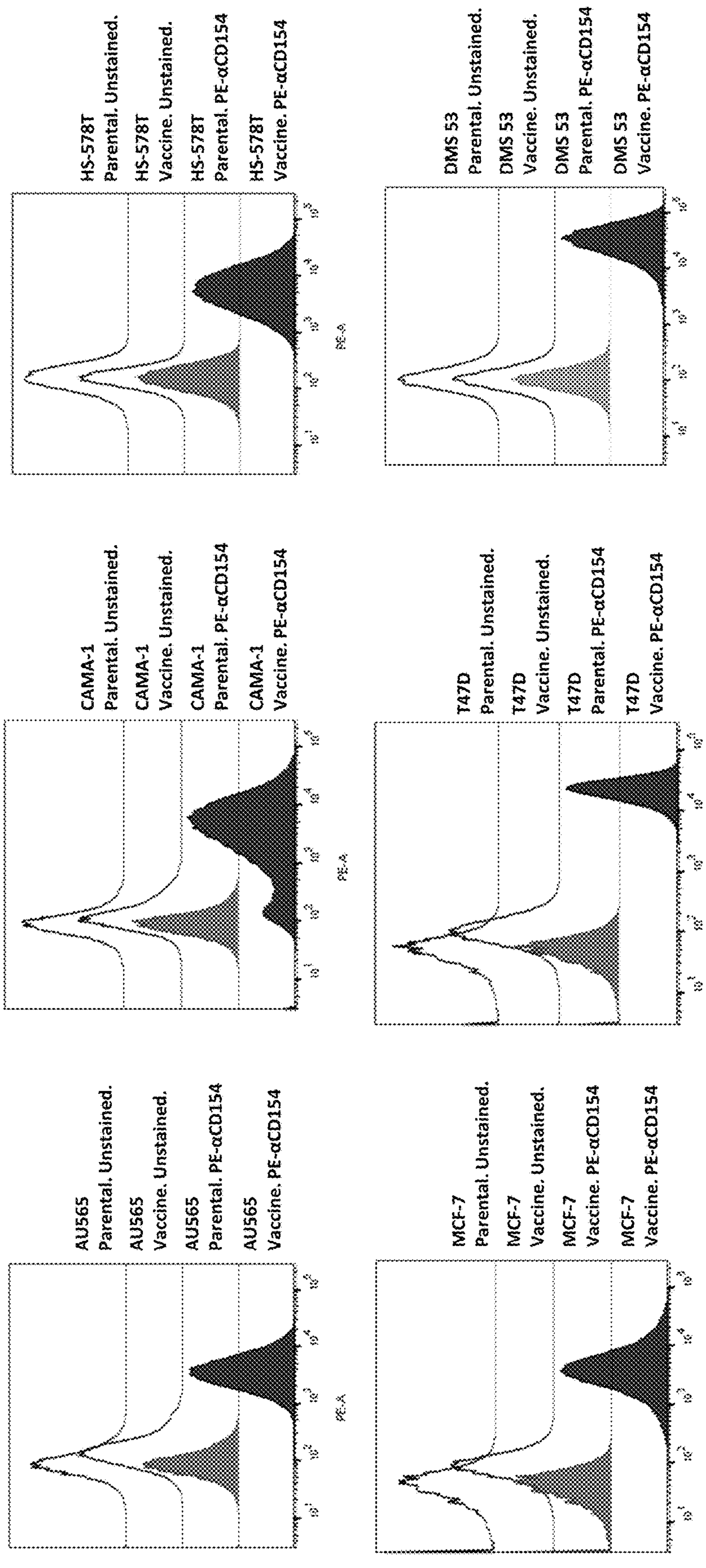

FIG. 125 shows expression of membrane bound CD40L by the BRC vaccine component cell lines.

Figure 126C:
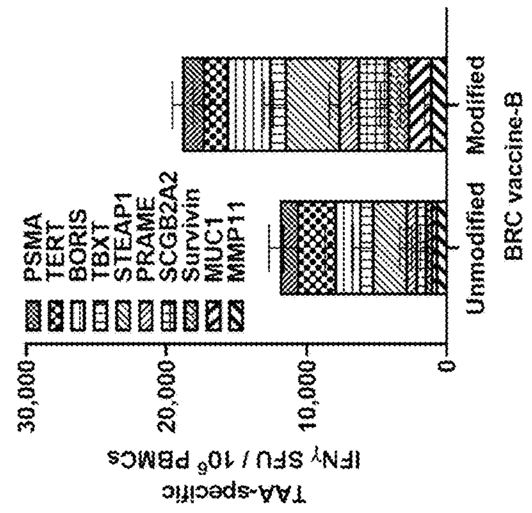
Figure 126B:
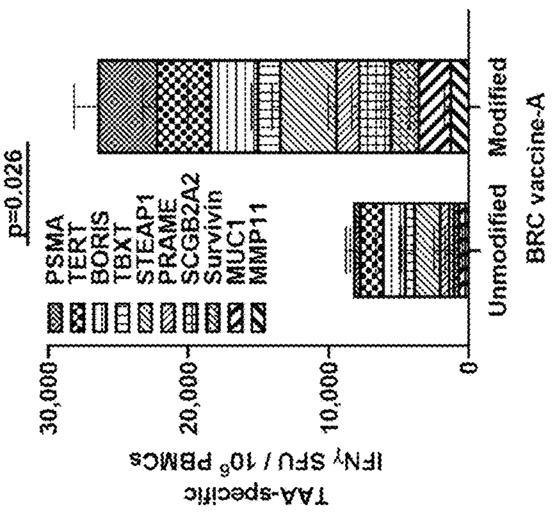
Figure 126A:
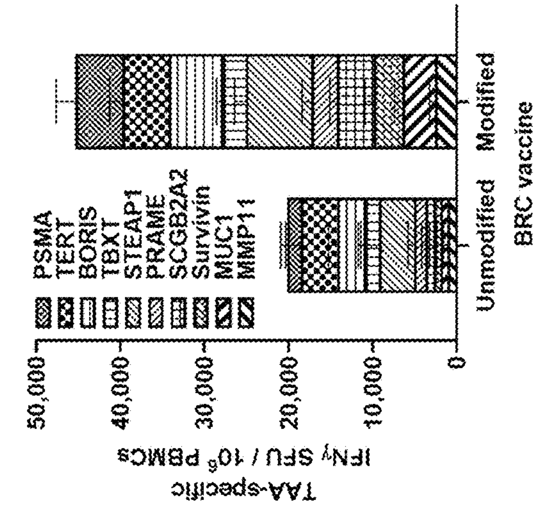

FIGS. 126A-C show antigen specific IFNγ responses induced by the unit dose of the BRC vaccine (FIG. 126A), BRC vaccine-A (FIG. 126B) and BRC vaccine-B (FIG. 126C) compared to unmodified controls.

Figure 127:
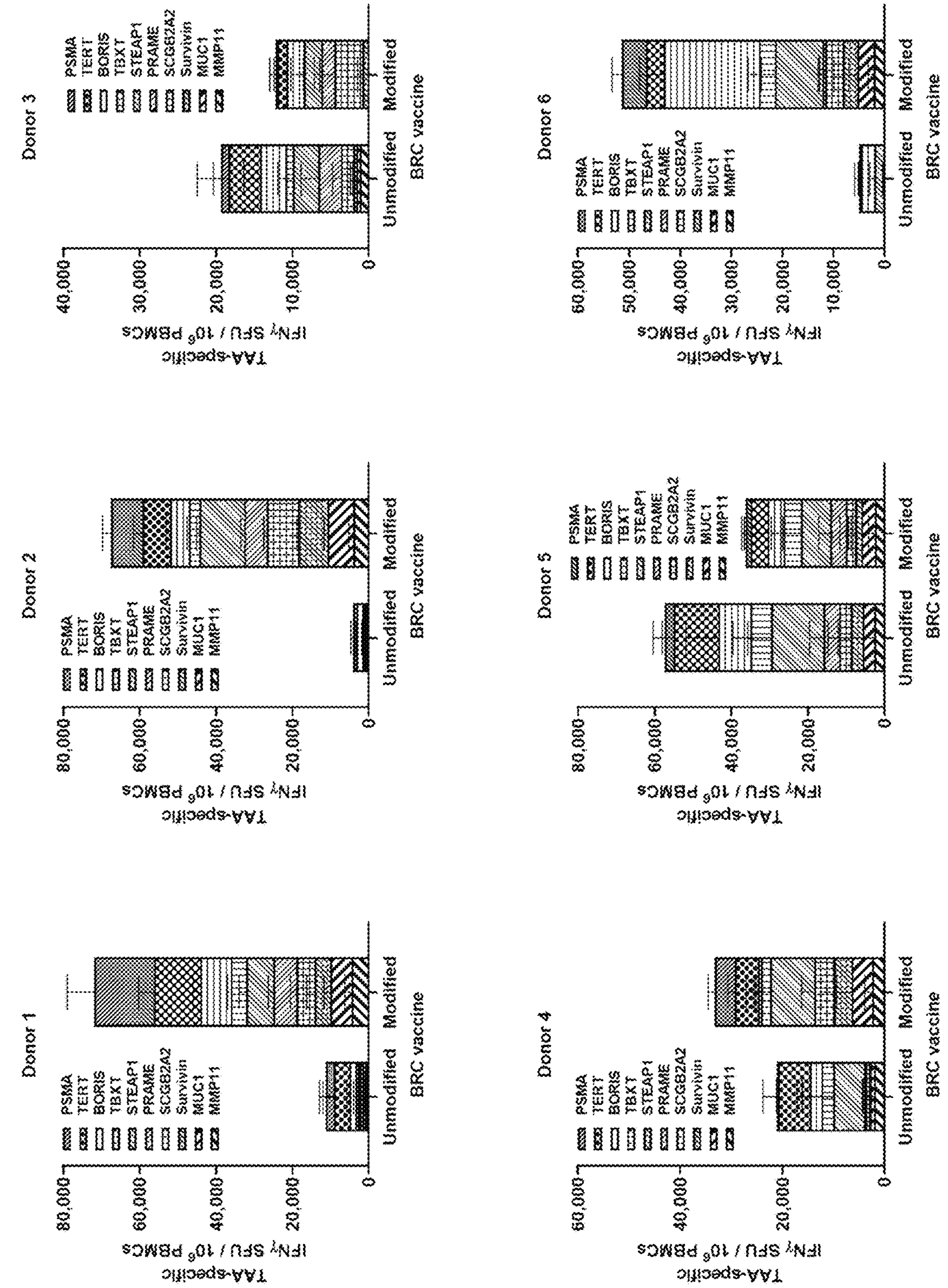

FIG. 127 shows antigen specific IFNγ responses induced by the unit dose of the BRC vaccine in individual donors compare to unmodified controls.

FIGS. 128A-D show BRC vaccine-A (FIG. 128A and FIG. 128C) and BRC vaccine-B (FIG. 128B and FIG. 128D) compositions induce a greater breadth and magnitude of antigen specific responses compared to single component cell lines.

FIG. 129 shows the sequence alignment between human native PSMA (huPSMA; SEQ ID NO: 70) and the designed PSMA with non-synonymous mutations (NSMs) (PSMAmod; SEQ ID NO: 38).

Figure 130A:
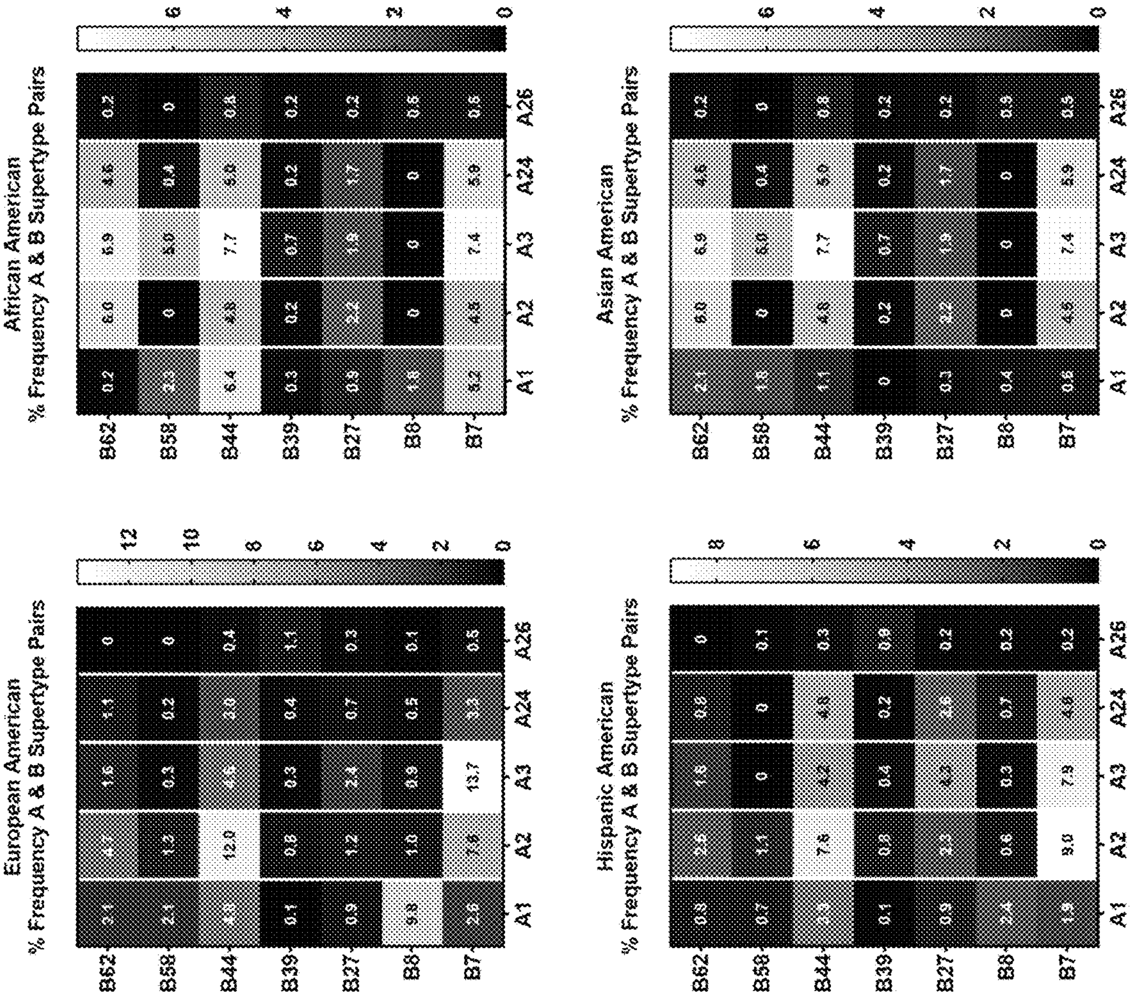

FIG. 130A-C shows HLA supertype frequency pairs in a population.

Figure 131:
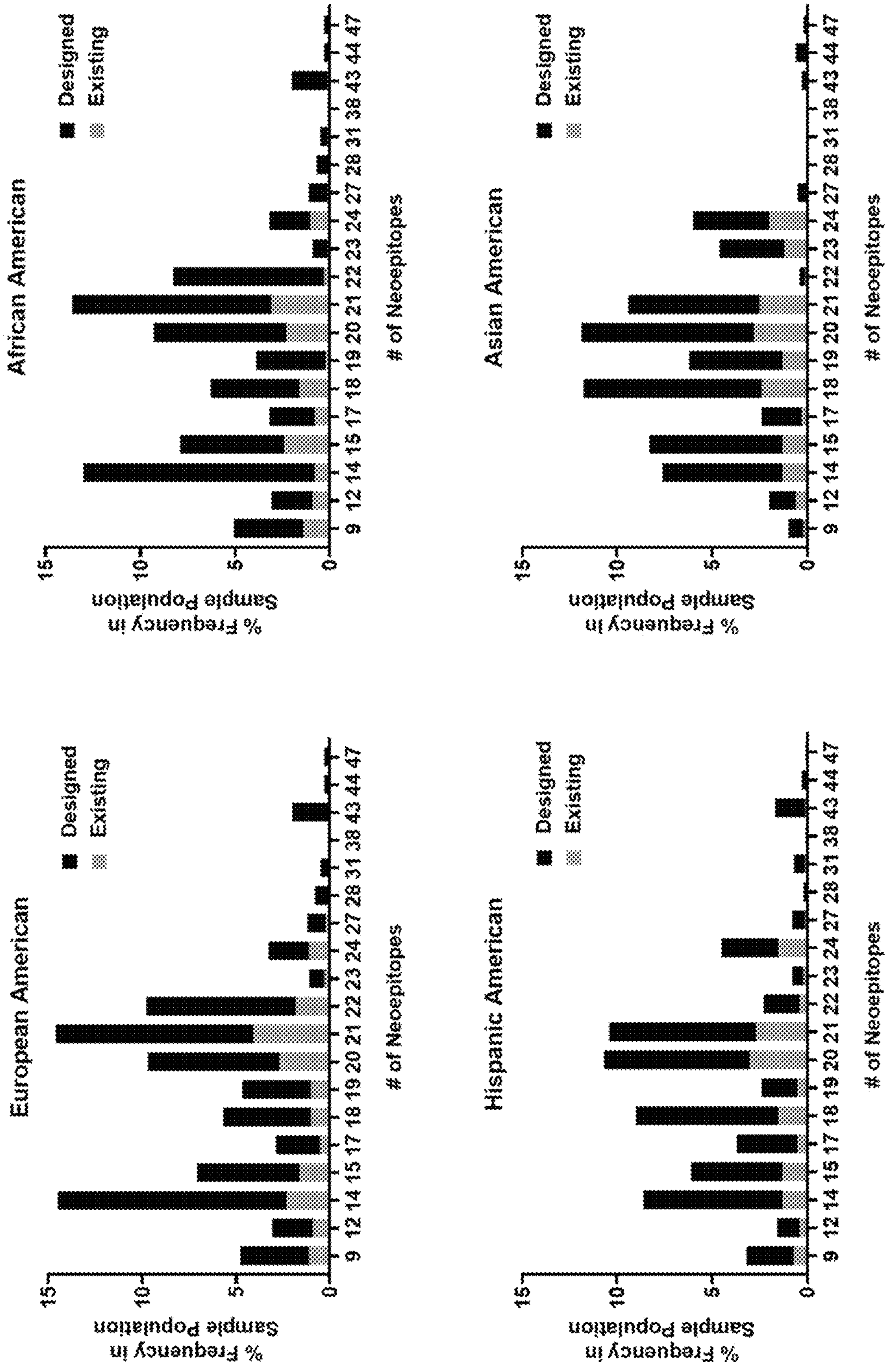

FIG. 131 shows the number of neoepitopes existing in the cell lines of a vaccine composition and designed neoepitopes in GBM recognized by donors expressing HLA-A and HLA-B supertype pairs within the population subsets described in FIG. 131.

Figure 132:
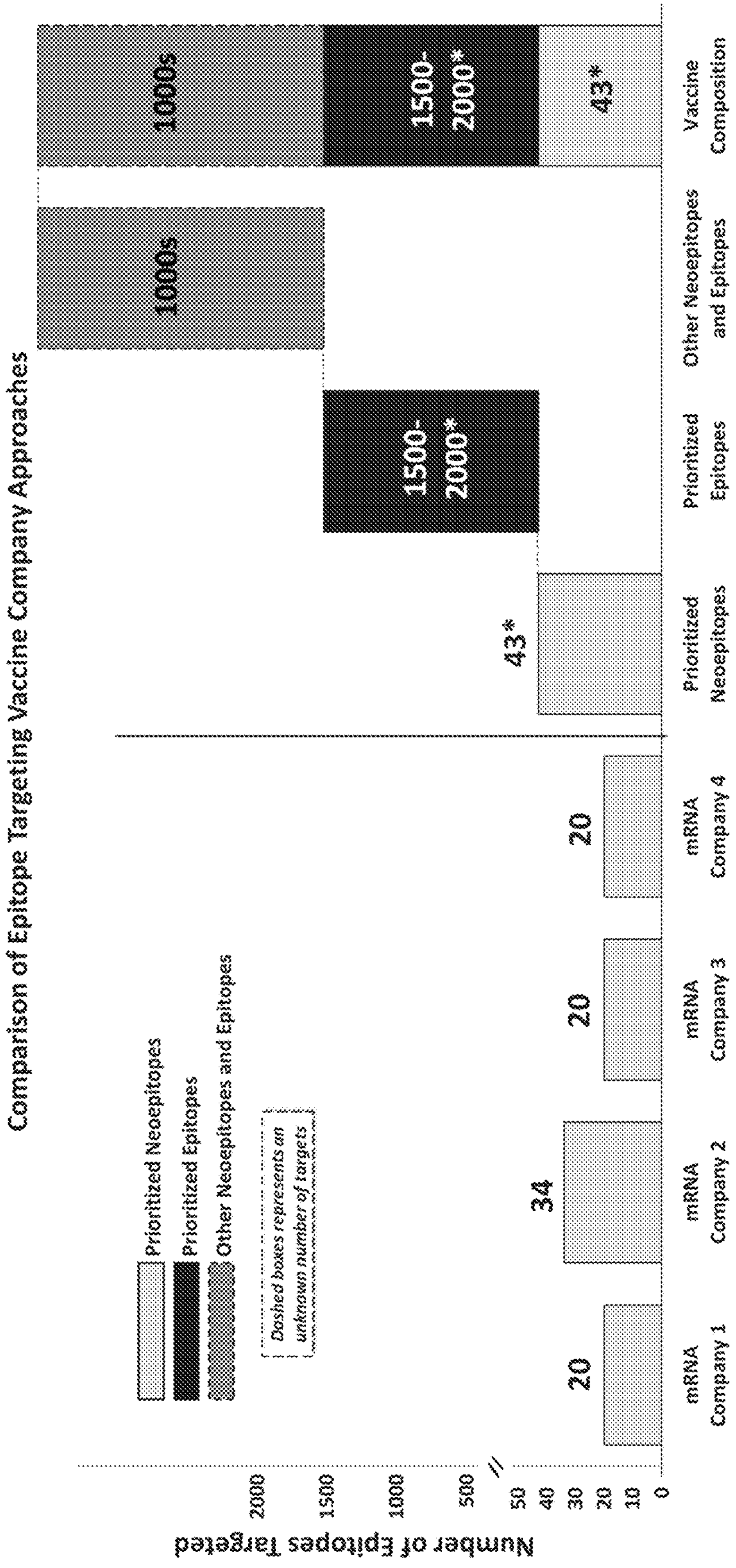

FIG. 132 shows the number of neoepitopes targeted by four different mRNA immunotherapies.

DETAILED DESCRIPTION

Embodiments of the present disclosure provide a platform approach to cancer vaccination that provides both breadth, in terms of the types of cancer amenable to treatment by the compositions, methods, and regimens disclosed, and magnitude, in terms of the immune responses elicited by the compositions, methods, and regimens disclosed.

In various embodiments of the present disclosure, intradermal injection of an allogenic whole cancer cell vaccine induces a localized inflammatory response recruiting immune cells to the injection site. Without being bound to any theory or mechanism, following administration of the vaccine, antigen presenting cells (APCs) that are present locally in the skin (vaccine microenvironment, VME), such as Langerhans cells (LCs) and dermal dendritic cells (DCs), uptake vaccine cell components by phagocytosis and then migrate through the dermis to a draining lymph node. At the draining lymph node, DCs or LCs that have phagocytized the vaccine cell line components can prime naïve T cells and B cells. Priming of naïve T and B cells initiates an adaptive immune response to tumor associated antigens (TAAs) expressed by the vaccine cell lines. In some embodiments of the present disclosure, the priming occurs in vivo and not in vitro or ex vivo. In embodiments of the vaccine compositions provided herein, the multitude of TAAs expressed by the vaccine cell lines are also expressed a subject's tumor. Expansion of antigen specific T cells at the draining lymph node and the trafficking of these T cells to the tumor microenvironment (TME) can initiate a vaccine-induced anti-tumor response.

Immunogenicity of an allogenic vaccine can be enhanced through genetic modifications of the cell lines comprising the vaccine composition to introduce TAAs (native/wild-type or designed/mutated as described herein). Immunogenicity of an allogenic vaccine can be further enhanced through genetic modifications of the cell lines comprising the vaccine composition to reduce expression of immunosuppressive factors and/or increase the expression or secretion of immunostimulatory signals. Modulation of these factors can enhance the uptake of vaccine cell components by LCs and DCs in the dermis, facilitate the trafficking of DCs and LCs to the draining lymph node, and enhance effector T cell and B cell priming in the draining lymph node, thereby providing more potent anti-tumor responses.

In various embodiments, the present disclosure provides an allogeneic whole cell cancer vaccine platform that includes compositions and methods for treating cancer, and/or preventing cancer, and/or stimulating an immune response. Criteria and methods according to embodiments of the present disclosure include without limitation: (i) criteria and methods for cell line selection for inclusion in a vaccine composition, (ii) criteria and methods for combining multiple cell lines into a therapeutic vaccine composition, (iii) criteria and methods for making cell line modifications, and (iv) criteria and methods for administering therapeutic compositions with and without additional therapeutic agents. In some embodiments, the present disclosure provides an allogeneic whole cell cancer vaccine platform that includes, without limitation, administration of multiple cocktails comprising combinations of cell lines that together comprise one unit dose, wherein unit doses are strategically administered over time, and additionally optionally includes administration of other therapeutic agents such as cyclophosphamide and additionally optionally a checkpoint inhibitor.

The present disclosure provides, in some embodiments, compositions and methods for tailoring a treatment regimen for a subject based on the subject's tumor type. In some embodiments, the present disclosure provides a cancer vaccine platform whereby allogeneic cell line(s) are identified and optionally modified and administered to a subject. In various embodiments, the tumor origin (primary site) of the cell line(s), the amount and number of TAAs expressed by the cell line(s), the number of cell line modifications, and the number of cell lines included in a unit dose are each customized based on the subject's tumor type, stage of cancer, and other considerations As described herein, the tumor origin of the cell lines may be the same or different than the tumor intended to be treated. In some embodiments, the cancer cell lines may be cancer stem cell lines.

Definitions

In this disclosure, "comprises", "comprising", "containing", "having", and the like have the meaning ascribed to them in U.S. patent law and mean "includes", "including", and the like; the terms "consisting essentially of" or "consists essentially" likewise have the meaning ascribed in U.S. patent law and these terms are open-ended, allowing for the presence of more than that which is recited so long as basic or novel characteristics of that which is recited are not changed by the presence of more than that which is recited, but excluding prior art embodiments.

Unless specifically otherwise stated or obvious from context, as used herein, the terms "a", "an", and "the" are understood to be singular or plural.

The terms "cell", "cell line", "cancer cell line", "tumor cell line", and the like as used interchangeably herein refers to a cell line that originated from a cancerous tumor as described herein, and/or originates from a parental cell line of a tumor originating from a specific source/organ/tissue. In some embodiments the cancer cell line is a cancer stem cell line as described herein. In certain embodiments, the cancer cell line is known to express or does express multiple tumor-associated antigens (TAAs) and/or tumor specific antigens (TSAs). In some embodiments of the disclosure, a cancer cell line is modified to express, or increase expression of, one or more TAAs. In certain embodiments, the cancer cell line includes a cell line following any number of cell passages, any variation in growth media or conditions, introduction of a modification that can change the characteristics of the cell line such as, for example, human telomerase reverse transcriptase (hTERT) immortalization, use of xenografting techniques including serial passage through xenogenic models such as, for example, patient-derived xenograft (PDX) or next generation sequencing (NGS) mice, and/or co-culture with one or more other cell lines to provide a mixed population of cell lines. As used herein, the term "cell line" includes all cell lines identified as having any overlap in profile or segment, as determined, in some embodiments, by Short Tandem Repeat (STR) sequencing, or as otherwise determined by one of skill in the art. As used herein, the term "cell line" also encompasses any genetically homogeneous cell lines, in that the cells that make up the cell line(s) are clonally derived from a single cell such that they are genetically identical. This can be accomplished, for example, by limiting dilution subcloning of a heterogeneous cell line. The term "cell line" also encompasses any genetically heterogeneous cell line, in that the cells that make up the cell line(s) are not expected to be genetically identical and contain multiple subpopulations of cancer cells. Various examples of cell lines are described herein. Unless otherwise specifically stated, the term "cell line" or "cancer cell line" encompasses the plural "cell lines."

As used herein, the term "tumor" refers to an accumulation or mass of abnormal cells. Tumors may be benign (non-cancerous), premalignant (pre-cancerous, including hyperplasia, atypia, metaplasia, dysplasia and carcinoma in situ), or malignant (cancerous). It is well known that tumors may be "hot" or "cold". Byway of example, melanoma and lung cancer, among others, demonstrate relatively high response rates to checkpoint inhibitors and are commonly referred to as "hot" tumors. These are in sharp contrast to tumors with low immune infiltrates called "cold" tumors or non-T-cell-inflamed cancers, such as those from the prostate, pancreas, glioblastoma, and bladder, among others. In some embodiments, the compositions and methods provided herein are useful to treat or prevent cancers with associated hot tumors. In some embodiments, the compositions and methods provided herein are useful to treat or prevent cancers with cold tumors. Embodiments of the vaccine compositions of the present disclosure can be used to convert cold (i.e., treatment-resistant or refractory) cancers or tumors to hot (i.e., amenable to treatment, including a checkpoint inhibition-based treatment) cancers or tumors. Immune responses against cold tumors are dampened because of the lack of neoepitopes associated with low mutational burden. In various embodiments, the compositions described herein comprise a multitude of potential neoepitopes arising from point-mutations that can generate a multitude of exogenous antigenic epitopes. In this way, the patients' immune system can recognize these epitopes as non-self, subsequently break self-tolerance, and mount an anti-tumor response to a cold tumor, including induction of an adaptive immune response to wide breadth of antigens (See Leko, V. et al. J Immunol (2019)).

Cancer stem cells are responsible for initiating tumor development, cell proliferation, and metastasis and are key components of relapse following chemotherapy and radiation therapy. In certain embodiments, a cancer stem cell line or a cell line that displays cancer stem cell characteristics is included in one or more of the vaccine compositions. As used herein, the phrase "cancer stem cell" (CSC) or "cancer stem cell line" refers to a cell or cell line within a tumor that possesses the capacity to self-renew and to cause the heterogeneous lineages of cancer cells that comprise the tumor. CSCs are highly resistant to traditional cancer therapies and are hypothesized to be the leading driver of metastasis and tumor recurrence. To clarify, a cell line that displays cancer stem cell characteristics is included within the definition of a "cancer stem cell". Exemplary cancer stem cell markers identified by primary tumor site are provided in Table 2 and described herein. Cell lines expressing one or more of these markers are encompassed by the definition of "cancer stem cell line". Exemplary cancer stem cell lines are described herein, each of which are encompassed by the definition of "cancer stem cell line".

As used herein, the phrase "each cell line or a combination of cell lines" refers to, where multiple cell lines are provided in a combination, 1, 2, 3, 4, 5, 6, 7, 8, 9, 10 or more or the combination of the cell lines. As used herein, the phrase "each cell line or a combination of cell lines have been modified" refers to, where multiple cell lines are provided in combination, modification of one, some, or all cell lines, and also refers to the possibility that not all of the cell lines included in the combination have been modified. By way of example, the phrase "a composition comprising a therapeutically effective amount of at least 2 cancer cell lines, wherein each cell line or a combination of the cell lines comprises cells that have been modified . . . " means that each of the two cell lines has been modified or one of the two cell lines has been modified. By way of another example, the phrase "a composition comprising a therapeutically effective amount of at least 3 cancer cell lines, wherein each cell line or a combination of the cell lines comprises cells that have been modified . . . " means that each (i.e., all three) of the cell lines have been modified or that one or two of the three cell lines have been modified.

The term "oncogene" as used herein refers to a gene involved in tumorigenesis. An oncogene is a mutated gene that contributes to the development of a cancer. In their normal, unmutated state, oncogenes are called proto-oncogenes, and they play roles in the regulation of cell division.

As used herein, the phrase "identifying one or more . . . mutations," for example in the process for preparing compositions useful for stimulating an immune response or treating cancer as described herein, refers to newly identifying, identifying within a database or dataset or otherwise using a series of criteria or one or more components thereof as described herein and, optionally, selecting the oncogene or mutation for use or inclusion in a vaccine composition as described herein.

The phrase " . . . cells that express at least [ ] tumor associated antigens (TAAs) associated with a cancer of a subject intended to receive said composition . . . " as used herein refers to cells that express, either natively or by way of genetic modification, the designated number of TAAs and wherein said same TAAs are expressed or known to be expressed by cells of a patient's tumor. The expression of specific TAAs by cells of a patient's tumor may be determined by assay, surgical procedures (e.g., biopsy), or other methods known in the art. In other embodiments, a clinician may consult the Cancer Cell Line Encyclopedia (CCLE) and other known resources to identify a list of TAAs known to be expressed by cells of a particular tumor type.

As used herein, the phrase " . . . that is either not expressed or minimally expressed . . . " means that the referenced gene or protein (e.g., a TAA or an immunosuppressive protein or an immunostimulatory protein) is not expressed by a cell line or is expressed at a low level, where such level is inconsequential to or has a limited impact on immunogenicity. For example, it is readily appreciated in the art that a TAA may be present or expressed in a cell line in an amount insufficient to have a desired impact on the therapeutic effect of a vaccine composition including said cell line. In such a scenario, the present disclosure provides compositions and methods to increase expression of such a TAA.

As used herein, the term "equal" generally means the same value+/−10%. In some embodiments, a measurement, such as number of cells, etc., can be +/−1, 2, 3, 4, 5, 6, 7, 8, 9, or 10%. Similarly, as used herein and as related to amino acid position or nucleotide position, the term "approximately" refers to within 1, 2, 3, 4, or 5 such residues. With respect to the number of cells, the term "approximately" refers to +/−1, 2, 3, 4, 5, 6, 7, 8, 9, or 10%.

As used herein, the phrase " . . . wherein said composition is capable of stimulating a 1.3-fold increase in IFNγ production compared to unmodified cancer cell lines . . . " means, when compared to a composition of the same cell line or cell lines that has/have not been modified, the composition comprising a modified cell line or modified cell lines is capable of stimulating at least 1.3-fold more IFNγ production. In this example, "at least 1.3" means 1.3, 1.4, 1.5, etc., or higher. This definition is used herein with respect to other values of IFNγ production, including, but not limited to, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 4.0, or 5.0-fold or higher increase in IFNγ production compared to unmodified cancer cell lines (e.g., a modified cell line compared to an modified cell line, a composition of 2 or 3 modified cell lines (e.g., a vaccine composition) compared cell lines to the same composition comprising unmodified cell lines, or a unit dose comprising 6 modified cell lines compared to the same unit dose comprising unmodified cell lines). In other embodiments, the IFNγ production is increased by approximately 1, 2, 3, 4, 5, 6, 7, 8, 9, 10, 11, 12, 13, 14, 15, 16, 17, 18, 19, 20, 21, 22, 23, 24, or 25-fold or higher compared to unmodified cancer cell lines. Similarly, in various embodiments, the present disclosure provides compositions of modified cells or cell lines that are compared to unmodified cells or cell lines on the basis of TAA expression, immunostimulatory factor expression, immunosuppressive factor expression, and/or immune response stimulation using the methods provided herein and the methods known in the art including, but not limited to, ELISA, IFNγ ELISpot, and flow cytometry.

As used herein, the phrase "fold increase" refers to the change in units of expression or units of response relative to a control. By way of example, ELISA fold change refers to the level of secreted protein detected for the modified cell line divided by the level of secreted protein detected, or the lower limit of detection, by the unmodified cell line. In another example, fold change in expression of an antigen by flow cytometry refers to the mean fluorescence intensity (MFI) of expression of the protein by a modified cell line divided by the MFI of the protein expression by the unmodified cell line. IFNγ ELISpot fold change refers to the average IFNγ spot-forming units (SFU) induced across HLA diverse donors by the test variable divided by the average IFNγ SFU induced by the control variable. For example, the average total antigen specific IFNγ SFU across donors by a composition of three modified cell lines divided by the IFNγ SFU across the same donors by a composition of the same three unmodified cell lines.

In some embodiments, the fold increase in IFNγ production will increase as the number of modifications (e.g., the number of immunostimulatory factors and the number of immunosuppressive factors) is increased in each cell line. In some embodiments, the fold increase in IFNγ production will increase as the number of cell lines (and thus, the number of TAAs), whether modified or unmodified, is increased. The fold increase in IFNγ production, in some embodiments, is therefore attributed to the number of TAAs and the number of modifications.

As used herein, the term "modified" means genetically modified to express, overexpress, increase, decrease, or inhibit the expression of one or more protein or nucleic acid. As described herein, exemplary proteins include, but are not limited to immunostimulatory factors. Exemplary nucleic acids include sequences that can be used to knockdown (KD) (i.e., decrease expression of) or knockout (KO) (i.e., completely inhibit expression of) immunosuppressive factors. As used herein, the term "decrease" is synonymous with "reduce" or "partial reduction" and may be used in association with gene knockdown. Likewise, the term "inhibit" is synonymous with "complete reduction" and may be used in the context of a gene knockout to describe the complete excision of a gene from a cell.

Unless specifically stated or obvious from context, as used herein, the term "or" is understood to be inclusive.

As used herein, the terms "patient", "subject", "recipient", and the like are used interchangeably herein to refer to any mammal, including humans, non-human primates, domestic and farm animals, and other animals, including, but not limited to dogs, horses, cats, cattle, sheep, pigs, mice, rats, and goats. Exemplary subjects are humans, including adults, children, and the elderly. In some embodiments, the subject can be a donor.

The terms "treat", "treating", "treatment", and the like, as used herein, unless otherwise indicated, refers to reversing, alleviating, inhibiting the process of disease, disorder or condition to which such term applies, or one or more symptoms of such disease, disorder or condition and includes the administration of any of the compositions, pharmaceutical compositions, or dosage forms described herein, to prevent the onset of the symptoms or the complications, alleviate the symptoms or the complications, or eliminate the disease, condition, or disorder. As used herein, treatment can be curative or ameliorating.

As used herein, "preventing" means preventing in whole or in part, controlling, reducing, or halting the production or occurrence of the thing or event to which such term applies, for example, a disease, disorder, or condition to be prevented.

Embodiments of the methods and compositions provided herein are useful for preventing a tumor or cancer, meaning the occurrence of the tumor is prevented or the onset of the tumor is significantly delayed. In some embodiments, the methods and compositions are useful for treating a tumor or cancer, meaning that tumor growth is significantly inhibited as demonstrated by various techniques well-known in the art such as, for example, by a reduction in tumor volume. Tumor volume may be determined by various known procedures, (e.g., obtaining two dimensional measurements with a dial caliper). Preventing and/or treating a tumor can result in the prolonged survival of the subject being treated.

As used herein, the term "stimulating", with respect to an immune response, is synonymous with "promoting", "generating", and "eliciting" and refers to the production of one or more indicators of an immune response. Indicators of an immune response are described herein. Immune responses may be determined and measured according to the assays described herein and by methods well-known in the art.

The phrases "therapeutically effective amount", "effective amount", "immunologically effective amount", "anti-tumor effective amount", and the like, as used herein, indicate an amount necessary to administer to a subject, or to a cell, tissue, or organ of a subject, to achieve a therapeutic effect, such as an ameliorating or a curative effect. The therapeutically effective amount is sufficient to elicit the biological or medical response of a cell, tissue, system, animal, or human that is being sought by a researcher, veterinarian, medical doctor, clinician, or healthcare provider. For example, a therapeutically effective amount of a composition is an amount of cell lines, whether modified or unmodified, sufficient to stimulate an immune response as described herein. In certain embodiments, a therapeutically effective amount of a composition is an amount of cell lines, whether modified or unmodified, sufficient to inhibit the growth of a tumor as described herein. Determination of the effective amount or therapeutically effective amount is, in certain embodiments, based on publications, data or other information such as, for example, dosing regimens and/or the experience of the clinician.

The terms "administering", "administer", "administration", and the like, as used herein, refer to any mode of transferring, delivering, introducing, or transporting a therapeutic agent to a subject in need of treatment with such an agent. Such modes include, but are not limited to, oral, topical, intravenous, intraarterial, intraperitoneal, intramuscular, intratumoral, intradermal, intranasal, and subcutaneous administration.

As used herein, the term "vaccine composition" refers to any of the vaccine compositions described herein containing one or more (e.g., 2, 3, 4, 5, 6, 7, 8, 9, 10, or more) cell lines. As described herein, one or more of the cell lines in the vaccine composition may be modified. In certain embodiments, one or more of the cell lines in the vaccine composition may not be modified. The terms "vaccine", "tumor cell vaccine", "cancer vaccine", "cancer cell vaccine", "whole cancer cell vaccine", "vaccine composition", "composition", "cocktail", "vaccine cocktail", and the like are used interchangeably herein. In some embodiments, the vaccine compositions described herein are useful to treat or prevent cancer. In some embodiments, the vaccine compositions described herein are useful to stimulate or elicit an immune response. In such embodiments, the term "immunogenic composition" is used. In some embodiments, the vaccine compositions described herein are useful as a component of a therapeutic regimen to increase immunogenicity of said regimen.

The terms "dose" or "unit dose" as used interchangeably herein refer to one or more vaccine compositions that comprise therapeutically effective amounts of one more cell lines. As described herein, a "dose" or "unit dose" of a composition may refer to 1, 2, 3, 4, 5, or more distinct compositions or cocktails. In some embodiments, a unit dose of a composition refers to 2 distinct compositions administered substantially concurrently (i.e., immediate series). In exemplary embodiments, one dose of a vaccine composition comprises 1, 2, 3, 4, 5, 6, 7, 8, 9, or 10 separate vials, where each vial comprises a cell line, and where cell lines, each from a separate vial, are mixed prior to administration. In some embodiments, a dose or unit dose includes 6 vials, each comprising a cell line, where 3 cell lines are mixed and administered at one site, and the other 3 cell lines are mixed and administered at a second site. Subsequent "doses" may be administered similarly. In still other embodiments, administering 2 vaccine cocktails at 2 sites on the body of a subject for a total of 4 concurrent injections is contemplated.

As used herein, the term "cancer" refers to diseases in which abnormal cells divide without control and are able to invade other tissues. Thus, as used herein, the phrase " . . . associated with a cancer of a subject" refers to the expression of tumor associated antigens, neoantigens, or other genotypic or phenotypic properties of a subject's cancer or cancers. TAAs associated with a cancer are TAAs that expressed at detectable levels in a majority of the cells of the cancer. Expression level can be detected and determined by methods described herein. There are more than 100 different types of cancer. Most cancers are named for the organ or type of cell in which they start; for example, cancer that begins in the colon is called colon cancer; cancer that begins in melanocytes of the skin is called melanoma. Cancer types can be grouped into broader categories. In some embodiments, cancers may be grouped as solid (i.e., tumor-forming) cancers and liquid (e.g., cancers of the blood such as leukemia, lymphoma and myeloma) cancers. Other categories of cancer include: carcinoma (meaning a cancer that begins in the skin or in tissues that line or cover internal organs, and its subtypes, including adenocarcinoma, basal cell carcinoma, squamous cell carcinoma, and transitional cell carcinoma); sarcoma (meaning a cancer that begins in bone, cartilage, fat, muscle, blood vessels, or other connective or supportive tissue); leukemia (meaning a cancer that starts in blood-forming tissue (e.g., bone marrow) and causes large numbers of abnormal blood cells to be produced and enter the blood; lymphoma and myeloma (meaning cancers that begin in the cells of the immune system); and central nervous system cancers (meaning cancers that begin in the tissues of the brain and spinal cord). The term myelodysplastic syndrome refers to a type of cancer in which the bone marrow does not make enough healthy blood cells (white blood cells, red blood cells, and platelets) and there are abnormal cells in the blood and/or bone marrow. Myelodysplastic syndrome may become acute myeloid leukemia (AML). By way of non-limiting examples, the compositions and methods described herein are used to treat and/or prevent the cancer described herein, including in various embodiments, lung cancer (e.g., non-small cell lung cancer or small cell lung cancer), prostate cancer, breast cancer, triple negative breast cancer, metastatic breast cancer, ductal carcinoma in situ, invasive breast cancer, inflammatory breast cancer, Paget disease, breast angiosarcoma, phyllodes tumor, testicular cancer, colorectal cancer, bladder cancer, gastric cancer, head and neck cancer, liver cancer, renal cancer, glioma, gliosarcoma, astrocytoma, ovarian cancer, neuroendocrine cancer, pancreatic cancer, esophageal cancer, endometrial cancer, melanoma, mesothelioma, and/or hepatocellular cancers.

Examples of carcinomas include, without limitation, giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma; cholangiocarcinoma; hepatocellular carcinoma; combined hepatocellular carcinoma and cholangiocarcinoma; trabecular adenocarcinoma; adenoid cystic carcinoma; adenocarcinoma in an adenomatous polyp; adenocarcinoma, familial polyposis coli; solid carcinoma; carcinoid tumor; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; non-encapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease; mammary acinar cell carcinoma; adenosquamous carcinoma; adenocarcinoma with squamous metaplasia; sertoli cell carcinoma; embryonal carcinoma; and choriocarcinoma.

Examples of sarcomas include, without limitation, glomangiosarcoma; sarcoma; fibrosarcoma; myxosarcoma; liposarcoma; leiomyosarcoma; rhabdomyosarcoma; embryonal rhabdomyo sarcoma; alveolar rhabdomyo sarcoma; stromal sarcoma; carcinosarcoma; synovial sarcoma; hemangiosarcoma; kaposi's sarcoma; lymphangiosarcoma; osteosarcoma; juxtacortical osteosarcoma; chondrosarcoma; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; myeloid sarcoma; and mast cell sarcoma.

Examples of leukemias include, without limitation, leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; and hairy cell leukemia.

Examples of lymphomas and myelomas include, without limitation, malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant melanoma; amelanotic melanoma; superficial spreading melanoma; malignant melanoma in giant pigmented nevus; epithelioid cell melanoma; and multiple myeloma.

Examples of brain/spinal cord cancers include, without limitation, pinealoma, malignant; chordoma; glioma, gliosarcoma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; and neurilemmoma, malignant.

Examples of other cancers include, without limitation, a thymoma; an ovarian stromal tumor; a thecoma; a granulosa cell tumor; an androblastoma; a leydig cell tumor; a lipid cell tumor; a paraganglioma; an extra-mammary paraganglioma; a pheochromocytoma; blue nevus, malignant; fibrous histiocytoma, malignant; mixed tumor, malignant; mullerian mixed tumor; nephroblastoma; hepatoblastoma; mesenchymoma, malignant; brenner tumor, malignant; phyllodes tumor, malignant; mesothelioma, malignant; dysgerminoma; teratoma, malignant; struma ovarii, malignant; mesonephroma, malignant; hemangioendothelioma, malignant; hemangiopericytoma, malignant; chondroblastoma, malignant; granular cell tumor, malignant; malignant histiocytosis; and immunoproliferative small intestinal disease.

All references, patents, and patent applications disclosed herein are incorporated by reference with respect to the subject matter for which each is cited, which in some cases may encompass the entirety of the document.

Vaccine Compositions

The present disclosure is directed to a platform approach to cancer vaccination that provides breadth, with regard to the scope of cancers and tumor types amenable to treatment with the compositions, methods, and regimens disclosed, as well as magnitude, with regard to the level of immune responses elicited by the compositions and regimens disclosed. Embodiments of the present disclosure provide compositions comprising cancer cell lines. In some embodiments, the cell lines have been modified as described herein.

The compositions of the disclosure are designed to increase immunogenicity and/or stimulate an immune response. For example, in some embodiments, the vaccines provided herein increase IFNγ production and the breadth of immune responses against multiple TAAs (e.g., the vaccines are capable of targeting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more TAAs, indicating the diversity of T cell receptor (TCR) repertoire of these anti-TAA T cell precursors. In some embodiments, the immune response produced by the vaccines provided herein is a response to more than one epitope associated with a given TAA (e.g., the vaccines are capable of targeting 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 epitopes or more on a given TAA), indicating the diversity of TCR repertoire of these anti-TAA T cell precursors.

This can be accomplished in certain embodiments by selecting cell lines that express numerous TAAs associated with the cancer to be treated; knocking down or knocking out expression of one or more immunosuppressive factors that facilitates tumor cell evasion of immune system surveillance; expressing or increasing expression of one or more immunostimulatory factors to increase immune activation within the vaccine microenvironment (VME); increasing expression of one or more tumor-associated antigens (TAAs) to increase the scope of relevant antigenic targets that are presented to the host immune system, optionally where the TAA or TAAs are designed or enhanced (e.g., modified by mutation) and comprise, for example, nonsynonymous mutations (NSMs) and/or neoepitopes; administering a vaccine composition comprising at least 1 cancer stem cell; and/or any combination thereof.

The one or more cell lines of the vaccine composition can be modified to reduce production of more than one immunosuppressive factor (e.g., 2, 3, 4, 5, 6, 7, 8, 9, 10, or more immunosuppressive factors). The one or more cell lines of a vaccine can be modified to increase production of more than one immunostimulatory factor (e.g., 2, 3, 4, 5, 6, 7, 8, 9, 10, or more immunostimulatory factors). The one or more cell lines of the vaccine composition can naturally express, or be modified to express more than one TAA, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more TAAs.

The vaccine compositions can comprise cells from 1, 2, 3, 4, 5, 6, 7, 8, 9, 10, or more cell lines. Further, as described herein, cell lines can be combined or mixed, e.g., prior to administration. In some embodiments, production of one or more immunosuppressive factors from one or more or the combination of the cell lines can be reduced or eliminated. In some embodiments, production of one or more immunostimulatory factors from one or more or the combination of the cell lines can be added or increased. In certain embodiments, the one or more or the combination of the cell lines can be selected to express a heterogeneity of TAAs. In some embodiments, the cell lines can be modified to increase the production of one or more immunostimulatory factors, TAAs, and/or neoantigens. In some embodiments, the cell line selection provides that a heterogeneity of HLA supertypes are represented in the vaccine composition. In some embodiments, the cells lines are chosen for inclusion in a vaccine composition such that a desired complement of TAAs are represented.

In various embodiments, the vaccine composition comprises a therapeutically effective amount of cells from at least one cancer cell line, wherein the cell line or the combination of cell lines expresses more than one of the TAAs of Tables 7-23. In some embodiments, a vaccine composition is provided comprising a therapeutically effective amount of cells from at least two cancer cell lines, wherein each cell line or the combination of cell lines expresses at least three, at least four, at least five, at least six, at least seven, at least eight, at least nine, or at least ten of the TAAs of Tables 7-23. In some embodiments, a vaccine composition is provided comprising a therapeutically effective amount of cells from at least one cancer cell line, wherein the at least one cell line is modified to express at least one of the immunostimulatory factors of Table 4, at least two of the immunostimulatory factors of Table 4, or at least three of the immunostimulatory factors of Table 4. In further embodiments, a vaccine composition is provided comprising a therapeutically effective amount of cells from at least one cancer cell line, wherein each cell line or combination of cell lines is modified to reduce at least one of the immunosuppressive factors of Table 6, or at least two of the immunosuppressive factors of Table 6.

In embodiments where the one or more cell lines are modified to increase the production of one or more TAAs, the expressed TAAs may or may not have the native coding sequence of DNA/protein. That is, expression may be codon optimized or modified. Such optimization or modification may enhance certain effects (e.g., may lead to reduced shedding of a TAA protein from the vaccine cell membrane). As described herein, in some embodiments the expressed TAA protein is a designed antigen comprising one or more nonsynonymous mutations (NSMs) identified in cancer patients. In some embodiments, the NSMs introduces CD4, CD8, or CD4 and CD8 neoepitopes.

Any of the vaccine compositions described herein can be administered to a subject in order to treat cancer, prevent cancer, prolong survival in a subject with cancer, and/or stimulate an immune response in a subject.

Cell Lines

In various embodiments of the disclosure, the cell lines comprising the vaccine compositions and used in the methods described herein originate from parental cancer cell lines.

Cell lines are available from numerous sources as described herein and are readily known in the art. For example, cancer cell lines can be obtained from the American Type Culture Collection (ATCC, Manassas, Va.), Japanese Collection of Research Bioresources cell bank (JCRB, Kansas City, Mo.), Cell Line Service (CLS, Eppelheim, Germany), German Collection of Microorganisms and Cell Cultures (DSMZ, Braunschweig, Germany), RIKEN BioResource Research Center (RCB, Tsukuba, Japan), Korean Cell Line Bank (KCLB, Seoul, South Korea), NIH AIDS Reagent Program (NIH-ARP/Fisher BioServices, Rockland, Md.), Bioresearch Collection and Research Center (BCRC, Hsinchu, Taiwan), Interlab Cell Line Collection (ICLC, Genova, Italy), European Collection of Authenticated Cell Cultures (ECACC, Salisbury, United Kingdom), Kunming Cell Bank (KCB, Yunnan, China), National Cancer Institute Development Therapeutics Program (NCI-DTP, Bethesda, Md.), Rio de Janeiro Cell Bank (BCRJ, Rio de Janeiro, Brazil), Experimental Zooprophylactic Institute of Lombardy and Emilia Romagna (IZSLER, Milan, Italy), Tohoku University cell line catalog (TKG, Miyagi, Japan), and National Cell Bank of Iran (NCBI, Tehran, Iran). In some embodiments, cell lines are identified through an examination of RNA-seq data with respect to TAAs, immunosuppressive factor expression, and/or other information readily available to those skilled in the art.

In various embodiments, the cell lines in the compositions and methods described herein are from parental cell lines of solid tumors originating from the lung, prostate, testis, breast, urinary tract, colon, rectum, stomach, head and neck, liver, kidney, nervous system, endocrine system, mesothelium, ovaries, pancreas, esophagus, uterus or skin. In certain embodiments, the parental cell lines comprise cells of the same or different histology selected from the group consisting of squamous cells, adenocarcinoma cells, adenosquamous cells, large cell cells, small cell cells, sarcoma cells, carcinosarcoma cells, mixed mesodermal cells, and teratocarcinoma cells. In related embodiments, the sarcoma cells comprise osteosarcoma, chondrosarcoma, leiomyosarcoma, rhabdomyosarcoma, mesothelioma, fibrosarcoma, angiosarcoma, liposarcoma, glioma, gliosarcoma, astrocytoma, myxosarcoma, mesenchymous or mixed mesodermal cells.

In certain embodiments, the cell lines comprise cancer cells originating from lung cancer, non-small cell lung cancer (NSCLC), small cell lung cancer (SCLC), prostate cancer, glioblastoma, colorectal cancer, breast cancer including triple negative breast cancer (TNBC), bladder or urinary tract cancer, squamous cell head and neck cancer (SCCHN), liver hepatocellular (HCC) cancer, kidney or renal cell carcinoma (RCC) cancer, gastric or stomach cancer, ovarian cancer, esophageal cancer, testicular cancer, pancreatic cancer, central nervous system cancers, endometrial cancer, melanoma, and mesothelium cancer.

According to various embodiments, the cell lines are allogeneic cell lines (i.e., cells that are genetically dissimilar and hence immunologically incompatible, although from individuals of the same species.) In certain embodiments, the cell lines are genetically heterogeneous allogeneic. In other embodiments, the cell lines are genetically homogeneous allogeneic.

Allogeneic cell-based vaccines differ from autologous vaccines in that they do not contain patient-specific tumor antigens. Embodiments of the allogeneic vaccine compositions disclosed herein comprise laboratory-grown cancer cell lines known to express TAAs of a specific tumor type. Embodiments of the allogeneic cell lines of the present disclosure are strategically selected, sourced, and modified prior to use in a vaccine composition. Vaccine compositions of embodiments of the present disclosure can be readily mass-produced. This efficiency in development, manufacturing, storage, and other areas can result in cost reductions and economic benefits relative to autologous-based therapies.

Tumors are typically made up of a highly heterogeneous population of cancer cells that evolve and change over time. Therefore, it can be hypothesized that a vaccine composition comprising only autologous cell lines that do not target this cancer evolution and progression may be insufficient in the elicitation of a broad immune response required for effective vaccination. As described in embodiments of the vaccine composition disclosed herein, use of one or more strategically selected allogeneic cell lines with certain genetic modification(s) addresses this disparity.

In some embodiments, the allogeneic cell-based vaccines are from cancer cell lines of the same type (e.g., breast, prostate, lung) of the cancer sought to be treated. In other embodiments, various types of cell lines (i.e., cell lines from different primary tumor origins) are combined (e.g., stem cell, prostate, testes). In some embodiments, the cell lines in the vaccine compositions are a mixture of cell lines of the same type of the cancer sought to be treated and cell lines from different primary tumor origins.

Exemplary cancer cell lines, including, but not limited to those provided in Table 1, below, are contemplated for use in the compositions and methods described herein. The Cell Line Sources identified herein are for exemplary purposes only. The cell lines described in various embodiments herein may be available from multiple sources.

TABLE 1

Exemplary vaccine composition cell lines per indication

| Anatomical Site of Primary Tumor | Cell Line Common Name | Cell Line Source | Cell Line Source Identification |
|---|---|---|---|
| Lung (Small Cell and Non-Small Cell) | ABC-1 | JCRB | JCRB0815 |
| | Calu-1 | ATCC | HTB-54 |
| | LOU-NH91 | DSMZ | ACC-393 |
| | NCI-H1581 | ATCC | CRL-5878 |
| | NCI-H1703 | ATCC | CRL-5889 |
| | NCI-H460 | ATCC | HTB-177 |
| | NCI-H520 | ATCC | HTB-182 |
| | A549 | ATCC | CCL-185 |
| | LK-2 | JCRB | JCRB0829 |
| | NCI-H23 | ATCC | CRL-5800 |
| | NCI-H2066 | ATCC | CRL-5917 |
| | NCI-H2009 | ATCC | CRL-5911 |
| | NCI-H2023 | ATCC | CRL-5912 |
| | RERF-LC-Ad1 | JCRB | JCRB1020 |
| | SK-LU-1 | ATCC | HTB-57 |
| | NCI-H2172 | ATCC | CRL-5930 |
| | NCI-H292 | ATCC | CRL-1848 |
| | NCI-H661 | ATCC | HTB-183 |
| | SQ-1 | RCB | RCB1905 |
| | RERF-LC-KJ | JCRB | JCRB0137 |
| | SW900 | ATCC | HTB-59 |
| | NCI-H838 | ATCC | CRL-5844 |
| | NCI-H1693 | ATCC | CRL-5887 |
| | HCC2935 | ATCC | CRL-2869 |
| | NCI-H226 | ATCC | CRL-5826 |
| | HCC4006 | ATCC | CRL-2871 |
| | DMS 53 | ATCC | CRL-2062 |
| | DMS 114 | ATCC | CRL-2066 |

TABLE 1-continued

Exemplary vaccine composition cell lines per indication

| Anatomical Site of Primary Tumor | Cell Line Common Name | Cell Line Source | Cell Line Source Identification |
|---|---|---|---|
| | NCl-H196 | ATCC | CRL-5823 |
| | NCl-H1092 | ATCC | CRL-5855 |
| | SBC-5 | JCRB | JCRB0819 |
| | NCl-H510A | ATCC | HTB-184 |
| | NCl-H889 | ATCC | CRL-5817 |
| | NCl-H1341 | ATCC | CRL-5864 |
| | NClH-1876 | ATCC | CRL-5902 |
| | NCl-H2029 | ATCC | CRL-5913 |
| | NCl-H841 | ATCC | CRL-5845 |
| | NCl-H1694 | ATCC | CRL-5888 |
| | DMS 79 | ATCC | CRL-20496 |
| | HCC33 | DSMZ | ACC-487 |
| | NCl-H1048 | ATCC | CRL-5853 |
| | NCl-H1105 | ATCC | CRL-5856 |
| | NCl-H1184 | ATCC | CRL-5858 |
| | NCl-H128 | ATCC | HTB-120 |
| | NCl-H1436 | ATCC | CRL-5871 |
| | DMS 153 | ATCC | CRL-2064 |
| | NCl-H1836 | ATCC | CRL-5898 |
| | NCl-H1963 | ATCC | CRL-5982 |
| | NCl-H2081 | ATCC | CRL-5920 |
| | NCl-H209 | ATCC | HTB-172 |
| | NCl-H211 | ATCC | CRL-524 |
| | NCl-H2171 | ATCC | CRL-5929 |
| | NCl-H2196 | ATCC | CRL-5932 |
| | NCl-H2227 | ATCC | CRL-5934 |
| | NCl-H446 | ATCC | HTB-171 |
| | NCl-H524 | ATCC | CRL-5831 |
| | NCl-H526 | ATCC | CRL-5811 |
| | NCl-H69 | ATCC | HTB-119 |
| | NCl-H82 | ATCC | HTB-175 |
| | SHP-77 | ATCC | CRL-2195 |
| | SW1271 | ATCC | CRL-2177 |
| Prostate or Testis | PC3 | ATCC | CRL-1435 |
| | DU145 | ATCC | HTB-81 |
| | LNCaP clone FGC | ATCC | CRL-2023 |
| | NCCIT | ATCC | CRL-2073 |
| | NEC-8 | JCRB | JCRB0250 |
| | NTERA-2cl-D1 | ATCC | CRL-1973 |
| | NCl-H660 | ATCC | CRL-5813 |
| | VCaP | ATCC | CRL-2876 |
| | MDA-PCa-2b | ATCC | CRL-2422 |
| | 22Rv1 | ATCC | CRL-2505 |
| | E006AA | Millipore | SCC102 |
| | NEC14 | JCRB | JCRB0162 |
| | SuSa | DSMZ | ACC-747 |
| | 833K-E | ECACC | 06072611 |
| Colorectal | LS123 | ATCC | CCL-255 |
| | HCT15 | ATCC | CCL-225 |
| | SW1463 | ATCC | CCL-234 |
| | RKO | ATCC | CRL-2577 |
| | HUTU80 | ATCC | HTB-40 |
| | HCT116 | ATCC | CCL-247 |
| | LOVO | ATCC | CCL-229 |
| | T84 | ATCC | CCL-248 |
| | LS411N | ATCC | CRL-2159 |
| | SW48 | ATCC | CCL-231 |
| | C2BBe1 | ATCC | CRL-2102 |
| | Caco-2 | ATCC | HTB-37 |
| | SNU-1033 | KCLB | 01033 |
| | COLO 201 | ATCC | CCL-224 |
| | GP2d | ECACC | 95090714 |
| | CL-14 | DSMZ | ACC-504 |
| | SW403 | ATCC | CCL-230 |
| | SW1116 | ATCC | CCL-233 |
| | SW837 | ATCC | CCL-235 |
| | SK-CO-1 | ATCC | HTB-39 |
| | CL-34 | DSMZ | ACC-520 |
| | NCl-H508 | ATCC | CCL-253 |
| | CCK-81 | JCRB | JCRB0208 |
| | SNU-C2A | ATCC | CCL-250.1 |
| | GP2d | ECACC | 95090714 |
| | HT-55 | ECACC | 85061105 |
| | MDST8 | ECACC | 99011801 |

TABLE 1-continued

Exemplary vaccine composition cell lines per indication

| Anatomical Site of Primary Tumor | Cell Line Common Name | Cell Line Source | Cell Line Source Identification |
|---|---|---|---|
| | RCM-1 | JCRB | JCRB0256 |
| | CL-40 | DSMZ | ACC-535 |
| | COLO 678 | DSMZ | ACC-194 |
| | LS180 | ATCC | CL-187 |
| Breast | BT20 | ATCC | HTB-19 |
| | BT549 | ATCC | HTB-122 |
| | MDA-MB-231 | ATCC | HTB-26 |
| | HS578T | ATCC | HTB-126 |
| | AU565 | ATCC | CRL-2351 |
| | CAMA1 | ATCC | HTB-21 |
| | MCF7 | ATCC | HTB-22 |
| | T-47D | ATCC | HTB-133 |
| | ZR-75-1 | ATCC | CRL-1500 |
| | MDA-MB-415 | ATCC | HTB-128 |
| | CAL-51 | DSMZ | ACC-302 |
| | CAL-120 | DSMZ | ACC-459 |
| | HCC1187 | ATCC | CRL-2322 |
| | HCC1395 | ATCC | CRL-2324 |
| | SK-BR-3 | ATCC | HTB-30 |
| | HDQ-P1 | DSMZ | ACC-494 |
| | HCC70 | ATCC | CRL-2315 |
| | HCC1937 | ATCC | CRL-2336 |
| | MDA-MB-436 | ATCC | HTB-130 |
| | MDA-MB-468 | ATCC | HTB-132 |
| | MDA-MB-157 | ATCC | HTB-24 |
| | HMC-1-8 | JCRB | JCRB0166 |
| | Hs 274.T | ATCC | CRL-7222 |
| | Hs 281.T | ATCC | CRL-7227 |
| | JIMT-1 | ATCC | ACC-589 |
| | Hs 343.T | ATCC | CRL-7245 |
| | Hs 606.T | ATCC | CRL-7368 |
| | UACC-812 | ATCC | CRL-1897 |
| | UACC-893 | ATCC | CRL-1902 |
| Urinary Tract | UM-UC-3 | ATCC | CRL-1749 |
| | 5637 | ATCC | HTB-9 |
| | J82 | ATCC | HTB-1 |
| | T24 | ATCC | HTB-4 |
| | HT-1197 | ATCC | CRL-1473 |
| | TCCSUP | ATCC | HTB-5 |
| | HT-1376 | ATCC | CRL-1472 |
| | SCaBER | ATCC | HTB-3 |
| | RT4 | ATCC | HTB-2 |
| | CAL-29 | DSMZ | ACC-515 |
| | AGS | ATCC | CRL-1739 |
| | KMBC-2 | JCRB | JCRB1148 |
| | 253J | KCLB | 080001 |
| | 253J-BV | KCLB | 080002 |
| | SW780 | ATCC | CRL-2169 |
| | SW1710 | DSMZ | ACC-426 |
| | VM-CUB-1 | DSMZ | ACC-400 |
| | BC-3C | DSMZ | ACC-450 |
| | U-BLC1 | ECACC | U-BLC1 |
| | KMBC-2 | JCRB | JCRB1148 |
| | RT112/84 | ECACC | 85061106 |
| | UM-UC-1 | ECACC | 06080301 |
| | RT-112 | DSMZ | ACC-418 |
| | KU-19-19 | DSMZ | ACC-395 |
| | 639V | DSMZ | ACC-413 |
| | 647V | DSMZ | ACC-414 |
| Kidney | A-498 | ATCC | HTB-44 |
| | A-704 | ATCC | HTB-45 |
| | 769-P | ATCC | CRL-1933 |
| | 786-O | ATCC | CRL-1932 |
| | ACHN | ATCC | CRL-1611 |
| | KMRC-1 | JCRB | JCRB1010 |
| | KMRC-2 | JCRB | JCRB1011 |
| | VMRC-RCZ | JCRB | JCRB0827 |
| | VMRC-RCW | JCRB | JCRB0813 |
| | UO-31 | NCl-DTP | UO-31 |
| | Caki-1 | ATCC | HTB-46 |
| | Caki-2 | ATCC | HTB-47 |
| | OS-RC-2 | RCB | RCB0735 |
| | TUHR-4TKB | RCB | RCB1198 |
| | RCC-10RGB | RCB | RCB1151 |

TABLE 1-continued

Exemplary vaccine composition cell lines per indication

| Anatomical Site of Primary Tumor | Cell Line Common Name | Cell Line Source | Cell Line Source Identification |
|---|---|---|---|
| | SNU-1272 | KCLB | 01272 |
| | SNU-349 | KCLB | 00349 |
| | TUHR-14TKB | RCB | RCB1383 |
| | TUHR-10TKB | RCB | RCB1275 |
| | BFTC-909 | DSMZ | ACC-367 |
| | CAL-54 | DSMZ | ACC-365 |
| | KMRC-3 | JCRB | JCRB1012 |
| | KMRC-20 | JCRB | JCRB1071 |
| Upper Aerodigestive Tract (Head and Neck) | HSC-4 | JCRB | JCRB0624 |
| | DETROIT 562 | ATCC | CCL-138 |
| | SCC-9 | ATCC | CRL-1629 |
| | SCC-4 | ATCC | CRL-1624 |
| | OSC-19 | JCRB | JCRB0198 |
| | KON | JCRB | JCRB0194 |
| | HO-1-N-1 | JCRB | JCRB0831 |
| | OSC-20 | JCRB | JCRB0197 |
| | HSC-3 | JCRB | JCRB0623 |
| | SNU-1066 | KCLB | 01066 |
| | SNU-1041 | KCLB | 01041 |
| | SNU-1076 | KCLB | 01076 |
| | BICR 18 | ECACC | 06051601 |
| | CAL-33 | DSMZ | ACC-447 |
| | YD-8 | KCLB | 60501 |
| | FaDu | ATCC | HTB-43 |
| | 2A3 | ATCC | CRL-3212 |
| | CAL-27 | ATCC | CRL-2095 |
| | SCC-25 | ATCC | CRL-1628 |
| | SCC-15 | ATCC | CRL-1623 |
| | HO-1-u-1 | JCRB | JCRB0828 |
| | KOSC-2 | JCRB | JCRB0126.1 |
| | RPMI-2650 | ATCC | CCL-30 |
| | SCC-90 | ATCC | CRL-3239 |
| | SKN-3 | JCRB | JCRB1039 |
| | HSC-2 | JCRB | JCRB0622 |
| | Hs 840.T | ATCC | CRL-7573 |
| | SAS | JCRB | JCRB0260 |
| | SAT | JCRB | JCRB1027 |
| | SNU-46 | KCLB | 00046 |
| | YD-38 | KCLB | 60508 |
| | SNU-899 | KCLB | 00899 |
| | HN | DSMZ | ACC-417 |
| | BICR 10 | ECACC | 04072103 |
| | BICR 78 | ECACC | 04072111 |
| Ovaries | OVCAR-3 | ATCC | HTB-161 |
| | TOV-112D | ATCC | CRL-11731 |
| | ES-2 | ATCC | CRL-1978 |
| | TOV-21G | ATCC | CRL-11730 |
| | OVTOKO | JCRB | JCRB1048 |
| | KURAMOCHI | JCRB | JCRB0098 |
| | MCAS | JCRB | JCRB0240 |
| | TYK-nu | JCRB | JCRB0234.0 |
| | OVSAHO | JCRB | JCRB1046 |
| | OVMANA | JCRB | JCRB1045 |
| | JHOM-2B | RCB | RCB1682 |
| | OV56 | ECACC | 96020759 |
| | JHOS-4 | RCB | RCB1678 |
| | JHOC-5 | RCB | RCB1520 |
| | OVCAR-4 | NCl-DTP | OVCAR-4 |
| | JHOS-2 | RCB | RCB1521 |
| | EFO-21 | DSMZ | ACC-235 |
| | OV-90 | ATCC | CRL-11732 |
| | OVKATE | JCRB | JCRB1044 |
| | SK-OV-3 | ATCC | HTB-77 |
| | Caov-4 | ATCC | HTB-76 |
| | Coav-3 | ATCC | HTB-75 |
| | JHOM-1 | RCB | RCB1676 |
| | COV318 | ECACC | 07071903 |
| | OVK-18 | RCB | RCB1903 |
| | SNU-119 | KCLB | 00119 |
| | SNU-840 | KCLB | 00840 |
| | SNU-8 | KCLB | 0008 |
| | COV362 | ECACC | 07071910 |
| | COV434 | ECACC | 07071909 |
| | COV644 | ECACC | 07071908 |

TABLE 1-continued

Exemplary vaccine composition cell lines per indication

| Anatomical Site of Primary Tumor | Cell Line Common Name | Cell Line Source | Cell Line Source Identification |
|---|---|---|---|
| | OV7 | ECACC | 96020764 |
| | OAW-28 | ECACC | 85101601 |
| | OVCAR-8 | NCl-DTP | OVCAR-8 |
| | 59M | ECACC | 89081802 |
| | EFO-27 | DSMZ | ACC-191 |
| Pancreas | PANC-1 | ATCC | CRL-1469 |
| | HPAC | ATCC | CRL-2119 |
| | KP-2 | JCRB | JCRB0181 |
| | KP-3 | JCRB | JCRB0178.0 |
| | KP-4 | JCRB | JCRB0182 |
| | HPAF-II | ATCC | CRL-1997 |
| | SUIT-2 | JCRB | JCRB1094 |
| | AsPC-1 | ATCC | CRL-1682 |
| | PSN1 | ATCC | CRL-3211 |
| | CFPAC-1 | ATCC | CRL-1918 |
| | Capan-1 | ATCC | HTB-79 |
| | Panc 02.13 | ATCC | CRL-2554 |
| | Panc 03.27 | ATCC | CRL-2549 |
| | BxPC-3 | ATCC | CRL-1687 |
| | SU.86.86 | ATCC | CRL-1837 |
| | Hs 766T | ATCC | HTB-134 |
| | Panc 10.05 | ATCC | CRL-2547 |
| | Panc 04.03 | ATCC | CRL-2555 |
| | PaTu 8988s | DSMZ | ACC-204 |
| | PaTu 8988t | DSMZ | ACC-162 |
| | SW1990 | ATCC | CRL-2172 |
| | SNU-324 | KCLB | 00324 |
| | SNU-213 | KCLB | 00213 |
| | DAN-G | DSMZ | ACC-249 |
| | Panc 02.03 | ATCC | CRL-2553 |
| | PaTu 8902 | DSMZ | ACC-179 |
| | Capan-2 | ATCC | HTB-80 |
| | MIA PaCa-2 | ATCC | CRL-1420 |
| | YAPC | DSMZ | ACC-382 |
| | HuP-T3 | DSMZ | ACC-259 |
| | T3M-4 | RCB | RCB1021 |
| | PK-45H | RCB | RCB1973 |
| | Panc 08.13 | ATCC | CRL-2551 |
| | PK-1 | RCB | RCB1972 |
| | PK-59 | RCB | RCB1901 |
| | HuP-T4 | DSMZ | ACC-223 |
| | Panc 05.04 | ATCC | CRL-2557 |
| Stomach | RERF-GC-1B | JCRB | JCRB1009 |
| | Fu97 | JCRB | JCRB1074 |
| | MKN74 | JCRB | JCRB0255 |
| | NCl-N87 | ATCC | CRL-5822 |
| | NUGC-2 | JCRB | JCRB0821 |
| | MKN45 | JCRB | JCRB0254 |
| | OCUM-1 | JCRB | JCRB0192 |
| | MKN7 | JCRB | JCRB1025 |
| | MKN1 | JCRB | JCRB0252 |
| | ECC10 | RCB | RCB0983 |
| | TGBC-11-TKB | RCB | RCB1148 |
| | SNU-620 | KCLB | 00620 |
| | GSU | RCB | RCB2278 |
| | KE-39 | RCB | RCB1434 |
| | HuG1-N | RCB | RCB1179 |
| | NUGC-4 | JCRB | JCRB0834 |
| | SNU-16 | ATCC | CRL-5974 |
| | SJSA-1 | ATCC | CRL-2098 |
| | RD-ES | ATCC | HTB-166 |
| | U2OS | ATCC | HTB-96 |
| | SaOS-2 | ATCC | HTB-85 |
| | Hs 746.T | ATCC | HTP-135 |
| | LMSU | RCB | RCB1062 |
| | SNU-520 | KCLB | 00520 |
| | GSS | RCB | RCB2277 |
| | ECC12 | RCB | RCB1009 |
| | GClY | RCB | RCB0555 |
| | SH-10-TC | RCB | RCB1940 |
| | HGC-27 | BCRJ | 0310 |
| | HuG1-N | RCB | RCB1179 |
| | SNU-601 | KCLB | KCLB00601 |
| | SNU-668 | KCLB | 00668 |

TABLE 1-continued

Exemplary vaccine composition cell lines per indication

| Anatomical Site of Primary Tumor | Cell Line Common Name | Cell Line Source | Cell Line Source Identification |
|---|---|---|---|
| | NCC-StC-K140 | JCRB | JCRB1228 |
| | SNU-719 | KCLB | 00719 |
| | SNU-216 | KCLB | 00216 |
| | NUGC-3 | JCRB | JCRB0822 |
| Liver | Hep-G2 | ATCC | HB-8065 |
| | JHH-2 | JCRB | JCRB1028 |
| | JHH-4 | JCRB | JCRB0435 |
| | JHH-6 | JCRB | JCRB1030 |
| | Li7 | RCB | RCB1941 |
| | HLF | JCRB | JCRB0405 |
| | HuH-6 | RCB | BRC1367 |
| | JHH-5 | JCRB | JCRB1029 |
| | HuH-7 | JCRB | JCRB0403 |
| | SNU-182 | ATCC | CRL-2235 |
| | JHH-7 | JCRB | JCRB1031 |
| | SK-HEP-1 | ATCC | HTB-52 |
| | Hep 3B2.1-7 | ATCC | HB-8064 |
| | SNU-449 | ATCC | CRL-2234 |
| | SNU-761 | KCLB | KCLB |
| | JHH-1 | JCRB | JCRB1062 |
| | SNU-398 | ATCC | CRL-2233 |
| | SNU-423 | ATCC | CRL-2238 |
| | SNU-387 | ATCC | CRL-2237 |
| | SNU-475 | ATCC | CRL-2236 |
| | SNU-886 | KCLB | KCLB 00886 |
| | SNU-878 | KCLB | KCLB 00878 |
| | NCl-H684 | KCLB | KCLB 90684 |
| | PLC/PRF/5 | ATCC | CRL-8024 |
| | HuH-1 | JCRB | JCRB0199 |
| | HLE | JCRB | JCRB0404 |
| | C3A | ATCC | HB-8065 |
| Central Nervous System | DBTRG-05MG | ATCC | CRL-2020 |
| | LN-229 | ATCC | CRL-2611 |
| | SF-126 | JCRB | IFO50286 |
| | M059K | ATCC | CRL-2365 |
| | M059KJ | ATCC | CRL-2366 |
| | U-251 MG | JCRB | IFO50288 |
| | A-172 | ATCC | CRL-1620 |
| | YKG-1 | ATCC | JCRB0746 |
| | GB-1 | ATCC | IFO50489 |
| | KNS-60 | ATCC | IFO50357 |
| | KNS-81 | JCRB | IFO50359 |
| | TM-31 | RCB | RCB1731 |
| | NMC-G1 | JCRB | IFO50467 |
| | SNU-201 | KCLB | 00201 |
| | SW1783 | ATCC | HTB-13 |
| | GOS-3 | DSMZ | ACC-408 |
| | KNS-81 | JCRB | IFO50359 |
| | KG-1-C | JCRB | JCRB0236 |
| | AM-38 | JCRB | IFO50492 |
| | CAS-1 | ILCL | HTL97009 |
| | H4 | ATCC | HTB-148 |
| | D283 Med | ATCC | HTB-185 |
| | DK-MG | DSMZ | ACC-277 |
| | U-118MG | ATCC | HTB-15 |
| | SNU-489 | KCLB | 00489 |
| | SNU-466 | KCLB | 00426 |
| | SNU-1105 | KCLB | 01105 |
| | SNU-738 | KCLB | 00738 |
| | SNU-626 | KCLB | 00626 |
| | Daoy | ATCC | HTB-186 |
| | D341 Med | ATCC | HTB-187 |
| | SW1088 | ATCC | HTB-12 |
| | Hs 683 | ATCC | HTB-138 |
| | ONS-76 | JCRB | IFO50355 |
| | LN-18 | ATCC | CRL-2610 |
| | T98G | ATCC | CRL-1690 |
| | GMS-10 | DSMZ | ACC-405 |
| | 42-MG-BA | DSMZ | ACC-431 |
| | GaMG | DSMZ | ACC-242 |
| | 8-MG-BA | DSMZ | ACC-432 |
| | IOMM-Lee | ATCC | CRL-3370 |
| | SF268 | NCl-DTP | SF-268 |
| | SF539 | NCl-DTP | SF-539 |
| | SNB75 | NCl-DTP | SNB-75 |
| Esophagus | TE-10 | RCB | RCB2099 |
| | TE-6 | RCB | RCB1950 |
| | TE-4 | RCB | RCB2097 |
| | EC-Gl-10 | RCB | RCB0774 |
| | OE33 | ECACC | 96070808 |
| | TE-9 | RCB | RCB1988 |
| | TT | JCRB | JCRB0262 |
| | TE-11 | RCB | RCB2100 |
| | OE19 | ECACC | 96071721 |
| | OE21 | ECACC | 96062201 |
| | KYSE-450 | JCRB | JCRB1430 |
| | TE-14 | RCB | RCB2101 |
| | TE-8 | RCB | RCB2098 |
| | KYSE-410 | JCRB | JCRB1419 |
| | KYSE-140 | DSMZ | ACC-348 |
| | KYSE-180 | JCRB | JCRB1083 |
| | KYSE-520 | JCRB | JCRB1439 |
| | KYSE-270 | JCRB | JCRB1087 |
| | KYSE-70 | JCRB | JCRB0190 |
| | TE-1 | RCB | RCB1894 |
| | TE-5 | RCB | RCB1949 |
| | TE-15 | RCB | RCB1951 |
| | KYSE-510 | JCRB | JCRB1436 |
| | KYSE-30 | ECACC | 94072011 |
| | KYSE-150 | DSMZ | ACC-375 |
| | COLO 680N | DSMZ | ACC-182 |
| | KYSE-450 | JCRB | JCRB1430 |
| | TE-10 | RCB | RCB2099 |
| | ESO-26 | ECACC | 11012009 |
| | ESO-51 | ECACC | 11012010 |
| | FLO-1 | ECACC | 11012001 |
| | KYAE-1 | ECACC | 11012002 |
| | KYSE-220 | JCRB | JCRB1086 |
| | KYSE-50 | JCRB | JCRB0189 |
| | OACM5.1 C | ECACC | 11012006 |
| | OACP4 C | ECACC | 11012005 |
| Endometrium | SNG-M | JCRB | IFO50313 |
| | HEC-1-B | ATCC | HTB-113 |
| | JHUEM-3 | Riken RCB | RCB1552 |
| | RL95-2 | ATCC | CRL-1671 |
| | MFE-280 | ECACC | 98050131 |
| | MFE-296 | ECACC | 98031101 |
| | TEN | Riken RCB | RCB1433 |
| | JHUEM-2 | Riken RCB | RCB1551 |
| | AN3-CA | ATCC | HTB-111 |
| | KLE | ATCC | CRL-1622 |
| | Ishikawa | ECACC | 99040201 |
| | HEC-151 | JCRB | JCRB1122 |
| | SNU-1077 | KCLB | 01077 |
| | MFE-319 | DSMZ | ACC-423 |
| | EFE-184 | DSMZ | ACC-230 |
| | HEC-108 | JCRB | JCRB1123 |
| | HEC-265 | JCRB | JCRB1142 |
| | HEC-6 | JCRB | JCRB1118 |
| | HEC-50B | JCRB | JCRB1145 |
| | JHUEM-1 | RCB | RCB1548 |
| | HEC-251 | JCRB | JCRB1141 |
| | COLO 684 | ECACC | 87061203 |
| | SNU-685 | KCLB | 00685 |
| | HEC-59 | JCRB | JCRB1120 |
| | EN | DSMZ | ACC-564 |
| | ESS-1 | DSMZ | ACC-461 |
| | HEC-1A | ATCC | HTB-112 |
| | JHUEM-7 | RCB | RCB1677 |
| | HEC-1 | JCRB | JCRB0042 |
| Skin | RPMI-7951 | ATCC | HTB-66 |
| | MeWo | ATCC | HTB-65 |
| | Hs 688(A).T | ATCC | CRL-7425 |
| | COLO 829 | ATCC | CRL-1974 |
| | C32 | ATCC | CRL-1585 |
| | A-375 | ATCC | CRL-1619 |
| | Hs 294T | ATCC | HTB-140 |

TABLE 1-continued

Exemplary vaccine composition cell lines per indication

| Anatomical Site of Primary Tumor | Cell Line Common Name | Cell Line Source | Cell Line Source Identification |
|---|---|---|---|
| | Hs 695T | ATCC | HTB-137 |
| | Hs 852T | ATCC | CRL-7585 |
| | A2058 | ATCC | CRL-11147 |
| | RVH-421 | DSMZ | ACC-127 |
| | Hs 895.T | ATCC | CRL-7637 |
| | Hs 940.T | ATCC | CRL-7691 |
| | SK-MEL-1 | ATCC | HTB-67 |
| | SK-MEL-28 | ATCC | HTB-72 |
| | SH-4 | ATCC | CRL-7724 |
| | COLO 800 | ECACC | 93051123 |
| | COLO 783 | DSMZ | ACC-257 |
| | MDA-MB-435S | ATCC | HTB-129 |
| | IGR-1 | CLS | 300219/p483_ IGR-1 |
| | IGR-39 | DSMZ | ACC-239 |
| | HT-144 | ATCC | HTB-63 |
| | SK-MEL-31 | ATCC | HTB-73 |
| | Hs 839.T | ATCC | CRL-7572 |
| | Hs 600.T | ATCC | CRL-7360 |
| | A101D | ATCC | CRL-7898 |
| | IPC-298 | DSMZ | ACC-251 |
| | SK-MEL-24 | ATCC | HTB-71 |
| | SK-MEL-3 | ATCC | HTB-69 |
| | HMCB | ATCC | CRL-9607 |
| | Malme-3M | ATCC | HTB-64 |
| | Mel JuSo | DSMZ | ACC-74 |
| | COLO 679 | RCB | RCB0989 |
| | COLO 741 | ECACC | 93052621 |
| | SK-MEL-5 | ATCC | HTB-70 |
| | WM266-4 | ATCC | CRL-1676 |
| | IGR-37 | DSMZ | ACC-237 |
| | Hs 934.T | ATCC | CRL-7684 |
| | UACC-257 | NCl-DTP | UACC-257 |
| Mesothelium | NCl-H28 | ATCC | CRL-5820 |
| | MSTO-211H | ATCC | CRL-2081 |
| | IST-Mes1 | ICLC | HTL01005 |
| | ACC-MESO-1 | RCB | RCB2292 |
| | NCl-H2052 | ATCC | CRL-5951 |
| | NCl-H2452 | ATCC | CRL-2081 |
| | MPP 89 | ICLC | HTL00012 |
| | IST-Mes2 | ICLC | HTL01007 |
| | RS-5 | DSMZ | ACC-604 |
| | DM-3 | DSMZ | ACC-595 |
| | JL-1 | DSMZ | ACC-596 |
| | COR-L321 | ECACC | 96020756 |

In addition to the cell lines identified in Table 1, the following cell lines are also contemplated in various embodiments.

In various embodiments, one or more non-small cell lung (NSCLC) cell lines are prepared and used according to the disclosure. By way of example, the following NSCLC cell lines are contemplated: NCI-H460, NCIH520, A549, DMS 53, LK-2, and NCI-H23. Additional NSCLC cell lines are also contemplated by the present disclosure. As described herein, inclusion of a cancer stem cell line such as DMS 53 in a vaccine comprising NSCLC cell lines is also contemplated.

In some embodiments, one or more prostate cancer cell lines are prepared and used according to the disclosure. By way of example, the following prostate cancer cell lines are contemplated: P03, DU-145, LNCAP, NEC8, and NTERA-2cl-Di. Additional prostate cancer cell lines are also contemplated by the present disclosure. As described herein, inclusion of a cancer stem cell line such as DMS 53 in a vaccine comprising prostate cancer cell lines is also contemplated.

In some embodiments, one or more colorectal cancer (CRC) cell lines are prepared and used according to the disclosure. By way of example, the following colorectal cancer cell lines are contemplated: HOT-15, RKO, HuTu-80, HCT-116, and LS411N. Additional colorectal cancer cell lines are also contemplated by the present disclosure. As described herein, inclusion of a cancer stem cell line such as DMS 53 in a vaccine comprising CRC cell lines is also contemplated.

In some embodiments, one or more breast cancer or triple negative breast cancer (TNBC) cell lines are prepared and used according to the disclosure. By way of example, the following TNBC cell lines are contemplated: Hs 578T, AU565, CAMA-1, MCF-7, and T-47D. Additional breast cancer cell lines are also contemplated by the present disclosure. As described herein, inclusion of a cancer stem cell line such as DMS 53 in a vaccine comprising breast and/or TNBC cancer cell lines is also contemplated.

In some embodiments, one or more bladder or urinary tract cancer cell lines are prepared and used according to the disclosure. By way of example, the following urinary tract or bladder cancer cell lines are contemplated: UM-UC-3, J82, TCCSUP, HT-1376, and SCaBER. Additional bladder cancer cell lines are also contemplated by the present disclosure. As described herein, inclusion of a cancer stem cell line such as DMS 53 in a vaccine comprising bladder or urinary tract cancer cell lines is also contemplated.

In some embodiments, one or more stomach or gastric cancer cell lines are prepared and used according to the disclosure. By way of example, the following stomach or gastric cancer cell lines are contemplated: Fu97, MKN74, MKN45, OCUM-1, and MKN1. Additional stomach cancer cell lines are also contemplated by the present disclosure. As described herein, inclusion of a cancer stem cell line such as DMS 53 in a vaccine comprising stomach or gastric cancer cell lines is also contemplated.

In some embodiments, one or more squamous cell head and neck cancer (SCCHN) cell lines are prepared and used according to the disclosure. By way of example, the following SCCHN cell lines are contemplated: HSC-4, Detroit 562, KON, HO-1-N-1, and OSC-20. Additional SCCHN cell lines are also contemplated by the present disclosure. As described herein, inclusion of a cancer stem cell line such as DMS 53 in a vaccine comprising SCCHN cancer cell lines is also contemplated.

In some embodiments, one or more small cell lung cancer (SCLC) cell lines are prepared and used according to the disclosure. By way of example, the following SCLC cell lines are contemplated: DMS 114, NCI-H196, NCI-H1092, SBC-5, NCI-H510A, NCI-H889, NCI-H1341, NCIH-1876, NCI-H2029, NCI-H841, and NCI-H1694. Additional SCLC cell lines are also contemplated by the present disclosure. As described herein, inclusion of a cancer stem cell line such as DMS 53 in a vaccine comprising SCLC cell lines is also contemplated.

In some embodiments, one or more liver or hepatocellular cancer (HCC) cell lines are prepared and used according to the disclosure. By way of example, the following HCC cell lines are contemplated: Hep-G2, JHH-2, JHH-4, JHH-6, Li7, HLF, HuH-6, JHH-5, and HuH-7. Additional HCC cell lines are also contemplated by the present disclosure. As described herein, inclusion of a cancer stem cell line such as DMS 53 in a vaccine comprising liver or HCC cancer cell lines is also contemplated.

In some embodiments, one or more kidney cancer such as renal cell carcinoma (RCC) cell lines are prepared and used according to the disclosure. By way of example, the following RCC cell lines are contemplated: A-498, A-704, 769-P, 786-0, ACHN, KMRC-1, KMRC-2, VMRC-RCZ, and VMRC-RCW. Additional RCC cell lines are also contemplated by the present disclosure. As described herein, inclusion of a cancer stem cell line such as DMS 53 in a vaccine comprising kidney or RCC cancer cell lines is also contemplated.

In some embodiments, one or more glioblastoma (GBM) cancer cell lines are prepared and used according to the disclosure. By way of example, the following GBM cell lines are contemplated: DBTRG-05MG, LN-229, SF-126, GB-1, and KNS-60. Additional GBM cell lines are also contemplated by the present disclosure. As described herein, inclusion of a cancer stem cell line such as DMS 53 in a vaccine comprising GBM cancer cell lines is also contemplated.

In some embodiments, one or more ovarian cancer cell lines are prepared and used according to the disclosure. By way of example, the following ovarian cell lines are contemplated: TOV-112D, ES-2, TOV-21G, OVTOKO, and MCAS. Additional ovarian cell lines are also contemplated by the present disclosure. As described herein, inclusion of a cancer stem cell line such as DMS 53 in a vaccine comprising ovarian cancer cell lines is also contemplated.

In some embodiments, one or more esophageal cancer cell lines are prepared and used according to the disclosure. By way of example, the following esophageal cell lines are contemplated: TE-10, TE-6, TE-4, EC-GI-10, OE33, TE-9, TT, TE-11, OE19, OE21. Additional esophageal cell lines are also contemplated by the present disclosure. As described herein, inclusion of a cancer stem cell line such as DMS 53 in a vaccine comprising esophageal cancer cell lines is also contemplated.

In some embodiments, one or more pancreatic cancer cell lines are prepared and used according to the disclosure. By way of example, the following pancreatic cell lines are contemplated: PANC-1, KP-3, KP-4, SUIT-2, and PSN1. Additional pancreatic cell lines are also contemplated by the present disclosure. As described herein, inclusion of a cancer stem cell line such as DMS 53 in a vaccine comprising pancreatic cancer cell lines is also contemplated.

In some embodiments, one or more endometrial cancer cell lines are prepared and used according to the disclosure. By way of example, the following endometrial cell lines are contemplated: SNG-M, HEC-1-B, JHUEM-3, RL95-2, MFE-280, MFE-296, TEN, JHUEM-2, AN3-CA, and Ishikawa. Additional endometrial cell lines are also contemplated by the present disclosure. As described herein, inclusion of a cancer stem cell line such as DMS 53 in a vaccine comprising endometrial cancer cell lines is also contemplated.

In some embodiments, one or more melanoma cancer cell lines are prepared and used according to the disclosure. By way of example, the following melanoma cell lines are contemplated: RPMI-7951, MeWo, Hs 688(A).T, COLO 829, C32, A-375, Hs 294T, Hs 695T, Hs 852T, and A2058. Additional melanoma cell lines are also contemplated by the present disclosure. As described herein, inclusion of a cancer stem cell line such as DMS 53 in a vaccine comprising melanoma cancer cell lines is also contemplated.

In some embodiments, one or more mesothelioma cancer cell lines are prepared and used according to the disclosure. By way of example, the following mesothelioma cell lines are contemplated: NCI-H28, MSTO-211H, IST-Mes1, ACC-MESO-1, NCI-H2052, NCI-H2452, MPP 89, and IST-Mes2. Additional mesothelioma cell lines are also contemplated by the present disclosure. As described herein, inclusion of a cancer stem cell line such as DMS 53 in a vaccine comprising mesothelioma cancer cell lines is also contemplated.

Embodiments of vaccine compositions according to the disclosure are used to treat and/or prevent various types of cancer. In some embodiments, a vaccine composition may comprise cancer cell lines that originated from the same type of cancer. For example, a vaccine composition may comprise 1, 2, 3, 4, 5, 6, 7, 8, 9, 10 or more NSCLC cell lines, and such a composition may be useful to treat or prevent NSCLC. According to certain embodiments, the vaccine composition comprising NCSLC cell lines may be used to treat or prevent cancers other than NSCLC, examples of which are described herein.

In some embodiments, a vaccine composition may comprise cancer cell lines that originated from different types of cancer. For example, a vaccine composition may comprise 1, 2, 3, 4, 5, 6, 7, 8, 9, 10 or more NSCLC cell lines, plus 1, 2, 3, 4, 5, 6, 7, 8, 9, 10 or more SCLC cancer cell lines, optionally plus one or other cancer cell lines, such as cancer stem cell lines, and so on, and such a composition may be useful to treat or prevent NSCLC, and/or prostate cancer, and/or breast cancer, and so on. According to some embodiments, the vaccine composition comprising different cancer cell lines as described herein may be used to treat or prevent various cancers. In some embodiments, the targeting of a TAA or multiple TAAs in a particular tumor is optimized by using cell lines derived from different tissues or organs within a biological system to target a cancer of primary origin within the same system. By way of non-limiting examples, cell lines derived from tumors of the reproductive system (e.g., ovaries, fallopian tubes, uterus, vagina, mammary glands, testes, vas deferens, seminal vesicles, and prostate) may be combined; cell lines derived from tumors of the digestive system (e.g., salivary glands, esophagus, stomach, liver, gallbladder, pancreas, intestines, rectum, and anus) may be combined; cell lines from tumors of the respiratory system (e.g., pharynx, larynx, bronchi, lungs, and diaphragm) may be combined; and cell lines derived from tumors of the urinary system (e.g., kidneys, ureters, bladder, and urethra) may be combined.

According to various embodiments of the vaccine compositions, the disclosure provides compositions comprising a combination of cell lines. By way of non-limiting examples, cell line combinations are provided below. In each of the following examples, cell line DMS 53, whether modified or unmodified, is combined with 5 other cancer cell lines in the associated list. One or more of the cell lines within each recited combination may be modified as described herein. In some embodiments, none of the cell lines in the combination of cell lines are modified.

(1) NCI-H460, NCIH520, A549, DMS 53, LK-2, and NCI-H23 for the treatment and/or prevention of NSCLC;

(2) DMS 114, NCI-H196, NCI-H1092, SBC-5, NCI-H510A, NCI-H889, NCI-H1341, NCIH-1876, NCI-H2029, NCI-H841, DMS 53, and NCI-H1694 for the treatment and/or prevention of SCLC;

(3) DMS 53, PC3, DU-145, LNCAP, NCC-IT, and NTERA-2cl-D1 for the treatment and/or prevention of prostate cancer;

(4) DMS 53, HCT-15, RKO, HuTu-80, HCT-116, and LS411 N for the treatment and/or prevention of colorectal cancer;

(5) DMS 53, Hs 578T, AU565, CAMA-1, MCF-7, and T-47D for the treatment and/or prevention of breast cancer including triple negative breast cancer (TNBC);

(6) DMS 53, UM-UC-3, J82, TCCSUP, HT-1376, and SCaBER for the treatment and/or prevention of bladder cancer;

(7) DMS 53, HSC-4, Detroit 562, KON, HO-1-N-1, and OSC-20 for the treatment and/or prevention of head and/or neck cancer;

(8) DMS 53, Fu97, MKN74, MKN45, OCUM-1, and MKN1 for the treatment and/or prevention of stomach cancer;

(9) DMS 53, Hep-G2, JHH-2, JHH-4, JHH-6, Li7, HLF, HuH-6, JHH-5, and HuH-7 for the treatment and/or prevention of liver cancer;

(10) DMS 53, DBTRG-05MG, LN-229, SF-126, GB-1, and KNS-60 for the treatment and/or prevention of glioblastoma;

(11) DMS 53, TOV-112D, ES-2, TOV-21G, OVTOKO, and MCAS for the treatment and/or prevention of ovarian cancer;

(12) DMS 53, TE-10, TE-6, TE-4, EC-GI-10, OE33, TE-9, TT, TE-11, OE19, and OE21 for the treatment and/or prevention of esophageal cancer;

(13) DMS 53, A-498, A-704, 769-P, 786-0, ACHN, KMRC-1, KMRC-2, VMRC-RCZ, and VMRC-RCW for the treatment and/or prevention of kidney cancer;

(14) DMS 53, PANC-1, KP-3, KP-4, SUIT-2, and PSN1 for the treatment and/or prevention of pancreatic cancer;

(15) DMS 53, SNG-M, HEC-1-B, JHUEM-3, RL95-2, MFE-280, MFE-296, TEN, JHUEM-2, AN3-CA, and Ishikawa for the treatment and/or prevention of endometrial cancer;

(16) DMS 53, RPMI-7951, MeWo, Hs 688(A).T, COLO 829, C32, A-375, Hs 294T, Hs 695T, Hs 852T, and A2058 for the treatment and/or prevention of skin cancer; and

(17) DMS 53, NCI-H28, MSTO-211H, IST-Mes1, ACC-MESO-1, NCI-H2052, NCI-H2452, MPP 89, and IST-Mes2 for the treatment and/or prevention of mesothelioma.

In some embodiments, the cell lines in the vaccine compositions and methods described herein include one or more cancer stem cell (CSC) cell lines, whether modified or unmodified. One example of a CSC cell line is small cell lung cancer cell line DMS 53, whether modified or unmodified. CSCs display unique markers that differ depending on the anatomical origin of the tumor. Exemplary CSC markers include: prominin-1 (CD133), A2B5, aldehyde dehydrogenase (ALDH1), polycomb protein (Bmi-1), integrin-β1 (CD29), hyaluronan receptor (CD44), Thy-1 (CD90), SCF receptor (CD117), TRA-1-60, nestin, Oct-4, stage-specific embryonic antigen-1 (CD15), GD3 (CD60a), stage-specific embryonic antigen-1 (SSEA-1) or (CD15), stage-specific embryonic antigen-4 (SSEA-4), stage-specific embryonic antigen-5 (SSEA-5), and Thomsen-Friedenreich antigen (CD176).

Expression markers that identify cancer cell lines with greater potential to have stem cell-like properties differ depending on various factors including anatomical origin, organ, or tissue of the primary tumor. Exemplary cancer stem cell markers identified by primary tumor site are provided in Table 2 and are disclosed across various references (e.g., Gilbert, C A & Ross, A H. J Cell Biochem. (2009); Karsten, U & Goletz, S. SpringerPlus (2013); Zhao, W et al. Cancer Transl Med. (2017)).

Exemplary cell lines expressing one or more markers of cancer stem cell-like properties specific for the anatomical site of the primary tumor from which the cell line was derived are listed in Table 2. Exemplary cancer stem cell lines are provided in Table 3. Expression of CSC markers was determined using RNA-seq data from the Cancer Cell Line Encyclopedia (CCLE) (retrieved from www.broadinstitute.org/ccle on Nov. 23, 2019; Barretina, J et al. Nature. (2012)). The HUGO Gene Nomenclature Committee gene symbol was entered into the CCLE search and mRNA expression downloaded for each CSC marker. The expression of a CSC marker was considered positive if the RNA-seq value (FPKM) was greater than 0.

TABLE 2

Exemplary CSC markers by primary tumor anatomical origin

| Anatomical Site of Primary Tumor | CSC Marker Common Name | CSC Marker Gene Symbol |
|---|---|---|
| Ovaries | Endoglin, CD105 | ENG |
| | CD117, cKIT | KIT |
| | CD44 | CD44 |
| | CD133 | PROM1 |
| | SALL4 | SAL4 |
| | Nanog | NANOG |
| | Oct-4 | POU5F1 |
| Pancreas | ALDH1A1 | ALDH1A1 |
| | c-Myc | MYC |
| | EpCAM, TROP1 | EPCAM |
| | CD44 | CD44 |
| | Cd133 | PROM1 |
| | CXCR4 | CXCR4 |
| | Oct-4 | POU5F1 |
| | Nestin | NES |
| | BMI-1 | BMI1 |
| Skin | CD27 | CD27 |
| | ABCB5 | ABCB5 |
| | ABCG2 | ABCG2 |
| | CD166 | ALCAM |
| | Nestin | NES |
| | CD133 | PROM1 |
| | CD20 | MS4A1 |
| | NGFR | NGFR |
| Lung | ALDH1A1 | ALDH1A1 |
| | EpCAM, TROP1 | EPCAM |
| | CD90 | THY1 |
| | CD117, cKIT | KIT |
| | CD133 | PROM1 |
| | ABCG2 | ABCG2 |
| | SOX2 | SOX2 |
| Liver | Nanog | NANOG |
| | CD90/thy1 | THY1 |
| | CD133 | PROM1 |
| | CD13 | ANPEP |
| | EpCAM, TROP1 | EPCAM |
| | CD117, cKIT | KIT |
| | SALL4 | SAL4 |
| | SOX2 | SOX2 |
| Upper Aerodigestive Tract (Head and Neck) | ABCG2 | ABCG2 |
| | ALDH1A1 | ALDH1A1 |
| | Lgr5, GPR49 | LGR5 |
| | BMI-1 | BMI1 |
| | CD44 | CD44 |
| | cMET | MET |
| Central Nervous System | ALDH1A1 | ALDH1A1 |
| | ABCG2 | ABCG2 |
| | BMI-1 | BMI1 |
| | CD15 | FUT4 |
| | CD44 | CD44 |
| | CD49f, Integrin α6 | ITGA6 |
| | CD90 | THYI |
| | CD133 | PROM1 |
| | CXCR4 | CXCR4 |
| | CX3CR1 | CX3CR1 |
| | SOX2 | SOX2 |
| | c-Myc | MYC |
| | Musashi-1 | MSI1 |
| | Nestin | NES |
| Stomach | ALDH1A1 | ALDH1A1 |
| | ABCB1 | ABCB1 |
| | ABCG2 | ABCG2 |
| | CD133 | PROM1 |
| | CD164 | CD164 |
| | CD15 | FUT4 |
| | Lgr5, GPR49 | LGR5 |
| | CD44 | CD44 |
| | MUC1 | MUC1 |
| | DLL4 | DLL4 |

TABLE 2-continued

| Exemplary CSC markers by primary tumor anatomical origin | | |
|---|---|---|
| Anatomical Site of Primary Tumor | CSC Marker Common Name | CSC Marker Gene Symbol |
| Colon (Large and Small Intestines) | ALDH1A1 | ALDH1A1 |
| | c-myc | MYC |
| | CD44 | CD44 |
| | CD133 | PROM1 |
| | Nanog | NANOG |
| | Musashi-1 | MSI1 |
| | EpCAM, TROP1 | EPCAM |
| | Lgr5, GPR49 | LGR5 |
| | SALL4 | SAL4 |
| Breast | ABCG2 | ABCG2 |
| | ALDH1A1 | ALDH1A1 |
| | BMI-1 | BMI1 |
| | CD133 | PROM1 |
| | CD44 | CD44 |
| | CD49f, Integrin α6 | ITGA6 |
| | CD90 | THY1 |
| | c-myc | MYC |
| | CXCR1 | CXCR1 |
| | CXCR4 | CXCR4 |
| | EpCAM, TROP1 | EPCAM |
| | KLF4 | KLF4 |
| | MUC1 | MUC1 |
| | Nanog | NANOG |
| | SALL4 | SAL4 |
| | SOX2 | SOX2 |
| Urinary Tract | ALDH1A1 | ALDH1A1 |
| | CEACAM6, CD66c | CEACAM6 |
| | Oct4 | OCT4 |
| | CD44 | CD44 |
| | YAP1 | YAP1 |
| Hematopoietic and Lymphoid Tissue | BMI-1 | BMI1 |
| | CD117, c-kit | KIT |
| | CD20 | MS4A1 |
| | CD27, TNFRSF7 | CD27 |
| | CD34 | CD34 |
| | CD38 | CD38 |
| | CD44 | CD44 |
| | CD96 | CD96 |
| | GLI-1 | GLI1 |
| | GLI-2 | GLI2 |
| | IL-3Rα | IL3RA |
| | MICL | CLEC12A |
| | Syndecan-1, CD138 | SDC1 |
| | TIM-3 | HAVCR2 |
| Bone | ABCG2 | ABCG2 |
| | CD44 | CD44 |
| | Endoglin, CD105 | ENG |
| | Nestin | NES |

TABLE 3

| Cell lines expressing CSC markers | | | |
|---|---|---|---|
| Anatomical Site of Primary Tumor | Cell Line Common Name | Cell Line Source | Cell Line Source Identification |
| Ovaries | JHOM-2B | RCB | RCB1682 |
| | OVCAR-3 | ATCC | HTB-161 |
| | OV56 | ECACC | 96020759 |
| | JHOS-4 | RCB | RCB1678 |
| | JHOC-5 | RCB | RCB1520 |
| | OVCAR-4 | NCI-DTP | OVCAR-4 |
| | JHOS-2 | RCB | RCB1521 |
| | EFO-21 | DSMZ | ACC-235 |
| Pancreas | CFPAC-1 | ATCC | CRL-1918 |
| | Capan-1 | ATCC | HTB-79 |
| | Panc 02.13 | ATCC | CRL-2554 |
| | SUIT-2 | JCRB | JCRB1094 |
| | Panc 03.27 | ATCC | CRL-2549 |
| Skin | SK-MEL-28 | ATCC | HTB-72 |
| | RVH-421 | DSMZ | ACC-127 |
| | Hs 895.T | ATCC | CRL-7637 |

TABLE 3-continued

| Cell lines expressing CSC markers | | | |
|---|---|---|---|
| Anatomical Site of Primary Tumor | Cell Line Common Name | Cell Line Source | Cell Line Source Identification |
| | Hs 940.T | ATCC | CRL-7691 |
| | SK-MEL-1 | ATCC | HTB-67 |
| | Hs 936.T | ATCC | CRL-7686 |
| | SH-4 | ATCC | CRL-7724 |
| | COLO 800 | DSMZ | ACC-193 |
| | UACC-62 | NCI-DTP | UACC-62 |
| Lung | NCI-H2066 | ATCC | CRL-5917 |
| | NCI-H1963 | ATCC | CRL-5982 |
| | NCI-H209 | ATCC | HTB-172 |
| | NCI-H889 | ATCC | CRL-5817 |
| | COR-L47 | ECACC | 92031915 |
| | NCI-H1092 | ATCC | CRL-5855 |
| | NCI-H1436 | ATCC | CRL-5871 |
| | COR-L95 | ECACC | 96020733 |
| | COR-L279 | ECACC | 96020724 |
| | NCI-H1048 | ATCC | CRL-5853 |
| | NCI-H69 | ATCC | HTB-119 |
| | DMS 53 | ATCC | CRL-2062 |
| Liver | HuH-6 | RCB | RCB1367 |
| | Li7 | RCB | RCB1941 |
| | SNU-182 | ATCC | CRL-2235 |
| | JHH-7 | JCRB | JCRB1031 |
| | SK-HEP-1 | ATCC | HTB-52 |
| | Hep 3B2.1-7 | ATCC | HB-8064 |
| Upper Aerodigestive Tract (Head and Neck) | SNU-1066 | KCLB | 01066 |
| | SNU-1041 | KCLB | 01041 |
| | SNU-1076 | KCLB | 01076 |
| | BICR 18 | ECACC | 06051601 |
| | CAL-33 | DSMZ | ACC-447 |
| | DETROIT 562 | ATCC | CCL-138 |
| | HSC-3 | JCRB | JCRB0623 |
| | HSC-4 | JCRB | JCRB0624 |
| | SCC-9 | ATCC | CRL-1629 |
| | YD-8 | KCLB | 60501 |
| Urinary Tract | CAL-29 | DSMZ | ACC-515 |
| | KMBC-2 | JCRB | JCRB1148 |
| | 253J | KCLB | 80001 |
| | 253J-BV | KCLB | 80002 |
| | SVV780 | ATCC | CRL-2169 |
| | SW1710 | DSMZ | ACC-426 |
| | VM-CUB-1 | DSMZ | ACC-400 |
| | BC-3C | DSMZ | ACC-450 |
| Central Nervous System | KNS-81 | JCRB | IF050359 |
| | TM-31 | RCB | RCB1731 |
| | NMC-G1 | JCRB | IF050467 |
| | GB-1 | JCRB | IF050489 |
| | SNU-201 | KCLB | 00201 |
| | DBTRG-05MG | ATCC | CRL-2020 |
| | YKG-1 | JCRB | JCRB0746 |
| Stomach | ECC10 | RCB | RCB0983 |
| | RERF-GC-1B | JCRB | JCRB1009 |
| | TGBC-11-TKB | RCB | RCB1148 |
| | SNU-620 | KCLB | 00620 |
| | GSU | RCB | RCB2278 |
| | KE-39 | RCB | RCB1434 |
| | HuG1-N | RCB | RCB1179 |
| | NUGC-4 | JCRB | JCRB0834 |
| | MKN-45 | JCRB | JCRB0254 |
| | SNU-16 | ATCC | CRL-5974 |
| | OCUM-1 | JCRB | JCRB0192 |
| Colon (Large and Small Intestines) | C2BBe1 | ATCC | CRL-2102 |
| | Caco-2 | ATCC | HTB-37 |
| | SNU-1033 | KCLB | 01033 |
| | SW1463 | ATCC | CCL-234 |
| | COLO 201 | ATCC | CCL-224 |
| | GP2d | ECACC | 95090714 |
| | LoVo | ATCC | CCL-229 |
| | SW403 | ATCC | CCL-230 |
| | CL-14 | DSMZ | ACC-504 |
| Breast | HCC2157 | ATCC | CRL-2340 |
| | HCC38 | ATCC | CRL-2314 |
| | HCC1954 | ATCC | CRL-2338 |
| | HCC1143 | ATCC | CRL-2321 |
| | HCC1806 | ATCC | CRL-2335 |
| | HCC1599 | ATCC | CRL-2331 |

TABLE 3-continued

| Cell lines expressing CSC markers | | | |
|---|---|---|---|
| Anatomical Site of Primary Tumor | Cell Line Common Name | Cell Line Source | Cell Line Source Identification |
| | MDA-MB-415 | ATCC | HTB-128 |
| | CAL-51 | DSMZ | ACC-302 |
| Hematopoietic and Lymphoid Tissue | KO52 | JCRB | JCRB0123 |
| | SKNO-1 | JCRB | JCRB1170 |
| | Kasumi-1 | ATCC | CRL-2724 |
| | Kasumi-6 | ATCC | CRL-2775 |
| | MHH-CALL-3 | DSMZ | ACC-339 |
| | MHH-CALL-2 | DSMZ | ACC-341 |
| | JVM-2 | ATCC | CRL-3002 |
| | HNT-34 | DSMZ | ACC-600 |
| Bone | HOS | ATCC | CRL-1543 |
| | OUMS-27 | JCRB | IFO50488 |
| | T1-73 | ATCC | CRL-7943 |
| | Hs 870.T | ATCC | CRL-7606 |
| | Hs 706.T | ATCC | CRL-7447 |
| | SJSA-1 | ATCC | CRL-2098 |
| | RD-ES | ATCC | HTB-166 |
| | U2OS | ATCC | HTB-96 |
| | SaOS-2 | ATCC | HTB-85 |
| | SK-ES-1 | ATCC | HTB-86 |

In certain embodiments, the vaccine compositions comprising a combination of cell lines are capable of stimulating an immune response and/or preventing cancer and/or treating cancer. The present disclosure provides compositions and methods of using one or more vaccine compositions comprising therapeutically effective amounts of cell lines.

The amount (e.g., number) of cells from the various individual cell lines in a cocktail or vaccine compositions can be equal (as defined herein) or different. In various embodiments, the number of cells from a cell line or from each cell line (in the case where multiple cell lines are administered) in a vaccine composition, is approximately $1.0\times10^6$, $2.0\times10^6$, $3.0\times10^6$, $4.0\times10^6$, $5.0\times10^6$, $6.0\times10^6$, $7.0\times10^6$, $8\times10^6$, $9.0\times10^6$, $1.0\times10^7$, $2.0\times10^7$, $3.0\times10^7$, $4.0\times10^7$, $5.0\times10^7$, $6.0\times10^7$, $8.0\times10^7$, or $9.0\times10^7$ cells.

The total number of cells administered to a subject, e.g., per administration site, can range from $1.0\times10^6$ to $9.0\times10^7$. For example, $2.0\times10^6$, $3.0\times10^6$, $4.0\times10^6$, $5.0\times10^6$, $6.0\times10^6$, $7.0\times10^6$, $8\times10^6$, $9.0\times10^6$, $1.0\times10^7$, $2.0\times10^7$, $3.0\times10^7$, $4.0\times10^7$, $5.0\times10^7$, $6.0\times10^7$, $8.0\times10^7$, $8.6\times10^7$, $8.8\times10^7$, or $9.0\times10^7$ cells are administered.

In certain embodiments, the number of cell lines included in each administration of the vaccine composition can range from 1 to 10 cell lines. In some embodiments, the number of cells from each cell line are not equal and different ratios of cell lines are used. For example, if one cocktail contains $5.0\times10^7$ total cells from 3 different cell lines, there could be $3.33\times10^7$ cells of one cell line and $8.33\times10^6$ of the remaining 2 cell lines.

HLA Diversity

HLA mismatch occurs when the subject's HLA molecules are different from those expressed by the cells of the administered vaccine compositions. The process of HLA matching involves characterizing 5 major HLA loci, which include the HLA alleles at three Class I loci HLA-A, —B and —C and two class II loci HLA-DRB1 and -DQB1. As every individual expresses two alleles at each loci, the degree of match or mismatch is calculated on a scale of 10, with 10/10 being a perfect match at all 10 alleles.

The response to mismatched HLA loci is mediated by both innate and adaptive cells of the immune system. Within the cells of the innate immune system, recognition of mismatches in HLA alleles is mediated to some extent by monocytes. Without being bound to any theory or mechanism, the sensing of "non-self" by monocytes triggers infiltration of monocyte-derived DCs, followed by their maturation, resulting in efficient antigen presentation to naïve T cells. Alloantigen-activated DCs produce increased amounts of IL-12 as compared to DCs activated by matched syngeneic antigens, and this increased IL-12 production results in the skewing of responses to Th1 T cells and increased IFN gamma production. HLA mismatch recognition by the adaptive immune system is driven to some extent by T cells. Without being bound to any theory or mechanism, 1-10% of all circulating T cells are alloreactive and respond to HLA molecules that are not present in self. This is several orders of magnitude greater than the frequency of endogenous T cells that are reactive to a conventional foreign antigen. The ability of the immune system to recognize these differences in HLA alleles and generate an immune response is a barrier to successful transplantation between donors and patients and has been viewed an obstacle in the development of cancer vaccines.

As many as 945 different HLA-A and -B alleles can be assigned to one of the nine supertypes based on the binding affinity of the HLA molecule to epitope anchor residues. In some embodiments, the vaccine compositions provided herein exhibit a heterogeneity of HLA supertypes, e.g., mixtures of HLA-A supertypes, and HLA-B supertypes. As described herein, various features and criteria may be considered to ensure the desired heterogeneity of the vaccine composition including, but not limited to, an individual's ethnicity (with regard to both cell donor and subject receiving the vaccine). Additional criteria are described herein (e.g., Example 22). In certain embodiments, a vaccine composition expresses a heterogeneity of HLA supertypes, wherein at least two different HLA-A and at least two HLA-B supertypes are represented.

In some embodiments, a composition comprising therapeutically effective amounts of multiple cell lines are provided to ensure a broad degree of HLA mismatch on multiple class I and class II HLA molecules between the tumor cell vaccine and the recipient.

In some embodiments, the vaccine composition expresses a heterogeneity of HLA supertypes, wherein the composition expresses a heterogeneity of major histocompatibility complex (MHC) molecules such that two of HLA-A24, HLA-A03, HLA-A01, and two of HLA-B07, HLA-B08, HLA-B27, and HLA-B44 supertypes are represented. In some embodiments, the vaccine composition expresses a heterogeneity HLA supertypes, wherein the composition expresses a heterogeneity of MHC molecules and at least the HLA-A24 is represented. In some exemplary embodiments, the composition expresses a heterogeneity of MHC molecules such that HLA-A24, HLA-A03, HLA-A01, HLA-B07, HLA-B27, and HLA-B44 supertypes are represented. In other exemplary embodiments, the composition expresses a genetic heterogeneity of MHC molecules such that HLA-A01, HLA-A03, HLA-B07, HLA-B08, and HLA-B44 supertypes are represented.

Patients display a wide breadth of HLA types that act as markers of self. A localized inflammatory response that promotes the release of cytokines, such as IFNγ and IL-2, is initiated upon encountering a non-self cell. In some embodiments, increasing the heterogeneity of HLA-supertypes within the vaccine cocktail has the potential to augment the localized inflammatory response when the vaccine is delivered conferring an adjuvant effect. As described herein, in some embodiments, increasing the breadth, magnitude, and immunogenicity of tumor reactive T cells primed by the cancer vaccine composition is accomplished by including multiple cell lines chosen to have mismatches in HLA types, chosen, for example, based on expression of certain TAAs. Embodiments of the vaccine compositions provided herein enable effective priming of a broad and effective anti-cancer response in the subject with the additional adjuvant effect generated by the HLA mismatch. Various embodiments of the cell line combinations in a vaccine composition express the HLA-A supertypes and HLA-B supertypes. Non-limiting examples are provided in Example 22 herein.

Cell Line Modifications

In certain embodiments, the vaccine compositions comprise cells that have been modified. Modified cell lines can be clonally derived from a single modified cell, i.e., genetically homogenous, or derived from a genetically heterogenous population.

Cell lines can be modified to express or increase expression of one or more immunostimulatory factors, to inhibit or decrease expression of one or more immunosuppressive factors, and/or to express or increase expression of one or more TAAs, including optionally TAAs that have been mutated in order to present neoepitopes (e.g., designed or enhanced antigens with NSMs) as described herein. Additionally, cell lines can be modified to express or increase expression of factors that can modulate pathways indirectly, such expression or inhibition of microRNAs. Further, cell lines can be modified to secrete non-endogenous or altered exosomes.

In addition to modifying cell lines to express a TAA or immunostimulatory factor, the present disclosure also contemplates co-administering one or more TAAs (e.g., an isolated TAA or purified and/or recombinant TAA) or immunostimulatory factors (e.g., recombinantly produced therapeutic protein) with the vaccines described herein.

Thus, in various embodiments, the present disclosure provides a unit dose of a vaccine comprising (i) a first composition comprising a therapeutically effective amount of at least 1, 2, 3, 4, 5 or 6 cancer cell lines, wherein the cell line or a combination of the cell lines comprises cells that express at least 5, 10, 15, 20, 25, 30, 35, or 40 tumor associated antigens (TAAs) associated with a cancer of a subject intended to receive said composition, and wherein the composition is capable of eliciting an immune response specific to the at least 5, 10, 15, 20, 25, 30, 35, or 40 TAAs, and (ii) a second composition comprising one or more isolated TAAs. In other embodiments, the first composition comprises a cell line or cell lines that is further modified to (a) express or increase expression of at least 1 immunostimulatory factor, and/or (ii) inhibit or decrease expression of at least 1 immunosuppressive factor.

Immunostimulatory Factors

An immunostimulatory protein is one that is membrane bound, secreted, or both that enhances and/or increases the effectiveness of effector T cell responses and/or humoral immune responses. Without being bound to any theory, immunostimulatory factors can potentiate antitumor immunity and increase cancer vaccine immunogenicity. There are many factors that potentiate the immune response. For example, these factors may impact the antigen-presentation mechanism or the T cell mechanism. Insertion of the genes for these factors may enhance the responses to the vaccine composition by making the vaccine more immunostimulatory of anti-tumor response.

Without being bound to any theory or mechanism, expression of immunostimulatory factors by the combination of cell lines included in the vaccine in the vaccine microenvironment (VME) can modulate multiple facets of the adaptive immune response. Expression of secreted cytokines such as GM-CSF and IL-15 by the cell lines can induce the differentiation of monocytes, recruited to the inflammatory environment of the vaccine delivery site, into dendritic cells (DCs), thereby enriching the pool of antigen presenting cells in the VME. Expression of certain cytokines can also mature and activate DCs and Langerhans cells (LCs) already present. Expression of certain cytokines can promote DCs and LCs to prime T cells towards an effector phenotype. DCs that encounter vaccine cells expressing IL-12 in the VME should prime effector T cells in the draining lymph node and mount a more efficient anti-tumor response. In addition to enhancing DC maturation, engagement of certain immunostimulatory factors with their receptors on DCs can promote the priming of T cells with an effector phenotype while suppressing the priming of T regulatory cells (Tregs). Engagement of certain immunostimulatory factors with their receptors on DCs can promote migration of DCs and T cell mediated acquired immunity.

In some embodiments of the vaccine compositions provided herein, modifications to express the immunostimulatory factors are not made to certain cell lines or, in other embodiments, all of the cell lines present in the vaccine composition.

Provided herein are embodiments of vaccine compositions comprising a therapeutically effective amount of cells from at least one cancer cell line (e.g., GBM cell line), wherein the cell line is modified to increase production of at least one (e.g., 2, 3, 4, 5, 6, 7, 8, 9, 10 or more) immunostimulatory factors. In some embodiments, the immunostimulatory factors are selected from those presented in Table 4. Also provided are exemplary NCBI Gene IDs that can be utilized by a skilled artisan to determine the sequences to be introduced in the vaccine compositions of the disclosure. These NCBI Gene IDs are exemplary only.

TABLE 4

Exemplary immunostimulatory factors

| Factor | NCBI Gene Symbol (Gene ID) |
|---|---|
| CCL5 | CCL5 (6352) |
| XCL1 | XCL1 (6375) |
| Soluble CD40L (CD154) | CD40LG (959) |
| Membrane-bound CD40L | CD40LG (959) |
| CD36 | CD36 (948) |
| GITR | TNFRSF18 (8784) |
| GM-CSF | CSF2 (1437) |
| OX-40 | TNFRSF4 (7293) |
| OX-40L | TNFSF4 (7292) |
| CD137 (41BB) | TNFRSF9 (13604) |
| CD80 (B7-1) | CD80 (941) |
| IFNγ | IFNG (3458) |
| IL-1pβ | ILI B (3553) |
| IL-2 | IL2 (3558) |
| IL-6 | IL6 (3569) |
| IL-7 | IL7 (3574) |
| IL-9 | IL9 (3578) |
| IL-12 | IL12A (3592) IL12B (3593) |
| IL-15 | IL15 (3600) |
| IL-18 | IL-18 (3606) |
| IL-21 | IL21 (59067) |
| IL-23 | IL23A (51561) IL12B (3593) |
| TNFα | TNF (7124) |

In some embodiments, the cell lines of the vaccine composition can be modified (e.g., genetically modified) to express overexpress, or increase the expression of one or more immunostimulatory factors selected from Table 4. In certain embodiments, the immunostimulatory sequence can be a native human sequence. In some embodiments, the immunostimulatory sequence can be a genetically engineered sequence. The genetically engineered sequence may be modified to increase expression of the protein through codon optimization, or to modify the cellular location of the protein (e.g., through mutation of protease cleavage sites).

For example, at least one (i.e., 1, 2, 3, 4, 5, 6, 7, 8, 9, 10, or more) of the cancer cell lines in any of the vaccine compositions described herein may be genetically modified to express or increase expression of one or more immunostimulatory factors. The immunostimulatory factors expressed by the cells within the composition may all be the same, may all be different, or any combination thereof.

In some embodiments, a vaccine composition comprises a therapeutically effective amount of cells from at least one cancer cell line, wherein the at least one cell line is modified to express 1, 2, 3, 4, 5, 6, 7, 8, 9, 10, or more of the immunostimulatory factors of Table 4. In some embodiments, the composition comprises a therapeutically effective amount of cells from 2, 3, 4, 5, 6, 7, 8, 9, or 10 cancer cell lines. In some embodiments, the at least one cell line is modified to increase the production of at least 2, 3, 4, 5, 6, 7, 8, 9 or 10 immunostimulatory factors of Table 5. In some embodiments, the composition comprises a therapeutically effective amount of cells from 2, 3, 4, 5, 6, 7, 8, 9, or 10 cancer cell lines, and each cell line is modified to increase the production of at least 2, 3, 4, 5, 6, 7, 8, 9 or 10 immunostimulatory factors of Table 4.

In some embodiments, the composition comprises a therapeutically effective amount of cells from 3 cancer cells lines wherein 1, 2, or all 3 of the cell lines have been modified to express or increase expression of GM-CSF, membrane bound CD40L, and IL-12.

Exemplary combinations of modifications, e.g., where a cell line or cell lines have been modified to express or increase expression of more than one immunostimulatory factor include but are not limited to: GM-CSF+IL-12; CD40L+IL-12; GM-CSF+CD40L; GM-CSF+IL-12+CD40L; GM-CSF+IL-15; CD40L+IL-15; GM-CSF+CD40L; and GM-CSF+IL-15+CD40L, among other possible combinations.

In certain instances, tumor cells express immunostimulatory factors including the IL-12A (p35 component of IL-12), GM-CSF (kidney cell lines), and CD40L (leukemia cell lines). Thus, in some embodiments, cell lines may also be modified to increase expression of one or more immunostimulatory factors.

In some embodiments, the cell line combination of or cell lines that have been modified as described herein to express or increase expression of one or more immunostimulatory factors will express the immunostimulatory factor or factors at least 2, 3, 4, 5, 6, 7, 8, 9, 10-fold or more relative to the same cell line or combination of cell lines that have not been modified to express or increase expression of the one or more immunostimulatory factors.

Methods to increase immunostimulatory factors in the vaccine compositions described herein include, but are not limited to, introduction of the nucleotide sequence to be expressed byway of a viral vector or DNA plasmid. The expression or increase in expression of the immunostimulatory factors can be stable expression or transient expression.

In some embodiments, the cancer cells in any of the vaccine compositions described herein are genetically modified to express CD40 ligand (CD40L). In some embodiments, the CD40L is membrane bound. In some embodiments, the CD40L is not membrane bound. Unless stated otherwise, as used herein CD4L refers to membrane bound CD40L. In some embodiments, the cancer cells in any of the vaccine compositions described herein are genetically modified to express GM-CSF, membrane bound CD40L, GITR, IL-12, and/or IL-15. Exemplary amino acid and nucleotide sequences useful for expression of the one or more of the immunostimulatory factors provided herein are presented in Table 5.

TABLE 5

Sequences of exemplary immunostimulatory factors

| Factor | Sequence |
|---|---|
| CD154 (CD40L) (membrane bound) | atgatcgaaacatacaaccaaacttctccccgatctgcggccactggactgcccatcagcatgaaaatttttatgtatttacttactgtttttct tatcacccagatgattgggtcagcacttttttgctgtgtatcttcatagaaggttggacaagatagaagatgaaaggaatcttcatgaagattttg tattcatgaaaacgatacagagatgcaacacaggagaaagatccttatccttactgaactgtgaggagattaaaagccagtttgaaggctttgtg aaggatataatgttaaacaaagaggagacgaagaaagaaaacagctttgaaatgcctcgtggtgaagaggatagtcaaattgcggcacatgtcat aagtgaggccagcagtaaaacaacatctgtgttacagtgggctgaaaaaggatactacaccatgagcaacaacttggtaaccctggaaaatggga aacagctgaccgttaaaagacaaggactctattatatctatgcccaagtcaccttctgttccaatcgggaagcttcgagtcaagctccatttat agccagcctctgcctaaagtcccccggtagattcgagagaatcttactcagagctgcaaatacccacagttccgccaaaccttgcgggcaacaa tccattcacttgggaggagtatttgaattgcaaccaggtgcttcggtgtttgtcaatgtgactgatccaagccaagtgagccatggcactggctt cacgtcctttggcttactcaaactctga (SEQ ID NO: 1) |
| CD154 (CD40L) (membrane bound) (codon-optimized) | Atgatcgaaacctacaaccagacctcaccacgaagtgccgccaccggactgcctattagtatgaaaatctttatgtacctgctgacagtgttcct gatcacccagatgatcggctccgccctgtttgccgtgtacctgcaccggagactggacaagatcgaggatgagcggaacctgcacgaggact tcgtgtttatgaagaccatccagcggtgcaacacaggcgagagaagcctgtccctgctgaattgtgaggagatcaagagccagttcgagggc tttgtgaaggacatcatgctgaacaaggaggagacaaagaaggagaacagcttcgagatgcccagaggcgaggaggattcccagatcgc cgcccacgtgatctctgaggccagctccaagaccacaagcgtgctgcagtgggccgagaagggctactataccatgtctaacaatctggtga cactggagaacggcaagcagctgaccgtgaagaggcagggcctgtactatatctatgcccaggtgacattctgcagcaatcgcgaggcctct agccaggcccccttttatcgccagcctgtgcctgaagagccctggcaggttcgagcgcatcctgctgagagccgccaacacccactcctctgcc aagccatgcggacagcagtcaatccacctgggaggcgtgttcgagctgcagccaggagcaagcgtgttcgtgaatgtgactgacccatcac aggtgtctcacggcactggattcacatcatttggactgctgaaactgtga (SEQ ID NO: 2) |
| CD154 (CD40L) (membrane bound) | MIETYNQTSPRSAATGLPISMKIFMYLLTVFLITQMIGSALFAVYLHRRLDKIEDERNLHEDFVFMKTIQR CNTGERSLSLLNCEEIKSQFEGFVKDIMLNKEETKKENSFEMPRGEEDSQIAAHVISEASSKTTSVLQ WAEKGYYTMSNNLVTLENGKQLTVKRQGLYYIYAQVTFCSNREASSQAPFIASLCLKSPGRFERILLR AANTHSSAKPCGQQSIHLGGVFELQPGASVFVNVTDPSQVSHGTGFTSFGLLKL (SEQ ID NO: 3) |
| GITR | Atggctcagcatggggctatgggggccttcagggctctgtgcggactggctctgctgtgcgctctgtcactggggcagagaccaacaggagg accaggatgcggacctggcaggctgctgctgggcaccggcacagacgcaaggtgctgtagagtgcacaccacaaggtgctgtcgcgacta ccctggcgaggagtgctgttctgagtgggattgcatgtgcgtgcagccagagtttcactgtggcgatccctgctgtaccacatgccgccaccacc catgtccacctggacagggagtgcagtctcagggcaagttcagctttggcttccagtgcatcgactgtgcaagcggcaccttttccggaggaca |

TABLE 5-continued

Sequences of exemplary immunostimulatory factors

| Factor | Sequence |
|---|---|
| | cgagggacactgcaagccctggaccgattgtacacagtttggcttcctgaccgtgttccctggcaacaagacacacaatgccgtgtgcgtgcct<br>ggctccccaccagcagagcccctgggctggctgaccgtggtgctgctggccgtggcagcatgcgtgctgctgctgacaagcgcccagctggg<br>actgcacatctggcagctgcggtcccagtgtatgtggccaagagagacccagctgctgctggaggtgcctccatccacagaggacgcccggt<br>cttgccagttccccgaagaggagagggggaaagaagtgccgaagaaaagggaaggctgggagacctgtgggtg (SEQ ID NO: 4) |
| GITR | MAQHGAMGAFRALCGLALLCALSLGQRPTGGPGCGPGRLLLGTGTDARCCRVHTTRCCRDYPGEE<br>CCSEWDCMCVQPEFHCGDPCCTTCRHHPCPPGQGVQSQGKFSFGFQCIDCASGTFSGGHEGHCK<br>PWTDCTQFGFLTVFPGNKTHNAVCVPGSPPAEPLGWLTWLLAVAACVLLLTSAQLGLHIWQLRSQC<br>MWPRETQLLLEVPPSTEDARSCQFPEEERGERSAEEKGRLGDLWV (SEQ ID NO: 5) |
| GM-CSF | atgtggctgcagagcctgctgctcttgggcactgtggcctgcagcatctctgcacccgcccgctcgcccagccccagcacgcagccctgggag<br>catgtgaatgccatccaggaggcccggcgtctcctgaacctgagtagagacactgctgctgagatgaatgaaacagtagaagtcatctcaga<br>aatgtttgacctccaggagccgacctgcctacagacccgcctggagctgtacaagcagggcctgcggggcagcctcaccaagctcaaggg<br>ccccttgaccatgatggccagccactacaagcagcactgccctccaaccccggaaacttcctgtgcaacccagattatcacctttgaaagtttc<br>aaagagaacctgaaggactttctgcttgtcatcccctttgactgctgggagccagtccaggagtga (SEQ ID NO: 6) |
| GM-CSF (codon-optimized) | atgtggctgcagtctctgctgctgctgggcaccgtcgcctgttctatttccgcacccgctcgctccccttctccctcaactcagccttgggagca<br>cgtgaacgccatccaggaggcccggagactgctgaatctgtcccgggacaccgccgccgagatgaacgagacagtggaagtgatctctgagat<br>gttcgatctgcaggagcccacctgcctgcagacaaggctggagctgtacaagcagggcctgcgcggctctctgaccaagctgaagggccca<br>ctgacaatgatggccagccactataagcagcactgccccctacccccgagacaagctgtgccacccagatcatcacattcgagtcctttaag<br>gagaacctgaaggactttctgctggtcattccatttgattgttgggagcccgtgcaggagtga (SEQ ID NO: 7) |
| GM-CSF | MWLQSLLLLGTVACSISAPARSPSPSTQPWEHVNAIQEARRLLNLSRDTAAEMNETVEVISEMFDLQE<br>PTCLQTRLELYKQGLRGSLTKLKGPLTMMASHYKQHCPPTPETSCATQIITFESFKENLKDFLLVIPFD<br>CWEPVQE (SEQ ID NO: 8) |
| IL-12 | atgtgccatcagcaactggttatatcttggttcagtctcgtctttctcgcgtcacccttggtcgctatctgggagcttaaaaaagatgtctacgt<br>cgttgaacttgattggtaccctgatgctccgggggaaatggtggttttgacttgcgatacgccagaagaggatggcataacgtggacactggacc<br>agtcttcagaggttctcgggtctggtaagacactcactatacaggtgaaggagtttggtgacgcaggacaatatacttgccataaaggcggcgag<br>gtgctctcccatagccttctgctccttcataaaaaagaggacgggatatggtcaactgacattctgaaggatcagaaagaaccgaagaacaaaac<br>tttcctcagatgcgaggcaaagaactattcaggccgctttacttgctggtggctcactaccatcagcactgacctcactttcagcgtcaagagca<br>gtagaggctcaagtgacccacaaggggttacatgcggggccgctacgttgtctgccgagcgagtcaggggagataataaggaatatgagtata<br>gcgttgaatgccaagaagattcagcctgcccagccgcagaagagagtcttcccatagaagttatggtggacgcagttcataaactgaagtatga<br>gaactatacatcttccttctttattcgcgatatcataaagcctgatcctccgaaaaacttgcaactcaagccgttgaagaatagccgacaggtcg<br>aggtctcttgggagtatccagatacgtggtctaccccgcactcctatttcagtctcaccttctgtgtgcaggtgcaggggaaaagtaagcgggaa<br>aaaaaggaccgggtatttactgataagacctccgctacagtgatttgtagaaagaacgcctctatcagcgtgagagcccaggatagatattatt<br>ctagtagttggtctgagtgggcctccgtcccttgttccggaagcggagccacgaacttctctctgttaaagcaagcaggagatgttgaagaaaac<br>cccgggcctatgtgtccagcgcgcagcctcctccttgtggctaccctggtcctcctggaccacctcagtttggcccgaaacctgccggtcgctac<br>acccgatcctggaatgtttccctgccttcatcacagccagaatctgctgagggcagtcagtaacatgctgcagaaggcgcggcaaactctgga<br>gttctatccatgtacctccgaggaaattgatcacgaggacattactaaggataaaacaagtacagtagaagcctgtttgcctcttgagctcacta<br>aaaatgagtcatgcttgaacagtcgagagacgagttttatcactaacggttcatgcttggcgtccaggaagacaagctttatgatggcgctctgc<br>ctgtcttctatatatgaagaccttaaaatgtaccaagttgagtttaagaccatgaacgccaaacttttgatggaccccaagaggcagatcttcct<br>tgatcagaatatgttggcggtgatcgatgaacttatgcaagctttgaacttcaacagtgagacagtgcctcagaaaagttccttggaggaaccgg<br>acttctataagaccaagatcaaactgtgcattttgctgcatgcatttagaattcgagccgttacaatcgaccgggtgatgtcatatttgaatgca<br>tcataa (SEQ ID NO: 9) |
| IL-12 | MCHQQLVISWFSLVFLASPLVAIWELKKDVYVVELDWYPDAPGEMVVLTCDTPEEDGITWTLDQSSE<br>VLGSGKTLTIQVKEFGDAGQYTCHKGGEVLSHSLLLLHKKEDGIWSTDILKDQKEPKNKTFLRCEAKN<br>YSGRFTCWWLTTISTDLTFSVKSSRGSSDPQGVTCGAATLSAERVRGDNKEYEYSVECQEDSACPA<br>AEESLPIEVMVDAVHKLKYENYTSSFFIRDIIKPDPPKNLQLKPLKNSRQVEVSWEYPDTWSTPHSYFS<br>LTFCVQVQGKSKREKKDRVFTDKTSATVICRKNASISVRAQDRYYSSSWSEWASVPCSGSGATNFSL<br>LKQAGDVEENPGPMCPARSLLLVATLVLLDHLSLARNLPVATPDPGMFPCLHHSQNLLRAVSNMLQK<br>ARQTLEFYPCTSEEIDHEDITKDKTSTVEACLPLELTKNESCLNSRETSFITNGSCLASRKTSFMMALC<br>LSSIYEDLKMYQVEFKTMNAKLLMDPKRQIFLDQNMLAVIDELMQALNFNSETVPQKSSLEEPDFYKT<br>KIKLCILLHAFRIRAVTIDRVMSYLNAS (SEQ ID NO: 10) |
| IL-15 | Atgtataggatgcagctgctgtcatgtatcgcactgtccctggcactggtgactaactctaactgggtgaatgtgatctccgacctgaagaagat<br>cgaggacctgatccagtctatgcacatcgatgccaccctgtacacagagtccgacgtgcaccccctcttgcaaggtgaccgccatgaagtgtttcc<br>tgctggagctgcaggtcatcagcctggagagcggcgacgcatccatccacgataccgtggagaacctgatcatcctggccaacaatagcctg<br>agctccaacggcaatgtgacagagtccggctgcaaggagtgtgaggagctggaggagaagaatatcaaagagttcctgcagtcattcgtcc<br>atatcgtccagatgtttatcaataccagt (SEQ ID NO: 11) |
| IL-15 | MYRMQLLSCIALSLALVTNSNWVNVISDLKKIEDLIQSMHIDATLYTESDVHPSCKVTAMKCFLLELQVI<br>SLESGDASIHDTVENLIILANNSLSSNGNVTESGCKECEELEEKNIKEFLQSFVHIVQMFINTS (SEQ ID<br>NO: 12) |
| IL-23 | atgtgccatcagcagctggtcattagttggtttagcctggtctttctggcctcacccctggtcgcaatctgggaactgaagaaggacgtgtacgt<br>ggtggagctggactggtatccagatgcaccaggagagatggtggtgctgacctgcgacacacctgaggaggatggcatcacctggacactgga<br>tcagagctccgaggtgctgggcagcggcaagaccctgacaatccaggtgaaggagttcggcgacgccggccagtacacatgtcacaagg<br>gcggcgaggtgctgtcccactctctgctgctgctgcacaagaaggaggacggcatctggtccacagacatcctgaaggatcagaaggagcc<br>aaagaacaagaccttcctgcggtgcgaggccaagaattatagcggccggttcacctgttggtggctgaccacaatctccaccgatctgacattt<br>tctgtgaagtctagcaggggctcctctgacccccagggagtgacatgcggagcagccaccctgagcgccgagcgggtgagaggcgataac<br>aaggagtacgagtattctgtggagtgccaggaggacagcgcctgtccagcagcagaggagtccctgcctatcgaagtgatggtggatgccgt<br>gcacaagctgaagtacgagaattatacaagctccttctttatcagggacatcatcaagccagatcccccctaagaacctgcagctgaagcccct<br>gaagaatagccgccaggtggaggtgtcctgggagtaccctgacacctggtccacaccacactcttatttcagcctgaccttttgcgtgcaggtgc<br>agggcaagagcaagagggagaagaaggaccgcgtgttcaccgataagacatccgccaccgtgatctgtcggaagaacgccagcatctcc |

TABLE 5-continued

Sequences of exemplary immunostimulatory factors

| Factor | Sequence |
|---|---|
| | gtgagggcccaggatcgctactattctagctcctggagcgagtgggcctccgtgccatgctctggaggaggaggcagcggcggaggaggct ccggaggcggcggctctggcggcggcggctccctgggctctcgggccgtgatgctgctgctgctgctgccctggaccgcacagggaagagc cgtgccaggaggctctagcccagcatggacacagtgccagcagctgtcccagaagctgtgcaccctggcatggtctgcccaccctctggtgg gccacatggacctgagagaggagggcgatgaggagaccacaaacgacgtgcctcacatccagtgcggcgacggctgtgatccacaggg cctgagggacaattctcagttctgtctgcagcgcatccaccagggcctgatcttctacgagaagctgctgggcagcgatatctttacaggagag cccagcctgctgcctgactccccagtgggacagctgcacgcctctctgctgggcctgagccagctgctgcagccagagggacaccactggg agacccagcagatcccttctctgagcccatcccagccttggcagcggctgctgctgcggttcaagatcctgagaagcctgcaggcattcgtcgc agtcgcagccagggtgttcgcccacggagccgctactctgagccca (SEQ ID NO: 13) |
| IL-23 | MCHQQLVISWFSLVFLASPLVAIWELKKDVYVVELDWYPDAPGEMVVLTCDTPEEDGITWTLDQSSE VLGSGKTLTIQVKEFGDAGQYTCHKGGEVLSHSLLLLHKKEDGIWSTDILKDQKEPKNKTFLRCEAKN YSGRFTCWWLTTISTDLTFSVKSSRGSSDPQGVTCGAATLSAERVRGDNKEYEYSVECQEDSACPA AEESLPIEVMVDAVHKLKYENYTSSFFIRDIIKPDPPKNLQLKPLKNSRQVEVSWEYPDTWSTPHSYFS LTFCVQVQGKSKREKKDRVFTDKTSATVICRKNASISVRAQDRYYSSSWSEWASVPCSGGGGSGGG GSGGGGSGGGGSLGSRAVMLLLLLPWTAQGRAVPGGSSPAWTQCQQLSQKLCTLAWSAHPLVGH MDLREEGDEETTNDVPHIQCGDGCDPQGLRDNSQFCLQRIHQGLIFYEKLLGSDIFTGEPSLLPDSPV GQLHASLLGLSQLLQPEGHHWETQQIPSLSPSQPWQRLLLRFKILRSLQAFVAVAARVFAHGAATLSP (SEQ ID NO: 14) |
| XCL1 | atgaggctgctgattctggcactgctgggcatctgctctctgaccgcttacatcgtggaaggagtcggctctgaagtctctgacaagcgcacatg cgtgtctctgaccacacagcgcctgcccgtgagccggatcaagacctacacaatcaccgagggcagcctgagagccgtgatcttcatcacaa agaggggcctgaaggtgtgcgccgaccctcaggcaacctgggtgcgggacgtggtgagaagcatggataggaagtccaacacccggaac aatatgatccagacaaaacccacaggaacccagcagagcactaatacagccgtgacactgaccggg (SEQ ID NO: 15) |
| XCL1 | MRLLILALLGICSLTAYIVEGVGSEVSDKRTCVSLTTQRLPVSRIKTYTITEGSLRAVIFITKRGLKVCADP QATWVRDWRSMDRKSNTRNNMIQTKPTGTQQSTNTAVTLTG (SEQ ID NO: 16) |

Provided herein is a GITR protein comprising the amino acid sequence of SEQ ID NO: 4, or a nucleic acid sequence encoding the same, e.g., SEQ ID NO: 5. Provided herein is a vaccine composition comprising one or more cell lines expressing the same.

Provided herein is a GM-CSF protein comprising the amino acid sequence of SEQ ID NO: 8, or a nucleic acid sequence encoding the same, e.g., SEQ ID NO: 6 or SEQ ID NO: 7. Provided herein is a vaccine composition comprising one or more cell lines expressing the same.

Provided herein is an IL-12 protein comprising the amino acid sequence of SEQ ID NO: 10, or a nucleic acid sequence encoding the same, e.g., SEQ ID NO: 9. Provided herein is a vaccine composition comprising one or more cell lines expressing the same.

Provided herein is an IL-15 protein comprising the amino acid sequence of SEQ ID NO: 12, or a nucleic acid sequence encoding the same, e.g., SEQ ID NO: 11. Provided herein is a vaccine composition comprising one or more cell lines expressing the same.

Provided herein is an IL-23 protein comprising the amino acid sequence of SEQ ID NO: 14, or a nucleic acid sequence encoding the same, e.g., SEQ ID NO: 13. Provided herein is a vaccine composition comprising one or more cell lines expressing the same.

Provided herein is a XCL1 protein comprising the amino acid sequence of SEQ ID NO: 16, or a nucleic acid sequence encoding the same, e.g., SEQ ID NO: 15. Provided herein is a vaccine composition comprising one or more cell lines expressing the same.

In some embodiments, the cancer cells in any of the vaccine compositions described herein are genetically modified to express one or more of CD28, B7-H2 (ICOS LG), CD70, CX3CL1, CXCL10 (IP10), CXCL9, LFA-1 (ITGB2), SELP, ICAM-1, ICOS, CD40, CD27 (TNFRSF7), TNFRSF14 (HVEM), BTN3A1, BTN3A2, ENTPD1, GZMA, and PERF1.

In some embodiments, vectors contain polynucleotide sequences that encode immunostimulatory molecules. Exemplary immunostimulatory molecules may include any of a variety of cytokines. The term "cytokine" as used herein refers to a protein released by one cell population that acts on one or more other cells as an intercellular mediator. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and —II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1 through IL-36, including, IL-1, IL-1alpha, IL-2, IL-3, IL-7, IL-8, IL-9, IL-11, IL-12; IL-15, IL-18, IL-21, IL-23, IL-27, TNF; and other polypeptide factors including LIF and kit ligand (KL). Other immunomodulatory molecules contemplated for use herein include IRF3, B7.1, B7.2, 4-1BB, CD40 ligand (CD40L), drug-inducible CD40 (iCD40), and the like.

In certain embodiments, polynucleotides encoding the immunostimulatory factors are under the control of one or more regulatory elements that direct the expression of the coding sequences. In various embodiments, more than one (i.e., 2, 3, or 4) immunostimulatory factors are encoded on one expression vector. In some embodiments, more than one (i.e., 2, 3, 4, 5, or 6) immunostimulatory factors are encoded on separate expression vectors. Lentivirus containing a gene or genes of interest (e.g., GM-CSF, CD40L, or IL-12 and other immunostimulatory molecules as described herein) are produced in various embodiments by transient co-transfection of 293T cells with lentiviral transfer vectors and packaging plasmids (OriGene) using LipoD293™ In Vitro DNA Transfection Reagent (SignaGen Laboratories).

For lentivirus infection, in some embodiments, cell lines are seeded in a well plate (e.g., 6-well, 12-well) at a density of 1-10×$10^5$ cells per well to achieve 50-80% cell confluency on the day of infection. Eighteen-24 hours after seeding, cells are infected with lentiviruses in the presence of 10 μg/mL of polybrene. Eighteen-24 hours after lentivirus infection, cells are detached and transferred to larger vessel. After 24-120 hours, medium is removed and replaced with fresh medium supplemented with antibiotics.

Immunosuppressive Factors

An immunosuppressive factor is a protein that is membrane bound, secreted, or both and capable of contributing to defective and reduced cellular responses. Various immunosuppressive factors have been characterized in the context of the tumor microenvironment (TME). In addition, certain immunosuppressive factors can negatively regulate migration of LCs and DCs from the dermis to the draining lymph node.

TGFβ1 is a suppressive cytokine that exerts its effects on multiple immune cell subsets in the periphery as well as in the TME. In the VME, TGFβ1 negatively regulates migration of LCs and DCs from the dermis to the draining lymph node. Similarly, TGFβ2 is secreted by most tumor cells and exerts immunosuppressive effects similar to TGFβ1. Modification of the vaccine cell lines to reduce TGFβ1 and/or TGFβ2 secretion in the VME ensures the vaccine does not further TGFβ-mediated suppression of LC or DC migration.

Within the TME, CD47 expression is increased on tumor cells as a mode of tumor escape by preventing macrophage phagocytosis and tumor clearance. DCs also express SIRPα, and ligation of SIRPα on DCs can suppress DC survival and activation. Additional immunosuppressive factors in the vaccine that could play a role in the TME and VME include CD276 (B7-H3) and CTLA4. DC contact with a tumor cell expressing CD276 or CTLA4 in the TME dampens DC stimulatory capabilities resulting in decreased T cell priming, proliferation, and/or promotes proliferation of T cells. Expression of CTLA4 and/or CD276 on the vaccine cell lines could confer the similar suppressive effects on DCs or LCs in the VME.

In certain embodiments of the vaccine compositions, production of one or more immunosuppressive factors can be inhibited or decreased in the cells of the cell lines contained therein. In some embodiments, production (i.e., expression) of one or more immunosuppressive factors is inhibited (i.e., knocked out or completely eliminated) in the cells of the cell lines contained in the vaccine compositions. In some embodiments, the cell lines can be genetically modified to decrease (i.e., reduce) or inhibit expression of the immunosuppressive factors. In some embodiments, the immunosuppressive factor is excised from the cells completely. In some embodiments, one or more of the cell lines are modified such that one or more immunosuppressive factor is produced (i.e., expressed) at levels decreased or reduced by at least 5, 10, 15, 20, 25, or 30% (i.e., at least 5, 10, 15, 20, 25, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In some embodiments, the one or more immunosuppressive factors is selected from the group presented in Table 6.

Simultaneously, production of one or more immunostimulatory factors, TAAs, and/or neoantigens can be increased in the vaccine compositions as described herein. In some embodiments of the vaccine compositions, in addition to the partial reduction or complete (e.g., excision and/or expression at undetectable levels) inhibition of expression of one or more immunosuppressive factors by the cell, one or more (i.e., 1, 2, 3, 4, 5, 6, 7, 8, 9, 10, or more) of the cell types within the compositions also can be genetically modified to increase the immunogenicity of the vaccine, e.g., by ensuring the expression of certain immunostimulatory factors, and/or TAAs.

Any combinations of these actions, modifications, and/or factors can be used to generate the vaccine compositions described herein. By way of non-limiting example, the combination of decreasing or reducing expression of immunosuppressive factors by at least 5, 10, 15, 20, 25, or 30% and increasing expression of immunostimulatory factors at least 2-fold higher than an unmodified cell line may be effective to improve the anti-tumor response of tumor cell vaccines. By way of another non-limiting example, the combination of reducing immunosuppressive factors by at least 5, 10, 15, 20, 25, or 30% and modifying cells to express certain TAAs in the vaccine composition, may be effective to improve the anti-tumor response of tumor cell vaccines.

In some embodiments, a cancer vaccine comprises a therapeutically effective amount of cells from at least one cancer cell line, wherein the cell line is modified to reduce production of at least one immunosuppressive factor by the cell line, and wherein the at least one immunosuppressive factor is CD47 or CD276. In some embodiments, expression of CTLA4, HLA-E, HLA-G, TGFβ1, and/or TGFβ2 are also reduced. In some embodiments, one or more, or all, cell lines in a vaccine composition are modified to inhibit or reduce expression of CD276, TGFβ1, and TGFβ2. In another embodiment, a vaccine composition is provided comprising three cell lines that have each been modified to inhibit (e.g., knockout) expression of CD276, and reduce expression of (e.g., knockdown) TGFβ1 and TGFβ2.

In some embodiments, a cancer vaccine composition comprises a therapeutically effective amount of cells from a cancer cell line wherein the cell line is modified to reduce expression of at least CD47. In some embodiments, the CD47 is excised from the cells or is produced at levels reduced by at least 5, 10, 15, 20, 25, or 30% (i.e., at least 5, 10, 15, 20, 25, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In some embodiments, CD47 is excised from the cells or is produced at levels reduced by at least 90%. Production of additional immunosuppressive factors can be reduced in one or more cell lines. In some embodiments, expression of CD276, CTLA4, HLA-E, HLA-G, TGFβ1, and/or TGFβ2 are also reduced or inhibited. Production of one or more immunostimulatory factors, TAAs, or neoantigens can be increased in one or more cell lines in these vaccine compositions.

In some embodiments, provided herein is a cancer vaccine composition comprising a therapeutically effective amount of cells from a cancer cell line wherein the cell line is modified to reduce production of at least CD276. In some embodiments, the CD276 is excised from the cells or is produced at levels reduced by at least 5, 10, 15, 20, 25, or 30% (i.e., at least 5, 10, 15, 20, 25, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In some embodiments, CD276 is excised from the cells or is produced at levels reduced by at least 90%. Production of additional immunosuppressive factors can be reduced in one or more cell lines. In some embodiments, expression of CD47, CTLA4, HLA-E, HLA-G, TGFβ1, and/or TGFβ2 are also reduced or inhibited. Production of one or more immunostimulatory factors, TAAs, or neoantigens can be increased in one or more cell lines in these vaccine compositions.

In some embodiments, provided herein is a cancer vaccine composition comprising a therapeutically effective amount of cells from a cancer cell line wherein the cell line is modified to reduce production of at least HLA-G. In some embodiments, the HLA-G is excised from the cells or is produced at levels reduced by at least 5, 10, 15, 20, 25, or 30% (i.e., at least 5, 10, 15, 20, 25, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In some embodiments, HLA-G is excised from the cells or is produced at levels reduced by at least 90%. Production of additional immunosuppressive factors can be reduced in one or more cell lines. In some embodiments, expression of CD47, CD276, CTLA4, HLA-E, TGFβ1, and/or TGFβ2 are also reduced or inhibited. Production of one or more immunostimulatory factors, TAAs, or neoantigens can be increased in one or more cell lines in these vaccine compositions.

In some embodiments, provided herein is a cancer vaccine composition comprising a therapeutically effective amount of cells from a cancer cell line wherein the cell line is modified to reduce production of at least CTLA4. In some embodiments, the CTLA4 is excised from the cells or is produced at levels reduced by at least 5, 10, 15, 20, 25, or 30% (i.e., at least 5, 10, 15, 20, 25, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In some embodiments, CTLA4 is excised from the cells or is produced at levels reduced by at least 90%. Production of additional immunosuppressive factors can be reduced in one or more cell lines. In some embodiments, expression of CD47, CD276, HLA-E, TGFβ1, and/or TGFβ2 are also reduced or inhibited. Production of one or more immunostimulatory factors, TAAs, or neoantigens can be increased in one or more cell lines in these vaccine compositions.

In some embodiments, provided herein is a cancer vaccine composition comprising a therapeutically effective amount of cells from a cancer cell line wherein the cell line is modified to reduce production of at least HLA-E. In some embodiments, the HLA-E is excised from the cells or is produced at levels reduced by at least 5, 10, 15, 20, 25, or 30% (i.e., at least 5, 10, 15, 20, 25, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In some embodiments, HLA-E is excised from the cells or is produced at levels reduced by at least 90%. Production of additional immunosuppressive factors can be reduced in one or more cell lines. In some embodiments, expression of CD47, CD276, CTLA4, TGFβ1, and/or TGFβ2 are also reduced or inhibited. Production of one or more immunostimulatory factors, TAAs, or neoantigens can be increased in one or more cell lines in these vaccine compositions.

In some embodiments, provided herein is a cancer vaccine composition comprising a therapeutically effective amount of cells from a cancer cell line wherein the cell line is modified to reduce production of TGFβ1, TGFβ2, or both TGFβ1 and TGFβ2. In some embodiments, TGFβ1, TGFβ2, or both TGFβ1 and TGFβ2 is excised from the cells or is produced at levels reduced by at least 5, 10, 15, 20, 25, or 30% (i.e., at least 5, 10, 15, 20, 25, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In some embodiments of the vaccine composition, TGFβ1, TGFβ2, or both TGFβ1 and TGFβ2 is excised from the cells or is produced at levels reduced by at least 90%.

In some embodiments, TGFβ1, TGFβ2, or both TGFβ1 and TGFβ2 expression is reduced via a short hairpin RNA (shRNA) delivered to the cells using a lentiviral vector. Production of additional immunosuppressive factors can be reduced. In some embodiments, expression of CD47, CD276, CTLA4, HLA-E, and/or HLA-G are also reduced in one or more cell lines where TGFβ1, TGFβ2, or both TGFβ1 and TGFβ2 expression is reduced. Production of one or more immunostimulatory factors, TAAs, or neoantigens can also be increased in one or more cell lines in embodiments of these vaccine compositions.

In some embodiments, the immunosuppressive factor selected for knockdown or knockout may be encoded by multiple native sequence variants. Accordingly, the reduction or inhibition of immunosuppressive factors can be accomplished using multiple gene editing/knockdown approaches known to those skilled in the art. As described herein, in some embodiments complete knockout of one or more immunosuppressive factors may be less desirable than knockdown. For example, TGFβ1 contributes to the regulation of the epithelial-mesenchymal transition, so complete lack of TGFβ1 (e.g., via knockout) may induce a less immunogenic phenotype in tumor cells.

Table 6 provides exemplary immunosuppressive factors that can be incorporated or modified as described herein, and combinations of the same. Also provided are exemplary NCBI Gene IDs that can be utilized for a skilled artisan to determine the sequence to be targeted for knockdown strategies. These NCBI Gene IDs are exemplary only.

TABLE 6

Exemplary immunosuppressive factors

| Factor | NCBI Gene Symbol (Gene ID) |
|---|---|
| B7-H3 (CD276) | CD276 (80381) |
| BST2 (CD317) | BST2 (684) |
| CD200 | CD200 (4345) |
| CD39 (ENTPD1) | ENTPD1 (953) |
| CD47 | CD47 (961) |
| CD73 (NT5E) | NT5E (4907) |
| COX-2 | PTGS2 (5743) |
| CTLA4 | CTLA4 (1493) |
| HLA-E | HLA-E (3133) |
| HLA-G | HLA-G (3135) |

TABLE 6-continued

| Exemplary immunosuppressive factors | |
|---|---|
| Factor | NCBI Gene Symbol (Gene ID) |
| IDO (indoleamine 2,3-dioxygenase) | IDO1 (3620) |
| IL-10 | IL10 (3586) |
| PD-L1 (CD274) | CD274 (29126) |
| TGFβ1 | TGFB1 (7040) |
| TGFβ2 | TGFB2 (7042) |
| TGFβ3 | TGFB3 (7043) |
| VISTA (VSIR) | VSIR (64115) |
| M-CSF | CSF1 (1435) |
| B751 (B7H4) | VTCN1 (79679) |
| PTPN2 | PTPN2 (5771) |

In exemplary embodiments, the production of the following combination of immunosuppressive factors is reduced or inhibited in the vaccine composition: CD47+TGFβ1, CD47+TGFβ2, or CD47+TGFβ1+TGFβ2. In exemplary embodiments, the production of the following combination of immunosuppressive factors is reduced or inhibited in the vaccine composition: CD276+TGFβ1, CD276+TGFβ2, or CD276+TGFβ1+TGFβ2. In exemplary embodiments, the production of the following combination of immunosuppressive factors is reduced or inhibited in the vaccine composition: CD47+TGFB1+CD276, CD47+TGFβ2+CD276, or CD47+TGFβ1+TGFβ2+CD276. In exemplary embodiments, the production of the following combination of immunosuppressive factors is reduced or inhibited in the vaccine composition: CD47+TGFβ1+B7-H3, CD47+TGFβ2+CD276, or CD47+TGFβ1+TGFβ2+CD276. In exemplary embodiments, the production of the following combination of immunosuppressive factors is reduced or inhibited in the vaccine composition: CD47+TGFβ1+CD276+BST2, CD47+TGFβ2+CD276+BST2, or CD47+TGFβ1+TGFβ2+CD276+BST2. In exemplary embodiments, the production of the following combination of immunosuppressive factors is reduced or inhibited in the vaccine composition: CD47+TGFβ1+CD276+CTLA4, CD47+TGFβ2+CD276+CTLA4, or CD47+TGFβ1+TGFβ2+CD276+CTLA4. In exemplary embodiments, the production of the following combination of immunosuppressive factors is reduced or inhibited in the vaccine composition: CD47+TGFβ1+CD276+CTLA4, CD47+TGFβ2+CD276+CTLA4, or CD47+TGFβ1+TGFβ2+CD276+CTLA4.

In exemplary embodiments, the production of the following combination of immunosuppressive factors is reduced or inhibited in the vaccine composition: CD47+TGFβ1+CD276+CTLA4, CD47+TGFβ2+CD276+CTLA4, or CD47+TGFβ1+TGFβ2+CD276+CTLA4, CD47+TGFβ2 or TGFβ1+CTLA4, or CD47+TGFβ1+TGFβ2+CD276+HLA-E or CD47+TGFβ1+TGFβ2+CD276+HLA-G, or CD47+TGFβ1+TGFβ2+CD276+HLA-G+CTLA-4, or CD47+TGFβ1+TGFβ2+CD276+HLA-E+CTLA-4.

Those skilled in the art will recognize that in embodiments of the vaccine compositions described herein, at least one (i.e., 1, 2, 3, 4, 5, 6, 7, 8, 9, 10, or more) of the cell lines within the composition has a knockdown or knockout of at least one immunosuppressive factor (e.g., one or more of the factors listed in Table 6). The cell lines within the composition may have a knockdown or knockout of the same immunosuppressive factor, or a different immunosuppressive factor for each cell line, or of some combination thereof.

Optionally, 1, 2, 3, 4, 5, 6, 7, 8, 9, 10, or more of the cell lines within the composition may be further genetically modified to have a knockdown or knockout of one or more additional immunosuppressive factors (e.g., one or more of the factors listed in Table 6). For example, 1, 2, 3, 4, 5, 6, 7, 8, 9, 10, or more of the cell lines within the composition may be further genetically modified to have a knockdown or knockout of the same additional immunosuppressive factor, of a different additional immunosuppressive factor for each cell line, or of some combination thereof.

In some embodiments, provided herein is a cancer vaccine composition comprising a therapeutically effective amount of cells from a cancer cell line wherein the cell line is modified to reduce production of SLAMF7, BTLA, EDNRB, TIGIT, KIR2DL1, KIR2DL2, KIR2DL3, TIM3 (HAVCR2), LAG3, ADORA2A and ARG1.

At least one of the cells within any of the vaccine compositions described herein may undergo one or more (i.e., 1, 2, 3, 4, 5, 6, 7, 8, 9, 10 or more) genetic modifications in order to achieve the partial or complete knockdown of immunosuppressive factor(s) described herein and/or the expression (or increased expression) of immunostimulatory factors described herein, TAAs, and/or neoantigens. In some embodiments, at least one cell line in the vaccine composition undergoes less than 5 (i.e., less than 4, less than 3, less than 2, 1, or 0) genetic modifications. In some embodiments, at least one cell in the vaccine composition undergoes no less than 5 genetic modifications.

Numerous methods of reducing or inhibiting expression of one or more immunosuppressive factors are known and available to those of ordinary skill in the art, embodiments of which are described herein.

Cancer cell lines are modified according to some embodiments to inhibit or reduce production of immunosuppressive factors. Provided herein are methods and techniques for selection of the appropriate technique(s) to be employed in order to inhibit production of an immunosuppressive factor and/or to reduce production of an immunosuppressive factor. Partial inhibition or reduction of the expression levels of an immunosuppressive factor may be accomplished using techniques known in the art.

In some embodiments, the cells of the cancer lines are genetically engineered in vitro using recombinant DNA techniques to introduce the genetic constructs into the cells. These DNA techniques include, but are not limited to, transduction (e.g., using viral vectors) or transfection procedures (e.g., using plasmids, cosmids, yeast artificial chromosomes (YACs), electroporation, liposomes). Any suitable method(s) known in the art to partially (e.g., reduce expression levels by at least 5, 10, 15, 20, 25, or 30%) or completely inhibit any immunosuppressive factor production by the cells can be employed.

In some embodiments, genome editing is used to inhibit or reduce production of an immunosuppressive factor by the cells in the vaccine. Non-limiting examples of genome editing techniques include meganucleases, zinc finger nucleases (ZFNs), transcription activator-like effector-based nucleases (TALEN), and the CRISPR-Cas system. In certain embodiments, the reduction of gene expression and subsequently of biological active protein expression can be achieved by insertion/deletion of nucleotides via non-homologous end joining (NHEJ) or the insertion of appropriate donor cassettes via homology directed repair (HDR) that lead to premature stop codons and the expression of non-functional proteins or by insertion of nucleotides.

In some embodiments, spontaneous site-specific homologous recombination techniques that may or may not include the Cre-Lox and FLP-FRT recombination systems are used. In some embodiments, methods applying transposons that integrate appropriate donor cassettes into genomic DNA with higher frequency, but with little site/gene-specificity are used in combination with required selection and identification techniques. Non-limiting examples are the piggyBac and Sleeping Beauty transposon systems that use TTAA and TA nucleotide sequences for integration, respectively.

Furthermore, combinatorial approaches of gene editing methods consisting of meganucleases and transposons can be used.

In certain embodiments, techniques for inhibition or reduction of immunosuppressive factor expression may include using antisense or ribozyme approaches to reduce or inhibit translation of mRNA transcripts of an immunosuppressive factor; triple helix approaches to inhibit transcription of the gene of an immunosuppressive factor; or targeted homologous recombination.

Antisense approaches involve the design of oligonucleotides (either DNA or RNA) that are complementary to mRNA of an immunosuppressive factor. The antisense oligonucleotides bind to the complementary mRNA transcripts of an immunosuppressive factor and prevent translation. Absolute complementarity may be preferred but is not required. A sequence "complementary" to a portion of an RNA, as referred to herein, means a sequence having sufficient complementarity to be able to hybridize with the RNA, forming a stable duplex. In the case of double-stranded antisense nucleic acids, a single strand of the duplex DNA may be tested, or triplex formation may be assayed. The ability to hybridize depends on both the degree of complementarity and the length of the antisense nucleic acid. In some embodiments, oligonucleotides complementary to either the 5' or 3-non-translated, non-coding regions of an immunosuppressive factor could be used in an antisense approach to inhibit translation of endogenous mRNA of an immunosuppressive factor. In some embodiments, inhibition or reduction of an immunosuppressive factor is carried out using an antisense oligonucleotide sequence within a short-hairpin RNA.

In some embodiments, lentivirus-mediated shRNA interference is used to silence the gene expressing the immunosuppressive factor. (See Wei et al., J. Immunother. 2012 35(3)267-275 (2012), incorporated by reference herein.)

MicroRNAs (miRNA) are stably expressed RNAi hairpins that may also be used for knocking down gene expression. In some embodiments, ribozyme molecules-designed to catalytically cleave mRNA transcripts are used to prevent translation of an immunosuppressive factor mRNA and expression. In certain embodiments, ribozymes that cleave mRNA at site specific recognition sequences can be used to destroy mRNAs. In some embodiments, the use of hammerhead ribozymes that cleave mRNAs at locations dictated by flanking regions that form complementary base pairs with the target mRNA are used. RNA endoribonucleases can also be used.

In some embodiments, endogenous gene expression of an immunosuppressive factor is reduced by inactivating or "knocking out" the gene or its promoter, for example, by using targeted homologous recombination. In some embodiments, endogenous gene expression is reduced by targeting deoxyribonucleotide sequences complementary to the regulatory region of the promoter and/or enhancer genes of an immunosuppressive factor to form triple helical structures that prevent transcription of the immunosuppressive factor gene in target cells. In some embodiments, promoter activity is inhibited by a nuclease dead version of Cas9 (dCas9) and its fusions with KRAB, VP64 and p65 that cannot cleave target DNA. The dCas9 molecule retains the ability to bind to target DNA based on the targeting sequence. This targeting of dCas9 to transcriptional start sites is sufficient to reduce or knockdown transcription by blocking transcription initiation.

In some embodiments, the activity of an immunosuppressive factor is reduced using a "dominant negative" approach in which genetic constructs that encode defective immunosuppressive factors are used to diminish the immunosuppressive activity on neighboring cells.

In some embodiments, the administration of genetic constructs encoding soluble peptides, proteins, fusion proteins, or antibodies that bind to and "neutralize" intracellularly any other immunosuppressive factors are used. To this end, genetic constructs encoding peptides corresponding to domains of immunosuppressive factor receptors, deletion mutants of immunosuppressive factor receptors, or either of these immunosuppressive factor receptor domains or mutants fused to another polypeptide (e.g., an IgFc polypeptide) can be utilized. In some embodiments, genetic constructs encoding anti-idiotypic antibodies or Fab fragments of anti-idiotypic antibodies that mimic the immunosuppressive factor receptors and neutralize the immunosuppressive factor are used. Genetic constructs encoding these immunosuppressive factor receptor peptides, proteins, fusion proteins, anti-idiotypic antibodies or Fabs can be administered to neutralize the immunosuppressive factor.

Likewise, genetic constructs encoding antibodies that specifically recognize one or more epitopes of an immunosuppressive factor, or epitopes of conserved variants of an immunosuppressive factor, or peptide fragments of an immunosuppressive factor can also be used. Such antibodies include but are not limited to polyclonal antibodies, monoclonal antibodies (mAbs), humanized or chimeric antibodies, single chain antibodies, Fab fragments, F(ab')2 fragments, fragments produced by a Fab expression library, and epitope binding fragments of any of the above. Any technique(s) known in the art can be used to produce genetic constructs encoding suitable antibodies.

In some embodiments, the enzymes that cleave an immunosuppressive factor precursor to the active isoforms are inhibited to block activation of the immunosuppressive factor. Transcription or translation of these enzymes may be blocked by a means known in the art.

In further embodiments, pharmacological inhibitors can be used to reduce enzyme activities including, but not limited to COX-2 and IDO to reduce the amounts of certain immunosuppressive factors.

Tumor Associated Antigens (TAAs)

Vector-based and protein-based vaccine approaches are limited in the number of TAAs that can be targeted in a single formulation. In contrast, embodiments of the allogenic whole cell vaccine platform as described herein allow for the targeting of numerous, diverse TAAs. The breadth of responses can be expanded and/or optimized by selecting allogenic cell line(s) that express a range of TAAs and optionally genetically modifying the cell lines to express additional antigens, including neoantigens or nonsynonymous mutations (NSMs), of interest for a desired therapeutic target (e.g., cancer type).

As used herein, the term "TAA" refers to tumor-associated antigen(s) and can refer to "wildtype" antigens as naturally expressed from a tumor cell or can optionally refer to a mutant antigen, e.g., a design antigen or designed antigen or enhanced antigen or engineered antigen, comprising one or more mutations such as a neoepitope or one or more NSMs as described herein.

TAAs are proteins that can be expressed in normal tissue and tumor tissue, but the expression of the TAA protein is significantly higher in tumor tissue relative to healthy tissue. TAAs may include cancer testis antigens (CTs), which are important for embryonic development but restricted to expression in male germ cells in healthy adults. CTs are often expressed in tumor cells.

Neoantigens or neoepitopes are aberrantly mutated genes expressed in cancer cells. In many cases, a neoantigen can be considered a TAA because it is expressed by tumor tissue and not by normal tissue. Targeting neoepitopes has many advantages since these neoepitopes are truly tumor specific and not subject to central tolerance in thymus. A cancer vaccine encoding full length TAAs with neoepitopes arising from nonsynonymous mutations (NSMs) has potential to elicit a more potent immune response with improved breadth and magnitude.

As used herein, a nonsynonymous mutation (NSM) is a nucleotide mutation that alters the amino acid sequence of a protein. In some embodiments, a missense mutation is a change in one amino acid in a protein, arising from a point mutation in a single nucleotide. A missense mutation is a type of nonsynonymous substitution in a DNA sequence. Additional mutations are also contemplated, including but limited to truncations, frameshifts, or any other mutation that change the amino acid sequence to be different than the native antigen protein.

As described herein, in some embodiments, an antigen is designed by (i) referencing one or more publicly-available databases to identify NSMs in a selected TAA; (ii) identifying NSMs that occur in greater than 2 patients; (iii) introducing each NSM identified in step (ii) into the related TAA sequence; (iv) identifying HLA-A and HLA-B supertype-restricted MHC class I epitopes in the TAA that now includes the NSM; and (v) including the NSMs that create new epitopes (SB and/or WB) or increases peptide-MHC affinity into a final TAA sequence. Exemplary NSMs predicted to create HLA-A and HLA-B supertype-restricted neoepitopes are provided herein (Table 135).

In some embodiments, an NSM identified in one patient tumor sample is included in the designed antigen (i.e., the mutant antigen arising from the introduction of the one or more NSMs). In various embodiments, 1, 2, 3, 4, 5, 6, 7, 8, 9, 10, 11, 12, 13, 14, 15, 16, 17, 18, 19, 20 or more NSMs are introduced into a TAA to generate the designed antigen. In some embodiments, target antigens could have a lower number NSMs and may need to use NSMs occurring only 1 time to reach the targeted homology to native antigen protein range (94-97%). In other embodiments, target antigens could have a high number of NSMs occurring at the 2 occurrence cut-off and may need to use NSMs occurring 3 times to reach the targeted homology to native antigen protein range (94-97%). Including a high number NSMs in the designed antigen would decrease the homology of the designed antigen to the native antigen below the target homology range (94-98%).

In some embodiments, 1, 2, 3, 4, 5 or 6 cell lines of a tumor cell vaccine according to the present disclosure comprise 1, 2, 3, 4, 5, 6, 7, 8, 9, 10, 11, 12, 13, 14, 15, 16, 17, 18, 19, 20 or more NSMs (and thus 1, 2, 3, 4, 5, 6, 7, 8, 9, 10, 11, 12, 13, 14, 15, 16, 17, 18, 19, 20 or more designed antigens) in at least one TAA.

In various embodiments, the sequence homology of the mutant (e.g., designed antigen) to the native full-length protein is 80%, 81%, 82%, 83%, 84%, 85%, 86%, 87%, 88%, 89%, 90%, 91%, 92%, 93%, 94%, 95%, 96%, 97%, 98%, 99% over the full length of the antigen.

In some embodiments, the designed antigen is incorporated into a therapeutic allogenic whole cell cancer vaccine to induce antigen-specific immune responses to the designed TAAs and existing TAAs.

In some embodiments, the vaccine can be comprised of a therapeutically effective amount of at least one cancer cell line, wherein the cell line or the combination of the cell lines express at least one designed TAA. In other embodiments, the vaccine comprises a therapeutically effective amount of at least one cancer cell line, wherein the cell line or the combination of the cell lines expresses at least 2, 3, 4, 5, 6, 7, 8, 9 10 or more designed TAAs.

Provided herein are embodiments of vaccine compositions comprising a therapeutically effective amount of cells from at least one cancer cell line, wherein the at least one cancer cell line expresses (either natively, or is designed to express) one or more TAAs, neoantigens (including TAAs comprising one or more NSMs), CTs, and/or TAAs. In some embodiments, the cells are transduced with a recombinant lentivector encoding one or more TAAs, including TAAs comprising one or more NSMs, to be expressed by the cells in the vaccine composition.

In some embodiments, the TAAs, including TAAs comprising one or more NSMs or neoepitopes, and/or other antigens may endogenously be expressed on the cells selected for inclusion in the vaccine composition. In some embodiments, the cell lines may be modified (e.g., genetically modified) to express selected TAAs, including TAAs comprising one or more NSMs, and/or other antigens (e.g., CTs, TSAs, neoantigens).

Any of the tumor cell vaccine compositions described herein may present one or more TAAs, including TAAs comprising one or more NSMs or neoepitopes, and induce a broad antitumor response in the subject. Ensuring such a heterogeneous immune response may obviate some issues, such as antigen escape, that are commonly associated with certain cancer monotherapies.

According to various embodiments of the vaccine composition provided herein, at least one cell line of the vaccine composition may be modified to express one or more neoantigens, e.g., neoantigens implicated in lung cancer, non-small cell lung cancer (NSCLC), small cell lung cancer (SCLC), prostate cancer, glioblastoma, colorectal cancer, breast cancer including triple negative breast cancer (TNBC), bladder or urinary tract cancer, squamous cell head and neck cancer (SCCHN), liver hepatocellular (HCC) cancer, kidney or renal cell carcinoma (RCC) cancer, gastric or stomach cancer, ovarian cancer, esophageal cancer, testicular cancer, pancreatic cancer, central nervous system cancers, endometrial cancer, melanoma, and mesothelium cancer. In some embodiments, one or more of the cell lines expresses an unmutated portion of a neoantigen protein. In some embodiments, one or more of the cell lines expresses a mutated portion of a neoantigen protein.

In some embodiments, at least one of the cancer cells in any of the vaccine compositions described herein may naturally express, or be modified to express one or more TAAs, including TAAs comprising one or more NSMs, CTs, or TSAs/neoantigens. In certain embodiments, more than one (e.g., 2, 3, 4, 5, 6, 7, 8, 9, 10, or more) of the cancer cell lines in the vaccine composition may express, or may be genetically modified to express one or more of the TAAs, including TAAs comprising one or more NSMs, CTs, or TSAs/neoantigens. The TAAs, including TAAs comprising one or more NSMs, CTs, or TSAs/neoantigens expressed by the cell lines within the composition may all be the same, may all be different, or any combination thereof.

Because the vaccine compositions may contain multiple (i.e., 2, 3, 4, 5, 6, 7, 8, 9, 10, or more) cancer cell lines of different types and histology, a wide range and variety of TAAs, including TAAs comprising one or more NSMs, and/or neoantigens may be present in the composition (Table 7-23). The number of TAAs that can be targeted using a combination of cell lines (e.g., 5-cell line combination, 6-cell line combination, 7-cell line combination, 8-cell line combination, 9-cell line combination, or 10-cell line combination) and expression levels of the TAAs is higher for the cell line combination compared to individual cell lines in the combination.

In embodiments of the vaccine compositions provided herein, at least one (i.e., 1, 2, 3, 4, 5, 6, 7, 8, 9, 10, or more) of the cancer cells in any of the vaccine compositions described herein may express, or be modified to express one or more TAAs, including TAAs comprising one or more NSMs or neoepitopes. The TAAs, including TAAs comprising one or more NSMs, expressed by the cells within the composition may all be the same, may all be different, or any combination thereof. Table 7 below lists exemplary non-small cell lung cancer TAAs, and exemplary subsets of lung cancer TAAs. In some embodiments, the TAAs are specific to NSCLC. In some embodiments, the TAAs are specific to GBM. In other embodiments, the TAAs are specific to prostate cancer.

In some embodiments, presented herein is a vaccine composition comprising a therapeutically effective amount of engineered cells from least one cancer cell line, wherein the cell lines or combination of cell lines express at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more of the TAAs in Tables 7-23. In other embodiments, the TAAs in Tables 7-23 are modified to include one or more NSM as described herein.

In some embodiments, a vaccine composition is provided comprising a therapeutically effective amount of engineered cells from at least one cancer cell line, wherein the cell lines express at least 2, 3, 4, 5, 6, 7, 8, 9, 10 of the TAAs in Tables 7-23 (or the TAAs in Tables 7-23 that have been modified to include one or more NSM). As provided herein, in various embodiments the cell lines express at least 2, 3, 4, 5, 6, 7, 8, 9, 10 of the TAAs in Tables 7-23 (or the TAAs in Tables 7-23 that have been modified to include one or more NSM) and are optionally modified to express or increase expression of one or more immunostimulatory factors of Table 4, and/or inhibit or decrease expression of one or more immunosuppressive factors in Table 6.

TABLE 7

Exemplary TAAs expressed in non-small cell lung cancer

| TAA Name | NCBI Gene Symbol (Gene ID) |
|---|---|
| Survivin | BIRC5 (332) |
| CD44 | CD44 (960) |
| CD44v6 | CD44 (960) |
| CEA | CEACAM5 (1048) |
| CT83 | CT83 (203413) |
| DEPDC1 | DEPDC1 (55635) |
| DLL3 | DLL3 (10683) |
| NYESO1 | CTAG1 (1485) |
| BORIS | CTCFL (140690) |
| EGFR | EGFR (1956) |
| Her2 | ERBB2 (2064) |
| PSMA | FOLH1 (2346) |
| KOC1 | IGF2BP3 (10643) |
| VEGFR | KDR (3791) FLT1 (2321) |
| KIF20A | KIF20A (10112) |

TABLE 7-continued

Exemplary TAAs expressed in non-small cell lung cancer

| TAA Name | NCBI Gene Symbol (Gene ID) |
|---|---|
| MPHOSPH1 | KIF20B (9585) |
| KRAS | KRAS (3845) |
| LY6K | LY6K (54742) |
| MAGE-A1 | MAGEA1 (4100) |
| MAGE-A3 | MAGEA3 (4102) |
| MAGE-A4 | MAGEA4 (4103) |
| MAGE-A6 | MAGEA6 (4105) |
| Mesothelin | MSLN (10232) |
| MUC1 | MUC1 (4582) |
| c-Myc | MYC (4609) |
| NUF2 | NUF2 (83540) |
| PRAME | PRAME (23532) |
| CD133 (Prominin-1) | PROM1 (8842) |
| PTK7 | PTK7 (5754) |
| Securin | PTTG1 (9232) |
| STEAP1 | STEAP1 (26872) |
| hTERT | TERT (7015) |
| p53 | TP53 (7157) |
| 5T4 | TPBG (7162) |
| TTK (CT96) | TTK (7272) |
| Brachyury/TBXT | T (6862) |
| WT1 | WT1 (7490 |
| XAGE1B | XAGE1B (653067) |

TABLE 8

Exemplary TAAs expressed in prostate cancer

| TAA Name | NCBI Gene Symbol (Gene ID) |
|---|---|
| PAP | ACP3 (55) |
| Androgen Receptor | AR (367) |
| Survivin | BIRC5 (332) |
| NYESO1 | CTAG1B (1485) |
| CXCL12 | CXCL12 (6387) |
| CXCR4 | CXCR4 (7852) |
| EGFR | EGFR (1956) |
| Her2 | ERBB2 (2064) |
| PSMA | FOLH1 (2346) |
| GCNT1 | GCNT1 (2650) |
| IDH1 | IDH1 (3417) |
| FAP | FAP (2191) |
| c-KIT/CD117 | KIT (3815) |
| PSA | KLK3 (354) |
| Galectin 8 | LGALS8 (3964) |
| MAGE-A1 | MAGEA1 (4100) |
| MAGE-A3 | MAGEA3 (4102) |
| MAGE-A4 | MAGEA4 (4103) |
| MAGE-C2 | MAGEC2 (51438) |
| Midkine | MDK (4192) |
| MUC1 | MUC1 (4582) |
| PDGF-B | PDGFB (5155) |
| PDGF-D | PDGFD (80310) |
| PDGFRβ | PDGFRB (5159) |
| PLAT (T-PA) | PLAT (5327) |
| uPA | PLAU (5328) |
| uPAR (CD87) | PLAUR (5329) |
| CD133 (Prominin-1) | PROM1 (8842) |
| PSCA | PSCA (8000) |
| SART3 | SART3 (9733) |
| Prostein | SLC45A3 (85414) |
| CD147 | SLC7A11 (23657) |
| SSX2 | SSX2 (6757) |
| STEAP1 | STEAP1 (26872) |
| Brachyury/TBXT | T (6862) |
| hTERT | TERT (7015) |
| 5T4 | TPBG (7162) |
| VEGF-A | VEGFA (7422) |

TABLE 9

Exemplary TAAs expressed in glioblastoma cancer

| TAA Name | NCBI Gene Symbol (Gene ID) |
|---|---|
| AIM2 | AIM2 (9447) |
| B4GALNT1 | B4GALNT1 (2583) |
| Survivin | BIRC5 (4582) |
| Basigin (BSG) | BSG (682) |
| Cyclin B1 | CCNB1 (891) |
| CDH5 | CDH5 (1003) |
| GP39 | CHI3L1 (1116) |
| Trp2 | DCT (1638) |
| DLL3 | DLL3 (10683) |
| DRD2 | DRD2 (1813) |
| EGFRyll I | EGFR (1956) |
| Epha2 | EPHA2 (1969) |
| Epha3 | EPHA3 (2042) |
| Her2 | ERBB2 (2064) |
| EZH2 | EZH2 (2146) |
| PSMA | FOLH1 (2346) |
| FOSL1 | FOSL1 (8061) |
| GSK3B | GSK3B (2932) |
| IDH1 | IDH1 (3417) |
| IDH2 | IDH2 (3418) |
| IL13RA2 | IL13RA2 (3598) |
| IL4R | IL4R (3566) |
| LRP1 | LRP1 (4035) |
| KOC1 | IGF2BP3 (10643) |
| MAGE-Al | MAGEA1 (4100) |
| MAGE-A4 | MAGEA4 (4103) |
| MUC1 | MUC1 (4582) |
| MUL1 | MUL1 (79594) |
| GP100 (PM EL) | PMEL (6490) |
| PRAME | PRAME (23532) |
| hCMV pp65 | ABQ23593 (UniProtKB-P06725 (PP65_HCMVA) |
| PROM1 | PROM1 (8842) |
| PTHLH | PTHLH (4744) |
| SART1 | SART1 (9092) |
| SART3 | SART3 (9733) |
| CD147 | SLC7A11 (23657) |
| SOX-2 | SOX2 (6657) |
| SOX-11 | SOX11 (6664) |
| STEAP1 | STEAP1 (26872) |
| hTERT | TERT (7015) |
| Tenascin-C (TNC) | TNC (3371) |
| TYR | TYR (7299) |
| Trpl (TYRP1) | TYRP1 (7306) |
| WT1 | WT1 (7490) |
| XPO1 | XPO1 (7514) |
| pp65* | ABQ23593 |

*Viral antigen, no Gene ID is available. Accession number is used instead.

TABLE 10

Exemplary TAAs expressed in ovarian cancer

| TAA Name | NCBI Gene Symbol (Gene ID) |
|---|---|
| OY-TES-1 | ACRBP (84519) |
| A-Kinase Anchoring Protein 3 | AKAP3 (10566) |
| Anti-Mullerian Hormone Receptor | AMHR2 (269) |
| Axl Receptor Tyrosine Kinase | AXL (558) |
| Suryiyin | BIRC5 (332) |
| Bruton's Tyrosine Kinase | BTK (695) |
| CD44 | CD44 (960) |
| Cell Cycle Checkpoint Kinase 1 (CHK1) | CHEK1 (1111) |
| Claudin 6 | CLDN6 ((074) |
| NY-ESO-1 | CTAG1B (1485) |
| LAGE1 | CTAG2 (30848) |
| BORIS | CTCFL (140690) |
| Dickkopf-1 | DKK1 (22943) |
| DLL4 | DLL4 (54567) |
| Her2 | ERBB2 (2064) |
| HER3 | ERBB3 (2065) |
| FOLR1/FBP | FOLR1 (2348) |
| GAGE1 | GAGE1 (2543) |
| GAGE2 | GAGE2A (729447) |

TABLE 10-continued

Exemplary TAAs expressed in ovarian cancer

| TAA Name | NCBI Gene Symbol (Gene ID) |
|---|---|
| IGFBP2 | IGFBP2 (3485) |
| FSHR | FSHR (3969) |
| PLU-1 | KDM5B (10765) |
| Luteinizing Hormone Receptor | LHCGR (3973) |
| MAGE-A1 | MAGEA1 (4100) |
| MAGE-A10 | MAGEA10 (4109) |
| MAGE-A4 | MAGEA4 (4103) |
| MAGE-A9 | MAGEA9 (4108) |
| MAGE-C1 | MAGEC1 (9947) |
| Mesothelin | MSLN (10232) |
| Muc1 | MUC1 (4582) |
| Muc16 | MUC16 (94025) |
| Glucocorticoid Receptor II | NR3C1 (2908) |
| PARP1 | PARP1 (142) |
| PIWIL1 | PIWIL1 (9271) |
| PIWIL2 | PIWIL2 (55124) |
| PIWIL3 | PIWIL3 (440822) |
| PIWIL4 | PIWIL4 (143689) |
| PRAME | PRAME (23532) |
| SP17 | SPA17 (53340) |
| SPAG-9 | SPAG9 (9043) |
| STEAP1 | STEAP1 (26872) |
| hTERT | TERT (7015) |
| WT1 | WT1 (7490) |

TABLE 11

Exemplary TAAs expressed in colorectal cancer

| TAA Name | NCBI Gene Symbol (Gene ID) |
|---|---|
| Survivin | BIRC5 (332) |
| B-RAF | BRAF (673) |
| CEA | CEACAM5 (1048) |
| βHCG | CGB3 (1082) |
| NYESO1 | CTAG1B (1485) |
| EPCAM | EPCAM (4072) |
| EPH receptor A2 | EPHA2 (1969) |
| Her2 | ERBB2 (2064) |
| GUCY2C | GUCY2C (2984) |
| PSMA | FOLH1 (2346) |
| KRAS | KRAS (3845) |
| MAGE-A1 | MAGEA1 (4100) |
| MAGE-A3 | MAGEA3 (4102) |
| MAGE-A4 | MAGEA4 (4103) |
| MAGE-A6 | MAGEA6 (4105) |
| Mesothelin | MSLN (10232) |
| MUC1 | MUC1 (4582) |
| PRAME | PRAME (23532) |
| CD133 | PROM1 (8842) |
| RNF43 | RNF43 (54894) |
| SART3 | SART3 (9733) |
| STEAP1 | STEAP1 (26872) |
| Brachyury/TBXT | T (6862) |
| TROP2 | TACSTD2 (4070) |
| hTERT | TERT (7015) |
| TOMM34 | TOMM34 (10953) |
| 5T4 | TPBG (7162) |
| WT1 | WT1 (7490) |

TABLE 12

Exemplary TAAs expressed in breast cancer

| TAA Name | NCBI Gene Symbol (Gene ID) |
|---|---|
| Survivin | BIRC5 (332) |
| Cyclin B1 | CCNB1 (891) |
| Cadherin-3 | CDH3 (1001) |
| CEA | CEACAM5 (1048) |
| CREB binding protein | CREBBP (1387) |

TABLE 12-continued

Exemplary TAAs expressed in breast cancer

| TAA Name | NCBI Gene Symbol (Gene ID) |
|---|---|
| CS1 | CSH1 (1442) |
| CT83 | CT83 (203413) |
| NYESO1 | CTAG1B (1485) |
| BORIS | CTCFL (140690) |
| Endoglin | ENG (2022) |
| PSMA | FOLH1 (2346) |
| FOS like 1 | FOSL1 (8061) |
| FOXM1 | FOXM1 (2305) |
| GPNMB | GPNMB (10457) |
| MAGE A1 | MAGEA1 (4100) |
| MAGE A3 | MAGEA3 (4102) |
| MAGE A4 | MAGEA4 (4103) |
| MAGE A6 | MAGEA6 (4105) |
| Mesothelin | MSLN (10232) |
| MMP11 | MMP11 (4320) |
| MUC1 | MUC1 (4582) |
| PRAME | PRAME (23532) |
| CD133 | PROM1 (8842) |
| PTK7 | PTK7 (5754) |
| ROR1 | ROR1 (4919) |
| Mammaglobin A | SCGB2A2 (4250) |
| Syndecan-1 | SDC1 (6382) |
| SOX2 | SOX2 (6657) |
| SPAG9 | SPAG9 (9043) |
| STEAP1 | STEAP1 (26872) |
| Brachyury/TBXT | T (6862) |
| TROP2 | TACSTD2 (4070) |
| hTERT | TERT (7015) |
| WT1 | WT1 (7490) |
| YB-1 | YBX1 (4904) |

TABLE 13

Exemplary TAAs expressed in bladder cancer

| | |
|---|---|
| Androgen Receptor | AR (367) |
| ATG7 | ATG7 (10533) |
| AXL Receptor Tyrosine Kinase | AXL (558) |
| Survivin | BIRC5 (332) |
| BTK | BTK (695) |
| CEACAM1 | CEACAM1 (634) |
| CEA | CEACAM5 (1048) |
| βHCG | CGB3 (1082) |
| NYESO1 | CTAG1B (1495) |
| LAGE1 | CTAG2 (30848) |
| DEPDC1 | DEPDC1 (55635) |
| EPH receptor B4 | EPHB4 (2050) |
| HER2 | ERBB2 (2064) |
| FGFR3 | FGFR3 (2261) |
| VEGFR | FLT3 (2322) |
| PSMA | FOLH1 (2346) |
| FOLR1α (FBP) | FOLR1 (2348) |
| IGF2BP3 | IGF2BP3 (10643) |
| MPHOSPH1 | KIF20B (9585) |
| LY6K | LY6K (54742) |
| MAGEA1 | MAGEA1 (4100) |
| MAGEA3 | MAGEA3 (4102) |
| MAGEA6 | MAGEA6 (4105) |
| MAGEC2 | MAGEC2 (51438) |
| c-Met | MET (4233) |
| MUC1 | MUC1 (4582) |
| Nectin-4 | NECTIN4 (81607) |
| NUF2 | NUF2 (83540) |
| RET | RET (5979) |
| STEAP1 | STEAP1 (26872) |
| TDGF1 (Cripto1) | TDGF1 (6997) |
| hTERT | TERT (7015) |
| TROP2 | TACSTD2 (4070) |
| WEE1 | WEE1 (7465) |
| WT1 | WT1 (7490) |

TABLE 14

Exemplary TAAs expressed in head and/or neck cancer

| TAA Name | NCBI Gene Symbol (Gene ID) |
|---|---|
| Survivin | BIRC5 (332) |
| BTK | BTK (695) |
| cyclin D1 | CCND1 (595) |
| CDK4 | CDK4 (1019) |
| CDK6 | CDK6 (1021) |
| P16 | CDKN2A (1029) |
| CEA | CEACAM5 (1048) |
| EGFR | EGFR (1956) |
| EPH receptor B4 | EPHB4 (2050) |
| Her2 | ERBB2 (2064) |
| HER3 | ERBB3 (2065) |
| FGFR1 | FGFR1 (2260) |
| FGFR2 | FGFR2 (2263) |
| FGFR3 | FGFR3 (2261) |
| PSMA | FOLH1 (2346) |
| IGF2BP3 | IGF2BP3 (10643) |
| IMP3 | IMP3 (55272) |
| MPHOSPH1 | KIF20B (9585) |
| LY6K | LY6K (54742) |
| MAGE-A10 | MAGEA10 (4109) |
| MAGE-A3 | MAGEA3 (4102) |
| MAGE-A4 | MAGE-A4 (4103) |
| MAGE-A6 | MAGE-A6 (4105) |
| MUC1 | MUC1 (4582) |
| NUF2 | NUF2 (83540) |
| PRAME | PRAME (23532) |
| STEAP1 | STEAP1 (26872) |
| Brachyury/TBXT | T (6862) |
| hTERT | TERT (7015) |
| p53 | TP53 (7157) |
| HPV16 E6* | AVN72023 |
| HPV16 E7* | AVN80203 |
| HPV18 E6* | ALA62736 |
| HPV18 E7* | ABP99745 |

*Viral antigen, no Gene ID is available; GenBank™ accession number is provided.

TABLE 15

Exemplary TAAs expressed in gastric cancer

| TAA Name | NCBI Gene Symbol (Gene ID) |
|---|---|
| TEM-8 (ANTXR1) | ANTXR1 (84168) |
| Annexin A2 (ANXA2) | ANXA2 (302) |
| Survivin | BIRC5 (332) |
| CCKBR | CCKBR (887) |
| Cadherin 17 | CDH17 (1015) |
| CDKN2A | CDKN2A (1029) |
| CEA | CEACAM5 (1048) |
| Claudin 18 | CLDN18 (51208) |
| CT83 | CT83 (203413) |
| EPCAM | EPCAM (4072) |
| Her2 | ERBB2 (2064) |
| Her3 | ERBB3 (2065) |
| PSMA | FOLH1 (2346) |
| FOLR1 | FOLR1 (2348) |
| FOXM1 | FOXM1 (2305) |
| FUT3 | FUT3 (2525) |
| Gastrin | GAST (2520) |
| KIF20A | KIF20A (10112) |
| LY6K | LY6K (54742) |
| MAGE-A1 | MAGEA1 (4100) |
| MAGE-A3 | MAGEA3 (4102) |
| MMP9 | MMP9 (4318) |
| Mesothelin | MSLN (10232) |
| MUC1 | MUC1 (4582) |
| MUC3A | MUC3A (4584) |
| PRAME | PRAME (23532) |
| PTPN11 | PTPN11 (5781) |
| SART3 | SART3 (9733) |
| SATB1 | SATB1 (6304) |
| STEAP1 | STEAP1 (26872) |

TABLE 15-continued

| Exemplary TAAs expressed in gastric cancer | |
|---|---|
| TAA Name | NCBI Gene Symbol (Gene ID) |
| hTERT | TERT (7015) |
| 5T4 (TPBG) | TPBG (7162) |
| VEGFR1 | FLT1 (2321) |
| WEE1 | WEE1 (7465) |
| WT1 | WT1 (7490) |

TABLE 16

| Exemplary TAAs expressed in liver cancer | |
|---|---|
| TAA Name | NCBI Gene Symbol (Gene ID) |
| AKR1C3 | AKR1C3 (8644) |
| MRP3 (ABCC3) | ABCC3 (8714) |
| AFP | AFP (174) |
| Annexin A2 (ANXA2) | ANXA2 (302) |
| Survivin | BIRC5 (4582) |
| Basigin (BSG) | BSG (682) |
| CEA | CEACAM5 (1048) |
| NYESO1 | CTAG1B (1485) |
| DKK-1 | DKK1 (22943) |
| SART-2 (DSE) | DSE (29940) |
| EpCAM | EPCAM (4072) |
| Glypican-3 | GPC3 (2719) |
| MAGE-A1 | MAGEA1 (4100) |
| MAGE-A3 | MAGEA3 (4102) |
| MAGE-A4 | MAGEA4 (4103) |
| MAGE-A10 | MAGEA10 (4109) |
| MAGE-C1 | MAGEC1 (9947) |
| MAGE-C2 | MAGEC2 (51438) |
| Midkine (MDK) | MDK (4192) |
| MUC-1 | MUC1 (4582) |
| PRAME | PRAME (23532) |
| SALL-4 | SALL4 (57167) |
| Spa17 | SPA17 (53340) |
| SPHK2 | SPHK2 (56848) |
| SSX-2 | SSX2 (6757) |
| STAT3 | STAT3 (6774) |
| hTERT | TERT (7015) |
| HCA661 (TFDP3) | TFDP3 (51270) |
| WT1 | WT1 (7490) |

TABLE 17

| Exemplary TAAs expressed in esophageal cancer | |
|---|---|
| TAA Name | NCBI Gene Symbol (Gene ID) |
| ABCA1 | ABCA1 (19) |
| NYESO1 | CTAG1B (1485) |
| LAGE1 | CTAG2 (30848) |
| DKK1 | DKK1 (22943) |
| EGFR | EGFR (1956) |
| EpCAM | EPCAM (4072) |
| Her2 | ERBB2 (2065) |
| Her3 | ERBB3 (2064) |
| FOLR1 | FOLR1 (2348) |
| Gastrin (GAST) | GAST (2520) |
| IGF2BP3 | IGF2BP3 (10643) |
| IMP3 | IMP3 (55272) |
| LY6K | LY6K (54742) |
| MAGE-A1 | MAGEA1 (4100) |
| MAGE-A3 | MAGEA3 (4102) |
| MAGE-A4 | MAGEA4 (4103) |
| MAGE-A11 | MAGEA11 (4110) |
| Mesothelin (MSLN) | MSLN (10232) |

TABLE 17-continued

| Exemplary TAAs expressed in esophageal cancer | |
|---|---|
| TAA Name | NCBI Gene Symbol (Gene ID) |
| NUF2 | NUF2 (83540) |
| PRAME | PRAME (23532) |
| PTPN11 | PTPN11 (5781) |
| hTERT | TERT (7015) |
| TTK | TTK (7272) |

TABLE 18

| Exemplary TAAs expressed in kidney cancer | |
|---|---|
| TAA Name | NCBI Gene Symbol (Gene ID) |
| apolipoprotein L1 | APOL1 (8542) |
| Axl Receptor Tyrosine Kinase | AXL (558) |
| Survivin | BIRC5 (332) |
| G250 | CA9 (768) |
| cyclin D1 | CCND1 (595) |
| CXCR4 | CXCR4 (7852) |
| EPH receptor B4 | EPHB4 (2050) |
| FAP | FAP (2191) |
| VEGFR | FLT3 (2322) |
| GUCY2C | GUCY2C (2984) |
| INTS1 | INTS1 (26173) |
| c-KIT/CD117 | KIT (3815) |
| c-Met | MET (4233) |
| MMP7 | MMP7 (4316) |
| RAGE1 | MOK (5891) |
| Muc1 | MUC1 (4582) |
| PDGFRα | PDGFRA (5156) |
| PDGFRβ | PDGFRB (5159) |
| M2PK | PKM (5315) |
| perilipin 2 | PLIN2 (123) |
| PRAME | PRAME (23532) |
| PRUNE2 | PRUNE2 (158471) |
| RET | RET (5979) |
| RGS5 | RGS5 (8490) |
| ROR2 | ROR2 (4920) |
| STEAP1 | STEAP1 (26872) |
| Tie-1 | TIE1 (7075) |
| 5T4 | TPBG (7162) |
| gp75 | TYRP1 (7306) |

TABLE 19

| Exemplary TAAs expressed in pancreatic cancer | |
|---|---|
| TAA Name | NCBI Gene Symbol (Gene ID) |
| Survivin | BIRC5 (332) |
| BTK | BTK (695) |
| Connective Tissue Growth Factor | CCN2 (1490) |
| CEA | CEACAM5 (1048) |
| Claudin 18 | CLDN18 (51208) |
| NYESO1 | CTAG1B (1495) |
| CXCR4 | CXCR4 (7852) |
| EGFR | EGFR (1956) |
| FAP | FAP (2191) |
| PSMA | FOLH1 (2346) |
| MAGE-A4 | MAGEA4 (4103) |
| Perlecan | HSPG2 (3339) |
| Mesothelin | MSLN (10232) |
| MUC1 | MUC1 (4582) |
| Muc16 | MUC16 (94025) |

TABLE 19-continued

Exemplary TAAs expressed in pancreatic cancer

| TAA Name | NCBI Gene Symbol (Gene ID) |
|---|---|
| Mucin 5AC | MUC5AC (4586) |
| CD73 | NT5E (4907) |
| G17 (gastrin1-17) | PBX2 (5089) |
| uPA | PLAU (5328) |
| uPAR (CD87) | PLAUR (5329) |
| PRAME | PRAME (23532) |
| PSCA | PSCA (8000) |
| Focal adhesion kinase | PTK2 (5747) |
| SSX2 | SSX2 (6757) |
| STEAP1 | STEAP1 (26872) |
| hTERT | TERT (7015) |
| Neurotensin Receptor 1 | TFIP11 (24144) |
| WT1 | WT1 (7490) |

TABLE 20

Exemplary TAAs expressed in endometrial cancer

| TAA Name | NCBI Gene Symbol (Gene ID) |
|---|---|
| OY-TES-1 | ACRBP (84519) |
| ARMC3 | ARMC3 (219681) |
| Survivin | BIRC5 (332) |
| BMI1 | BMI1 (648) |
| BST2 | BST2 (684) |
| BORIS | CTCFL (140690) |
| DKK1 | DKK1 (22943) |
| DRD2 | DRD2 (1813) |
| EpCam | EPCAM (4072) |
| EphA2 | EphA2 (1969) |
| HER2/neu | ERBB2 (2064) |
| HER3 | ERBB3 (2065 |
| ESR2 | ESR2 (2100) |
| MAGE-A3 | MAGEA3 (4102) |
| MAGE-A4 | MAGEA4 (4103) |
| MAGE-C1 | MAGEC1 (9947) |
| MUC-1 | MUC1 (4582) |
| MUC-16 | MUC16 (94025) |
| SPA17 | SPA17 (53340) |
| SSX-4 | SSX4 (6757) |
| hTERT | TERT (7015) |
| HE4 (WFDC2) | WFDC2 (10406) |
| WT1 | WT1 (7490) |
| XPO1 | XPO1 (7514) |

TABLE 21

Exemplary TAAs expressed in skin cancer

| TAA Name | NCBI Gene Symbol (Gene ID) |
|---|---|
| B4GALNT1 | B4GALNT1 (2583) |
| Survivin | BIRC5 (332) |
| Endosialin (CD248) | CD248 (57124) |
| CDKN2A | CDKN2A (1029) |
| CSAG2 | CSAG2 (102423547) |
| CSPG4 | CSPG4 (1464) |
| NYESO1 | CTAG1B (1485) |
| Trp2 (DCT) | DCT (1638) |
| MAGE-A1 | MAGEA1 (4100) |
| MAGE-A2 | MAGEA2 (4101) |
| MAGE-A3 | MAGEA3 (4102) |
| MAGE-A4 | MAGEA4 (4103) |
| MAGE-A6 | MAGEA6 (4105) |

TABLE 21-continued

Exemplary TAAs expressed in skin cancer

| TAA Name | NCBI Gene Symbol (Gene ID) |
|---|---|
| MAGE-A10 | MAGEA10 (4109) |
| MITF | MITF (4286) |
| MART-1 | MLANA (2315) |
| NFE2L2 | NFE2L2 (4780) |
| PMEL | PMEL (6490) |
| PRAME | PRAME (23532) |
| NY-MEL-1 | RAB38 (23682) |
| NEF | S100B (6285) |
| SEMA4D | SEMA4D (10507) |
| SSX2 | SSX2 (6757) |
| SSX4 | SSX4 (6759) |
| ST8SIA1 | ST8SIA1 (6489) |
| hTERT | TERT (7015) |
| TYR | TYR (7299) |
| Trp1 | TYRP1 (7306) |

TABLE 22

Exemplary TAAs expressed in mesothelial cancer

| TAA Name | NCBI Gene Symbol (Gene ID) |
|---|---|
| APEX1 | APEX1 (328) |
| CHEK1 | CHEK1 (1111) |
| NYESO1 | CTAG1B (1485) |
| DHFR | DHFR (1719) |
| DKK3 | DKK3 (27122) |
| EGFR | EGFR (1956) |
| ESR2 | ESR2 (2100) |
| EZH1 | EZH1 (2145) |
| EZH2 | EZH2 (2146) |
| MAGE-A1 | MAGEA1 (4100) |
| MAGE-A3 | MAGEA3 (4102) |
| MAGE-A4 | MAGEA4 (4103) |
| MCAM | MCAM (4162) |
| Mesothelin | MSLN (10232) |
| MUC1 | MUC1 (4582) |
| PTK2 | PTK2 (5747) |
| SSX-2 | SSX2 (6757) |
| STAT3 | STAT3 (6774) |
| THBS2 | THBS2 (7058) |
| 5T4 (TPBG) | TPBG (7162) |
| WT1 | WT1 (7490) |

TABLE 23

Exemplary TAAs expressed in small cell lung cancer

| TAA Name | NCBI Gene Symbol (Gene ID) |
|---|---|
| AIM2 | AIM2 (9447) |
| AKR1C3 | AKR1C3 (8644) |
| ASCL1 | ASCL1 (429) |
| B4GALNT1 | B4GALNT1 (2583) |
| Survivin | BIRC5 (332) |
| Cyclin B1 | CCNB1 (891) |
| CEA | CEACAM5 (1048) |
| CKB | CKB (1152) |
| DDC | DDC (1644) |
| DLL3 | DLL3 (10863) |
| Enolase 2 | ENO2 (2026) |
| Her2 | ERBB2 (2064) |
| EZH2 | EZH2 (2146) |
| Bombesin | GRP (2922) |
| KDM1A | KDM1A (23028) |
| MAGE-A1 | MAGEA1 (4100) |

TABLE 23-continued

| Exemplary TAAs expressed in small cell lung cancer | |
|---|---|
| TAA Name | NCBI Gene Symbol (Gene ID) |
| MAGE-A3 | MAGEA3 (4102) |
| MAGE-A4 | MAGA4 (4103) |
| MAGE-A10 | MAGEA10 (4109) |
| MDM2 | MDM2 (4193) |
| MUC1 | MUC1 (4582) |
| NCAM-1 | NCAM1 (4684) |
| GP100 | PMEL (6490) |
| SART-1 | SART1 (9092) |
| SART-3 | SART3 (9733) |
| SFRP1 | SFRP1 (6422) |
| SOX-2 | SOX2 (6657) |
| SSTR2 | SSTR2 (6752) |
| Trp1 (TYRP1) | TYRP1 (7306) |

In some embodiments of the vaccine compositions provided herein, 1, 2, 3, 4, 5, 6, 7, 8, 9, 10, or more of the cell lines within the composition may be genetically modified to express or increase expression of the same immunostimulatory factor, TAA, including TAAs comprising one or more NSMs, and/or neoantigen; of a different immunostimulatory factor, TAA, and/or neoantigen; or some combination thereof. In some embodiments, the TAA sequence can be the native, endogenous, human TAA sequence. In some embodiments, the TAA sequence can be a genetically engineered sequence of the native endogenous, human TAA sequence. The genetically engineered sequence may be modified to increase expression of the TAA through codon optimization or the genetically engineered sequence may be modified to change the cellular location of the TAA (e.g., through mutation of protease cleavage sites).

Exemplary NCBI Gene IDs are presented in Table 7-23. As provided herein, these Gene IDs can be used to express (or overexpress) certain TAAs in one or more cell lines of the vaccine compositions of the disclosure.

In various embodiments, one or more of the cell lines in a composition described herein is modified to express mesothelin (MSLN), CT83 (kita-kyushu lung cancer antigen 1) TERT, PSMA, MAGEA1, EGFRvIII, hCMV pp65, TBXT, BORIS, FSHR, MAGEA10, MAGEC2, WT1, FBP, TDGF1, Claudin 18, LY6K, PRAME, HPV16/18 E6/E7, FAP, or mutated versions thereof (Table 24). The phrase "or mutated versions thereof" refers to sequences of the aforementioned TAAs, or other TAAs provided herein, that comprise one or more mutations (e.g., 1, 2, 3, 4, 5, 6, 7, 8, 9, or 10 or more substitution mutations), including neopepitopes or NSMs, as described herein. Thus, in various embodiments, one or more of the cell lines in a composition described herein is modified to express modMesothelin (modMSLN), modTERT, modPSMA, modMAGEA1, modEGFRvIII, modhCMV pp65, modTBXT, modBORIS, modFSHR, modMAGEA10, modMAGEC2, modWT1, modKRAS, modFBP, modTDGF1, modClaudin 18, modLY6K, modFAP, modPRAME, KRAS G12D mutation, KRAS G12V mutation, and/or modHPV16/18 E6/E7. In other embodiments, the TAA or "mutated version thereof" may comprise fusions of 1, 2, or 3 or more of the TAAs or mutated versions provided herein. In some embodiments, the fusions comprises a native or wild-type sequence fused with a mutated TAA. In some embodiments, the individual TAAs in the fusion construct are separated by a cleavage site, such as a furin cleavage site. Thus the present disclosure provides TAA fusion proteins such as CT83-MSLN or modCT83-MSLN, modMAGEA1-EGFRvIII-pp65, modTBXT-modBORIS, modFSHR-modMAGEA10, modTBXT-modMAGEC2, modTBXT-modWT1, modTBXT-modWT1 (KRAS), modWT1-modFBP, modPSMA-modTDGF1, modWT1-modClaudin 18, modPSMA-modLY6K, modFAP-modClaudin 18, and modPRAME-modTBXT, Sequences for native TAAs can be readily obtained from the NCBI database (www.ncbi.nlm.nih.gov/protein). Sequences for the aforementioned TAAs, mutated versions, and fusions are provided in Table 24.

TABLE 24

Sequences for MSLN, CT83 and Exemplary Design Antigens

| TAA | Sequence |
|---|---|
| Mesothelin | atggctctgcctaccgcaagacccctgctgggctcctgtgggactcctgctctgggatcactgctgtttctgctgttttcactgggctgggtgca<br>gccttcccgcaccctggcaggagagacaggacaggaggcagcaccactggacggcgtgctggccaaccccccctaatatcagctccct<br>gtctcctcggcagctgctgggcttcccatgtgcagaggtgagcggactgtccaccgagagggtgcgcgagctggcagtggccctggcac<br>agaagaacgtgaagctgagcacagagcagctgaggtgcctggcacacaggctgtccgagccaccagaggacctggatgcactgcc<br>actggacctgctgctgttcctgaacccagatgccttttccggcccccaggcctgtaccaggttcttttctcgcatcacaaaggccaatgtggat<br>ctgctgcccagaggcgcacctgagaggcagagactgctgccagccgccctggcatgctggggcgtgaggggctctctgctgagcgag<br>gcagacgtgcgcgccctgggaggactggcctgtgatctgccaggccgctttgtggcagagagcgccgaggtgctgctgccacggctggt<br>gtcctgccctggcccactggaccaggatcagcaggaggcagcccgggccgccctgcagggcggcggccctccctacggcccccccttc<br>cacctggtctgtgagcacaatggacgcactgagaggactgctgcctgtgctgggacagccaatcatcaggtctatcccccagggcatcgt<br>ggcagcatggaggcagcggagcagccgggaccccagctggcggcagcctgagagaaccatcctgcggcctagattccggagagag<br>gtggagaagacagcctgtccatctggcaagaaggccagagagatcgacgagagcctgatcttttacaagaagtgggagctggaggcc<br>tgcgtggacgccgccctgctggctacccagatggacagggtgaatgccatccccttcacctacgagcagctggacgtgctgaagcaca<br>agctggatgagctgtacccacagggctatcccgagtccgtgatccagcacctgggctacctgtttctgaagatgtcccccgaggatatcag<br>aaagtggaacgtgacctctctggagacactgaaggccctgctggaggtcaataagggccacgagatgagccctcaggtggccaccct<br>gatcgaccggttcgtgaagggcagaggccagctggacaaggatacactggataccctgacagccttttaccccggctacctgtgctccct<br>gtctcctgaggagctgtcctctgtgccacccagctccatctgggccgtgcggccacaggacctggatacctgcgacccccggcagctgg<br>acgtgctgtaccctaaggccaggctggccttccagaacatgaatggctctgagtatttcgtgaagatccagagctttctgggaggagcacc<br>taccgaggacctgaaggccctgagccagcagaacgtgagcatggacctggccacctttatgaagctgcgcacagatgccgtgctgcca<br>ctgaccgtggcagaggtgcagaagctgctgggacctcacgtggagggcctgaaggcagaggagaggcacaggccagtgcgggact<br>ggattctgcggcagagacaggacgatctggataccctgggactgggactgcagggaggcatcccaaatggaggcagcacatccggct<br>ctggcaagccaggctccggagagggctctaccaagggaatgcaggaggccctgagcggcacaccttgcctgctgggacctggacctg<br>tgctgactgtgctggctctgctgctggcatctactctggct (SEQ ID NO: 17) |
| Mesothelin | MALPTARPLLGSCGTPALGSLLFLLFSLGINVQPSRTLAGETGQEAAPLDGVLANPPNISSLSPRQL<br>LGFPCAEVSGLSTERVRELAVALAQKNVKLSTEQLRCLAHRLSEPPEDLDALPLDLLLFLNPDAFS<br>GPQACTRFFSRITKANVDLLPRGAPERQRLLPAALACWGVRGSLLSEADVRALGGLACDLPGRFV<br>AESAEVLLPRLVSCPGPLDQDQQEAARAALQGGGPPYGPPSTWSVSTMDALRGLLPVLGQPIIRS<br>IPQGIVAAWRQRSSRDPSWRQPERTILRPRFRREVEKTACPSGKKAREIDESLIFYKKWELEACV<br>DAALLATQMDRVNAIPFTYEQLDVLKHKLDELYPQGYPESVIQHLGYLFLKMSPEDIRKWNVTSLE<br>TLKALLEVNKGHEMSPQVATLIDRFVKGRGQLDKDTLDTLTAFYPGYLCSLSPEELSSVPPSSIWA<br>VRPQDLDTCDPRQLDVLYPKARLAFQNMNGSEYFVKIQSFLGGAPTEDLKALSQQNVSMDLATF<br>MKLRTDAVLPLTVAEVQKLLGPHVEGLKAEERHRPVRDWILRQRQDDLDTLGLGLQGGIPNGGST<br>SGSGKPGSGEGSTKGMQEALSGTPCLLGPGPVLTVLALLLASTLA (SEQ ID NO: 18) |
| CT83 | atgaacttttacctgctgctggcatcctcaatcctgtgcgccctgatcgtgttttggaaataccgacgctttcagagaaatactggcgagatga<br>gcagcaacagcaccgccctggccctggtgcggccctctagctccggcctgatcaactctaatacagacaacaatctggccgtgtacgac<br>ctgtctcgggatatcctgaacaatttccctcacagcatcgcccggcagaagagaatcctggtgaacctgagcatggtggagaataagctg<br>gtggagctggaacatacactgctgagtaagggctttagggggcttcaccacatcgcaagtcaaca (SEQ ID NO: 19) |
| CT83 | MNFYLLLASSILCALIVFWKYRRFQRNTGEMSSNSTALALVRPSSSGLINSNTDNNLAVYDLSRDIL<br>NNFPHSIARQKRILVNLSMVENKLVELEHTLLSKGFRGASPHRKST (SEQ ID NO: 20) |
| CT83-Mesothelin | atgaatttctacctgctgctggcatcttcaatcctgtgcgccctgatcgtcttttggaagtatcgccgctttcagaggaacactggcgagatga<br>gcagcaacagcaccgccctggccctggtgcggccttctagctccggcctgatcaactctaatacagacaacaatctggccgtgtatgacc<br>tgtcccgggatatcctgaacaatttcccacactctatcgccaggcagaagcgcatcctggtgaacctgagcatggtggagaataagctgg<br>tggagctggagcacaccctgctgagcaagggcttccggggagcatccccacacagaaagtctaccggcagcggcgccacaaacttttt<br>ctctgctgaagcaggcaggcgacgtggaggagaatcctggaccagccctgccaaccgccagacccctgctgggcagctgtggcacac |

TABLE 24-continued

Sequences for MSLN, CT83 and Exemplary Design Antigens

| TAA | Sequence |
| --- | --- |
| | ccgccctgggctctctgctgttcctgctgtttagcctgggatgggtgcagccatcaaggaccctggcaggagagacaggacaggaggca<br>gcacccctggatggcgtgctggccaaccccctaatatctctagcctgagcccaagacagctgctgggcttcccatgtgcagaggtgtcc<br>ggactgtctaccgagagggtgcgcgagctggcagtggccctggcacagaagaatgtgaagctgtctacagagcagctgaggtgcctgg<br>cacacagactgagcgagccaccagaggacctggatgcactgcctctggacctgctgctgttcctgaaccccgatgcctttagcggacctc<br>aggcctgcacccggttcttttccagaatcacaaaggccaatgtggatctgctgcctaggggcgcaccagagaggcagagactgctgcca<br>gccgccctggcctgctggggcgtgaggggcagcctgctgtccgaggcagacgtgcgcgccctgggaggactggcctgtgatctgccag<br>gccgctttgtggcagagtctgccgaggtgctgctgcctaggctggtgagctgcccaggacctctggaccaggatcagcaggaggcagcc<br>cgggccgccctgcagggcggcggccctccatacggcccccccttccacctggtccgtgtctacaatggacgcactgagaggactgctgcc<br>agtgctgggacagccaatcatcaggagcatcccccagggcatcgtggcagcatggaggcagcggagcagccgggacccctcctgga<br>ggcagccagagaggaccatcctgcggccaagattccggagagaggtggagaagacagcatgtccatccggcaagaaggcccgcg<br>agatcgacgagtctctgatcttttacaagaagtgggagctggaggcctgcgtggacgccgccctgctggctacccagatggaccgggtg<br>aacgccatccccttcacctacgagcagctggacgtgctgaagcacaagctggatgagctgtacccccagggctatcctgagtccgtgatc<br>cagcacctgggctacctgtttctgaagatgagccccgaggatatccggaagtggaacgtgacctccctggagacactgaaggccctgct<br>ggaggtcaataagggccacgagatgagccctcaggtggccaccctgatcgacaggttcgtgaagggccgcggccagctggacaagg<br>atacactggataccctgacagccttttaccctggctacctgtgcagcctgtccccagaggagctgagctccgtgccaccctctagcatctgg<br>gccgtgcggccccaggacctggatacctgcgaccctagacagctggatgtgctgtacccaaaggccaggctggccttccagaacatga<br>atggctctgagtatttcgtgaagatccagagctttctgggaggagcaccaaccgaggacctgaaggccctgtcccagcagaacgtgtcta<br>tggacctggccacctttatgaagctgagaacagatgccgtgctgcctctgaccgtggcagaggtgcagaagctgctgggaccacacgtg<br>gagggcctgaaggcagaggagaggcacaggcctgtgagggactggattctgcggcagagacaggacgatctggataccctgggact<br>gggactgcagggaggcatccccaatggcggctctacaagcggctccggcaagcctggctctggagagggcagcaccaagggaatgc<br>aggaggccctgagcggcacaccctgtctgctgggacctggacccgtgctgactgtgctggctctgctgctggcttcaaccctggca<br>(SEQ ID NO: 21) |
| CT83-Mesothelin | MNFYLLLASSILCALIVFWKYRRFQRNTGEMSSNSTALALVRPSSSGLINSNTDNNLAVYDLSRDIL<br>NNFPHSIARQKRILVNLSMVENKLVELEHTLLSKGFRGASPHRKSTGSGATNFSLLKQAGDVEEN<br>PGPALPTARPLLGSCGTPALGSLLFLLFSLGWVQPSRTLAGETGQEAAPLDGVLANPPNISSLSPR<br>QLLGFPCAEVSGLSTERVRELAVALAQKNVKLSTEQLRCLAHRLSEPPEDLDALPLDLLLFLNPDA<br>FSGPQACTRFFSRITKANVDLLPRGAPERQRLLPAALACWGVRGSLLSEADVRALGGLACDLPGR<br>FVAESAEVLLPRLVSCPGPLDQDQQEAARAALQGGGPPYGPPSTWSVSTMDALRGLLPVLGQPII<br>RSIPQGIVAAWRQRSSRDPSWRQPERTILRPRFRREVEKTACPSGKKAREIDESLIFYKKWELEA<br>CVDAALLATQMDRVNAIPFTYEQLDVLKHKLDELYPQGYPESVIQHLGYLFLKMSPEDIRKWNVTS<br>LETLKALLEVNKGHEMSPQVATLIDRFVKGRGQLDKDTLDTLTAFYPGYLCSLSPEELSSVPPSSI<br>WAVRPQDLDTCDPRQLDVLYPKARLAFQNMNGSEYFVKIQSFLGGAPTEDLK5ALSQQNVSMDL<br>ATFMKLRTDAVLPLTVAEVQKLLGPHVEGLKAEERHRPVRDWILRQRQDDLDTLGLGLQGGIPNG<br>GSTSGSGKPGSGEGSTKGMQEALSGTPCLLGPGPVLTVLALLLASTLA (SEQ ID NO: 22) |
| modTERT | atgcctagagcacctagatgtagagctgtgcggagcctgctgcggagccactatagagaagttctgcccctggccaccttcgtgcgtaga<br>cttggacctcaaggatggcggctggtgcagagaggcgatcctgctgcttttagagccctggtggcccagtgtctcgtgtgcgttccatggga<br>tgctagacctccaccagctgctcccagcttcagacaggtgtcctgcctgaaagaactggtggccagagtgctgcagcggctgtgtgaaag<br>gggcgccaaaaatgtgctggccttcggctttgccctgctggatgaagctagaggcggacctcctgaggcctttacaacaagcgtgcgga<br>gctacctgcctaacaccgtgacagatgccctgagaggatctggcgcttggggactgctgctgagaagagtgggagatgacgtgctggtg<br>catctgctggcccactgtgctctgtttgtgctggtggctcctagctgcgcctaccaagtttgcggccctctgctgtatcagctgggcgctgctac<br>acaggctagaccacctccacatgccagcggacctagaagaaggctgggctgcgaaagagcctggaaccactctgttagagaagccg<br>gcgtgccactgggattgcctgcacctggtgctcggagaagagatggcagcgcctctagatctctgcctctgcctaagaggcccagaaga<br>ggcgcagcacctgagcctgagagaacccctatcggccaaggatcttgggcccatcctggcagaacaagaggccctagcgatagagg<br>cttctgcgtggtgtctcctgccagacctgccgaggaagctacatctcttgacggcgccctgagcggcacaagacactctcatccatctgtgg<br>gctgccagcaccatgccggacctccatctacaagcagaccacctagaccttgggacaccccttgtcctccagtgtacgccgagacaaa<br>gcacttcctgtacagcagcggcgacaaagagcagctgaggcctagcttcctgctgagctttctgaggccaagcctgacaggcgccaga<br>cggctgctggaaacaatcttcctgggcagcagaccctggatgcctggcacacttagaaggctgcctagactgccccagcggtactggca |

TABLE 24-continued

| Sequences for MSLN, CT83 and Exemplary Design Antigens | |
|---|---|
| TAA | Sequence |
| | aatgaggcccctgtttctggaactgctgggcaaccacgctcagtgcccttatggcgtgctgctgaaaacccactgtccactgagagccgtg<br>gttactccagctgctggcgtgtgtgccagagagaagccacagggatctgtggtggcccctgaggaagaggacaccgatcctagaaggc<br>tcgtgcagctgctgaggcagcatagctctccatggcaggtctacggattcgtgcgggcctgtctgcatagactggttccacctggactgtgg<br>ggctccagacacaacgagcggcggtttctgcggaacaccaagaagttcatcagcctgggaaagcacgccaagctgagcctgcaaga<br>gctgacctggaagatgagcgtgtgggattgtgcttggctgcggagaagtcctggcgtgggatgtgttcctgccgccgaacacagactgcg<br>ggaagagatcctggccaagttcctgcactggctgatgtccgtgtacgtggtcgaactgctgcggtccctgttctgcgtgaccgagacaacct<br>tccagaagaaccggctgttcttctaccggaagtccgtgtggtccaagctgcagagcatcggcatccggcagcatctgaagagagtgcag<br>ctgagagagctgctcgaagccgaagttcggcagcacagaaaagccagactggccctgctgaccagcaggctgagattcatccccaag<br>cacgatggcctgcggcctattgtgaacatggactacgttgtgggcgccagaaccttccaccgggaaaagagagccgagcggctgacct<br>ctagagtgaaggccctgtttagcgtgctgaactacgagcgggccagaaggccatctctgctgggagcctttgtgctcggcctggacgatat<br>tcatagagcctggcggacattcgtgctgagagtcagagcccaggatagccctcctgagctgtacttcgtgaaggccgatgtgatgggcgc<br>ctacaacacaatccctcaggaccggctgaccgagatcattgccagcatcatcaagccccagaacatgtactgtgtgcggagatacgcc<br>gtggtgcagaaagccacacatggccacgtgcgcaaggccttcaagagccatgtgtctaccctgaccgacctgcagccttacatgagac<br>agttcgtggcctatctgcaagagacaagccctctgagggacgccgtgatcatcgaacagagcagcagcctgaatgaggccagctccgg<br>cctgtttgacgtgttcctcagattcatgtgccaccacgccgtgcggatcagaggcaagagctacatccagtgccagggcattccacaggg<br>ctccatcctgagcacactgctgtgcagcctgtgctacggcgacatggaaaacaagctgttcgccggcattcggcgcgacggactgcttctt<br>agactggtggacgacttcctgctcgtgacccctcatctgacccacgccaagacctttctgaaaacactcgtgcggggcgtgcccgagtatg<br>gctgtgtggtcaatctgagaaagaccgtggtcaacttccccgtcgaggatgaagccctcggcggcacagcttttgtgcagatgcctgctca<br>cggactgttcccttggtgctccctgctgctggacactagaaccctggaagtgcagagcgactacagcagctatgcccggacctctatcag<br>agccagcctgaccttcaaccggggctttaaggccggcagaaacatgcggagaaagctgtttggagtgctgcggctgaagtgccacagc<br>ctgttcctcgacctgcaagtgaacagcctgcagaccgtgtgcaccaatatctacaagattctgctgctgcaagcctaccggttccacgcctg<br>tgttctgcagctgcccttccaccagcaagtgtggaagaaccctacattcttcctgcggatcatcagcgacaccgccagcctgtgttacagca<br>tcctgaaggccaagaacgccggcatgtctctgggagctaaaggcgctgcaggacccctgccttttgaagctgttcagtggctgtgtcacca<br>ggcctttctgctgaagctgacccggcacagagtgacatatgtgcccctgctgggctccctgagaacagctcagatgcagctgtccagaaa<br>gctgccaggcacaaccctgacagccctggaagctgctgctaaccctgctctgcccagcgacttcaagaccatcctggactgatga<br>(SEQ ID NO: 35) |
| modTERT | MPRAPRCRAVRSLLRSHYREVLPLATFVRRLGPQGWRLVQRGDPAAFRALVAQCLVCVPWDAR<br>PPPAAPSFRQVSCLKELVARVLQRLCERGAKNVLAFGFALLDEARGGPPEAFTTSVRSYLPNTVT<br>DALRGSGAWGLLLRRVGDDVLVHLLAHCALFVLVAPSCAYQVCGPLLYQLGAATQARPPPHASG<br>PRRRLGCERAWNHSVREAGVPLGLPAPGARRRDGSASRSLPLPKRPRRGAAPEPERTPIGQGS<br>WAHPGRTRGPSDRGFCVVSPARPAEEATSLDGALSGTRHSHPSVGCQHHAGPPSTSRPPRPW<br>DTPCPPVYAETKHFLYSSGDKEQLRPSFLLSFLRPSLTGARRLLETIFLGSRPWMPGTLRRLPRLP<br>QRYWQMRPLFLELLGNHAQCPYGVLLKTHCPLRAVVTPAAGVCAREKPQGSVVAPEEEDTDPR<br>RLVQLLRQHSSPWQVYGFVRACLHRLVPPGLWGSRHNERRFLRNTKKFISLGKHAKLSLQELTW<br>KMSVWDCAWLRRSPGVGCVPAAEHRLREEILAKFLHWLMSVYVVELLRSLFCVTETTFQKNRLF<br>FYRKSVWSKLQSIGIRQHLKRVQLRELLEAEVRQHRKARLALLTSRLRFIPKHDGLRPIVNMDYVV<br>GARTFHREKRAERLTSRVKALFSVLNYERARRPSLLGAFVLGLDDIHRAWRTFVLRVRAQDSPPE<br>LYFVKADVMGAYNTIPQDRLTEIIASIIKPQNMYCVRRYAVVQKATHGHVRKAFKSHVSTLTDLQPY<br>MRQFVAYLQETSPLRDAVIIEQSSSLNEASSGLFDVFLRFMCHHAVRIRGKSYIQCQGIPQGSILST<br>LLCSLCYGDMENKLFAGIRRDGLLLRLVDDFLLVTPHLTHAKTFLKTLVRGVPEYGCVVNLRKTVV<br>NFPVEDEALGGTAFVQMPAHGLFPWCSLLLDTRTLEVQSDYSSYARTSIRASLTFNRGFKAGRN<br>MRRKLFGVLRLKCHSLFLDLQVNSLQTVCTNIYKILLLQAYRFHACVLQLPFHQQVWKNPTFFLRII<br>SDTASLCYSILKAKNAGMSLGAKGAAGPLPFEAVQWLCHQAFLLKLTRHRVTYVPLLGSLRTAQM<br>QLSRKLPGTTLTALEAAANPALPSDFKTILD (SEQ ID NO: 36) |
| modPSMA | atgtggaatctgctgcacgagacagatagcgccgtggctaccgttagaaggcccagatggctttgtgctggcgctctggttctggctggcg<br>gctttttttctgctgggcttcctgttcggctggttcatcaagagcagcaacgaggccaccaacatcacccctaagcacaacatgaaggccttt<br>ctggacgagctgaaggccgagaatatcaagaagttcctgtacaacttcacgcacatccctcacctggccggcaccgagcagaattttca |

TABLE 24-continued

Sequences for MSLN, CT83 and Exemplary Design Antigens

| TAA | Sequence |
| --- | --- |
| | gctggccaagcagatccagagccagtggaaagagttcggcctggactctgtggaactggcccactacgatgtgctgctgagctacccca<br>acaagacacaccccaactacatcagcatcatcaacgaggacggcaacgagatcttcaacaccagcctgttcgagcctccacctcctgg<br>ctacgagaacgtgtccgatatcgtgcctccattcagcgctttcagcccacagcggatgcctgagggctacctggtgtacgtgaactacgcc<br>agaaccgaggacttcttcaagctggaatgggacatgaagatcagctgcagcggcaagatcgtgatcgcccggtacagaaaggtgttcc<br>gcgagaacaaagtgaagaacgcccagctggcaggcgccaaaggcgtgatcctgtatagcgaccccgccgactattttgcccctggcgt<br>gaagtcttaccccgacggctggaattttcctggcggcggagtgcagcggcggaacatccttaatcttaacggcgctggcgaccctctgac<br>acctggctatcctgccaatgagtacgcctacagacacggaattgccgaggctgtgggcctgccttctattcctgtgcaccctgtgcggtact<br>acgacgcccagaaactgctggaaaagatgggcggaagcgcccctcctgactcttcttggagaggctctctgaaggtgccctacaatgtc<br>ggcccaggcttcaccggcaacttcagcacccagaaagtgaaaatgcacatccacagcaccaacgaagtgacccggatctacaacgt<br>gatcggcacactgagaggcgccgtggaacccgacaaatacgtgatcctcggcggccacagagacagctgggtgttcggaggaatcg<br>accctcaatctggcgccgctgtggtgtatgagatcgtgcggtctttcggcaccctgaagaaagaaggatggcggcccagacggaccatc<br>ctgtttgcctcttgggacgccgaggaatttggcctgctgggatctacagagtgggccgaagagaacagcagactgctgcaagaaagag<br>gcgtggcctacatcaacgccgacagcagcatcgagggcaactacaccctgcggatcgattgcacccctctgatgtacagcctggtgcac<br>aacctgaccaaagagctgaagtcccctgacgagggctttgagggcaagagcctgtacaagagctggaccaagaagtccccatctcctg<br>agttcagcggcatgcccagaatctctaagctggaaagcggcaacaacttcgaggtgttcttccagcggctgggaatcgcctctggaatcg<br>ccagatacaccaagaactgggagacaaacaagttctccggctatcccctgtaccacagcgtgtacgagacatacgagctggtggaaa<br>agttctacgaccccatgttcaagtaccacctgacagtggcccaagtgcgcggaggcatggtgttcgaactggccaatagcatcgtgctgc<br>ccttcaactgcagagactacgccgtggtgctgcggaagtacgccgacaagatctacagcatcagcatgaagcacccgcaagagatga<br>agacctacagcgtgtccttcgactccctgttcttcgccgtgaagaacttcaccaagatcgccagcaagttcagcgagcggctgcaggactt<br>cgacaagagcaaccctatcgtgctgaggatgatgaacgaccagctgatgttcctggaacgggccttcatcaaccctctgggactgcccg<br>acagacccttctacaggcacgtgatctgtgcccctagcagccacaacaaatacgccggcgagagcttccccggcatctacgatgccctg<br>ttcgacatcgagagcaacgtgaaccctagcaaggcctggggcgaagtgaagagacagatctacgtggccgcattcacagtgcaggcc<br>gctgccgaaacactgtctgaggtggcctgatga (SEQ ID NO: 37) |
| modPSMA | MWNLLHETDSAVATVRRPRWLCAGALVLAGGFFLLGFLFGWFIKSSNEATNITPKHNMKAFLDEL<br>KAENIKKFLYNFTHIPHLAGTEQNFQLAKQIQSQWKEFGLDSVELAHYDVLLSYPNKTHPNYISIINE<br>DGNEIFNTSLFEPPPPGYENVSDIVPPFSAFSPQRMPEGYLVYVNYARTEDFFKLEWDMKISCSG<br>KIVIARYRKVFRENKVKNAQLAGAKGVILYSDPADYFAPGVKSYPDGWNFPGGGVQRRNILNLNG<br>AGDPLTPGYPANEYAYRHGIAEAVGLPSIPVHPVRYYDAQKLLEKMGGSAPPDSSWRGSLKVPY<br>NVGPGFTGNFSTQKVKMHIHSTNEVTRIYNVIGTLRGAVEPDKYVILGGHRDSWVFGGIDPQSGA<br>AVVYEIVRSFGTLKKEGWRPRRTILFASWDAEEFGLLGSTEWAEENSRLLQERGVAYINADSSIEG<br>NYTLRIDCTPLMYSLVHNLTKELKSPDEGFEGKSLYKSWTKKSPSPEFSGMPRISKLESGNNFEVF<br>FQRLGIASGIARYTKNWETNKFSGYPLYHSVYETYELVEKFYDPMFKYHLTVAQVRGGMVFELAN<br>SIVLPFNCRDYAVVLRKYADKIYSISMKHPQEMKTYSVSFDSLFFAVKNFTKIASKFSERLQDFDKS<br>NPIVLRMMNDQLMFLERAFINPLGLPDRPFYRHVICAPSSHNKYAGESFPGIYDALFDIESNVNPSK<br>AWGEVKRQIYVAAFTVQAAAETLSEVA (SEQ ID NO: 38) |
| modMAGEA1-EGFRvIII-pp65 | atgtctctcgaacagagaagcctgcactgcaagcccgaggaagctctggaagctcagcaagaggctctgggccttgtgtgtgttcaggc<br>cgctgccagcagcttttctcctctggtgctgggcacactggaagaggtgccaacagccggctctaccgatcctcctcaatctcctcaaggc<br>gccagcgcctttcctaccaccatcaacttcacccggcagagacagcctagcgagggctctagctctcacgaggaaaagggccctagca<br>ccagctgcatcctggaaagcctgttccgggccgtgatcacaaagaaagtggccgacctcgtgggcttcctgctgctgaagtacagagcc<br>agagaacccgtgaccaaggccgagatgctggaaagcgtgatcaagaactacaagcactgcttcagcgagatcttcggcaaggccag<br>cgagtctctgcagctcgtgtttggcatcgacgtgaaagaggccgatcctaccggccacagctacgtgttcgtgacatgtctgggcctgagct<br>acgatggcctgctgggcgacaatcagattatgctgaaaaccggcttcctgatcatcgtgctggtcatgatcgccatggaaggctctcacgc<br>ccctaaagaggaaatctgggaagaactgagcgtgatggaagtgtacgacggcagagagcatagcgcctacggcgagcctagaaaa<br>ctgctgacccaggacctggtgcaagagaagtacctcgagtacagacaggtgcccgacagcgaccctgccagatacgaatttctgtggg<br>gccctagagcactggccgagacaagctatgtgaaggtgctggaatacgtcatcaaggtgtccgccagagtgtgcttcttcttcccatctctg<br>cgggaagccgctctgcgcgaagaggaagaaggcgtcagaggccggaagagaagaagcctggaagagaaaaagggcaactacgt<br>ggtcaccgaccactgcagaggcagaaagcggagaagcgagtctagaggcagacggtgccctgagatgattagcgtgctgggccctat |

TABLE 24-continued

Sequences for MSLN, CT83 and Exemplary Design Antigens

| TAA | Sequence |
|---|---|
| | ctctggccacgtgctgaaggccgtgttcagcagaggcgatacacctgtgctgccccacgagacaagactgctgcagacaggcatccat<br>gtgcgggtgtcacagccaagcctgatcctggtgtctcagtacacccctgacagcaccccttgtcacagaggcgacaaccagctccaggt<br>gcagcacacctactttaccggcagcgaggtggaaaacgtgtccgtgaacgtgcacaatcccaccggcagatccatctgtcccagccaa<br>gagcctatgagcatctacgtgtacgccctgcctctgaagatgctgaacatccccagcatcaatgtgcatcactacccctctgccgccgagc<br>ggaaacacagacatctgcctgtggccgatgccgtgattcacgcctctggaaagcagatgtggcaggccagactgacagtgtccggact<br>ggcttggaccagacagcagaaccagtggaaagaacccgacgtgtactacacctccgccttcgtgttccccacaaaggacgtggccctg<br>agacacgttgtgtgcgcccatgaactcgtgtgcagcatggaaaacacccgggccaccaagatgcaagtgatcggcgaccagtacgtg<br>aaggtgtacctggaatccttctgcgaggacgtgccaagcggcaagctgttcatgcacgtgaccctgggctccgatgtggaagaggacct<br>gaccatgaccagaaatccccagcctttcatgcggcctcacgagagaaatggcttcaccgtgctgtgccccaagaacatgatcatcaagc<br>ccggcaagatcagccacatcatgctggatgtggccttcaccagccacgagcacttcggactgctgtgtcctaagagcatccccggcctga<br>gcatcagcggcaacctgctgatgaatggccagcagatcttcctggaagtgcaggccattcgggaaaccgtggaactgagacagtacga<br>ccctgtggctgccctgttcttcttcgacatcgatctgctgctccagagaggccctcagtacagcgagcacccaacctttaccagccagtaca<br>gaatccagggcaagctggaatatcggcacacctgggatagacacgatgagggtgctgcacagggcgacgatgatgtgtggacaagc<br>ggcagcgatagcgacgaggaactggtcaccaccgagagaaagacccctagagttacaggcggaggcgcaatggctggcgcttctac<br>atctgccggacgcaagagaaagagcgcctcttctgccaccgcctgtacaagcggcgtgatgacaagaggcaggctgaaagccgaga<br>gcacagtggcccctgaggaagatacagacgaggacagcgacaacgagattcacaaccccgccgtgtttacctggcctccttggcagg<br>ctggcattctggctagaaacctggtgcctatggtggccacagtgcagggccagaacctgaagtaccaagagttcttctgggacgccaac<br>gacatctaccggatcttcgccgaactggaaggcgtgtggcaaccagccgctcagcccaaaagacgcagacacagacaggacgctct<br>gcccggaccttgtattgccagcacacccaagaaacaccggggctgataa (SEQ ID NO: 39) |
| modMAGEA1-EGFRvIII-pp65 | MSLEQRSLHCKPEEALEAQQEALGLVCVQAAASSFSPLVLGTLEEVPTAGSTDPPQSPQGASAF<br>PTTINFTRQRQPSEGSSSHEEKGPSTSCILESLFRAVITKKVADLVGFLLLKYRAREPVTKAEMLES<br>VIKNYKHCFSEIFGKASESLQLVFGIDVKEADPTGHSYVFVTCLGLSYDGLLGDNQIMLKTGFLIIVL<br>VMIAMEGSHAPKEEIWEELSVMEVYDGREHSAYGEPRKLLTQDLVQEKYLEYRQVPDSDPARYE<br>FLWGPRALAETSYVKVLEYVIKVSARVCFFFPSLREAALREEEEGVRGRKRRSLEEKKGNYVVTD<br>HCRGRKRRSESRGRRCPEMISVLGPISGHVLKAVFSRGDTPVLPHETRLLQTGIHVRVSQPSLILV<br>SQYTPDSTPCHRGDNQLQVQHTYFTGSEVENVSVNVHNPTGRSICPSQEPMSIYVYALPLKMLNI<br>PSINVHHYPSAAERKHRHLPVADAVIHASGKQMWQARLTVSGLAWTRQQNQWKEPDVYYTSAF<br>VFPTKDVALRHVVCAHELVCSMENTRATKMQVIGDQYVKVYLESFCEDVPSGKLFMHVTLGSDV<br>EEDLTMTRNPQPFMRPHERNGFTVLCPKNMIIKPGKISHIMLDVAFTSHEHFGLLCPKSIPGLSISG<br>NLLMNGQQIFLEVQAIRETVELRQYDPVAALFFFDIDLLLQRGPQYSEHPTFTSQYRIQGKLEYRHT<br>WDRHDEGAAQGDDDVINTSGSDSDEELVTTERKTPRVTGGGAMAGASTSAGRKRKSASSATAC<br>TSGVMTRGRLKAESTVAPEEDTDEDSDNEIHNPAVFTWPPWQAGILARNLVPMVATVQGQNLKY<br>QEFFWDANDIYRIFAELEGVINQPAAQPKRRRHRQDALPGPCIASTPKKHRG (SEQ ID NO: 40) |
| modTBXT-modBORIS | atgtctagccctggaacagagtctgccggcaagagcctgcagtacagagtggaccatctgctgagcgccgtggaaaatgaactgcagg<br>ccggaagcgagaagggcgatcctacagagcacgagctgagagtcggcctggaagagtctgagctgtggctgcggttcaaagaactg<br>accaacgagatgatcgtgaccaagaacggcagacggatgttccccgtgctgaaagtgaacgtgtccggactggaccccaacgccatgt<br>acagctttctgctggacttcgtggtggccgacaaccacagatggaaatacgtgaacggcgagtgggtgccaggcggaaaacctcaact<br>gcaagcccctagctgcgtgtacattcaccctgacagccccaatttcggcgcccactggatgaaggcccctgtgtccttcagcaaagtgaa<br>gctgaccaacaagctgaacggcggaggccagatcatgctgaacagcctgcacaaatacgagcccagaatccacatcgtcagagtcg<br>gcggaccccagagaatgatcaccagccactgcttccccgagacacagtttatcgccgtgaccgcctaccagaacgaggaaatcacca<br>cactgaagatcaagtacaaccccttcgccaaggccttcctggacgccaaagagcggagcgaccacaaagagatgatcaaagagccc<br>ggcgacagccagcagccaggctattctcaatggggatggctgctgccaggcaccagcacattgtgccctccagccaatcctcacagcc<br>agtttggaggcgccctgagcctgtctagcacccacagctacgacagataccccacactgcggagccacagaagcagcccctatccttct<br>ccttacgctcaccggaacaacagccccacctacagcgataatagccccgcctgtctgagcatgctgcagtcccacgataactggtccag<br>cctgagaatgcctgctcacccttccatgctgcccgtgtctcacaatgcctctccacctaccagcagctctcagtaccctagcctttggagcgt<br>gtccaatggcgccgtgacactgggatctcaggcagccgctgtgtctaatggactgggagcccagttcttcagaggcagccctgctcacta<br>cacccctctgacacatcctgtgtctgcccctagcagcagcggcttccctatgtataagggcgctgccgccgctaccgacatcgtggattctc |

TABLE 24-continued

Sequences for MSLN, CT83 and Exemplary Design Antigens

| TAA | Sequence |
|---|---|
| | agtatgatgccgccgcacagggacacctgatcgcctcttggacacctgtgtctccaccttccatgagaggcagaaagagaagatccgcc<br>gccaccgagatcagcgtgctgagcgagcagttcaccaagatcaaagaattgaagctgatgctcgagaaggggctgaagaaagaaga<br>gaaggacggcgtctgccgcgagaagaatcacagaagccctagcgagctggaagcccagagaacatctggcgccttccaggacagc<br>atcctggaagaagaggtggaactggttctggcccctctggaagagagcaagaagtacatcctgacactgcagaccgtgcacttcacctc<br>tgaagccgtgcagctccaggacatgagcctgctgtctatccagcagcaagagggcgtgcaggttgtggttcagcaacctggacctggac<br>tgctctggctgcaagagggacctagacagtccctgcagcagtgtgtggccatcagcatccagcaagagctgtatagccctcaagagatg<br>gaagtgctgcagtttcacgccctcgaagagaacgtgatggtggccatcgaggacagcaagctggctgtgtctctggccgaaacaaccg<br>gcctgatcaagctggaagaggaacaagagaagaaccagctgctggccgagaaaacaaaaaagcaactgttcttcgtggaaaccatg<br>agcggcgacgagagaagcgacgagatcgtgctgacagtgtccaacagcaacgtggaagaacaagaggaccagcctaccgcctgtc<br>aggccgatgccgagaaagccaagtttaccaagaaccagagaaagaccaagggcgccaagggcaccttccactgcaacgtgtgcat<br>gttcaccagcagccggatgagcagcttcaactgccacatgaagacccacaccagcgagaagccccatctgtgtcacctgtgcctgaaa<br>accttccggacagtgacactgctgtggaactatgtgaacacccacacaggcacccggccttacaagtgcaacgactgcaacatggcctt<br>cgtgaccagcggagaactcgtgcggcacagaagatacaagcacacccacgagaaacccttcaagtgcagcatgtgcaaatacgcat<br>ccatggaagcctccaagctgaagtgccacgtgcgctctcacacaggcgagcaccctttccagtgctgtcagtgtagctacgccagccgg<br>gacacctataagctgaagcggcacatgagaacccactctggcgaaaagccctacgagtgccacatctgccacaccagattcacccag<br>agcggcaccatgaagattcacatcctgcagaaacacggcaagaacgtgcccaagtaccagtgtcctcactgcgccaccattatcgcca<br>gaaagtccgacctgcgggtgcacatgaggaatctgcacgcctattctgccgccgagctgaaatgcagatactgcagcgccgtgttccac<br>aagagatacgccctgatccagcaccagaaaacccacaagaacgagaagcggtttaagtgcaagcactgcagctacgcctgcaagca<br>agagcgccacatgatcgcccacatccacacacacaccggggagaagcctttttacctgcctgagctgcaacaagtgcttccggcagaaa<br>cagctgctcaacgcccacttcagaaagtaccacgacgccaacttcatccccaccgtgtacaagtgctccaagtgcggcaagggcttcag<br>ccggtggatcaatctgcaccggcacctggaaaagtgcgagtctggcgaagccaagtctgccgcctctggcaagggcagaagaacccg<br>gaagagaaagcagaccatcctgaaagaggccaccaagagccagaaagaagccgccaagcgctggaaagaggctgccaacggc<br>gacgaagctgctgccgaagaagccagcacaacaaagggcgaacagttccccgaagagatgttccctgtggcctgcagagaaaccac<br>agccagagtgaagcaagaggtcgaccagggcgtgacctgcgagatgctgctgaacaccatggacaagtgatga (SEQ ID NO: 41) |
| modTBXT-modBORIS | MSSPGTESAGKSLQYRVDHLLSAVENELQAGSEKGDPTEHELRVGLEESELWLRFKELTNEMIVT<br>KNGRRMFPVLKVNVSGLDPNAMYSFLLDFVVADNHRWKYVNGEWVPGGKPQLQAPSCVYIHPD<br>SPNFGAHWMKAPVSFSKVKLTNKLNGGGQIMLNSLHKYEPRIHIVRVGGPQRMITSHCFPETQFIA<br>VTAYQNEEITTLKIKYNPFAKAFLDAKERSDHKEMIKEPGDSQQPGYSQWGWLLPGTSTLCPPAN<br>PHSQFGGALSLSSTHSYDRYPTLRSHRSSPYPSPYAHRNNSPTYSDNSPACLSMLQSHDNWSSL<br>RMPAHPSMLPVSHNASPPTSSSQYPSLWSVSNGAVTLGSQAAAVSNGLGAQFFRGSPAHYTPL<br>THPVSAPSSSGFPMYKGAAAATDIVDSQYDAAAQGHLIASWTPVSPPSMRGRKRRSAATEISVLS<br>EQFTKIKELKLMLEKGLKKEEKDGVCREKNHRSPSELEAQRTSGAFQDSILEEEVELVLAPLEESK<br>KYILTLQTVHFTSEAVQLQDMSLLSIQQQEGVQVVVQQPGPGLLWLQEGPRQSLQQCVAISIQQE<br>LYSPQEMEVLQFHALEENVMVAIEDSKLAVSLAETTGLIKLEEEQEKNQLLAEKTKKQLFFVETMS<br>GDERSDEIVLTVSNSNVEEQEDQPTACQADAEKAKFTKNQRKTKGAKGTFHCNVCMFTSSRMSS<br>FNCHMKTHTSEKPHLCHLCLKTFRTVTLLWNYVNTHTGTRPYKCNDCNMAFVTSGELVRHRRYK<br>HTHEKPFKCSMCKYASMEASKLKCHVRSHTGEHPFQCCQCSYASRDTYKLKRHMRTHSGEKPY<br>ECHICHTRFTQSGTMKIHILQKHGKNVPKYQCPHCATIIARKSDLRVHMRNLHAYSAAELKCRYCS<br>AVFHKRYALIQHQKTHKNEKRFKCKHCSYACKQERHMIAHIHTHTGEKPFTCLSCNKCFRQKQLL<br>NAHFRKYHDANFIPTVYKCSKCGKGFSRWINLHRHLEKCESGEAKSAASGKGRRTRKRKQTILKE<br>ATKSQKEAAKRWKEAANGDEAAAEEASTTKGEQFPEEMFPVACRETTARVKQEVDQGVTCEML<br>LNTMDK (SEQ ID NO: 42) |
| modFSHR-modMAGEA10 | atggctctgctgctggtttctctgctggccctgctgtctctcggctctggatgtcaccacagaatctgccactgcagcaaccgggtgttcctgtg<br>ccagaaaagcaaagtgaccgagatcctgagcgacctgcagcggaatgccatcgagctgagattcgtgctgaccaagctgcaagtgat<br>ccagaagggcgccttcagcggcttcggcgacctggaaaagatcgagatcagccagaacaacgtgctggaagtgatcgaggcccacg<br>tgttcagcaacctgcctaagctgcacgagatcagaatcgagaaggccaacaacctgctgtacatcaaccccgaggccttccagaacttc<br>cccaacctgcagtacctgctgatctccaacaccggcatcaaacatctgcccgacgtgcacaagatccacagcctgcagaaggtgctgct |

TABLE 24-continued

| Sequences for MSLN, CT83 and Exemplary Design Antigens | |
|---|---|
| TAA | Sequence |
| | ggacatccaggacaacatcaacatccacacaatcgagcggaactacttcctgggcctgagcttcgagagcgtgatcctgtggctgaaca<br>agaacggcatccaagagatccacaactgcgccttcaatggcacccagctggacgagctgaacctgtccgacaacaacaatctggaag<br>aactgcccaacgacgtgttccacagagccagcggacctgtgatcctggacatcagcagaaccagaatccactctctgcccagctacgg<br>cctggaaaacctgaagaagctgcgggccagaagcacctacaatctgaaaaagctgcctacgctggaaaccctggtggccctgatgga<br>agccagcctgacataccctagccactgctgcgcctttgccaactggcggagacagatctctgagctgcaccccatctgcaacaagagca<br>tcctgcggcaagaggtggactacatgacacaggccagaggccagagattcagcctggccgaggataacgagagcagctacagcag<br>aggcttcgacatgacctacaccgagttcgactacgacctgtgcaacaaggtggtggacgtgacatgcagccccaagcctgatgccttca<br>atccctgcgaggacatcatgggctacaacatcctgagagtgctgatctggttcatcagcatcctggccatcaccgagaacatcatcgtgct<br>ggtcatcctgaccaccagccagtacaagctgaccgtgcctatgttcctgatgtgcaacctggccttcgccgatctgtgcatcggcatctacct<br>gctgctgatcgccagcgtggacattcacaccaagagccagtaccacaactacgccatcgactggcagacaggcgccggatgtgatgc<br>cgccggattctttacagtgttcgccagcgagctgtccgtgtacaccctgacagctatcaccctggaacggtggcacaccatcacacacgct<br>atgcagctggactgcaaagtgcacctgagacacagcgcctccgtgatggttatgggctggatcttcgccttcgctgccgctctgttccccatc<br>tttggcatcagctcctacatgaaggtgtccatctatctgcccatggacatcgacagccctctgagccagctgtacgtgatgagtctgctggtg<br>ctgaatgtgctggcctttgtggtcatctgcggctgctacatctatatctacctgacagtgcggaaccccaacatcgtgtccagctccagcgac<br>acccggatcgctaagagaatggccatgctgatcttcaccgactttctgtgcatggcccctatcagcctgttcgccattagcgctagcctgaa<br>ggtgcccctgatcaccgtgtccaaggccaagattctgctggtcctgttctaccccatcaacagctgcgccaatcctttcctgtacgccatcttc<br>accaagaacttcaggcggaacttcttcatcctgctgagcaagcggggctgttacaagatgcaggcccagatctaccggaccgagacact<br>gtccaccgtgcacaacacacaccccagaaacggccactgtagcagcgcccctagagtgacaaatggctccacctacatcctggtgcc<br>actgagccatctggcccagaacagaggccggaagagaagaagccccagggctcccaagagacagagatgcatgcccgaagagg<br>acctgcagagccagagcgaaacacagggactcgaaggtgctcaggctcctctggccgtggaagaagatgccagcagctctaccagc<br>acctccagcagcttccctagcagctttccattcagctcctctagctctagcagcagctgttaccctctgatccccagcacacccgagaaggt<br>gttcgccgacgacgagacacctaatccactgcagtctgcccagatcgcctgcagcagtacactggtggttgctagcctgcctctggacca<br>gtctgatgagggaagcagcagccagaaagaggaaagccctagcacactccaggtgctgcccgatagcgagagcctgcctagaagc<br>gagatctacaagaaaatgaccgacctggtgcagttcctcctgttcaagtaccagatgaaggaacccatcaccaaggccgaaatcctgg<br>aaagcgtgatcagaaactacgaggaccactttccactgctgttcagcgaggccagcgagtgcatgctgctcgtgtttagcatcgacgtga<br>agaaggtggaccccaccggccacagctttgtgctggttacaagcctgggactgacctacgacggcatgctgtccgatgtgcagagcatg<br>cctaagaccggcatcctgatcctgattctgagcatcgtgttcatcgagggctactgcacccctgaggaagtgatttgggaagccctgaacat<br>gatgggcctgtacgatggcatggaacacctgatctacggcgagcccagaaaactgctgacccaggactgggtgcaagagaactacct<br>ggaataccggcagatgcccggcagcgatcctgccagatatgagtttctgtggggccctagagcacatgccgagatccggaagatgagc<br>ctgctgaagttcctggccaaagtgaacggcagcgacccaatcagcttcccactttggtacgaagaggccctgaaggacgaggaagag<br>agagcccaggatagaatcgccaccaccgacgacacaacagccatggcctctgcctcttctagcgccaccggcagctttagctaccccg<br>agtgataa (SEQ ID NO: 43) |
| modFSHR-modMAGEA10 | MALLLVSLLALLSLGSGCHHRICHCSNRVFLCQKSKVTEILSDLQRNAIELRFVLTKLQVIQKGAFS<br>GFGDLEKIEISQNNVLEVIEAHVFSNLPKLHEIRIEKANNLLYINPEAFQNFPNLQYLLISNTGIKHLPD<br>VHKIHSLQKVLLDIQDNINIHTIERNYFLGLSFESVILWLNKNGIQEIHNCAFNGTQLDELNLSDNNNL<br>EELPNDVFHRASGPVILDISRTRIHSLPSYGLENLKKLRARSTYNLKKLPTLETLVALMEASLTYPSH<br>CCAFANWRRQISELHPICNKSILRQEVDYMTQARGQRFSLAEDNESSYSRGFDMTYTEFDYDLC<br>NKVVDVTCSPKPDAFNPCEDIMGYNILRVLIWFISILAITENIIVLVILTTSQYKLTVPMFLMCNLAFAD<br>LCIGIYLLLIASVDIHTKSQYHNYAIDWQTGAGCDAAGFFTVFASELSVYTLTAITLERWHTITHAMQ<br>LDCKVHLRHSASVMVMGWIFAFAAALFPIFGISSYMKVSIYLPMDIDSPLSQLYVMSLLVLNVLAFV<br>VICGCYIYIYLTVRNPNIVSSSSDTRIAKRMAMLIFTDFLCMAPISLFAISASLKVPLITVSKAKILLVLF<br>YPINSCANPFLYAIFTKNFRRNFFILLSKRGCYKMQAQIYRTETLSTVHNTHPRNGHCSSAPRVTN<br>GSTYILVPLSHLAQNRGRKRRSPRAPKRQRCMPEEDLQSQSETQGLEGAQAPLAVEEDASSSTS<br>TSSSFPSSFPFSSSSSSSSCYPLIPSTPEKVFADDETPNPLQSAQIACSSTLVVASLPLDQSDEGS |

TABLE 24-continued

| Sequences for MSLN, CT83 and Exemplary Design Antigens | |
|---|---|
| TAA | Sequence |
| | SSQKEESPSTLQVLPDSESLPRSEIYKKMTDLVQFLLFKYQMKEPITKAEILESVIRNYEDHFPLLFS<br>EASECMLLVFSIDVKKVDPTGHSFVLVTSLGLTYDGMLSDVQSMPKTGILILILSIVFIEGYCTPEEVI<br>WEALNMMGLYDGMEHLIYGEPRKLLTQDINVQENYLEYRQMPGSDPARYEFLWGPRAHAEIRKM<br>SLLKFLAKVNGSDPISFPLINYEEALKDEEERAQDRIATTDDTTAMASASSSATGSFSYPE (SEQ ID<br>NO: 44) |
| modTBXT-modMAGEC2 | atggctctgctgctggtttctctgctggccctgctgtctctcggctctggatgtcaccacagaatctgccactgcagcaaccgggtgttcctgtg<br>ccagaaaagcaaagtgaccgagatcctgagcgacctgcagcggaatgccatcgagctgagattcgtgctgaccaagctgcaagtgat<br>ccagaagggcgccttcagcggcttcggcgacctggaaaagatcgagatcagccagaacaacgtgctggaagtgatcgaggcccacg<br>tgttcagcaacctgcctaagctgcacgagatcagaatcgagaaggccaacaacctgctgtacatcaaccccgaggccttccagaacttc<br>cccaacctgcagtacctgctgatctccaacaccggcatcaaacatctgcccgacgtgcacaagatccacagcctgcagaaggtgctgct<br>ggacatccaggacaacatcaacatccacacaatcgagcggaactacttcctgggcctgagcttcgagagcgtgatcctgtggctgaaca<br>agaacggcatccaagagatccacaactgcgccttcaatggcacccagctggacgagctgaacctgtccgacaacaacaatctggaag<br>aactgcccaacgacgtgttccacagagccagcggacctgtgatcctggacatcagcagaaccagaatccactctctgcccagctacgg<br>cctggaaaacctgaagaagctgcgggccagaagcacctacaatctgaaaaagctgcctacgctggaaaccctggtggccctgatgga<br>agccagcctgacataccctagccactgctgcgcctttgccaactggcggagacagatctctgagctgcaccccatctgcaacaagagca<br>tcctgcggcaagaggtggactacatgacacaggccagaggccagagattcagcctggccgaggataacgagagcagctacagcag<br>aggcttcgacatgacctacaccgagttcgactacgacctgtgcaacaaggtggtggacgtgacatgcagccccaagcctgatgccttca<br>atccctgcgaggacatcatgggctacaacatcctgagagtgctgatctggttcatcagcatcctggccatcaccgagaacatcatcgtgct<br>ggtcatcctgaccaccagccagtacaagctgaccgtgcctatgttcctgatgtgcaacctggccttcgccgatctgtgcatcggcatctacct<br>gctgctgatcgccagcgtggacattcacaccaagagccagtaccacaactacgccatcgactggcagacaggcgccggatgtgatgc<br>cgccggattctttacagtgttcgccagcgagctgtccgtgtacaccctgacagctatcaccctggaacggtggcacaccatcacacacgct<br>atgcagctggactgcaaagtgcacctgagacacagcgcctccgtgatggttatgggctggatcttcgccttcgctgccgctctgttccccatc<br>tttggcatcagctcctacatgaaggtgtccatctatctgcccatggacatcgacagccctctgagccagctgtacgtgatgagtctgctggtg<br>ctgaatgtgctggcctttgtggtcatctgcggctgctacatctatatctacctgacagtgcggaaccccaacatcgtgtccagctccagcgac<br>acccggatcgctaagagaatggccatgctgatcttcaccgactttctgtgcatggcccctatcagcctgttcgccattagcgctagcctgaa<br>ggtgcccctgatcaccgtgtccaaggccaagattctgctggtcctgttctaccccatcaacagctgcgccaatcctttcctgtacgccatcttc<br>accaagaacttcaggcggaacttcttcatcctgctgagcaagcggggctgttacaagatgcaggcccagatctaccggaccgagacact<br>gtccaccgtgcacaacacacaccccagaaacggccactgtagcagcgcccctagagtgacaaatggctccacctacatcctggtgcc<br>actgagccatctggcccagaacagaggccggaagagaagaagccccagggctcccaagagacagagatgcatgcccgaagagg<br>acctgcagagccagagcgaaacacagggactcgaaggtgctcaggctcctctggccgtggaagaagatgccagcagctctaccagc<br>acctccagcagcttccctagcagctttccattcagctcctctagctctagcagcagctgttaccctctgatccccagcacacccgagaaggt<br>gttcgccgacgacgagacacctaatccactgcagtctgcccagatcgcctgcagcagtacactggtggttgctagcctgcctctggacca<br>gtctgatgagggaagcagcagccagaaagaggaaagccctagcacactccaggtgctgcccgatagcgagagcctgcctagaagc<br>gagatctacaagaaaatgaccgacctggtgcagttcctcctgttcaagtaccagatgaaggaacccatcaccaaggccgaaatcctgg<br>aaagcgtgatcagaaactacgaggaccactttccactgctgttcagcgaggccagcgagtgcatgctgctcgtgtttagcatcgacgtga<br>agaaggtggaccccaccggccacagctttgtgctggttacaagcctgggactgacctacgacggcatgctgtccgatgtgcagagcatg<br>cctaagaccggcatcctgatcctgattctgagcatcgtgttcatcgagggctactgcacccctgaggaagtgatttgggaagccctgaacat<br>gatgggcctgtacgatggcatggaacacctgatctacggcgagcccagaaaactgctgacccaggactgggtgcaagagaactacct<br>ggaataccggcagatgcccggcagcgatcctgccagatatgagtttctgtggggccctagagcacatgccgagatccggaagatgagc<br>ctgctgaagttcctggccaaagtgaacggcagcgacccaatcagcttcccactttggtacgaagaggccctgaaggacgaggaagag<br>agagcccaggatagaatcgccaccaccgacgacacaacagccatggcctctgcctcttctagcgccaccggcagctttagctaccccg<br>agtgataa (SEQ ID NO: 45) |
| modTBXT-modMAGEC2 | MSSPGTESAGKSLQYRVDHLLSAVENELQAGSEKGDPTEHELRVGLEESELWLRFKELTNEMIVT<br>KNGRRMFPVLKVNVSGLDPNAMYSFLLDFVVADNHRWKYVNGEWVPGGKPQLQAPSCVY1HPD<br>SPNFGAHWMKAPVSFSKVKLTNKLNGGGQIMLNSLHKYEPRIHIVRVGGPQRMITSHCFPETQFIA<br>VTAYQNEEITTLKIKYNPFAKAFLDAKERSDHKEMIKEPGDSQQPGYSQWGWLLPGTSTLCPPAN<br>PHSQFGGALSLSSTHSYDRYPTLRSHRSSPYPSPYAHRNNSPTYSDNSPACLSMLQSHDNWSSL |

TABLE 24-continued

| Sequences for MSLN, CT83 and Exemplary Design Antigens | |
|---|---|
| TAA | Sequence |
| | RMPAHPSMLPVSHNASPPTSSSQYPSLWSVSNGAVTLGSQAAAVSNGLGAQFFRGSPAHYTPL THPVSAPSSSGFPMYKGAAAATDIVDSQYDAAAQGHLIASWTPVSPPSMRGRKRRSPPVPGVPF RNVDNDSLTSVELEDWVDAQHPTDEEEEEASSASSTLYLVFSPSSFSTSSSLILGGPEEEEVPSG VIPNLTESIPSSPPQGPPQGPSQSPLSSCCSSFLWSSFSEESSSQKGEDTGTCQGLPDSESSFTY TLDEKVAKLVEFLLLKYEAEEPVTEAEMLMIVIKYKDYFPVILKRAREFMELLFGLALIEVGPDHFCV FANTVGLTDEGSDDEGMPENSLLIIILSVIFIKGNCASEEVIWEVLNAVGVYAGREHFVYGKPRELL TNVWVQGHYLEYWEVPHSSPLYYEFLWGPRAHSESIKKKVLEFLAKLNNTVPSFFPSWYKDALK DVEERVQATIDTADDATVMASESLSVMSSNVSFSE (SEQ ID NO: 46) |
| modTBXT-modWT1 | atgtctagccctggaacagagtctgccggcaagagcctgcagtacagagtggaccatctgctgagcgccgtggaaaatgaactgcagg ccggaagcgagaagggcgatcctacagagcacgagctgagagtcggcctggaagagtctgagctgtggctgcggttcaaagaactg accaacgagatgatcgtgaccaagaacggcagacggatgttccccgtgctgaaagtgaacgtgtccggactggaccccaacgccatgt acagctttctgctggacttcgtggtggccgacaaccacagatggaaatacgtgaacggcgagtgggtgccaggcggaaaacctcaact gcaagcccctagctgcgtgtacattcaccctgacagccccaatttcggcgcccactggatgaaggcccctgtgtccttcagcaaagtgaa gctgaccaacaagctgaacggcggaggccagatcatgctgaacagcctgcacaaatacgagcccagaatccacatcgtcagagtcg gcggaccccagagaatgatcaccagccactgcttccccgagacacagtttatcgccgtgaccgcctaccagaacgaggaaatcacca cactgaagatcaagtacaaccccttcgccaaggccttcctggacgccaaagagcggagcgaccacaaagagatgatcaaagagccc ggcgacagccagcagccaggctattctcaatggggatggctgctgccaggcaccagcacattgtgccctccagccaatcctcacagcc agtttggaggcgccctgagcctgtctagcacccacagctacgacagataccccacactgcggagccacagaagcagcccctatccttct ccttacgctcaccggaacaacagccccacctacagcgataatagccccgcctgtctgagcatgctgcagtcccacgataactggtccag cctgagaatgcctgctcacccttccatgctgcccgtgtctcacaatgcctctccacctaccagcagctctcagtaccctagcctttggagcgt gtccaatggcgccgtgacactgggatctcaggcagccgctgtgtctaatggactgggagcccagttcttcagaggcagccctgctcacta cacccctctgacacatcctgtgtctgcccctagcagcagcggcttccctatgtataagggcgctgccgccgctaccgacatcgtggattctc agtatgatgccgccgcacagggacacctgatcgcctcttggacacctgtgtctccaccttccatgagaggcagaaagcggagaagcga cttcctgctgctgcagaaccctgcctctacctgtgtgcctgaaccagcctctcagcacaccctgagatctggccctggatgtctccagcagc ctgaacagcagggcgttagagatcctggcggaatctgggccaaactgggagctgccgaagcctctgccgaatgtctgcagggcagaa gaagcagaggcgccagcggatctgaacctcaccagatgggaagcgacgtgcacgacctgaatgctctgttgcctgccgtgccatctctt ggcggaggcggaggatgtgctttgcctgtttctggtgctgcccagtgggctcccgtgctggattttgctcctcctggcgcttctgcctatggctct cttggaggacctgctcctccaccagctccacctccaccgccgcctccaccacctcacagctttatcaagcaagagccctcctggggcgga gccgagcctcacgaaaaacagtgtctgagcgccttcaccgtgcactttttcggccagtttaccggcaccgtgggcgcctgtagatacggcc cttttggaccaccaccacctagccaggcttctagcggacaggccagaatgttccccaacgctccttacctgcctagctgcctggaaagcc agcctaccatcagaaaccagggcttcagcaccgtgaccttcgacggcatgcctagctatggccacacaccatctcaccacgccgctcag ttccccaatcacagcttcaagcacgaggaccctatgggccagcagggatctctgggagagcagcagtatagcgtgccacctcctgtgta cggctgtcacacccctaccgatagctgcacaggcaatcaggctctgctgctgaggatgcctttcagcagcgacaacctgtaccagatgac aagccagctggaatgcatgatttggaaccagatgaacctgggcgccactctgaaaggcgtggccgctggatctagcagctccgtgaaat ggacagccggccagagcaatcactccaccggctacgagagcgacaatcacaccatgcctatcctgtgtggggcccagtaccggattca cacacacggcgtgttcaggggcattcaggatgtgcgaagagtgcctggcgtggcccctacacttgtgggatctgccagcgaaaccagcg agaagcaccccttcatgtgcgcctatccaggctgcaacaagcggtacttcaagctgagccacctgaagatgcacagccggaagcaca caggcgagaagctgtaccagtgcgacttcaaggactgcgagcggagattcagctgcagcgaccagctgaagagacaccagagaag gcacaccggcgtgaagccctttcagtgcaagacctgccagcggaccttctcctggtccaaccacctgaaaacccacacaagaacccac accggcaagaccatcgagaagcccttcagctgtagatggcccagctgccagaagaagttcgcccggtctaacgagctggtgcatcacc acaacatgcaccagaggaacatgaccaaactgcagctggtgctgtgatga (SEQ ID NO: 47) |
| modTBXT_WT1 | MSSPGTESAGKSLQYRVDHLLSAVENELQAGSEKGDPTEHELRVGLEESELWLRFKELTNEMIVT KNGRRMFPVLKVNVSGLDPNAMYSFLLDFVVADNHRWKYVNGEWVPGGKPQLQAPSCVYIHPD SPNFGAHWMKAPVSFSKVKLTNKLNGGGQIMLNSLHKYEPRIHIVRVGGPQRMITSHCFPETQFIA VTAYQNEEITTLKIKYNPFAKAFLDAKERSDHKEMIKEPGDSQQPGYSQWGWLLPGTSTLCPPAN PHSQFGGALSLSSTHSYDRYPTLRSHRSSPYPSPYAHRNNSPTYSDNSPACLSMLQSHDNWSSL RMPAHPSMLPVSHNASPPTSSSQYPSLWSVSNGAVTLGSQAAAVSNGLGAQFFRGSPAHYTPL |

TABLE 24-continued

| Sequences for MSLN, CT83 and Exemplary Design Antigens | |
|---|---|
| TAA | Sequence |
| | THPVSAPSSSGFPMYKGAAAATDIVDSQYDAAAQGHLIASWTPVSPPSMRGRKRRSDFLLLQNP<br>ASTCVPEPASQHTLRSGPGCLQQPEQQGVRDPGGIWAKLGAAEASAECLQGRRSRGASGSEPH<br>QMGSDVHDLNALLPAVPSLGGGGGCALPVSGAAQWAPVLDFAPPGASAYGSLGGPAPPPAPPP<br>PPPPPPHSFIKQEPSWGGAEPHEKQCLSAFTVHFFGQFTGTVGACRYGPFGPPPPSQASSGQA<br>RMFPNAPYLPSCLESQPTIRNQGFSTVTFDGMPSYGHTPSHHAAQFPNHSFKHEDPMGQQGSL<br>GEQQYSVPPPVYGCHTPTDSCTGNQALLLRMPFSSDNLYQMTSQLECMIWNQMNLGATLKGVA<br>AGSSSSVKWTAGQSNHSTGYESDNHTMPILCGAQYRIHTHGVFRGIQDVRRVPGVAPTLVGSAS<br>ETSEKHPFMCAYPGCNKRYFKLSHLKMHSRKHTGEKLYQCDFKDCERRFSCSDQLKRHQRRHT<br>GVKPFQCKTCQRTFSWSNHLKTHTRTHTGKTIEKPFSCRWPSCQKKFARSNELVHHHNMHQRN<br>MTKLQLVL (SEQ ID NO: 48) |
| modTBXT_WT1_(KRAS Mutations) | agagtctgagctgtggctgcggttcaaagaactgaccaacgagatgatcgtgaccaagaacggcagacggatgttccccgtgctgaaa<br>gtgaacgtgtccggactggaccccaacgccatgtacagctttctgctggacttcgtggtggccgacaaccacagatggaaatacgtgaac<br>ggcgagtgggtgccaggcggaaaacctcaactgcaagcccctagctgcgtgtacattcaccctgacagccccaatttcggcgcccactg<br>gatgaaggcccctgtgtccttcagcaaagtgaagctgaccaacaagctgaacggcggaggccagatcatgctgaacagcctgcacaa<br>atacgagcccagaatccacatcgtcagagtcggcggaccccagagaatgatcaccagccactgcttccccgagacacagtttatcgcc<br>gtgaccgcctaccagaacgaggaaatcaccacactgaagatcaagtacaaccccttcgccaaggccttcctggacgccaaagagcg<br>gagcgaccacaaagagatgatcaaagagcccggcgacagccagcagccaggctattctcaatggggatggctgctgccaggcacca<br>gcacattgtgccctccagccaatcctcacagccagtttggaggcgccctgagcctgtctagcacccacagctacgacagataccccaca<br>ctgcggagccacagaagcagcccctatccttctccttacgctcaccggaacaacagccccacctacagcgataatagccccgcctgtct<br>gagcatgctgcagtcccacgataactggtccagcctgagaatgcctgctcacccttccatgctgcccgtgtctcacaatgcctctccaccta<br>ccagcagctctcagtaccctagcctttggagcgtgtccaatggcgccgtgacactgggatctcaggcagccgctgtgtctaatggactggg<br>agcccagttcttcagaggcagccctgctcactacacccctctgacacatcctgtgtctgcccctagcagcagcggcttccctatgtataagg<br>gcgctgccgccgctaccgacatcgtggattctcagtatgatgccgccgcacagggacacctgatcgcctcttggacacctgtgtctccacc<br>ttccatgagaggcagaaagcggagaagcgacttcctgctgctgcagaaccctgcctctacctgtgtgcctgaaccagcctctcagcacac<br>cctgagatctggccctggatgtctccagcagcctgaacagcagggcgttagagatcctggcggaatctgggccaaactgggagctgccg<br>aagcctctgccgaatgtctgcagggcagaagaagcagaggcgccagcggatctgaacctcaccagatgggaagcgacgtgcacga<br>cctgaatgctctgttgcctgccgtgccatctcttggcggaggcggaggatgtgctttgcctgtttctggtgctgcccagtgggctcccgtgctgg<br>attttgctcctcctggcgcttctgcctatggctctcttggaggacctgctcctccaccagctccacctccaccgccgcctccaccacctcacag<br>ctttatcaagcaagagccctcctggggcggagccgagcctcacgaaaaacagtgtctgagcgccttcaccgtgcactttttcggccagttt<br>accggcaccgtgggcgcctgtagatacggcccttttggaccaccaccacctagccaggcttctagcggacaggccagaatgttccccaa<br>cgctccttacctgcctagctgcctggaaagccagcctaccatcagaaaccagggcttcagcaccgtgaccttcgacggcatgcctagcta<br>tggccacacaccatctcaccacgccgctcagttccccaatcacagcttcaagcacgaggaccctatgggccagcagggatctctggga<br>gagcagcagtatagcgtgccacctcctgtgtacggctgtcacacccctaccgatagctgcacaggcaatcaggctctgctgctgaggatg<br>cctttcagcagcgacaacctgtaccagatgacaagccagctggaatgcatgatttggaaccagatgaacctgggcgccactctgaaag<br>gcgtggccgctggatctagcagctccgtgaaatggacagccggccagagcaatcactccaccggctacgagagcgacaatcacacc<br>atgcctatcctgtgtggggcccagtaccggattcacacacacggcgtgttcaggggcattcaggatgtgcgaagagtgcctggcgtggcc<br>cctacacttgtgggatctgccagcgaaaccagcgagaagcaccccttcatgtgcgcctatccaggctgcaacaagcggtacttcaagct<br>gagccacctgaagatgcacagccggaagcacacaggcgagaagctgtaccagtgcgacttcaaggactgcgagcggagattcagct<br>gcagcgaccagctgaagagacaccagagaaggcacaccggcgtgaagccctttcagtgcaagacctgccagcggaccttctcctggt<br>ccaaccacctgaaaacccacacaagaacccacaccggcaagaccatcgagaagcccttcagctgtagatggcccagctgccagaa<br>gaagttcgcccggtctaacgagctggtgcatcaccacaacatgcaccagaggaacatgaccaaactgcagctggtgctgaggggaag<br>aaagaggcggtccaccgagtacaagctggtggttgttggagccgatggcgtgggaaagagcgccctgacaattcagctgatccagaac<br>cacttcgtgcgcggcagaaagagaagatctacagagtataagctcgtggtcgtgggcgctgtcggagtgggaaaatctgccctgaccat<br>ccaactcattcagaatcactttgtgtgatga (SEQ ID NO: 49) |
| modTBXT_WT1_(KRAS Mutations) | MSSPGTESAGKSLQYRVDHLLSAVENELQAGSEKGDPTEHELRVGLEESELWLRFKELTNEMIVT<br>KNGRRMFPVLKVNVSGLDPNAMYSFLLDFVVADNHRWKYVNGEWVPGGKPQLQAPSCVYIHPD<br>SPNFGAHWMKAPVSFSKVKLTNKLNGGGQIMLNSLHKYEPRIHIVRVGGPQRMITSHCFPETQFIA |

TABLE 24-continued

Sequences for MSLN, CT83 and Exemplary Design Antigens

| TAA | Sequence |
|---|---|
| | VTAYQNEEITTLKIKYNPFAKAFLDAKERSDKEMIKEPGDSQQPGYSQWGWLLPGTSTLCPPAN<br>PHSQFGGALSLSSTHSYDRYPTLRSHRSSPYPSPYAHRNNSPTYSDNSPACLSMLQSHDNWSSL<br>RMPAHPSMLPVSHNASPPTSSSQYPSLWSVSNGAVTLGSQAAAVSNGLGAQFFRGSPAHYTPL<br>THPVSAPSSSGFPMYKGAAAATDIVDSQYDAAAQGHLIASWTPVSPPSMRGRKRRSDFLLLQNP<br>ASTCVPEPASQHTLRSGPGCLQQPEQQGVRDPGGIWAKLGAAEASAECLQGRRSRGASGSEPH<br>QMGSDVHDLNALLPAVPSLGGGGGCALPVSGAAQWAPVLDFAPPGASAYGSLGGPAPPPAPPP<br>PPPPPPHSFIKQEPSWGGAEPHEKQCLSAFTVHFFGQFTGTVGACRYGPFGPPPPSQASSGQA<br>RMFPNAPYLPSCLESQPTIRNQGFSTVTFDGMPSYGHTPSHHAAQFPNHSFKHEDPMGQQGSL<br>GEQQYSVPPPVYGCHTPTDSCTGNQALLLRMPFSSDNLYQMTSQLECMIWNQMNLGATLKGVA<br>AGSSSSVKWTAGQSNHSTGYESDNHTMPILCGAQYRIHTHGVFRGIQDVRRVPGVAPTLVGSAS<br>ETSEKHPFMCAYPGCNKRYFKLSHLKMHSRKHTGEKLYQCDFKDCERRFSCSDQLKRHQRRHT<br>GVKPFQCKTCQRTFSWSNHLKTHTRTHTGKTIEKPFSCRWPSCQKKFARSNELVHHHNMHQRN<br>MTKLQLVLRGRKRRSTEYKLWVGADGVGKSALTIQLIQNHFVRGRKRRSTEYKLWVGAVGVGK<br>SALTIQLIQNHFV (SEQ ID NO: 50) |
| modWT1-modFBP | atggactttctgctgctgcagaaccctgccagcacctgtgttccagaacctgcctctcagcacaccctgagatctggccctggatgtctcca<br>gcagcctgaacagcagggcgttagagatcctggcggaatctgggccaaactgggagccgctgaagcctctgccgaatgtctgcaggg<br>cagaagaagcagaggcgccagcggatctgaacctcaccagatgggaagcgacgtgcacgacctgaatgctctgctgcctgccgtgcc<br>atctcttggcggaggcggaggatgtgctttgcctgtttctggtgctgcccagtgggctcccgtgctggattttgctcctcctggcgcttctgcctat<br>ggctctcttggaggacctgctcctccaccagctccacctccaccgccgcctccaccacctcacagctttatcaagcaagagccctcctggg<br>gcggagccgagcctcacgaaaaacagtgtctgagcgccttcaccgtgcactttttcggccagtttaccggcacagtgggcgcctgtagat<br>acggccctttggaccaccaccacctagccaggctagctctggacaggccagaatgttccccaacgctccctacctgcctagctgcctgg<br>aaagccagcctaccatcagaaaccagggcttcagcaccgtgaccttcgacggcatgcctagctatggccacacaccatctcaccacgc<br>cgctcagttccccaatcacagcttcaagcacgaggaccctatgggccagcagggatctctgggagagcagcagtatagcgtgccacct<br>cctgtgtacggctgtcacacccctaccgatagctgcacaggcaatcaggccctgctgctgaggatgcccttcagcagcgacaacctgtac<br>cagatgacaagccagctggaatgcatgatctggaaccagatgaacctgggcgccacactgaaaggcgtggccgctggatctagcagc<br>agcgtgaaatggacagccggccagagcaatcactccaccggctacgagtccgacaaccacaccatgcctattctgtgcggagcccagt<br>acagaatccacacacacggcgtgttccggggcattcaggatgtgcgaagagtgcctggcgtggcccctacacttgtgggatctgcctctg<br>agacaagcgagaagcaccccttcatgtgcgcctatcctggctgcaacaagcggtacttcaagctgagccacctgaagatgcacagccg<br>gaagcacacaggcgagaagctgtaccagtgcgacttcaaggactgcgagcggagattcagctgcagcgaccagctgaagagacac<br>cagagaaggcacaccggcgtgaagcccttccagtgcaagacctgccagcggacctttagctggtccaaccacctgaaaacccacaca<br>agaacccacaccggcaagaccatcgagaagcctttcagctgtagatggcccagctgccagaagaagttcgcccggtctaacgagctg<br>gtgcatcaccacaacatgcaccagaggaacatgaccaaactgcagctggtgctgaggggaagaaagcggagaagcgcccagaga<br>atgaccacacagttgctgctgctcctcgtgtgggttgccgttgtgggagaagtgcagaccagaatcgcctgggccagaaccgagctgctg<br>aacgtgtgcatgaacgccaagcaccacaagaagaagcccgatcctgaggacaagctgcacgagcagtgtcggccttggagaaaga<br>acgcctgctgtagcaccaacaccagccaagaggcccacaagaacgtgtcctacctgtaccggttcaactggaaccactgcggcgagat<br>gacacccgcctgcaagagacacttcatccaggatacctgcctgtacgagtgcagccccaatctcggcccctggattcagcaagtggacc<br>agagctggcggaaagaactggtcctgaatgtgcccctgtgcaaagaggattgcgagcagtggtgggaagattgcagaaccagctaca<br>catgcaagagcaactggcacaaaggctggaactggaccagcggcttcaacaagtgtgccgtgggagctgcctgtcagcctttccacttct<br>actttcacacacccaccgtgctgtgcaacaagatctggacccacagctacaaggtgtccaactacagcagaggcagcggccggtgtat<br>ccagatgtggttcgatcccgccaagggcaaccccaatgaggaagtggccagattctacgccgctgccatgtctggtgcaggaccttggg<br>ctgcttggccctttctgctttcactggccctgatgctgctgtggctgctgagctgataa (SEQ ID NO: 51) |
| modWT1-modFBP | MDFLLLQNPASTCVPEPASQHTLRSGPGCLQQPEQQGVRDPGGIWAKLGAAEASAECLQGRRS<br>RGASGSEPHQMGSDVHDLNALLPAVPSLGGGGGCALPVSGAAQWAPVLDFAPPGASAYGSLG<br>GPAPPPAPPPPPPPPPHSFIKQEPSWGGAEPHEKQCLSAFTVHFFGQFTGTVGACRYGPFGPPP<br>PSQASSGQARMFPNAPYLPSCLESQPTIRNQGFSTVTFDGMPSYGHTPSHHAAQFPNHSFKHED<br>PMGQQGSLGEQQYSVPPPVYGCHTPTDSCTGNQALLLRMPFSSDNLYQMTSQLECMIWNQMN<br>LGATLKGVAAGSSSSVKWTAGQSNHSTGYESDNHTMPILCGAQYRIHTHGVFRGIQDVRRVPGV |

TABLE 24-continued

Sequences for MSLN, CT83 and Exemplary Design Antigens

| TAA | Sequence |
| --- | --- |
| | APTLVGSASETSEKHPFMCAYPGCNKRYFKLSHLKMHSRKHTGEKLYQCDFKDCERRFSCSDQL<br>KRHQRRHTGVKPFQCKTCQRTFSWSNHLKTHTRTHTGKTIEKPFSCRWPSCQKKFARSNELVH<br>HHNMHQRNMTKLQLVLRGRKRRSAQRMTTQLLLLLVWVAVVGEVQTRIAWARTELLNVCMNAK<br>HHKKKPDPEDKLHEQCRPWRKNACCSTNTSQEAHKNVSYLYRFNWNHCGEMTPACKRHFIQDT<br>CLYECSPNLGPWIQQVDQSWRKELVLNVPLCKEDCEQWWEDCRTSYTCKSNWHKGWNWTSG<br>FNKCAVGAACQPFHFYFHTPTVLCNKIWTHSYKVSNYSRGSGRCIQMWFDPAKGNPNEEVARFY<br>AAAMSGAGPWAAWPFLLSLALMLLWLLS (SEQ ID NO: 52) |
| modPSMA-modTDGF1 | atgtggaatctgctgcacgagacagatagcgccgtggctaccgttagaaggcccagatggctttgtgctggcgctctggttctggctggcg<br>gctttttttctgctgggcttcctgttcggctggttcatcaagagcagcaacgaggccaccaacatcacccctaagcacaacatgaaggccttt<br>ctggacgagctgaaggccgagaatatcaagaagttcctgtacaacttcacgcacatccctcacctggccggcaccgagcagaattttca<br>gctggccaagcagatccagagccagtggaaagagttcggcctggactctgtggaactggcccactacgatgtgctgctgagctacccca<br>acaagacacaccccaactacatcagcatcatcaacgaggacggcaacgagatcttcaacaccagcctgttcgagcctccacctcctgg<br>ctacgagaacgtgtccgatatcgtgcctccattcagcgctttcagcccacagcggatgcctgagggctacctggtgtacgtgaactacgcc<br>agaaccgaggacttcttcaagctggaatgggacatgaagatcagctgcagcggcaagatcgtgatcgcccggtacagaaaggtgttcc<br>gcgagaacaaagtgaagaacgcccagctggcaggcgccaaaggcgtgatcctgtatagcgaccccgccgactattttgcccctggcgt<br>gaagtcttaccccgacggctggaatttcctggcggcggagtgcagcggcggaacatccttaatcttaacggcgctggcgaccctctgac<br>acctggctatcctgccaatgagtacgcctacagacacggaattgccgaggctgtgggcctgccttctattcctgtgcaccctgtgcggtact<br>acgacgcccagaaactgctggaaaagatgggcggaagcgcccctcctgactcttcttggagaggctctctgaaggtgccctacaatgtc<br>ggcccaggcttcaccggcaacttcagcacccagaaagtgaaaatgcacatccacagcaccaacgaagtgacccggatctacaacgt<br>gatcggcacactgagaggcgccgtggaacccgacaaatacgtgatcctcggcggccacagagacagctgggtgttcggaggaatcg<br>accctcaatctggcgccgctgtggtgtatgagatcgtgcggtctttcggcaccctgaagaaagaaggatggcggcccagacggaccatc<br>ctgtttgcctcttgggacgccgaggaatttggcctgctgggatctacagagtgggccgaagagaacagcagactgctgcaagaaagag<br>gcgtggcctacatcaacgccgacagcagcatcgagggcaactacaccctgcggatcgattgcacccctctgatgtacagcctggtgcac<br>aacctgaccaaagagctgaagtcccctgacgagggctttgagggcaagagcctgtacaagagctggaccaagaagtccccatctcctg<br>agttcagcggcatgcccagaatctctaagctggaaagcggcaacaacttcgaggtgttcttccagcggctgggaatcgcctctggaatcg<br>ccagatacaccaagaactgggagacaaacaagttctccggctatcccctgtaccacagcgtgtacgagacatacgagctggtggaaa<br>agttctacgaccccatgttcaagtaccacctgacagtggcccaagtgcgcggaggcatggtgttcgaactggccaatagcatcgtgctgc<br>ccttcaactgcagagactacgccgtggtgctgcggaagtacgccgacaagatctacagcatcagcatgaagcacccgcaagagatga<br>agacctacagcgtgtccttcgactccctgttcttcgccgtgaagaacttcaccaagatcgccagcaagttcagcgagcggctgcaggactt<br>cgacaagagcaaccctatcgtgctgaggatgatgaacgaccagctgatgttcctggaacgggccttcatcaaccctctgggactgcccg<br>acagacccttctacaggcacgtgatctgtgcccctagcagccacaacaaatacgccggcgagagcttccccggcatctacgatgccctg<br>ttcgacatcgagagcaacgtgaaccctagcaaggcctggggcgaagtgaagagacagatctacgtggccgcattcacagtgcaggcc<br>gctgccgaaacactgtctgaagtggccagaggccggaagagaagatccgactgcagaaagatggcccggttcagctactccgtgatct<br>ggatcatggccatctccaaggccttcgagctgagactggttgccggactgggccaccaagagtttgccagacctagctggggctatctgg<br>ccttccgggacgatagcatctggccccaagaggaacctgccatcagacccagatctagccagcgggtgccacctatggaaatccagca<br>cagcaaagaactgaaccggacctgctgcctgaacggcagaacctgtatgctgggcagcttctgcgcctgtcctcctagcttctacggccg<br>gaattgcgagcacgacgtgcggaaagaaaactgcggcagcgtgccacacgatacctggctgcctaagaaatgcagcctgtgcaagtg<br>ttggcacggccagctgcggtgtttccccagagcttttctgcccgtgtgtgacggcctggtcatggatgaacacctggtggccagcagaacc<br>cctgagcttcctccaagcgccaggaccaccacctttatgctcgtgggcatctgcctgagcatccagagctactactgatga (SEQ ID<br>NO: 53) |
| modPSMA-modTDGF1 | MWNLLHETDSAVATVRRPRWLCAGALVLAGGFFLLGFLFGWFIKSSNEATNITPKHNMKAFLDEL<br>KAENIKKFLYNFTHIPHLAGTEQNFQLAKQIQSQWKEFGLDSVELAHYDVLLSYPNKTHPNYISIINE<br>DGNEIFNTSLFEPPPPGYENVSDIVPPFSAFSPQRMPEGYLVYVNYARTEDFFKLEWDMKISCSG<br>KIVIARYRKVFRENKVKNAQLAGAKGVILYSDPADYFAPGVKSYPDGWNFPGGGVQRRNILNLNG<br>AGDPLTPGYPANEYAYRHGIAEAVGLPSIPVHPVRYYDAQKLLEKMGGSAPPDSSWRGSLKVPY<br>NVGPGFTGNFSTQKVKMHIHSTNEVTRIYNVIGTLRGAVEPDKYVILGGHRDSWVFGGIDPQSGA<br>AVVYEIVRSFGTLKKEGWRPRRTILFASWDAEEFGLLGSTEWAEENSRLLQERGVAYINADSSIEG |

TABLE 24-continued

| Sequences for MSLN, CT83 and Exemplary Design Antigens | |
|---|---|
| TAA | Sequence |
| | NYTLRIDCTPLMYSLVHNLTKELKSPDEGFEGKSLYKSWTKKSPSPEFSGMPRISKLESGNNFEVF<br>FQRLGIASGIARYTKNWETNKFSGYPLYHSVYETYELVEKFYDPMFKYHLTVAQVRGGMVFELAN<br>SIVLPFNCRDYAWLRKYADKIYSISMKHPQEMKTYSVSFDSLFFAVKNFTKIASKFSERLQDFDKS<br>NPIVLRMMNDQLMFLERAFINPLGLPDRPFYRHVICAPSSHNKYAGESFPGIYDALFDIESNVNPSK<br>AWGEVKRQIYVAAFTVQAAAETLSEVARGRKRRSDCRKMARFSYSVIWIMAISKAFELRLVAGLG<br>HQEFARPSWGYLAFRDDSIWPQEEPAIRPRSSQRVPPMEIQHSKELNRTCCLNGRTCMLGSFCA<br>CPPSFYGRNCEHDVRKENCGSVPHDTWLPKKCSLCKCWHGQLRCFPRAFLPVCDGLVMDEHLV<br>ASRTPELPPSARTTTFMLVGICLSIQSYY (SEQ ID NO: 54) |
| modWT1-modClaudin 18 | atggactttctgctgctgcagaaccctgccagcacctgtgttccagaacctgcctctcagcacaccctgagatctggccctggatgtctcca<br>gcagcctgaacagcagggcgttagagatcctggcggaatctgggccaaactgggagccgctgaagcctctgccgaatgtctgcaggg<br>cagaagaagcagaggcgccagcggatctgaacctcaccagatgggaagcgacgtgcacgacctgaatgctctgctgcctgccgtgcc<br>atctcttggcggaggcggaggatgtgctttgcctgtttctggtgctgcccagtgggctcccgtgctggattttgctcctcctggcgcttctgcctat<br>ggctctcttggaggacctgctcctccaccagctccacctccaccgccgcctccaccacctcacagctttatcaagcaagagccctcctggg<br>gcggagccgagcctcacgaaaaacagtgtctgagcgccttcaccgtgcactttttcggccagtttaccggcacagtgggcgcctgtagat<br>acggcccttttggaccaccaccacctagccaggctagctctggacaggccagaatgttccccaacgctccctacctgcctagctgcctgg<br>aaagccagcctaccatcagaaaccagggcttcagcaccgtgaccttcgacggcatgcctagctatggccacacaccatctcaccacgc<br>cgctcagttccccaatcacagcttcaagcacgaggaccctatgggccagcagggatctctgggagagcagcagtatagcgtgccacct<br>cctgtgtacggctgtcacacccctaccgatagctgcacaggcaatcaggccctgctgctgaggatgcccttcagcagcgacaacctgtac<br>cagatgacaagccagctggaatgcatgatctggaaccagatgaacctgggcgccacactgaaaggcgtggccgctggatctagcagc<br>agcgtgaaatggacagccggccagagcaatcactccaccggctacgagtccgacaaccacaccatgcctattctgtgcggagcccagt<br>acagaatccacacacacggcgtgttccggggcattcaggatgtgcgaagagtgcctggcgtggcccctacacttgtgggatctgcctctg<br>agacaagcgagaagcaccccttcatgtgcgcctatcctggctgcaacaagcggtacttcaagctgagccacctgaagatgcacagccg<br>gaagcacacaggcgagaagctgtaccagtgcgacttcaaggactgcgagcggagattcagctgcagcgaccagctgaagagacac<br>cagagaaggcacaccggcgtgaagcccttccagtgcaagacctgccagcggacctttagctggtccaaccacctgaaaacccacaca<br>agaacccacaccggcaagaccatcgagaagcctttcagctgtagatggcccagctgccagaagaagttcgcccggtctaacgagctg<br>gtgcatcaccacaacatgcaccagaggaacatgaccaaactgcagctggtgctgaggggaagaaagcggagatctgccgtgacagc<br>ctgtcagagcctgggctttgtggtgtccctgatcgagatcgtgggcatcattgccgctacctgcatggaccagtggtctacccaggacctgta<br>caacaaccctgtgaccgccgtgttcaactaccaaggcctgtggcacagctgcatgagagagagcagcggcttcaccgagtgcagagg<br>ctacttcaccctgctggaactgcctgccatgctgcaggctgtgcaggcccttatgatcgtgggaattgtgctgggagccatcggcctgctggt<br>gtccattttcgccctgaagtgcatccggatcggcagcatggaagatagcgccaaggccaacatgaccctgaccagcggcatcatgttcat<br>cgtgtccggcctgtgcgccattgctggcgtgtccgtgtttgccaatatgctcgtgaccaacttctggctgagcaccgccaacatgtacaccgg<br>catgggcgagatggtgcagaccgtgcagacacggtacacatttggcgccgctctgtttgtcggatgggttgcaggcggactgacactgatt<br>ggcggcgtgatgatgtgtatcgcctgcagaggactggcccctgaggaaacaaactacaaggccgtgtactaccacgcctccggacaca<br>gcgtggcatacaaacctggcggctttaaggccagcaccggcttcggcagcaacaccaagaacaagaagatctacgacggcggagca<br>cacaccgaggatgaggtgcagagctaccccagcaagcacgactacgtgtgatga (SEQ ID NO: 55) |
| modWT1-modClaudin 18 | MDFLLLQNPASTCVPEPASQHTLRSGPGCLQQPEQQGVRDPGGIWAKLGAAEASAECLQGRRS<br>RGASGSEPHQMGSDVHDLNALLPAVPSLGGGGGCALPVSGAAQWAPVLDFAPPGASAYGSLG<br>GPAPPPAPPPPPPPPPHSFIKQEPSWGGAEPHEKQCLSAFTVHFFGQFTGTVGACRYGPFGPPP<br>PSQASSGQARMFPNAPYLPSCLESQPTIRNQGFSTVTFDGMPSYGHTPSHHAAQFPNHSFKHED<br>PMGQQGSLGEQQYSVPPPVYGCHTPTDSCTGNQALLLRMPFSSDNLYQMTSQLECMIWNQMN<br>LGATLKGVAAGSSSSVKWTAGQSNHSTGYESDNHTMPILCGAQYRIHTHGVFRGIQDVRRVPGV<br>APTLVGSASETSEKHPFMCAYPGCNKRYFKLSHLKMHSRKHTGEKLYQCDFKDCERRFSCSDQL<br>KRHQRRHTGVKPFQCKTCQRTFSWSNHLKTHTRTHTGKTIEKPFSCRWPSCQKKFARSNELVH<br>HHNMHQRNMTKLQLVLRGRKRRSAVTACQSLGFVVSLIEIVGIIAATCMDQWSTQDLYNNPVTAV |

TABLE 24-continued

| Sequences for MSLN, CT83 and Exemplary Design Antigens | |
|---|---|
| TAA | Sequence |
| | FNYQGLWHSCMRESSGFTECRGYFTLLELPAMLQAVQALMIVGIVLGAIGLLVSIFALKCIRIGSME<br>DSAKANMTLTSGIMFIVSGLCAIAGVSVFANMLVTNFWLSTANMYTGMGEMVQTVQTRYTFGAAL<br>FVGWVAGGLTLIGGVMMCIACRGLAPEETNYKAVYYHASGHSVAYKPGGFKASTGFGSNTKNKK<br>IYDGGAHTEDEVQSYPSKHDYV (SEQ ID NO: 56) |
| modPSMA-modLY6K | atgtggaatctgctgcacgagacagatagcgccgtggctaccgttagaaggcccagatggctttgtgctggcgctctggttctggctggcg<br>gctttttctgctgggcttcctgttcggctggttcatcaagagcagcaacgaggccaccaacatcacccctaagcacaacatgaaggccttt<br>ctggacgagctgaaggccgagaatatcaagaagttcctgtacaacttcacgcacatccctcacctggccggcaccgagcagaattttca<br>gctggccaagcagatccagagccagtggaaagagttcggcctggactctgtggaactggcccactacgatgtgctgctgagctacccca<br>acaagacacaccccaactacatcagcatcatcaacgaggacggcaacgagatcttcaacaccagcctgttcgagcctccacctcctgg<br>ctacgagaacgtgtccgatatcgtgcctccattcagcgctttcagcccacagcggatgcctgagggctacctggtgtacgtgaactacgcc<br>agaaccgaggacttcttcaagctggaatgggacatgaagatcagctgcagcggcaagatcgtgatcgcccggtacagaaaggtgttcc<br>gcgagaacaaagtgaagaacgcccagctggcaggcgccaaaggcgtgatcctgtatagcgaccccgccgactattttgcccctggcgt<br>gaagtcttaccccgacggctggaatttcctggcggcggagtgcagcggcggaacatccttaatcttaacggcgctggcgaccctctgac<br>acctggctatcctgccaatgagtacgcctacagacacggaattgccgaggctgtgggcctgccttctattcctgtgcaccctgtgcggtact<br>acgacgcccagaaactgctggaaaagatgggcggaagcgcccctcctgactcttcttggagaggctctctgaaggtgccctacaatgtc<br>ggcccaggcttcaccggcaacttcagcacccagaaagtgaaaatgcacatccacagcaccaacgaagtgacccggatctacaacgt<br>gatcggcacactgagaggcgccgtggaacccgacaaatacgtgatcctcggcggccacagagacagctgggtgttcggaggaatcg<br>accctcaatctggcgccgctgtggtgtatgagatcgtgcggtctttcggcaccctgaagaaagaaggatggcggcccagacggaccatc<br>ctgtttgcctcttgggacgccgaggaatttggcctgctgggatctacagagtgggccgaagagaacagcagactgctgcaagaaagag<br>gcgtggcctacatcaacgccgacagcagcatcgagggcaactacaccctgcggatcgattgcacccctctgatgtacagcctggtgcac<br>aacctgaccaaagagctgaagtcccctgacgagggctttgagggcaagagcctgtacaagagctggaccaagaagtccccatctcctg<br>agttcagcggcatgcccagaatctctaagctggaaagcggcaacaacttcgaggtgttcttccagcggctgggaatcgcctctggaatcg<br>ccagatacaccaagaactgggagacaaacaagttctccggctatcccctgtaccacagcgtgtacgagacatacgagctggtggaaa<br>agttctacgaccccatgttcaagtaccacctgacagtggcccaagtgcgcggaggcatggtgttcgaactggccaatagcatcgtgctgc<br>ccttcaactgcagagactacgccgtggtgctgcggaagtacgccgacaagatctacagcatcagcatgaagcacccgcaagagatga<br>agacctacagcgtgtccttcgactccctgttcttcgccgtgaagaacttcaccaagatcgccagcaagttcagcgagcggctgcaggactt<br>cgacaagagcaaccctatcgtgctgaggatgatgaacgaccagctgatgttcctggaacgggccttcatcaaccctctgggactgcccg<br>acagacccttctacaggcacgtgatctgtgcccctagcagccacaacaaatacgccggcgagagcttccccggcatctacgatgccctg<br>ttcgacatcgagagcaacgtgaaccctagcaaggcctggggcgaagtgaagagacagatctacgtggccgcattcacagtgcaggcc<br>gctgccgaaacactgtctgaagtggccagaggccggaagagaagaagtgctctgctggcactgctgctggtggtggctttgcctagagtg<br>tggaccgacgccaatctgacagtgcggcagagagatcctgaggacagccagagaaccgacgacggcgataacagagtgtggtgcc<br>acgtgtgcgagcgcgagaataccttcgagtgtcagaaccccagacggtgcaagtggaccgagccttactgtgtgatcgccgccgtgaa<br>aatcttcccacggttcttcatggtggtcaagcagtgcagcgctggctgtgccgctatggaaagacccaagcctgaggaaaagcggttcct<br>gctcgaggaacccatgctgttcttctacctgaagtgctgcaaaatctgctactgcaacctggaaggccctcctatcaacagcagcgtcctg<br>aaagaatatgccggcagcatgggcgagtcttgtggtggactgtggctggccattctgctgctgcttgcctctattgccgcctctctgagcctga<br>gctgatga (SEQ ID NO: 57) |
| modPSMA-modLY6K | MWNLLHETDSAVATVRRPRWLCAGALVLAGGFFLLGFLFGWFIKSSNEATNITPKHNMKAFLDEL<br>KAENIKKFLYNFTHIPHLAGTEQNFQLAKQIQSQWKEFGLDSVELAHYDVLLSYPNKTHPNYISIINE<br>DGNEIFNTSLFEPPPPGYENVSDIVPPFSAFSPQRMPEGYLVYVNYARTEDFFKLEWDMKISCSG<br>KIVIARYRKVFRENKVKNAQLAGAKGVILYSDPADYFAPGVKSYPDGWNFPGGGVQRRNILNLNG<br>AGDPLTPGYPANEYAYRHGIAEAVGLPSIPVHPVRYYDAQKLLEKMGGSAPPDSSWRGSLKVPY<br>NVGPGFTGNFSTQKVKMHIHSTNEVTRIYNVIGTLRGAVEPDKYVILGGHRDSWVFGGIDPQSGA<br>AWYEIVRSFGTLKKEGWRPRRTILFASWDAEEFGLLGSTEWAEENSRLLQERGVAYINADSSIEG<br>NYTLRIDCTPLMYSLVHNLTKELKSPDEGFEGKSLYKSWTKKSPSPEFSGMPRISKLESGNNFEVF<br>FQRLGIASGIARYTKNWETNKFSGYPLYHSVYETYELVEKFYDPMFKYHLTVAQVRGGMVFELAN<br>SIVLPFNCRDYAWLRKYADKIYSISMKHPOEMKTYSVSFDSLFFAVKNFTKIASKFSERLQDFDKS<br>NPIVLRMMNDQLMFLERAFINPLGLPDRPFYRHVICAPSSHNKYAGESFPGIYDALFDIESNVNPSK |

TABLE 24-continued

| Sequences for MSLN, CT83 and Exemplary Design Antigens | |
|---|---|
| TAA | Sequence |
| | AWGEVKRQIYVAAFTVQAAAETLSEVARGRKRRSALLALLLWALPRVWTDANLTVRQRDPEDSQ RTDDGDNRVWCHVCERENTFECQNPRRCKWTEPYCVIAAVKIFPRFFMWKQCSAGCAAMERP KPEEKRFLLEEPMLFFYLKCCKICYCNLEGPPINSSVLKEYAGSMGESCGGLWLAILLLLASIAASL SLS (SEQ ID NO: 58) |
| modBORIS | atggccgctacagagattagcgtgctgagcgagcagttcaccaagatcaaagaactgaagctgatgctcgagaagggcctgaagaaa gaagagaaggacggcgtctgccgcgagaagaaccacagaagcccatctgagctggaagcccagagaacctctggcgccttccagg acagcatcctggaagaggaagtggaactggttctggcccctctggaagagagcaagaagtacatcctgacactgcagaccgtgcactt cacctctgaagccgtgcagctccaggacatgagcctgctgtctatccagcagcaagagggcgtgcaggttgtggttcagcaacctggac ctggactgctgtggctgcaagagggacctagacagagcctgcagcagtgtgtggccatcagcatccagcaagagctgtactcccctcaa gagatggaagtgctgcagtttcacgccctggaagaaaacgtgatggtggccatcgaggacagcaagctggctgtgtctctggccgaaac caccggcctgatcaagctggaagaagaacaagagaagaatcagctgctcgccgaaaagaccaaaaagcaactgttcttcgtggaaa ccatgagcggcgacgagcggagcgacgaaatcgtgctgaccgtgtccaacagcaacgtcgaggaacaagaggaccagcctacagc ctgtcaggccgatgccgagaaagccaagtttaccaagaaccagagaaagaccaagggcgccaagggcaccttccactgcaacgtgt gcatgttcaccagcagccggatgagcagcttcaactgccacatgaagacccacaccagcgagaagccccacctgtgccatctgtgcct gaaaaccttccggaccgtgactctgctgtggaactacgtgaacacccacacaggcacccggccttacaagtgcaacgactgcaacatg gccttcgtgaccagcggagaactcgtgcggcacagaagatacaagcacacccacgagaaacccttcaagtgcagcatgtgcaaatac gccagcatggaagcctccaagctgaagtgtcacgtgcggagccatacaggcgagcaccctttccagtgctgccagtgtagctacgcctc cagggacacctataagctgaagcggcacatgagaacccactctggggagaagccttacgagtgccacatctgccacaccagattcac ccagagcggcaccatgaagattcacatcctgcagaaacacggcaagaacgtgcccaagtaccagtgtcctcactgcgccaccattatc gccagaaagtccgacctgcgggtgcacatgaggaatctgcacgcctattctgccgccgagctgaaatgcagatactgcagcgccgtgtt ccacaagagatacgccctgatccagcaccagaaacccacaagaacgagaagcggtttaagtgcaagcactgctcctacgcctgca agcaagagcgccacatgatcgcccacatccacacacacaccggcgaaaagcctttcacctgtctgagctgcaacaagtgcttccggca gaaacagctgctgaacgcccacttcagaaagtaccacgacgccaacttcatccccaccgtgtacaagtgctccaagtgcggcaagggc ttcagccggtggatcaatctgcaccggcacctggaaaagtgcgagtctggcgaagccaagtctgccgcctctggcaagggcagaaga acccggaagagaaagcagaccattctgaaagaggccaccaagagccagaaagaagccgccaagcgctggaaagaggctgccaa cggcgacgaagctgccgctgaagaagccagcacaacaaagggcgaacagttccccgaagagatgttccccgtggcctgcagagaa accacagccagagtgaagcaagaggtggaccagggcgtcacatgcgagatgctgctgaataccatggacaagtgatga (SEQ ID NO: 59) |
| modBORIS | MAATEISVLSEQFTKIKELKLMLEKGLKKEEKDGVCREKNHRSPSELEAQRTSGAFQDSILEEEVE LVLAPLEESKKYILTLQTVHFTSEAVQLQDMSLLSIQQQEGVQVVVQQPGPGLLWLQEGPRQSLQ QCVAISIQQELYSPQEMEVLQFHALEENVMVAIEDSKLAVSLAETTGLIKLEEEQEKNQLLAEKTKK QLFFVETMSGDERSDEIVLTVSNSNVEEQEDQPTACQADAEKAKFTKNORKTKGAKGTFHCNVC MFTSSRMSSFNCHMKTHTSEKPHLCHLCLKTFRTVTLLWNYVNTHTGTRPYKCNDCNMAFVTSG ELVRHRRYKHTHEKPFKCSMCKYASMEASKLKCHVRSHTGEHPFQCCQCSYASRDTYKLKRHM RTHSGEKPYECHICHTRFTQSGTMKIHILQKHGKNVPKYQCPHCATIIARKSDLRVHMRNLHAYSA AELKCRYCSAVFHKRYALIQHQKTHKNEKRFKCKHCSYACKQERHMIAHIHTHTGEKPFTCLSCN KCFRQKQLLNAHFRKYHDANFIPTVYKCSKCGKGFSRWINLHRHLEKCESGEAKSAASGKGRRT RKRKQTILKEATKSQKEAAKRWKEAANGDEAAAEEASTTKGEQFPEEMFPVACRETTARVKQEV DQGVTCEMLLNTMDK (SEQ ID NO: 60) |
| modMesothelin | atggcattgcctacagctagacctctgctgggcagctgtggaacaccagctctgggaagcctgctgtttctgctgttcagcctcggatgggtg cagccttctagaacactggccggcgagacaggacaagaagctgctcctcttgacggcgtgctggccaatcctcctaatatcagctctctg agccccagacagctgctcggctttccttgtgccgaagtgtctggcctgagcaccgagagagtgtgggaacttgctgtggccctggctcaga aaaacgtgaagctgagcacagagcagctgagatgtctggcccaccagctgagtgaacctccagaggatctggatgccctgcctctgga cctgctgctgttcctgaatcctgacgcctttagcggccctcaggcctgcaccagattcttcagcagaatcaccaaggccaatgtggatctgct gcccagaggcgcccctgagagacaaagacttctgcctgctgctctggcctgttggggcgttagaggatctctgctgtctgaggccgatgtg ctggctcttggaggcctggcttgtaacctgcctggcagatttgtggccgagtctgctgaggtgctgctgcctagactggtgtcctgtcctggac |

TABLE 24-continued

Sequences for MSLN, CT83 and Exemplary Design Antigens

| TAA | Sequence |
|---|---|
| | ctctggatcaggaccagcaagaagccgctagagctgcacttcaaggcggcggacctccttatggacctcctctgacttggagcgtgtcca<br>ccatggacgctctgagaggactgctgcctgttctgggccagcctatcatccggtctatccctcagggaattgtggccgcttggcggcagag<br>aagcttcagagatccctcttggagacagcccaagcagaccatcctgtggcctcggttcagatgggaagtcgagaaaaccgcctgtccta<br>gcggcaagaaggccagagagatcgacgagagcctgatcttctacaagaagtgggaactcgaggcctgcgtggacgctgctctgctgg<br>ctacacagatggacagagtgaacgctatccccttcacctatgagcagctggacgtgctgaagcacaagctggatgagctgtaccctcag<br>ggctaccccgagtctgtgattcagcacctgggctacctgtttctgaagatgagccccgaggacatccggaagtggaacgtgaccagcctg<br>gaaaccctgaaggccctgctggaagtgaacaagggccacgagatgtccccacaggctcctagaaggcctctgcctcaagtggccaca<br>ctgatcgacagattcgtgaaaggcaggggccagctggacaaggacaccctggatacactgaccgccttctatcccggctatctgtgcag<br>cctgtctcctgaggaactgtcctctgtgcctcctagctctatttgggctgtgcggcctcaggacctggatacctgtgatcctagacagctggat<br>gtcctgtatcctaaggctcggctggccttccagaacatgaacggcagcgagtacttcgtgaagatccagttcttccttggcggcgctcccac<br>cgaggatctgaaagctctgtcccagcagaatgtgtctatggacctggccacctttatgaagctgcggaccgatgctgtgctgcctctgacag<br>tggccgaggtgcaaaaactgctgggccctcatgtggaaggactgaaggccgaagaacggcacagacccgtcagagactggattctga<br>gacagcggcaggacgacctggacacactggaacttggactgcaaggcggcatccccaatggctacctggtgctggatctgagcgtgca<br>agaggccctctctggcacaccttgtttgctcggacctggaccagtgctgacagtgttggctctgctgctggcctctacactggcctgataa<br>(SEQ ID NO: 61) |
| modMesothelin | MALPTARPLLGSCGTPALGSLLFLLFSLGINVQPSRTLAGETGQEAAPLDGVLANPPNISSLSPRQL<br>LGFPCAEVSGLSTERVWELAVALAQKNVKLSTEQLRCLAHQLSEPPEDLDALPLDLLLFLNPDAFS<br>GPQACTRFFSRITKANVDLLPRGAPERQRLLPAALACWGVRGSLLSEADVLALGGLACNLPGRFV<br>AESAEVLLPRLVSCPGPLDQDQQEAARAALQGGGPPYGPPLTWSVSTMDALRGLLPVLGQPIIRS<br>IPQGIVAAWRQRSFRDPSWRQPKQTILWPRFRWEVEKTACPSGKKAREIDESLIFYKKWELEACV<br>DAALLATQMDRVNAIPFTYEQLDVLKHKLDELYPQGYPESVIQHLGYLFLKMSPEDIRKWNVTSLE<br>TLKALLEVNKGHEMSPQAPRRPLPQVATLIDRFVKGRGQLDKDTLDTLTAFYPGYLCSLSPEELSS<br>VPPSSIWAVRPQDLDTCDPRQLDVLYPKARLAFQNMNGSEYFVKIQFFLGGAPTEDLKALSQQNV<br>SMDLATFMKLRTDAVLPLTVAEVQKLLGPHVEGLKAEERHRPVRDWILRQRQDDLDTLELGLQG<br>GIPNGYLVLDLSVQEALSGTPCLLGPGPVLTVLALLLASTLA (SEQ ID NO: 62) |
| modFAP-modClaudin 18 | cctgaacgtgaccttcagctacaagatattcttccccaactggatctccggccaagagtacctgcaccagagcgccgacaacaacatcgt<br>gctgtacaacatcgagacaggccagagctacaccatcatgagcaaccggaccatgaagtccgtgaacgccagcaactacggactga<br>gccccgattggcagttcgtgtacctggaaagcgactacagcaagctgtggcggtacagctacaccgccacctactacatctacgacctg<br>agcaacggcgagttcgtgaagggcaacgagctgccccatcctatccagtacctgtgttggagccctgtgggctccaagctggcctacgtg<br>taccagaacaacatctacctgaagcagcggcctggcgaccctccattccagatcaccttcaacggcagagagaacaagatctttaacg<br>gcatccccgactgggtgtacgaggaagagatgctggccaccaaatacgccctgtggtggtcccctaacggcaagtttctggcctatgccg<br>acttcaacgacacagacatccccgtgatcgcctacagctactacggcaatgagcagtaccccaggaccatcaacatcagctaccccaa<br>agccggcgctaagaaccctgtcgtgcggatcttcatcatcgacaccacctatcctgtgtacgtgggccctcaagaggtgccagtgcctgcc<br>atgattgccagcagcgactactacttcagctggctgacctgggtcaccgacgagcgagtttgtctgcagtggctgaagcgggtgcagaac<br>atcagcgtgctgagcatctgcgacttcagaaaggactggcagacatgggactgccccaacacacagcagcacatcgaggaaagcag<br>aaccggctgggctggcggcttctttgtgtctaccccctgtgttcagctacgacgccatcctgtactataagatcttcagcgacaaggacggcta<br>caagcacatccactacatcaagtacaccgtcgagaacgtgatccagattaccagcggcaagtgggaagccatcaatatcttcagagtg<br>atccagtacagcctgttctacagcagcaacgagttcgaggaataccccggcagacggaacatctacagaatcagcatcggcagctacc<br>cgcctagcaagaaatgcgtgacctgccacctgagaaaagagcggtgccagtactacacagccagcttctccaactacgccaagtacta<br>cgccctcgtgtgttacggccctggcatccctatcagcacactgcacgatggcagaaccgaccaagagatcaagatcctggaagaaaac<br>aaagagctggaaaacgccctgaagaacatccagctgcctaaagaggaaatcaagaagctggaagtcgacgagatcaccctgtggta<br>caagatgatcctgcctcctcagttcgaccggtccaagaagtaccctctgctgatccaggtgtacggcggaccttgttctcagtctgtgcgctc<br>cgtgttcgccgtgaattggatcagctatctggccagcaaagaaggcatggttatcgccctggtggacggcagaggcacagcttttcaagg<br>cgacaagctgctgtacgccgtgtatcagaaactgggcgtgtacgaagtggaagatcagatcaccgccgtgcggaagttcatcgagatgg<br>gcttcatcgacgagaagcggatcgccatctggggctggtcttacggcggctatattagctctctggccctggcctctggcaccggcctgttta<br>agtgtggaattgccgtggctcccgtgtccagctgggagtactataccagcgtgtacaccgagcggttcatgggcctgcctaccaaggacg<br>acaacctggaacactacaagaactctaccgtgatggccagagccgagtacttccggaacgtggactacctgctgattcacggcaccgc |

TABLE 24-continued

Sequences for MSLN, CT83 and Exemplary Design Antigens

| TAA | Sequence |
|---|---|
| | cgacgacaacgtgcacttccaaaacagcgcccagatcgctaaggccctcgtgaatgcccaggtggactttcaggccatgtggtacagc<br>gaccagaaccacggactgtctggcctgagcaccaaccacctgtacacccacatgacccactttctgaaacagtgcttcagcctgagcga<br>ccggggcagaaagagaagatctgccgtcacagcctgtcagagcctgggctttgtggtgtccctgatcgagatcgtgggcatcattgccgc<br>tacctgcatggaccagtggtctacccaggacctgtataacaaccccgtgaccgccgtgttcaactaccaaggcctgtggcacagctgcat<br>gagagagagcagcggcttcaccgagtgcaggggctactttaccctgctggaactgccagccatgctgcaggctgtgcaggcccttatgat<br>cgtgggaattgtgctgggcgccatcggcctgctggtgtctatttttgccctgaagtgcatccggatcggcagcatggaagatagcgccaag<br>gccaacatgaccctgacctccggcatcatgttcatcgtgtccggcctgtgtgccattgcaggcgtgtccgtgtttgccaatatgctcgtgacca<br>acttctggctgtccaccgccaacatgtacaccggcatgggcgagatggtgcagaccgtgcagacacggtacacatttggcgccgctctgt<br>ttgtcggatgggttgcaggcggactgactctgattggcggcgtgatgatgtgtatcgcctgcagaggactggcccctgaggaaacaaact<br>acaaggccgtgtactaccacgccagcggacacagcgtggcatacaaaccaggcggctttaaggccagcacaggcttcggcagcaac<br>accaagaacaagaagatctacgacggcggagcccataccgaggatgaggtgcagagctaccctagcaagcacgactacgtgtgatg<br>a (SEQ ID NO: 63) |
| modFAP-modClaudin 18 | MKTLVKIVFGVATSAVLALLVMCIVLHPSRVHNSEENTMRALTLKDILNVTFSYKIFFPNWISGQEYL<br>HQSADNNIVLYNIETGQSYTIMSNRTMKSVNASNYGLSPDWQFVYLESDYSKLWRYSYTATYYIY<br>DLSNGEFVKGNELPHPIQYLCWSPVGSKLAYVYQNNIYLKQRPGDPPFQITFNGRENKIFNGIPDW<br>VYEEEMLATKYALWWSPNGKFLAYADFNDTDIPVIAYSYYGNEQYPRTINISYPKAGAKNPVVRIFII<br>DTTYPVYVGPQEVPVPAMIASSDYYFSWLTWVTDERVCLQWLKRVQNISVLSICDFRKDWQTWD<br>CPNTQQHIEESRTGWAGGFFVSTPVFSYDAILYYKIFSDKDGYKHIHYIKYTVENVIQITSGKWEAIN<br>IFRVIQYSLFYSSNEFEEYPGRRNIYRISIGSYPPSKKCVTCHLRKERCQYYTASFSNYAKYYALVC<br>YGPGIPISTLHDGRTDQEIKILEENKELENALKNIQLPKEEIKKLEVDEITLWYKMILPPQFDRSKKYP<br>LLIQVYGGPCSQSVRSVFAVNWISYLASKEGMVIALVDGRGTAFQGDKLLYAVYQKLGVYEVEDQI<br>TAVRKFIEMGFIDEKRIAIWGWSYGGYISSLALASGTGLFKCGIAVAPVSSWEYYTSVYTERFMGL<br>PTKDDNLEHYKNSTVMARAEYFRNVDYLLIHGTADDNVHFQNSAQIAKALVNAQVDFQAMWYSD<br>QNHGLSGLSTNHLYTHMTHFLKQCFSLSDRGRKRRSAVTACQSLGFWSLIEIVGIIAATCMDQWS<br>TQDLYNNPVTAVFNYQGLWHSCMRESSGFTECRGYFTLLELPAMLQAVQALMIVGIVLGAIGLLV<br>SIFALKCIRIGSMEDSAKANMTLTSGIMFIVSGLCAIAGVSVFANMLVTNFWLSTANMYTGMGEMV<br>QTVQTRYTFGAALFVGINVAGGLTLIGGVMMCIACRGLAPEETNYKAVYYHASGHSVAYKPGGFK<br>ASTGFGSNTKNKKIYDGGAHTEDEVQSYPSKHDYV (SEQ ID NO: 64) |
| modPRAME-modTBXT | atggaaagaagaaggctctggggcagcatccagagccggtacatcagcatgagcgtgtggacaagccctcggagactggtggaact<br>ggctggacagagcctgctgaaggatgaggccctggccattgctgctctggaactgctgcctagagagctgttccctcctctgttcatggccg<br>ccttcgacggcagacacagccagacactgaaagccatggtgcaggcctggcctttcacctgtctgcctctgggagtgctgatgaagggc<br>cagcatctgcacctggaaaccttcaaggccgtgctggatggcctggatgtgctgctggctcaagaagtgcggcctcggcgttggaaactg<br>caggttctggatctgctgaagaacagccaccaggatttctggaccgtttggagcggcaacagagccagcctgtacagctttcctgagcctg<br>aagccgctcagcccatgaccaagaaaagaaaggtggacggcctgagcaccgaggccgagcagccttttattcccgtggaagtgctgg<br>tggacctgttcctgaaagaaggcgcctgcgacgagctgttcagctacctgaccgagaaagtgaagcagaagaagaacgtcctgcacct<br>gtgctgcaagaagctgaagatctttgccatgcctatgcaggacatcaagatgatcctgaagatggtgcagctggacagcatcgaggacct<br>ggaagtgacctgtacctggaagctgcccacactggccaagttctttagctacctgggccagatgatcaacctgcggagactgctgctgag<br>ccacatccacgccagctcctacatcagccccgagaaagaggaacagtacatctcccagttcacctctcagtttctgagcctgcagtgtctg<br>caggccctgtacgtggacagcctgttcttcctgagaggcaggctggaccagctgctgagacacgtgatgaaccctctggaaaccctgag<br>catcaccaactgcagactgctggaaggcgacgtgatgcacctgtctcagagcccatctgtgtcccagctgagcgtgctgtctctgtctggc<br>gtgatgctgaccgatgtgtcccctgaacctctgcaggcactgctgaaaaaggccagcgccactctgcaggacctggtgtttgatgagtgcg<br>gcatcatggacgaccagctgtttgccctgctgccaagcctgagccactgtagccaactgaccacactgagcttctacggcaacagcatct<br>acatctctgccctgcagagcctcctgcagcacctgatcggactgagcaatctgacccacgtgctgtacccagtgctgctcgagagctacg<br>aggacatccacgtgaccctgcaccaagagagactggcctatctgcatgcccggctgagagaactgctgtgcgaactgggcagaccca<br>gcatggtttggctgagcgctaatctgtgccctcactgcggcgacagaaccttctacgaccccaagctgatcatgtgcccctgcttcatgccc<br>aaccggggcagaaagagaagaagctctagccctggcacagagagcgccggaaagtccctgcagtacagagtggatcatctgctgag<br>cgccgtggaaaacgaactgcaggccggatctgagaagggcgatcctacagagcacgagctgagagtcggcctggaagagtctgagc |

TABLE 24-continued

Sequences for MSLN, CT83 and Exemplary Design Antigens

| TAA | Sequence |
|---|---|
| | tgtggctgcggttcaaagaactgaccaacgagatgatcgtcaccaagaacggcagacggatgttccccgtgctgaaagtgaacgtgtcc ggactggaccccaacgccatgtatagctttctgctggacttcgtggtggccgacaaccacagatggaaatacgtgaacggcgagtgggt gccaggcggaaaacctcaactgcaagcccctagctgcgtgtacattcaccctgacagccccaatttcggcgcccactggatgaaggcc cctgtgtcctttagcaaagtcaagctgaccaacaagctgaacggcggaggccagatcatgctgaactccctgcacaaatacgagccca gaatccacatcgtcagagtcggcggaccccagagaatgatcaccagccactgcttccccgagacacagtttatcgccgtgaccgcctac cagaacgaggaaatcacaaccctgaagatcaagtacaaccccttcgccaaggccttcctggacgccaaagagcggagcgaccaca aagaaatgatcaaagagcccggcgactcccagcagccaggctattctcaatggggatggctgctgccaggcaccagcacattgtgccc tccagccaatcctcacagccagtttggaggcgctctgtccctgagcagcacacacagctacgacagataccccacactgcggagccac agaagcagcccctatccttctccttacgctcaccggaacaacagccccacctacagcgataatagccccgcctgtctgagcatgctgcag tcccacgataattggagcagcctgcggatgcctgctcacccttctatgctgcccgtgtctcacaacgcctctccacctacaagcagctctca gtaccccagcctttggagcgtgtccaatggcgctgtgacactgggatctcaggccgctgctgtgtctaatggactgggagcccagttcttca gaggcagccctgctcactacacccctctgacacatcctgtgtcagccccttctagcagcggcttccctatgtacaaaggcgccgctgccgc caccgatatcgtggattctcagtacgatgccgccgctcagggccacctgattgcatcttggacacctgtgtctccaccttccatgtgatga (SEQ ID NO: 65) |
| modPRAME-modTBXT | MERRRLWGSIQSRYISMSVWTSPRRLVELAGQSLLKDEALAIAALELLPRELFPPLFMAAFDGRHS QTLKAMVQAWPFTCLPLGVLMKGQHLHLETFKAVLDGLDVLLAQEVRPRRWKLQVLDLLKNSHQ DFWTVWSGNRASLYSFPEPEAAQPMTKKRKVDGLSTEAEQPFIPVEVLVDLFLKEGACDELFSYL TEKVKQKKNVLHLCCKKLKIFAMPMQDIKMILKMVQLDSIEDLEVTCTWKLPTLAKFFSYLGQMINL RRLLLSHIHASSYISPEKEEQYISQFTSQFLSLQCLQALYVDSLFFLRGRLDQLLRHVMNPLETLSIT NCRLLEGDVMHLSQSPSVSQLSVLSLSGVMLTDVSPEPLQALLKKASATLQDLVFDECGIMDDQL FALLPSLSHCSQLTTLSFYGNSIYISALQSLLQHLIGLSNLTHVLYPVLLESYEDIHVTLHQERLAYLH ARLRELLCELGRPSMVWLSANLCPHCGDRTFYDPKLIMCPCFMPNRGRKRRSSSPGTESAGKSL QYRVDHLLSAVENELQAGSEKGDPTEHELRVGLEESELWLRFKELTNEMIVTKNGRRMFPVLKVN VSGLDPNAMYSFLLDFWADNHRWKYVNGEINVPGGKPQLQAPSCVYIHPDSPNFGAHWMKAPV SFSKVKLTNKLNGGGQIMLNSLHKYEPRIHIVRVGGPQRMITSHCFPETQFIAVTAYQNEEITTLKIK YNPFAKAFLDAKERSDHKEMIKEPGDSQQPGYSQWGWLLPGTSTLCPPANPHSQFGGALSLSST HSYDRYPTLRSHRSSPYPSPYAHRNNSPTYSDNSPACLSMLQSHDNWSSLRMPAHPSMLPVSH NASPPTSSSQYPSLWSVSNGAVTLGSQAAAVSNGLGAQFFRGSPAHYTPLTHPVSAPSSSGFPM YKGAAAATDIVDSQYDAAAQGHLIASWTPVSPPSM (SEQ ID NO: 66) |
| HPV16/18 E6/E7 | atgcaccagaaacggaccgccatgtttcaggaccctcaagagaggcccagaaagctgcctcacctgtgtaccgagctgcagaccacc atccacgacatcatcctggaatgcgtgtactgcaagcagcagctcctgcggagagaggtgtacgatttcgccttccgggacctgtgcatcg tgtacagagatggcaacccctacgccgtgtgcaacaagtgcctgaagttctacagcaagatcagcgagtaccgctactactgctacagc gtgtacggcaccacactggaacagcagtacaacaagcccctgtgcgacctgctgatccggtgcatcaactgccagaaacctctgtgccc cgaggaaaagcagcggcacctggacaagaagcagcggttccacaacatcagaggccggtggaccggcagatgcatgagctgttgtc ggagcagccggaccagaagagagacacagctgagaggccggaagagaagaagccacggcgataccccctacactgcacgagtac atgctggacctgcagcctgagacaaccgacctgtactgctacgagcagctgaacgacagcagcgaggaagaggacgagattgacgg acctgccggacaggccgaacctgatagagcccactacaatatcgtgaccttctgctgcaagtgcaacagcaccctgagactgtgcgtgc agagcacccacgtggacatcagaaccctggaagatctgctgatgggcaccctgggaatcgtgtgccctatctgcagccagaagcctag aggcagaaagcggagaagcgccagattcgacgaccccaccagaaggccttacaagctgcctgatctgtgcactgaactgaacacca gcctgcaggacatcgagattacctgtgtgtattgcaagaccgtgctggaactgaccgaggtgttcgagtttgcctttaaggacctgttcgtggt gtaccgggacagcattcctcacgccgcctgccacaagtgcatcgacttctacagccggatcagagagctgcggcactacagcgattctgt gtacggggacaccctggaaaagctgaccaacaccggcctgtacaacctgctcatcagatgcctgcggtgtcagaagcccctgaatcct gccgagaagctgagacacctgaacgagaagcggagattccacaatatcgccggccactacagaggccagtgccacagctgttgcaa ccgggccagacaagagagactgcagagaaggcgggaaacccaagtgcggggcagaaagagaagatctcacggccctaaggcca |

TABLE 24-continued

Sequences for MSLN, CT83 and Exemplary Design Antigens

| TAA | Sequence |
|---|---|
| | cactgcaggatatcgtgctgcacctggaacctcagaacgagatccccgtggatctgctgtgccatgagcagctgtccgactccaaagag<br>gaaaacgacgaaatcgacggcgtgaaccaccagcatctgcctgccagaagggccgaaccacagagacacaccatgctgtgcatgtg<br>ttgcaagtgcgaggcccggattgagctggtggtggaaagctctgccgacgacctgagagccttccagcagctgttcctgaacaccctgag<br>cttcgtgtgtccttggtgcgccagccagcagtgataa (SEQ ID NO: 67) |
| HPV16/18 E6/E7 | MHQKRTAMFQDPQERPRKLPHLCTELQTTIHDIILECVYCKQQLLRREVYDFAFRDLCIVYRDGNP<br>YAVCNKCLKFYSKISEYRYYCYSVYGTTLEQQYNKPLCDLLIRCINCQKPLCPEEKQRHLDKKQRF<br>HNIRGRWTGRCMSCCRSSRTRRETQLRGRKRRSHGDTPTLHEYMLDLQPETTDLYCYEQLNDS<br>SEEEDEIDGPAGQAEPDRAHYNIVTFCCKCNSTLRLCVQSTHVDIRTLEDLLMGTLGIVCPICSQKP<br>RGRKRRSARFDDPTRRPYKLPDLCTELNTSLQDIEITCVYCKTVLELTEVFEFAFKDLFVVYRDSIP<br>HAACHKCIDFYSRIRELRHYSDSVYGDTLEKLTNTGLYNLLIRCLRCQKPLNPAEKLRHLNEKRRF<br>HNIAGHYRGQCHSCCNRARQERLQRRRETQVRGRKRRSHGPKATLQDIVLHLEPQNEIPVDLLC<br>HEQLSDSKEENDEIDGVNHQHLPARRAEPQRHTMLCMCCKCEARIELVVESSADDLRAFQQLFL<br>NTLSFVCPWCASQQ (SEQ ID NO: 68) |
| huPSMA | atgtggaatctccttcacgaaaccgactcggctgtggccaccgcgcgccgcccgcgctggctgtgcgctggggcgctggtgctggcgggt<br>ggcttctttctcctcggcttcctcttcgggtggtttataaaatcctccaatgaagctactaacattactccaaagcataatatgaaagcatttttgg<br>atgaattgaaagctgagaacatcaagaagttcttatataattttacacagataccacatttagcaggaacagaacaaaactttcagcttgca<br>aagcaaattcaatcccagtggaaagaatttggcctggattctgttgagctagcacattatgatgtcctgttgtcctacccaaataagactcatc<br>ccaactacatctcaataattaatgaagatggaaatgagattttcaacacatcattatttgaaccacctcctccaggatatgaaaatgtttcgg<br>atattgtaccacctttcagtgctttctctcctcaaggaatgccagagggcgatctagtgtatgttaactatgcacgaactgaagacttctttaaat<br>tggaacgggacatgaaaatcaattgctctgggaaaattgtaattgccagatatgggaaagttttcagaggaaataaggttaaaaatgccc<br>agctggcaggggccaaaggagtcattctctactccgaccctgctgactactttgctcctggggtgaagtcctatccagatggttggaatcttc<br>ctggaggtggtgtccagcgtggaaatatcctaaatctgaatggtgcaggagaccctctcacaccaggttacccagcaaatgaatatgctta<br>taggcgtggaattgcagaggctgttggtcttccaagtattcctgttcatccaattggatactatgatgcacagaagctcctagaaaaaatggg<br>tggctcagcaccaccagatagcagctggagaggaagtctcaaagtgccctacaatgttggacctggctttactggaaacttttctacacaa<br>aaagtcaagatgcacatccactctaccaatgaagtgacaagaatttacaatgtgataggtactctcagaggagcagtggaaccagaca<br>gatatgtcattctgggaggtcaccggactcatgggtgtttggtggtattgaccctcagagtggagcagctgttgttcatgaaattgtgagga<br>gctttggaacactgaaaaaggaagggtggagacctagaagaacaattttgtttgcaagctgggatgcagaagaatttggtcttcttggttct<br>actgagtgggcagaggagaattcaagactccttcaagagcgtggcgtggcttatattaatgctgactcatctatagaaggaaactacactc<br>tgagagttgattgtacaccgctgatgtacagcttggtacacaacctaacaaaagagctgaaaagccctgatgaaggctttgaaggcaaat<br>ctctttatgaaagttggactaaaaaaagtccttccccagagttcagtggcatgcccaggataagcaaattgggatctggaaatgattttgag<br>gtgttcttccaacgacttggaattgcttcaggcagagcacggtatactaaaaattgggaaacaaacaaattcagcggctatccactgtatca<br>cagtgtctatgaaacatatgagttggtggaaaagttttatgatccaatgtttaaatatcacctcactgtggcccaggttcgaggagggatggt<br>gtttgagctagccaattccatagtgctcccttttgattgtcgagattatgctgtagttttaagaaagtatgctgacaaaatctacagtatttctatga<br>aacatccacaggaaatgaagacatacagtgtatcatttgattcactthttctgcagtaaagaattttacagaaattgcttccaagttcagtgag<br>agactccaggactttgacaaaagcaacccaatagtattaagaatgatgaatgatcaactcatgtttctggaaagagcatttattgatccatta<br>gggttaccagacaggcctttttataggcatgtcatctatgctccaagcagccacaacaagtatgcaggggagtcattcccaggaatttatga<br>tgctctgtttgatattgaaagcaaagtggacccttccaaggcctggggagaagtgaagagacagatttatgttgcagccttcacagtgcag<br>gcagctgcagagactttgagtgaagtagcctaa (SEQ ID NO: 69) |
| huPSMA | MWNLLHETDSAVATARRPRWLCAGALVLAGGFFLLGFLFGWFIKSSNEATNITPKHNMKAFLDEL<br>KAENIKKFLYNFTQIPHLAGTEQNFQLAKQIQSQWKEFGLDSVELAHYDVLLSYPNKTHPNYISIINE<br>DGNEIFNTSLFEPPPPGYENVSDIVPPFSAFSPQGMPEGDLVYVNYARTEDFFKLERDMKINCSG<br>KIVIARYGKVFRGNKVKNAQLAGAKGVILYSDPADYFAPGVKSYPDGWNLPGGGVQRGNILNLNG<br>AGDPLTPGYPANEYAYRRGIAEAVGLPSIPVHPIGYYDAQKLLEKMGGSAPPDSSWRGSLKVPYN<br>VGPGFTGNFSTQKVKMHIHSTNEVTRIYNVIGTLRGAVEPDRYVILGGHRDSINVFGGIDPQSGAA<br>VVHEIVRSFGTLKKEGWRPRRTILFASWDAEEFGLLGSTEWAEENSRLLQERGVAYINADSSIEG<br>NYTLRVDCTPLMYSLVHNLTKELKSPDEGFEGKSLYESWTKKSPSPEFSGMPRISKLGSGNDFEV |

TABLE 24-continued

Sequences for MSLN, CT83 and Exemplary Design Antigens

| TAA | Sequence |
|---|---|
| | FFQRLGIASGRARYTKNWETNKFSGYPLYHSVYETYELVEKFYDPMFKYHLIVAQVRGGMVFEL ANSIVLPFDCRDYAVVLRKYADKIYSISMKHPQEMKTYSVSFDSLFSAVKNFTEIASKFSERLQDFD KSNPIVLRMMNDQLMFLERAFIDPLGLPDRPFYRHVIYAPSSHNKYAGESFPGIYDALFDIESKVDP SKAWGEVKRQIYVAAFTVQAAAETLSEVA (SEQ ID NO: 70) |
| CD276 shRNA | ccggtgctggagaaagatcaaacagctcgagctgtttgatctttctccagcatttttt (SEQ ID NO: 71) |
| modMAGEA1 | atgtctctcgaacagagaagcctgcactgcaagcccgaggaagctctggaagctcagcaagaggctctgggccttgtgtgtgttcaggc cgctgccagcagcttttctcctctggtgctgggcacactggaagaggtgccaacagccggctctaccgatcctcctcaatctcctcaaggc gccagcgcctttcctaccaccatcaacttcacccggcagagacagcctagcgagggctctagctctcacgaggaaaagggccctagca ccagctgcatcctggaaagcctgttccgggccgtgatcacaaagaaagtggccgacctcgtgggcttcctgctgctgaagtacagagcc agagaacccgtgaccaaggccgagatgctggaaagcgtgatcaagaactacaagcactgcttcagcgagatcttcggcaaggccag cgagtctctgcagctcgtgtttggcatcgacgtgaaagaggccgatcctaccggccacagctacgtgttcgtgacatgtctgggcctgagct acgatggcctgctgggcgacaatcagattatgctgaaaaccggcttcctgatcatcgtgctggtcatgatcgccatggaaggctctcacgc ccctaaagaggaaatctgggaagaactgagcgtgatggaagtgtacgacggcagagagcatagcgcctacggcgagcctagaaaa ctgctgacccaggacctggtgcaagagaagtacctcgagtacagacaggtgcccgacagcgaccctgccagatacgaatttctgtggg gccctagagcactggccgagacaagctatgtgaaggtgctggaatacgtcatcaaggtgtccgccagagtgtgcttcttcttcccatctctg cgggaagccgctctgcgcgaagaggaagaaggcgtc (SEQ ID NO: 72) |
| modMAGEA1 | MSLEQRSLHCKPEEALEAQQEALGLVCVQAAASSFSPLVLGTLEEVPTAGSTDPPQSPQGASAF PTTINFTRQRQPSEGSSSHEEKGPSTSCILESLFRAVITKKVADLVGFLLLKYRAREPVTKAEMLES VIKNYKHCFSEIFGKASESLQLVFGIDVKEADPTGHSYVFVTCLGLSYDGLLGDNQIMLKTGFLIIVL VMIAMEGSHAPKEEIWEELSVMEVYDGREHSAYGEPRKLLTQDLVQEKYLEYRQVPDSDPARYE FLWGPRALAETSYVKVLEYVIKVSARVCFFFPSLREAALREEEEGV (SEQ ID NO: 73) |
| EGFRvIII | ctggaagagaaaaagggcaactacgtggtcaccgaccactgc (SEQ ID NO: 74) |
| EGFRvIII | LEEKKGNYVVTDHC (SEQ ID NO: 75) |
| hCMV pp65 | gagtctagaggcagacggtgccctgagatgattagcgtgctgggccctatctctggccacgtgctgaaggccgtgttcagcagaggcgat acacctgtgctgccccacgagacaagactgctgcagacaggcatccatgtgcgggtgtcacagccaagcctgatcctggtgtctcagta cacccctgacagcaccccttgtcacagaggcgacaaccagctccaggtgcagcacacctactttaccggcagcgaggtggaaaacgt gtccgtgaacgtgcacaatcccaccggcagatccatctgtcccagccaagagcctatgagcatctacgtgtacgccctgcctctgaagat gctgaacatccccagcatcaatgtgcatcactacccctctgccgccgagcggaaacacagacatctgcctgtggccgatgccgtgattca cgcctctggaaagcagatgtggcaggccagactgacagtgtccggactggcttggaccagacagcagaaccagtggaaagaacccg acgtgtactacacctccgccttcgtgttccccacaaaggacgtggccctgagacacgttgtgtgcgcccatgaactcgtgtgcagcatgga aaacacccgggccaccaagatgcaagtgatcggcgaccagtacgtgaaggtgtacctggaatccttctgcgaggacgtgccaagcgg caagctgttcatgcacgtgaccctgggctccgatgtggaagaggacctgaccatgaccagaaatccccagcctttcatgcggcctcacg agagaaatggcttcaccgtgctgtgccccaagaacatgatcatcaagcccggcaagatcagccacatcatgctggatgtggccttcacc agccacgagcacttcggactgctgtgtcctaagagcatccccggcctgagcatcagcggcaacctgctgatgaatggccagcagatctt cctggaagtgcaggccattcgggaaaccgtggaactgagacagtacgaccctgtggctgccctgttcttcttcgacatcgatctgctgctcc agagaggccctcagtacagcgagcacccaacctttaccagccagtacagaatccagggcaagctggaatatcggcacacctgggata gacacgatgagggtgctgcacagggcgacgatgatgtgtggacaagcggcagcgatagcgacgaggaactggtcaccaccgagag aaagacccctagagttacaggcggaggcgcaatggctggcgcttctacatctgccggacgcaagagaaagagcgcctcttctgccacc gcctgtacaagcggcgtgatgacaagaggcaggctgaaagccgagagcacagtggcccctgaggaagatacagacgaggacagc gacaacgagattcacaaccccgccgtgtttacctggcctccttggcaggctggcattctggctagaaacctggtgcctatggtggccacag tgcagggccagaacctgaagtaccaagagttcttctgggacgccaacgacatctaccggatcttcgccgaactggaaggcgtgtggca accagccgctcagcccaaaagacgcagacacagacaggacgctctgcccggaccttgtattgccagcacacccaagaaacaccgg ggc (SEQ ID NO: 76) |

TABLE 24-continued

Sequences for MSLN, CT83 and Exemplary Design Antigens

| TAA | Sequence |
|---|---|
| hCMV pp65 | ESRGRRCPEMISVLGPISGHVLKAVFSRGDTPVLPHETRLLQTGIHVRVSQPSLILVSQYTPDSTP<br>CHRGDNQLQVQHTYFTGSEVENVSVNVHNPTGRSICPSQEPMSIYVYALPLKMLNIPSINVHHYP<br>SAAERKHRHLPVADAVIHASGKQMWQARLTVSGLAWTRQQNQWKEPDVYYTSAFVFPTKDVAL<br>RHVVCAHELVCSMENTRATKMQVIGDQYVKVYLESFCEDVPSGKLFMHVTLGSDVEEDLTMTRN<br>PQPFMRPHERNGFTVLCPKNMIIKPGKISHIMLDVAFTSHEHFGLLCPKSIPGLSISGNLLMNGQQI<br>FLEVQAIRETVELRQYDPVAALFFFDIDLLLQRGPQYSEHPTFTSQYRIQGKLEYRHTWDRHDEGA<br>AQGDDDVWTSGSDSDEELVTTERKTPRVTGGGAMAGASTSAGRKRKSASSATACTSGVMTRG<br>RLKAESTVAPEEDTDEDSDNEIHNPAVFTWPPWQAGILARNLVPMVATVQGQNLKYQEFFWDAN<br>DIYRIFAELEGVWQPAAQPKRRRHRQDALPGPCIASTPKKHRG (SEQ ID NO: 77) |
| modTBXT | atgtctagccctggaacagagtctgccggcaagagcctgcagtacagagtggaccatctgctgagcgccgtggaaaatgaactgcagg<br>ccggaagcgagaagggcgatcctacagagcacgagctgagagtcggcctggaagagtctgagctgtggctgcggttcaaagaactg<br>accaacgagatgatcgtgaccaagaacggcagacggatgttccccgtgctgaaagtgaacgtgtccggactggaccccaacgccatgt<br>acagctttctgctggacttcgtggtggccgacaaccacagatggaaatacgtgaacggcgagtgggtgccaggcggaaaacctcaact<br>gcaagcccctagctgcgtgtacattcaccctgacagccccaatttcggcgcccactggatgaaggcccctgtgtccttcagcaaagtgaa<br>gctgaccaacaagctgaacggcggaggccagatcatgctgaacagcctgcacaaatacgagcccagaatccacatcgtcagagtcg<br>gcggaccccagagaatgatcaccagccactgcttccccgagacacagtttatcgccgtgaccgcctaccagaacgaggaaatcacca<br>cactgaagatcaagtacaaccccttcgccaaggccttcctggacgccaaagagcggagcgaccacaaagagatgatcaaagagccc<br>ggcgacagccagcagccaggctattctcaatggggatggctgctgccaggcaccagcacattgtgccctccagccaatcctcacagcc<br>agtttggaggcgccctgagcctgtctagcacccacagctacgacagataccccacactgcggagccacagaagcagcccctatccttct<br>ccttacgctcaccggaacaacagccccacctacagcgataatagccccgcctgtctgagcatgctgcagtcccacgataactggtccag<br>cctgagaatgcctgctcacccttccatgctgcccgtgtctcacaatgcctctccacctaccagcagctctcagtaccctagcctttggagcgt<br>gtccaatggcgccgtgacactgggatctcaggcagccgctgtgtctaatggactgggagcccagttcttcagaggcagccctgctcacta<br>cacccctctgacacatcctgtgtctgcccctagcagcagcggcttccctatgtataagggcgctgccgccgctaccgacatcgtggattctc<br>agtatgatgccgccgcacagggacacctgatcgcctcttggacacctgtgtctccaccttccatg (SEQ ID NO: 78) |
| modTBXT | MSSPGTESAGKSLQYRVDHLLSAVENELQAGSEKGDPTEHELRVGLEESELWLRFKELTNEMIVT<br>KNGRRMFPVLKVNVSGLDPNAMYSFLLDFVVADNHRWKYVNGEWVPGGKPQLQAPSCVYIHPD<br>SPNFGAHWMKAPVSFSKVKLTNKLNGGGQIMLNSLHKYEPRIHIVRVGGPQRMITSHCFPETQFIA<br>VTAYQNEEITTLKIKYNPFAKAFLDAKERSDHKEMIKEPGDSQQPGYSQWGWLLPGTSTLCPPAN<br>PHSQFGGALSLSSTHSYDRYPTLRSHRSSPYPSPYAHRNNSPTYSDNSPACLSMLQSHDNWSSL<br>RMPAHPSMLPVSHNASPPTSSSQYPSLWSVSNGAVTLGSQAAAVSNGLGAQFFRGSPAHYTPL<br>THPVSAPSSSGFPMYKGAAAATDIVDSQYDAAAQGHLIASWTPVSPPSM (SEQ ID NO: 79) |
| modWTI | gacttcctgctgctgcagaaccctgcctctacctgtgtgcctgaaccagcctctcagcacaccctgagatctggccctggatgtctccagca<br>gcctgaacagcagggcgttagagatcctggcggaatctgggccaaactgggagctgccgaagcctctgccgaatgtctgcagggcag<br>aagaagcagaggcgccagcggatctgaacctcaccagatgggaagcgacgtgcacgacctgaatgctctgttgcctgccgtgccatct<br>cttggcggaggcggaggatgtgctttgcctgtttctggtgctgcccagtgggctcccgtgctggattttgctcctcctggcgcttctgcctatggc<br>tctcttggaggacctgctcctccaccagctccacctccaccgccgcctccaccacctcacagctttatcaagcaagagccctcctggggcg<br>gagccgagcctcacgaaaaacagtgtctgagcgccttcaccgtgcacttttcggccagtttaccggcaccgtgggcgcctgtagatacg<br>gccctttggaccaccaccacctagccaggcttctagcggacaggccagaatgttccccaacgctccttacctgcctagctgcctggaaa<br>gccagcctaccatcagaaaccagggcttcagcaccgtgaccttcgacggcatgcctagctatggccacacaccatctcaccacgccgct<br>cagttccccaatcacagcttcaagcacgaggaccctatgggccagcagggatctctgggagagcagcagtatagcgtgccacctcctgt<br>gtacggctgtcacacccctaccgatagctgcacaggcaatcaggctctgctgctgaggatgcctttcagcagcgacaacctgtaccagat<br>gacaagccagctggaatgcatgatttggaaccagatgaacctgggcgccactctgaaaggcgtggccgctggatctagcagctccgtg<br>aaatggacagccggccagagcaatcactccaccggctacgagagcgacaatcacaccatgcctatcctgtgtggggcccagtaccgg<br>attcacacacacggcgtgttcaggggcattcaggatgtgcgaagagtgcctggcgtggcccctacacttgtgggatctgccagcgaaacc<br>agcgagaagcacccttcatgtgcgcctatccaggctgcaacaagcggtacttcaagctgagccacctgaagatgcacagccggaag |

TABLE 24-continued

Sequences for MSLN, CT83 and Exemplary Design Antigens

| TAA | Sequence |
|---|---|
| | cacacaggcgagaagctgtaccagtgcgacttcaaggactgcgagcggagattcagctgcagcgaccagctgaagagacaccaga gaaggcacaccggcgtgaagccctttcagtgcaagacctgccagcggaccttctcctggtccaaccacctgaaaacccacacaagaa cccacaccggcaagaccatcgagaagcccttcagctgtagatggcccagctgccagaagaagttcgcccggtctaacgagctggtgc atcaccacaacatgcaccagaggaacatgaccaaactgcagctggtgctg (SEQ ID NO: 80) |
| modWT1 | DFLLLQNPASTCVPEPASQHTLRSGPGCLQQPEQQGVRDPGGIWAKLGAAEASAECLQGRRSR GASGSEPHQMGSDVHDLNALLPAVPSLGGGGGCALPVSGAAQWAPVLDFAPPGASAYGSLGGP APPPAPPPPPPPPPHSFIKQEPSWGGAEPHEKQCLSAFTVHFFGQFTGTVGACRYGPFGPPPPS QASSGQARMFPNAPYLPSCLESQPTIRNQGFSTVTFDGMPSYGHTPSHHAAQFPNHSFKHEDP MGQQGSLGEQQYSVPPPVYGCHTPTDSCTGNQALLLRMPFSSDNLYQMTSQLECMIWNQMNL GATLKGVAAGSSSSVKWTAGQSNHSTGYESDNHTMPILCGAQYRIHTHGVFRGIQDVRRVPGVA PTLVGSASETSEKHPFMCAYPGCNKRYFKLSHLKMHSRKHTGEKLYQCDFKDCERRFSCSDQLK RHQRRHTGVKPFQCKTCQRTFSWSNHLKTHTRTHTGKTIEKPFSCRWPSCQKKFARSNELVHH HNMHQRNMTKLQLVL (SEQ ID NO: 81) |
| KRAS G12D mutation | accgagtacaagctggtggttgttggagccgatggcgtgggaaagagcgccctgacaattcagctgatccagaaccacttcgtg (SEQ ID NO: 82) |
| KRAS G12D mutation | TEYKLVVVGADGVGKSALTIQLIQNHFV (SEQ ID NO: 83) |
| KRAS G12V mutation | acagagtataagctcgtggtcgtgggcgctgtcggagtgggaaaatctgccctgaccatccaactcattcagaatcactttgtg (SEQ ID NO: 84) |
| KRAS G12V mutation | TEYKLVVVGAVGVGKSALTIQLIQNHFV (SEQ ID NO: 85) |
| modMAGEC2 | cctcctgtgcctggcgtgcccttcagaaacgtggacaacgatagcctgaccagcgtggaactggaagattgggtcgacgcccagcatcc taccgacgaggaagaggaagaagccagctctgccagcagcaccctgtacctggtgtttagccccagcagcttctccaccagctctagcc tgattctcggaggccccgaagaagaagaggtcccaagcggcgtgatccccaatctgacagagagcatcccaagcagccctccacag ggaccaccacaaggaccttctcagagccctctgagcagctgttgcagcagtttcctgtggtccagcttcagcgaggaaagcagctccca gaaaggcgaggataccggcacttgtcagggcctgccagatagcgagagcagcttcacctacacactggacgagaaggtggccaagc tggtcgagttcctgctgctgaagtacgaggccgaggaacctgtgacagaggccgagatgctgatgatcgtcatcaagtataaggactact tccccgtgatcctgaagcgggccagagaattcatggaactgctgttcggactggccctgatcgaagtgggccccgatcacttctgcgtgttc gctaacacagtgggcctgaccgatgagggctccgatgatgagggaatgcccgagaactccctgctgatcatcatcctgagcgtcatcttc atcaagggcaactgcgcctccgaggaagtgatctgggaagtcctgaatgccgtgggcgtttacgccggcagagaacactttgtgtacgg caagccccgcgagctgctgaccaatgtttgggtgcagggccactacctggaatactgggaagtgcctcactctagccctctgtactacga gtttctgtggggccctagagcacacagcgagtccatcaagaaaaaggtgctggaattcctggccaaactgaacaataccgtgcctagctt cttcccgtcctggtacaaggatgccctgaaggacgtggaagagagagtgcaggccaccatcgacaccgccgatgatgctacagtgatg gccagcgagagcctgagcgtgatgagcagcaacgtgtcctttagcgag (SEQ ID NO: 86) |
| modMAGEC2 | PPVPGVPFRNVDNDSLTSVELEDWVDAQHPTDEEEEEASSASSTLYLVFSPSSFSTSSSLILGGP EEEEVPSGVIPNLTESIPSSPPQGPPQGPSQSPLSSCCSSFLWSSFSEESSSQKGEDTGTCQGLP DSESSFTYTLDEKVAKLVEFLLLKYEAEEPVTEAEMLMIVIKYKDYFPVILKRAREFMELLFGLALIEV GPDHFCVFANTVGLTDEGSDDEGMPENSLLIIILSVIFIKGNCASEEVIWEVLNAVGVYAGREHFVY GKPRELLTNVINVQGHYLEYWEVPHSSPLYYEFLWGPRAHSESIKKKVLEFLAKLNNTVPSFFPS WYKDALKDVEERVQATIDTADDATVMASESLSVMSSNVSFSE (SEQ ID NO: 87) |
| modTDGF1 | gactgcagaaagatggcccggttcagctactccgtgatctggatcatggccatctccaaggccttcgagctgagactggttgccggactgg gccaccaagagtttgccagacctagctggggctatctggccttccgggacgatagcatctggccccaagaggaacctgccatcagaccc agatctagccagcgggtgccacctatggaaatccagcacagcaaagaactgaaccggacctgctgcctgaacggcagaacctgtatg |

TABLE 24-continued

Sequences for MSLN, CT83 and Exemplary Design Antigens

| TAA | Sequence |
|---|---|
| | ctgggcagcttctgcgcctgtcctcctagcttctacggccggaattgcgagcacgacgtgcggaaagaaaactgcggcagcgtgccaca cgatacctggctgcctaagaaatgcagcctgtgcaagtgttggcacggccagctgcggtgtttccccagagcttttctgcccgtgtgtgacg gcctggtcatggatgaacacctggtggccagcagaacccctgagcttcctccaagcgccaggaccaccacctttatgctcgtgggcatct gcctgagcatccagagctactac (SEQ ID NO: 88) |
| modTDGF1 | DCRKMARFSYSVIWIMAISKAFELRLVAGLGHQEFARPSWGYLAFRDDSIWPQEEPAIRPRSSQR VPPMEIQHSKELNRTCCLNGRTCMLGSFCACPPSFYGRNCEHDVRKENCGSVPHDTWLPKKCS LCKCWHGQLRCFPRAFLPVCDGLVMDEHLVASRTPELPPSARTTTFMLVGICLSIQSYY (SEQ ID NO: 89) |
| modPSMA in modPSMA_TDGF1 | ggatccgccaccatgtggaatctgctgcacgagacagatagcgccgtggctaccgttagaaggcccagatggctttgtgctggcgctctg gttctggctggcggctttttctgctgggcttcctgttcggctggttcatcaagagcagcaacgaggccaccaacatcacccctaagcacaa catgaaggcctttctggacgagctgaaggccgagaatatcaagaagttcctgtacaacttcacgcacatccctcacctggccggcaccg agcagaattttcagctggccaagcagatccagagccagtggaaagagttcggcctggactctgtggaactggcccactacgatgtgctg ctgagctaccccaacaagacacaccccaactacatcagcatcatcaacgaggacggcaacgagatcttcaacaccagcctgttcgag cctccacctcctggctacgagaacgtgtccgatatcgtgcctccattcagcgctttcagcccacagcggatgcctgagggctacctggtgta cgtgaactacgccagaaccgaggacttcttcaagctggaatgggacatgaagatcagctgcagcggcaagatcgtgatcgcccggtac agaaaggtgttccgcgagaacaaagtgaagaacgcccagctggcaggcgccaaaggcgtgatcctgtatagcgaccccgccgacta ttttgcccctggcgtgaagtcttaccccgacggctggaattttcctggcggcggagtgcagcggcggaacatccttaatcttaacggcgctg gcgaccctctgacacctggctatcctgccaatgagtacgcctacagacacggaattgccgaggctgtgggcctgccttctattcctgtgcac cctgtgcggtactacgacgcccagaaactgctggaaaagatgggcggaagcgcccctcctgactcttcttggagaggctctctgaaggtg ccctacaatgtcggcccaggcttcaccggcaacttcagcacccagaaagtgaaaatgcacatccacagcaccaacgaagtgacccgg atctacaacgtgatcggcacactgagaggcgccgtggaacccgacaaatacgtgatcctcggcggccacagagacagctgggtgttcg gaggaatcgaccctcaatctggcgccgctgtggtgtatgagatcgtgcggtctttcggcaccctgaagaaagaaggatggcggcccaga cggaccatcctgtttgcctcttgggacgccgaggaatttggcctgctgggatctacagagtgggccgaagagaacagcagactgctgca agaaagaggcgtggcctacatcaacgccgacagcagcatcgagggcaactacaccctgcggatcgattgcacccctctgatgtacag cctggtgcacaacctgaccaaagagctgaagtcccctgacgagggctttgagggcaagagcctgtacaagagctggaccaagaagtc cccatctcctgagttcagcggcatgcccagaatctctaagctggaaagcggcaacaacttcgaggtgttcttccagcggctgggaatcgc ctctggaatcgccagatacaccaagaactgggagacaaacaagttctccggctatcccctgtaccacagcgtgtacgagacatacgag ctggtggaaaagttctacgaccccatgttcaagtaccacctgacagtggcccaagtgcgcggaggcatggtgttcgaactggccaatag catcgtgctgcccttcaactgcagagactacgccgtggtgctgcggaagtacgccgacaagatctacagcatcagcatgaagcacccg caagagatgaagacctacagcgtgtccttcgactccctgttcttcgccgtgaagaacttcaccaagatcgccagcaagttcagcgagcgg ctgcaggacttcgacaagagcaaccctatcgtgctgaggatgatgaacgaccagctgatgttcctggaacgggccttcatcaaccctctg ggactgcccgacagacccttctacaggcacgtgatctgtgcccctagcagccacaacaaatacgccggcgagagcttccccggcatct acgatgccctgttcgacatcgagagcaacgtgaaccctagcaaggcctggggcgaagtgaagagacagatctacgtggccgcattca cagtgcaggccgctgccgaaacactgtctgaagtggccagaggc (SEQ ID NO: 90) |
| modWT1 in modWT1_FBP | atggactttctgctgctgcagaaccctgccagcacctgtgttccagaacctgcctctcagcacaccctgagatctggccctggatgtctcca gcagcctgaacagcagggcgttagagatcctggcggaatctgggccaaactgggagccgctgaagcctctgccgaatgtctgcaggg cagaagaagcagaggcgccagcggatctgaacctcaccagatgggaagcgacgtgcacgacctgaatgctctgctgcctgccgtgcc atctcttggcggaggcggaggatgtgctttgcctgtttctggtgctgcccagtgggctcccgtgctggattttgctcctcctggcgcttctgcctat ggctctcttggaggacctgctcctccaccagctccacctccaccgccgcctccaccacctcacagctttatcaagcaagagccctcctggg gcggagccgagcctcacgaaaaacagtgtctgagcgccttcaccgtgcactttttcggccagtttaccggcacagtgggcgcctgtagat acggcccttttggaccaccaccacctagccaggctagctctggacaggccagaatgttccccaacgctccctacctgcctagctgcctgg aaagccagcctaccatcagaaaccagggcttcagcaccgtgaccttcgacggcatgcctagctatggccacacaccatctcaccacgc cgctcagttccccaatcacagcttcaagcacgaggaccctatgggccagcagggatctctgggagagcagcagtatagcgtgccacct cctgtgtacggctgtcacacccctaccgatagctgcacaggcaatcaggccctgctgctgaggatgcccttcagcagcgacaacctgtac cagatgacaagccagctggaatgcatgatctggaaccagatgaacctgggcgccacactgaaaggcgtggccgctggatctagcagc agcgtgaaatggacagccggccagagcaatcactccaccggctacgagtccgacaaccacaccatgcctattctgtgcggagcccagt |

TABLE 24-continued

Sequences for MSLN, CT83 and Exemplary Design Antigens

| TAA | Sequence |
|---|---|
| | acagaatccacacacacggcgtgttccggggcattcaggatgtgcgaagagtgcctggcgtggcccctacacttgtgggatctgcctctg agacaagcgagaagcaccccttcatgtgcgcctatcctggctgcaacaagcggtacttcaagctgagccacctgaagatgcacagccg gaagcacacaggcgagaagctgtaccagtgcgacttcaaggactgcgagcggagattcagctgcagcgaccagctgaagagacac cagagaaggcacaccggcgtgaagcccttccagtgcaagacctgccagcggacctttagctggtccaaccacctgaaaacccacaca agaacccacaccggcaagaccatcgagaagcctttcagctgtagatggcccagctgccagaagaagttcgcccggtctaacgagctg gtgcatcaccacaacatgcaccagaggaacatgaccaaactgcagctggtgctg (SEQ ID NO: 91) |
| modFBP | gcccagagaatgaccacacagttgctgctgctcctcgtgtgggttgccgttgtgggagaagtgcagaccagaatcgcctgggccagaac cgagctgctgaacgtgtgcatgaacgccaagcaccacaagaagaagcccgatcctgaggacaagctgcacgagcagtgtcggccttg gagaaagaacgcctgctgtagcaccaacaccagccaagaggcccacaagaacgtgtcctacctgtaccggttcaactggaaccactg cggcgagatgacacccgcctgcaagagacacttcatccaggatacctgcctgtacgagtgcagccccaatctcggcccctggattcagc aagtggaccagagctggcggaaagaactggtcctgaatgtgcccctgtgcaaagaggattgcgagcagtggtgggaagattgcagaa ccagctacacatgcaagagcaactggcacaaaggctggaactggaccagcggcttcaacaagtgtgccgtgggagctgcctgtcagc ctttccacttctactttcacacacccaccgtgctgtgcaacaagatctggacccacagctacaaggtgtccaactacagcagaggcagcg gccggtgtatccagatgtggttcgatcccgccaagggcaaccccaatgaggaagtggccagattctacgccgctgccatgtctggtgcag gaccttgggctgcttggccctttctgctttcactggccctgatgctgctgtggctgctgagc (SEQ ID NO: 92) |
| modFBP | AQRMTTQLLLLLVWVAVVGEVQTRIAWARTELLNVCMNAKHHKKKPDPEDKLHEQCRPWRKNA CCSTNTSQEAHKNVSYLYRFNWNHCGEMTPACKRHFIQDTCLYECSPNLGPWIQQVDQSWRKE LVLNVPLCKEDCEQWWEDCRTSYTCKSNWHKGWNWTSGFNKCAVGAACQPFHFYFHTPTVLC NKIWTHSYKVSNYSRGSGRCIQMWFDPAKGNPNEEVARFYAAAMSGAGPWAAWPFLLSLALML LWLLS (SEQ ID NO: 93) |
| modFSHR | atggctctgctgctggtttctctgctggccctgctgtctctcggctctggatgtcaccacagaatctgccactgcagcaaccgggtgttcctgtg ccagaaaagcaaagtgaccgagatcctgagcgacctgcagcggaatgccatcgagctgagattcgtgctgaccaagctgcaagtgat ccagaagggcgccttcagcggcttcggcgacctggaaaagatcgagatcagccagaacaacgtgctggaagtgatcgaggcccacg tgttcagcaacctgcctaagctgcacgagatcagaatcgagaaggccaacaacctgctgtacatcaaccccgaggccttccagaacttc cccaacctgcagtacctgctgatctccaacaccggcatcaaacatctgcccgacgtgcacaagatccacagcctgcagaaggtgctgct ggacatccaggacaacatcaacatccacacaatcgagcggaactacttcctgggcctgagcttcgagagcgtgatcctgtggctgaaca agaacggcatccaagagatccacaactgcgccttcaatggcacccagctggacgagctgaacctgtccgacaacaacaatctggaag aactgcccaacgacgtgttccacagagccagcggacctgtgatcctggacatcagcagaaccagaatccactctctgcccagctacgg cctggaaaacctgaagaagctgcgggccagaagcacctacaatctgaaaaagctgcctacgctggaaaccctggtggccctgatgga agccagcctgacataccctagccactgctgcgcctttgccaactggcggagacagatctctgagctgcaccccatctgcaacaagagca tcctgcggcaagaggtggactacatgacacaggccagaggccagagattcagcctggccgaggataacgagagcagctacagcag aggcttcgacatgacctacaccgagttcgactacgacctgtgcaacaaggtggtggacgtgacatgcagccccaagcctgatgccttca atccctgcgaggacatcatgggctacaacatcctgagagtgctgatctggttcatcagcatcctggccatcaccgagaacatcatcgtgct ggtcatcctgaccaccagccagtacaagctgaccgtgcctatgttcctgatgtgcaacctggccttcgccgatctgtgcatcggcatctacct gctgctgatcgccagcgtggacattcacaccaagagccagtaccacaactacgccatcgactggcagacaggcgccggatgtgatgc cgccggattctttacagtgttcgccagcgagctgtccgtgtacaccctgacagctatcaccctggaacggtggcacaccatcacacacgct atgcagctggactgcaaagtgcacctgagacacagcgcctccgtgatggttatgggctggatcttcgccttcgctgccgctctgttccccatc tttggcatcagctcctacatgaaggtgtccatctatctgcccatggacatcgacagccctctgagccagctgtacgtgatgagtctgctggtg ctgaatgtgctggcctttgtggtcatctgcggctgctacatctatatctacctgacagtgcggaaccccaacatcgtgtccagctccagcgac acccggatcgctaagagaatggccatgctgatcttcaccgactttctgtgcatggcccctatcagcctgttcgccattagcgctagcctgaa ggtgcccctgatcaccgtgtccaaggccaagattctgctggtcctgttctaccccatcaacagctgcgccaatcctttcctgtacgccatcttc accaagaacttcaggcggaacttcttcatcctgctgagcaagcggggctgttacaagatgcaggcccagatctaccggaccgagacact gtccaccgtgcacaacacacaccccagaaacggccactgtagcagcgcccctagagtgacaaatggctccacctacatcctggtgcc actgagccatctggcccagaac (SEQ ID NO: 94) |

TABLE 24-continued

| Sequences for MSLN, CT83 and Exemplary Design Antigens | |
|---|---|
| TAA | Sequence |
| modFSHR | MALLLVSLLALLSLGSGCHHRICHCSNRVFLCQKSKVTEILSDLQRNAIELRFVLTKLQVIQKGAFS<br>GFGDLEKIEISQNNVLEVIEAHVFSNLPKLHEIRIEKANNLLYINPEAFQNFPNLQYLLISNTGIKHLPD<br>VHKIHSLQKVLLDIQDNINIHTIERNYFLGLSFESVILWLNKNGIQEIHNCAFNGTQLDELNLSDNNNL<br>EELPNDVFHRASGPVILDISRTRIHSLPSYGLENLKKLRARSTYNLKKLPTLETLVALMEASLTYPSH<br>CCAFANWRRQISELHPICNKSILRQEVDYMTQARGQRFSLAEDNESSYSRGFDMTYTEFDYDLC<br>NKVVDVTCSPKPDAFNPCEDIMGYNILRVLIWFISILAITENIIVLVILTTSQYKLTVPMFLMCNLAFAD<br>LCIGIYLLLIASVDIHTKSQYHNYAIDWQTGAGCDAAGFFTVFASELSVYTLTAITLERWHTITHAMQ<br>LDCKVHLRHSASVMVMGWIFAFAAALFPIFGISSYMKVSIYLPMDIDSPLSQLYVMSLLVLNVLAFV<br>VICGCYIYIYLTVRNPNIVSSSSDTRIAKRMAMLIFTDFLCMAPISLFAISASLKVPLITVSKAKILLVLF<br>YPINSCANPFLYAIFTKNFRRNFFILLSKRGCYKMQAQIYRTETLSTVHNTHPRNGHCSSAPRVTN<br>GSTYILVPLSHLAQN (SEQ ID NO: 95) |
| modMAGEA10 | cccagggctcccaagagacagagatgcatgcccgaagaggacctgcagagccagagcgaaacacagggactcgaaggtgctcag<br>gctcctctggccgtggaagaagatgccagcagctctaccagcacctccagcagcttccctagcagctttccattcagctcctctagctctag<br>cagcagctgttaccctctgatccccagcacacccgagaaggtgttcgccgacgacgagacacctaatccactgcagtctgcccagatcg<br>cctgcagcagtacactggtggttgctagcctgcctctggaccagtctgatgagggaagcagcagccagaaagaggaaagccctagca<br>cactccaggtgctgcccgatagcgagagcctgcctagaagcgagatctacaagaaaatgaccgacctggtgcagttcctcctgttcaagt<br>accagatgaaggaacccatcaccaaggccgaaatcctggaaagcgtgatcagaaactacgaggaccactttccactgctgttcagcga<br>ggccagcgagtgcatgctgctcgtgtttagcatcgacgtgaagaaggtggaccccaccggccacagctttgtgctggttacaagcctggg<br>actgacctacgacggcatgctgtccgatgtgcagagcatgcctaagaccggcatcctgatcctgattctgagcatcgtgttcatcgagggct<br>actgcaccccctgaggaagtgatttgggaagccctgaacatgatgggcctgtacgatggcatggaacacctgatctacggcgagcccag<br>aaaactgctgacccaggactgggtgcaagagaactacctggaataccggcagatgcccggcagcgatcctgccagatatgagtttctgt<br>ggggccctagagcacatgccgagatccggaagatgagcctgctgaagttcctggccaaagtgaacggcagcgacccaatcagcttcc<br>cactttggtacgaagaggccctgaaggacgaggaagagagagcccaggatagaatcgccaccaccgacgacacaacagccatgg<br>cctctgcctcttctagcgccaccggcagctttagctaccccgag (SEQ ID NO: 96) |
| modMAGEA10 | PRAPKRQRCMPEEDLQSQSETQGLEGAQAPLAVEEDASSSTSTSSSFPSSFPFSSSSSSSSCYP<br>LIPSTPEKVFADDETPNPLQSAQIACSSTLVVASLPLDQSDEGSSSQKEESPSTLQVLPDSESLPR<br>SEIYKKMTDLVQFLLFKYQMKEPITKAEILESVIRNYEDHFPLLFSEASECMLLVFSIDVKKVDPTGH<br>SFVLVTSLGLTYDGMLSDVQSMPKTGILILILSIVFIEGYCTPEEVIWEALNMMGLYDGMEHLIYGEP<br>RKLLTQDWVQENYLEYRQMPGSDPARYEFLWGPRAHAEIRKMSLLKFLAKVNGSDPISFPLWYE<br>EALKDEEERAQDRIATTDDTTAMASASSSATGSFSYPE (SEQ ID NO: 97) |
| modPRAME | atggaaagaagaaggctctggggcagcatccagagccggtacatcagcatgagcgtgtggacaagccctcggagactggtggaact<br>ggctggacagagcctgctgaaggatgaggccctggccattgctgctctggaactgctgcctagagagctgttccctcctctgttcatggccg<br>ccttcgacggcagacacagccagacactgaaagccatggtgcaggcctggcctttcacctgtctgcctctgggagtgctgatgaagggc<br>cagcatctgcacctggaaaccttcaaggccgtgctggatggcctggatgtgctgctggctcaagaagtgcggcctcggcgttggaaactg<br>caggttctggatctgctgaagaacagccaccaggatttctggaccgtttggagcggcaacagagccagcctgtacagctttcctgagcctg<br>aagccgctcagcccatgaccaagaaaagaaaggtggacggcctgagcaccgaggccgagcagccttttattcccgtggaagtgctgg<br>tggacctgttcctgaaagaaggcgcctgcgacgagctgttcagctacctgaccgagaaagtgaagcagaagaagaacgtcctgcacct<br>gtgctgcaagaagctgaagatctttgccatgcctatgcaggacatcaagatgatcctgaagatggtgcagctggacagcatcgaggacct<br>ggaagtgacctgtacctggaagctgcccacactggccaagttctttagctacctgggccagatgatcaacctgcggagactgctgctgag<br>ccacatccacgccagctcctacatcagccccgagaaagaggaacagtacatctcccagttcacctctcagtttctgagcctgcagtgtctg<br>caggccctgtacgtggacagcctgttcttcctgagaggcaggctggaccagctgctgagacacgtgatgaaccctctggaaaccctgag<br>catcaccaactgcagactgctggaaggcgacgtgatgcacctgtctcagagcccatctgtgtcccagctgagcgtgctgtctctgtctggc<br>gtgatgctgaccgatgtgtcccctgaacctctgcaggcactgctgaaaaaggccagcgccactctgcaggacctggtgtttgatgagtgcg<br>gcatcatggacgaccagctgtttgccctgctgccaagcctgagccactgtagccaactgaccacactgagcttctacggcaacagcatct<br>acatctctgccctgcagagcctcctgcagcacctgatcggactgagcaatctgacccacgtgctgtacccagtgctgctcgagagctacg |

TABLE 24-continued

Sequences for MSLN, CT83 and Exemplary Design Antigens

| TAA | Sequence |
|---|---|
| | aggacatccacgtgaccctgcaccaagagagactggcctatctgcatgcccggctgagagaactgctgtgcgaactgggcagaccca gcatggtttggctgagcgctaatctgtgccctcactgcggcgacagaaccttctacgaccccaagctgatcatgtgcccctgcttcatgccc aac (SEQ ID NO: 98) |
| modPRAME | MERRRLWGSIQSRYISMSVWTSPRRLVELAGQSLLKDEALAIAALELLPRELFPPLFMAAFDGRHS QTLKAMVQAWPFTCLPLGVLMKGQHLHLETFKAVLDGLDVLLAQEVRPRRWKLQVLDLLKNSHQ DFWTVWSGNRASLYSFPEPEAAQPMTKKRKVDGLSTEAEQPFIPVEVLVDLFLKEGACDELFSYL TEKVKQKKNVLHLCCKKLKIFAMPMQDIKMILKMVQLDSIEDLEVTCTWKLPTLAKFFSYLGQMINL RRLLLSHIHASSYISPEKEEQYISQFTSQFLSLQCLQALYVDSLFFLRGRLDQLLRHVMNPLETLSIT NCRLLEGDVMHLSQSPSVSQLSVLSLSGVMLTDVSPEPLQALLKKASATLQDLVFDECGIMDDQL FALLPSLSHCSQLTTLSFYGNSIYISALQSLLQHLIGLSNLTHVLYPVLLESYEDIHVTLHQERLAYLH ARLRELLCELGRPSMVWLSANLCPHCGDRTFYDPKLIMCPCFMPN (SEQ ID NO: 99) |
| modTBXT in modPRAME_TBXT | tctagccctggcacagagagcgccggaaagtccctgcagtacagagtggatcatctgctgagcgccgtggaaaacgaactgcaggcc ggatctgagaagggcgatcctacagagcacgagctgagagtcggcctggaagagtctgagctgtggctgcggttcaaagaactgacc aacgagatgatcgtcaccaagaacggcagacggatgttccccgtgctgaaagtgaacgtgtccggactggaccccaacgccatgtata gctttctgctggacttcgtggtggccgacaaccacagatggaaatacgtgaacggcgagtgggtgccaggcggaaaacctcaactgca agcccctagctgcgtgtacattcaccctgacagccccaatttcggcgcccactggatgaaggcccctgtgtcctttagcaaagtcaagctg accaacaagctgaacggcggaggccagatcatgctgaactccctgcacaaatacgagcccagaatccacatcgtcagagtcggcgg accccagagaatgatcaccagccactgcttccccgagacacagtttatcgccgtgaccgcctaccagaacgaggaaatcacaaccctg aagatcaagtacaaccccttcgccaaggccttcctggacgccaaagagcggagcgaccacaaagaaatgatcaaagagcccggcg actcccagcagccaggctattctcaatggggatggctgctgccaggcaccagcacattgtgccctccagccaatcctcacagccagtttg gaggcgctctgtccctgagcagcacacacagctacgacagataccccacactgcggagccacagaagcagcccctatccttctccttac gctcaccggaacaacagccccacctacagcgataatagccccgcctgtctgagcatgctgcagtcccacgataattggagcagcctgc ggatgcctgctcacccttctatgctgcccgtgtctcacaacgcctctccacctacaagcagctctcagtaccccagcctttggagcgtgtcca atggcgctgtgacactgggatctcaggccgctgctgtgtctaatggactgggagcccagttcttcagaggcagccctgctcactacacccc tctgacacatcctgtgtcagccccttctagcagcggcttccctatgtacaaaggcgccgctgccgccaccgatatcgtggattctcagtacg atgccgccgctcagggccacctgattgcatcttggacacctgtgtctccaccttccatg (SEQ ID NO: 100) |
| HPV16 E6 | atgcaccagaaacggaccgccatgtttcaggaccctcaagagaggcccagaaagctgcctcacctgtgtaccgagctgcagaccacc atccacgacatcatcctggaatgcgtgtactgcaagcagcagctcctgcggagagaggtgtacgatttcgccttccgggacctgtgcatcg tgtacagagatggcaacccctacgccgtgtgcaacaagtgcctgaagttctacagcaagatcagcgagtaccgctactactgctacagc gtgtacggcaccacactggaacagcagtacaacaagcccctgtgcgacctgctgatccggtgcatcaactgccagaaacctctgtgccc cgaggaaaagcagcggcacctggacaagaagcagcggttccacaacatcagaggccggtggaccggcagatgcatgagctgttgtc ggagcagccggaccagaagagagacacagctg (SEQ ID NO: 101) |
| HPV16 E6 | MHQKRTAMFQDPQERPRKLPHLCTELQTTIHDIILECVYCKQQLLRREVYDFAFRDLCIVYRDGNP YAVCNKCLKFYSKISEYRYYCYSVYGTTLEQQYNKPLCDLLIRC INCQKPLCPEEKQRHLDKKQRF HNIRGRWTGRCMSCCRSSRTRRETQL (SEQ ID NO: 102) |
| HPV16 E7 | cacggcgataccccctacactgcacgagtacatgctggacctgcagcctgagacaaccgacctgtactgctacgagcagctgaacgaca gcagcgaggaagaggacgagattgacggacctgccggacaggccgaacctgatagagcccactacaatatcgtgaccttctgctgca agtgcaacagcaccctgagactgtgcgtgcagagcacccacgtggacatcagaaccctggaagatctgctgatgggcaccctgggaat cgtgtgccctatctgcagccagaagcct (SEQ ID NO: 103) |
| HPV16 E7 | HGDTPTLHEYMLDLQPETTDLYCYEQLNDSSEEEDEIDGPAGQAEPDRAHYNIVTFCCKCNSTLR LCVQSTHVDIRTLEDLLMGTLGIVCPICSQKP (SEQ ID NO: 104) |

TABLE 24-continued

| Sequences for MSLN, CT83 and Exemplary Design Antigens | |
|---|---|
| TAA | Sequence |
| HPV18 E6 | gccagattcgacgaccccaccagaaggccttacaagctgcctgatctgtgcactgaactgaacaccagcctgcaggacatcgagatta<br>cctgtgtgtattgcaagaccgtgctggaactgaccgaggtgttcgagtttgcctttaaggacctgttcgtggtgtaccgggacagcattcctca<br>cgccgcctgccacaagtgcatcgacttctacagccggatcagagagctgcggcactacagcgattctgtgtacggggacaccctggaa<br>aagctgaccaacaccggcctgtacaacctgctcatcagatgcctgcggtgtcagaagcccctgaatcctgccgagaagctgagacacct<br>gaacgagaagcggagattccacaatatcgccggccactacagaggccagtgccacagctgttgcaaccgggccagacaagagaga<br>ctgcagagaaggcgggaaacccaagtg (SEQ ID NO: 105) |
| HPV18 E6 | ARFDDPTRRPYKLPDLCTELNTSLQDIEITCVYCKTVLELTEVFEFAFKDLFVVYRDSIPHAACHKCI<br>DFYSRIRELRHYSDSVYGDTLEKLTNTGLYNLLIRCLRCQKPLNPAEKLRHLNEKRRFHNIAGHYR<br>GQCHSCCNRARQERLQRRRETQV (SEQ ID NO: 106) |
| HPV18 E7 | cacggccctaaggccacactgcaggatatcgtgctgcacctggaacctcagaacgagatccccgtggatctgctgtgccatgagcagct<br>gtccgactccaaagaggaaaacgacgaaatcgacggcgtgaaccaccagcatctgcctgccagaagggccgaaccacagagaca<br>caccatgctgtgcatgtgttgcaagtgcgaggcccggattgagctggtggtggaaagctctgccgacgacctgagagccttccagcagct<br>gttcctgaacaccctgagcttcgtgtgtccttggtgcgccagccagcag (SEQ ID NO: 107) |
| HPV18 E7 | HGPKATLQDIVLHLEPQNEIPVDLLCHEQLSDSKEENDEIDGVNHQHLPARRAEPQRHTMLCMCC<br>KCEARIELWESSADDLRAFQQLFLNTLSFVCPWCASQQ (SEQ ID NO: 108) |
| modClaudin 18 (CLDN18) | gccgtgacagcctgtcagagcctgggctttgtggtgtccctgatcgagatcgtgggcatcattgccgctacctgcatggaccagtggtctac<br>ccaggacctgtacaacaaccctgtgaccgccgtgttcaactaccaaggcctgtggcacagctgcatgagagagagcagcggcttcacc<br>gagtgcagaggctacttcaccctgctggaactgcctgccatgctgcaggctgtgcaggcccttatgatcgtgggaattgtgctgggagcca<br>tcggcctgctggtgtccattttcgccctgaagtgcatccggatcggcagcatggaagatagcgccaaggccaacatgaccctgaccagc<br>ggcatcatgttcatcgtgtccggcctgtgcgccattgctggcgtgtccgtgtttgccaatatgctcgtgaccaacttctggctgagcaccgcca<br>acatgtacaccggcatgggcgagatggtgcagaccgtgcagacacggtacacatttggcgccgctctgtttgtcggatgggttgcaggcg<br>gactgacactgattggcggcgtgatgatgtgtatcgcctgcagaggactggcccctgaggaaacaaactacaaggccgtgtactaccac<br>gcctccggacacagcgtggcatacaaacctggcggctttaaggccagcaccggcttcggcagcaacaccaagaacaagaagatcta<br>cgacggcggagcacacaccgaggatgaggtgcagagctaccccagcaagcacgactacgtg (SEQ ID NO: 109) |
| modClaudin 18 (CLDN18) | AVTACQSLGFWSLIEIVGIIAATCMDQWSTQDLYNNPVTAVFNYQGLWHSCMRESSGFTECRGY<br>FTLLELPAMLQAVQALMIVGIVLGAIGLLVSIFALKCIRIGSMEDSAKANMTLTSGIMFIVSGLCAIAG<br>VSVFANMLVTNFWLSTANMYTGMGEMVQTVQTRYTFGAALFVGWVAGGLTLIGGVMMCIACRG<br>LAPEETNYKAVYYHASGHSVAYKPGGFKASTGFGSNTKNKKIYDGGAHTEDEVQSYPSKHDYV<br>(SEQ ID NO: 110) |
| modLY6K | gctctgctggcactgctgctggtggtggctttgcctagagtgtggaccgacgccaatctgacagtgcggcagagagatcctgaggacagc<br>cagagaaccgacgacggcgataacagagtgtggtgccacgtgtgcgagcgcgagaataccttcgagtgtcagaaccccagacggtg<br>caagtggaccgagccttactgtgtgatcgccgccgtgaaaatcttcccacggttcttcatggtggtcaagcagtgcagcgctggctgtgccg<br>ctatggaaagacccaagcctgaggaaaagcggttcctgctcgaggaacccatgctgttcttctacctgaagtgctgcaaaatctgctactg<br>caacctggaaggccctcctatcaacagcagcgtcctgaaagaatatgccggcagcatgggcgagtcttgtggtggactgtggctggcca<br>ttctgctgctgcttgcctctattgccgcctctctgagcctgagc (SEQ ID NO: 111) |
| modLY6K | ALLALLLWALPRVWTDANLTVRQRDPEDSQRTDDGDNRVWCHVCERENTFECQNPRRCKWTE<br>PYCVIAAVKIFPRFFMWKQCSAGCAAMERPKPEEKRFLLEEPML FFYLKCCKICYCNLEGPPINS<br>SVLKEYAGSMGESCGGLWLAILLLLASIAASLSLS (SEQ ID NO: 112) |
| modBORIS in modTBXT_BORIS | gccgccaccgagatcagcgtgctgagcgagcagttcaccaagatcaaagaattgaagctgatgctcgagaaggggctgaagaaaga<br>agagaaggacggcgtctgccgcgagaagaatcacagaagccctagcgagctggaagcccagagaacatctggcgccttccaggac |

TABLE 24-continued

Sequences for MSLN, CT83 and Exemplary Design Antigens

| TAA | Sequence |
| --- | --- |
| | agcatcctggaagaagaggtggaactggttctggcccctctggaagagagcaagaagtacatcctgacactgcagaccgtgcacttca<br>cctctgaagccgtgcagctccaggacatgagcctgctgtctatccagcagcaagagggcgtgcaggttgtggttcagcaacctggacctg<br>gactgctctggctgcaagagggacctagacagtccctgcagcagtgtgtggccatcagcatccagcaagagctgtatagccctcaagag<br>atggaagtgctgcagtttcacgccctcgaagagaacgtgatggtggccatcgaggacagcaagctggctgtgtctctggccgaaacaac<br>cggcctgatcaagctggaagaggaacaagagaagaaccagctgctggccgagaaaacaaaaaagcaactgttcttcgtggaaacc<br>atgagcggcgacgagagaagcgacgagatcgtgctgacagtgtccaacagcaacgtggaagaacaagaggaccagcctaccgcct<br>gtcaggccgatgccgagaaagccaagtttaccaagaaccagagaaagaccaagggcgccaagggcaccttccactgcaacgtgtgc<br>atgttcaccagcagccggatgagcagcttcaactgccacatgaagacccacaccagcgagaagccccatctgtgtcacctgtgcctgaa<br>aaccttccggacagtgacactgctgtggaactatgtgaacacccacacaggcacccggccttacaagtgcaacgactgcaacatggcc<br>ttcgtgaccagcggagaactcgtgcggcacagaagatacaagcacacccacgagaaacccttcaagtgcagcatgtgcaaatacgca<br>tccatggaagcctccaagctgaagtgccacgtgcgctctcacacaggcgagcaccctttccagtgctgtcagtgtagctacgccagccgg<br>gacacctataagctgaagcggcacatgagaacccactctggcgaaaagccctacgagtgccacatctgccacaccagattcacccag<br>agcggcaccatgaagattcacatcctgcagaaacacggcaagaacgtgcccaagtaccagtgtcctcactgcgccaccattatcgcca<br>gaaagtccgacctgcgggtgcacatgaggaatctgcacgcctattctgccgccgagctgaaatgcagatactgcagcgccgtgttccac<br>aagagatacgccctgatccagcaccagaaacccacaagaacgagaagcggtttaagtgcaagcactgcagctacgcctgcaagca<br>agagcgccacatgatcgcccacatccacacacacaccggggagaagccttttacctgcctgagctgcaacaagtgcttccggcagaaa<br>cagctgctcaacgcccacttcagaaagtaccacgacgccaacttcatccccaccgtgtacaagtgctccaagtgcggcaagggcttcag<br>ccggtggatcaatctgcaccggcacctggaaaagtgcgagtctggcgaagccaagtctgccgcctctggcaagggcagaagaacccg<br>gaagagaaagcagaccatcctgaaagaggccaccaagagccagaaagaagccgccaagcgctggaaagaggctgccaacggc<br>gacgaagctgctgccgaagaagccagcacaacaaagggcgaacagttccccgaagagatgttccctgtggcctgcagagaaaccac<br>agccagagtgaagcaagaggtcgaccagggcgtgacctgcgagatgctgctgaacaccatggacaag (SEQ ID NO: 113) |
| modFAP | atgaagaccctggtcaagatcgtgtttggcgtggccacatctgccgtgctggctctgctggtcatgtgcattgtgctgcaccccagcagagtg<br>cacaacagcgaagagaacaccatgcgggccctgacactgaaggacatcctgaacgtgaccttcagctacaagatattcttccccaact<br>ggatctccggccaagagtacctgcaccagagcgccgacaacaacatcgtgctgtacaacatcgagacaggccagagctacaccatc<br>atgagcaaccggaccatgaagtccgtgaacgccagcaactacggactgagccccgattggcagttcgtgtacctggaaagcgactaca<br>gcaagctgtggcggtacagctacaccgccacctactacatctacgacctgagcaacggcgagttcgtgaagggcaacgagctgcccc<br>atcctatccagtacctgtgttggagccctgtgggctccaagctggcctacgtgtaccagaacaacatctacctgaagcagcggcctggcg<br>accctccattccagatcaccttcaacggcagagagaacaagatctttaacggcatccccgactgggtgtacgaggaagagatgctggcc<br>accaaatacgccctgtggtggtcccctaacggcaagtttctggcctatgccgacttcaacgacacagacatccccgtgatcgcctacagct<br>actacggcaatgagcagtaccccaggaccatcaacatcagctaccccaaagccggcgctaagaaccctgtcgtgcggatcttcatcatc<br>gacaccacctatcctgtgtacgtgggccctcaagaggtgccagtgcctgccatgattgccagcagcgactactacttcagctggctgacct<br>gggtcaccgacgagcgagtttgtctgcagtggctgaagcgggtgcagaacatcagcgtgctgagcatctgcgacttcagaaaggactgg<br>cagacatgggactgccccaacacacagcagcacatcgaggaaagcagaaccggctgggctggcggcttctttgtgtctacccctgtgtt<br>cagctacgacgccatcctgtactataagatcttcagcgacaaggacggctacaagcacatccactacatcaagtacaccgtcgagaac<br>gtgatccagattaccagcggcaagtgggaagccatcaatatcttcagagtgatccagtacagcctgttctacagcagcaacgagttcgag<br>gaataccccggcagacggaacatctacagaatcagcatcggcagctacccgcctagcaagaaatgcgtgacctgccacctgagaaa<br>agagcggtgccagtactacacagccagcttctccaactacgccaagtactacgccctcgtgtgttacggccctggcatccctatcagcac<br>actgcacgatggcagaaccgaccaagagatcaagatcctggaagaaaacaaagagctggaaaacgccctgaagaacatccagctg<br>cctaaagaggaaatcaagaagctggaagtcgacgagatcaccctgtggtacaagatgatcctgcctcctcagttcgaccggtccaaga<br>agtaccctctgctgatccaggtgtacggcggaccttgttctcagtctgtgcgctccgtgttcgccgtgaattggatcagctatctggccagcaa<br>agaaggcatggttatcgccctggtggacggcagaggcacagcttttcaaggcgacaagctgctgtacgccgtgtatcagaaactgggcg<br>tgtacgaagtggaagatcagatcaccgccgtgcggaagttcatcgagatgggcttcatcgacgagaagcggatcgccatctggggctgg<br>tcttacggcggctatattagctctctggccctggcctctggcaccggcctgtttaagtgtggaattgccgtggctcccgtgtccagctgggagt<br>actataccagcgtgtacaccgagcggttcatgggcctgcctaccaaggacgacaacctggaacactacaagaactctaccgtgatggc<br>cagagccgagtacttccggaacgtggactacctgctgattcacggcaccgccgacgacaacgtgcacttccaaaacagcgcccagatc<br>gctaaggccctcgtgaatgcccaggtggactttcaggccatgtggtacagcgaccagaaccacggactgtctggcctgagcaccaacc<br>acctgtacacccacatgacccactttctgaaacagtgcttcagcctgagcgac (SEQ ID NO: 114) |

TABLE 24-continued

| Sequences for MSLN, CT83 and Exemplary Design Antigens | |
|---|---|
| TAA | Sequence |
| modFAP | MKTLVKIVFGVATSAVLALLVMCIVLHPSRVHNSEENTMRALTLKDILNVTFSYKIFFPNWISGQEYL<br>HQSADNNIVLYNIETGQSYTIMSNRTMKSVNASNYGLSPDWQFVYLESDYSKLWRYSYTATYYIY<br>DLSNGEFVKGNELPHPIQYLCWSPVGSKLAYVYQNNIYLKQRPGDPPFQITFNGRENKIFNGIPDW<br>VYEEEMLATKYALIMNSPNGKFLAYADFNDTDIPVIAYSYYGNEQYPRTINISYPKAGAKNPVVRIFII<br>DTTYPVYVGPQEVPVPAMIASSDYYFSWLTINVTDERVCLQWLKRVQNISVLSICDFRKDWQTWD<br>CPNTQQHIEESRTGWAGGFFVSTPVFSYDAILYYKIFSDKDGYKHIHYIKYTVENVIQITSGKWEAIN<br>IFRVIQYSLFYSSNEFEEYPGRRNIYRISIGSYPPSKKCVTCHLRKERCQYYTASFSNYAKYYALVC<br>YGPGIPISTLHDGRTDQEIKILEENKELENALKNIQLPKEEIKKLEVDEITLWYKMILPPQFDRSKKYP<br>LLIQVYGGPCSQSVRSVFAVNWISYLASKEGMVIALVDGRGTAFQGDKLLYAVYQKLGVYEVEDQI<br>TAVRKFIEMGFIDEKRIAIWGWSYGGYISSLALASGTGLFKCGIAVAPVSSWEYYTSVYTERFMGL<br>PTKDDNLEHYKNSTVMARAEYFRNVDYLLIHGTADDNVHFQNSAQIAKALVNAQVDFQAMWYSD<br>QNHGLSGLSTNHLYTHMTHFLKQCFSLSD (SEQ ID NO: 115) |
| modClaudin 18 in modFAP_Claudin 18 | gccgtcacagcctgtcagagcctgggctttgtggtgtccctgatcgagatcgtgggcatcattgccgctacctgcatggaccagtggtctac<br>ccaggacctgtataacaaccccgtgaccgccgtgttcaactaccaaggcctgtggcacagctgcatgagagagagcagcggcttcacc<br>gagtgcaggggctactttaccctgctggaactgccagccatgctgcaggctgtgcaggcccttatgatcgtgggaattgtgctgggcgcca<br>tcggcctgctggtgtctatttttgccctgaagtgcatccggatcggcagcatggaagatagcgccaaggccaacatgaccctgacctccgg<br>catcatgttcatcgtgtccggcctgtgtgccattgcaggcgtgtccgtgtttgccaatatgctcgtgaccaacttctggctgtccaccgccaaca<br>tgtacaccggcatgggcgagatggtgcagaccgtgcagacacggtacacatttggcgccgctctgtttgtcggatgggttgcaggcggac<br>tgactctgattggcggcgtgatgatgtgtatcgcctgcagaggactggcccctgaggaaacaaactacaaggccgtgtactaccacgcc<br>agcggacacagcgtggcatacaaaccaggcggctttaaggccagcacaggcttcggcagcaacaccaagaacaagaagatctacg<br>acggcggagcccataccgaggatgaggtgcagagctaccctagcaagcacgactacgtg (SEQ ID NO: 116) |

In some embodiments, provided herein is a vaccine composition comprising a therapeutically effective amount of cells from at least two cancer cell lines, wherein each cell line or a combination of the cell lines expresses at least 1, 2, 3, 4, 5, 6, 7, 8, 9, or 10 of the TAAs of Tables 7-23. In other embodiments, the TAAs in Tables 7-23 are modified to include one or more NSMs as described herein. In some embodiments, at least one cell line is modified to increase production of at least 1, 2, or 3 immunostimulatory factors, e.g., immunostimulatory factors from Table 4. In some embodiments, a vaccine composition is provided comprising a therapeutically effective amount of the cells from at least one cancer cell line, wherein each cell line or combination of cell lines is modified to reduce at least 1, 2, or 3 immunosuppressive factors, e.g., immunosuppressive factors from Table 6. In some embodiments, a vaccine composition is provided comprising two cocktails, wherein each cocktail comprises three cell lines modified to express 1, 2, or 3 immunostimulatory factors and to inhibit or reduce expression of 1, 2, or 3 immunosuppressive factors, and wherein each cell line expresses at least 10 TAAs or TAAs comprising one or more NSMs.

Methods and assays for determining the presence or expression level of a TAA in a cell line according to the disclosure or in a tumor from a subject are known in the art. By way of example, Warburg-Christian method, Lowry Assay, Bradford Assay, spectrometry methods such as high performance liquid chromatography (HPLC), liquid chromatography-mass spectrometry (LC/MS), immunoblotting and antibody-based techniques such as western blot, ELISA, immunoelectrophoresis, protein immunoprecipitation, flow cytometry, and protein immunostaining are all contemplated by the present disclosure.

The antigen repertoire displayed by a patient's tumor can be evaluated in some embodiments in a biopsy specimen using next generation sequencing and antibody-based approaches. Similarly, in some embodiments, the antigen repertoire of potential metastatic lesions can be evaluated using the same techniques to determine antigens expressed by circulating tumor cells (CTCs). Assessment of antigen expression in tumor biopsies and CTCs can be representative of a subset of antigens expressed. In some embodiments, a subset of the antigens expressed by a patient's primary tumor and/or CTCs are identified and, as described herein, informs the selection of cell lines to be included in the vaccine composition in order to provide the best possible match to the antigens expressed in a patient's tumor and/or metastatic lesions.

Embodiments of the present disclosure provides compositions of cell lines that (i) are modified as described herein and (ii) express a sufficient number and amount of TAAs such that, when administered to a patient afflicted with a cancer, cancers, or cancerous tumor(s), a TAA-specific immune response is generated.

Methods of Stimulating an Immune Response and Methods of Treatment

The vaccine compositions described herein may be administered to a subject in need thereof. Provided herein are methods for inducing an immune response in a subject, which involve administering to a subject an immunologically effective amount of the genetically modified cells. Also provided are methods for preventing or treating a tumor in a subject by administering an anti-tumor effective amount of the vaccine compositions described herein. Such compositions and methods may be effective to prolong the survival of the subject.

According to various embodiments, administration of any one of the vaccine compositions provided herein can increase pro-inflammatory cytokine production (e.g., IFNγ secretion) by leukocytes. In some embodiments, administration of any one of the vaccine compositions provided herein can increase pro-inflammatory cytokine production (e.g., IFNγ secretion) by leukocytes by at least 1.5-fold, 1.6-fold, 1.75-fold, 2-fold, 2.5-fold, 3.0-fold, 3.5-fold, 4.0-fold, 4.5-fold, 5.0-fold or more. In other embodiments, the IFNγ production is increased by approximately 1, 2, 3, 4, 5, 6, 7, 8, 9, 10, 11, 12, 13, 14, 15, 16, 17, 18, 19, 20, 21, 22, 23, 24, or 25-fold or higher compared to unmodified cancer cell lines. Without being bound to any theory or mechanism, the increase in pro-inflammatory cytokine production (e.g., IFNγ secretion) by leukocytes is a result of either indirect or direct interaction with the vaccine composition.

In some embodiments, administration of any one of the vaccine compositions provided herein comprising one or more modified cell lines as described herein can increase the uptake of cells of the vaccine composition by phagocytic cells, e.g., by at least 1.1-fold, 1.2-fold, 1.3-fold, 1.4-fold, 1.5-fold, 2-fold, 2.5-fold or more, as compared to a composition that does not comprise modified cells.

In some embodiments, the vaccine composition is provided to a subject by an intradermal injection. Without being bound to any theory or mechanism, the intradermal injection, in at least some embodiments, generates a localized inflammatory response recruiting immune cells to the injection site. Following administration of the vaccine, antigen presenting cells (APCs) in the skin, such as Langerhans cells (LCs) and dermal dendritic cells (DCs), uptake the vaccine cell line components by phagocytosis and then migrate through the dermis to the draining lymph node. At the draining lymph node, DCs or LCs that have phagocytized the vaccine cell line components are expected to prime naïve T cells and B cells. Priming of naïve T and B cells is expected to initiate an adaptive immune response to tumor associated antigens (TAAs) expressed by the vaccine cell line components. Certain TAAs expressed by the vaccine cell line components are also expressed by the patient's tumor. Expansion of antigen specific T cells at the draining lymph node and trafficking of these T cells to the tumor microenvironment (TME) is expected to generate a vaccine-induced anti-tumor response.

According to various embodiments, immunogenicity of the allogenic vaccine composition can be further enhanced through genetic modifications that reduce expression of immunosuppressive factors while increasing the expression or secretion of immunostimulatory signals. Modulation of these factors aims to enhance the uptake vaccine cell line components by LCs and DCs in the dermis, trafficking of DCs and LCs to the draining lymph node, T cell and B cell priming in the draining lymph node, and, thereby resulting in more potent anti-tumor responses.

In some embodiments, the breadth of TAAs targeted in the vaccine composition can be increased through the inclusion of multiple cell lines. For example, different histological subsets within a certain tumor type tend to express different TAA subsets. As a further example, in NSCLC, adenocarcinomas, and squamous cell carcinomas express different antigens. The magnitude and breadth of the adaptive immune response induced by the vaccine composition can, according to some embodiments of the disclosure, be enhanced through the inclusion of additional cell lines expressing the same or different immunostimulatory factors. For example, expression of an immunostimulatory factor, such as IL-12, by one cell line within a cocktail of three cell lines can act locally to enhance the immune responses to all cell lines delivered into the same site. The expression of an immunostimulatory factor by more than one cell line within a cocktail, such as GM-CSF, can increase the amount of the immunostimulatory factor in the injection site, thereby enhancing the immune responses induced to all components of the cocktail. The degree of HLA mismatch present within a vaccine cocktail may further enhance the immune responses induced by that cocktail.

As described herein, in various embodiments, a method of stimulating an immune response specific to at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more TAAs in a subject is provided comprising administering a therapeutically effective amount of a vaccine composition comprising modified cancer cell lines.

An "immune response" is a response of a cell of the immune system, such as a B cell, T cell, or monocyte, to a stimulus, such as a cell or antigen (e.g., formulated as an antigenic composition or a vaccine). An immune response can be a B cell response, which results in the production of specific antibodies, such as antigen specific neutralizing antibodies. An immune response can also be a T cell response, such as a CD4+ response or a CD8+ response. B cell and T cell responses are aspects of a "cellular" immune response. An immune response can also be a "humoral" immune response, which is mediated by antibodies. In some cases, the response is specific for a particular antigen (that is, an "antigen specific response"), such as one or more TAAs, and this specificity can include the production of antigen specific antibodies and/or production of a cytokine such as interferon gamma which is a key cytokine involved in the generation of a $Th_1$ T cell response and measurable by ELISpot and flow cytometry.

Vaccine efficacy can be tested by measuring the T cell response CD4+ and CD8+ after immunization, using flow cytometry (FACS) analysis, ELISpot assay, or other method known in the art. Exposure of a subject to an immunogenic stimulus, such as a cell or antigen (e.g., formulated as an antigenic composition or vaccine), elicits a primary immune response specific for the stimulus, that is, the exposure "primes" the immune response. A subsequent exposure, e.g., by immunization, to the stimulus can increase or "boost" the magnitude (or duration, or both) of the specific immune response. Thus, "boosting" a preexisting immune response by administering an antigenic composition increases the magnitude of an antigen (or cell) specific response, (e.g., by increasing antibody titer and/or affinity, by increasing the frequency of antigen specific B or T cells, by inducing maturation effector function, or a combination thereof).

The immune responses that are monitored/assayed or stimulated by the methods described herein include, but not limited to: (a) antigen specific or vaccine specific IgG antibodies; (b) changes in serum cytokine levels that may include and is not limited to: IL-1p, IL-4, IL-5, IL-6, IL-8, IL-10, IL-12, IL-17A, IL-20, IL-22, TNFα, IFNγ, TGFβ, CCL5, CXCL10; (c) IFNγ responses determined by ELISpot for CD4 and CD8 T cell vaccine and antigen specific responses; (d) changes in IFNγ responses to TAA or vaccine cell components; (e) increased T cell production of intracellular cytokines in response to antigen stimulation: IFNγ, TNFα, and IL-2 and indicators of cytolytic potential: Granzyme A, Granzyme B, Perforin, and CD107a; (f) decreased levels of regulatory T cells (Tregs), mononuclear monocyte derived suppressor cells (M-MDSCs), and polymorphonuclear derived suppressor cells (PMN-MDSCs); (g) decreased levels of circulating tumor cells (CTCs); (h) neutrophil to lymphocyte ratio (NLR) and platelet to lymphocyte ratio (PLR); (i) changes in immune infiltrate in the TME; and (j) dendritic cell maturation.

Assays for determining the immune responses are described herein and well known in the art. DC maturation can be assessed, for example, by assaying for the presence of DC maturation markers such as CD80, CD83, CD86, and MHC II. (See Dudek, A., et al., Front. Immunol., 4:438 (2013)). Antigen specific or vaccine specific IgG antibodies can be assessed by ELISA or flow cytometry. Serum cytokine levels can be measured using a multiplex approach such as Luminex or Meso Scale Discovery Electrochemiluminescence (MSD). T cell activation and changes in lymphocyte populations can be measured by flow cytometry. CTCs can be measured in PBMCs using a RT-PCR based approach. The NLR and PLR ratios can be determined using standard complete blood count (CBC) chemistry panels. Changes in immune infiltrate in the TME can be assessed by flow cytometry, tumor biopsy and next-generation sequencing (NGS), or positron emission tomography (PET) scan of a subject.

Given the overlap in TAA expression between cancers and tumors of different types, the present disclosure provides, in certain embodiments, compositions that can treat multiple different cancers. For example, one vaccine composition comprising two cocktails of three cell lines each may be administered to a subject suffering from two or more types of cancers and said vaccine composition is effective at treating both, additional or all types of cancers. In exemplary embodiments, and in consideration of the TAA expression profile, the same vaccine composition comprising modified cancer cell lines is used to treat prostate cancer and testicular cancer, gastric and esophageal cancer, or endometrial, ovarian, and breast cancer in the same patient (or different patients). TAA overlap can also occur within subsets of hot tumors or cold tumors. For example, TAA overlap occurs in GBM and SCLC, both considered cold tumors. Exemplary TAAs included in embodiments of the vaccine composition include GP100, MAGE-A1, MAGE-A4, MAGE-A10, Sart-1, Sart-3, Trp-1, and Sox2. In some embodiments, cell lines included in the vaccine composition can be selected from two tumor types of similar immune landscape to treat one or both of the tumor types in the same individual.

As used herein, changes in or "increased production" of, for example a cytokine such as IFNγ, refers to a change or increase above a control or baseline level of production/secretion/expression and that is indicative of an immunostimulatory response to an antigen or vaccine component.

Combination Treatments and Regimens

Formulations, Adjuvants, and Additional Therapeutic Agents

The compositions described herein may be formulated as pharmaceutical compositions. The term "pharmaceutically acceptable" as used herein refers to a pharmaceutically acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with tissue, organs or other human component without excessive toxicity, irritation, allergic response, immunogenicity, or other problems or complications, commensurate with a reasonable benefit/risk ratio. (See Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, Fla., 2004)).

Embodiments of the pharmaceutical composition of the disclosure is formulated to be compatible with its intended route of administration (i.e., parenteral, intravenous, intraarterial, intradermal, subcutaneous, oral, inhalation, transdermal, topical, intratumoral, transmucosal, intraperitoneal or intra-pleural, and/or rectal administration). Solutions or suspensions used for parenteral, intradermal, or subcutaneous application can include the following components: a sterile diluent such as water, saline solution, fixed oils, polyethylene glycols, glycerine, propylene glycol or other synthetic solvents; dimethyl sulfoxide (DMSO); antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes, or one or more vials comprising glass or polymer (e.g., polypropylene). The term "vial" as used herein means any kind of vessel, container, tube, bottle, or the like that is adapted to store embodiments of the vaccine composition as described herein.

In some embodiments, the composition further comprises a pharmaceutically acceptable carrier. The term "carrier" as used herein encompasses diluents, excipients, adjuvants, and combinations thereof. Pharmaceutically acceptable carriers are well known in the art (See Remington: The Science and Practice of Pharmacy, 21st Edition). Exemplary "diluents" include sterile liquids such as sterile water, saline solutions, and buffers (e.g., phosphate, tris, borate, succinate, or histidine). Exemplary "excipients" are inert substances that may enhance vaccine stability and include but are not limited to polymers (e.g., polyethylene glycol), carbohydrates (e.g., starch, glucose, lactose, sucrose, or cellulose), and alcohols (e.g., glycerol, sorbitol, or xylitol).

In various embodiments, the vaccine compositions and cell line components thereof are sterile and fluid to the extent that the compositions and/or cell line components can be loaded into one or more syringes. In various embodiments, the compositions are stable under the conditions of manufacture and storage and preserved against the contaminating action of microorganisms such as bacteria and fungi. In some embodiments, the carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, by the use of surfactants, and by other means known to one of skill in the art. Prevention of the action of microorganisms can be achieved by various antibacterial and antifungal agents, for example, parabens, chlorobutanol, phenol, ascorbic acid, thimerosal, and the like. In some embodiments, it may be desirable to include isotonic agents, for example, sugars, polyalcohols such as manitol, sorbitol, and/or sodium chloride in the composition. In some embodiments, prolonged absorption of the injectable compositions can be brought about by including in the composition an agent that delays absorption, for example, aluminum monostearate and gelatin.

In some embodiments, sterile injectable solutions can be prepared by incorporating the active compound(s) in the required amount(s) in an appropriate solvent with one or a combination of ingredients enumerated above, as required, followed by filtered sterilization. In certain embodiments, dispersions are prepared by incorporating the active compound into a sterile vehicle that contains a basic dispersion medium and the required other ingredients from those enumerated herein. In the case of sterile powders for the preparation of sterile injectable solutions, embodiments of methods of preparation include vacuum drying and freeze-drying that yield a powder of the active ingredient plus any additional desired ingredient from a previously sterile-filtered solution thereof.

The innate immune system comprises cells that provide defense in a non-specific manner to infection by other organisms. Innate immunity in a subject is an immediate defense, but it is not long-lasting or protective against future challenges. Immune system cells that generally have a role in innate immunity are phagocytic, such as macrophages and dendritic cells. The innate immune system interacts with the adaptive (also called acquired) immune system in a variety of ways.

In some embodiments, the vaccine compositions alone activate an immune response (i.e., an innate immune response, an adaptive immune response, and/or other immune response). In some embodiments, one or more adjuvants are optionally included in the vaccine composition or are administered concurrently or strategically in relation to the vaccine composition, to provide an agent(s) that supports activation of innate immunity in order to enhance the effectiveness of the vaccine composition. An "adjuvant" as used herein is an "agent" or substance incorporated into the vaccine composition or administered simultaneously or at a selected time point or manner relative to the administration of the vaccine composition. In some embodiments, the adjuvant is a small molecule, chemical composition, or therapeutic protein such as a cytokine or checkpoint inhibitor. A variety of mechanisms have been proposed to explain how different agents function (e.g., antigen depots, activators of dendritic cells, macrophages). An agent may act to enhance an acquired immune response in various ways and many types of agents can activate innate immunity. Organisms, like bacteria and viruses, can activate innate immunity, as can components of organisms, chemicals such as 2'-5' oligo A, bacterial endotoxins, RNA duplexes, single stranded RNA and other compositions. Many of the agents act through a family of molecules referred to herein as "toll-like receptors" (TLRs). Engaging a TLR can also lead to production of cytokines and chemokines and activation and maturation of dendritic cells, components involved in development of acquired immunity. The TLR family can respond to a variety of agents, including lipoprotein, peptidoglycan, flagellin, imidazoquinolines, CpG DNA, lipopolysaccharide and double stranded RNA. These types of agents are sometimes called pathogen (or microbe)-associated molecular patterns. In some embodiments, the adjuvant is a TLR4 agonist.

One adjuvant that in some embodiments may be used in the vaccine compositions is a monoacid lipid A (MALA) type molecule. An exemplary MALA is MPL® adjuvant as described in, e.g., Ulrich J. T. and Myers, K. R., Chapter 21 in Vaccine Design, the Subunit and Adjuvant Approach, Powell, M. F. and Newman, M. J., eds. Plenum Press, NY (1995).

In other embodiments, the adjuvant may be "alum", where this term refers to aluminum salts, such as aluminum phosphate and aluminum hydroxide.

In some embodiments, the adjuvant may be an emulsion having vaccine adjuvant properties. Such emulsions include oil-in-water emulsions. Incomplete Freund's adjuvant (IFA) is one such adjuvant. Another suitable oil-in-water emulsion is MF-59™ adjuvant which contains squalene, polyoxyethylene sorbitan monooleate (also known as Tween® 80 surfactant) and sorbitan trioleate. Other suitable emulsion adjuvants are Montanide™ adjuvants (Seppic Inc., Fairfield N.J.) including Montanide™ ISA 50V which is a mineral oil-based adjuvant, Montanide™ ISA 206, and Montanide™ IMS 1312. While mineral oil may be present in the adjuvant, in one embodiment, the oil component(s) of the compositions of the present disclosure are all metabolizable oils.

In some embodiments, the adjuvant may be AS02™ adjuvant or AS04™ adjuvant. AS02™ adjuvant is an oil-in-water emulsion that contains both MPL™ adjuvant and QS-21™ adjuvant (a saponin adjuvant discussed elsewhere herein). AS04™ adjuvant contains MPL™ adjuvant and alum. The adjuvant may be Matrix-M™ adjuvant. The adjuvant may be a saponin such as those derived from the bark of the Quillaja saponaria tree species, or a modified saponin, see, e.g., U.S. Pat. Nos. 5,057,540; 5,273,965; 5,352,449; 5,443,829; and 5,560,398. The product QS-21™ adjuvant sold by Antigenics, Inc. (Lexington, Mass.) is an exemplary saponin-containing co-adjuvant that may be used with embodiments of the composition described herein. In other embodiments, the adjuvant may be one or a combination of agents from the ISCOM™ family of adjuvants, originally developed by Iscotec (Sweden) and typically formed from saponins derived from Quillaja saponaria or synthetic analogs, cholesterol, and phospholipid, all formed into a honeycomb-like structure.

In some embodiments, the adjuvant or agent may be a cytokine that functions as an adjuvant, see, e.g., Lin R. et al. Clin. Infec. Dis. 21(6):1439-1449 (1995); Taylor, C. E., Infect. Immun. 63(9):3241-3244 (1995); and Egilmez, N. K., Chap. 14 in Vaccine Adjuvants and Delivery Systems, John Wiley & Sons, Inc. (2007). In various embodiments, the cytokine may be, e.g., granulocyte-macrophage colony-stimulating factor (GM-CSF); see, e.g., Change D. Z. et al. Hematology 9(3):207-215 (2004), Dranoff, G. Immunol. Rev. 188:147-154 (2002), and U.S. Pat. No. 5,679,356; or an interferon, such as a type I interferon, e.g., interferon-α (IFN-α) or interferon-β (IFN-β), or a type II interferon, e.g., interferon-γ (IFNγ), see, e.g., Boehm, U. et al. Ann. Rev. Immunol. 15:749-795 (1997); and Theofilopoulos, A. N. et al. Ann. Rev. Immunol. 23:307-336 (2005); an interleukin, specifically including interleukin-1a (IL-1a), interleukin-1p (IL-1β), interleukin-2 (IL-2); see, e.g., Nelson, B. H., J. Immunol. 172(7): 3983-3988 (2004); interleukin-4 (IL-4), interleukin-7 (IL-7), interleukin-12 (IL-12); see, e.g., Portielje, J. E., et al., Cancer Immunol. Immunother. 52(3): 133-144 (2003) and Trinchieri. G. Nat. Rev. Immunol. 3(2):133-146 (2003); interleukin-15 (II-15), interleukin-18 (IL-18); fetal liver tyrosine kinase 3 ligand (Flt3L), or tumor necrosis factor α (TNFα).

In some embodiments, the adjuvant may be unmethylated CpG dinucleotides, optionally conjugated to the antigens described herein.

Examples of immunopotentiators that may be used in the practice of the compositions and methods described herein as adjuvants include: MPL™; MDP and derivatives; oligonucleotides; double-stranded RNA; alternative pathogen-associated molecular patterns (PAMPS); saponins; small-molecule immune potentiators (SMIPs); cytokines; and chemokines.

When two or more adjuvants or agents are utilized in combination, the relative amounts of the multiple adjuvants may be selected to achieve the desired performance properties for the composition which contains the adjuvants, relative to the antigen alone. For example, an adjuvant combination may be selected to enhance the antibody response of the antigen, and/or to enhance the subject's innate immune system response. Activating the innate immune system results in the production of chemokines and cytokines, which in turn may activate an adaptive (acquired) immune response. An important consequence of activating the adaptive immune response is the formation of memory immune cells so that when the host re-encounters the antigen, the immune response occurs quicker and generally with better quality. In some embodiments, the adjuvant(s) may be pre-formulated prior to their combination with the compositions described herein.

Embodiments of the vaccine compositions described herein may be administered simultaneously with, prior to, or after administration of one or more other adjuvants or agents, including therapeutic agents. In certain embodiments, such agents may be accepted in the art as a standard treatment or prevention for a particular cancer. Exemplary agents contemplated include cytokines, growth factors, steroids, NSAIDs, DMARDs, anti-inflammatories, immune checkpoint inhibitors, chemotherapeutics, radiotherapeutics, or other active and ancillary agents. In other embodiments, the agent is one or more isolated TAA as described herein.

In some embodiments, a vaccine composition provided herein is administered to a subject that has not previously received certain treatment or treatments for cancer or other disease or disorder. As used herein, the phrase "wherein the subject refrains from treatment with other vaccines or therapeutic agents" refers to a subject that has not received a cancer treatment or other treatment or procedure prior to receiving a vaccine of the present disclosure. In some embodiments, the subject refrains from receiving one or more therapeutic vaccines (e.g. flu vaccine, covid-19 vaccine such as AZD1222, BNT162b2, mRNA-1273, and the like) prior to the administration of the therapeutic vaccine as described in various embodiments herein. In some embodiments, the subject refrains from receiving one or more antibiotics prior to the administration of the therapeutic vaccine as described in various embodiments herein. "Immune tolerance" is a state of unresponsiveness of the immune system to substances, antigens, or tissues that have the potential to induce an immune response. The vaccine compositions of the present disclosure, in certain embodiments, are administered to avoid the induction of immune tolerance or to reverse immune tolerance.

In various embodiments, the vaccine composition is administered in combination with one or more active agents used in the treatment of cancer, including one or more chemotherapeutic agents. Examples of such active agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (“Ara-C”); cyclophosphamide; thiotepa; taxoids, e.g., paclitaxel (TAXOL®, Bristol-Myers Squibb Oncology, Princeton, N.J.) and paclitaxel protein-bound particles (ABRAXANE®) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine, docetaxel, platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as TARGRETIN™ (bexarotene), PANRETIN™ (alitretinoin); and ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Further cancer active agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors.

In further embodiments, the vaccine composition is administered in combination with a TLR4 agonist, TLR8 agonist, or TLR9 agonist. Such an agonist may be selected from peptidoglycan, polyI:C, CpG, 3M003, flagellin, and *Leishmania* homolog of eukaryotic ribosomal elongation and initiation factor 4a (LeIF).

In some embodiments, the vaccine composition is administered in combination with a cytokine as described herein. In some embodiments, the compositions disclosed herein may be administered in conjunction with molecules targeting one or more of the following: Adhesion: MAdCAM1, ICAM1, VCAM1, CD103; Inhibitory Mediators: IDO, TDO; MDSCs/Tregs: NOS1, arginase, CSFR1, FOXP3, cyclophosphamide, PI3Kgamma, PI3Kdelta, tasquinimod; Immunosuppression: TGFβ, IL-10; Priming and Presenting: BATF3, XCR1/XCL1, STING, INFalpha; Apoptotic Recycling: IL-6, surviving, IAP, mTOR, MCL1, PI3K; T-Cell Trafficking: CXCL9/10/11, CXCL1/13, CCL2/5, anti-LIGHT, anti-CCR5; Oncogenic Activation: WNT-beta-cat, MEK, PPARgamma, FGFR3, TKIs, MET; Epigenetic Reprogramming: HDAC, HMA, BET; Angiogenesis immune modulation: VEGF (alpha, beta, gamma); Hypoxia: HIF1alpha, adenosine, anitADORA2A, anti-CD73, and anti-CD39.

In certain embodiments, the compositions disclosed herein may be administered in conjunction with a histone deacetylase (HDAC) inhibitor. HDAC inhibitors include hydroxamates, cyclic peptides, aliphatic acids and benzamides. Illustrative HDAC inhibitors contemplated for use herein include, but are not limited to, Suberoylanilide hydroxamic acid (SAHA/Vorinostat/Zolinza), Trichostatin A (TSA), PXD-101, Depsipeptide (FK228/romidepsin/ISTODAX®), panobinostat (LBH589), MS-275, Mocetinostat (MGCD0103), ACY-738, TMP195, Tucidinostat, valproic acid, sodium phenylbutyrate, 5-aza-2'-deoxycytidine (decitabine). See e.g., Kim and Bae, Am J Transl Res 2011; 3(2):166-179; Odunsi et al., Cancer Immunol Res. 2014 Jan. 1; 2(1): 37-49. Other HDAC inhibitors include Vorinostat (SAHA, MK0683), Entinostat (MS-275), Panobinostat (LBH589), Trichostatin A (TSA), Mocetinostat (MGCD0103), ACY-738, Tucidinostat (Chidamide), TMP195, Citarinostat (ACY-241), Belinostat (PXD101), Romidepsin (FK228, Depsipeptide), MC1568, Tubastatin A HCl, Givinostat (ITF2357), Dacinostat (LAQ824), CUDC-101, Quisinostat (JNJ-26481585) 2HCl, Pracinostat (SB939), PCI-34051, Droxinostat, Abexinostat (PCI-24781), RGFP966, AR-42, Ricolinostat (ACY-1215), Valproic acid sodium salt (Sodium valproate), Tacedinaline (C1994), CUDC-907, Sodium butyrate, Curcumin, M344, Tubacin, RG2833 (RGFP109), Resminostat, Divalproex Sodium, Scriptaid, and Tubastatin A.

In certain embodiments, the vaccine composition is administered in combination with chloroquine, a lysosomotropic agent that prevents endosomal acidification and which inhibits autophagy induced by tumor cells to survive accelerated cell growth and nutrient deprivation. More generally, the compositions comprising heterozygous viral vectors as described herein may be administered in combination with active agents that act as autophagy inhibitors, radiosensitizers or chemosensitizers, such as chloroquine, misonidazole, metronidazole, and hypoxic cytotoxins, such as tirapazamine. In this regard, such combinations of a heterozygous viral vector with chloroquine or other radio or chemo sensitizer, or autophagy inhibitor, can be used in further combination with other cancer active agents or with radiation therapy or surgery.

In other embodiments, the vaccine composition is administered in combination with one or more small molecule drugs that are known to result in killing of tumor cells with concomitant activation of immune responses, termed “immunogenic cell death”, such as cyclophosphamide, doxorubicin, oxaliplatin and mitoxantrone. Furthermore, combinations with drugs known to enhance the immunogenicity of tumor cells such as patupilone (epothilone B), epidermal-growth factor receptor (EGFR)-targeting monoclonal antibody 7A7.27, histone deacetylase inhibitors (e.g., vorinostat, romidepsin, panobinostat, belinostat, and entinostat), the n3-polyunsaturated fatty acid docosahexaenoic acid, furthermore proteasome inhibitors (e.g., bortezomib), shikonin (the major constituent of the root of Lithospermum erythrorhizon) and oncolytic viruses, such as TVec (talimogene laherparepvec). In some embodiments, the compositions comprising heterozygous viral vectors as described herein may be administered in combination with epigenetic therapies, such as DNA methyltransferase inhibitors (e.g., decitabine, 5-aza-2'-deoxycytidine) which may be administered locally or systemically.

In other embodiments, the vaccine composition is administered in combination with one or more antibodies that increase ADCC uptake of tumor by DCs. Thus, embodiments of the present disclosure contemplate combining cancer vaccine compositions with any molecule that induces or enhances the ingestion of a tumor cell or its fragments by an antigen presenting cell and subsequent presentation of tumor antigens to the immune system. These molecules include agents that induce receptor binding (e.g., Fc or mannose receptors) and transport into the antigen presenting cell such as antibodies, antibody-like molecules, multispecific multivalent molecules and polymers. Such molecules may either be administered intratumorally with the composition comprising heterozygous viral vector or administered by a different route. For example, a composition comprising heterozygous viral vector as described herein may be administered intratumorally in conjunction with intratumoral injection of rituximab, cetuximab, trastuzumab, Campath, panitumumab, ofatumumab, brentuximab, pertuzumab, Ado-trastuzumab emtansine, Obinutuzumab, anti-HER1, -HER2, or -HER3 antibodies (e.g., MEHD7945A; MM-111; MM-151; MM-121; AMG888), anti-EGFR antibodies (e.g., nimotuzumab, ABT-806), or other like antibodies. Any multivalent scaffold that is capable of engaging Fc receptors and other receptors that can induce internalization may be used in the combination therapies described herein (e.g., peptides and/or proteins capable of binding targets that are linked to Fc fragments or polymers capable of engaging receptors).

In certain embodiments, the vaccine composition may be further combined with an inhibitor of ALK, PARP, VEGFRs, EGFR, FGFR1-3, HIF1α, PDGFR1-2, c-Met, c-KIT, Her2, Her3, AR, PR, RET, EPHB4, STAT3, Ras, HDAC1-11, mTOR, and/or CXCR4.

In certain embodiments, a cancer vaccine composition may be further combined with an antibody that promotes a co-stimulatory signal (e.g., by blocking inhibitory pathways), such as anti-CTLA-4, or that activates co-stimulatory pathways such as an anti-CD40, anti-CD28, anti-ICOS, anti-OX40, anti-CD27, anti-ICOS, anti-CD127, anti-GITR, IL-2, IL-7, IL-15, IL-21, GM-CSF, IL-12, and INFα.

Checkpoint Inhibitors

In certain embodiments, a checkpoint inhibitor molecule is administered in combination with the vaccine compositions described herein. Immune checkpoints refer to a variety of inhibitory pathways of the immune system that are crucial for maintaining self-tolerance and for modulating the duration and amplitude of an immune responses. Tumors use certain immune-checkpoint pathways as a major mechanism of immune resistance, particularly against T cells that are specific for tumor antigens. (See Pardoll, 2012 Nature 12:252; Chen and Mellman Immunity 39:1 (2013)). Immune checkpoint inhibitors include any agent that blocks or inhibits in a statistically significant manner, the inhibitory pathways of the immune system. Such inhibitors may include antibodies, or antigen binding fragments thereof, that bind to and block or inhibit immune checkpoint receptors or antibodies that bind to and block or inhibit immune checkpoint receptor ligands. Illustrative immune checkpoint molecules that may be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, BTLA, SIGLEC9, 2B4 (belongs to the CD2 family of molecules and is expressed on all NK, γδ, and memory CD8+(αβ) T cells), CD160 (also referred to as BY55), and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, BTLA, SIGLEC9, 2B4, CD160, and CGEN-15049.

Illustrative immune checkpoint inhibitors include anti-PD1, anti-PDL1, and anti-PDL2 agents such as A167, AB122, ABBV-181, ADG-104, AK-103, AK-105, AK-106, AGEN2034, AM0001, AMG-404, ANB-030, APL-502, APL-501, zimberelimab, atezolizumab, AVA-040, AVA-040-100, avelumab, balstilimab, BAT-1306, BCD-135, BGB-A333, BI-754091, budigalimab, camrelizumab, CB-201, CBT-502, CCX-4503, cemiplimab, cosibelimab, cetrelimab, CS-1001, CS-1003, CX-072, CX-188, dostarlimab, durvalumab, envafolimab, sugemalimab, HBM9167, F-520, FAZ-053, genolimzumab, GLS-010, GS-4224, hAB21, HLX-10, HLX-20, HS-636, HX-008, IMC-001, IMM-25, INCB-86550, JS-003, JTX-4014, JYO-34, KL-A167, LBL-006, lodapolimab, LP-002, LVGN-3616, LYN-00102, LMZ-009, MAX-10181, MEDI-0680, MGA-012 (Retifanlimab), MSB-2311, nivolumab, pembrolizumab, prolgolimab, prololimab, sansalimab, SCT-110A, SG-001, SHR-1316, sintilimab, spartalizumab, RG6084, RG6139, RG6279, CA-170, CA-327, STI-3031, toleracyte, toca 521, Sym-021, TG-1501, tislelizumab, toripalimab, TT-01, ZKAB-001, and the anti-PD-1 antibodies capable of blocking interaction with its ligands PD-L1 and PD-L2 described in WO/2017/124050.

Illustrative multi-specific immune checkpoint inhibitors, where at least one target is anti-PD1, anti-PDL1, or anti-PDL2, include ABP-160 (CD47×PD-L1), AK-104 (PD-1×CTLA-4), AK-112 (PD-1×VEGF), ALPN-202 (PD-L1×CTLA-4×CD28), AP-201 (PD-L1×OX-40), AP-505 (PD-L1×VEGF), AVA-0017 (PD-L1×LAG-3), AVA-0021 (PD-L1×LAG-3), AUPM-170 (PD-L1×VISTA), BCD-217 (PD-1×CTLA-4), BH-2950 (PD-1×HER2), BH-2996h (PD-1×PD-L1), BH-29xx (PD-L1×CD47), bintrafusp alfa (PD-L1×TGFβ), CB-213 (PD-1×LAG-3), CDX-527 (CD27×PD-L1), CS-4100 (PD-1×PD-L1), DB-001 (PD-L1×HER2), DB-002 (PD-L1×CTLA-4), DSP-105 (PD-1×4-1BBL), DSP-106, (PD-1×CD70), FS-118 (LAG-3×PD-L1), FS-222 (CD137/4-1BB×PD-L1), GEN-1046 (PD-L1×CD137/4-1BB), IBI-318 (PD-1×PD-L1), IBI-322 (PD-L1×CD-47), KD-033 (PD-L1×IL-15), KN-046 (PD-L1×CTLA-4), KY-1043 (PD-L1×IL-2), LY-3434172 (PD-1×PD-L1), MCLA-145 (PD-L1×CD137), MEDI-5752 (PD-1×CTLA-4), MGD-013 (PD-1×LAG-3), MGD-019 (PD-1×CTLA-4), ND-021 (PD-L1×4-1BB×HSA), OSE-279 (PD-1×PD-L1), PRS-332 (PD-1×HER2), PRS-344 (PD-L1×CD137), PSB-205 (PD-1×CTLA-4), R-7015 (PD-L1×TGFβ), RO-7121661 (PD-1×

TIM-3), RO-7247669 (PD-1×LAG-3), SHR-1701 (PD-L1×TGFβ2), SL-279252 (PD-1×OX40L), TSR-075 (PD-1×LAG-3), XmAb-20717 (CTLA-4×PD-1), XmAb-23104 (PD-1×ICOS), and Y-111 (PD-L1×CD-3).

Additional illustrative immune checkpoint inhibitors include anti-CTLA4 agents such as: ADG-116, AGEN-2041, BA-3071, BCD-145, BJ-003, BMS-986218, BMS-986249, BPI-002, CBT-509, CG-0161, Olipass-1, HBM-4003, HLX-09, IBI-310, ipilimumab, JS-007, KN-044, MK-1308, ONC-392, REGN-4659, RP-2, tremelimumab, and zalifrelimab. Additional illustrative multi-specific immune checkpoint inhibitors, where at least one target is anti-CTLA4, include: AK-104 (PD-1×CTLA-4), ALPN-202 (PD-L1×CTLA-4×CD28), ATOR-1015 (CTLA-4×OX40), ATOR-1144 (CTLA-4×GITR), BCD-217 (PD-1×CTLA-4), DB-002 (PD-L1×CTLA-4), FPT-155 (CD28×CTLA-4), KN-046 (PD-L1×CTLA-4), MEDI-5752 (PD-1×CTLA-4), MGD-019 (PD-1×CTLA-4), PSB-205 (PD-1×CTLA-4), XmAb-20717 (CTLA-4×PD-1), and XmAb-22841 (CTLA-4×LAG-3). Additional illustrative immune checkpoint inhibitors include anti-LAG3 agents such as BI-754111, BJ-007, eftilagimod alfa, GSK-2831781, HLX-26, IBI-110, IMP-701, IMP-761, INCAGN-2385, LBL-007, MK-4280, REGN-3767, relatlimab, Sym-022, TJ-A3, and TSR-033. Additional illustrative multi-specific immune checkpoint inhibitors, where at least one target is anti-LAG3, include: CB-213 (PD-1×LAG-3), FS-118 (LAG-3×PD-L1), MGD-013 (PD-1×LAG-3), AVA-0017 (PD-L1×LAG-3), AVA-0021 (PD-L1×LAG-3), RO-7247669 (PD-1×LAG-3), TSR-075 (PD-1×LAG-3), and XmAb-22841 (CTLA-4×LAG-3). Additional illustrative immune checkpoint inhibitors include anti-TIGIT agents such as AB-154, ASP8374, BGB-A1217, BMS-986207, CASC-674, COM-902, EOS-884448, HLX-53, IBI-939, JS-006, MK-7684, NB-6253, RXI-804, tiragolumab, and YH-29143. Additional illustrative multi-specific immune checkpoint inhibitors, where at least one target is anti-TIGIT are contemplated. Additional illustrative immune checkpoint inhibitors include anti-TIM3 agents such as: BGB-A425, BMS-986258, ES-001, HLX-52, INCAGN-2390, LBL-003, LY-3321367, MBG-453, SHR-1702, Sym-023, and TSR-022. Additional illustrative multi-specific immune checkpoint inhibitors, where at least one target is anti-TIM3, include: AUPM-327 (PD-L1×TIM-3), and RO-7121661 (PD-1×TIM-3). Additional illustrative immune checkpoint inhibitors include anti-VISTA agents such as: HMBD-002, and PMC-309. Additional illustrative multi-specific immune checkpoint inhibitors, where at least one target is anti-VISTA, include CA-170 (PD-L1×VISTA). Additional illustrative immune checkpoint inhibitors include anti-BTLA agents such as: JS-004. Additional illustrative multi-specific immune checkpoint inhibitors, where at least one target is anti-BTLA are contemplated. Illustrative stimulatory immune checkpoints include anti-OX40 agents such as ABBV-368, GSK-3174998, HLX-51, IBI-101, INBRX-106, INCAGN-1949, INV-531, JNJ-6892, and KHK-4083. Additional illustrative multi-specific stimulatory immune checkpoints, where at least one target is anti-OX40, include AP-201 (PD-L1×OX-40), APVO-603 (CD138/4-1BB×OX-40), ATOR-1015 (CTLA-4×OX-40), and FS-120 (OX40×CD137/4-1BB). Additional illustrative stimulatory immune checkpoints include anti-GITR agents such as BMS-986256, CK-302, GWN-323, INCAGN-1876, MK-4166, PTZ-522, and TRX-518. Additional illustrative multi-specific stimulatory immune checkpoints, where at least one target is anti-GITR, include ATOR-1144 (CTLA-4×GITR). Additional illustrative stimulatory immune checkpoints include anti-CD137/4-1BB agents such a: ADG-106, AGEN-2373, AP-116, ATOR-1017, BCY-3814, CTX-471, EU-101, LB-001, LVGN-6051, RTX-4-1BBL, SCB-333, urelumab, utomilumab, and WTiNT. Additional illustrative multi-specific stimulatory immune checkpoints, where at least one target is anti-CD137/4-1BB, include ALG.APV-527 (CD137/4-1BB×5T4), APVO-603 (CD137/4-1BB×OX40), BT-7480 (Nectin-4×CD137/4-1BB), CB-307 (CD137/4-1BB×PSMA), CUE-201 (CD80×CD137/4-1BB), DSP-105 (PD-1×CD137/4-1BB), FS-120 (OX40×CD137/4-1BB), FS-222 (PD-L1×CD137/4-1BB), GEN-1042 (CD40×CD137/4-1BB), GEN-1046 (PD-L1×CD137/4-1BB), INBRX-105 (PD-L1×CD137/4-1BB), MCLA-145 (PD-L1×CD137/4-1BB), MP-0310 (CD137/4-1BB×FAP), ND-021 (PD-L1×CD137/4-1BB×HSA), PRS-343 (CD137/4-1BB×HER2), PRS-342 (CD137/4-1BB×GPC3), PRS-344 (CD137/4-1BB×PD-L1), RG-7827 (FAP×4-1BBL), and RO-7227166 (CD-19×4-1BBL).

Additional illustrative stimulatory immune checkpoints include anti-ICOS agents such as BMS-986226, GSK-3359609, KY-1044, and vopratelimab. Additional illustrative multi-specific stimulatory immune checkpoints, where at least one target is anti-ICOS, include XmAb-23104 (PD-1×ICOS). Additional illustrative stimulatory immune checkpoints include anti-CD127 agents such as MD-707 and OSE-703. Additional illustrative multi-specific stimulatory immune checkpoints, where at least one target is anti-CD127 are contemplated. Additional illustrative stimulatory immune checkpoints include anti-CD40 agents such as ABBV-428, ABBV-927, APG-1233, APX-005M, BI-655064, bleselumab, CD-40GEX, CDX-1140, LVGN-7408, MEDI-5083, mitazalimab, and selicrelumab. Additional Illustrative multi-specific stimulatory immune checkpoints, where at least one target is anti-CD40, include GEN-1042 (CD40×CD137/4-1BB). Additional illustrative stimulatory immune checkpoints include anti-CD28 agents such as FR-104 and theralizumab. Additional illustrative multi-specific stimulatory immune checkpoints, where at least one target is anti-CD28, include ALPN-101 (CD28×ICOS), ALPN-202 (PD-L1×CD28), CUE-201 (CD80×CD137/4-1BB), FPT-155 (CD28×CTLA-4), and REGN-5678 (PSMA×CD28). Additional illustrative stimulatory immune checkpoints include anti-CD27 agents such as: HLX-59 and varlilumab. Additional illustrative multi-specific stimulatory immune checkpoints, where at least one target is anti-CD27, include DSP-160 (PD-L1×CD27/CD70) and CDX-256 (PD-L1×CD27). Additional illustrative stimulatory immune checkpoints include anti-IL-2 agents such as ALKS-4230, BNT-151, CUE-103, NL-201, and THOR-707. Additional illustrative multi-specific stimulatory immune checkpoints, where at least one target is anti-IL-2, include CUE-102 (IL-2×WT1). Additional illustrative stimulatory immune checkpoints include anti-IL-7 agents such as BNT-152. Additional illustrative multi-specific stimulatory immune checkpoints, where at least one target is anti-IL-7 are contemplated. Additional illustrative stimulatory immune checkpoints include anti-IL-12 agents such as AK-101, M-9241, and ustekinumab. Additional illustrative multi-specific stimulatory immune checkpoints, where at least one target is antiIL-12 are contemplated.

As described herein, the present disclosure provides methods of administering vaccine compositions, cyclophosphamide, checkpoint inhibitors, and/or other therapeutic agents such as Treg inhibitors. Treg inhibitors are known in the art and include, for example, bempegaldesleukin, fludarabine, gemcitabine, mitoxantrone, Cyclosporine A, tacrolimus, paclitaxel, imatinib, dasatinib, bevacizumab, idelalisib, anti-CD25, anti-folate receptor 4, anti-CTLA4, anti-GITR, anti-OX40, anti-CCR4, anti-CCR5, anti-CCR8, or TLR8 ligands.

Dosing

A "dose" or "unit dose" as used herein refers to one or more vaccine compositions that comprise therapeutically effective amounts of one more cell lines. A dose can be a single vaccine composition, two separate vaccine compositions, or two separate vaccine compositions plus one or more compositions comprising one or more therapeutic agents described herein. When in separate compositions, the two or more compositions of the "dose" are meant to be administered "concurrently". In some embodiments, the two or more compositions are administered at different sites on the subject (e.g., arm, thigh, or back). As used herein, "concurrent" administration of two compositions or therapeutic agents indicates that within about 30 minutes of administration of a first composition or therapeutic agent, the second composition or therapeutic agent is administered. In cases where more than two compositions and/or therapeutic agents are administered concurrently, each composition or agent is administered within 30 minutes, wherein timing of such administration begins with the administration of the first composition or agent and ends with the beginning of administration of the last composition or agent. In some cases, concurrent administration can be completed (i.e., administration of the last composition or agent begins) within about 30 minutes, or within 15 minutes, or within 10 minutes, or within 5 minutes of start of administration of first composition or agent. Administration of a second (or multiple) therapeutic agents or compositions "prior to" or "subsequent to" administration of a first composition means that the administration of the first composition and another therapeutic agent is separated by at least 30 minutes, e.g., at least 1 hour, at least 2 hours, at least 4 hours, at least 6 hours, at least 8 hours, at least 10 hours, at least 12 hours, at least 18 hours, at least 24 hours, or at least 48 hours.

The amount (e.g., number) of cells from the various individual cell lines in the vaccine compositions can be equal (as defined herein), approximately (as defined herein) equal, or different. In various embodiments, each cell line of a vaccine composition is present in an approximately equal amount. In other embodiments, 2 or 3 cell lines of one vaccine composition are present in approximately equal amounts and 2 or 3 different cell lines of a second composition are present in approximately equal amounts.

In some embodiments, the number of cells from each cell line (in the case where multiple cell lines are administered), is approximately $5.0\times10^5$, $1.0\times10^6$, $2.0\times10^6$, $3.0\times10^6$, $4.0\times10^6$, $5.0\times10^6$, $6.0\times10^6$, $7.0\times10^6$, $8\times10^6$, $9.0\times10^6$, $1.0\times10^7$, $2.0\times10^7$, $3.0\times10^7$, $4.0\times10^7$, $5.0\times10^7$, $6.0\times10^7$, $8.0\times10^7$, $9.0\times10^7$, $1.0\times10^8$, $2.0\times10^8$, $3.0\times10^8$, $4.0\times10^8$ or $5.0\times10^8$ cells. In one embodiment, approximately 10 million (e.g., $1.0\times10^7$) cells from one cell line are contemplated. In another embodiment, where 6 separate cell lines are administered, approximately 10 million cells from each cell line, or 60 million (e.g., $6.0\times10^7$) total cells are contemplated.

The total number of cells administered in a vaccine composition, e.g., per administration site, can range from $1.0\times10^6$ to $3.0\times10^8$. For example, in some embodiments, $2.0\times10^6$, $3.0\times10^6$, $4.0\times10^6$, $5.0\times10^6$, $6.0\times10^6$, $7.0\times10^6$, $8\times10^6$, $9.0\times10^6$, $1.0\times10^7$, $2.0\times10^7$, $3.0\times10^7$, $4.0\times10^7$, $5.0\times10^7$, $6.0\times10^7$, $8.0\times10^7$, $9.0\times10^7$, $1.0\times10^8$, $2.0\times10^8$, or $3.0\times10^8$ cells are administered.

As described herein, the number of cell lines contained with each administration of a cocktail or vaccine composition can range from 1 to 10 cell lines. In some embodiments, the number of cells from each cell line are not equal, and different ratios of cell lines are included in the cocktail or vaccine composition. For example, if one cocktail contains $5.0\times10^7$ total cells from 3 different cell lines, there could be $3.33\times10^7$ cells of one cell line and $8.33\times10^6$ of the remaining 2 cell lines.

The vaccine compositions and compositions comprising additional therapeutic agents (e.g., chemotherapeutic agents, checkpoint inhibitors, and the like) may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial and sublingual injection or infusion techniques. Also envisioned are embodiments where the vaccine compositions and compositions comprising additional therapeutic agents (e.g., chemotherapeutic agents, checkpoint inhibitors, and the like) are administered intranodally or intratumorally.

In some embodiments, the vaccine compositions are administered intradermally. In related embodiments, the intradermal injection involves injecting the cocktail or vaccine composition at an angle of administration of 5 to 15 degrees.

The injections (e.g., intradermal or subcutaneous injections), can be provided at a single site (e.g. arm, thigh or back), or at multiple sites (e.g. arms and thighs). In some embodiments, the vaccine composition is administered concurrently at two sites, where each site receives a vaccine composition comprising a different composition (e.g., cocktail). For example, in some embodiments, the subject receives a composition comprising three cell lines in the arm, and three different, or partially overlapping cell lines in the thigh. In some embodiments, the subject receives a composition comprising one or more cell lines concurrently in each arm and in each thigh.

In some embodiments, the subject receives multiple doses of the cocktail or vaccine composition and the doses are administered at different sites on the subject to avoid potential antigen competition at certain (e.g., draining) lymph nodes. In some embodiments, the multiple doses are administered by alternating administration sites (e.g. left arm and right arm, or left thigh and right thigh) on the subject between doses. In some embodiments, the multiple doses are administered as follows: a first dose is administered in one arm, and second dose is administered in the other arm; subsequent doses, if administered, continue to alternate in this manner. In some embodiments, the multiple doses are administered as follows: a first dose is administered in one thigh, and second dose is administered in the other thigh; subsequent doses, if administered, continue to alternate in this manner. In some embodiments, the multiple doses are administered as follows: a first dose is administered in one thigh, and second dose is administered in one arm; subsequent doses if administered can alternate in any combination that is safe and efficacious for the subject. In some embodiments, the multiple doses are administered as follows: a first dose is administered in one thigh and one arm, and second dose is administered in the other arm and the other thigh; subsequent doses if administered can alternate in any combination that is safe and efficacious for the subject.

In some embodiments, the subject receives, via intradermal injection, a vaccine composition comprising a total of six cell lines (e.g., NCI-H460, NCI-H520, DMS 53, LK-2, NCI-H23, and A549 or other 6-cell line combinations described herein) in one, two or more separate cocktails, each cocktail comprising one or a mixture two or more of the 6-cell lines. In some embodiments, the subject receives, via intradermal injection, a vaccine composition comprising a mixture of three cell lines (e.g., three of NCI-H460, NCI-H520, DMS 53, LK-2, NCI-H23, and A549 or three cell lines from other 6-cell line combinations described herein). In some embodiments, the subject receives, via intradermal injection to the arm (e.g., upper arm), a vaccine composition comprising a mixture of three cell lines, comprising NCI-H460, NCI-H520, and A549; and the subject concurrently receives, via intradermal injection to the leg (e.g., thigh), a vaccine composition comprising a mixture of three cell lines, comprising DMS 53, LK-2, and NCI-H23.

Where an additional therapeutic agent is administered, the doses or multiple doses may be administered via the same or different route as the vaccine composition(s). By way of example, a composition comprising a checkpoint inhibitor is administered in some embodiments via intravenous injection, and the vaccine composition is administered via intradermal injection. In some embodiments, cyclophosphamide is administered orally, and the vaccine composition is administered intradermally.

Regimens

The vaccine compositions according to the disclosure may be administered at various administration sites on a subject, at various times, and in various amounts. The efficacy of a tumor cell vaccine may be impacted if the subject's immune system is in a state that is permissible to the activation of antitumor immune responses. The efficacy may also thus impacted if the subject is undergoing or has received radiation therapy, chemotherapy or other prior treatments. In some embodiments, this requires that the immunosuppressive elements of the immune system are inhibited while the activation and effector elements are fully functional. In addition to the immunosuppressive factors described herein, other elements that suppress antitumor immunity include, but are not limited to, T regulatory cells (Tregs) and checkpoint molecules such as CTLA-4, PD-1 and PD-L1.

In some embodiments, timing of the administration of the vaccine relative to previous chemotherapy and radiation therapy cycles is set in order to maximize the immune permissive state of the subject's immune system prior to vaccine administration. The present disclosure provides methods for conditioning the immune system with one or low dose administrations of a chemotherapeutic agent such as cyclophosphamide prior to vaccination to increase efficacy of whole cell tumor vaccines. In some embodiments, metronomic chemotherapy (e.g., frequent, low dose administration of chemotherapy drugs with no prolonged drug-free break) is used to condition the immune system. In some embodiments, metronomic chemotherapy allows for a low level of the drug to persist in the blood, without the complications of toxicity and side effects often seen at higher doses. By way of example, administering cyclophosphamide to condition the immune system includes, in some embodiments, administration of the drug at a time before the receipt of a vaccine dose (e.g., 15 days to 1 hour prior to administration of a vaccine composition) in order to maintain the ratio of effector T cells to regulatory T cells at a level less than 1.

In some embodiments, a chemotherapy regimen (e.g., myeloablative chemotherapy, cyclophosphamide, and/or fludarabine regimen) may be administered before some, or all of the administrations of the vaccine composition(s) provided herein. Cyclophosphamide (CYTOXAN™, NEOSAR™) is a well-known cancer medication that interferes with the growth and spread of cancer cells in the body. Cyclophosphamide may be administered as a pill (oral), liquid, or via intravenous injection. Numerous studies have shown that cyclophosphamide can enhance the efficacy of vaccines. (See, e.g., Machiels et al., Cancer Res., 61:3689, 2001; Greten, T. F., et al., J. Immunother., 2010, 33:211; Ghiringhelli et al., Cancer Immunol. Immunother., 56:641, 2007; Ge et al., Cancer Immunol. Immunother., 61:353, 2011; Laheru et al., Clin. Cancer Res., 14:1455, 2008; and Borch et al., OncoImmunol, e1207842, 2016). "Low dose" cyclophosphamide as described herein, in some embodiments, is effective in depleting Tregs, attenuating Treg activity, and enhancing effector T cell functions. In some embodiments, intravenous low dose administration of cyclophosphamide includes 40-50 mg/kg in divided doses over 2-5 days. Other low dose regimens include 1-15 mg/kg every 7-10 days or 3-5 mg/kg twice weekly. Low dose oral administration, in accordance with some embodiments of the present disclosure, includes 1-5 mg/kg per day for both initial and maintenance dosing. Dosage forms for the oral tablet are 25 mg and 50 mg. In some embodiments, cyclophosphamide is administered as an oral 50 mg tablet for the 7 days leading up to the first and optionally each subsequent doses of the vaccine compositions described herein.

In some embodiments, cyclophosphamide is administered as an oral 50 mg tablet on each of the 7 days leading up to the first, and optionally on each of the 7 days preceding each subsequent dose(s) of the vaccine compositions. In another embodiment, the patient takes or receives an oral dose of 25 mg of cyclophosphamide twice daily, with one dose being the morning upon rising and the second dose being at night before bed, 7 days prior to each administration of a cancer vaccine cocktail or unit dose. In certain embodiments, the vaccine compositions are administered intradermally multiple times over a period of years. In some embodiments, a checkpoint inhibitor is administered every two weeks or every three weeks following administration of the vaccine composition(s).

In another embodiment, the patient receives a single intravenous dose of cyclophosphamide of 200, 250, 300, 500 or 600 mg/m$^2$ at least one day prior to the administration of a cancer vaccine cocktail or unit dose of the vaccine composition. In another embodiment, the patient receives an intravenous dose of cyclophosphamide of 200, 250, 300, 500 or 600 mg/m$^2$ at least one day prior to the administration vaccine dose number 4, 8, 12 of a cancer vaccine cocktail or unit dose. In another embodiment, the patient receives a single dose of cyclophosphamide at 1000 mg/kg as an intravenous injection at least one hour prior to the administration of a cancer vaccine cocktail or unit dose. In some embodiments, an oral high dose of 200 mg/kg or an IV high dose of 500-1000 mg/m$^2$ of cyclophosphamide is administered.

The administration of cyclophosphamide can be via any of the following: oral (e.g., as a capsule, powder for solution, or a tablet); intravenous (e.g., administered through a vein (IV) by injection or infusion); intramuscular (e.g., via an injection into a muscle (IM)); intraperitoneal (e.g., via an injection into the abdominal lining (IP)); and intrapleural (e.g., via an injection into the lining of the lung).

In some embodiments, immunotherapy checkpoint inhibitors (e.g., anti-CTLA4, anti-PD-1 antibodies such as pembrolizumab, and nivolumab, anti-PDL1 such as durvalumab) may be administered before, concurrently, or after the vaccine composition. In certain embodiments, pembrolizumab is administered 2 mg/kg every 3 weeks as an intravenous infusion over 60 minutes. In some embodiments, pembrolizumab is administered 200 mg every 3 weeks as an intravenous infusion over 30 minutes. In some embodiments pembrolizumab is administered 400 mg every 6 weeks as an intravenous infusion over 30 minutes. In some embodiments, durvalumab is administered 10 mg/kg every two weeks. In some embodiments, nivolumab is administered 240 mg every 2 weeks (or 480 mg every 4 weeks). In some embodiments, nivolumab is administered 1 mg/kg followed by ipilimumab on the same day, every 3 weeks for 4 doses, then 240 mg every 2 weeks (or 480 mg every 4 weeks). In some embodiments, nivolumab is administered 3 mg/kg followed by ipilimumab 1 mg/kg on the same day every 3 weeks for 4 doses, then 240 mg every 2 weeks (or 480 mg every 4 weeks). In some embodiments, nivolumab is administered or 3 mg/kg every 2 weeks.

In some embodiments, durvalumab or pembrolizumab is administered every 2, 3, 4, 5, 6, 7 or 8 weeks for up to 8 administrations and then reduced to every 6, 7, 8, 9, 10, 11 or 12 weeks as appropriate.

In other embodiments, the present disclosure provides that PD-1 and PD-L1 inhibitors are administered with a fixed dosing regimen (i.e., not weight-based). In non-limiting examples, a PD-1 inhibitor is administered weekly or at weeks 2, 3, 4, 6 and 8 in an amount between 100-1200 mg. In non-limiting examples, a PD-L1 inhibitor is administered weekly or at weeks 2, 3, 4, 6 and 8 in an mount between 250-2000 mg.

In some embodiments, a vaccine composition or compositions as described herein is administered concurrently or in combination with a PD-1 inhibitor dosed either Q1W, Q2W, Q3W, Q4W, Q6W, or Q8W, between 100 mg and 1500 mg fixed or 0.5 mg/kg and 15 mg/kg based on weight. In another embodiment, a vaccine composition or compositions as described herein is administered concurrently in combination with PD-L1 inhibitor dosed either Q2W, Q3W, or Q4W between 250 mg and 2000 mg fixed or 2 mg/kg and 30 mg/kg based on weight. In other embodiments, the aforementioned regimen is administered but the compositions are administered in short succession or series such that the patient receives the vaccine composition or compositions and the checkpoint inhibitor during the same visit.

The plant *Cannabis sativa* L. has been used as an herbal remedy for centuries and is an important source of phytocannabinoids. The endocannabinoid system (ECS) consists of receptors, endogenous ligands (endocannabinoids) and metabolizing enzymes, and plays a role in different physiological and pathological processes. Phytocannabinoids and synthetic cannabinoids can interact with the components of ECS or other cellular pathways and thus may affect the development or progression of diseases, including cancer. In cancer patients, cannabinoids can be used as a part of palliative care to alleviate pain, relieve nausea and stimulate appetite. In addition, numerous cell culture and animal studies have demonstrated antitumor effects of cannabinoids in various cancer types. (For a review, see Daris, B., et al., Bosn. J. Basic. Med. Sci., 19(1):14-23 (2019).) Phytocannabinoids are a group of C21 terpenophenolic compounds predominately produced by the plants from the genus *Cannabis*. There are several different cannabinoids and related breakdown products. Among these are tetrahydrocannabinol (THC), cannabidiol (CBD), cannabinol (CBN), cannabichromene (CBC), A8-THC, cannabidiolic acid (CBDA), cannabidivarin (CBDV), and cannabigerol (CBG).

In certain embodiments of the present disclosure, use of all phytocannabinoids is stopped prior to or concurrent with the administration of a Treg cell inhibitor such as cyclophosphamide, and/or is otherwise stopped prior to or concurrent with the administration of a vaccine composition according to the present disclosure. In some embodiments, where multiple administrations of cyclophosphamide or vaccine compositions occur, the cessation optionally occurs prior to or concurrent with each administration. In certain embodiments, use of phytocannabinoids is not resumed until a period of time after the administration of the vaccine composition(s). For example, abstaining from cannabinoid administration for at least 1, 2, 3, 4, 5, 6, 7, 8, 9 or 10 days prior to administration and at least 1, 2, 3, 4, 5, 6, 7, 8, 9, or 10 days after administration of cyclophosphamide or a vaccine dose is contemplated.

In some embodiments, patients will receive the first dose of the vaccine within 6-12 weeks after completion of chemotherapy. High dose chemotherapy used in cancer treatment ablates proliferating cells and depletes immune cell subsets. Upon completion of chemotherapy, the immune system will begin to reconstitute. The time span for T cells to recur is roughly 2-3 weeks. Because T cells are an immunological cell subset targeted for activation, in some embodiments, the cancer vaccine is administered within a window where there are sufficient T cells to prime, yet the subject remains lymphopenic. This environment, in which there are less cells occupying the niche will allow the primed T cells to rapidly divide, undergoing "homeostatic proliferation" in response to increased availability of cytokines (e.g., IL7 and IL15). Thus, by dosing the vaccine at this window, the potential efficacy of embodiments of the cancer vaccine platform as described herein is maximized to allow for the priming of antigen specific T cells and expansion of the vaccine associated T cell response.

Methods of Selecting Cell Lines and Preparing Vaccines

Cell Line Selection

For a given cancer or in instances where a patient is suffering from more than one cancer, a cell line or combination of cell lines is identified for inclusion in a vaccine composition based on several criteria. In some embodiments, selection of cell lines is performed stepwise as provided below. Not all cancer indications will require all of the selection steps and/or criteria.

Step 1. Cell lines for each indication are selected based on the availability of RNA-seq data such as for example in the Cancer Cell Line Encyclopedia (CCLE) database. RNA-seq data allows for the identification of candidate cell lines that have the potential to display the greatest breadth of antigens specific to a cancer indication of interest and informs on the potential expression of immunosuppressive factors by the cell lines. If the availability of RNA-seq data in the CCLE is limited, RNA-seq data may be sourced from the European Molecular Biology Laboratory-European Bioinformatics Institute (EMBL-EBI) database or other sources known in the art. In some embodiments, potential expression of a protein of interest (e.g., a TAA) based on RNA-seq data is considered "positive" when the RNA-seq value is >0.

Step 2. For all indications, cell lines derived from metastatic sites are prioritized to diversify antigenic breadth and to more effectively target later-stage disease in patients with metastases. Cell lines derived from primary tumors are included in some embodiments to further diversify breadth of the vaccine composition. The location of the metastases from which the cell line are derived is also considered in some embodiments. For example, in some embodiments, cell lines can be selected that are derived from lymph node, ascites, and liver metastatic sites instead of all three cell lines derived from liver metastatic sites.

Step 3. Cell lines are selected to cover a broad range of classifications of cancer types. For example, tubular adenocarcinoma is a commonly diagnosed classification of gastric cancer. Thus, numerous cell lines may be chosen matching this classification. For indications where primary tumor sites vary, cell lines can be selected to meet this diversity. For example, for small cell carcinoma of the head and neck (SCCHN), cell lines were chosen, in some embodiments, to cover tumors originating from the oral cavity, buccal mucosa, and tongue. These selection criteria enable targeting a heterogeneous population of patient tumor types. In some embodiments, cell lines are selected to encompass an ethnically diverse population to generate a cell line candidate pool derived from diverse histological and ethnical backgrounds.

Step 4. In some embodiments, cell lines are selected based on additional factors. For example, in metastatic colorectal cancer (mCRC), cell lines reported as both microsatellite instable high (MSI-H) and microsatellite stable (MSS) may be included. As another example, for indications that are viral driven, cell lines encoding viral genomes may be excluded for safety and/or manufacturing complexity concerns.

Step 5. In some embodiments, cell lines are selected to cover a varying degree of genetic complexity in driver mutations or indication-associated mutations. Heterogeneity of cell line mutations can expand the antigen repertoire to target a larger population within patients with one or more tumor types. By way of example, breast cancer cell lines can be diversified on deletion status of Her2, progesterone receptor, and estrogen receptor such that the final unit dose includes triple negative, double negative, single negative, and wild type combinations. Each cancer type has a complex genomic landscape and, as a result, cell lines are selected for similar gene mutations for specific indications. For example, melanoma tumors most frequently harbor alterations in BRAF, CDKN2A, NRAS and TP53, therefore selected melanoma cell lines, in some embodiments, contain genetic alterations in one or more of these genes.

Step 6. In some embodiments, cell lines are further narrowed based on the TAA, TSA, and/or cancer/testis antigen expression based on RNA-seq data. An antigen or collection of antigens associated with a particular tumor or tumors is identified using search approaches evident to persons skilled in the art (See, e.g., such as www.ncbi.nlm.nih.gov/pubmed/, and clinicaltrials.gov). In some embodiments, antigens can be included if associated with a positive clinical outcome or identified as highly-expressed by the specific tumor or tumor types while expressed at lower levels in normal tissues.

Step 7. After Steps 1 through 6 are completed, in some embodiments, the list of remaining cell line candidates are consolidated based on cell culture properties and considerations such as doubling time, adherence, size, and serum requirements. For example, cell lines with a doubling time of less than 80 hours or cell lines requiring media serum (FBS, FCS)<10% can be selected. In some embodiments, adherent or suspension cell lines that do not form aggregates can be selected to ensure proper cell count and viability.

Step 8. In some embodiments, cell lines are selected based on the expression of immunosuppressive factors (e.g., based on RNA-seq data sourced from CCLE or EMBL as described in Step 1).

In some embodiments, a biopsy of a patient's tumor and subsequent TAA expression profile of the biopsied sample will assist in the selection of cell lines. Embodiments of the present disclosure therefore provide a method of preparing a vaccine composition comprising the steps of determining the TAA expression profile of the subject's tumor; selecting cancer cell lines; modifying cancer cell lines; and irradiating cell lines prior to administration to prevent proliferation after administration to patients.

Preparing Vaccine Compositions

In certain embodiments, after expansion in manufacturing, all of the cells in a modified cell line are irradiated, suspended, and cryopreserved. In some embodiments, cells are irradiated 10,000 cGy. According to some embodiments, cells are irradiated at 7,000 to 15,000 cGy. According to some embodiments, cells are irradiated at 7,000 to 15,000 cGy.

In certain embodiments, each vial contains a volume of 120±10 μL ($1.2\times10^7$ cells). In some embodiments, the total volume injected per site is 300 μL or less. In some embodiments, the total volume injected per site is 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 μL. Where, for example, the total volume injected is 300 μL, the present disclosure provides, in some embodiments that 3×100 μL volumes, or 2×150 μL, are injected, for a total of 300 μL.

In some embodiments, the vials of the component cell lines are stored in the liquid nitrogen vapor phase until ready for injection. In some embodiments, each of the component cell lines are packaged in separate vials.

As described herein, prior to administration, in some embodiments the contents of two vials are removed by needle and syringe and are injected into a third vial for mixing. In some embodiments, this mixing is repeated for each cocktail. In other embodiments, the contents of six vials are divided into two groups—A and B, where the contents of three vials are combined or mixed, optionally into a new vial (A), and the contents of the remaining three vials are combined or mixed, optionally into a new vial (B).

In certain embodiments, the cells will be irradiated prior to cryopreservation to prevent proliferation after administration to patients. In some embodiments, cells are irradiated at 7,000 to 15,000 cGy in order to render the cells proliferation incompetent.

In some embodiments, cell lines are grown separately and in the same growth culture media. In some embodiments, cell lines are grown separately and in different cell growth culture media.

Xeno-Free Conversion of Whole Tumor Cell Vaccine Component Cell Lines

Analysis of antibody responses in subjects treated with a whole tumor cell vaccine has suggested a negative correlation between survival and the development of IgG antibody responses to the bovine α-Gal antigen. (See Xia et al., Cell Chem Biol 23(12):1515-1525 (2016)). This is significant because most whole tumor cell vaccines are comprised of tumor cell lines that have been expanded and cryopreserved in media containing fetal bovine serum (FBS), which contains the bovine α-Gal antigen.

In some embodiments, to prevent the immune response to foreign antigens that are present in FBS, the cell lines disclosed herein are adapted to xeno-free media composed of growth factors and supplements essential for cell growth that are from human source, prior to large scale cGMP manufacturing. As used herein, the terms "adapting" and "converting" or "conversion" are used interchangeably to refer to transferring/changing cells to a different media as will be appreciated by those of skill in the art. The xeno-free media formulation chosen can be, in some embodiments, the same across all cell lines or, in other embodiments, can be different for different cell lines. In some embodiments, the media composition will not contain any non-human materials and can include human source proteins as a replacement for FBS alone, or a combination of human source proteins and human source recombinant cytokines and growth factors (e.g., EGF). Additionally, the xeno-free media compositions can, in some embodiments, also contain additional supplements (e.g., amino acids, energy sources) that enhance the growth of the tumor cell lines. The xeno-free media formulation will be selected for its ability to maintain cell line morphology and doubling time no greater than twice the doubling time in FBS and the ability to maintain expression of transgenes comparable to that in FBS.

A number of procedures may be instituted to minimize the possibility of inducing IgG, IgA, IgE, IgM and IgD antibodies to bovine antigens. These include but are not limited to: cell lines adapted to growth in xeno-free media; cell lines grown in FBS and placed in xeno-free media for a period of time (e.g., at least three days) prior to harvest; cell lines grown in FBS and washed in xeno-free media prior to harvest and cryopreservation; cell lines cryopreserved in media containing Buminate (a USP-grade pharmaceutical human serum albumin) as a substitute for FBS; and/or cell lines cryopreserved in a medial formulation that is xeno-free, and animal-component free (e.g., CryoStor). In some embodiments, implementation of one or more of these procedures may reduce the risk of inducing anti-bovine antibodies by removing the bovine antigens from the vaccine compositions.

According to one embodiment, the vaccine compositions described herein do not comprise non-human materials. In some embodiments, the cell lines described herein are formulated in xeno-free media. Use of xeno-free media avoids the use of immunodominant xenogeneic antigens and potential zoonotic organisms, such as the BSE prion. By way of example, following gene modification, the cell lines are transitioned to xeno-free media and are expanded to generate seed banks. The seed banks are cryopreserved and stored in vapor-phase in a liquid nitrogen cryogenic freezer.

Exemplary xeno-free conversions are provided herein for a NSCLC and GBM vaccine preparations.

In Vitro Assays

The ability of allogeneic whole cell cancer vaccines such as those described herein, to elicit anti-tumor immune responses, and to demonstrate that modifications to the vaccine cell lines enhance vaccine-associated immune responses, can be modelled with in vitro assays. Without being bound by any theory, the genetic modifications made to the vaccine cell line components augment adaptive immune responses through enhancing dendritic cell (DC) function in the vaccine microenvironment. The potential effects of expression of TAAs, immunosuppressive factors, and/or immunostimulatory factors can be modelled in vitro, for example, using flow cytometry-based assays and the IFNγ ELISpot assay.

In some embodiments, to model the effects of modifications to the vaccine cell line components in vitro, DCs are derived from monocytes isolated from healthy donor peripheral blood mononuclear cells (PBMCs) and used in downstream assays to characterize immune responses in the presence or absence of one or more immunostimulatory or immunosuppressive factors. The vaccine cell line components are phagocytized by donor-derived immature DCs during co-culture with the unmodified parental vaccine cell line (control) or the modified vaccine cell line components. The effect of modified vaccine cell line components on DC maturation, and thereby subsequent T cell priming, can be evaluated using flow cytometry to detect changes in markers of DC maturation such as CD40, CD83, CD86, and HLA-DR. Alternatively, the immature DCs are matured after co-culture with the vaccine cell line components, the mature DCs are magnetically separated from the vaccine cell line components, and then co-cultured with autologous CD14-PBMCs for 6 days to mimic in vivo presentation and stimulation of T cells. IFNγ production, a measurement of T cell stimulatory activity, is measured in the IFNγ ELISpot assay or the proliferation and characterization of immune cell subsets is evaluated by flow cytometry. In the IFNγ ELISpot assay, PBMCs are stimulated with autologous DCs loaded with the unmodified parental vaccine cell line components to assess potential responses against unmodified tumor cells in vivo.

The IFNγ ELISpot assay can be used to evaluate the potential of the allogenic vaccine to drive immune responses to clinically relevant TAAs expressed by the vaccine cell lines. To assess TAA-specific responses in the IFNγ ELISpot assay, following co-culture with DCs, the PBMCs are stimulated with peptide pools comprising known diverse MHC-I epitopes for TAAs of interest. In various embodiments, the vaccine composition may comprise 3 cell lines that induce IFNγ responses to at least 3, 4, 5, 6, 7, 8, 9, 10, or 11 non-viral antigens, or at least 30%, 40%, 50%, 60%, 70%, 80%, 90%, or 100% of the antigens evaluated for an IFNγ response. In some embodiments, the vaccine composition may be a unit dose of 6 cell lines that induce IFNγ responses to at least 5, 6, 7, 8, 9, 10 or 11 non-viral antigens, or at least 60%, 70%, 80%, 90%, or 100% of the antigens evaluated for an IFNγ response.

In Vivo Mouse Models

Induction of antigen specific T cells by the allogenic whole cell vaccine can be modeled in vivo using mouse tumor challenge models. The vaccines provided in embodiments herein may not be administered directly to mouse tumor model due to the diverse xenogeneic homology of TAAs between mouse and human. However, a murine homolog of the vaccines can be generated using mouse tumor cell lines. Some examples of additional immune readouts in a mouse model are: characterization of humoral immune responses specific to the vaccine or TAAs, boosting of cellular immune responses with subsequent immunizations, characterization of DC trafficking and DC subsets at draining lymph nodes, evaluation of cellular and humoral memory responses, reduction of tumor burden, and determining vaccine-associated immunological changes in the TME, such as the ratio of tumor infiltrating lymphocytes (TILs) to Tregs. Standard immunological methods such as ELISA, IFNγ ELISpot, and flow cytometry will be used.

Kits

The vaccine compositions described herein may be used in the manufacture of a medicament, for example, a medicament for treating or prolonging the survival of a subject with cancer, e.g., lung cancer, non-small cell lung cancer (NSCLC), small cell lung cancer (SCLC), prostate cancer, glioblastoma, colorectal cancer, breast cancer including triple negative breast cancer (TNBC), bladder or urinary tract cancer, squamous cell head and neck cancer (SCCHN), liver hepatocellular (HCC) cancer, kidney or renal cell carcinoma (RCC) cancer, gastric or stomach cancer, ovarian cancer, esophageal cancer, testicular cancer, pancreatic cancer, central nervous system cancers, endometrial cancer, melanoma, and mesothelium cancer.

Also provided are kits for treating or prolonging the survival of a subject with cancer containing any of the vaccine compositions described herein, optionally along with a syringe, needle, and/or instructions for use. Articles of manufacture are also provided, which include at least one vessel or vial containing any of the vaccine compositions described herein and instructions for use to treat or prolong the survival of a subject with cancer. Any of the vaccine compositions described herein can be included in a kit comprising a container, pack, or dispenser together with instructions for administration.

In some embodiments, provided herein is a kit comprising at least two vials, each vial comprising a vaccine composition (e.g., cocktail A and cocktail B), wherein each vial comprises at least 1, 2, 3, 4, 5, 6, 7, 8, 9, or 10 or more cell lines, wherein the cell lines are modified to inhibit or reduce production of one or more immunosuppressive factors, and/or express or increase expression of one or more immunostimulatory factors, and/or express a heterogeneity of tumor associated antigens, or neoantigens.

By way of example, a kit comprising 6 separate vials is provided, wherein each vial comprises one of the following cell lines: NCI-H460, NCI-H520, DMS 53, LK-2, NCI-H23, and A549. As another example, a kit comprising 6 separate vials is provided, wherein each vial comprises one of the following cell lines: DMS 53, DBTRG-05MG, LN-229, SF-126, GB-1, and KNS-60. As another example, a kit comprising 6 separate vials is provided, wherein each vial comprises one of the following cell lines: DMS53, PC3, NEC8, NTERA-2cl-D1, DU-145, and LNCAP. As another example, a kit comprising 6 separate vials is provided, wherein each vial comprises one of the following cell lines: DMS 53, HCT-15, HuTu80, LS411N, HCT-116 and RKO. As another example, a kit comprising 6 separate vials is provided, wherein each vial comprises one of the following cell lines: DMS 53, OVTOKO, MCAS, TOV-112D, TOV-21G, and ES-2. As another example, a kit comprising 6 separate vials is provided, wherein each vial comprises one of the following cell lines: DMS 53, HSC-4, HO-1-N-1, DETROIT 562, KON, and OSC-20. As another example, a kit comprising 6 separate vials is provided, wherein each vial comprises one of the following cell lines: DMS 53, J82, HT-1376, TCCSUP, SCaBER, and UM-UC-3. As another example, a kit comprising 6 separate vials is provided, wherein each vial comprises one of the following cell lines: DMS 53, MKN-1, MKN-45, MKN-74, OCUM-1, and Fu97. As another example, a kit comprising 6 separate vials is provided, wherein each vial comprises one of the following cell lines: DMS 53, AU565, CAMA-1, HS-578T, MCF-7, and T-47D. As another example, a kit comprising 6 separate vials is provided, wherein each vial comprises one of the following cell lines: DMS 53, PANC-1, KP-3, KP-4, SUIT-2, and PSN1.

In some embodiments, provided herein is a kit comprising at least two vials, each vial comprising a vaccine composition (e.g., cocktail A and cocktail B), wherein each vial comprises at least three cell lines, wherein the cell lines are modified to reduce production or expression of one or more immunosuppressive factors, and/or modified to increase expression of one or more immunostimulatory factors, and/or express a heterogeneity of tumor associated antigens, or neoantigens. The two vials in these embodiments together are a unit dose. Each unit dose can have from about $5\times10^6$ to about $5\times10^7$ cells per vial, e.g., from about $5\times10^6$ to about $3\times10^7$ cells per vial.

In some embodiments, provided herein is a kit comprising at least six vials, each vial comprising a vaccine composition, wherein each vaccine composition comprises one cell line, wherein the cell line is modified to inhibit or reduce production of one or more immunosuppressive factors, and/or modified to express or increase expression of one or more immunostimulatory factors, and/or expresses a heterogeneity of tumor associated antigens, or neoantigens. Each of the at least six vials in the embodiments provided herein can be a unit dose of the vaccine composition. Each unit dose can have from about $2\times10^6$ to about $50\times10^6$ cells per vial, e.g., from about $2\times10^6$ to about $10\times10^6$ cells per vial.

In some embodiments, provided herein is a kit comprising separate vials, each vial comprising a vaccine composition, wherein each vaccine composition comprises one cell line, wherein the cell line is modified to inhibit or reduce production of one or more immunosuppressive factors, and/or modified to express or increase expression of one or more immunostimulatory factors, and/or expresses, a heterogeneity of tumor associated antigens, or neoantigens. Each of the vials in the embodiments provided herein can be a unit dose of the vaccine composition. Each unit dose can have from about $2\times10^6$ to about $50\times10^6$ cells per vial, e.g., from about $2\times10^6$ to about $10\times10^6$ cells per vial.

In one exemplary embodiment, a kit is provide comprising two cocktails of 3 cell lines each (i.e., total of 6 cell lines in 2 different vaccine compositions) as follows: $8\times10^6$ cells per cell line; $2.4\times10^7$ cells per injection; and $4.8\times10^7$ cells total dose. In another exemplary embodiment, $1\times10^7$ cells per cell line; $3.0\times10^7$ cells per injection; and $6.0\times10^7$ cells total dose is provided. In some embodiments, a vial of any of the kits disclosed herein contains about 0.1, 0.2, 0.3, 0.4, 0.5, 0.6, 0.7, 0.8, 0.9, or 1.0 mL of a vaccine composition of the disclosure. In some embodiments, the concentration of cells in a vial is about $5\times10^7$ cells/mL to about $5\times10^8$/cells mL.

The kits as described herein can further comprise needles, syringes, and other accessories for administration.

EXAMPLES

Example 1: Reduction of HLA-G Expression in a Human Adenocarcinoma Cell Line of the Lung Increases IFNγ Secretion in a Co-Culture with Peripheral Blood Mononuclear Cells (PBMC Aberrant expression of HLA-G by tumor cell is associated with tumor immune escape, metastasis and poor prognosis. Ligation of HLA-G with its receptors ILT2 and ILT4 on DCs can promote immune tolerance and priming of T cells with an immunosuppressed phenotype. Reduction of HLA-G expression on cell line component of a whole cell vaccine could improve immunogenicity in the VME.

Reduction of HLA-G Expression in Human Adenocarcinoma Cell Line

Figure 1B:
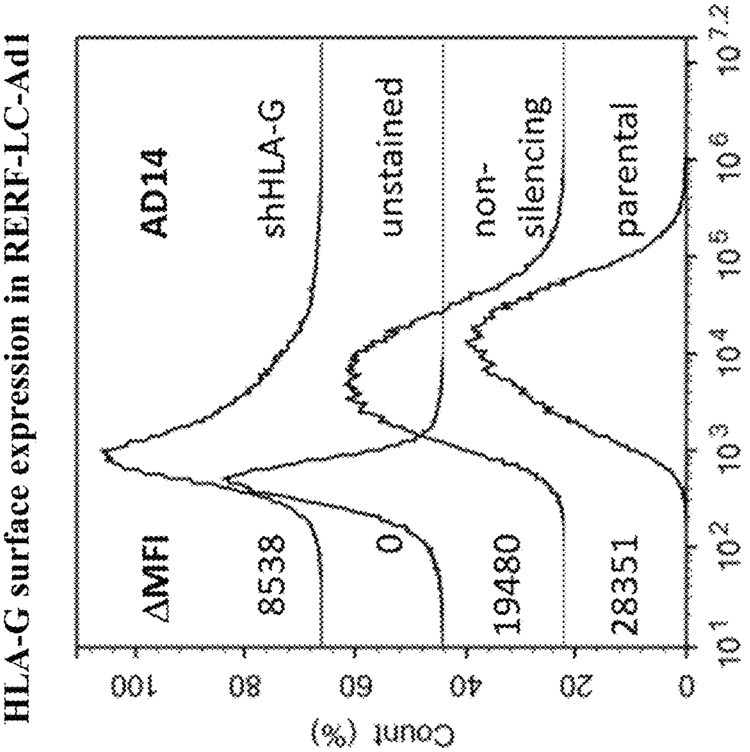
FIGS. 1A and B show reduction of HLA-G mRNA and protein expression in cells stably transduced with shRNA knocking down HLA-G in comparison to controls.
Figure 1A:
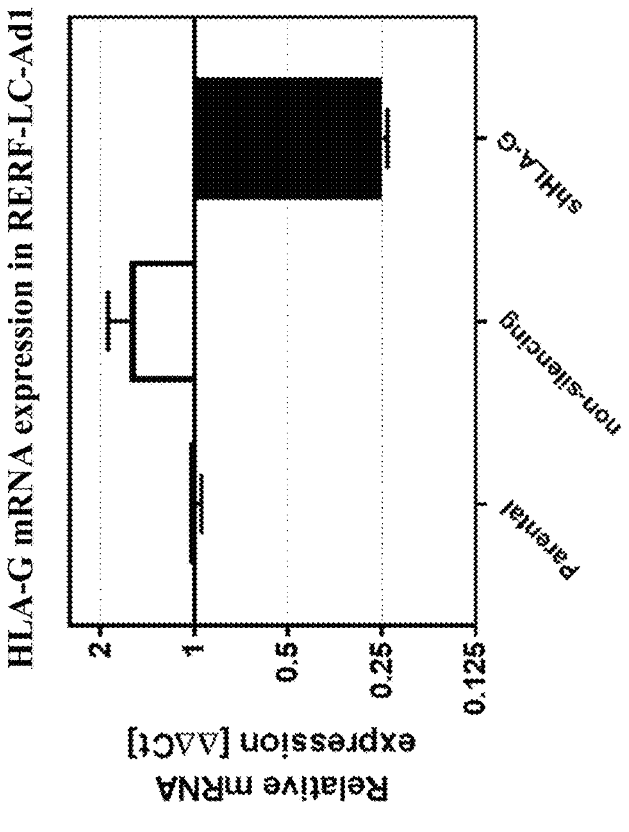

Human adenocarcinoma cell line RERF-LC-Ad1 was transduced with lentiviral particles expressing a short-hairpin ribonucleic acid (shRNA) specific for the knockdown of HLA-G (mature antisense sequence: TACAGCTGCAAGGACAACCAG) (SEQ ID NO: 23). Parental cells or cells transduced with control (non-silencing) shRNA served as controls. HLA-G expression levels following shRNA mediated HLA-G knockdown was determined by cytometry by staining with an APC-conjugated mouse monoclonal antibody human HLA-G (clone 87G) and then FACs sorted to enrich for the HLA-G low population. Modified and unmodified cells were detached and stained with an APC-conjugated mouse monoclonal antibody human HLA-G (clone 87G). After selection with puromycin to enrich for cells stable expressing the shRNA, cells were analyzed for expression of HLA-G at mRNA level by quantitative polymerase chain reaction (qPCR) and at protein level by flow cytometry. For qPCR cells were lysed in Trizol, total RNA isolated and then transcribed into complementary DNA (cDNA). Relative HLA-G mRNA expression was quantified with specific-probes for HLA-G and PSMB4 (for normalization) using the ΔΔCt method. HLA-G mRNA expression was reduced in cells stable transduced with shRNA for HLA-G in comparison to parental (non-transduced) cells and cells transduced with control (non-silencing) shRNA by at least 75% (FIG. 1A). HLA-G expression levels were following shRNA mediated HLA-G knockdown was determined by flow cytometry. Modified and unmodified cells were detached and stained with an APC-conjugated mouse monoclonal antibody human HLA-G (clone 87G). Fluorescence (expression) intensity was calculated as delta mean fluorescence intensity ($\Delta MFI=MFI_{anti\text{-}HLA\text{-}G}\text{-}MFI_{unstained}$). HLA-G cell surface expression was reduced in in cells stable transduced with shRNA for HLA-G in comparison to parental (non-transduced) cells by 70% (FIG. 1B).

Increase of IFNγ Secretion in Mixed Lymphocyte Tumor Reaction (MLR)

Figure 2B:
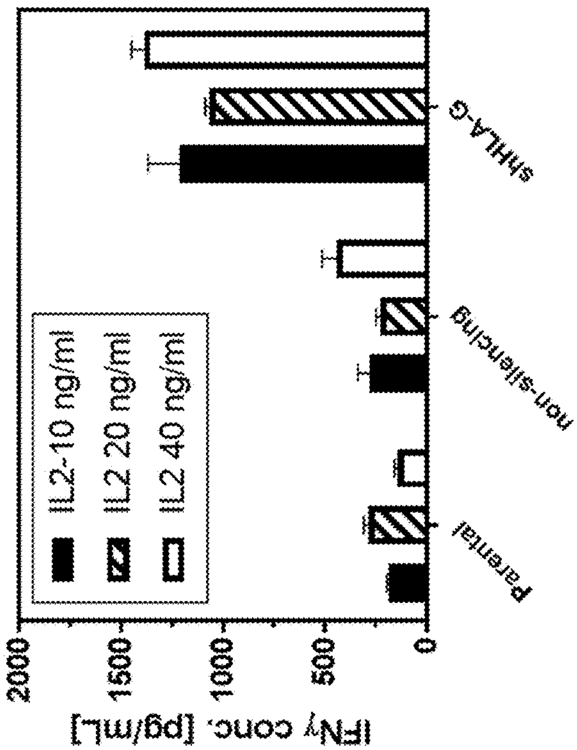
FIGS. 2A and B show reduction of HLA-G expression increases IFNγ production.
Figure 2A:
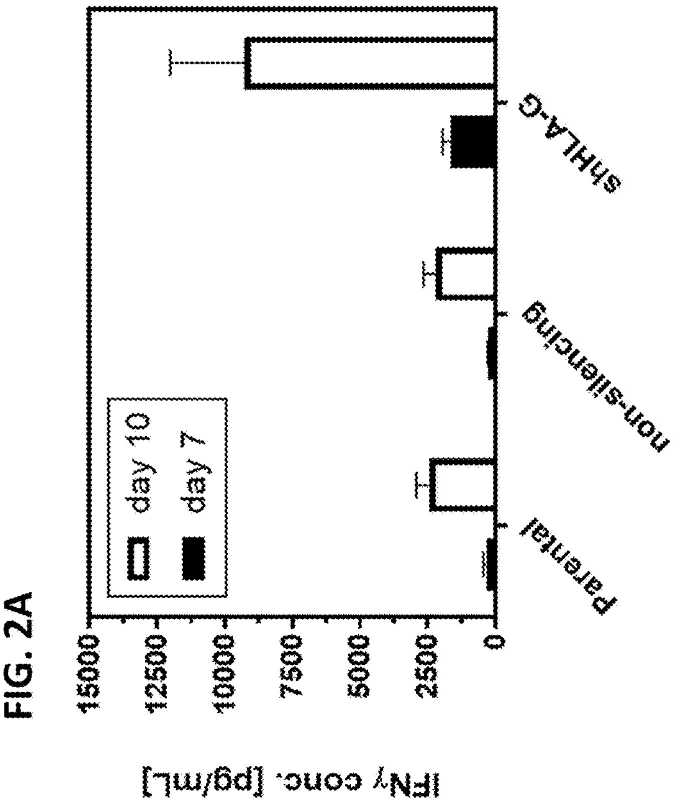

PBMCs were isolated from blood of healthy donors and co-incubated with adenocarcinoma lung cancer cell lines, that were pre-treated with mitomycin C (0.4 μg/ml for 16 hours) to prevent tumor cell growth and proliferation, at a PBMC to tumor cell ratio of 10 to 1. Interleukin-2 (IL2) was added on day 3 (and 7) of co-culture at different concentrations. On day 7 and/or 10 cell culture supernatant was harvested and IFNγ secretion was measured by ELISA. The increase of IFNγ in the co-culture of PBMCs with tumor cells with reduced HLA-G expression was significant ($p<0.01$) compared to parental and non-silencing tumor cells on day 10 (2way ANOVA with Sidak's multiple comparisons test) (FIG. 2A). In addition, the significant increase of IFNγ secretion was independent of the IL-2 concentration during co-culture ($p<0.0001$, 2way ANOVA with Tukey's multiple comparisons test) (FIG. 2B).

Example 2: Reduction of CD47 Expression Increases Phagocytosis of Tumor Cell Lines by Antigen Presenting Cells and Enhances Immunogenicity CD47 is a cell surface marker for "self" and thereby prevents immunological responses against healthy cells. Primary tumor cells as well as tumor cell lines can express high levels of CD47.

Reduction of CD47 Expression in Human Adenocarcinoma Cell Line

Figure 3A:
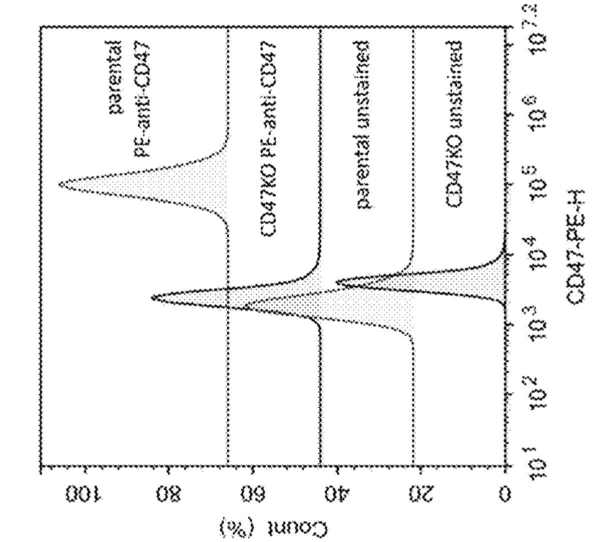
FIGS. 3A-C show reduction of CD47 expression in the A549 (FIG. 3A), NCI-H460 (FIG. 3B), and NCI-H520 (FIG. 3C) cell lines by zinc-finger nuclease (ZFN)-mediated gene editing.
Figure 3B:
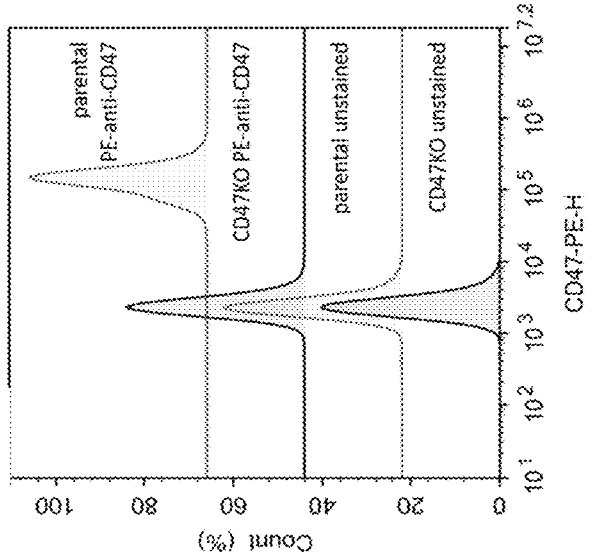
Figure 3C:
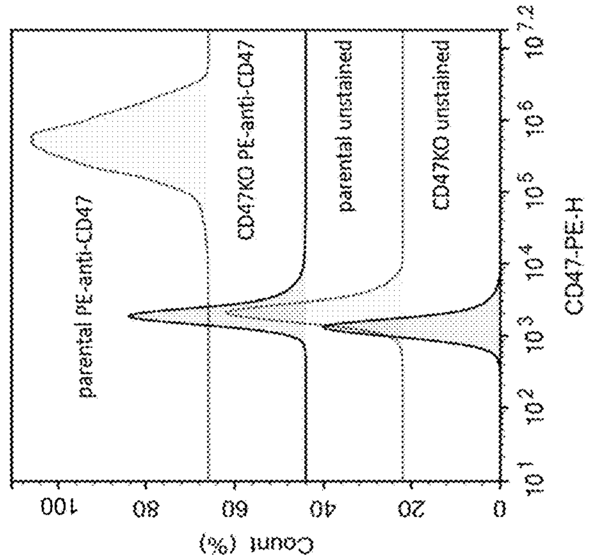

The human NSCLC cell lines A549, NCI-H460, and NCI-H520 were electroporated with a zinc finger nuclease (ZFN) pair specific for CD47 targeting the following genomic DNA sequence: CACACAGGAAACTACacttgtGAAGTAACAGAATTA (SEQ ID NO: 27). Full-allelic knockout cells were identified by flow cytometry after staining with PE-conjugated anti-human CD47 monoclonal antibody (clone CC2C6) and then FACS sorted to enrich for the CD47 negative population. Gene editing of CD47 by ZFN resulted in greater than 99% reduction in CD47 expression by the A549 (FIG. 3A), NCI-H460 (FIG. 3B), and NCI-H520 (FIG. 3C) cell lines.

Reduction of CD47 Increases Phagocytosis of Tumor Cell Lines by Antigen Presenting Cells and Enhances Immunogenicity The effect of reducing CD47 expression (CD47 KO) on phagocytosis and immunogenicity was determined using the NCI-H520 cell line. Specifically, the effect of CD47 KO on phagocytosis by human monocyte-derived professional antigen presenting cells (APCs), both DCs and macrophages, was determined using a phagocytosis assay. Immune responses induced by NCI-H520 unmodified parental and CD47 KO evaluated in the IFNγ ELISpot assay.

Generation of Human Dendritic Cells and Macrophages

Human immature dendritic cells (iDCs) and M1 macrophages (MDM) were derived from $CD14^+$ cells isolated from healthy donor leukopaks (StemCell Technologies, #70500) by magnetic separation according to the manufacturer's instructions. iDCs were generated by culturing $CD14^+$ cells in ImmunoCult™-ACF Dendritic Cell Medium (StemCell Technologies, #10986) in the presence of ImmunoCult™-ACF Dendritic Cell Differentiation Supplement (StemCell Technologies, #10988) according to the manufacturer's instructions. iDCs were harvested for use in the phagocytosis assay on Day 3 and on Day 6 for use in the IFNγ ELISpot assay. MDM were generated by culturing $CD14^+$ cells in RPMI supplemented with 10% FBS in the presence of 100 ng/mL GM-CSF (PeproTech, #300-03-100UG) for 7 days. To skew macrophages towards a M1 phenotype, on Day 7 the RPMI+10% FBS media was replaced with Macrophage-SFM (Gibco, #12065074) containing 20 ng/mL LPS (InvivoGen, #tlrl-3pelps) and 20 ng/mL IFNγ (PeproTech, 300-02-100UG). MDM were harvested on Day 9 for the phagocytosis assay.

Phagocytosis Assay

Unmodified parental and CD47 KO NCI-H520 cells were treated with 10 μg/mL mitomycin C (MMC) for 2 hours and rested overnight prior to labelling with 1 μM of CSFE (Invitrogen, #C34554) for 30 minutes at 37 □ C. iDC and MDM were co-cultured with the CSFE-labeled unmodified parental and CD47 KO NCI-H520 cells for 4 hours at 37 □ C. iDC and cell lines were co-cultured at a 1:1 effector to target ratio in 96-well low-adherence U bottom plates. MDM were co-cultured at a 1:4 effector to target ratio in 96-well plates. Following the 4 hour incubation, the co-cultures were surface stained with LIVE/DEAD Aqua (Molecular Probes, #L23105), αCD45-PE-Cy7 (BD Biosciences, clone H130), and αCD11c-BV605 (BD Biosciences, clone B-ly6) for iDCs or αCD11b-BV421 (BD Biosciences, clone ICRF44) for MDM. Flow cytometry data was analyzed using FlowJo (FlowJo LLC). MDM phagocytosis was defined as the percentage of live, $CD45^+$, $CD11b^+$ cells that were also CFSE (FITC) positive by flow cytometry. iDC phagocytosis was defined as the percent of live, $CD45^+$, $CD11c^+$ cells that were also CFSE ($FITC^+$) positive by flow cytometry. MDM and iDC that were not co-cultured with the unmodified parental or CD47 KO NCI-H520 cells served as controls.

IFNγ ELISpot Assay

Unmodified parental and CD47 KO NCI-H520 cells were x-ray irradiated at 100 Gy (Rad Source 1800 Q) 24 hours prior to loading of iDCs. To load iDCs, irradiated unmodified parental and CD47 KO NCI-H520 (ATCC HTB-182) were co-cultured with iDCs at a 1:1 ratio for 24 hours in the presence of 25 μg/mL of Keyhole Limpet Hemocyanin (KLH) (Calbiochem #374807) and 1 μg/mL soluble CD40L (sCD40L) (PeproTech, #AF31002100UG). Tumor cell loaded iDCs were than matured overnight by the addition of 100 IU/mL IFNγ (PeproTech, 300-02-100UG), 10 ng/mL LPS (InvivoGen, #tlrl-3pelps) and 2.5 μg/mL Resiquimod (R848) (InvivoGen, #tlrl-3r848). Mature DCs (mDCs) were labelled with αCD45-PE (BD Biosciences, clone H130) and magnetically separated from the co-culture using the EasySep™ Release Human PE Positive Selection Kit (StemCell Technologies, #17654) according to manufacturer's instructions. Isolated mDCs were then co-cultured with autologous CD14-PBMCs for 6 days at a 1:10 DC to PBMC ratio. For the IFNγ ELISpot assay (MabTech, 3420-4APT-10), CD14-PBMCs were isolated from co-culture with mDCs and stimulated with unmodified parental NCI-H520 loaded mDCs for 24 hours. IFNγ spot forming units (SFU) were detected following the manufacturer's instructions, counted (S6 Core Analyzer, ImmunoSpot), and expressed as the number of SFU/$10^6$ PBMCs above that of the controls.

Increased Phagocytosis of the NCI-H520 CD47KO Cell Line by Monocyte Derived Dendritic Cells and Macrophages Reduction of CD47 increased phagocytosis by MDM derived from 2 healthy donors by an average of 1.6-fold (11.1±1.9% live/CD45+/CD11b$^+$/CFSE$^+$) relative to phagocytosis of the unmodified parental cell line (7.0±1.2% live/CD45$^+$/CD11b$^+$/CFSE$^+$). Reduction of CD47 also increased phagocytosis by iDC derived from 2 healthy donors by an average of 2.2-fold (11.9±2.3% live/CD45+/CD11c$^+$/CFSE$^+$) relative to phagocytosis of the unmodified parental cell line (5.5±3.4% live/CD45$^+$/CD11c$^+$/CFSE$^+$) (FIG. 4A).

Reduction of CD47 Improves Immunogenicity of a Human Squamous Tumor Cell Line

Figure 4B:
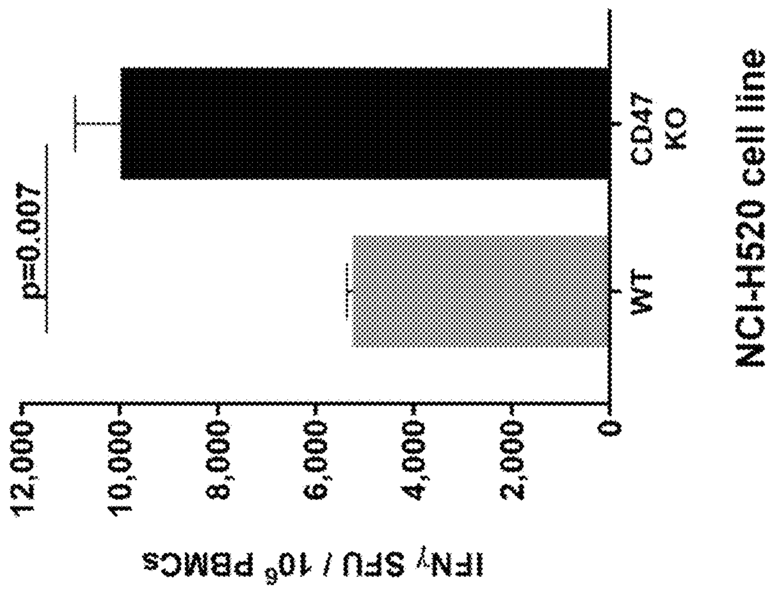
FIGS. 4A and B show reduction of CD47 in the NCI-H520 cell line increases phagocytosis (FIG. 4A) by monocyte-derived dendritic cells and macrophages and increases IFNγ responses (FIG. 4B) in the ELISpot assay.
Figure 4A:
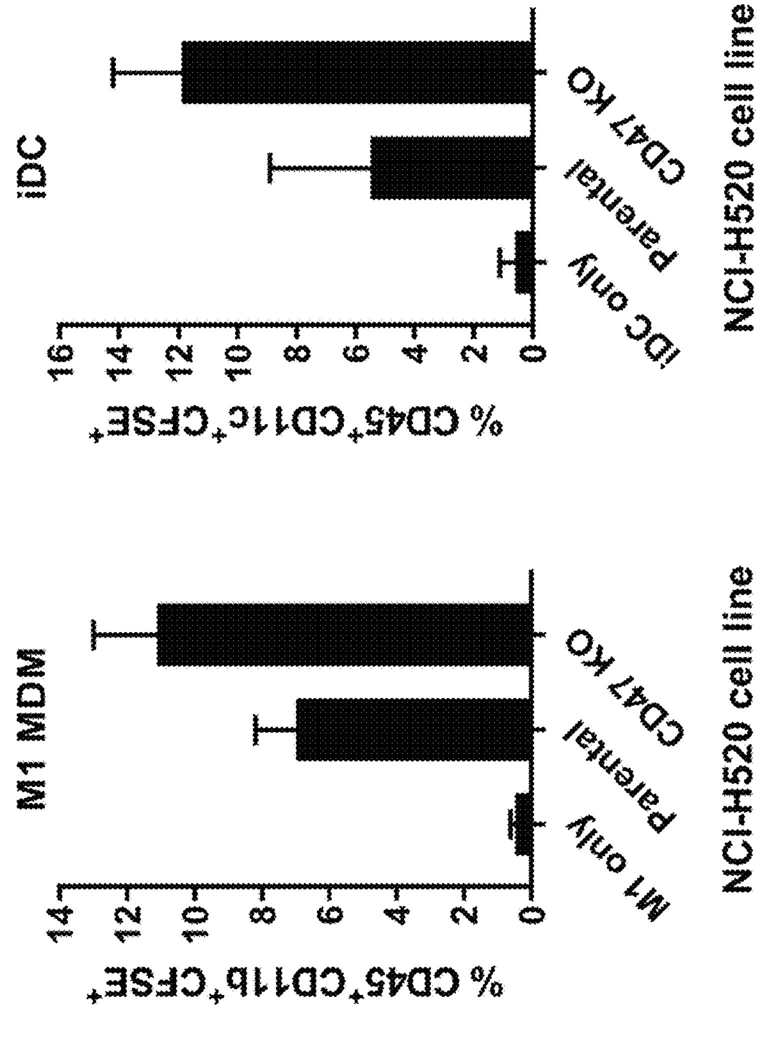

IFNγ responses by ELISpot were 1.9-fold higher when autologous PBMCs were co-cultured with DCs loaded with CD47 KO cells (9,980±903 SFU) relative to DCs loaded with the unmodified parental, CD47 positive cells (5,253±109 SFU) (p=0.007, Student's T-test) (n=3) (FIG. 4B).

Example 3: Reduction of Programmed Cell Death Ligand 1 Expression

Binding of PD1 on DCs to PDL1 (CD274) on tumor cells can suppress DC function and potentially reduce priming of inflammatory ($Th_1$) T cells and promote the priming of immunosuppressive (Th2) T cells.

Figure 5:
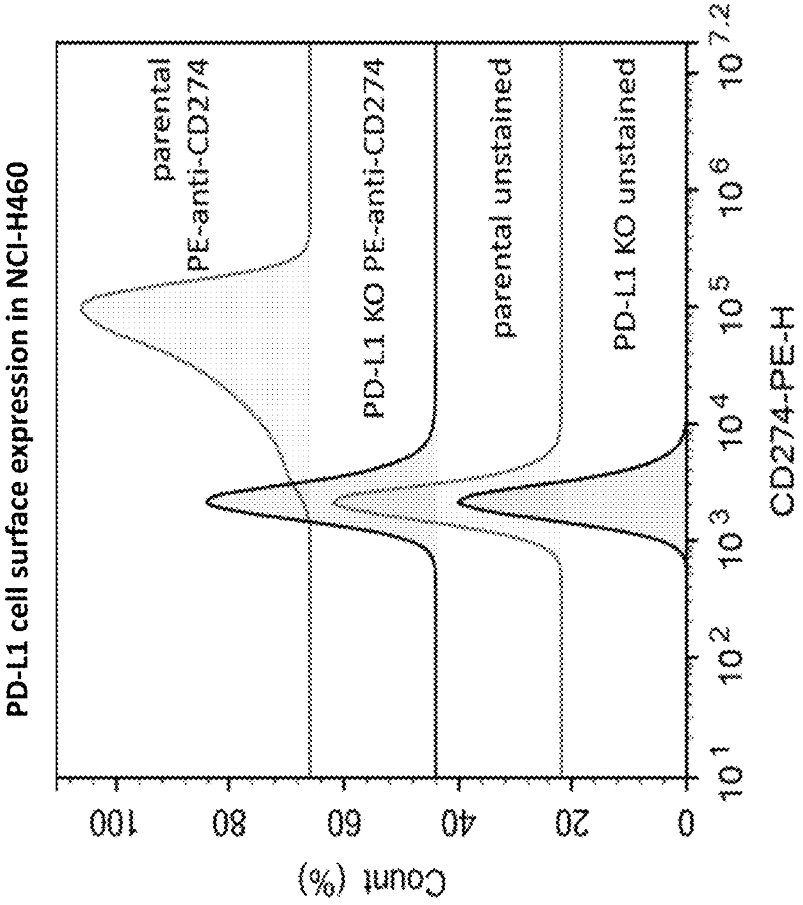
FIG. 5 shows ZFN-mediated gene editing of PD-L1 in the NCI-H460 cell line results in a 99% decrease in PD-L1 expression.

PDL1 expression by the NSCLC cell line NCI-H460 was reduced using zinc-finger mediated gene editing. The cell line was electroporated with DNA plasmids coding for a zinc finger nuclease (ZFN) pair specific for PD-L1 targeting the following genomic DNA sequence: CCAGTCACCTCTGAACATGaactgaCATGTCAGGCTGAGGGCT (SEQ ID NO: 28). Full-allelic knockout cells were identified by flow cytometry after staining with PE-conjugated anti-human CD274 monoclonal antibody (clone MIH1) and then FACS sorted. Gene editing of PD-L1 by ZFNs resulted in greater than 99% PD-L1 negative NCI-H460 cells after sorting (FIG. 5).

Example 4: Reduction of Bone Marrow Stromal Cell Antigen 2 (Bst2) Expression

BST2 is a cell surface marker on primary tumor cells and tumor cell lines that inhibits cytokine production (type I interferons) through interaction with ILT7 (CD85g) on plasmacytoid dendritic cells.

Figure 6:
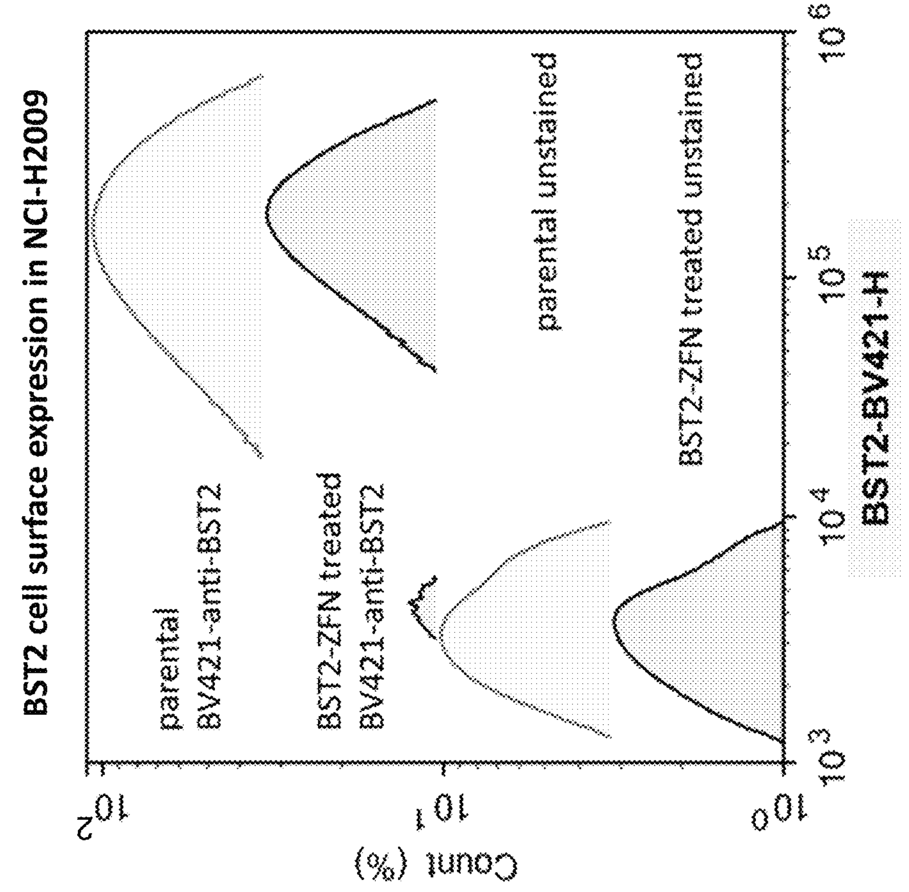
FIG. 6 shows ZFN-mediated gene editing of BST2 in the NCI-H2009 cell line results in a 98.5% reduction in BST2 expression.

The reduction of BST2 expression by the NCI-H2009 cell line was completed using ZFN mediated gene editing. The cell line was electroporated with DNA plasmids coding for a ZFN pair specific for BST2 targeting the following genomic DNA sequence: CCTAATGGCTTCCCTGGATgcagagAAGGCCCAAGGACAAAAG (SEQ ID NO: 34). Full-allelic knockout cells were identified by flow cytometry after staining with BV421-conjugated anti-human BST2 monoclonal antibody (clone HM1.24). Gene editing of BST2 by ZFNs resulted in 98.5% reduction in BST2 expression by NCI-H2009 cells (FIG. 6). The BST2 positive fraction of BST2-ZFN treated NCI-H2009 cells can subsequently be FACS sorted to purity.

Example 5: Reduction of TGFβ1 and/or TGFβ2 Secretion in Lung Cancer Cell Lines TGFβ1 and TGFβ2 are highly immunosuppressive molecules secreted by tumor cells to evade immune surveillance. This example describes the procedure to generate lung cancer cell lines with reduced or without secretion of TGFβ1 and TGFβ2 and how the changes in secretion were verified.

Cell Lines, Culture and Selection

The lung cancer cell lines NCI-H460 (ATCC HTB-177), DMS 53 (ATCC CRL-2062), NCI-H520 (ATCC HTB-182), A549 (ATCC CCL-185), NCI-H2023 (ATCC CRL-5912), NCI-H23 (ATCC CRL-5800), and NCI-H1703 (ATCC CRL-5889) were obtained from ATCC and cultured according to ATCC recommendations. LK-2 (JCRB0829) was obtained from the Japanese Collection of Research Biosources Cell Bank (JCRB) and cultured according to JCRB recommendations. For mammalian cell line selection after lentiviral transduction puromycin and blasticidin in concentrations ranging from 2 to 8 μg/mL were used for selection and maintenance.

shRNA Mediated Knockdown of TGFβ1 and TGFβ2

The cell lines NCI-H460, DMS 53, and NCI-H520, A549, NCI-H2023, NCI-H23, LK-2, and NCI-H1703 were transduced with lentiviral particles expressing short-hairpin ribonucleic acid (shRNA) specific for the knockdown of TGFβ1 (shTGFβ1, mature antisense sequence: TTTCCACCATTAGCACGCGGG (SEQ ID NO: 25)) and TGFβ2 (shTGFβ2, mature antisense sequence: AATCTGATATAGCTCAATCCG (SEQ ID NO: 24)). Cells transduced with control shRNA (NS) or parental unmodified cell lines served as controls. After antibiotic selection to enrich for cells stabling expressing shRNA(s), cells were analyzed for TGFβ1 and TGFβ2 secretion.

Knockout of TGFβ1 and TGFβ2

Knockout of TGFβ1 and TGFβ2 was completed using CRISPR-Cas9 and ZFN approaches. For CRISPR-Cas9 knockouts, the NCI-H460 and NCI-H520 cell lines were electroporated with plasmid DNA coding for Cas9 and guide RNA specific for TGFβ2 targeting the following gDNA sequence: GCTTGCTCAGGATCTGCCCG (SEQ ID NO: 29) or control guide RNA targeting the sequence: GCACTACCAGAGCTAACTCA (SEQ ID NO: 30). Full-allelic knockout clones were screened for secretion of TGFβ1 and TGFβ2 by ELISA. For ZFN-mediated knockout, the NCI-H460 cell line was electroporated with RNA coding for zinc finger nuclease (ZFN) pairs specific for TGFβ1 targeting the following genomic DNA (gDNA) sequence: CTCGCCAGCCCCCCGagccaGGGGGAGGTGCCGCCCGG (SEQ ID NO: 31) and for TGFβ2 targeting the following gDNA sequence: AGCTCACCAGTCCCCCAGAagactaTCCTGAGCCCGAGGAAGTC (SEQ ID NO: 32). Full-allelic knockout clones were screened by genomic DNA sequencing of expanded single cells and then analyzed for TGFβ1 and TGFβ2 secretion.

TGFβ1 and TGFβ2 Secretion Assay

TGFβ1 and TGFβ2 knockdown or knockout cells and unmodified or control modified parental cells were plated at $8.33\times10^4$ cells/well in a 24-well plated in regular growth medium (RPMI containing 10% FBS). Twenty-four hours after plating, adherent cells were thoroughly washed to remove FBS and culture was continued in RPMI+5% CTS. Forty-eight hours after media replacement, the cell culture supernatant was harvested, and stored at −70° C. until TGFβ1 and TGFβ2 secretion assays were initiated according to the manufacturer's instructions (DB100B and DB250, R&D Systems). TGFβ1 and TGFβ2 secretion levels are expressed as pg/$10^6$ cells/24 hours. The lower limit of quantification of human TGFβ1 and TGFβ2 are 15.4 pg/mL (92.4 pg/$10^6$ cells/24 hours) and 7.0 pg/mL (42.0 pg/$10^6$ cells/24 hours), respectively. The lower limit of quantification of the ELISA assay was used to approximate the percent reduction of TGFβ1 or TGFβ2 relative to the unmodified parental cell line shRNA when the modified cell lines secreted levels of TGFβ1 or TGFβ2 below the lower limit of quantification of the assay. In cases where TGFβ1 or TGFβ2 secretion were below the lower limit of quantification, the lower limit of quantification was used to determine statistical significance at the n for which the assay was completed.

Reduction of TGFβ1 and TGFβ2 Secretion in NCI-H460 Cells

Figure 7B:
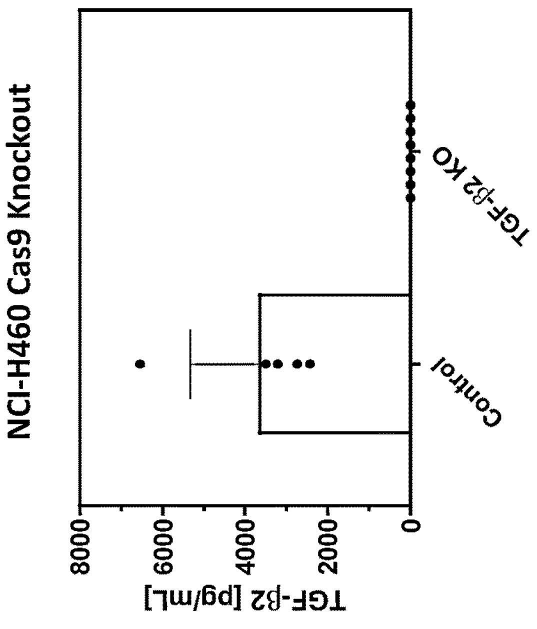
FIGS. 7A-C show reduction of TGFβ1 and TGFβ2 in NCI-H460 cell line by shRNA (FIG. 7A), Cas9 (FIG. 7B), and ZFN-mediated (FIG. 7C) gene editing.
Figure 7C:
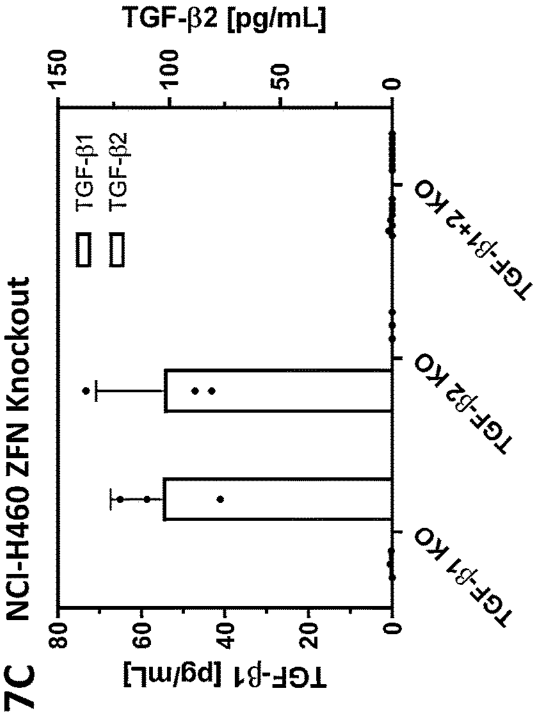
Figure 7A:
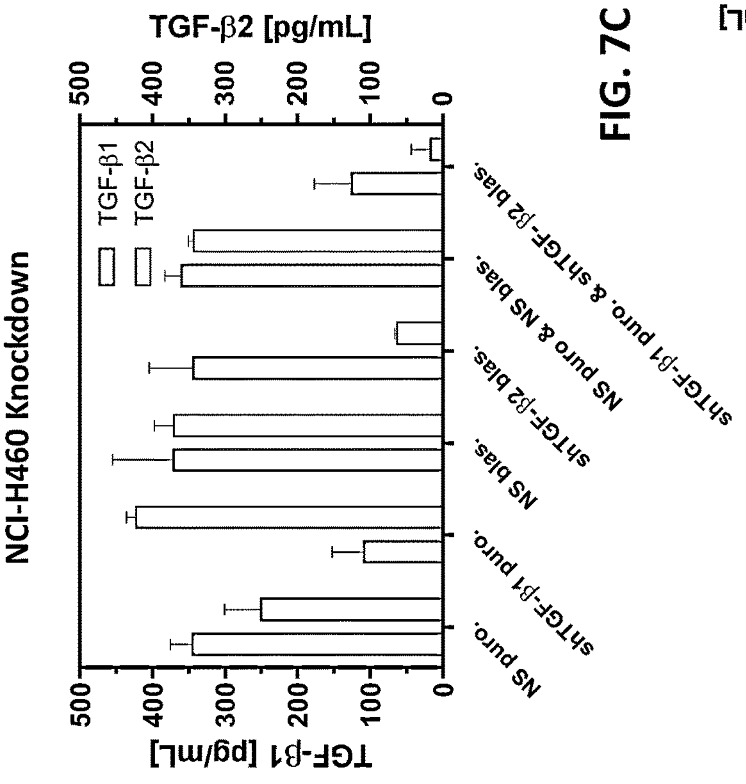

Knockdown of TGFβ1 in NCI-H460 reduced TGFβ1 secretion by 62%. Similarly, knockdown of TGFβ2 in NCI-H460 reduced TGFβ2 secretion by 84%. The combined knockdown of TGFβ1 and TGFβ2 in NCI-H460 reduced TGFβ1 secretion by 57% and TGFβ2 secretion by >98% (Table 26) (FIG. 7A). Clones derived from Cas9 mediated knockout using TGFβ2 specific guide RNA in NCI-H460 cells demonstrated clones did not secrete TGFβ2 (>99% reduction) above the lower limit of detect compared clones from NCI-H460 treated with control guide RNA (3686±1478 pg/$10^6$ cells/24 hours) (FIG. 7B). Clones derived from NCI-H460 treated with TGFβ1 specific ZFN pair did not secrete TGFβ1 above the lower limit of detection of the assay compared to clones from NCI-H460 treated with TGFβ2 specific ZFN pair. Clones derived from NCI-H460 treated with TGFβ2 specific ZFN pair did not secrete TGFβ2 above the lower limit of detection in contrast to clones from NCI-H460 treated with TGFβ1 specific ZFN pair. Clones derived from NCI-H460 treated with TGFβ1 specific ZFN pair and with TGFβ2 specific ZFN pair did not secrete TGFβ1 or TGFβ2 above the lower limit of detection (FIG. 7C).

Figure 8B:
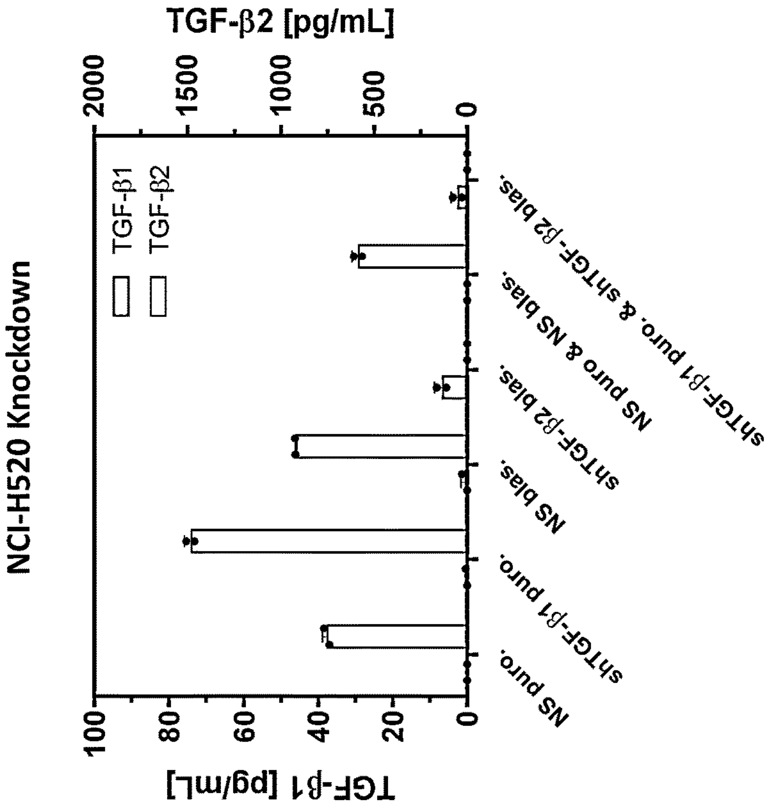
FIGS. 8A and B show shRNA mediated knockdown of TGFβ1 and/or TGFβ2 in the DMS 53 (FIG. 8A) cell line and NCI-H520 (FIG. 8B) cell line.
Figure 8A:
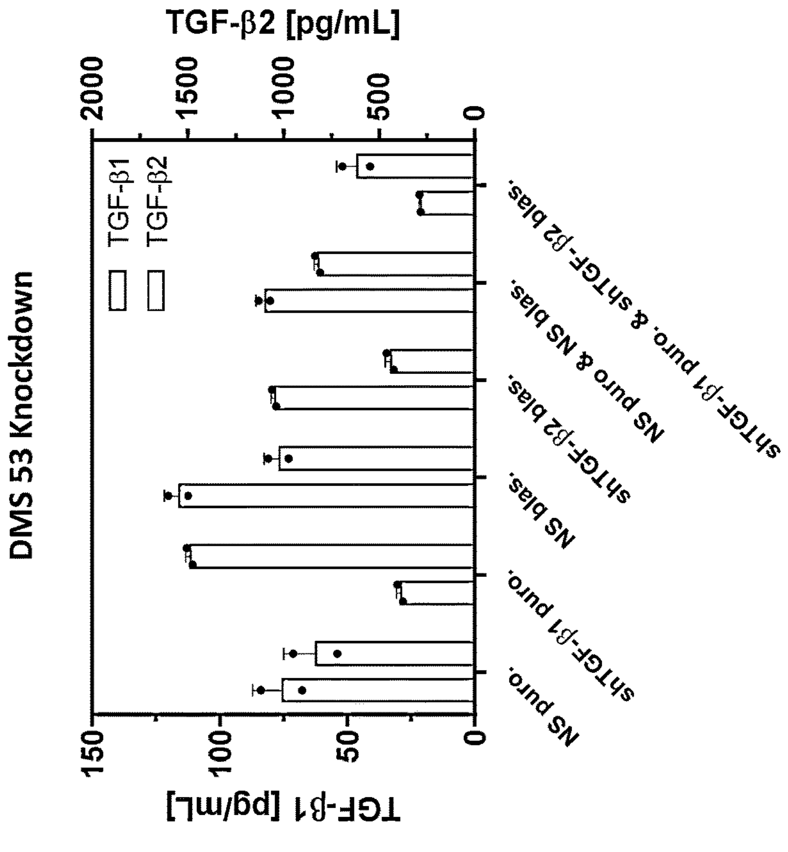

Knockdown of TGFβ1 and TGFβ2 in DMS 53 Cells shRNA mediated knockdown of TGFβ1 in DMS 53 reduced TGFβ1 secretion by 66%. Similarly, shRNA-mediated knockdown of TGFβ2 in DMS 53 reduced TGFβ2 secretion by 53%. The combined knockdown of TGFβ1 and TGFβ2 in DMS 53 reduced TGFβ1 secretion by 74% and TGFβ2 secretion by 32% (Table 26) (FIG. 8A).

Knockdown of TGFβ1 and TGFβ2 in NCI-H520 Cells

Knockdown of TGFβ1 in NCI-H520 could not be evaluated because of the lack of detectable TGFβ1 secretion by the parental cell line. Knockdown of TGFβ2 in NCI-H520 reduced TGFβ2 secretion by >99%. The combined knockdown of TGFβ1 and TGFβ2 in NCI-H520 (ATCC HTB-182) reduced TGFβ2 secretion by >99% (Table 26) (FIG. 8B).

Knockdown of TGFβ1 and TGFβ2 in NCI-H2023 Cells

Figure 9A:
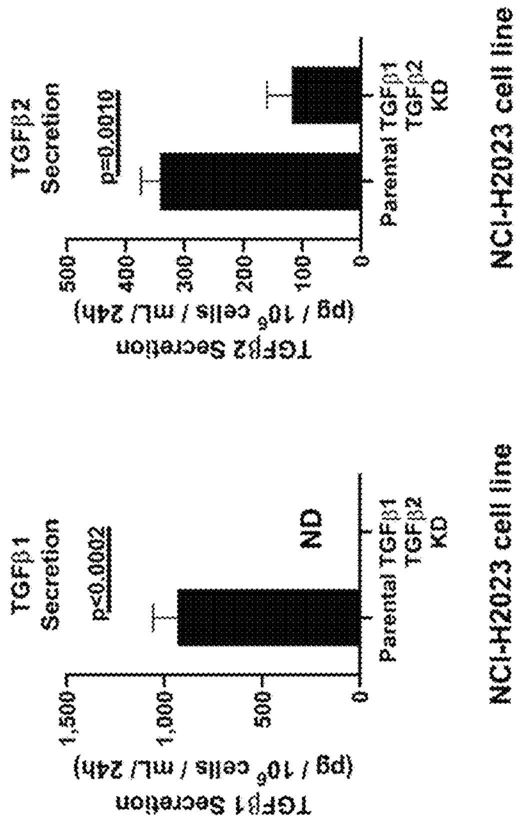
FIGS. 9A-E show the reduction of TGFβ1 and/or TGFβ2 in the NCI-H2023 (FIG. 9A), NCI-H23 (FIG. 9B), A549 (FIG. 9C), LK-2 (FIG. 9D), and NCI-H1703 (FIG. 9E) cell lines.

The combined knockdown of TGFβ1 and TGFβ2 in NCI-H2023 reduced TGFβ1 secretion below the lower limit of quantification (n=8) resulting in an estimated >90% decrease in TGFβ1 secretion compared to the unmodified parental cell line (933±125 pg/$10^6$ cells/24h) (n=8). TGFβ1 secretion was significantly reduced compared to the unmodified parental cell line (p<0.0002). The combined knockdown of TGFβ1 and TGFβ2 in NCI-H2023 reduced TGFβ2 secretion by 65% (118±42 pg/$10^6$ cells/24h) (n=8) compared to the unmodified parental cell line (341±32 pg/$10^6$ cells/24h) (n=8). TGFβ2 (p=0.0010) secretion was significantly decreased compared to the unmodified parental cell line (Mann-Whitney U Test) (Table 25) (FIG. 9A).

TABLE 25 shRNA mediate reduction of TGFβ1 and TGFβ2 secretion in lung cancer cell lines

| Cell line | TGFβ1 (pg/$10^6$cells/24 hours) | | | TGFβ2 (pg/$10^6$cells/24 hours) | | |
|---|---|---|---|---|---|---|
| | Parental | TGFβ1 KD | % Reduction | Parental | TGFβ2 KD | % Reduction |
| NCI-H460 | 2263 ± 2080 | 973 ± 551 | 57 | 2096 ± 1023 | <42 | 98 |
| NCI-H520 | <92 | <92 | NA | 3657 ± 3394 | <42 | >99* |
| DMS 53 | 504 ± 407 | 170 ± 128 | 53 | 4869 ± 5024 | 3293 ± 4161 | 32 |
| NCI-H2023 | 933 ± 125 | <92 | >90* | 341 ± 32 | 118 ± 42 | 65 |
| NCI-H23 | 1575 ± 125 | 644 ± 102 | 59 | 506 ± 42 | 48 ± 9 | 90 |
| A549 | 5796 ± 339 | 914 ± 54 | 84 | 772 + 49 | 42 ± 7 | 95 |
| NCI-H1703 | 1736 ± 177 | 429 ± 133 | 75 | <42 | <42 | NA |
| LK-2 | <92 | <92 | NA | 197 ± 34 | 77 ± 12 | 61 |

Parental indicates the unmodified cell line.
*Secretion levels are below the lower limit of quantification for TGFβ1 (92 pg/$10^6$ cells/24 hours) or TGFβ2 (42 pg/$10^6$ cells/24 hours). Lower limit of quantification used to approximate % reduction relative to parental.
NA: secretion levels are below the lower limit of quantification for both the parental and shRNA modified cell line.

Knockdown of TGFβ1 and TGFβ2 in NCI-H23 Cells

Figure 9B:
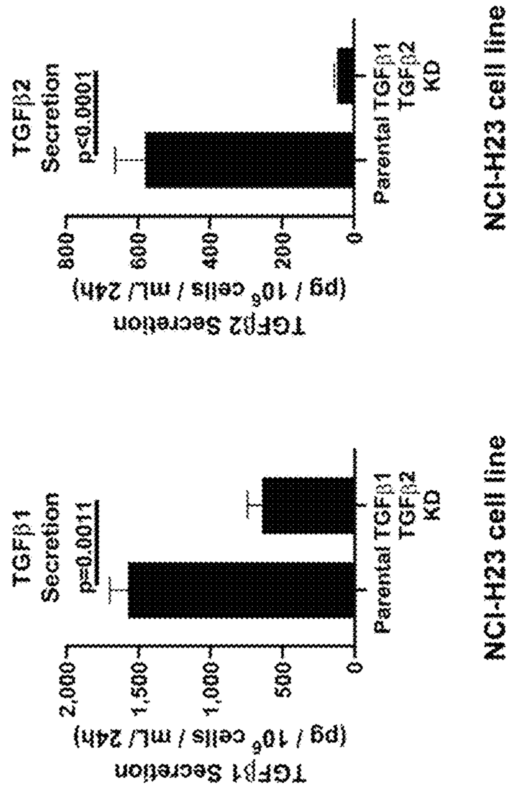

The combined knockdown of TGFβ1 and TGFβ2 in NCI-H23 (ATCC CRL-5800) reduced TGFβ1 secretion by 59% (644±102 pg/$10^6$ cells/24h) (n=8) compared to the unmodified parental cell line (1,575±125 pg/$10^6$ cells/24h) (n=8). The combined knockdown of TGFβ1 and TGFβ2 in NCI-H23 (ATCC CRL-5800) reduced TGFβ2 secretion 90% (48±9 pg/$10^6$ cells/24h (n=9) compared to the unmodified parental cell line (506±42 pg/$10^6$ cells/24h) (n=9). TGFβ1 (p=0.0011) and TGFβ2 (p<0.0001) secretion were significantly decreased compared to the unmodified parental cell line (Mann-Whitney U Test) (Table 25) (FIG. 9B).

Knockdown of TGFβ1 and TGFβ2 in A549 Cells

Figure 9C:
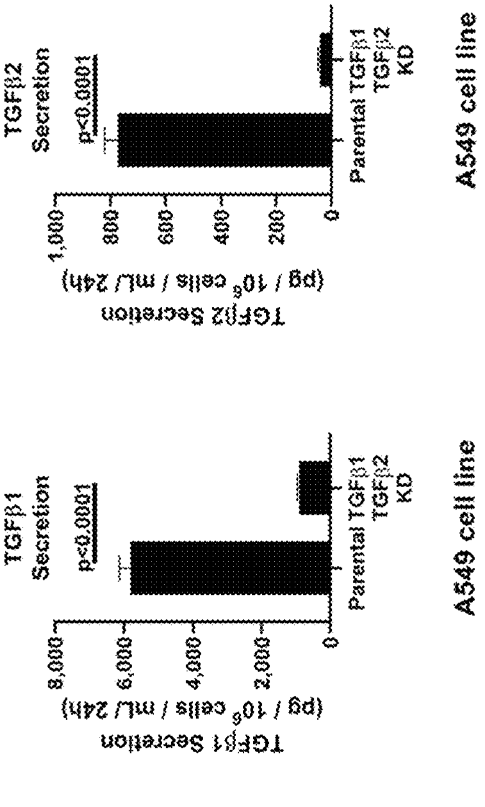

The combined knockdown of TGFβ1 and TGFβ2 in A549 reduced TGFβ1 secretion by 84% (914±54 pg/$10^6$ cells/24h) (n=11) compared to the unmodified parental cell line (5,796±339 pg/$10^6$ cells/24h) (n=11). The combined knockdown of TGFβ1 and TGFβ2 in A549 reduced TGFβ2 secretion by 95% (42±7 pg/$10^6$ cells/24h) (n=11) compared to the unmodified parental cell line (772±49 pg/$10^6$ cells/24h) (n=11). Both TGFβ1 (p=0.0128) and TGFβ2 (p=0.0042) secretion were significantly decreased compared to the unmodified parental cell line (Mann-Whitney U Test) (Table 25) (FIG. 9C).

Knockdown of TGFβ1 and TGFβ2 in LK-2 Cells

Figure 9D:
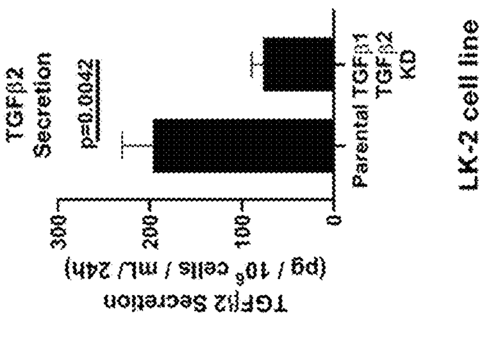

Neither the unmodified parental (n=9) nor the shRNA modified cell lines (n=9) secreted TGFβ1 above the lower limit of quantification of the ELISA assay. The combined knockdown of TGFβ1 and TGFβ2 in LK-2 reduced TGFβ2 secretion by 61% (77±12 pg/$10^6$ cells/24h) (n=10) compared to the unmodified parental cell line (197±34 pg/$10^6$ cells/24h) (n=10). TGFβ2 (p=0.0042) secretion were significantly decreased compared to the unmodified parental cell line (Mann-Whitney U Test) (Table 25) (FIG. 9D).

Knockdown of TGFβ1 and TGFβ2 in NCI-H1703 Cells

Figure 9E:
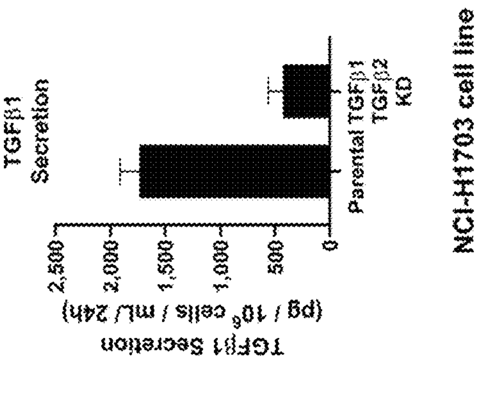

The combined knockdown of TGFβ1 and TGFβ2 in NCI-H1703 reduced TGFβ1 secretion by 75% (429±133 pg/$10^6$ cells/24h) (n=3) compared to the unmodified parental cell line (1,736±177 pg/$10^6$ cells/24h) (n=3). Both the unmodified parental (n=5) and shRNA modified cell lines (n=5) did not secret TGFβ2 above the lower limit of quantification of the ELISA assay (Table 25) (FIG. 9E).

Example 6: Downregulation of TGFβ1 and/or TGFβ2 Enhances Cellular Immune Responses Unmodified parental, TGFβ1 KD, TGFβ2 KD, or TGFβ1+R2 KD NCI-H460 cells were treated with 10 μg/mL MMC for 2 hours and then seeded in 6-well plate 24 hours prior to the addition of healthy donor PBMCs. PBMCs were co-cultured with the MMC treated NCI-H460 for 5-6 days in the presence of IL-2. On day 5 or 6, PBMCs were carefully isolated from the co-culture, counted, and loaded on pre-coated IFNγ ELISpot plates (MabTech). PBMCs were then stimulated with either MMC treated unmodified parental NCI-H460 cells or a mixture of 11 peptides comprising known MHC class I-restricted Survivin epitopes for 36-48 hours. IFNγ SFU were detected following the manufacturer's instructions, counted (CTL CRO Scanning Services), and expressed as the number of SFU/$10^6$ PBMCs.

Figure 10C:
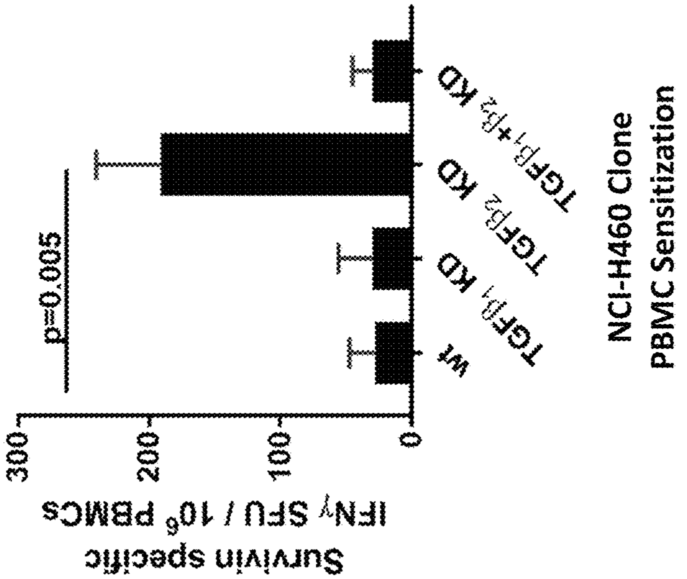
FIGS. 10A-C show that knockdown of TGFβ1, TGFβ2, or TGFβ1 and TGFβ2 in the NCI-H460 cell line significantly increases IFNγ responses against the parental NCI-H460 cells and the Survivin (BIRC5) antigen.
Figure 10B:
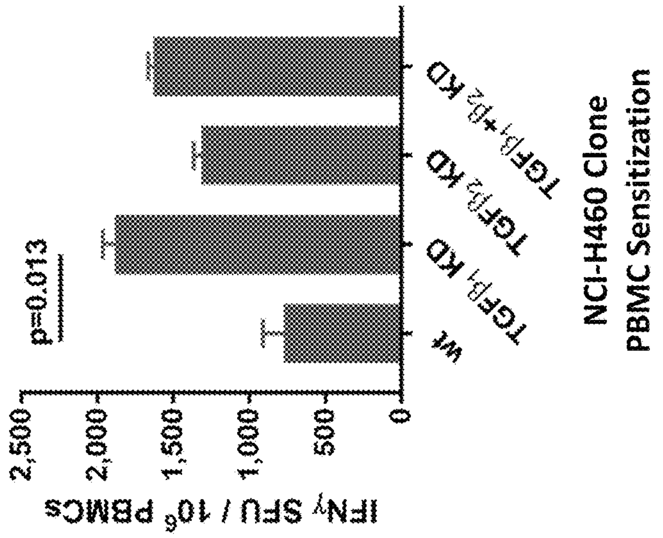
Figure 10A:
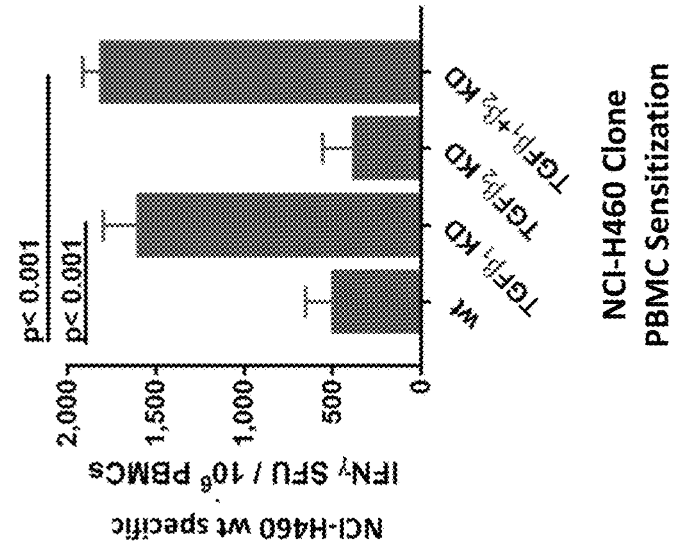

Healthy donor (HLA-A*01, HLA-A*02) derived PBMCs sensitized with TGFβ1 KD NCI-H460 significantly increases cellular immune responses (1613±187 SFU), compared to sensitization with the unmodified parental NCI-H460 (507±152 SFU) (p<0.001) (FIG. 10A). Knockdown of both TGFβ1 and TGFβ2 also significantly increased IFNγ responses (1823±93 SFU) (p<0.001) compared to unmodified parental NCI-H460. Knockdown of TGFβ2 did not increase IFNγ production relative to the unmodified parental cell line (390±170 SFU) (p=0.692). The increase in immune responses with knockdown of TGFβ1 and TGFβ2 is likely attributed to the effects of TGFβ1 knockdown because TGFβ2 knockdown alone did not enhance immunogenicity. In PBMCs derived from a different donor (HLA-A*01, HLA-A*11) knockdown of TGFβ1 in NCI-H460 significantly increased cellular immune responses (1883±144 SFU), compared to sensitization with the unmodified parental NCI-H460 (773±236 SFU) (p=0.013) (FIG. 10B). Knockdown of TGFβ2 alone (1317±85 SFU (p>0.999) and of both TGFβ1 and TGFβ2 (1630±62) (p=0.249) also increased IFNγ responses relative to sensitization with unmodified parental NCI-H460 cells but did not reach statistical significance.

Survivin (BIRC5) is a well characterized TAA that is overexpressed in multiple cancer immunotherapy indications. FIG. 10C demonstrates significantly more robust MHC class I-restricted responses to Survivin in the IFNγ ELISpot assay when donor PBMCs are sensitized with NCI-H460 TGFβ2 KD cells (192±120 SFU) compared to unmodified parental NCI-H460 cells (28±44) (p=0.005). PBMC sensitization with NCI-H460 TGFβ1 KD (30±64) (p=0.999) or TGFβ1 and TGFβ2 KD (30±38) (p=0.999) did not demonstrate a significant increase in Survivin specific IFNγ production in two independent experiments.

Figure 11A:
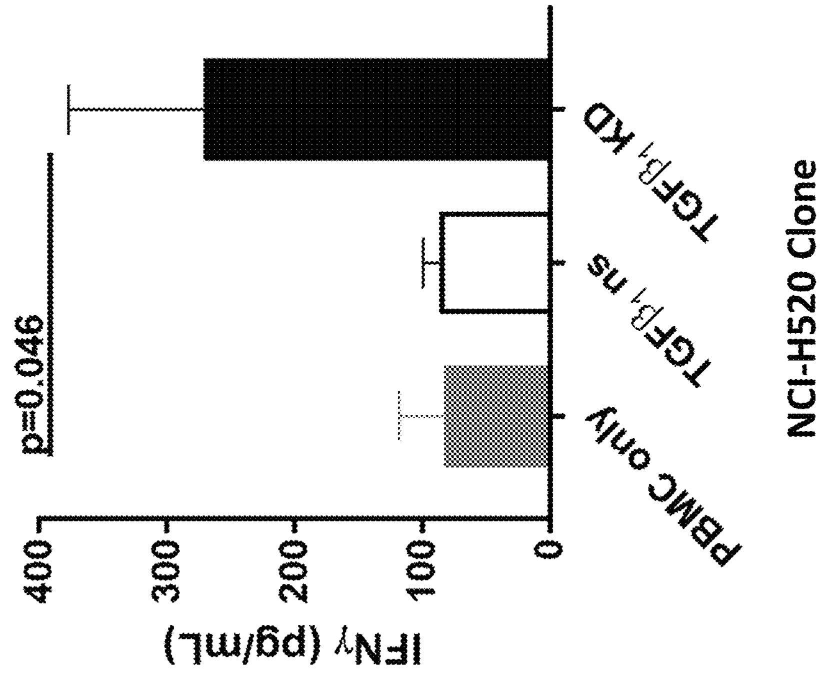
FIGS. 11A and B show that loading dendritic cells (DCs) with lysate from NCI-H520 TGFβ1 KD cells increases IFNγ responses against parental NCI-H460 cells upon re-stimulation in the IFNγ ELISpot assay and in the mixed lymphocyte co-culture assay.

The effect of TGFβ1 KD on immunogenicity of this vaccine approach was further characterized in PBMCs isolated from the two healthy donors (HLA-A*24, HLA-A*30) (HLA-A*02, HLA-A*68) in the mixed lymphocyte co-culture reaction (n=3/donor). PBMCs cultured alone, or co-cultured with NCI-H520 TGFβ1 nonsense control or TGFβ1 KD cells in the presence of IL-2 for 10 days. PBMCs cultured without tumor cells served as an additional control. IFNγ secretion was measured in the co-culture supernatant by ELISA on day 10 (FIG. 11A). IFNγ secretion was significantly increased, compared to PBMCs alone (83±86 μg/mL), in the supernatant of PBMCs co-cultured with NCI-H520 TGFβ1 KD cells (272±259 pg/mL) (p=0.046). There was not a significant increase in IFNγ secretion in the supernatant of the NCI-H520 TGFβ1 nonsense KD (86±32 pg/mL) (p=0.512) compared to PBMCs alone.

Figure 11B:
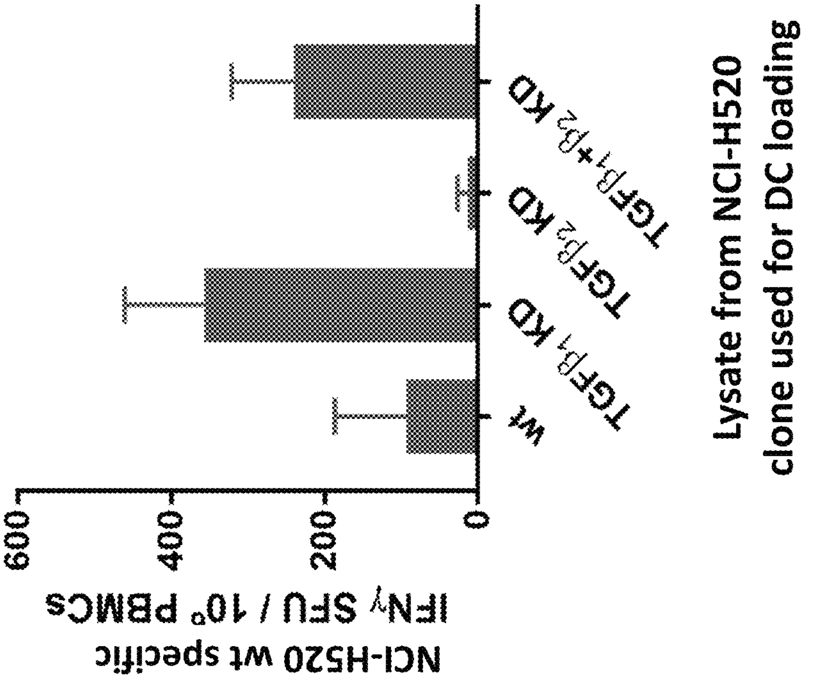

The impact of TGFβ1 knockdown on the immunogenicity of NCI-H520 was further evaluated in an autologous PBMC DC co-culture assay. DCs, differentiated from monocytes isolated from a healthy donor (HLA-A*24, HLA-A*30), were loaded with cell lysate from NCI-H520 unmodified parental cells, TGFβ1 KD, TGFβ2 KD, or TGFβ1+R2 KD cells. Autologous PBMCs were co-cultured with lysate loaded DCs for 5-6 days in the presence of 20 U/mL of IL-2. On day 5 or 6, PBMCs were carefully isolated from the co-culture, counted, and $1\times10^5$ plated per well on pre-coated IFNγ ELISpot plates (MabTech). PBMCs were then stimulated with MMC treated unmodified parental NCI-H520 cells for 36-48 hours. The results indicated that there was a trend towards TGFβ1 KD increasing cellular immune responses to NCI-H520 unmodified parental cells (357±181 SFU), assayed by IFNγ ELISpot, compared to unmodified parental NCI-H520 cells (93±162 SFU) (p=0.181) (FIG. 11B). IFNγ responses to unmodified parental NCI-H520 cells induced in autologous PBMCs co-cultured with lysate from NCI-H520 TGFβ2 KD (13±23 SFU) (p=0.897) and TGFβ1 and TGFβ2 KD (240±142 SFU) (p=0.603) did not significantly increase IFNγ responses compared to autologous PBMCs co-cultured with NCI-H520 (ATCC HTB-182) unmodified parental lysate loaded DCs. Despite not reaching statistical significance, cellular immune responses induced by co-culture of autologous PBMCs with DCs loaded with NCI-H520 TGFβ1 KD and TGFβ1 and TGFβ2 KD were more robust than those with NCI-H520 TGFβ2 KD and unmodified parental lysate.

Figure 12:
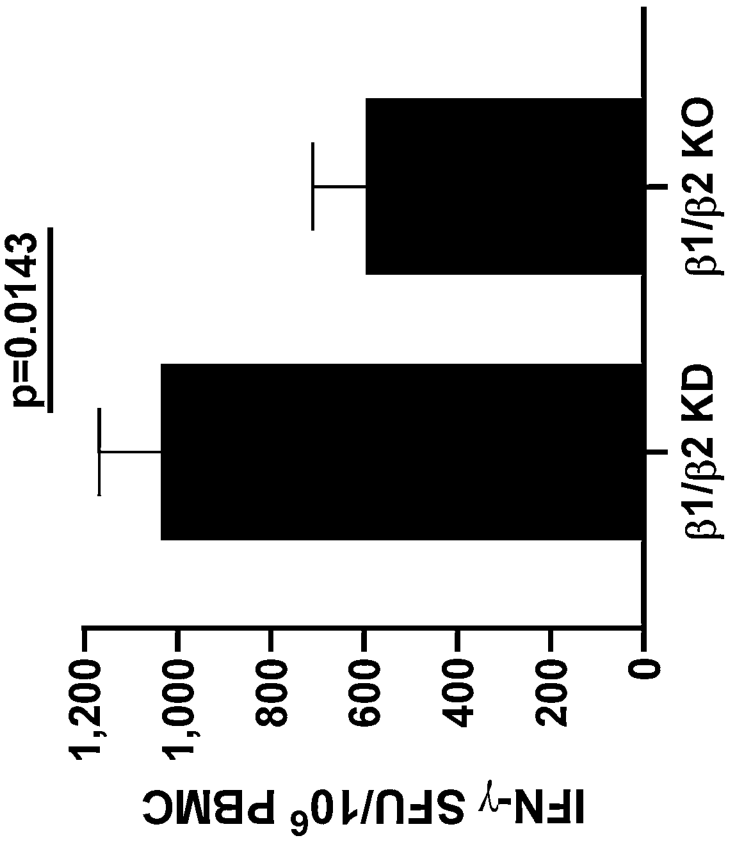
FIG. 12 shows the IFNγ response comparison between TGFβ1 TGFβ2 knockdown and knockout.

Example 7: shRNA Downregulation of TGFβ Induces Stronger Immune Responses than TGFβ Knockout in Cell Lines In vitro data suggest that a complete knockout of TGFβ1 and TGFβ2 was less effective at inducing responses against tumor cells than shRNA knockdown of the two molecules. A representative assay is shown in FIG. 12. Normal donor PBMC were cocultured with either TGFβ1/TGFβ2 shRNA modified or NCI-H460 or TGFβ1/TGFβ2 ZFN knockout NCI-H460 prior to analysis in an IFNγ ELISpot assay. The data show that the shRNA modified cells induced significantly better IFNγ secretion than ZFN-knockout cells (p=0.0143, unpaired t-test). For this experiment, 5 individual donors were tested for a total of 24 replicates for the shRNA modified cells and 31 replicates for the knockout cells.

Figure 13:
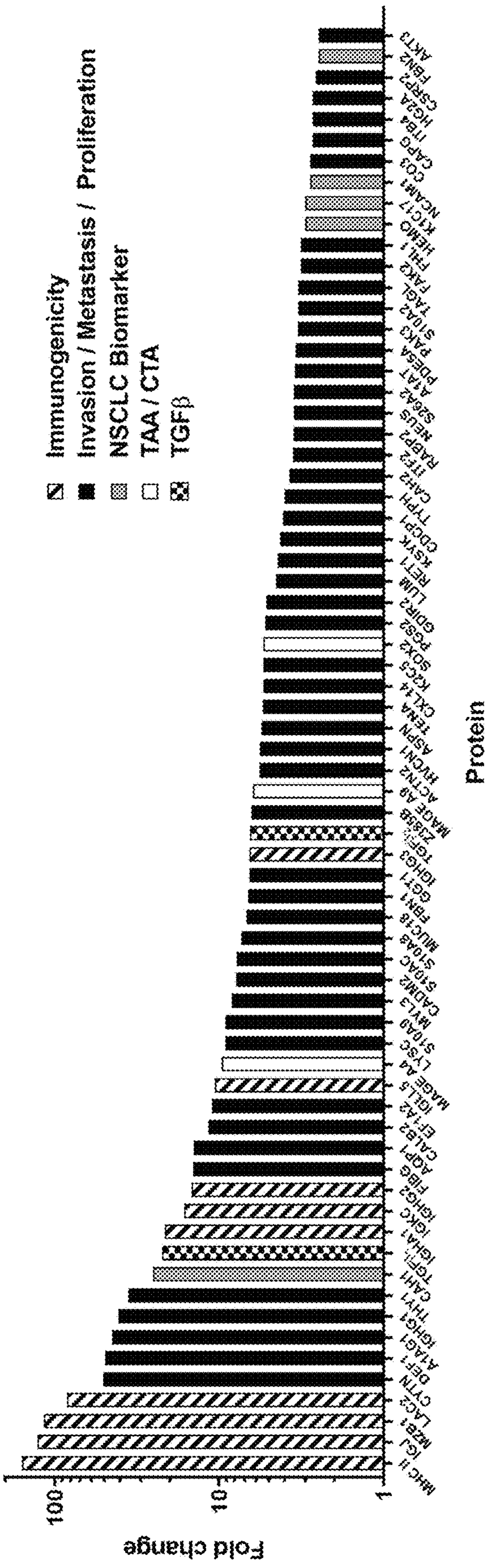
FIG. 13 shows the proteomic comparison between TGFβ1 TGFβ2 knockdown and knockout.
Figure 14A:
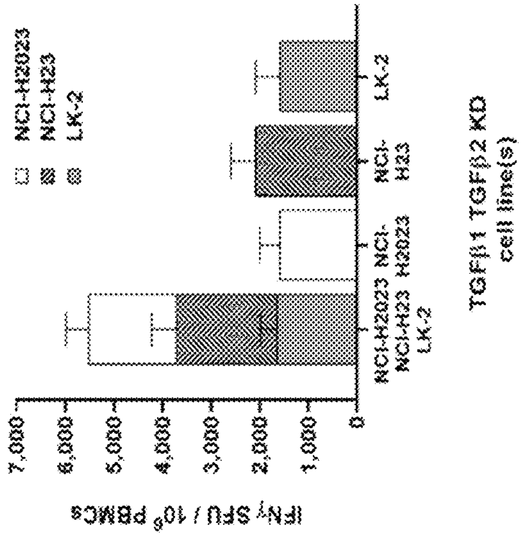
FIGS. 14A-F show IFNγ responses against unmodified parental cell lines elicited by exemplary combinations of TGFβ1 and/or TGFβ2 modified cell lines.
Figure 14B:
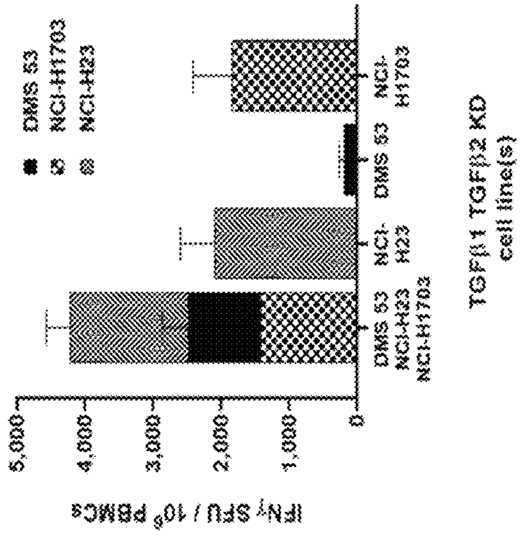
Figure 14C:
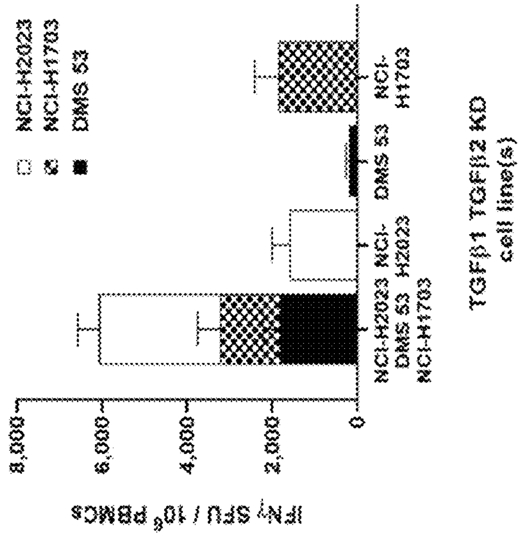
Figure 14D:
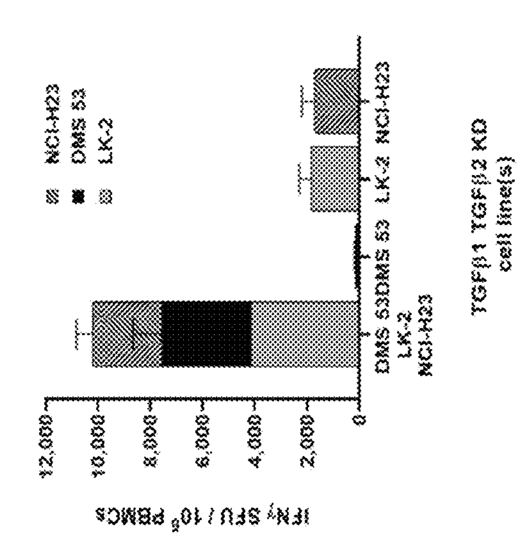
Figure 14E:
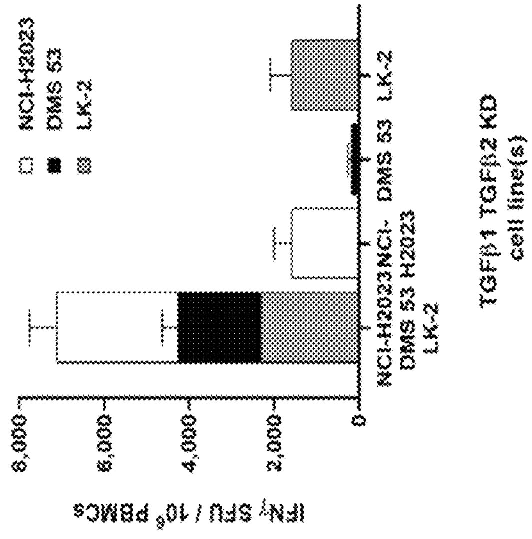
Figure 14F:
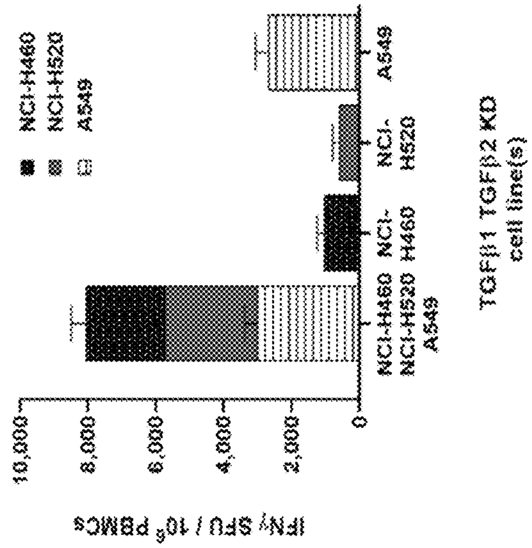

Because TGFβ1 is a key player in regulating the epithelial-mesenchymal transition, complete lack of TGFβ1 induces a less immunogenic phenotype in tumor cells (Miyazono, K et al., Frontiers of Medicine. 2018). This was discernable when compared the ratio of the expression of important immune response-related proteins in TGFβ1 TGFβ2 shRNA knockdown in NCI-H460 compared to knockout (FIG. 13). The knockdown cells expressed high levels of immunogenic proteins and TAAs compared to the knockout cells.

Collectively, the data presented in Examples 6 and 7 demonstrate that reduction of TGFβ1 and/or TGFβ2 can increase cellular immune responses to unmodified parental tumor cells and antigens in the context of an allogenic whole cell vaccine. Further, these data demonstrate that shRNA mediated knockdown induces more robust immune responses compared to knockout of TGFβ1 and TGFβ2.

Example 8. Immunogenicity of Combinations of Cell Lines with shRNA Mediated Downregulated TGFβ1 and/or TGFβ2 Secretion Immunogenicity of example combinations of cell lines with reduced TGFβ1 and/or TGFβ2 secretion were determined by IFNγ ELISpot as described in Example 2 with modifications. Two different responses were evaluated, first for the combinations of cell lines and second for known tumor associated, tumor-specific, and cancer-testis antigens (collectively referred to as antigens). To assess immune responses generated by the combinations of cell lines, DCs were loaded at a 1.0:0.33 DC to cell line ratio such that the ratio of DCs to total cell line was 1:1. Specifically, $1.5\times10^6$ DCs were cocultured with $5.0\times10^6$ cell line 1, $5.0e^5$ cell line 2, and $5.0e^5$ cell line 3.

To assess responses to antigens, CD14-PBMCs isolated from co-culture with mDCs on day 6 were stimulated with antigen specific peptide pools in the IFNγ ELISpot assay for 24 hours prior to detection of IFNγ SFU. Antigen specific responses are expressed as the number of SFU/$10^6$ PBMCs above that of the controls. Antigen peptide pools were acquired from the commercial sources as follows: Mage A1 (JPT, PM-MAGEA1), Mage A3 (JPT, PM-MAGEA3), Mage A4 (JPT, PM-MAGEA4), CEACAM (CEA) (JPT, PM-CEA), MUC1 (JPT, PM-MUC1), Survivin (thinkpeptides, 7769_001-011), PRAME (Miltenyi Biotec, 130-097-286), WT1 (JPT, PM-WT1), TERT (JPT, PM-TERT), STEAP (PM-STEAP1), and HER2 (JPT, PM-ERB_ECD). Immune responses were determined in using cells derived from HLA-A02 (Donors 1-3) and HLA-A11 (Donor 4) healthy donors (n=2-3/cell line/donor).

Immunogenicity of the six example combinations of three TGFβ1 and/or TGFβ2 modified cell lines were determined by IFNγ ELISpot (FIG. 14).

Example vaccine cell line Combination 1 was composed of NCI-2023, NCI-H23, and LK-2 TGFβ1 and TGFβ2 modified cell lines. The cell line combination elicited a total IFNγ response of 5,499±1,016 SFU (n=9/3 donors) consisting of 1,800±553 SFU to NCI-2023, 2,069±393 SFU to NCI-H23, and 1,630±102 SFU to LK-2 (FIG. 14A) (Table 26). Example vaccine cell line Combination 2 was composed of the NCI-H23, DMS 53, and NCI-H1703 TGFβ1 and/or TGFβ2 modified cell lines. This example vaccine combination elicited a total IFNγ response of 3,604±1,491 SFU (n=9/3 donors) consisting of 1,738±529 SFU to NCI-H23, 826±457 SFU to DMS 53, and 1,041±555 SFU to NCI-H1703 (FIG. 14B) (Table 26). Example vaccine cell line Combination 3 was composed of NCI-H2023, DMS 53, and NCI-H1703 TGFβ1 and/or TGFβ2 modified cell lines. This example cell line combination induced a total IFNγ response of 6,065±941 SFU (n=9/3 donors) consisting of 2,847±484 SFU to NCI-H2023, 1,820±260 SFU to DMS 53, and 1,398±309 SFU to NCI-H1703 (FIG. 14C) (Table 26). Example vaccine cell line Combination 4 consisted of NCI-H23, DMS 53, and LK-2 TGFβ1 and/or TGFβ2 modified cell lines. This example cell line combination induced a total IFNγ response of 9,612±5,293 SFU (n=12/4 donors) consisting of 2,654±1,091 SFU to NCI-H23, 3,017±1,914 SFU to DMS 53, and 3,942±2,474 SFU to LK-2. (FIG. 14D) (Table 26). Example vaccine cell line Combination 5 consisted of NCI-H2023, DMS 53, and LK-2 TGFβ1 and/or TGFβ2 modified cell lines. This example cell line combination induced a total IFNγ response of 6,358±2,278 SFU (n=9/3 donors) consisting of 2,869±1,150 SFU to NCI-H2023, 1,698±568 SFU to DMS 53, and 1,791±637 SFU to LK-2 (FIG. 14E) (Table 26). Example vaccine cell line Combination 6 consisted of NCI-H460, NCI-H520, and A549 TGFβ1 and TGFβ2 modified cell lines. This example cell line combination induced a total IFNγ of 8,407±1,535 SFU (n=12/4 donors) comprising of 2,320±666 SFU to NCI-H460, 2,723±644 SFU to NCI-H520, and 3,005±487 SFU to A549 (FIG. 14F) (Table 26).

For some exemplary cell line combinations, IFNγ responses against the individual unmodified parental cell lines were enhanced when PBMCs were co-cultured with DCs presenting antigens from three vaccine cell line combinations relative to PBMCs co-cultured with DCs presenting antigens from a single vaccine cell line component (Table 26). The immune responses induced by three cell line combinations were more robust than the response induced by each individual cell line.

TABLE 26

IFNγ responses against cell lines in example combinations or against single individual vaccine component cell lines

| | Three Vaccine Cell Line Combination (SFU) | Single Vaccine Cell Line Component (SFU) |
|---|---|---|
| Cell Line Combination 1 | | |
| NCI-2023 | 1,800 ± 553 | 903 ± 136 |
| NCI-H23 | 2,069 ± 393 | 1,014 ± 773 |
| LK-2 | 1,630 ± 102 | 1,573 ± 935 |
| Cell Line Combination 2 | | |
| NCI-H23 | 1,738 ± 529 | 1,014 ± 773 |
| DMS 53 | 826 ± 457 | 227 ± 227 |
| NCI-H1703 | 1,041 ± 555 | 724 ± 724 |
| Cell Line Combination 3 | | |
| NCI-H2023 | 2,847 ± 484 | 903 ± 136 |
| DMS 53 | 1,820 ± 260 | 227 ± 227 |
| NCI-H1703 | 1,398 ± 309 | 724 ± 724 |
| Cell Line Combination 4 | | |
| NCI-H23 | 2,654 ± 1,091 | 1,567 ± 788 |
| DMS 53 | 3,017 ± 1,914 | 138 ± 85 |
| LK-2 | 3,942 ± 2,474 | 1,592 ± 965 |

TABLE 26-continued

IFNγ responses against cell lines in example combinations or against single individual vaccine component cell lines

| | Three Vaccine Cell Line Combination (SFU) | Single Vaccine Cell Line Component (SFU) |
|---|---|---|
| Cell Line Combination 5 | | |
| NCI-H2023 | 2,869 ± 1,150 | 903 ± 136 |
| DMS 53 | 1,698 ± 568 | 227 ± 227 |
| LK-2 | 1,791 ± 637 | 1,573 ± 935 |
| Cell Line Combination 6 | | |
| NCI-H460 | 2,320 ± 666 | 970 ± 281 |
| NCI-H520 | 2,723 ± 644 | 596 ± 336 |
| A549 | 3,005 ± 487 | 2,677 ± 632 |

Figure 15B:
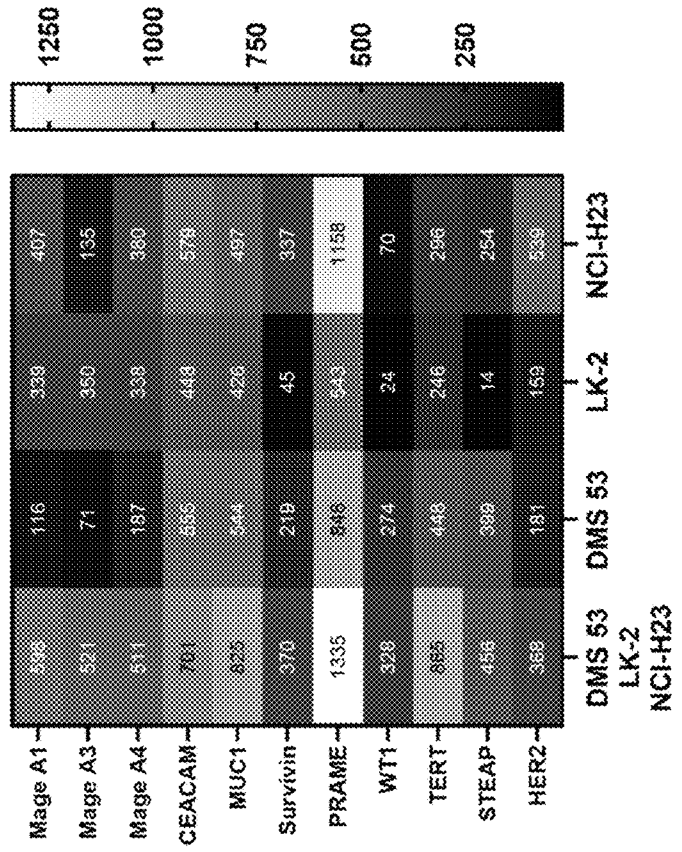
FIGS. 15A and B show IFNγ responses to cancer antigens elicited by exemplary combinations of TGFβ1 and/or TGFβ2 modified cell lines.
Figure 15A:
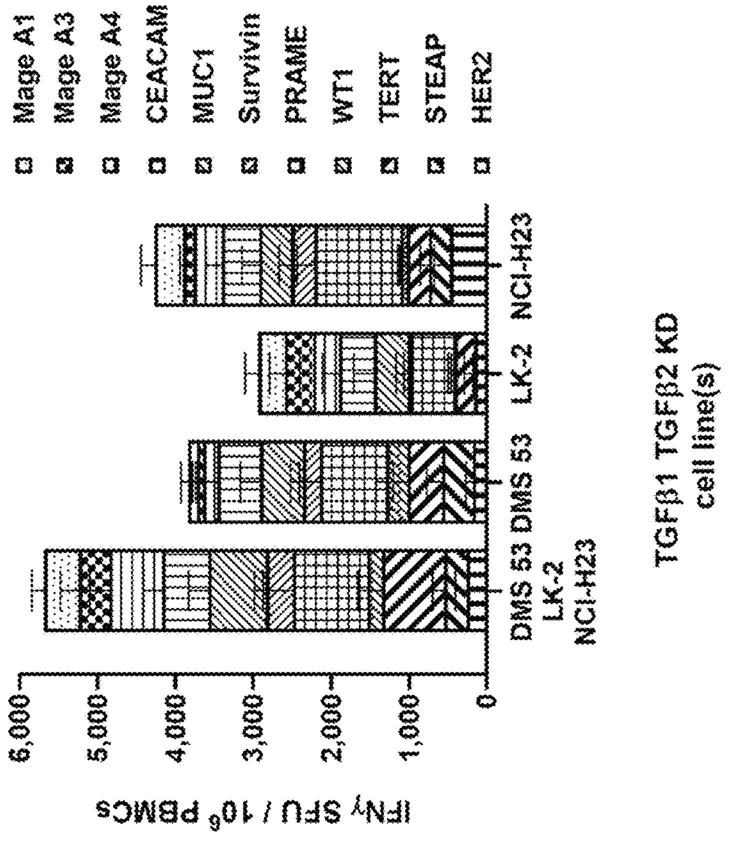

IFNγ responses to 11 antigens were determined for the example vaccine Combination 4 (NCI-H23, DMS 53, and LK-2 TGFβ1 and/or TGFβ2 modified cell lines). Responses against the antigens Mage A1, Mage A3, Mage A4, CEACAM (CEA), MUC1, Survivin, PRAME, WT1, TERT, STEAP, and HER2 were assessed in 3 HLA-A02 health donors (n=3/donor). Example vaccine Combination 4 induced antigen specific IFNγ responses greater in magnitude 5,423±427 SFU (FIG. 15A) and breadth (FIG. 15B) compared to the single vaccine component TGFβ1 and/or TGFβ2 modified cell lines; NCI-H23 (4,1115±2,118 SFU), DMS 53 (3,661±1,982 SFU), and LK-2 (2,772±2,936 SFU). Responses to specific antigens are in the order indicated in the figure legends. The average IFNγ response to each antigen induced by the single component and combination cell line vaccines are detailed in FIG. 15B.

Example 9: Reduction of HLA-E Expression Improves Cellular Immune Responses

HLA-E belongs to the HLA class I heavy chain paralogues. Human tumor cell surface expression of HLA-E can inhibit the anti-tumor functions of NK, DC, and CD8 T cells through binding to the NKG2A receptor on these immune cell subsets.

Reduction of HLA-E Expression in the RERF-LC-Ad1 Cell Line (JCRB1020)

The human adenocarcinoma cell line RERF-LC-Ad1 was electroporated with a zinc finger nuclease (ZFN) pair specific for HLA-E targeting the following genomic DNA sequence: TACTCCTCTCGGAGGCCCTGgcccttACCCAGACCTGGGCGGGT (SEQ ID NO: 33). Full-allelic knockout cells were identified by flow cytometry after staining with PE-conjugated anti-human HLA-E (BioLegend, clone 3D12) then FACS sorted. Cells were expanded after sorting and percent knockout determined. The MFI of the unstained control of the HLA-E KO or unmodified parental cell was subtracted from the MFI of the HLA-E KO or unmodified parental cells stained with PE-conjugated anti-human HLA-E (BioLegend, clone 3D12). Gene editing of HLA-E by ZFN resulted in greater than 99% HLA-E negative cells after FACS sorting (FIG. 16A). Knockout percentage is expressed as: (RERF-LC-Ad1 HLA-E KO MFI/Parental MFI)×100.

Reduction of HLA-E Expression Improves Immune Responses

IFNγ ELISpot was completed as described in Example 8 with one modification. In this experiment iDC were loaded with only one cell line, RERF-LC-Ad1 parental or HLA-E KO cell lines. Here, $1.5\times10^6$ DCs were loaded with $1.5\times10^6$ RERF-LC-Ad1 parental or HLA-E KO cells. IFNγ responses were 1.8-fold higher when autologous PBMCs were co-cultured with DCs loaded with HLA-E negative cells (5085±1157 SFU) relative to DCs loaded with the unmodified parental HLA-E positive cells (2810±491 SFU). Student's test, p=0.012. n=12, 3 HLA-A diverse donors (FIG. 16B).

Example 10: Reduction of Cytotoxic T-Lymphocyte-Associated Protein 4 (CTLA-4) Expression Increases Cellular Immune Responses CTLA-4 (CD152) functions as an immune checkpoint and is constitutively expressed on some tumor cells. CTLA-4 binding to CD80 or CD86 on the surface of DCs can negatively regulate DC maturation and inhibit proliferation and effector function of T cells.

Reduction of CTLA-4 Expression in Human Squamous Cell Line

Figure 17A:
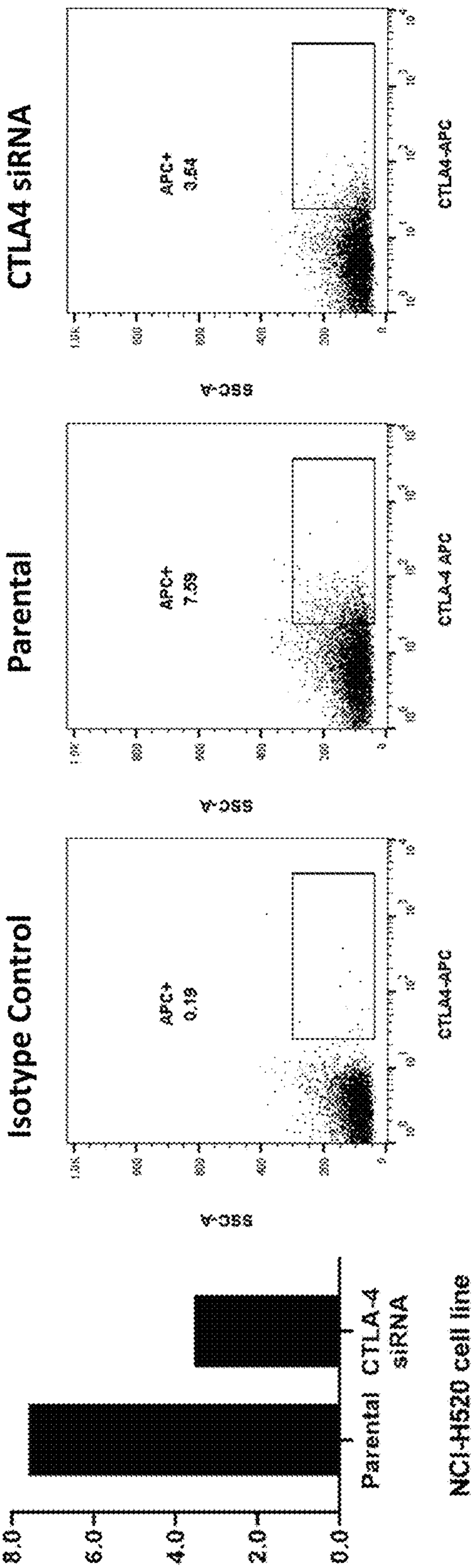
FIGS. 17A and B show reduction of CTLA-4 expression in the NCI-H520 cell line increases cellular immune responses.

The NCI-H520 cell line was transfected with siRNA targeting CTLA-4 (Dharmacon, L-016267-00-0050). Cells were seeded at $6\times10^5$ in each well of a six well plate in antibiotic-free media and incubated at 37° C. in 5% $CO_2$. Following DharmaFect siRNA transfection protocol, each well was transfected with a 25 nM final concentration of CTLA-4 siRNA using 4 uL of DharmaFECT 1 Transfection Reagent (Dharmacon, T-20001-01) per well. Reduction of CTLA-4 expression on live cells was determined by flow cytometry 72 hours after siRNA transfection prior to use in the IFNγ ELISpot assay. Specifically, NCI-H520 cells were stained with LIVE/DEAD™ Aqua (Invitrogen, L34965) and human α-CTLA4-APC (BioLegend, clone L3D10). siRNA reduced NCI-H520 cell surface expression of CTLA-4 (3.59%) 2.1-fold compared to unmodified parental NCI-H520 (7.59%) (FIG. 17A).

Figure 17B:
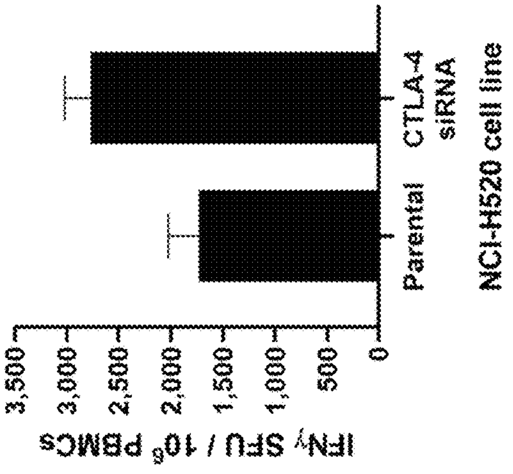

Reduction of CTLA-4 Expression in the NCI-H520 (ATCC HTB-182) Cell Line Increases Cellular Immune Responses The impact of reducing cell surface expression of CTLA-4 on cellular immune responses was evaluated in the IFNγ ELISpot assay using cells derived from an HLA-A 02:01 donor. The ELISpot was initiated 72 hours after siRNA transfection and carried out as described in Example 9. Reduction of CTLA-4 expression in NCI-H520 was associated with a 1.6-fold increase in IFNγ responses (2,770±180 SFU) (n=2) compared to the unmodified parental cell line (1,730±210 SFU) (n=2) (FIG. 17B).

Example 11. Reduction of CD276 Expression in the A549 Cell Line Enhances Cellular Immune Responses CD276 (B7-H3) is an immune checkpoint member of the B7 and CD28 families. Over expression of CD276 in human solid cancers can induce an immunosuppressive phenotype and preferentially down-regulates Th1-mediated immune responses.

Figure 18B:
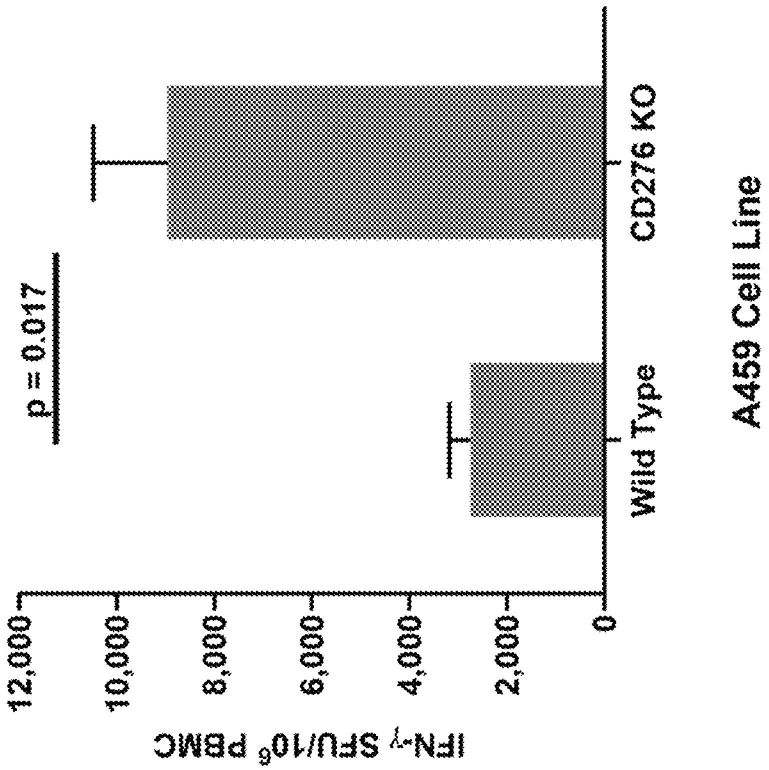
FIGS. 18A and B show reduction of CD276 in the A549 cell line increases cellular immune responses.
Figure 18A:
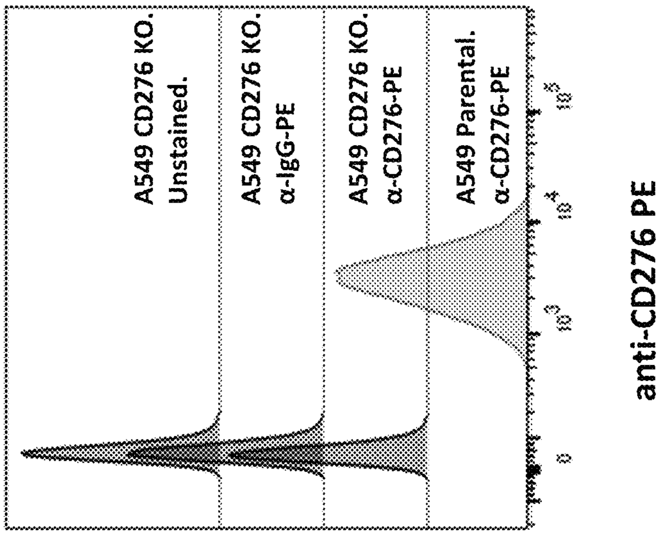

Reduction of CD276 expression in A549 was completed using the CRISPR-Cas9 system with guide RNA specific for TGCCCACCAGTGCCACCACT (SEQ ID NO: 117) (Synthego). The initial heterogenous population contained 71% A549 cells where CD276 expression was reduced. The heterogenous population was surface stained with BB700-conjugated α-human CD276 (BD Biosciences, clone 7-517) and full allelic knockout cells enriched by cell sorting (BioRad S3e Cell Sorter). The reduction of CD276 was confirmed by extracellular staining of the sort enriched A540 CD276 KO cells and parental A549 cells with PE α-human CD276 (BioLegend, clone DCN.70). Unstained and isotype control PE α-mouse IgG1 (BioLegend, clone MOPC-21) stained A549 CD276 KO cells served as controls. Cas9-mediated gene editing of CD276 resulted in >99% reduction of CD276 compared to controls (FIG. 18A).

In a representative experiment, iDCs were loaded A549 parental cells or A549 CD276 KO cells and co-cultured with autologous CD14-PBMCs for 6 days prior to stimulation with autologous DCs loaded with cell lysate from wild type A549. Cells were then assayed for IFNγ secretion against wild type A549 cells in an ELISpot assay. These data show that CD276 KO cells are better stimulators than the wild type cells (p=0.017; unpaired t test) (FIG. 18B).

Example 12: Reduction of CD47 Expression and TGFβ1 and/or TGFβ2 Secretion

Methods for shRNA downregulation of TGFβ1 and TGFβ1 and determine levels of secreted TGFβ1 and TGFβ2 are described in Example 5.

Reduction of CD47 Expression in Human Lung Cancer Lines with shRNA Downregulated TGFβ1 and or TGFβ2

The A549, NCI-H460, NCI-H2023, NCI-H23, NCI-H520, LK-2, and NCI-H1703 that were modified to decrease secretion of TGFβ1 and/or TGFβ2 were further modified to reduce expression of CD47 as described in Example 2 and additional methods described here. Following ZEN-mediated knockout of CD47, the cell lines were surface stained with FITC-conjugated α-CD47 (BD Biosciences, clone B6H12) and full allelic knockout cells enriched by cell sorting (BioRad S3e Cell Sorter). The cells were collected using a purity sorting strategy to ensure the collection of only CD47 negative cells. The sorted cells were plated in an appropriately sized vessel based on cell number, grown and expanded. After cell enrichment for full allelic knockouts, the TGFβ1 and/or TGFβ2 KID CD47 KO cells were passaged 2-5 times and CD47 knockout percentage determined by flow cytometry (BV421-conjugated human αCD47, BD Biosciences, clone 1B61H12). The MFI of the unstained controls for the modified or unmodified parental cells were subtracted from the MFI of the modified or unmodified parental cells stained with BV421-conjugated human α-CD47. CD47 knockout percentage is expressed as: (1−(TGFβ1/TGFβ2 KD CD47 KO MFI/Parental MFI))×100).

Figures 19A, 19B, 19C, 19D:
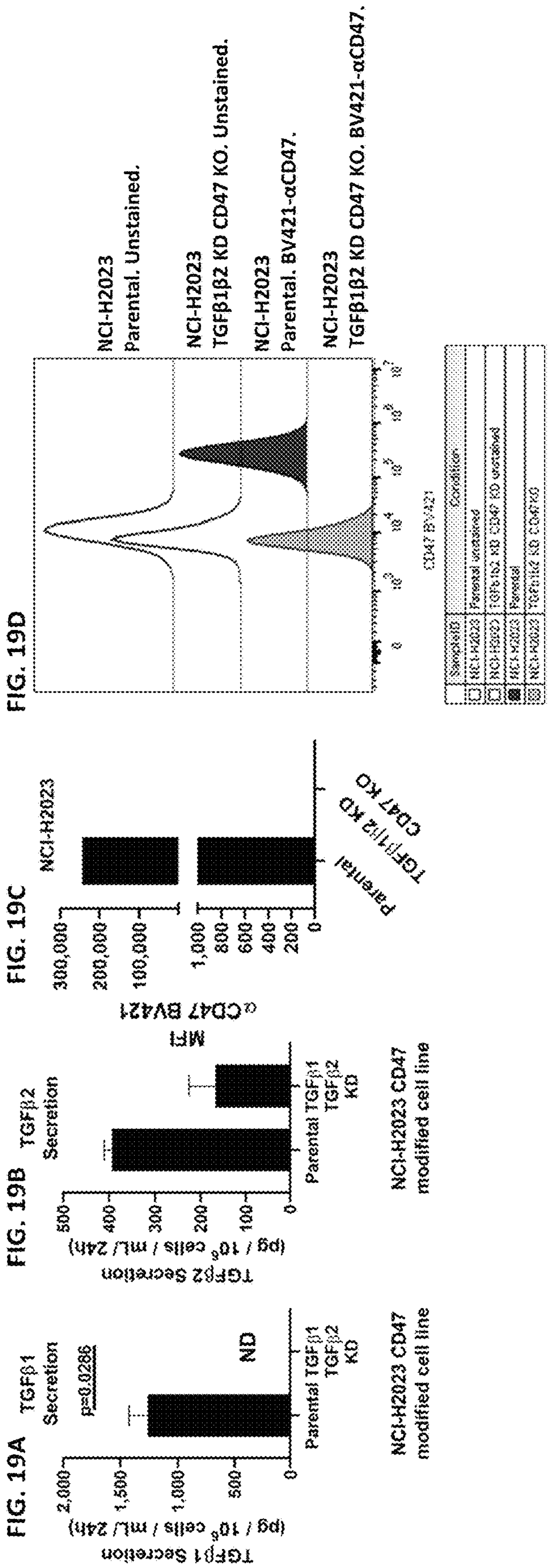
FIGS. 19A-D show reduction of CD47 expression and TGFβ1 and TGFβ2 secretion in the NCI-H2023 cell line.
Figure 20A:
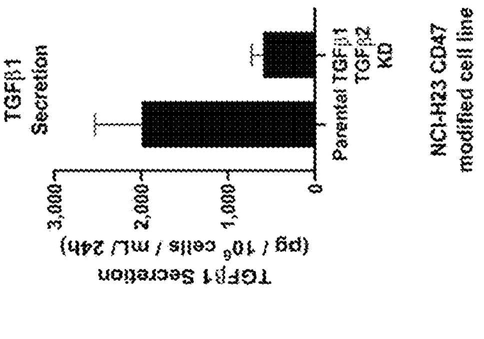
FIGS. 20A-D show reduction of CD47 expression and TGFβ1 and TGFβ2 secretion in the NCI-H23 cell line.
Figure 20B:
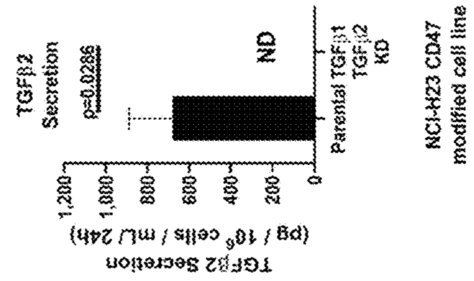
Figure 20C:
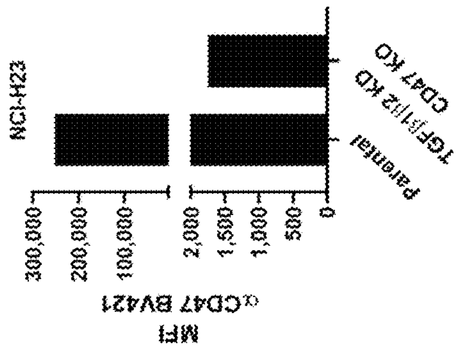
Figure 20D:
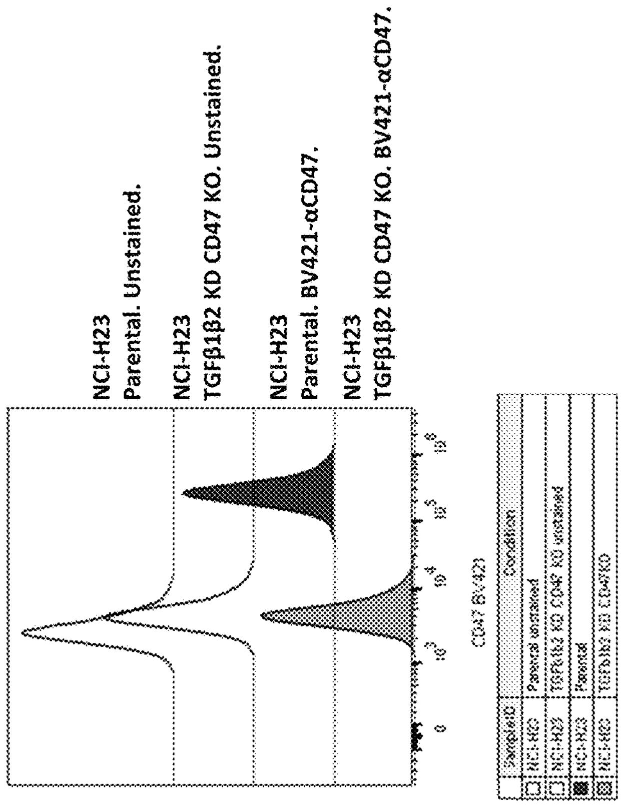
Figure 21A:
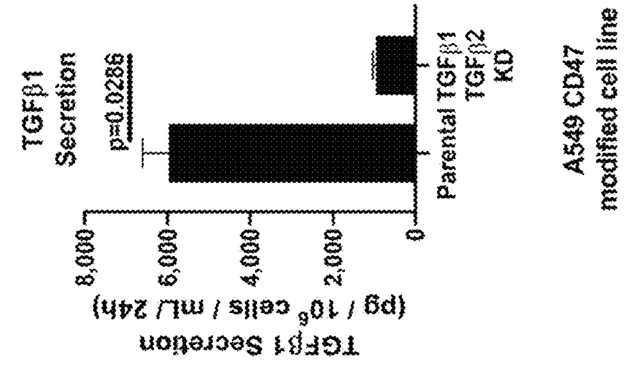
FIGS. 21A-D show reduction of CD47 expression and TGFβ1 and TGFβ2 secretion in the A549 cell line.
Figure 21B:
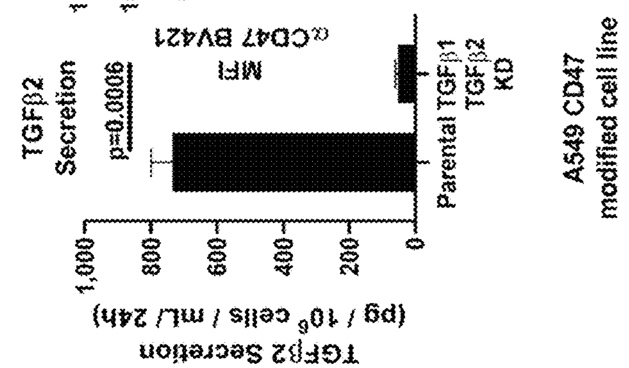
Figure 21C:
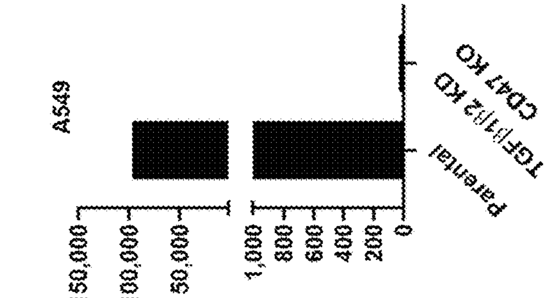
Figure 21D:
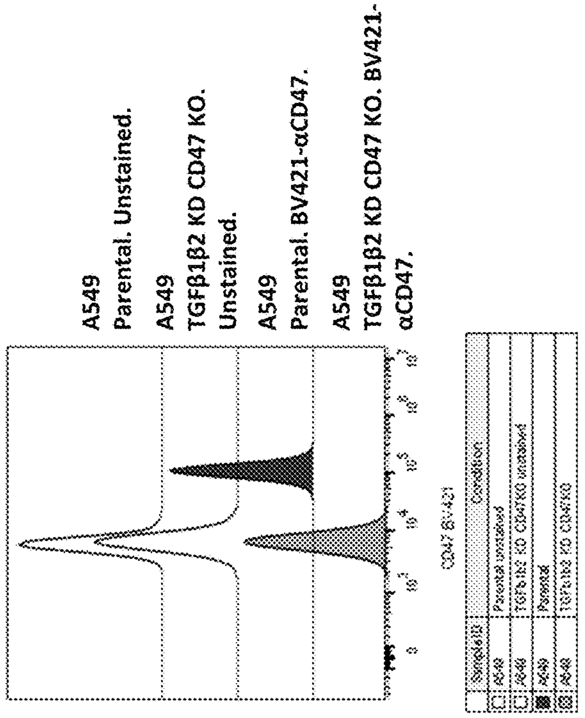
Figure 22A:
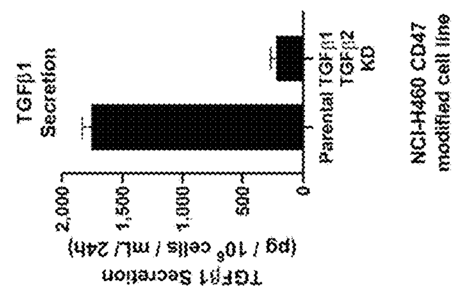
FIGS. 22A-D show reduction of CD47 expression and TGFβ1 and TGFβ2 secretion in the NCI-H460 cell line.
Figure 22B:
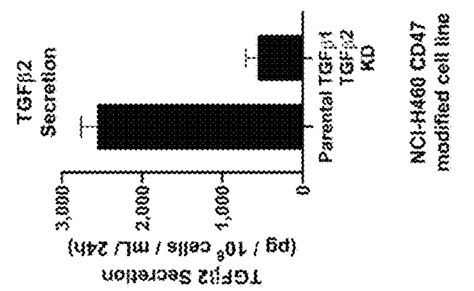
Figure 22C:
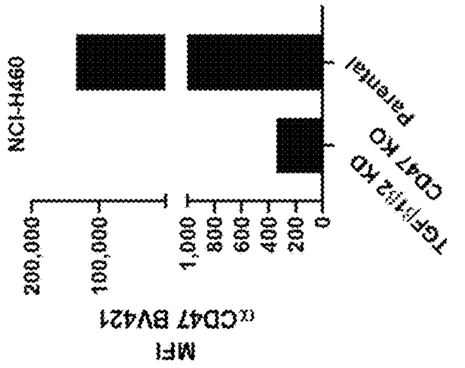
Figure 22D:
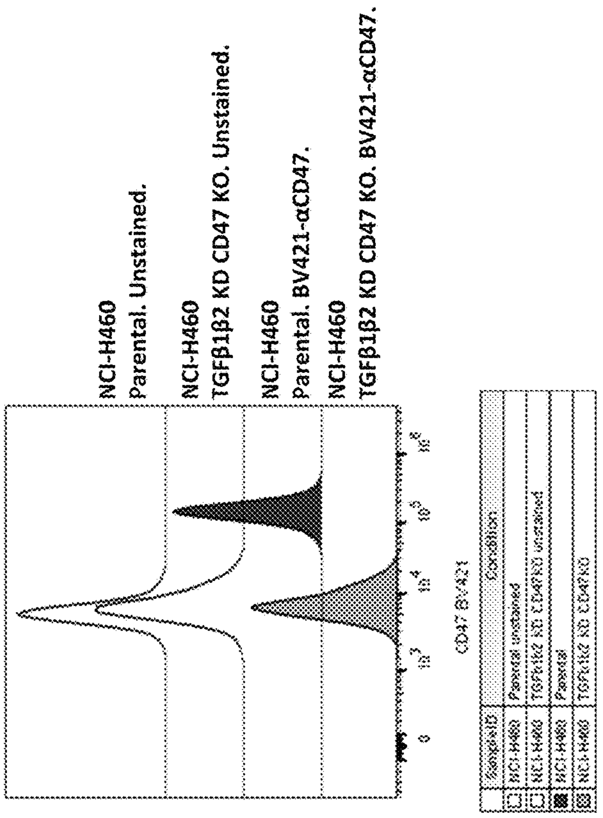
Figure 23A:
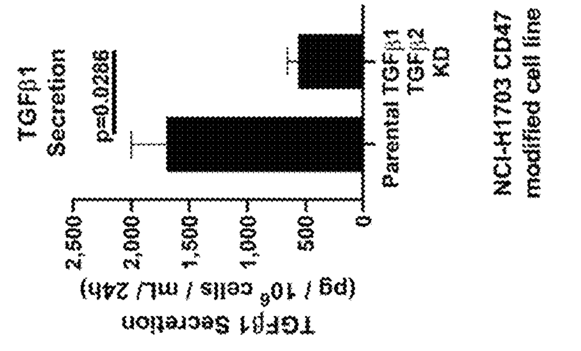
FIGS. 23A-C show reduction of CD47 expression and TGFβ1 secretion in the NCI-H1703 cell line.
Figure 23B:
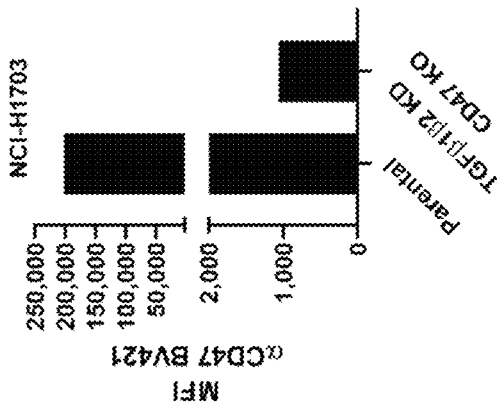
Figure 23C:
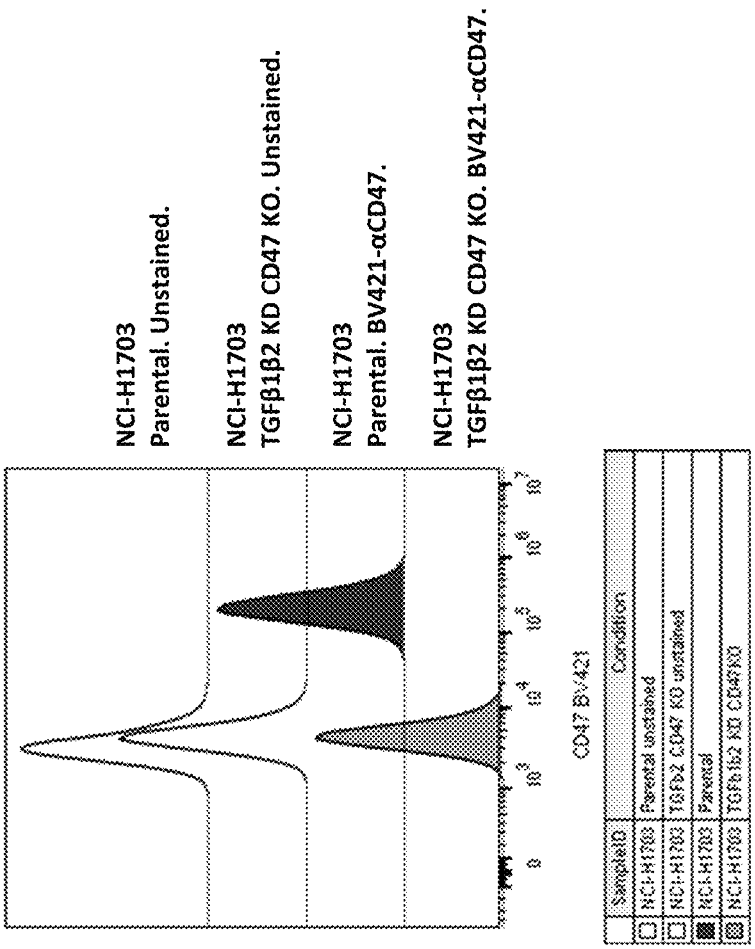
Figure 24A:
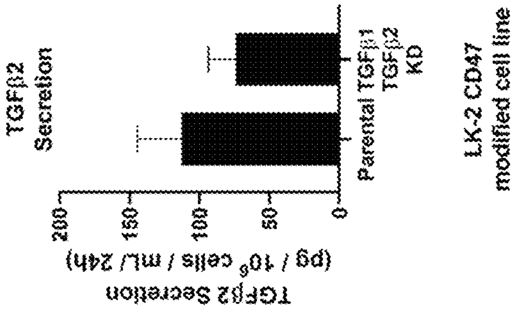
FIGS. 24A-C show reduction of CD47 expression and TGFβ2 secretion in the LK-2 cell line.
Figure 24B:
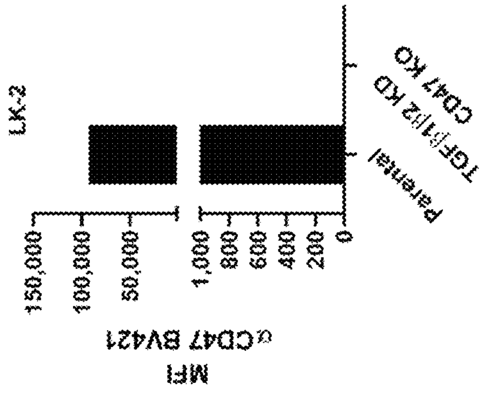
Figure 24C:
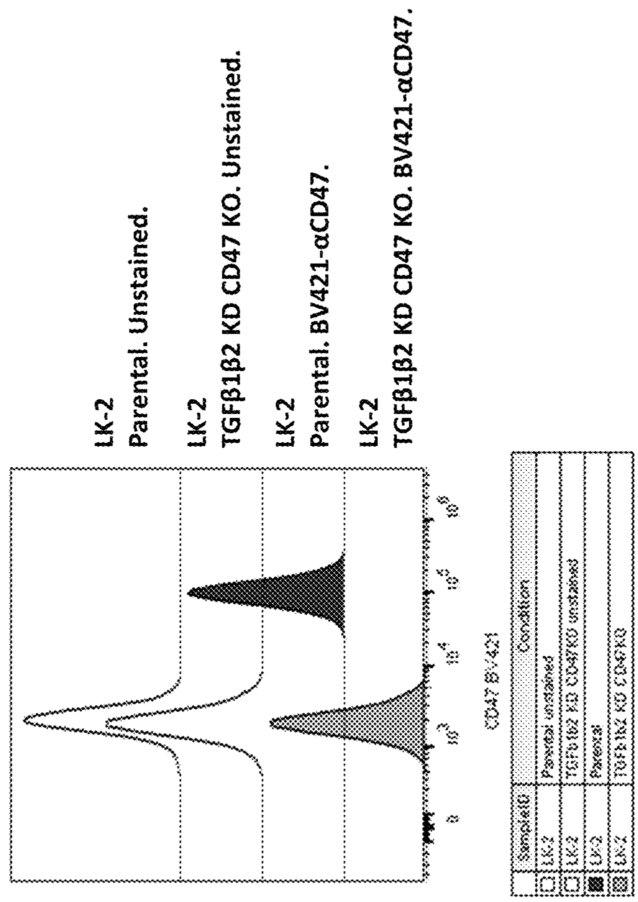
Figure 25A:
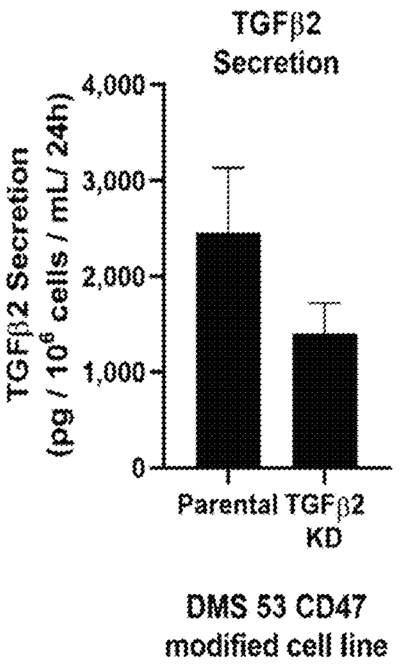
FIGS. 25A-C show reduction of CD47 expression and TGFβ2 secretion in the DMS 53 cell line.
Figure 25B:
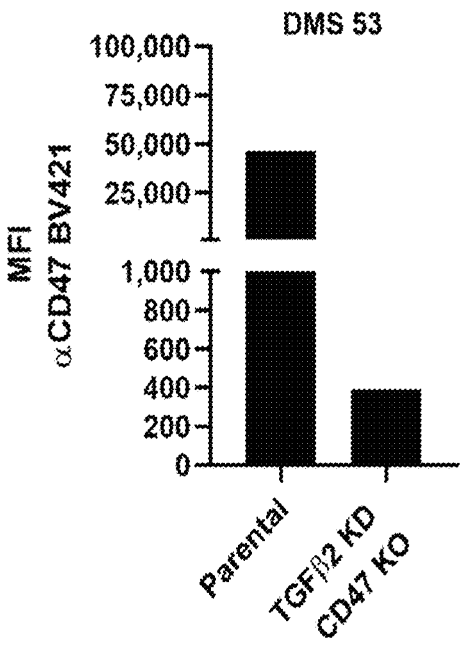
Figure 25C:
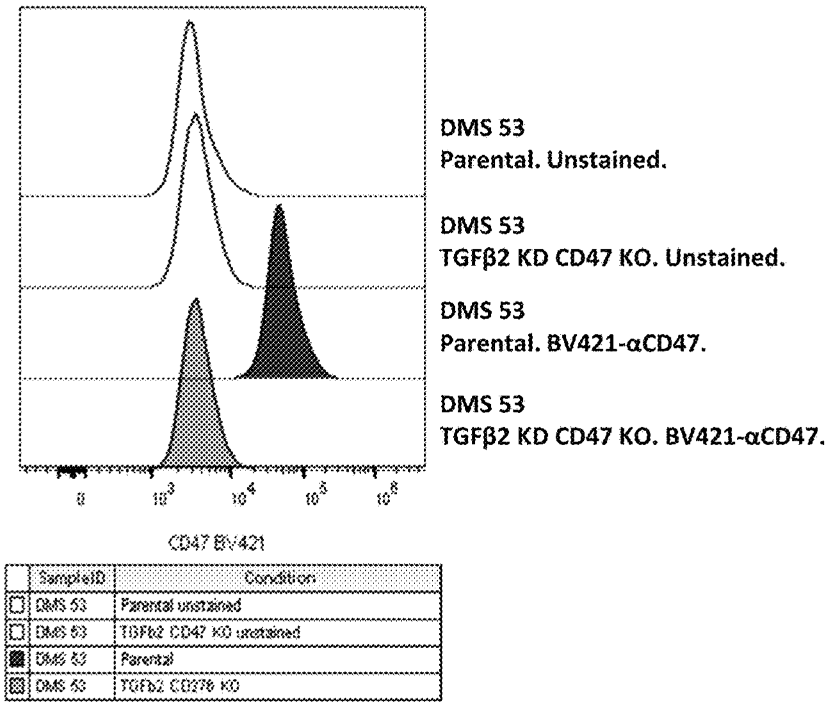
Figure 26A:
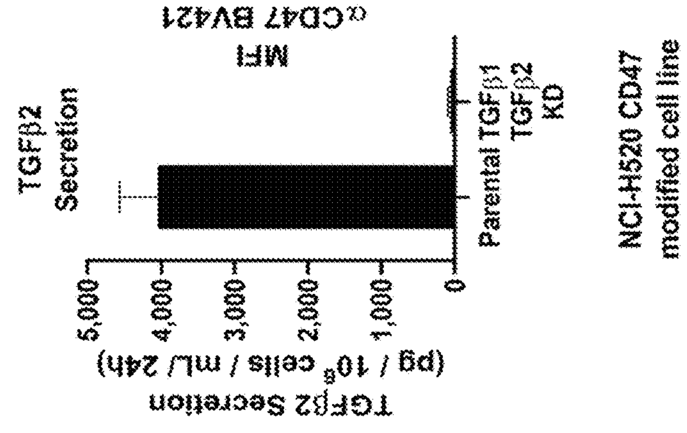
FIGS. 26A-C show reduction of CD47 expression and TGFβ2 secretion in the NCI-H520 cell line.
Figure 26B:
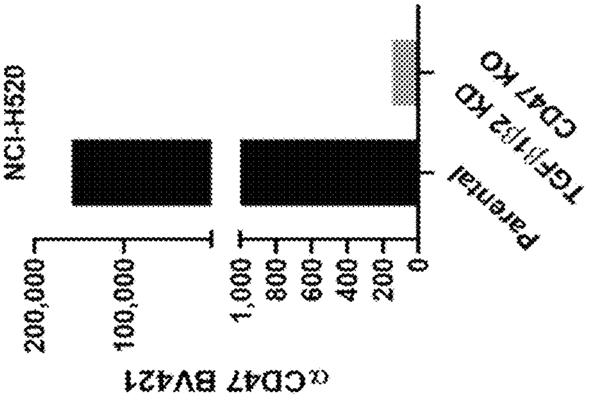
Figure 26C:
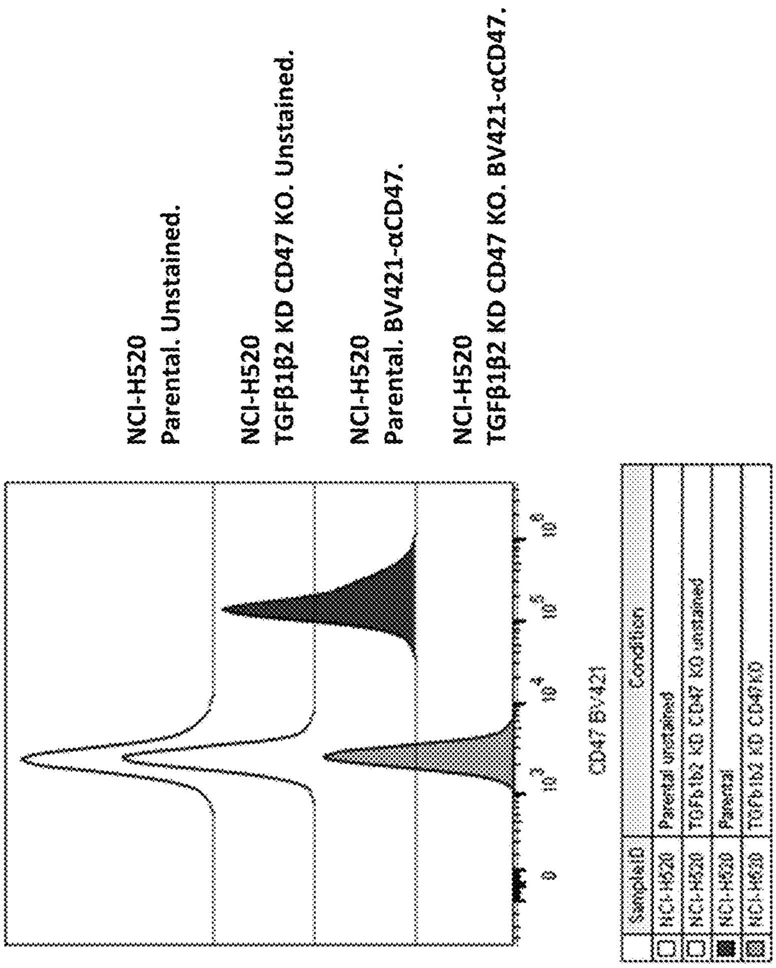
Figure 27A:
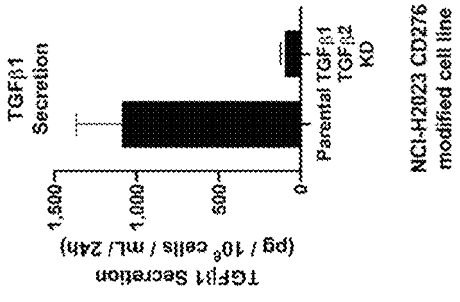
FIGS. 27A-D show reduction of CD276 expression and TGFβ1 and TGFβ2 secretion in the NCI-H2023 cell line.
Figure 27B:
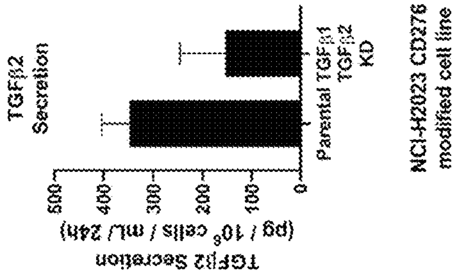
Figure 27C:
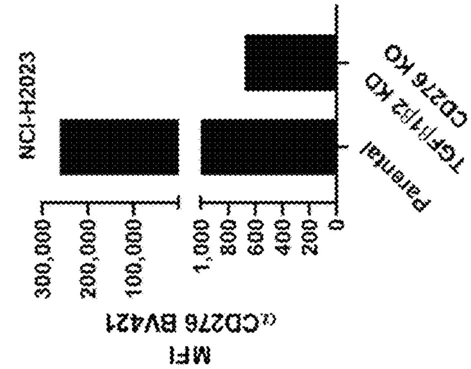
Figure 27D:
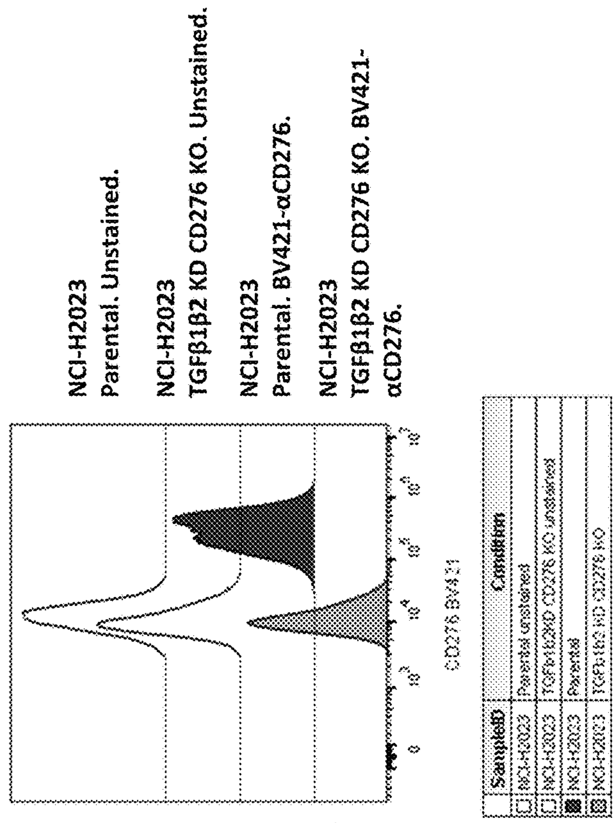
Figure 28A:
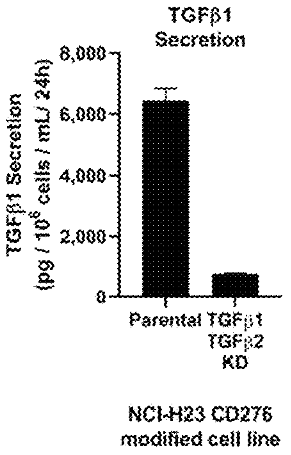
FIGS. 28A-D show reduction of CD276 expression and TGFβ1 and TGFβ2 secretion in the NCI-H23 cell line.
Figure 28B:
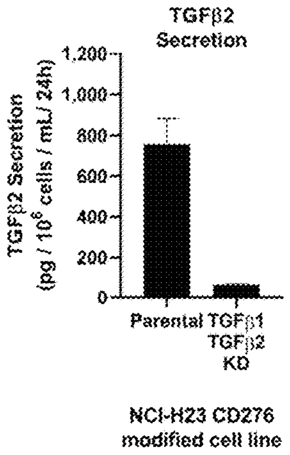
Figure 28C:
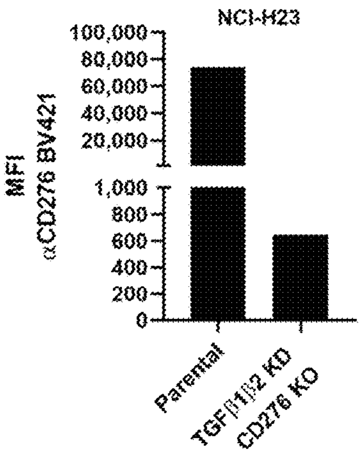
Figure 28D:
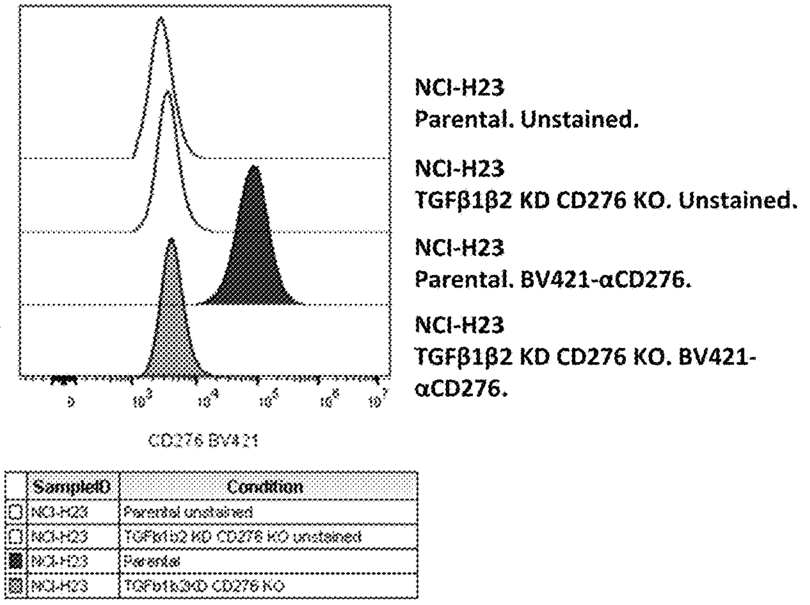
Figure 29A:
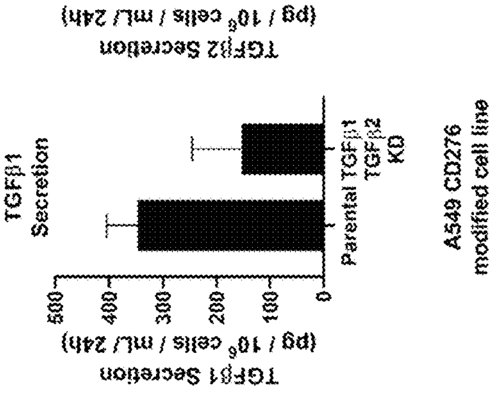
FIGS. 29A-D show reduction of CD276 expression and TGFβ1 and TGFβ2 secretion in the A549 cell line.
Figure 29B:
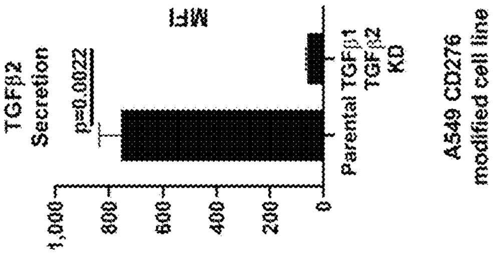
Figure 29C:
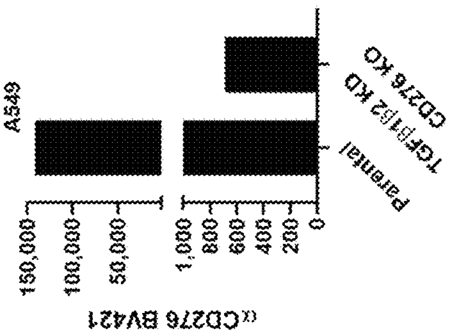
Figure 29D:
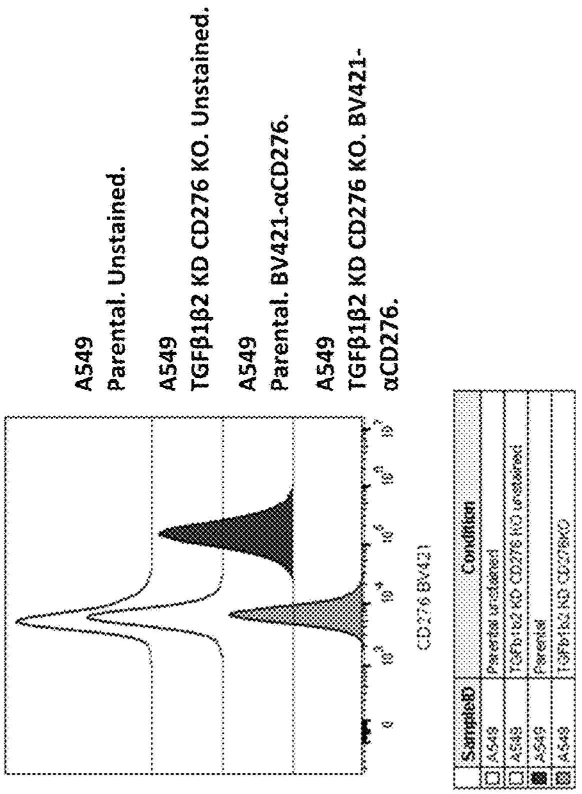

Gene editing of CD47 by ZFN resulted in greater than 99% CD47 negative cells after FACS sorting in the cell lines (Table 27) while maintaining reduced secretion of TGFβ1 and/or TGFβ2 (Table 28). The downregulation of TGFβ1 and/or TGFβ2 with reduction of CD47 expression is shown as follows: NCI-H2023 in FIG. 19, NCI-H23 in FIG. 20, A549 in FIG. 21, NCI-H460 in FIG. 22, NCI-H1703 in FIG. 23, LK-2 in FIG. 24, DMS 53 in FIG. 25, and NCI-H520 in FIG. 26.

TABLE 27

CD47 KO in TGFβ1 and/or TGFβ2 KD cell lines

| Cell line | Parental CD47 MFI | Modified CD47 MFI | % Reduction CD47 |
|---|---|---|---|
| NCI-H2023 | 244,674 | 0 | 100.0 |
| NCI-H23 | 252,210 | 1745 | 99.3 |
| A549 | 96,845 | 29 | 99.9 |
| NCI-H460 | 134,473 | 343 | 99.7 |
| NCI-H1703 | 202,482 | 1069 | 99.5 |
| LK-2 | 92,360 | 0 | 100.0 |
| DMS 53 | 46,399 | 389 | 99.2 |
| NCI-H520 | 158,037 | 145 | 99.9 |

MFI reported with unstained controls subtracted. Parental indicates the unmodified cell line.

TABLE 28

TGFβ1 and TGFβ2 secretion in TGFβ1 and/or TGFβ2 KD cell lines CD47 KO cell lines

| Cell line | TGFβ1 (pg/$10^6$cells/24 hours) | | | TGFβ2 (pg/$10^6$cells/24 hours) | | |
|---|---|---|---|---|---|---|
| | Parental | TGFβ1 KD | % Reduction | Parental | TGFβ2 KD | % Reduction |
| NCI-H2023 | 1262 ± 163 | <92 | >93* | 393 ± 168 | 168 ± 57 | 57 |
| NCI-H23 | 1993 ± 540 | 590 ± 136 | 70 | 679 ± 211 | <42 | >94* |
| A549 | 5962 ± 636 | 952 ± 77 | 84 | 718 ± 82 | 45 ± 12 | 94 |
| NCI-H460 | 1758 ± 75 | 227 ± 45 | 87 | 2564 ± 200 | 559 ± 147 | 57 |
| NCI-H1703 | 1700 ± 300 | 565 ± 91 | 67 | <42 | <42 | NA |
| LK-2 | <92 | <92 | NA | 111 ± 41 | 58 ± 13 | 48 |
| DMS 53 | | Not completed | | 2458 ± 675 | 1409 ± 313 | 43 |
| NCI-H520 | <92 | <92 | NA | 3278 ± 837 | 151 ± 13 | 95 |

Parental indicates the unmodified cell line.
*Secretion levels are below the lower limit of quantification for TGFβ1 (92 pg/$10^6$cells/24 hours) or TGFβ2 (42 pg/$10^6$ cells/24 hours). Lower limit of quantification used to approximate % reduction relative to parental.
NA: secretion levels are below the lower limit of quantification for both the parental and shRNA modified cell line.

Example 13: Reduction of CD276 Expression and TGFβ1 and/or TGFβ2 Secretion Increases Cellular Immune Responses The human tumor cell lines NCI-H460, NCI-H520, DMS 53, A549, NCI-H2023, NCI-H23, LK-2 and NCI-H1703, in which TGFβ1 and/or TGFβ2 secretion was reduced by shRNA in Example 5 were electroporated with a zinc finger nuclease (ZFN) pair specific for CD276 targeting the genomic DNA sequence: GGCAGCCCTGGCATGggtgtg-CATGTGGGTGCAGCC. (SEQ ID NO: 26). Following ZFN-mediated knockout of CD276 in the TGFβ1 and/or TGFβ2 KD lines, the cell lines were surface stained with BB700-conjugated α-human CD276 (BD Biosciences, clone 7-517) and full allelic knockout cells enriched by cell sorting (BioRad S3e Cell Sorter). The cells were collected using a purity sorting strategy to ensure the collection of only CD276 negative cells. The sorted cells were plated in an appropriately sized vessel based on cell number, grown and expanded. After cell enrichment for full allelic knockouts, the TGFβ1 and/or TGFβ2 KD CD276 KO cells were passaged 2-5 times and CD276 knockout percentage by flow cytometry (BV421-conjugated human α-CD276, BD Biosciences, clone 7-517). The MFI of the unstained controls for modified cells or unmodified parental cells were subtracted from the MFI of the modified cells or unmodified parental cells stained with BV421-conjugated human α-CD276. Percent reduction is expressed as: (1-(TGFβ1/β2 KD CD276 KO MFI/Parental MFI))×100).

Figure 31A:
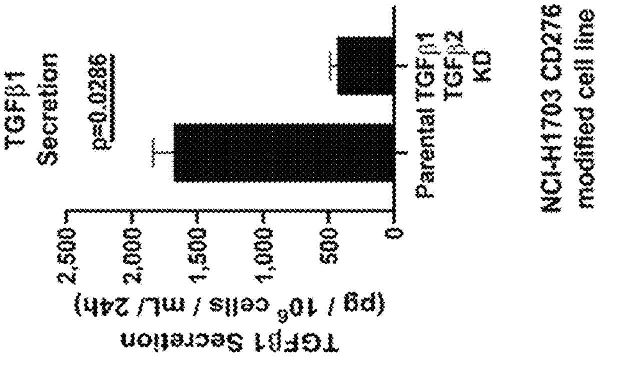
FIGS. 31A-C show reduction of CD276 expression and TGFβ1 secretion in the NCI-H1703 cell line.
Figure 31B:
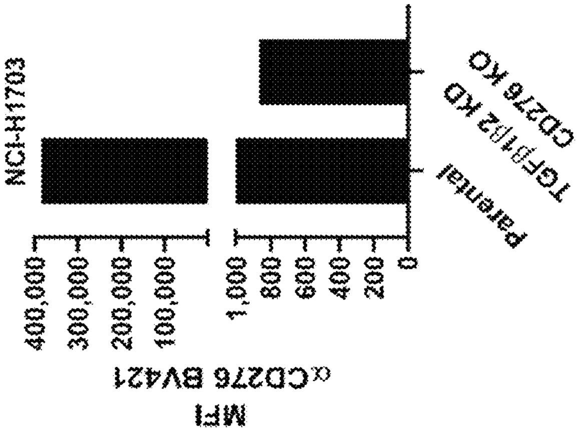
Figure 31C:
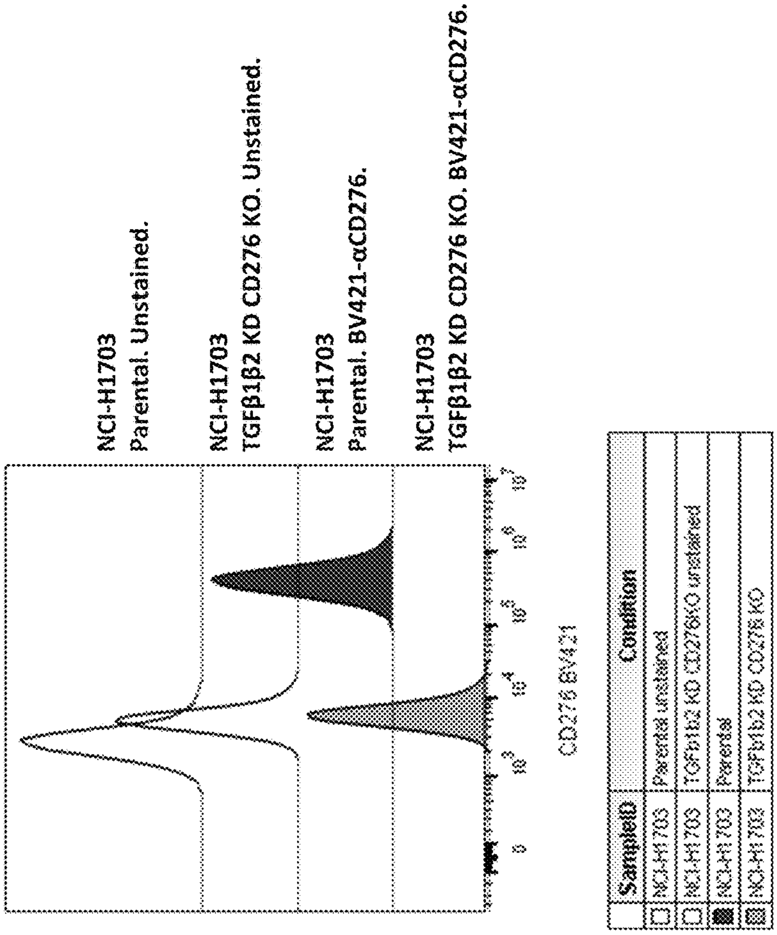
Figures 32A, 32B, 32C:
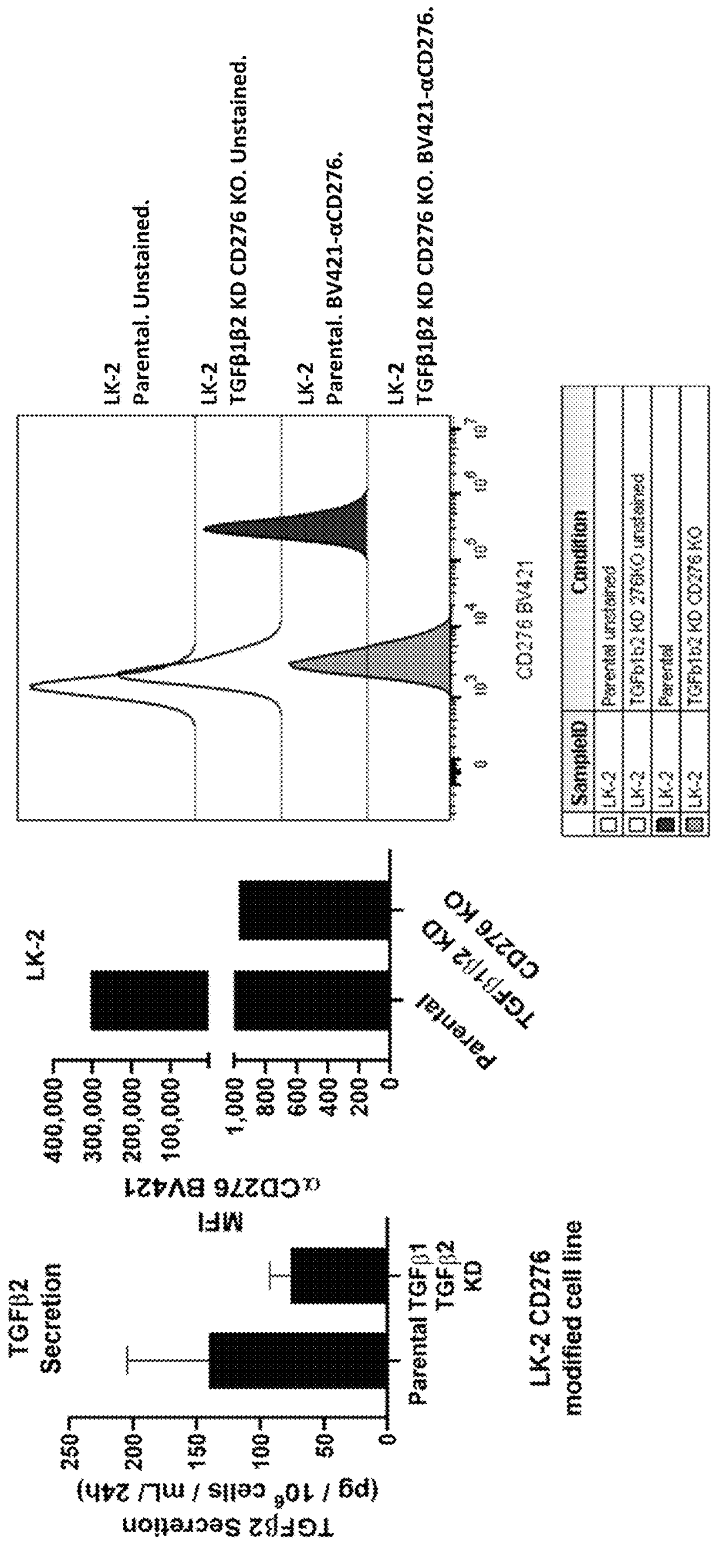
FIGS. 32A-C show reduction of CD276 expression and TGFβ2 secretion in the LK-2 cell line.
Figure 33A:
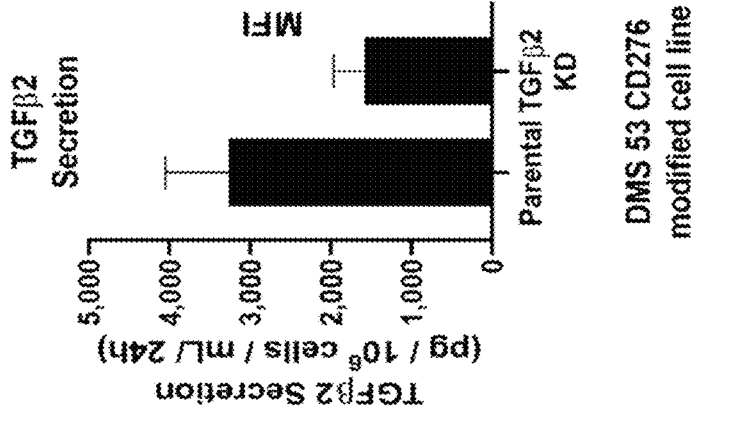
FIGS. 33A-C show reduction of CD276 expression an TGFβ2 secretion in the DMS 53 cell line.
Figure 33B:
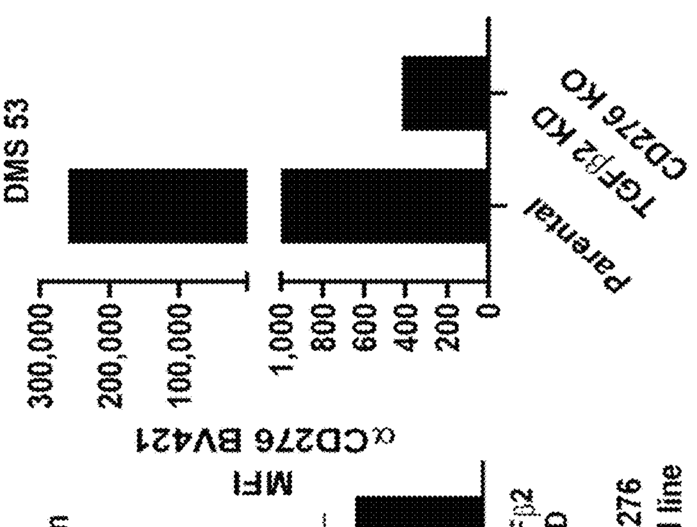
Figure 33C:
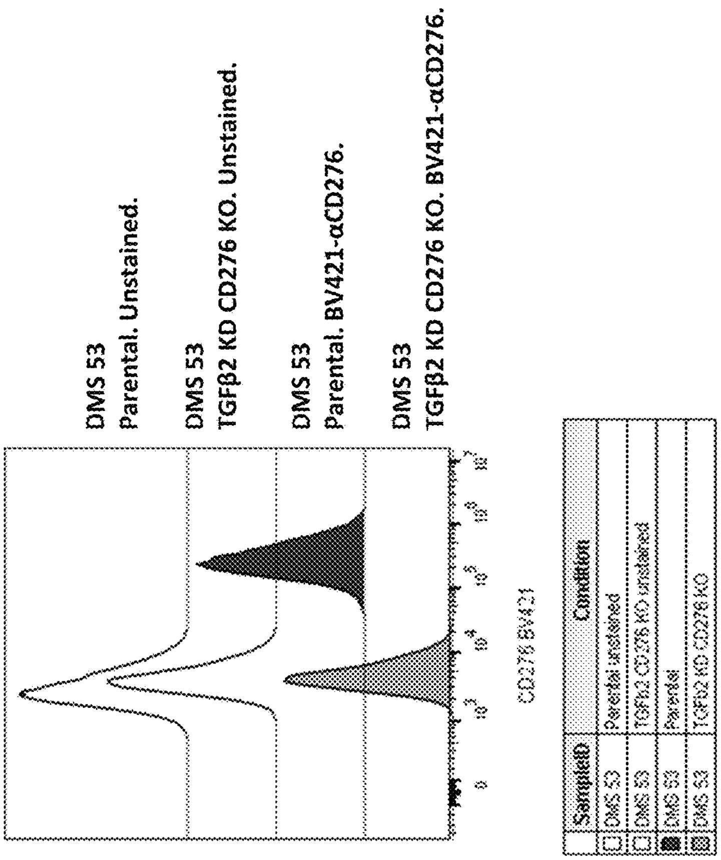
Figures 34A, 34B, 34C:
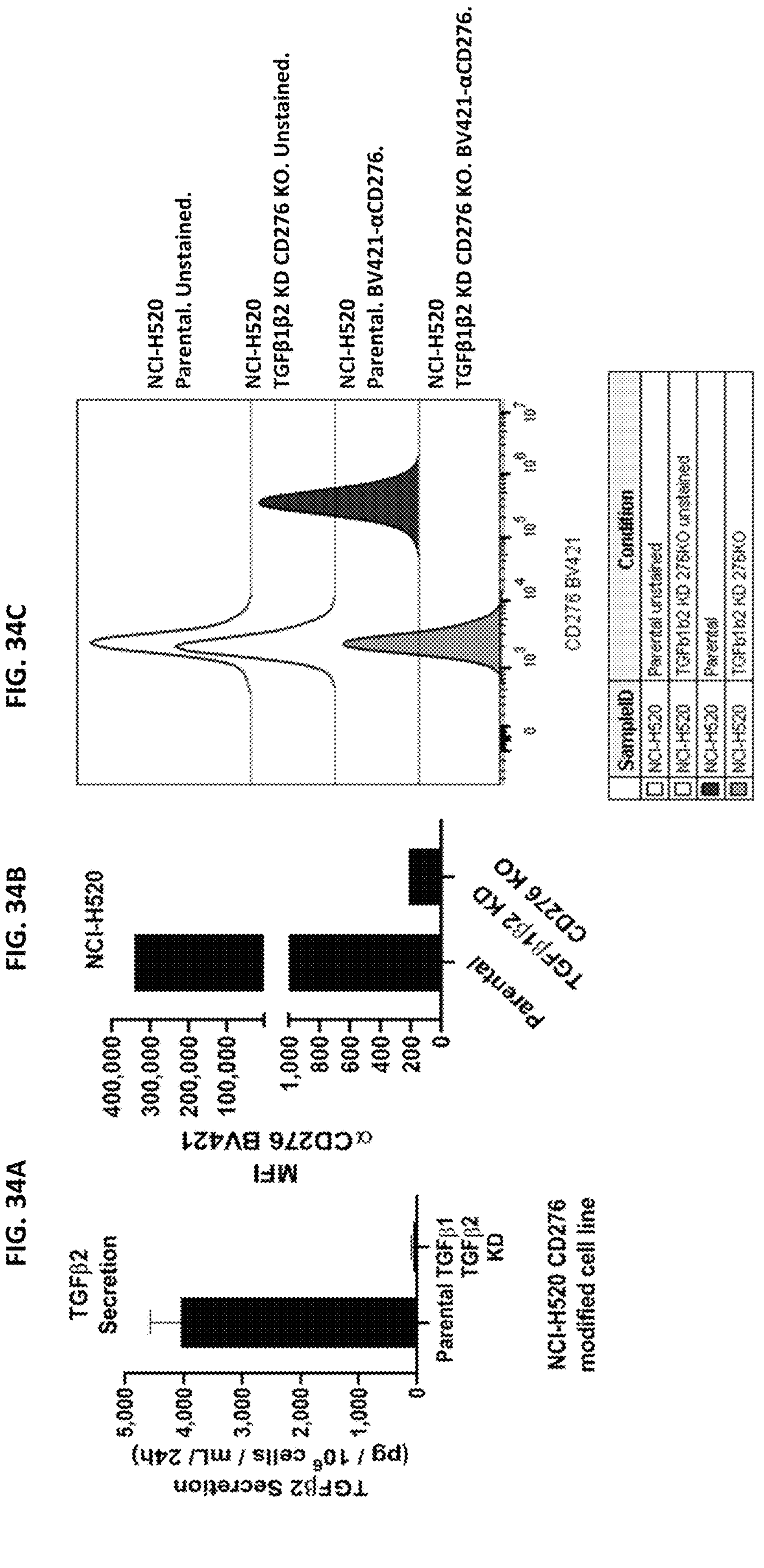
FIGS. 34A-C show reduction of CD276 expression and TGFβ2 secretion in the NCI-H520 cell line.

Gene editing of CD276 by ZFN resulted in greater than 99% CD276 negative cells (Table 29) in the cell lines with reduced secretion of TGFβ1 and/or TGFβ2 (Table 31). The downregulation of TGFβ1 and/or TGFβ2 with reduction of CD276 expression is shown as follows: NCI-H2023 in FIG. 27, NCI-H23 in FIG. 28, A549 in FIG. 29, NCI-H460 in FIG. 30, NCI-H1703 in FIG. 31, LK-2 in FIG. 32, DMS 53 in FIG. 33, and NCI-H520 in FIG. 34.

TABLE 29

CD276 knockout in cell lines with reduced TGFβ1 and/or TGFβ2 secretion.

| Cell line | Parental CD276 MFI | Modified CD276 MFI | % Reduction CD276 |
|---|---|---|---|
| NCI-H2023 | 262,460 | 680 | 99.7 |
| NCI-H23 | 74,176 | 648 | 99.1 |
| A549 | 141,009 | 688 | 99.5 |
| NCI-H460 | 366,565 | 838 | 99.8 |
| NCI-H1703 | 262,386 | 417 | 99.9 |
| LK-2 | 385,535 | 867 | 99.8 |
| DMS 53 | 304,637 | 972 | 99.7 |
| NCI-H520 | 341,202 | 212 | 99.9 |

MFI reported with unstained controls subtracted. Parental indicates the unmodified cell line.

TABLE 30

TGFβ1 and TGFβ2 secretion in TGFβ1 and/or TGFβ2 KD CD276 KO cell lines.

| | TGFβ1 (pg/$10^6$cells/24 hours) | | | TGFβ2 (pg/$10^6$cells/24 hours) | | |
|---|---|---|---|---|---|---|
| Cell line | Parental | TGFβ1 KD | % Reduction | Parental | TGFβ2 KD | % Reduction |
| NCI-H2023 | 1090 ± 279 | 97 ± 23 | 91 | 347 ± 57 | 153 ± 93 | 56 |
| NCI-H23 | 1683 ± 111 | 706 ± 180 | 58 | 523 ± 37 | 55 ± 18 | 89 |
| A549 | 6443 ± 406 | 770 ± 29 | 88 | 757 ± 125 | 61 ± 8 | 92 |
| NCI-H460 | 1415 ± 282 | 390 ± 14 | 72 | 2100 ± 542 | 680 ± 166 | 68 |
| NCI-H1703 | 1682 ± 155 | 434 ± 53 | 74 | <42 | <42 | NA |
| LK-2 | <92 | <92 | NA | 140 ± 64 | 76 ± 16 | 46 |
| DMS 53 | | Not completed | | 4053 ± 2548 | 2329 ± 1175 | 52 |
| NCI-H520 | <92 | <92 | NA | 4045 ± 525 | 59 ± 34 | 99 |

Parental indicates the unmodified cell line
NA: secretion levels are below the lower limit of quantification for both the parental and shRNA modified cell line.

TGFβ1 and TGFβ2 KD and CD276 KO Increases Cellular Immune Responses

Figure 35B:
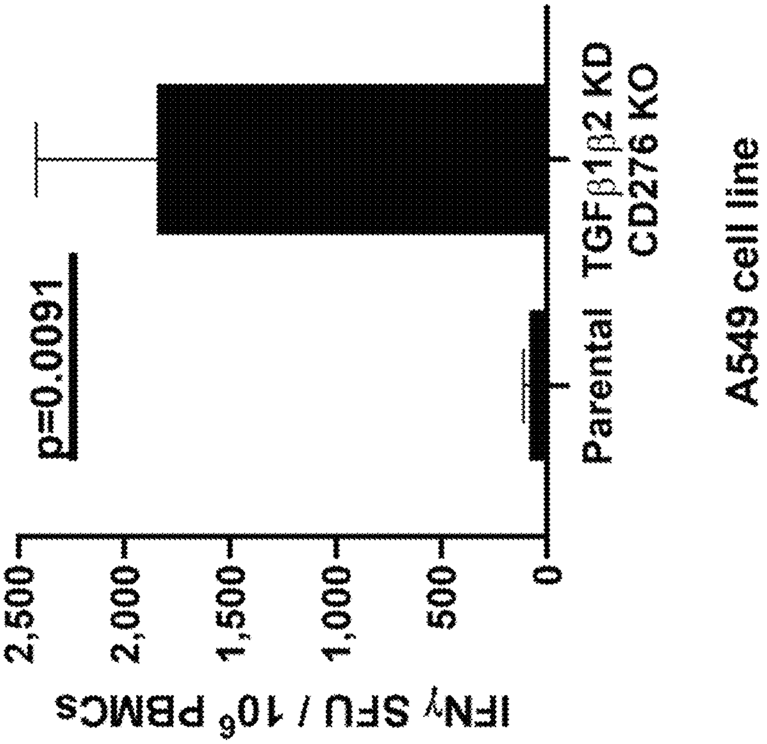
FIGS. 35A and B show reduction of CD276 expression and TGFβ1 and TGFβ2 secretion in the NCI-H460 (FIG. 35A) and A549 (FIG. 35B) cell lines increases cellular immune responses.
Figure 35A:
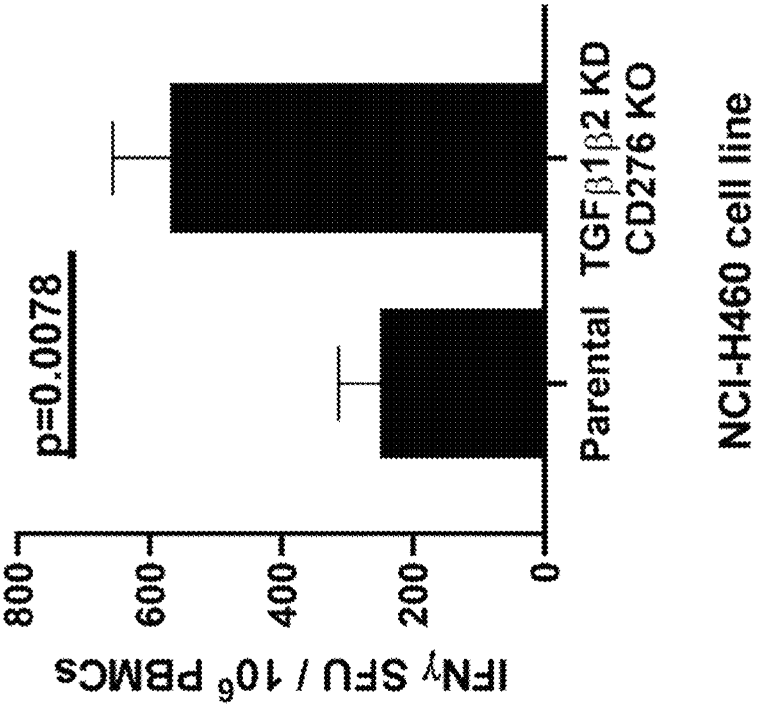

IFNγ ELISpot was carried out as described in Example 9. Cells derived from HLA-A02 and HLA-A03 healthy donors were used to evaluate if reduction of TGFβ1 and TGFβ2 secretion and CD276 expression could improve immune responses compared to the unmodified parental cell lines. In the NCI-H460 cell line, modification of TGFβ1, TGFβ2, and CD276 increased IFNγ responses 2.3-fold (569±87 SFU) (n=11) relative to the unmodified parental cell line (250±63 SFU) (n=11) (p=0.0078, Mann-Whitney U Test) (FIG. 35A). In the A549 cell line, modification of TGFβ1, TGFβ2 and CD276 increased IFNγ responses 22.2-fold (83±29 SFU) (n=11) relative to the unmodified parental cell line (1,848±569 SFU) (n=11) (p=0.0091, Mann-Whitney U Test) (FIG. 35B).

Example 14: Reduction of CD276 and CD47 Expression and TGFβ1 and TGFβ2 Secretion Increases Cellular Immune Responses The A549 cell line was modified to reduce TGFβ1 and TGFβ2 secretion using shRNA and reduce expression of CD47 and CD276. Methods used to secretion and determine levels of TGFβ1 and TGFβ2 are described in Example 5. Methods employed to reduce expression of CD47 and CD276 and determine expression levels are described in Example 12 and Example 13, respectively. IFNγ ELISpot was completed as described in Example 9.

Figure 36A:
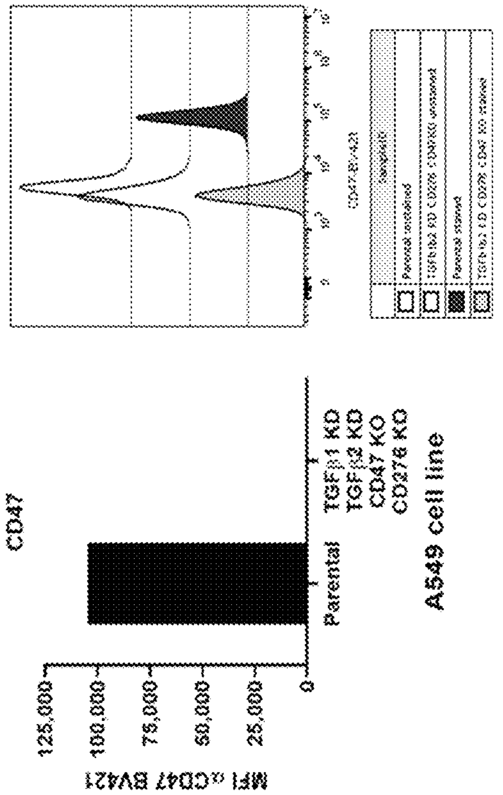
FIGS. 36A-D show reduction of CD47 and CD276 expression and TGFβ1 and TGFβ2 secretion in the A549 cell line.
Figure 36B:
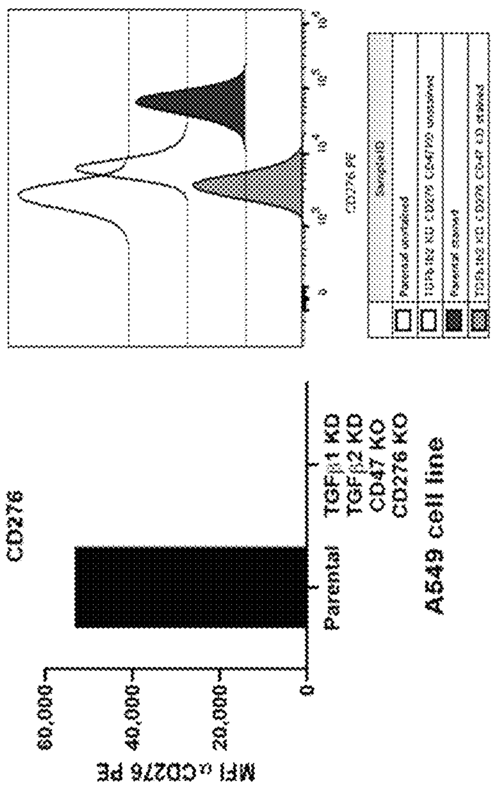
Figure 36C:
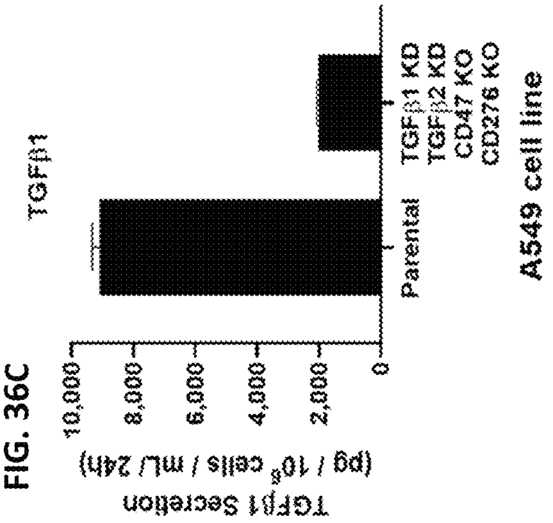
Figure 36D:
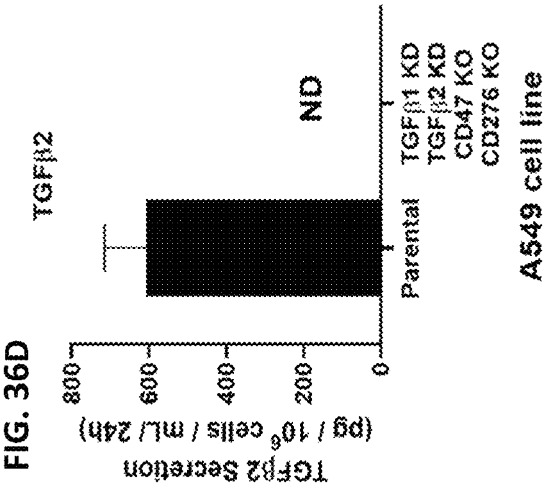

Characterization of A549 Cells with Reduced Expression of CD276 and CD47 and TGFβ1 and TGFβ2 Secretion CD47 expression was reduced 99.9% on the modified cell line (136 MFI) relative to the unmodified parental cell line (104,442 MFI) (FIG. 36A) (Table 31). CD276 expression was reduced 100% on the modified cell line (0 MFI) relative to the unmodified parental cell line (53,196 MFI) (FIG. 36B) (Table 31). TGFβ1 secretion was by the modified cell line (2027±31 pg/$10^6$ cells/24 hours) (n=2) was reduced 78% compared to the unmodified parental cell line (9093±175 pg/$10^6$ cells/24 hours) (n=2) (FIG. 36C). TGFβ2 secretion by the modified cell line was below the lower limit of quantification of the ELISA assay (n=2), resulting in a 100% reduction in secretion levels relative to the unmodified parental cell line (607±76 pg/$10^6$ cells/24 hours) (n=2) (FIG. 36D).

Figure 37B:
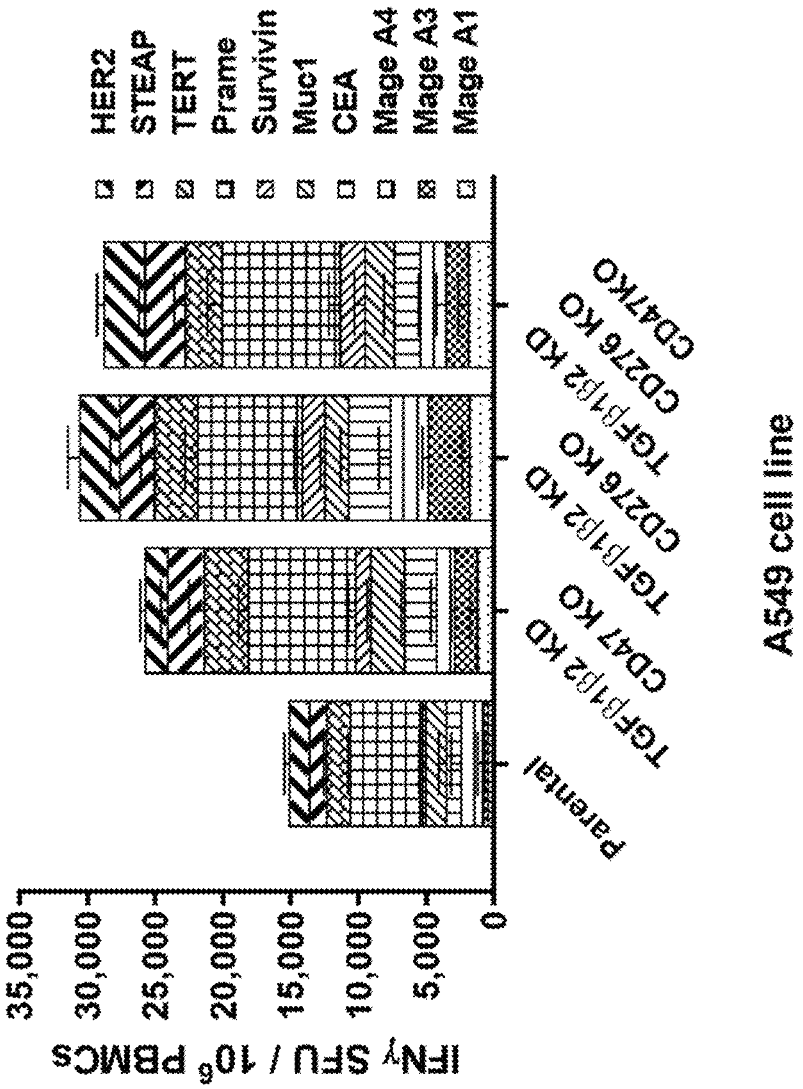
FIGS. 37A and B show reduction of CD47 and CD276 expression and TGFβ1 and TGFβ2 secretion increases immunogenicity.
Figure 37A:
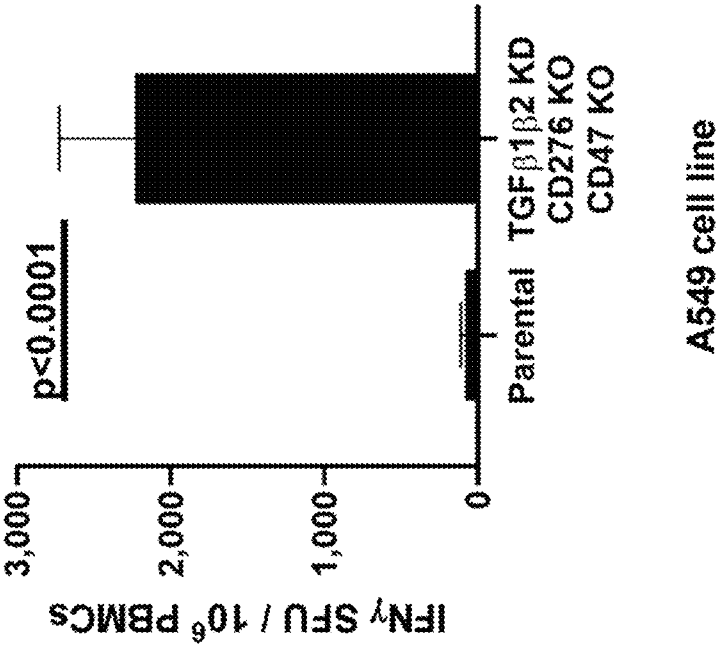

Reduction of CD276 and CD47 Expression and TGFβ1 and TGFβ2 Secretion Increases Cellular Immune Responses Cells derived from HLA-A02 (FIG. 37A), HLA-A03 (FIG. 37A), and HLA-A24 (FIG. 37B) healthy donors were utilized in the IFNγ ELISpot assay to determine if modification of TGFβ1 and TGFβ2, CD276, and CD47 in the A549 cell line enhanced immune responses relative to the unmodified parental cell line. IFNγ ELISpot was completed as described in Examples 9. The modified cell line increased IFNγ responses 26.8-fold (83±29 SFU) (n=11) relative to the unmodified parental cell line (2,233±493 SFU) (n=11) (p=0.0091, Mann-Whitney U test) (FIG. 37A). Responses against 10 antigens were assessed for the unmodified parental, TGFβ1 TGFβ2 KD CD47KO, TGFβ1 TGFβ2 KD CD276 KO, and TGFβ1 TGFβ2 KD CD276 CD47KO A549 modified cell lines. Relative to the total TAA response induced by the unmodified parental cell line (15,140 SFU) (n=3), reduction of TGFβ1, TGFβ2, and CD47 increased the total antigen specific response 1.7-fold (25,813 SFU) (n=3), reduction of TGFβ1, TGFβ2, and CD276 increased the total antigen specific response 2.0-fold (30,640 SFU) (n=3), and reduction of TGFβ1, TGFβ2, CD47 and CD276 increased the total TAA response 2.0-fold (29,993 SFU) (n=3) (FIG. 37B). Responses to specific antigens are in the order indicated in the figure legends. The data suggests that both reduction of CD47 and/or CD276 concurrently with reduction in TGFβ1 and TGFβ2 secretion can promote increased TAA-specific IFNγ production.

TABLE 31

Knockout of CD47 or CD276 in TGFβ1 and TGFβ2 KD cell lines modified to secrete GM-CSF, express membrane bound CD40L, and secrete IL-12.

| Cell line | Parental MFI | CD47 MFI | % Reduction |
|---|---|---|---|
| A549 | 100,228 | 33 | 99.9 |
| NCI-H460 | 140,990 | 6 | >99.9 |
| **Cell line** | **Parental MFI** | **CD276 MFI** | **% Reduction** |
| A549 | 30,636 | 326 | 98.9 |
| NCI-H460 | 82,858 | 1,467 | 98.2 |

MFI reported with unstained controls subtracted. Parental indicates the unmodified cell line.

Example 15: Expression of Membrane Bound CD154 (Membrane Bound CD40 Ligand) Enhances Cellular Immune Responses CD40 Ligand (CD40L) is transiently expressed on T cells and other non-immune cells under inflammatory condition and binds to the costimulatory molecule CD40 on B cells and professional antigen-presenting cells. The binding of CD40L to CD40 upregulates multiple facets of adaptive cellular and humoral immunity.

Expression of Membrane Bound CD40L in the A549 Cell Line

The cell line A549 cell line was transduced with lentiviral particles expressing a CD40L sequence modified to reduce cleavage by ADAM17 and, thereby, promote membrane bound CD40L expression. Parental, unmodified cell lines served as controls. After antibiotic selection in 200 μg/mL to enrich for cells stable expressing CD40L, cells were analyzed for CD40L expression on the cell surface using flow cytometry and solubilized CD40L detected by ELISA. The sequence of membrane bound CD40L used in this example is shown in SEQ ID NO: 1.

Figure 38A:
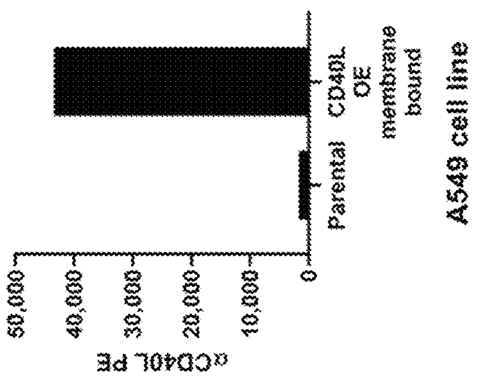
FIGS. 38A-D show expression of membrane bound CD40L in the A549 cell line increases dendritic cell (DC) maturation and cellular immune responses.

To determine the level of membrane bound CD40L expression, unmodified parental and modified cells were stained with PE-conjugated human α-CD40L (BD Biosciences, clone TRAP1). There was a 25.5-fold increase in the expression of CD40L on the cell surface (43,466 MFI) compared to the unmodified parental A549 cell line (1702 MFI) (FIG. 38A).

Figure 38B:
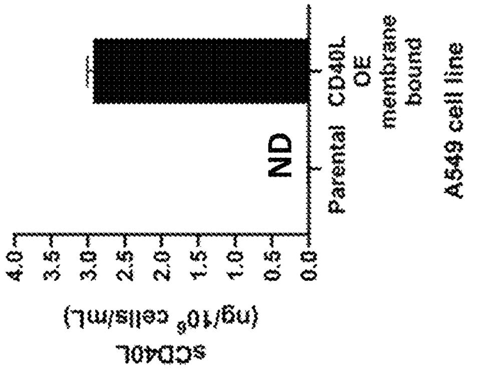

Solubilized CD40L was quantified by ELISA. CD40L-transduced and unmodified parental cells were plated at $8.33\times10^1$ cells/well in a 24-well plated in regular growth medium (RPMI containing 10% FBS). Twenty-four hours after plating, adherent cells were thoroughly washed to remove FBS and culture was continued in RPMI+5% CTS. Forty-eight hours after media replacement, the cell culture supernatant was harvested, and stored at −70° C. until the assays were completed according to the manufacturers instructions (BioLegend, DCDL40). The lower limit of quantification of human CD40L is 62.5 pg/mL, or 0.375 ng/$10^6$ cells/24 hours. Overexpression of CD40L resulted in 2.93 ng/$10^6$ cells/24 hours of sCD40L (FIG. 38B).

The effect of A549 CD40L expression on DC maturation was characterized by flow cytometry. iDCs and A549 unmodified parental cells, unmodified parental cells with exogenous sCD40L (1 μg/mL) (PeproTech, #AF31002100UG), or A549 cells overexpressing membrane-bound CD40L were co-cultured at a 1:1 ratio in 96-well low-adherence U bottom plates. Following the 24 hours incubation, the co-cultures were surface stained with LIVE/DEAD Aqua (Molecular Probes, #L23105), αCD45-PE-Cy7 (BD Biosciences, clone H130), and αCD11c-BV605 (BD Biosciences, clone B-Iy6), and αCD83-APC (BD Biosciences, clone HB15e). Flow cytometry data was analyzed using FlowJo (FlowJo LLC). Increased DC maturation was defined as an increase in the % live, $CD45^+$ $CD11c^+CD83^+$ DCs. DC maturation was evaluated for 7 HLA diverse healthy donors.

Figure 38C:
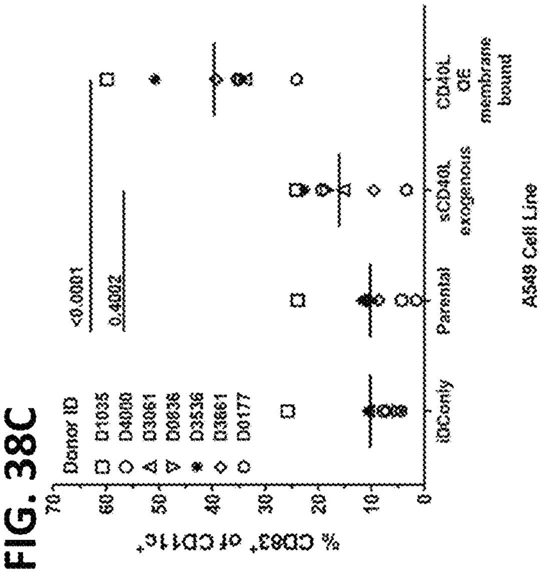

A549 expression of CD40L significantly increased the % of live, $CD45^+CD11c^+CD83^+$ DCs 3.9-fold (40±5) relative to the unmodified parental cell line (10±3) ($p<0.001$, Holm-Sidak's multiple comparisons test) (n=7). Exogenous sCD40L did not significantly increase the % of live, $CD45^+$ $CD11c^+CD83^+$ DCs (16±3) (p=0.4402, Holm-Sidak's multiple comparisons test) (n=7) (FIG. 38C).

Expression of Membrane Bound CD40L Enhances Cellular Immune Responses

Figure 38D:
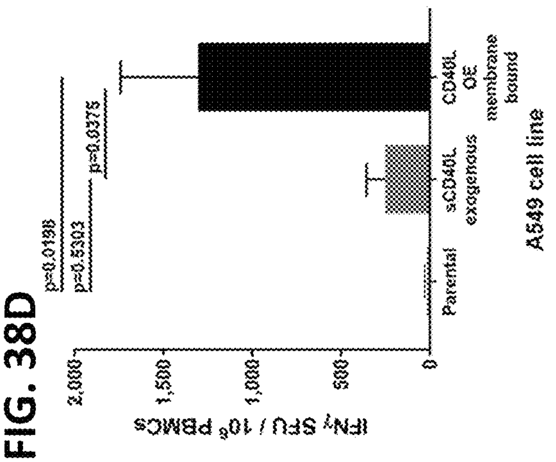

The effect of overexpression of CD40L on induction of cellular immune responses was evaluated by IFNγ ELISpot assay as described in Example 9. iDCs loaded were loaded with A549 cells, A549 cells with 1 μg/mL exogenous sCD40L, or A549 cells overexpressing CD40L. Expression of CD40L by A549 cells increased IFNγ responses 87-fold (1,305±438 SFU) compared to the unmodified parental cell line (15±15 SFU) (p=0.0198, Holm-Sidak's multiple comparisons test) (n=4). Inclusion of exogenous sCD40L in the co-culture did not significantly increase IFNγ responses (255±103 SFU) relative to the unmodified parental cell line (p=0.5303, Holm-Sidak's multiple comparisons test) (n=4). IFNγ responses elicited by overexpression of CD40L on A549 cells were significantly greater than the responses detected with the addition of exogenous sCD40L (p=0.0375, Holm-Sidak's multiple comparisons test) (n=4) (FIG. 38D).

Example 16: Expression of GM-CSF Enhances Cellular Immune Responses

Figure 39:
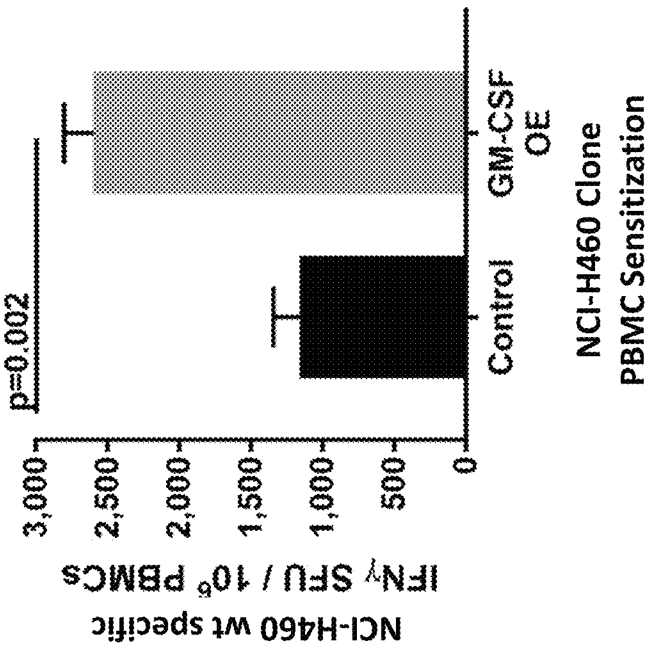
FIG. 39 shows overexpression of GM-CSF in the NCI-H460 cell line increases cellular immune responses.

Unmodified parental NCI-H460 cells were transfected with either empty lentiviral vector (control) or a lentiviral vector designed to overexpress GM-CSF (SEQ ID NO: 6). The control and GM-CSF over expressing cell line were grown in the presence of Puromycin (2 μg/mL) prior to use in the IFNγ ELISpot assay. IFNγ ELISpot was performed as described in Example 6. FIG. 39 demonstrates that sensitization of healthy donor (HLA-A*01, HLA-A*02) derived PBMCs with GM-CSF overexpressing NCI-H460 cells significantly increases cellular immune responses to unmodified parental NCI-H460 cells (2600±207 SFU) when compared to sensitization with the Control NCI-H460 cells (1163±183 SFU) (p=0.002).

Example 17: Expression of Interleukin-12 (IL-12) Enhances Cellular Immune Responses IL-12 is a proinflammatory cytokine that promotes DCs and LCs to prime T cells towards an effector phenotype.

IL-12 can also act directly on DCs to reverse or prevent the induction of immune tolerance.

Figure 40:
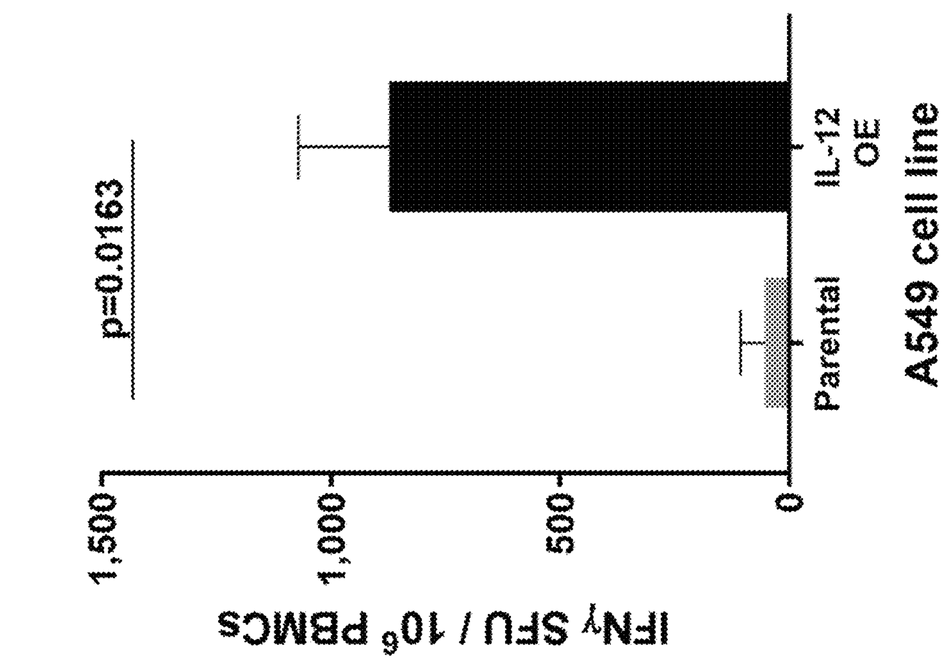
FIG. 40 shows expression of IL-12 in the A549 cell line increases cellular immune responses.

The A549 cells were transduced with lentiviral particles expressing both the p40 and p35 chains of IL-12 to form the functional IL-12 p70 cytokine protein. The p40 and p35 sequences are separated by a P2A cleavage sequence. The sequence of IL-12 used in this example is shown in SEQ ID NO: 9. Unmodified parental, unmodified cell lines served as controls. After antibiotic selection in 600 μg/mL zeocin to enrich for cells stably expressing IL-12 immune responses generated by the parental and IL-12 modified cell lines were determined as described in Example 9. There was a 16-fold increase in IFNγ SFU with the expression of IL-12 (873±199 SFU) (n=3) compared to IFNγ responses induced by the unmodified parental cells (53±53 SFU) (p=0.0163, Mann-Whitney U test) (n=3) (FIG. 40).

Example 18: Expression of Glucocorticoid-Induced TNFR Family Related Gene (GITR) Enhances Cellular Immune Responses GITR is surface receptor molecule involved in inhibiting the suppressive activity of T-regulatory cells (Tregs) and extending the survival of T-effector cells. Binding of GITR to its ligand, GITR, on APCs triggers signaling which co-stimulates both $CD8^+$ and $CD4^+$ effector T cells, leading to enhanced T cell expansion and effector function, while suppressing the activity of Tregs.

Expression of GITR

A codon optimized sequence was generated based on the native, membrane bound variant of GITR (NP_004186) as and cloned in to the BamHI and XhoI restriction endonuclease site of pVAX1 (Invitrogen, #V26020) (GenScript). The sequence of GITR used in this example is shown in SEQ ID NO: 4. For transfections of cells using pVAX1 encoding GITR, A549 (5.38×106 cells), NCI-H460 (1.79×107 cells), LK-2 (2.39×107 cells) or NCI-H520 (1.02×107 cells) were plated into T175 flasks using 45 mL of complete culture media 18-24 hours prior to transfection and maintained at 37° C./5% CO2. Plasmid DNA transfections were performed using the Lipofectamine™ transfection reagent (Invitrogen, #2075084) according to the manufacturer's instructions. Cells were incubated at 37° C. and 5% CO2 for 72 hours prior to assessment of GITR expression by flow cytometry.

Figure 41A:
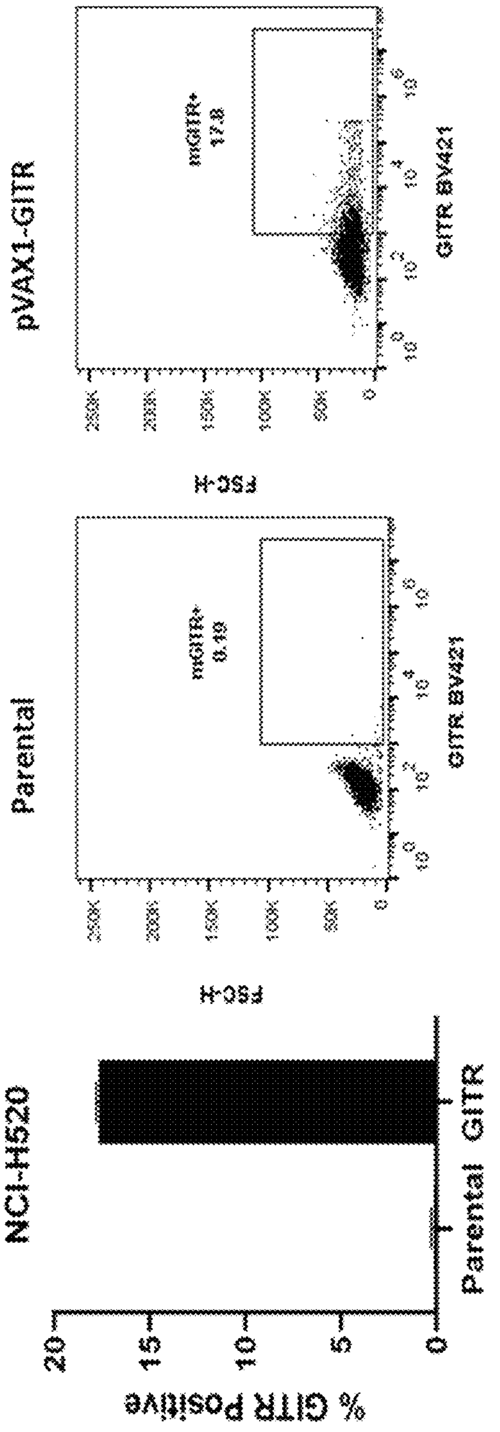
FIGS. 41A-D show expression of GITR in the NCI-H520 (FIG. 41A), A549 (FIG. 41B), LK-2 (FIG. 41C), and NCI-H460 (FIG. 41D) cell lines.
Figure 41B:
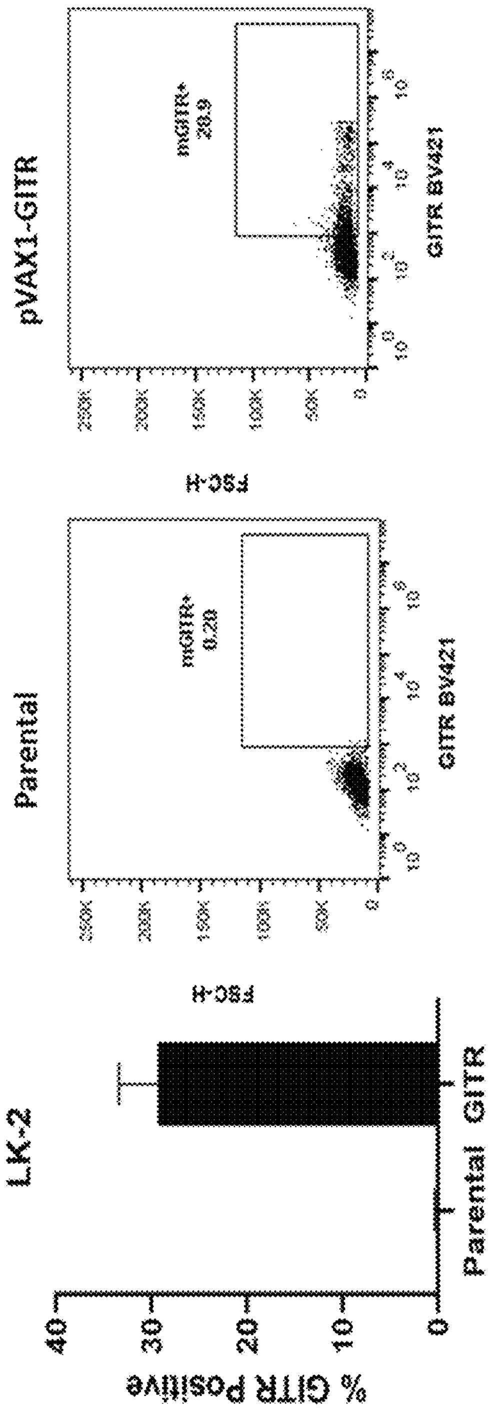
Figure 41C:
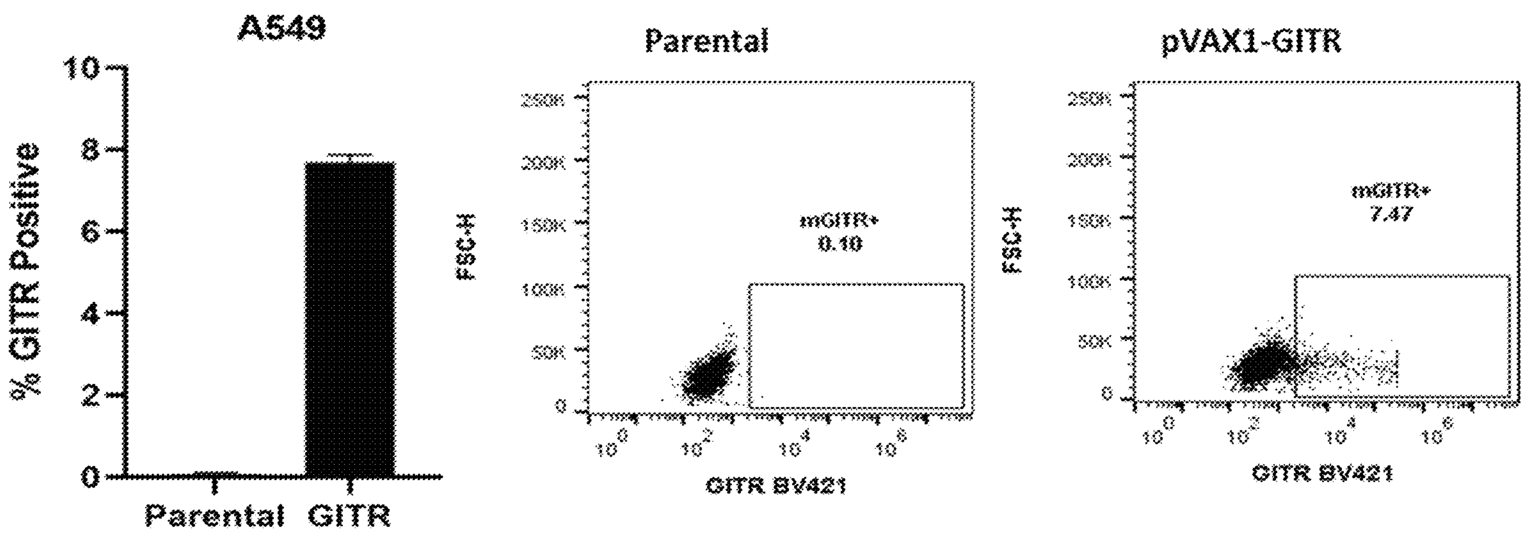
Figure 41D:
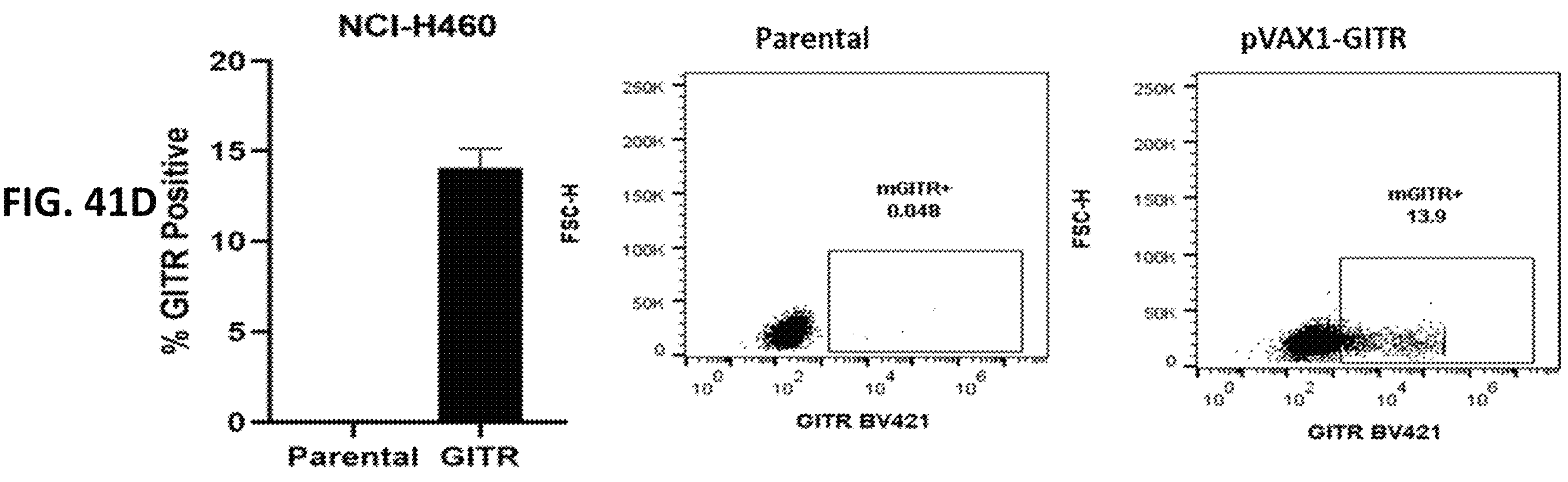

To determine cell surface expression of GITR, transfected cells and unmodified parental controls were surfaced stained with BV421-conjugated mouse anti-human GITR antibody (BD Biosciences, clone V27-580). Flow cytometry data was acquired on a BD LSRFortessa and analyzed using FlowJo software. Minimal expression of GITR was detected on untransfected unmodified parental cell lines (n=3 for each cell line) (FIG. 41). GITR was expressed on 17.7±0.1% of transfected NCI-H520 cells (n=3) (FIG. 41A), 29.3±3.3% of transfected LK-2 cells (n=3) (FIG. 41B), 7.7±0.2% of transfected A549 cells (n=3) (FIG. 41C), and 14.1±0.9% of transfected NCI-H460 cells (n=3) (FIG. 41D).

Expression of GITR Enhances Cellular Immune Responses

Figure 42D:
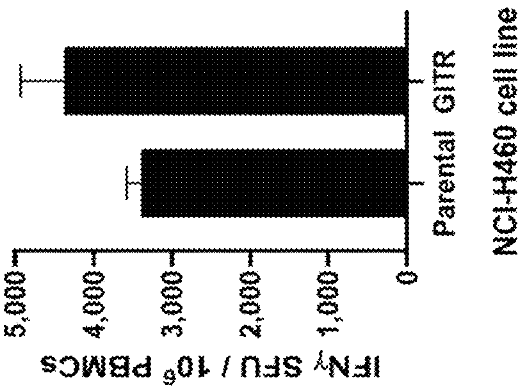
FIGS. 42A-D show expression of GITR enhances cellular immune responses.
Figure 42C:
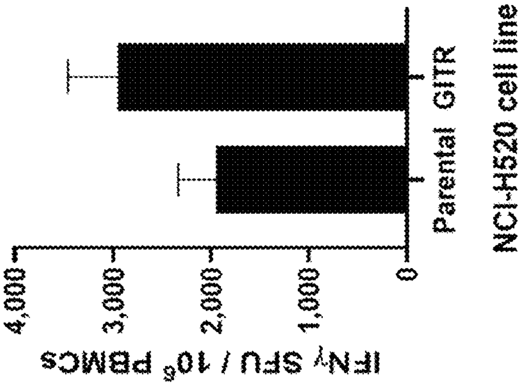
Figure 42B:
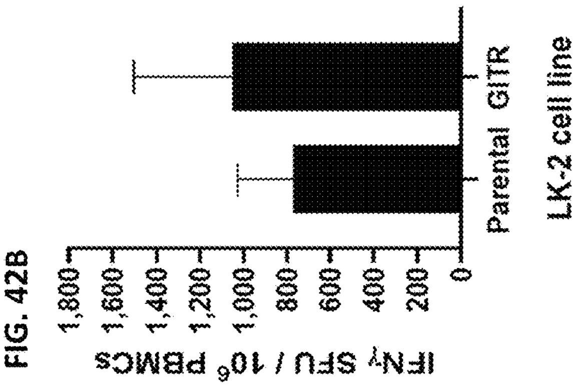
Figure 42A:
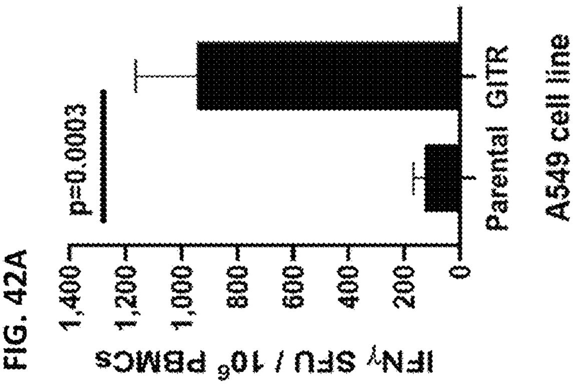

The effect of expression of GITR on cellular immunogenicity was evaluated by IFNγ ELISpot as described in Example 9 using cells derived from two HLA-A02 donors and one HLA-A24 healthy donor (n=3/donor). Expression of GITR by the A549 cell line significantly increased IFNγ production 7.4-fold (947±217 SFU) (n=9) compared to the unmodified parental A549 cell line (128±38 SFU) (n=9) (p=0.0003, Mann-Whitney U test) (FIG. 42A). There was a trend towards increased IFNγ production with expression of GITR in the LK-2 cell line (1,053±449 SFU) (n=9) compared the unmodified parental cell line (773±255 SFU) (n=9) (FIG. 42B). There was a trend towards increased immunogenicity with GITR expression in the NCI-H520 cell line (2,953±504 SFU) (n=3) compared to the unmodified parental, unmodified cells (1,953±385 SFU) (n=3) (FIG. 42C). There was also a trend towards increased immunogenicity with GITR expression in the NCI-H460 (4,940±557 SFU) cell line compared to the unmodified parental cells (3,400±181 SFU) (n=3) (FIG. 42D).

Example 19: Expression of Interleukin-15 (IL-15) Enhances Cellular Immune Responses IL-15 is a member of the four α-helix bundle family of cytokines and is produced by a wide range of cells including DCs and is essential for the differentiation of CH' memory T cells. Two isoforms of IL-15 are natively expressed that encode two different N-terminal signal peptides. These signal peptides function to decrease or inhibit secretion of the IL-15 protein from tumor cells. A codon optimized sequence of IL-15 was generated where the native IL-15 long signal peptide region was replaced with IL-2 signal peptide to promote secretion of the IL-15 protein (GenScript). The codon optimized sequence was cloned into the BamHI and XhoI restriction sites of pVAX1. The sequence of IL-15 used in this example is shown in SEQ ID NO: 11.

Quantification of IL-15 Secretion

Figure 43A:
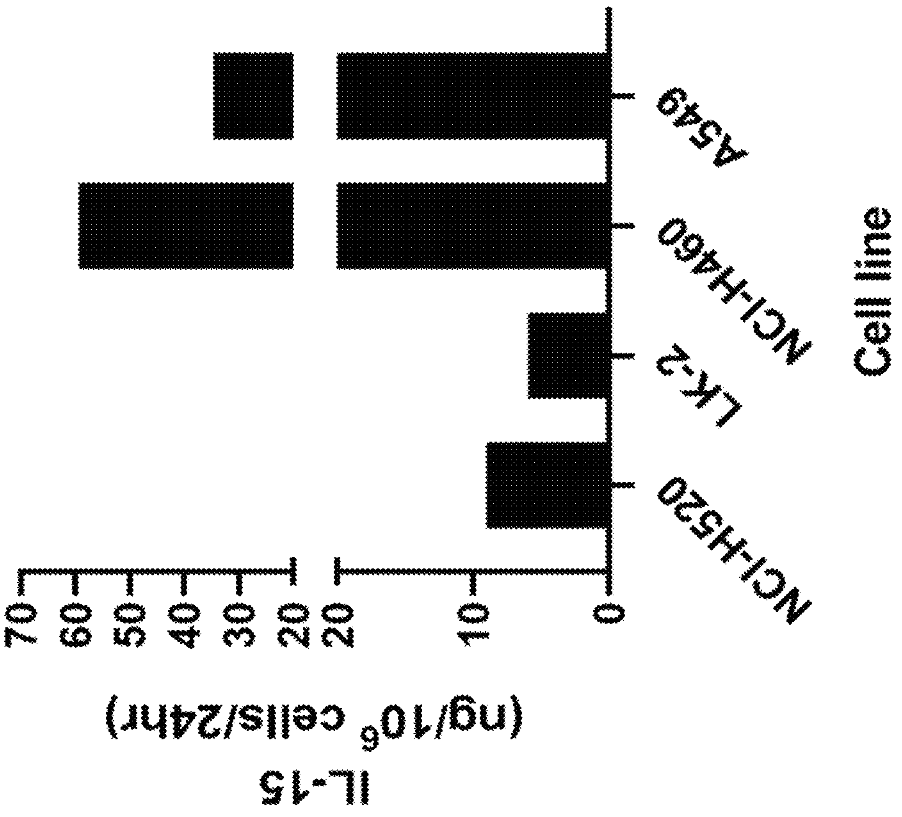
FIGS. 43A and B show expression of IL-15 enhances cellular immune responses.

Transfections of the IL-15 encoding plasmid were completed as described in Example 18. Supernatants were assayed for the presence of secreted IL-15 by ELISA using the Human IL-15 Quantikine ELISA Kit (R&D Systems, D1500) and following the manufacturers instructions. The lower limit of quantification of the IL-15 ELISA is 3.98 pg/mL, or 0.0239 ng/$10^6$ cells/24 hours. The NCI-H520, LK-2, NCI-H460, and A549 cell lines expressed 9.04, 5.99, 59.43, and 34.74 ng/$10^6$ cells/24 hours of IL-15, respectively (FIG. 43A).

IL-15 Enhances Cellular Immune Responses

Figure 43B:
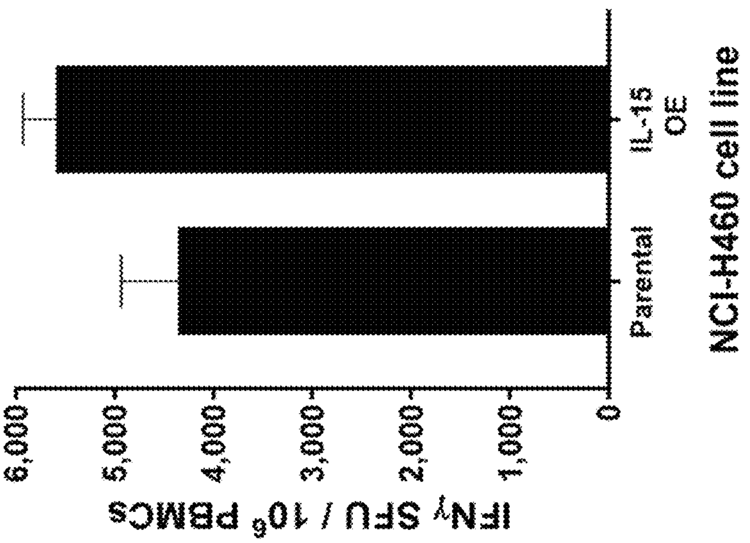

IFNγ ELISpot to evaluate the effect of IL-15 on cellular immune responses was completed as described in Example 9. The effect of IL-15 secretion by the NCI-H460 cell line on cellular immune responses was evaluated using immune cells derived from an HLA-A02 healthy donor (n=3). There was a trend towards increased IFNγ production with IL-15 overexpression (5,593±474 SFU) relative to the unmodified parental NCI-H460 cell line (4,360±806 SFU) (FIG. 43B).

Example 20: Expression of Interleukin-23 (IL-23) Enhances Cellular Immune Responses IL-23 is a binary complex of a four-helix bundle cytokine (p19) and a soluble class I cytokine receptor p40. IL-23 acts as a proinflammatory cytokine that enhances DC maturation and suppresses DC activation of naive T cell-derived Tregs.

Expression of IL-23

Human codon optimized IL-23 p19 and p40 sequences were generated and cloned into the BamHI and XhoI restriction sites of pVAX1 (GenScript). The p19 and p40 sequences were separated by a flexible linker $GS_3$ linker. The sequence of IL-23 used in this example is shown in SEQ ID NO: 13. Transfections were completed as described in Example 18.

Figure 44B:
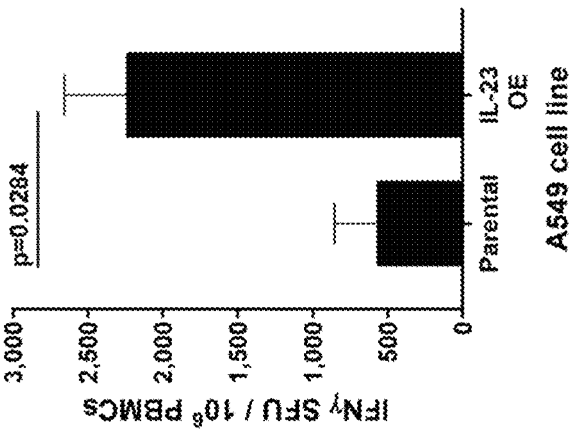
FIGS. 44A and B show expression of IL-23 enhances cellular immune responses.
Figure 44A:
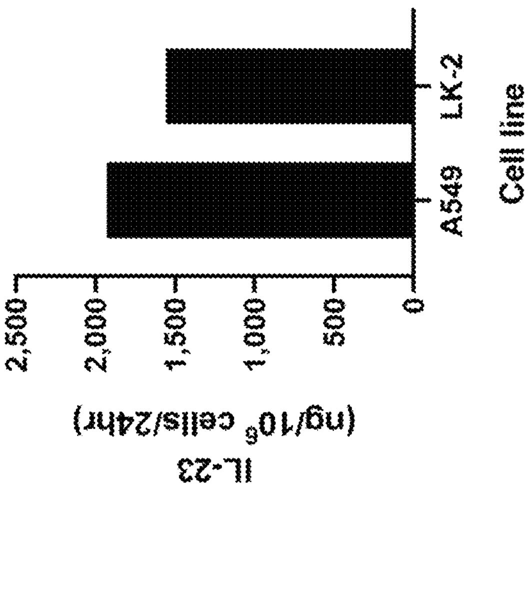

Supernatants were assayed for the presence of functional (p19 and p40 dimers) secreted IL-23 using the Human IL-23 Quantikine ELISA Kit (R&D Systems, D2300B) according to the manufacturer's instructions. The lower limit of quantification of the IL-23 ELISA is 39.1 pg/mL, or 0.235 ng/$10^6$ cells/24 hours. The LK-2 and A549 cell lines expressed 1,559 and 1,929 ng/$10^6$ cells/24 hours of IL-23, respectively (FIG. 44A).

Secretion of IL-23 Increases Cellular Immune Responses

IFNγ ELISpot to evaluate the effect of IL-23 on cellular immune responses was completed as described in Example 9. The effect of IL-15 secretion by the A549 (ATCC CCL-185) cell line on cellular immune responses was evaluated using immune cells derived from an HLA-A02 healthy donor. There was a significant 3.9-fold increase in IFNγ production with IL-23 overexpression (2,247±580 SFU) relative to the unmodified parental A549 (ATCC CCL-185) cell line (573±401 SFU) (FIG. 44B) (p=0.0284, Student's T-test) (n=3).

Example 21: Expression of X-C Motif Chemokine Ligand 1 (XCL1)

The cytokine XCL1, also known as Lymphotactin, binds to the chemokine receptor XCR1, which is selectively expressed on antigen cross-presenting DCs. Expression of XCL1 has the potential to function as an adjuvant for intradermal vaccine administration.

Expression of XCL1

A human codon optimized sequence was generated encoding human XCL1 (GenScript) and cloned into the BamHI and XhoI restriction sites of the pVAX1 plasmid. Transient expression and secretion of XCL1 was characterized by ELISA. The sequence of XCL1 used in this example is shown in SEQ ID NO: 15.

Quantification of XCL1 Secretion

Figure 45:
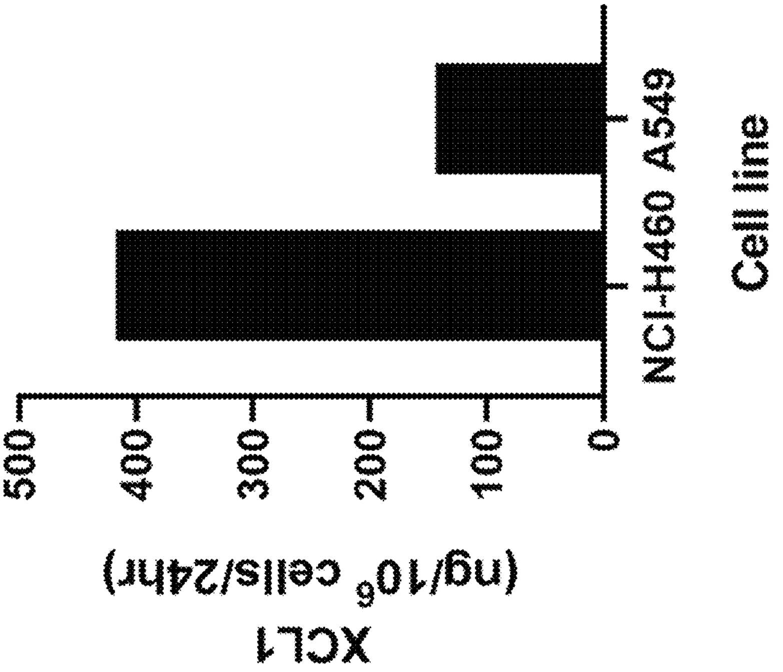
FIG. 45 shows the expression of XCL1.

NCI-H460 and A549 cells were transfected with pVAX1 encoding codon optimized XCL1 as described in Example 18. Twenty-four hours after transfection, supernatants were removed from the cells and assayed for the presence of secreted XCL1 by ELISA. Supernatants were assayed for XCL1 secretion according to the manufacturer's instructions (R&D Systems, #DXCL10). The NCI-H460 and A549 cell lines transiently expressed 418 and 144 and ng/$10^6$ cells/24 hours of XCL1, respectively (FIG. 45).

Example 22: Expression of Mesothelin (MSLN

MSLN is expressed on the surface of many lung adenocarcinomas and expression is correlated with poor prognosis. MSLN is an attractive TAA targeted because antigen specific immune responses to MSLN can predict the survival of patients with brain metastasis resulting from several different primary tumors including ovarian, lung and melanoma. A small subset of lung cancer cell lines express MSLN despite expression of MSLN in many patient tumors. In Example 22, the expression of MSLN was genetically introduced in exemplary vaccine cell lines that do not natively express MSLN to broaden the coverage TMs potentially important to patients with NSCLC.

Expression of MSLN

A codon optimized human MSLN sequence was generated in which the ADAM17 cleavage site replaced with a flexible linker to promote retention of MSLN in the cell membrane (GenScript). The codon optimized sequence was cloned into the BamHI and XhoI restriction sites of pVAX1. The sequence of MSLN used in this example is SEQ ID NO: 17.

Quantification of MSLN Expression

Figure 46A:
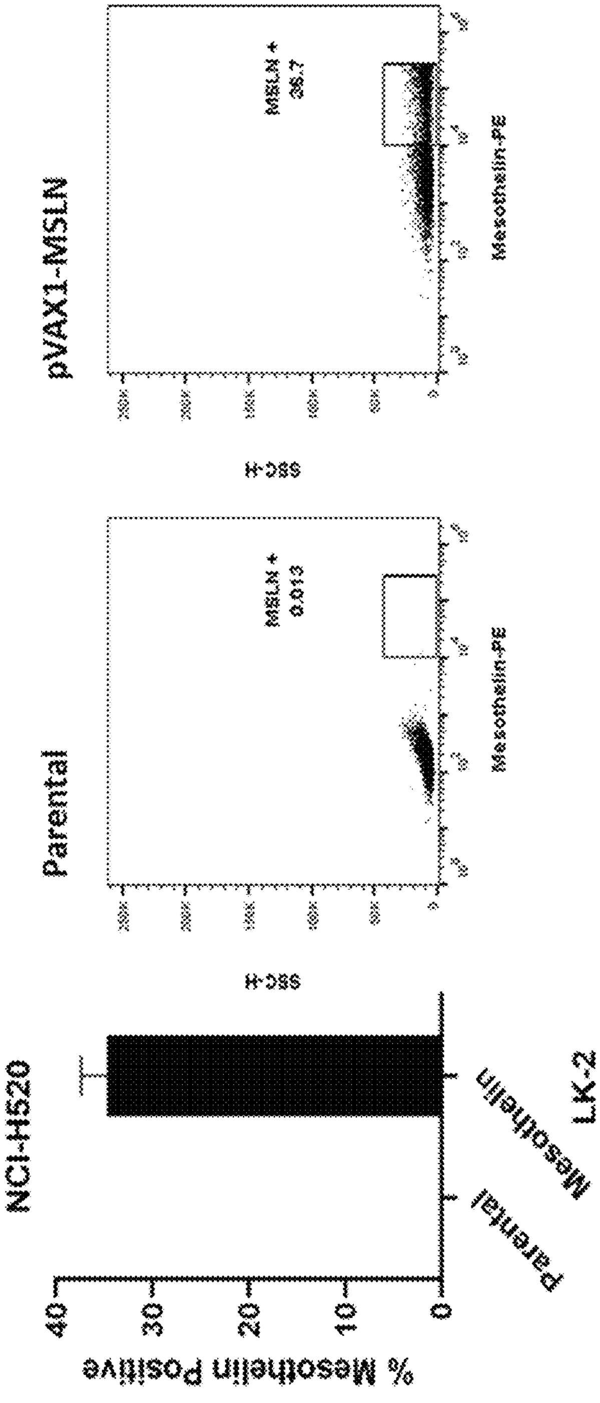
FIGS. 46A-E show expression of Mesothelin and increased mesothelin-specific IFNγ responses in the NCI-H520 cell line (FIG. 46A), LK-2 cell line (FIG. 46B and FIG. 46E), A549 cell line (FIG. 46C), and NCI-H460 cell line (FIG. 46D).
Figure 46B:
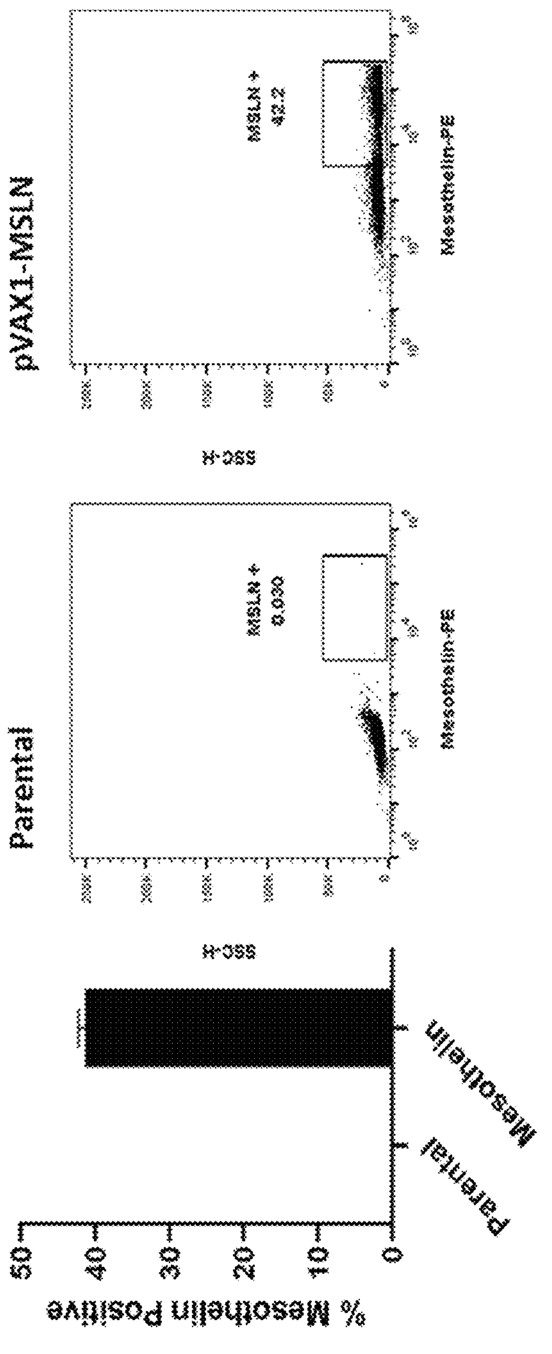
Figure 46C:
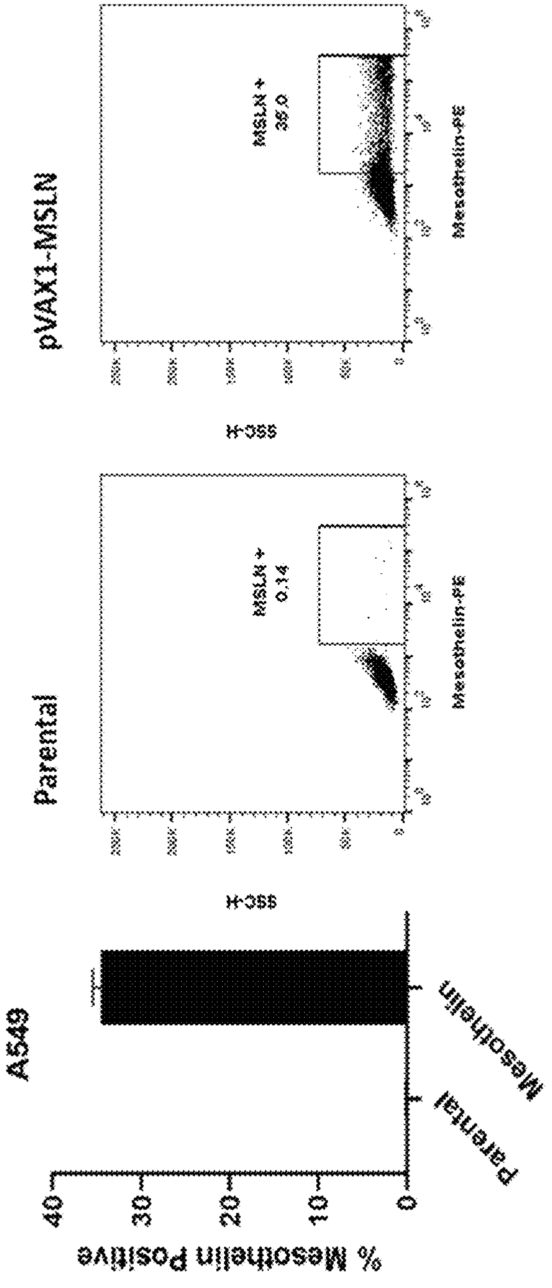
Figure 46D:
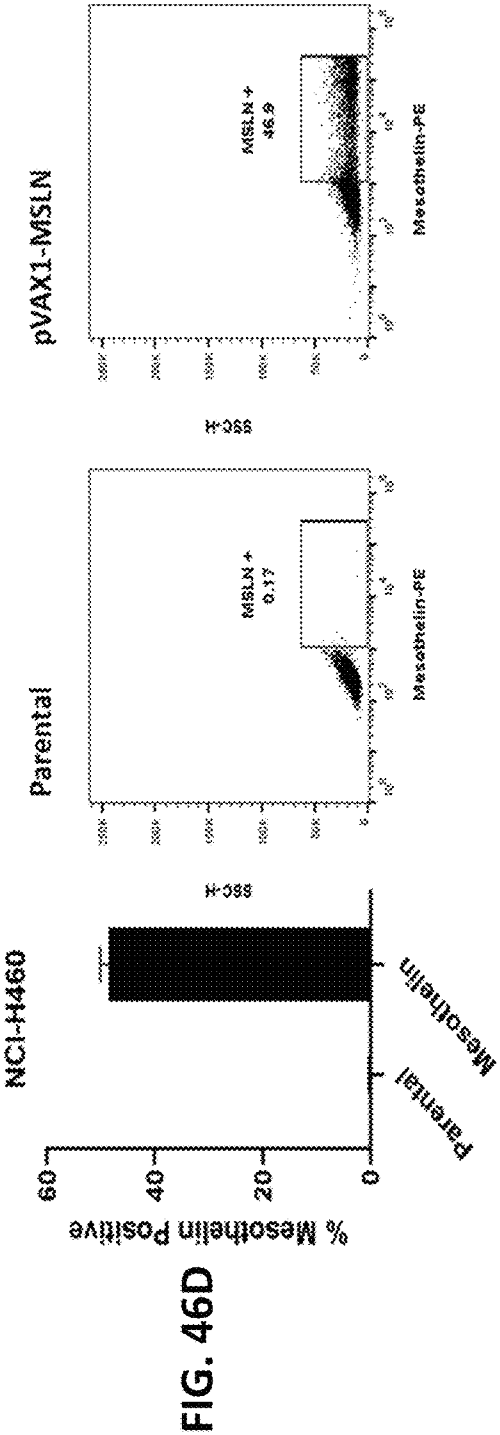

Transfections of the MSLN encoding plasmid were completed as described in Example 18. To determine cell surface expression of MSLN, transfected cells and unmodified parental controls were surfaced stained with PE-conjugated rat anti-human MSLN antibody (R&D Systems, FAB32652P). Flow cytometry data was acquired on a BD LSRFortessa and analyzed using FlowJo software. Minimal expression of MSLN was detected on untransfected, unmodified parental cell lines (n=3/cell line) (FIG. 46). MSLN was expressed on 34.7±2.2% of transfected NCI-H520 cells (n=3) (FIG. 46A), 41.4±0.7% of transfected LK-2 cells (n=3) (FIG. 46B), 34.6±0.7% of transfected A549 cells (n=3) (FIG. 46C), and 48.5±1.3% of transfected NCI-H460 cells (n=3) (FIG. 46D).

MSLN-Specific IFNγ Responses

Figure 46E:
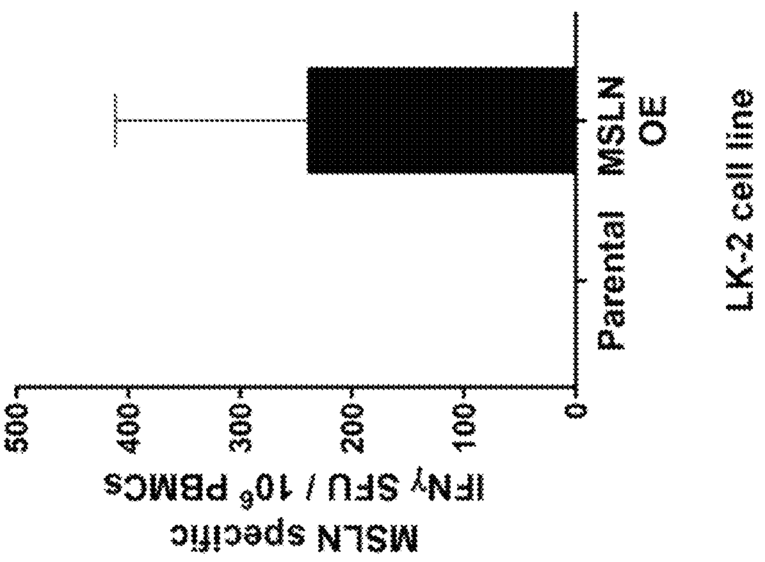

Immune responses to the overexpressed MSLN antigen were characterized by IFNγ ELISpot. To detect MSLN-specific responses in this assay, peptides 15 amino acids in length, overlapping by 11 amino acids, were generated to cover the native protein MSLN protein and used to stimulate PBMCs as described in Example 8. IFNγ responses to the overexpressed MSLN protein (240 SFU) in LK-2 (FIG. 46E).

Example 23: Expression of Kita-Kyushu Lung Cancer Antigen 1 (CT83)

CT83 is expressed by 40% non-small-cell lung cancer tissues and by 31% Stage 1 NSCLC. CT83 is highly expressed in lung tumors compared to normal tissue. Expression of CT83 is also typically associated with poor prognosis. In Example 23, the expression of CT83 was genetically introduced in exemplary vaccine cell lines that do not natively express CT83 to broaden the coverage TAAs potentially relevant to some NSCLC patients.

Expression of CT83

A codon optimized sequence of human CT83 was generated and cloned in frame with codon optimized MSLN (Example 17). SEQ ID NO: 21 was used. The MSLN and CT83 coding sequences were separated by a P2A cleavage site and cloned into the BamHI and XhoI restriction sites of pVAX1.

Characterization of CT83 Expression

Figure 47:
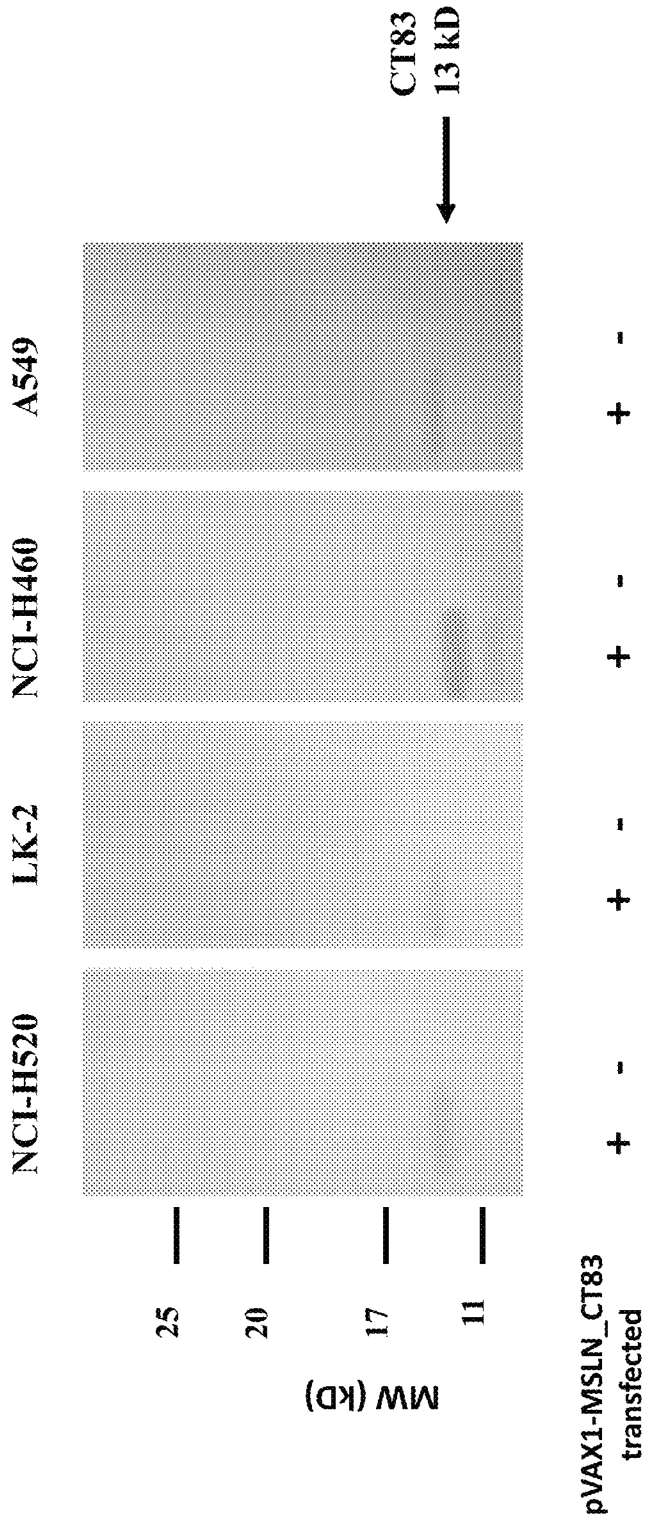
FIG. 47 shows the expression of CT83.

Expression of CT83 by pVAX1-MSLN-CT83 was determined by western blot. Transfections were completed as described in described in Example 18. Transfected cells were lysed by the addition of 100 μL 1× NuPAGE® LDS Sample Buffer (Invitrogen, #NP0007) and incubated for 5 minutes at room temperature. The cell lysate was transferred to Eppendorf tubes and sonicated for 5 minutes to reduce viscosity. Samples were heated for 10 minutes at 70° C. and then loaded onto 4-12% NuPAGE® Bis-Tris gels. BLUelf Pre-stained Protein Ladder (FroggaBio, PM008-0500) was included as a protein sizing standard. Gels were electrophoresed at 200 Volts for ~1 hour under reducing conditions using 1×MES SDS Running Buffer (Invitrogen, NP0002). Proteins were then transferred to nitrocellulose using NuPAGE® Transfer Buffer (Invitrogen, NP0006) plus 20% methanol under reducing conditions. Blotting was performed for 1 hour at 30 Volts. After blotting, membranes were blocked with 5% Blotto (ChemCruz, DC2324) in Tris-Buffered Saline plus Tween (TBST: 10 mM Tris pH 8.0, 150 mM NaCl, 0.1% Tween 20) for 1 hour at room temperature with shaking (100 rpm). Blots were then probed with primary antibody anti-CT83 rabbit polyclonal (Sigma, HPA004773) in TBST-5% Blotto at 4 μg/mL overnight at 4° C. The next day, blots were washed 5× with TBST and then probed with a 1:5,000 dilution of anti-rabbit IgG HRP conjugated antibody (Southern Biotech, 4030-05) in TBST-5% Blotto for 1 hour at room temperature with shaking. Blots were washed 5× with TBST and developed by the addition of 1-Step Ultra TMB Blotting Solution (Pierce, #37574) (FIG. 47).

Example 24: Expression of Immunostimulatory Factors in A549 and NCI-H460 with Reduced Expression of Immunosuppressive Factors The reduction of immunosuppressive suppressive factors in the VME can enhance cellular immune responses. Expression of immunostimulatory factors in the VME, in the context of reduced production of immunosuppressive factors, should further enhance the ability of the vaccine to elicit robust immune responses.

In this Example, the A549 and NCI-H460 component vaccine cell lines with reduced expression of three immunosuppressive factors were modified to secrete GM-CSF, express membrane bound CD40L, and/or secrete the functional heterodimeric IL-12 p70 cytokine. The ability for GM-CSF to increase IFNγ responses in vitro is described in Example 16. In vivo expression of GM-CSF in the skin enhances DC activation, maturation, and the ability for DCs to promote a more functional, Th1-biased immune response. The immunostimulatory functions of membrane bound CD40L and IL-12 p70 when expressed alone are described in Example 15 and Example 17, respectively. The methods used for shRNA mediated knockdown TGFβ1 and TGFβ2 secretion, and to determine resulting secretion levels, are described in Example 5. The methods used for ZFN-mediated knockout of CD47 and CD276, and to determine resulting cell surface expression levels, are described in Example 12 and Example 13, respectively.

In some examples, the component vaccine cell lines with three reduced immunosuppressive factors were modified to secrete GM-CSF and to express membrane bound CD40L. In some examples, the component vaccine cell lines with three reduced immunosuppressive factors were modified to secrete GM-CSF, express membrane bound CD40L, and to secrete the functional IL-12 p70 cytokine. Methods used to quantify the expression of membrane bound CD40L are described herein.

Secretion of GM-CSF by A549 and NCI-H460

The vaccine component cell lines A549 and NCI-H460 were transduced with lentiviral particles expressing native human GM-CSF. Unmodified parental, unmodified cell lines served as controls. After antibiotic selection in 100 μg/mL to enrich for cells stable expressing GM-CSF, cells were analyzed for GM-CSF secretion by ELISA. The sequence of GM-CSF used in this example is shown in SEQ ID NO: 6.

Quantification of Secreted GM-CSF

GM-CSF-transduced and unmodified parental cells were plated at $8.33\times10^1$ cells/well in a 24-well plated in regular growth medium (RPMI containing 10% FBS). Twenty-four hours after plating, adherent cells were thoroughly washed to remove FBS and culture was continued in RPMI+5% CTS. Forty-eight hours after media replacement, the cell culture supernatant was harvested, and stored at −70° C. until the GM-CSF secretion assay was completed according to the manufacturers specifications (human GM-CSF Quantikine ELISA kit #DGM00, R&D Systems). The lower limit of quantitation of human GM-CSF in the ELISA assay is less than 3.0 pg/mL, or 0.018 ng/$10^6$ cells/24 hours. GM-CSF secretion by the unmodified parental cell lines was below the lower limit of quantitation of the ELISA assay.

Quantification of Secreted IL-12 p70

IL-12-transduced and unmodified parental cells were plated at $8.33\times10^1$ cells/well in a 24-well plated in regular growth medium (RPMI containing 10% FBS). Twenty-four hours after plating, adherent cells were thoroughly washed to remove FBS and culture was continued in RPMI+5% CTS. Forty-eight hours after media replacement, the cell culture supernatant was harvested, and stored at −70° C. until the IL-12 secretion assays for p40 and p70 were completed according to the manufacturers specifications (BioLegend, human IL-12 p40 LEGEND MAX ELISA kit #430707 and human IL-12 p70 LEGEND MAX ELISA kit #431707). The lower limit of quantification of human IL-12 p40 is 9.5 pg/mL, or 0.057 ng/$10^6$ cells/24 hours. The lower limit of quantification of human IL-12 p70 is 1.2 pg/mL, or 0.007 ng/$10^6$ cells/24 hours. IL-12 secretion by the unmodified parental cell lines was below the lower limit of quantitation of the ELISA assay.

Figure 48A:
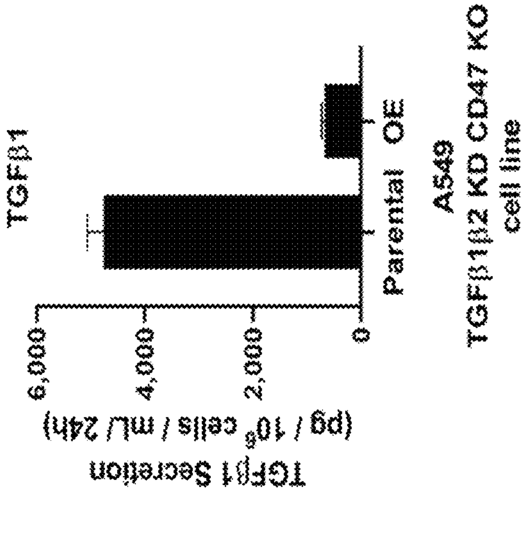
FIGS. 48A-E show secretion of GM-CSF and expression of membrane bound CD40L in the A549 TGFβ1 TGFβ2 KD CD47 KO cell line.
Figure 48B:
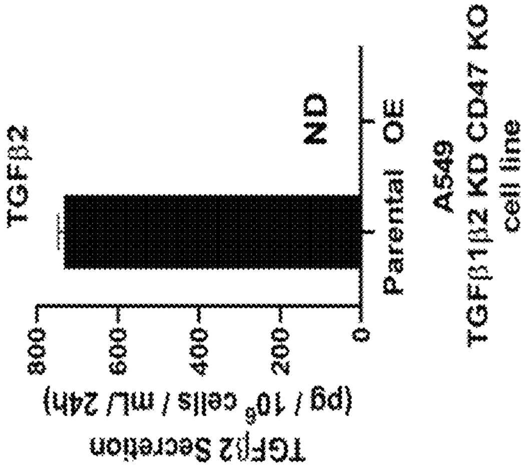
Figure 48C:
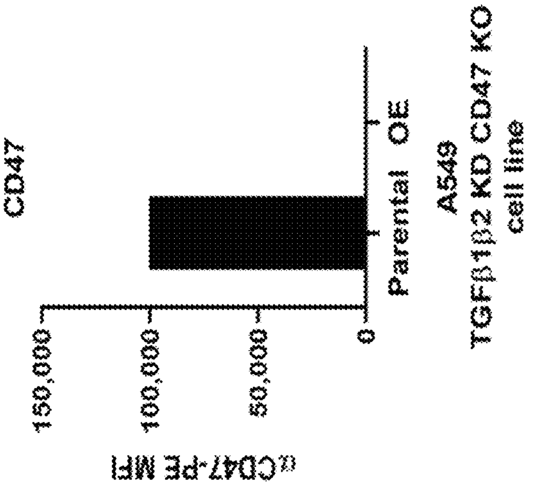
Figure 48D:
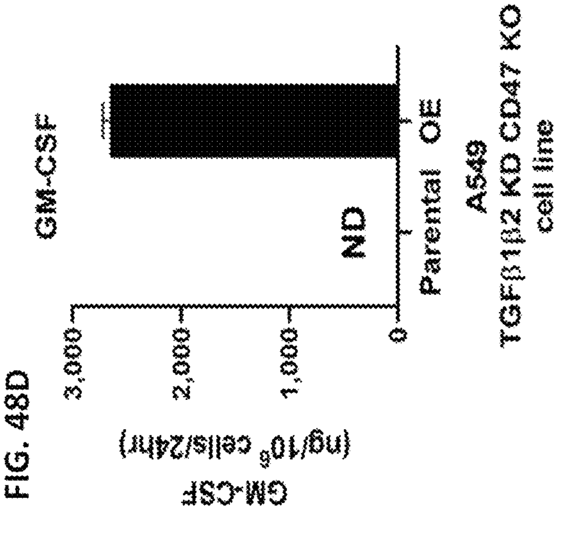
Figure 48E:
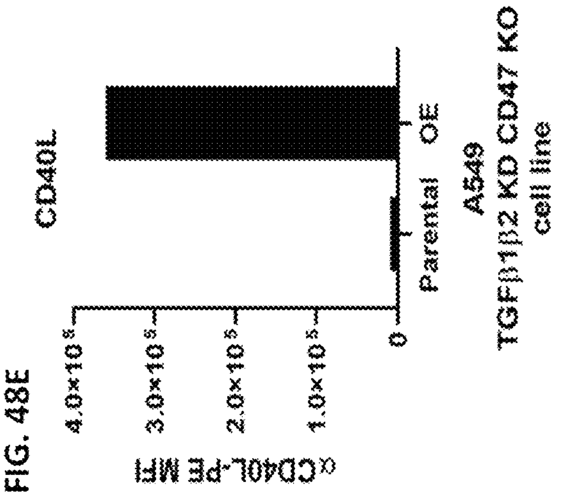
Figure 49A:
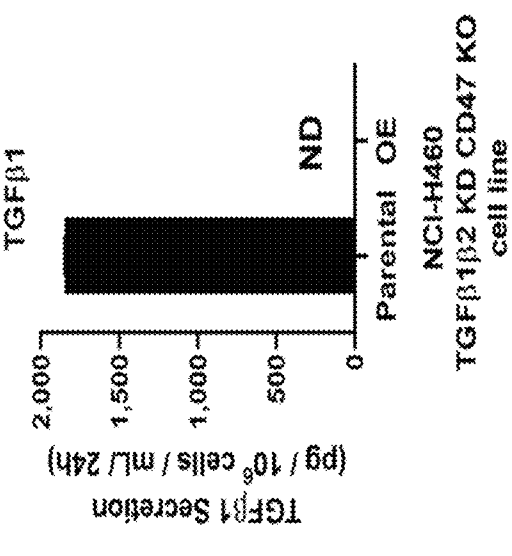
FIGS. 49A-E show secretion of GM-CSF and expression of membrane bound CD40L in the NCI-H460 TGFβ1 TGFβ2 KD CD47 KO cell line.
Figure 49B:
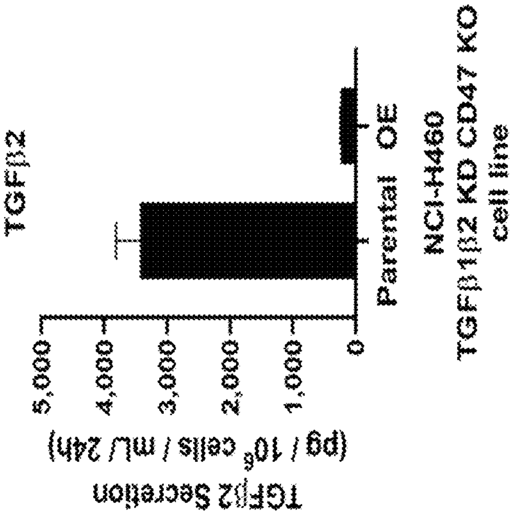
Figure 49C:
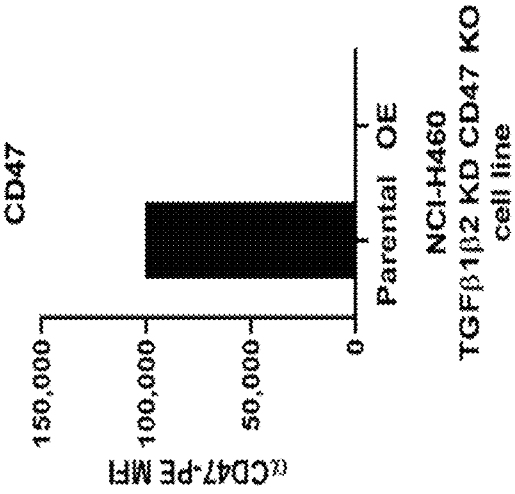
Figure 49D:
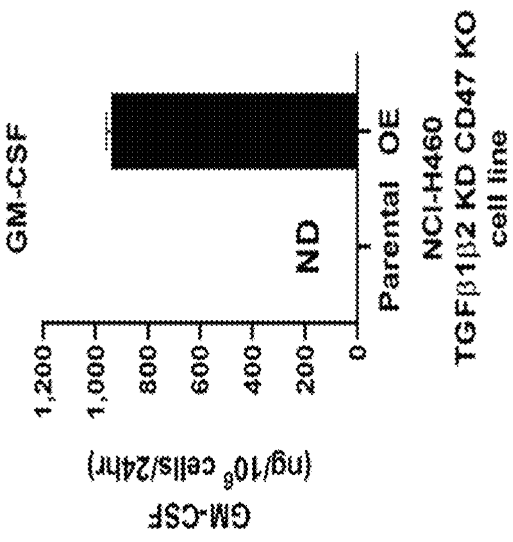
Figure 49E:
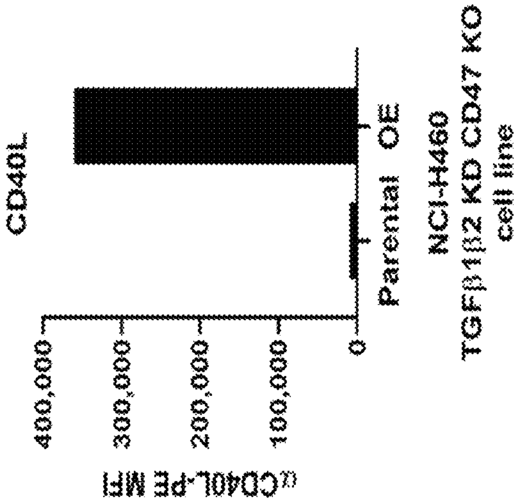

GM-CSF Secretion and Membrane Bound CD40L Expression by TGFβ1 TGFβ2 KD CD47 KO A549 and NCI-H460 Cell Lines The A549 cell line was modified to reduce secretion of TGFβ1 86% (n=2) (FIG. 48A) (Table 32), and TGFβ2>89% (n=2) (FIG. 48B) (Table 32), reduce the expression of CD47 99.9% (FIG. 48C) (Table 33), secrete 2,656±69 ng/$10^6$ cells/24 hours of GM-CSF (FIG. 48D) (Table 34), and express a 38-fold increase in membrane bound CD40L (FIG. 48E) (Table 34). The NCI-H460 cell line was modified to reduce secretion of TGFβ1>95% (n=2) (FIG. 49A) (Table 32), and TGFβ2 93% (n=2) (FIG. 49B) (Table 32), reduce the expression of CD47 99.9% (FIG. 49C) (Table 33), secrete 940±19 ng/$10^6$ cells/24 hours of GM-CSF (FIG. 49D) (Table 35), and express a 5-fold increase in membrane bound CD40L (FIG. 49E) (Table 34).

TABLE 32

TGFβ1 and TGFβ2 secretion in CD47 KO cell lines that secrete GM-CSF and express membrane bound CD40L

| | TGFβ1 (pg/$10^6$cells/24 hours) | | | TGFβ2 (pg/$10^6$cells/24 hours) | | |
|---|---|---|---|---|---|---|
| Cell line | Parental | TGFβ1 KD | % Reduction | Parental | TGFβ2 KD | % Reduction |
| A549 | 4,767 ± 300 | 679 + 51 | 86 | 732 ± 14 | <42 | >89* |
| NCI-H460 | 1,850 ± 1 | <92 | >95* | 3,433 ± 271 | 239 ± 13 | 93 |

Parental indicates the unmodified cell line.

*Secretion levels are below the lower limit of quantification for TGFβ1 (92 pg/$10^6$ cells/24 hours) or TGFβ2 (42 pg/$10^6$ cells/24 hours). Lower limit of quantification used to approximate % reduction relative to parental.

NA: secretion levels are below the lower limit of quantification for both the parental and shRNA modified cell line.

TABLE 33

| CD47 KO or CD276 KO in TGFβ1 and TGFβ2 KD cell lines that secrete GM-CSF and express membrane bound CD40L | | | |
|---|---|---|---|
| Cell line | Parental CD47 MFI | Modified CD47 MFI | % Reduction |
| A549 | 100,228 | 74 | 99.9 |
| NCI-H460 | 140,990 | 30 | 99.9 |
| Cell line | Parental MFI | Modified CD276 MFI | % Reduction |
| A549 | 30,636 | 1,983 | 93.5 |
| NCI-H460 | 82,858 | 712 | 99.1 |

MFI reported with unstained controls subtracted. Parental indicates the unmodified cell line.

TABLE 34

GM-CSF secretion and membrane bound CD40L expression by TGFβ1 TGFβ2 KD CD47 KO and TGFβ1 TGFβ2 KD CD276 KO cell lines

| Cell line | GMCSF ($ng/10^6$ cells/24 hours) | Parental CD40L MFI | Modified CD40L MFI | CD40L Fold Increase |
|---|---|---|---|---|
| A549 TGFβ1 and TGFβ2 KD, CD47 KO | 2,656 ± 69 | 9,537 | 360,236 | 38 |
| NCI-H460 TGFβ1 and TGFβ2 KD, CD47 KO | 940 ± 19 | 16,992 | 84,924 | 5 |
| A549 TGFβ1 and TGFβ2 KD, CD276 KO | 1,704 ± 60 | 41,076 | 1,660,242 | 40 |
| NCI-H460 TGFβ1 and TGFβ2 KD, CD276 KO | 943 ± 13 | 16,992 | 121,555 | 7 |

Figures 50A, 50B, 50C, 50D, 50E:
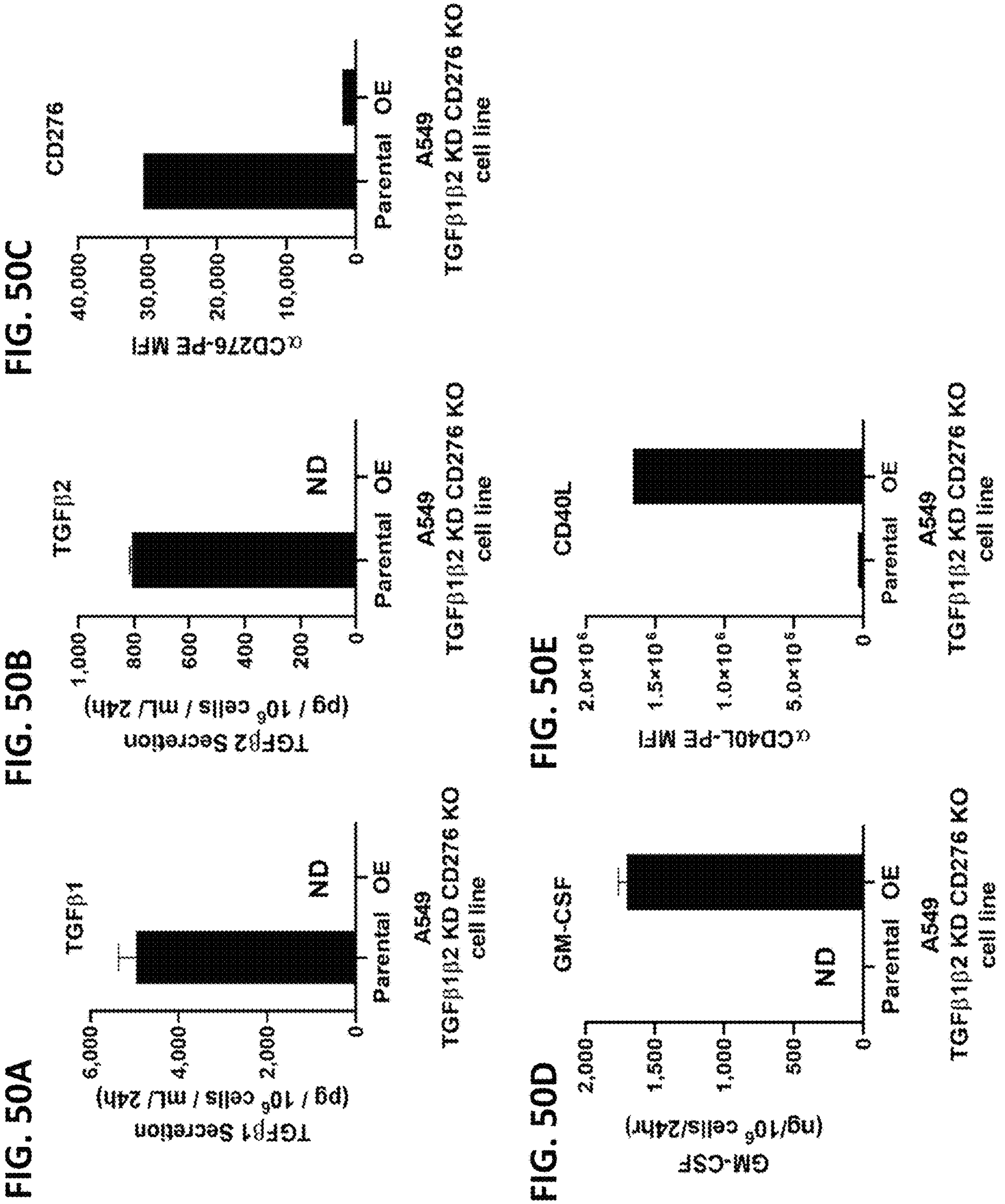
FIGS. 50A-E show secretion of GM-CSF and expression of membrane bound CD40L in the A549 TGFβ1 TGFβ2 KD CD276 KO cell line.
Figure 51A:
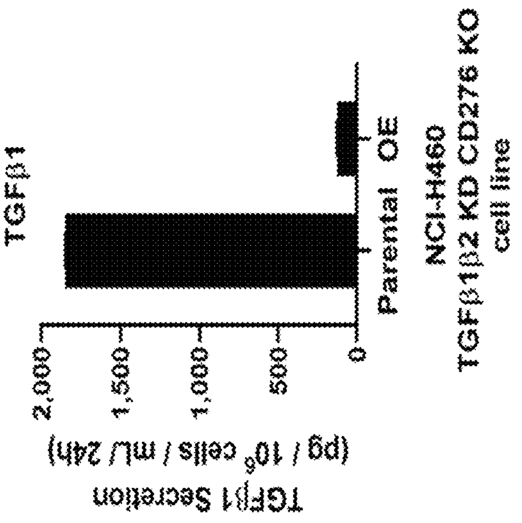
FIGS. 51A-E show secretion of GM-CSF and expression of membrane bound CD40L in the NCI-H460 TGFβ1 TGFβ2 KD CD276 KO cell line.
Figure 51B:
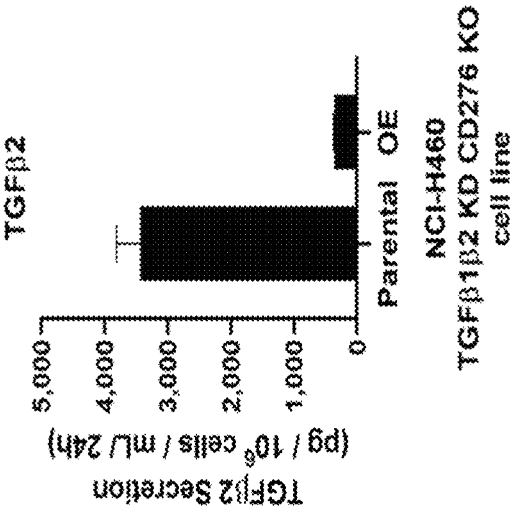
Figure 51C:
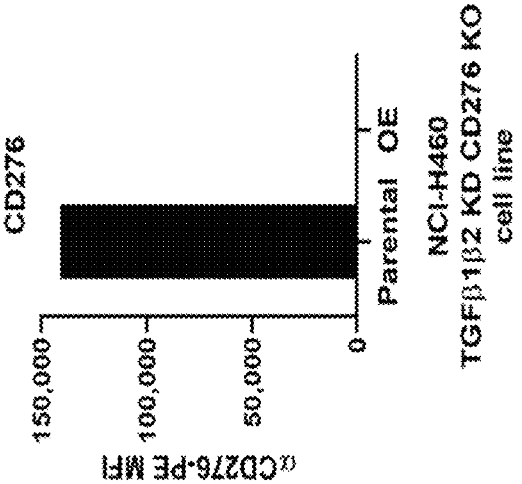
Figure 51D:
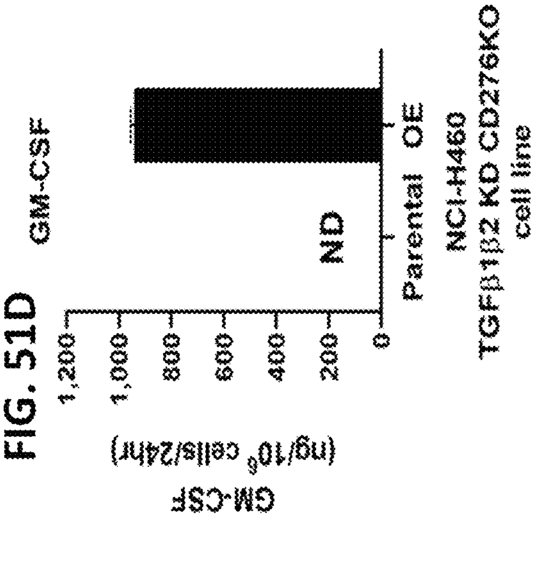
Figure 51E:
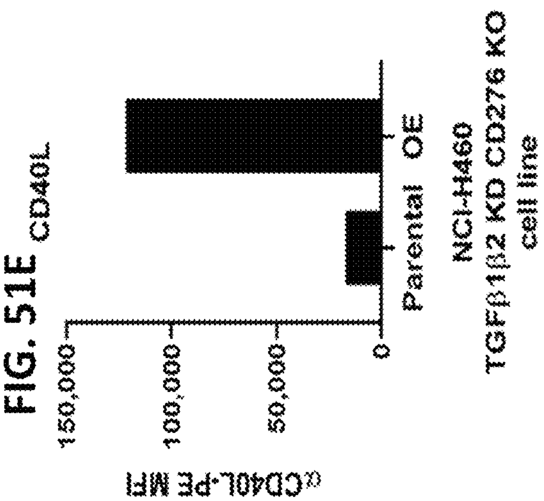

GM-CSF Secretion and Membrane Bound CD40L Expression by TGFβ1 TGFβ2 KD CD276 KO A549 and NCI-H460 Cell Lines The A549 cell line was modified to reduce secretion of TGFβ1>98% (n=2) (FIG. 50A) (Table 35), and TGFβ2>89% (n=2) (FIG. 50B) (Table 35), reduce the expression of CD276 93.5% (FIG. 50C) (Table 33), secrete 1,704±60 $ng/10^6$ cells/24 hours of GM-CSF (FIG. 50D) (Table 34), and express a 40-fold increase in membrane bound CD40L (FIG. 50E) (Table 34). The NCI-H460 cell line was modified to reduce secretion of TGFβ1 93% (n=2) (FIG. 51A) (Table 32), and TGFβ2 89% (n=2) (FIG. 51B) (Table 32), reduce the expression of CD276 99.1% (FIG. 51C) (Table 33), secrete 943±13 $ng/10^6$ cells/24 hours of GM-CSF (FIG. 51D) (Table 34), and express a 7-fold increase in membrane bound CD40L (FIG. 51D) (Table 34).

Figure 52A:
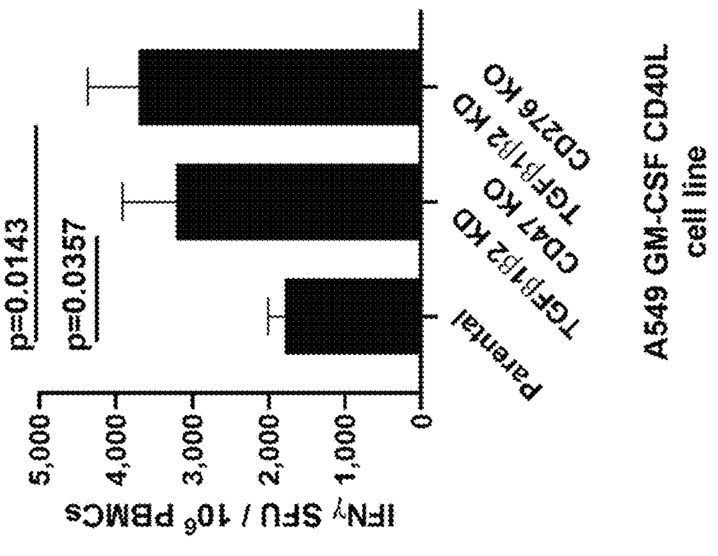
FIGS. 52A-C show secretion of GM-CSF and expression of membrane bound CD40L in TGFβ1 TGFβ2 KD CD47 KO or TGFβ1 TGFβ2 KD CD276 KO cell lines increases cellular immune responses and DC maturation.

GM-CSF Secretion and Membrane Bound CD40L Expression by TGFβ1 TGFβ2 KD CD47 KO and TGFβ1 TGFβ2 KD CD276 KO A549 Cell Line Increases Cellular Immune Responses IFNγ ELISpot was used to evaluate the effect GM-CSF secretion and membrane bound CD40L expression by TGFβ1 TGFβ2 KD CD47 KO and GM-CSF secretion and membrane bound CD40L expression by TGFβ1 TGFβ2 KD CD276 KO on cellular immune responses in the A549 cell line. IFNγ ELISpot was completed as described in Example 9 using cells derived from two HLA-A02 healthy donors (n=3/donor). GM-CSF secretion and membrane bound CD40L expression by TGFβ1 TGFβ2 KD CD47 KO (3,213±287) (n=6) (p=0.0357) and TGFβ1 TGFβ2 KD CD276 KO (3,207±663) (n=6) (p=0.0143) significantly increase IFNγ responses compared to the unmodified parental A549 cell line (1,793±215 SFU) (n=6) (FIG. 52A). Statistical significance was determined using One-Way ANOVA and Holm-Sidak's multiple comparisons test.

Figure 52B:
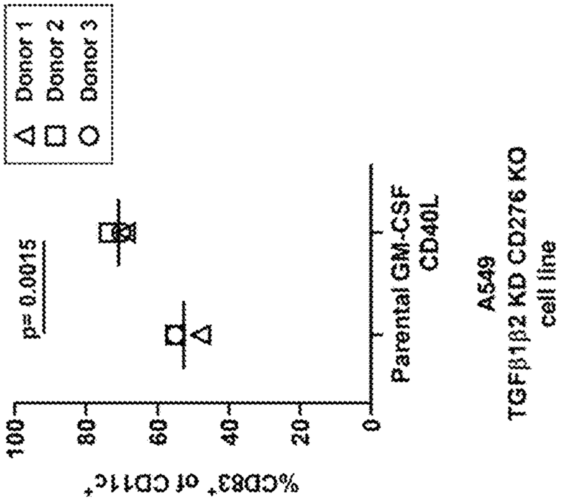
Figure 52C:
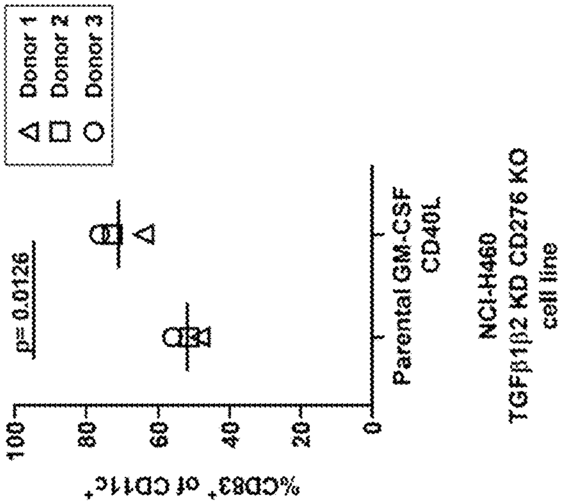

GM-CSF Secretion and Membrane Bound CD40L Expression by TGFβ1 TGFβ2 KD CD276 KO A549 and NCI-H460 Cell Lines Increase DC Maturation The maturation of iDCs was determined by flow cytometry as described in Example 15. In this Example, iDCs derived from three HLA-A02 donors were co-cultured with the unmodified parental A549 or unmodified parental NCI-H460 cell lines, or the modified A549 or NCI-H460 TGFβ1 and TGFβ2 KD CD276 KO, that secrete GM-CSF and express membrane bound CD40L. Expression of the DC maturation marker CD83 was significantly increased on DCs co-cultured with the modified A549 (71±2%) compared to DCs co-cultured with the unmodified parental A549 cell line (53±3%) (p=0.0015) (FIG. 52B). Similarly, CD83 was significantly increased on DCs co-cultured with the modified NCI-H460 (71±5%) compared to DCs co-cultured with the unmodified parental H460 (ATCC HTB-177) cell line (52±3%) (p=0.0126) (FIG. 52C). Statistical significance was determined using One-Way ANOVA and Holm-Sidak's multiple comparisons test.

GM-CSF Secretion, Membrane Bound CD40L Expression, and IL-12 Secretion by TGFβ1 TGFβ2 KD CD47 KO A549 and NCI-H460 Vaccine Component Cell Lines The A549 cell line was modified to reduce secretion of TGFβ1 84% (n=2) (FIG. 53A) (Table 36), and TGFβ2>89% (n=2) (FIG. 53B) (Table 36), reduce the expression of CD47 99.9% (FIG. 53C) (Table 33), secrete 2,295±60 $ng/10^6$ cells/24 hours of GM-CSF (FIG. 53D) (Table 37), express a 56-fold increase in membrane bound CD40L (FIG. 53E) (Table 37), and secrete 300±24 $ng/10^6$ cells/24 hours of IL-12 p70 (FIG. 53F) (Table 37).

TABLE 35

TGFβ1 and TGFβ2 secretion in CD276 KO cell lines that secrete GM-CSF and express membrane bound CD40L

| Cell line | TGFβ1 ($pg/10^6$cells/24 hours) Parental | TGFβ1 KD | % Reduction | TGFβ2 ($pg/10^6$cells/24 hours) Parental | TGFβ2 KD | % Reduction |
|---|---|---|---|---|---|---|
| A549 | 4,967 ± 399 | <92 | >98* | 807 ± 8 | <42 | >89* |
| NCI-H460 | 1,850 ± 1 | 126 ± 5 | 93 | 3,433 ± 271 | 366 ± 5 | 89 |

Parental indicates the unmodified cell line.

*Secretion levels are below the lower limit of quantification for TGFβ1 (92 $pg/10^6$ cells/24 hours) or TGFβ2 (42 $pg/10^6$ cells/24 hours). Lower limit of quantification used to approximate % reduction relative to parental.

TABLE 36

TGFβ1 and TGFβ2 secretion in TGFβ1 and TGFβ KD, CD47 KO cell lines that secrete GM-CSF, express membrane bound CD40L, and secrete IL-12

| | TGFβ1 ($pg/10^6$cells/24 hours) | | | TGFβ2 ($pg/10^6$cells/24 hours) | | |
|---|---|---|---|---|---|---|
| Cell line | Parental | TGFβ1 KD | % Reduction | Parental | TGFβ2 KD | % Reduction |
| A549 | 4,767 ± 300 | 760 ± 55 | 84 | 732 ± 14 | <42 | >89* |
| NCl-H460 | 1,850 ± 1 | <92 | >95* | 3,433 ± 271 | 492 ± 10 | 86 |

Parental refers to the unmodified cell line.
*Secretion levels are below the lower limit of quantification for TGFβ1 (92 $pg/10^6$ cells/24 hours) or TGFβ2 (42 $pg/10^6$ cells/24 hours). Lower limit of quantification used to approximate % reduction relative to parental.

TABLE 37

GM-CSF secretion, membrane bound CD40L expression, and IL-12 secretion by TGFβ1 TGFβ2 KD CD47 KO and TGFβ1 TGFβ2 KD CD276 KO cell lines

| Cell line | GMCSF ($ng/10^6$ cells/24 hours) | Parental CD40L MFI | Modified CD40L MFI | CD40L Fold Increase | IL-12 p70 (n/ $10^6$ cells/24 hours) |
|---|---|---|---|---|---|
| A549 TGFβ1 and TGFβ2 KD, CD47 KO | 2,295 ± 60 | 9,537 | 536,953 | 56 | 300 ± 24 |
| NCl-H460 TGFβ1 and TGFβ2 KD, CD47 KO | 1,586 ± 24 | 16,992 | 154,964 | 9 | 434 ± 15 |
| A549 TGFβ1 and TGFβ2 KD, CD276 KO | 1,113 ± 51 | 41,076 | 1,476,699 | 36 | 263 ± 24 |
| NCl-H460 TGFβ1 and TGFβ2 KD, CD276 KO | 1,234 ± 24 | 16,992 | 267,023 | 16 | 312 ± 50 |

Figures 54A, 54B, 54C, 54D, 54E, 54F:
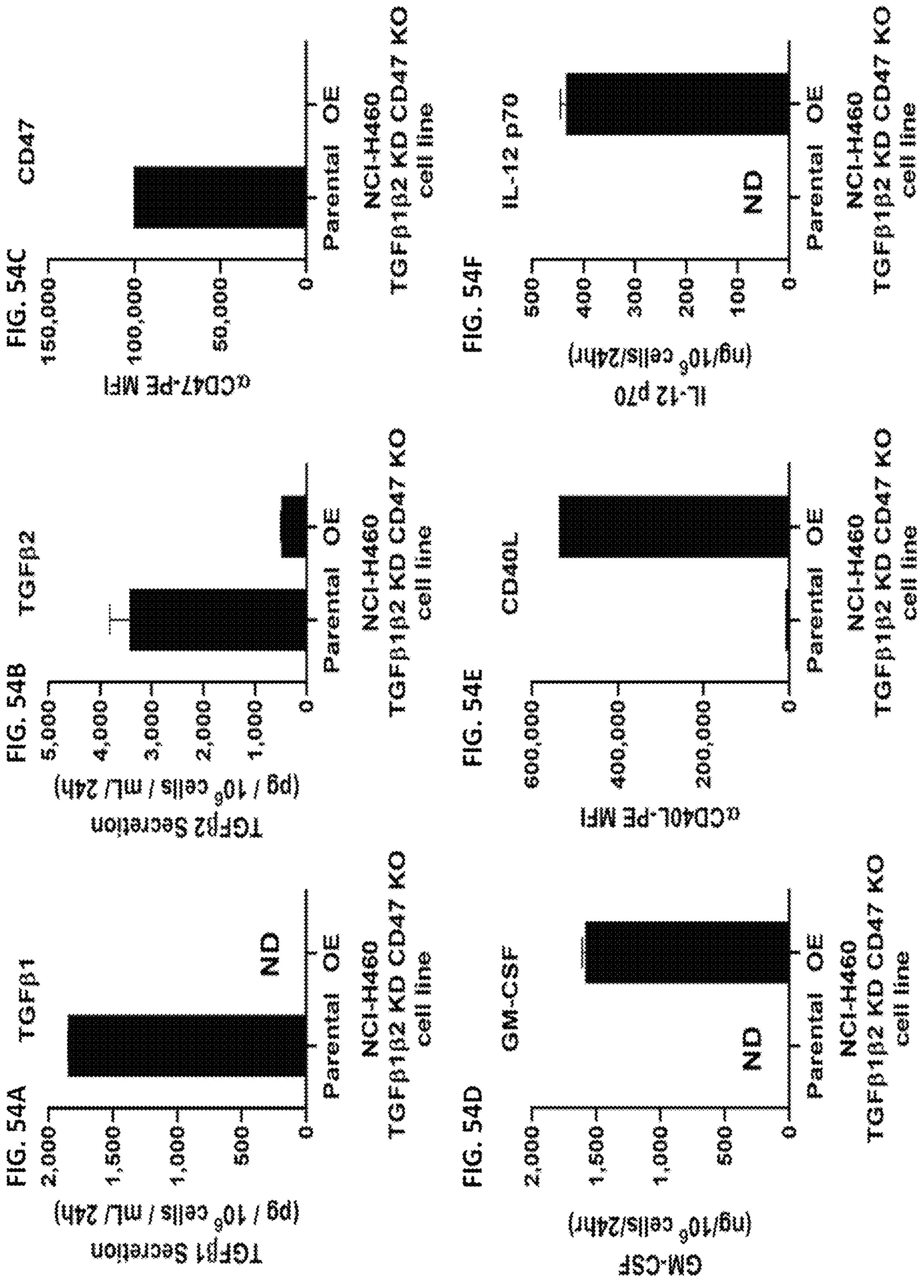
FIGS. 54A-F show secretion of GM-CSF, expression of membrane bound CD40L, and secretion of IL-12 in the NCI-H460 TGFβ1 TGFβ2 KD CD47 KO cell line.

The NCI-H460 cell line was modified to reduce secretion of TGFβ1>95% (n=2) (FIG. 54A) (Table 36), and TGFβ2 86% (n=2) (FIG. 54B) (Table 36), reduce the expression of CD47>99.9% (FIG. 54C) (Table 33), secrete 1,586±24 $ng/10^6$ cells/24 hours of GM-CSF (FIG. 54C) (Table 37), express a 9-fold increase in membrane bound CD40L (FIG. 54E) (Table 36), add secrete 434±15 $ng/10^6$ cells/24 hours of IL-12 p70 (FIG. 54F) (Table 36).

Figure 55B:
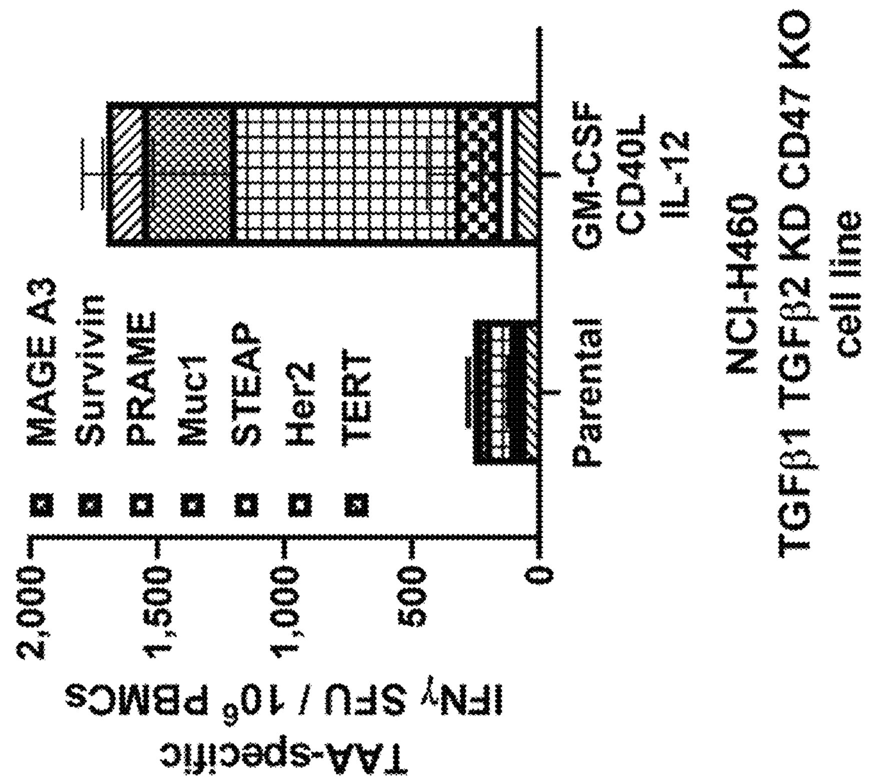
FIGS. 55A and B show secretion of GM-CSF, expression of membrane bound CD40L, and secretion of IL-12 by the A549 (FIG. 55A) and NCI-H460 (FIG. 55B) TGFβ1 TGFβ2 KD CD47 KO cell lines increases antigen specific responses.
Figure 55A:
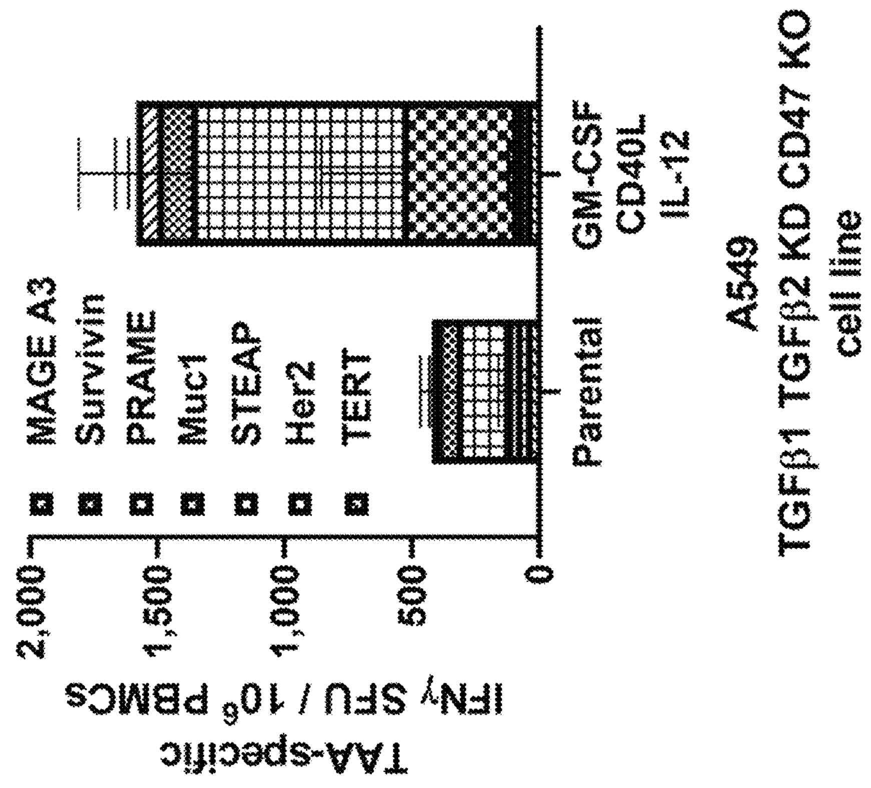

GM-CSF Secretion, Membrane Bound CD40L Expression, and IL-12 Secretion by TGFβ1 TGFβ2 KD CD47 KO A549 (ATCC CCL-185) and NCI-H460 (ATCC HTB-177) Cell Lines Increases TAA-Specific IFNγ Responses IFNγ ELISpot was used to evaluate the effect GM-CSF secretion, expression of membrane bound CD40L, and secretion of IL-12 by the TGFβ1 TGFβ2 KD CD47 KO A549 and by the TGFβ1 TGFβ2 KD CD47 KO NCI-H460 cell lines on IFNγ responses to antigens. IFNγ ELISpot was completed as described in Example 9 using cells derived from two HLA-A02 healthy donors (n=3/donor). The total IFNγ response to the TAAs MAGE A3, Survivin, PRAME, Muc1, STEAP1, Her2, and TERT was increased by the A549 TGFβ1 TGFβ2 KD CD47 KO cells (1,586±887 SFU) (n=6) compared to the unmodified parental cell line (382±96 SFU) (n=6) (p=0.5887) (FIG. 55A). Similarly, the total antigen specific IFNγ response elicited by the NCI-H460 TGFβ1 TGFβ2 KD CD47 KO cell line (1702±682 SFU) (n=6) was increased relative to the unmodified parental cell line (262±105 SFU) (n=6) (p=0.1385) (FIG. 55B). Responses to specific antigens are in the order indicated in the figure legends.

Figure 56:
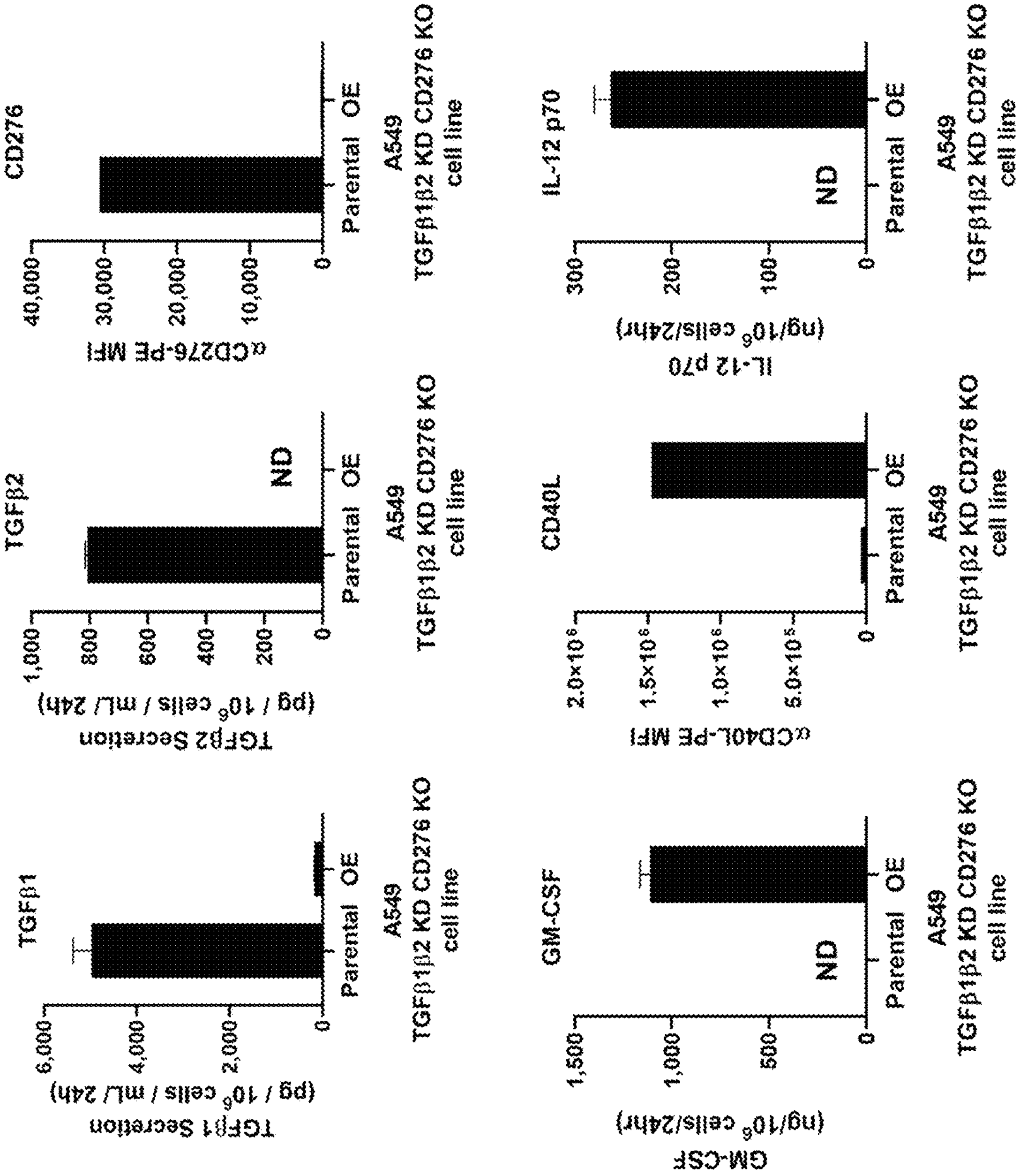
FIG. 56 shows the secretion of GM-CSF, expression of membrane bound CD40L, and secretion of IL-12 in the A549 TGFβ1 TGFβ2 KD CD276 KO cell line.

GM-CSF Secretion, Membrane Bound CD40L Expression, and IL-12 Secretion by TGFβ1 TGFβ2 KD CD276 KO A549 and NCI-H460 Vaccine Component Cell Lines The A549 cell line was modified to reduce the secretion of TGFβ1 96% (n=2) (FIG. 56A) (Table 38), and TGFβ2>89% (n=2) (FIG. 56B) (Table 38), reduce the expression of CD276 98.9% (FIG. 56C) (Table 33), secrete 1,113±51 $ng/10^6$ cells/24 hours of GM-CSF (FIG. 56D) (Table 37), express a 36-fold increase in membrane bound CD40L (FIG. 56E) (Table 37), add secrete 263±24 $ng/10^6$ cells/24 hours of IL-12 p70 (FIG. 56F) (Table 37).

Figure 57A:
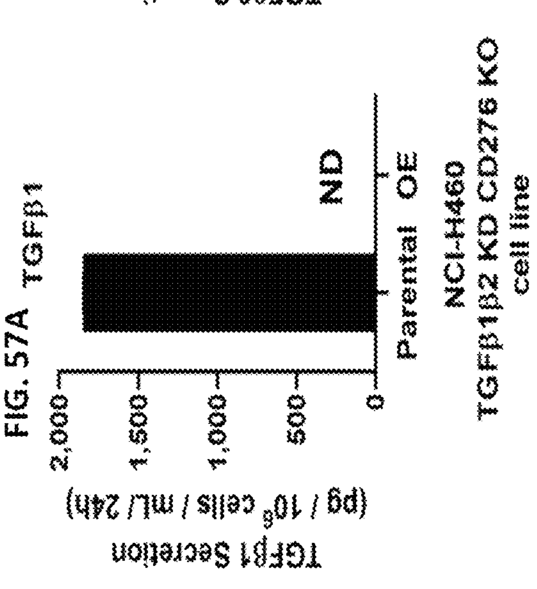
FIGS. 57A-F show secretion of GM-CSF, expression of membrane bound CD40L, and secretion of IL-12 in the NCI-H460 TGFβ1 TGFβ2 KD CD276 KO cell line.
Figure 57B:
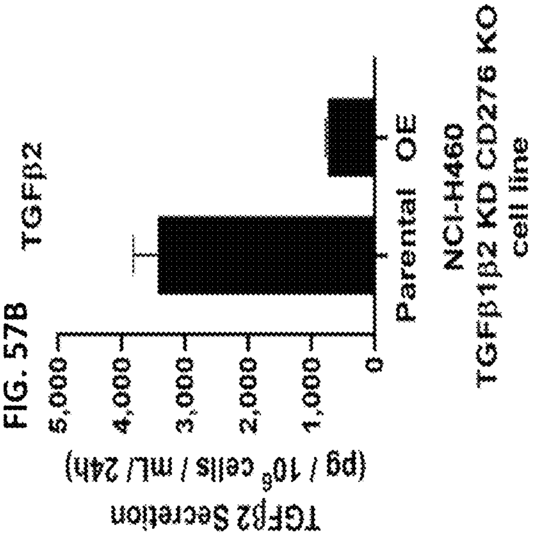
Figure 57C:
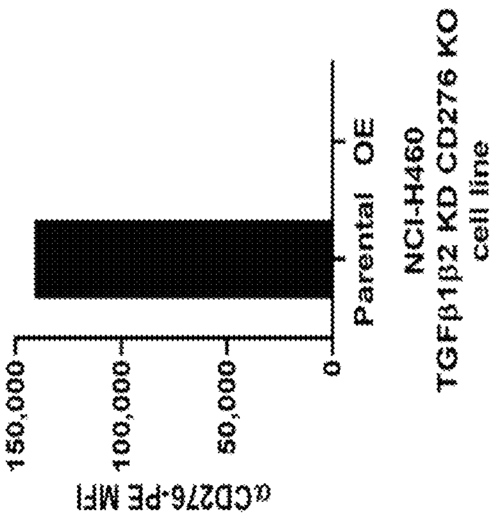
Figure 57D:
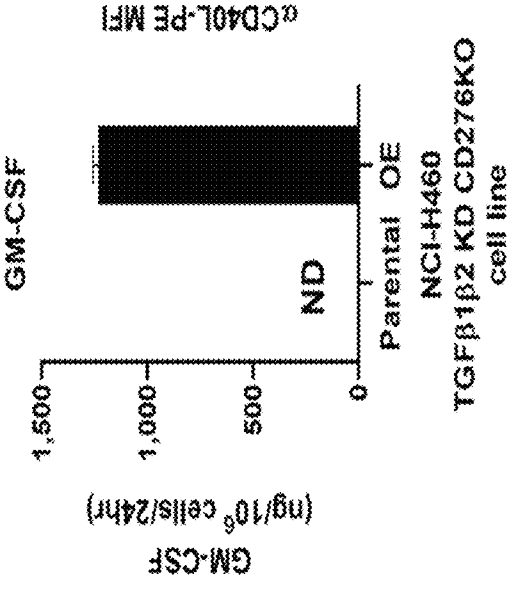
Figure 57E:
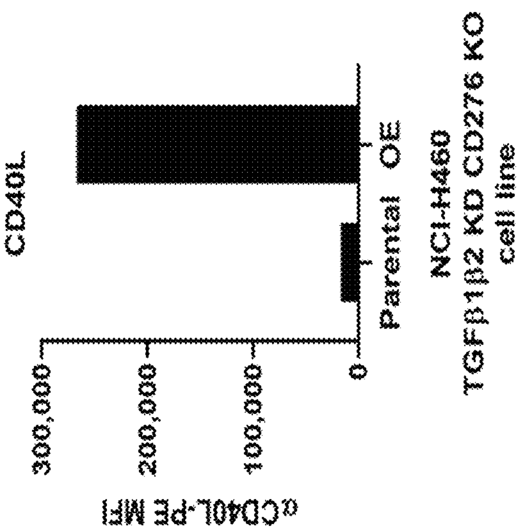
Figure 57F:
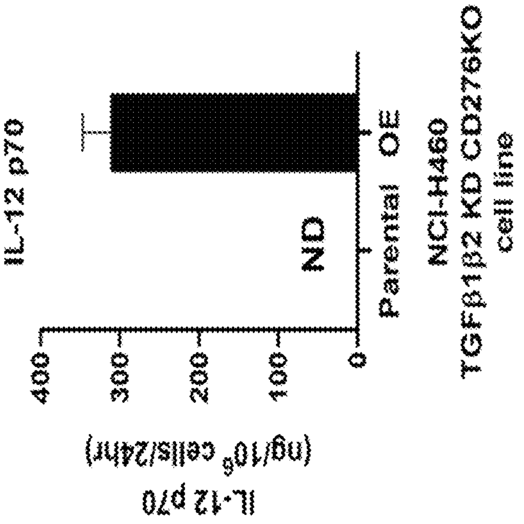

NCI-H460 cell line was modified to reduce secretion of TGFβ1>95% (n=2) (FIG. 57A) (Table 38), and TGFβ2 78% (n=2) (FIG. 57B) (Table 38), reduce the expression of CD276 98.2% (FIG. 57C) (Table 33), secrete 1,234±24 $ng/10^6$ cells/24 hours of GM-CSF (FIG. 57D) (Table 37), express a 16-fold increase in membrane bound CD40L (FIG. 57E) (Table 37), add secrete 312±50 $ng/10^6$ cells/24 hours of IL-12 p70 (FIG. 57F) (Table 37).

TABLE 38

TGFβ1 and TGFβ2 secretion in cell lines with reduced CD276 expression modified to express CD40L, GM-CSF, and IL-12 p70

| | TGFβ1 (pg/$10^6$cells/24 hours) | | | TGFβ2 (pg/$10^6$cells/24 hours) | | |
|---|---|---|---|---|---|---|
| Cell line | Parental | TGFβ1 | % Reduction | Parental | TGFβ2 | % Reduction |
| A549 | 4,967 ± 399 | 179 ± 6 | 96 | 807 ± 8 | <42 | >89* |
| NCI-H460 | 1,850 ± 1 | <92 | >95* | 3,433 ± 271 | 738 ± 34 | 78 |

Parental indicates the unmodified cell line.

*Secretion levels are below the lower limit of quantification for TGFβ1 (92 pg/$10^6$ cells/24 hours) or TGFβ2 (42 pg/$10^6$ cells/24 hours). Lower limit of quantification used to approximate % reduction relative to parental.

NA: secretion levels are below the lower limit of quantification for both the parental and shRNA modified cell line.

Figure 58A:
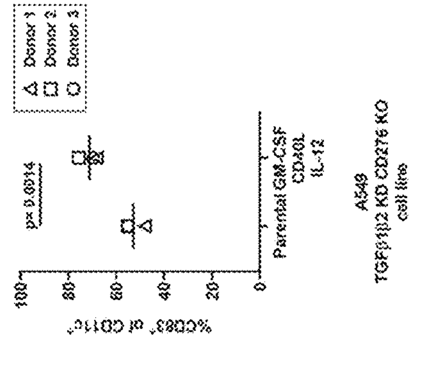
FIGS. 58A-D show secretion of GM-CSF, expression of membrane bound CD40L, and secretion of IL-12 by the A549 and NCI-H460 TGFβ1 TGFβ2 KD CD276 KO cell lines increases DC maturation and antigen specific responses.
Figure 58B:
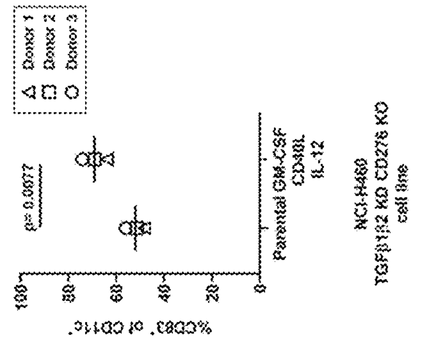

GM-CSF Secretion, Membrane Bound CD40L Expression, and IL-12 Secretion by TGFβ1 TGFβ2 KD CD276 KO A549 and NCI-H460 Cell Lines Increases DC Maturation The effect of GM-CSF secretion, expression of membrane bound CD40L, and secretion of IL-12 by the component vaccine cell lines on the maturation of DCs was determined by flow cytometry as described in Example 15. Specifically, iDCs derived from three HLA-A02 donors were co-cultured with the unmodified parental A549 (ATCC CCL-185) or NCI-H460 (ATCC HTB-177) cell lines, or the modified TGFβ1 and TGFβ2 KD CD276 KO A549 (ATCC CCL-185) or NCI-H460 (ATCC HTB-177) that secrete GM-CSF, express membrane bound CD40L, and secrete IL-12. Expression of the DC maturation marker CD83 was significantly increased on DCs co-cultured with the modified A549 (ATCC CCL-185) (71±3%) cell line compared to DCs co-cultured with the unmodified parental A549 (ATCC CCL-185) cell line (53±3%) (p=0.0014) (FIG. 58A). Similarly, CD83 was significantly increased on DCs co-cultured with the modified NCI-H460 (69±4%) cell line compared to DCs co-cultured with the unmodified parental H460 (ATCC HTB-177) cell line (52±3%) (p=0.0077) (FIG. 58B). Statistical significance was determined using One-Way ANOVA and Holm-Sidak's multiple comparisons test.

Figure 58C:
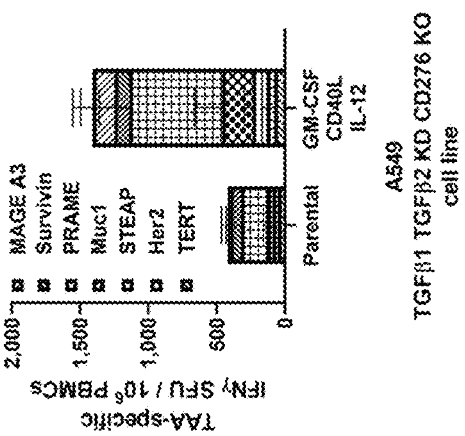
Figure 58D:
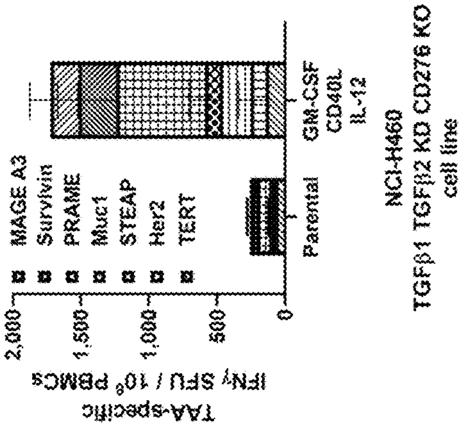

GM-CSF Secretion, Membrane Bound CD40L Expression, and IL-12 Secretion by TGFβ1 TGFβ2 KD CD276 KO A549 (ATCC CCL-185) and NCI-H460 (ATCC HTB-177) Cell Lines Increases TAA-Specific IFNγ Responses IFNγ ELISpot was used to evaluate the effect GM-CSF secretion, expression of membrane bound CD40L, and secretion of IL-12 by the TGFβ1 TGFβ2 KD CD276 KO A549 and by the TGFβ1 TGFβ2 KD CD276 KO NCI-H460 cell lines on IFNγ responses to antigens. IFNγ ELISpot was completed as described in Example 9 using cells derived from two HLA-A02 healthy donors (n=3/donor). The total IFNγ response to the antigens MAGE A3, Survivin, PRAME, Muc1, STEAP1, Her2, and TERT was markedly increased by the A549 TGFβ1 TGFβ2 KD CD47 KO cells (1,408±738 SFU) (n=6) compared to the unmodified parental cell line (421±149 SFU) (n=6) (p=0.1385) (FIG. 58C). Similarly, the total antigen specific IFNγ response elicited by the NCI-H460 TGFβ1 TGFβ2 KD CD276 KO cell line (1725±735 SFU) (n=6) was increased relative to the unmodified parental cell line (262±105 SFU) (n=6) (p=0.1385) (FIG. 58D). Responses to specific antigen are in the order indicated in the figure legends.

Example 25: HLA Mismatch Results in Increased Immunogenicity

Immune cells respond to "non-self"-proteins by generating an immune response. In the case of HLA mismatch, the immune response is against HLA proteins that are not expressed on the individual's cells and this response can be measured by the production of interferon gamma. Interferon gamma is a key cytokine involved in the generation of a $Th_1$ T cell response and $Th_1$ T cells are the essential mediators of an anti-cancer response. Unlike in stem cell or organ transplants, the HLA mismatch immune response plays a highly beneficial role in increasing the immunogenicity of a whole cell tumor vaccine by acting as an adjuvant that boosts the priming of T cells to TMs expressed within the tumor vaccine.

According to various embodiments of the present disclosure, the design of a cocktail of cell lines comprising the final vaccine product to include HLA mismatches at the two most immunogenic HLA loci—HLA-A and HLA-B, between the vaccine and the patient results in beneficial inflammatory responses at the vaccine site that results in increased vaccine uptake and presentation by DCs and the activation of a larger number of T cells, thus ultimately increasing the breadth, magnitude and immunogenicity of tumor reactive T cells primed by the cancer vaccine cocktail. By including multiple cell lines chosen to have mismatches in HLA types, and chosen for expression of key TAAs, the vaccine enables effective priming of a broad and effective anti-cancer response with the additional adjuvant effect generated by the HLA mismatch.

In one example, a vaccine composition according to the present disclosure includes multiple cell lines chosen to ensure a breadth of TMs as well as a diversity in the most immunogenic HLA proteins (HLA-A and HLA-B) in order to stimulate a maximal, effective immune response against the tumor. Inclusion of HLA mismatch augments the immune response, acting as an adjuvant to result in increased total anti-TAA interferon gamma production measurable by ELISpot and flow cytometry. The following features and selection criteria can be followed according to various embodiments:

Since HLA genes are inherited, the degree of HLA mismatch increases amongst individuals from different ethnicities. The cell line selection process may thus include, in some embodiments, obtaining cells from banks around the world in order to design a cocktail to include diversity in HLA alleles.

Disparities in HLA-C, -DRB1 and -DPB1 have been identified to be potentially less immunogenic, therefore in some embodiments the cell lines of a vaccine composition may be selected to ensure a mismatch of at least 2 of the highly immunogenic HLA-A and HLA-B alleles.

Increasing the number of mismatched HLA-A and HLA B loci between the cell lines selected may result, according to some embodiments, in a greater degree of mismatch across all patients receiving the vaccine to ensure the adjuvant effect measurable by interferon gamma ELISpot.

Dendritic cells were incubated with cancer cell line to allow for antigen uptake and DC maturation. The DCs were then co-cultured with PBMCs from donors, re-stimulated with the same cell line or a cocktail of cell lines chosen to have heterogeneity in their HLA subtypes and in order to create a mismatch with the donor PBMC HLA type. The cells were plated on an ELISpot plate and activated. Tumor specific T cells were measured by counting interferon γ spots/well as described in Example 6.

Figure 59:
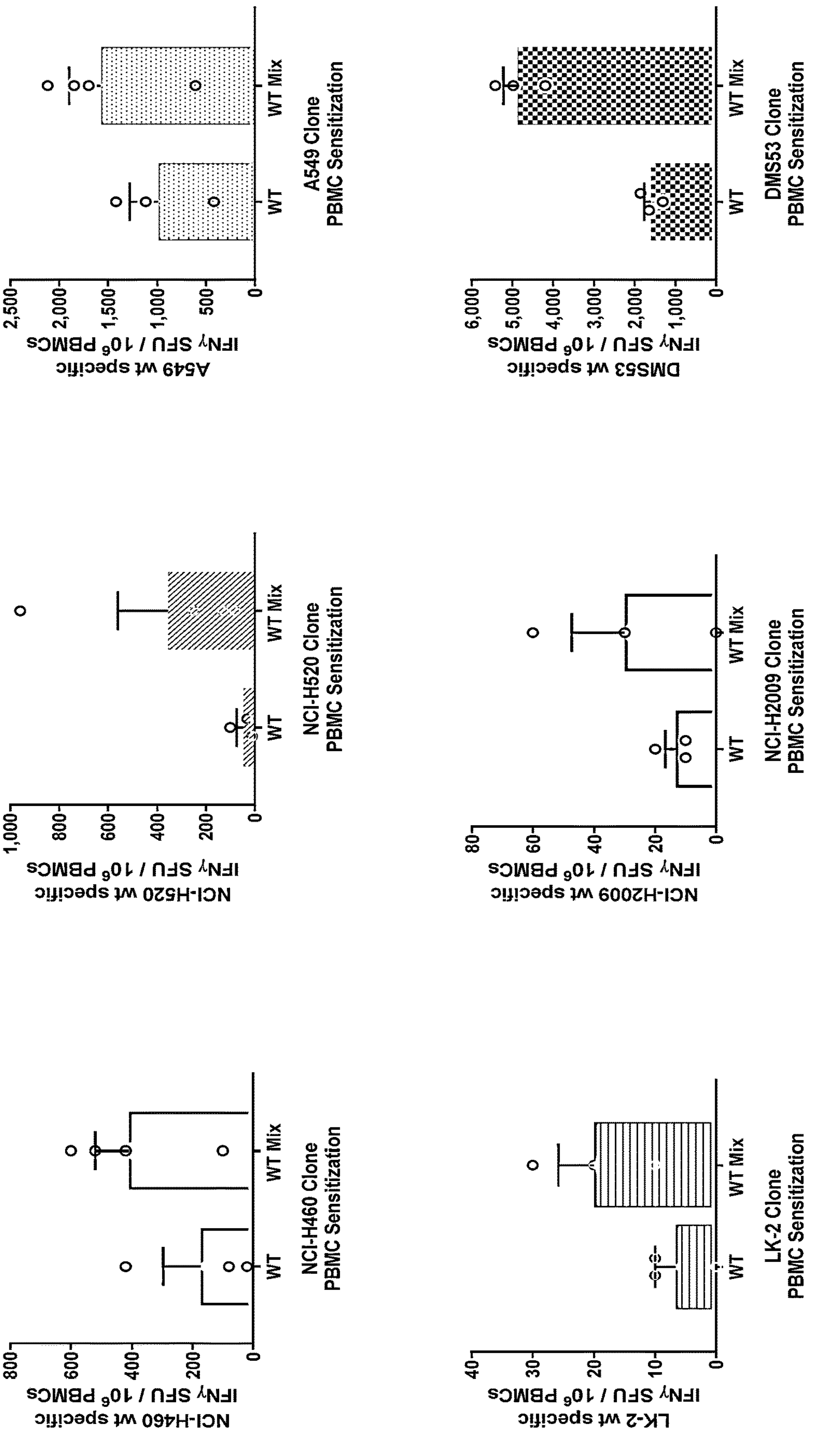
FIG. 59 shows that HLA mismatch results in increased immunogenicity.

As shown in FIG. 59, inclusion of a combination of lung cancer cell lines with a greater degree of HLA mismatch to the donor across multiple HLA molecules results in increased anti-tumor T cell responses. The immune response due to HLA mismatch acts as an adjuvant to boost overall responses. These data indicated that inclusion of multiple cell lines to ensure a broad degree of HLA mismatch on multiple class I and class II HLA molecules between whole tumor cancer vaccine cocktail and recipient can generate an increased allogeneic response.

Example 26: Preparation of Non-Small Cell Lung Cancer (NSCLC) Vaccines

Tumors and tumor cell lines are highly heterogeneous. The subpopulations within the tumor express different phenotypes with different biological potential and different antigenic profiles. One of the driving purposes behind a whole tumor cell vaccine is to present a wide array of tumor cells to the immune system. By doing this, the immune response is generated against multiple TAAs, bypassing issues related to antigen loss, which can lead to antigen escape (or immune relapse) and patient relapse (Keenan B P, et al., Semin Oncol. 2012; 39: 276-86). Antigen escape was first observed in the treatment of B-cell lymphoma with anti-idiotype monoclonal antibodies (Meeker T, et al., N Engl J Med. 1985; 312: 1658-65) and has since been observed in other immunotherapy treatments such as CAR-T therapy (Majzner R G, et al., Cancer Discov. 2018; 8: 1219-26).

Expression of NSCLC TAAs

Figure 60:
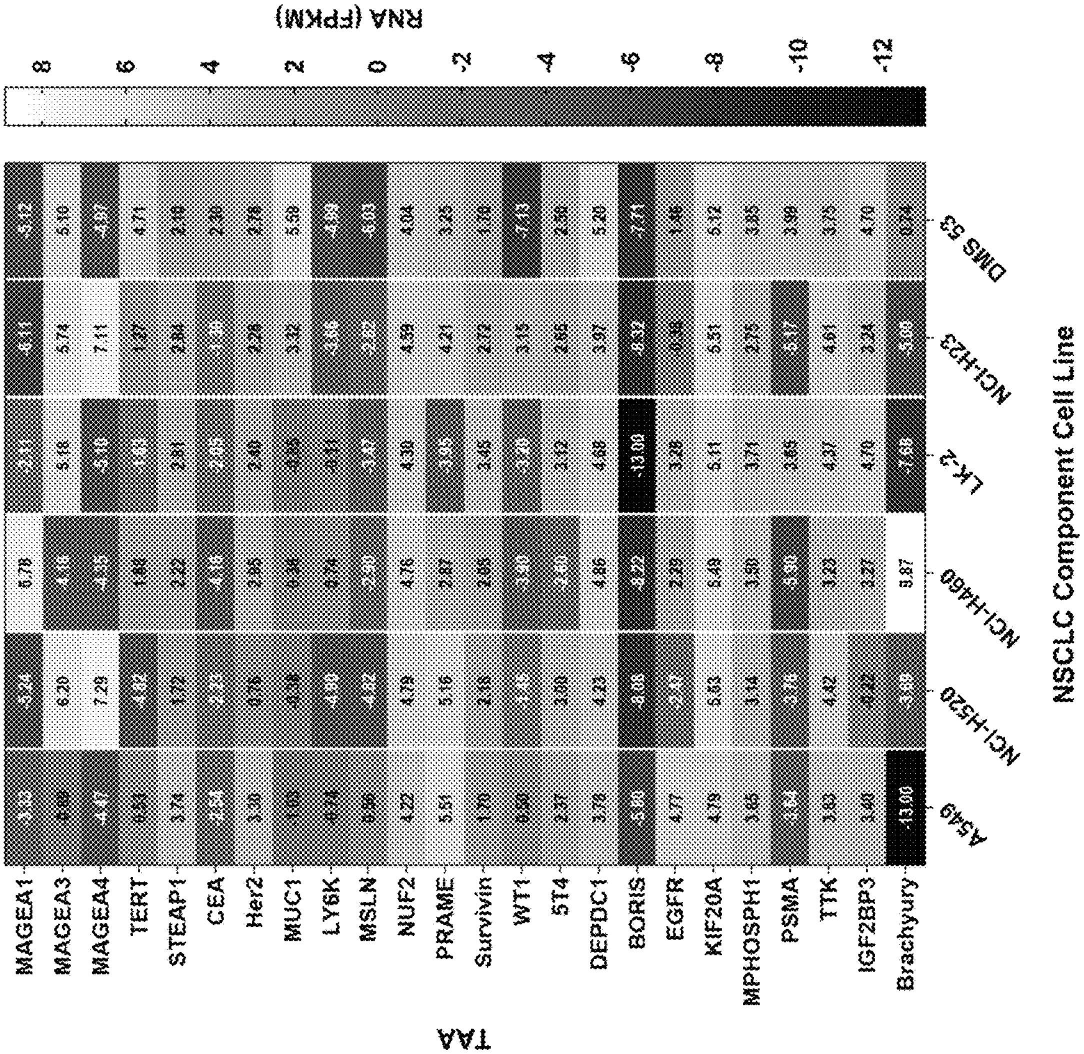
FIG. 60 shows the expression of NSCLC antigens in certain cell lines.

Expression of twenty-four TAAs by candidate component cell lines was determined by RNA expression data sourced from Broad Institute Cancer Cell Line Encyclopedia (CCLE). The HGNC gene symbol was included in the CCLE search and mRNA expression was downloaded for each TAA. Expression of a TAA by a cell line was considered positive if the RNA-seq value (FPKM) was greater than 0.5. Collectively, the six component cell lines expressed twenty-three of the twenty-four identified TMs at a mRNA level>0.5 FPKM (FIG. 60). Specifically, five TAAs were expressed by one cell line, four TAAs were expressed by two cell lines, four TAAs were expressed by three cell lines, five TAAs were expressed by three cell lines, and six TMs were expressed by eight cell lines. The minimum number of TMs expressed by a single cell line was twelve (NCI-H520) and the maximum number of TMs expressed by a single cell was eighteen (DMS 53). The number of antigens that can be targeted by the exemplary 6-cell line unit dose comprised of A549, NCI-H520, NCI-H460, DMS 53, LK-2, NCI-H23 is higher than the individual cell lines.

The cells in the vaccine described herein were selected to express a wide array of TMs, including those known to be important to antitumor immunity. To further enhance the array of TMs, one cell line (LK-2) was also transduced with the genes for CT83 and mesothelin, as described herein (FIG. 65). CT83 mRNA was endogenously expressed at a low level in two of the six cell lines and mesothelin was endogenously expressed by one of the six component cell lines.

Because of the need to maintain maximal heterogeneity of TMs, the gene modified cell lines utilized in the present vaccine have been established using antibiotic selection and flow cytometry and not through limiting dilution subcloning.

Cumulatively, the cells in the present vaccine express more of the TMs that have been demonstrated to be important in antitumor immunity. The cell lines in Table 39 are used in the present NSCLC vaccine.

TABLE 39

NSCLC vaccine cell lines and histology

| Cocktail | Cell Line Name | Histology |
|---|---|---|
| A | NCl-H520 | Squamous |
| A | A549 | Adenocarcinoma |
| A | NCl-H460 | Large cell |
| B | LK-2 | Squamous |
| B | NCl-H23 | Adenocarcinoma |
| B | DMS 53 | SCLC |

shRNA Downregulates TGF-β Secretion

TGFβ1 and TGFβ2 was knocked down and resulting secretion levels determined as described in Example 5. Of the parental cell lines in Cocktail A, NCI-H460 and A549 secrete measurable levels of TGFβ1 and TGFβ2 while LK-2 secretes TGFβ2 but not TGFβ1. Of the parental cell lines in Cocktail B, NCI-H23 secretes measurable levels of TGFβ1 and TGFβ2 and LK-2 secretes TGFβ2 but not TGFβ1. DMS 53 secretes measurable levels of TGFβ1 and TGFβ2, but TGFβ1 secretion is low.

With the exception of DMS 53, the component cell lines were all transduced with TGFβ1 shRNA and TGFβ2 shRNA to knockdown secretion of the two molecules. DMS 53 was gene modified with TGFβ2 shRNA only because multiple attempts to modify with both TGFβ1 and TGFβ2 shRNA were not successful. TGFβ1 knockdown was chosen to move forward because the secretion levels of TGFβ2 were already low in this cell line. These cells are described by the clonal designation DK4. The remaining cell lines were double modified with TGFβ1 and TGFβ2 shRNA. These cells are described by the clonal designation DK6.

Table 40 shows the TGF-β secretion in gene modified component cell lines compared to wild type cell lines. Reduction of TGFβ1 ranged from 59% to 90%. Reduction of TGFβ2 ranged from 42% to 97%.

TABLE 40

TGF-β Secretion (pg/$10^6$ cells/24 hr) in Component Cell Lines

| Cell Line | Cocktail | Clone | TGFβ1 | TGFβ2 |
|---|---|---|---|---|
| NCl-H520 | A | Wild type | ND | 3872 |
| NCl-H520 | A | DK6 | ND | 124 |
| NCl-H520 | A | Percent reduction | NA | 97% |
| A549 | A | Wild type | 5727 | 775 |
| A549 | A | DK6 | 577 | 42 |
| A549 | A | Percent reduction | 90% | 95% |
| NCl-H460 | A | Wild type | 1573 | 2307 |
| NCl-H460 | A | DK6 | 287 | 533 |
| NCl-H460 | A | Percent reduction | 82% | 77% |
| LK-2 | B | Wild type | ND | 161 |
| LK-2 | B | DK6 | ND | 69 |
| LK-2 | B | Percent reduction | NA | 55% |
| NCl-H23 | B | Wild type | 1761 | 588 |

TABLE 40-continued

| TGF-β Secretion (pg/$10^6$ cells/24 hr) in Component Cell Lines | | | | |
|---|---|---|---|---|
| Cell Line | Cocktail | Clone | TGFβ1 | TGFβ2 |
| NCl-H23 | B | DK6 | 719 | 61 |
| NCl-H23 | B | Percent reduction | 59% | 90% |
| DMS 53 | B | Wild type | 261 | 2833 |
| DMS 53 | B | DK4 | 286 | 1640 |
| DMS 53 | B | Percent reduction | 0% | 42% |

DK6: TGFβ1/TGFβ2 double knockdown; DK4: TGFβ2 single knockdown; ND=not detectable; NA=not applicable Based on an injected dose of $8\times10^6$ of each component cell line, the total TGF-β secretion in Cocktails A and B is shown in Table 41. Secretion in the wild type cells in the cocktail is also shown. Cocktail A shows a total secretion of 9679 pg per injected dose per 24 hours for TGFβ1 and 5600 μg per injected dose per 24 hours for TGFβ2. Cocktail B shows a total secretion of 8220 pg per injected dose per 24 hours for TGFβ1 and 14163 pg per injected dose per 24 hours for TGFβ2.

Belagenpumatucel-L had a total TGFβ2 secretion of 18,813 pg per injected dose per 24 hours (Nemunaitis, J. et al. JCO. (2006) 24:29, 4721-4730) (Fakhrai, H 2010). The total TGFβ2 secretion in the NSCLC vaccine (19,763 pg per injected dose per 24 hours) is roughly equivalent to the TGFβ2 secretion in belagenpumatucel-L despite the higher injected cell number of $4.8\times10^7$ cells in the NSCLC vaccine compared to $2.5\times10^7$ cells in belagenpumatucel-L.

TABLE 41

| Total TGF-β Secretion (pg/dose/24 hr) in NSCLC vaccine Cocktails | | | |
|---|---|---|---|
| Cocktail | Clones | TGFβ31 | TGFβ2 |
| A | Wild type | 58592 | 55638 |
| | DK6 | 9679 | 5600 |
| | Percent reduction | 83% | 90% |
| B | Wild type | 16735 | 28654 |
| | DK6/4 | 8220 | 14163 |
| | Percent reduction | 51% | 51% |

The total TGFβ1 secretion in the NSCLC vaccine (17,899 pg per injected dose per 24 hours) is 31% of the estimated TGFβ1 secretion in belagenpumatucel-L.

CD276 Expression

All component cell lines expressed CD276 and CD276 expression was knocked out by electroporation with ZFN as described in Example 13 and herein. The component cell lines had previously been gene modified with shRNA to knockdown expression of TGFβ1 and TGFβ2 (termed DK6), apart from DMS 53, where only TGFβ2 was knocked down (termed DK4). Because it was desirable to maintain as much tumor heterogeneity as possible, the electroporated cells were not cloned by limiting dilution. Instead, the cells were subjected to multiple rounds of cell sorting by FACS. Reduction of CD276 expression is described in Table 42. The absence of protein expression in the knockout cells was also confirmed by western blot analysis using (data not shown). These data show that gene editing of CD276 resulted in greater than 99% CD276-negative cells in all six component cell lines.

TABLE 42

| Reduction of CD276 expression | | | |
|---|---|---|---|
| Cell line | Parental Cell Line MFI | TGFβ1/β2 KD CD276 KO MFI | % Reduction CD276 |
| NCl-H460 | 366,565 | 838 | 99.8 |
| NCl-H520 | 341,202 | 212 | 99.9 |
| A549 | 141,009 | 688 | 99.5 |
| DMS 53 | 304,637 | 972 | 99.7 |
| LK-2 | 385,535 | 867 | 99.8 |
| NCI-H23 | 74,176 | 648 | 99.1 |

MFI reported with unstained controls subtracted

GM-CSF Secretion

Component cell lines were transduced with the GM-CSF as described herein and Example 24. The results are shown in Table 43.

TABLE 43

| GM-CSF Secretion in Component Cell Lines | | |
|---|---|---|
| Cell Line | GM-CSF (ng/$10^6$ cells/24 hr) | GM-CSF (ng/dose/24 hr) |
| NCl-H520 | 10 | 80 |
| A549 | 2880 | 23,040 |
| NCl-H460 | 1330 | 10,640 |
| Cocktail A Total | 4220 | 33,760 |
| LK-2 | 2 | 16 |
| NCl-H23 | 2310 | 18,480 |
| DMS 53 | 170 | 1,360 |
| Cocktail B Total | 2482 | 19,856 |

Based on an injected dose of $8\times10^6$ of each component cell line, the total GM-CSF secretion for Cocktail A is 33,760 ng per injected dose per 24 hours. The total GM-CSF secretion for Cocktail B is 19,856 ng per injected dose per 24 hours. The total secretion per injection is therefore 43,616 ng per 24 hours.

CD40L Expression

Figure 74:
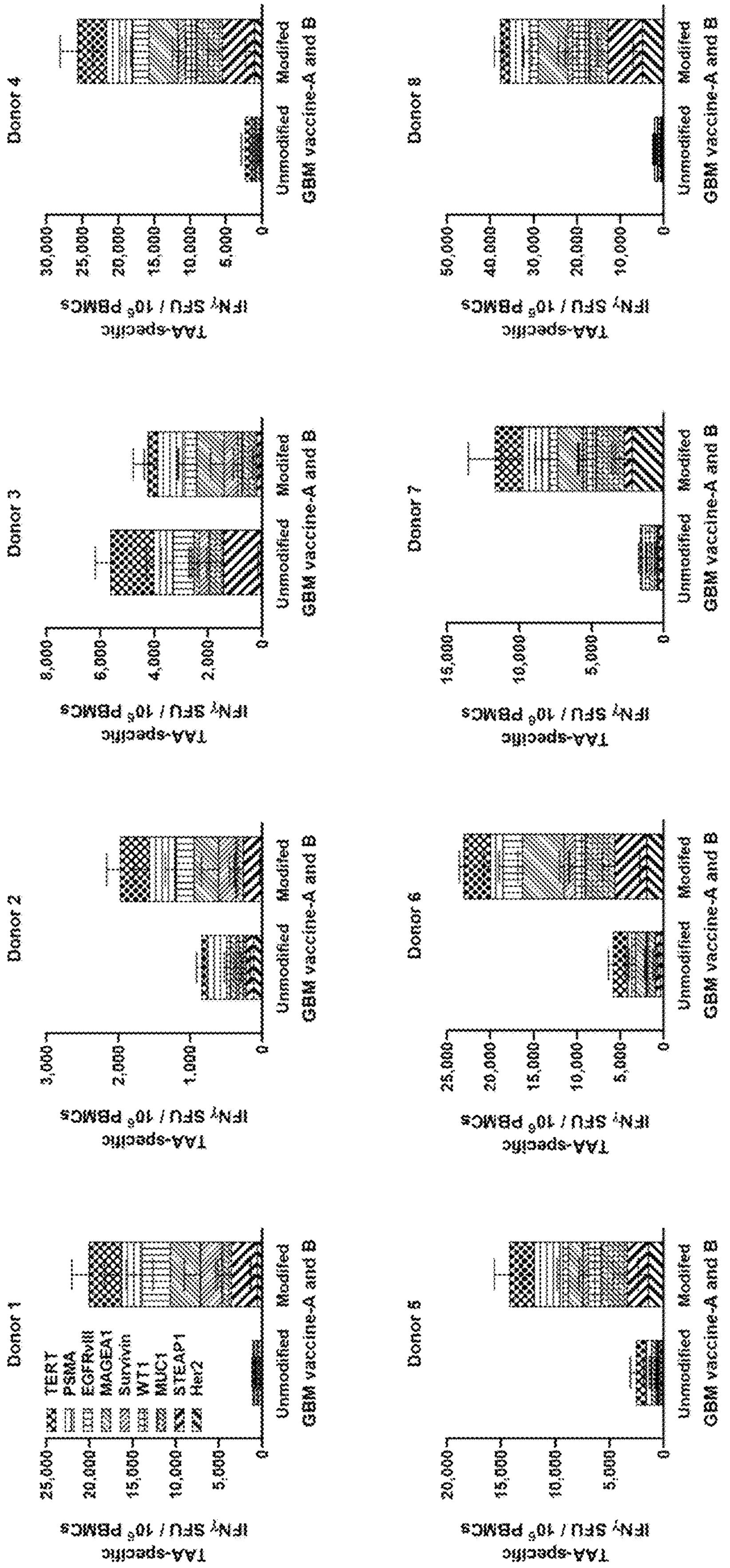
FIG. 74 shows antigen specific IFNγ responses induced by the unit dose of the GBM vaccine in individual donors compared to unmodified controls.

The component cell lines were transduced with a CD40L vector as described herein and by the methods described in Example 15. CD40L expression was evaluated by flow cytometry with an anti-CD40L monoclonal antibody as described in Example 15. The results, shown in FIG. 74, demonstrated significant CD40L membrane expression in all six cell lines.

IL-12 Expression

The component cell lines were transduced with the IL-12 vector and resulting IL-12 p70 expression determined as described in Example 24 and herein the results are shown in Table 44.

TABLE 44

| IL-12 secretion in component cell lines | | |
|---|---|---|
| Cell Line | IL-12 (ng/$10^6$ cells/24 hr) | IL-12 (ng/dose/24 hr) |
| NCl-H520 | NA | NA |
| A549 | 440 | 3520 |
| NCl-H460 | 420 | 3360 |
| Cocktail A Total | 860 | 6880 |
| LK-2 | NA | NA |
| NCl-H23 | 580 | 4640 |
| DMS 53 | 140 | 1120 |
| Cocktail B Total | 720 | 5760 |

Based on an injected dose of $8\times10^6$ of each component cell line, the total IL-12 secretion for Cocktail A is 6880 ng per injected dose per 24 hours. The total IL-12 secretion for Cocktail B is 5760 ng per injected dose per 24 hours. The total IL-12 secretion per injection is therefore 12,640 ng per 24 hours.

Stable Expression of Mesothelin and CT83 by the LK-2 Cell Line

As described above, the cells in the vaccine described herein were selected to express a wide array of TAAs, including those known to be important to antitumor immunity. To further enhance the array of antigens, the LK-2 cell line that was modified to reduce the secretion of TGFβ2, reduced the expression of CD276, and to express GM-CSF and membrane bound CD40L was also transduced with lentiviral particles expressing the CT83 and Mesothelin antigens. The CT83 and mesothelin antigens are linked by a P2A cleavage site (SEQ ID NO: 21).

Figure 65A:
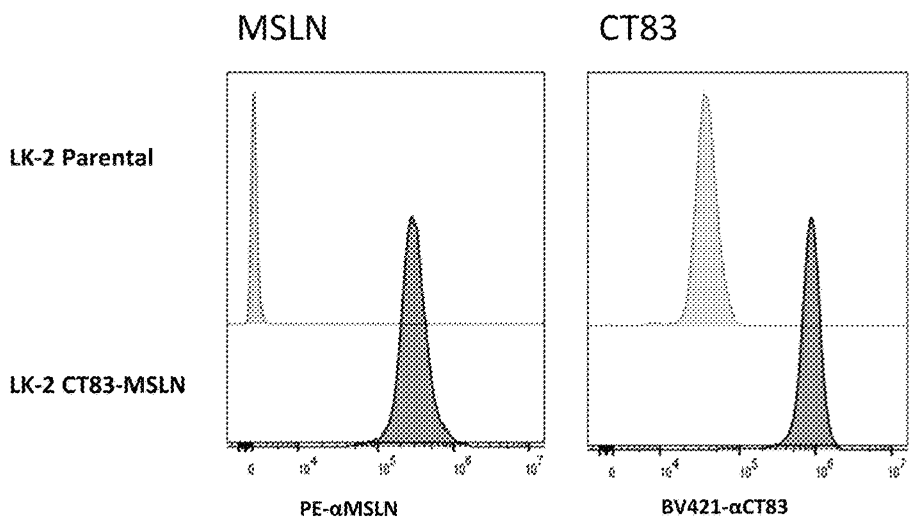
FIGS. 65A and B show expression of CT83 and Mesothelin by the LK-2 cell line and IFNγ responses to the CT83 and mesothelin antigens.

The expression of membrane bound Mesothelin and CT83 was characterized by flow cytometry. Unmodified parental and modified cells were stained extracellular with anti-mesothelin-PE (R&D Systems FAB32652P) according to the manufacturers instructions. Unmodified parental and modified cells were stained intracellular with anti-CT83 (Abcam, ab121219) followed by goat anti-rabbit Alex488 (Invitrogen, A-11034). The MFI of the unstained unmodified parental cells was subtracted from the MFI of the stained unmodified cells for both CT83 and mesothelin. The MFI of the modified parental cells was subtracted from the MFI of the modified cells for both CT83 and mesothelin. Percent increase in expression is calculated as: (1-(background subtracted modified MFI/background subtracted unmodified MFI))×100). Expression of CT83 increased in the modified cell line (934,985 MFI) 3-fold over that of the parental cell line (323,878 MFI). Expression of mesothelin by the modified cell line (123,128 MFI) increased 85-fold over the that of the parental cell line (1443 MFI) (FIG. 65A).

Figure 65B:
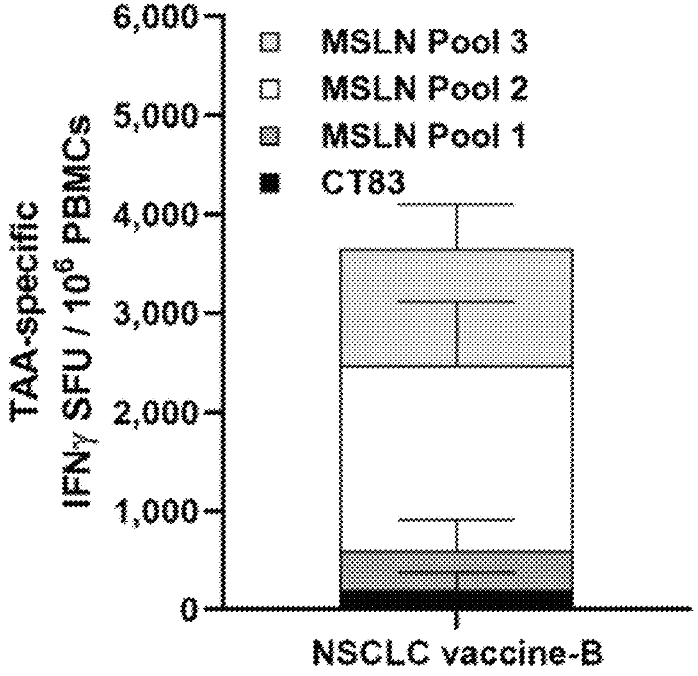

IFNγ responses to the CT83 and mesothelin antigens were determined by autologous DC and CD14-PBMC co-culture followed by ELISpot as described in Example 8. IFNγ responses to the CT83 and mesothelin antigens expressed by the modified LK-2 cell line were evaluated in the context of the NSCLC-vaccine B. Specifically, $5\times10^5$ of the modified DMS 53, NCI-H23, and LK-2 cells, $1.5\times10^6$ total modified cells, were co-cultured with $1.5\times10^6$ iDCs from 3 HLA diverse donors (n=3/donor). CD14-PBMCs isolated from co-culture with mDCs on day 6 were stimulated with the CT83 and mesothelin peptide pools, 15-mers overlapping by 11 amino acids spanning the native protein sequences, in the IFNγ ELISpot assay for 24 hours prior to detection of IFNγ SFU. IFNγ production was detected to both CT83 (205±158 SFU) (n=9) and mesothelin (3449±889 SFU) (n=9) (FIG. 65B).

Figure 62:
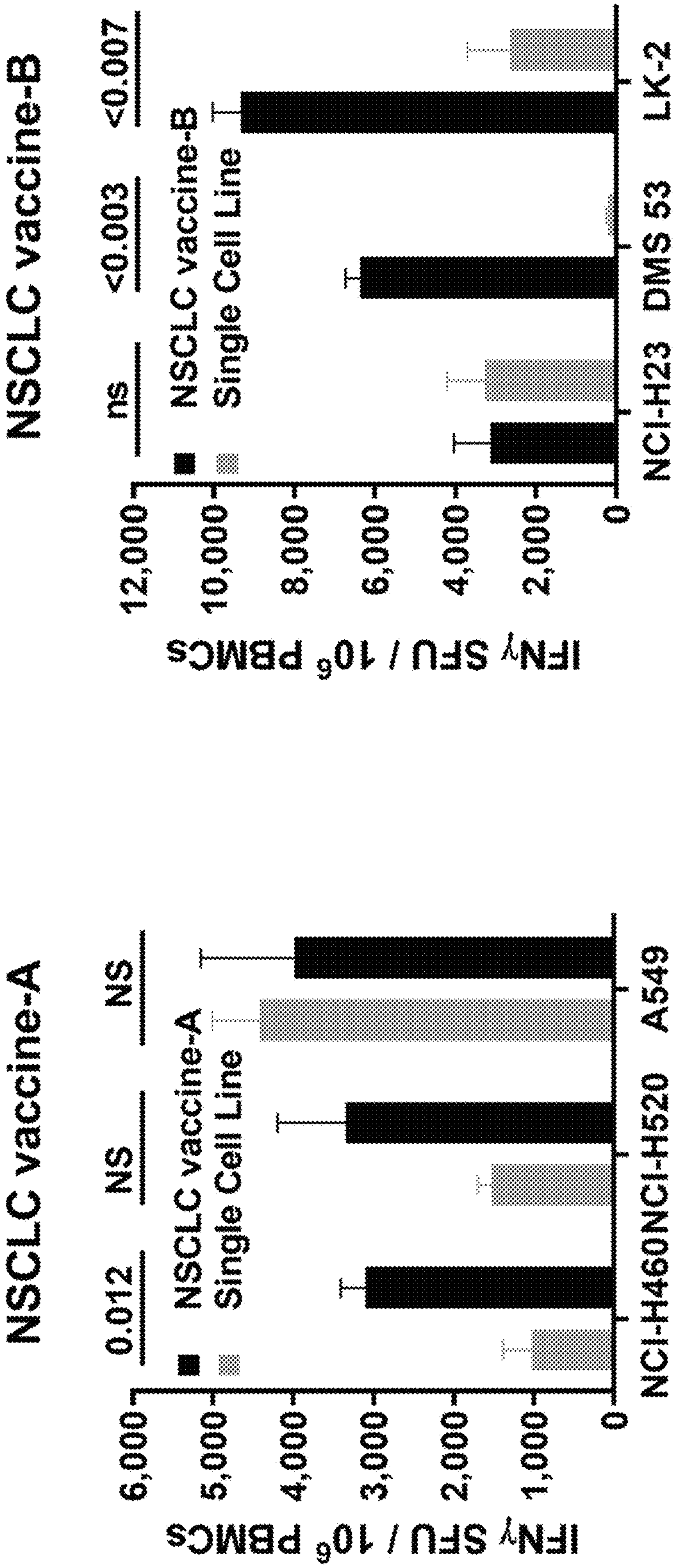
FIGS. 62A and B show IFNγ responses elicited by single lines compared to cocktails of cell lines.

Vaccine Cocktails Elicited Stronger and Broader Cellular Immune Responses Compared to Individual Component Cell Lines The ability of the individual NSCLC vaccine component cell lines to induce IFNγ responses against themselves compared to the ability of the NSCLC vaccine cocktails to induce IFNγ responses against the individual cell lines was measured by IFNγ ELISpot as described in Examples 8 and 9. The data in FIG. 62 demonstrate that the cocktails (NSCLC-A and NSCLC-B) elicited stronger immune responses than the individual component cell lines for 4 of the 6 cell lines.

Figure 63:
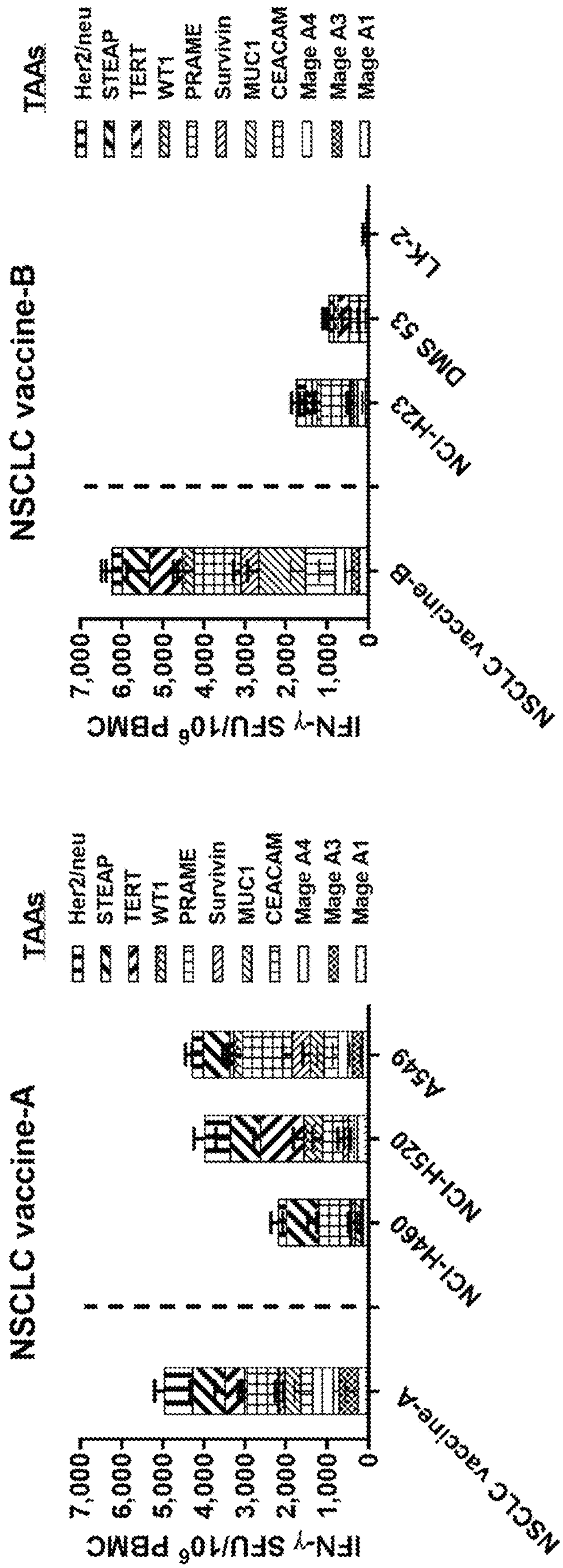
FIG. 63 shows IFNγ responses against selected antigens.
Figure 64:
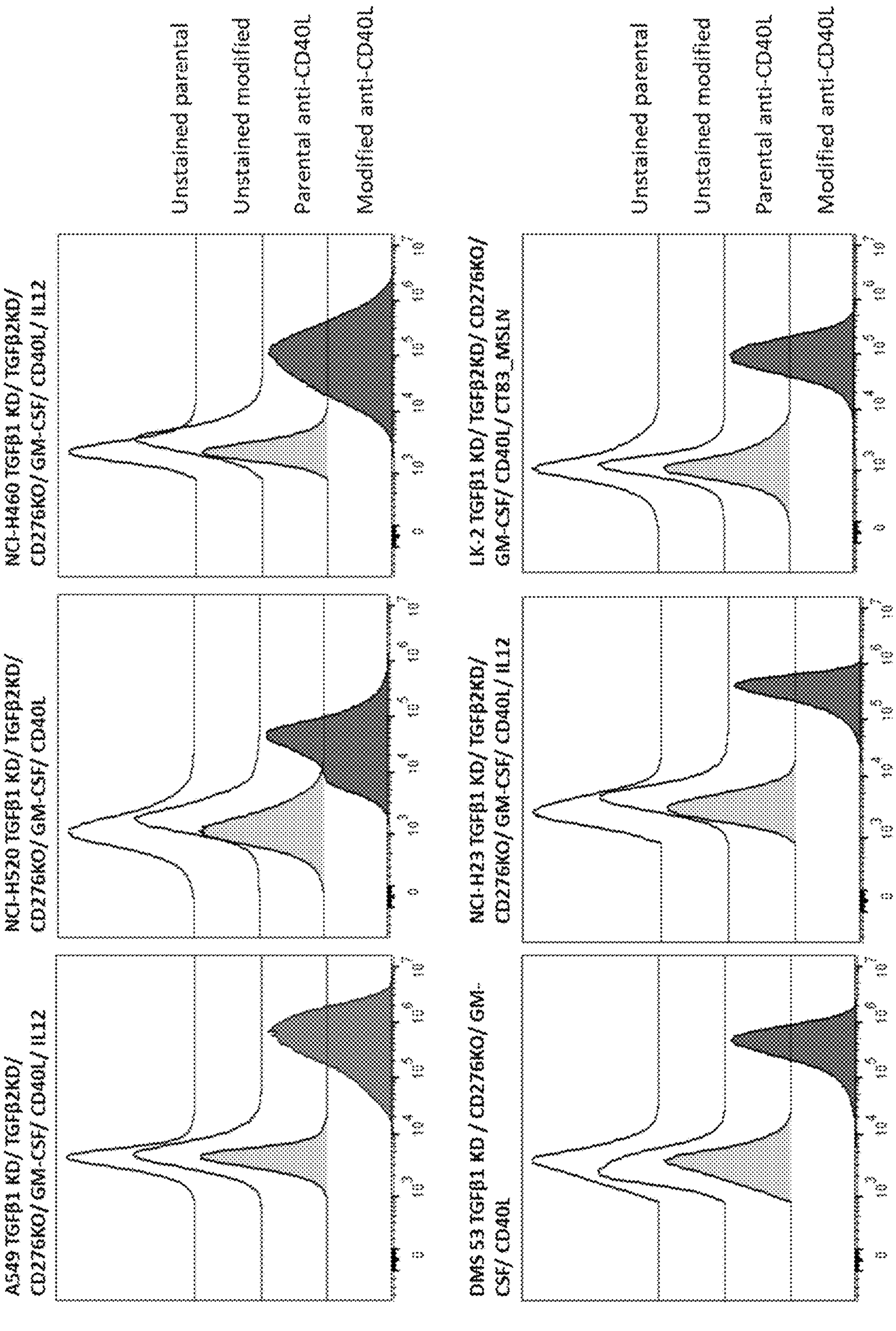
FIG. 64 shows expression of membrane bound CD40L on the NSCLC vaccine cell lines.

The immune response induced by the vaccine cocktails against relevant TAAs was then measured. Normal donor PBMCs were co-cultured with individual component cell lines or with the NSCLC-A or NSCLC-B cocktails for 6 days prior to stimulation with autologous DCs loaded with TAA-specific peptide pools containing known MHC-I restricted epitopes. Cells were then assayed for IFNγ secretion in the IFNγ ELISpot assay. The data shown in FIG. 63 demonstrate that each of the NSCLC vaccine component cell lines is capable of inducing TAA-specific IFNγ responses. More importantly, the two NSCLC vaccine cocktails induced stronger IFNγ responses against more TAAs compared to the individual component cell lines, indicating that the vaccine cocktails were capable of inducing broader immune responses.

Example 27: Non-Small Cell Lung Cancer (NSLC) Vaccines

Based on the disclosure and data provided herein, the following Example provides a whole cell vaccine for NSCLC comprised of the six lung cancer cell lines shown below in Table 45. The cell lines represent two adenocarcinomas (A549 and NCI-H23), two squamous cell carcinomas (NCI-H520 and LK-2), one large cell carcinoma (NCI-H460), and one small cell lung cancer (SCLC) (DMS 53). The cell lines have been divided into two groupings: vaccine cocktail A and vaccine cocktail B (i.e., NSCLC-A and NSCLC-B). Cocktail A is designed to be administered intradermally in the upper arm and Cocktail B is designed to be administered intradermally in the thigh. Cocktail A and B together comprise a unit dose of cancer vaccine.

TABLE 45

Cell line nomenclature and modifications

| Cocktail | Cell Line | TGFβ1 KD | TGFβ2 KD | CD276 KO | GM-CSF | CD40L | IL-12 | MSLN | CT83 |
|---|---|---|---|---|---|---|---|---|---|
| A | NCI-H520 | X | X | X | X | X | ND | ND | ND |
| A | A549 | X | X | X | X | X | X | ND | ND |
| A | NCI-H460 | X | X | X | X | X | X | ND | ND |
| B | LK-2 | X | X | X | X | X | ND | X | X |
| B | NCI-H23 | X | X | X | X | X | X | ND | ND |
| B | DMS 53 | ND | X | X | X | X | X | ND | ND |

ND = Not done

Where indicated in the above table, the genes for the immunosuppressive factors transforming growth factor-beta 1 (TGFβ1) and transforming growth factor-beta 2 (TGFβ2) have been knocked down using shRNA transduction with a lentiviral vector. The gene for CD276 has been knocked out by electroporation using zinc-finger nuclease (ZFN). The genes for granulocyte macrophage-colony stimulating factor (GM-CSF), IL-12, CD40L, mesothelin, and CT83 have been added by lentiviral vector transduction.

Five of the six established lung cancer cell lines were obtained from the American Type Culture Collection (ATCC, Manassas, Va.) and one was obtained from the Japanese Collection of Research Bioresources cell bank (JCRB, Kansas City, Mo.).

Example 28: Comparison of Belagenpumatucel-L and NSCLC Vaccine

The results of the clinical studies of belagenpumatucel-L were published in peer-reviewed journals and included two Phase II trials (Nemunaitis J, et al., J Clin Oncol. 2006; 24: 4721-30; Nemunaitis J, et al., Cancer Gene Ther. 2009; 16: 620-4) and a Phase III trial (Giaccone G, et al., Eur J Cancer. 2015; 51: 2321-9) in NSCLC.

Belagenpumatucel-L was a vaccine in which TGFβ2 secretion in four allogeneic NSCLC tumor cell lines was downregulated using a TGFβ2 antisense plasmid. However, Belagenpumatucel-L did not address the issue of TGFβ1 secretion. Recent studies have shown that TGFβ1 is the predominant isoform expressed in the immune system. TGFβ1 binds to the TGFβRII receptor at high affinity, whereas TGFβ2 only binds with high affinity in the presence of the TGFβRIII co-receptor (also called betaglycan). Betaglycan is downregulated in NSCLC, which makes TGFβ1 the predominant TGFβ isoform.

The NSCLC vaccine described in Example 27 introduces great improvement over belagenpumatucel-L relative to secretion of TGFβ1 and TGFβ2, among other modifications and improvements. The lower level of TGFβ2 secretion in the NSCLC vaccine is important, but even more significant is the decreased level of TGFβ1. The present NSCLC vaccine also introduces the following improvements: use of lentiviral transduction of shRNA is being used to knockdown the expression of TGFβ2 and TGFβ1 providing a major improvement over antisense for both expression and stability; use of zinc-finger nuclease electroporation to knockout the expression of CD276; use of lentiviral transduction to induce expression of the immunostimulatory molecules GM-CSF, IL-12, and CD40L; use of a SCLC cell line noting recent observations that NSCLC tumors contain a significant SCLC component and that component is responsible for drug resistance, metastasis, and relapse; and use of a serum-free media formulation.

Figure 61C:
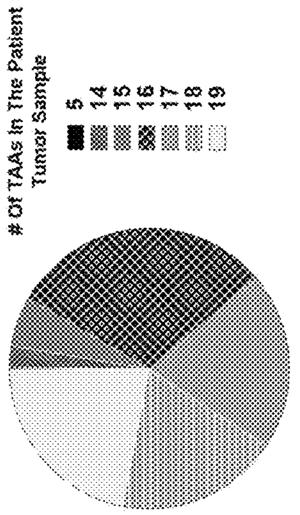
FIGS. 61A-C show a comparison of endogenous TAA expression profiles of NSCLC vaccines and Belagenpumatucel-L.
Figure 61B:
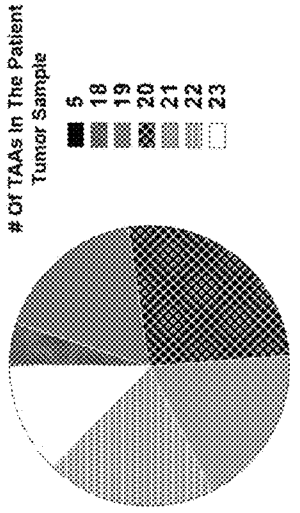
Figure 61A:
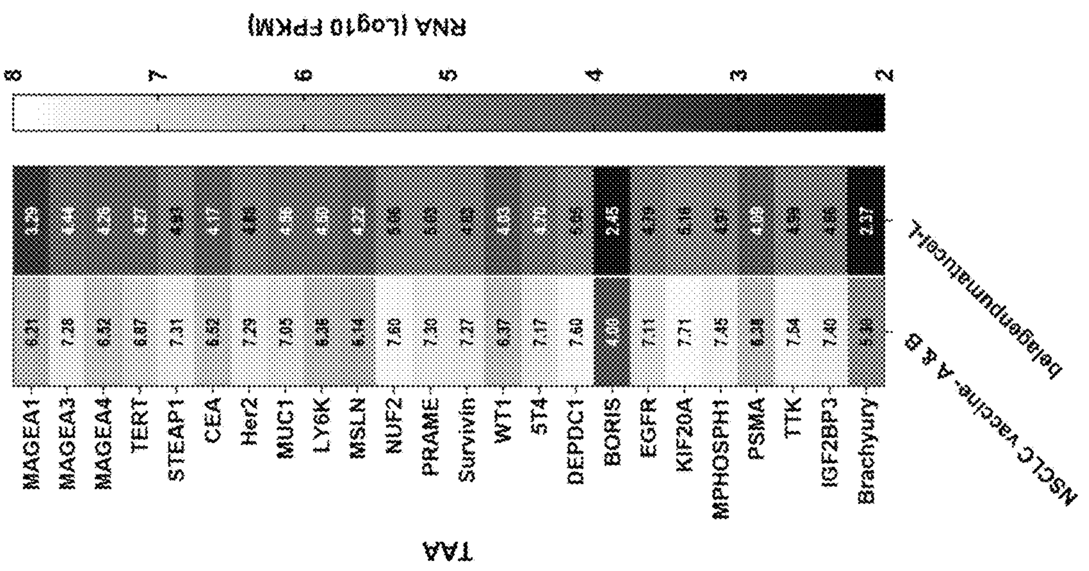

As described above, twenty-four TAAs that could potentially generate a relevant antitumor immune response in NSCLC patients were identified. mRNA expression of these twenty-four antigens in the NSCLC vaccine and belagenpumatucel-L is shown in FIG. 61A. The data in FIG. 61 is illustrated as the sum of $Log_{10}$ FPKM+14 mRNA expression of each antigen in the respective belagenpumatucel-L and NSCLC vaccine cell line components. The FPKM mRNA value was adjusted by 14.0 to account for the negative base value (−13.00 FPKM) to allow for addition of mRNA levels with positive values. Expression of the twenty-three prioritized NSCLC TAAs expressed by the NSCLC vaccine cell components was determined in 573 NSCLC patient samples. The NSCLC patient data was downloaded from the publicly available database, cBioPortal (cbioportal.org) (Cerami, E. et al. Cancer Discovery. 2012; Gao, J. et al. Sci Signal. 2013) between Feb. 23, 2020 through Jul. 2, 2020 (FIG. 78C). The HUGO Gene Nomenclature Committee (HGNC) gene symbol was included in the search and mRNA expression was downloaded for each TAA.

The NSCLC vaccine potentially targets a median of 21 TAAs (FIG. 61B) and belagenpumatucel-L targets a median of 17 TAAs (FIG. 61C) expressed by the 573 patient tumor samples. The NSCLC vaccine and belagenpumatucel-L both have the potential to induce an antitumor response to at least five antigens in all 573 patients. The NSCLC vaccine has the potential to induce an antitumor response to at least 17 antigens in 572 patients (99.8%), at least 18 antigens in 565 patients (98.6%), at least 19 antigens in 538 patients (93.9%), at least 20 antigens in 438 patients (76.4%), at least 21 antigens in 290 patients (50.6%), at least 22 antigens in 183 patients (31.9%) and at least 23 antigens in 73 patients (12.7%). In comparison, belagenpumatucel-L could only induce an antitumor response to at least 14 antigens in 572 patients (99.8%), at least 15 antigens in 558 patients (97.4%), at least 16 antigens in 525 patients (91.6%), at least 17 antigens in 351 patients (61.3%), at least 18 antigens in 233 patients (40.7%) and at least 19 antigens in 126 patients (22.0%). The above analysis includes antigens prioritized to induce and antitumor response in NSCLC patients and does not account for the additional, and potentially clinically relevant, antigens expressed by the component cell lines.

The six cell lines included in the NSCLC vaccine described herein were selected to express a wide array of TMs, including those known to be important to antitumor immunity. As a result, the number of TAAs that can be targeted using the exemplary six-cell line composition, and the expression levels of the antigens, is higher than belagenpumatucel-L. As described earlier, to further enhance antigenic breadth, one cell line (LK-2) was also transduced with the genes for CT83 (SEQ ID NO: 19, SEQ ID NO: 20) and mesothelin (SEQ ID NO: 17, SEQ ID NO: 18), two TMs for which mRNA was endogenously expressed at low levels in any of the six component cell lines.

This Example demonstrates that the reduction of TGFβ1, TGFβ2, and CD276 expression with concurrent overexpression of GM-CSF, CD40L, and IL-12 in of the NSCLC vaccine comprising two cocktails, each cocktail composed of three cell line components, a total of 6 component cell lines, significantly increases the antigenic breadth and magnitude of cellular immune responses compared to belagenpumatucel-L.

Reduction of TGFβ2 Secretion in the Belagenpumatucel-L Cell Lines

The cell line components of the belagenpumatucel-L cocktail, NCI-H460, NCI-H520, SK-LU-1, and Rh2 were transduced with lentiviral particles expressing shRNA specifically targeting TGFβ2 (SEQ ID NO: 24) and resulting TGFβ2 levels in the modified cell lines was determined as described in Example 5. TGFβ2 secretion levels in the modified cells were below the lower limit of quantification of the ELISA assay for NCI-H520 and SK-LU-1 and the MDD (42.0 pg/$10^6$ cells/24 hours was used to estimate the percent reduction relative to the parental cell line. Compared to the parental, unmodified cell lines, TGFβ2 secretion was reduced 84% in NCI-H460, 99% in NCI-H520, 84% in SK-LU-1, and 74% in Rh2. Reduction of TGFβ1 and TGFβ2 for NSCLC cocktail A and cocktail B levels are described in Table 41. The NSCLC vaccine was prepared as described in Example 27.

Antigen Specific and Tumor Cell Specific IFNγ Production to NSCLC Vaccine-A, NSCLC Vaccine-B, and Belagenpumatucel-L Cellular immune responses to antigens and parental, unmodified cells were determined by IFNγ ELISpot following autologous DC and PBMC co-culture as described in Example 8 with modifications as described below.

The autologous DC and PBMC co-cultures were adjusted to model the in vivo administration of the belagenpumatucel-L and the NSCLC vaccine. Belagenpumatucel-L was administered in a single site and NSCLC vaccine-A and NSCLC vaccine-B are administered in two separate injection sites. In the autologous DC and PBMC co-culture representing Belagenpumatucel-L, $3.75\times10^5$ of NCI-H460, NCI-H520, SK-LU-1, Rh2 modified cells, $1.5\times10^6$ total modified cells, were co-cultured with $1.5\times10^6$ iDCs. NSCLC vaccine-A, $5.00\times10^5$ of the modified NCI-H460, NCI-H520, A549 cells, $1.5\times10^6$ total modified cells, were co-cultured with $1.5\times10^6$ iDCs. For NSCLC vaccine-B, $5.0\times10^5$ of the modified DMS 53, NCI-H23, and LK-2 cells, $1.5\times10^6$ total modified cells, were co-cultured with $1.5\times10^6$ iDCs. Following co-culture, cellular immune responses directed against parental tumor cell lines and antigens were determined by IFNγ ELISpot. CD14-PBMCs from the Belagenpumatucel-L co-culture were stimulated in separate wells with unmodified NCI-H460, NCI-H520, SK-LU-1, or Rh2 (n=4/cell line/donor). $CD14^-$ PBMCs from NSCLC vaccine-A cocktail were stimulated in separate wells with either NCI-H460, NCI-H520, or A549 (n=4/cell line/donor). $CD14^-$ PBMCs from NSCLC vaccine-B cocktail were stimulated in separate wells with either DMS 53, LK-2, or NCI-H23 (n=4/cell line/donor). Antigen specific responses were determined using $CD14^-$ PBMCs isolated from the same belagenpumatucel-L, NSCLC vaccine-A, and NSCLC vaccine-B co-cultures (n=4/donor/antigen). IFNγ production responses were determined against the parental, unmodified cell lines comprising the belagenpumatucel-L vaccine, NSCLC vaccine-A and NSCLC vaccine-B and to exemplary tumor-associated antigens (TAAs), tumor-specific antigens (TSA), and cancer/testis antigens (CTA).

Figure 66B:
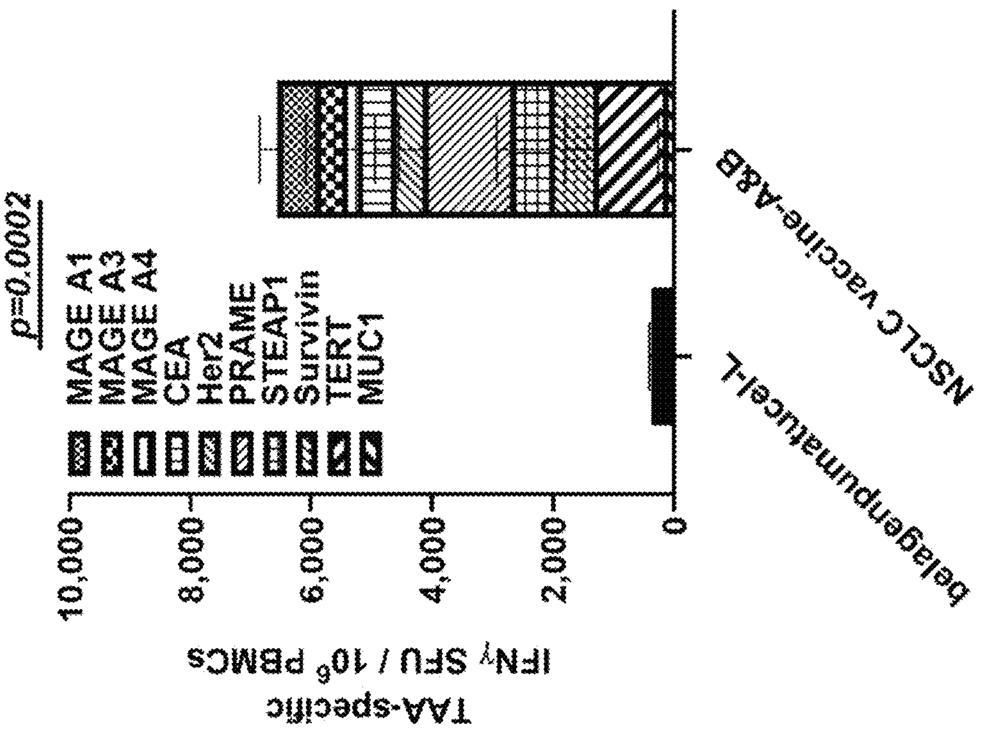
FIGS. 66A and B show a comparison of IFNγ responses generated by belagenpumatucel-L and NSCLC vaccine.
Figure 66A:
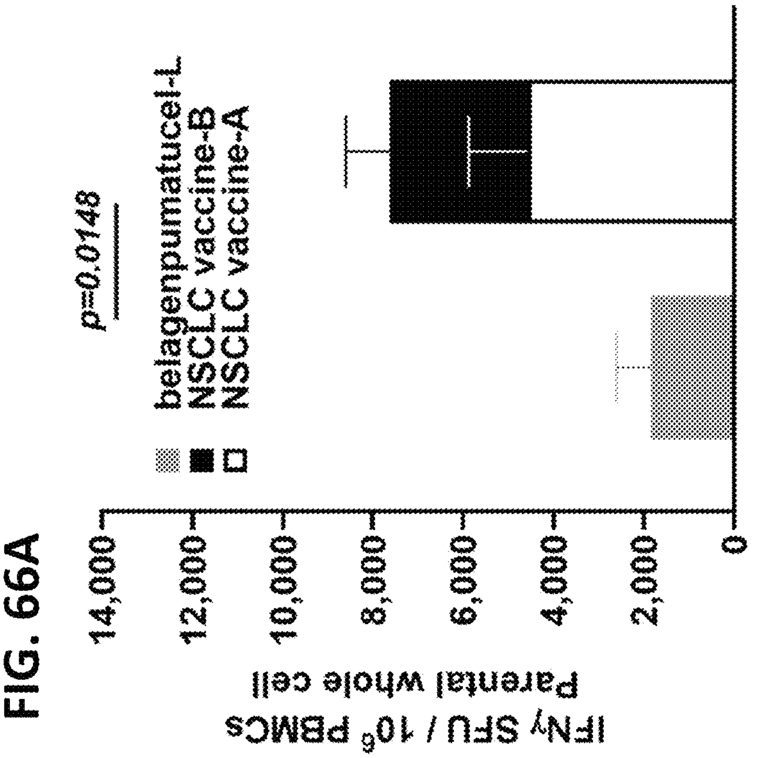
Figure 67A:
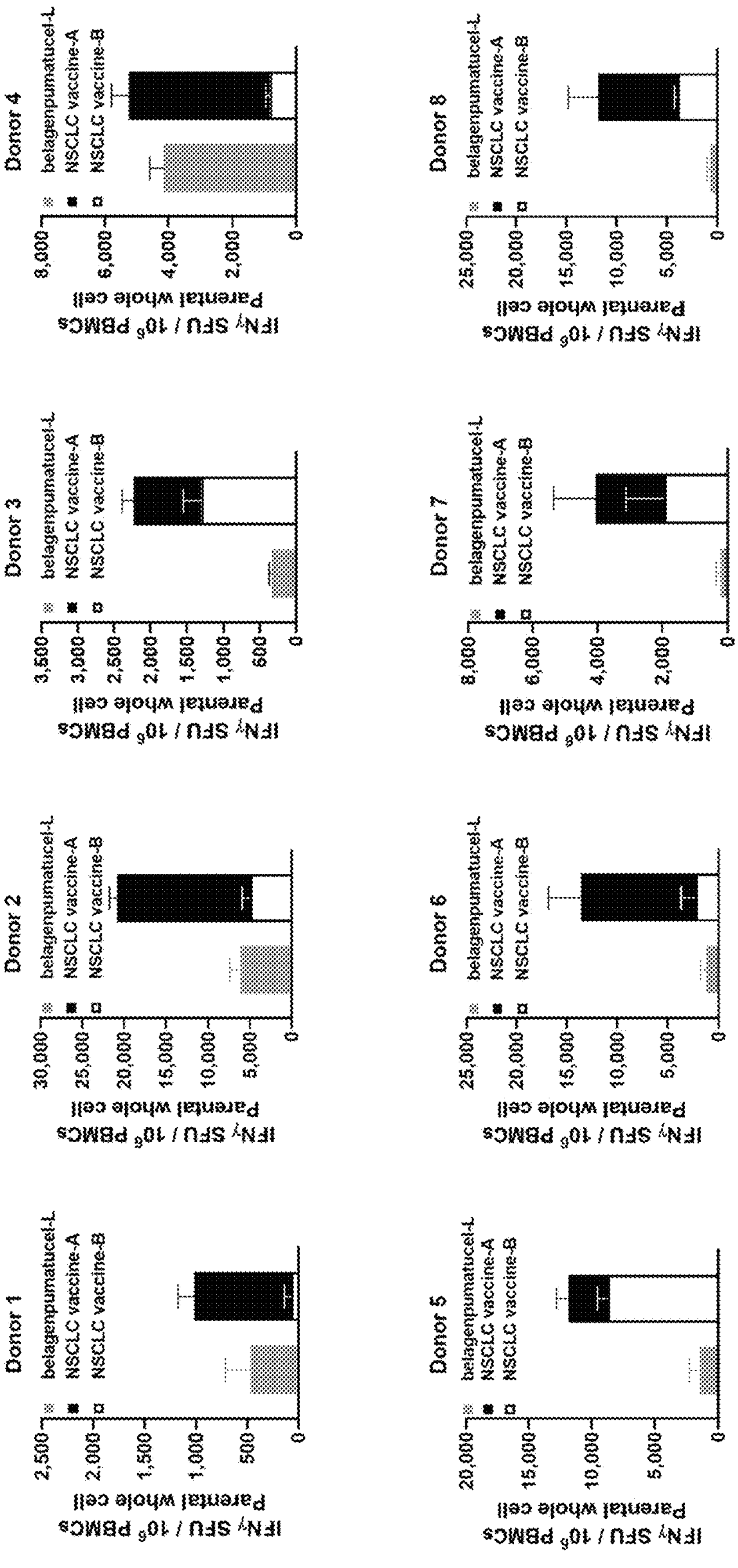
FIGS. 67A and B show a comparison of IFNγ responses generated by belagenpumatucel-L and NSCLC vaccine in individual donors.

Reduction of TGFβ1, TGFβ2, and CD276 Expression with Concurrent Overexpression of GM-CSF, CD40L, and IL-12 in 6 Component Cell Line, 2 Cocktail Approach, Significantly Increases Cellular Immune Responses Compared to Reduction of TGFβ2 in a 4-Component Cell Line, Single Cocktail Immunotherapy Approach IFNγ responses induced by the belagenpumatucel-L, Cocktail A and Cocktail B, against parental tumor cells and antigens were determined with following co-culture of CD14-PBMCs and DCs derived from 8 healthy, HLA diverse donors. PBMCs co-cultured with DCs loaded with the modified belagenpumatucel-L NCI-H460, NCI-H520, SK-LU-1, Rh2 component cell lines were stimulated with parental, unmodified, NCI-H460, NCI-H520, SK-LU-1, Rh2 cells (n=4/donor/cell line). PBMCs co-cultured with DCs loaded with Cocktail A were stimulated with parental, unmodified, NCI-H460, NCI-H520, A549 cells (n=4/donor/cell line). PBMCs co-cultured with DCs loaded with Cocktail B were stimulated with parental, unmodified, DMS 53, NCI-H23, and LK-2 cells (n=4/donor/cell line). The average SFU of the replicates (n=4) for each donor variable is reported ±SEM. The NSCLC vaccine unit dose elicited significantly more robust tumor cell specific IFNγ responses (7,613±1,763 SFU) (n=8) compared to belagenpumatucel-L (1,850±764 SFU) (n=8) (p=0.0148, Mann-Whitney U test) (FIG. 66A). Donor-specific IFNγ responses to belagenpumatucel-L, NSCLC vaccine Cocktail A, NSCLC vaccine Cocktail B, and NSCLC vaccine unit dose are shown in FIG. 67A.

Table 46 shows that the distribution of IFNγ responses to Cocktail A and Cocktail B varied on a per donor basis emphasizing that that increasing the number of cell lines of cell line components and delivery sites has the potential to reach a boarder population than a single composition of 4 cell lines.

TABLE 46

| IFNγ responses | | | | | |
|---|---|---|---|---|---|
| | belagenpumatucel-L | Cocktail A | Cocktail B | NSCLC Vaccine Unit Dose | Fold Increase* |
| Donor 1 | 473 | 943 | 75 | 1,018 | 2.2 |
| Donor 2 | 6,180 | 6,180 | 4,983 | 11,163 | 3.4 |
| Donor 3 | 339 | 926 | 1,303 | 2,229 | 6.6 |
| Donor 4 | 4,163 | 4,413 | 829 | 5,242 | 1.3 |
| Donor 5 | 1,476 | 3,039 | 8,780 | 11,819 | 8.0 |
| Donor 6 | 1,200 | 11,240 | 2,330 | 13,570 | 11.3 |
| Donor 7 | 225 | 2,107 | 1,956 | 4,063 | 18.1 |
| Donor 8 | 740 | 7,848 | 3,950 | 11,798 | 15.9 |
| Mean | 1,850 | 4,587 | 3,026 | 7,613 | |
| SEM | 764 | 1,287 | 999 | 1,763 | |

*Fold Increase of IFNγ SFU induced by IA Unit Dose relative to belagenpumatucel-L. (n = 4/Donor)

Figure 67B:
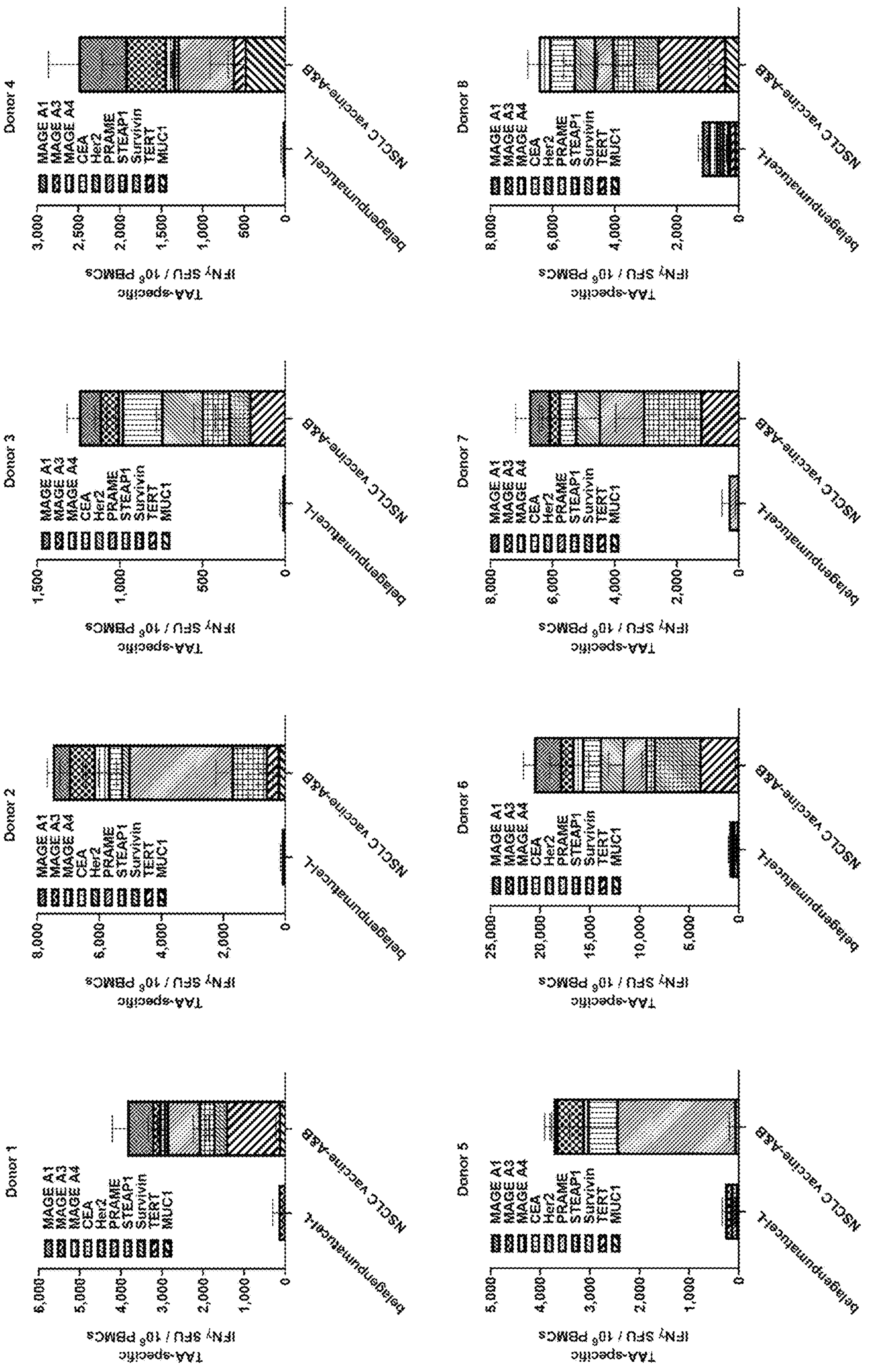

NSCLC vaccine Cocktail A and Cocktail B also induced more robust antigen specific IFNγ responses to an exemplary panel of antigens associated with NSCLC and other solid tumor indications. PBMCs co-cultured with DCs loaded with the belagenpumatucel-L, NSCLC vaccine Cocktail A, or NSCLC vaccine Cocktail B were stimulated with peptides pools containing known antigen specific T cell epitopes for a broad range of HLA haplotypes (n=4/donor/antigen). The average SFU of the replicates for each antigen and donor (n=4) is reported ±SEM in Table 47 and in FIG. 67B. The NSCLC vaccine unit dose significantly increased the mean magnitude and breadth of antigen specific IFNγ production (6,576±2,147 SFU) (n=8) relative to the belagenpumatucel-L (392±157 SFU) in 8 Donors (p=0.0002, Mann-Whitney U test) (FIG. 66B).

TABLE 47

| Mean magnitude of antigen specific IFNγ production | | | |
|---|---|---|---|
| | belagenpumatucel-L | NSCLC Vaccine Unit Dose | Fold Increase* |
| Donor 1 | 172 | 3,847 | 22.4 |
| Donor 2 | 125 | 7,493 | 59.9 |
| Donor 3 | 23 | 1,248 | 55.4 |
| Donor 4 | 35 | 2,500 | 71.4 |
| Donor 5 | 275 | 3,723 | 13.5 |
| Donor 6 | 977 | 20,603 | 21.1 |
| Donor 7 | 340 | 6,748 | 19.8 |
| Donor 8 | 1,191 | 6,447 | 5.4 |
| Mean | 392 | 6,576 | |
| SEM | 157 | 2,147 | |

*Fold Increase of IFNγ SFU induced by NSCLC vaccine Unit Dose relative to belagenpumatucel-L. (n = 4/Donor)

Example 29: Preparation of Glioblastoma Multiforme (GBM) Cancer Vaccine

This Example demonstrates that reduction of TGFβ1, TGFβ2, and CD276 expression with concurrent overexpression of GM-CSF, CD40L, and IL-12 in a vaccine composition of two cocktails, each cocktail composed of three cell lines for a total of 6 cell lines, significantly increased the magnitude of cellular immune responses to at least 10 GBM-associated antigens in an HLA-diverse population. As described herein, the first cocktail, GBM vaccine-A, is composed of cell line LN-229 that was also modified to express modPSMA, cell line GB-1, and cell line SF-126 that was also modified to express modTERT. The second cocktail, GBM vaccine-B, is composed of cell line DBTRG-05MG, cell line KNS 60 that was also modified to express modMAGEA1, hCMV pp65, and EGFRvIII, and cell line DMS 53. The 6 component cell lines collectively express at least twenty-two antigens that can provide an anti-GBM tumor response.

Identification of Glioblastoma Multiforme Vaccine Components

Initial cell line selection criteria identified seventeen vaccine component cell lines for potential inclusion in the GBM vaccine. Additional selection criteria were applied to narrow the seventeen candidate cell lines to eight cell lines for further evaluation in immunogenicity assays. These criteria included: endogenous GBM associated antigen expression, lack of expression of additional immunosuppressive factors, such as IL-10 or IDO1, expression of GBM specific CSC markers, ethnicity and age of the patient from which the cell line was derived, GBM histological and molecular subtype (when available), and the methylation status of the $O^6$-methylguanine-DNA methyltransferase (MGMT) promoter (when available).

Figure 68A:
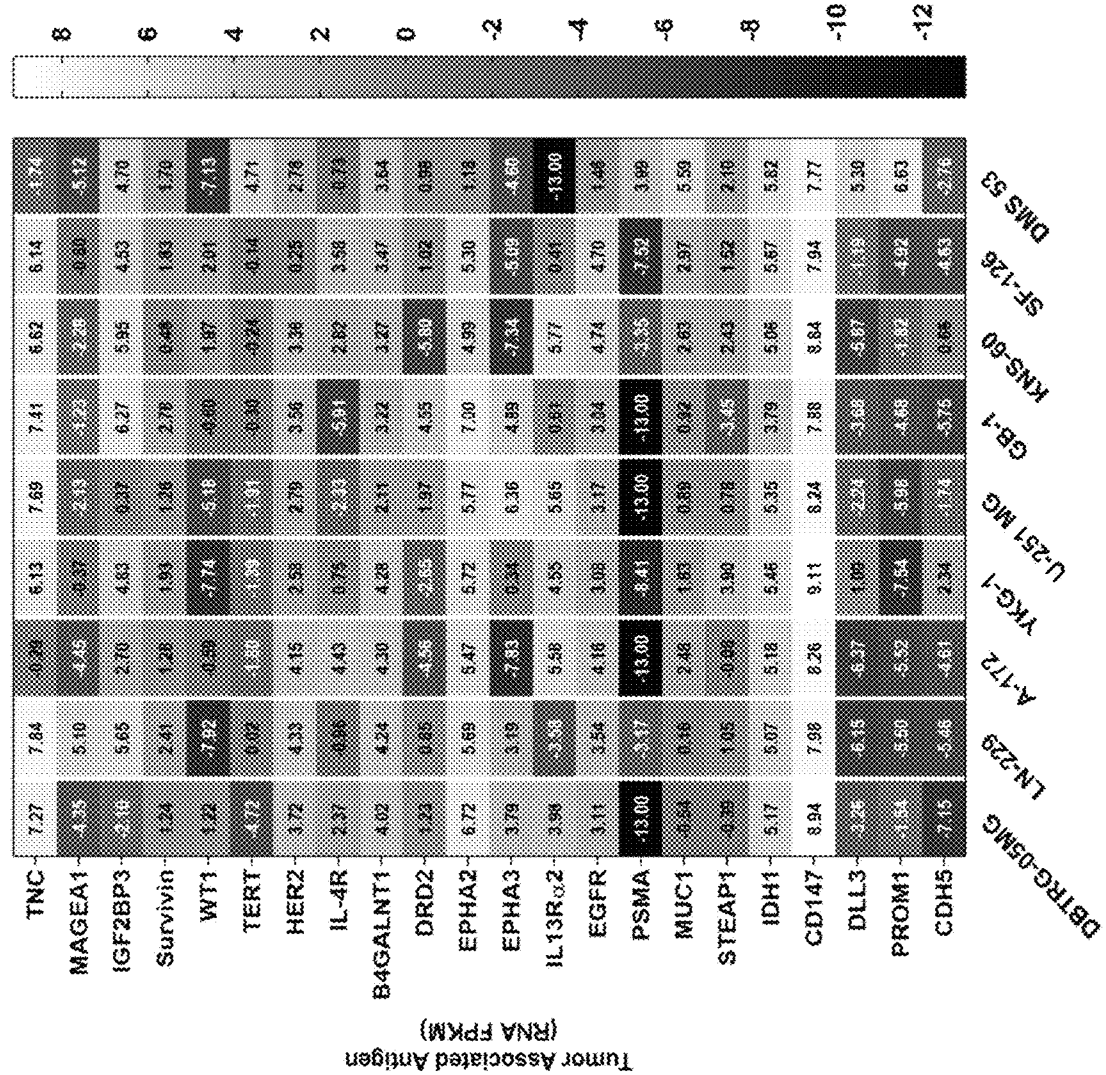
FIGS. 68A-C show endogenous expression of GBM antigens (FIG. 68A) and GBM CSC-like markers in candidate vaccine cell lines (FIG. 68B) and GBM patient tumor samples (FIG. 68C).
Figure 68C:
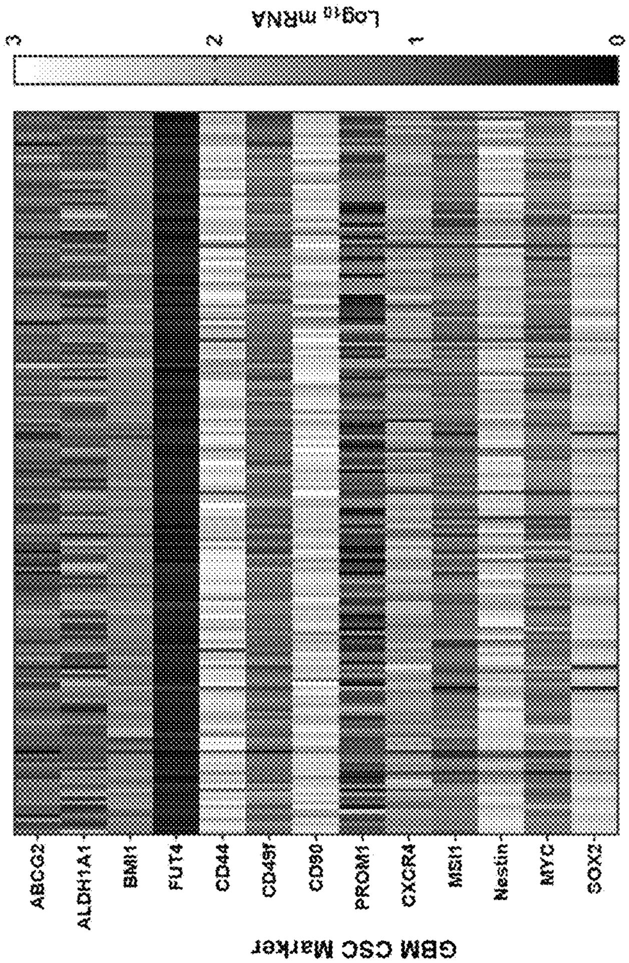

GBM tumors are enriched with a heterogenous population of CSCs that express a diverse array of CSC markers (Table 2). Expression of thirteen GBM associated CSC markers, ABCG2, ALDH1A1, BMI-1, FUT4, CD44, CD49f, CD90, PROM1, CXCR4, Musashi-1, Nestin, MYC, and SOX2 by GBM tumors was confirmed in patient tumor sample data downloaded from the publicly available database, cBioPortal (cbioportal.org) (Cerami, E. et al. Cancer Discovery. 2012; Gao, J. et al. Sci Signal. 2013) between Feb. 23, 2020 through Jul. 2, 2020 (FIG. 68C). The HUGO Gene Nomenclature Committee (HGNC) gene symbol was included in the search and mRNA expression was downloaded for each CSC marker.

Figure 68B:
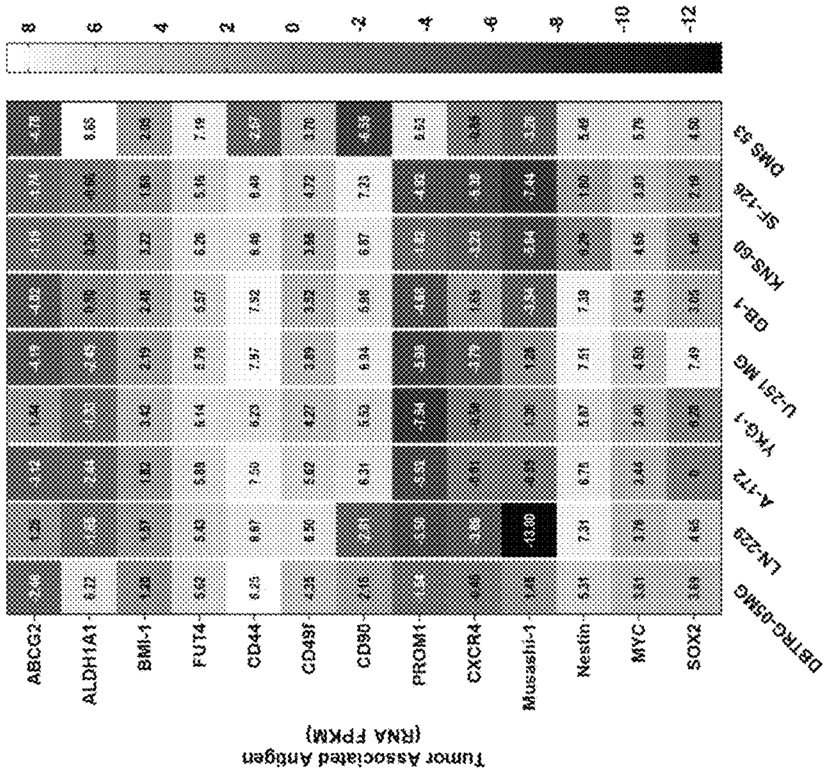

Expression of TAAs and CSC markers by candidate component cell lines was determined by RNA expression data sourced from Broad Institute Cancer Cell Line Encyclopedia (CCLE). The HGNC gene symbol was included in the CCLE search and mRNA expression was downloaded for each TAA or CSC marker. Expression of a TAA or CSC marker by a cell line was considered positive if the RNA-seq value (FPKM) was greater than one. Eight of the seventeen GBM vaccine candidate components were identified for further evaluation: DBTRG-05MG, LN-229, A-172, YKG-1, U-251 MG, GB-1, KNS 60, and SF-126 based on the selection criteria described above. The eight candidate component cell lines expressed seven to ten CSC markers (FIG. 68B) and eleven to fourteen TAAs (FIG. 68A). As described herein, the CSC-like cell line DMS 53 is included as one of the 6 cell lines.

Immunogenicity of the unmodified GBM component cell line candidates was evaluated by IFNγ ELISpot as described in Example 9 for three HLA diverse healthy donors (n=4 per donor). Donor HLA-A and HLA-B alleles were as follows: Donor 1, A*02:01 B*35:01 and A*31:01 B*35:03; Donor 2, A*01:01 B*30:01 and A*02:01 B*12:02, Donor 3, A*02:01 B*15:07 and A24:02 B*18:01. LN-229 (5,039±637 SFU) and DBTRG-05MG (6,094±734 SFU) were more immunogenic than A-172 (808±152 SFU), YKG-1 (576±154), U-251 MG (2,314±434), GB-1 (908±284 SFU), KNS-60 (2,177±415 SFU) and SF-126 (1,716±332 SFU). (FIG. 69A) LN-229 was selected to be included in vaccine cocktail A and DBTRG-05MG was selected to be included in vaccine cocktail B as described further herein.

Immunogenicity of DBTRG-05MG and LN-229 was evaluated in eight different combinations of three component cell lines, four combinations contained DBTRG-05MG and four combinations contained LN-229 (FIG. 69C). IFNγ responses were determined against the three component cell lines within in the eight potential vaccine cocktails by IFNγ ELISpot as described in Example 8 using the same three healthy donors described above (n=4/donor). IFNγ responses were detected for all eight cocktails and to each cell line component in each cocktail. Responses to the individual cocktail component cell lines were notably decreased compared to IFNγ responses detected for single cell line components. In all eight combinations evaluated, DBTRG-05MG and LN-229 remained the most immunogenic (FIG. 69B).

The cells in the vaccine described herein were selected to express a wide array of TAAs, including those known to be important specifically for GBM antitumor responses, such as IL13Rα2, and also TAAs known to be important for targets for GBM and other solid tumors, such TERT. As shown herein, to further enhance the array of TAAs, LN-229 was transduced with a gene encoding modPSMA, SF-126 was transduced with a gene encoding modTERT and KNS-60 was transduced with genes encoding modMAGEA1, hCMV pp65, and the 14 amino sequence spanning the in-frame deletion of 267 amino acids of EGFR that results in an activating mutated form of EGFR, EGFRvIII, as described herein.

TERT, PSMA and MAGEA1 were endogenously expressed in one of the six component cell lines, and the activating mutation EGFRvIII and GBM associated viral antigen hCMV pp65 were not endogenously expressed in one or more cell lines at >1.0 FPKM as described below (FIG. 70). Expression of the transduced antigens modTERT (SEQ ID NO: 35; SEQ ID NO: 36) by SF-126 (FIG. 71A), modPSMA (SEQ ID NO: 37; SEQ ID NO: 38) by LN-229 (FIG. 71B), modMAGEA1 (SEQ ID NO: 39; SEQ ID NO: 40) by KNS 60 (FIG. 71C), EGFRvIII (SEQ ID NO: 39; SEQ ID NO: 40) by KNS 60 (FIG. 71D), and hCMV pp65 (SEQ ID NO: 39; SEQ ID NO: 40) by KNS 60 (FIG. 71E), were detected by flow cytometry as described herein. Expression of EGFRvIII and hCMV pp65 by KNS 60 were also detected by RT-PCR as described herein (FIG. 71F). The genes for MAGEA1, EGFRvIII, and hCMV pp65 are encoded in the same lentiviral transfer vector separated by furin cleavage sites. IFNγ production to the transduced antigens is described herein.

Because of the need to maintain maximal heterogeneity of antigens and clonal subpopulations the comprise each cell line, the gene modified cell lines utilized in the present vaccine have been established using antibiotic selection and flow cytometry and not through limiting dilution subcloning.

Figure 70A:
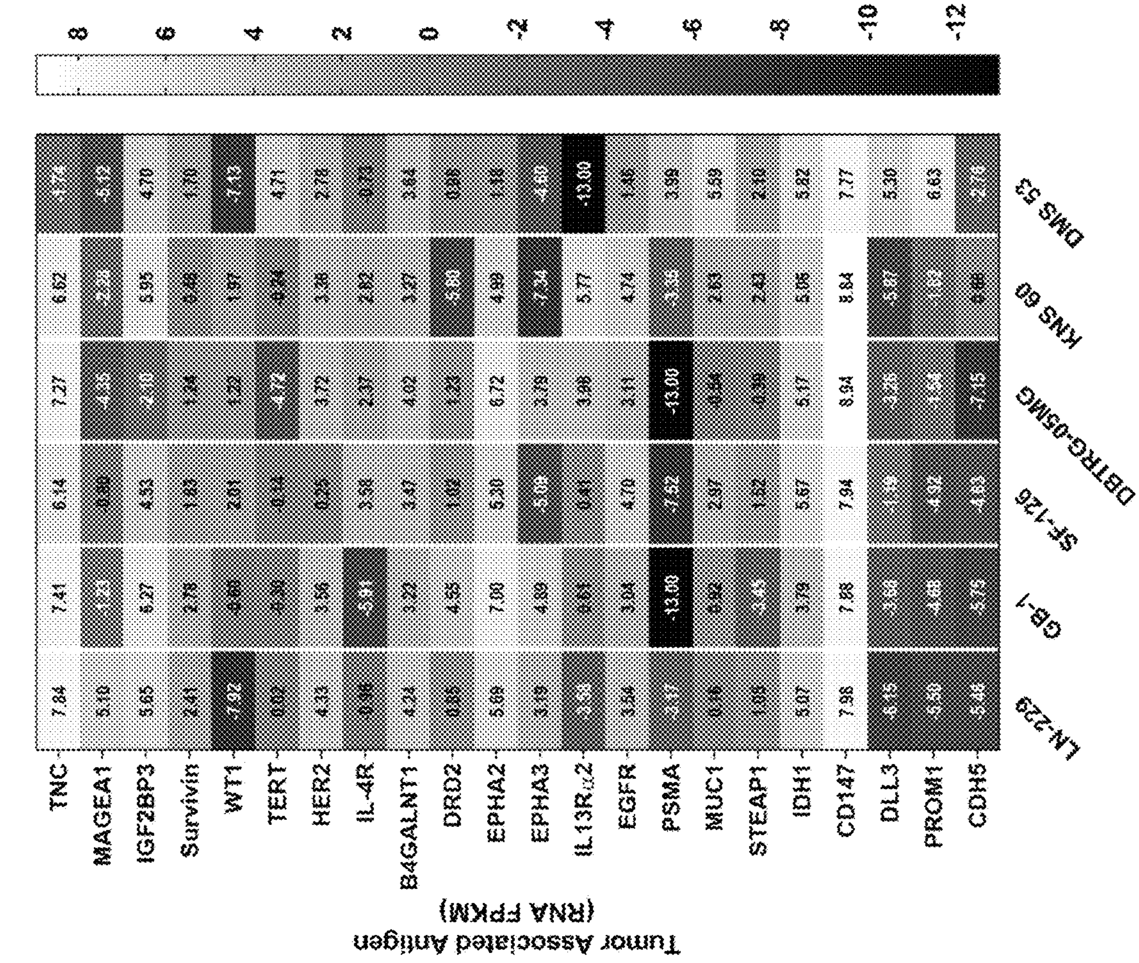
FIGS. 70A and B show endogenous expression of GBM antigens by the GBM vaccine cell lines (FIG. 70A) and the number of GBM antigens expressed by the vaccine cell lines also expressed in GBM patient tumors (FIG. 70B).
Figure 70B:
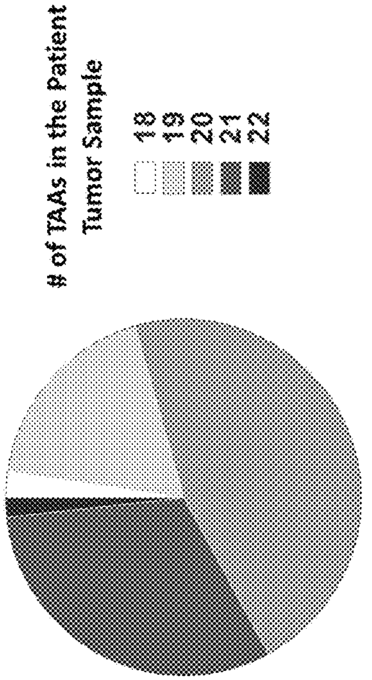
Figure 71A:
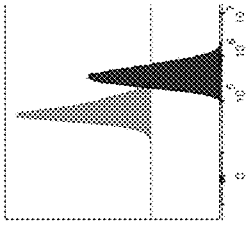
FIGS. 71A-K show the expression of and IFNγ responses to antigens introduced in the GBM vaccine cell lines compared to unmodified controls. Expression of modTERT by SF-126 (FIG. 71A) and IFNγ responses to TERT (FIG. 71G) in GBM-vaccine A. Expression of modPSMA by LN-229 (FIG. 71B) and IFNγ responses to PSMA (FIG. 71H) in GBM-vaccine A. Expression of modMAGEA1, EGFRvIII and pp65 by KNS 60 (FIGS. 71C-F) and IFNγ responses to MAGEA1, EGFRvIII and pp65 (FIGS. 71I-K) in GBM-vaccine B.

The mRNA expression of representative TAAs in the present vaccine are shown in FIG. 70A. The present vaccine has high expression of all identified twenty-two commonly targeted and potentially clinically relevant TAAs for inducing a GBM antitumor response. Some of these TAAs are known to be primarily enriched in GBM tumors and some can also induce an immune response to GBM and other solid tumors. Expression of the twenty-two prioritized GBM TAAs was determined in 170 GBM patient samples using the same methods and 170 patient samples used to confirm the expression of GBM CSC markers described above. Eighteen of the prioritized GBM TAAs were expressed by 100% of samples, 19 TAAs were expressed by 97.2% of samples, 20 TAAs were expressed by 79.4% of samples, 21 TAAs were expressed by 32.9% of samples, and 22 TAAs were expressed by 1.8% samples (FIG. 70B). Based on the expression and immunogenicity data presented herein, the cell lines identified in Table 48 were selected to comprise the present GBM vaccine.

TABLE 48

Glioblastoma vaccine cell lines and histology

| Cocktail | Cell Line | Name Histology |
|---|---|---|
| A | LN-229 | Glioblastoma Multiforme |
| A | GB-1 | Glioblastoma Multiforme |
| A | SF-126 | Glioblastoma Multiforme |
| B | DBTRG-05MG | Glioblastoma Multiforme |
| B | KNS-60 | Glioblastoma Multiforme |
| B | DMS 53 | Lung Small Cell Carcinoma |

CD276 Expression

The LN-229, GB-1, SF-126, KNS-60, and DMS 53 component cell lines expressed CD276 and expression was knocked out by electroporation with ZFN as described in Example 13 and elsewhere herein. DBTRG-05MG was transduced with lentiviral particles expressing shRNA specific for knockdown of CD276 (shCD276, ccggtgctggagaaagatcaaacagctcgagctgtttgatctttctccagcatttttt (SEQ ID NO: 71). Because it was desirable to maintain as much tumor heterogeneity as possible, the electroporated and shRNA modified cells were not cloned by limiting dilution. Instead, the cells were subjected to multiple rounds of cell sorting by FACS as described in Example 13.

Expression of CD276 was determined by extracellular staining of modified and parental cell lines with PE α-human CD276 (BioLegend, clone DCN.70) on Day 1 (before irradiation) and Day 3 (48 hours post-irradiation). Irradiation did not impact CD276 expression levels and Day 1 MFI values are reported. Unstained cells and isotype control PE α-mouse IgG1 (BioLegend, clone MOPC-21) stained parental and CD276 KO cells served as controls. The MFI of the isotype control was subtracted from reported values for both the parental and modified cell lines. Percent reduction of CD276 expression is expressed as: (1-(MFI of the CD276KO cell line/MFI of the parental))×100). MFI is normalized to 100,000 cells. Reduction of CD276 expression is described in Table 49. These data show that gene editing of CD276 with shRNA or ZFN resulted in greater than 58.5% CD276-negative cells in all six vaccine component cell lines.

TABLE 49

Reduction of CD276 expression

| Cell line | Parental Cell Line MFI | Modified Cell Line MFI | % Reduction CD276 |
|---|---|---|---|
| LN-229 | 17,549 | 176 | 99.0 |
| GB-1 | 31,439 | 137 | 99.6 |
| SF-126 | 25,608 | 18 | 99.9 |
| DBTRG-05MG | 67,196 | 27,879 | 58.5 |
| KNS-60 | 12,218 | 122 | 99.0 |
| DMS 53 | 11,928 | 24 | 99.8 |

MFI reported with isotype controls subtracted

Cytokine Secretion Assays for TGFβ1, TGFβ2, GM-CSF, and IL-12

Cell lines were X-ray irradiated at 100 Gy prior to plating in 6-well plates at 2 cell densities (5.0e5 and 7.5e5) in duplicate. The following day, cells were washed with PBS and the media was changed to Secretion Assay Media (Base Media+5% CTS). After 48 hours, media was collected for ELISAs. The number of cells per well was counted using the Luna cell counter (Logos Biosystems). Total cell count and viable cell count were recorded. The secretion of cytokines in the media, as determined by ELISA, was normalized to the total cell count recorded.

TGFβ1 secretion was determined by ELISA according to manufacturers instructions (Human TGFβ1 Quantikine ELISA, R&D Systems #SB100B). Four dilutions were plated in duplicate for each supernatant sample. If the results of the ELISA assay were below the LLD, the percentage decrease relative to parental cell lines was estimated by the number of cells recovered from the assay and the lower limit of detection, 15.4 pg/mL. If TGFβ1 was detected in >2 samples or dilutions the average of the positive values was reported with the n of samples run.

TGFβ2 secretion was determined by ELISA according to manufacturers instructions (Human TGFβ2 Quantikine ELISA, R&D Systems # SB250). Four dilutions were plated in duplicate for each supernatant sample. If the results of the ELISA assay were below the LLD, the percentage decrease relative to parental cell lines was estimated by the number of cells recovered from the assay and the lower limit of detection, 7.0 pg/mL. If TGFβ2 was detected in >2 samples or dilutions the average of the positive values was reported with the n of samples run.

GM-CSF secretion was determined by ELISA according to manufacturers instructions (GM-CSF Quantikine ELISA, R&D Systems #SGM00). Four dilutions were plated in duplicate for each supernatant sample. If the results of the ELISA assay were below the LLD, the percentage increase relative to parental cell lines was estimated by the number of cells recovered from the assay and the lower limit of detection, 3.0 pg/mL. If GM-CSF was detected in >2 samples or dilutions the average of the positive values was reported with the n of samples run.

IL-12 secretion was determined by ELISA according to manufacturer's instructions (LEGEND MAX Human IL-12 (p70) ELISA, Biolegend #431707). Four dilutions were plated in duplicate for each supernatant sample. If the results of the ELISA assay were below the LLD, the percentage increase was estimated by the number of cells recovered from the assay and the lower limit of detection, 1.2 pg/mL. If IL-12 was detected in >2 samples or dilutions the average of the positive values was reported with the n of samples run.

shRNA Downregulates TGF-β Secretion

Following CD276 knockout, TGFβ1 and TGFβ2 secretion levels were reduced using shRNA and resulting levels determined as described above. Of the parental cell lines in GBM vaccine-A, LN-229, GB-1 and SF-126 secreted measurable levels of TGFβ1 and TGFβ2. Of the parental cell lines in GBM vaccine-B, DBTRG-05MG, KNS 60, and DMS 53 secreted measurable levels of TGFβ1 and TGFβ2. Reduction of TGFβ2 secretion by the DMS 53 cell line is described in Example 5 and resulting levels determined as described above.

The five component cell lines of GBM origin were transduced with TGFβ1 shRNA to decrease secretion of TGFβ1. The lentiviral particles encoding TGFβ1 shRNA also encoded the gene for expression of membrane bound CD40L under the control of a different promoter. This allowed for simultaneous reduction of TGFβ1 and expression of membrane bound CD40L. SF-126 and KNS 60 were subsequently transduced with lentiviral particles encoding TGFβ2 shRNA and GM-CSF (SEQ ID NO: 6). This allowed for simultaneous reduction of TGFβ2 and expression of GM-CSF in both cell lines.

DBTRG-05MG and GB-1 were gene modified with only TGFβ1 shRNA. TGFβ1 and TGFβ2 promote cell proliferation and survival. In some cell lines, as in some tumors, reduction of TGFβ signaling can induce growth arrest and lead to cell death. In neuronal cells, such as GBM, loss of TGFβ signaling is also associated with cell death. TGFβ1 knockdown was selected for modification because it is considered a more potent immunosuppressive factor relative to TGFβ2 and retaining some TGFβ signaling is likely necessary for proliferation and survival of these cell lines. LN-229 secreted TGFβ2 at a detectable, but low, level and was not modified with TGFβ2 shRNA. These cells are described by the clonal designation DK2. As described in Example 26, DMS 53 was modified with shRNA to reduce secretion of TGFβ2 and not TGFβ1. These cells are described by the clonal designation DK4. The remaining cell lines were double modified with TGFβ1 shRNA and TGFβ2 shRNA. These cells are described by the clonal designation DK6.

Table 50 shows the percent reduction in TGFβ1 and/or TGFβ2 secretion in gene modified component cell lines compared to unmodified, parental, cell lines. Gene modification resulted in 49% to 80% reduction of TGFβ1 secretion. Gene modification of TGFβ2 resulted in 51% to 99% reduction in secretion of TGFβ2. TGFβ1 shRNA modified DBTRG-05MG secreted less TGFβ2 than the unmodified, parental cell line. Lower secretion of TGFβ2 by the modified cell line was confirmed in multiple independent experiments. Lower secretion of TGFβ2 following TGFβ1 knockdown was not observed in other component cell lines.

TABLE 50

TGF-β Secretion (pg/$10^6$ cells/24 hr) in Component Cell Lines

| Cell Line | Cocktail | Clone | TGFβ1 | TGFβ2 |
|---|---|---|---|---|
| LN-229 | A | Wild type | 1,874 ± 294 | 116 ± 19 |
| LN-229 | A | DK2 | 384 ± 47 | 73 ± 41 |
| LN-229 | A | Percent reduction | 80% | NA |
| GB-1 | A | Wild type | 204 ± 28 | 481 ± 51 |
| GB-1 | A | DK2 | 66 ± 16 | 438 ± 59 |
| GB-1 | A | Percent reduction | 68% | NA |
| SF-126 | A | Wild type | 2,818 ± 258 | 784 ± 98 |
| SF-126 | A | DK6 | 792 ± 188 | * ≤11 |
| SF-126 | A | Percent reduction | 72% | 99% |
| DBTRG-05MG | B | Wild type | 6,626 ± 389 | 2,664 ± 461 |
| DBTRG-05MG | B | DK2 | 3,365 ± 653 | 612 ± 190 |
| DBTRG-05MG | B | Percent reduction | 49% | NA |
| KNS 60 | B | Wild type | 3,308 ± 615 | 1,451 ± 235 |
| KNS 60 | B | DK6 | 1,296 ± 110 | 36 ± 11 |
| KNS 60 | B | Percent reduction | 61% | 97% |

TABLE 50-continued

TGF-β Secretion (pg/$10^6$ cells/24 hr) in Component Cell Lines

| Cell Line | Cocktail | Clone | TGFβ1 | TGFβ2 |
|---|---|---|---|---|
| DMS 53 | B | Wild type | 106 ± 10 | 486 ± 35 |
| DMS 53 | B | DK4 | 219 ± 33 | 238 ± 40 |
| DMS 53 | B | Percent reduction | NA | 51% |

DK6: TGFβ1/TGFβ2 double knockdown; DK4: TGFβ2 single knockdown; DK2: TGFβ1 single knockdown;
* = estimated using LLD, not detected; NA=not applicable Based on a dose of $5\times10^5$ of each component cell line, the total TGFβ1 and TGFβ2 secretion by the modified GBM vaccine-A and GBM vaccine-B and respective unmodified parental cell lines are shown in Table 51. The secretion of TGFβ1 by GBM vaccine-A was reduced by 75% and TGFβ2 by 62% pg/dose/24 hr. The secretion of TGFβ1 by GBM vaccine-B was reduced by 51% and TGFβ2 by 74% pg/dose/24 hr.

TABLE 51

Total TGF-β Secretion (pg/dose/24 hr) in GBM vaccine-A and GBM vaccine-B

| Cocktail | Clones | TGFβ1 | TGFβ2 |
|---|---|---|---|
| A | Wild type | 2,448 | 691 |
| | DK2/6 | 621 | 261 |
| | Percent reduction | 75% | 62% |
| B | Wild type | 5,020 | 2,301 |
| | DK2/4/6 | 2,440 | 600 |
| | Percent reduction | 51% | 74% |

GM-CSF Secretion

Two GBM component cell lines, KNS 60 and SF-126, were transduced with lentiviral particles containing both TGFβ2 shRNA and the gene to express GM-CSF (SEQ ID NO: 6) under the control of a different promoter. This allowed for simultaneous reduction of TGFβ2 secretion and expression of GM-CSF. The DBTRG-05MG, LN-229 and GB-1 cell lines were transduced with lentiviral particles to only express GM-CSF (SEQ ID NO: 7). DMS 53 was modified to secrete GM-CSF as described in Example 24 and elsewhere herein. The results are shown in Table 52 and described below.

Secretion of GM-CSF increased at least 19,000-fold in all modified component cell lines compared to unmodified, parental cell lines. In GBM vaccine-A component cell lines, secretion of GM-CSF increased 303,000-fold by LN-229 compared to the parental cell line (≤0.002 ng/$10^6$ cells/24 hr), 409,000-fold by GB-1 compared to the parental cell line (≤0.001 ng/$10^6$ cells/24 hr), and 19,000-fold by SF-126 compared to the parental cell line (≤0.003 ng/$10^6$ cells/24 hr). In GBM vaccine-B component cell lines secretion of GM-CSF increased 1,209,500-fold by DBTRG-05MG compared to the parental cell line (≤0.002 ng/$10^6$ cells/24 hr), 109,667-fold by KNS 60 compared to the parental cell line (≤0.003 ng/$10^6$ cells/24 hr) and 39,450-fold by DMS 53 compared to the parental cell line (≤0.004 ng/$10^6$ cells/24 hr).

TABLE 52

GM-CSF Secretion in Component Cell Lines

| Cell Line | GM-CSF (ng/106 cells/24 hr) | GM-CSF (ng/dose/24 hr) |
|---|---|---|
| LN-229 | 606 ± 228 | 303 |
| GB-1 | 409 ± 161 | 205 |

TABLE 52-continued

GM-CSF Secretion in Component Cell Lines

| Cell Line | GM-CSF (ng/106 cells/24 hr) | GM-CSF (ng/dose/24 hr) |
|---|---|---|
| SF-126 | 57 ± 13 | 29 |
| Cocktail A Total | 1,072 | 537 |
| DBTRG-05MG | 2,419 ± 721 | 1,210 |
| KNS 60 | 329 ± 45 | 165 |
| DMS 53 | 158 ± 15 | 79 |
| Cocktail B Total | 2,906 | 1,454 |

Based on a dose of $5\times10^5$ of each component cell line, the total GM-CSF secretion for GBM vaccine-A was 537 ng per dose per 24 hours. The total GM-CSF secretion for GBM vaccine-B was 1,454 ng per dose per 24 hours. The total GM-CSF secretion per dose was therefore 1,991 ng per 24 hours.

Membrane Bound CD40L (CD154) Expression

The component cell lines were transduced with lentiviral particles to express membrane bound CD40L vector as described above. The methods to detect expression of CD40L by the five GBM cell line components are described herein. The methods used to modify DMS 53 to express CD40L are described in Example 15. Evaluation of membrane bound CD40L by all six vaccine component cell lines is described below.

CD40L expression was evaluated by flow cytometry with an anti-CD40L monoclonal antibody as described in Example 15. CD40L expression was determined on Day 1 (pre-irradiation) and Day 3 (post-irradiation). Irradiation did not impact expression levels and Day 1 CD40L expression is reported. If subtraction of the MFI of the isotype control resulted in a negative value, an MFI of 1.0 was used to calculate the fold increase in expression of CD40L by the modified component cell line relative to the unmodified cell line. The results shown in FIG. 72 and described below demonstrate CD40L membrane expression was substantially increased in all six cell GBM vaccine component cell lines.

Figure 72:
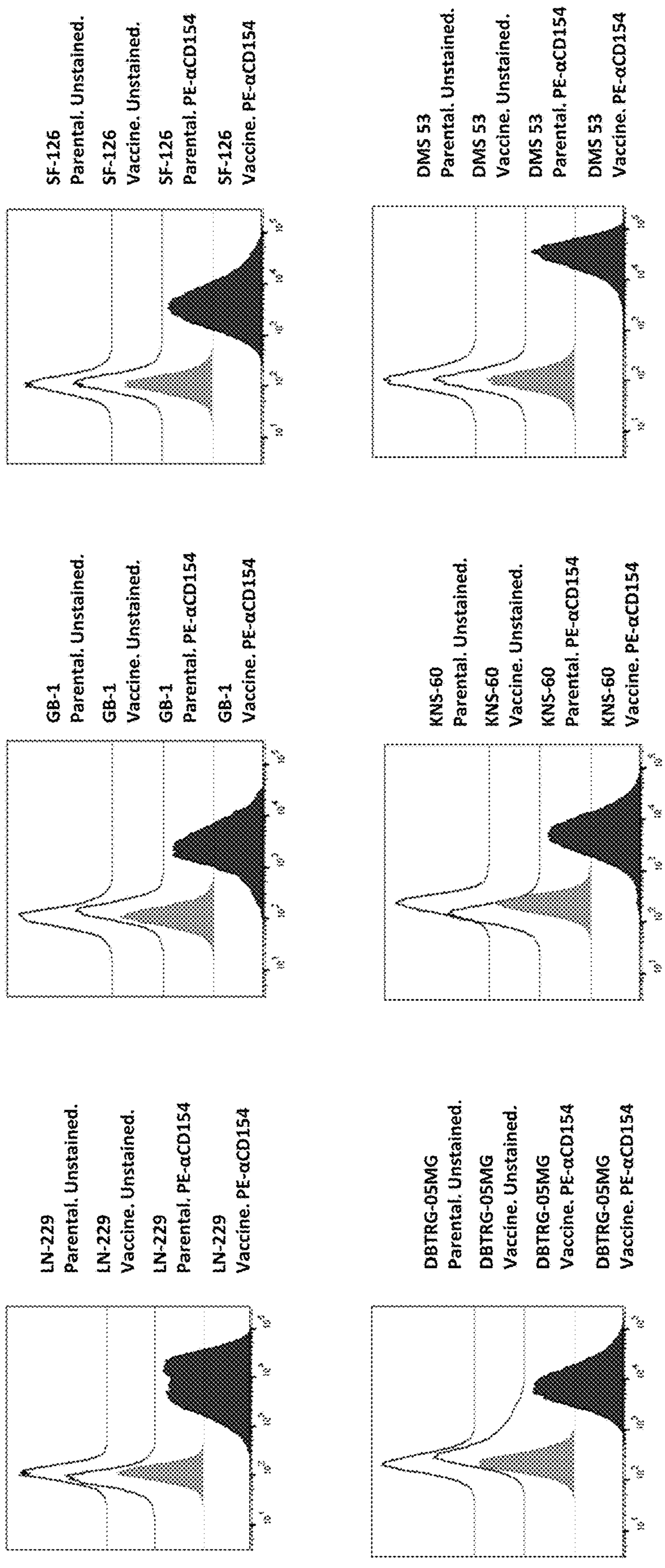
FIG. 72 shows expression of membrane bound CD40L by the GBM vaccine component cell lines.

FIG. 72 shows the expression of membrane bound CD40L by the GBM vaccine component cell lines. Expression of membrane bound CD40L increased at least 172-fold in all component cell lines compared to unmodified, parental cell lines. In GBM vaccine-A component cell lines, expression of CD40L increased 11,628-fold by LN-229 (11,628 MFI) compared to the parental cell line (0 MFI), 233-fold by GB-1 (4,464 MFI) compared to the parental cell line (19 MFI), and 172-fold by SF-126 (5,526) compared to the parental cell line (32 MFI). In GBM vaccine-B component cell lines expression of CD40L increased 20,510-fold by DBTRG-05MG compared to the parental cell line (0 MFI), 5,599-fold by KNS 60 compared to the parental cell line (0 MFI), and 88,261-fold by DMS 53 compared to the parental cell line (0 MFI).

IL-12 Expression

The component cell lines were transduced with the IL-12 vector as described in Example 17 and resulting IL-12 p70 expression determined as described above and herein. The results are shown in Table 53 and described below.

Secretion of IL-12 increased at least 45,000-fold in all component cell lines modified to secrete IL-12 p70 compared to unmodified, parental cell lines. In GBM vaccine-A component cell lines, secretion of IL-12 increased 81,000-fold by LN-229 compared to the parental cell line (≤0.001 ng/$10^6$ cells/24 hr), 50,000-fold by GB-1 compared to the parental cell line (≤0.0002 ng/$10^6$ cells/24 hr), and 45,000-fold by SF-126 compared to the parental cell line (≤0.001 ng/$10^6$ cells/24 hr). In GBM vaccine-B component cell lines expression of IL-12 increased 133,560-fold by DBTRG-05MG compared to the parental cell line (≤0.001 ng/$10^6$ cells/24 hr) and 116,000-fold by KNS 60 compared to the parental cell line (≤0.001 ng/$10^6$ cells/24 hr). DMS 53 was not modified to secrete IL-12.

TABLE 53

IL-12 secretion in component cell lines

| Cell Line | IL-12 (ng/$10^6$ cells/24 hr) | IL-12 (ng/dose/24 hr) |
|---|---|---|
| LN-229 | 81 ± 4 | 41 |
| GB-1 | 10 ± 1 | 5 |
| SF-126 | 45 ± 7 | 23 |
| Cocktail A Total | 136 | 69 |
| DBTRG-05MG | 134 ± 24 | 67 |
| KNS 60 | 116 ± 5 | 58 |
| DMS 53 | NA | NA |
| Cocktail B Total | 250 | 125 |

Based on a dose of $5\times10^5$ of each component cell line, the total IL-12 secretion for GBM vaccine-A was 69 ng per dose per 24 hours. The total IL-12 secretion for GBM vaccine-B was 125 ng per dose per 24 hours. The total IL-12 secretion per dose was therefore 194 ng per 24 hours.

Stable Expression of modPSMA by the LN-229 Cell Line

As described above, the cells in the vaccine described herein were selected to express a wide array of TAAs, including those known to be important to GBM antitumor immunity. To further enhance the array of antigens, the LN-229 cell line that was modified to reduce the secretion of TGFβ1, reduce the expression of CD276, and to express GM-CSF, membrane bound CD40L, and IL-12 was also transduced with lentiviral particles expressing the modPSMA antigen (SEQ ID NO: 37, SEQ ID NO: 38).

Figure 71B:
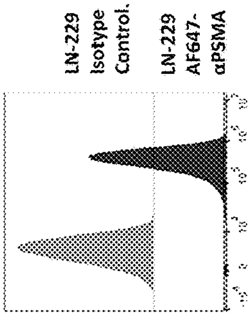

The expression of modPSMA was characterized by flow cytometry. Unmodified parental and modified cells were stained intracellular with 0.06 μg/test anti-mouse IgG1 anti-PSMA antibody (AbCam ab268061, Clone FOLH1/3734) followed by 0.125 ug/test AF647-conjugated goat anti-mouse IgG1 antibody (Biolegend #405322). The MFI of the isotype control stained parental and modified cells was subtracted from the MFI of cells stained anti-PSMA. MFI was normalized to 100,000 events. Fold increase in antigen expression was calculated as: (background subtracted modified MFI/background subtracted parental MFI). Expression of PSMA increased in the modified cell line (533,577 MFI) 38-fold over that of the parental cell line (14,008 MFI) (FIG. 71B).

Stable Expression of modMAGEA1, EGFRvIII, hCMV-Pp65 by the KNS 60 Cell Line

As described above, the cells in the vaccine described herein were selected to express a wide array of TAAs, including those known to be important to antitumor immunity. To further enhance the array of antigens, the KNS 60 cell line that was modified to reduce the secretion of TGFβ1 and TGFβ2, reduce the expression of CD276, and to express GM-CSF, membrane bound CD40L and IL-12 was also transduced with lentiviral particles expressing the modMAGEA1, hCMV pp65, and EGFRvIII antigens. The modMAGEA1, hCMV pp65, and EGFRvIII antigens are linked by a furin cleavage site (SEQ ID NO: 39, SEQ ID NO: 40).

The expression of modMAGEA1, hCMV pp65, and EGFRvIII was characterized by flow cytometry. Unmodified parental and modified cells were stained intracellular to detect the expression of each antigen as follows. For the detection of modMAGEA1, cells were first stained with mouse IgG1 anti-MAGEA1 antibody (SC-71539, Clone 3F256) (0.03 ug/test) followed by AF647-conjugated goat anti-mouse IgG1 antibody (Biolegend #405322) (0.125 ug/test). For the detection of hCMVpp65, cells were first stained with mouse IgG1 anti-pp65 antibody (AbCam ab31624, Clone 1-L-11) (0.06 ug/test) followed by AF647-conjugated goat anti-mouse IgG1 antibody (Biolegend #405322) (0.125 ug/test). For the detection of EGFRvIII, cells were first stained with mouse IgG1 anti-EGFRvIII antibody (Novus NBP2-50599, Clone DH8.3) (0.06 ug/test) followed by AF647-conjugated goat anti-mouse IgG1 antibody (Biolegend #405322) (0.125 ug/test). The MFI of the isotype control stained cells was subtracted from the MFI of the cells stained for MAGEA1, hCMV pp65, or EGFRvIII. MFI was normalized to 100,000 events. Fold increase in antigen expression was calculated as: (background subtracted modified MFI/background subtracted parental MFI).

Expression of hCMV pp65 and EGFRvIII was also confirmed by RT-PCR (FIG. 81F). 1.0-3.0×106 cell were used for RNA isolation. RNA was isolated using Direct-zol™ RNA MiniPrep kit (ZYMO RESEARCH, catalog number: R2051) per the manufacturer's instructions. RNA quantification was performed using NanoDrop™ OneC (Thermo Scientific™, catalogue number 13-400-519). For reverse transcription, 1 μg of RNA was reverse transcribed using qScript cDNA SuperMix (Quantabio, catalogue number: 95048-025) per the manufacturer's instructions to cDNA. After completion of cDNA synthesis, the reaction was diluted two times and 2 μL of cDNA were used for amplification. For hCMV pp65, the forward primer designed to anneal at the 1925-1945 base pair (bp) location in the transgene (CGGACTGCTGTGTCCTAAGAG (SEQ ID NO: 118)) and reverse primer designed to anneal at 2414-2435 bp location in the transgene (GCTGTCCTCGTCTGTATCTTCC (SEQ ID NO: 119)) and yield 511 bp product. For EGFRvIII, the forward primer was designed to anneal at the 839-858 bp location in the transgene (TGTGAAGGTGCTGGAATACG (SEQ ID NO: 120)) and reverse primer designed to anneal at the 1252-1271 bp location in the transgene (GCCGGTAAAGTAGGTGTGCT (SEQ ID NO: 121)) and yield 433 bp product. β-tubulin primers that anneal to variant 1, exon 1 (TGTCTAGGGGAAGGGTGTGG (SEQ ID NO: 122) and exon 4 (TGCCCCAGACTGACCAAATAC (SEQ ID NO: 123)) were used as a control. PCR to detect hCMV pp65, EGFRvIII and β-tubulin was completed as follows: initial denaturation, 98° C. for 30 seconds, followed by 25 cycles of denaturation at 98° C. for 5 to 10 seconds, annealing at 58° C. for 10 to 30 seconds, and extension at 72° C. for 30 seconds. After the 25 cycles final extension of 2 min at 72° C. was completed and the reaction held at 10° C. until detection of the PCR products by gel electrophoresis. After completion of PCR, Lel Loading Dye, Purple (6×) (New England BioLabs, # B7024S) was added at a 1× concentration. The PCR product was then run a 2% agarose gel (Lonza SeaKem® LE Agarose, #50004) along with 8 μL of of exACT Gene 100 bp ladder (Fisher BioReagents, # BP2573100) for band size estimation. After the bands were appropriately separated, the gels were imaged using ChemiDoc Imaging System (BioRAD, #17001401). For relative quantification with β-tubulin gene, Image Lab Software v6.0 (BioRAD) was used.

Figure 71C:
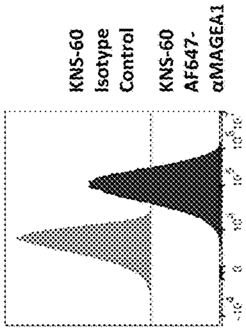
Figure 71D:
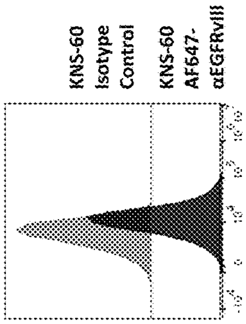
Figure 71E:
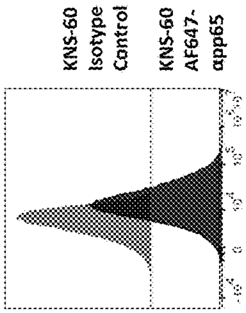
Figure 71F:
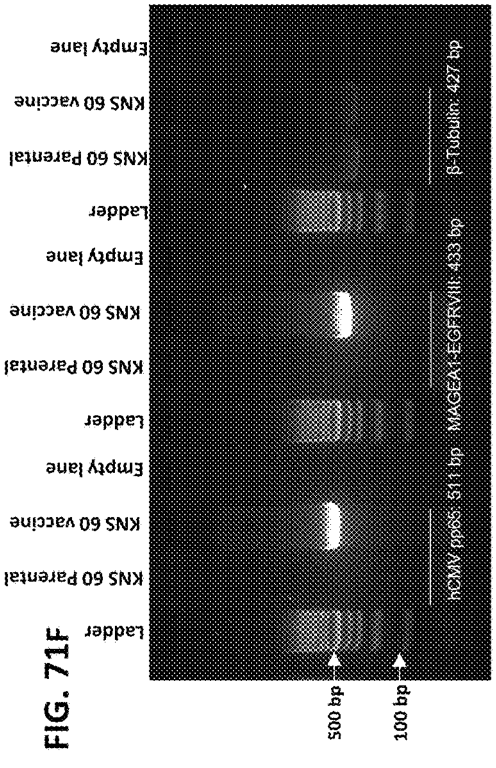

Expression of modMAGEA1 increased in the modified cell line (140,342 MFI) 41-fold over that of the parental cell line (3,460 MFI) (FIG. 71C). Expression of hCMV pp65 by the modified cell line (9,545 MFI) increased 9,545-fold over the that of the parental cell line (0 MFI). Subtraction of the MFI of the isotype control from the MFI of the pp65 stained parental KNS 60 resulted in negative value. The fold increase of pp65 expression in the modified cell line was calculated using 1 MFI (FIG. 71E). Expression of EGFRvIII by the modified cell line (4,925 MFI) increased 5-fold over the that of the parental cell line (1,053 MFI) (FIG. 71D).

Stable Expression of modTERT by the SF-126 Cell Line

As described above, the cells in the vaccine described herein were selected to express a wide array of TAAs, including those known to be important to antitumor immunity. To further enhance the array of antigens, the SF-126 cell line that was modified to reduce the secretion of TGFβ1 and TGFβ2, reduce the expression of CD276, and to express GM-CSF, membrane bound CD40L and IL-12 was also transduced with lentiviral particles expressing the modTERT antigen (SEQ ID NO: 35, SEQ ID NO: 36).

The expression of modTERT was characterized by flow cytometry. Unmodified parental and modified cells were stained intracellular with anti-rabbit IgG1 anti-TERT antibody (AbCam ab32020, Clone Y182) (0.03 μg/test) followed by AF647-conjugated donkey anti-rabbit IgG1 antibody (Biolegend #406414) (0.125 ug/test). MFI was normalized to 100,000 events. The MFI of the isotype control stained parental and modified cells was subtracted from the MFI of cells stained for parental and modified cells. Fold increase in antigen expression was calculated as: (background subtracted modified MFI/background subtracted parental MFI). Expression of modTERT increased in the modified cell line (281,904 MFI) 27-fold over that of the parental cell line (10,578 MFI) (FIG. 71A).

Immune Responses to MAGEA1, EGFRvIII, and hCMV Pp65 in GBM-Vaccine B

Figure 71G:
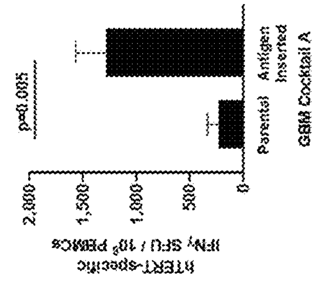
Figure 71H:
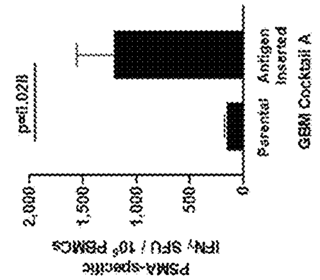
Figure 71I:
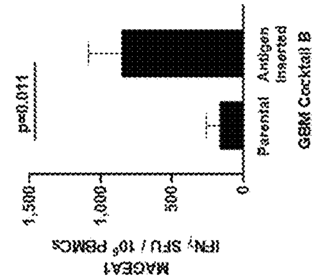
Figure 71J:
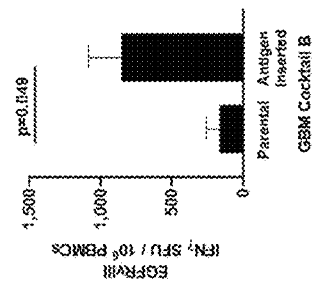
Figure 71K:
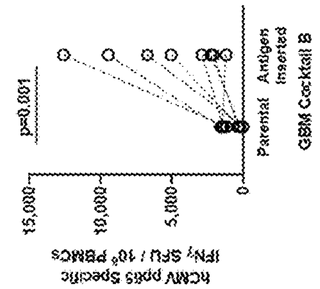

IFNγ responses to the MAGEA1, EGFRvIII, and hCMV pp65 antigens were evaluated in the context of the GBM-vaccine B. Specifically, $5\times10^5$ of the modified DMS 53, DBTRG-05MG and KNS 60 cell lines, a total of $1.5\times10^6$ total modified cells, were co-cultured with $1.5\times10^6$ iDCs from eight HLA diverse donors (n=4/donor). The HLA-A, HLA-B, and HLA-C alleles for each of the eight donors are shown in Table 54. The ability to generate and immune responses in MHC Class I diverse donors demonstrates the GBM vaccine is has the potential to elicit CD8+ T cell responses in a diverse patient population and is not class restricted to a specific MHC allele. CD14-PBMCs were isolated from co-culture with DCs on day 6 and stimulated with peptide pools, 15-mers overlapping by 11 amino acids or 15-mers overlapping by 9 amino acids, spanning the native protein sequences, in the IFNγ ELISpot assay for 24 hours prior to detection of IFNγ producing cells. Peptides were sourced as follows: EGFRvIII, 15-mers overlapping by 9 amino acids, were purchased from Thermo Scientific Custom Peptide Service, MAGE A1 (JPT, PM-MAGEA1) and hCMV pp65 (JPT, PM-PP65-1). IFNγ responses to MAGEA1 significantly increased with the modified GBM vaccine-B (1,323±442 SFU) compared to the unmodified GBM vaccine-B (225±64 SFU) (p=0.005, Mann-Whitney U test) (n=8) (FIG. 71I). EGFRvIII specific IFNγ responses significantly increased with the modified GBM vaccine-B (855±231 SFU) compared unmodified GBM vaccine-B (165±93 SFU) (p=0.049, Mann-Whitney U test) (FIG. 71J). hCMV pp65 specific IFNγ responses significantly increased with modified GBM vaccine-B (5,283±1,434 SFU) compared to the unmodified GBM vaccine-B (814±229 SFU) (p=0.001, Mann-Whitney U test) (FIG. 71K).

Immune Responses to PSMA and TERT in GBM-Vaccine A

IFNγ responses to the PSMA and TERT were evaluated in the context of GBM-vaccine A. Specifically, $5\times10^5$ of the modified LN-229, GB-1 and SF-126 cell lines, a total of $1.5\times10^6$ modified cells, were co-cultured with $1.5\times10^6$ iDCs from 8 HLA diverse donors (n=4/donor) (Table 54) and IFNγ responses determined by ELISpot as described above. PSMA peptides, 15-mers overlapping by 9 amino acids spanning the length of the native antigen, were purchased from Thermo Scientific Custom Peptide Service. TERT peptides cover the full-length native antigen were purchased from JPT (PM-TERT). TERT specific IFNγ responses with were significantly increased with the modified GBM vaccine-A (1,284±258 SFU) compared to the parental, unmodified GBM vaccine-A (231±102 SFU) (p=0.011, Mann-Whitney U test) (n=8) (FIG. 71G). PSMA specific IFNγ responses with the were significantly increased with the modified GBM vaccine-A (1,210±348 SFU) compared to the parental, unmodified GBM vaccine-A (154±22 SFU) (p=0.028, Mann-Whitney U test) (n=8) (FIG. 71H).

TABLE 54

Healthy Donor MHC-I characteristics

| Donor # | HLA-A | HLA-B | HLA-C |
|---|---|---|---|
| 1 | *02:01 *03:01 | *18:01 *38:01 | *07:01 *12:03 |
| 2 | *03:01 *25:01 | *07:02 *18:01 | *07:02 *12:03 |
| 3 | *02:01 *24:02 | *08:01 *44:02 | *05:01 *07:01 |
| 4 | *02:01 *03:01 | *08:01 *51:01 | *07:01 *14:02 |
| 5 | *02:05 *31:01 | *27:25 *50:01 | *07:01 *07:02 |
| 6 | *23:01 *24:02 | *35:03 *55:01 | *27:25 *50:01 |
| 7 | *30:02 *30:04 | *15:10 *58:02 | *03:04 *06:02 |
| 8 | *03:01 *32:01 | *07:02 *15:17 | *07:01 *07:02 |

Cocktails Induce Immune Responses Against Relevant TAAs

The ability of the individual component cell lines and the two GBM vaccine cocktails to induce IFNγ production against relevant GBM antigens was measured by ELISpot. PBMCs from eight HLA-diverse healthy donors (Table 54) were co-cultured with the GBM-A or GBM-B cocktails for 6 days prior to stimulation with autologous DCs loaded with TAA-specific specific peptide pools containing known MHC-I restricted epitopes. Peptides for stimulation of CD14-PBMCs were sourced as follows. Custom peptide libraries of 15-mers overlapping by 9 amino acids were ordered from Pierce for PSMA, WT1 and EGFRvIII. Additional 15-mer overlapping by 11 amino acid peptide pools were sourced as follows: TERT (JPT, PM-TERT), MAGE A1 (JPT, PM-MAGEA1), Survivin (thinkpeptides, 7769_001-011), WT1 (HER2 (JPT, PM-ERB_ECD), STEAP (PM-STEAP1), MUC1 (JPT, PM-MUC1), and hCMV pp65 (JPT, PM-PP65-1). Cells were then assayed for IFNγ secretion in the IFNγ ELISpot assay.

Approximately 60-70% of developed nations populations are hCMV positive (Hyun et al. Front. Immunol. 2017) and the hCMV status of the healthy donors in unknown. It is possible that the hCMV pp65 antigen in the GBM vaccine boosted a preexisting memory response in healthy donor PBMCs and did not prime a de novo response. For this reason, responses to hCMV are shown separately from the other nine prioritized TAAs and are not included in the TAA responses illustrated in FIG. 73, FIG. 74 or Table 55. Responses to the hCMV pp65 antigen in donor PBMCs when stimulated with parental controls or the GBM vaccine are shown in FIG. 71J. IFNγ responses to pp65 significantly increased with the GBM vaccine in seven of eight donors compared to parental controls. Specifically, expression of hCMV pp65 by KNS 60 significantly increased pp65 specific IFNγ responses in the context of the modified GBM vaccine-A (5,283±1,434 SFU) compared to the parental, unmodified GBM vaccine-A (814±229 SFU) (p=0.001, Mann-Whitney U test).

Figure 73C:
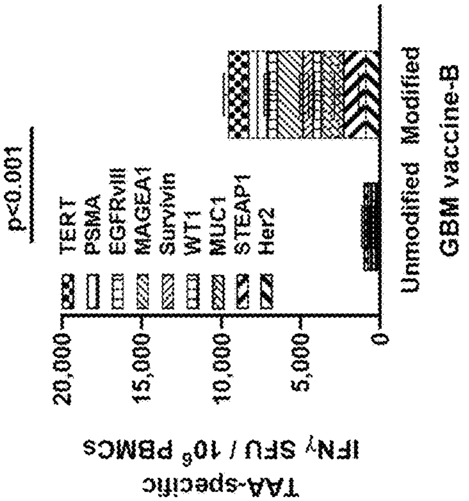
FIG. 73A-C shows antigen specific IFNγ responses induced by the unit dose of the GBM vaccine (FIG. 73A), GBM vaccine-A (FIG. 73B), and GBM vaccine-B (FIG. 73C) compared to unmodified controls.
Figure 73B:
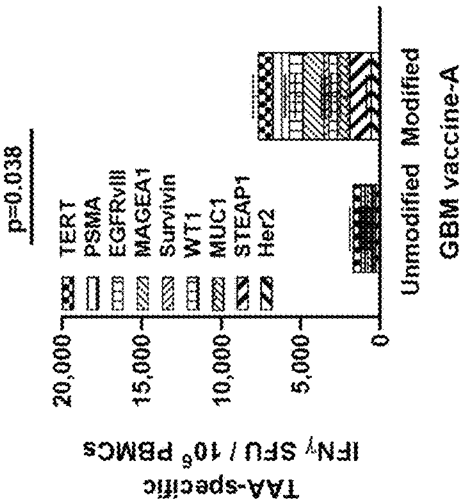
Figure 73A:
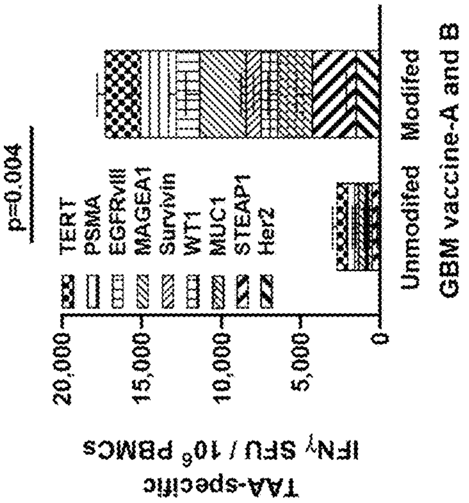

FIG. 73 demonstrates the GBM vaccine is capable of inducing antigen specific IFNγ responses in eight HLA-diverse donors that are significantly more robust (17,316±4,171 SFU) compared to the unmodified parental controls (2,769±691 SFU) (p=0.004, Mann-Whitney U test) (n=8) (FIG. 73A). GBM vaccine-A and GBM vaccine-B independently demonstrated antigen specific responses significantly greater compared to parental controls. Specifically, GBM vaccine-A elicited 7,716±2,308 SFU compared to the unmodified controls (1,718±556 SFU) (p=0.038, Mann-Whitney U test) (FIG. 73B). For GBM vaccine-A, excluding hCMV (n=9 antigens), one donor responded to four, three donors responded to seven antigens, one donor responded to eight antigens, and three donors responded to nine antigens. GBM vaccine-B elicited 9,601±2,413 SFU compared to parental controls (1,051±365 SFU) (p<0.001, Mann-Whitney U test) (FIG. 73C). For GBM vaccine-B, excluding hCMV (n=9 antigens), two donors responded to seven antigens, three donors responded to eight antigens, and three donors responded to nine antigens. The GBM vaccine (vaccine-A and vaccine-B) induced IFNγ production to all nine non-viral antigens in seven of eight donors (FIG. 74) (Table 55).

TABLE 55

IFNγ Responses to unmodified and modified GBM vaccine components

| | Unmodified (SFU ± SEM) | | | Modified (SFU ± SEM) | | |
|---|---|---|---|---|---|---|
| Donor (n = 4) | GBM vaccine-A | GBM vaccine-B | GBM Vaccine | GBM vaccine-A | GBM vaccine-B | GBM Vaccine |
| 1 | 89 ± 73 | 738 ± 401 | 826 ± 469 | 8,653 ± 4,964 | 11,450 ± 6,712 | 20,103 ± 11,633 |
| 2 | 246 ± 75 | 594 ± 58 | 840 ± 112 | 888 ± 383 | 1,086 ± 642 | 1,974 ± 956 |
| 3 | 5,204 ± 1,111 | 433 ± 145 | 5,636± | 669 ± 634 | 3,535 ± 2,146 | 4,234 ± 2,748 |
| 4 | 1,877 ± 1,002 | 450 ± 317 | 2,327± | 5,314 ± 3,529 | 20,347 ± 9856 | 25,661 ± 13,310 |
| 5 | 1,295 ± 732 | 1,268 ± 433 | 2,563 | 6,005 ± 2,330 | 8,130 ± 2,423 | 14,135 ± 4,605 |
| 6 | 2,330 ± 677 | 3,525 ± 330 | 5,858± | 15,253 ± 4,183 | 7,795 ± 2,324 | 23,048 ± 5,931 |
| 7 | 1,103 ± 503 | 751 ± 223 | 1,638± | 5,710 ± 4,657 | 5,965 ± 4,267 | 11,675 ± 8,893 |
| 8 | 1,600 ± 863 | 751 ± 223 | 2,351± | 19,204 ± 6,757 | 18,497 ± 5,934 | 37,701 ± 12,442 |

Based on the disclosure and data provided herein, a whole cell vaccine for Glioblastoma Multiforme comprising the six cancer cell lines, sourced from ATCC or JCRB, LN-229

(ATCC, CRL-2611), GB-1 (JCRB, IFO50489), SF-126 (JCRB, IFO50286), DBTRG-05MG (ATCC, CRL-2020), KNS 60 (JCRB, IFO50357) and DMS 53 (ATCC, CRL-2062) is shown in Table 56. The cell lines represent five glioblastoma cell lines and one small cell lung cancer (SCLC) cell line (DMS 53, ATCC CRL-2062). The cell lines have been divided into two groupings: vaccine-A and vaccine-B. Vaccine-A is designed to be administered intradermally in the upper arm and vaccine-B is designed to be administered intradermally in the thigh. Vaccine A and B together comprise a unit dose of cancer vaccine.

TABLE 56

| Cell line nomenclature and modifications | | | | | | | | |
|---|---|---|---|---|---|---|---|---|
| Cocktail | Cell Line | TGFβ1 KD | TGFβ2 KD | CD276 KO/KD | GM-CSF | CD40L | IL-12 | TAA(s) |
| A | LN-229 | X | ND | X | X | X | X | X |
| A | GB-1* | X | ND | X | X | X | X | ND |
| A | SF-126 | X | X | X | X | X | X | X |
| B | DBTRG-05MG* | X | ND | X^ | X | X | X | ND |
| B | KNS 60 | X | X | X | X | X | X | X |
| B | DMS 53* | ND | X | X | X | X | X | ND |

ND = Not done.
^CD276 KD.
*Cell lines identified as CSC-like cells.

Where indicated in the above table, the genes for the immunosuppressive factors transforming growth factor-beta 1 (TGFβ1) and transforming growth factor-beta 2 (TGFβ2) have been knocked down using shRNA transduction with a lentiviral vector. The gene for CD276 has been knocked out by electroporation using zinc-finger nuclease (ZFN) or knocked down using shRNA transduction with a lentiviral vector. The genes for granulocyte macrophage-colony stimulating factor (GM-CSF), IL-12, CD40L, modPSMA (LN-229), modTERT (SF-126), modMAGEA1 (KNS 60), EGFRvIII (KNS 60) and hCMV pp65 (KNS 60) have been added by lentiviral vector transduction.

Example 30: Preparation of Colorectal Cancer (CRC) Vaccine

This Example demonstrates that reduction of TGFβ1, TGFβ2, and CD276 expression with concurrent overexpression of GM-CSF, CD40L, and IL-12 in a vaccine composition of two cocktails, each cocktail composed of three cell lines for a total of 6 cell lines, significantly increased the magnitude of cellular immune responses to at least 10 CRC-associated antigens in an HLA-diverse population. As described herein, the first cocktail, CRC vaccine-A, is composed of cell line HCT-15, cell line HuTu-80 that was also modified to express modPSMA, and cell line LS411N. The second cocktail, CRC vaccine-B, is composed of cell line HCT-116 that was also modified to express modTBXT, modWT1, and the KRAS mutations G12D and G12V, cell line RKO, and cell line DMS 53. The six component cell lines collectively express at least twenty antigens that can provide an anti-CRC tumor response.

Identification of Colorectal Vaccine Components

Sixteen vaccine component cell lines were identified using initial cell line selection criteria for potential inclusion in the CRC vaccine. Additional selection criteria were applied to narrow the sixteen candidate cell lines to eight cell lines for further evaluation in immunogenicity assays. These criteria included: endogenous CRC associated antigen expression, lack of expression of additional immunosuppressive factors, such as IL-10 or IDO1, expression of CRC-associated CSC markers ALDH1, c-myc, CD44, CD133, Nanog, Musashi-1, EpCAM, Lgr-5 and SALL4, ethnicity and age of the patient from which the cell line was derived, microsatellite instability and CRC histological subtype.

Figure 75A:
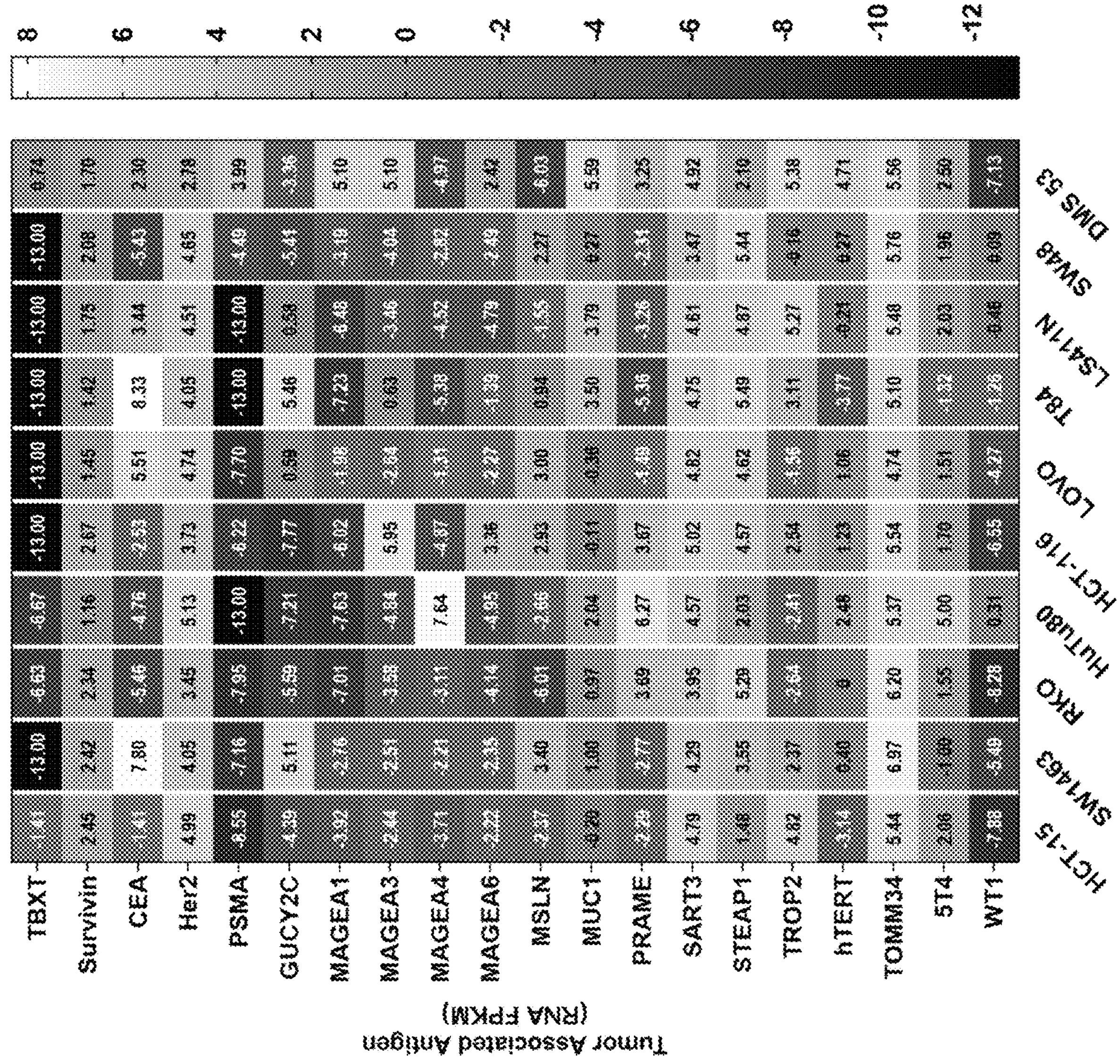
FIGS. 75A-C show endogenous expression of CRC antigens (FIG. 75A) and CRC CSC-like markers in selected cell lines (FIG. 75B) and CRC patient tumor samples (FIG. 75C).
Figure 75C:
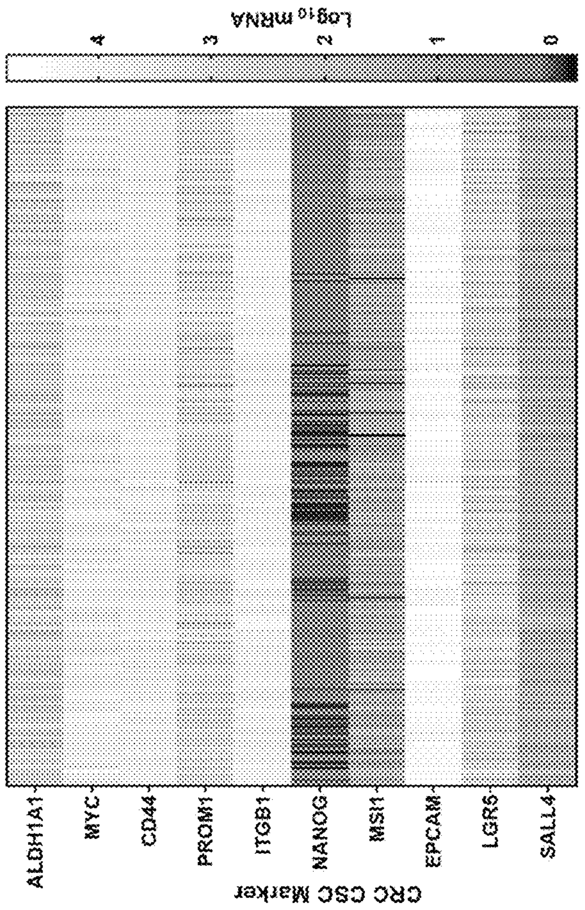

CSCs play a critical role in the metastasis and relapse of colorectal cancer (Table 2). Expression of nine CRC-associated CSC markers, by CRC tumors was confirmed in patient tumor sample data downloaded from the publicly available database, cBioPortal (cbioportal.org) (Cerami, E. et al. Cancer Discovery. 2012; Gao, J. et al. Sci Signal. 2013) between Oct. 1, 2019 through Oct. 20, 2020 (FIG. 75C). The HUGO Gene Nomenclature Committee (HGNC) gene symbol was included in the search and RSEM normalized mRNA abundance was downloaded for each CSC marker. Of 1,534 CRC patient samples 592 samples had mRNA expression data available for the ten CSC markers described above. A sample was considered positive for expression of a CRC CSC marker if $\text{Log}_{10}$ (RSEM+1)>0. Within the 592 samples 0.8% expressed 8 CSC markers (n=5), 43.9% expressed 9 CSC markers (n=260) and 55.2% expressed 10 CSC markers.

Figure 75B:
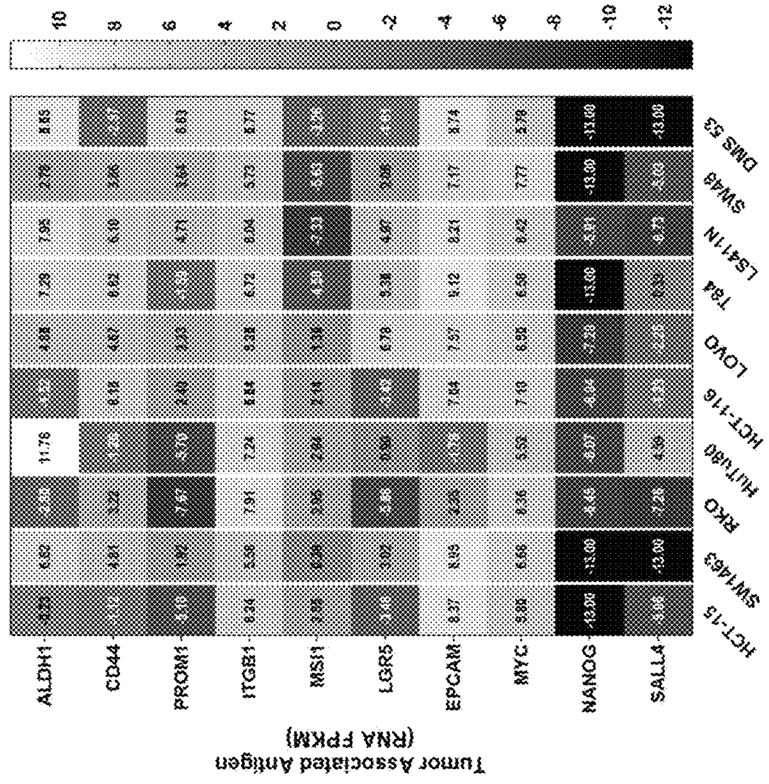

Expression of TAAs and CSC markers by candidate component cell lines was determined by RNA expression data sourced from Broad Institute Cancer Cell Line Encyclopedia (CCLE). The HGNC gene symbol was included in the CCLE search and mRNA expression was downloaded for each TAA or CSC marker. Expression of a TAA or CSC marker by a cell line was considered positive if the RNA-seq value (FPKM) was greater than one. Nine of the sixteen CRC vaccine candidate components were identified for further evaluation: HCT-15, SW1463, RKO, HuTu80, HCT-116, LoVo, T84, LS411N and SW48 based on the selection criteria described above. The nine candidate component cell lines expressed four to eight CSC markers (FIG. 75B) and seven to twelve TAAs (FIG. 75A). As described herein, the CSC-like cell line DMS 53 is included as one of the 6 cell lines and expressed fifteen CRC TMs.

Immunogenicity of the unmodified CRC component cell line candidates was evaluated by IFNγ ELISpot as described in Example 9 for two HLA diverse healthy donors (n=4 per donor). HLA-A and HLA-B alleles for Donor 1 were A*02:01 B*40:01 and A*30:01 B*57:01. HLA-A and HLA-B alleles for Donor 2 were A*24:02 B*18:01 and A*02:01 B*15:07. HCT-15 (2,375±774 SFU) and LoVo (1,758±311 SFU) were more immunogenic than SW1463 (170±90 SFU), RKO (280±102), HuTu80 (80±47), HCT-116 (981±433 SFU), T84 (406±185 SFU), LS411N (496±213)

and SW48 (636±289 SFU)(FIG. 76A). HCT-15 and LoVo were selected to be included in vaccine cocktail A or vaccine cocktail B as described further herein.

Immunogenicity of HCT-15 and LoVo was evaluated in eight different combinations of three component cell lines, four combinations contained HCT-15 and four combinations contained LoVo (FIG. 76C). IFNγ responses were determined against the three component cell lines within in the eight potential vaccine cocktails by IFNγ ELISpot as described in Example 8 using the same two donors described above (n=4/donor). IFNγ responses were detected for all eight cocktails and to each cell line component in each cocktail (FIG. 76B).

Figure 77:
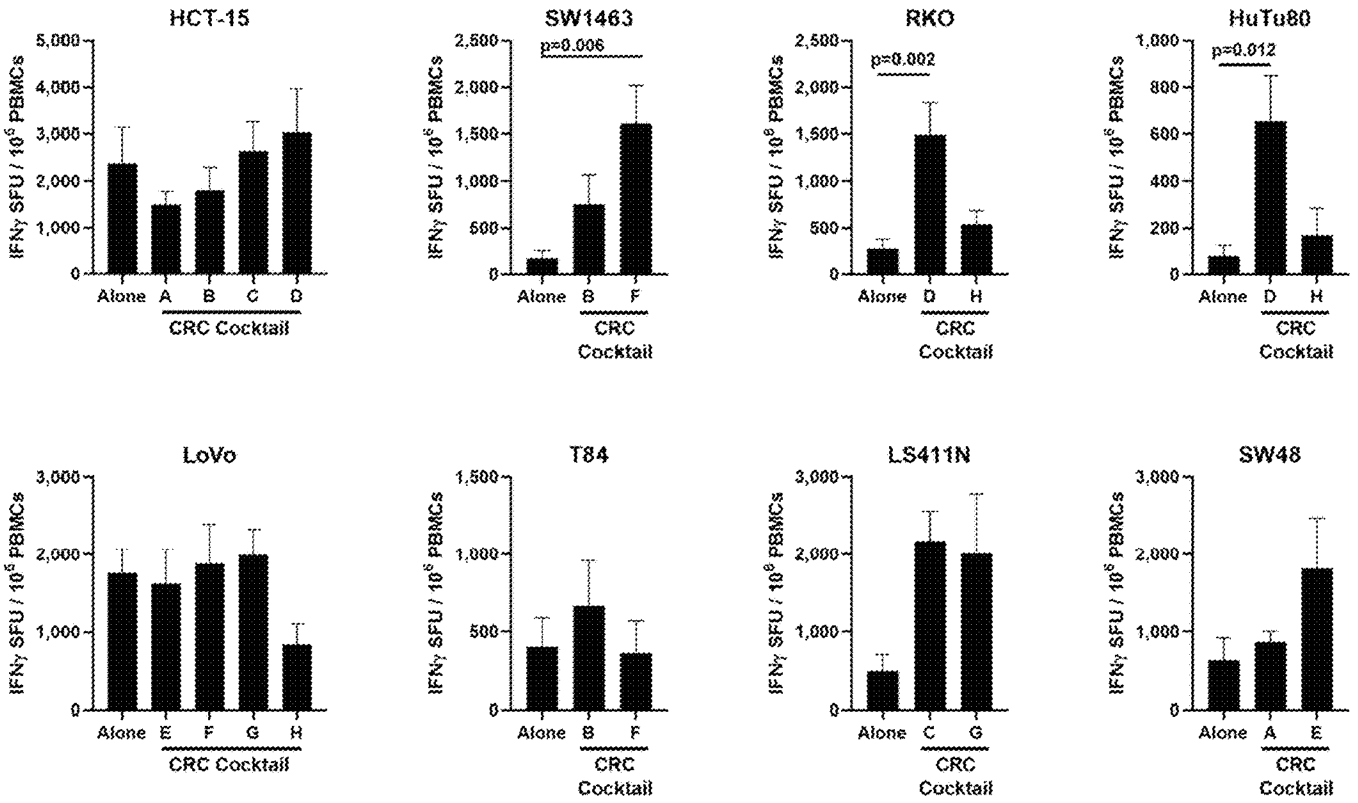
FIG. 77 shows IFNγ responses elicited by single candidate CRC vaccine cell lines alone compared to cocktails of cell lines.

The ability of the individual CRC vaccine component cell lines to induce IFNγ responses against themselves compared to the ability of the potential CRC vaccine cocktails to induce IFNγ responses against the individual cell lines was measured by IFNγ ELISpot as described in Examples 8 and 9. The data in FIG. 77 demonstrate that the cocktails CRC-A, CRC-B, CRC-C, CRC-D, CRC-E, CRC-F, CRC-G and CRC-H (FIG. 76C) in some cases, trend toward or are significantly better stimulators of antitumor immunity than the individual component cell lines and suggests that the breadth of response is increased by administering more than one cell line at a time.

The cells in the vaccine described herein were selected to express a wide array of TAAs, including those known to be important specifically for CRC antitumor responses, such as CEA, and also TAAs known to be important for targets for CRC and other solid tumors, such as TERT. As shown herein, to further enhance the array of TAAs, HuTu80 was transduced with a gene encoding modPSMA and HCT-116 was also modified to express modTBXT, modWT1, and the 28 amino acids spanning the KRAS mutations G12D and G12V respectively that result in an activating mutated form of KRAS, as described herein. KRAS mutations occur in approximately 35% to 45% of CRC patients. KRAS G12V and G12D are the most frequently occurring of multiple KRAS mutations in CRC patients.

Figure 78A:
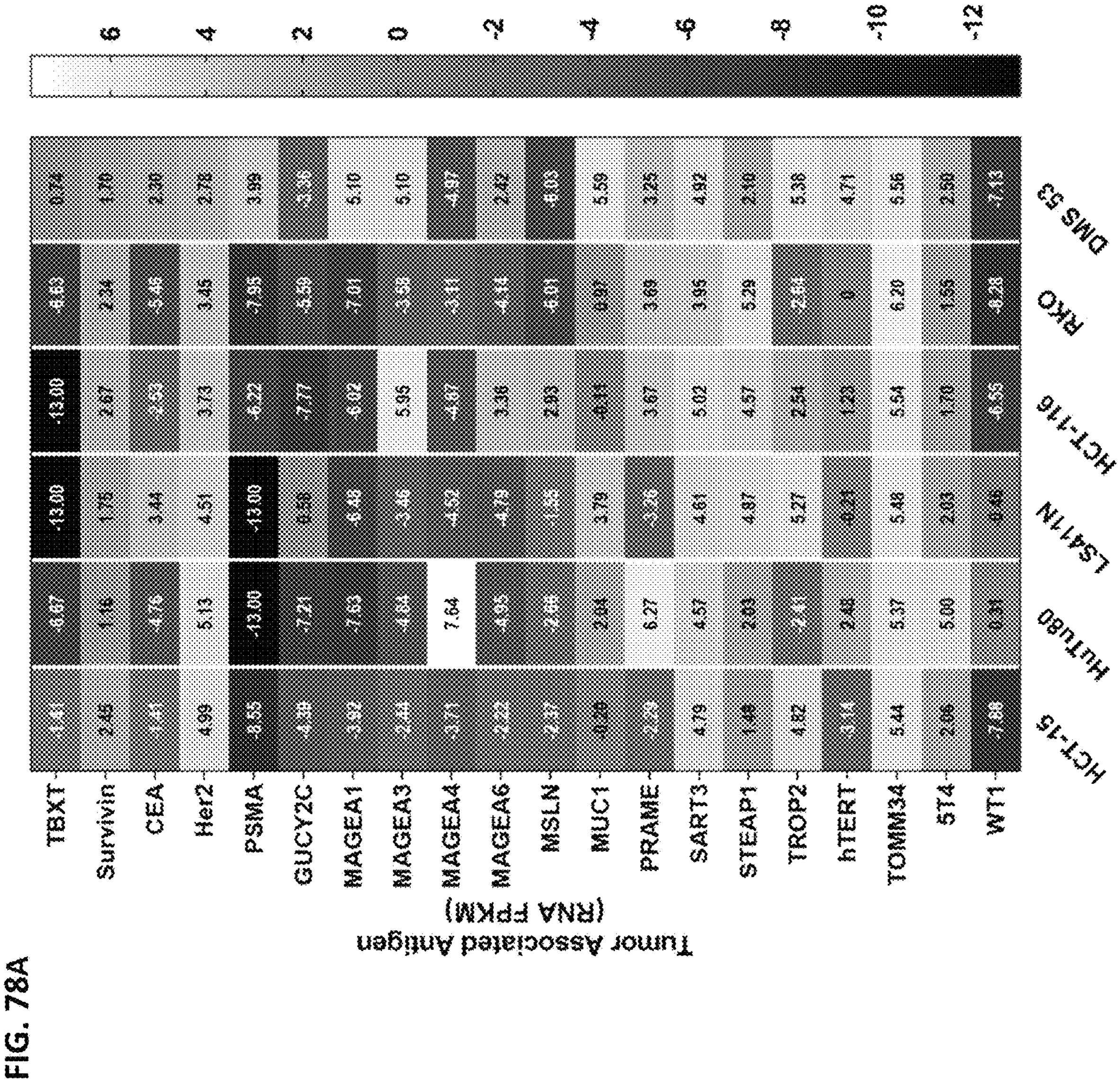
FIGS. 78A and B shows endogenous expression of CRC antigens by the CRC vaccine cell lines (FIG. 78A) and the number of CRC antigens expressed by the vaccine cell lines also expressed in CRC patient tumors (FIG. 78B).

PSMA was endogenously expressed in one of the six component cell lines at >1.0 FPKM as described below. TBXT and WT1 were not expressed endogenously in any of the six component cell lines at >1.0 FPKM (FIG. 78A). The KRAS mutations G12D and G12V were not expressed endogenously by any of the six component cell lines. Endogenous expression of KRAS mutations was determined using cBioPortal. The cell line data sets were searched with the HGNC gene symbol (KRAS) and each cell line was searched within the "mutations" data set. The KRAS G13D mutation, also expressed frequently in CRC tumors, was endogenously expressed by HCT-15 and HCT-116.

Figure 78B:
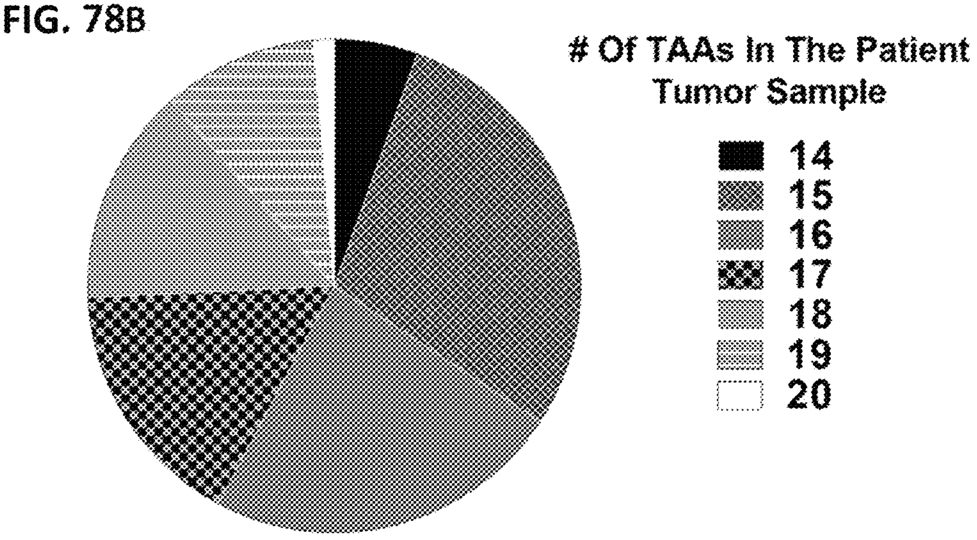

The mRNA expression of representative TAAs in the present vaccine are shown in FIG. 78A. The present vaccine has high expression of all identified twenty commonly targeted and potentially clinically relevant TAAs for inducing a CRC antitumor response. Some of these TAAs are known to be primarily enriched in CRC tumors and some can also induce an immune response to CRC and other solid tumors. RNA abundance of the twenty prioritized CRC TAAs was determined in 365 CRC patient samples with expression data available for all TAAs as described above to determine CSC marker expression patient samples. Fourteen of the prioritized CRC TAAs were expressed by 100% of samples, 15 TAAs were expressed by 94.5% of samples, 16 TAAs were expressed by 65.8% of samples, 17 TAAs were expressed by 42.2% of samples, 18 TAAs were expressed by 25.8% of samples, 19 TAAs were expressed by 11.5% of samples and 20 TAAs were expressed by 1.4% samples (FIG. 78B). The KRAS G12D (n=40) or G12V (n=37) mutation were expressed by 21.1% (n=77) of the 365 CRC patient tumor samples. The KRAS G13D mutation, that is endogenously expressed by two component cell lines, was expressed by 7.7% (n=28) of the 365 CRC patient tumor samples. Thus, provided herein are two compositions comprising a therapeutically effective amount of three cancer cell lines, wherein the combination of the cell lines express at least 14 TAAs associated with a cancer of a subset of CRC cancer subjects intended to receive said composition.

Expression of the transduced antigens modPSMA (SEQ ID NO: 37; SEQ ID NO: 38) by HuTu80 (FIG. 79A), and modTBXT (SEQ ID NO: 49; SEQ ID NO: 50) (FIG. 79B) and modWT1 (SEQ ID NO: 49; SEQ ID NO: 50) (FIG. 79C) by HCT-116 were detected by flow cytometry as described herein. The genes encoding KRAS G12D (SEQ ID NO: 49; SEQ ID NO: 50) (FIG. 89D) and G12V (SEQ ID NO: 49; SEQ ID NO: 50) (FIG. 79D) were detected by RT-PCR as described in Example 29 herein. The genes encoding modTBXT, modWT1, KRAS G12D and KRAS G12V are subcloned into the same lentiviral transfer vector separated by furin cleavage sites SEQ ID: X). IFNγ production to the transduced antigens is described herein.

Because of the need to maintain maximal heterogeneity of antigens and clonal subpopulations the comprise each cell line, the gene modified cell lines utilized in the present vaccine have been established using antibiotic selection and flow cytometry and not through limiting dilution subcloning.

Based on the expression and immunogenicity data presented herein, the cell lines identified in Table 57 were selected to comprise the present CRC vaccine.

TABLE 57

CRC vaccine cell lines and histology

| Cocktail | Cell Line Name | Histology |
|---|---|---|
| A | HCT-15 | Colorectal Adenocarcinoma |
| A | HuTu-80 | Duodenum Adenocarcinoma |
| A | LS411N | Colorectal Adenocarcinoma |
| B | HCT-116 | Colorectal Carcinoma |
| B | RKO | Colorectal Carcinoma |
| B | DMS 53 | Lung Small Cell Carcinoma |

Reduction of CD276 Expression

The HCT-15, HuTu-80, LS411N, HCT-116, RKO and DMS 53 component cell lines expressed CD276 and expression was knocked out by electroporation with ZFN as described in Example 13 and elsewhere herein. Because it was desirable to maintain as much tumor heterogeneity as possible, the electroporated and shRNA modified cells were not cloned by limiting dilution. Instead, the cells were subjected to multiple rounds of cell sorting by FACS as described in Example 13. Expression of CD276 was determined as described in Example 29. Reduction of CD276 expression is described in Table 58. These data show that gene editing of CD276 with ZFN resulted in greater than 99.6% CD276-negative cells in all six vaccine component cell lines.

TABLE 58

Reduction of CD276 expression

| Cell line | Parental Cell Line MFI | Modified Cell Line MFI | % Reduction CD276 |
|---|---|---|---|
| HCT-15 | 6,737 | 26 | 99.6 |
| HuTu-80 | 10,389 | 0 | 100.0 |
| LS411N | 34,278 | 4 | 100.0 |
| HCT-116 | 12,782 | 0 | 100.0 |

TABLE 58-continued

| Reduction of CD276 expression | | | |
|---|---|---|---|
| Cell line | Parental Cell Line MFI | Modified Cell Line MFI | % Reduction CD276 |
| RKO | 3,632 | 0 | 100.0 |
| DMS 53 | 11,928 | 24 | 99.8 |

MFI reported with isotype controls subtracted

Cytokine Secretion Assays for TGFβ1, TGFβ2, GM-CSF, and IL-12

Cytokine Secretion Assays for TGFβ1, TGFβ2, GM-CSF, and IL-12 were Completed as Described in Example 29.

shRNA Downregulates TGF-6 Secretion

Following CD276 knockout, TGFβ1 and TGFβ2 secretion levels were reduced using shRNA and resulting levels determined as described in Example 29. All parental cell lines in CRC vaccine-A secreted measurable levels of TGFβ1 and HuTu80 also secreted a measurable level of TGFβ2. Of the parental cell lines in CRC vaccine-B, HCT-116 and RKO secreted measurable levels of TGFβ1. Reduction of TGFβ2 secretion by the DMS 53 cell line is described in Example 5 and resulting levels determined as described above.

The five component cell lines of CRC origin were transduced with TGFβ1 shRNA to decrease secretion of TGFβ1 and increase expression of membrane bound CD40L as described in Example 29. These cells are described by the clonal designation DK2. HuTu80 was subsequently transduced with lentiviral particles encoding TGFβ2 shRNA and GM-CSF (SEQ ID NO: 6) Example 29. These cells are described by the clonal designation DK6. As described in Example 26, DMS 53 was modified with shRNA to reduce secretion of TGFβ2 and not TGFβ1. These cells are described by the clonal designation DK4. The remaining cell lines were double modified with TGFβ1 shRNA and TGFβ2 shRNA.

Table 59 shows the percent reduction in TGFβ1 and/or TGFβ2 secretion in gene modified component cell lines compared to unmodified, parental cell lines. If TGFβ1 or TGFβ2 secretion was only detected in 1 of 16 replicates run in the ELISA assay the value is reported without standard error of the mean. Gene modification resulted in at least 49% reduction of TGFβ1 secretion. Gene modification of TGFβ2 resulted in at least 51% reduction in secretion of TGFβ2.

TABLE 59

| TGF-β Secretion (pg/$10^6$ cells/24 hr) in Component Cell Lines | | | | |
|---|---|---|---|---|
| Cell Line | Cocktail | Clone | TGFβ1 | TGFβ2 |
| HCT-15 | A | Wild type | 369 ± 69 | 21 |
| HCT-15 | A | DK2 | 189 ± 23 | 21 ± 5 |
| HCT-15 | A | Percent reduction | 49% | NA |
| HuTu-80 | A | Wild type | 2,529 ± 549 | 4,299 ± 821 |
| HuTu-80 | A | DK6 | 327 ± 76 | 115 ± 42 |
| HuTu-80 | A | Percent reduction | 87% | 97% |
| LS411N | A | Wild type | 413 ± 125 | * ≤9 |
| LS411N | A | DK2 | 89 ± 5 | 78 ± 13 |
| LS411N | A | Percent reduction | 78% | NA |
| HCT-116 | B | Wild type | 2,400 ± 250 | * ≤8 |
| HCT-116 | B | DK2 | 990 ± 72 | * ≤8 |
| HCT-116 | B | Percent reduction | 59% | NA |
| RKO | B | Wild type | 971 ± 120 | * ≤6 |
| RKO | B | DK2 | 206 ± 10 | * ≤11 |
| RKO | B | Percent reduction | 79% | NA |

TABLE 59-continued

| TGF-β Secretion (pg/$10^6$ cells/24 hr) in Component Cell Lines | | | | |
|---|---|---|---|---|
| Cell Line | Cocktail | Clone | TGFβ1 | TGFβ2 |
| DMS 53 | B | Wild type | 106 ± 10 | 486 ± 35 |
| DMS 53 | B | DK4 | 219 ± 33 | 238 ± 40 |
| DMS 53 | B | Percent reduction | NA | 51% |

DK6: TGβ1/TGFβ2 double knockdown;

DK4: TGFβ2 single knockdown;

DK2: TGFβ1 single knockdown;

* = estimated using LLD, not detected;

NA = not applicable

Based on a dose of $5\times10^5$ of each component cell line, the total TGFβ1 and TGFβ2 secretion by the modified CRC vaccine-A and CRC vaccine-B and respective unmodified parental cell lines are shown in Table 60. The secretion of TGFβ1 by CRC vaccine-A was reduced by 82% and TGFβ2 by 95% pg/dose/24 hr. The secretion of TGFβ1 by CRC vaccine-B was reduced by 59% and TGFβ2 by 49% pg/dose/24 hr.

TABLE 60

| Total TGF-β Secretion (pg/dose/24 hr) in CRC vaccine-A and CRC vaccine-B | | | |
|---|---|---|---|
| Cocktail | Clones | TGFβ1 | TGFβ2 |
| A | Wild type | 1,656 | 2,165 |
| | DK2/DK6 | 303 | 107 |
| | Percent reduction | 82% | 95% |
| B | Wild type | 1,739 | 250 |
| | DK2/DK4 | 708 | 129 |
| | Percent reduction | 59% | 49% |

GM-CSF Secretion

The HuTu80 cell line was transduced with lentiviral particles containing both TGFβ2 shRNA and the gene to express GM-CSF (SEQ ID NO: 6) under the control of a different promoter. The HCT-15, LS411N, HCT-116 and RKO cell lines were transduced with lentiviral particles to only express GM-CSF (SEQ ID NO: 7). DMS 53 was modified to secrete GM-CSF as described in Example 24 and elsewhere herein. The results are shown in Table 61 and described below.

Secretion of GM-CSF increased at least 9,182-fold in all modified component cell lines compared to unmodified, parental cell lines. In CRC vaccine-A component cell lines, secretion of GM-CSF increased 29,500-fold by HCT-15 compared to the parental cell line (≤0.002 ng/$10^6$ cells/24 hr), 9,182-fold by HuTu80 compared to the parental cell line (≤0.011 ng/$10^6$ cells/24 hr), and 36,250-fold by LS411N compared to the parental cell line (≤0.004 ng/$10^6$ cells/24 hr). In CRC vaccine-B component cell lines secretion of GM-CSF increased 114,000-fold by HCT-116 compared to the parental cell line (≤0.003 ng/$10^6$ cells/24 hr), 43,667-fold by RKO compared to the parental cell line (≤0.003 ng/$10^6$ cells/24 hr) and 39,450-fold by DMS 53 compared to the parental cell line (≤0.004 ng/$10^6$ cells/24 hr).

TABLE 61

| GM-CSF Secretion in Component Cell Lines | | |
|---|---|---|
| Cell Line | GM-CSF ($ng/10^6$ cells/24 hr) | GM-CSF (ng/dose/24 hr) |
| HCT-15 | 59 ± 9 | 30 |
| HuTu80 | 101 ± 40 | 51 |
| LS411N | 145 ± 17 | 73 |
| Cocktail A Total | 305 | 154 |
| HCT-116 | 342 ± 97 | 171 |
| RKO | 131 ± 13 | 66 |
| DMS 53 | 158 ± 15 | 79 |
| Cocktail B Total | 631 | 316 |

Based on a dose of $5\times10^5$ of each component cell line, the total GM-CSF secretion for CRC vaccine-A was 154 ng per dose per 24 hours. The total GM-CSF secretion for CRC vaccine-B was 316 ng per dose per 24 hours. The total GM-CSF secretion per dose was therefore 470 ng per 24 hours.

Membrane Bound CD40L (CD154) Expression

The component cell lines were transduced with lentiviral particles to express membrane bound CD40L as described above. The methods to detect expression of CD40L by the five CRC cell line components are described in Example 29. The methods used to modify DMS 53 to express CD40L are described in Example 15. Evaluation of membrane bound CD40L by all six vaccine component cell lines is described below. The results shown in FIG. 80 and described below demonstrate CD40L membrane expression was substantially increased in all six cell CRC vaccine component cell lines.

Figure 80:
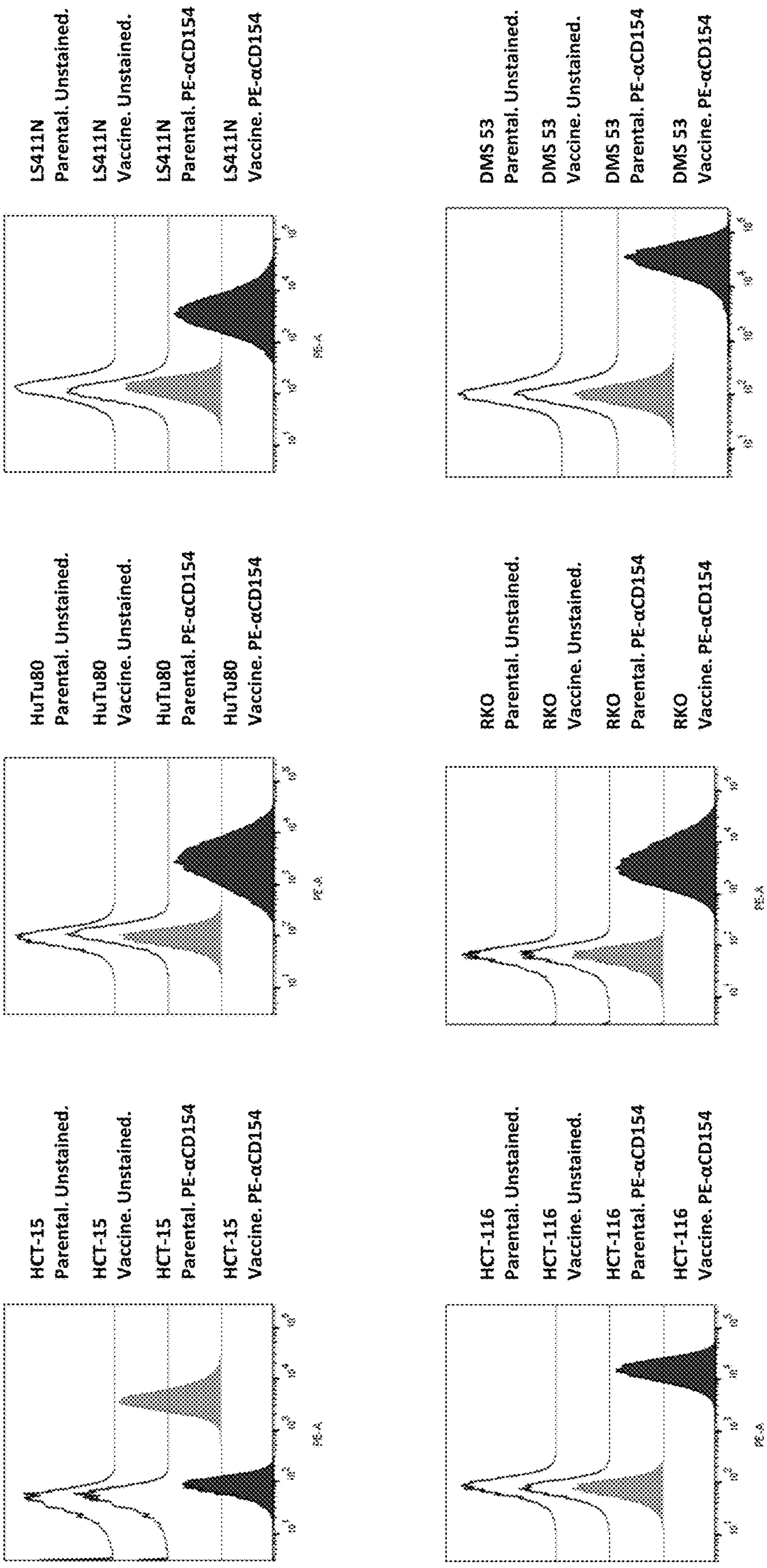
FIG. 80 shows expression of membrane bound CD40L by the CRC vaccine component cell lines.

FIG. 80 shows expression of membrane bound CD40L by the CRC vaccine component cell lines. Membrane bound CD40L increased at least 669-fold in all component cell lines compared to unmodified, parental cell lines. In CRC vaccine-A component cell lines, expression of CD40L increased 669-fold by HCT-15 (669 MFI) compared to the parental cell line (0 MFI), 1,178-fold by HuTu80 (5,890 MFI) compared to the parental cell line (5 MFI), and 4,703-fold by LS411N (4,703) compared to the parental cell line (0 MFI). In CRC vaccine-B component cell lines expression of CD40L increased 21,549-fold by HCT-116 compared to the parental cell line (0 MFI), 7,107-fold by RKO compared to the parental cell line (0 MFI), and 88,261-fold by DMS 53 compared to the parental cell line (0 MFI).

IL-12 Expression

The component cell lines were transduced with the IL-12 vector as described in Example 17 and resulting IL-12 p70 expression determined as described above and herein. The results are shown in Table 52 and described below.

Secretion of IL-12 increased at least 10,200-fold in all component cell lines modified to secrete IL-12 p70 compared to unmodified, parental cell lines. In CRC vaccine-A component cell lines, secretion of IL-12 increased 27,000-fold by HCT-15 compared to the parental cell line (≤0.001 $ng/10^6$ cells/24 hr), 10,200-fold by HuTu80 compared to the parental cell line (≤0.005 $ng/10^6$ cells/24 hr), and 13,000-fold by LS411N compared to the parental cell line (≤0.002 $ng/10^6$ cells/24 hr). In CRC vaccine-B component cell lines expression of IL-12 increased 186,000-fold by HCT-116 compared to the parental cell line (≤0.001 $ng/10^6$ cells/24 hr) and 43,000-fold by RKO compared to the parental cell line (≤0.001 $ng/10^6$ cells/24 hr). DMS 53 was not modified to secrete IL-12.

TABLE 52

| IL-12 secretion in component cell lines | | |
|---|---|---|
| Cell Line | IL-12 ($ng/10^6$ cells/24 hr) | IL-12 (ng/dose/24 hr) |
| HCT-15 | 27 ± 3 | 14 |
| HuTu80 | 51 ± 14 | 26 |
| LS411N | 26 ± 6 | 13 |
| Cocktail A Total | 104 | 52 |
| HCT-116 | 186 ± 16 | 93 |
| RKO | 43 ± 8 | 22 |
| DMS 53 | NA | NA |
| Cocktail B Total | 229 | 115 |

Based on a dose of $5\times10^5$ of each component cell line, the total IL-12 secretion for CRC vaccine-A was 52 ng per dose per 24 hours. The total IL-12 secretion for CRC vaccine-B was 115 ng per dose per 24 hours. The total IL-12 secretion per dose was therefore 167 ng per 24 hours.

Stable Expression of modPSMA by the HuTu80 Cell Line

Figure 79A:
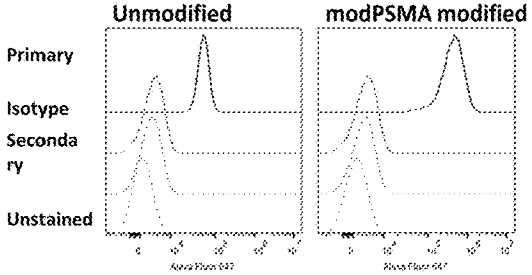
FIGS. 79A-J show the expression of and IFNγ responses to antigens introduced in the CRC vaccine cell lines compared to unmodified controls. Expression of modPSMA by HuTu80 (FIG. 79A) and IFNγ responses to PSMA (FIG. 79F) in CRC-vaccine A. Expression of modTBXT, modWT1, KRAS G12D and KRAS G12V by HCT-116 (FIG. 79B-C) and IFNγ responses to TBXT (FIG. 79G), WT1 (FIG. 79H), KRAS G12D (FIG. 79I) and KRAS G12D (FIG. 79J) in CRC-vaccine B.

As described above, the cells in the vaccine described herein were selected to express a wide array of TAAs, including those known to be important to CRC antitumor immunity. To further enhance the array of antigens, the HuTu80 cell line that was modified to reduce the secretion of TGFβ1 and TGFβ2, reduce the expression of CD276, and to express GM-CSF, membrane bound CD40L, and IL-12 was also transduced with lentiviral particles expressing the modPSMA antigen. The expression of modPSMA was characterized by flow cytometry. The cell line that was modified to reduce the secretion of TGFβ1 and TGFβ2, reduce the expression of CD276, and to express GM-CSF, membrane bound CD40L, and IL-12 (antigen unmodified) and the cell line that was modified to reduce the secretion of TGFβ1 and TGFβ2, reduce the expression of CD276, and to express GM-CSF, membrane bound CD40L, IL-12 and modPSMA were stained intracellularly with 0.06 μg/test anti-mouse IgG1 anti-PSMA antibody (AbCam ab268061, Clone FOLH1/3734) followed by 0.125 ug/test AF647-conjugated goat anti-mouse IgG1 antibody (Biolegend #405322). The MFI of the isotype control stained PSMA unmodified and PSMA modified cells was subtracted from the MFI of cells stained PSMA. MFI was normalized to 100,000 events. Fold increase in antigen expression was calculated as: (background subtracted modified MFI/background subtracted parental MFI). Expression of modPSMA increased in the modified cell line (756,908 MFI) 9.1-fold over that of the PSMA unmodified cell line (82,993 MFI) (FIG. 79A).

Figure 79B:
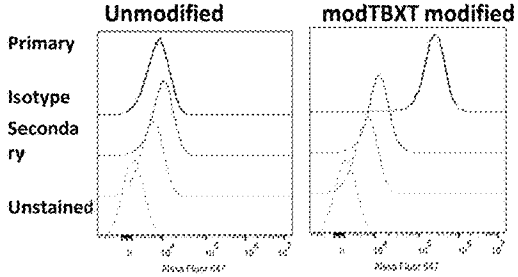
Figure 79C:
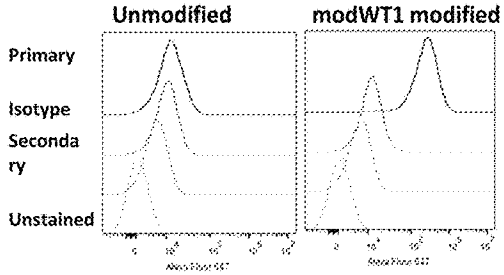

Stable Expression of modTBXT, modWT1, KRAS G12D and KRAS G12V by the HCT-116 Cell Line As described above, the cells in the vaccine described herein were selected to express a wide array of TAAs, including those known to be important to antitumor immunity. To further enhance the array of antigens, the HCT-116 cell line that was modified to reduce the secretion of TGFβ1, reduce the expression of CD276, and to express GM-CSF, membrane bound CD40L and IL-12 was also transduced with lentiviral particles expressing the modTBXT, modWT1, KRAS G12V and KRAS G12D antigens. The antigen unmodified and antigen modified cells were stained intracellular to detect the expression of each antigen as follows. For the detection of modTBXT, cells were first stained with rabbit IgG1 anti-TBXT antibody (Abcam ab209665, Clone EPR18113) (0.06 μg/test) followed by AF647-conjugated donkey anti-rabbit IgG1 antibody (Biolegend #406414) (0.125 μg/test). For the detection of modWT1, cells were first stained with rabbit IgG1 anti-WT1 antibody (AbCam ab89901, Clone CAN-R9) (0.06 ug/test) followed by AF647-conjugated donkey anti-rabbit IgG1 antibody (Biolegend #406414) (0.125 μg/test). The MFI of the isotype control stained cells was subtracted from the MFI of the cells stained for TBXT or WT1. MFI was normalized to 100,000 events. Fold increase in antigen expression was calculated as: (background subtracted modified MFI/background subtracted parental MFI). Expression of modTBXT increased in the modified cell line (356,691 MFI) 356,691-fold over that of the unmodified cell line (0 MFI) (FIG. 79B). Subtraction of the MFI of the isotype control from the MFI of the TBXT stained unmodified HCT-116 cell line resulted in negative value. The fold increase of TBXT expression in the modified cell line was calculated using 1 MFI. Expression of modWT1 by the modified cell line (362,698 MFI) increased 69.3-fold over the that of the unmodified cell line (5,235 MFI) (FIG. 79C).

Figure 79D:
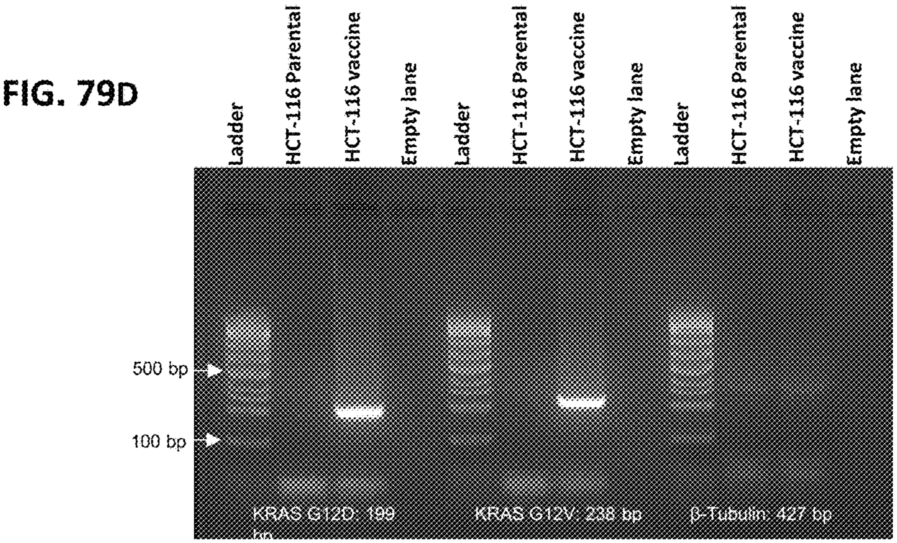
Figure 79E:
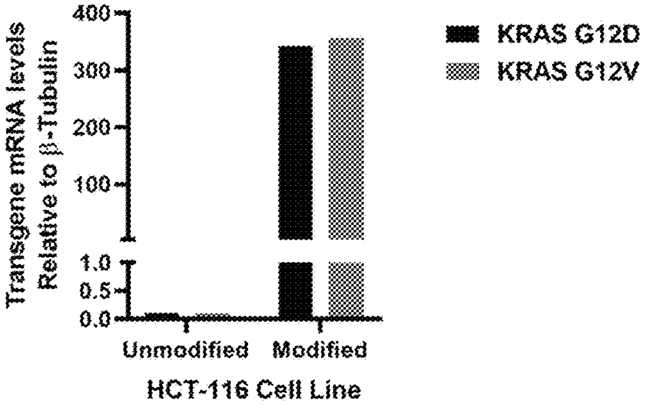

Expression of KRAS G12D and KRAS G12V by HCT-116 was determined using RT-PCR as described in Example 29 and herein. For KRAS G12D, the forward primer designed to anneal at the 2786-2807 base pair (bp) location in the transgene (GAAGCCCTTCAGCTGTAGATGG (SEQ ID NO: 124)) and reverse primer designed to anneal at 2966-2984 bp location in the transgene (CTGAATTGTCAGGGCGCTC (SEQ ID NO: 125)) and yield 199 bp product. For KRAS G12V, the forward primer was designed to anneal at the 2861-2882 bp location in the transgene (CATGCACCAGAGGAACATGACC (SEQ ID NO: 126)) and reverse primer designed to anneal at the 3071-3094 bp location in the transgene (GAGTTGGATGGTCAGGGCAGAT (SEQ ID NO: 127)) and yield 238 bp product. Control primers for β-tubulin are described in Example 29. Gene products for both KRAS G12D and KRAS G12V were detected at the expected size, 199 bp and 238 bp, respectively (FIG. 79D). KRAS G12D mRNA increased 3,127-fold and KRAS G12V mRNA increased 4,095-fold relative to parental controls (FIG. 79E).

Immune Responses to PSMA in CRC-Vaccine A

Figure 79F:
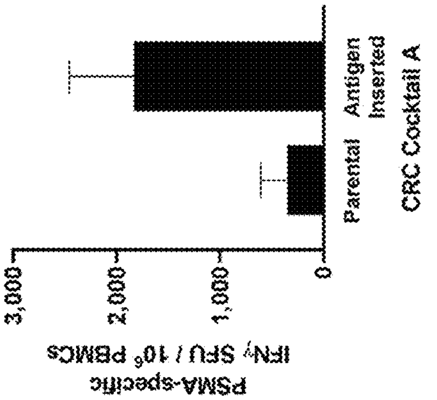

IFNγ responses to the PSMA were evaluated in the context of the CRC-vaccine A in four HLA diverse donors (n=4/donor) (Table 63 Donors 1, 3, 5 and 6) as described in Example 29 and IFNγ responses determined by ELISpot as described below. PSMA peptides, 15-mers overlapping by 9 amino acids spanning the native antigen sequence, were purchased from Thermo Scientific Custom Peptide Service. PSMA specific IFNγ responses were increased with the modified CRC vaccine-A (1,832±627 SFU) compared to the parental, unmodified CRC vaccine-A (350±260 SFU) (n=4) (FIG. 79F).

Immune Responses to TBXT, WT1, and KRAS Mutations in CRC-Vaccine B

Figure 79G:
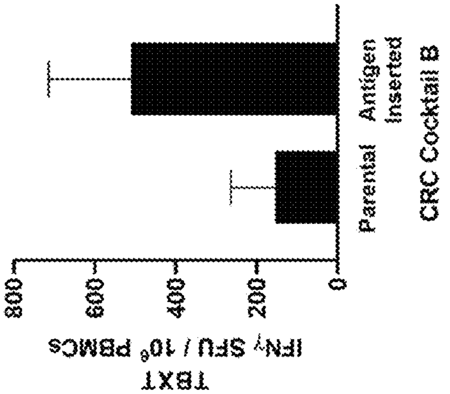
Figure 79H:
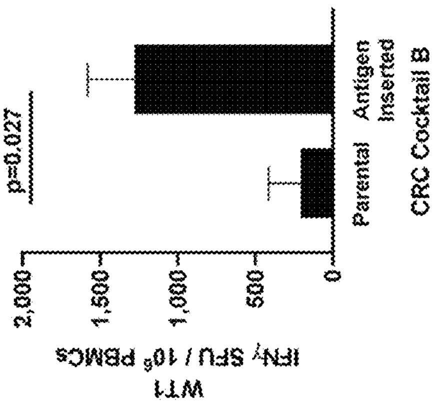
Figure 79I:
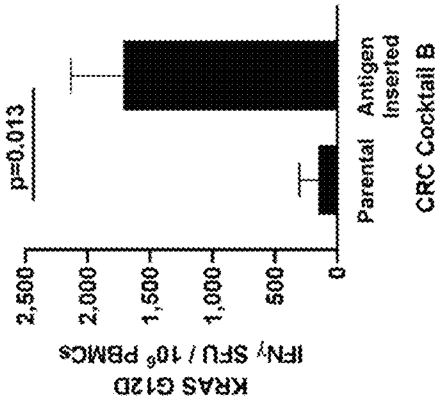
Figure 79J:
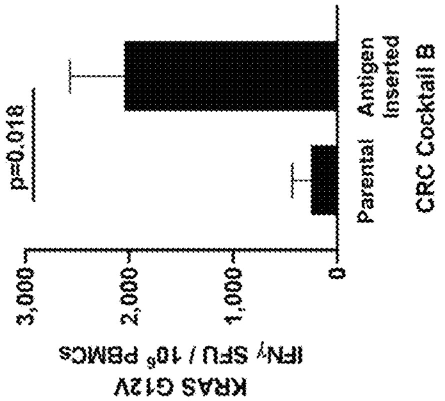

IFNγ responses to TBXT, WT1, KRAS G12D and KRAS G12V antigens were evaluated in the context of the CRC-vaccine B in four HLA diverse donors (n=4/donor) (Table 63. Donors 1, 3, 5 and 6) as described in Example 29. Peptides for were sourced as follows: TBXT (JPT, PM-BRAC), WT1 (JPT, PM-WT1), KRAS G12D and KRAS G12V 15-mers overlapping by 9 amino acids, were purchased from Thermo Scientific Custom Peptide Service. IFNγ responses to TBXT increased with the modified CRC vaccine-B (511±203 SFU) compared to the unmodified CRC vaccine-B (154±111 SFU) (n=4) (FIG. 79G). WT1 specific IFNγ responses significantly increased with the modified CRC vaccine-B (1,278±303 SFU) compared unmodified CRC vaccine-B (208±208 SFU) (p=0.027, Student's T test) (FIG. 79H). KRAS G12D specific IFNγ responses significantly increased with the modified CRC vaccine-B (1,716±420 SFU) compared unmodified CRC vaccine-B (153±153 SFU) (p=0.013, Student's T test) (FIG. 79I). KRAS G12V specific IFNγ responses significantly increased with the modified CRC vaccine-B (2,047±420 SFU) compared unmodified CRC vaccine-B (254±525 SFU) (p=0.018, Student's T test) (FIG. 79J).

TABLE 63

| Healthy Donor MHC-I characteristics | | | |
|---|---|---|---|
| Donor # | HLA-A | HLA-B | HLA-C |
| 1 | *02:01 *03:01 | *08:01 *51:01 | *07:01 *14:02 |
| 2 | *30:02 *30:04 | *15:10 *58:02 | *03:04 *06:02 |
| 3 | *01:01 *30:01 | *08:01 *13:02 | *06:02 *07:01 |
| 4 | *03:01 *25:01 | *17:02 *18:01 | *07:02 *12:03 |
| 5 | *02:05 *29:02 | *15:01 *44:03 | *03:04 *16:01 |
| 6 | *02:01 *03:01 | *18:01 *31:08 | *07:01 *12:03 |

Cocktails Induce Immune Responses Against Relevant TAAs

The ability of the individual component cell lines and the two CRC vaccine cocktails to induce IFNγ production against relevant CRC antigens was measured by ELISpot as described in Example 29 using PBMCs from six HLA-diverse healthy donors (Table 63). Peptides for PSMA, WT1, TBXT, KRAS G12D and KRAS G12V were sourced as described above. Peptides for the remaining antigens were sourced as follows: Survivin (thinkpeptides, 7769_001-011), PRAME (Miltenyi Biotech, 130-097-286), STEAP (PM-STEAP1), TERT (JPT, PM-TERT), MUC1 (JPT, PM-MUC1), and CEACAM (CEA) (JPT, PM-CEA). Cells were then assayed for IFNγ secretion in the IFNγ ELISpot assay.

Figure 81A:
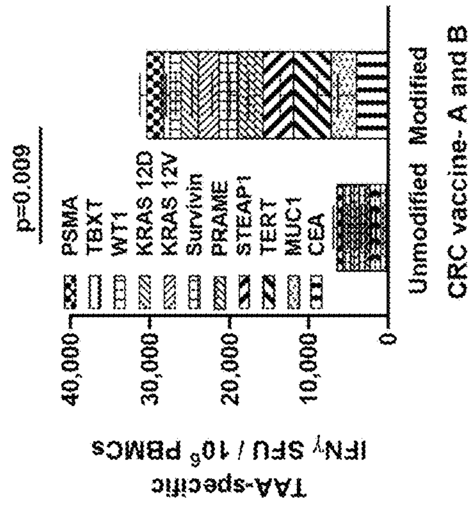
FIGS. 81A-C show antigen specific IFNγ responses induced by the unit dose of the CRC vaccine (FIG. 81A), CRC vaccine-A (FIG. 81B) and CRC vaccine-B (FIG. 81C) compared to unmodified controls.
Figure 81B:
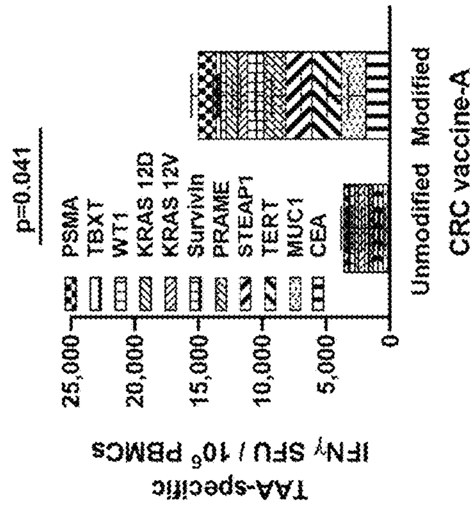
Figure 81C:
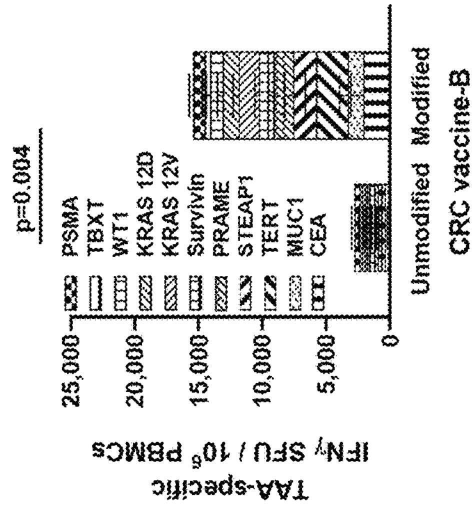
Figure 82:
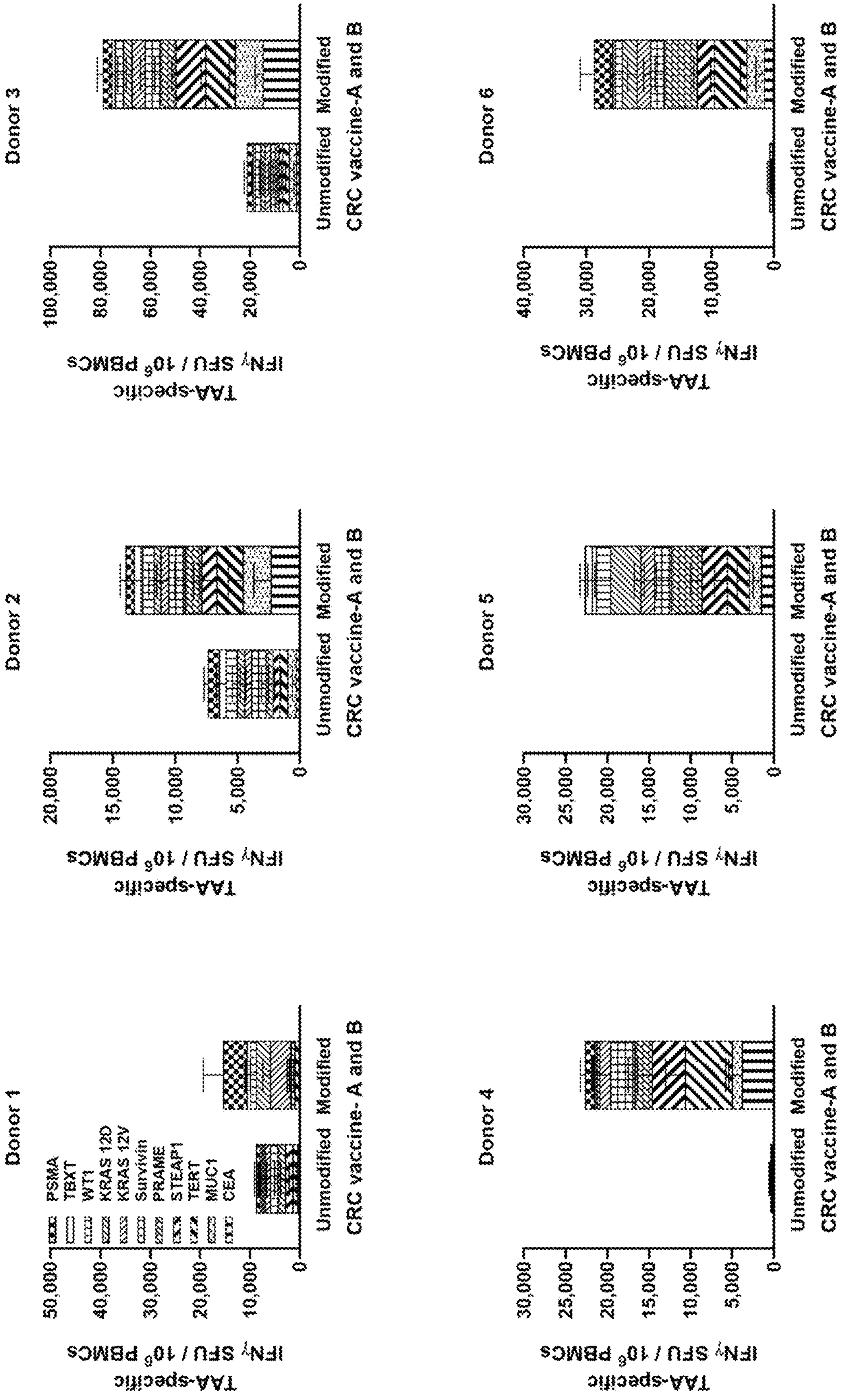
FIG. 82 shows antigen specific IFNγ responses induced by the unit dose of the CRC vaccine in individual donors compared to unmodified controls.

FIG. 81 demonstrates the CRC vaccine is capable of inducing antigen specific IFNγ responses in six HLA-diverse donors that are significantly more robust (30,480±9,980 SFU) compared to the unmodified parental controls (6,470±3,361SFU) (p=0.009, Mann-Whitney U test) (n=8) (FIG. 81A). CRC vaccine-A and CRC vaccine-B independently demonstrated antigen specific responses significantly greater compared to parental controls. Specifically, CRC vaccine-A elicited 12,080±3,569 SFU compared to the unmodified controls (3,665±1,849 SFU) (p=0.041, Mann-Whitney U test) (FIG. 81B). For CRC vaccine-A, one donor responded to five antigens, one donor responded to nine antigens, two donors responded to ten antigens, and two donors responded to eleven antigens. CRC vaccine-B (n=11 antigens) elicited 15,417±4,127 SFU compared to parental controls (2,805±1,549 SFU) (p=0.004, Mann-Whitney U test) (FIG. 81C). For CRC vaccine-B (n=11 antigens), one donor responded to nine antigens, two donors responded to ten antigens, and three donors responded to eleven antigens. The CRC vaccine (vaccine-A and vaccine-B) induced IFNγ production to ten antigens in two of six donors and all eleven antigens in four of six donors (FIG. 82) (Table 64). Thus, provided herein are two compositions comprising a therapeutically effective amount of three cancer cell lines (e.g., a unit dose of six cell lines) wherein said unit dose is capable of eliciting an immune response 4.7-fold greater than the unmodified composition specific to at least ten TAAs expressed in CRC patient tumors. CRC vaccine A increased IFNγ responses to at least five TAAs 4.1-fold and CRC vaccine-B increased IFNγ responses to at least nine TAAs 5.5-fold.

Figure 83:
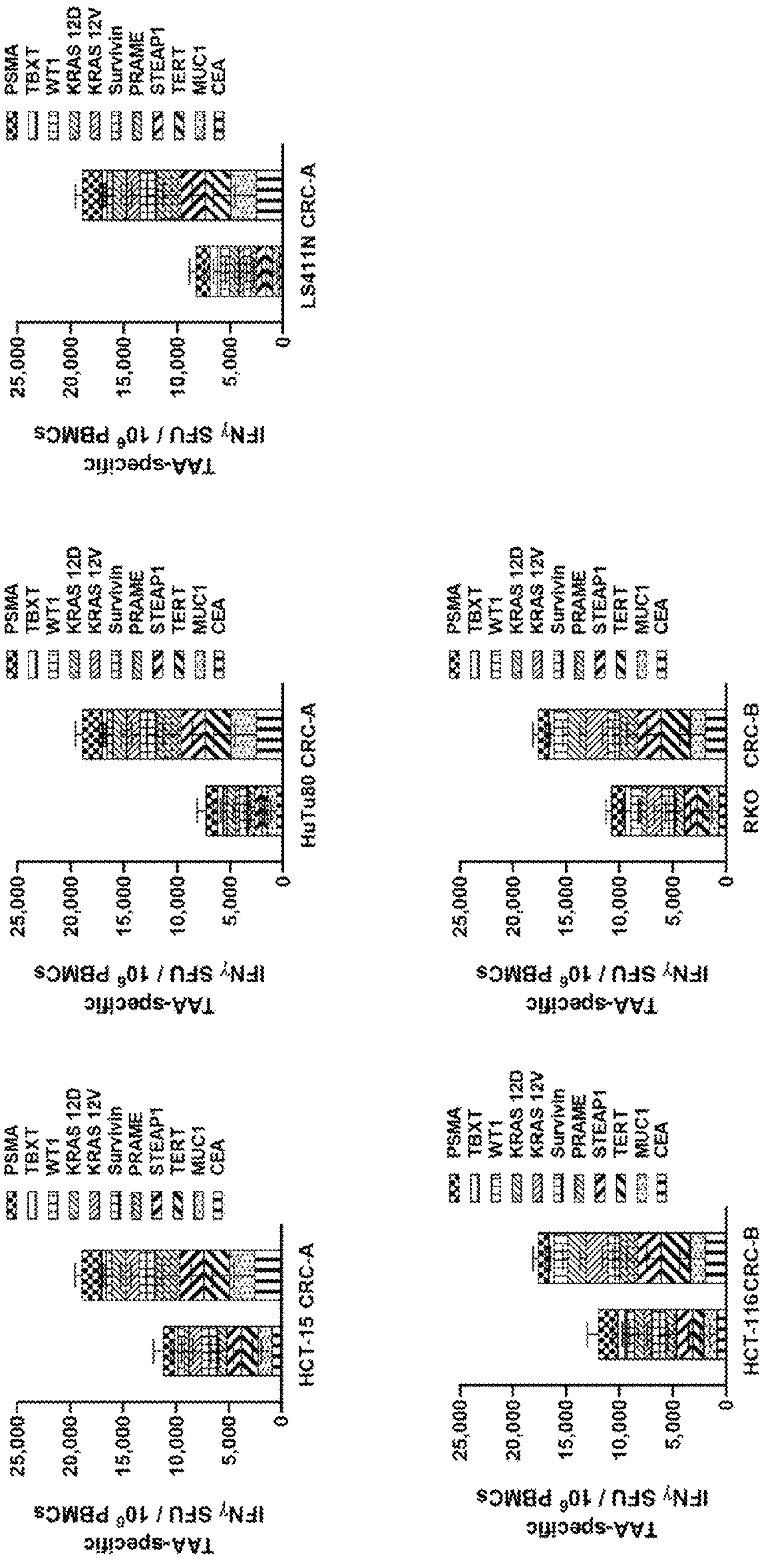
FIG. 83 shows antigen specific IFNγ responses induced by CRC vaccine cell lines alone and in cocktails of cell lines.

IFNγ responses to TAAs induced by CRC vaccine-A and CRC vaccine-B were more robust than compared to responses induced by the individual modified CRC cell line components. Specifically, CRC vaccine-A associated responses against the eleven assayed antigens (18,910±8,852 SFU) were greater than responses induced by modified HCT-15 (11,255±6,354 SFU), HuTu80 (7,332±2,814 SFU) and LS411N (8,277±3,187 SFU). Similarly, CRC vaccine-B associated responses against the eleven assayed antigens (17,635±6,056 SFU) were greater than responses induced by modified HCT-116 (11,984±5,085 SFU) and RKO (10,740±5,216 SFU) (FIG. 83).

TABLE 64

IFNγ Responses to TAAs induced by the unmodified and modified CRC vaccine

| Donor (n = 4) | Unmodified (SFU ± SEM) CRC vaccine-A | CRC vaccine-B | CRC vaccine | Modified (SFU ± SEM) CRC vaccine-A | CRC vaccine-B | CRC vaccine |
|---|---|---|---|---|---|---|
| 1 | 6,101 ± 2,763 | 2,659 ± 1,128 | 8,760 ± 3,640 | 3,969 ± 2,029 | 11,498 ± 3,813 | 15,466 ± 5,590 |
| 2 | 3,694 ± 1,363 | 3,699 ± 1,868 | 7,394 ± 3,217 | 5,465 ± 2,522 | 8,543 ± 4,763 | 14,008 ± 7,258 |
| 3 | 11,488 ± 1,912 | 9,910 ± 3,165 | 21,398 ± 4,907 | 43,448 ± 7,892 | 35,693 ± 4,638 | 79,140 ± 11,908 |
| 4 | 100 ± 50 | 388 ± 130 | 488 ± 84 | 9,276 ± 3,150 | 13,419 ± 5,196 | 22,694 ± 7,650 |
| 5 | 0 ± 0 | 0 ± 0 | 0 ± 0 | 12,666 ± 5,766 | 10,052 ± 6,559 | 22,718 ± 11,181 |
| 6 | 608 ± 334 | 173 ± 103 | 781 ± 436 | 15,557 ± 3,291 | 13,296 ± 2,843 | 28,853 ± 5,346 |

Provided herein are two compositions comprising a therapeutically effective amount of three cancer cell lines, a unit dose of six cancer cell lines, modified to reduce the expression of at least two immunosuppressive factors and to express at least two immunostimulatory factors. One composition, CRC vaccine-A, was modified to increase the expression of one TAA, modPSMA, and the second composition, CRC vaccine-B, was modified to expresses four TAAs, modTBXT, modWT1, KRAS G12D and KRAS G12V. The unit dose of six cancer cell lines expresses at least fifteen TAAs in CRC patient tumors and induces IFNγ responses 4.7-fold greater than the unmodified composition components.

Based on the disclosure and data provided herein, a whole cell vaccine for Colorectal Carcinoma comprising the six cancer cell lines, sourced from ATCC, HCT-15 (ATCC, CCL-225), HuTu80 (ATCC, HTB-40), LS411N (ATCC, CRL-2159), HCT-116 (ATCC, CCL-247), RKO (ATCC, CRL-2577) and DMS 53 (ATCC, CRL-2062) is shown in Table 65. The cell lines represent five colorectal cell lines and one small cell lung cancer (SCLC) cell line (DMS 53 ATCC CRL-2062). The cell lines have been divided into two groupings: vaccine-A and vaccine-B. Vaccine-A is designed to be administered intradermally in the upper arm and vaccine-B is designed to be administered intradermally in the thigh. Vaccine A and B together comprise a unit dose of cancer vaccine.

TABLE 65

Cell line nomenclature and modifications

| Cocktail | Cell Line | TGFβ1 KD | TGFβ2 KD | CD276 KO | GM-CSF | CD40L | IL-12 | TAA(s) |
|---|---|---|---|---|---|---|---|---|
| A | HCT-15 | X | ND | X | X | X | X | ND |
| A | HuTu80 | X | X | X | X | X | X | X |
| A | LS411N | X | ND | X | X | X | X | ND |
| B | HCT-116 | X | ND | X | X | X | X | X |
| B | RKO | X | ND | X | X | X | X | ND |
| B | DMS 53* | ND | X | X | X | X | ND | ND |

ND = Not done.
*Cell lines identified as CSC-like cells.

Where indicated in the above table, the genes for the immunosuppressive factors transforming growth factor-beta 1 (TGFβ1) and transforming growth factor-beta 2 (TGFβ2) have been knocked down using shRNA transduction with a lentiviral vector. The gene for CD276 has been knocked out by electroporation using zinc-finger nuclease (ZFN). The genes for granulocyte macrophage-colony stimulating factor (GM-CSF), IL-12, CD40L, modPSMA (HuTu80), modTBXT (HCT-116), modWT1 (HCT-116), KRAS G12D (HCT-116) and KRAS G12V (HCT-116) have been added by lentiviral vector transduction.

Example 31: Preparation of Prostate Cancer (PCa) Vaccine

This Example demonstrates that reduction of TGFβ1, TGFβ2, and CD276 expression with concurrent overexpression of GM-CSF, CD40L, and IL-12 in a vaccine composition of two cocktails, each cocktail composed of three cell lines for a total of 6 cell lines, significantly increased the magnitude of cellular immune responses to at least 10 PCa-associated antigens in an HLA-diverse population. As described herein, the first cocktail, PCa vaccine-A, is composed of cell line PC3 that was also modified to express modTBXT and modMAGEC2, cell line NEC8, and cell line NTERA-2cl-D1. The second cocktail, PCa vaccine-B, is composed of cell line DU145 that was also modified to express modPSMA, cell line LNCaP, and cell line DMS 53. The six component cell lines collectively express at least twenty-two antigens that can provide an anti-PCa tumor response.

Identification of PCa Vaccine Components

Initial cell line selection criteria identified sixteen vaccine component cell lines for potential inclusion in the PCa vaccine. Additional selection criteria were applied to narrow the fourteen candidate cell lines to six cell lines for further evaluation in immunogenicity assays. These criteria included: endogenous PCa associated antigen expression, lack of expression of additional immunosuppressive factors, such as IL-10 or IDO1, ethnicity and age of the patient from which the cell line was derived, if the cell line was derived from a primary tumor or metastatic site, and histological subtype.

Figure 84:
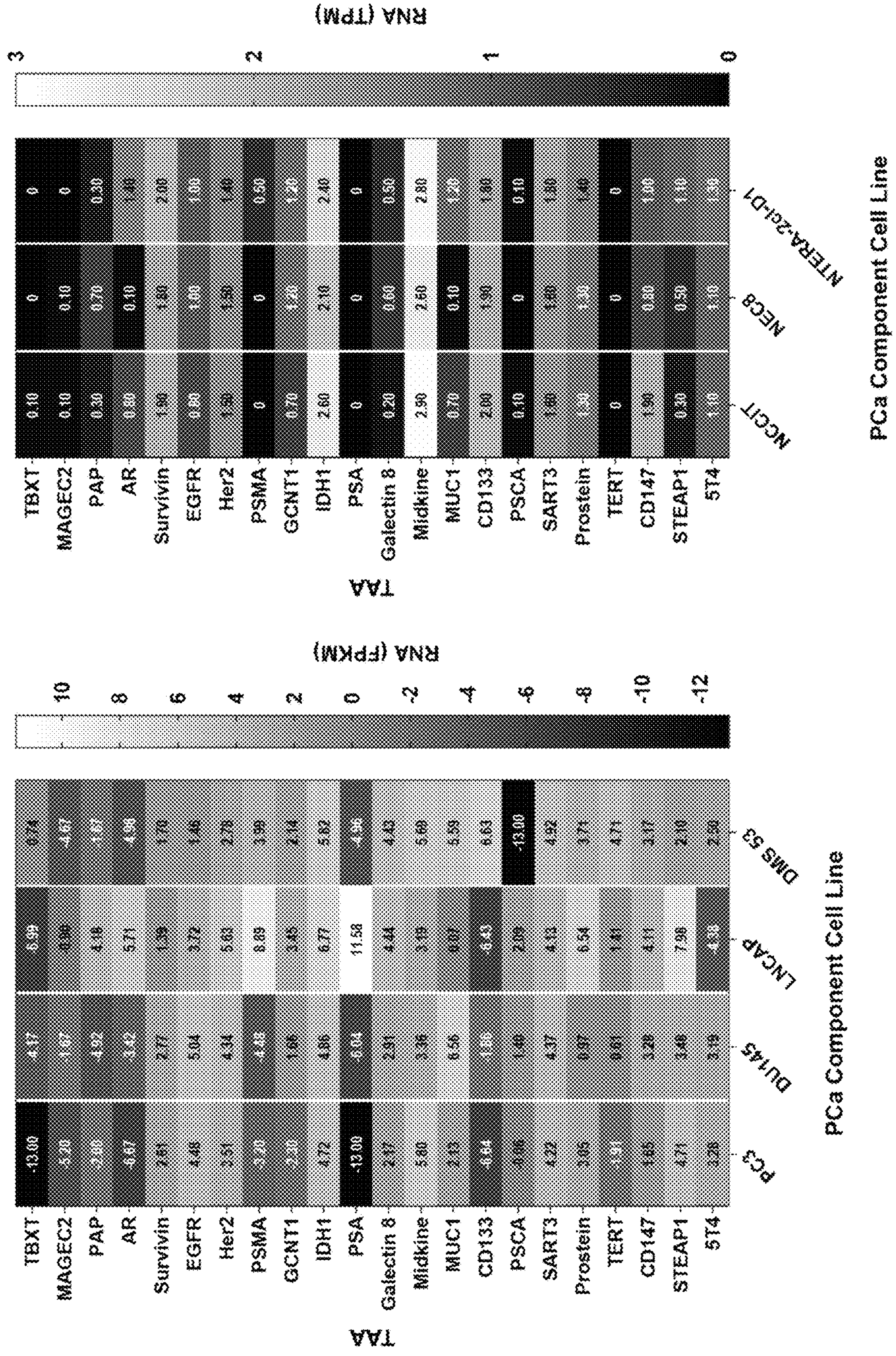
FIG. 84 shows endogenous expression of PCa antigens in candidate and final PCa vaccine cell line components.

Expression of TMs by candidate component cell lines was determined by RNA expression data sourced from the Broad Institute Cancer Cell Line Encyclopedia (CCLE) and from the European Molecular Biology Laboratory-European Bioinformatics Institute (EMBL-EBI) for NCCIT, NEC8 and NTERA-2cl-D1. The HGNC gene symbol was included in the CCLE search and mRNA expression was downloaded for each TAA. Expression of a TAA by a cell line was considered positive if the RNA-seq value was greater than one (CCLE, FPKM) or zero (EMBL-EBI, TPM). Six of the fourteen PCa vaccine candidate components were identified for further evaluation: PC3, DU145, LNCaP, NCCIT, NEC8 and NTERA-2cl-D1 based on the selection criteria described above. The six candidate component cell lines expressed twelve to nineteen TMs (FIG. 84). As described herein, the CSC-like cell line DMS 53 is included as one of the six cell lines and expressed sixteen PCa TMs.

Immunogenicity of the unmodified PCa individual component cell line candidates was evaluated by IFNγ ELISpot as described in Example 9 for four HLA diverse healthy donors (n=4 per donor). HLA-A and HLA-B alleles for the donors were as follows: Donor 1, A*02:01 B*35:01 and A*31:01 B*35:03; Donor 2, A*02:02 B*15:03 and A*30:02 B*57:03; Donor 3, A*02:01 B*40:01 and A*30:01 B*57:01; Donor 4, A*24:02 B*18:01 and A*02:01 B*15:07. PC3 (3,409±672 SFU) and DU145 (1,497±231 SFU) were more immunogenic than LNCaP (428±204 SFU), NCCIT (25±11 SFU), NEC8 (80±47 SFU) and NTERA-2cl-D1 (188±93 SFU) (FIG. 86A). NCCIT was poorly immunogenic and excluded from further analysis. PC3 and DU145 were selected to be included in vaccine cocktail A and vaccine cocktail B, respectively, as described further herein.

Immunogenicity of five selected PCa cell lines and the CSC cell line DMS 53 was evaluated in two different combinations of three component cell lines (FIG. 86C). IFNγ responses were determined against the three component cell lines within the two potential vaccine cocktails by IFNγ ELISpot as described in Example 8 in five HLA diverse healthy donors (n=4 per donor). HLA-A and HLA-B alleles for the donors were as follows: Donor 1, A*02:01 B*08:01 and A*03:01 B*51:01; Donor 2, A*30:02 B*18:01 and A*30:04 B*58:02, Donor 3, A*02:01 B*18:01 and A*25:01 B*27:05; Donor 4, A*03:01 B*07:02 and A*25:01 B*18:01; Donor 5, A*02:01 B*07:02 and A*33:01 B*14:02. IFNγ responses were detected for both cocktails and to each cell line component in each cocktail. (FIG. 86B).

The ability of the individual PCa vaccine component cell lines to induce IFNγ responses against themselves compared to the ability of the potential PCa vaccine cocktails to induce IFNγ responses against the individual cell lines was also measured by IFNγ ELISpot as described in Examples 8 and 9. IFNγ responses to the NEC8 cell line in PCa-A (1,963±863 SFU) were significantly increased compared to responses the cell line alone (283±101 SFU) (Mann-Whitney U test, p=0.032). Similarly, IFNγ responses to the NTERA-2cl-D1 cell line in PCa-A (630±280 SFU) were significantly increased compared to responses the cell line alone (283±101 SFU) (Mann-Whitney U test, p=0.032). IFNγ responses to the LNCaP cell line in PCa-B (624±254 SFU) were significantly increased compared to responses the cell line alone (139±111 SFU) (Mann-Whitney U test, p=0.032). The data in FIG. 86D demonstrate that the cocktails PCa-A and PCa-B, in some cases, trend toward or are significantly better stimulators of antitumor immunity than the individual component cell lines and suggest that the breadth and magnitude of response is increased by administering multiple cell lines with different HLA supertypes. Specifically, PCa-A cell lines are the following HLA supertypes: PC3, A01 A24 and B07; NTERA-2cl-D1, A01, B08, and B44. The HLA type of NEC8 is unavailable. PCa-B cell lines are the following HLA supertypes: DU145, A03, B44, and B58; LNCaP, A01, A02 B08, B44; DMS 53, A03, B08 and B07. The data above supports that HLA mismatch of cell lines comprising cocktails can improve immune responses to individual cell line components.

The cells in the vaccine described herein were selected to express a wide array of TAAs, including those known to be important specifically for PCa antitumor responses, such as PSA or PAP, and also TAAs known to be important for targets for PCa and other solid tumors, such TERT. As shown herein, to further enhance the array of TAAs, DU145 was transduced with a gene encoding modPSMA and PC3 was modified to express modTBXT and modMAGEC2. PSMA was endogenously expressed in three of the six component cell lines at >1.0 FPKM or >0 TPM. TBXT and MAGEC2 were endogenously in two of the six component cell lines at >1.0 FPKM or >0 TPM (FIG. 84).

Expression of the transduced antigens modTBXT (FIG. 87A) and modMAGEC2 (FIG. 87B) (SEQ ID NO: 45; SEQ ID NO: 46) by PC3, and modPSMA (SEQ ID NO: 37; SEQ ID NO: 38) by DU145 (FIG. 87C) were detected by flow cytometry or RT-PCR described in Example 29 and herein. The genes encoding modTBXT and modMAGEC2 are encoded in the same lentiviral transfer vector separated by a furin cleavage site.

Because of the need to maintain maximal heterogeneity of antigens and clonal subpopulations the comprise each cell line, the gene modified cell lines utilized in the present vaccine have been established using antibiotic selection and flow cytometry and not through limiting dilution subcloning.

Figure 85A:
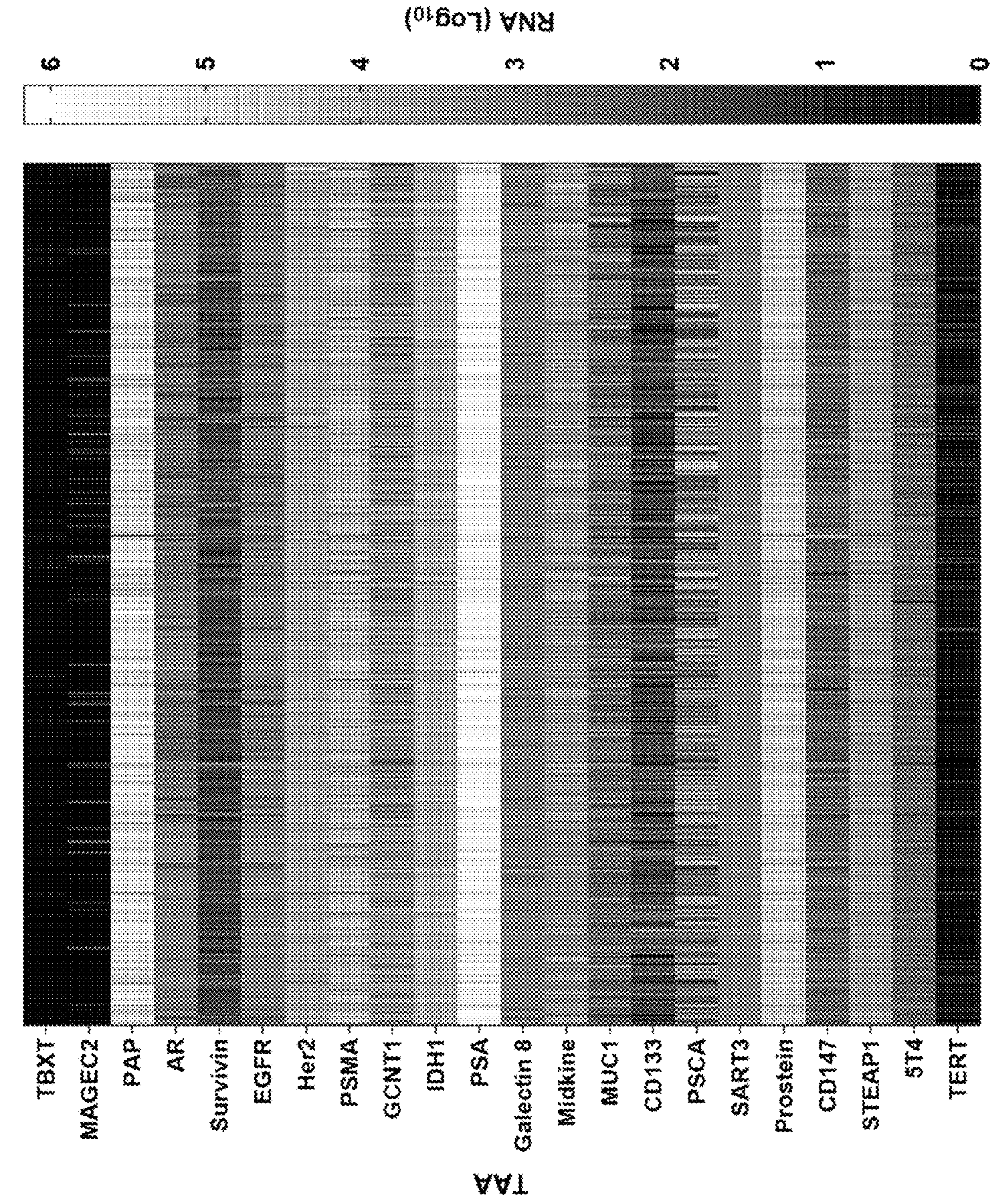
FIGS. 85A and B show antigens expressed by the PCa vaccine in PCa patient tumors (FIG. 85A) and the number of PCa antigens expressed by the vaccine cell lines also expressed in PCa patient tumors (FIG. 85B).
Figure 85B:
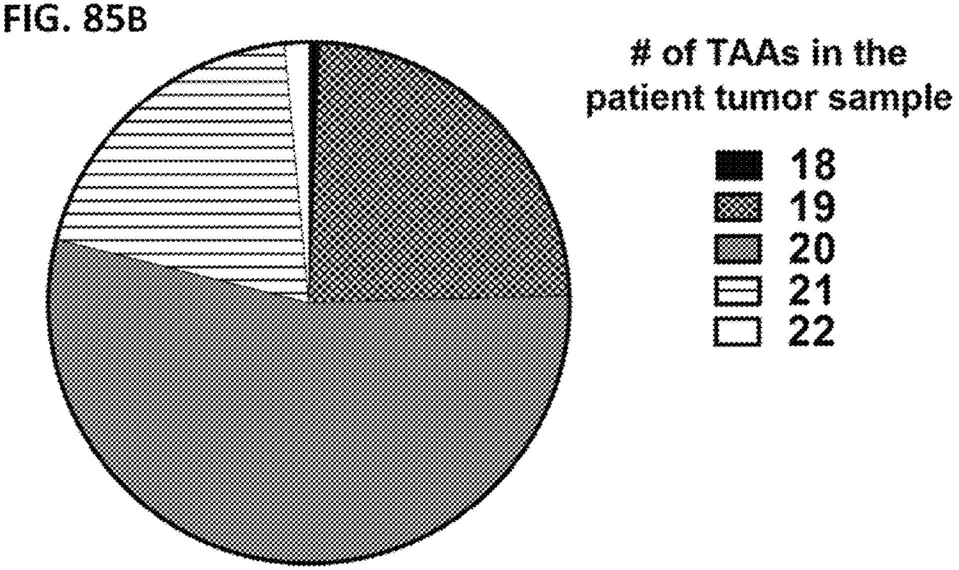

The mRNA expression of twenty-two representative TAAs in the present vaccine are shown in FIG. 84. NCCIT is the only cell line in FIG. 84 that is not included in the present vaccine. The present vaccine has high expression of all identified twenty-two commonly targeted and potentially clinically relevant TAAs for inducing a PCa antitumor response. Some of these TAAs are known to be primarily enriched in PCa tumors and some can also induce an immune response to PCa and other solid tumors. RNA abundance of the twenty-two prioritized PCa TAAs was determined in 460 PCa patient samples (FIG. 85A) with expression data available for all TAAs as described in Example 29. Eighteen of the prioritized PCa TAAs were expressed by 100% of samples, 19 TAAs were expressed by 99.3% of samples, 20 TAAs were expressed by 75.4% of samples, 21 TAAs were expressed by 21.1% of samples, 22 TAAs were expressed by 1.5% of samples (FIG. 85B). Provided herein are two compositions comprising a therapeutically effective amount of three cancer cell lines, wherein the combination of the cell lines comprises cells express at least 18 TAAs associated with a cancer of a subset of PCa cancer subjects intended to receive said composition. Based on the expression and immunogenicity data presented herein, the cell lines identified in Table 66 were selected to comprise the present PCa vaccine.

TABLE 66

| PCa vaccine cell lines and histology | | |
|---|---|---|
| Cocktail | Cell Line Name | Histology |
| A | PC3 | Prostate Carcinoma derived from metastatic site (bone) |
| A | NEC8 | Testicular Germ Cell Tumor |
| A | NTERA-2cl-D1 | Testis Embryonal Carcinoma derived from metastatic site (lung) |
| B | DU145 | Prostate Carcinoma derived from metastatic site (bone) |
| B | LNCaP | Prostate Carcinoma derived from metastatic site (lymph node) |
| B | DMS 53 | Lung Small Cell Carcinoma |

Reduction of CD276 Expression

The PC3, NEC8, NTERA-2cl-D1, DU145, LNCaP and DMS 53 component cell lines expressed CD276 and expression was knocked out by electroporation with ZFN as described in Example 13 and elsewhere herein. Because it was desirable to maintain as much tumor heterogeneity as possible, the electroporated and shRNA modified cells were not cloned by limiting dilution. Instead, the cells were subjected to multiple rounds of cell sorting by FACS as described in Example 13. Expression of CD276 was determined as described in Example 29. Reduction of CD276 expression is described in Table 67. These data show that gene editing of CD276 with ZFN resulted in greater than 98.7% CD276-negative cells in all six vaccine component cell lines.

TABLE 67

| Reduction of CD276 expression | | | |
|---|---|---|---|
| Cell line | Parental Cell Line MFI | Modified Cell Line MFI | % Reduction CD276 |
| PC3 | 6,645 | 0 | 100.0 |
| NEC8 | 6,317 | 33 | 99.5 |
| NTERA-2cl-D1 | 7,240 | 95 | 98.7 |
| DU145 | 8,461 | 8 | 99.9 |
| LNCaP | 41,563 | 3 | 99.9 |
| DMS 53 | 11,928 | 24 | 99.8 |

MFI reported with isotype controls subtracted

Cytokine Secretion Assays for TGFβ1, TGFβ2, GM-CSF, and IL-12

Cytokine Secretion Assays for TGFβ1, TGFβ2, GM-CSF, and IL-12 were Completed as Described in Example 29.

shRNA Downregulates TGF-6 Secretion

Following CD276 knockout, TGFβ1 and TGFβ2 secretion levels were reduced using shRNA and resulting levels determined as described in Example 29. The PC3 and NEC8 parental cell lines in PCa vaccine-A secreted measurable levels of TGFβ1. PC3 also secreted a measurable level of TGFβ2. NEC8 secreted relatively low levels of TGFβ1 and did not secrete measurable levels of TGFβ2. NTERA-2cl-D1 did not secreted measurable levels of TGFβ1 or TGFβ2. Of the parental cell lines in PCa vaccine-B, DU145 secreted measurable, but relatively low levels of TGFβ1 and TGFβ2, and LNCaP did not secrete measurable levels of TGFβ1 or TGFβ2. Reduction of TGFβ2 secretion by the DMS 53 cell line is described in Example 26 and resulting levels determined as described above.

The PC3 component cell line was transduced with TGFβ1 shRNA to decrease secretion of TGFβ1 and increase expression of membrane bound CD40L as described in Example 29 and was subsequently transduced with lentiviral particles encoding TGFβ2 shRNA and GM-CSF (SEQ ID NO: 6) Example 29. These cells are described by the clonal designation DK6. As described in Example 26, DMS 53 was modified with shRNA to reduce secretion of TGFβ2 and not TGFβ1. These cells are described by the clonal designation DK4. The remaining cell lines were not modified with TGFβ1 shRNA or TGFβ2 shRNA.

Table 68 shows the percent reduction in TGFβ1 and/or TGFβ2 secretion in gene modified component cell lines compared to unmodified, parental, cell lines. If TGFβ1 or TGFβ2 secretion was only detected in 1 of 16 replicates run in the ELISA assay the value is reported without standard error of the mean. Gene modification resulted in 82% reduction of TGFβ1 secretion. Gene modification of TGFβ2 resulted in at least 51% reduction in secretion of TGFβ2.

TABLE 68

| TGF-β Secretion (pg/$10^6$ cells/24 hr) in Component Cell Lines | | | | |
|---|---|---|---|---|
| Cell Line | Cocktail | Clone | TGFβ1 | TGFβ2 |
| PC3 | A | Wild type | 686 ± 93 | 3,878 ± 556 |
| PC3 | A | DK6 | 122 ± 119 | 382 ± 89 |
| PC3 | A | Percent reduction | 82% | 90% |
| NEC8 | A | Wild type | 97 ± 26 | * ≤4 |
| NEC8 | A | NA | NA | NA |
| NEC8 | A | Percent reduction | NA | NA |
| NTERA-2cl-D1 | A | Wild type | * ≤304 | * ≤138 |
| NTERA-2cl-D1 | A | NA | NA | NA |
| NTERA-2cl-D1 | A | Percent reduction | NA | NA |
| DU145 | B | Wild type | 161 ± 28 | 435 ± 64 |
| DU145 | B | NA | NA | NA |
| DU145 | B | Percent reduction | NA | NA |
| LNCaP | B | Wild type | * ≤63 | * ≤28 |
| LNCaP | B | NA | NA | NA |
| LNCaP | B | Percent reduction | NA | NA |
| DMS 53 | B | Wild type | 106 ± 10 | 486 ± 35 |
| DMS 53 | B | DK4 | NA | 238 ± 40 |
| DMS 53 | B | Percent reduction | NA | 51% |

DK6: TGβ1/TGFβ2 double knockdown;
DK4: TGFβ2 single knockdown;
DK2: TGFβ1 single knockdown;
* = estimated using LLD, not detected;
NA = not applicable Based on a dose of $5\times10^5$ of each component cell line, the total TGFβ1 and TGFβ2 secretion by the modified PCa vaccine-A and PCa vaccine-B and respective unmodified parental cell lines are shown in Table 69. The secretion of TGFβ1 by PCa vaccine-A was reduced by 52% pg/dose/24 hr and TGFβ2 by 87% pg/dose/24 hr. The secretion of TGFβ2 by PCa vaccine-B was reduced by 26% pg/dose/24 hr.

TABLE 69

| Total TGF-β Secretion (pg/dose/24 hr) in PCa vaccine-A and PCa vaccine-B | | | |
|---|---|---|---|
| Cocktail | Clones | TGFβ1 | TGFβ2 |
| A | Wild type | 544 | 2,010 |
| | DK6 | 262 | 262 |
| | Percent reduction | 52% | 87% |
| B | Wild type | 166 | 475 |
| | DK4 | NA | 351 |
| | Percent reduction | NA | 26% |

GM-CSF Secretion

The PC3 cell line was transduced with lentiviral particles containing both TGFβ2 shRNA and the gene to express GM-CSF (SEQ ID NO: 6) under the control of a different promoter. The NEC8, NTERA-2cl-D1, DU145 and LNCaP cell lines were transduced with lentiviral particles to only express GM-CSF (SEQ ID NO: 7). DMS 53 was modified to secrete GM-CSF as described in Example 24 and elsewhere herein. The results are shown in Table 70 and described below.

Secretion of GM-CSF increased at least 68-fold in all modified component cell lines compared to unmodified, parental cell lines. In PCa vaccine-A component cell lines, secretion of GM-CSF increased 67,987-fold by PC3 compared to the parental cell line (≤0.003 ng/$10^6$ cells/24 hr), 128,543-fold by NEC-8 compared to the parental cell line (≤0.002 ng/$10^6$ cells/24 hr), and 68-fold by NTERA-2cl-D1 compared to the parental cell line (≤0.059 ng/$10^6$ cells/24 hr). In PCa vaccine-B component cell lines secretion of GM-CSF increased 119,645-fold by DU145 compared to the parental cell line (≤0.003 ng/$10^6$ cells/24 hr), 10,151-fold by LNCaP compared to the parental cell line (≤0.012 ng/$10^6$ cells/24 hr) and 39,450-fold by DMS 53 compared to the parental cell line 004 ng/$10^6$ cells/24 hr).

TABLE 70

GM-CSF Secretion in Component Cell Lines

| Cell Line | GM-CSF (ng/$10^6$ cells/24 hr) | GM-CSF (ng/dose/24 hr) |
|---|---|---|
| PC3 | 187 ± 16 | 94 |
| NEC-8 | 208 ± 9 | 104 |
| NTERA-2cl-D1 | 4 ± 0.2 | 2 |
| Cocktail A Total | 399 | 200 |
| DU145 | 386 ± 71 | 193 |
| LNCaP | 124 ± 11 | 62 |
| DMS 53 | 158 ± 15 | 79 |
| Cocktail B Total | 668 | 334 |

Based on a dose of 5×$10^5$ of each component cell line, the total GM-CSF secretion for PCa vaccine-A was 200 ng per dose per 24 hours. The total GM-CSF secretion for PCa vaccine-B was 334 ng per dose per 24 hours. The total GM-CSF secretion per dose was therefore 534 ng per 24 hours.

Membrane Bound CD40L (CD154) Expression

The component cell lines were transduced with lentiviral particles to express membrane bound CD40L vector as described above. The methods to detect expression of CD40L by the five PCa cell line components are described in Example 29. The methods used to modify DMS 53 to express CD40L are described in Example 15. Evaluation of membrane bound CD40L by all six vaccine component cell lines is described below. The results shown in FIG. 88 and described below demonstrate CD40L membrane expression was substantially increased in all six cell PCa vaccine component cell lines.

Figure 88:
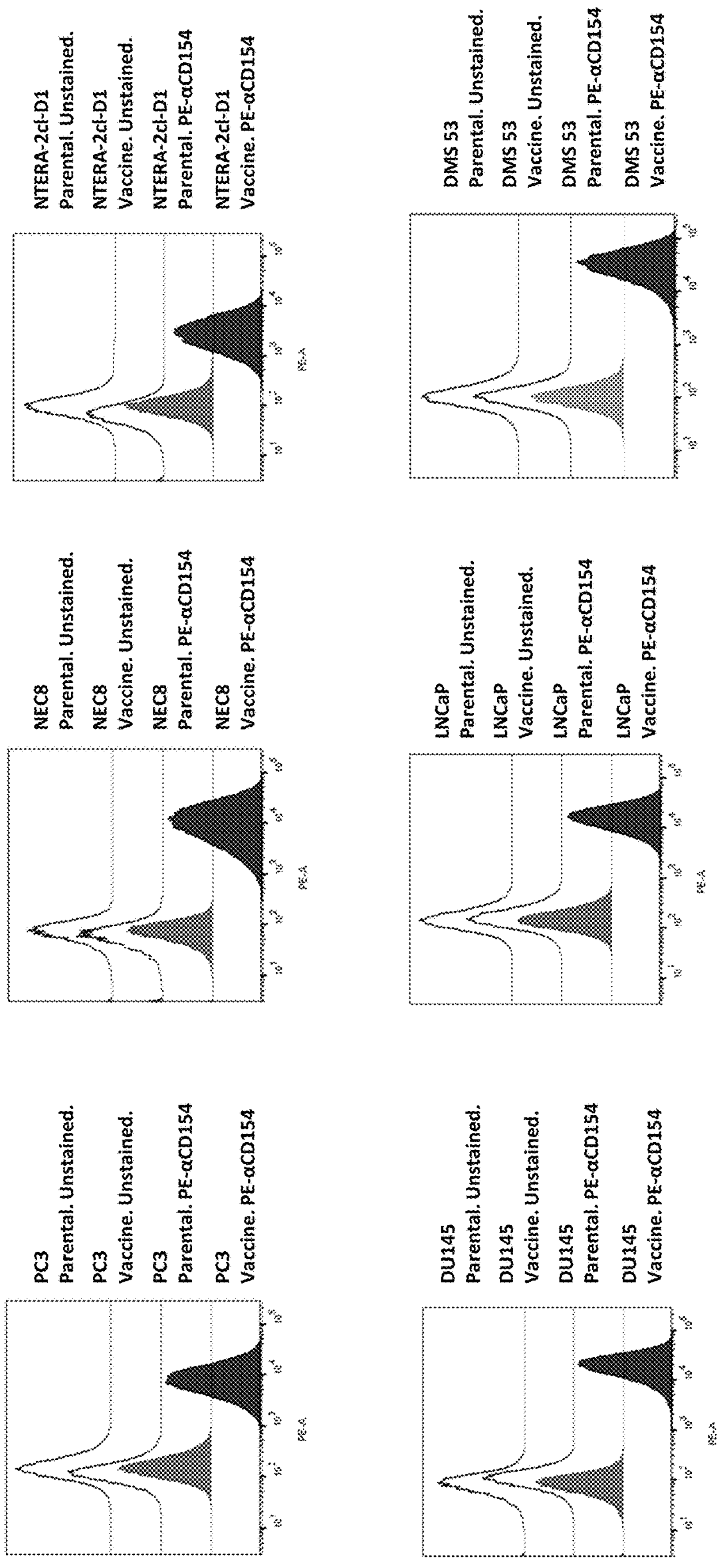
FIG. 88 shows expression of membrane bound CD40L by the PCa vaccine component cell lines.

Expression of membrane bound CD40L by the PCa vaccine cell lines is shown in FIG. 88. Membrane-bound CD40L expression increased at least 9,019-fold in all component cell lines compared to unmodified, parental cell lines. In PCa vaccine-A component cell lines, expression of CD40L increased 9,019-fold by PC3 (9,019 MFI) compared to the parental cell line (0 MFI), 11,571-fold by NEC8 (11,571 MFI) compared to the parental cell line (0 MFI), and 15,609-fold by NTERA-2cl-D1 (15,609 MFI) compared to the parental cell line (0 MFI). In PCa vaccine-B component cell lines expression of CD40L increased 18,699-fold by DU145 compared to the parental cell line (0 MFI), 30,243-fold by LNCaP compared to the parental cell line (0 MFI), and 88,261-fold by DMS 53 compared to the parental cell line (0 MFI).

IL-12 Expression

The component cell lines were transduced with the IL-12 vector as described in Example 17 and resulting IL-12 p70 expression determined as described above and herein. The results are shown in Table 71 and described below.

Secretion of IL-12 increased at least 507-fold in all component cell lines modified to secrete IL-12 p70 compared to unmodified, parental cell lines. In PCa vaccine-A component cell lines, secretion of IL-12 increased 42,727-fold by PC3 compared to the parental cell line (≤0.001 ng/$10^6$ cells/24 hr), 30,769-fold by NEC8 compared to the parental cell line (≤0.001 ng/$10^6$ cells/24 hr), and 507-fold by NTERA-2cl-D1 compared to the parental cell line (≤0.024 ng/$10^6$ cells/24 hr). In PCa vaccine-B component cell lines expression of IL-12 increased 13,178-fold by DU145 compared to the parental cell line (≤0.001 ng/$10^6$ cells/24 hr) and 3,901-fold by LNCaP compared to the parental cell line (≤0.005 ng/$10^6$ cells/24 hr). DMS 53 was not modified to secrete IL-12.

TABLE 71

IL-12 secretion in component cell lines

| Cell Line | IL-12 (ng/$10^6$ cells/24 hr) | IL-12 (ng/dose/24 hr) |
|---|---|---|
| PC3 | 47 ± 24 | 24 |
| NEC-8 | 20 ± 3 | 10 |
| NTERA-2cl-D1 | 12 | 6 |
| Cocktail A Total | 79 | 40 |
| DU145 | 17 ± 4 | 9 |
| LNCaP | 19 ± 6 | 10 |
| DMS 53 | NA | NA |
| Cocktail B Total | 36 | 19 |

Based on a dose of 5×$10^5$ of each component cell line, the total IL-12 secretion for PCa vaccine-A was 40 ng per dose per 24 hours. The total IL-12 secretion for PCa vaccine-B was 19 ng per dose per 24 hours. The total IL-12 secretion per dose was therefore 59 ng per 24 hours.

Stable Expression of modTBXT and modMAGEC2 by the PC3 Cell Line

As described above, the cells in the vaccine described herein were selected to express a wide array of TAAs, including those known to be important to antitumor immunity. To further enhance the array of antigens, the PC3 cell line that was modified to reduce the secretion of TGFβ1 and TGFβ2, reduce the expression of CD276, and to express GM-CSF, membrane bound CD40L and IL-12 was also transduced with lentiviral particles expressing the modTBXT and modMAGEC2 antigens. The genes encoding the modTBXT and modMAGEC2 antigens are linked by a furin cleavage site (SEQ ID NO: 45, SEQ ID NO: 46).

Figures 87A, 87B, 87C, 87D, 87E, 87F:
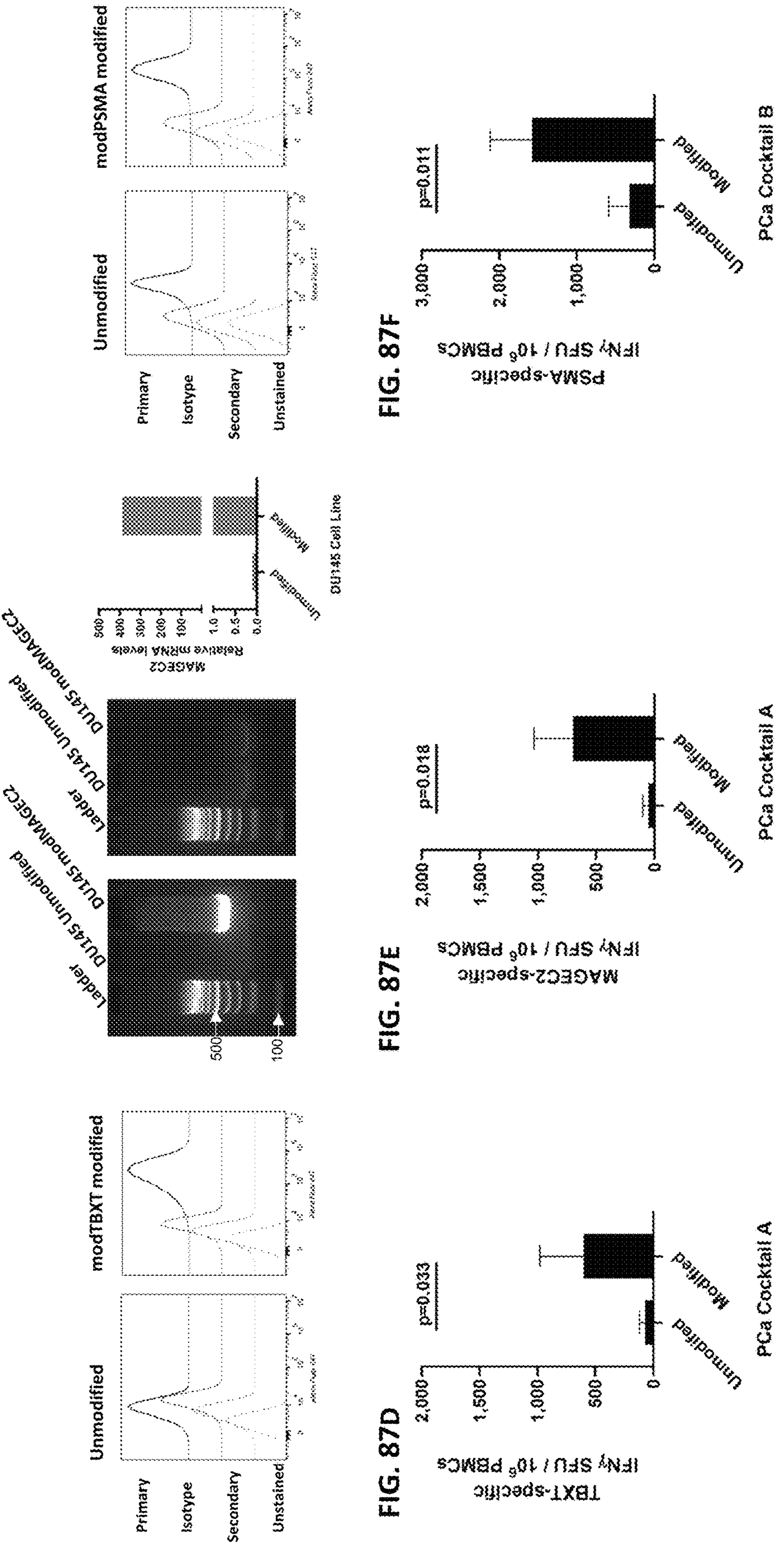
FIGS. 87A-F show the expression of and IFNγ responses to antigens introduced in the PCa vaccine cell lines compared to unmodified controls. Expression of modTBXT (FIG. 87A) by PC3 and IFNγ responses to TBXT (FIG. 87D) in PCa-vaccine A. Expression of modMAGEC2 (FIG. 87B) by PC3 and IFNγ responses to MAGEC2 (FIG. 87E) in PCa-vaccine A. Expression of modPSMA (FIG. 87C) by DU145 and IFNγ responses to PSMA (FIG. 87F) in PCa-vaccine B.

The expression of modTBXT by PC3 was characterized by flow cytometry. For the detection of modTBXT expression cells were first stained intracellular with rabbit IgG1 anti-TBXT antibody (Abcam ab209665, Clone EPR18113) (0.06 μg/test) followed by AF647-conjugated donkey anti-rabbit IgG1 antibody (Biolegend #4406414) (0.125 μg/test). Expression of modTBXT increased in the modified cell line (1,209,613 MFI) 1,209,613-fold over that of the unmodified cell line (0 MFI) (FIG. 87A). The expression of modMAGEC2 by PC3 was determined using RT-PCR as described in Example 29 and herein. The forward primer designed to anneal at the 604-631 base pair (bp) location in the transgene (GAT-CACTTCTGCGTGTTCGCTAACACAG (SEQ ID NO: 128)) and reverse primer designed to anneal at the 1072-1094 bp location in the transgene (CTCAT-CACGCTCAGGCTCTCGCT (SEQ ID NO: 129)) and yield 491 bp product. Control primers and resulting product for 3-tubulin are described in Example 29. The gene product for MAGEC2 was detected at the expected size (FIG. 97B). modMAGEC2 mRNA increased 3,914-fold relative to the parental control (FIG. 87B).

Stable Expression of modPSMA by the DU145 Cell Line

The DU145 cell line that was modified to reduce the expression of CD276, and to express GM-CSF, membrane bound CD40L, and IL-12 was also transduced with lentiviral particles expressing the modPSMA antigen (SEQ ID NO: 37, SEQ ID NO: 38). The expression of modPSMA was characterized by flow cytometry. Antigen unmodified and antigen modified cells were stained intracellular with 0.06 μg/test anti-mouse IgG1 anti-PSMA antibody (AbCam ab268061, Clone FOLH1/3734) followed by 0.125 ug/test AF647-conjugated goat anti-mouse IgG1 antibody (Biolegend #405322). Expression of modPSMA increased in the modified cell line (249,632 MFI) 6-fold over that of the parental cell line (42,196 MFI) (FIG. 87C).

Immune Responses to TBXT and MAGEC2 in PCa Vaccine-A

IFNγ responses to TBXT and MAGEC2 antigens were evaluated in the context of the modified PCa vaccine-A as described in Example 29, and herein, in seven HLA diverse donors (n=4/donor. The HLA-A, HLA-B, and HLA-C alleles for each of the seven donors are shown in Table 72. IFNγ responses to TBXT were determined by ELISpot using 15-mers peptides overlapping by 11 amino acids (JPT, PM-BRAC) spanning the entire length of the native TBXT antigen. IFNγ responses to TBXT significantly increased with the modified PCa vaccine-B (605±615 SFU) compared to the unmodified PCa vaccine-A (73±70 SFU) (p=0.033, Mann-Whitney U test) (n=7) (FIG. 87D). IFNγ responses to MAGEC2 were determined by ELISpot using 15-mers peptides overlapping by 9 amino acids spanning the entire length of the native antigen, purchased from Thermo Scientific Custom Peptide Service. IFNγ responses to MAGEC2 significantly increased with the modified PCa vaccine-B (697±536 SFU) compared to the unmodified PCa vaccine-B (SFU) (p=0.018, Mann-Whitney U test) (n=7) (FIG. 87E).

Immune Responses to PSMA in PCa-Vaccine B

IFNγ responses to the PSMA antigen were evaluated in the context of the PCa-vaccine B as described in Example 29, and herein, in seven HLA diverse donors (n=4/donor) (Table 72). IFNγ responses determined by ELISpot as described in Example 29. PSMA peptides, 15-mers overlapping by 9 amino acids spanning the native antigen sequence, were purchased from Thermo Scientific Custom Peptide Service. PSMA specific IFNγ responses with the were significantly increased with the modified PCa vaccine-B (1,580±847 SFU) compared to the parental, unmodified PCa vaccine-A (327±33 SFU) (p=0.011, Mann-Whitney U test) (n=7) (FIG. 87F).

TABLE 72

| Healthy Donor MHC-I characteristics | | | |
|---|---|---|---|
| Donor # | HLA-A | HLA-B | HLA-C |
| 1 | *02:01 *03:01 | *08:01 *51:01 | *07:01 *14:02 |
| 2 | *30:02 *30:01 | *15:10 *58:02 | *03:04 *06:02 |
| 3 | *03:01 *32:01 | *07:02 *15:17 | *07:01 *07:02 |
| 4 | *03:01 *25:01 | *07:02 *18:01 | *07:02 *12:03 |
| 5 | *02:01 *33:01 | *07:02 *14:02 | *07:02 *08:02 |
| 6 | *01:01 *30:01 | *08:01 *13:02 | *06:02 *07:01 |
| 7 | *26:01 *68:02 | *08:01 *15:03 | *03:04 *12:03 |

Cocktails Induce Immune Responses Against Relevant TAAs

The ability of the two PCa vaccine cocktails to induce IFNγ production against relevant PCa antigens was measured by ELISpot. PBMCs from seven HLA-diverse healthy donors (Table 72) were co-cultured with the PCA vaccine-A or PCa vaccine-B cocktails for 6 days prior to stimulation with autologous DCs loaded with TAA-specific specific peptide pools containing known MHC-I restricted epitopes. Peptides for stimulation of CD14-PBMCs for detection of IFNγ responses to TBXT, MAGEC2 and PSMA are described above. Additional 15-mer overlapping by 11 amino acid peptide pools were sourced as follows: TERT (JPT, PM-TERT), Survivin (thinkpeptides, 7769_001-011), HER2 (JPT, PM-ERB_ECD), STEAP (PM-STEAP1), MUC1 (JPT, PM-MUC1), PAP (JPT, PM-PAP), and PSA (JPT, PM-PSA). Cells were then assayed for IFNγ secretion in the IFNγ ELISpot assay.

Figure 89A:
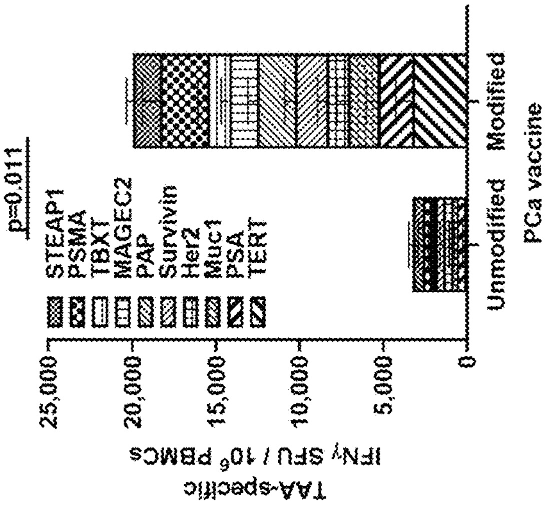
FIGS. 89A-C show antigen specific IFNγ responses induced by the unit dose of the PCa vaccine (FIG. 89A), PCa vaccine-A (FIG. 89B) and PCa vaccine-B (FIG. 89C) compared to unmodified controls.
Figure 89B:
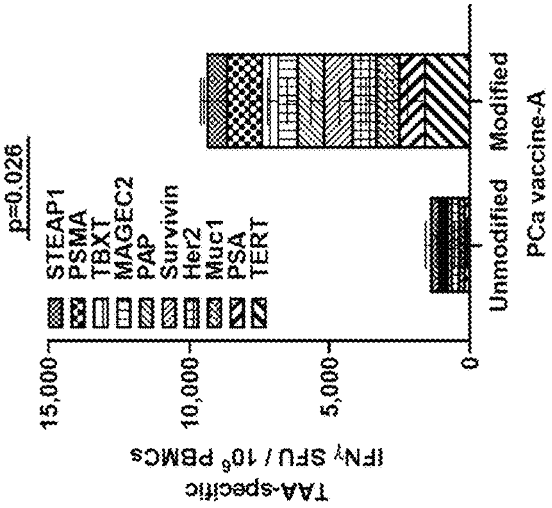
Figure 89C:
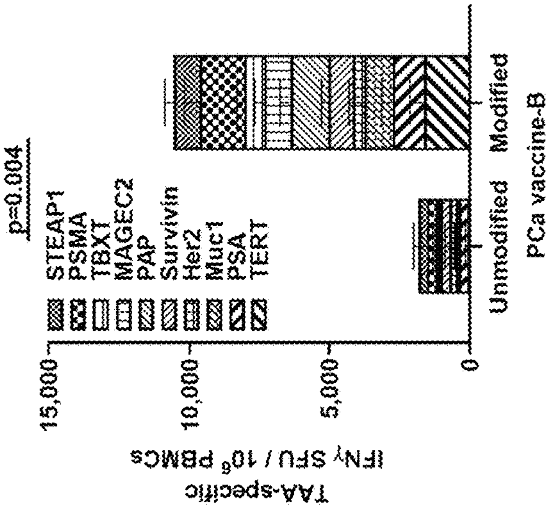
Figure 90:
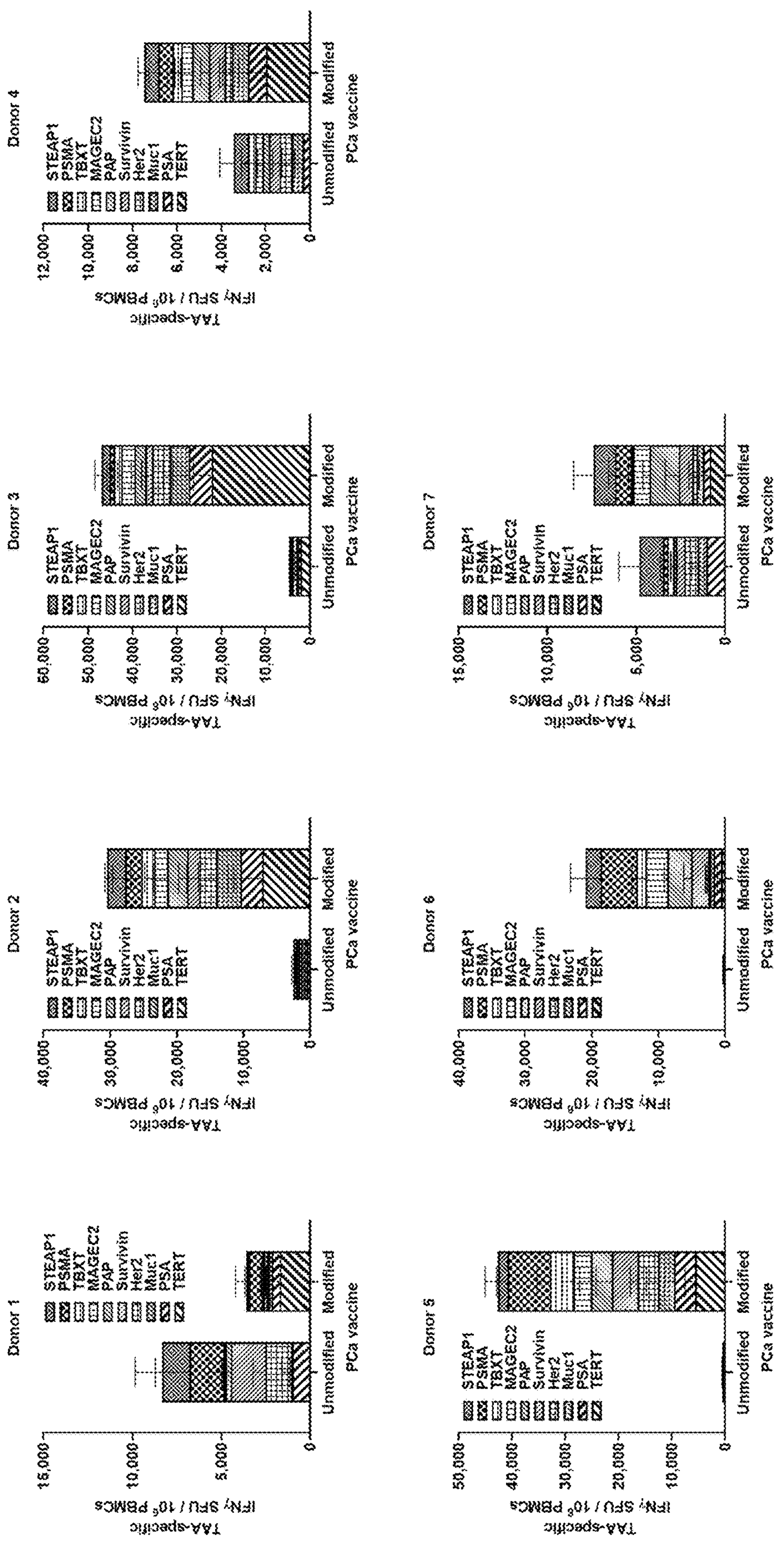
FIG. 90 shows antigen specific IFNγ responses induced by the unit dose of the PCa vaccine in individual donors compared to unmodified controls.

FIG. 89 demonstrates the PCa vaccine is capable of inducing antigen specific IFNγ responses in seven HLA-diverse donors to ten PCa antigens that are significantly more robust (19,982±5,480 SFU) compared to the unmodified parental controls (3,259±1,046 SFU) (p=0.011, Mann-Whitney U test) (n=7) (FIG. 89A). The unit dose of PCa vaccine-A and PCa vaccine-B elicited IFNγ responses to eight antigens in one of seven donors and ten antigens in six of the seven donors. PCa vaccine-A and PCa vaccine-B independently demonstrated antigen specific responses significantly greater compared to parental controls. For PCa vaccine-A, one donor responded to three antigens, one donor responded to eight antigens, one donor responded to nine antigens, and four donors responded ten antigens. Specifically, PCa vaccine-A elicited 9,412±6,170 SFU compared to the unmodified controls (1,430±911 SFU) (p=0.026, Mann-Whitney U test) (FIG. 89B). For PCa vaccine-B, one donor responded to six antigens, three donors responded to nine antigens, and three donors responded to ten antigens. PCa vaccine-B elicited 10,570±2,913 SFU compared to parental controls (1,830±371 SFU) (p=0.004, Mann-Whitney U test) (FIG. 89C). The PCA vaccine (vaccine-A and vaccine-B) induced IFNγ production to nine antigens in one of seven donors and all ten antigens in six of seven donors (FIG. 90) (Table 73). Described above are two compositions comprising a therapeutically effective amount of three cancer cell lines, a unit dose of six cell lines, wherein said unit dose is capable of eliciting an immune response 6.1-fold greater than the unmodified composition specific to at least eight TAAs expressed in PCA patient tumors. PCA vaccine-A increased IFNγ responses to at least three TAAs 6.6-fold and PCA vaccine-B increased IFNγ responses 5.8-fold to at least six TAAs.

The ability of the individual modified PCa vaccine component cell lines to induce IFNγ responses against matched unmodified cell line components was measured by IFNγ

Figure 91A:
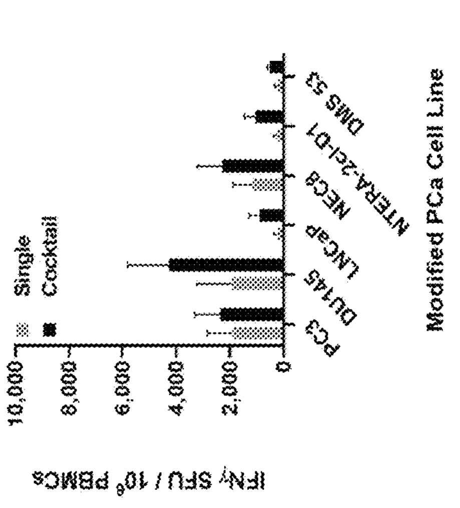
FIGS. 91A-E show the Pca vaccine cell lines as cocktails of cell lines are more immunogenic than single cell lines.

ELISpot as described in Examples 8 and 9 for four HLA diverse donors (n=4/donor) (Table 73. Donors 1, 2, 4 and 5). IFNγ responses were detected against parental unmodified cell lines for both cocktails and each modified cell line component in each cocktail. There was a trend towards increased IFNγ production for PCa vaccine-A and PCa vaccine-B compared to individual modified cell lines, but this trend did not reach statistical significance likely due to the low n of Donors (n=4) Mann Whitney U test for all comparisons) (FIG. 91A).

Figure 91B:
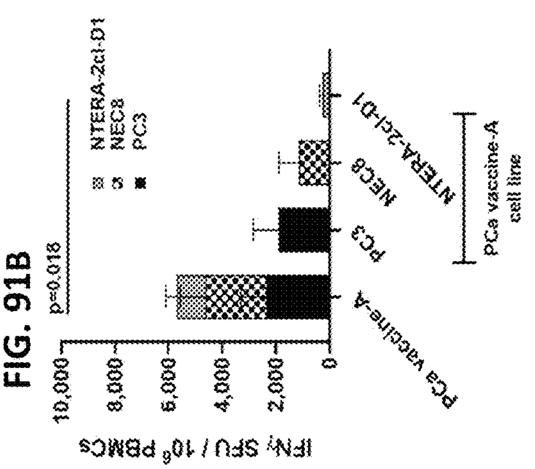
Figure 91C:
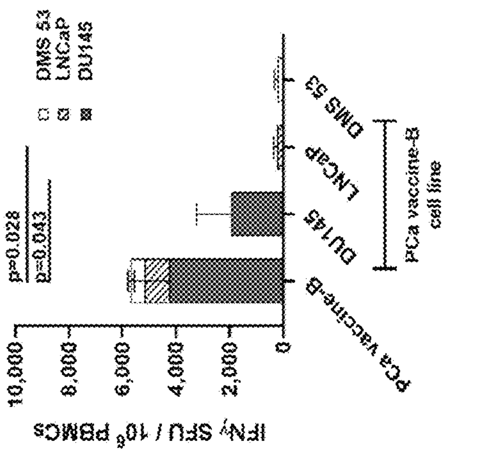
Figure 91D:
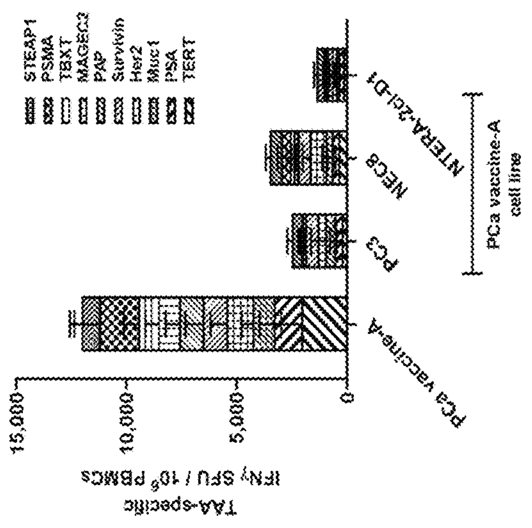

There was a significant difference in IFNγ production between PCa vaccine-A and the individual modified cell line components (p=0.036, Kruskal Wallis test). Specifically, PCa vaccine-A induced significantly greater IFNγ production (5,685±2,060 SFU) than the modified NTERA-2cl-D1 (253±136) (p=0.019) component cell line but not the NEC8 (1,151±735 SFU) (p=0.307) and PC3 component cell line (1,898±947 SFU) (p=0.621) (post-hoc Dunn's test for multiple comparisons) (FIG. 91B). There was also a significant difference in IFNγ production between PCa vaccine-B and the individual modified cell line components (p=0.006, Kruskal Wallis test). Specifically, PCa vaccine-B induced significantly greater IFNγ production (5,686±1,866 SFU) than the modified LNCaP (240±122 SFU) (p=0.043) and DMS 53 (222±113) (p=0.028) component cell lines but not the DU145 component cell line (1,943±1,291 SFU) (p=0.704) (post-hoc Dunn's test for multiple comparisons). (FIG. 91C).

Figure 91E:
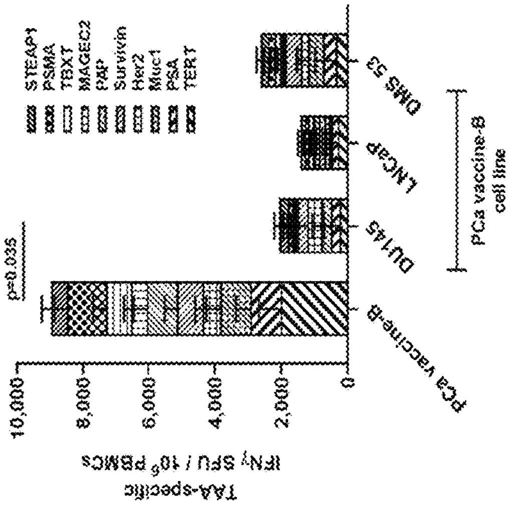

Antigen specific responses against ten PCa antigens was determined for the same four donors described above for the individual modified cell lines comprising PCa vaccine-A and PCa vaccine-B (Table 73. Donors 1, 2, 4 and 5). IFNγ responses to TAAs induced by PCa vaccine-A and PCa vaccine-B were more robust than compared to responses induced by the individual modified PCa cell line components. Specifically, PCa vaccine-A associated responses against the ten assayed antigens (9,412±6,170 SFU) were greater than responses induced by modified PC3 (2,357±1,076 SFU), NEC8 (3,491±1,196 SFU) and NTERA-2cl-D1 (1,381±429 SFU SFU). There was a trend towards increased IFNγ production for PCa vaccine-A compared to individual modified cell lines, but this trend did not reach statistical significance likely due to the low n of Donors (n=4) (FIG. 100D). PCa vaccine-B induced responses against the ten assayed antigens (12,067±6,694 SFU) were significantly different than the individual component cell lines (p=0.047, Kruskal Wallis test). Specifically, PCa vaccine-B antigen specific responses were significantly greater then responses those induced by modified DU145 (2,064±1,604 SFU) (p=0.0345), but not LNCaP (1,419±189 SFU) (p=0.113) or DMS 53 (2,615±1,044 SFU) (p=0.544) (post-hoc Dunn's test for multiple comparisons) (FIG. 91E). Collectively, the data described above demonstrate that compositions comprising a therapeutically effective amount of three cancer cell lines induce more robust IFNγ responses to unmodified parental cell lines and PCa antigens than a single cell line composition.

TABLE 73

IFNγ Responses to unmodified and modified PCa vaccine components

| Donor (n = 4) | Unmodified (SFU ± SEM) PCa vaccine-A | Unmodified (SFU ± SEM) PCa vaccine-B | Unmodified (SFU ± SEM) PCa Vaccine | Modified (SFU ± SEM) PCa vaccine-A | Modified (SFU ± SEM) PCa vaccine-B | Modified (SFU ± SEM) PCa Vaccine |
|---|---|---|---|---|---|---|
| 1 | 729 ± 243 | 7,608 ± 2,463 | 8,337 ± 2,584 | 251 ± 251 | 1,652 ± 882 | 3,588 ± 1,844 |
| 2 | 320 ± 241 | 1,545 ± 663 | 2,430 ± 841 | 10,603 ± 6,129 | 12,750 ± 8,596 | 30,478 ± 18,894 |
| 3 | 1,608 ± 360 | 461 ± 272 | 4,519 ± 1,314 | 8,400 ± 2,027 | 13,863 ± 3,296 | 46,955 ± 10,118 |
| 4 | 3,781 ± 2,630 | 3 ± 3 | 3,784 ± 2,630 | 2,753 ± 630 | 2,749 ± 1,141 | 7,471 ± 2,329 |
| 5 | 25 ± 25 | 505 ± 221 | 530 ± 243 | 26,323 ± 12,033 | 10,649 ± 6,413 | 42,613 ± 19,867 |
| 6 | 56 ± 45 | 214 ± 93 | 270 ± 124 | 3,621 ± 1,500 | 16,753 ± 1,766 | 20,961 ± 3,534 |
| 7 | 3,028 ± 1,007 | 1,789 ± 561 | 4,824 ± 1,363 | 2,395 ± 1,031 | 4,135 ± 1,811 | 7,399 ± 2,637 |

Based on the disclosure and data provided herein, a whole cell vaccine for prostate cancer comprising the six cancer cell lines, sourced from ATCC or JCRB, PC-3 (ATCC, CRL-1435), NEC-8 (JCRB, JCRB0250), NTERA-2cl-D1 (ATCC, CRL-1973), DU145 (ATCC, HTB-81), LNCaP (ATCC, CRL-2023) and DMS 53 (ATCC, CRL-2062) is shown in Table 74. The cell lines represent five prostate cancer and testicular cancer cell lines and one small cell lung cancer (SCLC) cell line (DMS 53 ATCC CRL-2062). The cell lines have been divided into two groupings: vaccine-A and vaccine-B. Vaccine-A is designed to be administered intradermally in the upper arm and vaccine-B is designed to be administered intradermally in the thigh. Vaccine A and B together comprise a unit dose of cancer vaccine.

TABLE 74

Cell line nomenclature and modifications

| Cocktail | Cell Line | TGFβ1 KD | TGFβ2 KD | CD276 KO | GM-CSF | CD40L | IL-12 | TAA(s) |
|---|---|---|---|---|---|---|---|---|
| A | PC3 | X | X | X | X | X | X | X |
| A | NEC8 | ND | ND | X | X | X | X | ND |
| A | NTERA-2cl-D1 | ND | ND | X | X | X | X | ND |
| B | DU-145 | ND | ND | X | X | X | X | X |

TABLE 74-continued

| Cell line nomenclature and modifications | | | | | | | | |
|---|---|---|---|---|---|---|---|---|
| Cocktail | Cell Line | TGFβ1 KD | TGFβ2 KD | CD276 KO | GM-CSF | CD40L | IL-12 | TAA(s) |
| B | LNCaP | ND | ND | X | X | X | X | ND |
| B | DMS 53* | ND | X | X | X | X | X | ND |

ND = Not done.
^ CD276 KD.
*Cell lines identified as CSC-like cells.

Where indicated in the above table, the genes for the immunosuppressive factors transforming growth factor-beta 1 (TGFβ1) and transforming growth factor-beta 2 (TGFβ2) have been knocked down using shRNA transduction with a lentiviral vector. The gene for CD276 has been knocked out by electroporation using zinc-finger nuclease (ZFN) or knocked down using shRNA transduction with a lentiviral vector. The genes for granulocyte macrophage-colony stimulating factor (GM-CSF), IL-12, CD40L, modTBXT (PC3), modMAGEC2 (PC3), and modPSMA (DU145) have been added by lentiviral vector transduction.

The present Example thus provides two compositions comprising a therapeutically effective amount of three cancer cell lines each (i.e., a unit dose of six cancer cell lines), modified to reduce the expression of at least one immunosuppressive factor and to express at least two immunostimulatory factors. One composition, PCa vaccine-A, was modified to increase the expression of two TAAs, modTBXT and modMAGEC2. The second composition, PCa vaccine-B, was modified to expresses one TAA, modPSMA. The unit dose of six cancer cell lines expresses at least at least 18 TAAs associated with a cancer of a subset of PCa cancer subjects intended to receive said composition and induces IFNγ responses 6.1-fold greater than the unmodified composition components.

Example 32: Preparation of Urinary Bladder Cancer (UBC) Vaccine

This Example demonstrates that reduction of TGFβ1, TGFβ2, and CD276 expression with concurrent overexpression of GM-CSF, CD40L, and IL-12 in a vaccine composition of two cocktails, each cocktail composed of three cell lines for a total of 6 cell lines, significantly increased the magnitude of cellular immune responses to at least 10 UBC-associated antigens in an HLA-diverse population. As described herein, the first cocktail, UBC vaccine-A, is composed of cell line J82 that was also modified to express modPSMA and modCripto1 (modTDGF1), cell line HT-1376, and cell line TCCSUP. The second cocktail, UBC vaccine-B, is composed of cell line SCaBER that was also modified to express modWT1 and modFOLR1 (modFBP), cell line UM-UC-3, and cell line DMS 53. The six component cell lines collectively express at least twenty-four antigens that can provide an anti-UBC tumor response.

Identification of UBC Vaccine Components

Initial cell line selection criteria identified twenty-six vaccine component cell lines for potential inclusion in the UBC vaccine. Additional selection criteria described herein were applied to narrow the twenty-six cell lines to eight cell lines for further evaluation in immunogenicity assays. These criteria included: endogenous UBC associated antigen expression, lack of expression of additional immunosuppressive factors, such as IL-10 or IDO1, expression of UBC-associated CSC-like markers YAP1, ALDH1A, CD44, CEACAM6, and Oct4, ethnicity and age of the patient from which the cell line was derived, site and stage of the bladder cancer, and histological subtype.

Figure 92A:
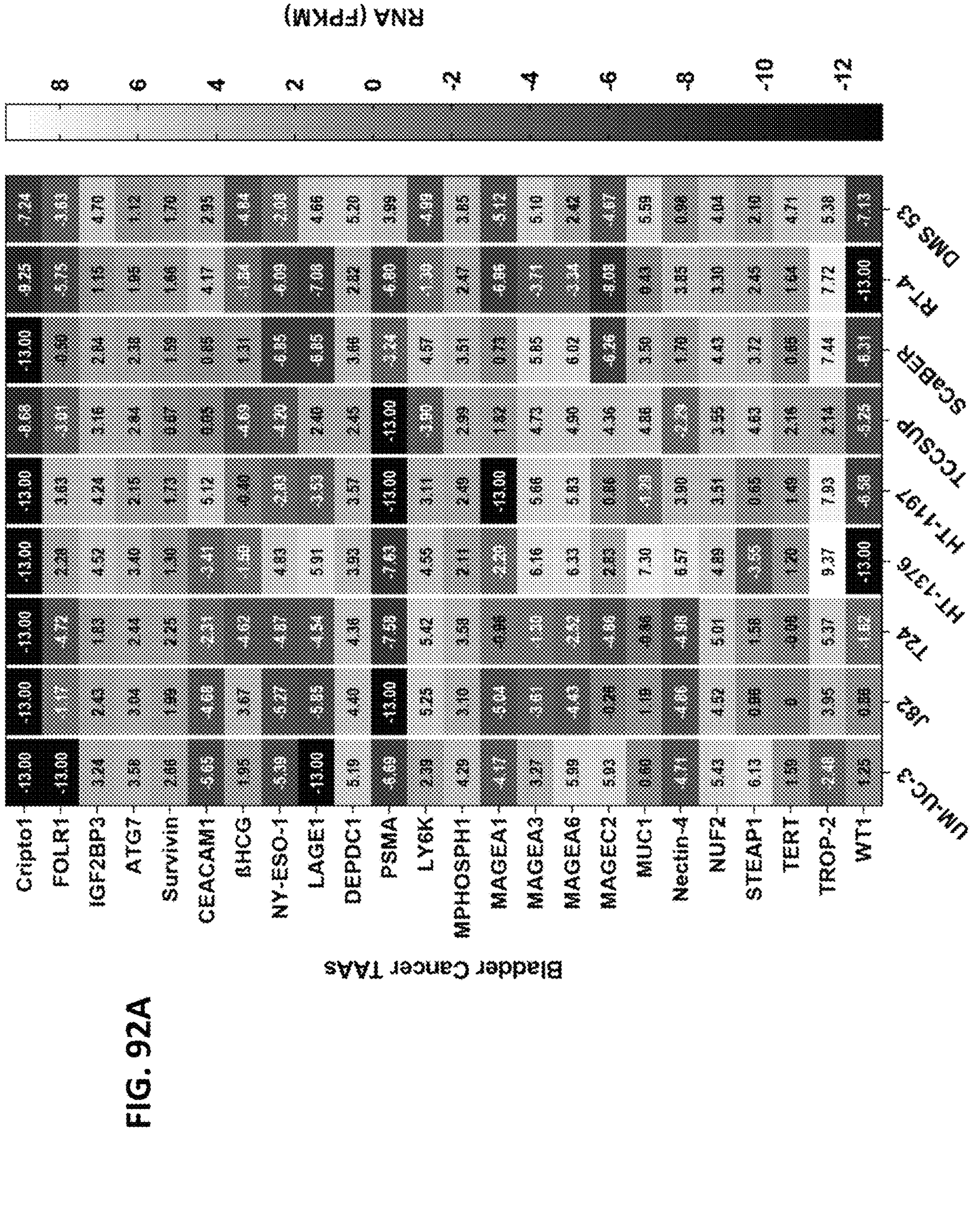
FIGS. 92A and B show endogenous expression of bladder cancer antigens (FIG. 92A) and bladder cancer CSC-like markers (FIG. 92B) by candidate UBC vaccine cell lines.
Figure 92B:
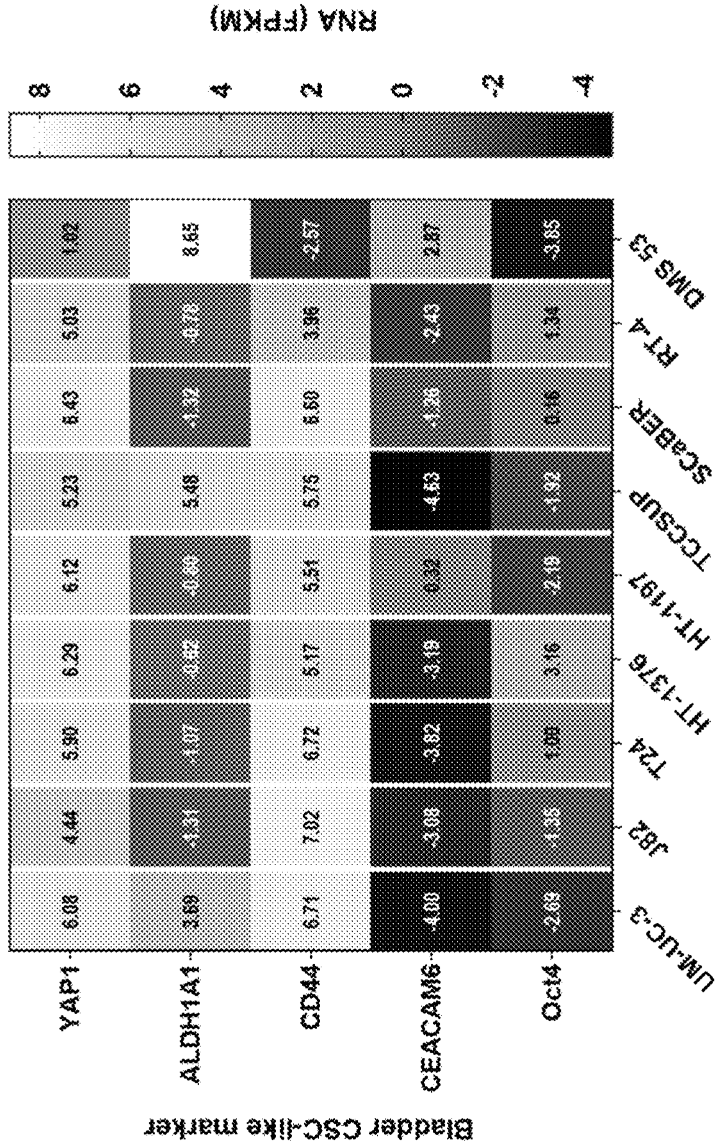

CSCs play a critical role in the metastasis, treatment resistance, and relapse of bladder cancer (Table 2). Expression of TMs and UBC specific CSC-like markers by candidate component cell lines was determined by RNA expression data sourced from the Broad Institute Cancer Cell Line Encyclopedia (CCLE). The HGNC gene symbol was included in the CCLE search and mRNA expression was downloaded for each TAA. Expression of a TAA or CSC marker by a cell line was considered positive if the RNA-seq value was greater than one. Selection criteria identified eight candidate UBC vaccine components for further evaluation: UM-UC-3, J82, T24, HT-1376, HT-1197, TCCSUP, SCaBER, and RT-4. The eight candidate component cell lines expressed nine to seventeen TAAs (FIG. 92A) and two or three CSC markers (FIG. 92B). As described herein, the CSC-like cell line DMS 53 is included as one of the six vaccine cell lines and expressed fifteen UBC TAAs and three UBC CSC-like markers.

Immunogenicity of the eight unmodified UBC vaccine component candidates was evaluated by IFNγ ELISpot as described in Example 9 using three HLA diverse healthy donors (n=4 per donor). HLA-A and HLA-B alleles for Donor 1 were A*02:01 B*35:02 and A*02:01 B*49:01. HLA-A and HLA-B alleles for Donor 2 were A*32:01 B*27:05 and A*68:05 B*39:08. HLA-A alleles for Donor 3 were A*01:01 and A*03:01. HLA-B typing was not available for Donor 3. J82 (5,420±577 SFU), TCCSUP (3,504±702 SFU) and SCaBER (2,903±654 SFU) were more immunogenic than UM-UC-3 (1,022±284 SFU), T24 (1,492±211 SFU), HT-1376 (922±230 SFU), HT-1197 (63±63 SFU) and RT-4 (13±13 SFU) (FIG. 93A).

Immunogenicity of J82 and TCCSUP was evaluated in eight different combinations of three component cell lines, four combinations contained J82 and four combinations contained TCCSUP (FIG. 93C). IFNγ responses were determined against the three component cell lines within in the eight potential vaccine cocktails by IFNγ ELISpot as described in Example 8 using the three healthy donors (n=4/donor). HLA-A and HLA-B alleles for Donor 1 were A*01:01 B*08:01 and A*02:01 B*15:01. HLA-A and HLA-B alleles for Donor 2 were A*03:01 B*15:01 and A*24:02 B*07:02. HLA-typing was only available for one HLA-A allele for Donor 3, which was A*02:01. Donor 3 HLA-B alleles were B*15:01 and B*51:01. IFNγ responses were detected for all eight cocktails and to each cell line component in each cocktail. Responses to the individual cocktail component cell lines were notably decreased compared to IFNγ responses detected for single cell line components (FIG. 93B). In all eight combinations evaluated, TCCSUP remained the most immunogenic. HT-1197 was poorly immunogenic alone and in three cell line component cocktails and therefore not included in the UBC vaccine.

The immunogenicity of J82, T24 and SCaBER was similar when evaluated in three cell line component cocktails. Of these three cell lines, T24 endogenously expressed the least number of TAAs (nine TAAs>1.0 FPKM) (FIG. 92A) and was excluded from the UBC vaccine. J82 and SCaBER were selected to express UBC antigens by lentiviral transduction as described above and placed in separate vaccine cocktails to mitigate any potential for antigen competition when delivered in the same vaccine cocktail. TCCSUP and J82 were selected to be included in vaccine cocktail A and SCaBER selected to be included in vaccine cocktail B as described above and further herein.

The cells in the vaccine described herein were selected to express a wide array of TAAs, including those known to be important specifically for UBC antitumor responses, such as Cripto1 or DEPDC1, and also TAAs known to be important for targets for UBC and other solid tumors, such TERT. As shown herein, to further enhance the array of TAAs, J82 was modified to express modPSMA and modCripto1 (TDGF1) and SCaBER was modified to express modWT1 and modFOLR1 (FBP). Cripto1 (TDGF1) was not endogenously expressed in any of the six component cell lines at >1.0 FPKM. PSMA, FOLR1 (FBP) and WT1 were endogenously expressed by one of the six component cell lines at >1.0 FPKM (FIG. 94A).

Expression of the transduced antigens modPSMA (FIG. 95A) and modCripto1 (modTDGF1) (FIG. 95B) by J82 (SEQ ID NO: 53; SEQ ID NO: 54), and modWT1 (FIG. 95C) and modFOLR1 (modFBP) (FIG. 94D) (SEQ ID NO: 51; SEQ ID NO: 52) by SCaBER, were detected by flow cytometry or RT-PCR as described in Example 29 and herein. The modPSMA and Cripto1 (TDGF1) antigens are encoded in the same lentiviral transfer vector separated by a furin cleavage site (SEQ ID NO: 53; SEQ ID NO: 54). The modWT1 and modFOLR1 (FBP) are encoded in the same lentiviral transfer vector separated by a furin cleavage site (SEQ ID NO: 52).

Because of the need to maintain maximal heterogeneity of antigens and clonal subpopulations the comprise each cell line, the gene modified cell lines utilized in the present vaccine have been established using antibiotic selection and flow cytometry and not through limiting dilution subcloning.

Figure 94A:
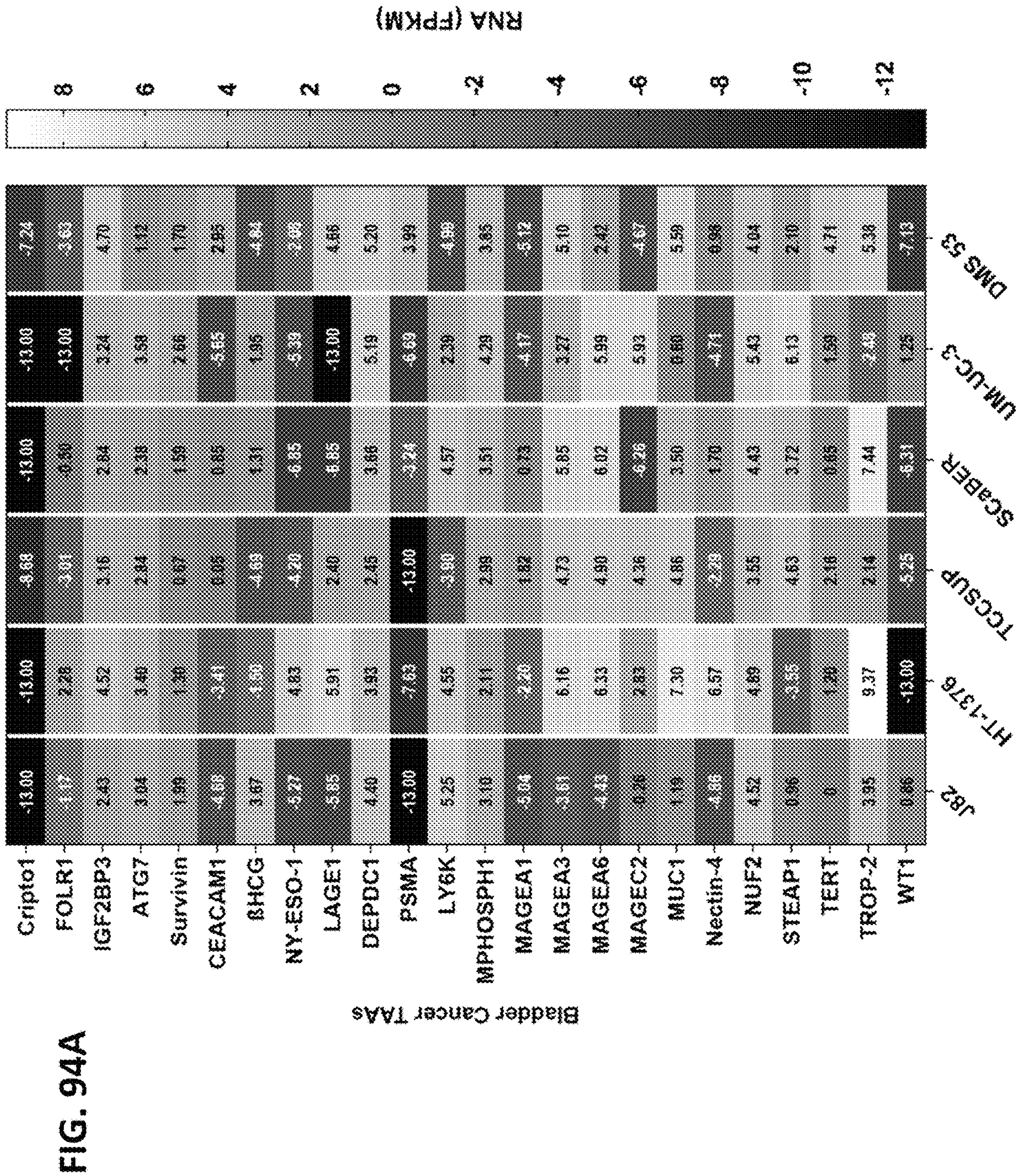
FIGS. 94A-C show endogenous expression of bladder cancer antigens by UBC vaccine cell lines (94A), expression of these antigens patient tumors (FIG. 94B) and the number of bladder cancer antigens expressed by the UBC vaccine cell lines also expressed in bladder cancer patient tumors (FIG. 94C).
Figure 94B:
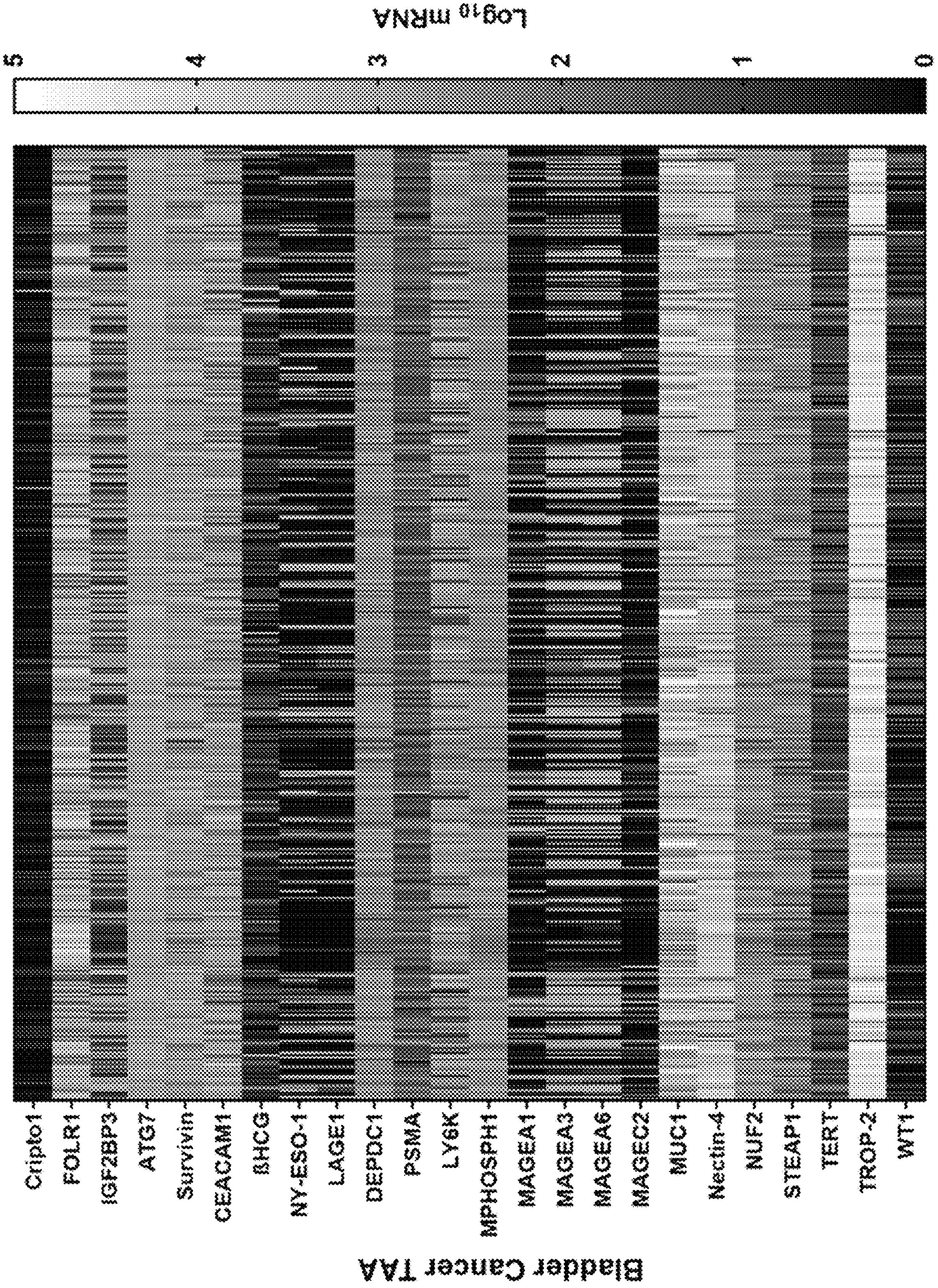
Figure 94C:
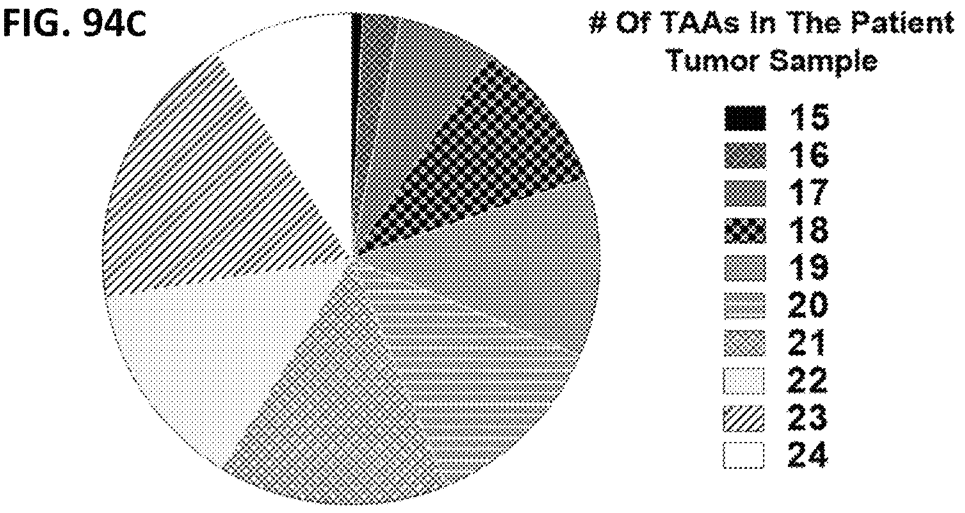

The endogenous mRNA expression of twenty-four representative UBC TAAs in the present vaccine are shown in FIG. 94A. The present vaccine, after introduction antigens described above, expresses of all identified twenty-four commonly targeted and potentially clinically relevant TAAs capable of inducing a UBC antitumor response. Some of these TAAs are known to be primarily enriched in UBC tumors and some can also induce an immune response to UBC and other solid tumors. RNA abundance of the twenty-four prioritized UBC TAAs was determined in 407 UBC patient samples with available mRNA data expression as described in Example 29 (FIG. 94B). Fifteen of the prioritized UBC TAAs were expressed by 100% of samples, 16 TAAs were expressed by 99.3% of samples, 17 TAAs were expressed by 96.8% of samples, 18 TAAs were expressed by 90.7% of samples, 19 TAAs were expressed by 80.3% of samples, 20 TAAs were expressed by 68.6% of samples, 21 TAAs were expressed by 56.3% of samples, 22 TAAs were expressed by 41.3% of samples, 23 TAAs were expressed by 27.5% of samples and 24 TAAs were expressed by 9.1% of samples (FIG. 94C). Thus, provided herein are two compositions comprising a therapeutically effective amount of three cancer cell lines, wherein the combination of the cell lines, a unit dose of six cell lines, comprises cells that express at least 15 TAAs associated with a subset of UBC cancer subjects intended to receive said composition. Based on the expression and immunogenicity data presented herein, the cell lines identified in Table 75 were selected to comprise the present UBC vaccine.

TABLE 75

Bladder vaccine cell lines and histology

| Cocktail | Cell Line Name | Histology |
|---|---|---|
| A | J82 | Bladder Transitional Cell Carcinoma |
| A | HT-1376 | Bladder Grade III Carcinoma |
| A | TCCSUP | Bladder Anaplastic Grade IV Transitional Cell Carcinoma |
| B | SCaBER | Bladder Squamous Cell Carcinoma |
| B | UM-UC-3 | Bladder Transitional Cell Carcinoma |
| B | DMS 53 | Lung Small Cell Carcinoma |

Reduction of CD276 Expression

The J82, HT-1376, TCCSUP, SCaBER, UM-UC-3 and DMS 53 component cell lines expressed CD276 and expression was knocked out by electroporation with ZFN as described in Example 13 and elsewhere herein. Because it was desirable to maintain as much tumor heterogeneity as possible, the electroporated and shRNA modified cells were not cloned by limiting dilution. Instead, the cells were subjected to multiple rounds of cell sorting by FACS as described in Example 13. Expression of CD276 was determined as described in Example 29. Reduction of CD276 expression is described in Table 76. These data show that gene editing of CD276 with ZFN resulted in greater than 99.8% CD276-negative cells in all six vaccine component cell lines.

TABLE 76

Reduction of CD276 expression

| Cell line | Parental Cell Line MFI | Modified Cell Line MFI | % Reduction CD276 |
|---|---|---|---|
| J82 | 13,721 | 27 | 99.8 |
| HT-1376 | 27,871 | 0 | >99.9 |
| TCCSUP | 21,401 | 37 | 99.8 |
| SCaBER | 31,950 | 29 | 99.9 |
| UM-UC-3 | 2,135 | 2 | 99.9 |
| DMS 53 | 11,928 | 24 | 99.8 |

MFI reported with isotype controls subtracted

Cytokine Secretion Assays for TGFβ1, TGFβ2, GM-CSF, and IL-12 were Completed as Described in Example 29.

shRNA Downregulates TGF-6 Secretion

Following CD276 knockout, TGFβ1 and TGFβ2 secretion levels were reduced using shRNA and resulting levels determined as described in Example 29. The J82, HT-1376 and TCCSUP parental cell lines in UBC vaccine-A secreted measurable levels of TGFβ1 and TGFβ2. J82 secreted low levels of TGFβ1 and was not modified to reduce TGFβ1 secretion. The SCaBER and UM-UC-3 component cell lines of UBC vaccine-B secreted measurable levels of TGFβ1. SCaBER also secreted measurable levels of TGFβ2. Reduction of TGFβ2 secretion by the DMS 53 cell line is described in Example 26 and resulting levels determined as described above and herein.

The HT-1376, TCCSUP, SCaBER component cell lines were transduced with TGFβ1 shRNA to decrease TGFβ1 secretion concurrently with the transgene to increase expression of membrane bound CD40L as described in Example 29. HT-1376, TCCSUP, SCaBER were also transduced with lentiviral particles encoding TGFβ2 shRNA to decrease the secretion of TGFβ2 and concurrently increase expression of GM-CSF (SEQ ID NO: 6) as described in Example 29. These cells are described by the clonal designation DK6. The UM-UC-3 cell line was transduced with TGFβ1 shRNA to decrease TGFβ1 secretion and concurrently increase expression of membrane bound CD40L as described in Example 29. These cells, modified to reduce TGFβ1 secretion and not TGFβ2 secretion, are described by the clonal designation DK2. J82 was transduced with lentiviral particles encoding TGFβ2 shRNA to decrease the secretion of TGFβ2 and concurrently increase expression of GM-CSF (SEQ ID NO: 6) as described in Example 29. DMS 53 was modified with shRNA to reduce secretion of TGFβ2 as described in Example 26. The J82 and DMS 53 cells modified to reduce secretion of TGFβ2 and not TGFβ1 are described by the clonal designation DK4.

Table 77 shows the percent reduction in TGFβ1 and/or TGFβ2 secretion in gene modified component cell lines compared to unmodified, parental, cell lines. Gene modification resulted in at least 78% reduction of TGFβ1 secretion. Gene modification of TGFβ2 resulted in at least 51% reduction in secretion of TGFβ2.

TABLE 77

TGF-β Secretion (pg/$10^6$ cells/24 hr) in Component Cell Lines

| Cell Line | Cocktail | Clone | TGFβ1 | TGFβ2 |
|---|---|---|---|---|
| J82 | A | Wild type | *≤24 | 955 ± 462 |
| J82 | A | DK4 | NA | *<8 |
| J82 | A | Percent reduction | NA | ≥99% |
| HT-1376 | A | Wild type | 817 ± 206 | 230 ± 86 |
| HT-1376 | A | DK6 | *≤49 | *≤23 |
| HT-1376 | A | Percent reduction | ≥94% | ≥90% |
| TCCSUP | A | Wild type | 2,273 ± 502 | 675 ± 157 |
| TCCSUP | A | DK6 | 133 ± 26 | 62 ± 24 |
| TCCSUP | A | Percent reduction | 94% | 91% |
| SCaBER | B | Wild type | 85 ± 13 | 1,954 ± 341 |
| SCaBER | B | DK6 | *≤18 | 224 ± 35 |
| SCaBER | B | Percent reduction | 79% | 89% |
| UM-UC-3 | B | Wild type | 375 ± 80 | *≤8 |
| UM-UC-3 | B | DK2 | 81 ± 12 | NA |
| UM-UC-3 | B | Percent reduction | 78% | NA |
| DMS 53 | B | Wild type | 106 ± 10 | 486 ± 35 |
| DMS 53 | B | DK4 | NA | 238 ± 40 |
| DMS 53 | B | Percent reduction | NA | 51% |

DK6: TGFβ1/TGFβ2 double knockdown;
DK4: TGFβ2 single knockdown;
DK2: TGFβ1 single knockdown;
* = estimated using LLD, not detected;
NA = not applicable.

Based on a dose of $5\times10^5$ of each component cell line, the total TGFβ1 and TGFβ2 secretion by the modified UBC vaccine-A and UBC vaccine-B and respective unmodified parental cell lines are shown in Table 78. The secretion of TGFβ1 by UBC vaccine-A was reduced by 93% pg/dose/24 hr and TGFβ2 by 95% pg/dose/24 hr. The secretion of TGFβ1 by UBC vaccine-B was reduced by 64% pg/dose/24 hr and TGFβ2 by 81% pg/dose/24 hr.

TABLE 78

Total TGF-β Secretion (pg/dose/24 hr) in UBC vaccine-A and UBC vaccine-B

| Cocktail | Clones | TGFβ1 | TGFβ2 |
|---|---|---|---|
| A | Wild type | 1,557 | 930 |
| | DK4/DK6 | 103 | 47 |
| | Percent reduction | 93% | 95% |

TABLE 78-continued

Total TGF-β Secretion (pg/dose/24 hr) in UBC vaccine-A and UBC vaccine-B

| Cocktail | Clones | TGFβ1 | TGFβ2 |
|---|---|---|---|
| B | Wild type | 283 | 1,224 |
| | DK2/DK4/DK6 | 103 | 235 |
| | Percent reduction | 64% | 81% |

GM-CSF Secretion

The HT-1376, TCCSUP, SCaBER and J82 cell lines were transduced with lentiviral particles containing both TGFβ2 shRNA and the gene to express GM-CSF (SEQ ID NO: 6) as described above. The UM-UC-3 cell line was transduced with lentiviral particles to only express GM-CSF (SEQ ID NO: 7). DMS 53 was modified to secrete GM-CSF as described in Example 24 and elsewhere herein. The results are shown in Table 79 and described below.

Secretion of GM-CSF increased at least 2,700-fold in all modified component cell lines compared to unmodified, parental cell lines. Fold increase in expression of GM-CSF by the UBC vaccine-A component cell lines was as follows: J82 increased 2,700-fold relative to the unmodified cell line (≤0.010 ng/$10^6$ cells/24 hr); HT-1376 increased 6,500-fold relative to the unmodified cell line (≤0.030 ng/$10^6$ cells/24 hr); TCCSUP increased 2,500-fold relative to the unmodified cell line (≤0.012 ng/$10^6$ cells/24 hr). Fold increase in expression of GM-CSF by the UBC vaccine-B component cell lines was as follows: SCaBER increased 12,556-fold relative to the unmodified cell line (≤0.009 ng/$10^6$ cells/24 hr); UM-UC-3 increased 15,500-fold relative to the unmodified cell line (≤0.008 ng/$10^6$ cells/24 hr); DMS 53 increased 39,450-fold relative to the unmodified cell line 0.004 ng/$10^6$ cells/24 hr).

TABLE 79

GM-CSF Secretion in Component Cell Lines

| Cell Line | GM-CSF (ng/$10^6$ cells/24 hr) | GM-CSF (ng/dose/24 hr) |
|---|---|---|
| J82 | 27 ± 8 | 14 |
| HT-1376 | 195 ± 59 | 98 |
| TCCSUP | 30 ± 9 | 15 |
| Cocktail A Total | 252 | 127 |
| SCaBER | 113 ± 30 | 57 |
| UM-UC-3 | 124 ± 35 | 62 |
| DMS 53 | 158 ± 15 | 79 |
| Cocktail B Total | 395 | 198 |

Based on a dose of $5\times10^5$ of each component cell line, the total GM-CSF secretion for UBC vaccine-A was 127 ng per dose per 24 hours. The total GM-CSF secretion for UBC vaccine-B was 198 ng per dose per 24 hours. The total GM-CSF secretion per dose was therefore 325 ng per 24 hours.

Membrane Bound CD40L (CD154) Expression

Figure 96:
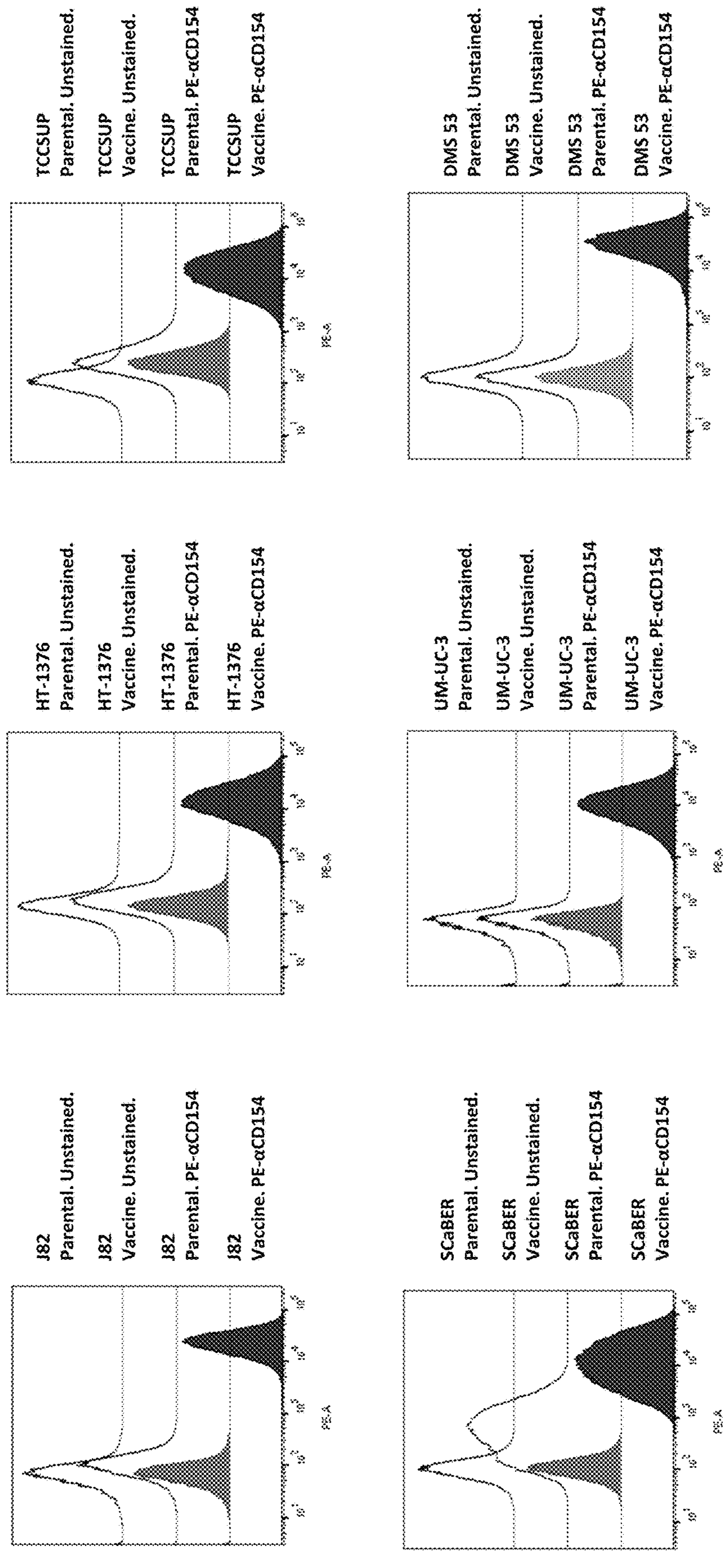
FIG. 96 shows expression of membrane bound CD40L by the UBC vaccine component cell lines.

The component cell lines were transduced with lentiviral particles to express membrane bound CD40L vector as described above. The methods to detect expression of CD40L by the five UBC cell line components are described in Example 29. Modification of DMS 53 to express membrane bound CD40L is described in Example 15. Evaluation of membrane bound CD40L by all six vaccine component cell lines is described below. The results shown in FIG. 96 and described below demonstrate CD40L membrane expression was substantially increased in all six UBC vaccine component cell lines.

Expression of membrane bound CD40L increased at least 851-fold in all component cell lines compared to unmodified, parental cell lines. In UBC vaccine-A component cell lines expression of CD40L increased 37,196-fold by J82 (37,196 MFI) compared to the parental cell line (0 MFI), 851-fold by HT-1376 (37,444 MFI) compared to the parental cell line (44 MFI), and 1,062-fold by TCCSUP (199,687 MFI) compared to the parental cell line (188 MFI). In UBC vaccine-B component cell lines expression of CD40L increased 13,772-fold by SCaBER (13,772 MFI) compared to the parental cell line (0 MFI), 11,301-fold by UM-UC-3 (11,301 MFI) compared to the parental cell line (0 MFI), and 88,261-fold by DMS 53 compared to the parental cell line (0 MFI).

IL-12 Expression

The component cell lines were transduced with the IL-12 vector as described in Example 17 and resulting IL-12 p70 expression determined as described above and herein. The results are shown in Table 80 and described below.

Secretion of IL-12 increased at least 1,400-fold in all component cell lines modified to secrete IL-12 p70 compared to unmodified, parental cell lines. In UBC vaccine-A component cell lines, secretion of IL-12 increased 3,500-fold by J82 compared to the parental cell line (≤0.004 ng/$10^6$ cells/24 hr), 609,000-fold by HT-1376 compared to the parental cell line (≤0.001 ng/$10^6$ cells/24 hr), and 1,400-fold by TCCSUP compared to the parental cell line (≤0.005 ng/$10^6$ cells/24 hr). In UBC vaccine-B component cell lines expression of IL-12 increased 6,750-fold by SCaBER compared to the parental cell line (≤0.004 ng/$10^6$ cells/24 hr) and 6,000-fold by UM-UC-3 compared to the parental cell line (≤0.003 ng/$10^6$ cells/24 hr). DMS 53 was not modified to secrete IL-12.

TABLE 80

IL-12 Secretion in Component Cell Lines

| Cell Line | IL-12 (ng/$10^6$ cells/24 hr) | IL-12 (ng/dose/24 hr) |
|---|---|---|
| J82 | 14 ± 4 | 7 |
| HT-1376 | 609 ± 51 | 305 |
| TCCSUP | 7 ± 3 | 4 |
| Cocktail A Total | 630 | 316 |
| SCaBER | 27 ± 12 | 14 |
| UM-UC-3 | 18 ± 19 | 9 |
| DMS 53 | NA | NA |
| Cocktail B Total | 45 | 23 |

Based on a dose of 5×$10^5$ of each component cell line, the total IL-12 secretion for UBC vaccine-A was 316 ng per dose per 24 hours. The total IL-12 secretion for UBC vaccine-B was 23 ng per dose per 24 hours. The total IL-12 secretion per dose was therefore 339 ng per 24 hours.

Stable Expression of modPSMA and modCripto1 (modTDGF1) by the J82 Cell Line

As described above, the cells in the vaccine described herein were selected to express a wide array of TAAs, including those known to be important to antitumor immunity. To further enhance the array of antigens, the J82 cell line that was modified to reduce the secretion of TGFβ2, reduce the expression of CD276, and to express GM-CSF, membrane bound CD40L and IL-12 was also transduced with lentiviral particles expressing the modPSMA and modCripto1 antigens. The genes encoding the modPSMA and modCripto1 antigens are linked by a furin cleavage site (SEQ ID NO: 53, SEQ ID NO: 54).

Figure 95A:
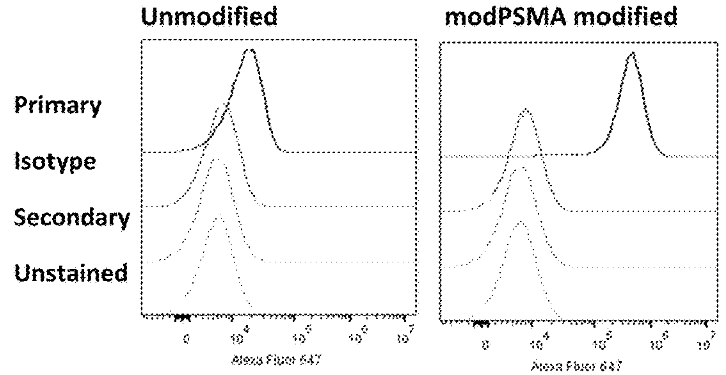
FIGS. 95A-H show the expression of and IFNγ responses to antigens introduced in the UBC vaccine cell lines compared to unmodified controls. Expression of modPSMA (FIG. 95A) and modCripto1 (FIG. 95B) by J82 and IFNγ responses to PSMA (FIG. 95E) and Cripto1 (FIG. 95F) induced by UBC-vaccine A. Expression of modWT1 (FIG. 95C) and modFOLR1 (FIG. 95D) by SCaBER and IFNγ responses to WT1 (FIG. 95G) and FOLR1 (FIG. 95H) in UBC-vaccine B.
Figure 95B:
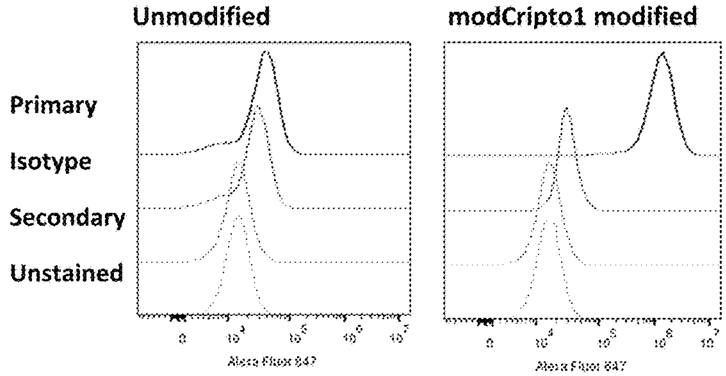
Figure 95C:
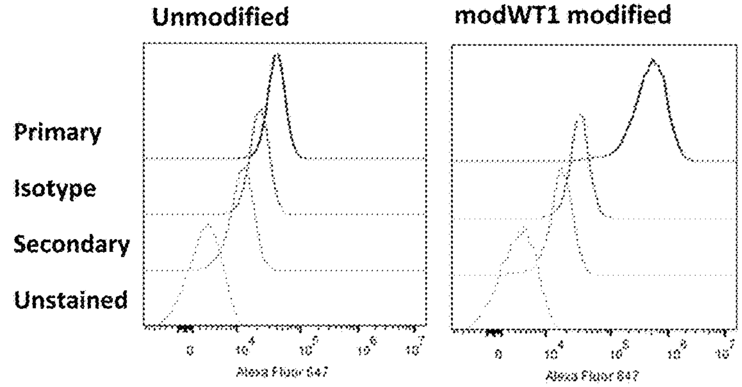

The expression of modPSMA by J82 was characterized by flow cytometry. Unmodified and antigen modified cells were stained intracellular with 0.03 μg/test anti-mouse IgG1 anti-PSMA antibody (Abcam, ab268061) followed by 0.125 ug/test AF647-conjugated goat anti-mouse IgG1 antibody (BioLegend #405322). Expression of modPSMA was increased in the modified cell line (249,632 MFI) 60-fold over that of the parental cell line (16,481 MFI) (FIG. 95A). Expression of modCripto1 by J82 was also characterized by flow cytometry. Cells were first stained intracellular with rabbit IgG anti-Cripto1 antibody (Abcam, ab108391) (0.03 μg/test) followed by AF647-conjugated donkey anti-rabbit IgG1 antibody (BioLegend #406414) (0.125 μg/test). Expression of modCripto1 increased in the modified cell line (3,330,400 MFI) 255-fold over the unmodified cell line (13,042 MFI) (FIG. 94B).

Stable Expression of modWT1 and modFOLR1 (modFBP) by the SCaBER Cell Line

Figure 95D:
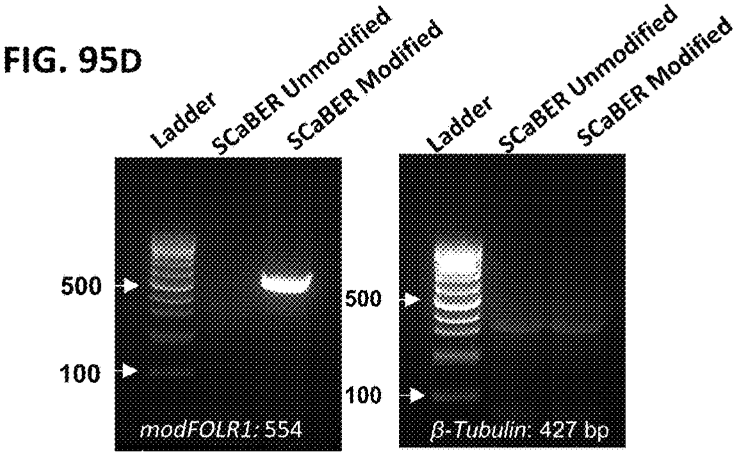

The SCaBER cell line that was modified to reduce the secretion of TGFβ1 and TGFβ2, reduce the expression of CD276, and to express GM-CSF, membrane bound CD40L, and IL-12 was also transduced with lentiviral particles expressing the modWT1 and modFOLR1 antigens (SEQ ID NO: 51, SEQ ID NO: 52). Expression of modWT1 by SCaBER was characterized by flow cytometry. Unmodified and antigen modified cells were stained intracellular with 0.03 μg/test anti-rabbit IgG1 anti-WT1 antibody (Abcam, ab89901) followed by 0.125 ug/test AF647-conjugated donkey anti-rabbit IgG1 antibody (BioLegend #406414). Expression of modWT1 increased in the modified cell line (4,121,028 MFI) 90-fold over that of the unmodified cell line (46,012 MFI) (FIG. 94C). Expression of modFOLR1 by SCaBER was determined by RT-PCR as described in Example 29 and herein. The forward primer was designed to anneal at the 56-76 bp location in the transgene (GAGAAGTGCAGACCAGAATCG (SEQ ID NO: 130)) and reverse primer designed to anneal at the 588-609 bp location in the transgene (TCTGCTGTAGTTGGACACCTTG (SEQ ID NO: 131)) yielding a 554 bp product. Control primers for β-tubulin are described in Example 29. The gene product for modFOLR1 was detected at the expected size (FIG. 95D) and mRNA increased 249,810-fold relative to the parental control.

Immune Responses to PSMA and Cripto1 (TDGF1) in UBC Vaccine-A

IFNγ responses to PSMA and Cripto1 were evaluated in the context of UBC vaccine-A as described in Example 29, and herein, in seven HLA diverse donors (n=4/donor). The HLA-A, HLA-B, and HLA-C alleles for each of the seven donors are shown in Table 81. IFNγ responses were determined by ELISpot as described in Example 29.

Figure 95H:
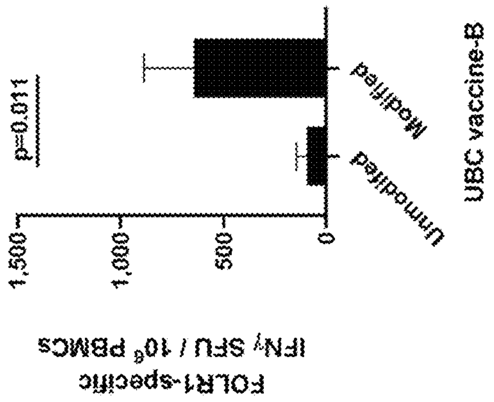
Figure 95G:
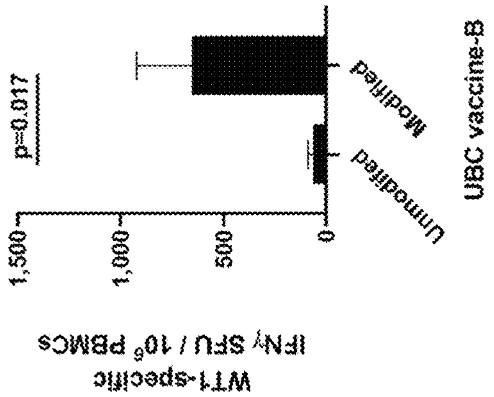
Figure 95F:
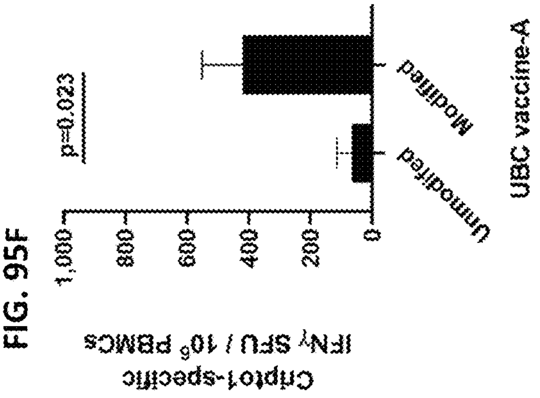
Figure 95E:
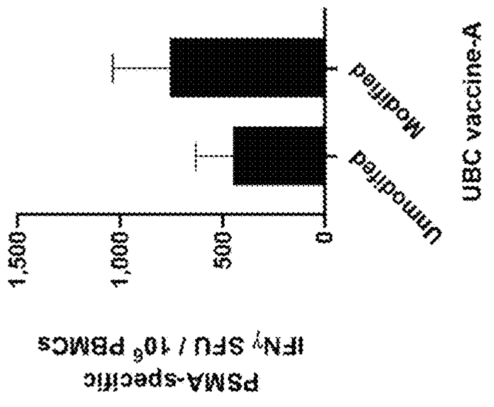

PSMA specific IFNγ responses with the were increased with the modified UBC vaccine-A (757±278 SFU) compared to the parental, unmodified UBC vaccine-A (450±179 SFU (FIG. 95E). IFNγ responses to Cripto1 were determined by ELISpot using 15-mers peptides overlapping by 9 amino acids spanning the entire length of the native Cripto1 antigen purchased from Thermo Scientific Custom Peptide Service. IFNγ responses to Cripto1 significantly increased with the modified UBC vaccine-A (420±132 SFU) compared to the unmodified UBC vaccine-A (67±47 SFU) (p=0.023, Mann-Whitney U test) (n=7) (FIG. 95F).

Immune Responses to WT1 and FOLR1 (FBP) in UBC Vaccine-B

IFNγ responses to WT1 and FOLR1 were evaluated in the context of UBC-vaccine B as described in Example 29, and herein, in seven HLA diverse donors (n=4/donor) (Table 81). IFNγ responses against WT1 and FOLR1 were determined by ELISpot using 15-mers peptides overlapping by 9 amino acids spanning the entire length of the native antigen protein purchased from Thermo Scientific Custom Peptide Service. WT1 specific IFNγ responses were significantly increased by UBC vaccine-B (654±268 SFU) compared to the unmodified UBC vaccine-B (65±23 SFU) (p=0.017, Mann-Whitney U test) (n=7) (FIG. 95G). FOLR1 specific IFNγ responses were significantly increased by UBC vaccine-B (643±244 SFU) compared to the unmodified UBC vaccine-B (95±51 SFU) (p=0.011, Mann-Whitney U test) (n=7) (FIG. 95H).

TABLE 81

Healthy Donor MHC-I characteristics

| Donor # | HLA-A | HLA-B | HLA-C |
|---|---|---|---|
| 1 | *02:01 *11:01 | *07:02 *37:02 | *06:02 *07:02 |
| 2 | *03:01 *03:01 | *07:02 *18:01 | *07:02 *12:03 |
| 3 | *02:01 *02:01 | *15:01 *51:01 | *02:02 *03:04 |
| 4 | *01:01 *30:01 | *08:01 *13:02 | *06:02 *07:02 |
| 5 | *02:01 *30:02 | *14:02 *13:02 | *08:02 *18:02 |
| 6 | *03:01 *32:01 | *07:02 *15:17 | *07:01 *07:02 |
| 7 | *02:01 *25:01 | *18:01 *27:05 | *02:02 *12:03 |

Figure 97C:
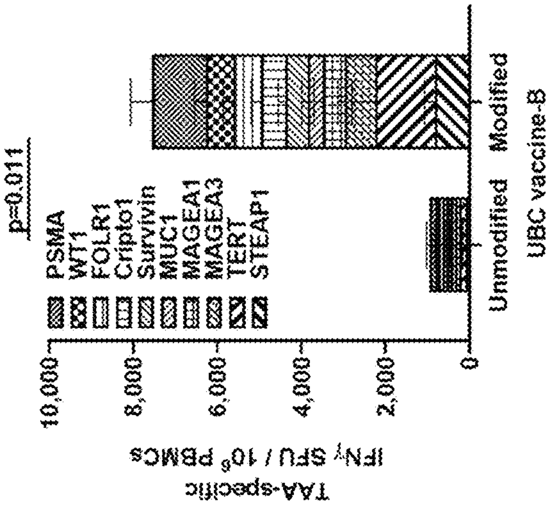
FIGS. 97A-C show antigen specific IFNγ responses induced by the unit dose of the UBC vaccine (FIG. 97A), UBC vaccine-A (FIG. 97B), and UBC vaccine-B (FIG. 97C) compared to unmodified controls.
Figure 97B:
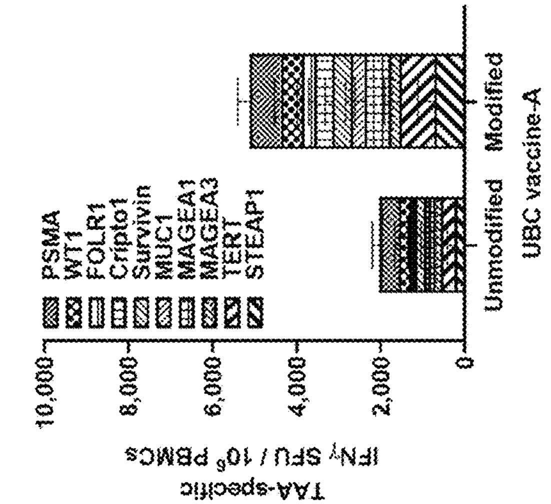
Figure 97A:
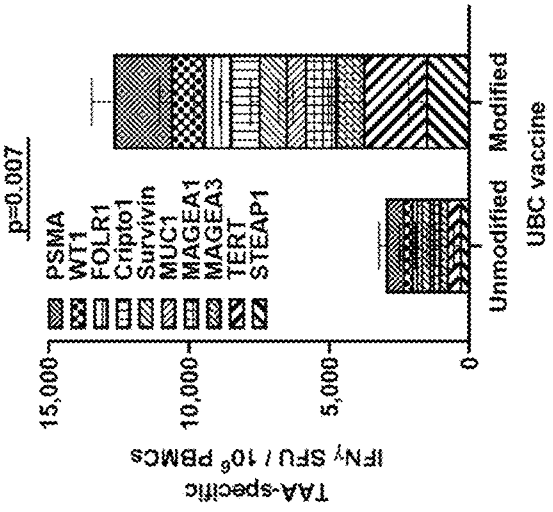
Figure 98:
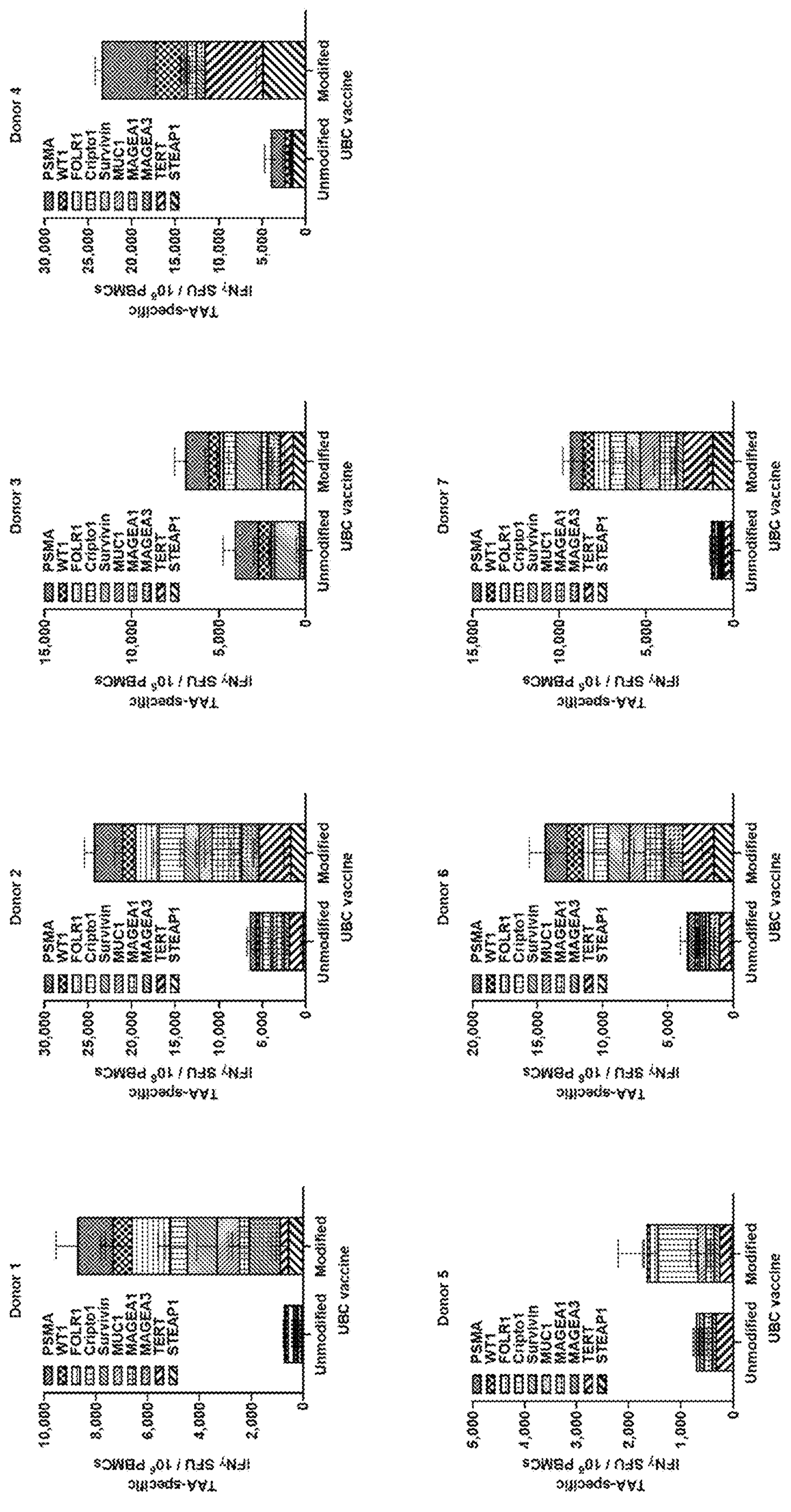
FIG. 98 shows antigen specific IFNγ responses induced by the unit dose of the UBC vaccine in individual donors compared to unmodified controls.

FIG. 97 demonstrates the UBC vaccine is capable of inducing antigen specific IFNγ responses in seven HLA-diverse donors to ten UBC antigens that are 4.3-fold more robust (12,706±3,223 SFU) compared to the unmodified parental control (2,986±813 SFU) (p=0.007, Mann-Whitney U test) (n=7) (FIG. 97A) (Table 82). The unit dose of UBC vaccine-A and UBC vaccine-B elicited IFNγ responses to eight antigens in two donors, nine antigens in one donor and ten antigens in four donors (FIG. 98). UBC vaccine-A and UBC vaccine-B independently demonstrated a 2.5-fold and 7.9-fold increase antigen specific responses compared to parental controls, respectively. Specifically, UBC vaccine-A elicited 5,140±1,422 SFU compared to the unmodified controls (2,027±573 SFU) (FIG. 97B). For UBC vaccine-A, one donor responded to four antigens, one donor responded to six antigens, one donor responded to seven antigens, one donor responded to seven antigens, and three donors responded ten antigens. UBC vaccine-B elicited 7,565±1,933 SFU compared to parental controls (959±331 SFU) (p=0.011, Mann-Whitney U test) (FIG. 97C). For UBC vaccine-B, one donor responded to four antigens, one donor responded to eight antigens, one donor responded to nine antigens, and four donors responded to ten antigens. Described above are two compositions comprising a therapeutically effective amount of three cancer cell lines, a unit dose of six cell lines, wherein said unit dose is capable of eliciting an immune response 4.3-fold greater than the unmodified composition specific to at least eight TMs expressed in UBC patient tumors. UBC vaccine-A increased IFNγ responses to at least four TMs 2.5-fold and UBC vaccine-B increased IFNγ responses 7.9-fold to at least four TMs.

TABLE 82

IFNγ Responses to unmodified and modified UBC vaccine components

| | Unmodified (SFU ± SEM) | | | Modified (SFU ± SEM) | | |
|---|---|---|---|---|---|---|
| Donor (n = 4) | UBC vaccine-A | UBC vaccine-B | UBC Vaccine | UBC vaccine-A | UBC vaccine-B | UBC Vaccine |
| 1 | 319 ± 71 | 415 ± 18 | 734 ± 78 | 2,058 ± 1,247 | 6,667 ± 4,459 | 8,725 ± 5,658 |
| 2 | 3,568 ± 268 | 2,905 ± 300 | 6,473 ± 128 | 9,138 ± 2,363 | 15,225 ± 1,123 | 24,363 ± 3,099 |
| 3 | 3,270 ± 1,234 | 845 ± 339 | 4,115 ± 1,022 | 1,549 ± 343 | 5,376 ± 1,730 | 6,924 ± 1,986 |
| 4 | 3,141 ± 715 | 841 ± 527 | 3,982 ± 788 | 9,881 ± 1,359 | 13,551 ± 1,749 | 23,432 ± 2,220 |
| 5 | 318 ± 183 | 405 ± 268 | 723 ± 440 | 1,100 ± 902 | 551 ± 551 | 1,651 ± 1,452 |
| 6* | 2,945 ± 816 | 614 ± 406 | 3,559 ± 1,031 | 7,838 ± 3,795 | 6,603 ± 3,431 | 14,440 ± 7,091 |
| 7 | 628 ± 146 | 688 ± 193 | 1,315 ± 327 | 4,420 ± 1,896 | 4,985 ± 1,725 | 9,405 ± 3,522 |

*Donor 6, n = 3. All other donors, n = 4.

Cocktails Induce Immune Responses Against Relevant TAAs

The ability of UBC vaccine-A and UBC vaccine-B to induce IFNγ production against ten UBC antigens was measured by ELISpot. PBMCs from seven HLA-diverse healthy donors (Table 81) were co-cultured with autologous DCs loaded with UBC vaccine-A or UBC vaccine-B for 6 days prior to stimulation with TAA-specific specific peptide pools containing known MHC-I restricted epitopes. Peptides for stimulation of CD14-PBMCs to detect IFNγ responses to PSMA, Cripto1, WT1 and FOLR1 are described above. Additional 15-mer peptides overlapping by 11 amino acid peptide pools were sourced as follows: Survivin (thinkpeptides, 7769_001-011), MUC1 (JPT, PM-MUC1), MAGEA1 (JPT, PM-MAGEA1), MAGEA3 (JPT, PM-MAGEA3), TERT (JPT, PM-TERT) and STEAP1 (PM-STEAP1).

Based on the disclosure and data provided herein, a whole cell vaccine for Bladder Cancer comprising the six cancer cell lines, sourced from ATCC, J82 (ATCC, HTB-1), HT-1376 (ATCC, CRL-1472), TCCSUP (ATCC, HTB-5), SCaBER (ATCC, HTB-3), UM-UC-3 (ATCC, CRL-1749) and DMS 53 (ATCC, CRL-2062) is shown in Table 83. The cell lines represent five bladder cancer cell lines and one small cell lung cancer (SCLC) cell line (DMS 53 ATCC CRL-2062). The cell lines have been divided into two groupings: vaccine-A and vaccine-B. Vaccine-A is designed to be administered intradermally in the upper arm and vaccine-B is designed to be administered intradermally in the thigh. Vaccine A and B together comprise a unit dose of cancer vaccine.

TABLE 83

| Cell line nomenclature and modifications | | | | | | | | |
|---|---|---|---|---|---|---|---|---|
| Cocktail | Cell Line | TGFβ1 KD | TGFβ2 KD | CD276 KO | GM-CSF | CD40L | IL-12 | TAA(s) |
| A | J82 | ND | X | X | X | X | X | X |
| A | HT-1376 | X | X | X | X | X | X | ND |
| A | TCCSUP | X | X | X | X | X | X | ND |
| B | SCaBER | X | X | X | X | X | X | X |
| B | UM-UC-3 | X | ND | X | X | X | X | ND |
| B | DMS 53* | ND | X | X | X | X | X | ND |

ND = Not done.
*Cell lines identified as CSC-like cells.

Where indicated in the above table, the genes for the immunosuppressive factors transforming growth factor-beta 1 (TGFβ1) and transforming growth factor-beta 2 (TGFβ2) have been knocked down using shRNA transduction with a lentiviral vector. The gene for CD276 has been knocked out by electroporation using zinc-finger nuclease (ZFN) or knocked down using shRNA transduction with a lentiviral vector. The genes for granulocyte macrophage-colony stimulating factor (GM-CSF), IL-12, CD40L, modPSMA (J82), modCripto1 (modTDGF1) (J82), modWT1 (SCaBER) and modFOLR1 (modFBP) (SCaBER) have been added by lentiviral vector transduction.

The present Example thus provides re two compositions comprising a therapeutically effective amount of three cancer cell lines, a unit dose of six cancer cell lines, modified to reduce the expression of at least two immunosuppressive factors and to express at least two immunostimulatory factors. One composition, UBC vaccine-A, was modified to increase the expression of two TAAs, modPSMA and modCripto1 (modTDGF1). The second composition, UBC vaccine-B, was modified to expresses two TAAs, modWT1 and modFOLR1 (modFBP). The unit dose of six cancer cell lines expresses at least at least 15 TAAs associated with a cancer of a subset of bladder cancer subjects intended to receive said composition and induces IFNγ responses 4.3-fold greater than the unmodified composition components.

Example 33: Preparation of Ovarian Cancer (OC) Vaccine

This Example demonstrates that reduction of TGFβ1, TGFβ2, and CD276 expression with concurrent overexpression of GM-CSF, CD40L, and IL-12 in a vaccine composition of two cocktails, each cocktail composed of three cell lines for a total of 6 cell lines, significantly increased the magnitude of cellular immune responses to at least 10 OC-associated antigens in an HLA-diverse population. As described herein, the first cocktail, OC vaccine-A, is composed of cell line OVTOKO, cell line MCAS that was also modified to express modTERT, and cell line TOV-112D that was also modified to express modFSHR and modMAGEA10. The second cocktail, OC vaccine-B, is composed of cell line TOV-21G that was also modified to express modWT1 and modFOLR1 (modFBP), cell line ES-2 that was also modified to express modBORIS, and cell line DMS 53. The six component cell lines collectively express at least twenty antigens that can provide an anti-OC tumor response.

Identification of OC Vaccine Components

Initial cell line selection criteria identified thirty-six vaccine component cell lines for potential inclusion in the OC vaccine. Additional selection criteria described herein were applied to narrow the thirty-six cell lines to ten cell lines for further evaluation in immunogenicity assays. These criteria included: endogenous OC associated antigen expression, lack of expression of additional immunosuppressive factors, such as IL-10 or IDO1, expression of OC-associated CSC-like markers ALDH1A, EPCAM, CD44, CD133, CD117, Endoglin, Oct4, NANOG and SAL4, ethnicity and age of the patient from which the cell line was derived, if the cell line was derived from a primary tumor or metastatic site, and ovarian histological subtype.

Figure 99B:
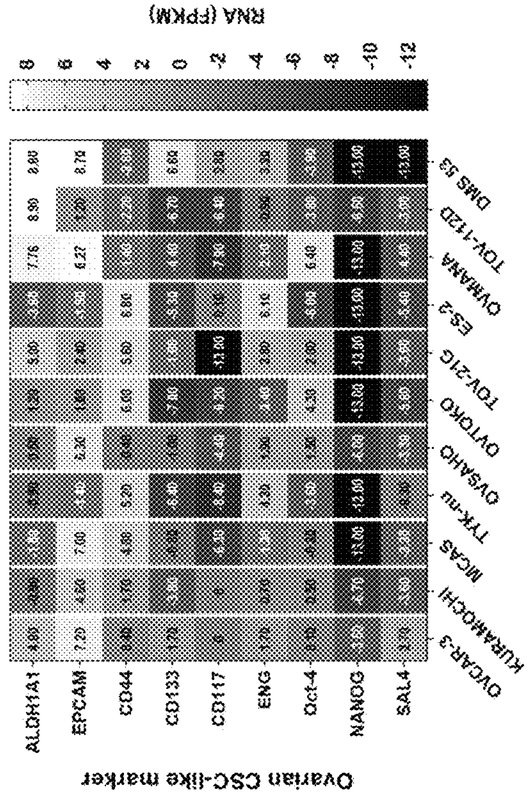
FIGS. 99A and B show endogenous expression of ovarian cancer antigens (FIG. 99A) and ovarian cancer CSC-like markers (FIG. 99B) by candidate ovarian cancer vaccine component cell lines.
Figure 99A:
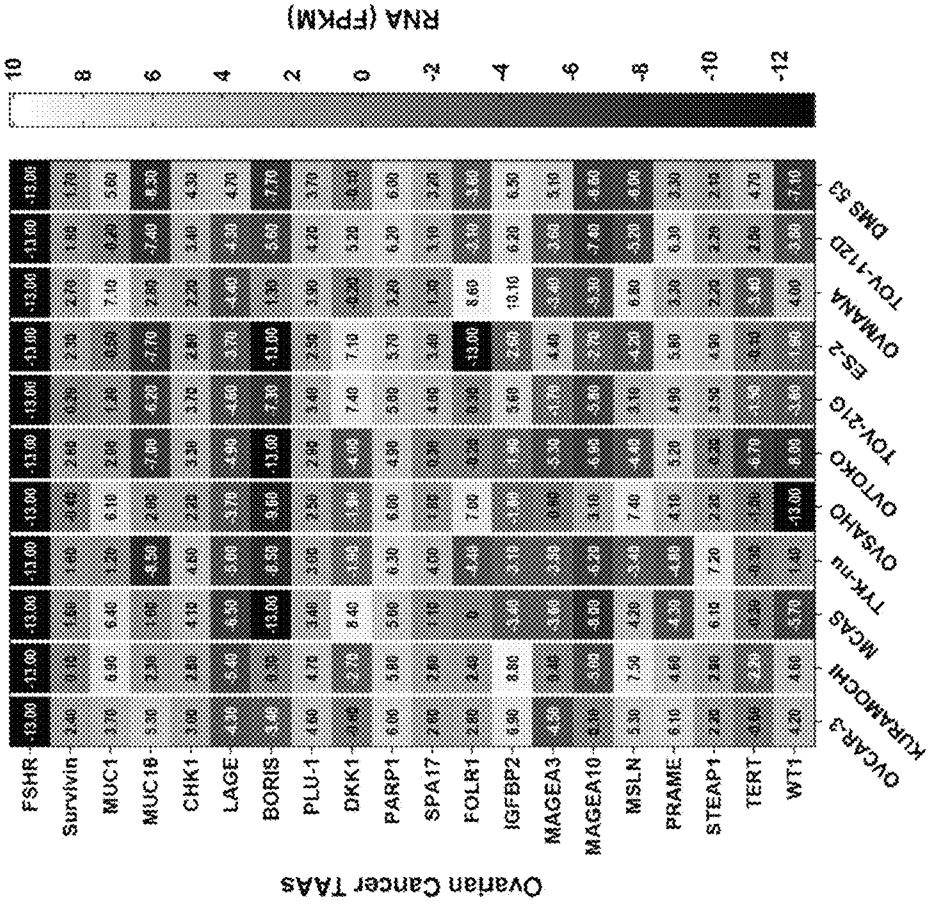

CSCs play a critical role in the metastasis, treatment resistance, and relapse of ovarian cancer (Table 2). Expression of TMs and CSC-like markers by candidate component cell lines was determined by RNA expression data sourced from the Broad Institute Cancer Cell Line Encyclopedia (CCLE). The HGNC gene symbol was included in the CCLE search and mRNA expression was downloaded for each TAA or CSC marker. Expression of a TAA or CSC marker by a cell line was considered positive if the RNA-seq value was greater than one. Selection criteria identified ten candidate OC vaccine components for further evaluation: OVCAR-3, KURAMOCHI, MCAS, TYK-nu, OVSAHO, OVTOKO, TOV-21G, ES-2, OVMANA, and TOV-112D. The ten candidate component cell lines expressed six to fourteen TAAs (FIG. 99A) and two to five CSC-like markers (FIG. 99B). As described herein, the CSC-like cell line DMS 53 is included as one of the six vaccine cell lines and expressed twelve OC TMs and five OC CSC-like markers.

Immunogenicity of the ten unmodified OC vaccine component candidates was evaluated by IFNγ ELISpot as described in Example 9 for three HLA diverse healthy donors (n=4 per donor). HLA-A and HLA-B alleles for the three Donors were as follows: Donor 1, A*02:01 B*35:01 and A*31:01 B*35:03; Donor 2, A*01:01 B*07:02 and A*30:01 B*12:02; Donor 3, A*02:01 B*15:07 and A*24:02 B*18:01. KURAMOCHI (1,896±421 SFU), OVTOKO (2,124±591 SFU) and TOV-21G (1,559±273 SFU) were more immunogenic than OVCAR-3 (54±24 SFU), MCAS (420±218 SFU), TYK-nu (339±109 SFU), OVSAHO (404±163 SFU), ES-2 (215±117 SFU), OVMANA (46±29) and TOV-112D (89±62) (FIG. 100A).

Immunogenicity of KURAMOCHI, OVTOKO and TOV-21G was evaluated in eleven different combinations of three component cell lines, three combinations contained KURAMOCHI, four combinations contained OVTOKO and four combinations contained TOV-21G (FIG. 100C). OVMANA (JCRB, JCRB1045) was not included in the eleven cocktails due to poor viability post-cryopreservation noted by JCRB that was confirmed prior to completion of the experiments described herein. IFNγ responses were determined against three component cell lines in the eleven potential vaccine cocktails by IFNγ ELISpot as described in Example 8 for three healthy donors (n=4/donor). HLA-A and HLA-B alleles for the Donors were as follows: Donor 1, A*02:01 B*07:02 and A*23:01 B*14:02; Donor 2, A*32:01 B*27:05 and A*68:05 B*39:08; Donor 3, A*02:02 B*15:03 and A*30:02 B*57:03. IFNγ responses were detected for all eleven cocktails and to each cell line component in each cocktail. IFNγ responses against most cocktail component cell lines were similar or notably increased compared to responses detected for single cell lines. In all eleven combinations evaluated, KURAMOCHI, OVTOKO and TOV-21G remained the most immunogenic (FIG. 100B). KURAMOCHI was not selected for inclusion in the final OC vaccine due to potential large-scale manufacturing concerns based on growth morphology following genetic modifications. OVTOKO and TOV-21G were selected to be included in vaccine cocktail A and vaccine cocktail B, respectively, as described further herein.

The cells in the vaccine described herein were selected to express a wide array of TAAs, including those known to be important specifically for OC antitumor responses, such as FOLR1 or FSHR, and also TAAs known to be important for targets for OC and other solid tumors, such TERT.

As shown herein, to further enhance the array of TAAs, MCAS was modified to express modTERT, TOV-112D was modified to express modFSHR and modMAGEA10, TOV-21G was modified to express modWT1 and modFOLR1 (modFBP) and ES-2 was modified to express modBORIS. FSHR, MAGEA10, WT1, FOLR1 and BORIS were not endogenously expressed in the six component cell lines at >1.0 FPKM. TERT was endogenously expressed by two of the six component cell lines at >1.0 FPKM (FIG. 101A).

Figure 112A:
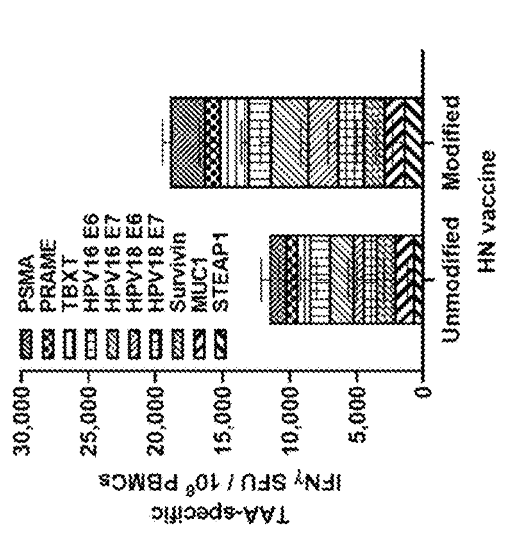
FIGS. 112A-F show antigen specific IFNγ responses induced by the unit dose of the HN vaccine (FIG. 112A) all HN antigens and non-viral HN antigens (FIG. 112D), HN vaccine-A (FIG. 112B) to all HN antigens and to non-viral HN antigens (FIG. 112E) and HN vaccine-B to all HN antigens (FIG. 112C) and non-viral HN antigens (FIG. 112F) compared to unmodified controls.
Figure 112B:
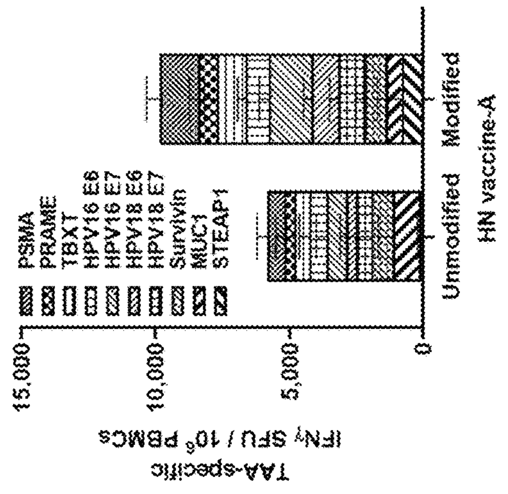
Figure 112C:
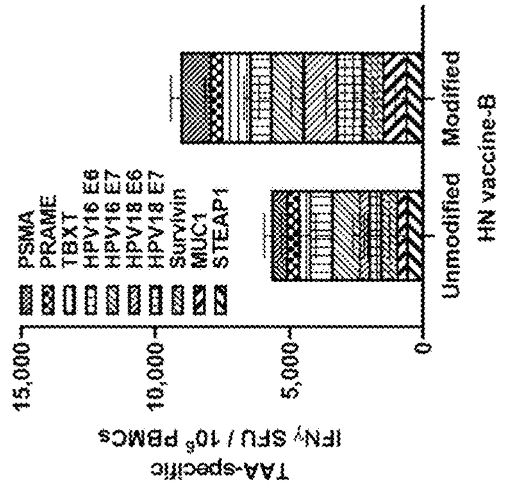
Figure 112D:
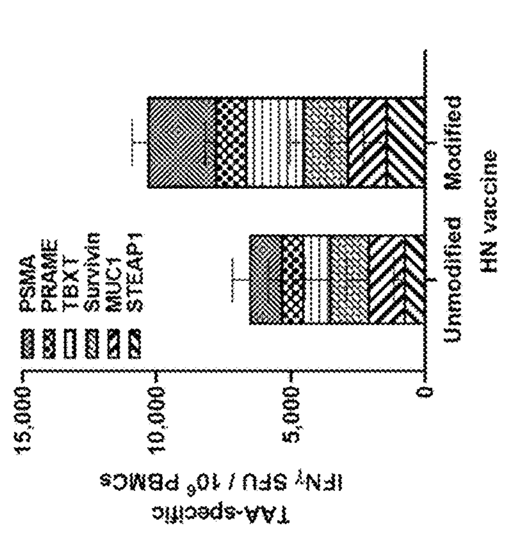
Figure 112E:
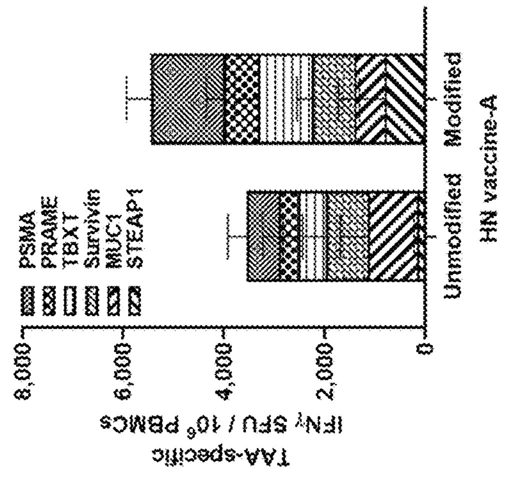
Figure 112F:
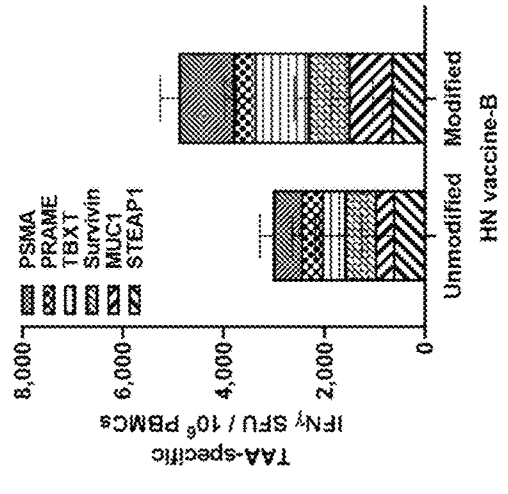

Expression of the transduced antigens modTERT (FIG. 102A) (SEQ ID NO: 35; SEQ ID NO: 36) by MCAS, modFSHR (FIG. 112B) and modMAGEA10 (FIG. 102C) (SEQ ID NO: 43; SEQ ID NO: 44) by TOV-112D, modWT1 (FIG. 102D) and modFOLR1 (modFBP) (FIG. 102E) (SEQ ID NO: 51; SEQ ID NO: 52) by TOV-21G and modBORIS (FIG. 102F) (SEQ ID NO: 59; SEQ ID NO: 60) by ES-2 were detected by flow cytometry or RT-PCR as described in Example 29 and herein. modFSHR and modMAGEA10 were encoded in the same lentiviral transfer vector separated by a furin cleavage site. modWT1 and modFOLR1 were also encoded in the same lentiviral transfer vector separated by a furin cleavage site.

Because of the need to maintain maximal heterogeneity of antigens and clonal subpopulations the comprise each cell line, the gene modified cell lines utilized in the present vaccine have been established using antibiotic selection and flow cytometry and not through limiting dilution subcloning.

Figure 101A:
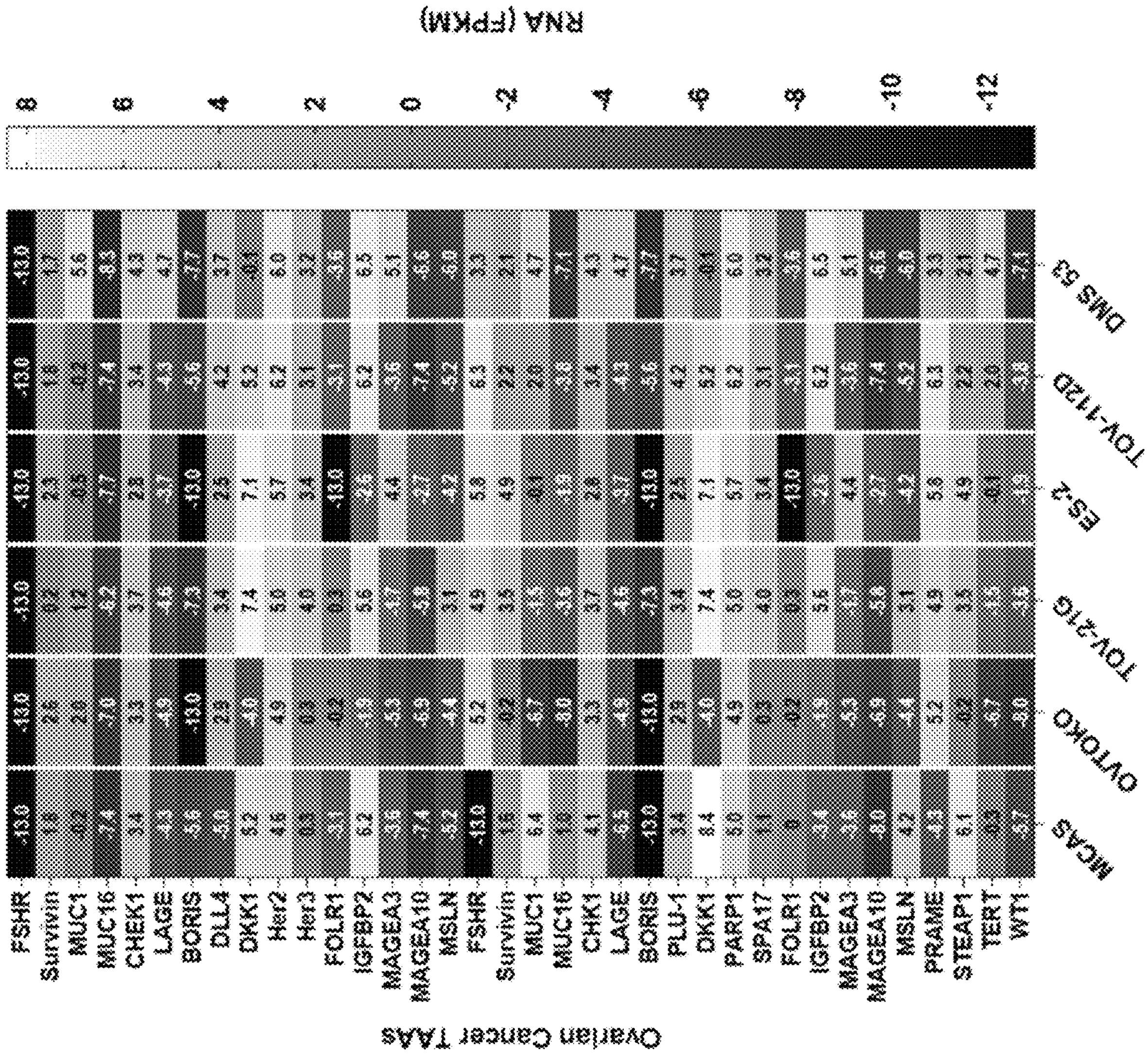
FIGS. 101A-C show endogenous antigen expression by selected OC vaccine component cell lines (FIG. 101A) expression of these antigens patient tumors (FIG. 101B) and the number of ovarian cancer antigens expressed by the OC vaccine cell lines also expressed in ovarian cancer patient tumors (FIG. 101C).
Figure 101B:
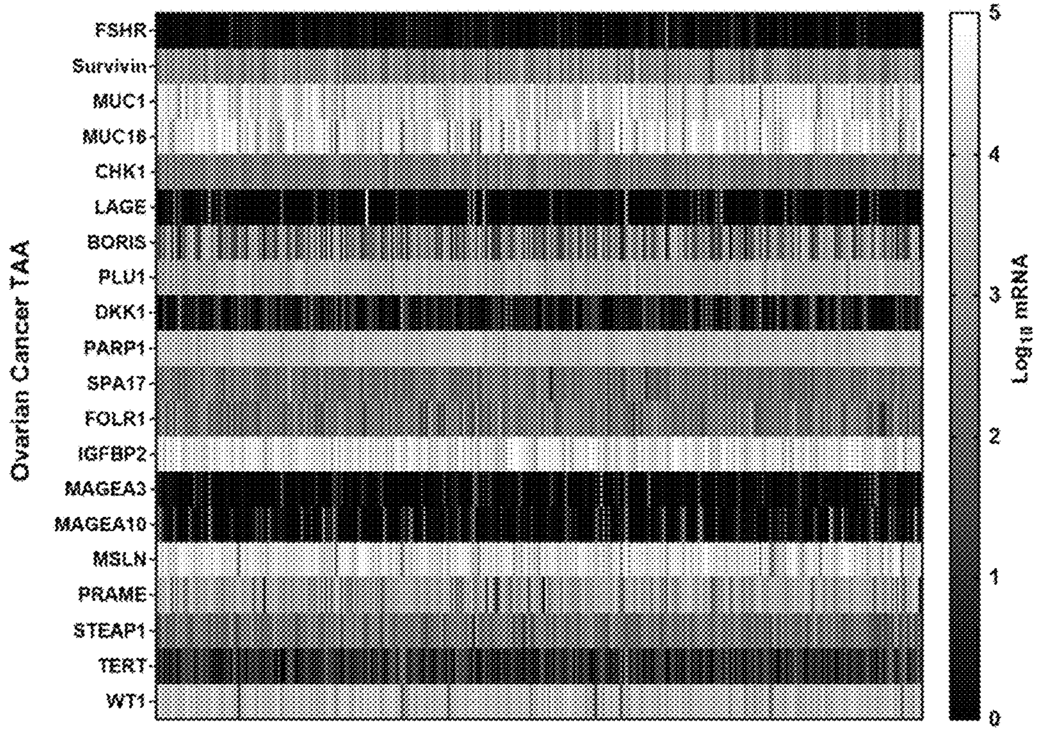
Figure 101C:
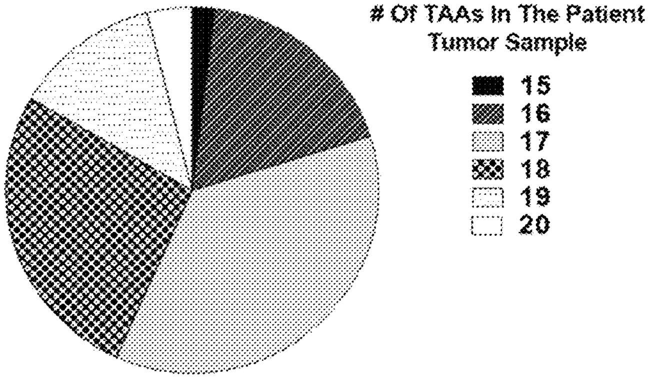

The endogenous mRNA expression of twenty representative OC TAAs in the present vaccine are shown in FIG. 101A. The present vaccine, after introduction of antigens described above, expresses all identified twenty commonly targeted or potentially clinically relevant TAAs capable of inducing an OC antitumor response. Some of these TAAs are known to be primarily enriched in OC tumors, such as FOLR1 (FBP) or FSHR, and some can also induce an immune response to OC and other solid tumors, such as TERT. RNA abundance of the twenty prioritized OC TAAs was determined in 307 OC patient samples with available mRNA data expression as described in Example 29 (FIG. 101B). Fifteen of the prioritized OC TAAs were expressed by 100% of samples, 16 TAAs were expressed by 98.0% of samples, 17 TAAs were expressed by 79.8% of samples, 18 TAAs were expressed by 43.3% of samples, 19 TAAs were expressed by 16.6% of samples and 20 TAAs were expressed by 3.9% of samples (FIG. 101C). The present Example thus provides two compositions comprising a therapeutically effective amount of three cancer cell lines, wherein the combination of the cell lines, a unit dose of six cell lines, comprises cells that express at least 15 TAAs associated with a subset of OC cancer subjects intended to receive said composition. Based on the expression and immunogenicity data presented herein, the cell lines identified in Table 84 were selected to comprise the present OC vaccine.

TABLE 84

Ovarian vaccine cell lines and histology

| Cocktail | Cell Line Name | Histology |
|---|---|---|
| A | OVTOKO | Ovarian Clear Cell Carcinoma derived from metastatic site (spleen) |
| A | MCAS | Ovarian Mucinous Cystadenocarcinoma |
| A | TOV-112D | Ovarian Endometrioid Adenocarcinoma |
| B | TOV-21G | Ovarian Clear Cell Carcinoma |
| B | ES-2 | Ovarian Poorly Differentiated Clear Cell Adenocarcinoma |
| B | DMS 53 | Lung Small Cell Carcinoma |

Reduction of CD276 Expression

The OVTOKO, MCAS, TOV-112D, TOV-21G, ES-2, and DMS 53 component cell lines expressed CD276 and expression was knocked out by electroporation with ZFN as described in Example 13 and elsewhere herein. Because it was desirable to maintain as much tumor heterogeneity as possible, the electroporated and shRNA modified cells were not cloned by limiting dilution. Instead, the cells were subjected to multiple rounds of cell sorting by FACS as described in Example 13. Expression of CD276 was determined as described in Example 29. Reduction of CD276 expression is described in Table 85. These data show that gene editing of CD276 with ZFN resulted in greater than 98.1% CD276-negative cells in all six vaccine component cell lines.

TABLE 85

Reduction of CD276 expression

| Cell line | Parental Cell Line MFI | Modified Cell Line MFI | % Reduction CD276 |
|---|---|---|---|
| OVTOKO | 108,003 | 705 | 99.3 |
| MCAS | 2,356 | 44 | 98.1 |
| TOV-112D | 2,969 | 7 | 99.8 |
| TOV-21G | 13,475 | 0 | 99.9 |
| ES-2 | 3,216 | 0 | 99.9 |
| DMS 53 | 11,928 | 24 | 99.8 |

MFI reported with isotype controls subtracted

Cytokine Secretion Assays for TGFβ1, TGFβ2, GM-CSF, and IL-12

Cytokine Secretion Assays for TGFβ1, TGFβ2, GM-CSF, and IL-12 were Completed as Described in Example 29.

shRNA Downregulates TGF-β Secretion

Following CD276 knockout, TGFβ1 and/or TGFβ2 secretion levels were reduced using shRNA and resulting levels determined as described in Example 29. The OVTOKO, MCAS and TOV-112D parental cell lines in OC vaccine-A secreted measurable levels of TGFβ1 and TGFβ2. The TOV-21G and ES-2 component cell lines of OC vaccine-B secreted measurable levels of TGFβ1 and TGFβ2. Reduction of TGFβ2 secretion by the DMS 53 cell line is described in Example 5 and resulting levels determined as described above and herein.

The MCAS, TOV-112D, and ES-2 component cell lines were transduced with TGFβ1 shRNA to decrease TGFβ1 secretion concurrently with the transgene to increase expression of membrane bound CD40L as described in Example 29. MCAS, TOV-112D and ES-2 were also transduced with lentiviral particles encoding TGFβ2 shRNA to decrease the secretion of TGFβ2 and concurrently increase expression of GM-CSF (SEQ ID NO: 6) as described in Example 29. These cells are described by the clonal designation DK6. The OVTOKO and TOV-21G cell lines was transduced with TGFβ1 shRNA to decrease TGFβ1 secretion and concurrently increase expression of membrane bound CD40L as described in Example 29. These cells, modified to reduce TGFβ1 secretion and not TGFβ2 secretion, are described by the clonal designation DK2. DMS 53 was modified with shRNA to reduce secretion of TGFβ2 as described in Example 26. The J82 and DMS 53 cells modified to reduce secretion of TGFβ2 and not TGFβ1 are described by the clonal designation DK4.

Figure 103B:
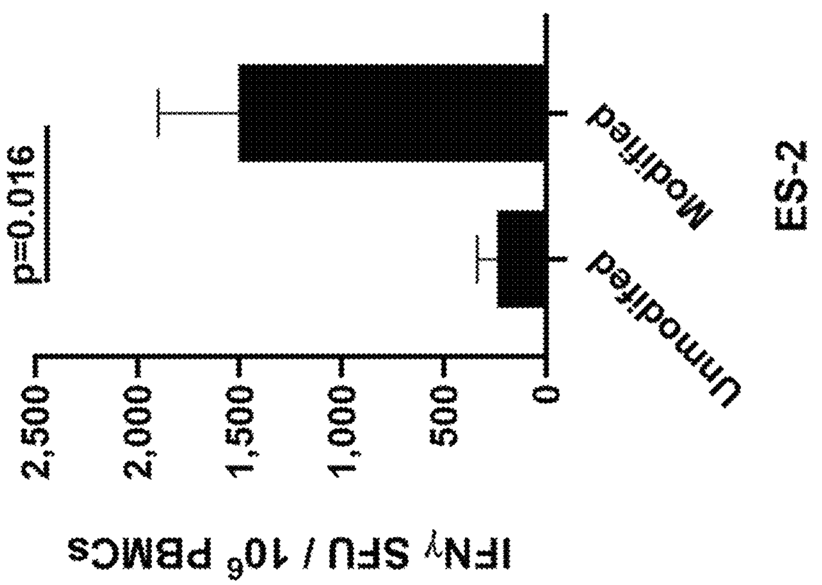
FIGS. 103A and B show IFNγ responses to the unmodified and vaccine component cell lines TOV-21G (FIG. 103A) and ES-2 (FIG. 103B) cell lines.
Figure 103A:
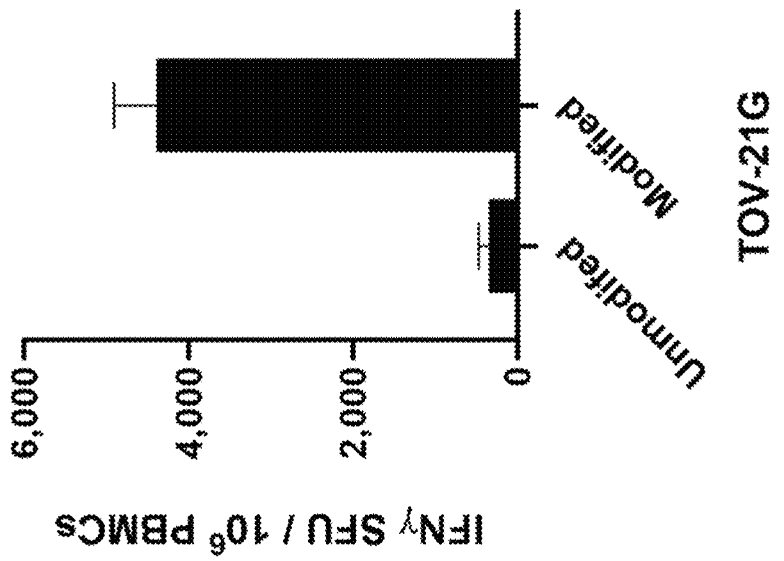

Modification of TOV-21G with TGFβ1 shRNA initially decreased TGFβ1 secretion, but TGFβ1 secretion was increased after further genetic modification potentially through a compensatory mechanism to maintain cell proliferation and survival. There was a 19% decrease in TGFβ2 secretion by the ES-2 cell line resulting from transduction with TGFβ2 shRNA. Immunogenicity of the OC vaccine-B component cell lines TOV-21G and ES-2 was compared with the immunogenicity of unmodified controls in five HLA diverse donors as described in Example 9. HLA-A and HLA-B alleles for Donors 1-3 is described in Table 74. HLA-A and HLA-B alleles for the other two donors were as follows: Donor 7, A*03:01 B*07:02 and A*25:01 B*18:01; and Donor 8, A*30:02 B*15:10 and A*30:04 B*58:02. The data indicated that the TOV-21G OC vaccine B component cell line was more immunogenic (4,390±517 SFU) than unmodified TOV-21G (349±121 SFU) (FIG. 103A). The data further indicated that OC vaccine B component cell line ES-2 was significantly more immunogenic (1,505±394 SFU) than unmodified ES-2 (238±100 SFU) (p=0.016, Mann-Whitney U) (FIG. 103B). The data described above indicate the immunological benefit obtained through multiple modifications.

Table 86 shows the percent reduction in TGFβ1 and/or TGFβ2 secretion in genetically modified component cell lines compared to unmodified parental cell lines. If TGFβ1 or TGFβ2 secretion was only detected in 1 of 16 replicates run in the ELISA assay the value is reported without standard error of the mean. Gene modification resulted in at least 70% reduction of TGFβ1 secretion (excluding TOV-21G). Gene modification of TGFβ2 resulted at least 19% reduction in secretion of TGFβ2.

TABLE 86

TGF-β Secretion (pg/$10^6$ cells/24 hr) in Component Cell Lines

| Cell Line | Cocktail | Clone | TGFβ1 | TGFβ2 |
|---|---|---|---|---|
| OVTOKO | A | Wild type | 517 ± 148 | 124 ± 35 |
| OVTOKO | A | DK2 | 157 ± 36 | NA |
| OVTOKO | A | Percent reduction | 70% | NA |
| MCAS | A | Wild type | 1,506 ± 203 | 871 ± 193 |
| MCAS | A | DK6 | 161 ± 35 | 61 ± 37 |
| MCAS | A | Percent reduction | 89% | 93% |
| TOV-112D | A | Wild type | 490 ± 91 | 2,397 ± 635 |
| TOV-112D | A | DK6 | *≤62 | *≤28 |
| TOV-112D | A | Percent reduction | ≥87% | ≥99% |
| TOV-21G | B | Wild type | 1,102 ± 150 | 526 ± 712 |
| TOV-21G | B | DK2 | 1,401 ± 370 | NA |

TABLE 86-continued

TGF-β Secretion (pg/$10^6$ cells/24 hr) in Component Cell Lines

| Cell Line | Cocktail | Clone | TGFβ1 | TGFβ2 |
|---|---|---|---|---|
| TOV-21G | B | Percent reduction | NA | NA |
| ES-2 | B | Wild type | 987 ± 209 | 272 ± 115 |
| ES-2 | B | DK6 | *≤19 | 220 ± 26 |
| ES-2 | B | Percent reduction | ≥98% | 19% |
| DMS 53 | B | Wild type | 106 ± 10 | 486 ± 35 |
| DMS 53 | B | DK4 | NA | 238 ± 40 |
| DMS 53 | B | Percent reduction | NA | 51% |

DK6: TGFβ1/TGFβ2 double knockdown;
DK4: TGFβ2 single knockdown;
DK2: TGFβ1 single knockdown;
* = estimated using LLD, not detected;
NA = not applicable.

Based on a dose of $5\times10^5$ of each component cell line, the total TGFβ1 and TGFβ2 secretion by the modified OC vaccine-A and OC vaccine-B and respective unmodified parental cell lines are shown in Table 87. The secretion of TGFβ1 by OC vaccine-A was reduced by 85% pg/dose/24 hr and TGFβ2 by 94% pg/dose/24 hr. The secretion of TGFβ1 by OC vaccine-A was reduced by 31% pg/dose/24 hr TGFβ2 by OC vaccine-B was reduced by 23% pg/dose/24 hr.

TABLE 87

Total TGF-β Secretion (pg/dose/24 hr) in OC vaccine-A and OC vaccine-B

| Cocktail | Clones | TGFβ1 | TGFβ2 |
|---|---|---|---|
| A | Wild type | 1,257 | 1,696 |
| | DK2/DK6 | 190 | 107 |
| | Percent reduction | 85% | 94% |
| B | Wild type | 1,098 | 642 |
| | DK2/DK4/DK6 | 763 | 492 |
| | Percent reduction | 31% | 23% |

GM-CSF Secretion

The MCAS, TOV-112D and ES-2 cell lines were transduced with lentiviral particles containing both TGFβ2 shRNA and the gene to express GM-CSF (SEQ ID NO: 6) as described above. The OVTOKO and TOV-21G cell lines were transduced with lentiviral particles to only express GM-CSF (SEQ ID NO: 7). DMS 53 was modified to secrete GM-CSF as described in Example 26 and elsewhere herein. The results are shown in Table 87 and described below.

Secretion of GM-CSF increased at least 656-fold in all modified component cell lines compared to unmodified, parental cell lines. In OC vaccine-A component cell lines, secretion of GM-CSF increased 656-fold by OVTOKO compared to the parental cell line (≤0.003 ng/$10^6$ cells/24 hr), 13,280-fold by MCAS compared to the parental cell line (≤0.003 ng/$10^6$ cells/24 hr), and 1,875-fold by TOV-112D compared to the parental cell line (≤0.014 ng/$10^6$ cells/24 hr). In OC vaccine-B component cell lines secretion of GM-CSF increased 426,660-fold by TOV-21G compared to the parental cell line (≤0.003 ng/$10^6$ cells/24 hr), 22,047-fold by ES-2 compared to the parental cell line (≤0.003 ng/$10^6$ cells/24 hr) and 49,313-fold by DMS 53 compared to the parental cell line (≤0.003 ng/$10^6$ cells/24 hr).

TABLE 88

| GM-CSF Secretion in Component Cell Lines | | |
|---|---|---|
| Cell Line | GM-CSF ($ng/10^6$ cells/24 hr) | GM-CSF (ng/dose/24 hr) |
| OVTOKO | 2 ± 0.6 | 1 |
| MCAS | 41 ± 13 | 21 |
| TOV-112D | 27 ± 8 | 14 |
| Cocktail A Total | 70 | 36 |
| TOV-21G | 1,382 ± 302 | 691 |
| ES-2 | 64 ± 19 | 32 |
| DMS 53 | 158 ± 15 | 79 |
| Cocktail B Total | 1,604 | 802 |

Based on a dose of $5\times10^5$ of each component cell line, the total GM-CSF secretion for OC vaccine-A was 36 ng per dose per 24 hours. The total GM-CSF secretion for OC vaccine-B was 802 ng per dose per 24 hours. The total GM-CSF secretion per dose was therefore 838 ng per 24 hours.

Membrane Bound CD40L (CD154) Expression

The component cell lines were transduced with lentiviral particles to express membrane bound CD40L as described above. The methods to detect expression of CD40L by the five OC cell line components are described in Example 29. Modification of DMS 53 to express membrane bound CD40L is described in Example 15. Evaluation of membrane bound CD40L by all six vaccine component cell lines is described below. The results shown in FIG. 104 and described below demonstrate CD40L membrane expression was substantially increased in all six OC vaccine component cell lines.

Figure 104:
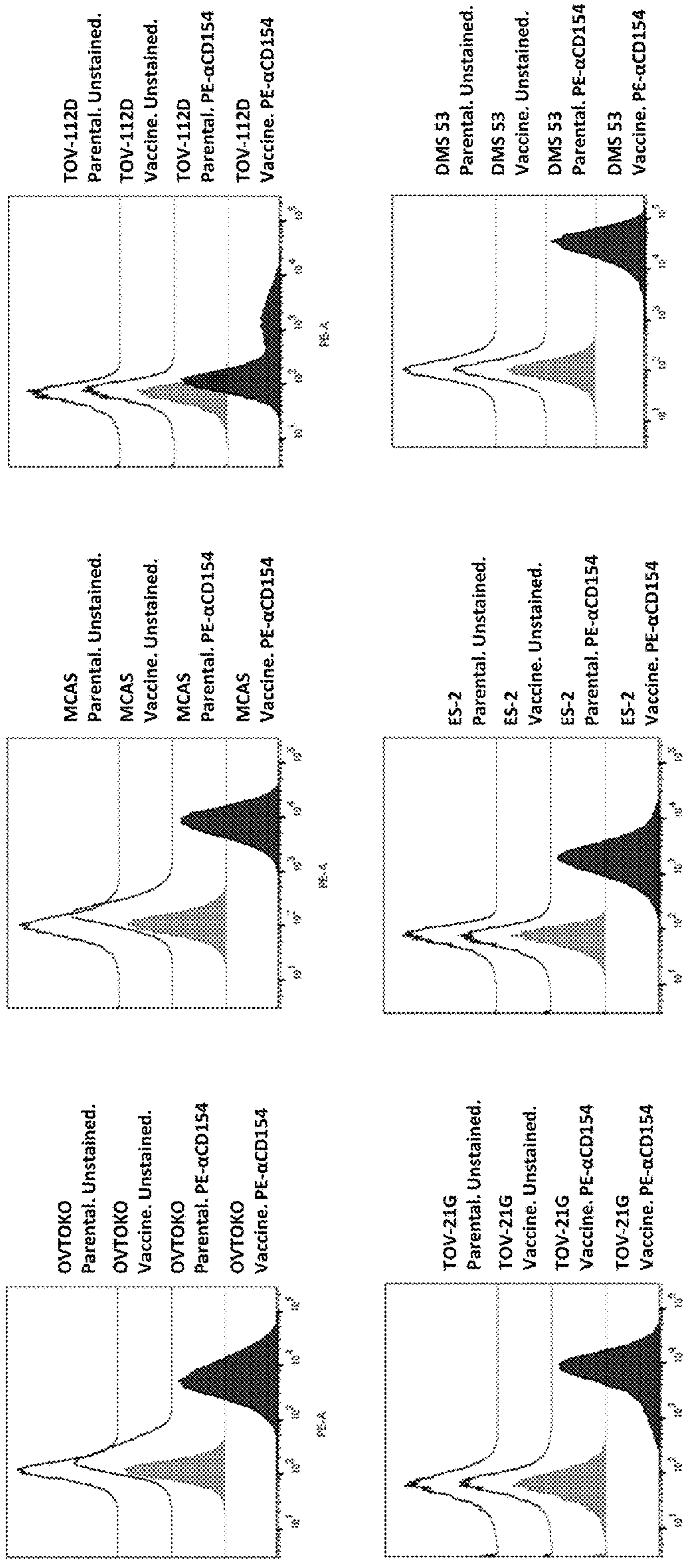
FIG. 104 shows expression of membrane bound CD40L by the OC vaccine component cell lines.

Expression of membrane bound CD40L increased at least 288-fold in all component cell lines compared to unmodified, parental cell lines. In OC vaccine-A component cell lines, expression of CD40L increased 18,046-fold by OVTOKO (13,661 MFI) compared to the parental cell line (0 MFI), 1,068-fold by MCAS (18,150 MFI) compared to the parental cell line (17 MFI), and 288-fold by TOV-112D (288 MFI) compared to the parental cell line (0 MFI). TOV-112D was subsequently sorted to enrich membrane-bound CD40L expression. After sorting, expression of membrane bound CD40L increased 728-fold compared to the parental cell line. The TOV-112D component cell line with 288-fold increased expression of membrane-bound CD40L was used to generate the described herein and is shown in FIG. 104. In OC vaccine-B component cell lines expression of CD40L increased 18,874-fold by TOV-21G compared to the parental cell line (0 MFI), 2,823-fold by ES-2 (2,823 MFI) compared to the parental cell line (0 MFI), and 88,261-fold by DMS 53 (88,261 MFI) compared to the parental cell line (0 MFI).

IL-12 Expression

The component cell lines were transduced with the IL-12 vector as described in Example 17 and resulting IL-12 p70 expression determined as described above and herein. The results are shown in Table 89 and described below.

Secretion of IL-12 increased at least 1,739-fold in all component cell lines modified to secrete IL-12 p70 compared to unmodified, parental cell lines. In OC vaccine-A component cell lines, secretion of IL-12 increased 35-fold by OVTOKO compared to the parental cell line (≤0.0014 $ng/10^6$ cells/24 hr), 11-fold by MCAS compared to the parental cell line (≤0.001 $ng/10^6$ cells/24 hr), and 1,739-fold by TOV-112D compared to the parental cell line (≤0.006 $ng/10^6$ cells/24 hr). Expression of IL-12 by the unmodified TOV-112D cell line was determined in a separate experiment than secretion of IL-12 by the modified cell line. In OC vaccine-B component cell lines expression of IL-12 increased 137-fold by TOV-21G compared to the parental cell line 0.001 $ng/10^6$ cells/24 hr) and 43-fold by ES-2 compared to the parental cell line (≤0.001 $ng/10^6$ cells/24 hr). DMS 53 was not modified to secrete IL-12.

TABLE 89

| IL-12 Secretion in Component Cell Lines | | |
|---|---|---|
| Cell Line | IL-12 ($ng/10^6$ cells/24 hr) | IL-12 (ng/dose/24 hr) |
| OVTOKO | 16 ± 3 | 8 |
| MCAS | 31 ± 7 | 16 |
| TOV-112D | 10 ± 7 | 5 |
| Cocktail A Total | 57 | 29 |
| TOV-21G | 38 ± 9 | 19 |
| ES-2 | 26 ± 5 | 13 |
| DMS 53 | NA | NA |
| Cocktail B Total | 64 | 32 |

Based on a dose of $5\times10^5$ of each component cell line, the total IL-12 secretion for OC vaccine-A was 29 ng per dose per 24 hours. The total IL-12 secretion for OC vaccine-B was 32 ng per dose per 24 hours. The total IL-12 secretion per dose was therefore 61 ng per 24 hours.

Stable Expression of modTERT by the MCAS Cell Line

Figure 102A:
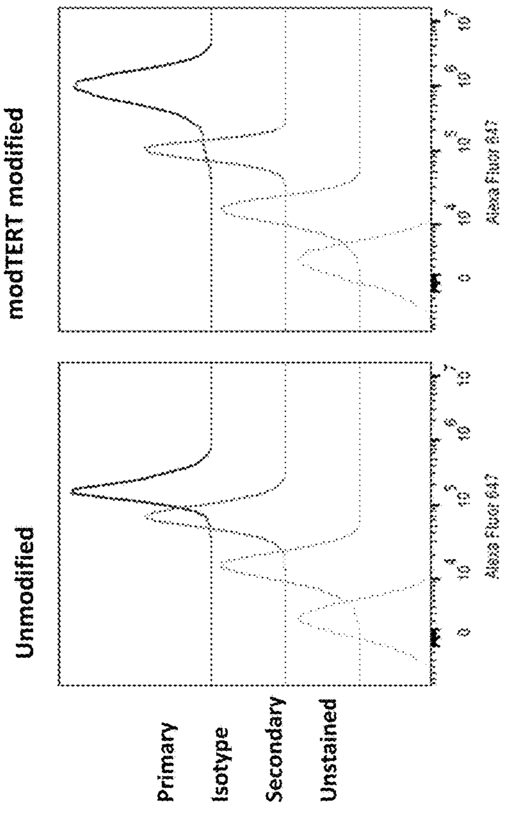
FIGS. 102A-L show the expression of and IFNγ responses to antigens introduced in the OC vaccine cell lines compared to unmodified controls. Expression of modTERT (FIG. 102A) by MCAS and IFNγ responses to TERT by OC-vaccine A (FIG. 102G), expression of modFSHR (FIG. 102B) and modMAGEA10 (FIG. 102D) by TOV-112D and IFNγ responses to FSHR (FIG. 102H) and MAGEA10 (FIG. 102I) by OC-vaccine A. Expression of modWT1 (FIG. 102C) and modFOLR1 (FIG. 102E) by TOV-21G and IFNγ responses to WT1 (FIG. 102K) and FOLR1 (FIG. 102J) by OC vaccine-B. Expression of modBORIS by ES-2 (FIG. 102F) and IFNγ responses to BORIS by OC vaccine-B (FIG. 102L).

As described above, the cells in the vaccine components described herein were selected to express a wide array of TAAs, including those known to be important to antitumor immunity. To further enhance the array of antigens, the MCAS cell line that was modified to reduce the secretion of TGFβ2, reduce the expression of CD276, and to express GM-CSF, membrane bound CD40L and IL-12 was also transduced with lentiviral particles expressing the modTERT antigen (SEQ ID NO: 35, SEQ ID NO: 36). The expression of modTERT by MCAS was characterized by flow cytometry. Unmodified and antigen modified cells were stained intracellular with 0.03 μg/test anti-rabbit IgG anti-TERT (Abcam ab32020) followed by 0.125 ug/test AF647-conjugated donkey anti-rabbit IgG1 antibody (BioLegend #406414). Expression of modTERT increased in the modified cell line (1,558,528 MFI) 6.8-fold over that of the unmodified cell line (227,724 MFI) (FIG. 102A).

Stable Expression of modFSHR and modMAGEA10 by the TOV-112D Cell Line

Figure 102B:
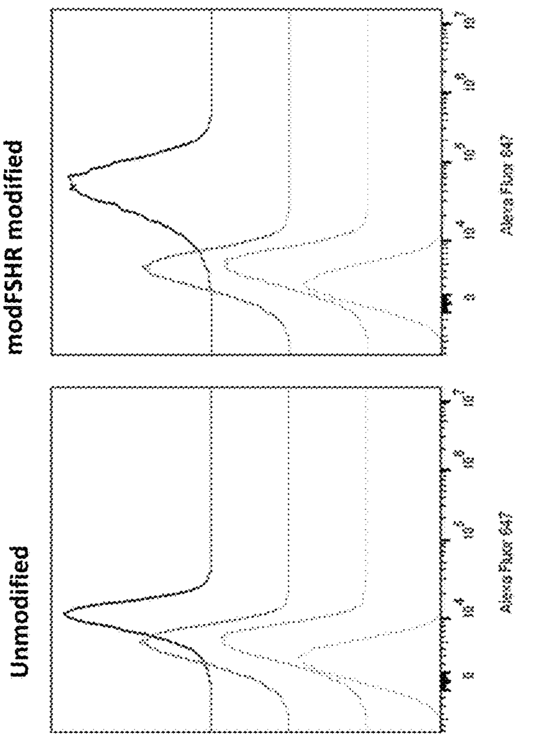

The TOV-112D cell line that was modified to reduce the secretion of TGFβ1 and TGFβ2, reduce the expression of CD276, and to express GM-CSF, membrane bound CD40L, and IL-12 was also transduced with lentiviral particles expressing the modFSHR and modMAGEA10 antigens (SEQ ID NO: 43, SEQ ID NO: 44). Expression of modFSHR by TOV-112D was determined by flow cytometry. Unmodified and antigen modified cells were stained intracellular with 0.03 μg/test anti-mouse IgG1 anti-FSHR antibody (Novus Biologicals, NBP2-36489) followed by 0.125 ug/test AF647-conjugated goat anti-mouse IgG1 antibody (Biolegend #405322). Expression of modFSHR increased in the modified cell line (86,796 MFI) 6.6-fold over that of the unmodified cell line (13,249 MFI) (FIG. 102B). Expression of modMAGEA10 by TOV-112D was determined by RT-PCR as described in Example 29 and herein. The forward primer was designed to anneal at the 24-50 bp location in the transgene (ATG-CATGCCCGAAGAGGACCTGCAGAG (SEQ ID NO: 132)) and reverse primer designed to anneal at the 637-659 bp location in the transgene (GCTCTGCACATCGGACAG-CAT (SEQ ID NO: 133)) yielding a 634 bp product. Control primers for 3-tubulin are described in Example 29. The gene product for modMAGEA10 was detected at the expected size (FIG. 102D) and mRNA increased 141,476-fold relative to the parental control.

Stable Expression of Mod WT1 and modFOLR1 (modFBP) by the TOV-21G Cell Line

Figure 102C:
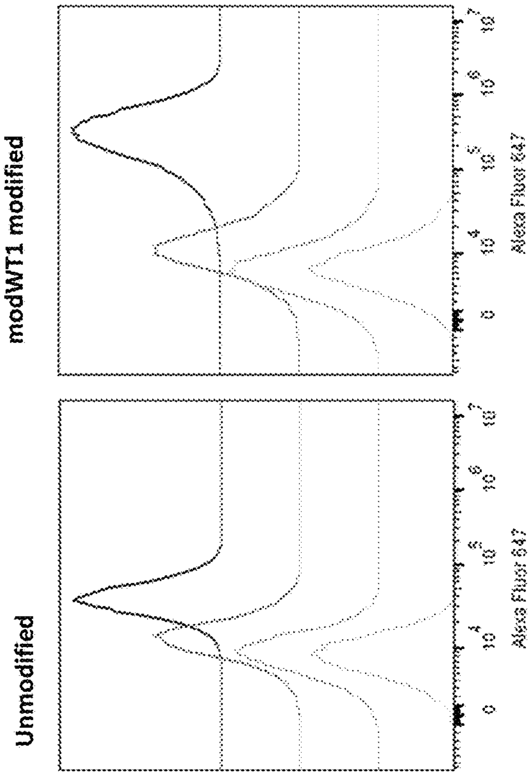
Figure 102D:
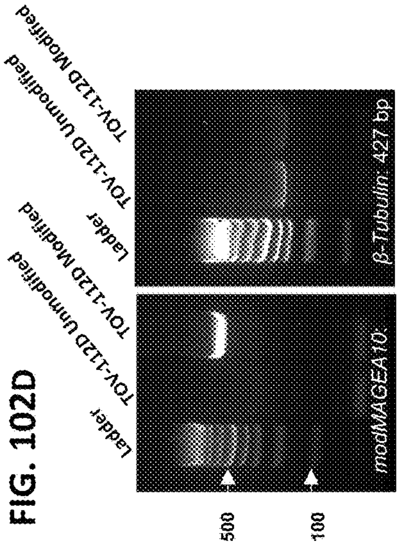
Figure 102E:
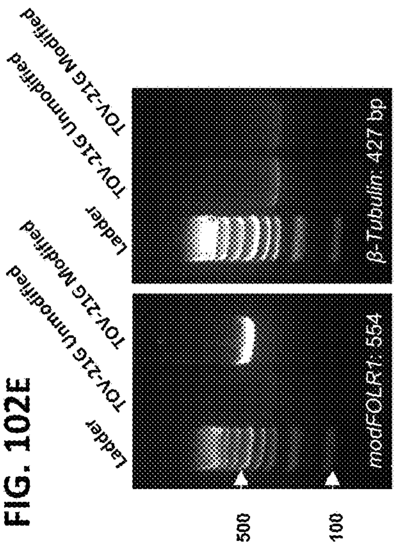
Figure 102F:
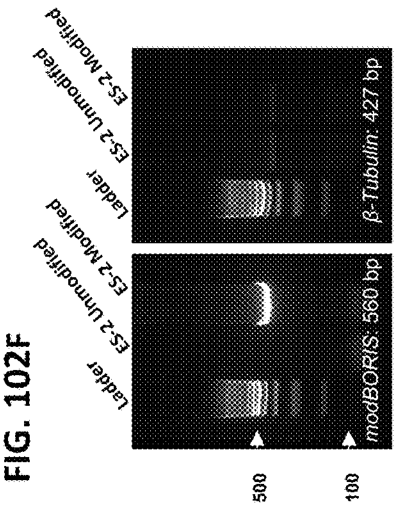

The TOV-21G cell line that was modified to reduce the secretion of TGFβ1, reduce the expression of CD276, and to express GM-CSF, membrane bound CD40L, and IL-12 was also transduced with lentiviral particles expressing the modWT1 and modFOLR1 antigens (SEQ ID NO: 51, SEQ ID NO: 52). Expression of modWT1 by TOV-21G was characterized by flow cytometry. Unmodified and antigen modified cells were stained intracellular with 0.03 μg/test anti-rabbit IgG1 anti-WT1 antibody (Abcam, ab89901) followed by 0.125 ug/test AF647-conjugated donkey anti-rabbit IgG1 antibody (BioLegend #406414). Expression of modWT1 increased in the modified cell line (687,582 MFI) 4.9-fold over that of the unmodified cell line (140,770 MFI) (FIG. 102C).

Expression of modFOLR1 by TOV-21G was determined by RT-PCR as described in Example 29 and herein. The forward primer was designed to anneal at the 56-76 bp location in the transgene (GAGAAGTGCA-GACCAGAATCG (SEQ ID NO: 130)) and reverse primer designed to anneal at the 588-609 bp location in the transgene (TCTGCTGTAGTTGGACACCTTG (SEQ ID NO: 131)) yielding a 554 bp product. Control primers for β-tubulin are described in Example 29. The gene product for modFOLR1 was detected at the expected size (FIG. 102E) and mRNA increased 170,855-fold relative to the parental control.

Stable Expression of modBORIS by the ES-2 Cell Line

The ES-2 cell line that was modified to reduce the secretion of TGFβ1 and TGFβ2, reduce the expression of CD276, and to express GM-CSF, membrane bound CD40L and IL-12 was also transduced with lentiviral particles expressing the modBORIS antigen (SEQ ID NO: 59, SEQ ID NO: 60). Expression of modBORIS by ES-2 was determined by RT-PCR as described in Example 29 and herein. The forward primer was designed to anneal at the 1119-1138 bp location in the transgene (TTCCAGTGCTGCCAGTGTAG (SEQ ID NO: 134)) and reverse primer designed to anneal at the 1559-1578 bp location in the transgene (AGCACTTGTTGCAGCTCAGA (SEQ ID NO: 135)) yielding a 460 bp product. Control primers for β-tubulin are described in Example 29. The gene product for modBORIS was detected at the expected size (FIG. 102F) and mRNA increased 4,196-fold relative to the parental control.

Immune Responses to TERT in OC Vaccine-A

Figures 102G, 102H, 102I, 102J, 102K, 102L:
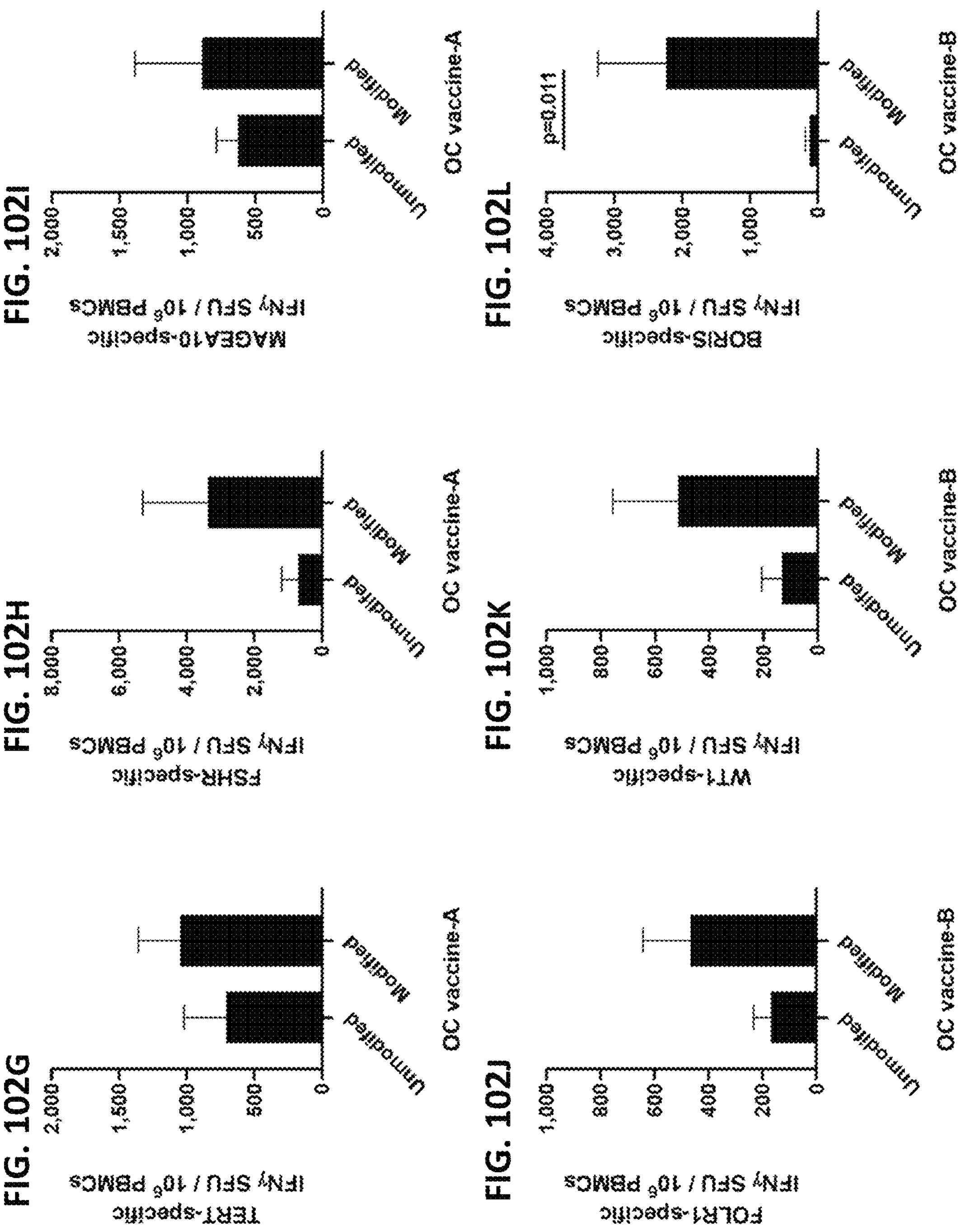

IFNγ responses to TERT were evaluated in the context of OC vaccine-A as described in Example 29, and herein, in seven HLA diverse donors (n=4/donor). The HLA-A, HLA-B, and HLA-C alleles for each of the seven donors are shown in Table 90. IFNγ responses were determined by ELISpot as described in Example 29. IFNγ responses to TERT were determined by ELISpot using 15-mers peptides overlapping by 11 amino acids spanning the entire length of the native TERT antigen (JPT, PM-TERT). IFNγ responses to TERT increased with the modified OC vaccine-A (1047±313 SFU) compared to the unmodified OC vaccine-A (707±314 SFU) but did not reach statistical significance (n=7) (FIG. 102G).

Immune Responses to FSHR and MAGEA10 in OC Vaccine-A

IFNγ responses to FSHR and MAGEA10 antigens were evaluated in the context of OC vaccine-A as described in Example 29, and herein, in seven HLA diverse donors (n=4/donor). The HLA-A, HLA-B, and HLA-C alleles for each of the seven donors are shown in Table 90. IFNγ responses were determined by ELISpot as described in Example 29. IFNγ responses to FSHR were determined by ELISpot using 15-mers peptides overlapping by 9 amino acids spanning the entire length of the native FSHR antigen purchased from Thermo Scientific Custom Peptide Service. FSHR specific IFNγ responses induced by the modified OC vaccine-A (3,379±1,923 SFU) were increased compared to the parental, unmodified OC vaccine-A (709±482 SFU) but did not reach statistical significance (n=7) (FIG. 102H). IFNγ responses to MAGEA10 were determined by ELISpot using 15-mers peptides overlapping by 9 amino acids spanning the entire length of the native MAGEA10 antigen purchased from Thermo Scientific Custom Peptide Service. IFNγ responses to MAGEA10 increased with the modified OC vaccine-A (893±495 SFU) compared to the unmodified OC vaccine-A (630±156 SFU) but did not reach statistical significance (n=7) (FIG. 102I).

Immune Responses to WT1 and FOLR1 (FBP) in OC Vaccine-B

IFNγ responses to the WT1 and FOLR1 were evaluated in the context of OC-vaccine B as described in Example 29, and herein, in seven HLA diverse donors (n=4/donor) (Table 90). IFNγ responses against WT1 and FOLR1 (FBP) were determined by ELISpot using 15-mers peptides overlapping by 9 amino acids spanning the entire length of the native antigen protein purchased from Thermo Scientific Custom Peptide Service. WT1 specific IFNγ responses were increased by OC vaccine-B (516±241 SFU) compared to the unmodified OC vaccine-B (132±74 SFU) (n=7) but did not reach statistical significance (n=7) (FIG. 102K). FOLR1 (FBP) specific IFNγ responses were increased by OC vaccine-B (467±175 SFU) compared to the unmodified OC vaccine-B (168±65 SFU) but did not reach statistical significance (n=7) (FIG. 102J).

Immune Responses to BORIS in OC Vaccine-B

IFNγ responses to BORIS were evaluated in the context of OC-vaccine B as described in Example 29, and herein, in seven HLA diverse donors (n=4/donor) (Table 90). IFNγ responses against BORIS were determined by ELISpot using 15-mers peptides overlapping by 9 amino acids spanning the entire length of the native antigen protein purchased from Thermo Scientific Custom Peptide Service. BORIS specific IFNγ responses were significantly increased by OC vaccine-B (2,234±1,011 SFU) compared to the unmodified OC vaccine-B (121±65 SFU) (p=0.011, Mann-Whitney U test) (n=7) (FIG. 102L).

TABLE 90

Healthy Donor MHC-I characteristics

| Donor # | HLA-A | HLA-B | HLA-C |
|---|---|---|---|
| 1 | *02:01 *24:02 | *08:01 *44:02 | *05:01 *07:01 |
| 2 | *02:01 *25:01 | *18:01 *27:05 | *02:02 *12:03 |
| 3 | *02:01 *33:01 | *07:02 *14:02 | *07:02 *08:02 |
| 4 | *02:01 *02:01 | *15:01 *51:01 | *02:02 *03:04 |
| 5 | *01:01 *30:01 | *08:01 *13:02 | *06:02 *07:01 |
| 6 | *02:01 *03:01 | *07:02 *44:03 | *07:02 *16:01 |
| 7 | *29:02 *31:01 | *40:01 *55:01 | *03:04 *16:01 |

Cocktails Induce Immune Responses Against Relevant TAAs

The ability of OC vaccine-A and OC vaccine-B to induce IFNγ responses against ten OC antigens was measured by ELISpot. PBMCs from seven HLA-diverse healthy donors (Table 90) were co-cultured with autologous DCs loaded with OC vaccine-A or OC vaccine-B for 6 days prior to stimulation with TAA-specific specific peptide pools containing known MHC-I restricted epitopes. Peptides for stimulation of CD14-PBMCs to detect IFNγ responses to TERT, FSHR, MAGEA10, WT1, FOLR1 and BORIS are described above. Additional 15-mer peptides overlapping by 11 amino acid peptide pools were sourced as follows: MSLN (GeneScript custom library), Survivin (thinkpeptides, 7769_001-011), PRAME (JPT, PM-01P4) and STEAP1 (PM-STEAP1).

Figure 105C:
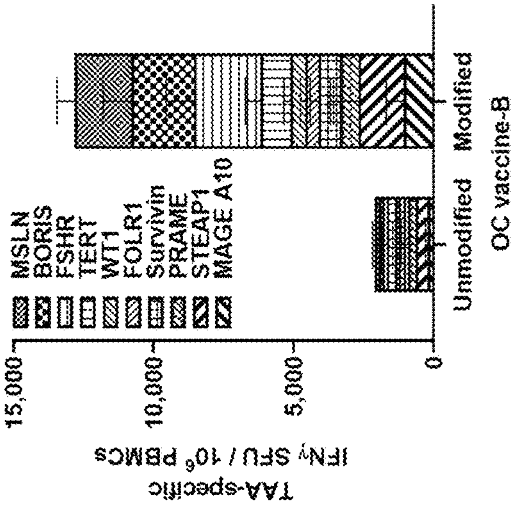
FIGS. 105A-C show antigen specific IFNγ responses induced by the unit dose of the OC vaccine (FIG. 105A), OC vaccine-A (FIG. 105B), and OC vaccine-B (FIG. 105C) compared to unmodified controls.
Figure 105B:
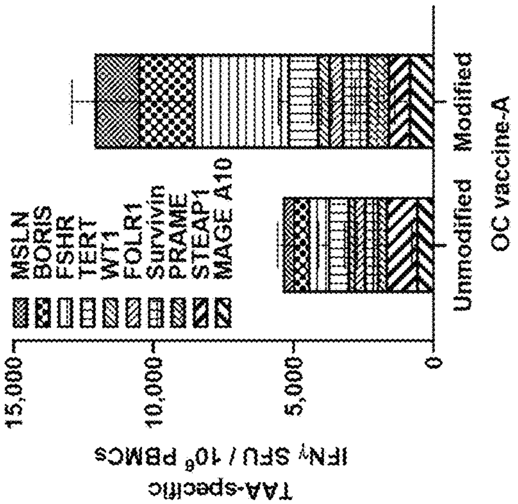
Figure 105A:
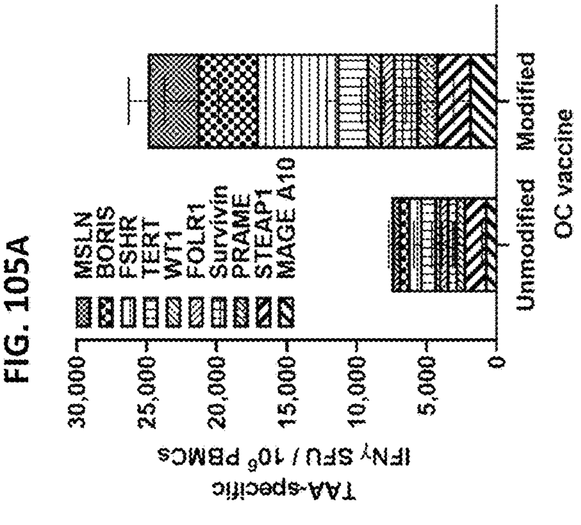
Figure 106:
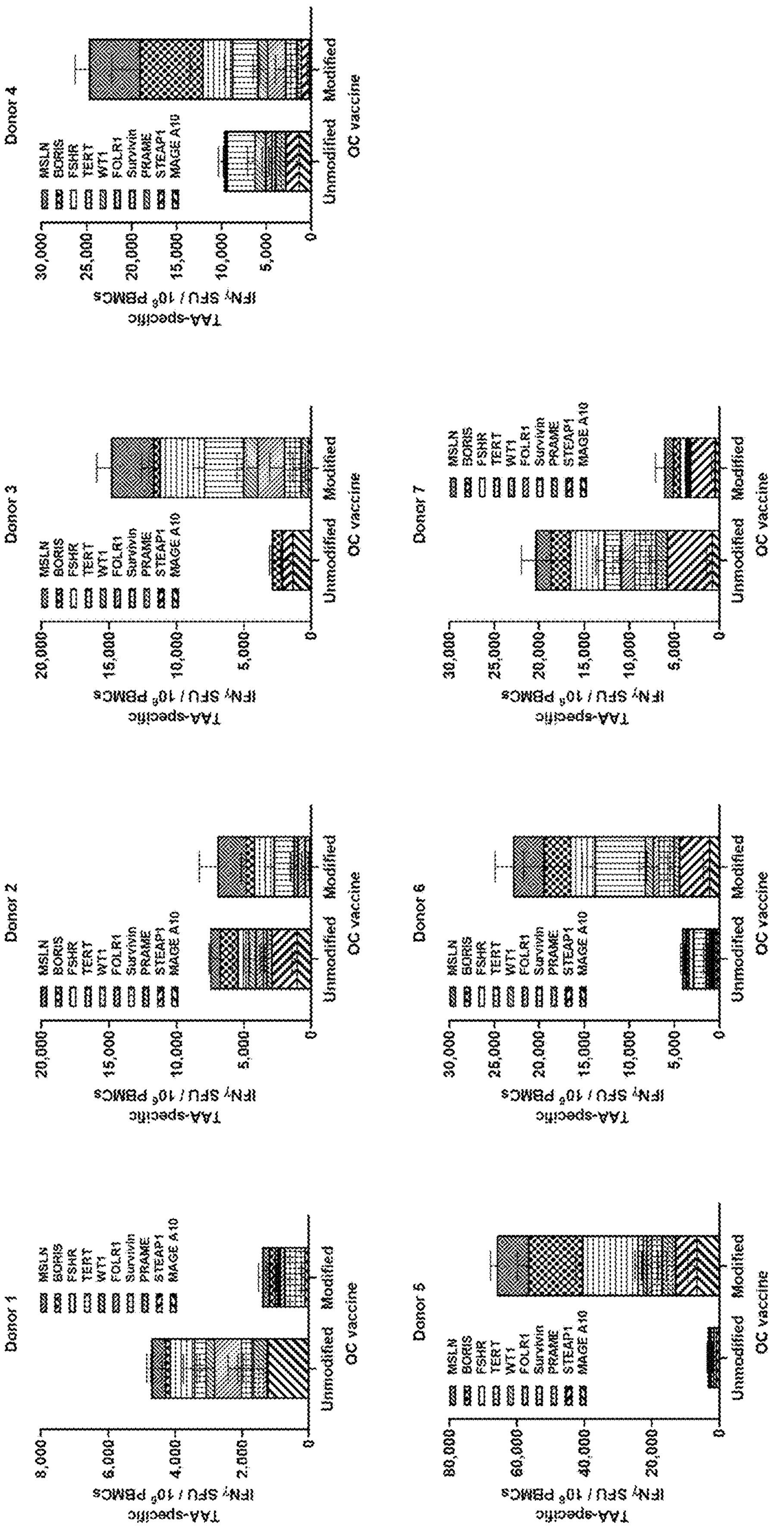
FIG. 106 shows antigen specific IFNγ responses induced by the unit dose of the OC vaccine in individual donors compared to unmodified controls.

FIG. 105 demonstrates the OC vaccine is capable of inducing antigen specific IFNγ responses in seven HLA-diverse donors to ten OC antigens that are 3.3-fold more robust (24,942±10,138 SFU) compared to the unmodified parental control (7,495±2,317 SFU) (n=7) (FIG. 105A) (Table 91). The unit dose of OC vaccine-A and OC vaccine-B elicited IFNγ responses to seven antigens in one donor, nine antigens in two donors and ten antigens in four donors (FIG. 106). OC vaccine-A and OC vaccine-B independently demonstrated a 2.2-fold and 6.1-fold increase in antigen specific responses compared to parental controls, respectively. Specifically, OC vaccine-A elicited 12,116±5,813 SFU compared to the unmodified controls (5,385±1,892 SFU) (FIG. 105B). For OC vaccine-A, one donor responded to six antigens, two donors responded to seven antigens, two donors responded to eight antigens, one donor responded to seven antigens, and two donors responded ten antigens. OC vaccine-B elicited 12,826±4,780 SFU compared to parental controls (2,110±529 SFU) (p=0.011, Mann-Whitney U test) (FIG. 105C). For OC vaccine-B, one donor responded to six antigens, one donor responded to seven antigens, two donors responded to eight antigens, and three donors responded to ten antigens. The present Example thus provides two compositions comprising a therapeutically effective amount of three cancer cell lines, a unit dose of six cell lines, wherein said unit dose is capable of eliciting an immune response 3.3-fold greater than the unmodified composition specific to at least seven TAAs expressed in OC patient tumors. OC vaccine-A increased IFNγ responses to at least six TAAs 2.2-fold and OC vaccine-B increased IFNγ responses 6.1-fold to at least six TAAs.

TABLE 91

IFNγ Responses to unmodified and modified OC vaccine components

| | Unmodified (SFU ± SEM) | | | Modified (SFU ± SEM) | | |
|---|---|---|---|---|---|---|
| Donor (n = 4) | OC vaccine-A | OC vaccine-B | OC Vaccine | OC vaccine-A | OC vaccine-B | OC Vaccine |
| 1 | 4,459 ± 2,295 | 260 ± 101 | 4,719 ± 2,970 | 386 ± 115 | 998 ± 446 | 1,383 ± 537 |
| 2 | 5,910 ± 1,175 | 2,240 ± 1,648 | 7,530 ± 1,735 | 2,188 ± 1,211 | 4,801 ± 1,430 | 6,989 ± 2,542 |
| 3 | 2,097 ± 1,631 | 813 ± 369 | 2,910 ± 1,933 | 9,273 ± 2,655 | 5,615 ± 1,764 | 14,888 ± 4,156 |
| 4 | 5,910 ± 1,175 | 3,331 ± 1,964 | 9,241 ± 3,012 | 22,102 ± 7,899 | 27,321 | 49,423 ± 18,471 |
| 5 | 1,962 ± 863 | 1,414 ± 617 | 3,376 ± 1,398 | 42,826 ± 2,276 | 23,162 ± 7,880 | 65,985 ± 8,801 |
| 6^ | 1,418 ± 636 | 1,686 ± 683 | 4,138 ± 1,060 | 2,433 ± 1,859 | 14,107 ± 8,825 | 22,053 ± 12,915 |
| 7 | 16,072 ± 4,222 | 4,333 ± 1,591 | 20,405± | 4,797 ± 1,783 | 1,358 ± 826 | 6,154 ± 2,592 |

^n = 3 for Donor 6. All others n = 4

Based on the disclosure and data provided herein, a whole cell vaccine for Ovarian Cancer comprising the six cancer cell lines, sourced from ATCC or JCRB, OVTOKO (JCRB, JCRB1048), MCAS (JCRB, JCRB0240), TOV-112D (ATCC, CRL-11731), TOV-21G (ATCC, CRL-11730), ES-2 (ATCC, CRL-1978) and DMS 53 (ATCC, CRL-2062) is shown in Table 92. The cell lines represent five ovarian cancer cell lines and one small cell lung cancer (SCLC) cell line (DMS 53). The cell lines have been divided into two groupings: vaccine-A and vaccine-B. Vaccine-A is designed to be administered intradermally in the upper arm and vaccine-B is designed to be administered intradermally in the thigh. Vaccine A and B together comprise a unit dose of cancer vaccine.

TABLE 92

Cell line nomenclature and modifications

| Cocktail | Cell Line | TGFβ1 KD | TGFβ2 KD | CD276 KO | GM-CSF | CD40L | IL-12 | TAA(s) |
|---|---|---|---|---|---|---|---|---|
| A | OVTOKO | X | ND | X | X | X | X | ND |
| A | MCAS | X | X | X | X | X | X | X |
| A | TOV-112D | X | X | X | X | X | X | X |
| B | TOV-21G | ND | ND | X | X | X | X | X |
| B | ES-2 | X | X | X | X | X | X | X |
| B | DMS 53* | ND | X | X | X | X | X | ND |

ND = Not done.

*Cell lines identified as CSC-like cells.

Where indicated in the above table, the genes for the immunosuppressive factors transforming growth factor-beta 1 (TGFβ1) and transforming growth factor-beta 2 (TGFβ2) have been knocked down using shRNA transduction with a lentiviral vector. The gene for CD276 has been knocked out by electroporation using zinc-finger nuclease (ZFN) or knocked down using shRNA transduction with a lentiviral vector. The genes for granulocyte macrophage-colony stimulating factor (GM-CSF), IL-12, CD40L, modTERT (MCAS), modFSHR (TOV-112D), modMAGEA10 (TOV-112D), modWT1 (TOV-21G), modFOLR1 (modFBP) (TOV-21G) and modBORIS (ES-2) have been added by lentiviral vector transduction.

Provided herein are two compositions comprising a therapeutically effective amount of three cancer cell lines, a unit dose of six cancer cell lines, modified to reduce the expression of at least one immunosuppressive factor and to express at least two immunostimulatory factors. One composition, OC vaccine-A, was modified to increase the expression of three TAAs modhTERT, modFSHR and modMAGEA10. The second composition, OC vaccine-B, was modified to expresses three TAAs, modWT1, modFOLR1 (modFBP) and modBORIS. The unit dose of six cancer cell lines expresses at least at least 15 TAAs associated with a cancer of a subset of ovarian cancer subjects intended to receive said composition and induces IFNγ responses 2.2-fold greater than the unmodified composition components.

Example 34: Preparation of Squamous Cell Head and Neck Cancer (SCCHN) Cancer Vaccine This Example demonstrates that reduction of TGFβ1, TGFβ2, and CD276 expression with concurrent overexpression of GM-CSF, CD40L, and IL-12 in a vaccine composition of two cocktails, each cocktail composed of three cell lines for a total of 6 cell lines, significantly increased the magnitude of cellular immune responses to at least 10 HN-associated antigens in an HLA-diverse population. As described herein, the first cocktail, HN vaccine-A, is composed of cell line HSC-4 that was also modified to express modPSMA, cell line HO-1-N-1 that was also modified to express modPRAME and modTBXT, and cell line DETROIT 562. The second cocktail, HN vaccine-B, is composed of cell line KON that was also modified to express HPV16 and HPV18 E6/E7, cell line OSC-20, and cell line DMS 53. The six component cell lines collectively express at least twenty non-viral antigens, and at least twenty-four, that can provide an anti-HN tumor response.

Identification of HN Vaccine Components

Initial cell line selection criteria identified thirty-five vaccine component cell lines for potential inclusion in the HN vaccine. Additional selection criteria described herein were applied to narrow the thirty-five cell lines to six cell lines for further evaluation in immunogenicity assays. These criteria included: endogenous HN associated antigen expression, lack of expression of additional immunosuppressive factors, such as IL-10 or IDO1, expression of associated CSC-like markers CD44, cMET, ABCG2, LRG5, ALDH1, and BMI-1, ethnicity and age of the patient from which the cell line was derived, primary site and stage of the HN cancer, and site from which the cell line was derived (primary or metastatic).

CSCs play a critical role in the metastasis, treatment resistance, and relapse of head and neck cancer (Table 2). Expression of TAAs and CSC-like markers by candidate component cell lines was determined by RNA expression data sourced from the Broad Institute Cancer Cell Line Encyclopedia (CCLE) and from the European Molecular Biology Laboratory-European Bioinformatics Institute (EMBL-EBI) (OSC-20, HO-1-N-1 and KON). The HGNC gene symbol was included in the CCLE search and mRNA expression was downloaded for each TAA. Expression of a TAA or CSC-like marker by a cell line was considered positive if the RNA-seq value was greater than one (CCLE, FPKM) or zero (EMBL-EBI, TPM). Selection criteria identified six candidate HN vaccine components for further evaluation: DETROIT 562, SCC-9, HSC-4, OSC-20, HO-1-N-1 and KON. The six candidate component cell lines expressed nine to seventeen TAAs (FIG. 107A) and four to six CSC-like markers (FIG. 107B). As described herein, the CSC-like cell line DMS 53 is included as one of the six vaccine cell lines and expressed fifteen HN TAAs and three HN CSC-like markers.

Immunogenicity of the six unmodified HN vaccine component candidates was evaluated by IFNγ ELISpot as described in Example 9 using three HLA diverse healthy donors (n=4 per donor). HLA-A and HLA-B alleles for the three donors were as follows: Donor 1, A*01:01 B*08:01 and A*02:01 B*15:01; Donor 2, A*03:01 B*15:01 and A*24:02 B*07:02; Donor 3, A*01:01 B*07:02 and A*30:01 B*12:02. KON (1,645±215 SFU) and HSC-4 (1,124±394 SFU) were more immunogenic than DETROIT 562 (372±132 SFU), SCC-9 (0±0 SFU), OSC-20 (985±265 SFU), and HO-1-N-1 (486±137 SFU) (FIG. 109A). SCC-9 was poorly immunogenic and excluded from further analysis. HSC-4 and KON were selected to be included in vaccine cocktail A and vaccine cocktail B, respectively, as described further herein.

Immunogenicity of five selected HN cell lines and the CSC-like cell line DMS 53 was evaluated in two different combinations of three component cell lines (FIG. 109C). IFNγ responses were determined against the three component cell lines within the two potential vaccine cocktails by IFNγ ELISpot as described in Example 8 in five HLA diverse healthy donors (n=4 per donor) (Table 99, Donors 1-3, 5 and 6). IFNγ responses were detected for both cocktails and to each cell line component in each cocktail (FIG. 109B). The ability of the individual HN vaccine component cell lines to induce IFNγ responses against themselves compared to the ability of the potential HN vaccine cocktails to induce IFNγ responses against the individual cell lines was also measured by IFNγ ELISpot as described in Examples 8 and 9. There was a trend towards increased IFNγ responses to each HN cell line included in the vaccine cocktails, with the exception of HSC-4, compared to responses to the cell line alone (FIG. 109D).

The cells in the vaccine described herein were selected to express a wide array of TMs, including those known to be important specifically for HN antitumor responses, such as NUF2 or PSMA, and also TMs known to be important for targets for HN and other solid tumors, such as TERT. Additionally, one of the six cell lines was also modified to express HPV16 and 18 viral antigens E6 and E7 since about 25-50% of HNCs are HPV-driven and high risk strains HPV16 and HPV18 contribute to the majority (~85%) of $HPV^-$ HNC cases worldwide. Viral oncoproteins E6 and E7 represent good targets for immunotherapy, as they are continuously expressed by tumor cells and are essential to maintain the transformation status of HPV+ cancer cells. As shown herein, to further enhance the array of TMs and HPV viral antigens, HSC-4 was modified to express modPSMA, HO-1-N-1 was modified to express modPRAME and modTBXT, and KON was modified to express HPV16 and HPV18 E6/E7. TBXT was not endogenously expressed in the six component cell lines at >1.0 FPKM or >0 TPM. HPV16 E6/E7 or HPV18 E6/E7 were not expressed by the HN vaccine component cell lines according to product information provided by ATCC or JCRB. Expression data of the HPV 16 or 18 viral antigens was not available in CCLE or EMBL. PSMA was endogenously expressed by one of the six component cell lines at >1.0 FPKM or >0 TPM. PRAME was endogenously expressed by two of the six component cell lines at >1.0 FPKM or >0 TPM. (FIG. 107A).

Expression of the transduced antigens modPSMA (FIG. 110A) by HSC-4 (SEQ ID NO: 37; SEQ ID NO: 38), modPRAME (FIG. 110B) and TBXT (FIG. 120C) by HO-1-N-1 (SEQ ID NO: 65; SEQ ID NO: 66) and HPV16 E6/E7 and HPV18 E6/E7 (FIG. 110D) (SEQ ID NO: 67; SEQ ID NO: 68) by KON, were detected by flow cytometry or RT-PCR as described in Example 29 and herein. The modPRAME and modTBXT antigens are encoded in the same lentiviral transfer vector separated by a furin cleavage site (SEQ ID NO: 65 and SEQ ID NO: 66).

Because of the need to maintain maximal heterogeneity of antigens and clonal subpopulations the comprise each cell line, the gene modified cell lines utilized in the present vaccine have been established using antibiotic selection and flow cytometry and not through limiting dilution subcloning.

Figure 107A:
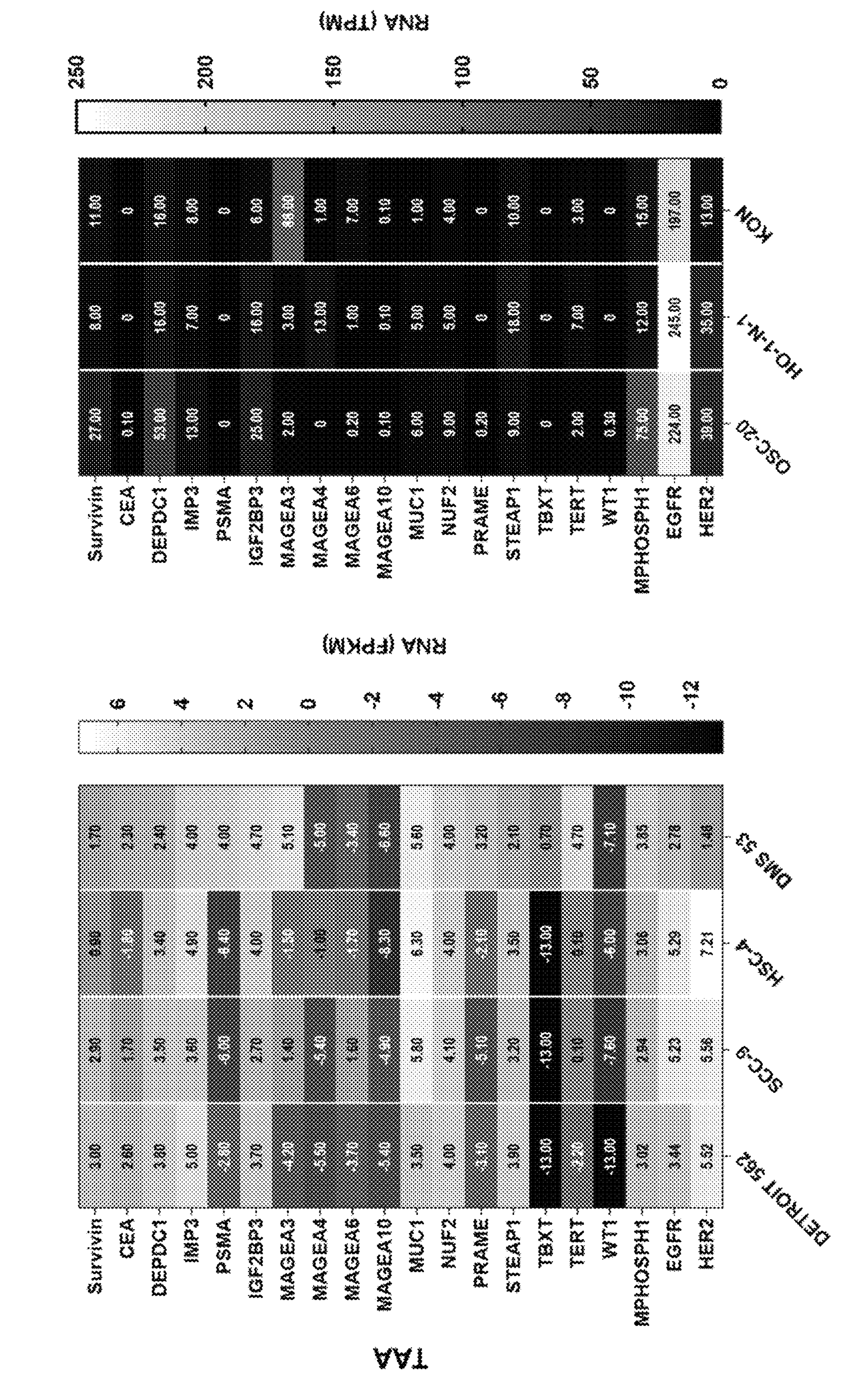
FIGS. 107A and B show endogenous expression of head and neck cancer antigens (FIG. 107A) and of head and neck cancer CSC-like markers (FIG. 107B) by candidate and selected head and neck cancer vaccine component cell lines.
Figure 107B:
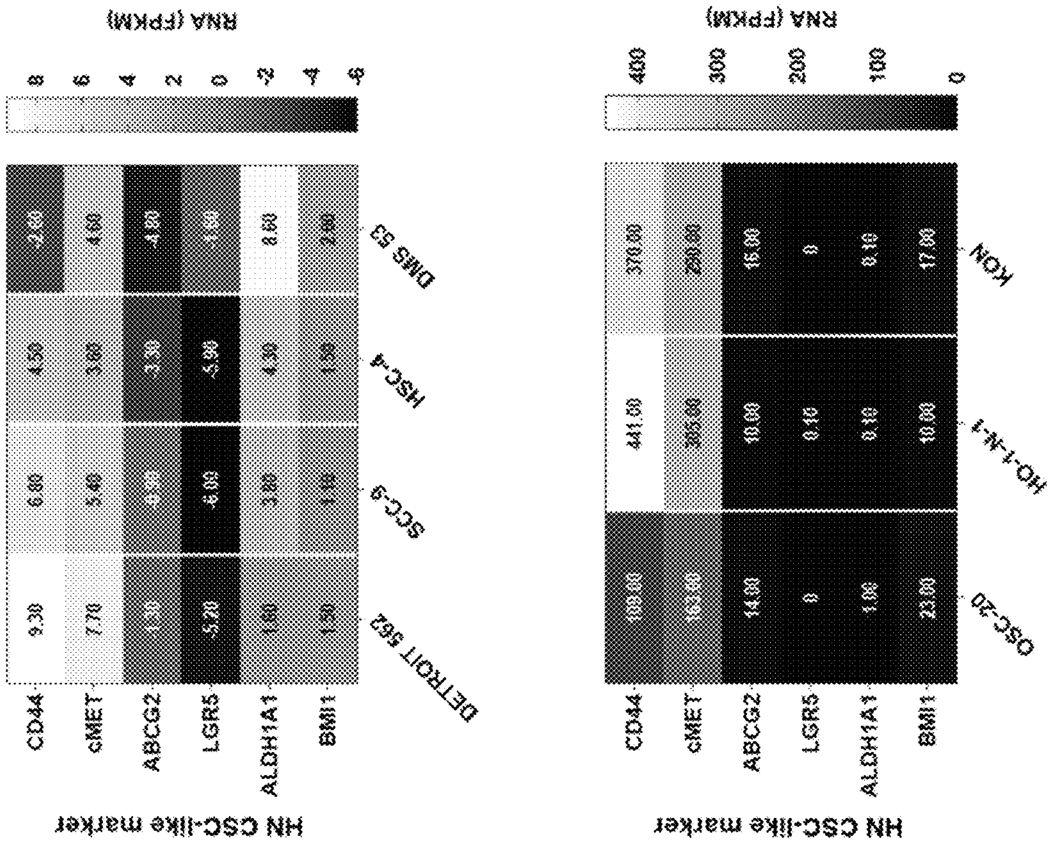
Figure 108A:
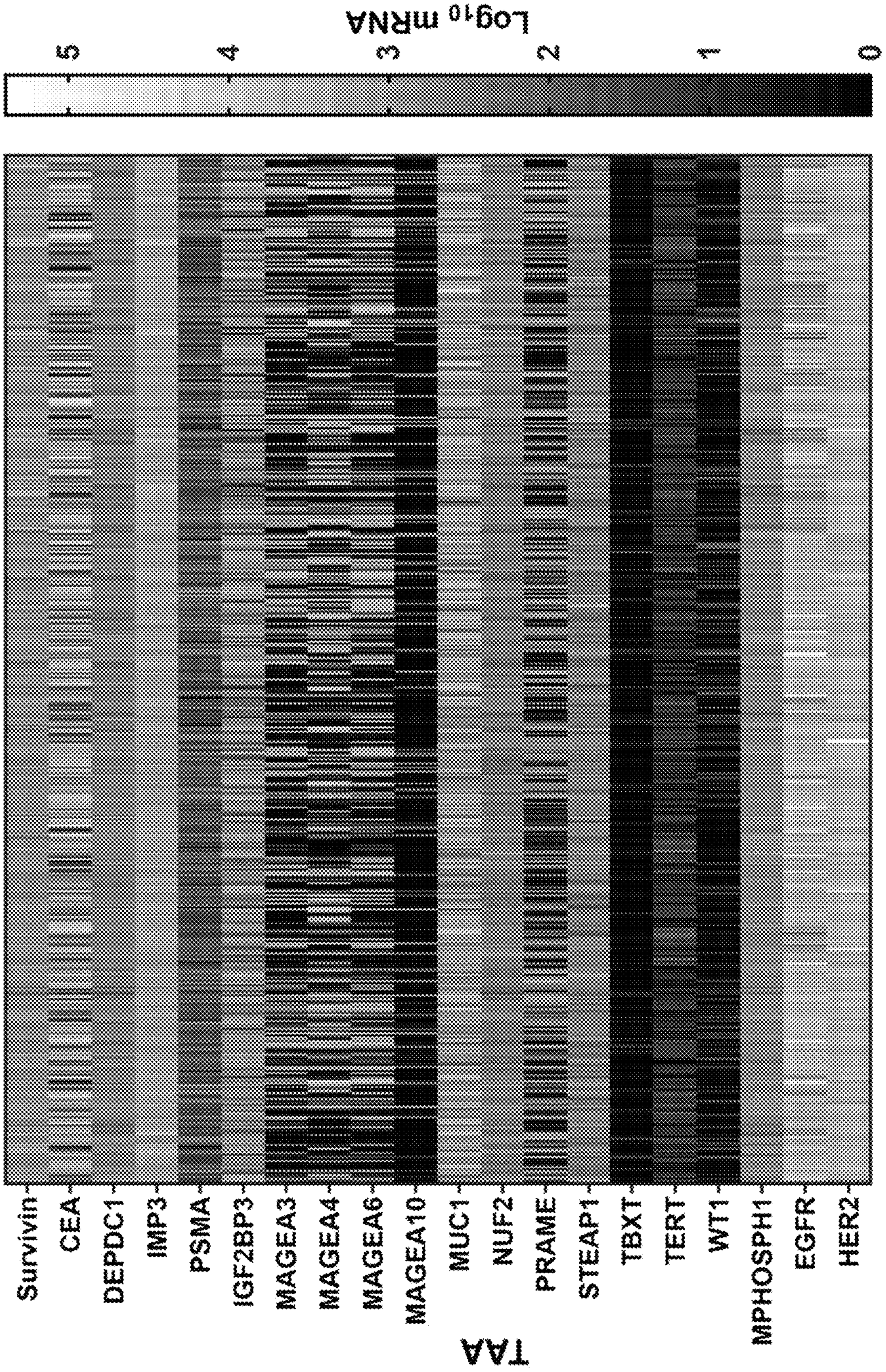
FIGS. 108A and B show expression of antigens in patient tumors also expressed by selected HN vaccine component cell lines (FIG. 108A) and the number of head and neck cancer antigens expressed by the HN vaccine cell lines also expressed in head and neck cancer patient tumors (FIG. 108B).
Figure 108B:
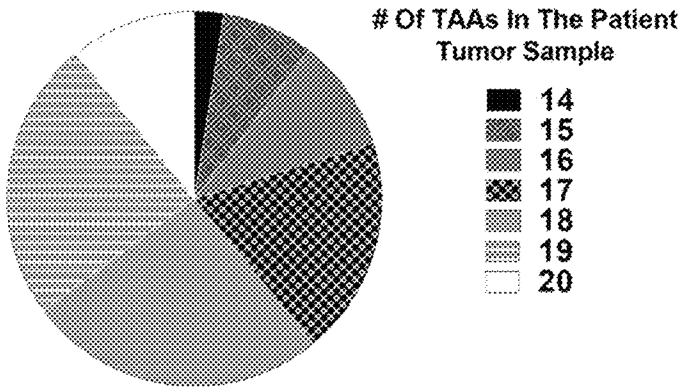

The endogenous mRNA expression of twenty representative HN TAAs in the present vaccine are shown in FIG. 107A. SCC-9 is the only cell line in FIG. 107 that is not included in the present vaccine. The present vaccine, after introduction antigens described above, expresses of all identified twenty commonly targeted and potentially clinically relevant TAAs capable of inducing a HN antitumor response. Some of these TAAs are known to be primarily enriched in HN tumors and some can also induce an immune response to HN and other solid tumors. RNA abundance of the twenty-four prioritized HN TAAs was determined in 515 HN patient samples with available mRNA data expression as described in Example 29 (FIG. 108A). Fourteen of the prioritized TAAs were expressed by 100% of samples, 15 TAAs were expressed by 97.5% of samples, 16 TAAs were expressed by 89.5% of samples, 17 TAAs were expressed by 79.8% of samples, 18 TAAs were expressed by 61.0% of samples, 19 TAAs were expressed by 35.1% of samples and 20 TAAs were expressed by 10.9% of samples (FIG. 108B). Provided herein are two compositions comprising a therapeutically effective amount of three cancer cell lines, wherein the combination of the cell lines, a unit dose of six cell lines, comprises cells that express at least 14 TAAs associated with a subset of HN cancer subjects intended to receive said composition. Based on the expression and immunogenicity data presented herein, the cell lines identified in Table 93 were selected to comprise the present HN vaccine.

TABLE 93

Head and neck vaccine cell lines and histology

| Cocktail | Cell Line Name | Histology |
|---|---|---|
| A | HSC-4 | Tongue Squamous Cell Carcinoma derived from metastatic site (cervical lymph node) |
| A | HO-1-N-1 | Buccal Mucosa Squamous Cell Carcinoma |
| A | DETROIT 562 | Pharynx Squamous Cell Carcinoma derived from metastatic site (pleural effusion) |
| B | KON | Mouth Floor Squamous Cell Carcinoma derived from metastatic site (cervical lymph node) |
| B | OSC-20 | Tongue Squamous Cell Carcinoma derived from metastatic site (cervical lymph node) |
| B | DMS 53 | Lung Small Cell Carcinoma |

Reduction of CD276 Expression

The HSC-4, HO-1-N-1, DETROIT 562, KON, OSC-2, and DMS 53 component cell lines expressed CD276 and expression was knocked out by electroporation with ZFN as described in Example 13 and elsewhere herein. Because it was desirable to maintain as much tumor heterogeneity as possible, the electroporated and shRNA modified cells were not cloned by limiting dilution. Instead, the cells were subjected to multiple rounds of cell sorting by FACS as described in Example 13. Expression of CD276 was determined as described in Example 29. Reduction of CD276 expression is described in Table 94. These data show that gene editing of CD276 with ZFN resulted in greater than 98.9% CD276-negative cells in all six vaccine component cell lines.

TABLE 94

Reduction of CD276 expression

| Cell line | Parental Cell Line MFI | Modified Cell Line MFI | % Reduction CD276 |
|---|---|---|---|
| HSC-4 | 21,934 | 15 | 99.9 |
| HO-1-N-1 | 12,200 | 139 | 98.9 |
| DETROIT 562 | 9,434 | 79 | 99.2 |
| KON | 14,762 | 6 | ≥99.9 |
| OSC-20 | 8,357 | 33 | 99.6 |
| DMS 53 | 11,928 | 24 | 99.8 |

MFI reported with isotype controls subtracted

Cytokine Secretion Assays for TGFβ1, TGFβ2, GM-CSF, and IL-12

Cytokine Secretion Assays for TGFβ1, TGFβ2, GM-CSF, and IL-12 were Completed as Described in Example 29.

shRNA Downregulates TGF-β Secretion

Following CD276 knockout, TGFβ1 and TGFβ2 secretion levels were reduced using shRNA and resulting levels determined as described in Example 29. The HSC-4, HO-1-N-1 and DETROIT 562 parental cell lines in HN vaccine-A secreted measurable levels of TGFβ1 and TGFβ2. The KON and OSC-2 component cell lines of HN vaccine-B secreted measurable levels of TGFβ1 and TGFβ2. OSC-2 secreted low levels of TGFβ1 and was not modified to reduce TGFβ1 secretion. Reduction of TGFβ2 secretion by the DMS 53 cell line is described in Example 26 and resulting levels determined as described above and herein.

The HSC-4, HO-1-N-1, DETROIT 562 and KON component cell lines were transduced with TGFβ131 shRNA to decrease TGFβ131 secretion and concurrently increase the expression of membrane bound CD40L as described in Example 29. The HSC-4, HO-1-N-1, DETROIT 562 and KON were also transduced with lentiviral particles encoding TGFβ2 shRNA to decrease the secretion of TGFβ2 and concurrently increase expression of GM-CSF (SEQ ID NO: 6) as described in Example 29. These cells are described by the clonal designation DK6. Modification of HSC-4 with TGFβ131 shRNA initially decreased the secretion of TGFβ131. Subsequent modification of HSC-4 with TGFβ2 shRNA decreased secretion of TGFβ2 but resulted in TGFβ131 secretion levels similar to the parental cell line (Table 95). TGFβ131 and TGFβ2 promote cell proliferation and survival and retaining some TGFβ signaling is likely necessary for proliferation and survival of some cell lines. Immunogenicity of the individual unmodified and modified HN cell vaccine cell line components was evaluated in five HLA diverse donors (Table 99, Donors 1-3, 5 and 6) as described in Example 9. The modified HSC-4 cell line remained more immunogenic (1,108±628 SFU) than the unmodified cell line (400±183 SFU) despite secreting similar TGFβ131 levels as the unmodified cell line (FIG. 109E). Increased secretion of TGFβ131 following reduction of TGFβ2 in the HSC-4 cell line potentially was a compensatory survival mechanism. OSC-20 was transduced with lentiviral particles encoding TGFβ2 shRNA to decrease the secretion of TGFβ2 and concurrently increase expression of GM-CSF (SEQ ID NO: 6) as described in Example 29. OSC-20 was subsequently transduced with lentiviral particles to increase the expression of membrane bound CD40L. DMS 53 was modified with shRNA to reduce secretion of TGFβ2 as described in Example 26. The OCS-20 and DMS 53 cells modified to reduce secretion of TGFβ2 and not TGFβ131 are described by the clonal designation DK4.

Table 95 shows the percent reduction in TGFβ131 and/or TGFβ2 secretion in gene modified component cell lines compared to unmodified, parental, cell lines. Gene modification resulted in at least 79% reduction of TGFβ131 secretion. Gene modification of TGFβ2 resulted in at least 51% reduction in secretion of TGFβ2.

TABLE 95

TGF-β Secretion (pg/$10^6$ cells/24 hr) in Component Cell Lines

| Cell Line | Cocktail | Clone | TGFβ1 | TGFβ2 |
|---|---|---|---|---|
| HSC-4 | A | Wild type | 477 ± 88 | 252 ± 46 |
| HSC-4 | A | DK6 | 515 ± 69 | * ≤15 |
| HSC-4 | A | Percent reduction | NA | 94% |
| HO-1-N-1 | A | Wild type | 1,226 ± 183 | 2,238 ± 488 |
| HO-1-N-1 | A | DK6 | 254 ± 60 | 224 ± 114 |
| HO-1-N-1 | A | Percent reduction | 79% | 90% |
| DETROIT 562 | A | Wild type | 361 ± 86 | 1,037 ± 392 |
| DETROIT 562 | A | DK6 | * ≤29 | * ≤15 |
| DETROIT 562 | A | Percent reduction | 92% | ≥99% |
| KON | B | Wild type | 863 ± 375 | 675 ± 243 |
| KON | B | DK6 | * ≤32 | 268 ± 148 |
| KON | B | Percent reduction | 96% | 60% |
| OSC-2 | B | Wild type | 268 ± 46 | 1,249 ± 383 |
| OSC-2 | B | DK4 | NA | 94 ± 31 |
| OSC-2 | B | Percent reduction | NA | 92% |
| DMS 53 | B | Wild type | 106 ± 10 | 486 ± 35 |
| DMS 53 | B | DK4 | NA | 238 ± 40 |
| DMS 53 | B | Percent reduction | NA | 51% |

DK6: TGFβ1/TGFβ2 double knockdown;
DK4: TGFβ2 single knockdown;
DK2: TGFβ1 single knockdown;
* estimated using LLD, not detected;
NA = not applicable Based on a dose of $5\times10^5$ of each component cell line, the total TGFβ1 and TGFβ2 secretion by the modified HN vaccine-A and HN vaccine-B and respective unmodified parental cell lines are shown in Table 96. The secretion of TGFβ1 by HN vaccine-A was reduced by 61% and TGFβ2 by 93% pg/dose/24 hr. The secretion of TGFβ1 by HN vaccine-B was reduced by 67% and TGFβ2 by 75% pg/dose/24 hr.

TABLE 96

Total TGF-β Secretion (pg/dose/24 hr) in HN vaccine-A and HN vaccine-B

| Cocktail | Clones | TGFβ1 | TGFβ2 |
|---|---|---|---|
| A | Wild type | 1,032 | 1,764 |
| | DK6 | 399 | 127 |
| | Percent reduction | 61% | 93% |
| B | Wild type | 619 | 1,205 |
| | DK4/DK6 | 203 | 300 |
| | Percent reduction | 67% | 75% |

GM-CSF Secretion

The HSC-4, HO-1-N-1, DETROIT 562 and KON cell lines were transduced with lentiviral particles containing both TGFβ2 shRNA and the gene to express GM-CSF (SEQ ID NO: 6) as described above. DMS 53 was modified to secrete GM-CSF as described in Example 26 and elsewhere herein. The results are shown in Table 96 and described below.

Secretion of GM-CSF increased at least 9,578-fold in all modified component cell lines compared to unmodified, parental cell lines. In HN vaccine-A component cell lines, secretion of GM-CSF increased 53,794-fold by HSC-4 compared to the parental cell line (≤0.0042 ng/$10^6$ cells/24 hr), 13,703-fold by HO-1-N-1 compared to the parental cell line (≤0.0039 ng/$10^6$ cells/24 hr), and 13,235-fold by DETROIT 562 compared to the parental cell line (≤0.0038 ng/$10^6$ cells/24 hr). In HN vaccine-B component cell lines secretion of GM-CSF increased 14,867-fold by KON compared to the parental cell line (≤0.0047 ng/$10^6$ cells/24 hr), 9,578-fold by OSC-2 compared to the parental cell line (≤0.0039 ng/$10^6$ cells/24 hr) and 49,313-fold by DMS 53 compared to the parental cell line (≤0.0032 ng/$10^6$ cells/24 hr).

TABLE 97

GM-CSF Secretion in Component Cell Lines

| Cell Line | GM-CSF (ng/$10^6$ cells/24 hr) | GM-CSF (ng/dose/24 hr) |
|---|---|---|
| HSC-4 | 226 ± 84 | 113 |
| HO-1-N-1 | 53 ± 11 | 27 |
| DETROIT 562 | 50 ± 11 | 25 |
| Cocktail A Total | 329 | 165 |
| KON | 70 ± 21 | 35 |
| OSC-2 | 37 ± 11 | 19 |
| DMS 53 | 158 ± 15 | 79 |
| Cocktail B Total | 265 | 133 |

Based on a dose of $5\times10^5$ of each component cell line, the total GM-CSF secretion for HN vaccine-A was 165 ng per dose per 24 hours. The total GM-CSF secretion for HN vaccine-B was 133 ng per dose per 24 hours. The total GM-CSF secretion per dose was therefore 298 ng per 24 hours.

Membrane Bound CD40L (CD154) Expression

Figure 111:
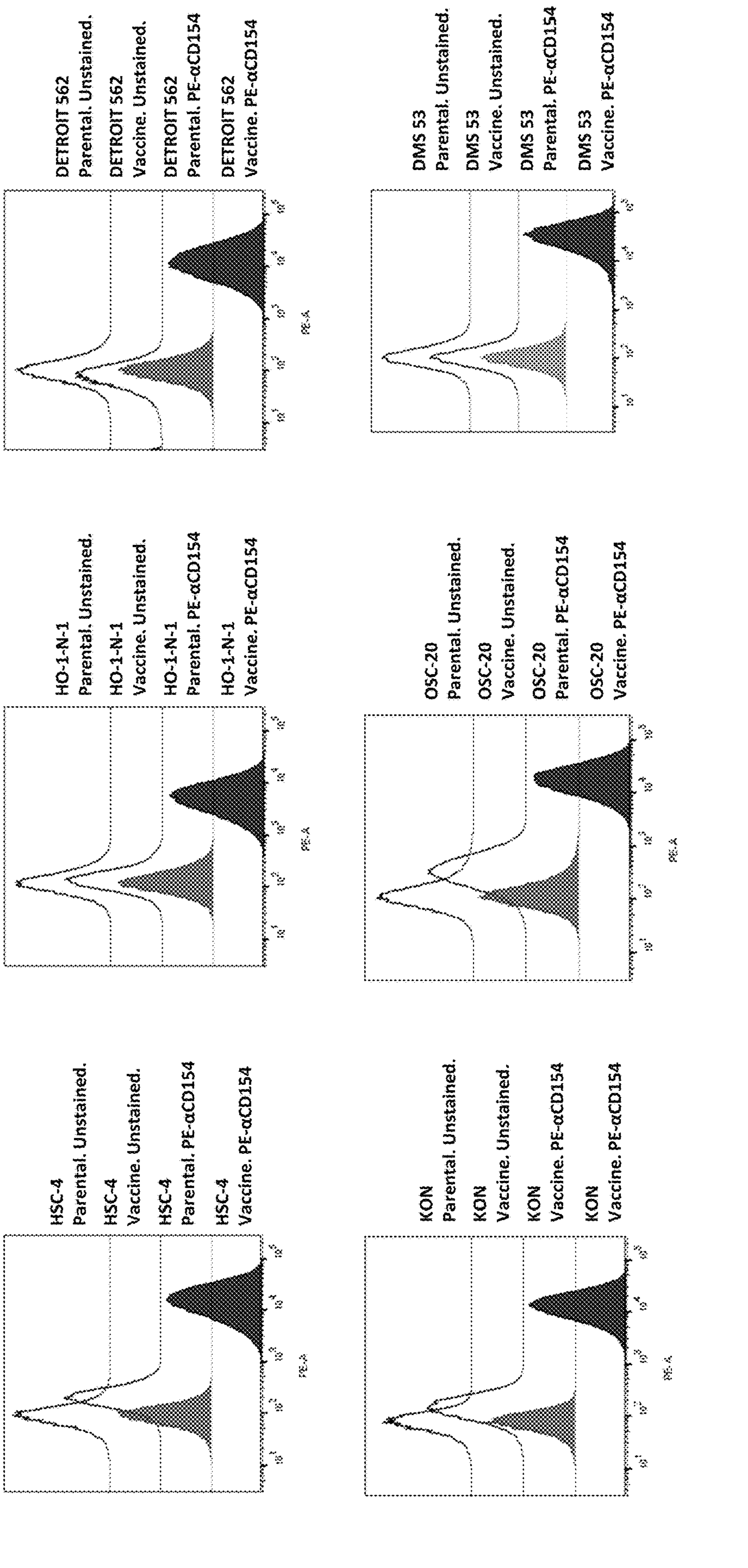
FIG. 111 shows expression of membrane bound CD40L by the HN vaccine component cell lines.

The component cell lines were transduced with lentiviral particles to express membrane bound CD40L vector as described above. The methods to detect expression of CD40L by the five HN cell line components are described in Example 29. Modification of DMS 53 to express membrane bound CD40L is described in Example 15. Evaluation of membrane bound CD40L by all six vaccine component cell lines is described below. The results shown in FIG. 111 and described below demonstrate CD40L membrane expression was substantially increased in all six HN vaccine component cell lines.

Expression of membrane bound CD40L increased at least 2,144-fold in all component cell lines compared to unmodified, parental cell lines. In HN vaccine-A component cell lines, expression of CD40L increased 18,046-fold by HSC-4 (18,046 MFI) compared to the parental cell line (0 MFI), 9,796-fold by HO-1-N-1 (9,796 MFI) compared to the parental cell line (0 MFI), and 18,374-fold by DETROIT 562 (18,374 MFI) compared to the parental cell line (0 MFI). In HN vaccine-B component cell lines expression of CD40L increased 15,603-fold by KON compared to the parental cell line (0 MFI), 2,144-fold by OSC-20 (40,738 MFI) compared to the parental cell line (19 MFI), and 88,261-fold by DMS 53 compared to the parental cell line (0 MFI).

IL-12 Expression

The component cell lines were transduced with the IL-12 vector as described in Example 17 and resulting IL-12 p70 expression determined as described above and herein. The results are shown in Table 98 and described below.

Secretion of IL-12 increased at least 11,274-fold in all component cell lines modified to secrete IL-12 p70 compared to unmodified, parental cell lines. In HN vaccine-A component cell lines, secretion of IL-12 increased 148,017-fold by HSC-4 compared to the parental cell line (≤0.0017 ng/$10^6$ cells/24 hr), 33,271-fold by HO-1-N-1 compared to the parental cell line 0.0016 ng/$10^6$ cells/24 hr), and 21,272-fold by DETROIT 562 compared to the parental cell line (≤0.0015 ng/$10^6$ cells/24 hr). In HN vaccine-B component cell lines expression of IL-12 increased 11,274-fold by KON compared to the parental cell line 0.0019 ng/$10^6$ cells/24 hr) and 22,641-fold by OSC-2 compared to the parental cell line (≤0.0016 ng/$10^6$ cells/24 hr). DMS 53 was not modified to secrete IL-12.

TABLE 98

IL-12 Secretion in Component Cell Lines

| Cell Line | IL-12 (ng/$10^6$ cells/24 hr) | IL-12 (ng/dose/24 hr) |
|---|---|---|
| HSC-4 | 249 ± 120 | 125 |
| HO-1-N-1 | 52 ± 11 | 26 |
| DETROIT 562 | 32 ± 6 | 16 |
| Cocktail A Total | 333 | 167 |
| KON | 21 ± 15 | 11 |
| OSC-2 | 35 ± 12 | 18 |
| DMS 53 | NA | NA |
| Cocktail B Total | 56 | 29 |

Based on a dose of 5×$10^5$ of each component cell line, the total IL-12 secretion for HN vaccine-A was 167 ng per dose per 24 hours. The total IL-12 secretion for HN vaccine-B was 29 ng per dose per 24 hours. The total IL-12 secretion per dose was therefore 196 ng per 24 hours.

Stable Expression of modPSMA by the HSC-4 Cell Line

As described above, the cells in the vaccine described herein were selected to express a wide array of TAAs, including those known to be important to antitumor immunity. To further enhance the array of antigens, the HSC-4 cell line that was modified to reduce the secretion of TGFβ2, reduce the expression of CD276, and to express GM-CSF, membrane bound CD40L and IL-12 was also transduced with lentiviral particles expressing the modPSMA antigen (SEQ ID NO: 37, SEQ ID NO: 38).

Figure 110A:
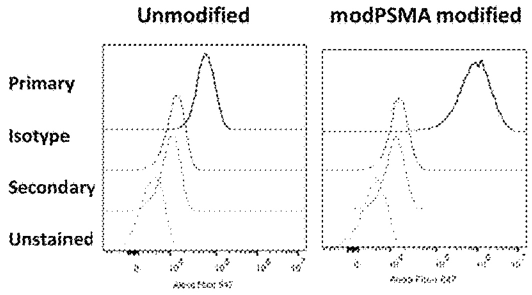
FIGS. 110A-K show expression of modPSMA by HSC-4 (FIG. 110A) and IFNγ responses to PSMA (FIG. 110E), expression of modPRAME (FIG. 110B) and modTBXT (FIG. 110C) by HO-1-N-1 (FIG. 110A) and IFNγ responses to PRAME (FIG. 110F) and TBXT (FIG. 110G), expression of HPV16 and HPV18 E6 and E7 by KON (FIG. 110D) and IFNγ responses to HPV16 E6 and E7 in all donors (FIG. 110H) and individual donors (FIG. 110I), and IFNγ responses to HPV18 E6 and E7 in all donors (FIG. 110J) and individual donors (FIG. 110K).

The expression of modPSMA by HSC-4 was characterized by flow cytometry. Unmodified and antigen modified cells were stained intracellular with 0.03 μg/test anti-mouse IgG1 anti-PSMA antibody (Abcam, ab268061) followed by 0.125 ug/test AF647-conjugated goat anti-mouse IgG1 antibody (BioLegend #405322). Expression of modPSMA was increased in the modified cell line (4,473,981 MFI) 25-fold over that of the parental cell line (174,545 MFI) (FIG. 110A).

Stable Expression of modPRAME and modTBXT by the HO-1-N-1 Cell Line

Figure 110B:
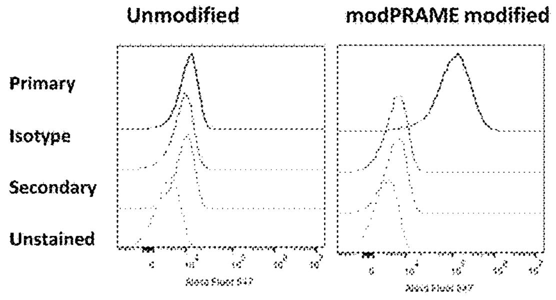
Figure 110C:
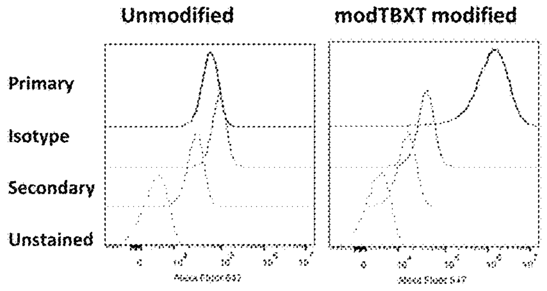
Figure 110D:
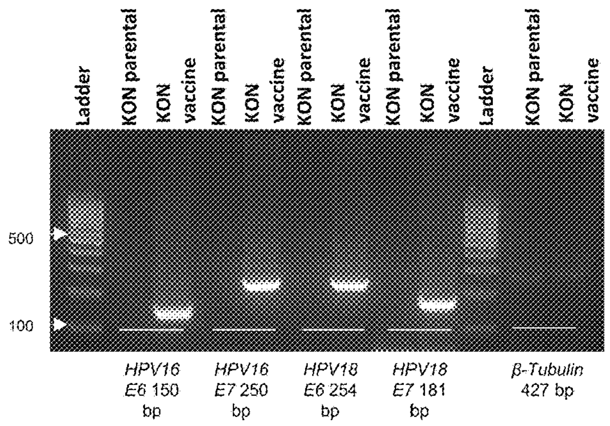

The HO-1-N-1 cell line that was modified to reduce the secretion of TGFβ1 and TGFβ2, reduce the expression of CD276, and to express GM-CSF, membrane bound CD40L, and IL-12 was also transduced with lentiviral particles expressing the modPRAME and modTBXT antigens (SEQ ID NO: 65, SEQ ID NO: 66). Expression of modPRAME by HO-1-N-1 was characterized by flow cytometry. Unmodified and antigen modified cells were stained intracellular with 0.015 μg/test anti-mouse IgG1 anti-PRAME antibody (Thermo Scientific, MA5-31909) followed by followed by 0.125 ug/test AF647-conjugated goat anti-mouse IgG1 antibody (BioLegend #405322). Expression of modPRAME increased in the modified cell line (290,436 MFI) 27-fold over that of the unmodified cell line (10,846 MFI) (FIG. 110B). Expression of modTBXT by HO-1-N-1 was also characterized by flow cytometry. Unmodified and antigen modified cells were stained intracellular with 0.06 μg/test rabbit anti-TBXT antibody (Abcam, ab209665) followed by 0.125 ug/test AF647-conjugated donkey anti-rabbit IgG1 antibody (BioLegend #406414). Expression of modTBXT increased in the modified cell line (3,338,324 MFI) 3,338,324-fold over that of the unmodified cell line (0 MFI) (FIG. 110C).

Stable Expression of HPV16 E6/E7 HPV18 E6/E7 by the KON Cell Line

The KON cell line that was modified to reduce the secretion of TGFβ1 and TGFβ2, reduce the expression of CD276, and to express GM-CSF, membrane bound CD40L and IL-12 was also transduced with lentiviral particles expressing the HPV16 and HPV18 E6 and E7 antigens (SEQ ID NO: 67, SEQ ID NO: 68). Expression of HPV16 and HPV18 E6/E7 by KON was determined by RT-PCR as described in Example 29 and herein. The forward primer to detect HPV16 E6 was designed to anneal at the 33-54 bp location in the transgene (CCCT-CAAGAGAGGCCCAGAAAG (SEQ ID NO: 136)) and reverse primer designed to anneal at the 160-182 bp location in the transgene (TACACGATGCACAGGTCCCGGAA (SEQ ID NO: 137)) yielding a 150 bp product. The gene product for HPV16 E6 was detected at the expected size (FIG. 110D) and mRNA increased 8,422-fold relative to the parental control. The forward primer to detect HPV16 E7 was designed to anneal at the 1-21 bp location in the transgene (CACGGCGATACCCCTACACTG (SEQ ID NO: 138)) and reverse primer designed to anneal at the 228-250 bp location in the transgene (CCATCAGCA-GATCTTCCAGGGTT (SEQ ID NO: 139)) yielding a 250 bp product. The gene product for HPV16 E7 was detected at the expected size (FIG. 110D) and mRNA increased 7,816-fold relative to the parental control. The forward primer to detect HPV18 E6 was designed to anneal at the 59-81 bp location in the transgene (TGAACACCAGCCTGCAGGA-CATC (SEQ ID NO: 140)) and reverse primer designed to anneal at the 287-312 bp location in the transgene (GCATCTGATGAGCAGGTTGTACAGGC (SEQ ID NO: 141)) yielding a 254 bp product. The gene product for HPV18 E6 was detected at the expected size (FIG. 110D) and mRNA increased 1,224-fold relative to the parental control. The forward primer to detect HPV18 E7 was designed to anneal at the 74-97 bp location in the transgene (TGTGCCATGAGCAGCTGTCCGACT (SEQ ID NO: 142)) and reverse primer designed to anneal at the 232-254 bp location in the transgene (AAGGCTCTCAGGTCGTCGGCAGA (SEQ ID NO: 143)) yielding a 181 bp product. The gene product for HPV18 E7 was detected at the expected size (FIG. 110D) and mRNA increased 1,684-fold relative to the parental control. Control primers for β-tubulin are described in Example 29.

Immune Responses to PSMA in HN Vaccine-A

Figure 110E:
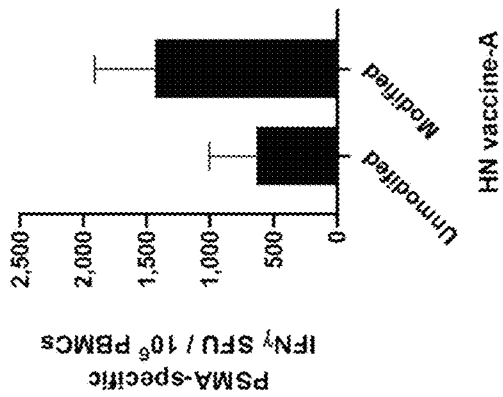

IFNγ responses to PSMA were evaluated in the context of HN vaccine-A as described in Example 32, and herein, in six HLA diverse donors (n=4/donor). The HLA-A, HLA-B, and HLA-C alleles for each of the seven donors are shown in Table 99. IFNγ responses were determined by ELISpot as described in Example 29. PSMA specific IFNγ responses were increased with the modified HN vaccine-A (1,433±479 SFU) compared to the parental unmodified HN vaccine-A (637±369 SFU (FIG. 110E).

Immune Responses to PRAME and TBXT in HN Vaccine-A

Figure 110F:
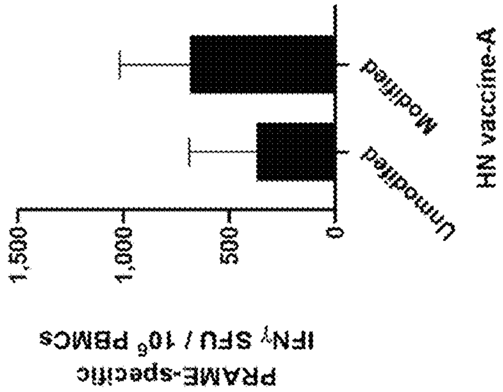
Figure 110G:
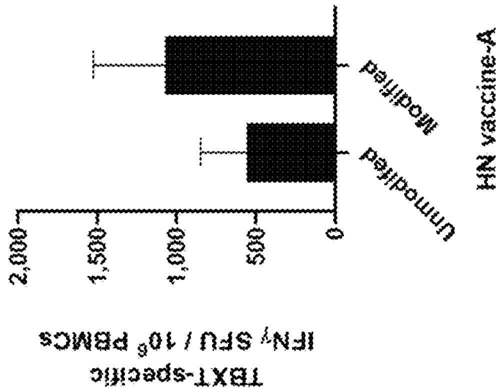

IFNγ responses to PRAME and FOLR1 were evaluated in the context of HN-vaccine A as described in Example 29, and herein, in six HLA diverse donors (n=4/donor) (Table 99). IFNγ responses against modPRAME were determined by ELISpot using 15-mer peptides overlapping by 11 amino acids spanning the entire length of the native antigen protein PRAME (JPT, PM-01P4). modPRAME specific IFNγ responses were increased by HN vaccine-A (687±333 SFU) compared to the unmodified HN vaccine-A (375±314 SFU) (FIG. 110F). IFNγ responses to TBXT were determined by ELISpot using 15-mers peptides overlapping by 11 amino acids (JPT, PM-BRAC) spanning the entire length of the native TBXT antigen. modTBXT specific IFNγ responses were increased by HN vaccine-A (1,071±455 SFU) compared to the unmodified HN vaccine-A (559±289 SFU) (FIG. 110G).

Immune Responses to HPV16 and HPV18 E6/E7 in HN Vaccine-B

IFNγ responses to the HPV16 and HPV18 E6/E7 antigens introduced into the KON cell line was evaluated in the context of HN-vaccine B as described in Example 29, and herein, in six HLA diverse donors (n=4/donor) (Table 99). Healthy donors from which the immune cells are derived to complete these studies are not screened for HPV16 and HPV18 and responses against the HPV16 E6/E7 and HPV18 E6/E7 antigens could be a boosted memory response, and not primed de novo, if the donor was HPV16 or HPV18 positive.

Figure 110H:
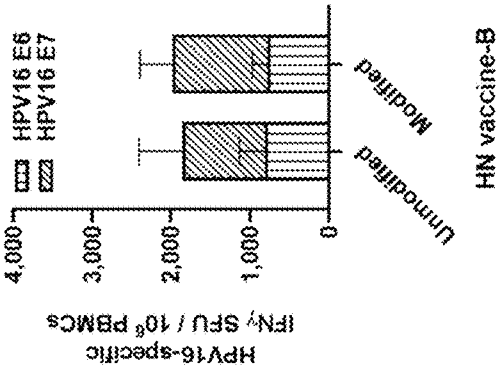
Figure 110I:
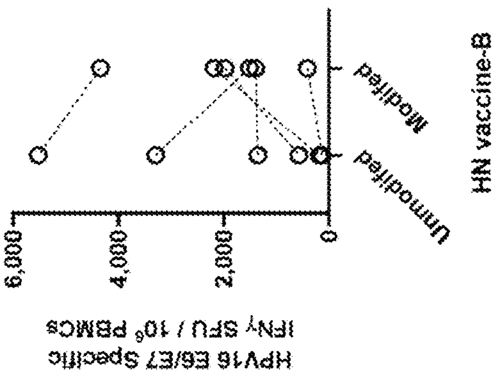
Figure 110J:
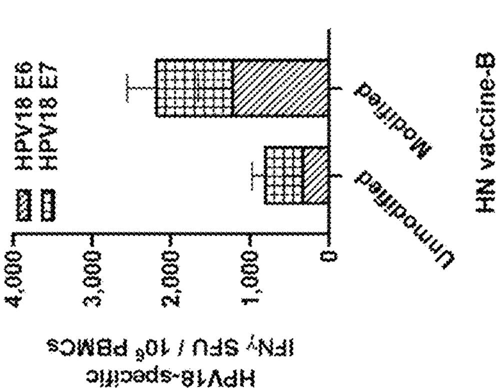
Figure 110K:
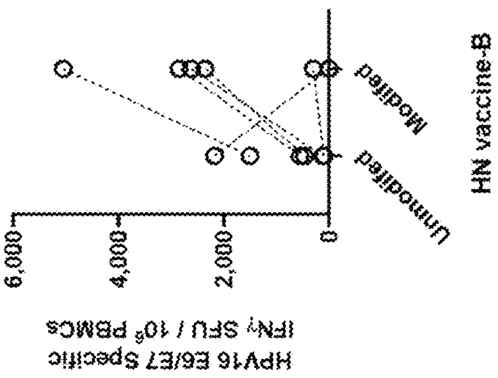

IFNγ responses to the HPV16 and HPV18 E6/E7 antigens were determined by ELISpot using 15-mers peptides overlapping by 9 amino acids spanning the entire length of the HPV16 and HPV18 E6/E7 antigens purchased from Thermo Scientific Custom Peptide Service. The average IFNγ response to HPV16 E6/E7 was similar with the modified HN vaccine-B (1,974±537 SFU) compared to the unmodified HN vaccine-B (1,845±878 SFU) (FIG. 110H). HPV16 E6/E7 responses were decreased in two of six donors (Donor 2 and Donor 6) primed with HN vaccine-B compared to unmodified HN vaccine-B (FIG. 1101). HPV16 E6/E7 responses were increased with HN vaccine-B in the other four Donors. It is possible that Donor 2 and Donor 6 were HPV16 positive and continuous stimulation in the context of the in vitro co-culture assay with HPV16 E6/E7 expressed by HN vaccine-B induced T cell exhaustion thereby decreasing IFNγ production when stimulated with peptides in the ELISpot assay. The HN vaccine should not induce T cell exhaustion in HPV16 or HPV18 positive patients because of the differences in the mechanism of inducing an immune response in vitro and in vivo. The average IFNγ response to HPV18 E6/E7 was increased by modified HN vaccine-B (2,195±757 SFU) compared to the unmodified HN vaccine-B (822±342 SFU) (FIG. 110J). HPV18 E6/E7 responses were decreased in Donor 6 when primed with HN vaccine-B compared to unmodified HN vaccine-B but increased in the other five Donors (FIG. 110K).

TABLE 99

| Healthy Donor MHC-I characteristics | | | |
|---|---|---|---|
| Donor # | HLA-A | HLA-B | HLA-C |
| 1 | *02:01 *02:01 | *15:01 *51:01 | *02:02 *03:04 |
| 2 | *02:01 *03:01 | *07:02 *49:01 | *07:01 *07:02 |
| 3 | *03:01 *32:01 | *07:02 *15:17 | *07:01 *07:02 |
| 4 | *01:01 *30:01 | *08:01 *13:02 | *06:02 *07:02 |
| 5 | *02:01 *30:02 | *14:02 *13:02 | *08:02 *18:02 |
| 6 | *30:02 *30:04 | *15:10 *58:02 | *03:04 *06:02 |

Cocktails Induce Immune Responses Against Relevant TAAs

The ability of HN vaccine-A and HN vaccine-B to induce IFNγ production against ten HN antigens was measured by ELISpot. PBMCs from six HLA-diverse healthy donors (Table 99) were co-cultured with autologous DCs loaded with HN vaccine-A or HN vaccine-B for 6 days prior to stimulation with TAA-specific specific peptide pools containing known MHC-I restricted epitopes. Peptides for stimulation of CD14-PBMCs to detect IFNγ responses to PSMA, PRAME, TBXT, HPV16 E6/E7 and HPV18 E6/E7 are described above. Additional 15-mer peptides overlapping by 11 amino acid peptide pools were sourced as follows: Survivin (thinkpeptides, 7769_001-011), MUC1 (JPT, PM-MUC1), and STEAP1 (PM-STEAP1).

Figure 113A:
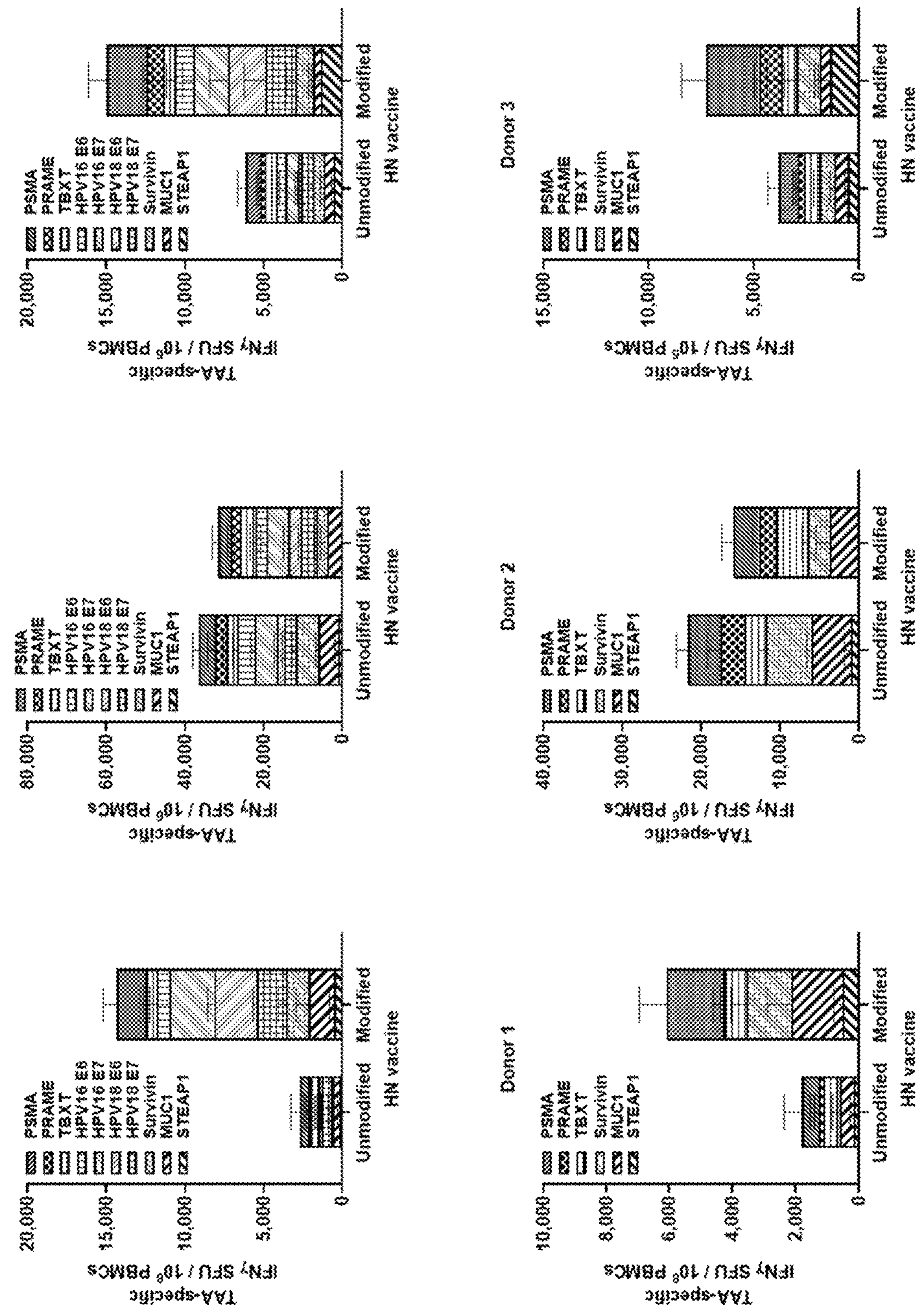
FIGS. 113A and B show antigen specific responses in individual donors to all HN antigens (top panel) and to non-viral HN antigens (bottom panel).
Figure 113B:
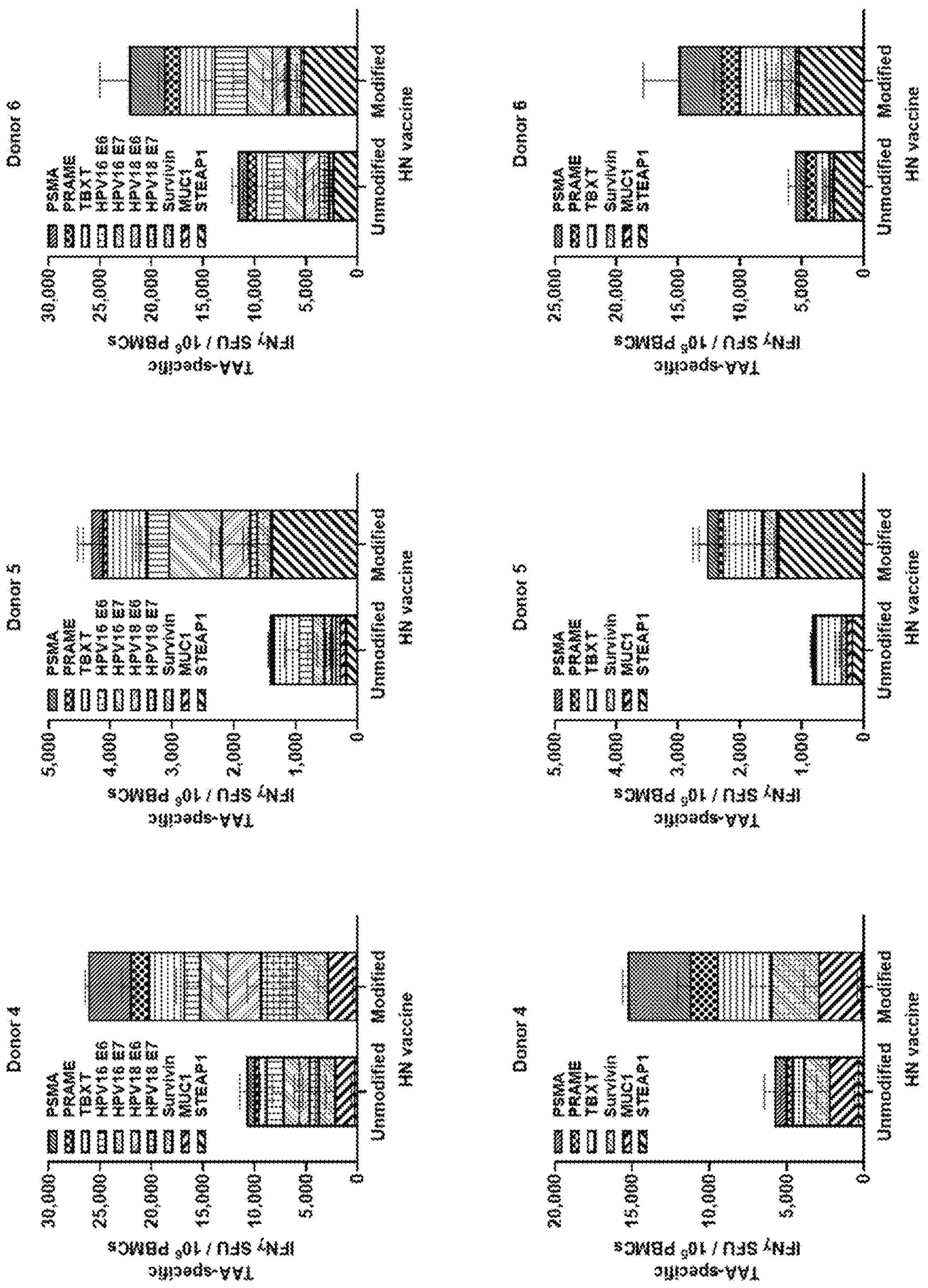

FIG. 112 demonstrates the HN vaccine is capable of inducing antigen specific IFNγ responses in six HLA-diverse donors to ten HN antigens that are 1.6-fold more robust (18,901±3,963 SFU) compared to the unmodified parental control (11,537±5,281 SFU) (FIG. 109A) (Table 100). The HN vaccine also increased IFNγ responses to non-viral antigens 1.6-fold (10,331±2,342 SFU) compared to unmodified parental control (6,568±3,112 SFU) (FIG. 112D). The unit dose of HN vaccine-A and HN vaccine-B elicited IFNγ responses to nine antigens in one donor and ten antigens in five donors (FIGS. 113A and 113B, upper panel). The unit dose of HN vaccine-A and HN vaccine-B elicited IFNγ responses to five non-viral antigens in one donor and six non-viral antigens in five donors (FIGS. 113A and 113B, lower panel) (Table 101). HN vaccine-A and HN vaccine-B independently demonstrated a 1.7-fold and 1.6-fold increase in antigen specific responses compared to parental controls, respectively, for all antigens.

HN vaccine-A and HN vaccine-B independently demonstrated a 1.5-fold and 1.6-fold increase in non-viral antigen specific responses compared to parental controls, respectively. Specifically, HN vaccine-A elicited 9,843±2,539 SFU compared to the unmodified controls (5,848±3,222 SFU) for all antigens and (FIG. 112B) (Table 100) and 5,441±1,694 SFU to non-viral antigens compared to the unmodified controls (3,547±1,990 SFU) (FIG. 112E) (Table 101). For HN vaccine-A, one donor responded to seven antigens, two donors responded to nine antigens, and three donors responded to ten antigens. HN vaccine-A elicited IFNγ responses to four non-viral antigens in one donor, five non-viral antigens in two donors and six non-viral antigens in three donors. HN vaccine-B elicited 9,058±1,715 SFU compared to the unmodified controls (5,688±2,472 SFU) for all antigens and (FIG. 112C) (Table 100) and 4,890±932 SFU to non-viral antigens compared to the unmodified controls (3,022±1,333 SFU) (FIG. 112F) (Table 101). For HN vaccine-B, one donor responded to six antigens, one donor responded to seven antigens, and two donors responded to nine antigens and two donors responded to ten antigens. HN vaccine-A elicited IFNγ responses to three non-viral antigens in one donor, four non-viral antigens in one donor, five non-viral antigens in two donors and six non-viral antigens in two donors.

Described above are two compositions comprising a therapeutically effective amount of three cancer cell lines, a unit dose of six cell lines, wherein said unit dose is capable of eliciting an immune response 1.6-fold greater than the unmodified composition specific to at least nine TAAs expressed in HN patient tumors. HN vaccine-A increased IFNγ responses to at least seven TAAs 1.7-fold and HN vaccine-B increased IFNγ responses 1.6-fold to at least six TAAs.

TABLE 100

IFNy Responses to unmodified and modified HN vaccine components

| | Unmodified (SFU ± SEM) | | | Modified (SFU ± SEM) | | |
|---|---|---|---|---|---|---|
| Donor (n = 4) | HN vaccine-A | HN vaccine-B | HN Vaccine | HN vaccine-A | HN vaccine-B | HN Vaccine |
| 1 | 542 ± 306 | 2,149 ± 1,421 | 2,691 ± 1,718 | 4,209 ± 1,876 | 10,106 ± 2,386 | 14,314 ± 1,483 |
| 2 | 20,690 ± 3,007 | 15,873 ± 4,506 | 36,563 ± 6,481 | 17,240 ± 5,541 | 14,265 ± 3,225 | 31,505 ± 3,770 |
| 3 | 3,500 ± 2,201 | 2,663 ± 450 | 6,133 ± 2,484 | 6,055 ± 2,562 | 8,905 ± 2,398 | 14,960 ± 4,113 |
| 4 | 8,620 ± 2,267 | 2,158 ± 1,092 | 10,778 ± 2,642 | 15,348 ± 5,682 | 10,780 ± 2,484 | 26,128 ± 7,506 |
| 5 | 520 ± 263 | 903 ± 572 | 1,423 ± 802 | 2,800 ± 1,336 | 1,513 ± 725 | 4,313 ± 1,640 |
| 6 | 1,218 ± 652 | 10,415 ± 3,103 | 11,633 ± 3,700 | 13,405 ± 2,355 | 8,783 ± 3,081 | 22,188 ± 2,851 |

TABLE 101

IFNy Responses to non-viral antigens by unmodified and modified HN vaccine components

| | Unmodified (SFU ± SEM) | | | Modified (SFU ± SEM) | | |
|---|---|---|---|---|---|---|
| Donor (n = 4) | HN vaccine-A | HN vaccine-B | HN Vaccine | HN vaccine-A | HN vaccine-B | HN Vaccine |
| 1 | 405 ± 313 | 1,408 ± 1,127 | 1,294 ± 737 | 1,003 ± 420 | 5,078 ± 833 | 3,709 ± 1,241 |
| 2 | 12,757 ± 2,435 | 8,840 ± 2,337 | 16,102 ± 3,210 | 10,984 ± 3,964 | 4,863 ± 1,434 | 12,679 ± 4,886 |
| 3 | 2,223 ± 1,278 | 1,583 ± 294 | 2,815 ± 1,076 | 2,700 ± 1,782 | 4,568 ± 1,385 | 4,813 ± 1,368 |
| 4 | 5,098 ± 1,131 | 683 ± 383 | 5,013 ± 1,069 | 8,513 ± 2,941 | 6,770 ± 1,525 | 9,655 ± 2,574 |
| 5 | 168 ± 89 | 665 ± 344 | 958 ± 516 | 1,745 ± 692 | 795 ± 541 | 2,493 ± 1,137 |
| 6 | 630 ± 514 | 4,953 ± 1,337 | 6,008 ± 1,624 | 7,700 ± 692 | 7,265 ± 1,702 | 13,590 ± 1,823 |

Based on the disclosure and data provided herein, a whole cell vaccine for Head and Neck Cancer comprising the six cancer cell lines, sourced from ATCC or JCRB, HSC-4 (JCRB, JCRB0624), HO-1-N-1 (JCRB, JCRB0831), DETROIT 562 (ATCC, CCL-138), KON (JCRB, JCRB0194), OSC-20 (JCRB, JCRB0197) and DMS 53 (ATCC, CRL-2062) is shown in Table 101A. The cell lines represent five head and neck cancer cell lines and one small cell lung cancer (SCLC) cell line (DMS 53 ATCC CRL-2062). The cell lines have been divided into two groupings: vaccine-A and vaccine-B. Vaccine-A is designed to be administered intradermally in the upper arm and vaccine-B is designed to be administered intradermally in the thigh. Vaccine A and B together comprise a unit dose of cancer vaccine.

TABLE 101A

| Cell line nomenclature and modifications | | | | | | | | |
|---|---|---|---|---|---|---|---|---|
| Cocktail | Cell Line | TGFβ1 KD | TGFβ2 KD | CD276 KO | GM-CSF | CD40L | IL-12 | TAA(s) |
| A | HSC-4* | X | X | X | X | X | X | X |
| A | HO-1-N-1 | X | X | X | X | X | X | X |
| A | DETROIT 562* | X | X | X | X | X | X | ND |
| B | KON | X | X | X | X | X | X | X |
| B | OSC-20 | ND | X | X | X | X | X | ND |
| B | DMS 53* | ND | X | X | X | X | X | ND |

ND = Not done.
*Cell lines identified as CSC-like cells.

Where indicated in the above table, the genes for the immunosuppressive factors transforming growth factor-beta 1 (TGFβ1) and transforming growth factor-beta 2 (TGFβ2) have been knocked down using shRNA transduction with a lentiviral vector. The gene for CD276 has been knocked out by electroporation using zinc-finger nuclease (ZFN) or knocked down using shRNA transduction with a lentiviral vector. The genes for granulocyte macrophage-colony stimulating factor (GM-CSF), IL-12, CD40L, modPSMA (HSC-4), modPRAME (HO-1-N-1), modTBXT (HO-1-N-1), HPV16 E6 and E7 (KON) and HPV18 E6 and E7 (KON) were added by lentiviral vector transduction.

Provided herein are two compositions comprising a therapeutically effective amount of three cancer cell lines, a unit dose of six cancer cell lines, modified to reduce the expression of at least two immunosuppressive factors and to express at least two immunostimulatory factors. One composition, HN vaccine-A, was modified to increase the expression of three TAAs, modPSMA, modPRAME and modTBXT. The second composition, HN vaccine-B, was modified to expresses four viral tumor associated antigens, HPV16 E6 and E7 and HPV18 E6 and E7. The unit dose of six cancer cell lines expresses at least at least 14 non-viral TAAs associated with a cancer of a subset of head and neck cancer subjects intended to receive said composition and induces IFNγ responses 1.6-fold greater than the unmodified composition components.

Example 35: Preparation of Gastric Cancer Vaccine

This Example demonstrates that reduction of TGFβ131, TGFβ2, and CD276 expression with concurrent overexpression of GM-CSF, CD40L, and IL-12 in a vaccine composition of two cocktails, each cocktail composed of three cell lines for a total of 6 cell lines, significantly increased the magnitude of cellular immune responses to at least 10 GCA-associated antigens in an HLA-diverse population. As described herein, the first cocktail, GCA vaccine-A, is composed of cell line MKN-1 that was also modified to express modPSMA and modLYK6, cell line MKN-45, and cell line MKN-74. The second cocktail, GCA vaccine-B, is composed of cell line OCUM-1, cell line Fu97 that was also modified to express modWT1 and modCLDN18 (Claudin 18), and cell line DMS 53. The six component cell lines collectively express at least twenty antigens that can provide an anti-GCA tumor response.

Identification of GCA Vaccine Components

Initial cell line selection criteria identified thirty-six vaccine component cell lines for potential inclusion in the GCA vaccine. Additional selection criteria described herein were applied to narrow the thirty-six cell lines to seven cell lines for further evaluation in immunogenicity assays. These criteria included: endogenous GCA associated antigen expression, lack of expression of additional immunosuppressive factors, such as IL-10 or IDO1, expression of GCA-associated CSC-like markers ABCB1, ABCG2, ALDH1A, CD133, CD164, FUT4, LGR5, CD44, MUC1 and DLL4, ethnicity and age of the patient from which the cell line was derived, cancer stage and site from which the cell line was derived, and histological subtype.

Figure 114B:
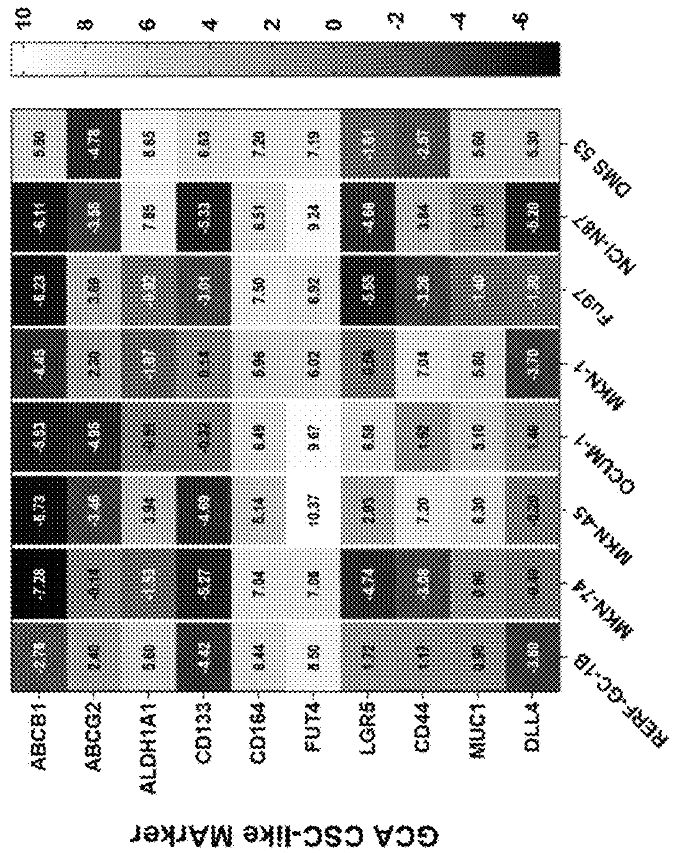
FIGS. 114A and B show endogenous expression of gastric cancer antigens (FIG. 114A) and gastric cancer CSC-like markers (FIG. 114B) by candidate ovarian cancer vaccine component cell lines.
Figure 114A:
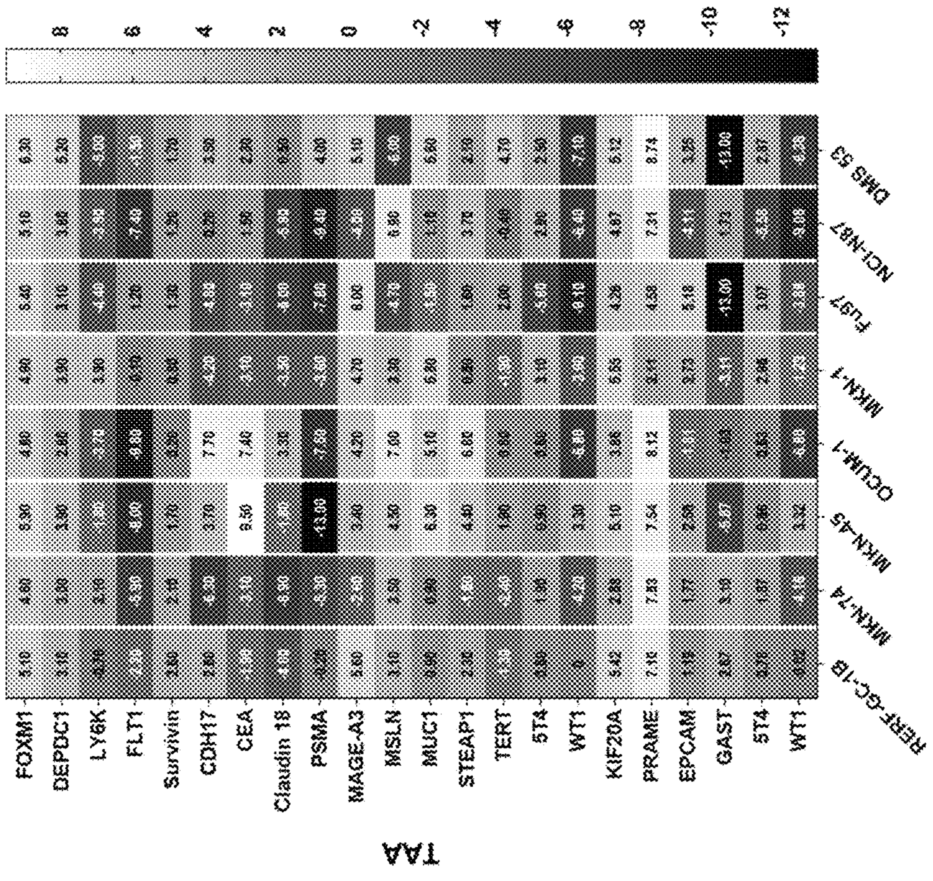

CSCs play a critical role in the metastasis, treatment resistance, and relapse of gastric cancer (Table 2). Expression of TAAs and GCA specific CSC-like markers by candidate component cell lines was determined by RNA expression data sourced from the Broad Institute Cancer Cell Line Encyclopedia (CCLE). The HGNC gene symbol was included in the CCLE search and mRNA expression was downloaded for each TAA. Expression of a TAA or CSC-like marker by a cell line was considered positive if the RNA-seq value was greater than one. Selection criteria identified seven candidate GCA vaccine components for further evaluation: RERF-GC-1B, MKN-74, MKN-45, OCUM-1, MKN-1, Fu97 and NCI-N87. The seven candidate component cell lines expressed ten to fourteen TAAs (FIG. 114A) and two to six CSC markers (FIG. 114B). As described herein, the CSC-like cell line DMS 53 is included as one of the six vaccine cell lines and expressed fourteen GCA TAAs and seven GCA CSC-like markers.

Immunogenicity of the seven unmodified GCA vaccine component candidates was evaluated by IFNγ ELISpot as described in Example 9 using three HLA diverse healthy donors (n=4 per donor). HLA-A and HLA-B alleles for Donors were as follows: Donor 1, A*01:01 B*08:01 and A*02:01 B*15:01; Donor 2, A*01:01 B*08:01 and A*02:01 B*57:03; and Donor 3, A*02:01 B*40:01 and A*30:01 B*57:01. MKN-1 (5,417±152 SFU) and OCUM-1 (1,123±258 SFU) were more immunogenic than RERF-GC- 1B (120±56 SFU), MKN-74 (241±107 SFU), MKN-45 (0±0 SFU), Fu97 (578±209 SFU) and NCI-N87 (0±0 SFU) (FIG. 115A).

Immunogenicity of MKN-1 and OCUM-1 was evaluated in eight different combinations of three component cell lines, four combinations contained MKN-1 and four combinations contained OCUM-1 (FIG. 115C). IFNγ responses were determined against the three component cell lines within the eight potential vaccine cocktails by IFNγ ELISpot as described in Example 8 using the three healthy donors (n=4/donor). HLA-A and HLA-B alleles for the donors were as follows: Donor 1, A*02:06 B*15:01 and A*34:02 B*51:01; Donor 2, A*03:01 B*07:02 and A*24:02 B*15:09; and Donor 3, A*02:01 B*40:01 and A*30:01 B*57:01. IFNγ responses were detected for all eight cocktails and to each cell line component in each cocktail. Responses to the individual cocktail component cell lines were notably increased for most cell lines compared to IFNγ responses detected for single cell line components (FIG. 115B). In all eight combinations evaluated, MKN-1 remained the most immunogenic. MKN-1 was selected to be included in vaccine cocktail A and OCUM-1 was selected to be included in vaccine cocktail B as described above and further herein.

The cells in the vaccine described herein were selected to express a wide array of TAAs, including those known to be important specifically for GCA antitumor responses, such as LY6K or MUC1, and also TAAs known to be important for targets for GCA and other solid tumors, such TERT. As shown herein, to further enhance the array of TMs, MKN-1 was modified to express modPSMA and modLY6K, and Fu97 was modified to express modWT1 and modCLDN18. PSMA, CLDN18 and WT1 were endogenously expressed by one of the six component cell lines and LY6K was endogenously expressed by two of the six component cell lines at >1.0 FPKM (FIG. 116A).

Expression of the transduced antigens modPSMA (FIG. 117A) and modLY6K (FIG. 117B) by MKN-1 (SEQ ID NO: 57; SEQ ID NO: 58), and modWT1 (FIG. 114C) and modCLDN18 (FIG. 114D) (SEQ ID NO: 55; SEQ ID NO: 56) by Fu97, were detected by flow cytometry as described in Example 29 and herein. The modPSMA and modLY6K antigens are encoded in the same lentiviral transfer vector separated by a furin cleavage site. The modWT1 and modCLDN18 are encoded in the same lentiviral transfer vector separated by a furin cleavage site.

Because of the need to maintain maximal heterogeneity of antigens and clonal subpopulations the comprise each cell line, the gene modified cell lines utilized in the present vaccine have been established using antibiotic selection and flow cytometry and not through limiting dilution subcloning.

Figure 116A:
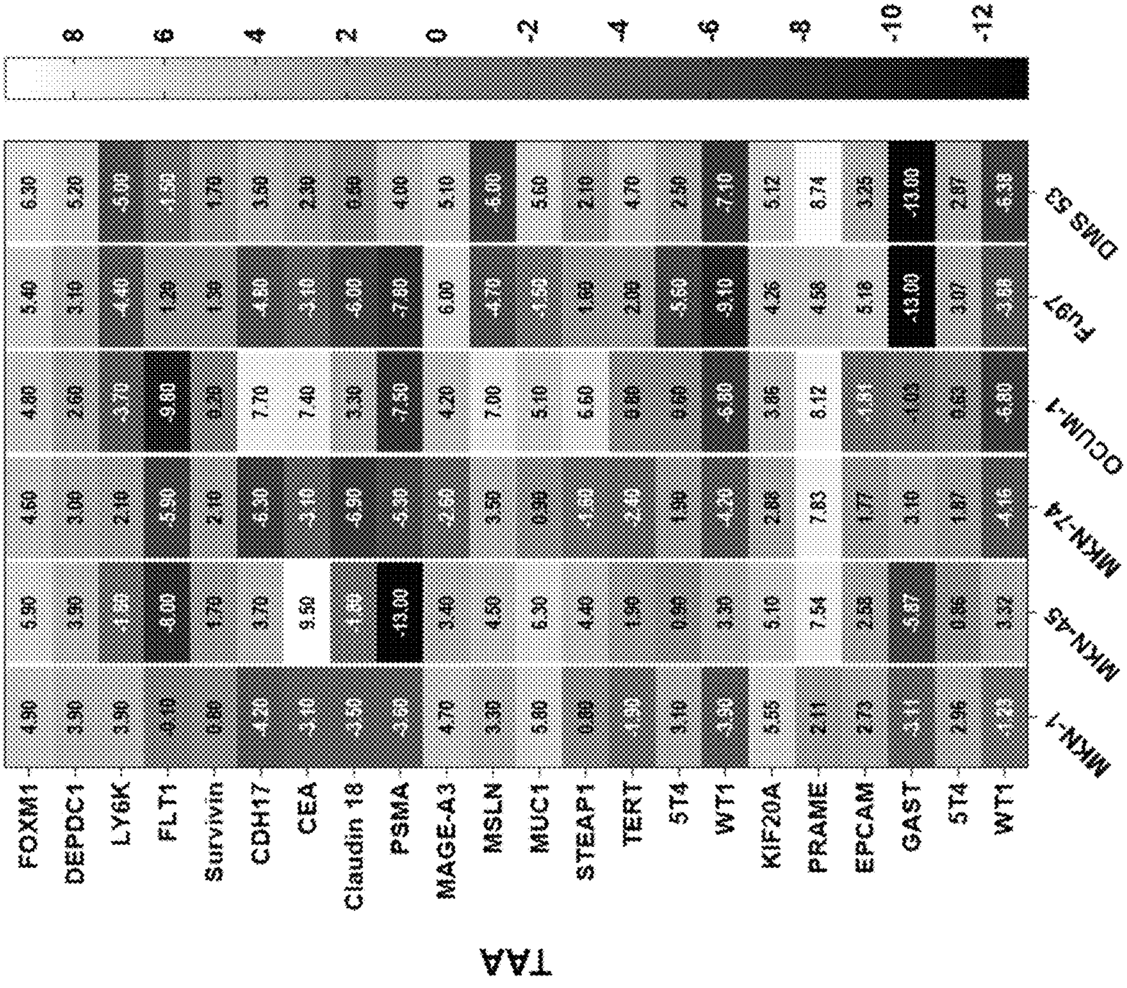
FIGS. 116A-C show endogenous antigen expression by selected GCA vaccine component cell lines (FIG. 116A) expression of these antigens patient tumors (FIG. 116B) and the number of gastric cancer antigens expressed by the GCA vaccine cell lines also expressed in gastric cancer patient tumors (FIG. 116C).
Figure 116B:
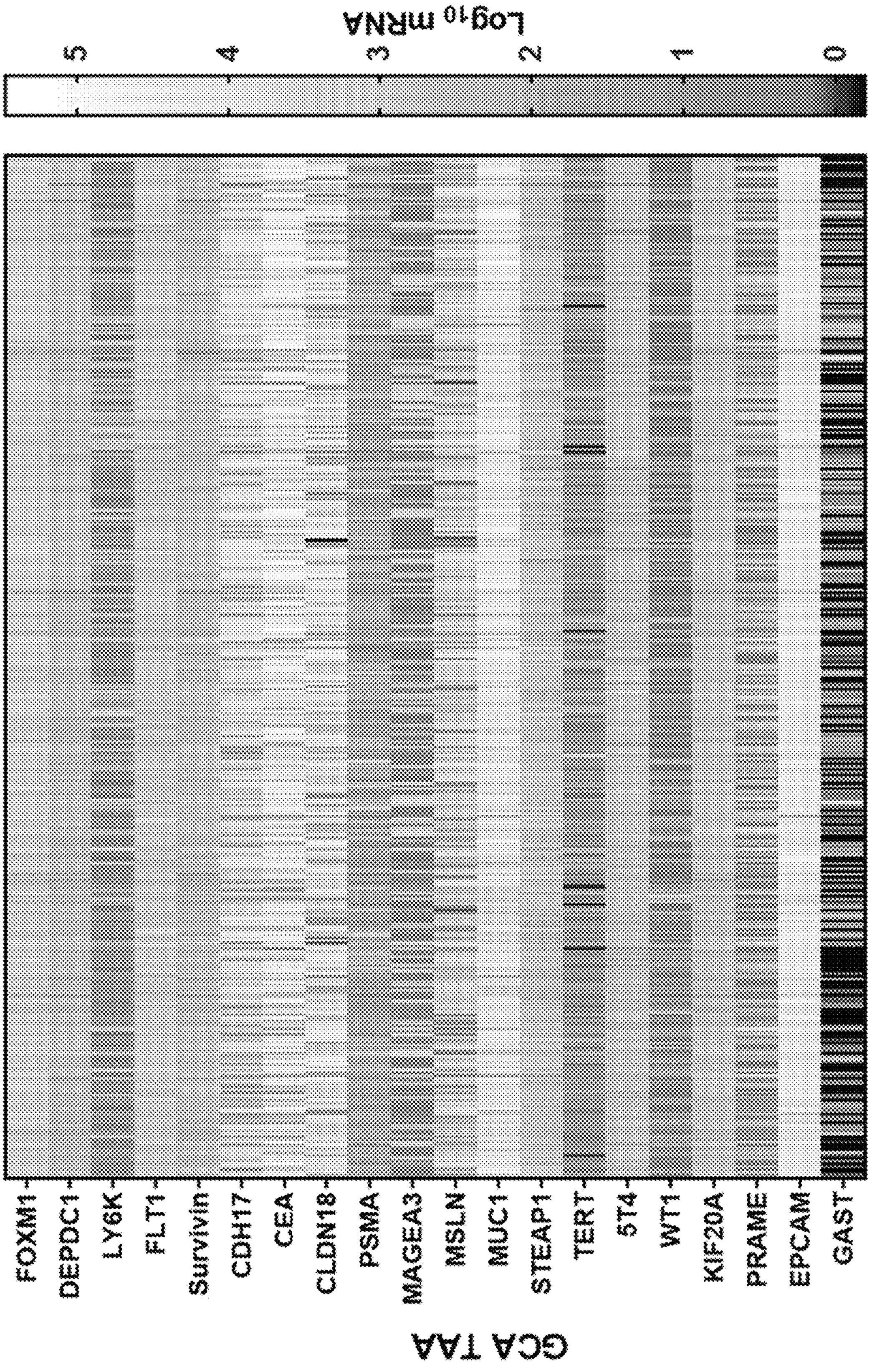
Figure 116C:
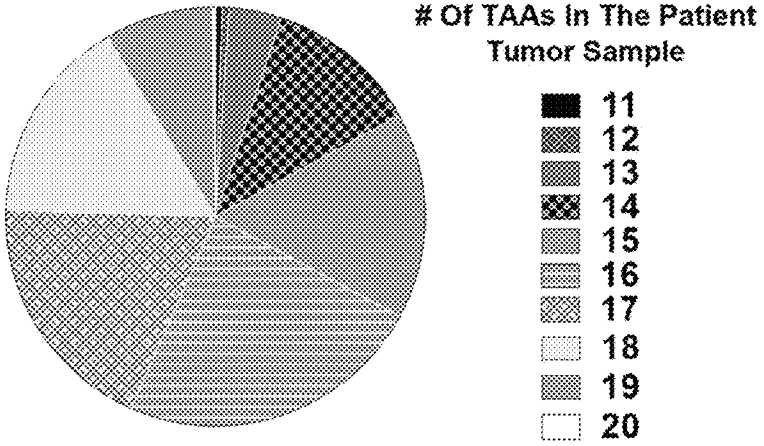

The endogenous mRNA expression of twenty representative GCA TAAs in the present vaccine are shown in FIG. 116A. The present vaccine, after introduction antigens described above, expresses of all identified twenty commonly targeted and potentially clinically relevant TAAs capable of inducing a GCA antitumor response. Some of these TAAs are known to be primarily enriched in GCA tumors and some can also induce an immune response to GCA and other solid tumors. RNA abundance of the twenty prioritized GCA TAAs was determined in 371 GCA patient samples with available mRNA data expression as described in Example 29 (FIG. 116B). Eleven of the prioritized GCA TAAs were expressed by 100% of samples, 12 TAAs were expressed by 99.5% of samples, 13 TAAs were expressed by 98.9% of samples, 14 TAAs were expressed by 94.9% of samples, 15 TAAs were expressed by 83.0% of samples, 16 TAAs were expressed by 67.1% of samples, 17 TAAs were expressed by 43.4% of samples, 18 TAAs were expressed by 24.5% of samples, 19 TAAs were expressed by 8.6% of samples and 20 TAAs were expressed by 0.3% of samples (FIG. 116C). Provided herein are two compositions comprising a therapeutically effective amount of three cancer cell lines, wherein the combination of the cell lines, a unit dose of six cell lines, comprises cells that express at least 11 TAAs associated with a subset of GCA cancer subjects intended to receive said composition. Based on the expression and immunogenicity data presented herein, the cell lines identified in Table 102 were selected to comprise the present GCA vaccine.

TABLE 102

Gastric vaccine cell lines and histology

| Cocktail | Cell Line Name | Histology |
|---|---|---|
| A | MKN-1 | Gastric Adenocarcinoma; derived from metastatic site (lymph node) |
| A | MKN-45 | Gastric Adenocarcinoma; derived from metastatic site (liver) |
| A | MKN-74 | Gastric Tubular Adenocarcinoma |
| B | OCUM-1 | Signet Ring Cell Gastric Adenocarcinoma; derived from metastatic site (pleural effusion) |
| B | Fu97 | Gastric Adenocarcinoma; derived from metastatic site (lymph node) |
| B | DMS 53 | Lung Small Cell Carcinoma |

Reduction of CD276 Expression

The MKN-1, MKN-45, MKN-74, OCUM-1, FU97, and DMS 53 component cell lines expressed CD276 and expression was knocked out by electroporation with ZFN as described in Example 13 and elsewhere herein. Because it was desirable to maintain as much tumor heterogeneity as possible, the electroporated and shRNA modified cells were not cloned by limiting dilution. Instead, the cells were subjected to multiple rounds of cell sorting by FACS as described in Example 13. Expression of CD276 was determined as described in Example 29. Reduction of CD276 expression is described in Table 103. These data show that gene editing of CD276 with ZFN resulted in greater than 83.3% CD276-negative cells in all six vaccine component cell lines.

TABLE 103

Reduction of CD276 expression

| Cell line | Parental Cell Line MFI | Modified Cell Line MFI | % Reduction CD276 |
|---|---|---|---|
| MKN-1 | 35,503 | 6 | 99.9 |
| MKN-45 | 8,479 | 11 | 99.9 |
| MKN-74 | 11,335 | 3 | 99.9 |
| OCUM-1 | 13,474 | 2,244 | 83.3 |
| FU97 | 178,603 | 394 | 99.8 |
| DMS-53 | 11,928 | 24 | 99.8 |

MFI reported with isotype controls subtracted

Cytokine Secretion Assays for TGFβ1, TGFβ2, GM-CSF, and IL-12

Cytokine Secretion Assays for TGFβ1, TGFβ2, GM-CSF, and IL-12 were Completed as Described in Example 29.

shRNA Downregulates TGF-β Secretion

Following CD276 knockout, TGFβ1 and TGFβ2 secretion levels were reduced using shRNA and resulting levels determined as described in Example 26. The MKN-1, MKN-45, and MKN-74 cell lines in GCA vaccine-A secreted measurable levels of TGFβ1. MKN-1 also secreted measurable levels of TGFβ2. The Fu97 and DMS 53 component cell lines of GCA vaccine-B secreted measurable levels of TGFβ1. DMS 53 also secreted measurable levels of TGFβ2. OCUM-1 did not secrete measurable levels of TGFβ1 or TGFβ2. Reduction of TGFβ2 secretion by the DMS 53 cell line is described in Example 26 and resulting levels determined as described above and herein.

The MKN-1 component cell lines were transduced with TGFβ1 shRNA to decrease TGFβ1 secretion concurrently with the transgene to increase expression of membrane bound CD40L as described in Example 29. MKN-1 was also transduced with lentiviral particles encoding TGFβ2 shRNA to decrease the secretion of TGFβ2 and concurrently increase expression of GM-CSF (SEQ ID NO: 6) as described in Example 29. These cells are described by the clonal designation DK6. The MKN-45, MKN-74 and Fu97 cell lines were transduced with TGFβ1 shRNA to decrease TGFβ1 secretion and concurrently increase expression of membrane bound CD40L as described in Example 29. These cells, modified to reduce TGFβ1 secretion and not TGFβ2 secretion, are described by the clonal designation DK2. DMS 53 was modified with shRNA to reduce secretion of TGFβ2 as described in Example 26. Modification of DMS 53 cells to reduce secretion of TGFβ2 and not TGFβ1 are described by the clonal designation DK4. OCUM-1 was not modified to reduce TGFβ1 or TGFβ2 secretion because the parental line did not secrete detective levels of TGFβ1 or TGFβ2.

Table 104 shows the percent reduction in TGFβ1 and/or TGFβ2 secretion in gene modified component cell lines compared to unmodified parental, cell lines. Gene modification resulted in at least 72% reduction of TGFβ1 secretion. Gene modification of TGFβ2 resulted in at least 51% reduction in secretion of TGFβ2.

TABLE 104

TGF-β Secretion (pg/$10^6$ cells/24 hr) in Component Cell Lines

| Cell Line | Cocktail | Clone | TGFβ1 | TGFβ2 |
|---|---|---|---|---|
| MKN-1 | A | Wild type | 2,539 ± 670 | 1,634 ± 670 |
| MKN-1 | A | DK6 | 218 ± 58 | * >12 |
| MKN-1 | A | Percent reduction | 91% | ≥99% |
| MKN-45 | A | Wild type | 704 ± 101 | * >11 |
| MKN-45 | A | DK2 | 98 ± 49 | NA |
| MKN-45 | A | Percent reduction | 86% | NA |
| MKN-74 | A | Wild type | 753 ± 104 | * >6 |
| MKN-74 | A | DK2 | 119 ± 18 | NA |
| MKN-74 | A | Percent reduction | 84% | NA |
| OCUM-1 | B | Wild type | * >22 | * >10 |
| OCUM-1 | B | NA | NA | NA |
| OCUM-1 | B | Percent reduction | NA | NA |
| Fu97 | B | Wild type | 402 ± 103 | * >11 |
| Fu97 | B | DK2 | 113 ± 14 | NA |
| Fu97 | B | Percent reduction | 72% | NA |
| DMS 53 | B | Wild type | 106 ± 10 | 486 ± 35 |
| DMS 53 | B | DK4 | NA | 238 ± 40 |
| DMS 53 | B | Percent reduction | NA | 51% |

DK6: TGFβ1/TGFβ2 double knockdown;
DK4: TGFβ2 single knockdown;
DK2: TGFβ1 single knockdown;
* = estimated using LLD, not detected;
NA = not applicable Based on a dose of $5\times10^5$ of each component cell line, the total TGFβ1 and TGFβ2 secretion by the modified GCA vaccine-A and GCA vaccine-B and respective unmodified parental cell lines are shown in Table 105. The secretion of TGFβ1 by GCA vaccine-A was reduced by 89% and TGFβ2 by 98% pg/dose/24 hr. The secretion of TGFβ1 by GCA vaccine-B was reduced by 54% and TGFβ2 by 49% pg/dose/24 hr.

TABLE 105

Total TGF-β Secretion (pg/dose/24 hr) in GCA vaccine-A and GCA vaccine-B

| Cocktail | Clones | TGFβ1 | TGFβ2 |
|---|---|---|---|
| A | Wild type | 1,998 | 826 |
| | DK2/DK6 | 218 | 15 |
| | Percent reduction | 89% | 98% |
| B | Wild type | 265 | 254 |
| | DK2/DK4 | 121 | 130 |
| | Percent reduction | 54% | 49% |

GM-CSF Secretion

The MKN-1 cell line was transduced with lentiviral particles containing both TGFβ2 shRNA and the gene to express GM-CSF (SEQ ID NO: 6) as described above. The MKN-45, MKN-74, OCUM-1 and Fu97 cell lines were transduced with lentiviral particles to only express GM-CSF (SEQ ID NO: 7). DMS 53 was modified to secrete GM-CSF as described in Example 26 and elsewhere herein. The results are shown in Table 106 and described below.

Secretion of GM-CSF increased at least 3,941-fold in all modified component cell lines compared to unmodified parental cell lines. In GCA vaccine-A component cell lines, secretion of GM-CSF increased 46,419-fold by MKN-1 compared to the parental cell line (≤0.0028 ng/$10^6$ cells/24 hr), 3,941-fold by MKN-45 compared to the parental cell line (≤0.0051 ng/$10^6$ cells/24 hr), and 242,155-fold by MKN-74 compared to the parental cell line (≤0.0027 ng/$10^6$ cells/24 hr). In GCA vaccine-B component cell lines secretion of GM-CSF increased 7,866-fold by OCUM-1 compared to the parental cell line (≤0.0043 ng/$10^6$ cells/24 hr), 193,248-fold by Fu97 compared to the parental cell line (≤0.0046 ng/$10^6$ cells/24 hr) and 49,313-fold by DMS 53 compared to the parental cell line (≤0.0032 ng/$10^6$ cells/24 hr).

TABLE 106

GM-CSF Secretion in Component Cell Lines

| Cell Line | GM-CSF (ng/$10^6$ cells/24 hr) | GM-CSF (ng/dose/24 hr) |
|---|---|---|
| MKN-1 | 130 ± 66 | 65 |
| MKN-45 | 20 ± 8 | 10 |
| MKN-74 | 664 ± 374 | 332 |
| Cocktail A Total | 814 | 407 |
| OCUM-1 | 34 ± 17 | 17 |
| FU97 | 893 ± 422 | 447 |
| DMS 53 | 158 ± 15 | 79 |
| Cocktail B Total | 1,085 | 543 |

Based on a dose of $5\times10^5$ of each component cell line, the total GM-CSF secretion for GCA vaccine-A was 407 ng per dose per 24 hours. The total GM-CSF secretion for GCA vaccine-B was 543 ng per dose per 24 hours. The total GM-CSF secretion per dose was therefore 950 ng per 24 hours.

Membrane Bound CD40L (CD154) Expression

Figure 118:
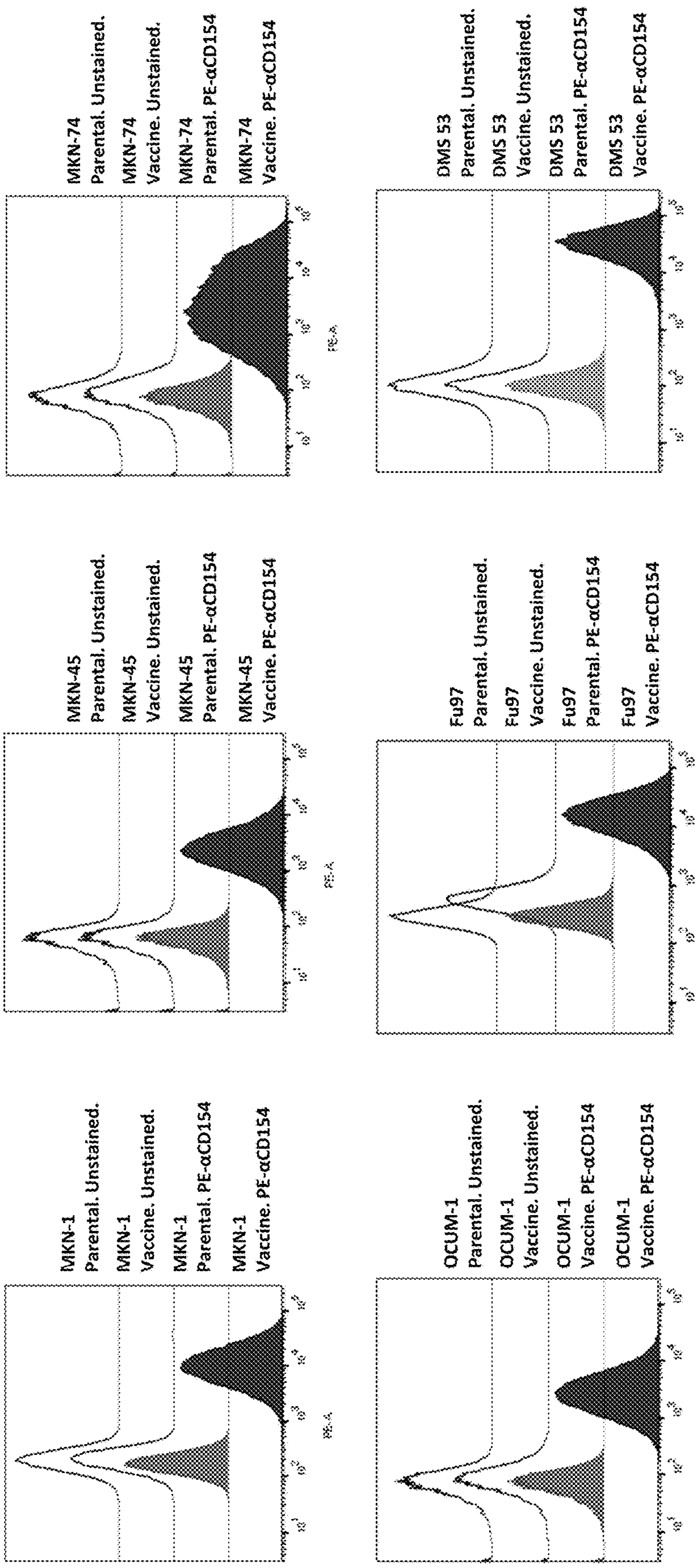
FIG. 118 shows expression of membrane bound CD40L by the GCA vaccine component cell lines.

The component cell lines were transduced with lentiviral particles to express membrane bound CD40L vector as described above. The methods to detect expression of CD40L by the five GCA cell line components are described in Example 29. Modification of DMS 53 to express membrane bound CD40L is described in Example 15. Evaluation of membrane bound CD40L by all six vaccine component cell lines is described below. The results shown in FIG. 118 and described below demonstrate CD40L membrane expression was substantially increased in all six GCA vaccine component cell lines.

Expression of membrane bound CD40L increased at least 374-fold in all component cell lines compared to unmodified, parental cell lines. In GCA vaccine-A component cell lines, expression of CD40L increased 15,941-fold by MKN-1 (15,941 MFI) compared to the parental cell line (0 MFI), 374-fold by MKN-45 (3,397 MFI) compared to the parental cell line (9 MFI), and 4,914-fold by MKN-74 (4,914 MFI) compared to the parental cell line (0 MFI). In GCA vaccine-B component cell lines expression of CD40L increased 3,741-fold by OCUM-1 (3,741 MFI) compared to the parental cell line (0 MFI), 1,569-fold by FU97 (26,449 MFI) compared to the parental cell line (17 MFI), and 88,261-fold by DMS 53 compared to the parental cell line (0 MFI).

IL-12 Expression

The MKN-1, MKN-45, MKN-74, and Fu97 component cell lines were transduced with the IL-12 vector as described in Example 17 and resulting IL-12 p70 expression determined as described above and herein. The results are shown in Table 107 and described below.

Secretion of IL-12 increased at least 1,715-fold in all component cell lines modified to secrete IL-12 p70 compared to unmodified, parental cell lines. In GCA vaccine-A component cell lines, secretion of IL-12 increased 53,185-fold by MKN-1 compared to the parental cell line (≤0.0011 ng/$10^6$ cells/24 hr), 1,715-fold by MKN-45 compared to the parental cell line 0.0021 ng/$10^6$ cells/24 hr), and 56,743-fold by MKN-74 compared to the parental cell line (≤0.0011 ng/$10^6$ cells/24 hr). In GCA vaccine-B component cell lines expression of IL-12 increased 13,078-fold by FU97 compared to the parental cell line (≤0.0037 ng/$10^6$ cells/24 hr). OCUM-1 and DMS 53 were not modified to secrete IL-12.

TABLE 107

IL-12 Secretion in Component Cell Lines

| Cell Line | IL-12 (ng/$10^6$ cells/24 hr) | IL-12 (ng/dose/24 hr) |
|---|---|---|
| MKN-1 | 60 ± 25 | 30 |
| MKN-45 | 4 ± 2 | 2 |
| MKN-74 | 62 ± 7 | 31 |
| Cocktail A Total | 126 | 63 |
| OCUM-1 | NA | NA |
| FU97 | 48 ± 11 | 24 |
| DMS 53 | NA | NA |
| Cocktail B Total | 48 | 24 |

Based on a dose of $5\times10^5$ of each component cell line, the total IL-12 secretion for GCA vaccine-A was 63 ng per dose per 24 hours. The total IL-12 secretion for GCA vaccine-B was 24 ng per dose per 24 hours. The total IL-12 secretion per dose was therefore 87 ng per 24 hours.

Stable Expression of modPSMA and modLY6K by the MKN-1 Cell Line

Figure 117A:
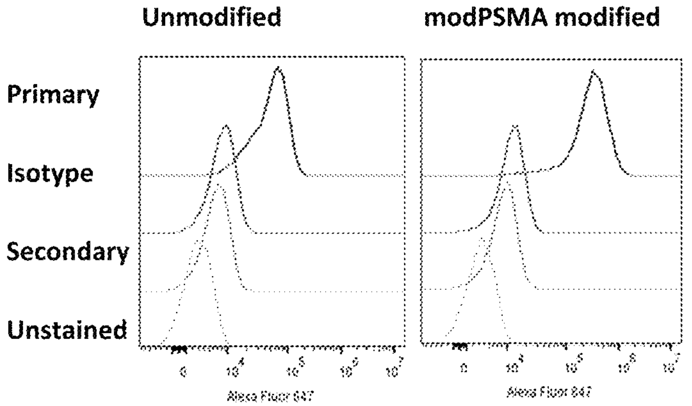
FIGS. 117A-H show expression of modPSMA (FIG. 117A) and modLY6K (FIG. 117B) by MKN-1 and IFNγ responses to PSMA (FIG. 117E) and LY6K (FIG. 117F), show expression of modWT1 (FIG. 117C) and modCLDN18 (FIG. 117D) by Fu97 and IFNγ responses to WT1 (FIG. 117G) and CLDN18 (FIG. 117H).
Figure 117B:
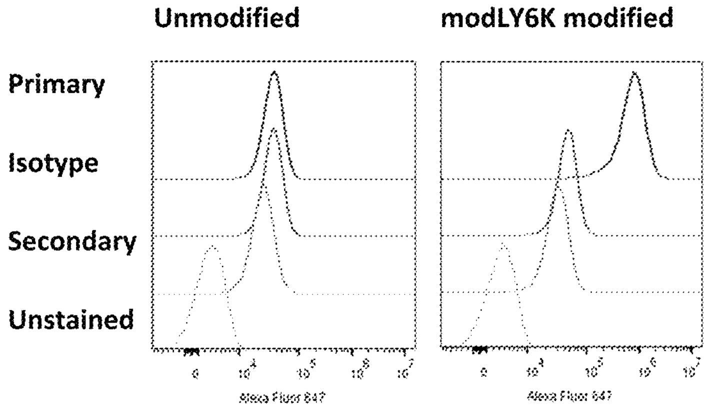

As described above, the cells in the vaccine described herein were selected to express a wide array of TAAs, including those known to be important to antitumor immunity. To further enhance the array of antigens, the MKN-1 cell line that was modified to reduce the secretion of TGFβ1 and TGFβ2, reduce the expression of CD276, and to express GM-CSF, membrane bound CD40L and IL-12 was also transduced with lentiviral particles expressing the modPSMA and modLY6K antigens. RNA expression data sourced from CCLE suggested that MKN-1 endogenously expressed LYK6 (FIG. 116A) but the LYK6 protein was not detected in unmodified MKN-1 cells by flow cytometry (FIG. 117B). The genes encoding the modPSMA and modLY6K antigens (SEQ ID NO: 57, SEQ ID NO: 58) are linked by a furin cleavage site.

The expression of modPSMA by MKN-1 was characterized by flow cytometry. Unmodified and antigen modified cells were stained intracellular with 0.03 μg/test anti-mouse IgG1 anti-PSMA antibody (Abcam, ab268061) followed by 0.125 μg/test AF647-conjugated goat anti-mouse IgG1 antibody (BioLegend #405322). Expression of modPSMA was increased in the modified cell line (697,744 MFI) 15-fold over that of the parental cell line (46,955 MFI) (FIG. 117A). Expression of modLY6K by MKN-1 was also characterized by flow cytometry. Cells were first stained intracellular with rabbit IgG anti-LY6K antibody (Abcam, ab246486) (0.03 μg/test) followed by AF647-conjugated donkey anti-rabbit IgG1 antibody (BioLegend #406414) (0.125 pg/test). Expression of modLY6K increased in the modified cell line (2,890,315 MFI) 2,890,315-fold over the unmodified cell line (0 MFI) (FIG. 117B).

Stable Expression of modWT1 and modCLDN18 by the Fu97 Cell Line

Figure 117C:
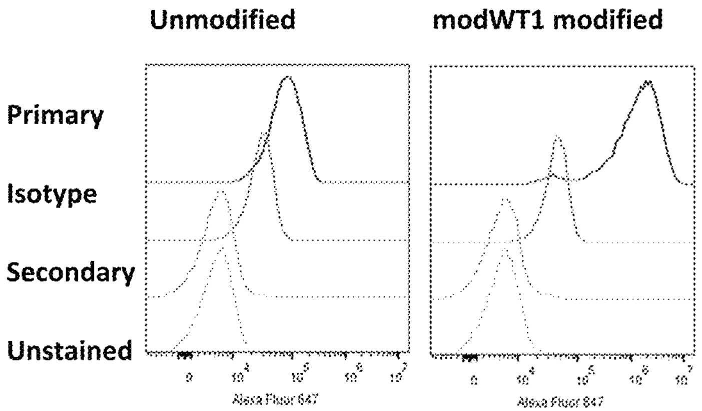
Figure 117D:
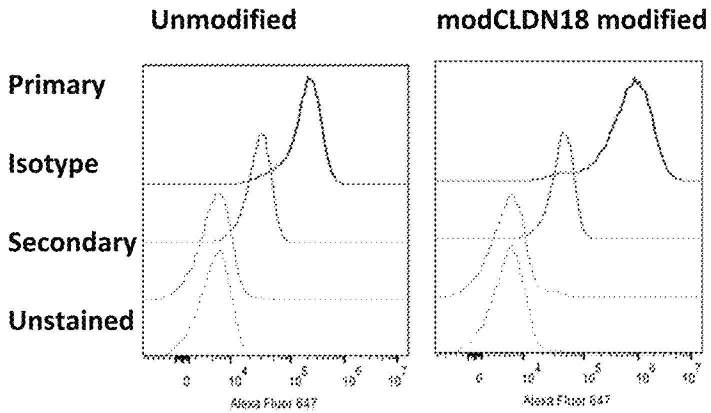

The Fu97 cell line that was modified to reduce the secretion of TGFβ1, reduce the expression of CD276, and to express GM-CSF, membrane bound CD40L, and IL-12 was also transduced with lentiviral particles expressing the modWT1 and modCLDN18 antigens (SEQ ID NO: 55, SEQ ID NO: 56). Expression of modWT1 by Fu97 was characterized by flow cytometry. Unmodified and antigen modified cells were stained intracellular with 0.03 μg/test anti-rabbit IgG1 anti-WT1 antibody (Abcam, ab89901) followed by 0.125 ug/test AF647-conjugated donkey anti-rabbit IgG1 antibody (BioLegend #406414). Expression of modWT1 increased in the modified cell line (7,418,365 MFI) 57-fold over that of the unmodified cell line (129,611 MFI) (FIG. 117C). Expression of modCLDN18 by Fu97 was characterized by flow cytometry. Unmodified and antigen modified cells were stained intracellular with 0.03 μg/test anti-rabbit IgG1 anti-CLDN18 antibody (Abcam, ab203563) followed by 0.125 ug/test AF647-conjugated donkey anti-rabbit IgG1 antibody (BioLegend #406414). Expression of modCLDN18 increased in the modified cell line (3,168,563 MFI) 5.7-fold over that of the unmodified cell line (558,211 MFI) (FIG. 117D).

Immune Responses to PSMA and LY6K in GCA Vaccine-A

IFNγ responses to PSMA and LY6K were evaluated in the context of GCA vaccine-A as described in Example 29 and herein, in six HLA diverse donors (n=4/donor). The HLA-A, HLA-B, and HLA-C alleles for each of the six donors are shown in Table 108. IFNγ responses were determined by ELISpot as described in Example 29.

Figure 117E:
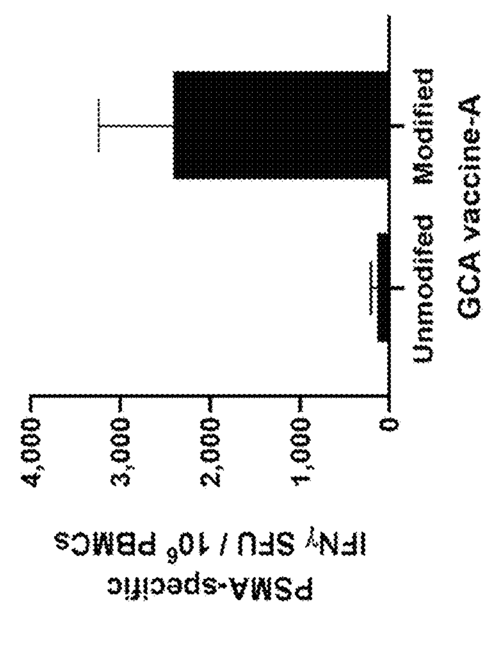

PSMA specific IFNγ responses were increased with the modified GCA vaccine-A (2,413±829 SFU) compared to the parental, unmodified GCA vaccine-A (137±82 SFU (FIG. 117E). IFNγ responses to LY6K were determined by ELISpot using 15-mers peptides overlapping by 9 amino acids spanning the entire length of the native LY6K antigen purchased from Thermo Scientific Custom Peptide Service.

Figure 117F:
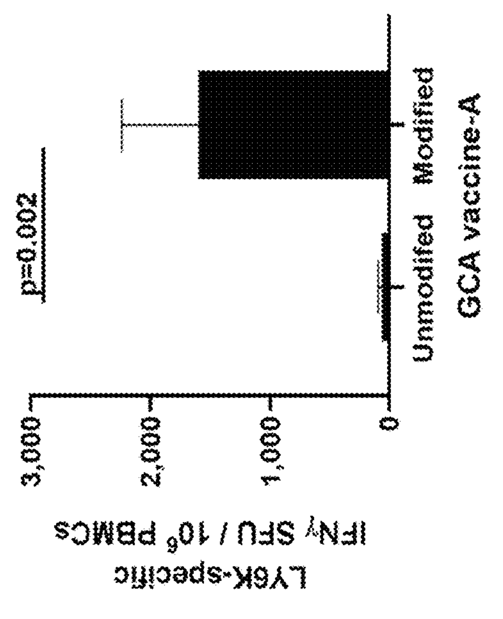

IFNγ responses to LY6K significantly increased with the modified GCA vaccine-A (1,598±639 SFU) compared to the unmodified GCA vaccine-A (63±30 SFU) (p=0.002, Mann-Whitney U test) (n=6) (FIG. 117F).

Immune Responses to WT1 and CLDN18 in GCA Vaccine-B

Figure 117G:
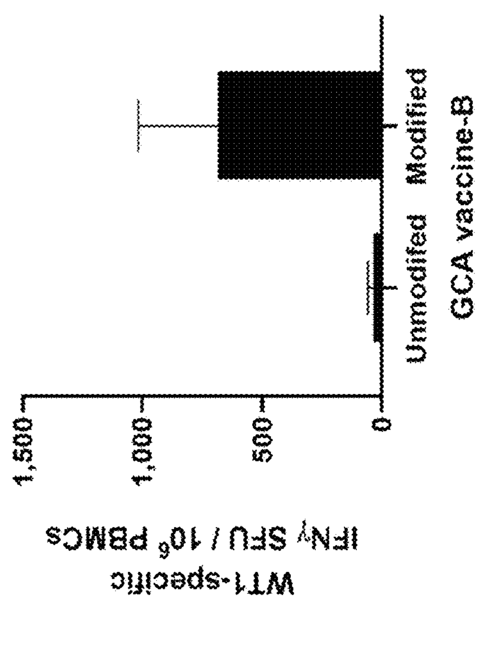
Figure 117H:
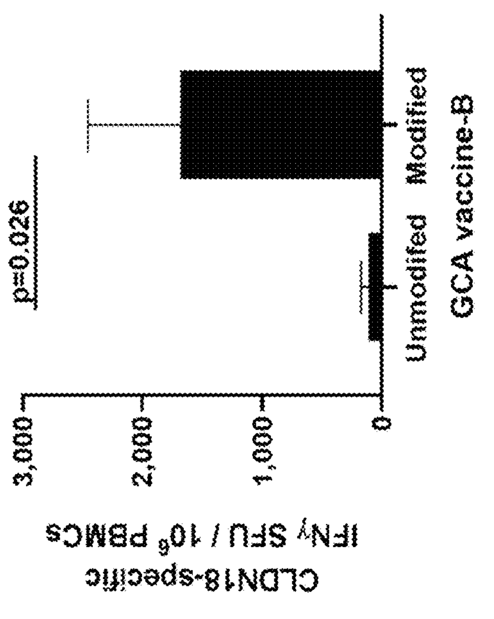

IFNγ responses to WT1 and CLDN18 were evaluated in the context of GCA-vaccine B as described in Example 29 and herein, in six HLA diverse donors (n=4/donor) (Table 108). IFNγ responses against WT1 and CLDN18 were determined by ELISpot using 15-mers peptides overlapping by 9 amino acids spanning the entire length of the native antigen protein purchased from Thermo Scientific Custom Peptide Service. WT1 specific IFNγ responses increased with GCA vaccine-B (686±330 SFU) compared to the unmodified GCA vaccine-B (37±22 SFU) (n=6) (FIG. 117G). CLDN18 specific IFNγ responses were significantly increased by GCA vaccine-B (1,682±773 SFU) compared to the unmodified GCA vaccine-B (113±65 SFU) (p=0.026, Mann-Whitney U test) (n=6) (FIG. 117H).

TABLE 108

Healthy Donor MHC-I characteristics

| Donor # | HLA-A | HLA-B | HLA-C |
|---|---|---|---|
| 1 | *02:01 *02:01 | *15:01 *51:01 | *02:02 *03:04 |
| 2 | *01:01 *32:01 | *08:01 *14:01 | *07:01 *08:01 |
| 3 | *03:01 *25:01 | *07:02 *18:01 | *07:02 *12:03 |
| 4 | *02:01 *30:02 | *14:02 *57:02 | *08:02 *18:02 |
| 5 | *02:01 *33:01 | *07:02 *14:02 | *07:02 *08:02 |
| 6 | *01:01 *32:01 | *35:01 *40:06 | *04:01 *15:02 |

Cocktails Induce Immune Responses Against Relevant TAAs

The ability of GCA vaccine-A and GCA vaccine-B to induce IFNγ production against ten GCA antigens was measured by ELISpot. PBMCs from seven HLA-diverse healthy donors (Table 108) were co-cultured with autologous DCs loaded with GCA vaccine-A or GCA vaccine-B for 6 days prior to stimulation with TAA-specific specific peptide pools containing known MHC-I restricted epitopes. Peptides for stimulation of CD14-PBMCs to detect IFNγ responses to PSMA, LY6K, WT1 and CLDN18 are described above. Additional 15-mer peptides overlapping by 11 amino acid peptide pools were sourced as follows: MSLN (GenScript custom peptide library), MAGEA3 (JPT, PM-MAGEA3), CEA (JPT, PM-CEA), Survivin (thinkpeptides, 7769_001-011), STEAP1 (PM-STEAP1) and MUC1 (JPT, PM-MUC1).

FIG. 119 demonstrates the GCA vaccine is capable of inducing antigen specific IFNγ responses in six HLA-diverse donors to ten GCA antigens that are 17.5-fold more robust (32,898±13,617 SFU) compared to the unmodified parental control (1,879±463 SFU) (p=0.009, Mann-Whitney U test) (n=6) (FIG. 119A) (Table 109). The unit dose of GCA vaccine-A and GCA vaccine-B elicited IFNγ responses to eight antigens in two donors, nine antigens in one donor and ten antigens in four donors (FIG. 120). GCA vaccine-A and GCA vaccine-B independently demonstrated a 17.4-fold and 17.7-fold increase antigen specific responses compared to parental controls, respectively. Specifically, GCA vaccine-A elicited 18,332±6,823 SFU compared to the unmodified controls (1,055±518 SFU) (p=0.004, Mann-Whitney U test) (FIG. 119B). For GCA vaccine-A, one donor responded to five antigens, two donors responded to nine antigens, and three donors responded ten antigens. GCA vaccine-B elicited 14,566±7,499 SFU compared to parental controls (823±287 SFU) (p=0.015, Mann-Whitney U test) (FIG. 119C). For GCA vaccine-B, one donor responded to five antigens, two donors responded to nine antigens, and three donors responded ten antigens. Described above are two compositions comprising a therapeutically effective amount of three cancer cell lines, a unit dose of six cell lines, wherein said unit dose is capable of eliciting an immune response 17.5-fold greater than the unmodified composition specific to at least eight TAAs expressed in GCA patient tumors. GCA vaccine-A increased IFNγ responses to at least five TAAs 17.4 and GCA vaccine-B increased IFNγ responses 17.7 to at least five TAAs.

TABLE 109

IFNy Responses to unmodified and modified GCA vaccine components

| Donor (n = 4) | Unmodified (SFU ± SEM) | | | Modified (SFU ± SEM) | | |
|---|---|---|---|---|---|---|
| | GCA Vaccine-A | GCA Vaccine-B | GCA Vaccine | GCA Vaccine-A | GCA Vaccine-B | GCA Vaccine |
| 1 | 305 ± 107 | 73 ± 73 | 378 ± 173 | 5,616 ± 1,720 | 5,438 ± 3,569 | 11,054 ± 4,736 |
| 2 | 3,542 ± 1,184 | 24 ± 24 | 3,566 ± 1,193 | 35,007 ± 15,203 | 51,023 ± 17,176 | 86,030 ± 32,196 |
| 3 | 811 ± 119 | 1,366 ± 468 | 2,176 ± 531 | 25,519 ± 11,590 | 11,586 ± 7,416 | 37,105 ± 18,093 |
| 4 | 0 ± 0 | 1,313 ± 533 | 1,313 ± 533 | 1,869 ± 632 | 675 ± 236 | 2,544 ± 673 |
| 5 | 530 ± 215 | 400 ± 173 | 1,240 ± 329 | 32,064 ± 1,785 | 9,261 ± 3,145 | 41,326 ± 2,571 |
| 6 | 968 ± 236 | 1,631 ± 701 | 2,599 ± 927 | 2,920 ± 1,014 | 4,743 ± 1,593 | 10,218 ± 585 |

Based on the disclosure and data provided herein, a whole cell vaccine for Gastric Cancer comprising the six cancer cell lines, sourced from ATCC or JCRB, MKN-1 (JCRB, JCRB0252), MKN-45 (JCRB, JCRB0254), MKN-74 (JCRB, JCRB0255), OCUM-1 (JCRB, JCRB0192), Fu97 (JCRB, JCRB1074) and DMS 53 (ATCC, CRL-2062) is shown in Table 110. The cell lines represent five gastric cancer cell lines and one small cell lung cancer (SCLC) cell line (DMS 53 ATCC CRL-2062). The cell lines have been divided into two groupings: vaccine-A and vaccine-B. Vaccine-A is designed to be administered intradermally in the upper arm and vaccine-B is designed to be administered intradermally in the thigh. Vaccine A and B together comprise a unit dose of cancer vaccine.

TABLE 110

| Cell line nomenclature and modifications | | | | | | | | |
|---|---|---|---|---|---|---|---|---|
| Cocktail | Cell Line | TGFβ1 KD | TGFβ2 KD | CD276 KO | GM-CSF | CD40L | IL-12 | TAA(s) |
| A | MKN-1 | X | X | X | X | X | X | X |
| A | MKN-45* | X | ND | X | X | X | X | ND |
| A | MKN-74 | X | ND | X | X | X | X | ND |
| B | OCUM-1* | ND | ND | X | X | X | ND | ND |
| B | Fu97 | X | ND | X | X | X | X | X |
| B | DMS 53* | ND | X | X | X | X | ND | ND |

ND = Not done.
*Cell lines identified as CSC-like cells.

Where indicated in the above table, the genes for the immunosuppressive factors transforming growth factor-beta 1 (TGFβ1) and transforming growth factor-beta 2 (TGFβ2) have been knocked down using shRNA transduction with a lentiviral vector. The gene for CD276 has been knocked out by electroporation using zinc-finger nuclease (ZFN) or knocked down using shRNA transduction with a lentiviral vector. The genes for granulocyte macrophage-colony stimulating factor (GM-CSF), IL-12, CD40L, modPSMA (MKN-1), modLY6K (MKN-1), modWT1 (Fu97) and mod-CLDN18 (Fu97) have been added by lentiviral vector transduction.

Provided herein are two compositions comprising a therapeutically effective amount of three cancer cell lines, a unit dose of six cancer cell lines, modified to reduce the expression of at least one immunosuppressive factor and to express at least two immunostimulatory factors. One composition, GCA vaccine-A, was modified to increase the expression of two TAAs, modPSMA and modLY6K. The second composition, GCA vaccine-B, was modified to expresses two TAAs, modWT1 and modCLDN18. The unit dose of six cancer cell lines expresses at least at least 11 TAAs associated with a cancer of a subset of gastric cancer subjects intended to receive said composition and induces IFNγ responses 17.5-fold greater than the unmodified composition components.

Example 36: Preparation of Breast Cancer (BRCA) Vaccine

This Example demonstrates that reduction of TGFβ1, TGFβ2, and CD276 expression with concurrent overexpression of GM-CSF, CD40L, and IL-12 in a vaccine composition of two cocktails, each cocktail composed of three cell lines for a total of 6 cell lines, significantly increased the magnitude of cellular immune responses to at least 10 BRC-associated antigens in an HLA-diverse population. As described herein, the first cocktail, BRC vaccine-A, is composed of cell line CAMA-1 that was also modified to express modPSMA, cell line AU565 that was also modified to express modTERT, and cell line HS-578T. The second cocktail, BRC vaccine-B, is composed of cell line MCF-7, cell line T47D that was also modified to express modTBXT and modBORIS, and cell line DMS 53. The six component cell lines collectively express at least twenty-two antigens that can provide an anti-BRC tumor response.

Identification of BRC Vaccine Components

Initial cell line selection criteria identified twenty-nine vaccine component cell lines for potential inclusion in the BRC vaccine. Additional selection criteria described herein were applied to narrow the twenty-nine cell lines to seven cell lines for further evaluation in immunogenicity assays. These criteria included: endogenous BRC associated antigen expression, endogenous expression of antigens enriched in triple negative breast cancer, lack of expression of additional immunosuppressive factors, such as IL-10 or IDO1, expression of BRC-associated CSC-like markers ABCG2, ALDH1A, BMI1, CD133, CD44, ITGA6, CD90, c-myc, CXCR1 CXCR4, EPCAM, KLF4, MUC1, NANOG, SAL4 and SOX2, ethnicity and age of the patient from which the cell line was derived, site and stage of the breast cancer, molecular subtype and histological subtype.

Figure 121B:
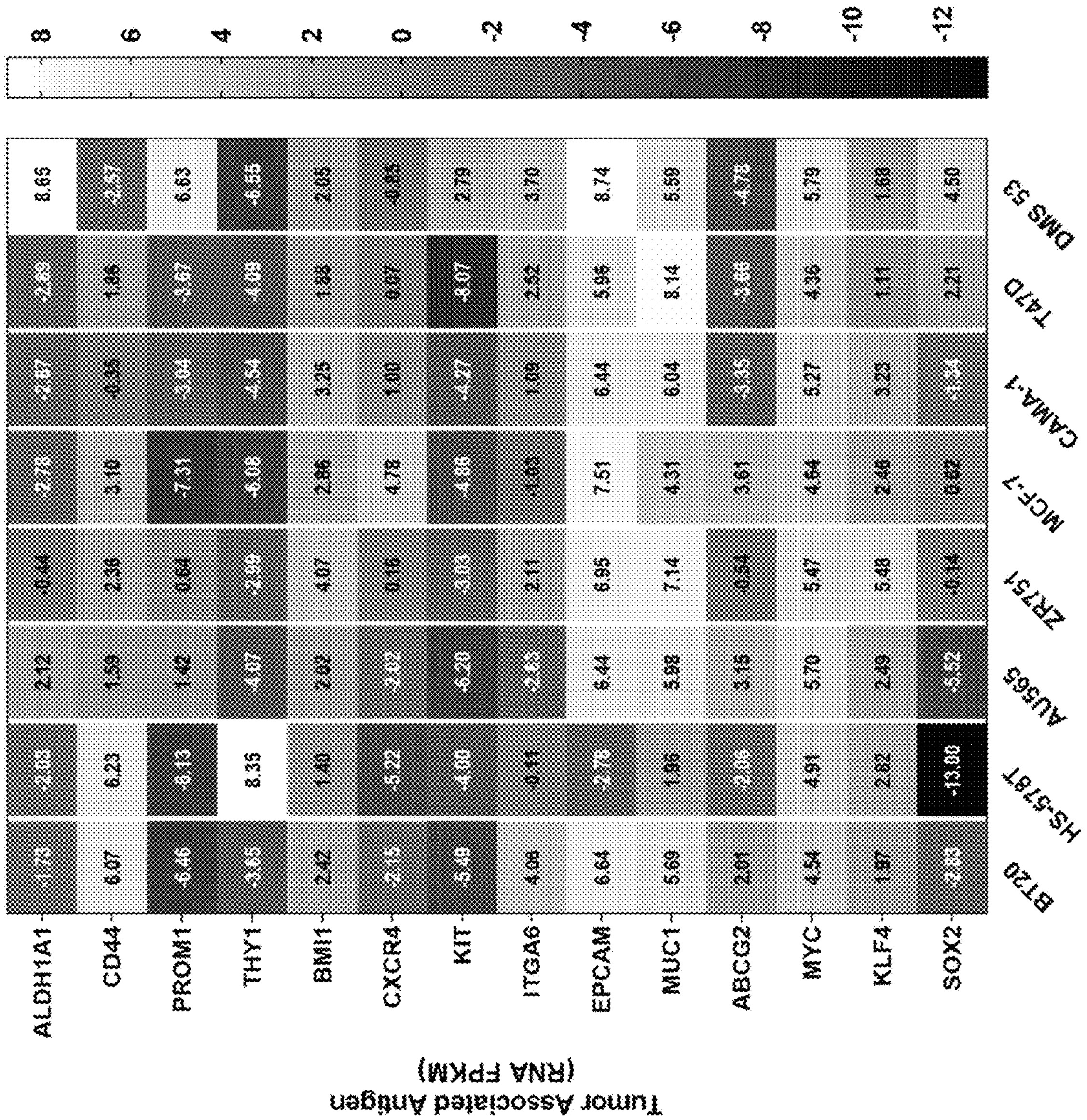

CSCs play a critical role in the metastasis, treatment resistance, and relapse of breast cancer (Table 2). Expression of TMs and BRC specific CSC-like markers by candidate component cell lines was determined by RNA expression data sourced from the Broad Institute Cancer Cell Line Encyclopedia (CCLE). The HGNC gene symbol was included in the CCLE search and mRNA expression was downloaded for each TAA. Expression of a TAA or CSC marker by a cell line was considered positive if the RNA-seq value was greater than one. Selection criteria identified seven candidate BRC vaccine components for further evaluation: BT20, HS-578T, AU565, ZR751, MCF-7, CAMA-1 and T47D. The seven candidate component cell lines expressed seven to eleven TAAs (FIG. 121A) and six to nine CSC markers (FIG. 121B). As described herein, the CSC-like cell line DMS 53 is included as one of the six vaccine cell lines and expressed fifteen BRC TMs and three BRC CSC-like markers.

Immunogenicity of the seven unmodified BRC vaccine component candidates were evaluated by IFNγ ELISpot as described in Example 9 using three HLA diverse healthy donors (n=4 per donor). HLA-A and HLA-B alleles for Donor 1 were A*02:01 B*57:03 and A*01:01 B*08:01. HLA-A and HLA-B alleles for Donor 2 were A*30:01 B*57:01 and A*02:01 B*40:01. HLA-A alleles for Donor 3 were A*01:01 and A*02:01. HLA-B typing was not available for Donor 3. Immunogenicity of T47D was evaluated separately in five HLA diverse donors (Table 117, Donors 2-6). MCF-7 (2,314±448 SFU) and CAMA-1 (990±223 SFU) were more immunogenic than AU565 (274±87 SFU), ZR751 (292±133 SFU), BT20 (524±192 SFU), HS-578T (281±81 SFU) (FIG. 122A) and T47D (491±202 SFU) (FIG. 122C).

Immunogenicity of MCF-7 and CAMA-1 were evaluated in eight different combinations of three component cell lines, four combinations contained MCF-7 and four combinations contained CAMA-1 (FIG. 122D). IFNγ responses were determined against the three component cell lines within the eight potential vaccine cocktails by IFNγ ELISpot as described in Example 8 using the three healthy donors (n=4/donor). HLA-A and HLA-B alleles for the Donors were as follows: Donor 1, A*01:01 B*08:01 and A*02:01

B*15:01; Donor 2, A*03:01 B*15:01 and A*24:02 B*07:02; Donor 3, A*01:01 B*30:01 and A*02:01 B*12:02. One additional cocktail combination of three component cell lines including T47D, MCF-7 and DMS 53 T47D was also evaluated (FIG. 122C) in the same five HLA-diverse donors (Table 117, Donors 2-6). IFNγ responses were detected for all nine cocktails and to each cell line component in each cocktail.

In all eight combinations evaluated, MCF-7 and CAMA-1 remained the most immunogenic. Responses to the individual cocktail component cell lines were similar, except for CAMA-1 and ZR751. IFNγ responses to CAMA-1 slightly decreased in the three component cell line combinations. IFNγ responses to ZR751 also slightly decreased in the three cell line component cocktails and therefore ZR751 was not included in the BRC vaccine (FIG. 122B-C). Triple negative breast cancer comprises approximately 15% of breast cancers. For this reason, one triple negative breast cancer cell line, 17% of the unit dose of the BRC vaccine, was included in the composition vaccine. The immunogenicity of the triple negative breast cancer cell lines, BT20 and HS-578T, was similar when evaluated in three cell line component cocktails. Of these two cell lines, HS-578T endogenously expressed more TAAs (eleven TAAs>1.0 FPKM) than BT20 (nine TAAs>1.0 FPKM) (FIG. 121A) and was selected for inclusion in the BRC vaccine. CAMA-1 was selected to be included in vaccine cocktail A and MCF-7 selected to be included in vaccine cocktail B as described above and further herein.

The cells in the vaccine described herein were selected to express a wide array of TAAs, including those known to be important specifically for BRC antitumor responses, such as mammaglobin A (SCGB2A2) and MUC1, enriched in triple negative breast cancer, such as TBXT and NY-ESO-1, and also TAAs known to be important for targets for BRC and other solid tumors, such TERT. As shown herein, to further enhance the array of TAAs, CAMA-1 was modified to express modPSMA, AU565 was modified to express modTERT, and T47D that was also modified to express modTBXT and modBORIS.

TBXT and BORIS were not endogenously expressed in any of the six component cell lines at >1.0 FPKM. TERT and PSMA were endogenously expressed by one of the six component cell lines at >1.0 FPKM (FIG. 123A).

Expression of the transduced antigens modPSMA (FIG. 124A) by CAMA-1 (SEQ ID NO: 37; SEQ ID NO: 38), modTERT (FIG. 124B) by AU565 (SEQ ID NO: 35; SEQ ID NO: 36), and modTBXT (FIG. 124C) and modBORIS (FIG. 124D) (SEQ ID NO: 41; SEQ ID NO: 42) by T47D, were detected by flow cytometry or RT-PCR as described in Example 29 and herein. The modTBXT and modBORIS antigens are encoded in the same lentiviral transfer vector separated by a furin cleavage site (SEQ ID NO: 41 and SEQ ID NO: 42).

Because of the need to maintain maximal heterogeneity of antigens and clonal subpopulations the comprise each cell line, the gene modified cell lines utilized in the present vaccine have been established using antibiotic selection and flow cytometry and not through limiting dilution subcloning.

The endogenous mRNA expression of twenty-two representative BRC TAAs in the present vaccine are shown in FIG. 123A. The present vaccine, after introduction of the antigens described above, expresses of all identified twenty-two commonly targeted and potentially clinically relevant TAAs capable of inducing a BRC antitumor response. Some of these TAAs are known to be primarily enriched in BRC tumors and some can also induce an immune response to BRC and other solid tumors. RNA abundance of the twenty-two prioritized BRC TAAs was determined in 1082 BRC patient samples with available mRNA data expression as described in Example 29 (FIG. 123B). Fifteen of the prioritized BRC TAAs were expressed by 100% of samples, 16 TAAs were expressed by 99.9% of samples, 17 TAAs were expressed by 99.3% of samples, 18 TAAs were expressed by 95.1% of samples, 19 TAAs were expressed by 79.9% of samples, 20 TAAs were expressed by 47.6% of samples, 21 TAAs were expressed by 17.1% of samples, and 22 TAAs were expressed by 3.4% of samples (FIG. 123C). Provided herein are two compositions comprising a therapeutically effective amount of three cancer cell lines, wherein the combination of the cell lines, a unit dose of six cell lines, comprises cells that express at least 15 TAAs associated with a subset of BRC cancer subjects intended to receive said composition. Based on the expression and immunogenicity data presented herein, the cell lines identified in Table 111 were selected to comprise the present BRC vaccine.

TABLE 111

Breast vaccine cell lines and histology

| Cocktail | Cell Line Name | Histology |
|---|---|---|
| A | CAMA-1 | Breast Luminal A Adenocarcinoma, ER+, PR+, Her2−; derived from metastatic site (pleural effusion) |
| A | AU565 | Breast Luminal Adenocarcinoma, ER−, PR−, Her2+; derived from metastatic site (pleural effusion) |
| A | HS-578T | Breast Triple Negative Ductal Carcinoma, ER−, PR−, Her2− |
| B | MCF-7 | Breast Luminal A Adenocarcinoma, ER+, PR+, Her2; derived from metastatic site (pleural effusion) |
| B | T47D | Breast Luminal A Ductal Carcinoma, ER+, PR+, Her2; derived from metastatic site (pleural effusion) |
| B | DMS 53 | Lung Small Cell Carcinoma |

Reduction of CD276 Expression

The CAMA-1, AU565, HS-578T, MCF-7, T47D, and DMS 53 component cell lines expressed CD276 and expression was knocked out by electroporation with ZFN as described in Example 13 and elsewhere herein. Because it was desirable to maintain as much tumor heterogeneity as possible, the electroporated and shRNA modified cells were not cloned by limiting dilution. Instead, the cells were subjected to multiple rounds of cell sorting by FACS as described in Example 13. Expression of CD276 was determined as described in Example 29. Reduction of CD276 expression is described in Table 112. These data show that gene editing of CD276 with ZFN resulted in greater than 95.2% CD276-negative cells in all six vaccine component cell lines.

TABLE 112

Reduction of CD276 expression

| Cell line | Parental Cell Line MFI | Modified Cell Line MFI | % Reduction CD276 |
|---|---|---|---|
| CAMA-1 | 14,699 | 75 | 99.5 |
| AU565 | 4,085 | 0 | 99.9 |
| HS-578T | 33,832 | 234 | 99.3 |
| MCF-7 | 25,952 | 1,243 | 95.2 |
| T47D | 11,737 | 3 | 99.9 |
| DMS 53 | 11,928 | 24 | 99.8 |

MFI reported with isotype controls subtracted

Cytokine Secretion Assays for TGFβ1, TGFβ2, GM-CSF, and IL-12

Cytokine Secretion Assays for TGFβ1, TGFβ2, GM-CSF, and IL-12 were Completed as Described in Example 29. shRNA Downregulates TGF-6 Secretion Following CD276 knockout, TGFβ1 and TGFβ2 secretion levels were reduced using shRNA and resulting levels determined as described in Example 29. The AU565 and HS-578T parental cell lines in BRC vaccine-A secreted measurable levels of TGFβ1 and TGFβ2. CAMA-1 secreted detectable levels of TGFβ2 but not TGFβ1. The MCF-7 component cell line of BRC vaccine-B secreted measurable levels of TGFβ1 and TGFβ2. T47D did not secreted measurable levels of TGFβ1 or TGFβ2 and therefore was not modified to reduce secretion of TGFβ1 or TGFβ2. Reduction of TGFβ2 secretion by the DMS 53 cell line is described in Example 26 and resulting levels determined as described above and herein.

The component HS-578T and MCF-7 cell lines were transduced with TGFβ1 shRNA to decrease TGFβ1 secretion concurrently with the transgene to increase expression of membrane bound CD40L as described in Example 29. HS-578T and MCF-7 were also transduced with lentiviral particles encoding TGFβ2 shRNA to decrease the secretion of TGFβ2 and concurrently increase expression of GM-CSF (SEQ ID NO: 6) as described in Example 29. These cells are described by the clonal designation DK6. The HS-578T, MCF-7, CAMA-1 and AU565 cell lines were transduced with lentiviral particles encoding TGFβ2 shRNA to decrease the secretion of TGFβ2 and concurrently increase expression of GM-CSF (SEQ ID NO: 6) as described in Example 29. DMS 53 was modified with shRNA to reduce secretion of TGFβ2 as described in Example 26. The cell lines modified to reduce secretion of TGFβ2 and not TGFβ1 are described by the clonal designation DK4.

Table 113 shows the percent reduction in TGFβ1 and/or TGFβ2 secretion in gene modified component cell lines compared to unmodified, parental cell lines. If TGFβ1 or TGFβ2 secretion was only detected in 1 of 16 replicates run in the ELISA assay the value is reported without standard error of the mean. Gene modification resulted at least 44% reduction of TGFβ1 secretion. Gene modification of TGFβ2 resulted in at least 51% reduction in secretion of TGFβ2.

TABLE 113

TGF-β Secretion (pg/$10^6$ cells/24 hr) in Component Cell Lines

| Cell Line | Cocktail | Clone | TGFβ1 | TGFβ2 |
|---|---|---|---|---|
| CAMA-1 | A | Wild type | *≤20 | 249 ± 59 |
| CAMA-1 | A | DK4 | NA | *≤11 |
| CAMA-1 | A | Percent reduction | 79% | ≥96% |
| AU565 | A | Wild type | 325 ± 219 | 306 ± 294 |
| AU565 | A | DK4 | NA | *≤23 |
| AU565 | A | Percent reduction | ≥85% | ≥92% |
| HS-578T | A | Wild type | 3,574 ± 690 | 615 ± 247 |
| HS-578T | A | DK6 | 1,989 ± 200 | 118 ± 26 |
| HS-578T | A | Percent reduction | 44% | 81% |
| MCF-7 | B | Wild type | 1,279 ± 174 | 411 ± 149 |
| MCF-7 | B | DK6 | 306 ± 48 | *≤14 |
| MCF-7 | B | Percent reduction | 76% | 60% |
| T47D | B | Wild type | *≤32 | *≤15 |
| T47D | B | NA | NA | NA |
| T47D | B | Percent reduction | NA | NA |
| DMS 53 | B | Wild type | 106 ± 10 | 486 ± 35 |
| DMS 53 | B | DK4 | NA | 238 ± 40 |
| DMS 53 | B | Percent reduction | NA | 51% |

DK6: TGFβ1/TGFβ2 double knockdown;

DK4: TGFβ2 single knockdown;

DK2: TGFβ1 single knockdown;

*= estimated using LLD, not detected;

NA = not applicable

Based on a dose of $5\times10^5$ of each component cell line, the total TGFβ1 and TGFβ2 secretion by the modified BRC vaccine-A and BRC vaccine-B and respective unmodified parental cell lines are shown in Table 114. The secretion of TGFβ1 by BRC vaccine-A was reduced by 49% and TGFβ2 by 87% pg/dose/24 hr. The secretion of TGFβ1 by BRC vaccine-B was reduced by 67% and TGFβ2 by 71% pg/dose/24 hr.

TABLE 114

Total TGF-β Secretion (pg/dose/24 hr) in BRC vaccine-A and BRC vaccine-B

| Cocktail | Clones | TGFβ1 | TGFβ2 |
|---|---|---|---|
| A | Wild type | 1,960 | 585 |
| | DK4/DK6 | 995 | 76 |
| | Percent reduction | 49% | 87% |
| B | Wild type | 709 | 456 |
| | DK4/DK6 | 222 | 134 |
| | Percent reduction | 67% | 71% |

GM-CSF Secretion

The HS-578T, MCF-7, CAMA-1 and AU565 cell lines were transduced with lentiviral particles containing both TGFβ2 shRNA and the gene to express GM-CSF (SEQ ID NO: 6) as described above. The T47D cell line was transduced with lentiviral particles to only express GM-CSF (SEQ ID NO: 7). DMS 53 was modified to secrete GM-CSF as described in Example 26 and elsewhere herein. The results are shown in Table 115 and described below.

Secretion of GM-CSF increased at least 15,714-fold in all modified component cell lines compared to unmodified, parental cell lines. In BRC vaccine-A component cell lines, secretion of GM-CSF increased 36,990-fold by CAMA-1 compared to the parental cell line (≤0.0039 ng/$10^6$ cells/24 hr), 15,714-fold by AU565 compared to the parental cell line (≤0.0042 ng/$10^6$ cells/24 hr), and 21,061-fold by HS-578T compared to the parental cell line (≤0.0064 ng/$10^6$ cells/24 hr). In BRC vaccine-B component cell lines secretion of GM-CSF increased 25,528-fold by MCF-7 compared to the parental cell line (≤0.0118 ng/$10^6$ cells/24 hr), 33,920-fold by T47D compared to the parental cell line (≤0.0063 ng/$10^6$ cells/24 hr) and 49,313-fold by DMS 53 compared to the parental cell line (≤0.0032 ng/$10^6$ cells/24 hr).

TABLE 115

GM-CSF Secretion in Component Cell Lines

| Cell Line | GM-CSF (ng/$10^6$ cells/24 hr) | GM-CSF (ng/dose/24 hr) |
|---|---|---|
| CAMA-1 | 145 ± 30 | 73 |
| AU565 | 66 ± 37 | 33 |
| HS-578T | 135 ± 20 | 68 |
| Cocktail A Total | 346 | 174 |
| MCF-7 | 302 ± 66 | 151 |
| T47D | 212 ± 40 | 106 |
| DMS 53 | 158 ± 15 | 79 |
| Cocktail B Total | 672 | 336 |

Based on a dose of $5\times10^5$ of each component cell line, the total GM-CSF secretion for BRC vaccine-A was 174 ng per dose per 24 hours. The total GM-CSF secretion for BRC vaccine-B was 336 ng per dose per 24 hours. The total GM-CSF secretion per dose was therefore 510 ng per 24 hours.

Membrane Bound CD40L (CD154) Expression

The component cell lines were transduced with lentiviral particles to express membrane bound CD40L vector as described above. The methods to detect expression of CD40L by the five BRC cell line components are described in Example 29. Modification of DMS 53 to express membrane bound CD40L is described in Example 15. Evaluation of membrane bound CD40L by all six vaccine component cell lines is described below. The results shown in FIG. 125 and described below demonstrate CD40L membrane expression was substantially increased in all six BRC vaccine component cell lines.

Expression of membrane bound CD40L increased at least 3,417-fold in all component cell lines compared to unmodified, parental cell lines. In BRC vaccine-A component cell lines, expression of CD40L increased 3,417-fold by CAMA-1 (3,417 MFI) compared to the parental cell line (0 MFI), 6,527-fold by AU565 (6,527 MFI) compared to the parental cell line (0 MFI), and 6,560-fold by HS-578T (6,560 MFI) compared to the parental cell line (0 MFI). In BR-BT vaccine-B component cell lines expression of CD40L increased 5,986-fold by MCF-7 (5,986 MFI) compared to the parental cell line (0 MFI), 45,071-fold by T47D (45,071 MFI) compared to the parental cell line (0 MFI), and 88,261-fold by DMS 53 compared to the parental cell line (0 MFI).

IL-12 Expression

The component cell lines were transduced with the IL-12 vector as described in Example 17 and resulting IL-12 p70 expression determined as described above and herein. The results are shown in Table 116 and described below.

Secretion of IL-12 increased at least 4,034-fold in all component cell lines modified to secrete IL-12 p70 compared to unmodified, parental cell lines. In BRC vaccine-A component cell lines, secretion of IL-12 increased 39,490-fold by CAMA-1 compared to the parental cell line (≤0.0016 ng/$10^6$ cells/24 hr), 14,793-fold by AU565 compared to the parental cell line 0.0017 ng/$10^6$ cells/24 hr), and 19,141-fold by HS-578T compared to the parental cell line (≤0.0026 ng/$10^6$ cells/24 hr). In BRC vaccine-B component cell lines expression of IL-12 increased 4,034-fold by MCF-7 compared to the parental cell line 0.0047 ng/$10^6$ cells/24 hr) and 43,655-fold by T47D compared to the parental cell line (≤0.002 ng/$10^6$ cells/24 hr). DMS 53 was not modified to secrete IL-12.

TABLE 116

IL-12 Secretion in Component Cell Lines

| Cell Line | IL-12 (ng/106 cells/24 hr) | IL-12 (ng/dose/24 hr) |
|---|---|---|
| CAMA-1 | 62 ± 13 | 31 |
| AU565 | 25 ± 12 | 13 |
| HS-578T | 49 ± 11 | 25 |
| Cocktail A Total | 136 | 69 |
| MCF-7 | 19 ± 13 | 10 |
| T47D | 86 ± 17 | 43 |
| DMS 53 | NA | NA |
| Cocktail B Total | 105 | 53 |

Based on a dose of $5\times10^5$ of each component cell line, the total IL-12 secretion for BRC vaccine-A was 69 ng per dose per 24 hours. The total IL-12 secretion for BRC vaccine-B was 53 ng per dose per 24 hours. The total IL-12 secretion per dose was therefore 122 ng per 24 hours.

Stable Expression of modPSMA by the CAMA-1 Cell Line

As described above, the cells in the vaccine described herein were selected to express a wide array of TAAs, including those known to be important to antitumor immunity. To further enhance the array of antigens, the CAMA-1 cell line that was modified to reduce the secretion of TGFβ2, reduce the expression of CD276, and to express GM-CSF, membrane bound CD40L and IL-12 was also transduced with lentiviral particles expressing the modPSMA antigen (SEQ ID NO: 37, SEQ ID NO: 38). The expression of modPSMA by CAMA1 was characterized by flow cytometry. Unmodified and antigen modified cells were stained intracellular with 0.03 μg/test anti-mouse IgG1 anti-PSMA antibody (Abcam, ab268061) followed by 0.125 ug/test AF647-conjugated goat anti-mouse IgG1 antibody (BioLegend #405322). Expression of modPSMA was increased in the modified cell line (77,718 MFI) 17-fold over that of the parental cell line (4,269 MFI) (FIG. 124A).

Stable Expression of modTERT by the AU565 Cell Line

Figure 124B:
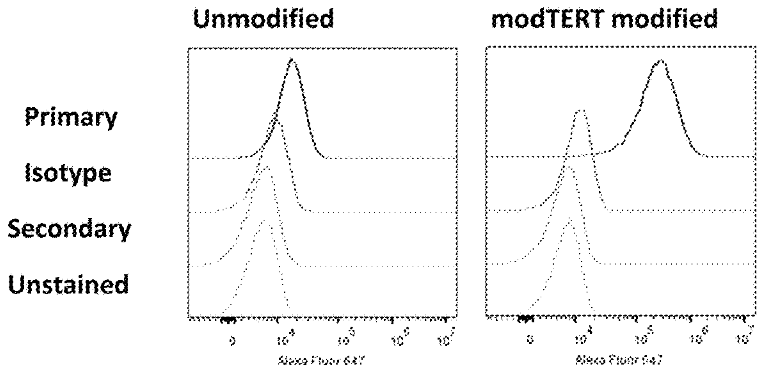

The AU565 cell line that was modified to reduce the secretion of TGFβ2, reduce the expression of CD276, and to express GM-CSF, membrane bound CD40L and IL-12 was also transduced with lentiviral particles expressing the modTERT antigen (SEQ ID NO: 35, SEQ ID NO: 36). Expression of modTERT by AU565 was characterized by flow cytometry. Unmodified and antigen modified cells were stained intracellular with 0.03 μg/test anti-mouse IgG1 anti-TERT antibody (Abcam, ab32020) followed by 0.125 ug/test donkey anti-rabbit IgG1 antibody (BioLegend #406414). Expression of modTERT was increased in the modified cell line (957,873 MFI) 31-fold over that of the unmodified cell line (30,743 MFI) (FIG. 124B).

Stable Expression of modTBXT and modBORIS by the T47D Cell Line

Figure 124C:
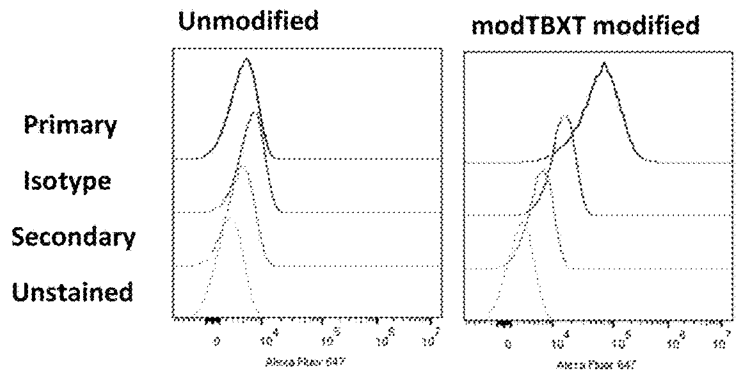
Figure 124D:
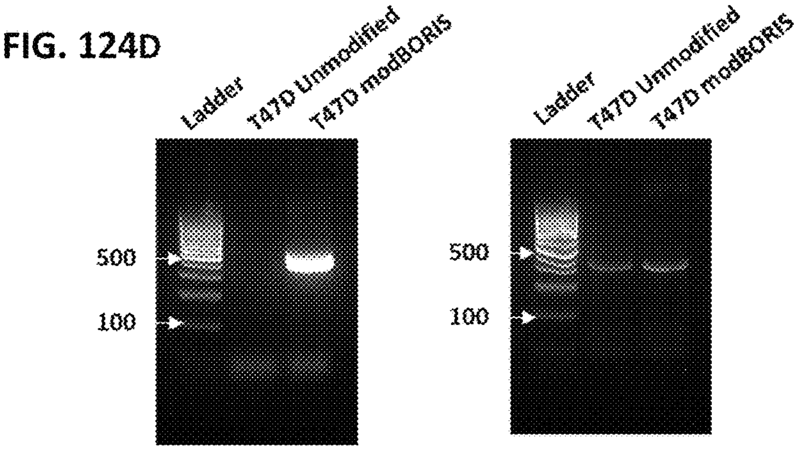

The T47D cell line that was modified to reduce the reduce the expression of CD276, and to express GM-CSF, membrane bound CD40L, and IL-12 was also transduced with lentiviral particles expressing the modTBXT and modBORIS antigens (SEQ ID NO: 41, SEQ ID NO: 42). Expression of modTBXT by T47D was characterized by flow cytometry. Unmodified and antigen modified cells were stained intracellular with 0.06 μg/test anti-rabbit IgG1 anti-TBXT antibody (Abcam, ab209665) followed by 0.125 ug/test AF647-conjugated donkey anti-rabbit IgG1 antibody (BioLegend #406414). Expression of modTBXT increased in the modified cell line (147,610 MFI) 147,610-fold over that of the unmodified cell line (0 MFI) (FIG. 124C). Expression of BORIS by SCaBER was determined by RT-PCR as described in Example 29 and herein. The forward primer was designed to anneal at the 1119-1138 bp location in the transgene (TTCCAGTGCTGCCAGTGTAG (SEQ ID NO:134)) and reverse primer designed to anneal at the 1159-1178 bp location in the transgene (AGCACTTGTTGCAGCTCAGA (SEQ ID NO: 135)) yielding a 460 bp product. Control primers for β-tubulin are described in Example 29. The gene product for modBORIS was detected at the expected size (FIG. 124D) and mRNA increased 2,198-fold relative to the parental control.

Immune Responses to PSMA in BRC Vaccine-A

IFNγ responses to PSMA were evaluated in the context of BRC vaccine-A as described in Example 29, and herein, in six HLA diverse donors (n=4/donor). The HLA-A, HLA-B, and HLA-C alleles for each of the six donors are shown in Table 117. IFNγ responses were determined by ELISpot as described in Example 29 using 15-mers peptides overlapping by 9 amino acids spanning the entire length of the native PSMA antigen purchased from Thermo Scientific Custom Peptide Service. PSMA specific IFNγ responses with the were significantly increased with the modified BRC vaccine-A (4,166±1,647 SFU) compared to the parental, unmodified BRC vaccine-A (393±210 SFU (p=0.041, Mann-Whitney U test) (n=6) (FIG. 124E).

Immune Responses to TERT in BRC Vaccine-A

IFNγ responses to TERT were evaluated in the context of BRC vaccine-A as described in Example 29, and herein, in six HLA diverse donors (n=4/donor). The HLA-A, HLA-B, and HLA-C alleles for each of the six donors are shown in Table 117. IFNγ responses were determined by ELISpot using 15-mers peptides overlapping by 11 amino acids spanning the entire length of the native TERT antigen (JPT, PM-TERT). IFNγ responses to TERT increased with the modified BRC vaccine-A (3,807±927 SFU) compared to the unmodified BRC vaccine-A (1,670±918) SFU (FIG. 124F).

Immune Responses to TBXT and BORIS in BRC Vaccine-B

IFNγ responses to TBXT and BORIS were evaluated in the context of BRC-vaccine B as described in Example 32, and herein, in six HLA diverse donors (n=4/donor) (Table 117). IFNγ responses against TBXT were determined by ELISpot using 15-mers peptides overlapping by 11 amino acids spanning the entire length of the native antigen (JPT, PM-BRAC). IFNγ responses against BORIS were determined by ELISpot using 15-mers peptides overlapping by 9 amino acids spanning the entire length of the native antigen protein purchased from Thermo Scientific Custom Peptide Service.

TBXT specific IFNγ responses were increased by BRC vaccine-B (1,102±366 SFU) compared to the unmodified BRC vaccine-B (930±496 SFU) (n=6) (FIG. 124G). BORIS specific IFNγ responses were also increased by BRC vaccine-B (3,054±1,155 SFU) compared to the unmodified BRC vaccine-B (1,757±661 SFU) (n=6) (FIG. 124H).

TABLE 117

| Healthy Donor MHC-I characteristics | | | |
|---|---|---|---|
| Donor # | HLA-A | HLA-B | HLA-C |
| 1 | *03:01 *07:02 | *07:02 *35:01 | *04:01 *07:02 |
| 2 | *02:01 *03:01 | *27:05 *27:05 | *01:02 *01:02 |
| 3 | *02:01 *33:01 | *07:02 *14:02 | *07:02 *08:02 |

TABLE 117-continued

| Healthy Donor MHC-I characteristics | | | |
|---|---|---|---|
| Donor # | HLA-A | HLA-B | HLA-C |
| 4 | *02:01 *02:01 | *15:01 *44:02 | *03:04 *14:02 |
| 5 | *24:02 *02:01 | *08:01 *51:01 | *14:02 *03:04 |
| 6 | *01:01 *02:01 | *35:01 *50:01 | *04:01 *06:02 |

Cocktails Induce Immune Responses Against Relevant TAAs

The ability of BRC vaccine-A and BRC vaccine-B to induce IFNγ production against ten BRC antigens was measured by ELISpot. PBMCs from six HLA-diverse healthy donors (Table 117) were co-cultured with autologous DCs loaded with BRC vaccine-A or BRC vaccine-B for 6 days prior to stimulation with TAA-specific specific peptide pools containing known MHC-I restricted epitopes. Peptides for stimulation of CD14-PBMCs to detect IFNγ responses to PSMA, TERT, TBXT and BORIS are described above. Additional 15-mer peptides overlapping by 11 amino acid peptide pools were sourced as follows: STEAP1 (PM-STEAP1), PRAME (JPT, PM-01P4), SCGB2A2 (Mammaglobin-A) (JPT, PM-MamA), Survivin (thinkpeptides, 7769_001-011), MUC1 (JPT, PM-MUC1) and MMP11 (JPT, PM-MMP11).

FIG. 126 demonstrates the BRC vaccine is capable of inducing antigen specific IFNγ responses in six HLA-diverse donors to ten BRC antigens that are 2.2-fold more robust (45,370±9,212 SFU) compared to the unmodified parental control (20,183±7,978 SFU) (n=6) (FIG. 136A) (Table 118). The unit dose of BRC vaccine-A and BRC vaccine-B elicited IFNγ responses to nine antigens in two donors and ten antigens in four donors (FIG. 127). The BRC vaccine increase IFNγ responses to PRAME 2.2-fold (3,049±1,079 SFU) and TBXT 1.7-fold, (3,049±1,079 SFU), two antigens enriched in the triple negative molecular subset of breast cancer, compared to the unmodified controls, 1,380±697 SFU and 1,601±810 SFU, respectively. BRC vaccine-A and BRC vaccine-B independently demonstrated a 2.6-fold and 1.4-fold increase antigen specific responses compared to parental controls, respectively. Specifically, BRC vaccine-A significantly increase antigen specific response 23,944±3,971 SFU compared to the unmodified controls (9,197±3,433 SFU) (p=0.026, Mann-Whitney U test) (FIG. 127B). For BRC vaccine-A, two donors responded to nine antigens and four donors responded ten antigens. BRC vaccine-B elicited 17,032±3,861 SFU compared to parental controls (11,975±4,510 SFU) (n=6) (FIG. 127C). For BRC vaccine-B, one donor responded to five antigens, two donors responded to nine antigens, and three donors responded to ten antigens. Described above are two compositions comprising a therapeutically effective amount of three cancer cell lines, a unit dose of six cell lines, wherein said unit dose is capable of eliciting an immune response 2.2-fold greater than the unmodified composition specific to at least nine TMs expressed in BRC patient tumors. BRC vaccine-A increased IFNγ responses to at least nine TMs 2.6-fold and BRC vaccine-B increased IFNγ responses 1.4-fold to at least five TMs.

TABLE 118

| IFNγ Responses to unmodified and modified BRC vaccine components | | | | | | |
|---|---|---|---|---|---|---|
| | Unmodified (SFU ± SEM) | | | Modified (SFU ± SEM) | | |
| Donor (n = 4) | BRC Vaccine-A | BRC Vaccine-B | BRC Vaccine | BRC Vaccine-A | BRC Vaccine-B | BRC Vaccine |
| 1 | 2,590 ± 924 | 4,896 ± 2,759 | 14,248 ± 9,736 | 41,841 ± 10,934 | 29,895 ± 9,674 | 71,736 ± 19,975 |
| 2 | 2,134 ± 434 | 1,697 ± 197 | 4,061 ± 761 | 36,234 ± 4,700 | 31,114 ± 1,918 | 67,349 ± 6,540 |
| 3* | 4,867 ± 4,503 | 11,522 ± 6,462 | 19,399 ± 14,052 | 6,345 ± 3,166 | 2,802 ± 1,446 | 12,196 ± 4,892 |
| 4 | 9,535 ± 7,710 | 14,104 ± 8,363 | 21,073 ± 16,703 | 23,510 ± 10,746 | 9,724 ± 5,389 | 33,234 ± 16,056 |
| 5 | 23,976 ± 17,601 | 38,089 ± 18,754 | 57,350 ± 38,795 | 17,257 ± 7,954 | 17,712 ± 11,548 | 36,268 ± 18,735 |
| 6 | 3,397 ± 992 | 659 ± 331 | 4,968 ± 2,159 | 30,599 ± 10,330 | 20,841 ± 5,625 | 51,440 ± 15,727 |

*Donor 3 n = 3. All other Donors n = 4.

Cocktails Increase the Breadth and Magnitude of IFNγ Responses to TAAs

Figure 128A:
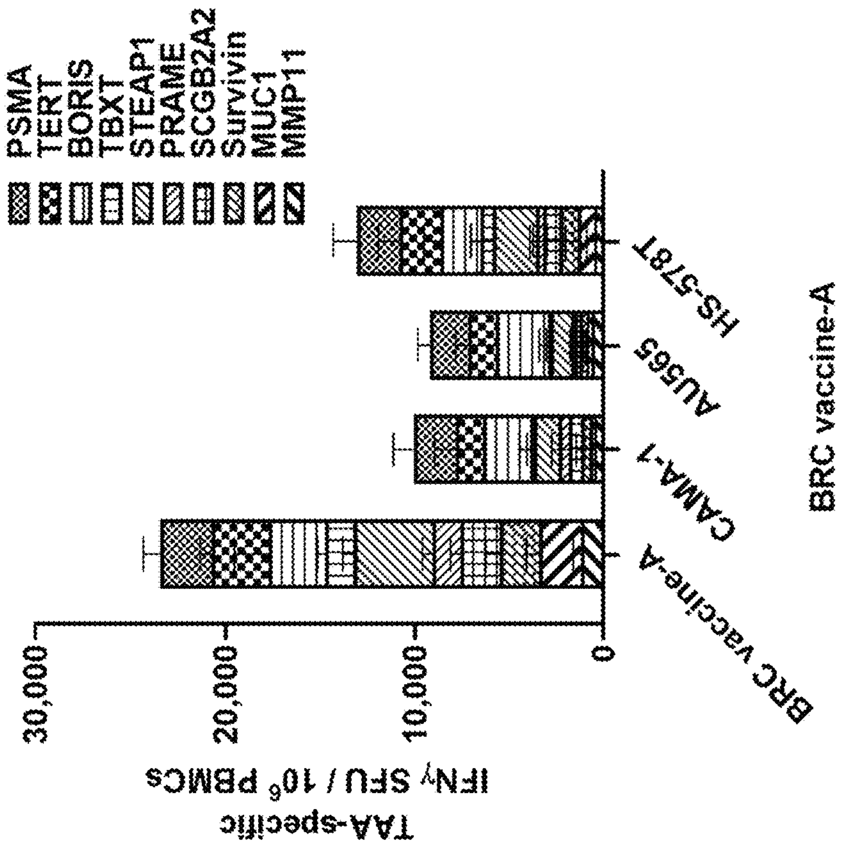
Figure 128B:
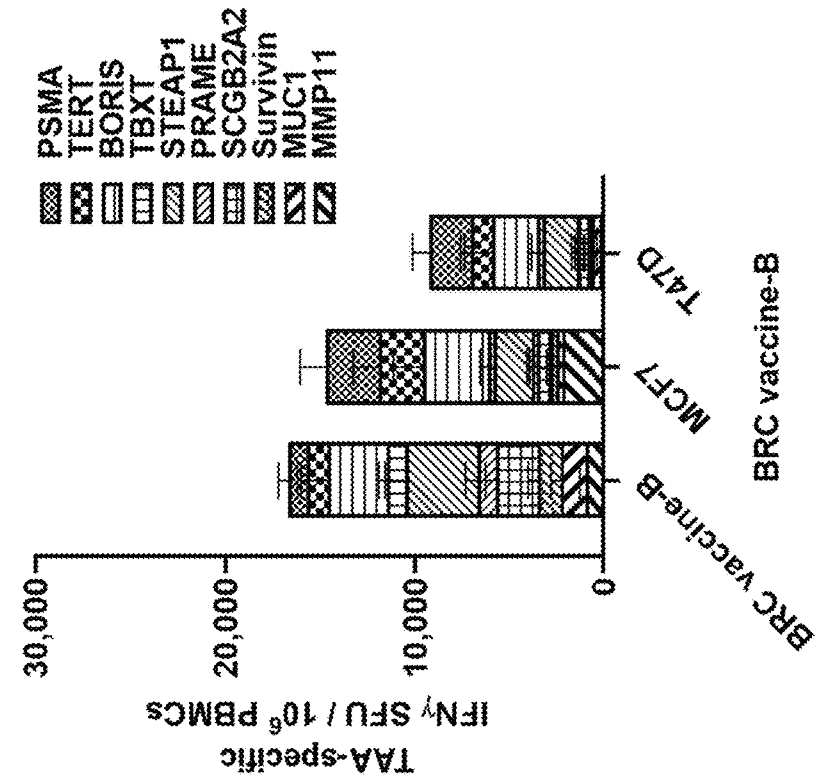
Figure 128C:
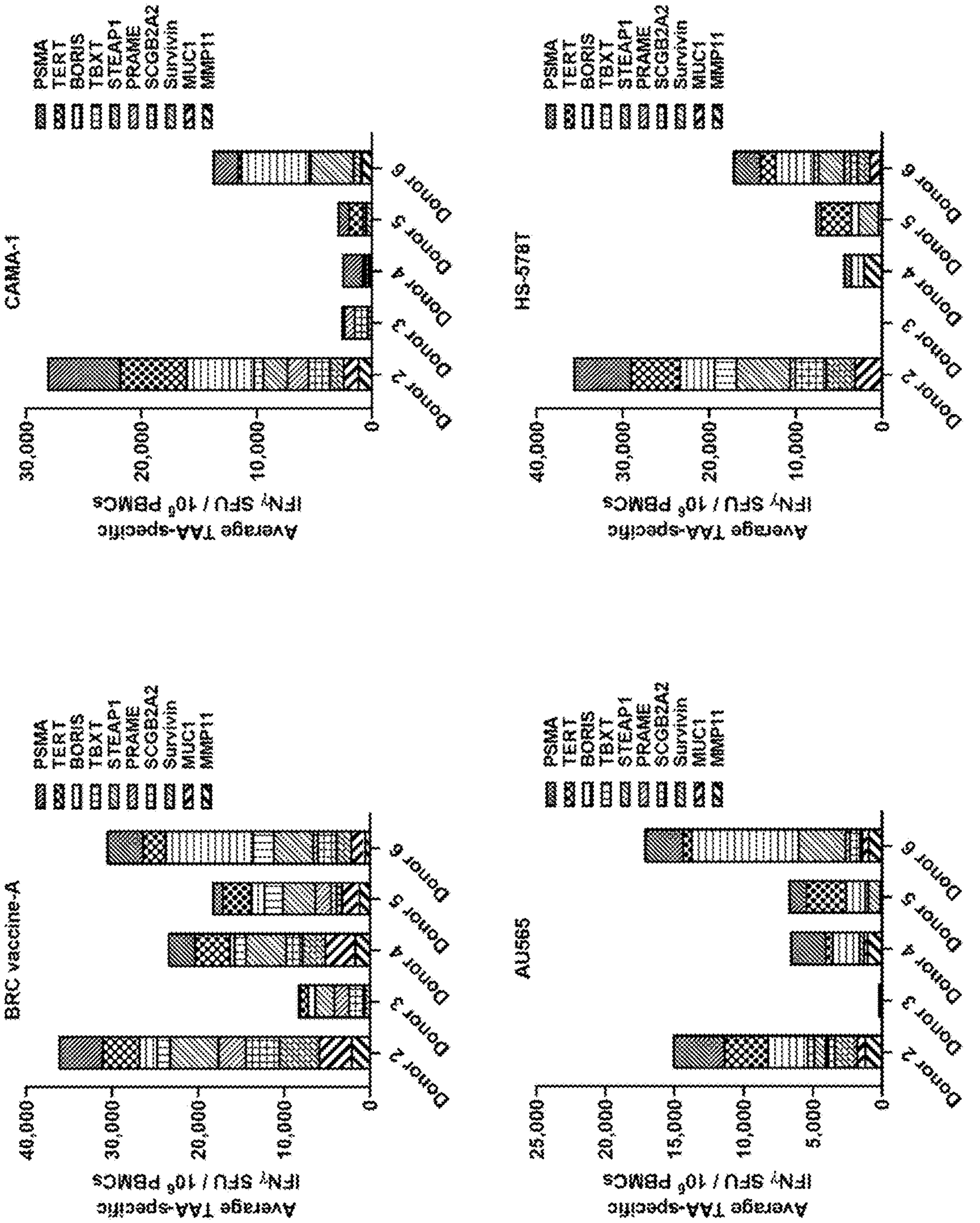
Figure 128D:
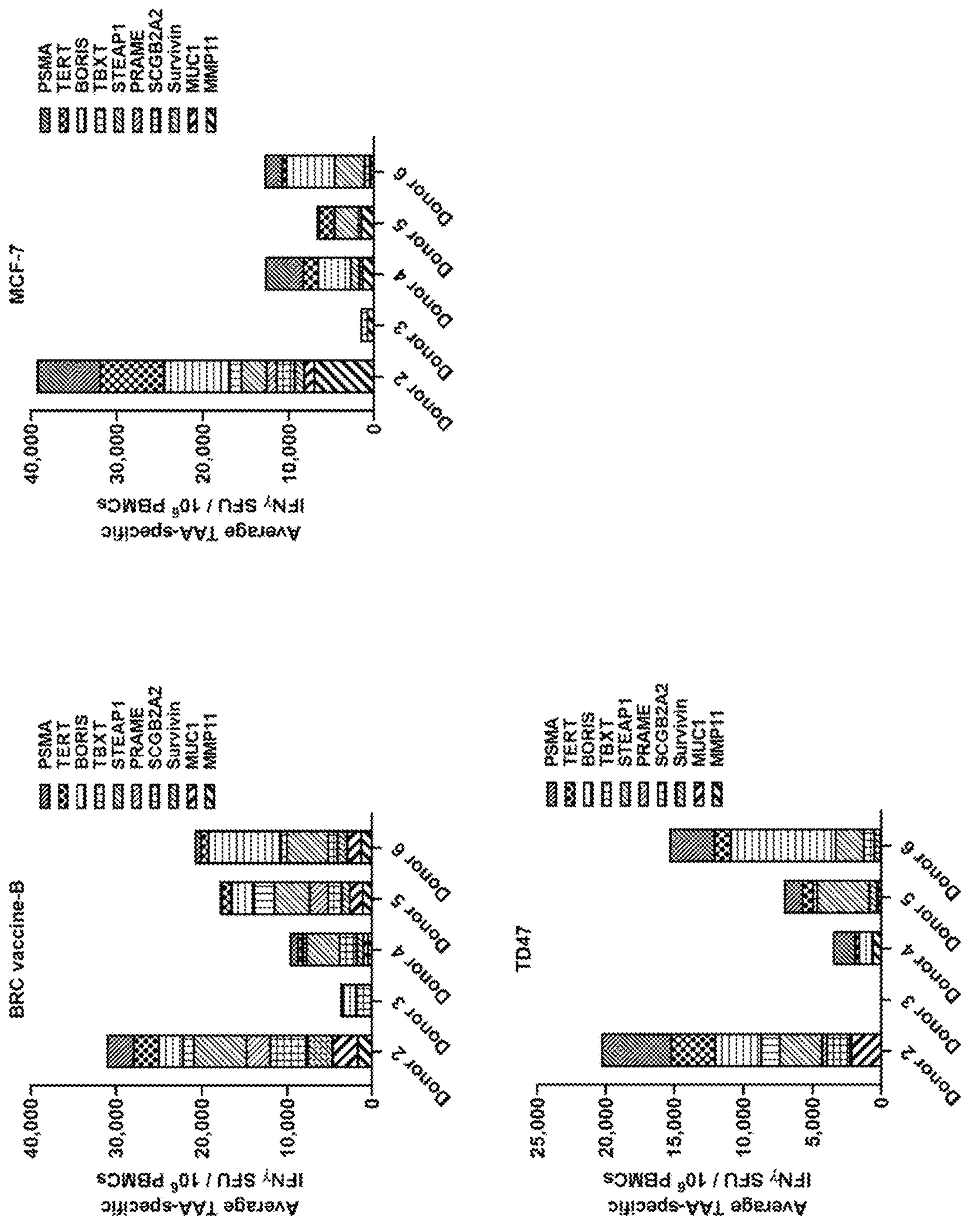

The ability of BRC vaccine-A and BRC vaccine-B to elicit a greater antigenic breadth and magnitude of IFNγ production, as described in Example 8, compared to the single component cell lines, as described in Example 9, was evaluated by IFNγ ELISpot in Donors 2-6 (Table 117). BRC vaccine-A (FIG. 128A) and BRC vaccine-B (FIG. 128B) induced more robust responses to breast cancer antigens. Importantly, BRC vaccine-A and BRC vaccine-B induced IFNγ responses to a greater number of antigens compared to single component cell lines. In this subset of five donors, for BRC vaccine-A induced IFNγ responses to nine antigens in two donors and ten antigens in three donors. CAMA-1 alone induced IFNγ responses to four antigens in one donor, six antigens in two donors, eight antigens in 1 donor and ten antigens in one donor. AU565 alone induced IFNγ responses to two antigens in one donor, six antigens in two donors, nine antigens in one donor and ten antigens in one donor. HS-578T alone induced IFNγ responses to zero antigens in one donor, three antigens in one donor, five antigens in one donor, nine antigens in one donor and ten antigens in one donor (FIG. 128C). In this subset of five donors, for BRC vaccine-B induced IFNγ responses to five antigens in one donor, nine antigens in two donors and ten antigens in two donors. MCF-7 alone induced IFNγ responses to three antigens in one donor, five antigens in one donor, seven antigens in one donor, eight antigens in 1 donor and ten antigens in one donor. T47D alone induced IFNγ responses to zero antigens in one donor, five antigens in one donor, seven antigens in two donors, and nine antigens in one donor (FIG. 128D).

Based on the disclosure and data provided herein, a whole cell vaccine for Breast Cancer comprising the six cancer cell lines, sourced from ATCC, CAMA-1 (ATCC, HTB-21), AU565 (ATCC, CRL-2351), HS-578T (ATCC, HTB-126), MCF-7 (ATCC, HTB-22), T47D (ATCC, HTB-133) and DMS 53 (ATCC, CRL-2062) is shown in Table 119. The cell lines represent five breast cancer cell lines and one small cell lung cancer (SCLC) cell line (DMS 53 ATCC CRL-2062). The cell lines have been divided into two groupings: vaccine-A and vaccine-B. Vaccine-A is designed to be administered intradermally in the upper arm and vaccine-B is designed to be administered intradermally in the thigh. Vaccine A and B together comprise a unit dose of cancer vaccine.

TABLE 119

| Cell line nomenclature and modifications | | | | | | | | |
|---|---|---|---|---|---|---|---|---|
| Cocktail | Cell Line | TGFβ1 KD | TGFβ2 KD | CD276 KO | GM-CSF | CD40L | IL-12 | TAA(s) |
| A | CAMA-1 | ND | X | X | X | X | X | X |
| A | AU565 | ND | X | X | X | X | X | X |
| A | HS-578T | X | X | X | X | X | X | ND |
| B | MCF-7 | X | X | X | X | X | X | ND |
| B | T47D | ND | ND | X | X | X | X | X |
| B | DMS 53* | ND | X | X | X | X | X | ND |

ND = Not done.
*Cell lines identified as CSC-like cells.

Where indicated in the above table, the genes for the immunosuppressive factors transforming growth factor-beta 1 (TGFβ1) and transforming growth factor-beta 2 (TGFβ2) have been knocked down using shRNA transduction with a lentiviral vector. The gene for CD276 has been knocked out by electroporation using zinc-finger nuclease (ZFN) or knocked down using shRNA transduction with a lentiviral vector. The genes for granulocyte macrophage-colony stimulating factor (GM-CSF), IL-12, CD40L, modTERT (AU565), modPSMA (CAMA-1), modTBXT (T47D), and modBORIS (T47D) have been added by lentiviral vector transduction.

Provided herein are two compositions comprising a therapeutically effective amount of three cancer cell lines, a unit dose of six cancer cell lines, modified to reduce the expression of at least one immunosuppressive factor and to express at least two immunostimulatory factors. One composition, BRC vaccine-A, was modified to increase the expression of two TAAs, modTERT and modPSMA. The second composition, BRC vaccine-B, was modified to expresses two TAAs, modTBXT and modBORIS. The unit dose of six cancer cell lines expresses at least at least 15 TAAs associated with a cancer of a subset of breast cancer subjects intended to receive said composition and induces IFNγ responses 2.2-fold greater than the unmodified composition components.

Example 37: Adaptation of GBM Vaccine Component Cell Lines to Growth in Xeno-Free Media

Overview of Adaptation Process

Five component cell lines of the GBM vaccine composition (DBTRG-05MG, LN-229, GB1, KNS-60 and SF-126) were directly cultured in (A1D, A2D) or sequentially adapted (A1W, A2W) to growth in media that is xeno-free, serum-free and devoid of non-human elements. For each cell line, two media formulations were tested. Conventional culture media consisted of RPMI (DBTRG-05MG, LN-229) or DMEM (GB1, KNS-60, SF-126), supplemented with 10% FBS, L-Glutamine, sodium pyruvate, HEPES, MEM-NEAA (non-essential amino acids used only in DMEM), and antibiotics (Table 120). Xeno-free media contained 15% xeno-free replacement (XFR) to replace FBS, and different antibiotics concentrations than in conventional media (A1-XFR media: RPMI- or DMEM-based media formulated with antibiotics shown in Table 121; A2-XFR media: RPMI- or DMEM-based media formulated with antibiotics shown in Table 122). Notably, antibiotics that are added to the media formulation for selection of transgenes bind to protein present in the media. Due to lower protein concentrations in xeno-free media compared to FBS-containing media, antibiotics concentrations were lowered to test two different concentrations, respectively, in A1-XFR and A2-XFR media. Each of the five GBM vaccine component cell lines were screened for growth in 2 media formulations A1-XFR and A2-XFR, and two adaptation conditions—comparing direct plating (A1 D, A2D) to sequential weaning (A1 W, A2W).

To confirm adaptation to xeno-free media formulations, cell morphology and proliferation were monitored. Culture conditions that showed non-adherent floating cells that were non-viable upon Trypan Blue staining were terminated. Cell lines with similar morphology to their control in FBS-containing media that were stably growing in xeno-free media and were under antibiotic selection for at least 3 weeks were harvested and analyzed for expression of modified genes.

TABLE 120

Base media (containing FBS) antibiotic concentrations for selection of inserted transgenes

| Cell Line | Blasticidin | Hygromycin | Puromycin |
|---|---|---|---|
| DBTRG-05MG | 4 | 300 | n/a |
| LN-229 | 4 | 300 | 2 |
| GB1 | 4 | 500 | n/a |
| KNS-60 | 4 | 500 | 2 |
| SF-126 | 4 | 500 | 2 |

All selection antibiotic concentrations are in μg/mL.
n/a, selection antibiotic not used for cell line.

TABLE 121

A1-XFR media antibiotic concentrations for selection of inserted transgenes

| Cell Line | Blasticidin | Hygromycin | Puromycin |
|---|---|---|---|
| DBTRG-05MG | 1.25 | 100 | n/a |
| LN-229 | 1.25 | 100 | 0.4 |
| GB1 | 1.25 | 100 | n/a |
| KNS-60 | 1.25 | 100 | 0.4 |
| SF-126 | 1.25 | 100 | 0.4 |

All selection antibiotic concentrations are in μg/mL.
n/a, selection antibiotic not used for cell line.

TABLE 122

A2-XFR media antibiotic concentrations for selection of inserted transgenes

| Cell Line | Blasticidin | Hygromycin | Puromycin |
|---|---|---|---|
| DBTRG-05MG | 2 | 200 | n/a |
| LN-229 | 2 | 200 | 1 |
| GB1 | 2 | 200 | n/a |
| KNS-60 | 2 | 200 | 1 |
| SF-126 | 2 | 200 | 1 |

All selection antibiotic concentrations are in μg/mL.
n/a, selection antibiotic not used for cell line.

Analysis of Transgene Expression in Cell Lines Grown in Xeno-Free Media

Each of the five modified GBM vaccine component cell lines were screened for growth in 2 media formulations A1-XFR and A2-XFR, and two adaptation conditions—comparing direct plating (A1 D) to sequential weaning (A1 W, A2W). The conditions that showed stable cell growth, minimal cell death and morphology comparable to cells grown in FBS were analyzed for expression of transgenes.

To obtain reproducible measurements of secreted cytokines, secretion assays were performed. Cells were seeded in duplicates of 0.7 $5\times10^6$ and $0.5\times10^6$ cells per well of a vitronectin-coated 6-well plate in xeno-free media. After 24 hours, the media was replaced with fresh xeno-free media. After another 48 hours, supernatants were harvested for analysis by ELISA. At the same time, cells were harvested for evaluation of CD40L expression by flow cytometry. Briefly, after harvest, cells were stained with phycoerythrin-conjugated anti-human CD40L (clone TRAP1). Labelled cells were analyzed by flow cytometry using a LSR Fortessa Flow cytometer. Secreted cytokines were measured using an enzyme linked immunosorbent assay (ELISA). Briefly, for each sample, two-four dilutions of the supernatant were run. TGFβ1 and TGFβ2 levels were determined using an enzyme-linked immunosorbent assay (ELISA) (R&D Systems). TGFβ1 and TGFβ2 secretion is reported in units of pg/$10^6$ cells/24 hours. GM-CSF and IL-12 levels were determined using an enzyme-linked immunosorbent assay (ELISA) with kits from R&D Systems and Biolegend, respectively. GM-CSF and IL-12 secretion levels are reported in units of ng/$10^6$ cells/24 hours.

Results of Transgene Expression in the Individual Cell Lines after Adaptation to Xeno-Free Media DBTRG-05MG cells used for the adaptation process were modified to reduce TGFβ1 expression and to express CD40L and IL-12. Cells proliferated stably when weaned to grow in 100% A1-XFR media over the course of 4-6 weeks, but doubling times increased to 586.8 hours compared to 38.3 hours of unmodified parental cells grown in FBS-containing media (Table 123). Direct plating in A1-XFR media resulted in proliferation arrest and cell death. Analysis of modified DBTRG-05MG cells adapted to grow in A1-XFR media showed that CD40L is expressed and secretion of IL-12 is detected and quantified to be 196.5 ng/$10^6$/24 hrs, while secretion of TGFβ1 is reduced by 88% from compared to unmodified parental DBTRG-05MG cells grown in FBS Unmodified DBTR-05MG cells do not express CD40L or produce IL-12.

LN-229 cells used for the adaptation process were modified to reduce TGFβ1 expression and to overexpress CD40L, GM-CSF and IL-12. Cells proliferated stably when directly plated in 100% A1-XFR media with a doubling time of 59.7 hours compared to 34.5 hours of unmodified parental cells grown in FBS-containing media (Table 123). When weaned to grow in 100% A2-XFR media over the course of 4-6 weeks, doubling time was 71 hours (Table 4). Analysis of modified LN-229 cells adapted to grow in A1-XFR and A2-XFR media showed that CD40L is expressed and secretion of IL-12 is detected and quantified to be 527 ng/$10^6$/24 hrs (A1 D) and 603 ng/$10^6$/24 hrs (A2W), GM-CSF detected and quantified to be 2029.8 ng/$10^6$/24 hrs (A1 D) and 2505.8 ng/$10^6$/24 hrs (A2W) and TGFβ1 levels were decreased by 79.2% (A1 D) or 78.9% (A2W) compared to unmodified parental cells grown in FBS. Unmodified LN-229 cells do not express CD40L or produce IL-12 or GM-CSF.

GB1 cells used for the adaptation process were modified to have decreased TGFβ1 expression and to overexpress CD40L and IL-12. Cells proliferated stably when plated directly in 100% A1-XFR media with a doubling time of 144.1 hours compared to 37.9 hours of unmodified parental cells grown in FBS-containing media (Table 123). When weaned to grow in 100% A1-XFR media over the course of 4-6 weeks, the doubling time was 597.2 hours, and 266.8 hours in A2-XFR media (Table 4). Analysis of modified GB1 cells adapted to grow in A1-XFR and A2-XFR media showed that CD40L is expressed and secretion of IL-12 is detected and quantified to be 117.5 ng/$10^6$/24 hrs (A1 D), 76.6 ng/$10^6$/24 hrs (A1W) and 72.0 ng/$10^6$/24 hrs (A2W), and TGFβ1 levels were decreased by 64.3% (A1 D), 74.6% (A1W) and 90.8% (A2W) compared to unmodified parental cells grown in FBS. Unmodified GB1 cells do not express CD40L or produce IL-12.

KNS-60 cells used for the adaptation process were modified to express decreased levels of TGFβ1 and TGFβ2, and to overexpress CD40L, GM-CSF and IL-12. Cells proliferated stably when weaned to grow in 100% A1-XFR media with a doubling time of 674.2 hours compared to 40.0 hours of unmodified parental cells grown in FBS-containing media (Table 123). When weaned to grow in 100% A2-XFR media over the course of 4-6 weeks, the doubling time was 303.8 hours (Table 4). Analysis of modified KNS-60 cells adapted to grow in A1-XFR and A2-XFR media showed that CD40L is expressed and secretion of IL-12 is detected and quantified to be 700.0 ng/$10^6$/24 hrs (A1W) and 482.2 ng/$10^6$/24 hrs (A2W), secretion of GM-CSF is detected and quantified to be 182.5 ng/$10^6$/24 hrs (A1W) and 156.9 ng/$10^6$/24 hrs (A2W), and TGFβ1 levels were decreased by 83.2% (A1W) and 87.7% (A2W) and TGFβ2 levels were decreased by 92.6% (A1W) and 94.7% (A2W) compared to unmodified parental cells grown in FBS. Unmodified KNS-60 cells do not express CD40L or produce IL-12 or GM-CSF.

SF-126 cells used for the adaptation process were modified to express decreased levels of TGFβ1 and TGFβ2, and to overexpress CD40L, GM-CSF and IL-12. Cells proliferated stably when weaned to grow in 100% A1-XFR media with a doubling time of 172.1 hours compared to 28.3 hours of unmodified parental cells grown in FBS-containing media (Table 123). When weaned to grow in 100% A2-XFR media over the course of 4-6 weeks, the doubling time was 456.6 hours (Table 4). Analysis of modified SF-126 cells adapted to grow in A1-XFR and A2-XFR media showed that CD40L is expressed and secretion of IL-12 is detected and quantified to be 671.2 ng/$10^6$/24 hrs (A1W) and 684.9 ng/$10^6$/24 hrs (A2W), secretion of GM-CSF is detected and quantified to be 51.2 ng/$10^6$/24 hrs (A1W) and 39.3 ng/$10^6$/24 hrs (A2W), and TGFβ1 levels were decreased by 86.9% (A1W) and 91.2% (A2W) and TGFβ2 levels were decreased by 80.4% (A1W) and 98.8% (A2W) compared to unmodified parental cells grown in FBS. Unmodified SF-126 cells do not express CD40L or produce IL-12 or GM-CSF.

In conclusion, all five modified GBM vaccine component cell lines stably adapted to xeno-free media formulations. The cells proliferated at a steady rate, inserted transgene expression was maintained and the reduction of TGFβ1 and TGFβ2 was also retained.

TABLE 123

Doubling time of vaccine component cell lines in FBS-containing media and xeno-free media

| Cell line | DT [hours] of parental cell line | DT [hours] A1 media Direct (A1D) | DT [hours] A1 media, Wean (A1W) | DT [hours] A2 media, Wean (A2W) |
|---|---|---|---|---|
| DBTRG-05MG | 38.3 | n/a | 586.8 | n/a |
| LN-229 | 34.5 | 59.7 | n/a | 71 |
| GB1 | 37.9 | 144.1 | 597.2 | 266.8 |
| KNS-60 | 40 | n/a | 674.2 | 303.8 |
| SF-126 | 28.3 | n/a | 172.1 | 456.6 |

DT: doubling time;

DT represents average values according to Conversion Reports

Example 38: Adaptation of NSCLC Vaccine Component Cell Lines to Growth in Xeno-Free Media Overview of Adaptation Process The six component cell lines (NCI-H23, A549, NCI-H460, DMS 53, LK-2 and NCI-H520) of the NSCLC vaccine composition were sequentially adapted to growth in media that is xeno-free, serum-free and containing no non-human elements. For each of the six cell lines, four xeno-free media formulations were tested. The media formulations are KSC pH 7.2, KSC pH 6.8, KSR pH 7.2 and KSR pH 6.8. An additional control condition of cells in regular culture media composed of RPMI supplemented with 10% FBS, L-Glutamine, sodium pyruvate and HEPES was also maintained. Each xeno-free media formulation was composed of a different base medium (KSC or KSR) with 10% human serum albumin (HSA) as a xeno-free serum replacement and antibiotics were added to the media to maintain the expression of the inserted transgenes as shown in Table 124. As the total protein content of the xeno-free media was comparable to that of media containing FBS, the antibiotic levels used for selection was the same as in FBS-based media. Additionally, each media formulation was tested at two levels of oxygen—normal 21% oxygen and low 3% oxygen. To confirm adaptation to the xeno-free media formulations, the cells were observed for their ability to proliferate in the test media. Conditions that showed cell death based on visual observation of non-adherent floaters that were non-viable upon staining with a viability dye were terminated. The cells that had a morphology similar to the control FBS wells, were stably growing in XF media and were under antibiotic selection for at least 3 weeks were harvested and the expression of inserted transgenes analyzed.

TABLE 124

NSCLC antibiotic concentrations for selection of inserted transgenes

| Cell Line | Pure | Blast* | Hygro* | Neo* | Zeo* |
|---|---|---|---|---|---|
| NCI-H23 | 1 | 2 | 300 | 600 | 50 |
| A549 | 1 | 2 | 800 | 600 | 1200 |
| NCI-H460 | 1 | 2 | 300 | 600 | 1200 |
| DMS 53 | n/a | 4 | 200 | 600 | n/a |
| LK-2 | 1 | 2 | 200 | 200 | n/a |
| NCI-H520 | 1 | 2 | 300 | 600 | n/a |

*All selection antibiotic concentrations are in μg/mL.
n/a, selection antibiotic not used for cell line.
Puro, Puromycin.
Blast, Blasticidin.
Hygro, Hygromycin.
Neo, Neomycin (G418).
Zeo, Zeocin.

Analysis of Transgene Expression in Cell Lines Grown in Xeno-Free Media

Each of the six vaccine component cell lines were screened for growth in 4 media formulations and 2 oxygen levels. The conditions that showed stable cell growth, minimal cell death and morphology comparable to the cells grown in FBS were analyzed for expression of transgenes. Secreted cytokines were measured using an enzyme linked immunosorbent assay (ELISA). Briefly, for each sample, two-four dilutions of the supernatant were run, and the data shown is the average of all conditions tested, normalized for dilution factor and cell count. TGFβ1 and TGFβ2 levels were determined using an enzyme-linked immunosorbent assay (ELISA) (R&D Systems). TGFβ1 and TGFβ2 secretion is reported in units of pg/ml/$10^6$ cells. GM-CSF and IL-12 levels were determined using an enzyme-linked immunosorbent assay (ELISA) with kits from R&D Systems and Biolegend respectively. GM-CSF and IL-12 secretion levels are reported in units of ng/ml/$10^6$ cells. The expression of CD40L was assessed by flow cytometry. Briefly, after being harvested the cells were stained with phycoerythrin-conjugated anti-human CD40L (clone TRAP1). The labelled cells were analyzed by flow cytometry using a LSR Fortessa Flow cytometer.

Results of Transgene Expression in the Individual Cell Lines after Adaptation to Xeno-Free Media NCI-H23 cells showed stable growth in treatment medias 4 (KSR pH 7.2) and 5 (KSR pH 6.8) under normal 21% oxygen condition. The cells failed to proliferate in the other treatment conditions. The expression of the surface protein CD40L was found to be stable and expressed at levels comparable to the cells grown in FBS. Secretion of IL-12 and GM-CSF were found to be increased in the xeno-free media formulations when compared to FBS 1.7-fold (IL-12 media 4 and 5) and 2.3-fold (GM-CSF media 4 and 5) respectively. The reduction of TGFβ1 and TGFβ2 was found to be greater in the XF media with the levels of TGFβ1 10-fold less in media 4 and 7-fold less in media 5, while TGFβ2 was not detectable in the XF media, when compared to cells in FBS containing media.

A549 cells showed stable growth in treatment medias 4 (KSR pH 7.2) and 5 (KSR pH 6.8) under normal 21% oxygen, and in treatment media 5 under low 3% oxygen conditions. The cells failed to proliferate in the other treatment conditions. The expression of the surface protein CD40L was found to be stable and expressed at levels comparable to the cells grown in FBS.

Secretion of IL-12 was found to be comparable to FBS in xeno-free media 4 grown in normal 21% oxygen, increased by 1.6-fold in media 5 in normal 21% oxygen condition and decreased by 0.6-fold in media 5 under low 3% oxygen condition. Secretion of GM-CSF was found to be comparable to FBS in xeno-free media 4 grown in normal 21% condition, increased by 1.4-fold in media 5 in normal 21% oxygen condition and decreased by 0.6-fold in media 5 under low 3% oxygen condition. The reduction of TGFβ1 and TGFβ2 was found to be greater in the XF media with the levels of TGFβ1 3.4-fold less in media 4 under normal 21% oxygen and 3.1-fold less in media 5 under normal 21% oxygen and 2-fold less in media 5 under low 3% oxygen, while TGFβ2 was reduced by 2.2-fold in treatment media 4 under normal 21% oxygen and was not detectable in the XF media 5 in low 3% or normal 21% oxygen condition, when compared to cells in FBS containing media.

NCI-H460 cells showed stable growth in treatment medias 4 (KSR pH 7.2) and 5 (KSR pH 6.8) under normal 21% oxygen condition. The cells failed to proliferate in the other treatment conditions. The expression of the surface protein CD40L was found to be stable and expressed at levels comparable to the cells grown in FBS. Secretion of IL-12 was found to be increased in the xeno-free media formulations when compared to FBS, 3.2-fold in media 4 and 1.7-fold in media 5. GM-CSF was also increased in the xeno-free medias, 3.5-fold in media 4 and 1.8-fold in media 5. The reduction of TGFβ1 and TGFβ2 was found to be greater in the XF media with the levels of TGFβ1 not detectable in the XF medias 4 and 5 and TGFβ2 reduced 1.6-fold in media 4 and 3.4-fold in media 5, when compared to cells in FBS containing media.

DMS 53 cells showed stable growth in treatment medias 4 (KSR pH 7.2) and 5 (KSR pH 6.8) under normal 21% oxygen condition. The cells failed to proliferate in the other treatment conditions. The expression of the surface protein CD40L was found to be stable and expressed at levels comparable to the cells grown in FBS. GM-CSF secretion was increased in the xeno-free medias, 3.5-fold in media 4 and 1.8-fold in media 5. TGFβ2 levels was found to be greater in the XF media 4 by 1.2-fold and decreased by 1.8-fold in media 5, when compared to cells in FBS containing media. The cell line was not modified to overexpress IL-12 or have a knock down in TGFβ1 levels.

LK-2 cells showed stable growth in treatment medias 4 (KSR pH 7.2) and 5 (KSR pH 6.8) under normal 21% oxygen condition. The cells failed to proliferate in the other treatment conditions. The expression of the surface protein CD40L was found to be stable and expressed at levels comparable to the cells grown in FBS. GM-CSF secretion was increased in the xeno-free medias, 2.8-fold in media 4 and 3.1-fold in media 5. TGFβ1 levels were not detectable in xeno-free media, and TGFβ2 levels were decreased by 6-fold in media 4 and 2.3-fold in media 5, when compared to cells in FBS containing media. The cell line was not modified to overexpress IL-12.

NCI-H520 cells showed stable growth in treatment medias 4 (KSR pH 7.2) and 5 (KSR pH 6.8) under normal 21% oxygen and low 3% oxygen conditions. The cells failed to proliferate in the other treatment conditions. The expression of the surface protein CD40L was found to be stable and expressed at levels comparable to the cells grown in FBS. Secretion of GM-CSF was increased in xeno-free media 4 and 5 grown in normal 21% conditions by 1.5 and 1.3-fold respectively. GM-CSF secretion was also increased in cells grown in low 3% oxygen conditions—2.1-fold in media 4 and 2.2-fold in media 5. Secretion of TGFβ1 was increased 10-fold in medias 4 and 5 under normal 21% oxygen, and not detectable when the cells were grown in low 3% oxygen. Secretion of TGFβ2 was decreased 3-fold and 1.2-fold in medias 4 and 5 under normal 21% oxygen, and not detectable when the cells were grown in low 3% oxygen. The cell line was not modified to overexpress IL-12.

In conclusion, all six modified NSCLC vaccine component cell lines were stably adapted to growth in xeno-free media conditions. The cells retained the reduction of TGFβ1 and TGFβ2 secretion and the secretion of GM-CSF and IL-12 was found to be comparable to or increased in the xeno-free formulations when compared to the modified cells grown in FBS. Expression of the surface protein CD40L was detected at levels similar to cells grown in FBS across all conditions tested.

Example 39: Allogeneic Tumor Cell Vaccine Platform

This Example provides the compositions and methods for using various allogeneic tumor cell vaccines for the treatment and/or prevention of cancer and/or to stimulate an immune response. Given the teaching provided herein, in some embodiments the following cell line combinations and modifications are embraced by the present disclosure. Other embodiments (e.g., alternative cell lines and/or modifications as provided herein) are also contemplated.

TABLE 125

Small cell lung cancer vaccine

| Cell Line | TGFβ1 KD | TGFβ2 KD | CD276 KO | CD40L | GM-CSF | IL-12 | TAAs |
|---|---|---|---|---|---|---|---|
| 1. DMS 114 | X | ND | X | X | * | * | ** |
| 2. NCl-H196 | X | X | X | X | * | * | ** |
| 3. NCl-H1092 | ND | X | X | X | * | * | ** |
| 4. SBC-5 | X | ND | X | X | * | * | ** |
| 5. NCl-H510A | X | X | X | X | * | * | ** |
| 6. NCl-H889 | X | X | X | X | * | * | ** |
| 7. NCl-H1341 | X | ND | X | X | * | * | ** |
| 8. NClH-1876 | X | X | X | X | * | * | ** |
| 9. NCl-H2029 | ND | X | X | X | * | * | ** |
| 10. NCl-H841 | X | ND | X | X | * | * | ** |
| 11. NCl-H1694 | X | ND | X | X | * | * | ** |
| DMS 53 | ND | X | X | X | X | X | ND |

ND = not done

*= One or more cell lines will be transduced in some embodiments to produce at least 15,000 ng per cocktail of GM-CSF and at least 4,000 ng of IL-12 per cocktail

**= Small cell lung cancer vaccine will be modified in some embodiments to express one or more of the following TAAs: MAGEA1 and DLL3.

TABLE 126

Liver cancer vaccine

| Cell Line | TGFβ1 KD | TGFβ2 KD | CD276 KO | CD40L | GM-CSF | IL-12 | TAAs |
|---|---|---|---|---|---|---|---|
| 1. Hep-G2 | X | ND | X | X | * | * | ** |
| 2. JHH-2 | X | X | X | X | * | * | ** |
| 3. JHH-4 | X | X | X | X | * | * | ** |
| 4. JHH-6 | X | X | X | X | * | * | ** |
| 5. Li7 | X | X | X | X | * | * | ** |
| 6. HLF | X | X | X | X | * | * | ** |
| 7. HuH-6 | X | ND | X | X | * | * | ** |
| 8. JHH-5 | X | X | X | X | * | * | ** |
| 9. HuH-7 | X | X | X | X | * | * | ** |
| DMS 53 | ND | X | X | X | X | X | ND |

ND = not done

*= One or more cell lines will be transduced in some embodiments to produce at least 15,000 ng per cocktail of GM-CSF and at least 4,000 ng of IL-12 per cocktail

**= Liver cancer vaccine will be modified in some embodiments to express one or more of the following TAAs: CEA (CEACAM5), MAGEA1, WT1, and PSMA (FOLH1).

TABLE 127

Kidney cancer vaccine

| Cell Line | TGFβ1 KD | TGFβ2 KD | CD276 KO | CD40L | GM-CSF | IL-12 | TAAs |
|---|---|---|---|---|---|---|---|
| 1. A-498 | X | X | X | X | * | * | ** |
| 2. A-704 | X | X | X | X | * | * | ** |
| 3. 769-P | X | ND | X | X | * | * | ** |
| 4. 786-O | X | X | X | X | * | * | ** |

TABLE 127-continued

| Kidney cancer vaccine | | | | | | | |
|---|---|---|---|---|---|---|---|
| Cell Line | TGFβ1 KD | TGFβ2 KD | CD276 KO | CD40L | GM-CSF | IL-12 | TAAs |
| 5. ACHN | X | X | X | X | * | * | ** |
| 6. KMRC-1 | X | X | X | X | * | * | ** |
| 7. KMRC-2 | X | X | X | X | * | * | ** |
| 8. VMRC-RCZ | X | X | X | X | * | * | ** |
| 9. VMRC-RCW | X | X | X | X | * | * | ** |
| DMS 53 | ND | X | X | X | X | X | ND |

ND = not done

*= One or more cell lines will be transduced in some embodiments to produce at least 15,000 ng per cocktail of GM-CSF and at least 4,000 ng of IL-12 per cocktail

**= Kidney cancer vaccine will be modified in some embodiments to express one or more of the following TAAs: MAGEA1, DLL3, CEA (CEACAM5), and PSMA (FOLH1)

TABLE 128

| Pancreatic cancer vaccine | | | | | | | |
|---|---|---|---|---|---|---|---|
| Cell Line | TGFβ1 KD | TGFβ2 KD | CD276 KO | CD40L | GM-CSF | IL-12 | TAAs |
| 1. PANC-1 | X | X | X | X | * | * | ** |
| 4. KP-3 | X | X | X | X | * | * | ** |
| 5. KP-4 | X | ND | X | X | * | * | ** |
| 7. SUIT-2 | X | X | X | X | * | * | ** |
| 8. AsPC-1 | X | X | X | X | * | * | ** |
| 9. PSN1 | X | X | X | X | * | * | ** |
| DMS 53 | ND | X | X | X | X | X | ND |

ND = not done

*= One or more cell lines will be transduced in some embodiments to produce at least 15,000 ng per cocktail of GM-CSF and at least 4,000 ng of IL-12 per cocktail

**= Pancreatic cancer vaccine will be modified in some embodiments to express one or more of the following TAAs: PSMA (FOLH1), BORIS (CTCFL), DLL3

TABLE 129

| Esophageal cancer vaccine | | | | | | | |
|---|---|---|---|---|---|---|---|
| Cell Line | TGFβ1 KD | TGFβ2 KD | CD276 KO | CD40L | GM-CSF | IL-12 | TAAs |
| 1. TE-10 | X | X | X | X | * | * | ** |
| 2. TE-6 | X | X | X | X | * | * | ** |
| 3. TE-4 | X | X | X | X | * | * | ** |
| 4. EC-GI-10 | X | X | X | X | * | * | ** |
| 5. OE33 | X | X | X | X | * | * | ** |
| 6. TE-9 | X | X | X | X | * | * | ** |
| 7. TT | X | ND | X | X | * | * | ** |
| 8. TE-11 | X | X | X | X | * | * | ** |
| 9. OE19 | X | ND | X | X | * | * | ** |
| 10. OE21 | X | X | X | X | * | * | ** |
| DMS 53 | ND | X | X | X | X | X | ND |

ND = not done

*= One or more cell lines will be transduced in some embodiments to produce at least 15,000 ng per cocktail of GM-CSF and at least 4,000 ng of IL-12 per cocktail

**= Esophageal cancer vaccine will be modified in some embodiments to express one or more of the following TAAs: WT1 and PSMA (FOLH1).

TABLE 130

| Endometrial cancer vaccine | | | | | | | |
|---|---|---|---|---|---|---|---|
| Cell Line | TGFβ1 KD | TGFβ2 KD | CD276 KO | CD40L | GM-CSF | IL-12 | TAAs |
| 1. SNG-M | X | ND | X | X | * | * | ** |
| 2. HEC-1-B | X | ND | X | X | * | * | ** |
| 3. JHUEM-3 | X | X | X | X | * | * | ** |
| 4. RL95-2 | ND | ND | X | X | * | * | ** |
| 5. MFE-280 | X | ND | X | X | * | * | ** |
| 6. MFE-296 | X | X | X | X | * | * | ** |
| 7. TEN | X | ND | X | X | * | * | ** |

TABLE 130-continued

| Endometrial cancer vaccine | | | | | | | |
|---|---|---|---|---|---|---|---|
| Cell Line | TGFβ1 KD | TGFβ2 KD | CD276 KO | CD40L | GM-CSF | IL-12 | TAAs |
| 8. JHUEM-2 | X | ND | X | X | * | * | ** |
| 9. AN3-CA | ND | X | X | X | * | * | ** |
| 10. Ishikawa | X | X | X | X | * | * | ** |
| DMS 53 | ND | X | X | X | X | X | ND |

ND = not done
*= One or more cell lines will be transduced in some embodiments to produce at least 15,000 ng per cocktail of GM-CSF and at least 4,000 ng of IL-12 per cocktail
**= Endometrial cancer vaccine will be modified in some embodiments to express one or more of the following TAAs: BORIS (CTCFL), WT1, PSMA (FOLH1)

TABLE 131

| Melanoma cancer vaccine | | | | | | | |
|---|---|---|---|---|---|---|---|
| Cell Line | TGFβ1 KD | TGFβ2 KD | CD276 KO | CD40L | GM-CSF | IL-12 | TAAs |
| 1. RPMI-7951 | X | X | X | X | * | * | ** |
| 2. MeWo | X | ND | X | X | * | * | ** |
| 3. Hs 688(A).T | X | ND | X | X | * | * | ** |
| 4. COLO 829 | X | ND | X | X | * | * | ** |
| 5. C32 | X | X | X | X | * | * | ** |
| 6. A-375 | X | ND | X | X | * | * | ** |
| 7. Hs 294T | X | X | X | X | * | * | ** |
| 8. Hs 695T | X | ND | X | X | * | * | ** |
| 9. Hs 852T | X | ND | X | X | * | * | ** |
| 10. A2058 | X | ND | X | X | * | * | ** |
| DMS 53 | ND | X | X | X | X | X | ND |

ND = not done
*= One or more cell lines will be transduced in some embodiments to produce at least 15,000 ng per cocktail of GM-CSF and at least 4,000 ng of IL-12 per cocktail
**= Melanoma cancer vaccine will be modified in some embodiments to express one or more of the following TAAs: MART-1 (MLANA), TYRP1, and PSMA (FOLH1)

TABLE 132

| Mesothelioma cancer vaccine | | | | | | | |
|---|---|---|---|---|---|---|---|
| Cell Line | TGFβ1 KD | TGFβ2 KD | CD276 KO | CD40L | GM-CSF | IL-12 | TAAs |
| 1. NCl-H28 | X | ND | X | X | * | * | ** |
| 2. MSTO-211H | X | ND | X | X | * | * | ** |
| 3. IST-Mes1 | X | X | X | X | * | * | ** |
| 4. ACC-MESO-1 | X | X | X | X | * | * | ** |
| 5. NCl-H2052 | X | X | X | X | * | * | ** |
| 6. NCl-H2452 | X | ND | X | X | * | * | ** |
| 7. MPP 89 | X | X | X | X | * | * | ** |
| 8. IST-Mes2 | X | ND | X | X | * | * | ** |
| DMS 53 | ND | X | X | X | X | X | ND |

ND = not done
*= One or more cell lines will be transduced in some embodiments to produce at least 15,000 ng per cocktail of GM-CSF and at least 4,000 ng of IL-12 per cocktail
**= Mesothelioma cancer vaccine will be modified in some embodiments to express one or more of the following TAAs: WT1, BORIS (CTCFL), and MAGEA1.

Example 40: Improving Breadth and Magnitude of Vaccine-Induced Cellular Immune Responses by Introducing Non-Synonymous Mutations (NSM) into Prioritized Full-Length Tumor Associated Antigens (TAAs Cancer immunotherapy through induction of anti-tumor cellular immunity has become a promising approach targeting cancer. Many therapeutic cancer vaccine platforms are targeting tumor associated antigens (TAAs) that are over-expressed in tumor cells, however, a cancer vaccine using these antigens must be potent enough to break tolerance. The cancer vaccines described in various embodiments herein are designed with the capacity to elicit broad and robust cellular responses against tumors. Neoepitopes are non-self epitopes generated from somatic mutations arising during tumor growth. Tumor types with higher mutational burden are correlated with durable clinical benefit in response to checkpoint inhibitor therapies. Targeting neoepitopes has many advantages because these neoepitopes are truly tumor specific and not subject to central tolerance in the thymus. A cancer vaccine encoding full length TAAs with neoepitopes arising from nonsynonymous mutations (NSMs) has potential to elicit a more potent immune response with improved breadth and magnitude.

Antigen Design Process

TAA Selection and Prioritization

TAAs are self-antigens that are either preferentially or abnormally expressed in tumors, but may be expressed at some level in normal cells as well. As described herein, selecting and prioritizing TAAs as vaccine targets is a critical step for cancer vaccine development. Multiple criteria were utilized for TAA evaluation and selection. First, TAAs were identified and grouped into multiple categories including:

A. Proliferation

B. Adhesion, migration and metastasis

C. Angiogenesis

D. Cancer stem cell targets

E. Unknown function

Additionally, the tissue specificity of the TMs in each group was evaluated and the percentage of tumor samples with overexpression of each TAA was determined. Protein expression data measured by IHC are preferred whenever it is applicable. Expression data from The Human Protein Atlas were collected where no expression data is available. Lastly, TMs in each group were prioritized and TAAs were selected based on the criteria described. As an example, the GBM TAAs are summarized in Table 133 below after TAA selection and prioritization.

TABLE 133

GBM Prioritized TAAs

| | TAA |
|---|---|
| Group A: Cell proliferation | IL-13Ra |
| | Survivin |
| | MAGE- 1 |
| | hTERT |
| | WT1 |
| Group B: Angiogenesis | PSMA |
| | EphA2 |
| Group C: CSC targets | Tenascin C (TNC) |
| | hTERT |

Expression Profile for Component Tumor Cell Lines and TAA Identification for Design and Insertion In order to determine whether the selected prioritized TAAs needed to be overexpressed in the component cell lines that comprise the vaccine compositions, expression profiles of all component cell lines for each indication was created to determine whether the endogenous expression of selected TAAs in these cell lines could be found. Expression of TAAs in the potential component cell lines was determined using RNA-seq data downloaded from the publicly available Cancer Cell Line Encyclopedia (CCLE) database (www.broadinstitute.org/ccle; Barretina, J et al. Nature. 2012) between Oct. 7, 2019-May 20, 2020. The HUGO Gene Nomenclature Committee gene symbol was entered into the CCLE search and mRNA expression was downloaded for each TAA. The expression of a TAA was considered positive if the RNA-seq value (FPKM) was greater than 0. Among the prioritized TAAs, those that were not expressed by any cell lines or only expressed by one cell line comprising the therapeutic combination of cell lines were identified for design and insertion. An antigen could also be selected for design and insertion when it is expressed by more than one cell line but its RNA expression level is above 1.0 FPKM in only one cell line. An example of TAA expression profile (heat map) of various GBM cell lines is shown in FIG. 78.

The expression of prioritized TMs listed in Table 66 in GBM cell lines was determined using the data in FIG. 78. As indicated in FIG. 78, no cell lines exhibit positive hTERT or PSMA expression (the RNA-seq values for hTERT and PSMA are all negative), while GB49 is the only cell line that expresses MAGE-A1. As a result, design/enhancement and overexpression of hTERT, PSMA and MAGE-A1 in selected GBM cell lines was performed.

Antigen Design Methods

After the TMs that need to be overexpressed were selected, in order to increase the breadth and magnitude of antigen-specific cellular immune responses, a multiphase design strategy was utilized to generate modified TMs with frequently occurring non-synonymous mutations in cancer patients.

Patient tumor sample data were downloaded from the publicly available database cBioPortal (cbioportal.org) database (Cerami, E. et al. Cancer Discovery. 2012; Gao, J. et al. Sci Signal. 2013) between Feb. 23, 2020-Jun. 2, 2020. The dataset of "curated set of nonredundant studies" was used and it contained 176 studies with whole exome or transcriptome sequencing of 46,706 tumor samples derived from 44,354 cancer patients. Table 134 lists the name, site of the primary tumor(s), number of samples, and the cBioPortal literature citation of the queried 176 studies.

TABLE 134

| Study Name | Cancer Type/ Primary Organ Site | Sample # | cBioPortal Study Citation |
|---|---|---|---|
| Adenoid Cystic Carcinoma Project | Adrenal Gland | 1049 | Multi-Institute, 2019 |
| Adrenocortical Carcinoma | Adrenal Gland | 92 | TCGA, PanCancer Atlas |
| Ampullary Carcinoma | Ampulla of Vater | 160 | Baylor, Cell Reports 2016 |
| Cholangiocarcinoma | Biliary Tract | 15 | National Cancer Center of Singapore, Nat Genet 2013 |
| Cholangiocarcinoma | Biliary Tract | 8 | National University of Singapore, Nat Genet 2013 |
| Cholangiocarcinoma | Biliary Tract | 36 | TCGA, PanCancer Atlas |
| Intrahepatic Cholangiocarcinoma | Biliary Tract | 40 | JHU, Nat Genet 2013 |
| Intrahepatic Cholangiocarcinoma | Biliary Tract | 103 | Shanghai, Nat Commun 2014 |
| Gallbladder Carcinoma | Biliary Tract | 32 | Shanghai, Nat Genet 2014 |
| Bladder Cancer | Bladder/Urinary Tract | 109 | MSKCC, Eur Urol 2014 |
| Bladder Cancer | Bladder/Urinary Tract | 97 | MSKCC, J Clin Onco 2013 |
| Bladder Urothelial Carcinoma | Bladder/Urinary Tract | 99 | BGI, Nat Genet 2013 |
| Bladder Urothelial Carcinoma | Bladder/Urinary Tract | 50 | DFCI/MSKCC Cancer Discov 2014 |
| Bladder Urothelial Carcinoma | Bladder/Urinary Tract | 411 | TCGA, PanCancer Atlas |
| Urothelial Carcinoma | Bladder/Urinary Tract | 72 | Cornell/Trento, Nat Genet 2016 |
| Upper Tract Urothelial Cancer | Bladder/Urinary Tract | 85 | MSK, Eur Urol 2015 |
| Upper Tract Urothelial Carcinoma | Bladder/Urinary Tract | 47 | Cornell/Baylor/MDACC, Nat Commun 2019 |

TABLE 134-continued

| Study Name | Cancer Type/ Primary Organ Site | Sample # | cBioPortal Study Citation |
|---|---|---|---|
| Ewing Sarcoma | Bone | 112 | Institute Curie, Cancer Discov 2014 |
| Pediatric Ewing Sarcoma | Bone | 107 | DFCI, Cancer Discov 2014 |
| Colorectal Adenocarcinoma | Bowel | 619 | DFCI, Cell Reports 2016 |
| Colorectal Adenocarcinoma | Bowel | 74 | Genentech, Nature 2012 |
| Colorectal Adenocarcinoma | Bowel | 594 | TCGA, PanCancer Atlas |
| Colorectal Adenocarcinoma Triplets | Bowel | 138 | MSKCC, Genome Biol 2014 |
| Colon Adenocarcinoma | Bowel | 29 | CaseCCC, PNAS 2015 |
| Colon Cancer | Bowel | 110 | CPTAC-2 Prospective, Cell 2019 |
| Breast Fibroepithelial Tumors | Breast | 22 | Duke-MUS, Nat Genet 2015 |
| Breast Cancer | Breast | 2509 | METRABRIC, Nature 2012 & Nat Commun 2016 |
| Breast Cancer | Breast | 70 | MSKCC, 2019 |
| Breast Invasive Carcinoma | Breast | 65 | British Columbia, Nature 2012 |
| Breast Invasive Carcinoma | Breast | 103 | Broad, Nature 2012 |
| Breast Invasive Carcinoma | Breast | 100 | Sanger, Nature 2012 |
| Breast Invasive Carcinoma | Breast | 1084 | TCGA, PanCancer Atlas |
| Metastatic Breast Cancer | Breast | 216 | INSERM, PLoS Med 2016 |
| Metastatic Breast Cancer Project | Breast | 237 | MBCP Provisional Data Set, February 2020 |
| Adenoid Cystic Carcinoma Breast | Breast | 12 | MSKCC, J Pathol 2015 |
| Brain Lower Grade Glioma | CNS/Brain | 514 | TCGA, PanCancer Atlas |
| Glioma | CNS/Brain | 91 | MSK, 2018 |
| Low Grade Gliomas | CNS/Brain | 61 | UCSF, Science 2014 |
| Glioblastoma Multiforme | CNS/Brain | 592 | TCGA, PanCancer Atlas |
| Medulloblastoma | CNS/Brain | 92 | Broad, Nature 2012 |
| Medulloblastoma | CNS/Brain | 37 | PCGP, Nature 2012 |
| Medulloblastoma | CNS/Brain | 46 | Sickkids, Nature 2016 |
| Cervical Squamous Cell Carcinoma | Cervix | 297 | TCGA, PanCancer Atlas |
| Esophageal Squamous Cell Carcinoma | Esophagus/Stomach | 88 | ICGC, Nature 2014 |
| Esophageal Squamous Cell Carcinoma | Esophagus/Stomach | 139 | UCLA, Nat Genet 2014 |
| Gastric Adenocarcinoma | Esophagus/Stomach | 78 | TMUCIH, PNAS 2015 |
| Esophageal Adenocarcinoma | Esophagus/Stomach | 151 | DFCI, Nat Genet 2013 |
| Esophageal Adenocarcinoma | Esophagus/Stomach | 182 | TCGA, PanCancer Atlas |
| Stomach Adenocarcinoma | Esophagus/Stomach | 100 | Pfizer and UHK, Nat Genet 2014 |
| Esophageal Adenocarcinoma | Esophagus/Stomach | 440 | TCGA, PanCancer Atlas |
| Esophageal Adenocarcinoma | Esophagus/Stomach | 30 | U Tokyo, Nat Genet 2014 |
| Uveal Melanoma | Eye | 28 | QIMR, Oncotarget 2016 |
| Uveal Melanoma | Eye | 80 | TCGA, PanCancer Atlas |
| Head and Neck Squamous Cell Carcinoma | Head and Neck | 74 | Broad, Science 2011 |
| Head and Neck Squamous Cell Carcinoma | Head and Neck | 32 | Johns Hopkins, Science 2011 |
| Head and Neck Squamous Cell Carcinoma | Head and Neck | 523 | TCGA, PanCancer Atlas |
| Oral Squamous Cell Carcinoma | Head and Neck | 40 | MD Anderson, Cancer Discov 2013 |
| Nasopharyngeal Carcinoma | Head and Neck | 56 | Singapore, Nat Genet 2014 |
| Adenoid Cystic Carcinoma | Head and Neck | 28 | FMI, Am J Surg Pathl 2014 |
| Adenoid Cystic Carcinoma | Head and Neck | 25 | JHU, Cancer Prey Res 2016 |
| Adenoid Cystic Carcinoma | Head and Neck | 102 | MDA, Clin Cancer Res 2015 |
| Adenoid Cystic Carcinoma | Head and Neck | 10 | MGH, Nat Gen 2016 |
| Adenoid Cystic Carcinoma | Head and Neck | 60 | MSKCC, Nat Genet 2013 |
| Adenoid Cystic Carcinoma | Head and Neck | 24 | Sanger/MDA, JCI 2013 |
| Clear Cell Renal Cell Carcinoma | Kidney | 35 | DFCI, Science 2019 |
| Kidney Renal Clear Cell Carcinoma | Kidney | 98 | BGI, Nat Genet 2012 |
| Kidney Renal Clear Cell Carcinoma | Kidney | 78 | IRC, Nat Genet 2014 |
| Kidney Renal Clear Cell Carcinoma | Kidney | 512 | TCGA, PanCancer Atlas |
| Renal Clear Cell Carcinoma | Kidney | 106 | U Tokyo, Nat Genet 2013 |
| Kidney Chromophobe | Kidney | 65 | TCGA, PanCancer Atlas |
| Kidney Renal Papillary Cell Carcinoma | Kidney | 283 | TCGA, PanCancer Atlas |
| Renal Non-Clear Cell Carcinoma | Kidney | 146 | Genentech, Nat Genet 2014 |
| Unclassified Renal Cell Carcinoma | Kidney | 62 | MSK, Nature 2016 |
| Pediatric Rhabdoid Tumor | Kidney | 72 | TARGET, 2018 |
| Rhabdoid Cancer | Kidney | 40 | BCGSC, Cancer Cell 2016 |
| Pediatric Wilms' Tumor | Kidney | 657 | TARGET, 2018 |
| Hepatocellular Adenoma | Liver | 46 | INSERM, Cancer Cell 2014 |
| Hepatocellular Carcinomas | Liver | 243 | INSERM, Nat Genet 2015 |
| Liver Hepatocellular Adenoma and Carcinomas | Liver | 19 | MSK, PLoS One 2018 |
| Liver Hepatocellular Carcinoma | Liver | 231 | AMC, Hepatology 2014 |
| Liver Hepatocellular Carcinoma | Liver | 27 | RIKEN, Nat Genet 2012 |
| Liver Hepatocellular Carcinoma | Liver | 372 | TCGA, PanCancer Atlas |

TABLE 134-continued

| Study Name | Cancer Type/ Primary Organ Site | Sample # | cBioPortal Study Citation |
|---|---|---|---|
| Thoracic PDX | Lung | 139 | MSK, Provisional |
| Small Cell Lung Cancer | Lung | 80 | Johns Hopkins, Nat Genet 2012 |
| Small Cell Lung Cancer | Lung | 110 | U Cologne, Nature 2015 |
| Small Cell Lung Cancer | Lung | 20 | Multi-Institute, Cancer Cell 2017 |
| Non-Small Cell Lung Cancer | Lung | 75 | MSK, Cancer Cell 2018 |
| Non-Small Cell Lung Cancer | Lung | 327 | TRACERx, NEJM 2017 |
| Non-Small Cell Lung Cancer | Lung | 41 | University of Turin, Lung Cancer 2017 |
| Lung Adenocarcinoma | Lung | 183 | Broad, Cell 2012 |
| Lung Adenocarcinoma | Lung | 566 | TCGA, PanCancer Atlas |
| Lung Adenocarcinoma | Lung | 163 | TSP, Nature 2008 |
| Lung Squamous Cell Carcinoma | Lung | 487 | TCGA, PanCancer Atlas |
| Acute Lymphoid Leukemia | Lymphoid | 73 | St. Jude, Nat Genet, 2016 |
| Pediatric Acute Lymphoid Leukemia-Phase II | Lymphoid | 1978 | TARGET, 2018 |
| Chronic Lymphocytic Leukemia | Lymphoid | 160 | Broad, Cell 2013 |
| Chronic Lymphocytic Leukemia | Lymphoid | 537 | Broad, Nature 2015 |
| Chronic Lymphocytic Leukemia | Lymphoid | 506 | I UOPA, Nature 2015 |
| Chronic Lymphocytic Leukemia | Lymphoid | 105 | ICGC, Nat Genet 2011 |
| Cutaneous T cell Lymphoma | Lymphoid | 43 | Columbia U, Nat Genet 2015 |
| Diffuse Large B Cell Lymphoma | Lymphoid | 135 | DFCI, Nat Med 2018 |
| Diffuse Large B Cell Lymphoma | Lymphoid | 1001 | Duke, Cell 2017 |
| Diffuse Large B Cell Lymphoma | Lymphoid | 48 | TCGA, PanCancer Atlas |
| Diffuse Large B Cell Lymphoma | Lymphoid | 53 | BCGSC, Blood 2013 |
| Mantel Cell Lymphoma | Lymphoid | 29 | IDIBIPS, PNAS 2013 |
| Multiple Myeloma | Lymphoid | 211 | Broad, Cancer Cell 2014 |
| Non-Hodgkin Lymphoma | Lymphoid | 14 | BCGSC, Nature 2011 |
| Primary Central Nervous System Lymphoma | Lymphoid | 19 | Mayo Clinic, Clin Cancer Res 2015 |
| Acute Myeloid Leukemia or Myelodysplastic Syndromes | Myeloid | 136 | WashU, 2016 |
| Acute Myeloid Leukemia | Myeloid | 672 | OHSU, Nature 2018 |
| Acute Myeloid Leukemia | Myeloid | 200 | TCGA, PanCancer Atlas |
| Pediatric Acute Myeloid Leukemia | Myeloid | 1025 | TARGET, 2018 |
| Histiocytosis Cobimetinib | Myeloid | 52 | MSK, 2019 |
| Myelodysplasia | Myeloid | 29 | UTokyo, Nature 2011 |
| Myeloproliferative Neoplasms | Myeloid | 151 | CIMR, NEJM 2013 |
| MSK-IMPACT | Mixed Cancer Types | 10,945 | MSKCC, Nat Med. 2017 |
| MSS Mixed Solid Tumors | Mixed Cancer Types | 249 | Broad/Dana-Farber, Nat Genet 2018 |
| Metastatic Solid Cancers | Mixed Cancer Types | 500 | UMich, Nature. 2017 |
| Pediatric Pan-Cancer | Mixed Cancer Types | 961 | DKFZ, Nature 2017 |
| Pediatric Pan-cancer | Mixed Cancer Types | 103 | Columbia U, Genome Med 2016 |
| Pediatric Preclinical Testing Consortium | Mixed Cancer Types | 261 | Maris, 2019 |
| SUMMIT-Neratinib Basket Study | Mixed Cancer Types | 141 | Multi-Institute, Nature 2018 |
| Ovarian Serous Cystadenocarcinoma | Ovarian/Fallopian | 585 | TCGA, PanCancer Atlas |
| Small Cell Carcinoma of the Ovary | Ovarian/Fallopian | 12 | MSKCC, Nat Genet 2014 |
| Acinar Cell Carcinoma of the Pancreas | Pancreas | 23 | JHU, J Pathol 2014 |
| Cystic Tumor of the Pancreas | Pancreas | 32 | Johns Hopkins, PNAS 2011 |
| Pancreatic Adenocarcinoma | Pancreas | 456 | QCMG, Nature 2016 |
| Pancreatic Adenocarcinoma | Pancreas | 184 | TCGA, PanCancer Atlas |
| Pancreatic Cancer | Pancreas | 109 | UTSW, Nat Commun 2015 |
| Insulinoma | Pancreas | 10 | Shanghai, Nat Commun 2013 |
| Pancreatic Neuroendocrine Tumors | Pancreas | 10 | Johns Hopkins, Science 2011 |
| Pancreatic Neuroendocrine Tumors | Pancreas | 98 | Multi-Institute, Nature 2017 |
| Malignant Peripheral Nerve Sheath Tumor | Peripheral Nervous | 15 | MSKCC, Nat Genet 2014 |
| Neuroblastoma | Peripheral Nervous | 87 | AMC Amsterdam, Nature 2012 |
| Neuroblastoma | Peripheral Nervous | 56 | Broad, Nature 2015 |
| Pediatric Neuroblastoma | Peripheral Nervous | 1089 | TARGET, 2018 |
| Mesothelioma | Pleura | 87 | TCGA, PanCancer Atlas |
| Pleural Mesothelioma | Pleura | 22 | NYU, Cancer Res 2015 |
| Prostate Cancer | Prostate | 18 | MSK, 2019 |
| Metastatic Prostate Adenocarcinoma | Prostate | 61 | MCTP, Nature 2012 |
| Metastatic Prostate Adenocarcinoma | Prostate | 444 | SU2C/PCF Dream Team, PNAS 2019 |
| Neuroendocrine Prostate Cancer | Prostate | 114 | Multi-Institute, Nat Med 2016 |
| Prostate Adenocarcinoma | Prostate | 112 | Broad/Cornell, Nat Genet 2012 |
| Prostate Adenocarcinoma | Prostate | 176 | Fred Hutchinson CRC, Nat Med 2016 |
| Prostate Adenocarcinoma | Prostate | 240 | MSKCC, Cancer Cell 2010 |
| Prostate Adenocarcinoma | Prostate | 65 | SMMU, Eur Urol 2017 |

TABLE 134-continued

| Study Name | Cancer Type/ Primary Organ Site | Sample # | cBioPortal Study Citation |
|---|---|---|---|
| Prostate Adenocarcinoma | Prostate | 494 | TCGA, PanCancer Atlas |
| Prostate Adenocarcinoma Organoids | Prostate | 12 | MSKCC, Cell 2014 |
| Metastatic Prostate Cancer Project | Prostate | 75 | Provisional, November 2019 |
| Basal Cell Carcinoma | Skin | 293 | UNIGE, Nat Genet 2016 |
| Cutaneous Squamous Cell Carcinoma | Skin | 29 | DFCI, Clin Cancer Res 2015 |
| Cutaneous Squamous Cell Carcinoma | Skin | 39 | MD Anderson, Clin Cancer Res 2014 |
| Acral Melanoma | Skin | 38 | TGEN, Genome Res 2017 |
| Metastatic Melanoma | Skin | 38 | UCLA, Cell 2016 |
| Melanoma | Skin | 64 | MSKCC, NEJM 2014 |
| Metastatic Melanoma | Skin | 110 | DFCI, Science 2015 |
| Metastatic Melanoma | Skin | 66 | MSKCC, JCO Precis Oncol 2017 |
| Skin Cutaneous Melanoma | Skin | 121 | Broad, Cell 2012 |
| Skin Cutaneous Melanoma | Skin | 448 | TCGA, PanCancer Atlas |
| Skin Cutaneous Melanoma | Skin | 147 | Yale, Nat Genet 2012 |
| Skin Cutaneous Melanoma | Skin | 78 | Broad, Cancer Discov 2014 |
| Desmoplastic Melanoma | Skin | 20 | Broad Institute, Nat Genet 2015 |
| Pheochromocytoma and Paraganglioma | Soft Tissue | 178 | TCGA, PanCancer Atlas |
| Sarcoma | Soft Tissue | 216 | MSKCC/Broad, Nat Genet 2010 |
| Sarcoma | Soft Tissue | 255 | TCGA, PanCancer Atlas |
| The Angiosarcoma Project | Soft Tissue | 48 | Provisional, September 2018 |
| Rhabdomyosarcoma | Soft Tissue | 43 | NIH, Cancer Discov 2014 |
| Testicular Germ Cell Tumors | Testis | 149 | TCGA, PanCancer Atlas |
| Thymic Epithelial Tumors | Thymus | 32 | NCI, Nat Genet 2014 |
| Thymoma | Thymus | 123 | TCGA, PanCancer Atlas |
| Thyroid Carcinoma | Thyroid | 500 | TCGA, PanCancer Atlas |
| Uterine Corpus Endometrial Carcinoma | Uterus | 529 | TCGA, PanCancer Atlas |
| Uterine Carcinosarcoma | Uterus | 22 | Johns Hopkins, Nat Commun 2014 |
| Uterine Carcinosarcoma | Uterus | 57 | TCGA, PanCancer Atlas |
| Uterine Clear Cell Carcinoma | Uterus | 16 | NIH, Cancer 2017 |
| Squamous Cell Carcinoma of the Vulva | Vulva/Vagina | 15 | CUK, Exp Mol Med 2018 |

The non-redundant data set was queried with the HUGO Gene Nomenclature Committee gene symbol for the antigen of interest. Missense mutations occurring in the target antigen were downloaded and sorted by frequency of occurrence. Missense mutations occurring in 2 patient samples were identified and evaluated for the potential to induce neoepitopes using the publicly available NetMHCpan 4.0 database (https://services.healthtech.dtu.dk/service.php?NetMHCpan-4.0) (Jurtz V, et al. J Immunol. 2017). The HLA supertypes included are HLA-A*01:01, HLA-A*02:01, HLA-A*03:01, HLA-A*24:02, HLA-A*26:01, HLA-B*07:02, HLA-B*08:01, HLA-B*27:05, HLA-B*39:01, HLA-B*40:01, HLA-B*58:01, and HLA-B*15:01.

TABLE 135

| Supertype | Representative |
|---|---|
| A01 | HLA-A*01:01 |
| A02 | HLA-A*02:01 |
| A03 | HLA-A*03:01 |
| A24 | HLA-A*24:02 |
| A26 | HLA-A*26:01 |
| B07 | HLA-B*07:02 |
| B08 | HLA-B*08:01 |
| B27 | HLA-B*27:05 |
| B39 | HLA-B*39:01 |
| B44 | HLA-B*40:01 |
| B58 | HLA-B*58:01 |
| B62 | HLA-B*15:01 |

The threshold for strong binder was set at the recommended threshold of 0.5, which means any peptides with predicted % rank lower than 0.5 will be annotated as strong binders. The threshold for weak binder was set at the recommended 2.0, which means any peptides with predicted % rank lower than 2.0 but higher than 0.5 will be annotated as weak binders.

To determine whether introduction of a NSM occurring≥2 patient samples into the human native antigen would create a new epitope or change a weak binder to strong binder, a list of HLA-A and HLA-B supertype-restricted 9-mer epitopes including both strong binders and weak binders was first generated using human native TAA protein sequence (List #1). Then, starting from 5' end of the human native antigen, each specific NSM was introduced to the human native antigen by replacing the native residue at the same position with the NSM. The resulting antigen with the NSM was used to generate a new list of HLA-A and HLA-B supertype-restricted epitopes including both strong binders and weak binders (List #2). By comparing List #2 with List #1, the numbers of new epitopes (strong binders and weak binders) and abrogated epitopes were calculated. If introduction of one specific NSM resulted in more new epitopes, then this NSM would be included in the human native TAA. If introduction of one specific NSM created the same number of new epitopes and abrogated epitopes, but it changed more weak binders to strong binders, the decision would still be made to include this NSM in the human native TAA. If there were fewer than 9 amino acid residues between two NSMs, then evaluation were performed for each individual NSM and the combination of two NSMs as well. Once the evaluation was completed, sequence alignment was performed to determine the protein sequence identity between the human native TAA and human TAA with NSMs. If the sequence identity is below 90%, then only NSMs occurring in 2 patient samples that either creates new epitopes or change weaker binders to strong binders were included.

As an example, the PSMA with NSMs was designed using the method described above. FIG. 129 shows the sequence alignment between human native PSMA (NCBI Gene ID: 2346) and the designed PSMA with NSMs (modPSMA; SEQ ID NO: 38). The NSMs (the residues that are different between huPSMA and modPSMA) are highlighted in gray. The sequence identity between huPSMA and modPSMA is 96.4%.

The HLA-A and HLA-B supertype-restricted epitopes for huPSMA and the modPSMA are summarized in Table 136. 49 NSMs occurring≥2 times were identified for PSMA 27 were included in the modPSMA antigen sequence. Compared to native PSMA, modPSMA contains an additional 41 neoepitopes due to the introduction of NSMs.

TABLE 136

Epitopes in Native and Designed (mod) PSMA

| HLA | Native | | | Designed | | |
|---|---|---|---|---|---|---|
| Supertype | SB | WB | Total | SB | WB | Total |
| A01 | 3 | 16 | 19 | 3 | 17 | 20 |
| A02 | 6 | 11 | 17 | 6 | 13 | 19 |
| A03 | 6 | 9 | 15 | 7 | 12 | 19 |
| A24 | 7 | 12 | 19 | 8 | 14 | 22 |
| A26 | 8 | 28 | 36 | 10 | 24 | 34 |
| B07 | 6 | 9 | 15 | 9 | 8 | 17 |
| B08 | 4 | 17 | 21 | 4 | 25 | 29 |
| B27 | 5 | 16 | 21 | 8 | 16 | 24 |
| B39 | 8 | 16 | 24 | 9 | 26 | 35 |
| B44 | 5 | 12 | 17 | 7 | 13 | 20 |
| B58 | 9 | 10 | 19 | 9 | 13 | 22 |
| B62 | 10 | 15 | 25 | 11 | 17 | 28 |
| Total Epitopes | 77 | 171 | 248 | 91 | 198 | 289 |

The HLA-A and HLA-B supertype-restricted epitopes for human WT1 (NCBI Gene ID: 7490) and the modWT1 (SEQ ID NO: 81) are summarized in Table 137. 46 NSMs occurring≥2 times were identified for WT1 and 28 were included in the modWT1 antigen sequence. When compared to native WT1, modWT1 contains an additional 33 more neoepitopes due to the introduction of NSMs.

TABLE 137

Epitopes in Native and Designed (mod) WT1

| HLA | Native | | | Designed | | |
|---|---|---|---|---|---|---|
| Supertype | SB | WB | Total | SB | WB | Total |
| A01 | 1 | 7 | 8 | 2 | 9 | 11 |
| A02 | 3 | 3 | 6 | 3 | 5 | 8 |
| A03 | 4 | 4 | 8 | 4 | 6 | 10 |
| A24 | 0 | 5 | 5 | 0 | 7 | 7 |
| A26 | 7 | 5 | 12 | 8 | 8 | 16 |
| B07 | 3 | 11 | 14 | 2 | 15 | 17 |
| B08 | 0 | 6 | 6 | 0 | 8 | 8 |
| B27 | 4 | 6 | 10 | 4 | 6 | 10 |
| B39 | 6 | 15 | 21 | 6 | 17 | 23 |
| B44 | 1 | 10 | 11 | 2 | 11 | 13 |
| B58 | 2 | 6 | 8 | 4 | 11 | 15 |
| B62 | 6 | 6 | 12 | 6 | 10 | 16 |
| Total Epitopes | 37 | 84 | 121 | 41 | 113 | 154 |

The HLA-A and HLA-B supertype-restricted epitopes for human FSHR (NCBI Gene ID: 2492) and the modFSHR (SEQ ID NO: 95) are summarized in Table 138. 70 NSMs occurring≥2 times were identified for FSHR and 26 were included in the modFSHR antigen sequence. When compared to native FSHR, modFSHR contains 47 more neoepitopes due to the introduction of NSMs.

TABLE 138

Epitopes in Native and Designed (mod) FSHR

| HLA | Native | | | Designed | | |
|---|---|---|---|---|---|---|
| Supertype | SB | WB | Total | SB | WB | Total |
| A01 | 4 | 12 | 16 | 5 | 17 | 22 |
| A02 | 12 | 24 | 36 | 14 | 28 | 42 |
| A03 | 7 | 7 | 14 | 8 | 8 | 16 |
| A24 | 12 | 18 | 30 | 12 | 19 | 31 |
| A26 | 10 | 15 | 25 | 10 | 21 | 31 |
| B07 | 7 | 16 | 23 | 8 | 15 | 23 |
| B08 | 7 | 28 | 35 | 9 | 27 | 36 |
| B27 | 6 | 10 | 16 | 7 | 12 | 19 |
| B39 | 17 | 23 | 40 | 19 | 30 | 49 |
| B44 | 3 | 13 | 16 | 4 | 15 | 19 |
| B58 | 6 | 24 | 30 | 6 | 26 | 32 |
| B62 | 13 | 14 | 27 | 15 | 20 | 35 |
| Total Epitopes | 104 | 204 | 308 | 117 | 238 | 355 |

The HLA-A and HLA-B supertype-restricted epitopes for human TERT (NCBI Gene ID: 7015) and the modTERT (SEQ ID NO: 36) are summarized in Table 139. 75 NSMs occurring≥2 times were identified for TERT and 43 were included in the modTERT antigen sequence. When compared to native TERT, modTERT contains 47 more neoepitopes due to the introduction of NSMs.

TABLE 139

Epitopes in Native and Design (mod) TERT

| | Native | | | Designed | | |
|---|---|---|---|---|---|---|
| HLA Supertype | SB | WB | Total | SB | WB | Total |
| A01 | 4 | 15 | 19 | 4 | 15 | 19 |
| A02 | 12 | 25 | 37 | 16 | 26 | 42 |
| A03 | 9 | 18 | 27 | 9 | 19 | 28 |
| A24 | 11 | 20 | 31 | 12 | 24 | 36 |
| A26 | 9 | 21 | 30 | 10 | 24 | 34 |
| B07 | 21 | 48 | 69 | 18 | 47 | 65 |
| B08 | 28 | 39 | 67 | 30 | 42 | 72 |
| B27 | 23 | 39 | 62 | 27 | 35 | 62 |
| B39 | 24 | 43 | 67 | 22 | 59 | 81 |
| B44 | 8 | 15 | 23 | 8 | 15 | 23 |
| B58 | 10 | 16 | 26 | 10 | 18 | 28 |
| B62 | 12 | 35 | 47 | 12 | 37 | 49 |
| Total Epitopes | 171 | 334 | 505 | 178 | 361 | 539 |

The HLA-A and HLA-B supertype-restricted epitopes for BORIS (NCBI Gene ID: 140690) and the modBORIS (SEQ ID NO: 60) are summarized in Table 140. 51 NSMs occurring≥2 times were identified for BORIS and 33 were included in the modBORIS antigen sequence. When compared to native BORIS, modBORIS contains 27 more neoepitopes due to the introduction of NSMs.

TABLE 140

| Epitopes in Native and Designed (mod) BORIS (CTCFL) | | | | | | |
|---|---|---|---|---|---|---|
| | Native | | | Designed | | |
| HLA Supertype | SB | WB | Total | SB | WB | Total |
| A01 | 2 | 10 | 12 | 2 | 11 | 13 |
| A02 | 0 | 5 | 5 | 1 | 4 | 5 |
| A03 | 4 | 12 | 16 | 6 | 16 | 22 |
| A24 | 2 | 4 | 6 | 5 | 3 | 8 |
| A26 | 3 | 10 | 13 | 5 | 15 | 20 |
| B07 | 1 | 10 | 11 | 2 | 9 | 11 |
| B08 | 6 | 14 | 20 | 8 | 14 | 22 |
| B27 | 1 | 10 | 11 | 1 | 13 | 14 |
| B39 | 10 | 15 | 25 | 9 | 18 | 27 |
| B44 | 9 | 16 | 25 | 6 | 18 | 24 |
| B58 | 1 | 10 | 11 | 2 | 11 | 13 |
| B62 | 4 | 13 | 17 | 4 | 16 | 20 |
| Total Epitopes | 43 | 129 | 172 | 51 | 148 | 199 |

The HLA-A and HLA-B supertype-restricted epitopes for MSLN (NCBI Gene ID: 10232) and the modMSLN (SEQ ID NO: 62) are summarized in Table 141. 23 NSMs occurring≥2 times were identified for MSLN and 13 were included in the modMSLN antigen sequence. When compared to native MSLN, modMSLN contains 23 more neoepitopes due to the introduction of NSMs.

TABLE 141

| Epitopes in Native and Designed (mod) MSLN | | | | | | |
|---|---|---|---|---|---|---|
| | Native | | | Designed | | |
| HLA Supertype | SB | WB | Total | SB | WB | Total |
| A01 | 3 | 10 | 13 | 3 | 12 | 15 |
| A02 | 5 | 12 | 17 | 6 | 12 | 18 |
| A03 | 4 | 6 | 10 | 4 | 6 | 10 |
| A24 | 4 | 8 | 12 | 6 | 11 | 17 |
| A26 | 11 | 14 | 25 | 11 | 14 | 25 |
| B07 | 11 | 16 | 27 | 9 | 19 | 28 |
| B08 | 5 | 13 | 18 | 6 | 13 | 19 |
| B27 | 2 | 6 | 8 | 2 | 8 | 10 |
| B39 | 12 | 18 | 30 | 12 | 20 | 32 |
| B44 | 4 | 12 | 16 | 6 | 14 | 20 |
| B58 | 3 | 7 | 10 | 3 | 12 | 15 |
| B62 | 4 | 14 | 18 | 4 | 14 | 18 |
| Total Epitopes | 68 | 136 | 204 | 72 | 155 | 227 |

The HLA-A and HLA-B supertype-restricted epitopes for TBXT (NCBI Gene ID: 6862) and the modTBXT (SEQ ID NO: 79) are summarized in Table 142. 44 NSMs occurring≥2 times were identified for TBXT and 16 were included in the modTBXT antigen sequence. When compared to native TBXT, modTBXT contains 34 more neoepitopes due to the introduction of NSMs.

TABLE 142

| Epitopes in Native and Designed (mod) TBXT | | | | | | |
|---|---|---|---|---|---|---|
| | Native | | | Designed | | |
| HLA Supertype | SB | WB | Total | SB | WB | Total |
| A01 | 6 | 4 | 10 | 8 | 5 | 13 |
| A02 | 4 | 5 | 9 | 4 | 9 | 13 |
| A03 | 2 | 4 | 6 | 3 | 6 | 9 |
| A24 | 5 | 6 | 11 | 5 | 7 | 12 |
| A26 | 2 | 5 | 7 | 2 | 8 | 10 |
| B07 | 5 | 14 | 19 | 4 | 12 | 16 |
| B08 | 4 | 6 | 10 | 5 | 9 | 14 |
| B27 | 5 | 2 | 7 | 6 | 3 | 9 |
| B39 | 6 | 18 | 24 | 9 | 23 | 32 |

TABLE 142-continued

| Epitopes in Native and Designed (mod) TBXT | | | | | | |
|---|---|---|---|---|---|---|
| | Native | | | Designed | | |
| HLA Supertype | SB | WB | Total | SB | WB | Total |
| B44 | 3 | 7 | 10 | 4 | 6 | 10 |
| B58 | 6 | 2 | 8 | 7 | 4 | 11 |
| B62 | 4 | 12 | 16 | 8 | 14 | 22 |
| Total Epitopes | 52 | 85 | 137 | 65 | 106 | 171 |

The HLA-A and HLA-B supertype-restricted epitopes for PRAME (NCBI Gene ID: 23532) and the modPRAME (SEQ ID NO: 99) are summarized in Table 143. 27 NSMs occurring≥2 times were identified for PRAME and 20 were included in the modPRAME antigen sequence. When compared to native PRAME, modPRAME contains 35 more neoepitopes due to the introduction of NSMs.

TABLE 143

| Epitopes in Native and Designed (mod) FRAME | | | | | | |
|---|---|---|---|---|---|---|
| | Native | | | Designed | | |
| HLA Supertype | SB | WB | Total | SB | WB | Total |
| A01 | 5 | 14 | 19 | 5 | 14 | 19 |
| A02 | 16 | 20 | 36 | 17 | 25 | 42 |
| A03 | 5 | 14 | 19 | 5 | 14 | 19 |
| A24 | 5 | 18 | 23 | 7 | 22 | 29 |
| A26 | 2 | 20 | 22 | 3 | 23 | 26 |
| B07 | 9 | 17 | 26 | 9 | 18 | 27 |
| B08 | 13 | 33 | 46 | 17 | 37 | 54 |
| B27 | 4 | 10 | 14 | 3 | 10 | 13 |
| B39 | 13 | 23 | 36 | 16 | 24 | 40 |
| B44 | 7 | 15 | 22 | 7 | 16 | 23 |
| B58 | 2 | 19 | 21 | 1 | 21 | 22 |
| B62 | 8 | 22 | 30 | 12 | 23 | 35 |
| Total Epitopes | 89 | 225 | 314 | 102 | 247 | 349 |

The HLA-A and HLA-B supertype-restricted epitopes for TDGF1 (NCBI Gene ID: 6997) and the modTDGF1 (SEQ ID NO: 89) are summarized in Table 144. 9 NSMs occurring≥2 times were identified for TDGF1 and 7 were included in the modTDGF1 antigen sequence. When compared to native TDGF1, modTDGF1 contains 11 more neoepitopes due to the introduction of NSMs.

TABLE 144

| Epitopes in Native and Designed (mod) TDGF1 | | | | | | |
|---|---|---|---|---|---|---|
| | Native | | | Designed | | |
| HLA Supertype | SB | WB | Total | SB | WB | Total |
| A01 | 0 | 1 | 1 | 0 | 1 | 1 |
| A02 | 2 | 5 | 7 | 2 | 4 | 6 |
| A03 | 1 | 1 | 2 | 1 | 1 | 2 |
| A24 | 1 | 5 | 6 | 1 | 5 | 6 |
| A26 | 0 | 7 | 7 | 2 | 6 | 8 |
| B07 | 5 | 6 | 11 | 6 | 8 | 14 |
| B08 | 2 | 11 | 13 | 3 | 10 | 13 |
| B27 | 1 | 3 | 4 | 2 | 5 | 7 |
| B39 | 2 | 4 | 6 | 2 | 7 | 9 |
| B44 | 1 | 1 | 2 | 2 | 1 | 3 |
| B58 | 2 | 6 | 8 | 2 | 7 | 9 |
| B62 | 2 | 4 | 6 | 2 | 4 | 6 |
| Total Epitopes | 19 | 54 | 73 | 25 | 59 | 84 |

The HLA-A and HLA-B supertype-restricted epitopes for FOLR1 (FBP) (NCBI Gene ID: 2348) and the modFOLR1 (SEQ ID NO: 93) are summarized in Table 145. 15 NSMs occurring≥2 times were identified for FOLR1 and 9 were included in the modFOLR1 antigen sequence. When compared to native FOLR1, modFOLR1 contains 7 more neoepitopes due to the introduction of NSMs.

TABLE 145

| Epitopes in Native and Designed (mod) FOLR1 | | | | | | |
|---|---|---|---|---|---|---|
| | Native | | | Designed | | |
| HLA Supertype | SB | WB | Total | SB | WB | Total |
| A01 | 1 | 4 | 5 | 0 | 5 | 5 |
| A02 | 3 | 8 | 11 | 4 | 8 | 12 |
| A03 | 2 | 2 | 4 | 3 | 4 | 7 |
| A24 | 2 | 6 | 8 | 2 | 8 | 10 |
| A26 | 1 | 4 | 5 | 1 | 5 | 6 |
| B07 | 5 | 5 | 10 | 5 | 3 | 8 |
| B08 | 5 | 5 | 10 | 4 | 4 | 8 |
| B27 | 1 | 2 | 3 | 2 | 1 | 3 |
| B39 | 5 | 6 | 11 | 5 | 8 | 13 |
| B44 | 1 | 3 | 4 | 1 | 3 | 4 |
| B58 | 7 | 9 | 16 | 7 | 11 | 18 |
| B62 | 2 | 5 | 7 | 2 | 5 | 7 |
| Total Epitopes | 35 | 59 | 94 | 36 | 65 | 101 |

The HLA-A and HLA-B supertype-restricted epitopes for CLDN18 (NCBI Gene ID: 51208) and the modCLDN18 (SEQ ID NO: 110) are summarized in Table 146. 22 NSMs occurring≥2 times were identified for CLDN18 and 11 were included in the modCLDN18 antigen sequence. When compared to native CLDN18, modCLDN18 contains 22 more neoepitopes due to the introduction of NSMs.

TABLE 146

| Epitopes in Native and Designed (mod) CLDN18 | | | | | | |
|---|---|---|---|---|---|---|
| | Native | | | Designed | | |
| HLA Supertype | SB | WB | Total | SB | WB | Total |
| A01 | 5 | 3 | 8 | 5 | 3 | 8 |
| A02 | 7 | 10 | 17 | 6 | 17 | 23 |
| A03 | 3 | 6 | 9 | 4 | 4 | 8 |
| A24 | 3 | 8 | 11 | 3 | 10 | 13 |
| A26 | 9 | 13 | 22 | 9 | 17 | 26 |
| B07 | 0 | 1 | 1 | 0 | 1 | 1 |
| B08 | 0 | 3 | 3 | 0 | 5 | 5 |
| B27 | 2 | 0 | 2 | 1 | 0 | 1 |
| B39 | 2 | 6 | 8 | 2 | 8 | 10 |
| B44 | 2 | 2 | 4 | 2 | 5 | 7 |
| B58 | 7 | 6 | 13 | 6 | 10 | 16 |
| B62 | 5 | 11 | 16 | 4 | 14 | 18 |
| Total Epitopes | 45 | 69 | 114 | 42 | 94 | 136 |

The HLA-A and HLA-B supertype-restricted epitopes for Ly6K (NCBI Gene ID: 54742) and the modLy6K (SEQ ID NO: 112) are summarized in Table 147. 9 NSMs occurring≥2 times were identified for Ly6K and 7 were included in the modLy6K antigen sequence. When compared to native Ly6K, modLy6K contains 6 more neoepitopes due to the introduction of NSMs.

TABLE 147

| Epitopes in Native and Designed (mod) Ly6K | | | | | | |
|---|---|---|---|---|---|---|
| | Native | | | Designed | | |
| HLA Supertype | SB | WB | Total | SB | WB | Total |
| A01 | 1 | 4 | 5 | 0 | 6 | 6 |
| A02 | 6 | 3 | 9 | 6 | 2 | 8 |
| A03 | 0 | 2 | 2 | 0 | 2 | 2 |

TABLE 147-continued

| Epitopes in Native and Designed (mod) Ly6K | | | | | | |
|---|---|---|---|---|---|---|
| | Native | | | Designed | | |
| HLA Supertype | SB | WB | Total | SB | WB | Total |
| A24 | 0 | 5 | 5 | 1 | 7 | 8 |
| A26 | 0 | 7 | 7 | 0 | 6 | 6 |
| B07 | 2 | 2 | 4 | 3 | 1 | 4 |
| B08 | 1 | 7 | 8 | 2 | 7 | 9 |
| B27 | 2 | 1 | 3 | 2 | 1 | 3 |
| B39 | 0 | 2 | 2 | 0 | 2 | 2 |
| B44 | 1 | 2 | 3 | 1 | 1 | 2 |
| B58 | 2 | 4 | 6 | 2 | 6 | 8 |
| B62 | 1 | 8 | 9 | 1 | 10 | 11 |
| Total Epitopes | 16 | 47 | 63 | 18 | 51 | 69 |

The HLA-A and HLA-B supertype-restricted epitopes for MAGEA10 (NCBI Gene ID: 4109) and the modMAGEA10 (SEQ ID NO: 97) are summarized in Table 148. 38 NSMs occurring≥2 times were identified for MAGEA10 and 13 were included in the modMAGEA10 antigen sequence. When compared to native MAGEA10, modMAGEA10 contains 29 more neoepitopes due to the introduction of NSMs.

TABLE 148

| Epitopes in Native and Designed (mod) MAGEA10 | | | | | | |
|---|---|---|---|---|---|---|
| | Native | | | Designed | | |
| HLA Supertype | SB | WB | Total | SB | WB | Total |
| A01 | 7 | 13 | 20 | 7 | 15 | 22 |
| A02 | 2 | 8 | 10 | 4 | 8 | 12 |
| A03 | 2 | 6 | 8 | 2 | 9 | 11 |
| A24 | 0 | 4 | 4 | 2 | 4 | 6 |
| A26 | 4 | 12 | 16 | 4 | 15 | 19 |
| B07 | 2 | 7 | 9 | 2 | 8 | 10 |
| B08 | 2 | 3 | 5 | 2 | 5 | 7 |
| B27 | 1 | 3 | 4 | 1 | 3 | 4 |
| B39 | 4 | 12 | 16 | 5 | 17 | 22 |
| B44 | 5 | 6 | 11 | 5 | 9 | 14 |
| B58 | 0 | 13 | 13 | 2 | 14 | 16 |
| B62 | 3 | 9 | 12 | 5 | 9 | 14 |
| Total Epitopes | 32 | 96 | 128 | 41 | 116 | 157 |

The HLA-A and HLA-B supertype-restricted epitopes for MAGEC2 (NCBI Gene ID: 51438) and the modMAGEC2 (SEQ ID NO:87) are summarized in Table 149. 45 NSMs occurring≥2 times were identified for MAGEC2 and 8 were included in the modMAGEC2 antigen sequence. When compared to native MAGEC2, modMAGEC2 contains 14 more neoepitopes due to the introduction of NSMs.

TABLE 149

| Epitopes in Native and Designed (mod) MAGEC2 | | | | | | |
|---|---|---|---|---|---|---|
| | Native | | | Designed | | |
| HLA Supertype | SB | W6 | Total | SB | WB | Total |
| A01 | 4 | 14 | 18 | 6 | 13 | 19 |
| A02 | 9 | 10 | 19 | 8 | 11 | 19 |
| A03 | 3 | 3 | 6 | 4 | 5 | 9 |
| A24 | 5 | 13 | 18 | 5 | 14 | 19 |
| A26 | 10 | 19 | 29 | 10 | 21 | 31 |
| B07 | 5 | 15 | 20 | 5 | 14 | 19 |
| B08 | 4 | 10 | 14 | 5 | 12 | 17 |
| B27 | 2 | 0 | 2 | 3 | 1 | 4 |
| B39 | 5 | 11 | 16 | 7 | 10 | 17 |

TABLE 149-continued

| Epitopes in Native and Designed (mod) MAGEC2 | | | | | | |
|---|---|---|---|---|---|---|
| | Native | | | Designed | | |
| HLA Supertype | SB | W6 | Total | SB | WB | Total |
| B44 | 7 | 13 | 20 | 7 | 12 | 19 |
| B58 | 5 | 17 | 22 | 7 | 18 | 25 |
| B62 | 8 | 12 | 20 | 8 | 12 | 20 |
| Total Epitopes | 67 | 137 | 204 | 75 | 143 | 218 |

The HLA-A and HLA-B supertype-restricted epitopes for FAP (NCBI Gene ID: 2191) and the modFAP (SEQ ID NO:115) are summarized in Table 150. 59 NSMs occurring≥2 times were identified for FAP and 25 were included in the modFAP antigen sequence. When compared to native FAP, modFAP contains 22 more neoepitopes due to the introduction of NSMs.

TABLE 150

| Epitopes in Native and Designed (mod) FAP | | | | | | |
|---|---|---|---|---|---|---|
| | Native | | | Designed | | |
| HLA Supertype | SB | WB | Total | SB | WB | Total |
| A01 | 15 | 38 | 53 | 14 | 40 | 54 |
| A02 | 11 | 14 | 25 | 16 | 13 | 29 |
| A03 | 11 | 18 | 29 | 14 | 17 | 31 |
| A24 | 12 | 36 | 48 | 15 | 36 | 51 |
| A26 | 24 | 35 | 59 | 27 | 37 | 64 |
| B07 | 7 | 13 | 20 | 7 | 11 | 18 |
| B08 | 14 | 21 | 35 | 16 | 20 | 36 |
| B27 | 9 | 13 | 22 | 9 | 12 | 21 |
| B39 | 9 | 34 | 43 | 8 | 36 | 44 |
| B44 | 6 | 15 | 21 | 6 | 15 | 21 |
| B58 | 12 | 32 | 44 | 13 | 34 | 47 |
| B62 | 17 | 28 | 45 | 17 | 33 | 50 |
| Total Epitopes | 147 | 297 | 444 | 162 | 304 | 466 |

The HLA-A and HLA-B supertype-restricted epitopes for MAGEA1 (NCBI Gene ID: 4100) and the modMAGEA1 (SEQ ID NO: 73) are summarized in Table 151. 16 NSMs occurring≥2 times were identified for MAGEA1 and 10 were included in the modMAGEA1 antigen sequence. When compared to native MAGEA1, modMAGEA1 contains 7 more neoepitopes due to the introduction of NSMs.

TABLE 151

| Epitopes in Native and Designed (mod) MAGEA1 | | | | | | |
|---|---|---|---|---|---|---|
| | Native | | | Designed | | |
| HLA Supertype | SB | WB | Total | SB | WB | Total |
| A01 | 5 | 7 | 12 | 6 | 6 | 12 |
| A02 | 3 | 8 | 11 | 5 | 7 | 12 |
| A03 | 2 | 3 | 5 | 2 | 4 | 6 |
| A24 | 3 | 3 | 6 | 4 | 4 | 8 |
| A26 | 2 | 13 | 15 | 3 | 16 | 19 |
| B07 | 3 | 4 | 7 | 2 | 2 | 4 |
| B08 | 3 | 4 | 7 | 3 | 3 | 6 |
| B27 | 2 | 3 | 5 | 1 | 3 | 4 |

TABLE 151-continued

| Epitopes in Native and Designed (mod) MAGEA1 | | | | | | |
|---|---|---|---|---|---|---|
| | Native | | | Designed | | |
| HLA Supertype | SB | WB | Total | SB | WB | Total |
| B39 | 2 | 8 | 10 | 2 | 10 | 12 |
| B44 | 4 | 7 | 11 | 4 | 6 | 10 |
| B58 | 2 | 11 | 13 | 2 | 12 | 14 |
| B62 | 1 | 6 | 7 | 2 | 7 | 9 |
| Total Epitopes | 32 | 77 | 109 | 36 | 80 | 116 |

TABLE 152

| Native Sequences for Designed (mod) Antigens | |
|---|---|
| TAA Name | NCBI Gene Symbol (Gene ID) |
| TERT | TERT (7015) |
| PSMA (FOLH1) | FOLH1 (2346) |
| MAGE A1 | MAGEA1 (4100) |
| TBXT | TBXT (6862) |
| BORIS | CTCFL (140690) |
| FSHR | FSHR (2492) |
| MAGEA10 | MAGEA10 (4109) |
| MAGEC2 | MAGEC2 (51438) |
| WT1 | WT1 (7490) |
| FBP | FOLR1 (2348) |
| TDGF1 | TDGF1 (6997) |
| Claudin 18 | CLDN18 (51208) |
| LY6K | LY6K (54742) |
| Mesothelin | MSLN (10232) |
| FAP | FAP (2191) |
| FRAME | PRAME (23532) |

The following table describes predicted epitopes for HLA-A and HLA-B supertypes for an exemplary combination of TAAs in GBM. Predicted epitopes for PSMA (SEQ ID NO: 70), modPSMA (SEQ ID NO: 38), native TERT (Gene ID 7015), modTERT (SEQ ID NO: 36), native MAGEA1 (Gene ID 4100), and modMAGEA1 (SEQ ID NO: 73) are indicated by HLA-A and HLA-B supertype. Table 153 demonstrates the combination of designed antigens creates a total of 82 neoepitopes: modPSMA creates 41 neoepitopes, modTERT 34 neoepitopes, and modMAGEA1 7 neoepitopes. FIG. 130A shows the frequency of HLA-A and HLA-B supertype pairs in a subset of 28,034 high-resolution HLA allele and haplotype frequency data available from donors in the National Marrow Donor Program databases from four major U.S. census categories of race and ethnicity (L Maiers, M., et al. (2007)). The HLA-A and HLA-B supertypes were assigned to HLA-A and HLA-B allele pairs occurring in the top 25th percentile of HLA-A and HLA-B haplotype pairs for each ethnic subgroup (FIG. 130B) according to Lundt et al. (2004). If either the HLA A or B haplotype was not classified into a supertype it was not included in the analysis (Outlier). Data for HLA-A and HLA-B pairs was downloaded from the publicly available database https://bioinformatics.bethematchclinical.org/hla-resources/haplotype-frequencies/high-resolution-hla-alleles-and-haplotypes-in-the-us-population/on Mar. 15, 2020. If an HLA-A or HLA-B allele in the data set did not fall into an HLA-A and HLA-B supertype according to Lundt et al. it was excluded from the data subset (FIG. 130C).

TABLE 153

| | PSMA | | TERT | | MAGE A1 | |
|---|---|---|---|---|---|---|
| HLA Supertype | Native | Designed | Native | Designed | Native | Designed |
| A01 | 19 | 20 | 19 | 19 | 12 | 12 |
| A02 | 17 | 19 | 37 | 42 | 11 | 12 |
| A03 | 15 | 19 | 27 | 28 | 5 | 6 |
| A24 | 19 | 22 | 31 | 36 | 6 | 8 |
| A26 | 36 | 34 | 30 | 34 | 15 | 19 |
| B07 | 15 | 17 | 69 | 65 | 7 | 4 |
| B08 | 21 | 29 | 67 | 72 | 7 | 6 |
| B27 | 21 | 24 | 62 | 62 | 5 | 4 |
| B39 | 24 | 35 | 67 | 81 | 10 | 12 |
| B44 | 17 | 20 | 23 | 23 | 11 | 10 |
| B58 | 19 | 22 | 26 | 28 | 13 | 14 |
| B62 | 25 | 28 | 47 | 49 | 7 | 9 |
| Total Epitopes | 248 | 289 | 505 | 539 | 109 | 116 |

In one exemplary embodiment, neoepitopes existing in the cell lines of a vaccine composition and induced by design in GBM are provided in Table 154.

TABLE 154

| Super type | Mod PSMA | Mod TERT | Mod MAGE Al | LN229 | A172 | YKG1 | KNS60 | SF126 | DMS53 | Design Total | Existing Total | Total |
|---|---|---|---|---|---|---|---|---|---|---|---|---|
| A01 | 2 | 0 | 1 | 1 | 0 | 0 | 0 | 1 | 0 | 3 | 2 | 5 |
| A02 | 2 | 5 | 1 | 0 | 0 | 1 | 1 | 0 | 0 | 8 | 2 | 10 |
| A03 | 4 | 3 | 2 | 0 | 0 | 0 | 2 | 0 | 0 | 9 | 2 | 11 |
| A24 | 3 | 5 | 2 | 1 | 0 | 1 | 0 | 0 | 2 | 10 | 4 | 14 |
| A26 | 2 | 5 | 3 | 0 | 0 | 0 | 0 | 0 | 0 | 10 | 0 | 10 |
| B07 | 2 | 2 | 2 | 0 | 1 | 0 | 0 | 1 | 2 | 6 | 4 | 10 |
| B08 | 9 | 6 | 0 | 0 | 0 | 0 | 1 | 1 | 0 | 15 | 2 | 17 |
| B27 | 4 | 3 | 0 | 0 | 0 | 0 | 0 | 0 | 0 | 7 | 0 | 7 |
| B39 | 12 | 16 | 4 | 0 | 0 | 1 | 0 | 0 | 0 | 32 | 1 | 33 |
| B44 | 3 | 1 | 0 | 0 | 0 | 0 | 0 | 0 | 0 | 4 | 0 | 4 |
| B58 | 3 | 2 | 0 | 1 | 0 | 1 | 0 | 0 | 0 | 5 | 2 | 7 |
| B62 | 3 | 3 | 1 | 1 | 0 | 0 | 1 | 0 | 0 | 7 | 2 | 9 |
| Total | 49 | 51 | 16 | 4 | 1 | 4 | 5 | 3 | 4 | 116 | 21 | 137 |

FIG. 131 shows the number of neoepitopes existing in the cell lines of a vaccine composition and created by design in GBM recognized by donors expressing HLA-A and HLA-B supertype pairs within the population subsets described in Example 29 herein. The median number of neoepitopes recognized in the four ethnic subpopulations is twenty.

FIG. 132 depicts the number of neoepitopes targeted by four different mRNA immunotherapies. One mRNA immunotherapy targets a total of 34 neoepitopes and the other three mRNA therapies target a total of 20 neoepitopes. Humans express two pairs of HLA-A and HLA-B alleles. The number of neoepitopes that an exemplary patient expressing the HLA-A and HLA-B allelic pairs in the HLA-A3 HLA-B7 and HLA-A1 HLA-B-8 supertypes would recognize of the neoepitopes existing in the cell lines of a vaccine composition and created by design in GBM is forty-three. The number of epitopes recognized in twenty prioritized TAAs existing in a vaccine composition GBM by all HLA-A and HLA-B supertype pairs ranges from 1,500 to 2,000.

Example 41: Clinical Protocol

An exemplary clinical protocol is provided in the following Example.

Dosage form: The vaccine composition is provided to a clinical site in a package containing six vials, each vial comprising a therapeutically effective amount of cells from a cancer cell line, as described in embodiments disclosed herein (thus six cell lines total). Three of the cell lines constitute Cocktail A and the other three cell lines constitute Cocktail B, thus resulting in three Cocktail A vials, and three Cocktail B vials. At the time of administration, the vials are removed from the freezeer and thawed at room temperature for about 5 to about 15 minutes. The contents of two of the Cocktail A vials are removed by needle and syringe and are injected into the third Cocktail A vial. Similarly, the contents of two of the Cocktail B vials are removed by needle and syringe and injected into the third Cocktail B vial.

Route of Administration: After mixing, 0.3 mL Cocktail A is drawn into a syringe and administered as an intradermal injection in the upper arm. Similarly and concurrently, 0.3 mL Cocktail B is drawn into a syringe and administered as an intradermal injection in the thigh. The dose administered is about $8\times10^6$ (or optionally $1\times10^7$) of each cell line for a total dose of about $2.4\times10^7$ (or optionally $3\times10^7$) cells at each injection site. Multiple doses are administered, and administration is alternated between the left and right arms and left and right thighs. As described herein, the 0.3 mL injection volume can be split into 3×0.1 mL or 2×0.15 mL.

In one embodiment, Cocktail A and Cocktail B comprises the modified cell lines as set out in Table 45, 56, 65, 74, 83, 92, 101, 110, 119. According to some embodiments, the clinical protocol may be used for other indications and using other cocktails of cell line combinations, as described herein.

Dosing Regimen: In various embodiments, three cohorts will receive administration of the vaccine in combination with a checkpoint inhibitor (CPI) such as pembrolizumab. In these cohorts, the vaccine will be administered in 21-day cycles to match administration of the CPI. The first four doses will be administered every 21 days (up to day 63) and then every 42 days for three additional doses (up to day 189). Patients who continue to benefit from treatment will be allowed to continue to receive the vaccine in combination with a CPI for five additional doses at 42-day intervals (up to day 399) and then at 84-day intervals.

In a fourth cohort, the vaccine will be administered in combination with durvalumab. The vaccine will be administered in either 14-day, 21-day or 28-day cycles to match administration of durvalumab. For example, the first three doses will be administered every 14 days (up to day 28) and then every 42 days for four additional doses (up to day 196). Patients who continue to benefit from treatment will be allowed to continue to receive the vaccine in combination with durvalumab for five additional doses at 42-day intervals (up to day 406) and then at 84-day intervals. As another example, the first three doses will be administered every 28 days.

All patients will receive an oral dose of 50 mg/day (or 100 mg/day) cyclophosphamide for seven days prior to each administration of the investigational product.

A number of embodiments have been described. Nevertheless, it will be understood that various modifications may be made without departing from the spirit and scope of the disclosure. Accordingly, other embodiments are within the scope of the following claims.

The invention claimed is:

1. A composition comprising a modified cancer cell line version of cell line designated DMS 53 available under ATCC CRL-2062, wherein the modified cell line is modified in vitro to: 1) knockout expression of the gene encoding CD276, 2) express GM-CSF from an expression vector, 3) express TGFβ2 shRNA from an expression vector, 4) express IL-12 from an expression vector, 5) express membrane bound CD40L from an expression vector, and 6) express TGFβ1 shRNA from an expression vector.

2. The composition of claim 1, wherein the composition comprises approximately $1.0\times10^6$-$6.0\times10^7$ cells.

3. The composition of claim 1, wherein the modified cell line is irradiated.

4. A kit comprising at least one vial, wherein said vial comprises a composition according to claim 1.

* * * * *